US008569336B2

(12) United States Patent  (10) Patent No.: US 8,569,336 B2
Tong et al.  (45) Date of Patent: Oct. 29, 2013

(54) COMPOUNDS FOR THE TREATMENT OF INFLAMMATORY DISORDERS

(76) Inventors: Ling Tong, Warren, NJ (US); Brian J. Lavey, New Providence, NJ (US); Bandarpalle B. Shankar, Branchburg, NJ (US); Seong Heon Kim, Livington, NJ (US); Wensheng Yu, Edison, NJ (US); Joseph A. Kozlowski, Princeton, NJ (US); Michael K. C. Wong, Somerset, NJ (US); Lei Chen, Roselle Park, NJ (US); Guowei Zhou, Somerset, NJ (US); Razia K. Rizvi, Bloomfield, NJ (US); Robert Feltz, Washington, PA (US); Aneta Maria Kosinski, South Amboy, NJ (US); De-Yi Yang, Morris Plains, NJ (US); Chaoyang Dai, Acton, MA (US); Luke Fire, Cambridge, MA (US); Vinay Girijavallabhan, Denville, NJ (US); Dansu Li, Reading, MA (US); Janeta Popovici-Muller, Waltham, MA (US); Judson E. Richard, Kittery, ME (US); Kristin E. Rosner, Watertown, MA (US); M. Arshad Siddiqui, Newton, MA (US); Liping Yang, Arlington, MA (US)

( * ) Notice: Subject to any disclaimer, the term of this patent is extended or adjusted under 35 U.S.C. 154(b) by 108 days.

(21) Appl. No.: 13/127,953

(22) PCT Filed: Nov. 9, 2009

(86) PCT No.: PCT/US2009/063669
§ 371 (c)(1),
(2), (4) Date: Sep. 23, 2011

(87) PCT Pub. No.: WO2010/054278
PCT Pub. Date: May 14, 2010

(65) Prior Publication Data
US 2012/0015926 A1 Jan. 19, 2012

Related U.S. Application Data

(60) Provisional application No. 61/113,085, filed on Nov. 10, 2008.

(51) Int. Cl.
A61K 31/4166 (2006.01)
A61K 31/4178 (2006.01)
A61K 31/4439 (2006.01)
A61K 31/454 (2006.01)
A61K 31/506 (2006.01)
C07D 233/76 (2006.01)
C07D 213/24 (2006.01)

(52) U.S. Cl.
USPC ........... 514/302; 544/333; 546/115; 546/193; 548/311.1; 514/269; 514/317; 514/386

(58) Field of Classification Search
USPC ........... 548/397; 514/269, 302, 317; 546/115, 546/193; 544/333
See application file for complete search history.

(56) References Cited

U.S. PATENT DOCUMENTS

| | | | |
|---|---|---|---|
| 6,495,565 B2 | 12/2002 | Duan et al. |
| 6,534,491 B2 | 3/2003 | Levin et al. |
| 6,677,355 B1 | 1/2004 | Conrad et al. |
| 7,041,693 B2 | 5/2006 | Sheppeck |
| 7,482,370 B2 | 1/2009 | Yu et al. |
| 7,488,745 B2 | 2/2009 | Yu et al. |
| 7,504,424 B2 | 3/2009 | Yu et al. |
| 7,524,842 B2 | 4/2009 | Lavey et al. |
| 7,683,085 B2 | 3/2010 | Yu et al. |
| 7,687,527 B2 | 3/2010 | Yu et al. |
| 7,772,263 B2 | 8/2010 | Lavey et al. |
| 7,879,890 B2 | 2/2011 | Yu et al. |
| 7,998,961 B2 | 8/2011 | Mansoor et al. |
| 8,178,553 B2 | 5/2012 | Lavey et al. |
| 2011/0288054 A1 | 11/2011 | Bandarpalle et al. |
| 2011/0288077 A1 | 11/2011 | Wong et al. |
| 2012/0010181 A1 | 1/2012 | Kozlowski et al. |

FOREIGN PATENT DOCUMENTS

| | | |
|---|---|---|
| WO | WO02/074750 A1 | 9/2002 |
| WO | WO02/096426 A1 | 12/2002 |
| WO | WO03/053940 A1 | 7/2003 |
| WO | WO03/053941 A2 | 7/2003 |

(Continued)

OTHER PUBLICATIONS

U.S. Appl. No. 13/120,728, commonly assigned.*
U.S. Appl. No. 13/120,730, commonly assigned.*
PCT International Search Report dated May 10, 2011 corresponding to PCT Application No. PCT/US2009/063669.
Knaggs, A., et al., "Biotransfonnation of Alosetron: Mechanism of Hydantoin Formation", Tetrahedron Letters, vol. 36, No. 3, pp. 477-480 (1995).

(Continued)

Primary Examiner — Kamal Saeed
Assistant Examiner — Janet L Coppins
(74) Attorney, Agent, or Firm — Eric A. Meade; Valerie J. Camara

(57) ABSTRACT

This invention relates to compounds of the Formula (I): (Chemical formula should be inserted here as it appears on abstract in paper form) (I) or a pharmaceutically acceptable salt thereof, which can be useful for the treatment of diseases or conditions mediated by MMPs, ADAMs, TACE, aggrecanase, TNF- or combinations thereof.

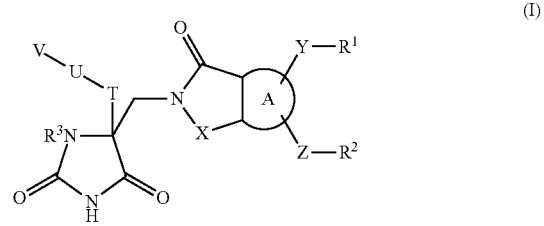

4 Claims, No Drawings

(56) References Cited

FOREIGN PATENT DOCUMENTS

| WO | WO2004/012663 A2 | 2/2004 |
| WO | WO2004/024698 A1 | 3/2004 |
| WO | WO2004/024715 A1 | 3/2004 |
| WO | WO2004/024721 A1 | 3/2004 |
| WO | WO2004/056766 A1 | 7/2004 |
| WO | WO2006/019768 A1 | 2/2006 |
| WO | WO 2007/084415 A2 * | 6/2007 |
| WO | WO2007/084415 A2 | 7/2007 |
| WO | WO2007/084451 A1 | 7/2007 |
| WO | WO2010/054279 A1 | 5/2010 |

OTHER PUBLICATIONS

Notice of Allowance mailed Jan. 3, 2013 from U.S. Appl. No. 13/120,730, which application published as US2011/0288077.

* cited by examiner

COMPOUNDS FOR THE TREATMENT OF INFLAMMATORY DISORDERS

CROSS-REFERENCE TO RELATED APPLICATIONS

This application is a 371 application filed Sep. 23, 2011, which is a national stage application of PCT/US09/63669 filed Nov. 9, 2009, which claims the priority of U.S. Provisional Application No. 61/113,085, filed Nov. 10, 2008, which is herein incorporated by reference in its entirety.

FIELD OF THE INVENTION

This invention relates generally to novel hydantoin derivatives that can inhibit matrix metalloproteinases (MMPs), disintegrin and metalloproteases (ADAMs) and/or tumor necrosis factor alpha-converting enzyme (TACE) and in so doing prevent the release of tumor necrosis factor alpha (TNF-α), pharmaceutical compositions comprising such compounds, and methods of treatment using such compounds.

BACKGROUND OF THE INVENTION

Osteo- and rheumatoid arthritis (OA and RA, respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A (1970) 424-434). There are four classes of protein degradative enzymes in mammalian cells: serine, cysteine, aspartic and metalloproteases. The available evidence supports the belief that it is the metalloproteases that are responsible for the degradation of the extracellular matrix of articular cartilage in OA and RA. Increased activities of collagenases and stromelysin have been found in OA cartilage and the activity correlates with severity of the lesion (Mankin et al. Arthritis Rheum. 21, 1978, 761-766, Woessner et al. Arthritis Rheum. 26, 1983, 63-68 and Ibid. 27, 1984, 305-312). In addition, aggrecanase (a newly identified metalloprotease) has been identified that provides the specific cleavage product of proteoglycan, found in RA and OA patients (Lohmander L. S. et al. Arthritis Rheum. 36, 1993, 1214-22).

Metalloproteases (MPs) have been implicated as the key enzymes in the destruction of mammalian cartilage and bone. It can be expected that the pathogenesis of such diseases can be modified in a beneficial manner by the administration of MP inhibitors (see Wahl et al. Ann. Rep. Med. Chem. 25, 175-184, AP, San Diego, 1990).

MMPs are a family of over 20 different enzymes that are involved in a variety of biological processes important in the uncontrolled breakdown of connective tissue, including proteoglycan and collagen, leading to resorption of the extracellular matrix. This is a feature of many pathological conditions, such as RA and OA, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMPs (tissue inhibitor of MPs), which form inactive complexes with the MMP's.

Tumor necrosis factor alpha (TNF-α) is a cell-associated cytokine that is processed from a 26 kDa precursor form to a 17 kd active form. See Black R. A. "Tumor necrosis factor-alpha converting enzyme" Int J Biochem Cell Biol. 2002 January; 34(1):1-5 and Moss M L, White J M, Lambert M H, Andrews R C. "TACE and other ADAM proteases as targets for drug discovery" Drug Discov Today. 2001 Apr. 1; 6(8): 417-426, each of which is incorporated by reference herein.

TNF-α has been shown to play a pivotal role in immune and inflammatory responses. Inappropriate or over-expression of TNF-α is a hallmark of a number of diseases, including RA, Crohn's disease, multiple sclerosis, psoriasis and sepsis. Inhibition of TNF-α production has been shown to be beneficial in many preclinical models of inflammatory disease, making inhibition of TNF-α production or signaling an appealing target for the development of novel anti-inflammatory drugs.

TNF-α is a primary mediator in humans and animals of inflammation, fever and acute phase responses, similar to those observed during acute infection and shock. Excess TNF-α has been shown to be lethal. Blocking the effects of TNF-α with specific antibodies can be beneficial in a variety of conditions, including autoimmune diseases such as RA (Feldman et al, Lancet, (1994) 344, 1105), non-insulin dependent diabetes mellitus (Lohmander L. S. et al., Arthritis Rheum. 36 (1993) 1214-22) and Crohn's disease (Macdonald T. et al., Clin. Exp. Immunol. 81 (1990) 301).

Compounds that inhibit the production of TNF-α are therefore of therapeutic importance for the treatment of inflammatory disorders. Recently it has been shown that metalloproteases, such as TACE, are capable of converting TNF-α from its inactive to active form (Gearing et al Nature, 1994, 370, 555). Since excessive TNF-α production has been noted in several disease conditions also characterized by MMP-mediated tissue degradation, compounds which inhibit both MMPs and TNF-α production may also have a particular advantage in diseases where both mechanisms are involved.

One approach to inhibiting the harmful effects of TNF-α is to inhibit the enzyme, TACE before it can process TNF-α to its soluble form. TACE is a member of the ADAM family of type I membrane proteins and mediates the ectodomain shedding of various membrane-anchored signaling and adhesion proteins. TACE has become increasingly important in the study of several diseases, including inflammatory disease, because of its role in cleaving TNF-α from its "stalk" sequence and thus releasing the soluble form of the TNF-α protein (Black R. A. Int J Biochem Cell Biol. 2002 34, 1-5).

There are numerous patents and publications which disclose hydroxamate, sulphonamide, hydantoin, carboxylate and/or lactam based MMP inhibitors.

U.S. Pat. No. 6,677,355 and U.S. Pat. No. 6,534,491(B2) describe compounds that are hydroxamic acid derivatives and MMP inhibitors.

U.S. Pat. No. 6,495,565 discloses lactam derivatives that are potential inhibitors of MMPs and/or TNF-α.

PCT Publications WO2002/074750, WO2002/096426, WO20040067996, WO2004012663, WO200274750 and WO2004024721 disclose hydantoin derivatives that are potential inhibitors of MMPs.

PCT Publications WO2004024698 and WO2004024715 disclose sulphonamide derivatives that are potential inhibitors of MMPs.

PCT Publications WO2004056766, WO2003053940 and WO2003053941 also describe potential inhibitors of TACE and MMPs.

PCT Publications WO2007/084415 and WO2007/084455 refer to hydantoin derivatives that are TACE inhibitors.

There is a need in the art for inhibitors of MMPs, ADAMs, TACE, and TNF-α, which can be useful as anti-inflammatory compounds and cartilage protecting therapeutics. The inhibition of TNF-α, TACE and or other MMPs can prevent the degradation of cartilage by these enzymes, thereby alleviating the pathological conditions of OA and RA as well as many other auto-immune diseases.

SUMMARY OF THE INVENTION

The present invention relates to compounds having the general structure shown in Formula (I):

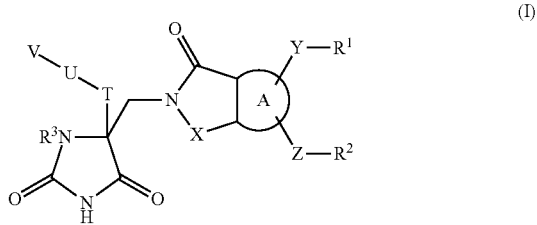

or a pharmaceutically acceptable salt thereof, wherein:
ring A is selected from the group consisting of aryl and heteroaryl, each of which is substituted with —Y—$R^1$ and —Z—$R^2$ as shown;
X is selected from the group consisting of —S—, —O—, —S(O)$_2$, —S(O)—, —(C(R)$^2$)$_m$— and —N($R^3$)—;
T is absent or present, and if present, T is selected from the group consisting of alkyl, aryl, and heteroaryl, wherein when each of said T aryl and heteroaryl contains two radicals on adjacent carbon atoms, said radicals may optionally be taken together with the carbon atoms to which they are attached to form a five- to eight-membered aryl or heteroaryl ring, wherein each of the aforementioned T aryl, and heteroaryl, optionally with said five- to eight-membered aryl or heteroaryl is independently unsubstituted or substituted with one to four $R^{10}$ moieties which can be the same or different;
U is absent or present or absent, and if present, U is selected from the group consisting of —O—, —O—C(O)NH—, —OC(O)N(alkyl)-, —C(O)—, —C(O)O—, —C(O)NH—, —C(O)N(alkyl)-, —C(=N—OH)-alkyl-, and —C(=N—O-alkyl)-alkyl-;
V is absent or present, and if present V is selected from the group consisting of alkyl, alkynyl, cycloalkyl, heterocyclyl, aryl, heteroaryl, and N-oxides of said heterocyclyl and heteroaryl, wherein when each of said V cycloalkyl, heterocyclyl, aryl, heteroaryl, and N-oxides of said heterocycyl and heteroaryl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of said V alkyl, alkynyl, cycloalkyl, heterocyclyl, aryl, and heteroaryl heterocyclyl, optionally with said five- to eight-membered cycloalkyl, aryl, heterocyclyl, or heteroaryl is independently unsubstituted or substituted with one to four $R^{10}$ moieties which can be the same or different;
Y is selected from the group consisting of a covalent bond, —(C($R^4$)$_2$)$_n$—, —N($R^4$)—, —C(O)N($R^4$)—, —N($R^4$)C(O)—, —N($R^4$)C(O)N($R^4$)—, —S(O)$_2$N($R^4$)—, —N($R^4$)S(O)$_2$, —O—, —S—, —C(O)—, —S(O)—, and —S(O)$_2$—;
Z is selected from the group consisting of a covalent bond, —(C($R^4$)$_2$)$_n$—, —N($R^4$)—, —C(O)N($R^4$)—, —N($R^4$)C(O)—, —N($R^4$)C(O)N($R^4$)—, —S(O)$_2$N($R^4$)—, —N($R^4$)S(O)$_2$—, —O—, —S—, —C(O)—, —S(O)—, and —S(O)$_2$—;

m is 1 to 3;
n is 1 to 3;
$R^1$ is selected from the group consisting of H, cyano, —C(O)OH, —C(O)O-alkyl, —C(O)NH$_2$, —C(O)NH(alkyl), —C(O)N(alkyl)$_2$, alkynyl, halogen, alkyl, cycloalkyl, haloalkyl, aryl, heteroaryl, and heterocyclyl, wherein when each of said cycloalkyl, heterocyclyl, aryl and heteroaryl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of the $R^1$ alkyl, alkynyl, aryl, heteroaryl, and heterocyclyl, optionally with the five or six-membered cycloalkyl, aryl, heterocyclyl or heteroaryl ring is unsubstituted or optionally independently substituted with one to four $R^{20}$ moieties which can be the same or different; with the proviso that when Y is —N($R^4$)—, —S— or —O—, then $R^1$ is not halogen or cyano;
$R^2$ is selected from the group consisting of H, cyano, —C(O)OH, —C(O)O-alkyl, —C(O)NH$_2$, —C(O)NH(alkyl), —C(O)N(alkyl)$_2$, alkynyl, halogen, alkyl, cycloalkyl, haloalkyl, aryl, heteroaryl, and heterocyclyl, wherein when each of said cycloalkyl, heterocyclyl, aryl and heteroaryl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of the $R^2$ alkyl, cycloalkyl, aryl, heteroaryl, and heterocyclyl, optionally with the five or six-membered cycloalkyl, aryl, heterocyclyl or heteroaryl ring is unsubstituted or optionally independently substituted with one to four $R^{20}$ moieties which can be the same or different; with the proviso that when Y is —N($R^4$)—, —S— or —O—, then $R^2$ is not halogen or cyano;
each $R^3$ is the same of different and is independently selected from the group consisting of H, alkyl, and aryl;
each $R^4$ is the same or different and is independently selected from the group consisting of H, alkyl, cycloalkyl, haloalkyl, hydroxy, -alkylcycloalkyl, -alkyl-N(alkyl)$_2$, heterocyclyl, aryl, and heteroaryl, wherein when each of said cycloalkyl, heterocyclyl, ayl, and heteroaryl contains two radicals on adjacent carbon atoms, said radicals may optionally be taken together with the carbon atoms to which they are attached to form a five- to eight-membered cycloalkyl, aryl, heterocyclyl or heteroaryl ring;
$R^{10}$ is selected from the group consisting of hydrogen, cyano, nitro, —C($R^4$)=N—O$R^4$, —O$R^4$, —S$R^4$, —N($R^4$)$_2$, —S(O)$R^4$, —S(O)$_2R^4$, —N($R^4$)S(O)$_2R^4$, —N($R^4$)—C(O)—$R^4$, —N($R^4$)—C(O)—N($R^4$)$_2$, —N($R^4$)—C(O)—O$R^4$, —OC(O)N($R^4$)$_2$, —C(O)N($R^4$)—S(O)$_2R^4$, —S(O)$_2$N(R$_4$)—C(O)—$R^4$, —C(O)N($R^4$)C(O)$R^4$, —C(O)N($R^4$)C(O)NR$^4$, —S(O)$_2$N($R^4$)$_2$, —N($R^4$)—C(=N$R^4$)—N($R^4$)$_2$, —N($R^4$)—C(=N—CN)—N($R^4$)$_2$, -haloalkoxy, —C(O)O$R^4$, —C(O)$R^4$, —C(O)N($R^4$)$_2$, halogen, alkyl, haloalkyl, aryl, heteroaryl, heterocyclyl, and cycloalkyl, wherein each of the $R^{10}$ alkyl, aryl, heteroaryl, heterocyclyl, and cycloalkyl is unsubstituted or optionally independently substituted with one to four $R^{30}$ moieties which can be the same or different;
or wherein two $R^{10}$ moieties, when attached to the same or adjacent carbon atoms may optionally be taken together with the carbon atom(s) to which they are attached to form a cycloalkyl, cycloalkenyl, heterocyclyl, aryl, or heteroaryl ring;
$R^{20}$ is selected from the group consisting of cyano, nitro, —C($R^4$)=N—O$R^4$, —O$R^4$, —S$R^4$, —N($R^4$)$_2$, —S(O)$R^4$, —S(O)$_2R^4$, —N($R^4$)S(O)$_2R^4$, —N($R^4$)—C(O)—$R^4$, —N($R^4$)—C(O)—N($R^4$)$_2$, —N($R^4$)—C(O)—O$R^4$, —OC(O)N($R^4$)$_2$, —C(O)N($R^4$)—S(O)$_2R^4$, —S(O)$_2$N(R$_4$)—C (O)—R⁴, —C(O)N(R⁴)C(O)R⁴, —C(O)N(R⁴)C(O)NR⁴, —S(O)₂N(R⁴)₂, —N(R⁴)—C(=NR⁴)—N(R⁴)₂, —N(R⁴)—C(=N—CN)—N(R⁴)₂, -haloalkoxy, —C(O)OR⁴, —C(O)R⁴, —C(O)N(R⁴)₂, halogen, alkyl, haloalkyl, aryl, heteroaryl, heterocyclyl, and cycloalkyl; wherein when each of said R²⁰ aryl, heteroaryl, heterocyclyl and cycloalkyl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of said R²⁰ alkyl, aryl, heteroaryl, heterocyclyl, and cycloalkyl, optionally with said five- to eight-membered cycloalkyl, aryl, heterocyclyl or heteroaryl ring is unsubstituted or substituted with one to four moieties selected independently from the group consisting of alkyl, halo, haloalkyl, hydroxy, alkoxy, haloalkoxy, hydroxyalkyl, cyano, nitro, —NH₂, —NH(alkyl), and —N(alkyl)₂;

or when two R²⁰ moieties when attached to the same or adjacent carbon atoms may optionally be taken together with the carbon atom(s) to which they are attached to form a cycloalkyl, cycloalkenyl, heterocyclyl, aryl, or heteroaryl ring;

R³⁰ is selected from the group consisting of cyano, nitro, —C(R⁴)=N—OR⁴, —OR⁴, —SR⁴, —N(R⁴)₂, —S(O)R⁴, —S(O)₂R⁴, —N(R⁴)S(O)₂R⁴, —N(R⁴)—C(O)—R⁴, —N(R⁴)—C(O)—N(R⁴)₂, —N(R⁴)—C(O)—OR⁴, —OC(O)N(R⁴)₂, —C(O)N(R⁴)—S(O)₂R⁴, —S(O)₂N(R₄)—C(O)—R⁴, —C(O)N(R⁴)C(O)R⁴, —C(O)N(R⁴)C(O)NR⁴, —S(O)₂N(R⁴)₂, —N(R⁴)—C(=NR⁴)—N(R⁴)₂, —N(R⁴)—C(=N—CN)—N(R⁴)₂, -haloalkoxy, —C(O)OR⁴, —C(O)R⁴, —C(O)N(R⁴)₂, halogen, alkyl, haloalkyl, aryl, heteroaryl, heterocyclyl, and cycloalkyl; wherein when each of said R³⁰ aryl, heteroaryl, heterocyclyl and cycloalkyl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of said R³⁰ alkyl, aryl, heteroaryl, heterocyclyl, and cycloalkyl, optionally with said five- to eight-membered cycloalkyl, aryl, heterocyclyl or heteroaryl ring is unsubstituted or substituted with one to four moieties selected independently from the group consisting of alkyl, halo, haloalkyl, hydroxy, alkoxy, haloalkoxy, cyano, nitro, —NH₂, —NH(alkyl), and —N(alkyl)₂;

or when two R³⁰ moieties when attached to the same or adjacent carbon atoms may optionally be taken together with the carbon atom(s) to which they are attached to form a cycloalkyl, cycloalkenyl, heterocyclyl, aryl, or heteroaryl ring;

with the proviso that at least one of T, U, and V must be present.

The present invention also relates to a compound selected from the group consisting of:

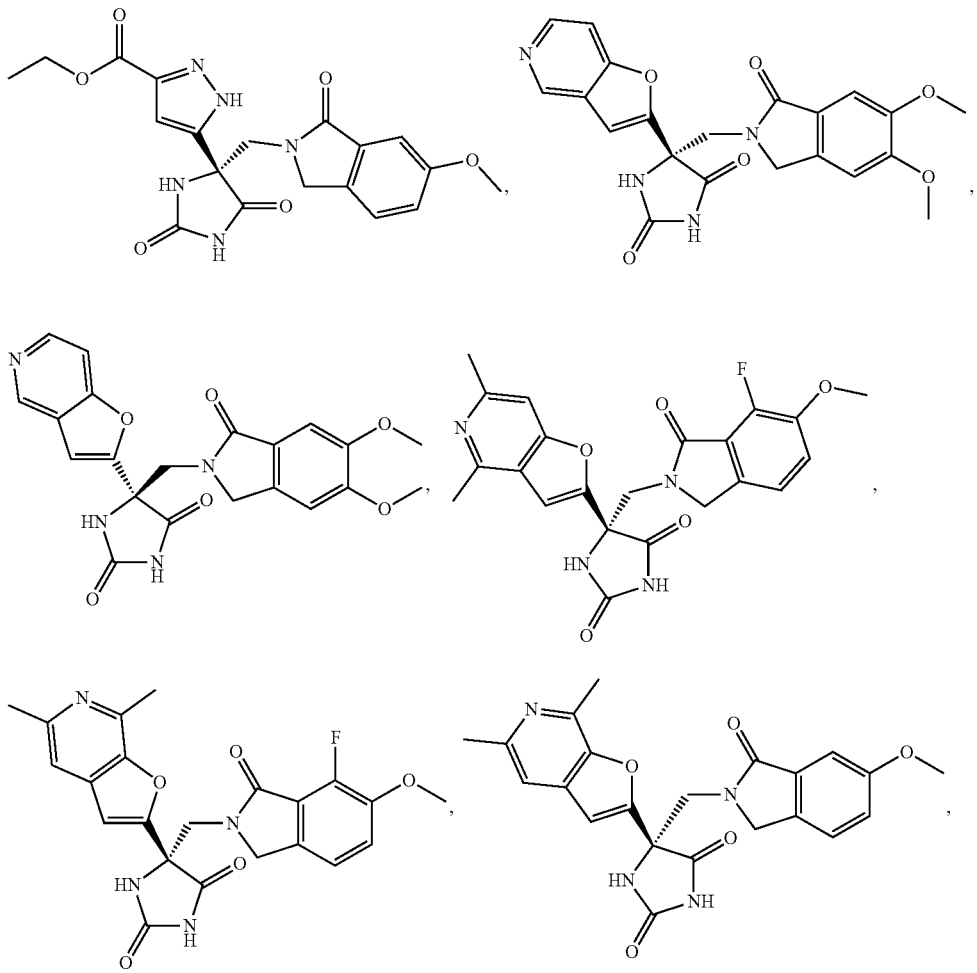

-continued
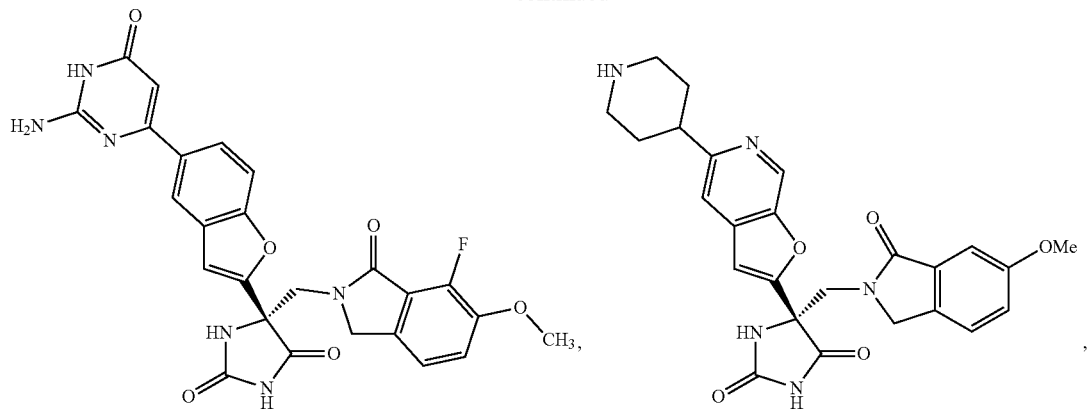
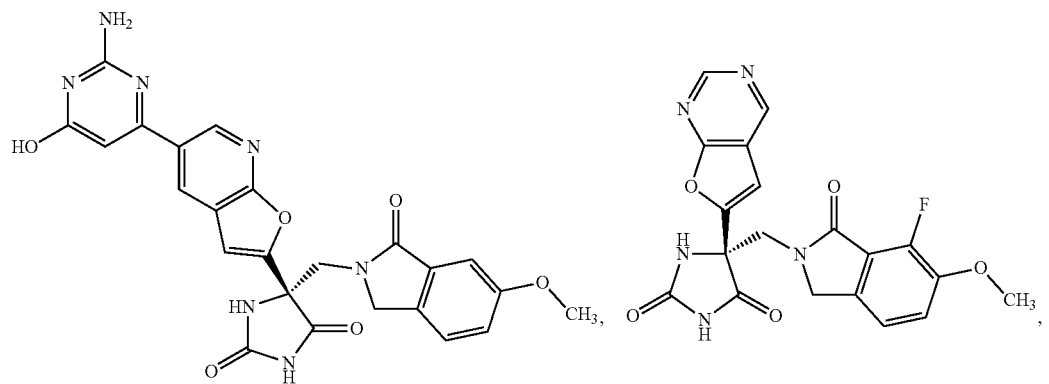
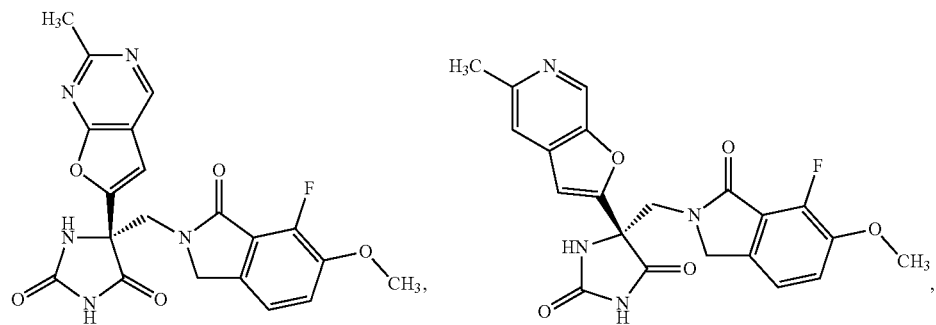
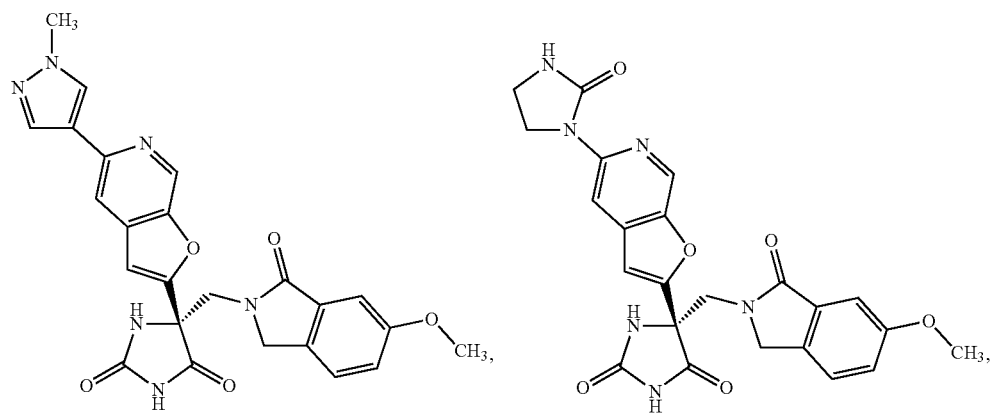

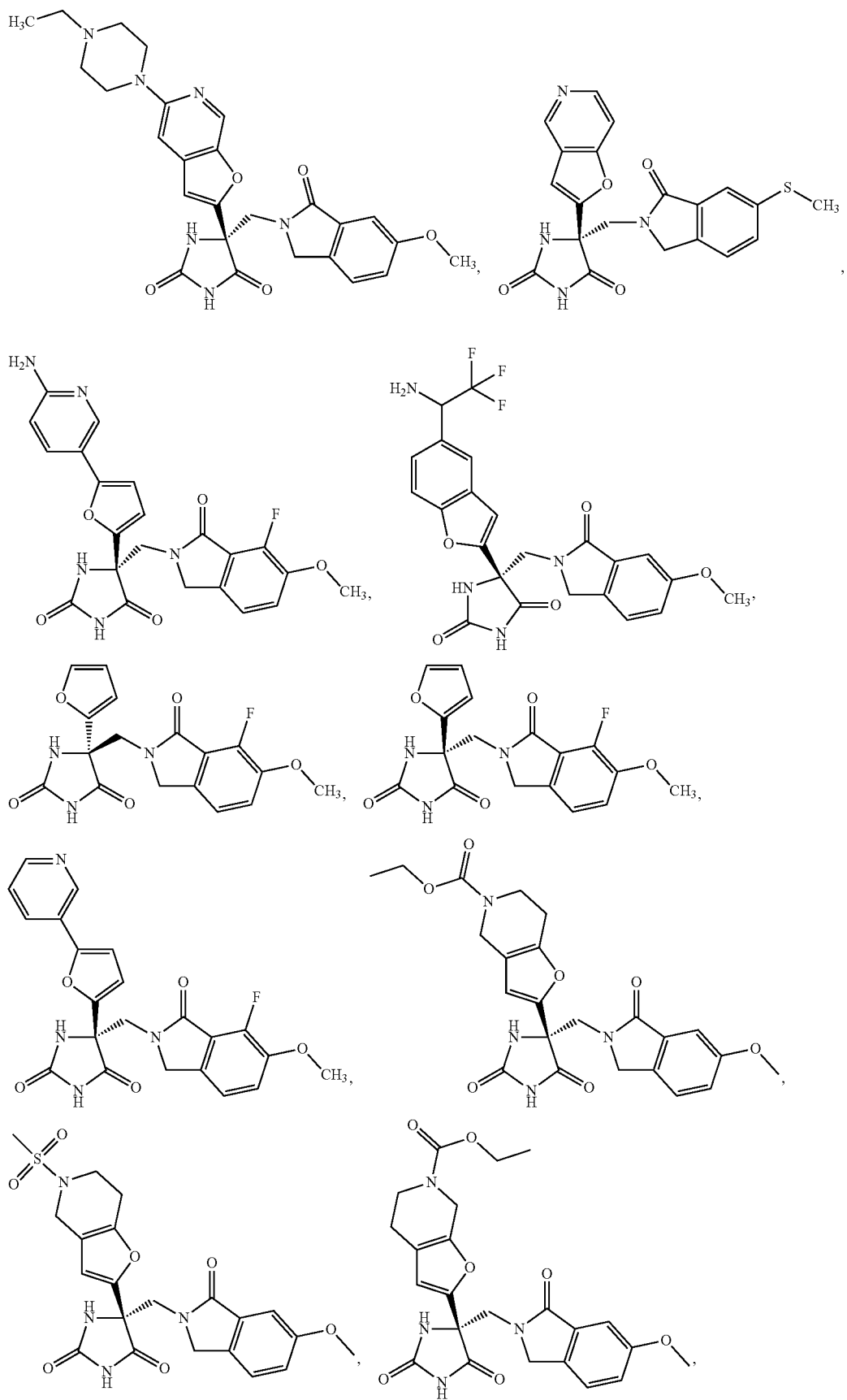

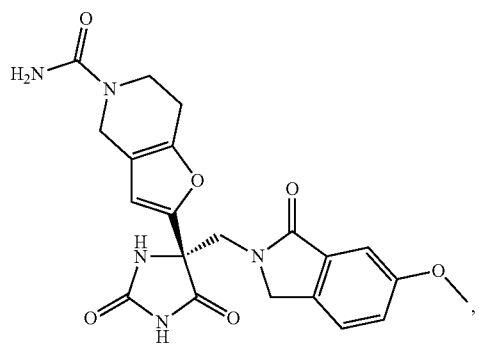
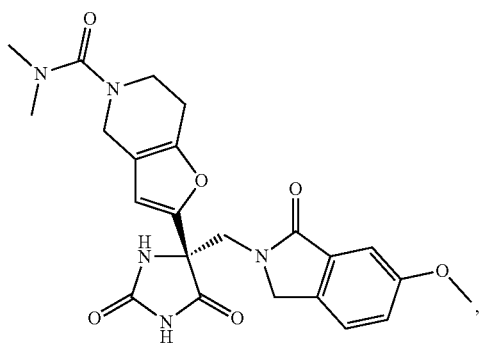
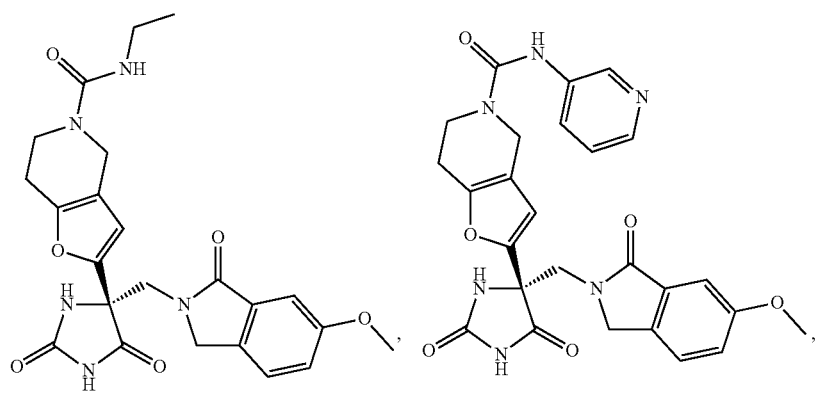
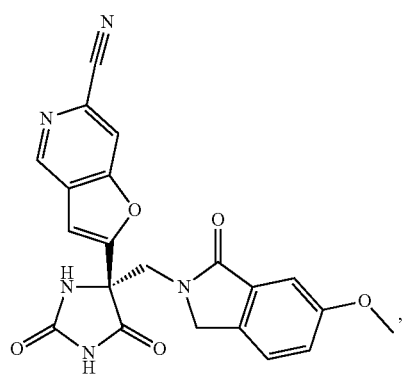
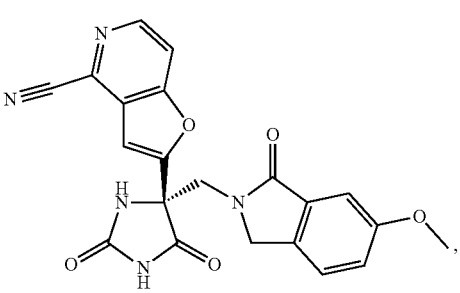
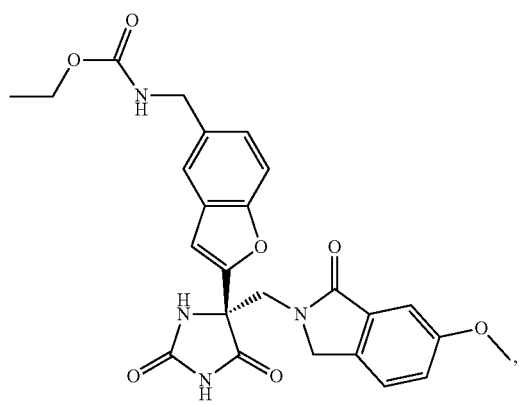
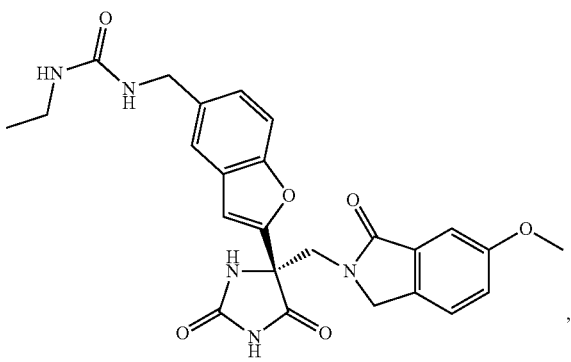

-continued
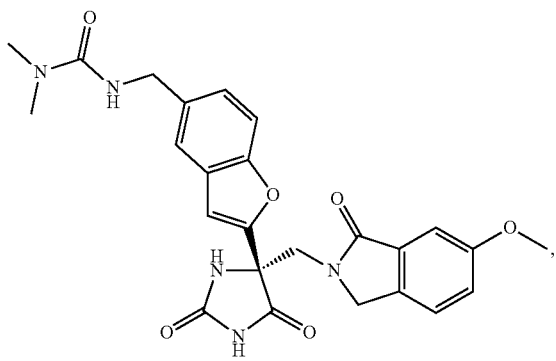
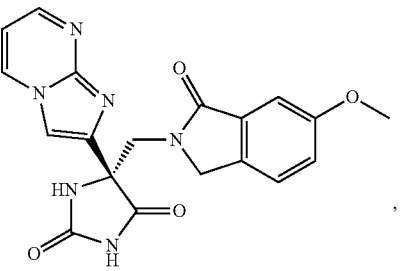
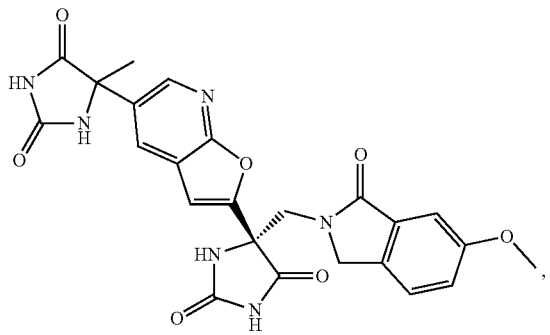
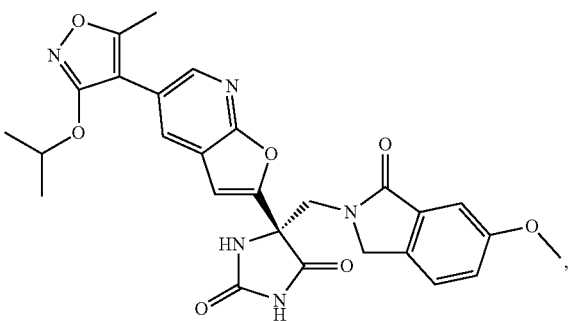
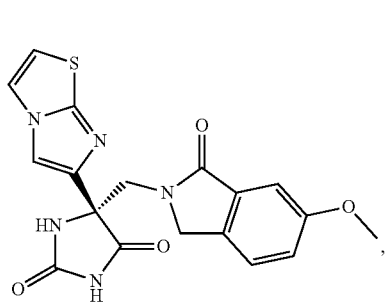
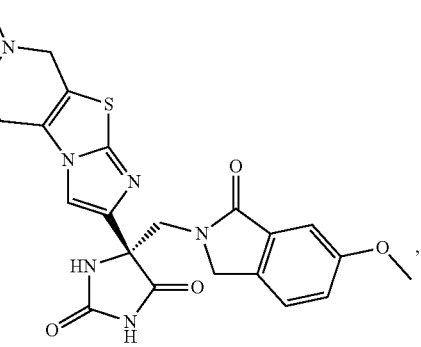
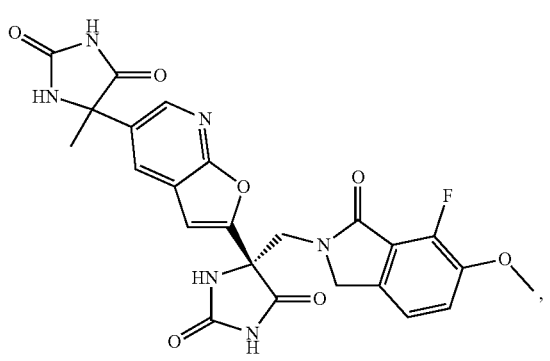
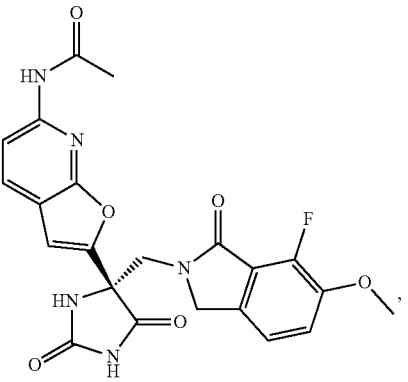

-continued
| 15 | 16 |
|---|---|
| 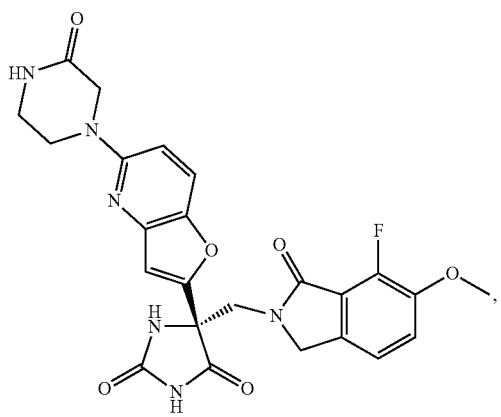 | 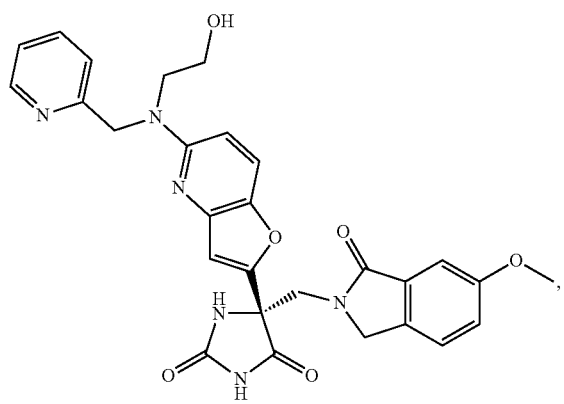 |
| 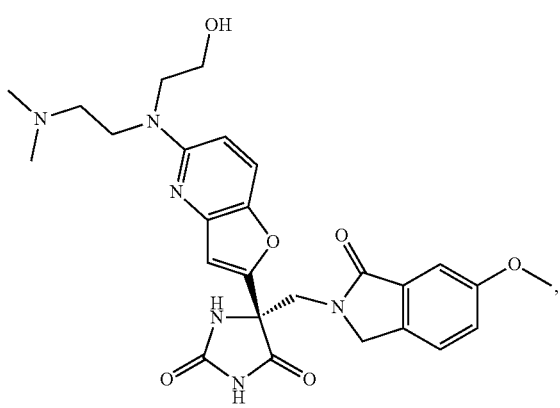 | 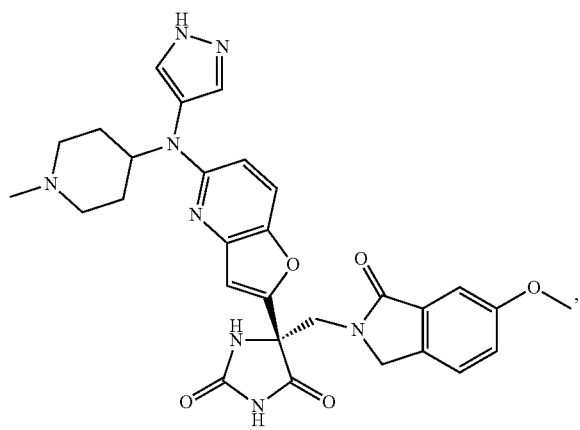 |
| 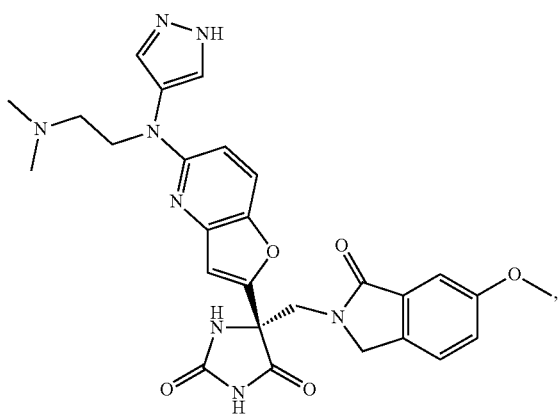 | 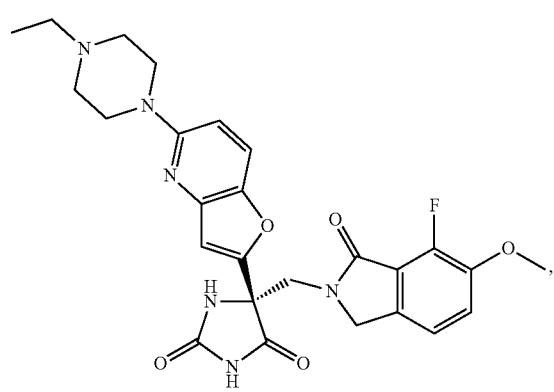 |
| 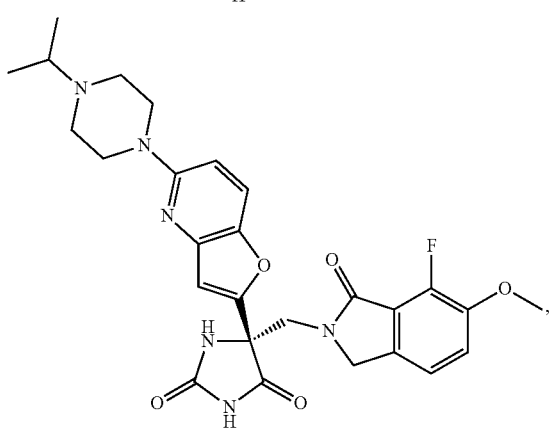 | 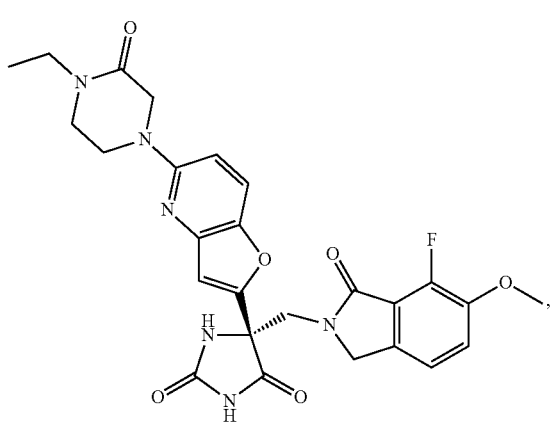 |

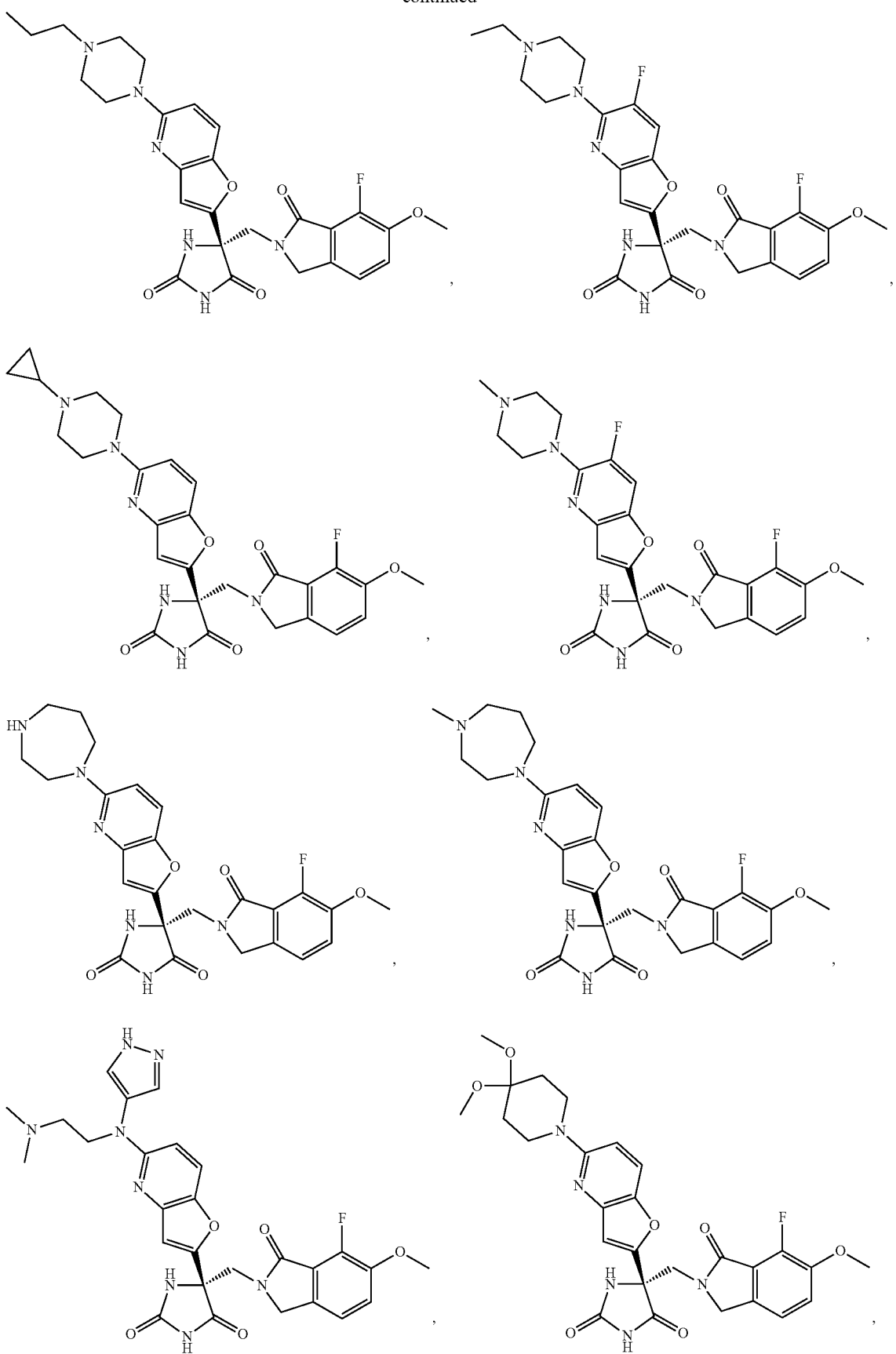

-continued
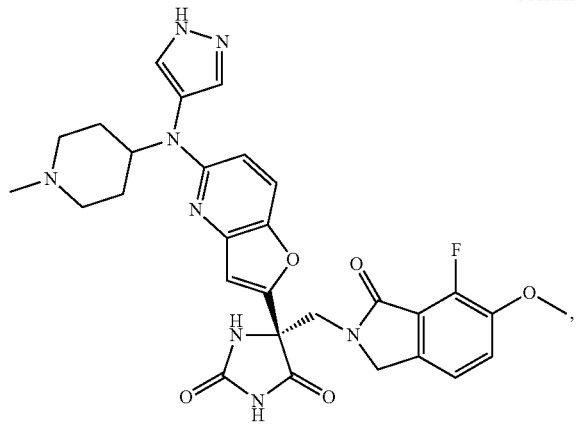
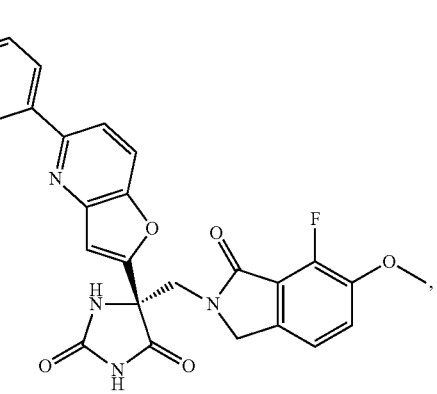
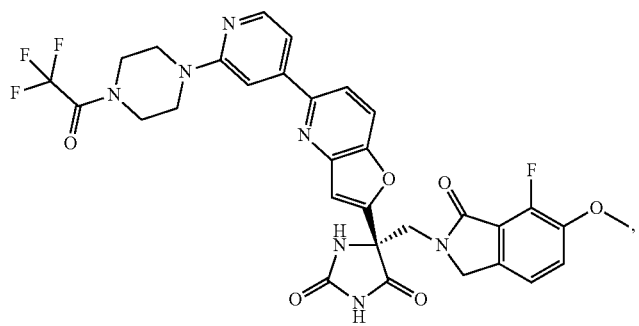
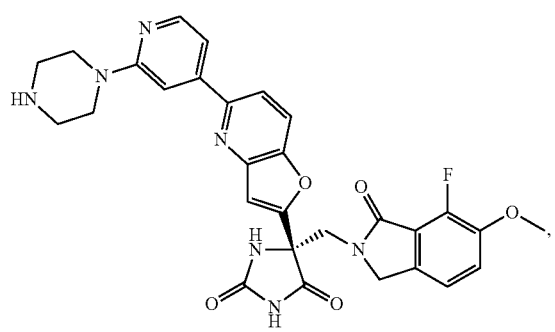
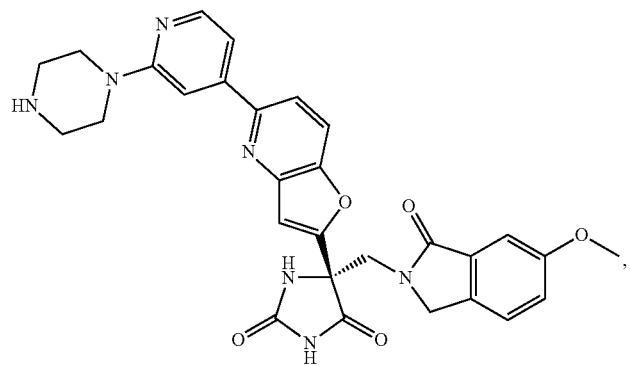
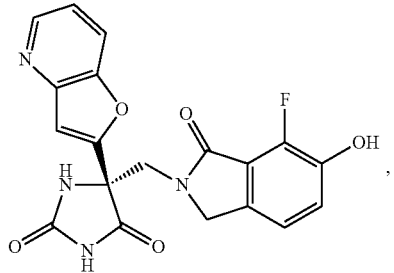
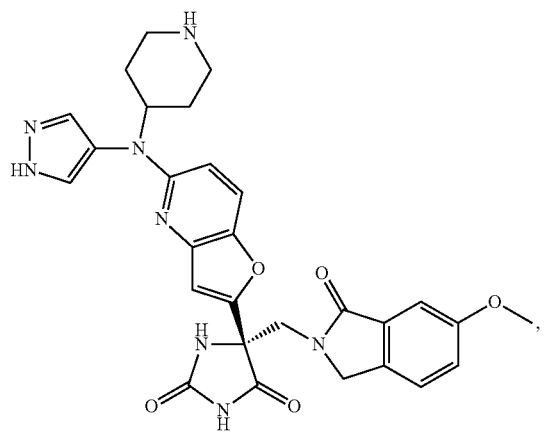
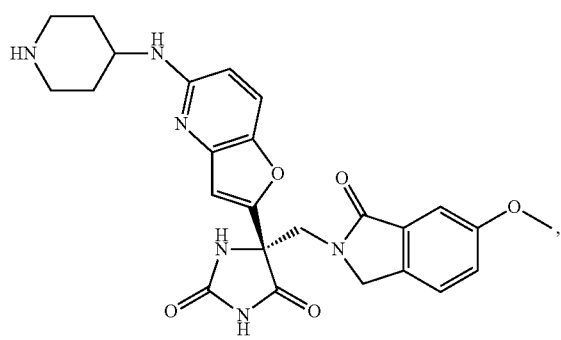

-continued
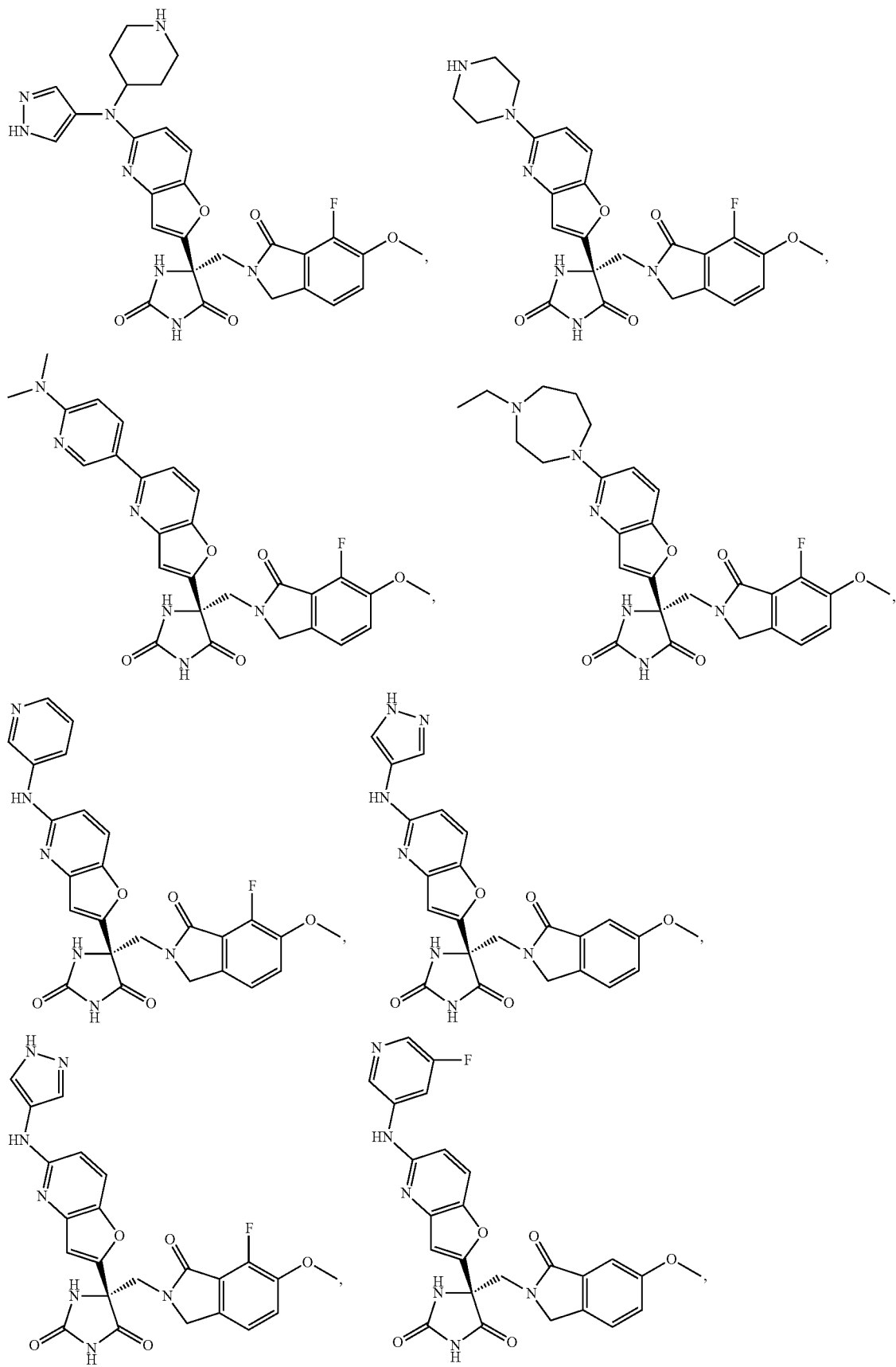

-continued
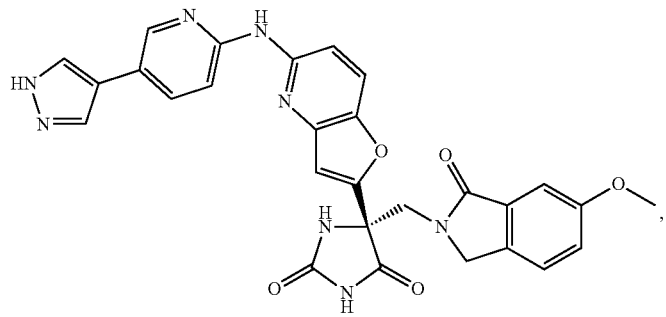
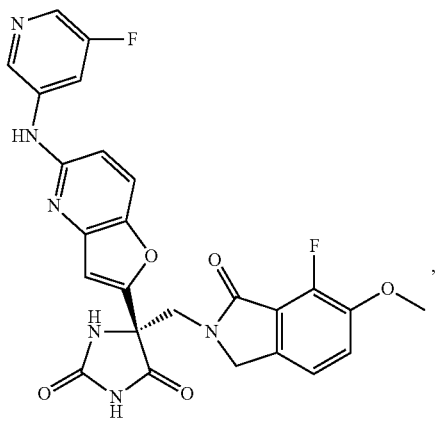
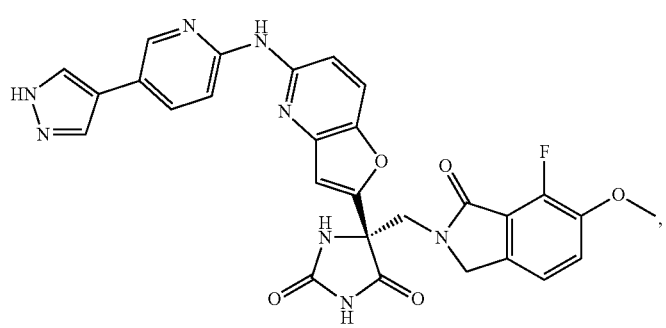
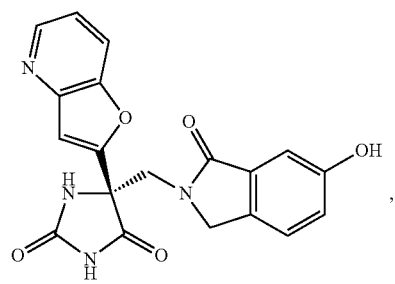
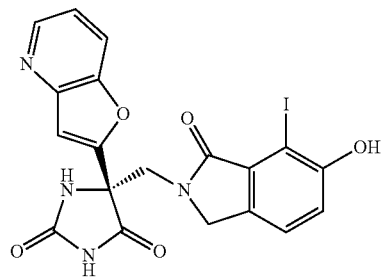
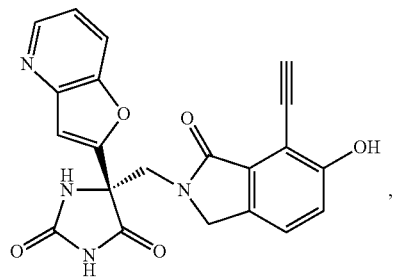
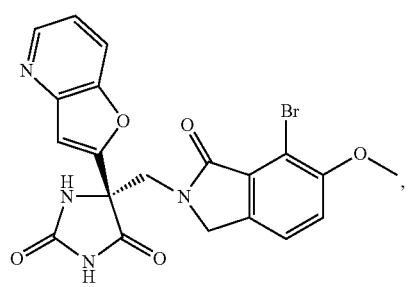
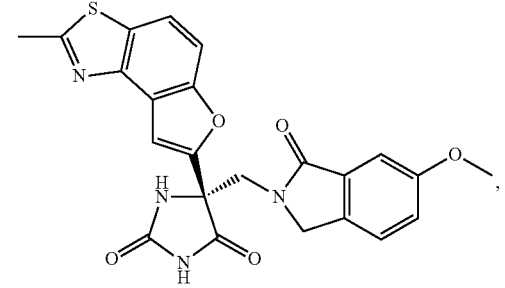
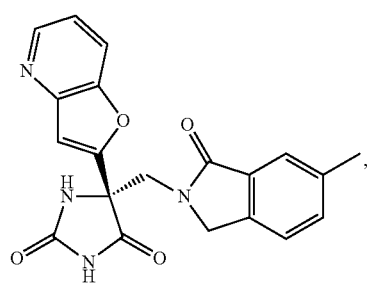
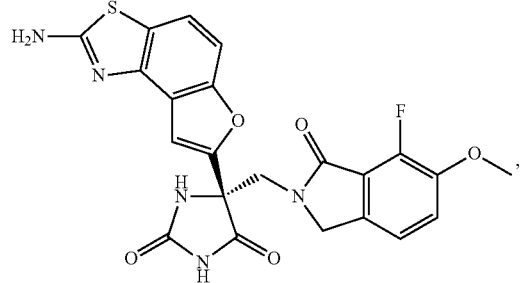

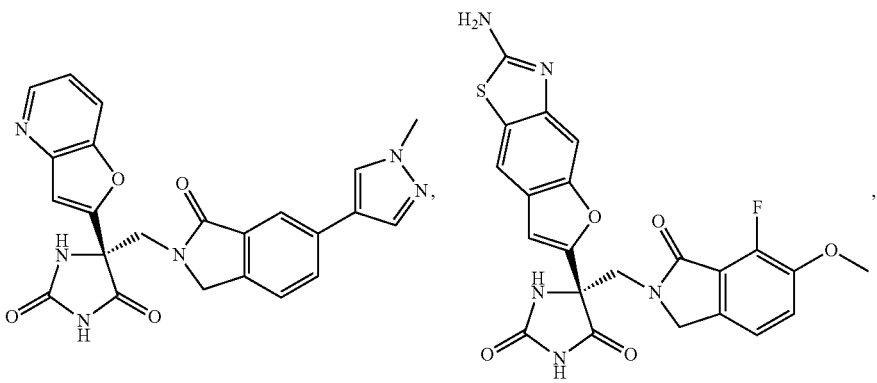
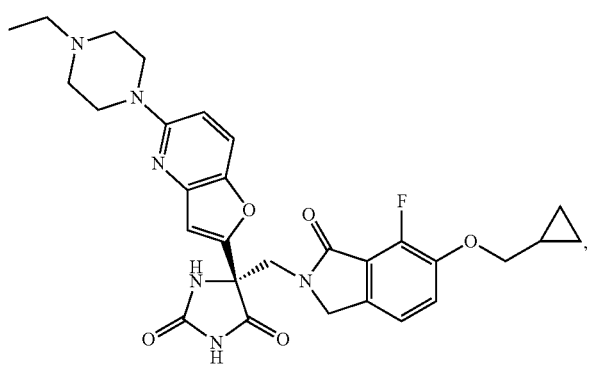
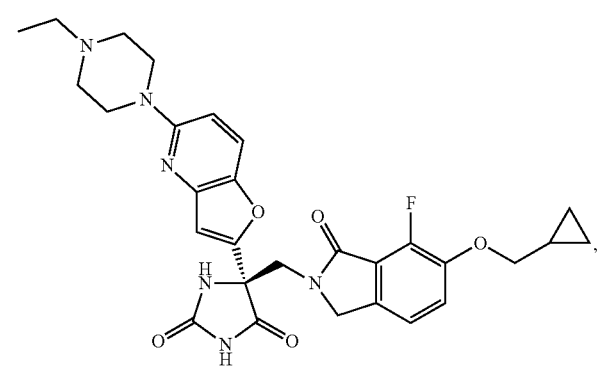
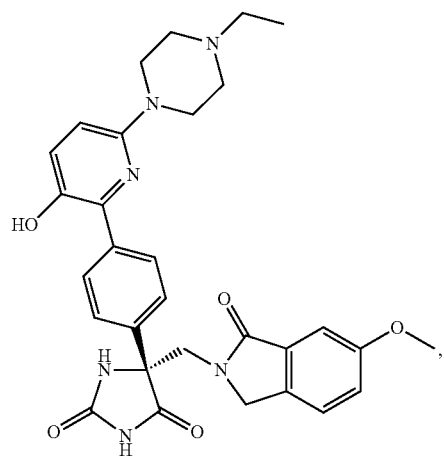
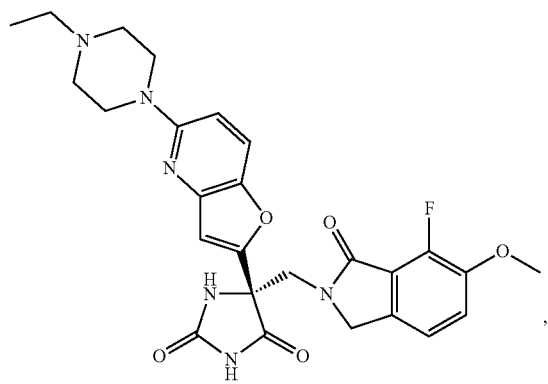
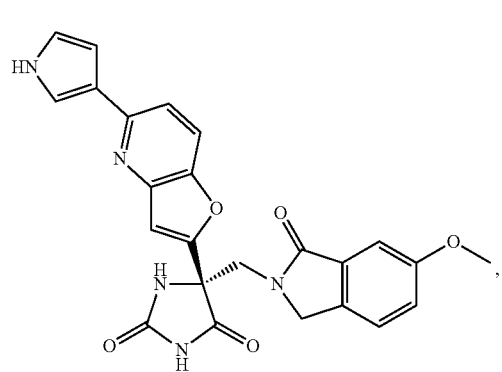
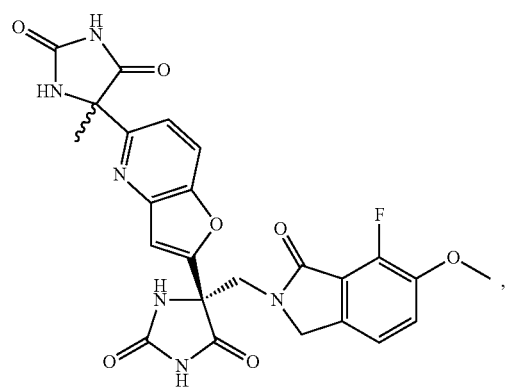

-continued
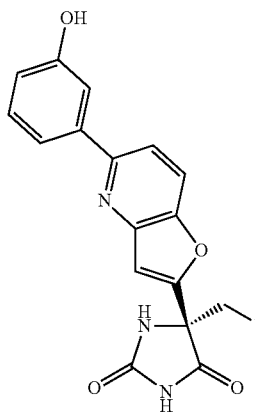 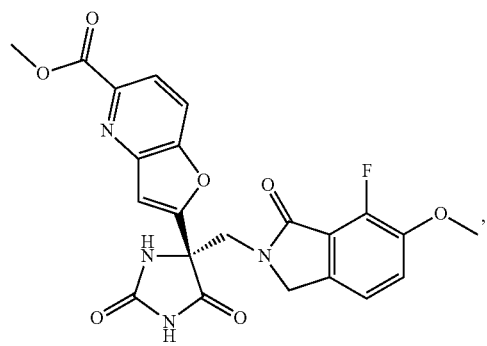
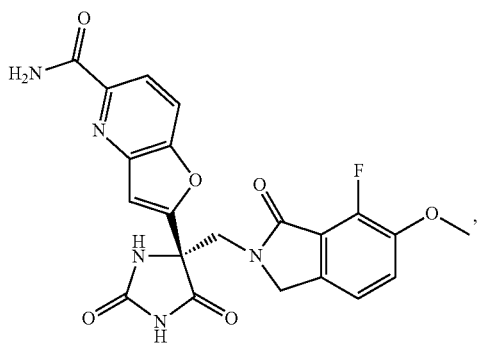 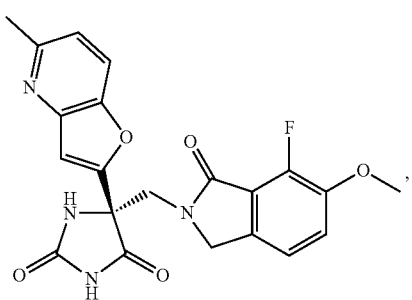
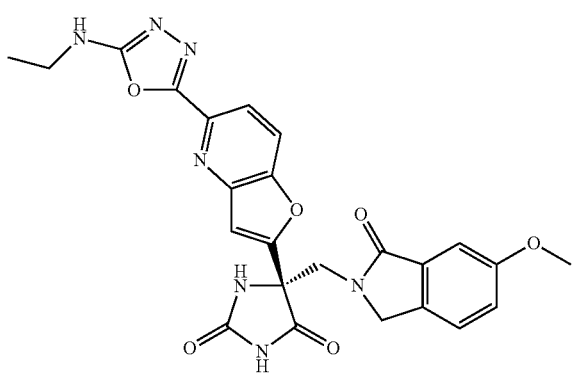 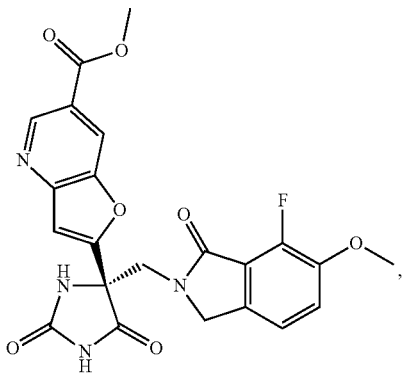
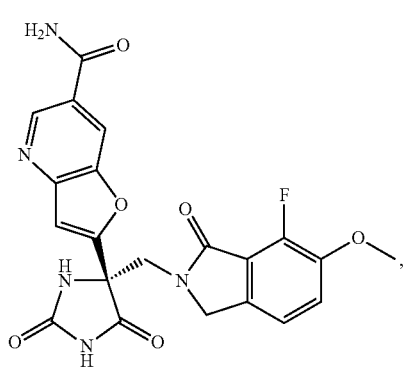 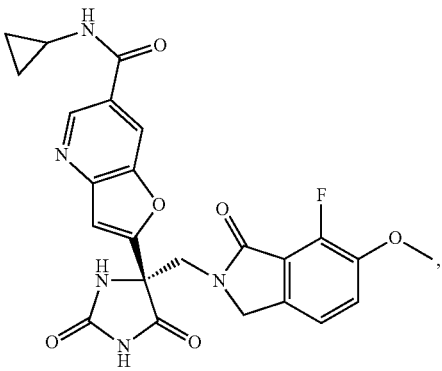

-continued
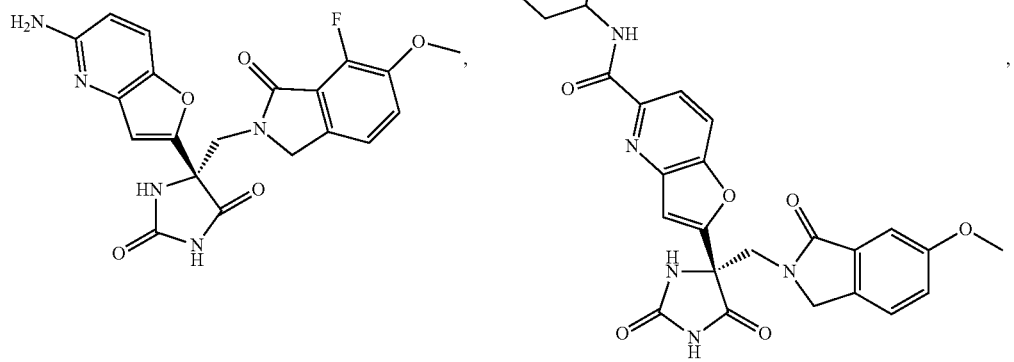
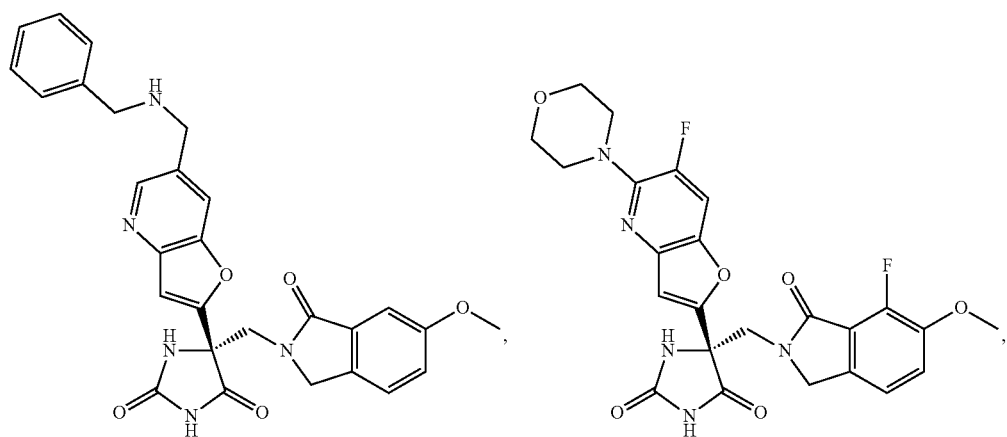
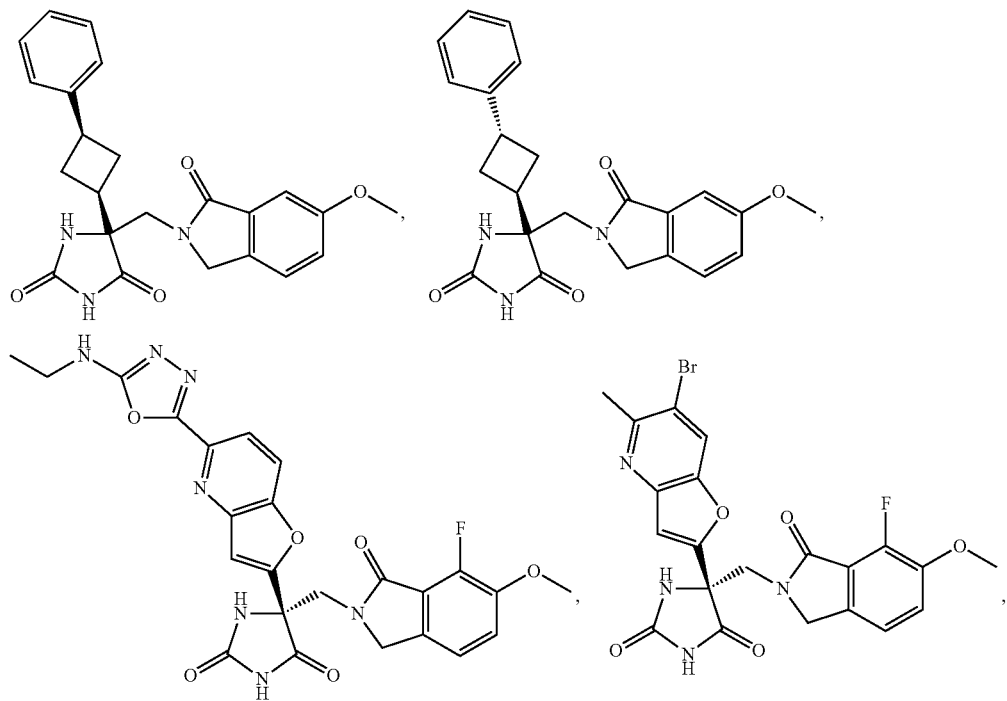

-continued
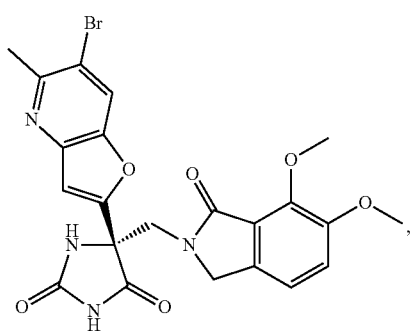
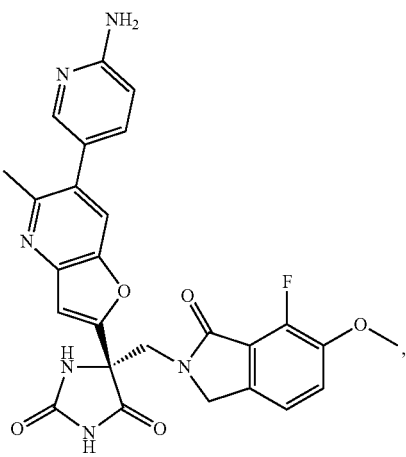
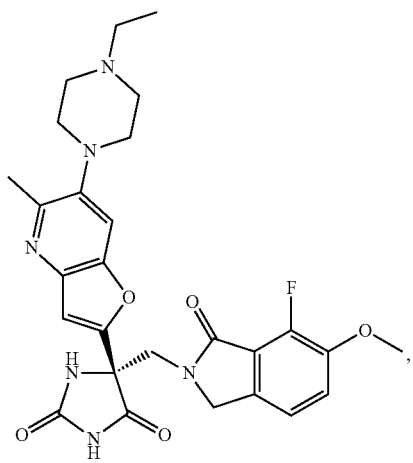
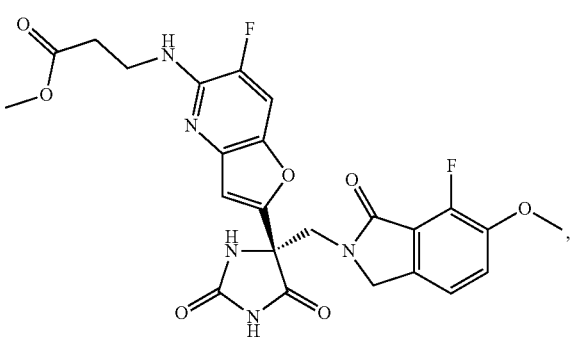
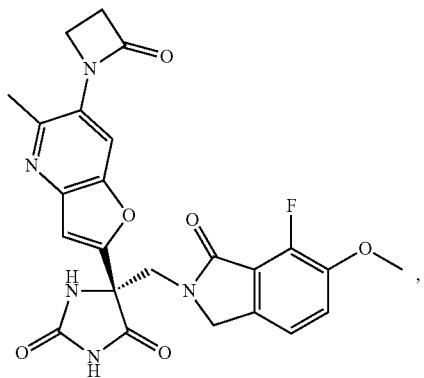
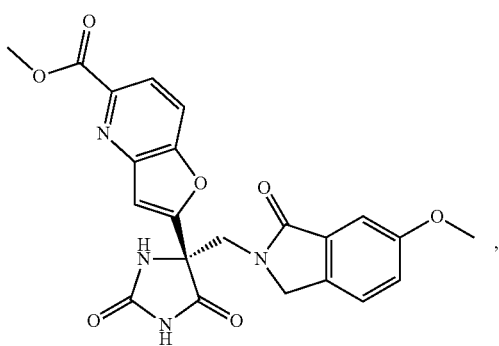
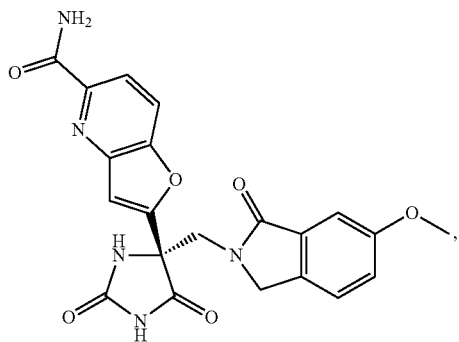
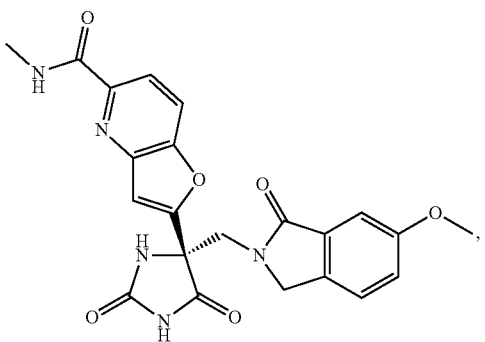

-continued
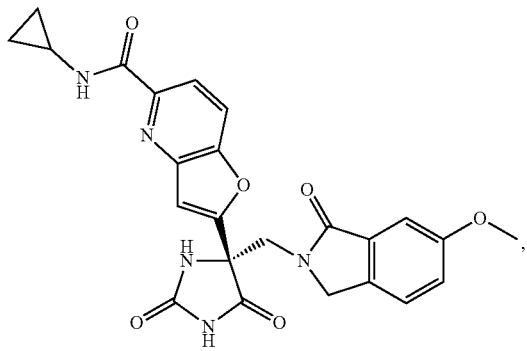
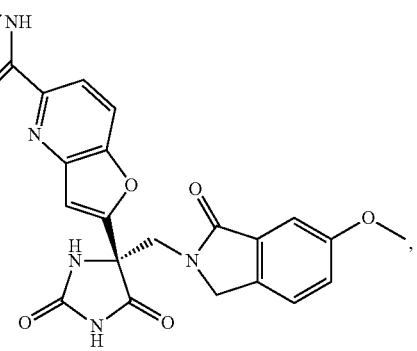
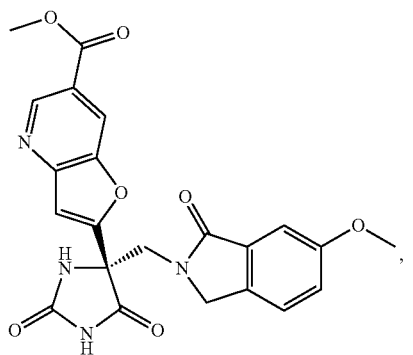
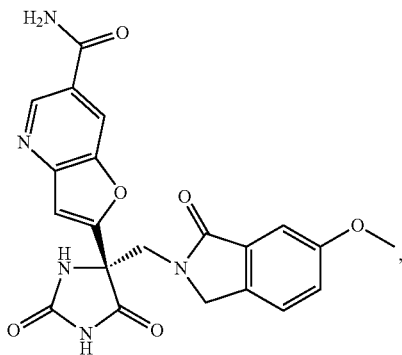
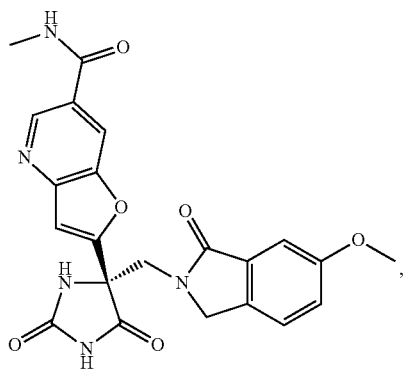
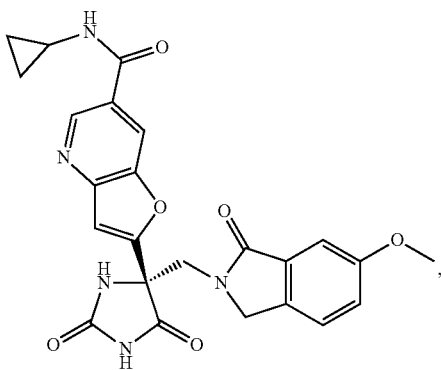
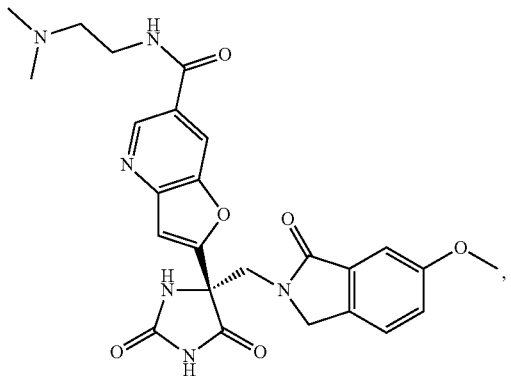
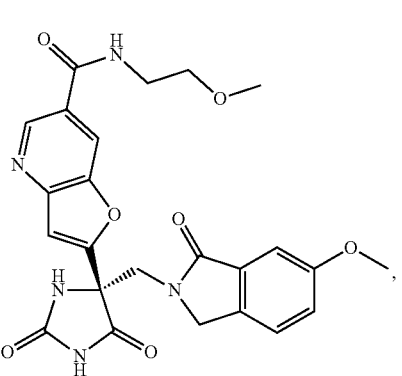

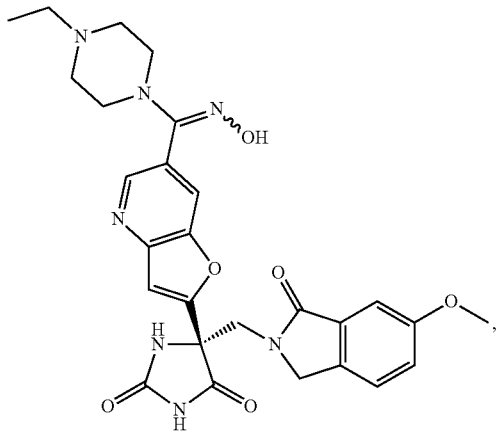
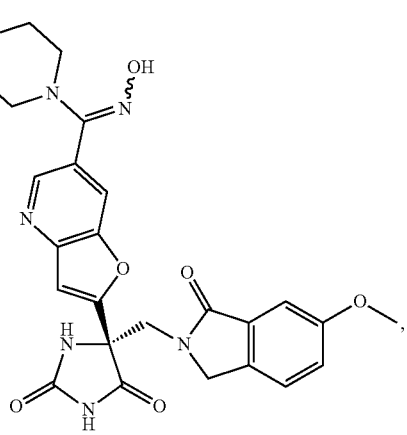
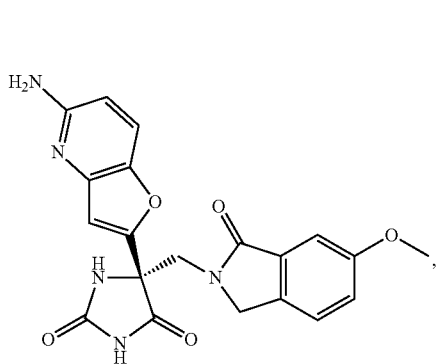
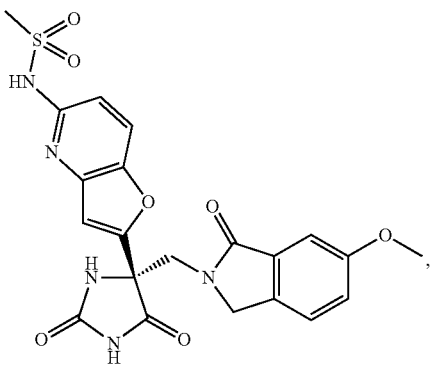
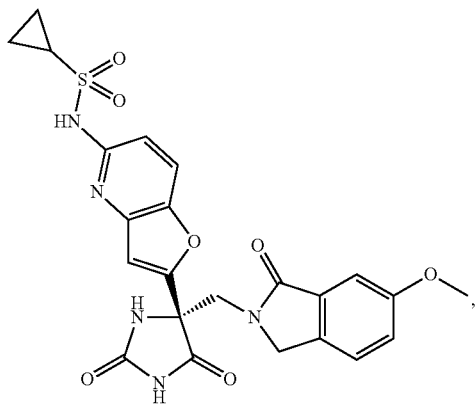
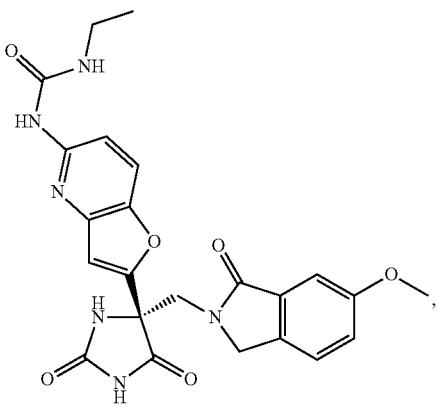
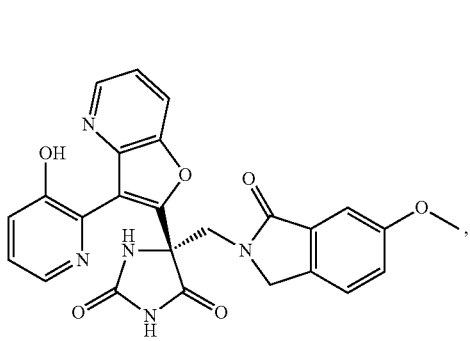
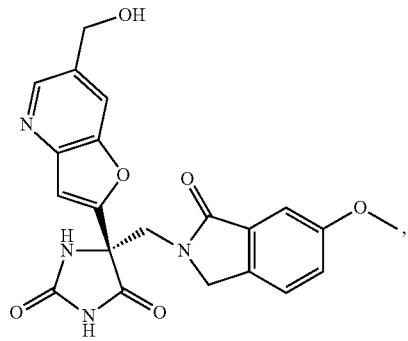

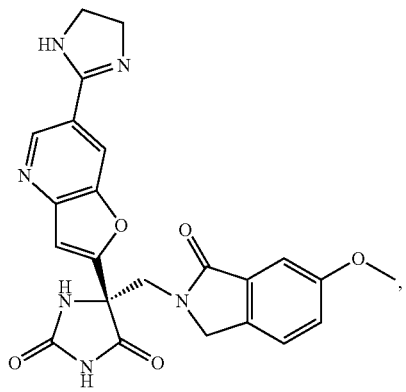
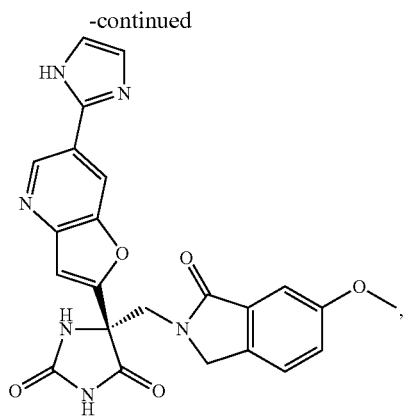
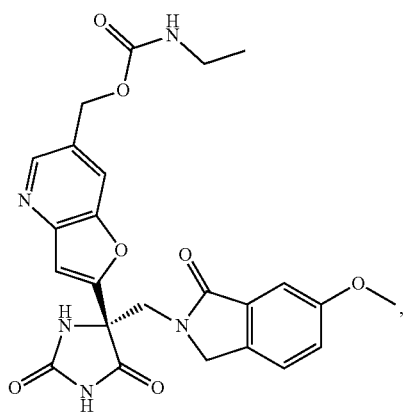
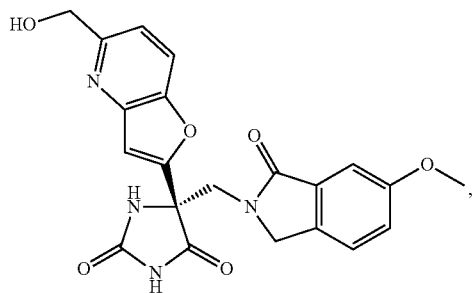
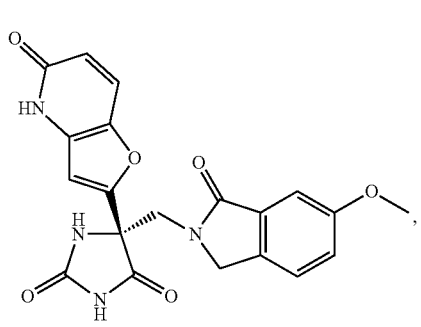
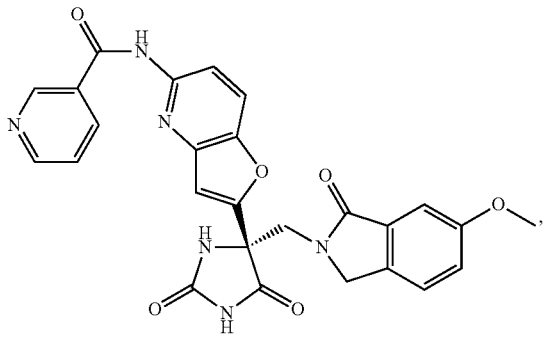
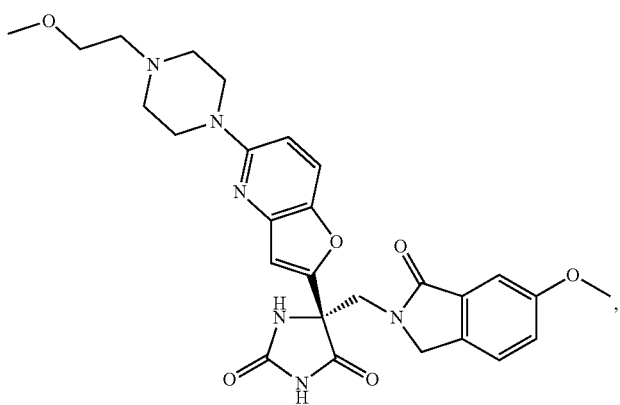

39 40
-continued
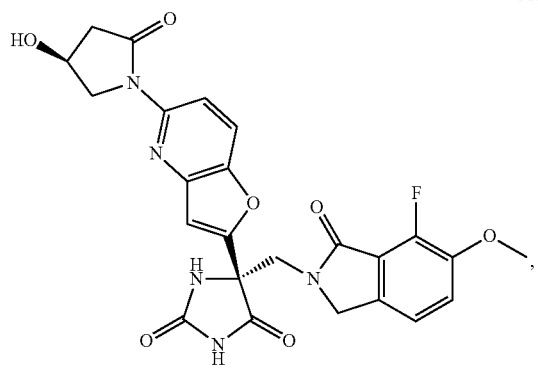
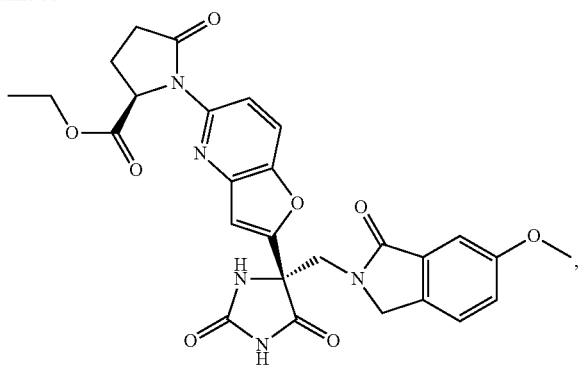
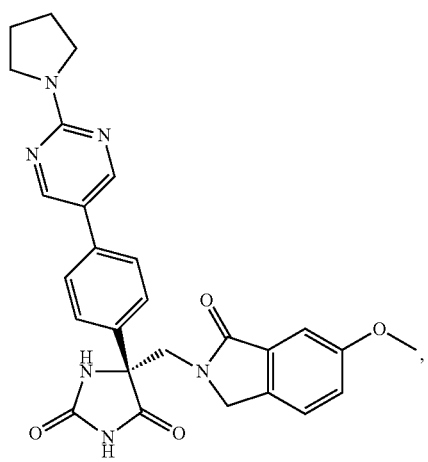
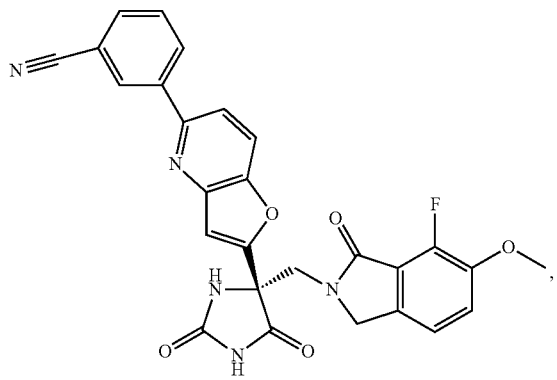
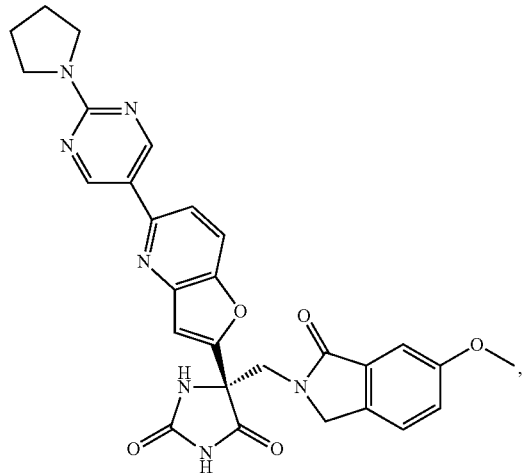
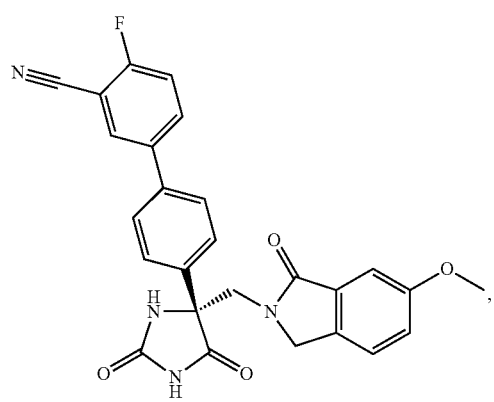
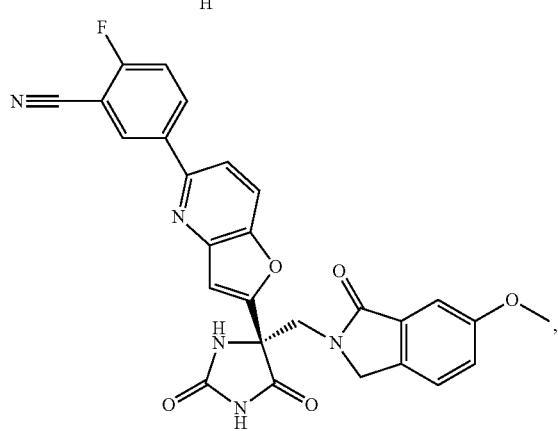
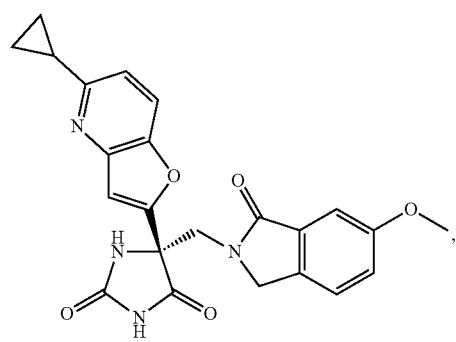

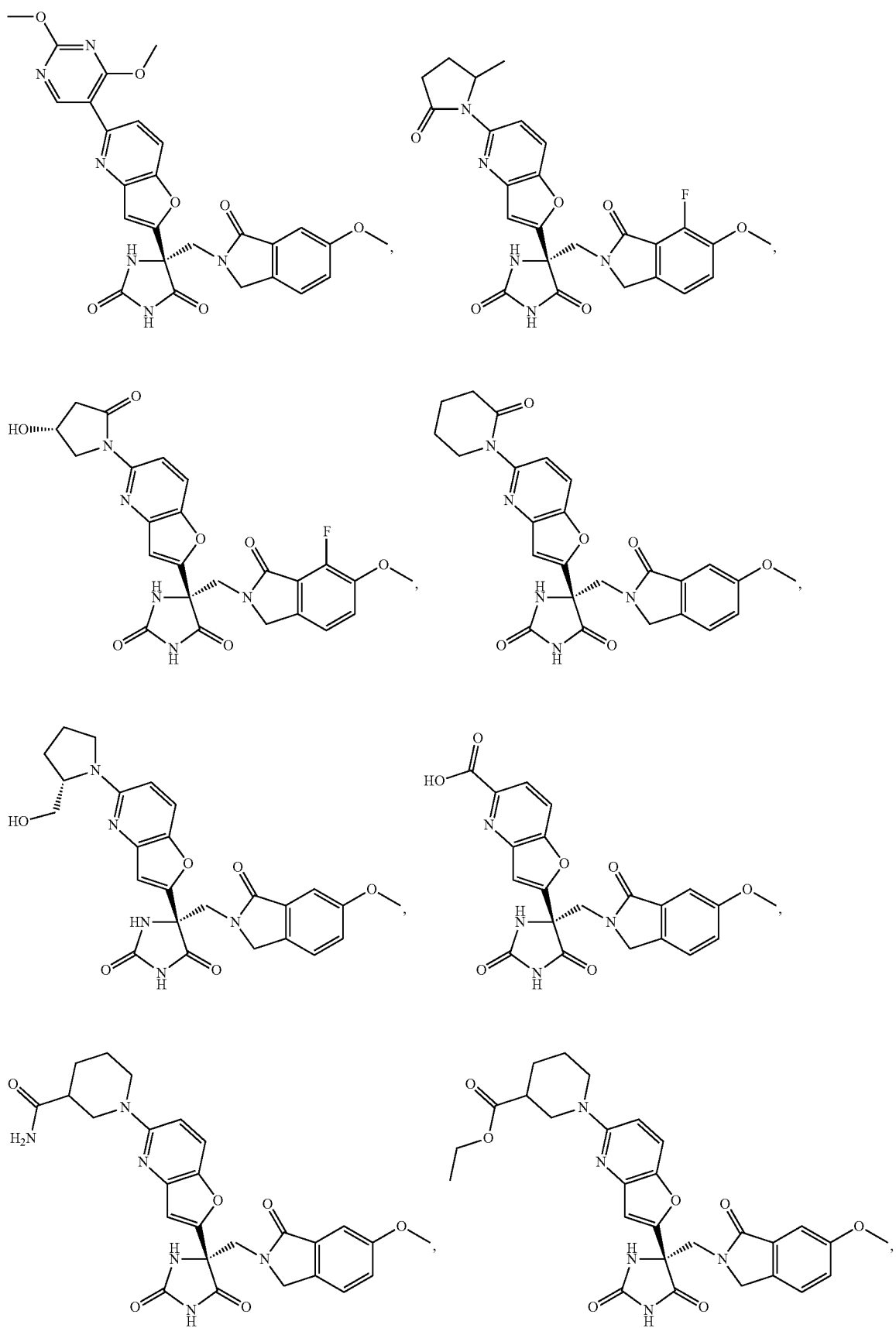

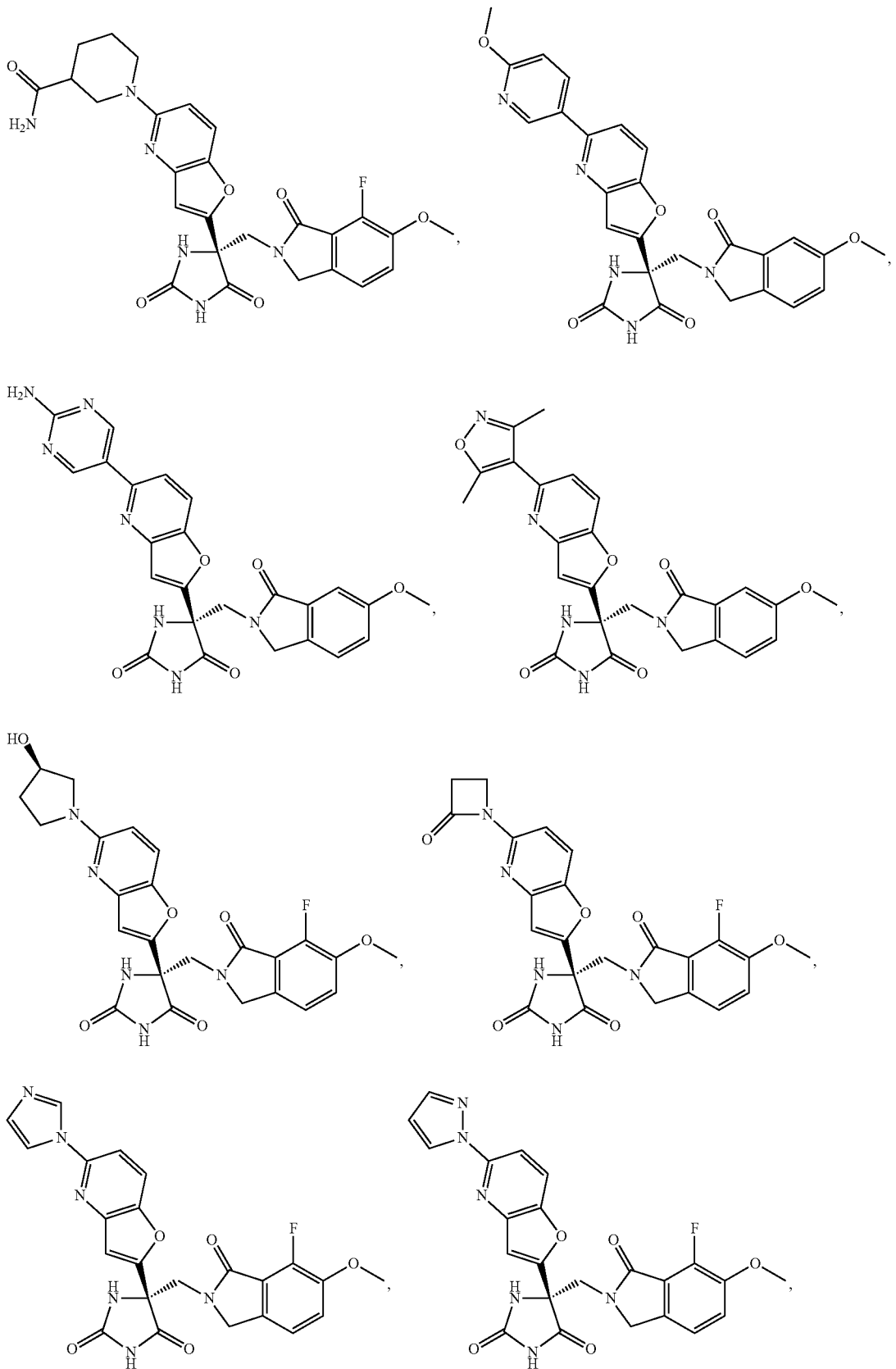

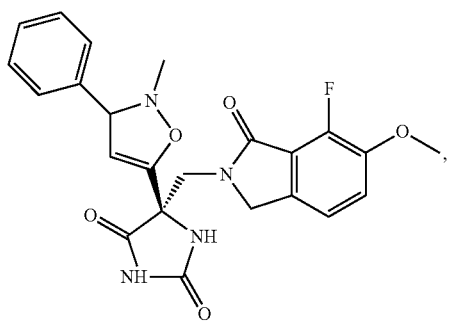
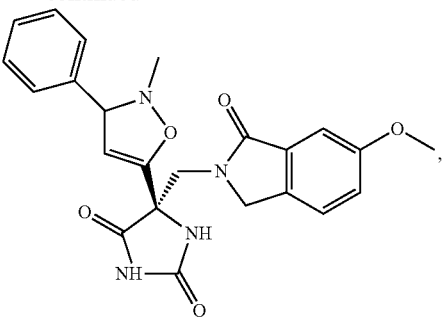
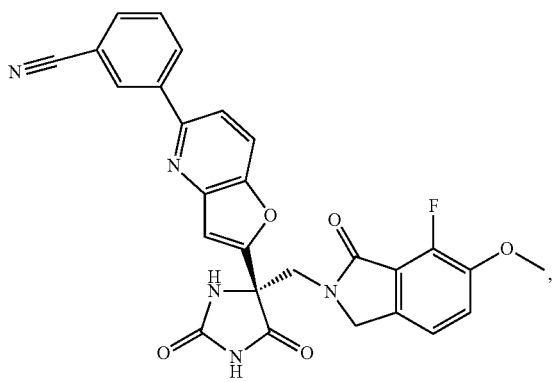
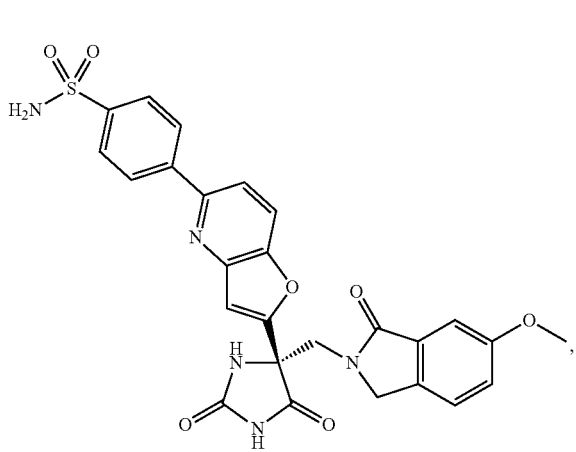
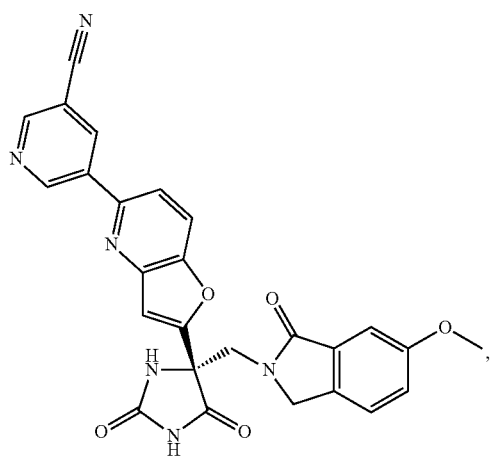
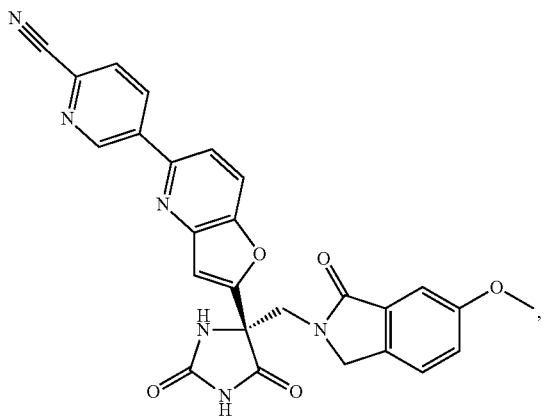
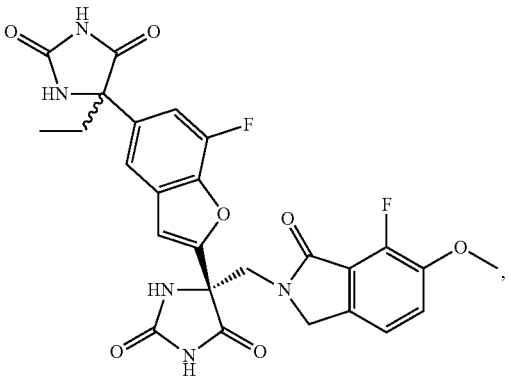

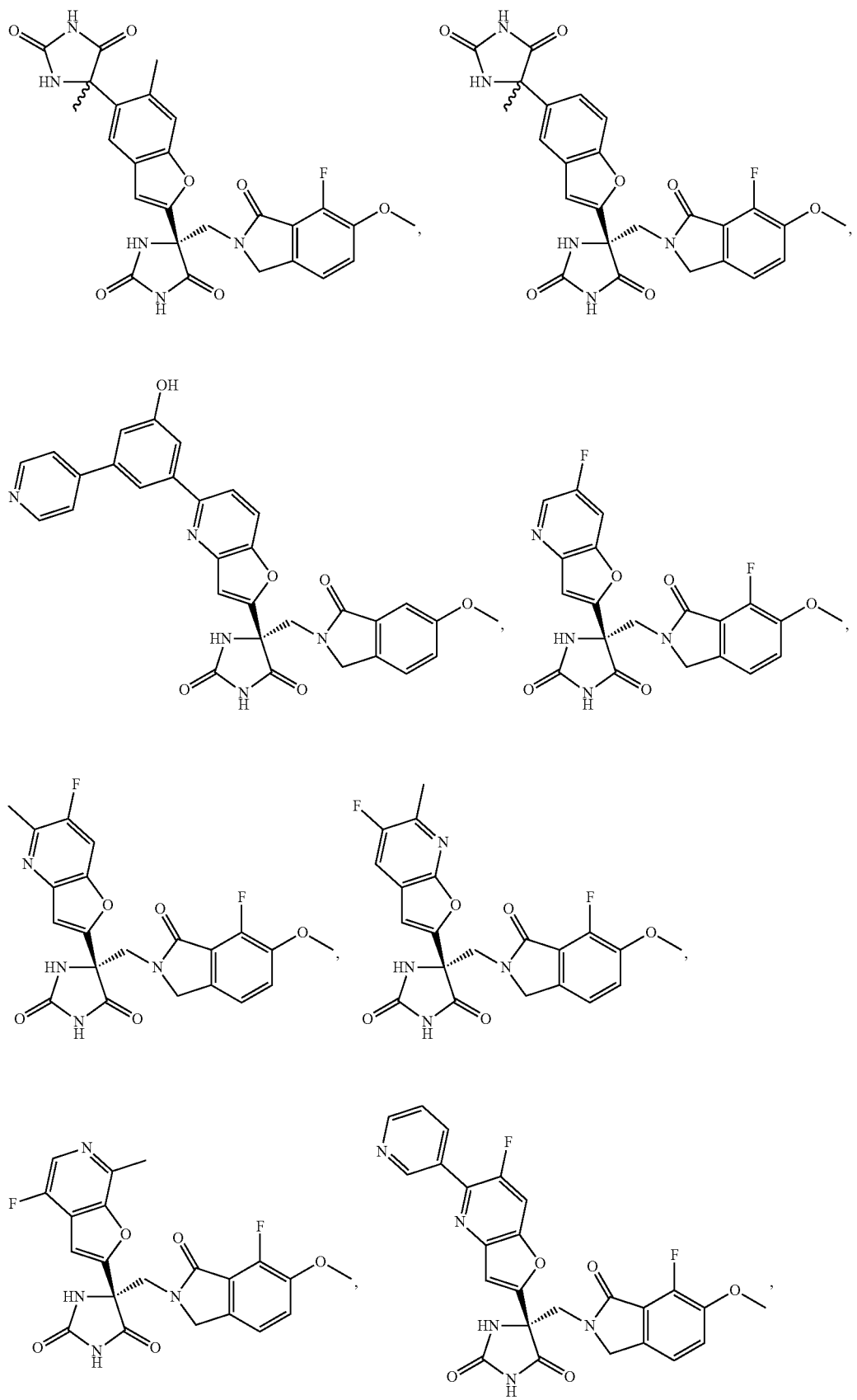

49
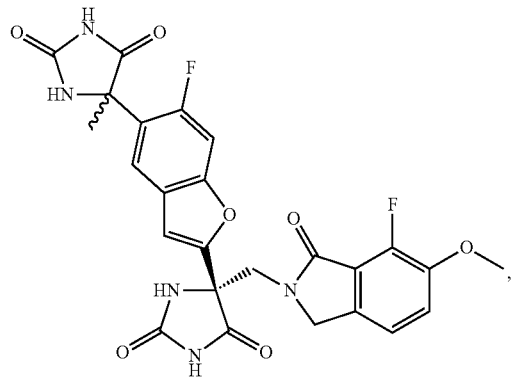
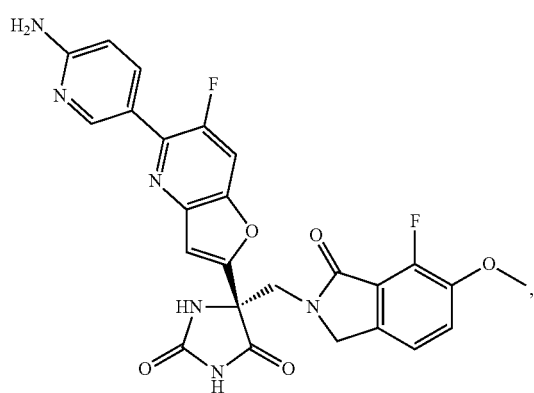
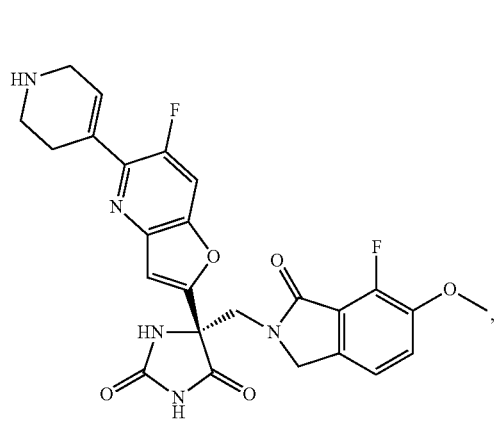
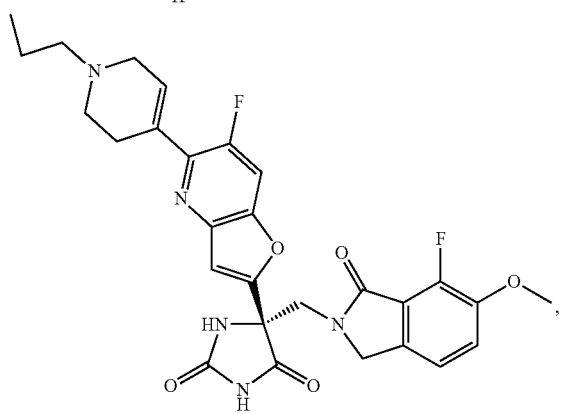
-continued
50
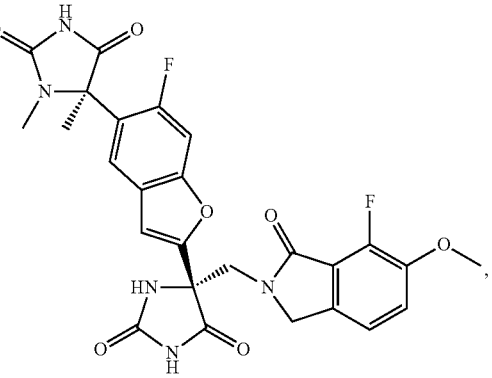
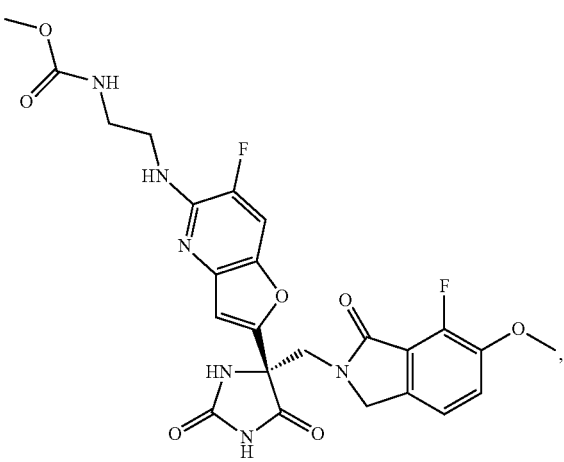
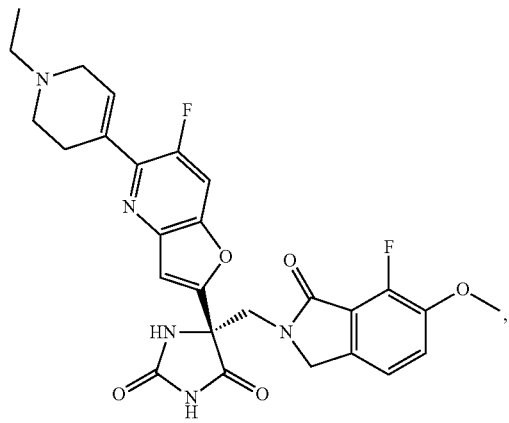
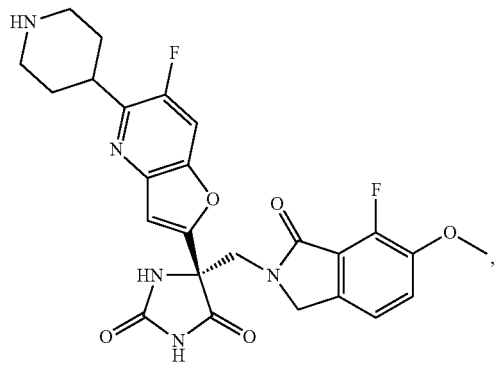

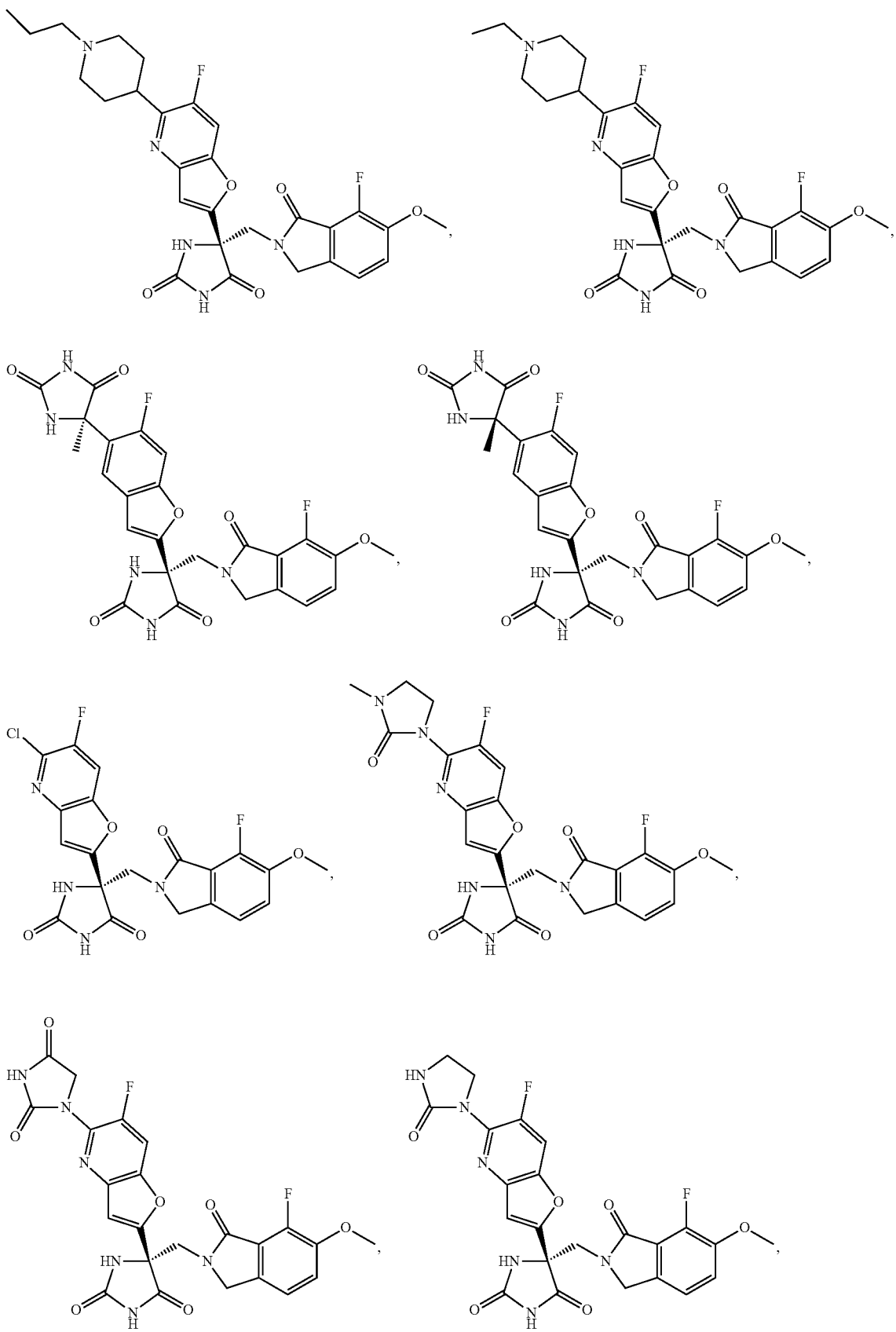

53
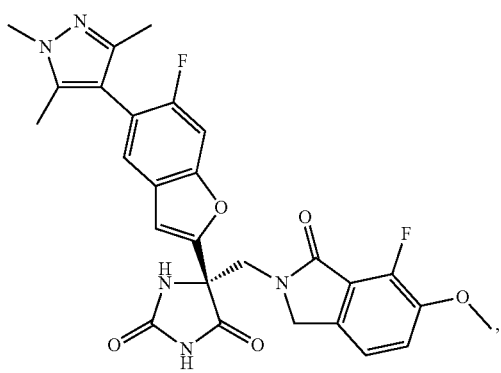
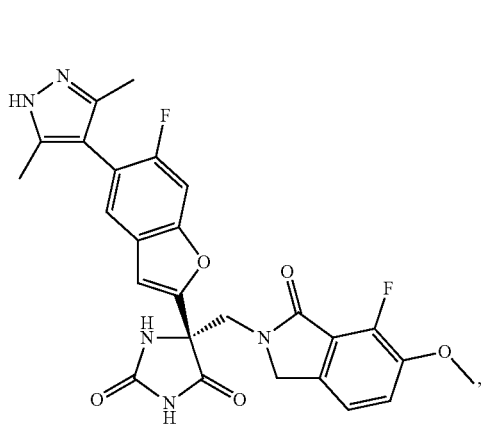
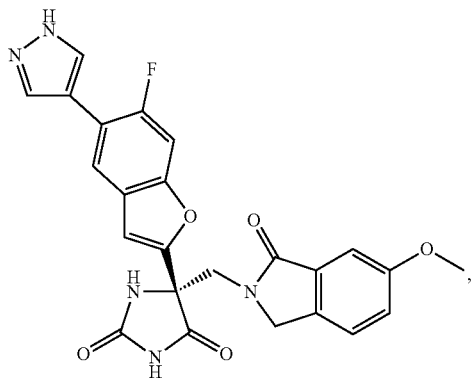
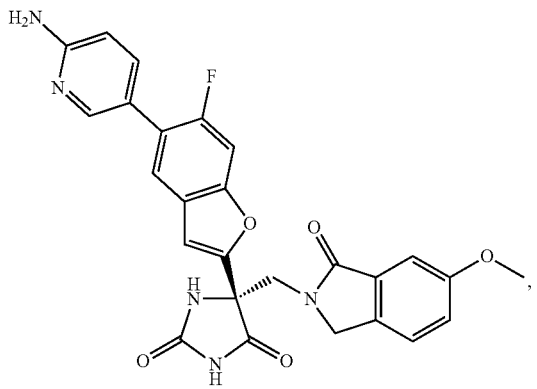
-continued
54
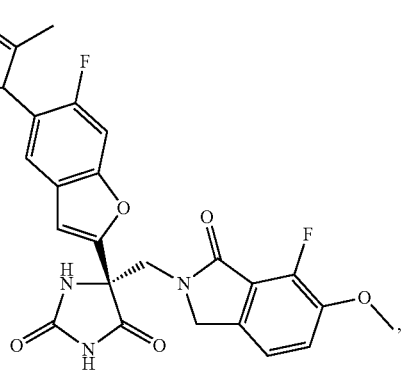
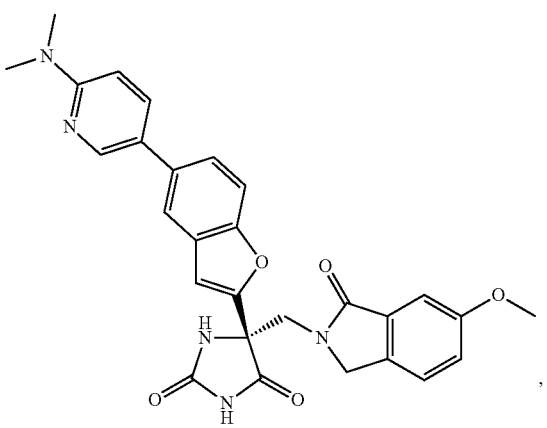
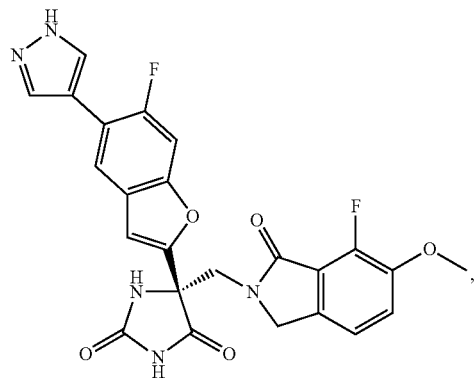
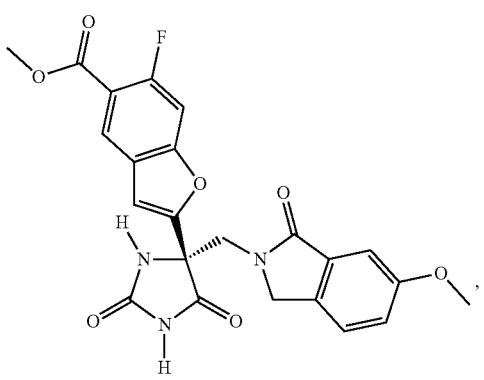

55
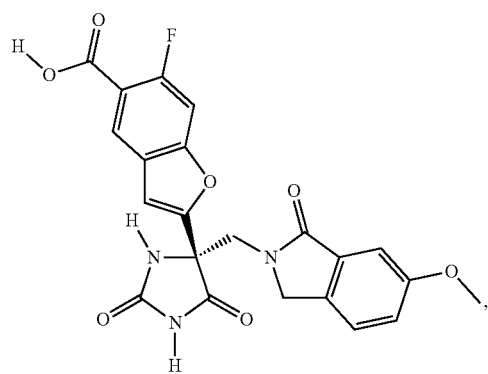
56
-continued
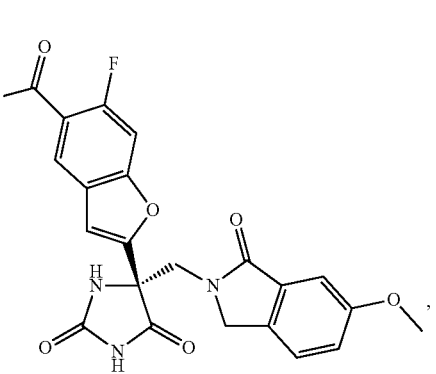
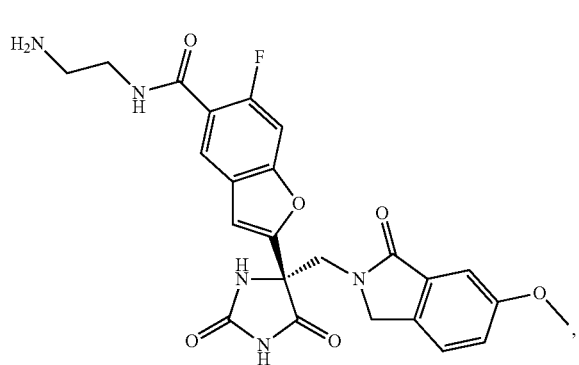
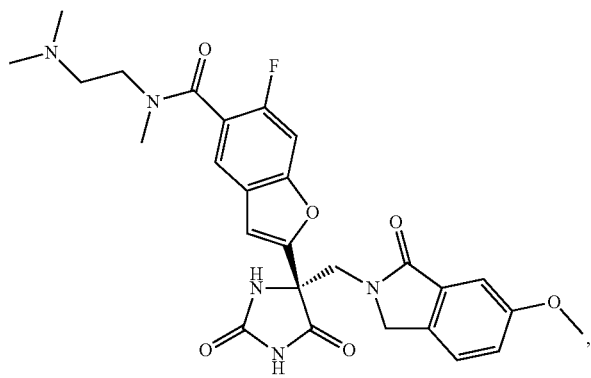
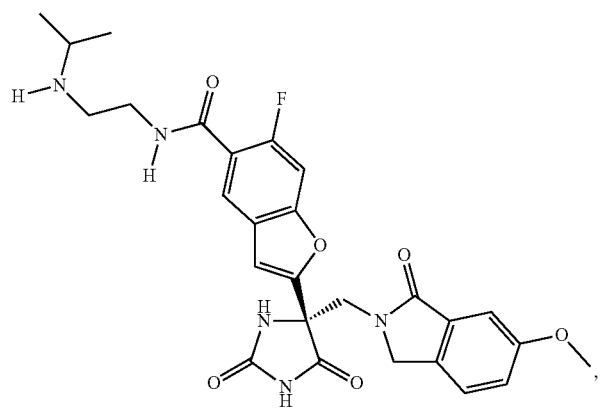
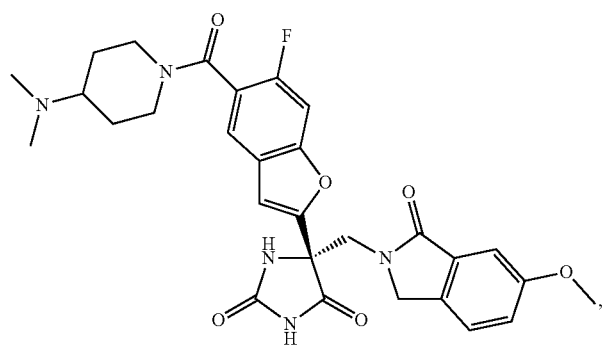

-continued
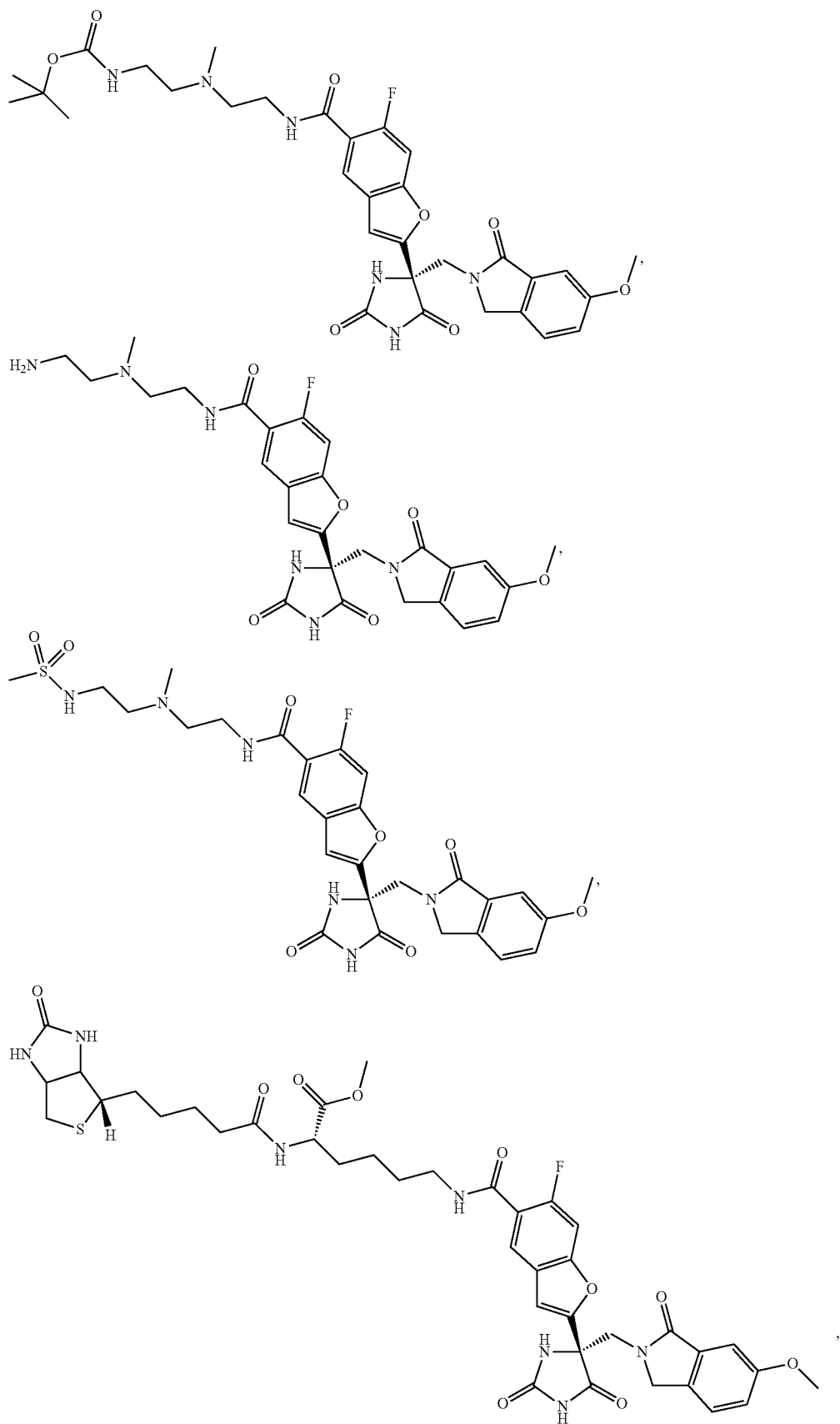

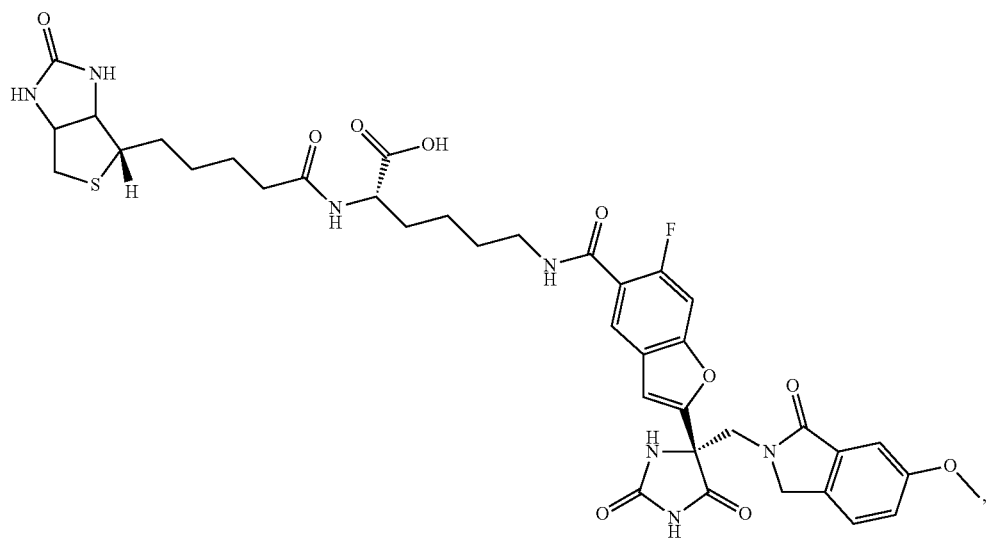
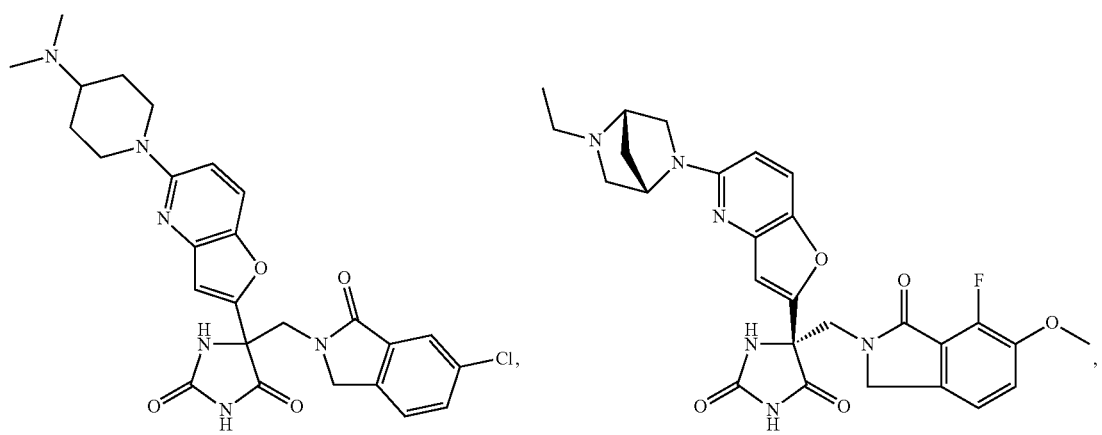
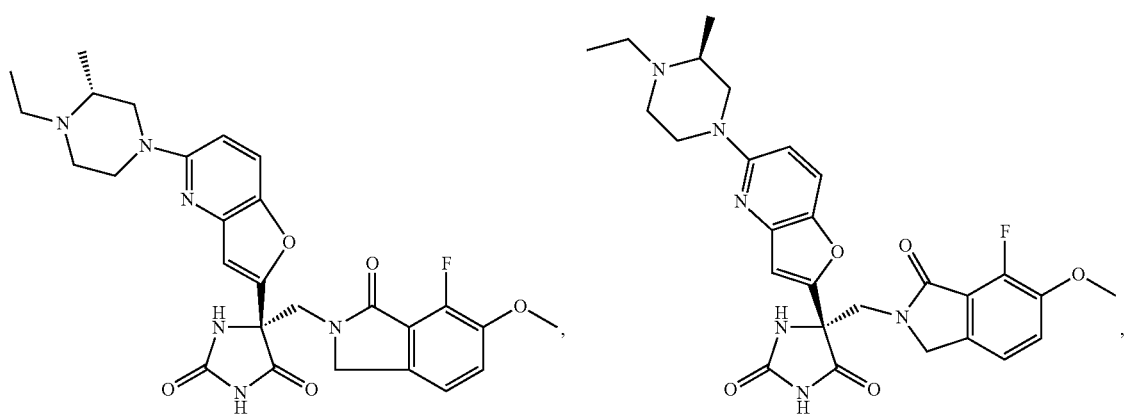
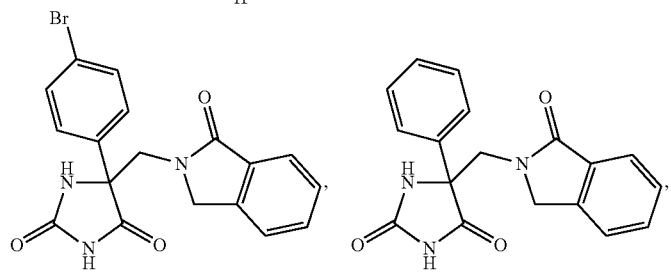

-continued
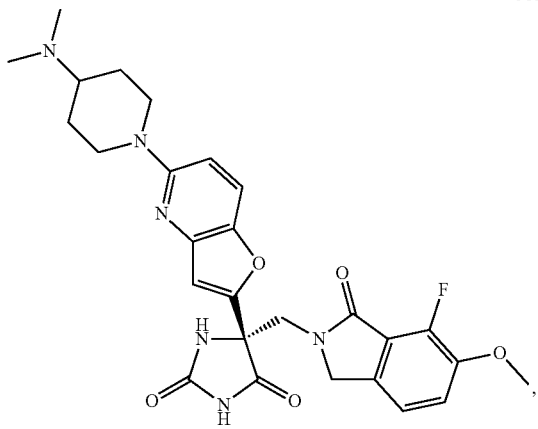
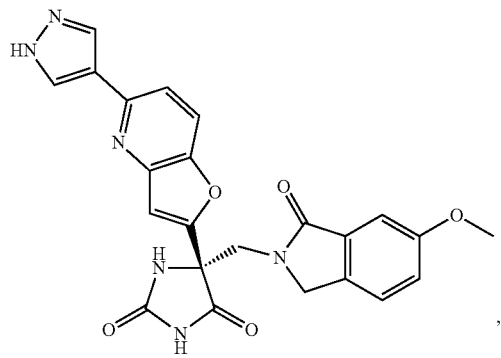
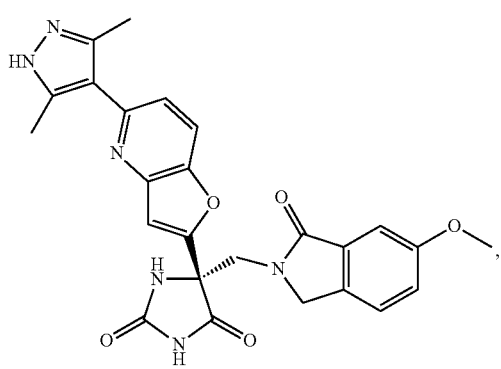
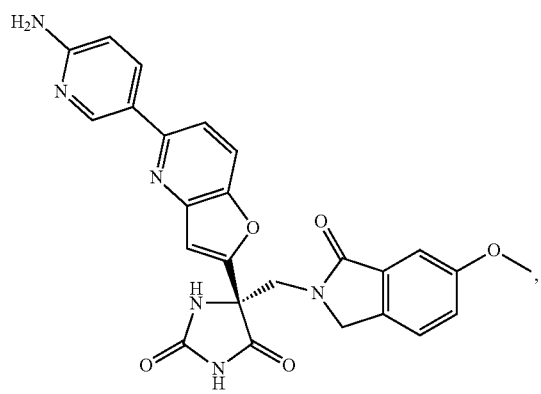
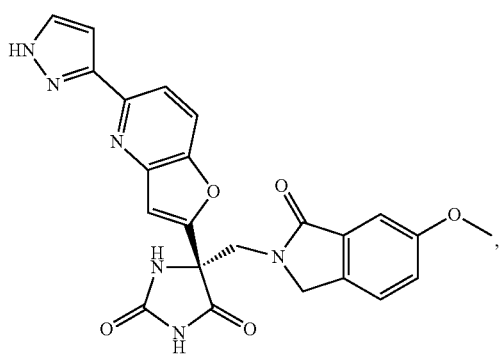
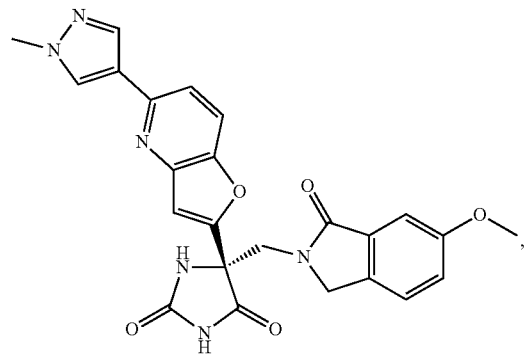
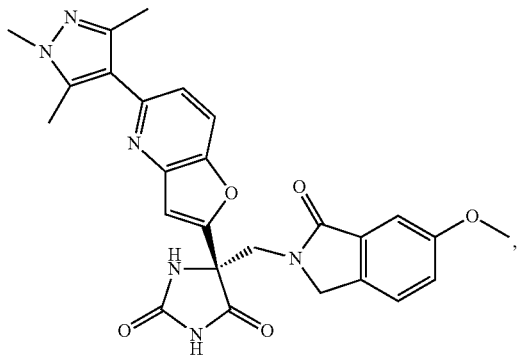
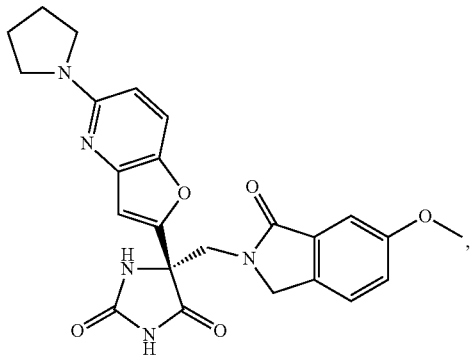

63
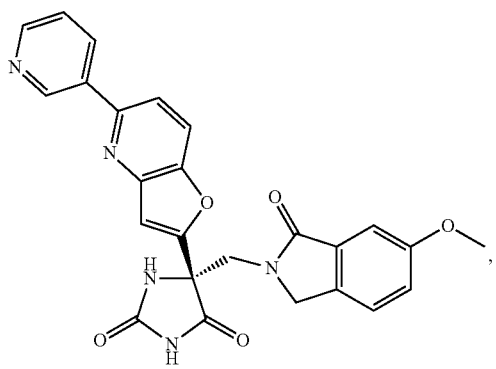
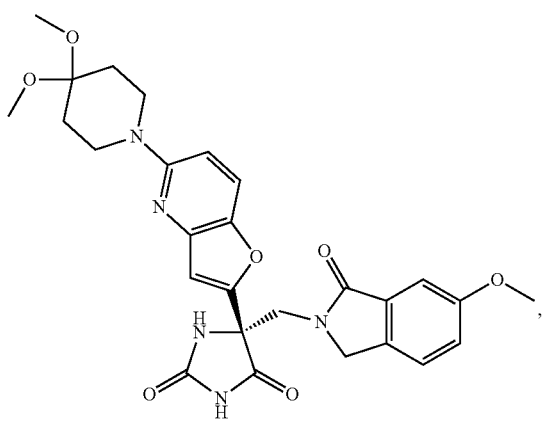
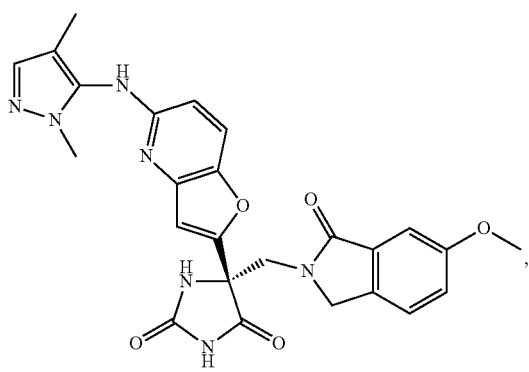
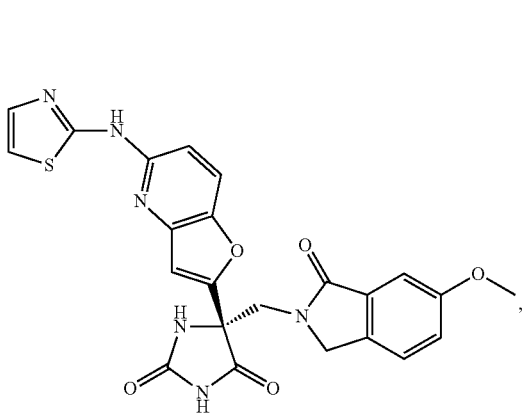
-continued
64
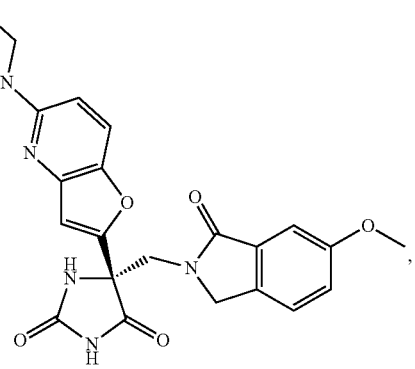
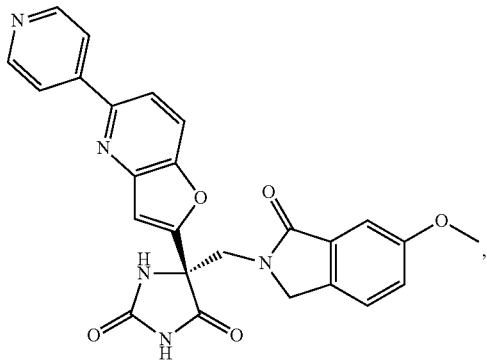
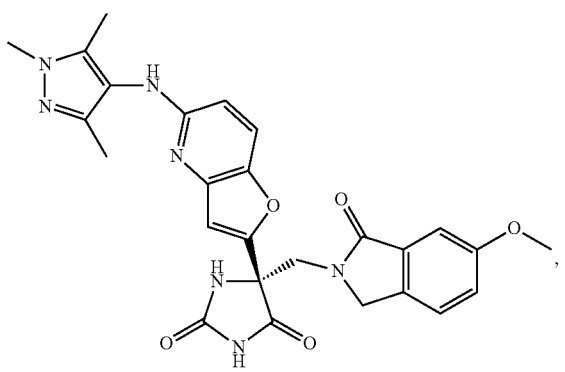
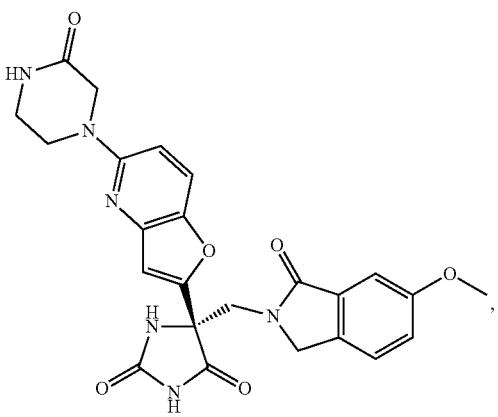

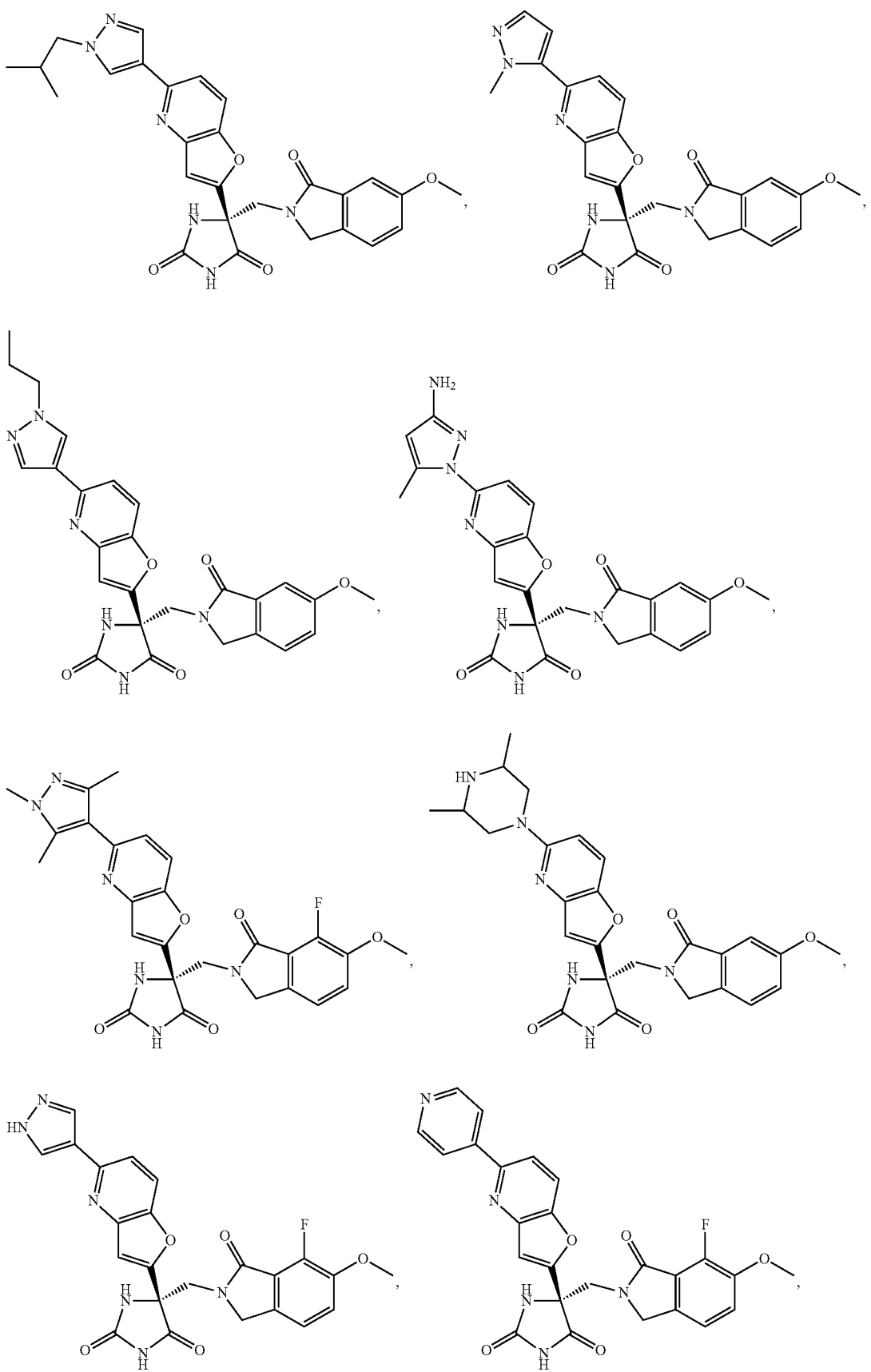

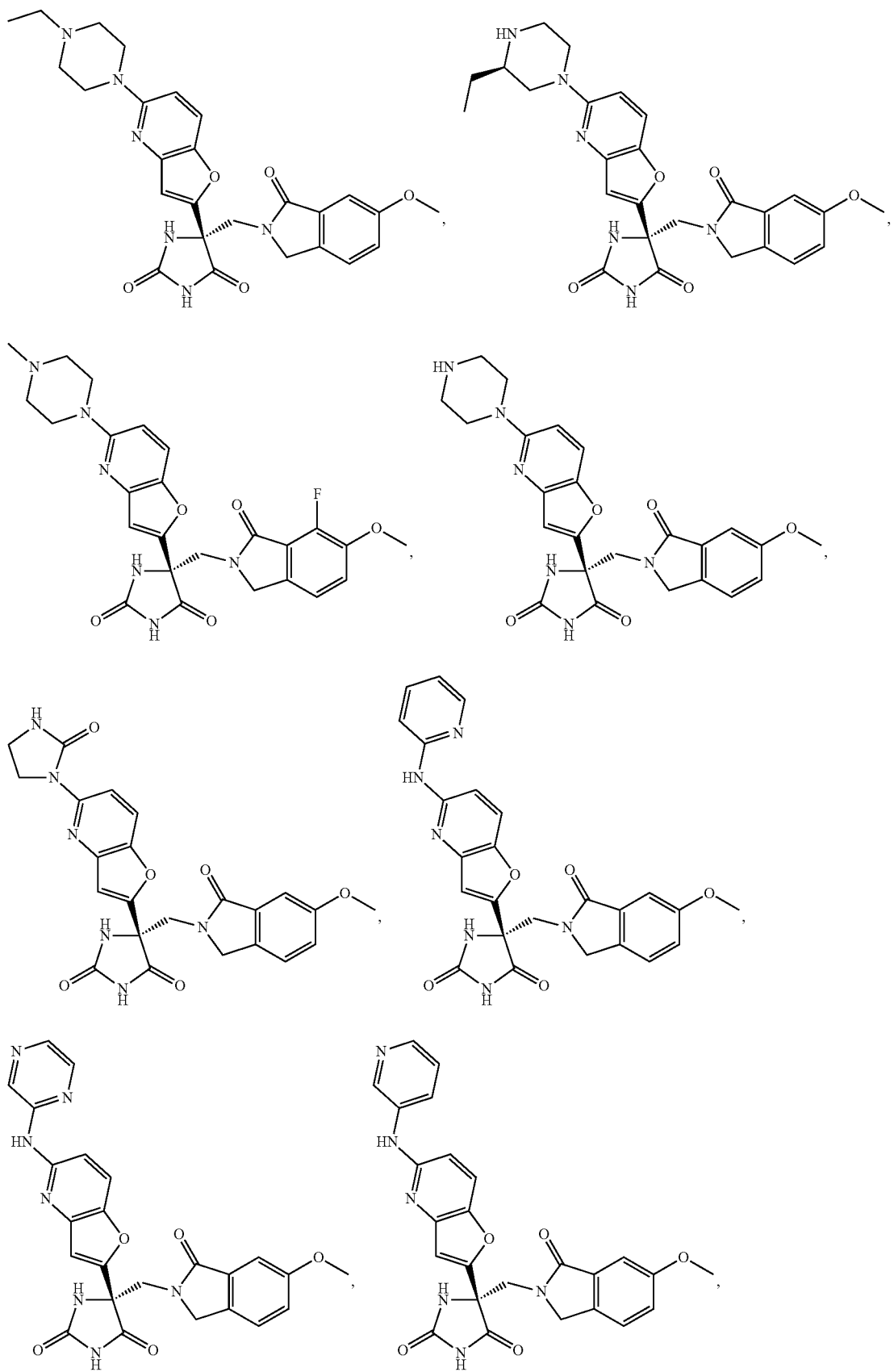

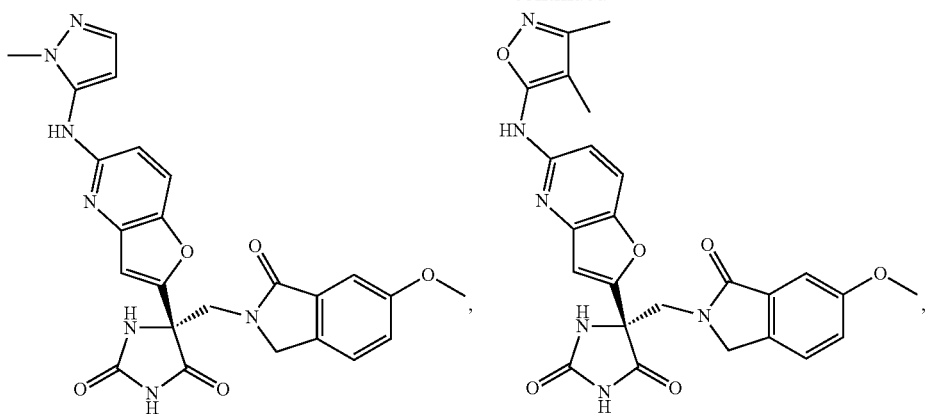
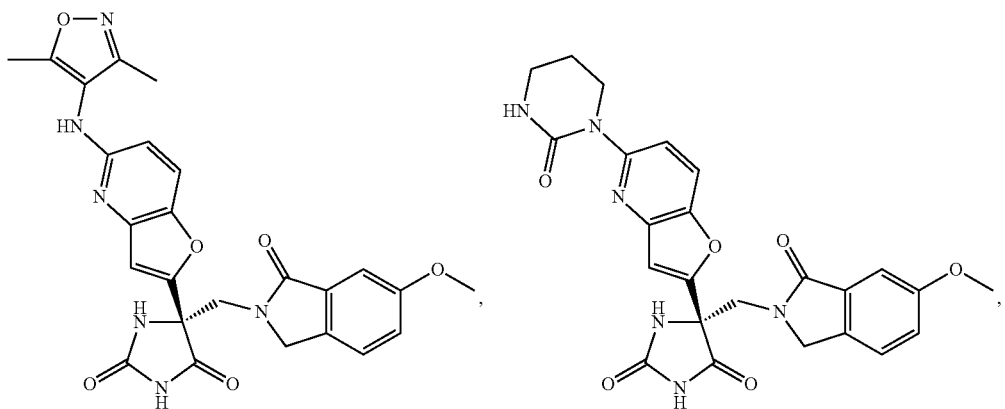
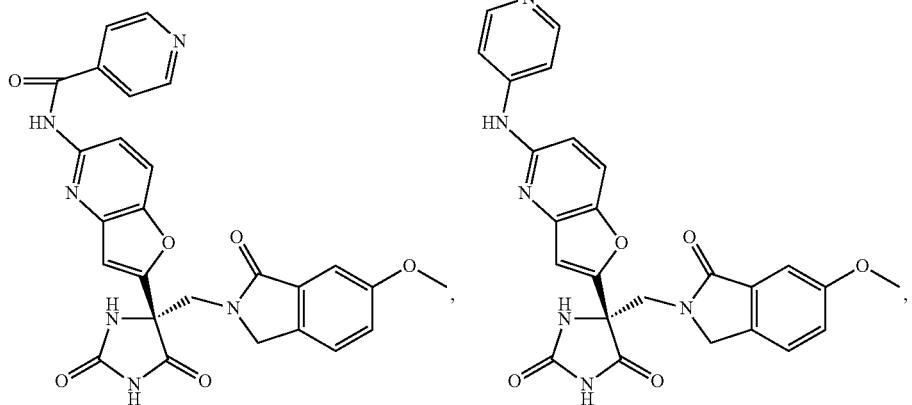
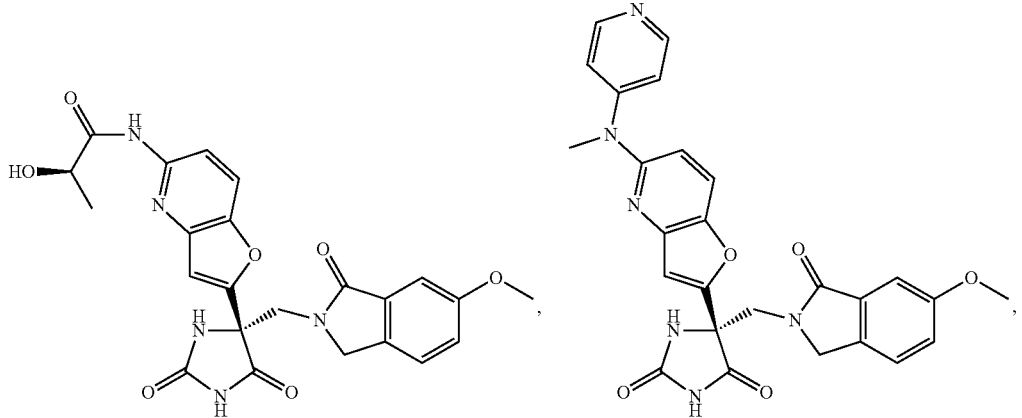

-continued
71
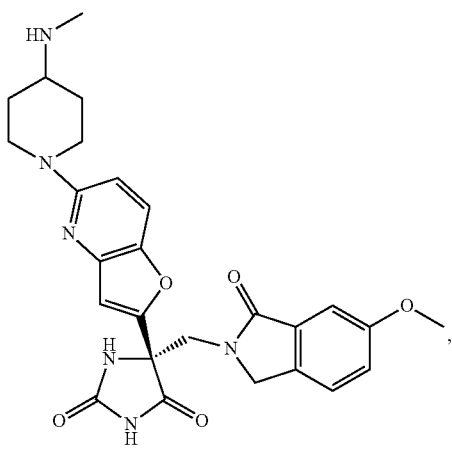
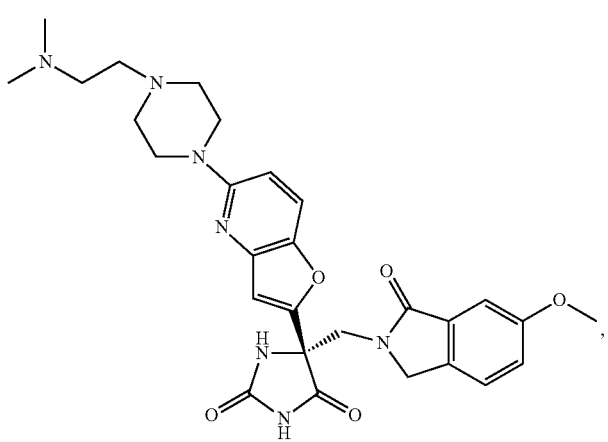
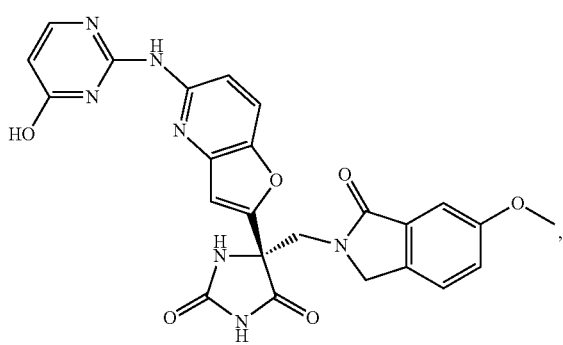
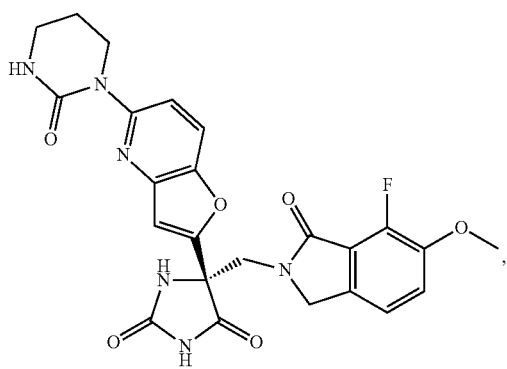
72
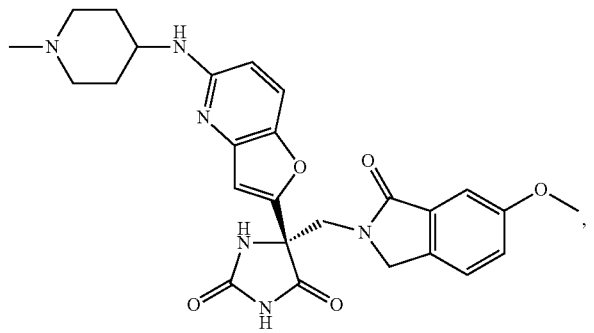
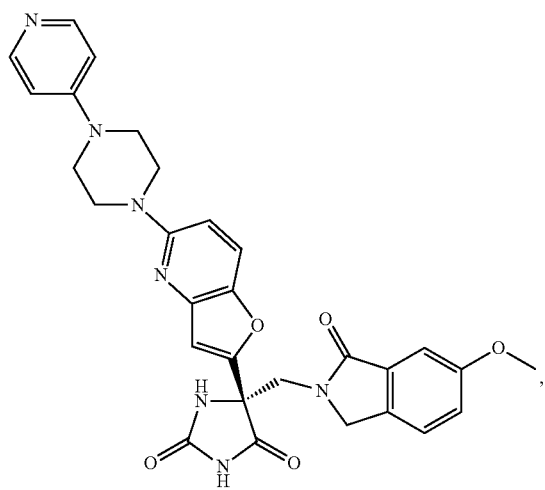
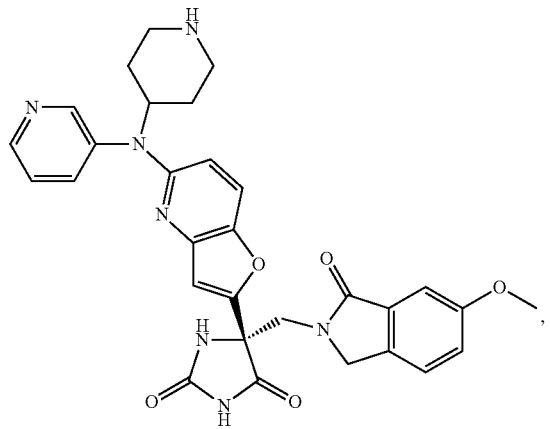
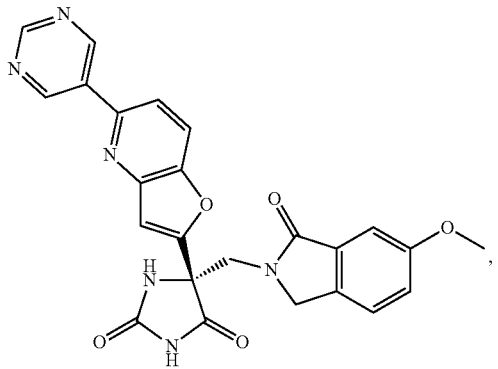

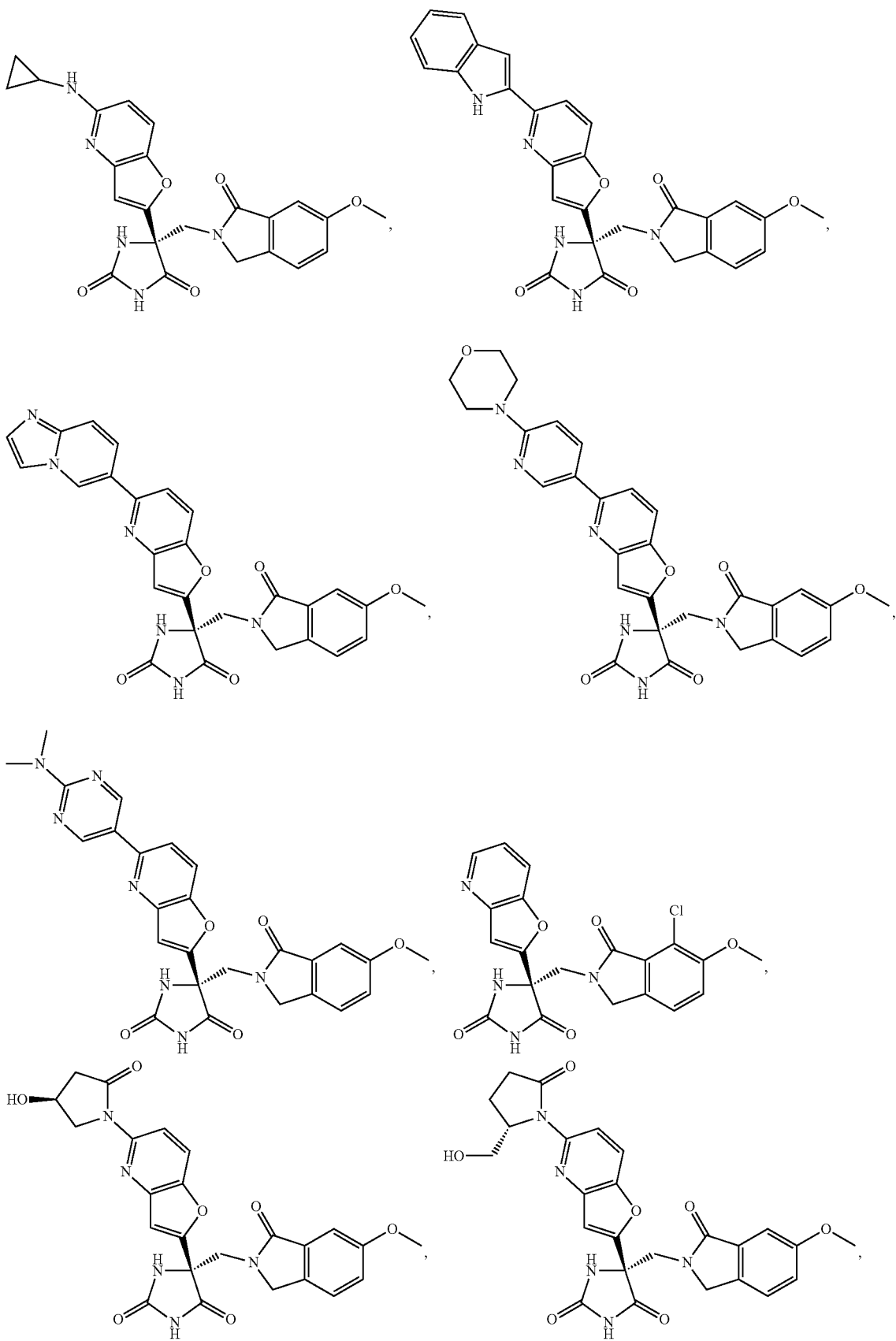

75
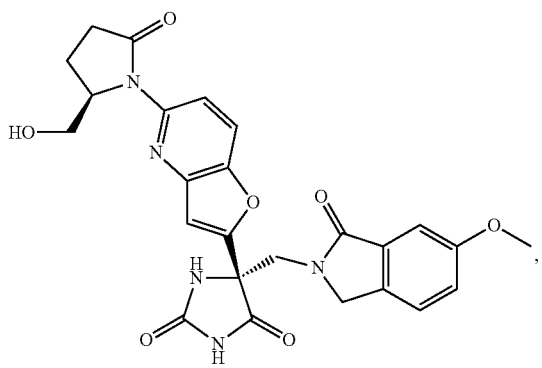
76
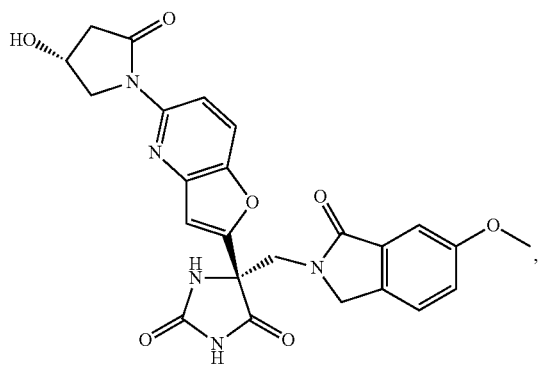
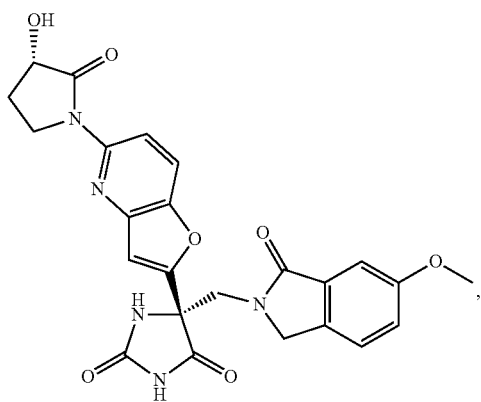
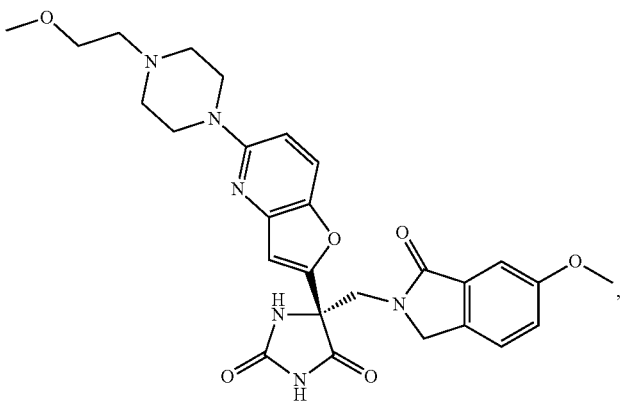
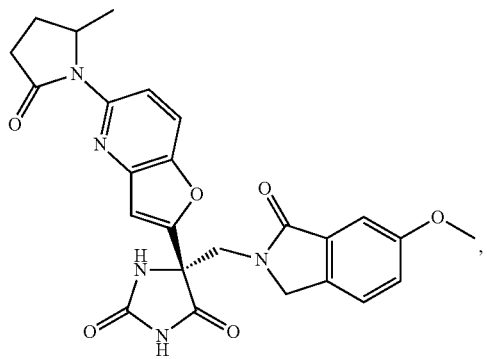
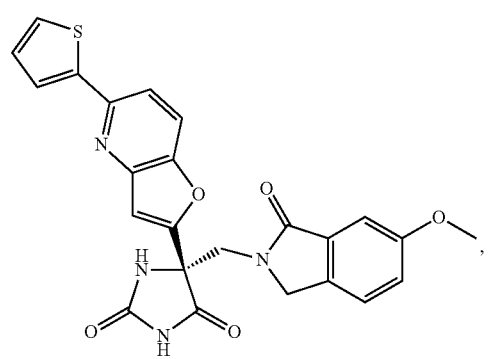
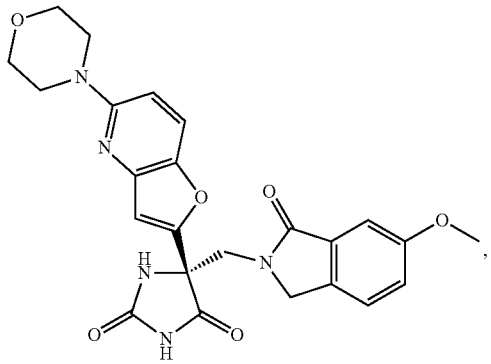
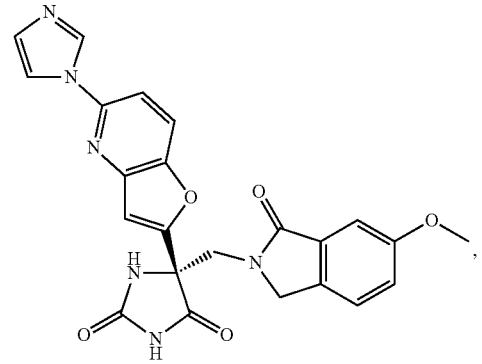

-continued
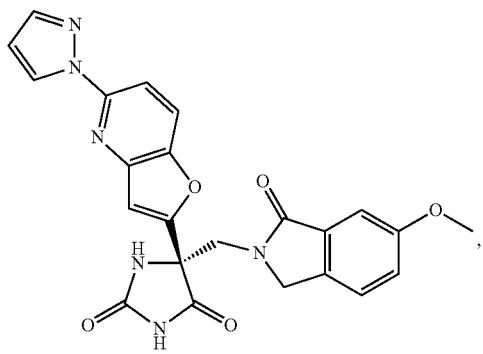,
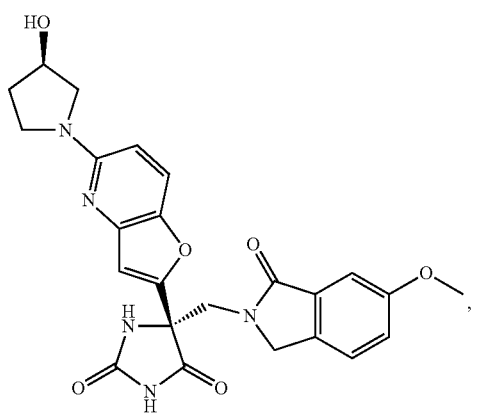,
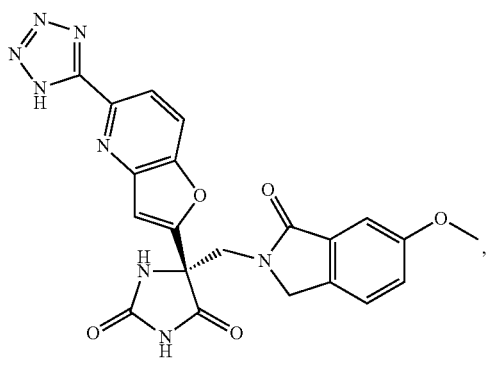,
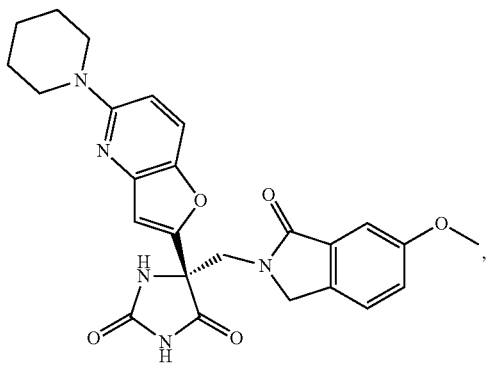,
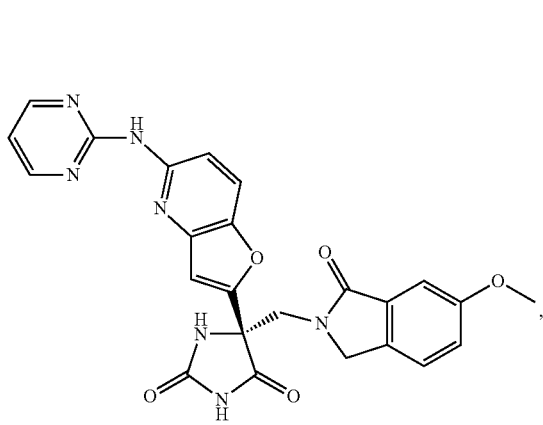,
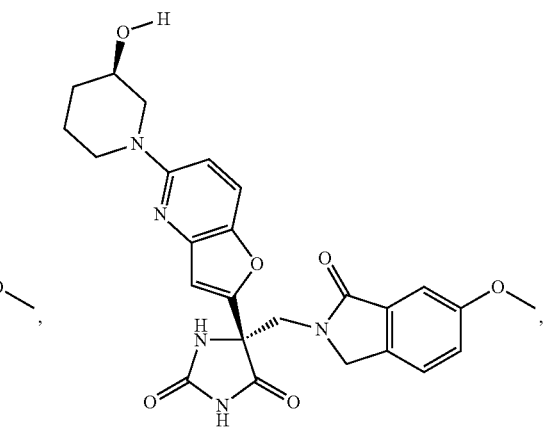,
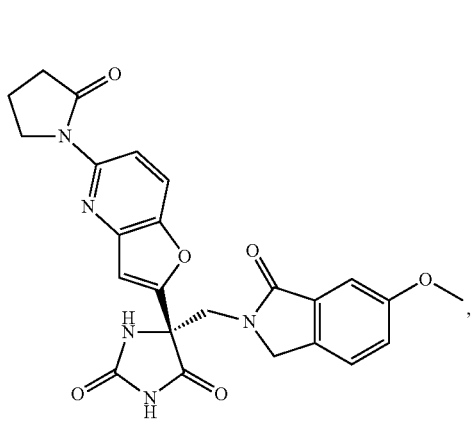,
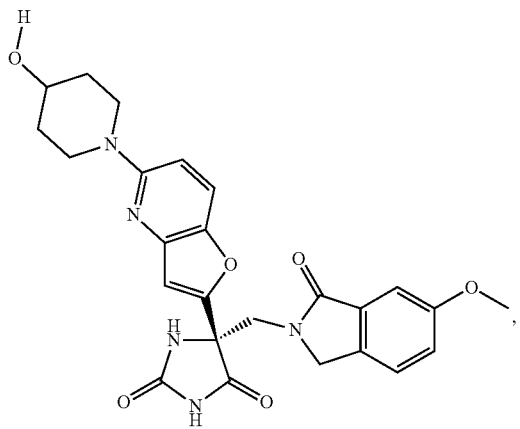, -continued
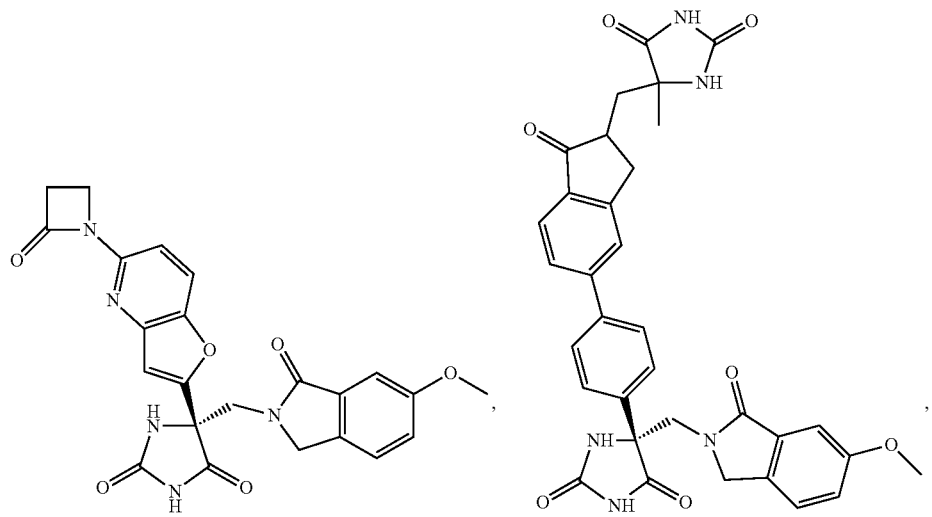
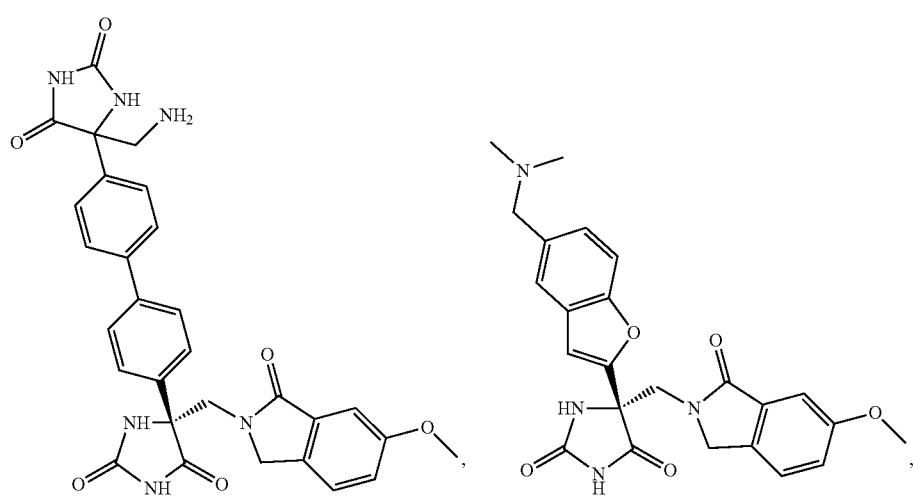
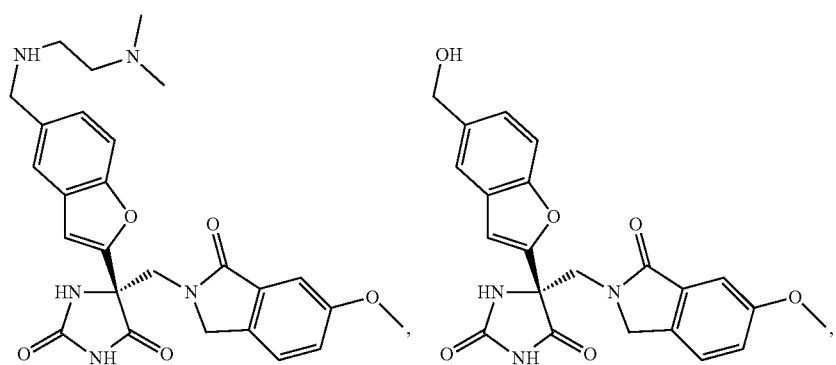

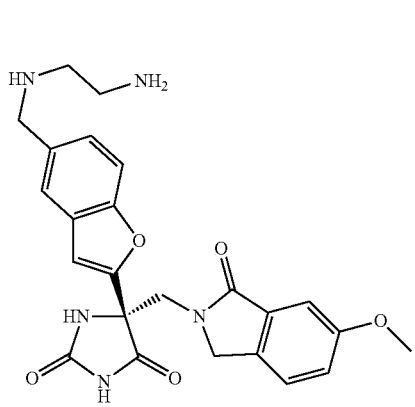
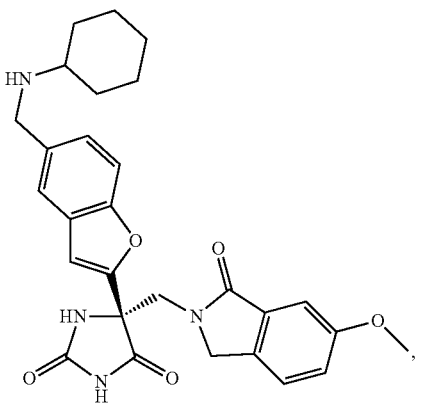
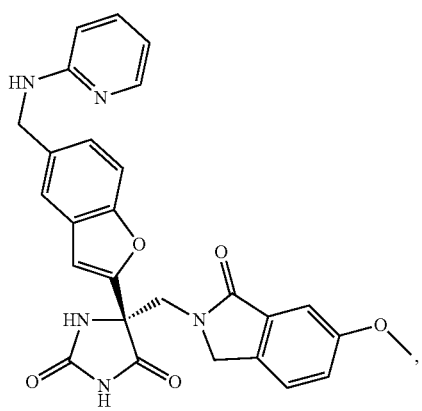
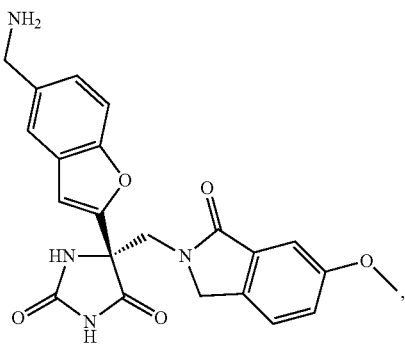
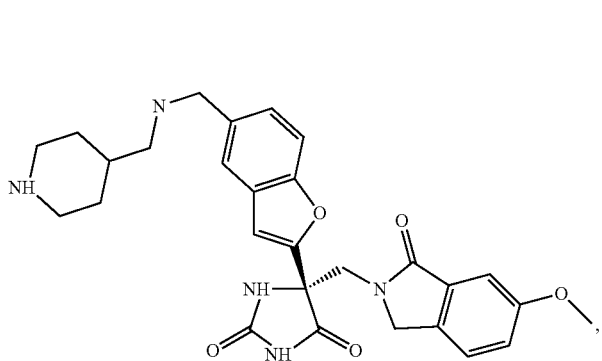
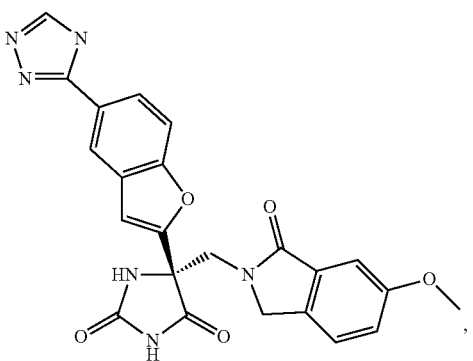
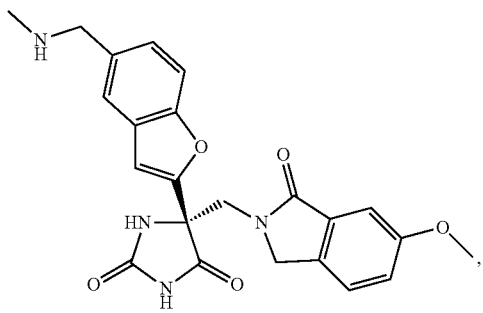
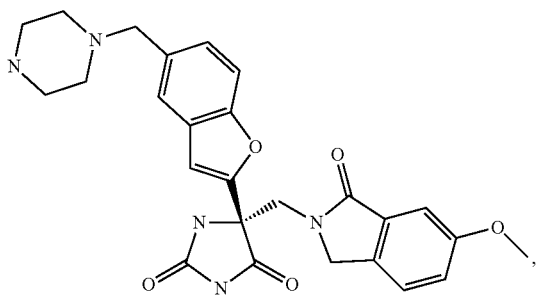

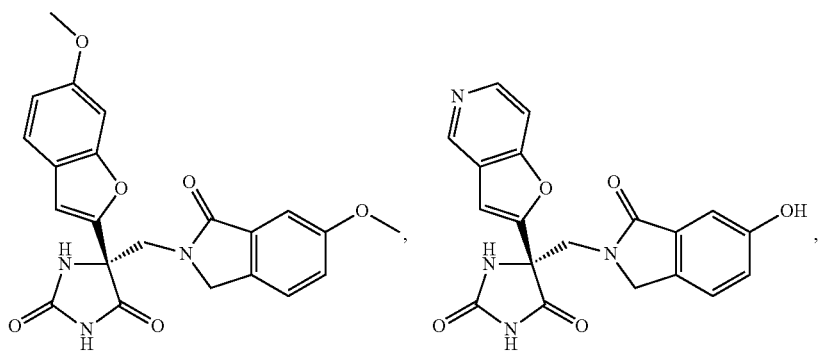
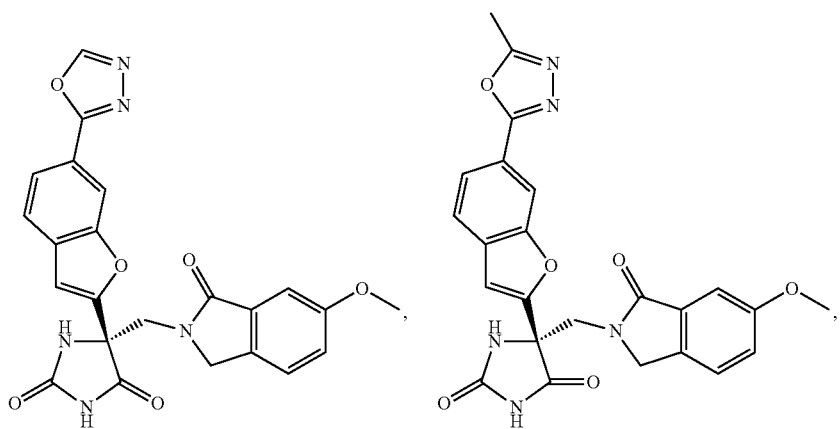
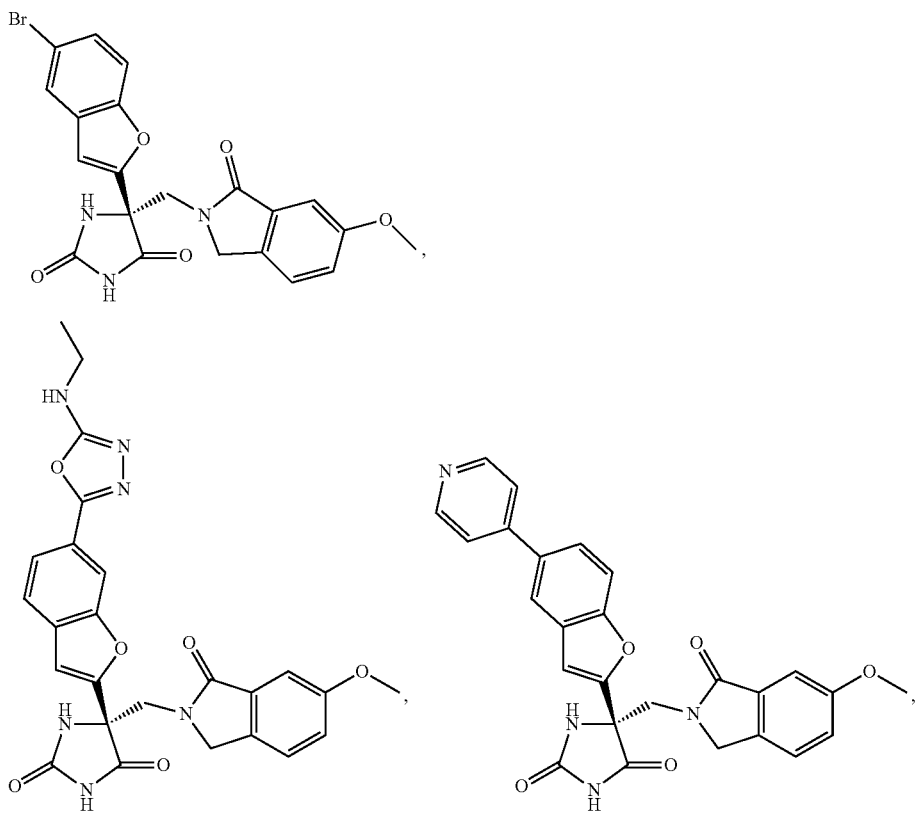

85
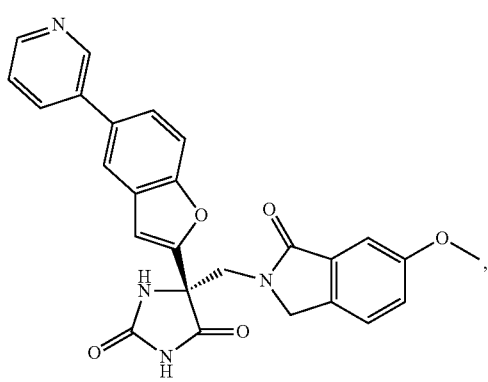
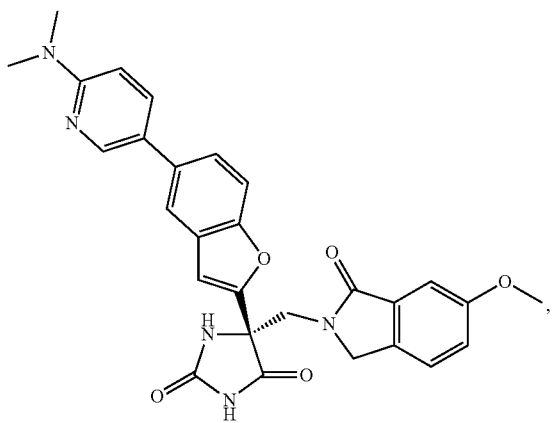
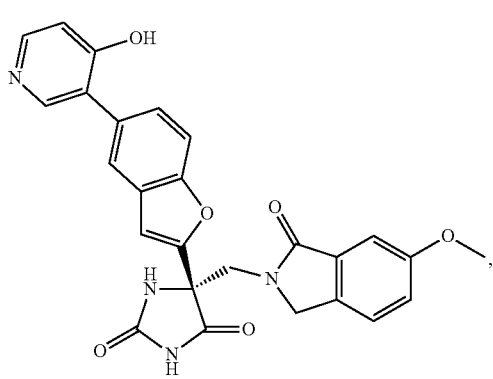
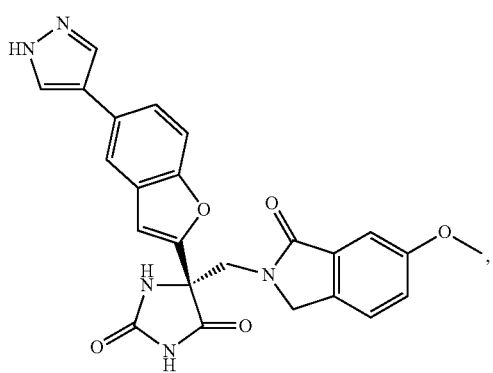
86
-continued
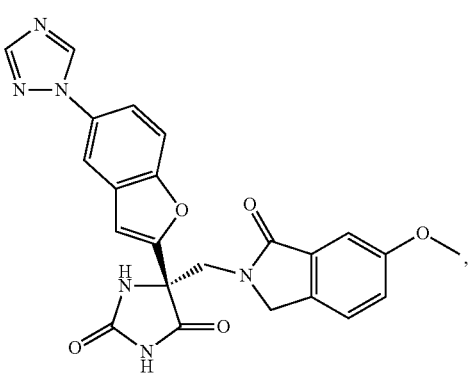
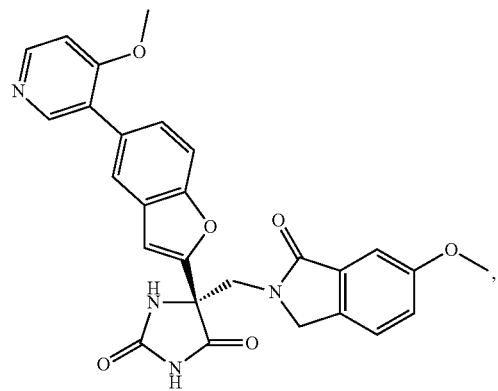
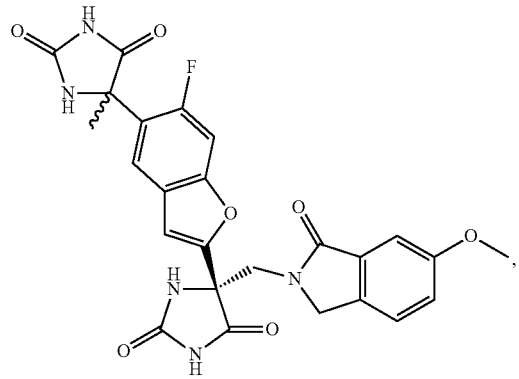
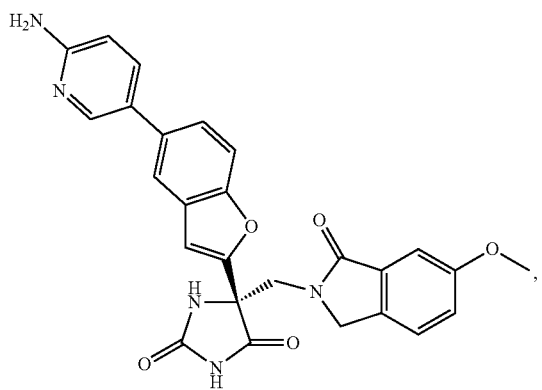

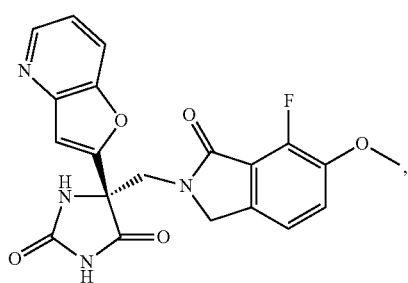 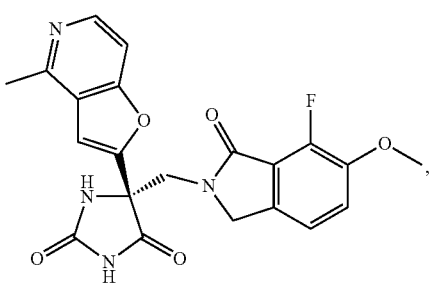
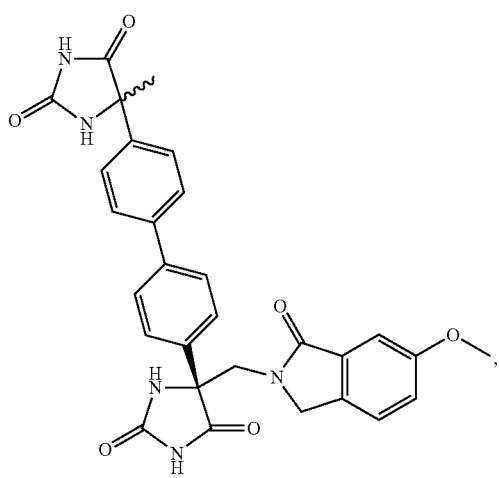 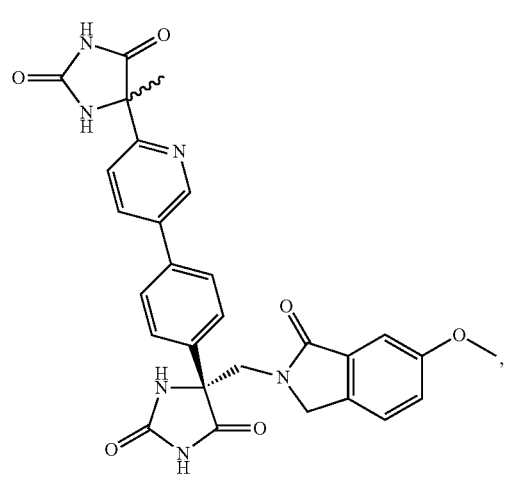
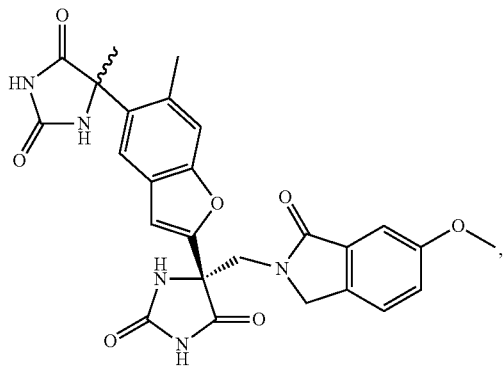 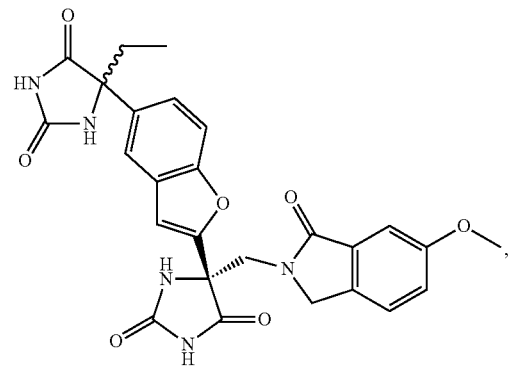
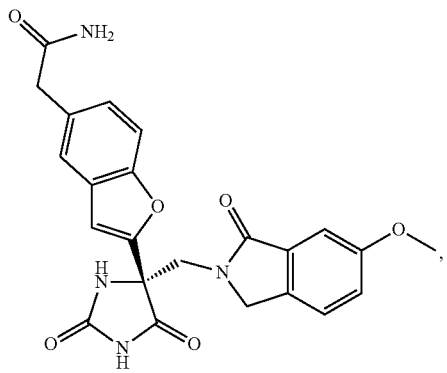 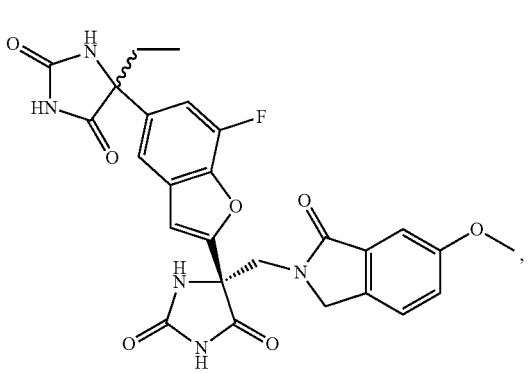

-continued
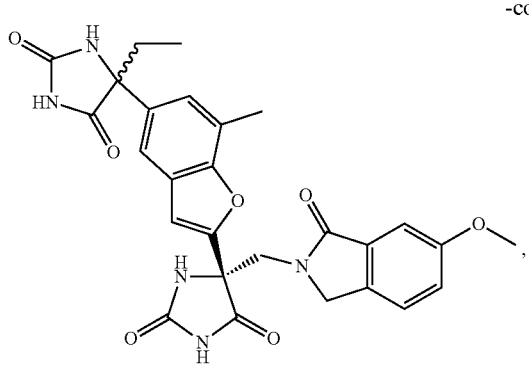
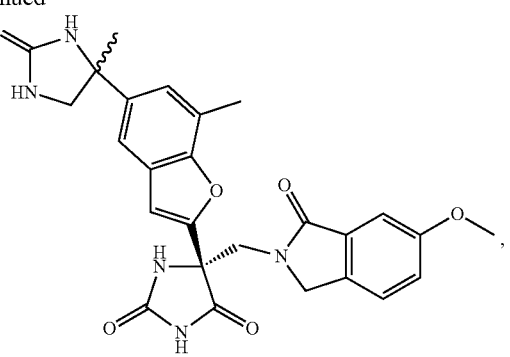
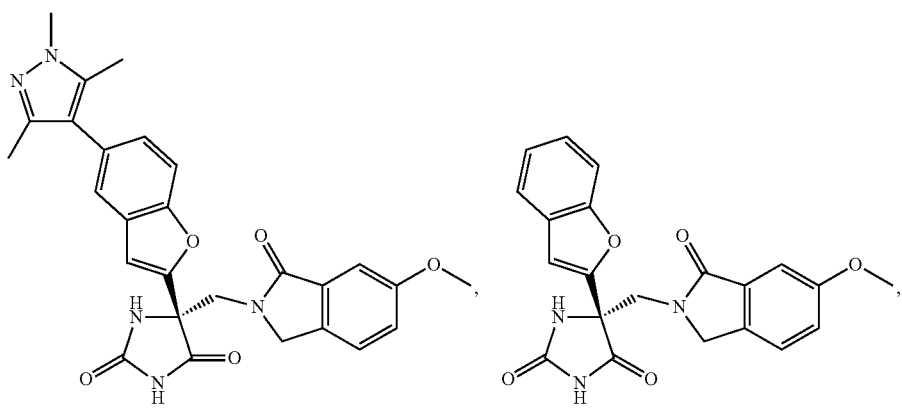
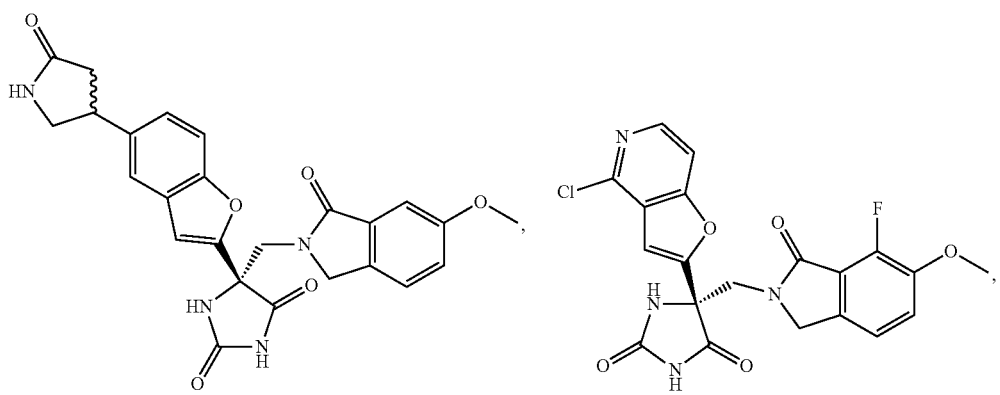
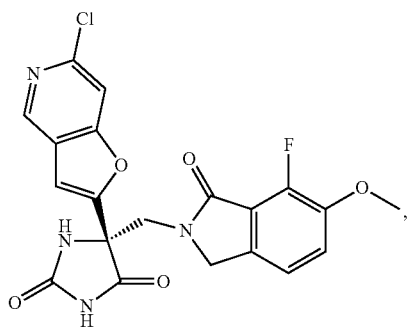

-continued
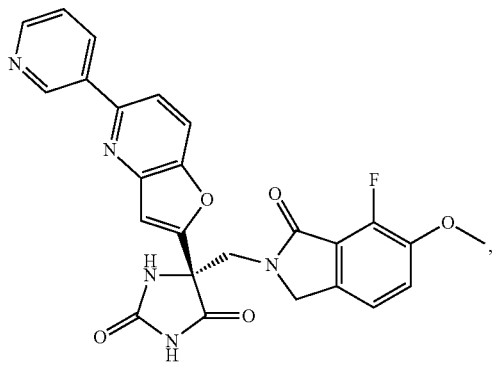
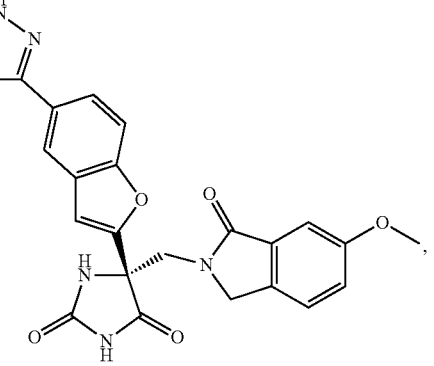
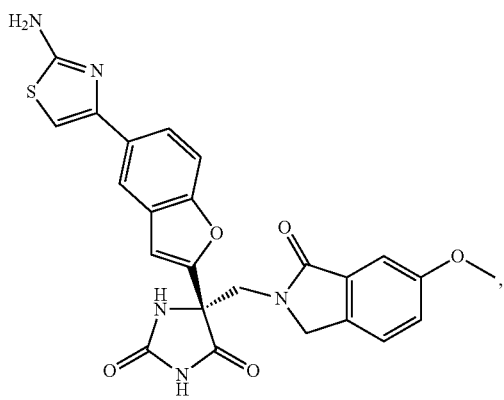
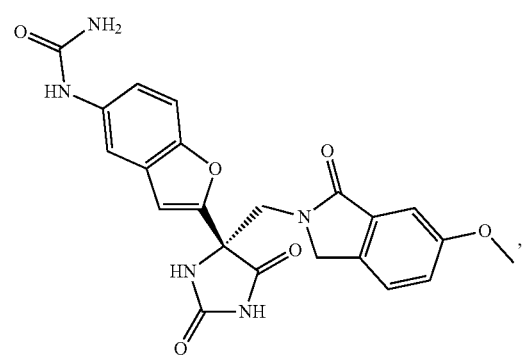
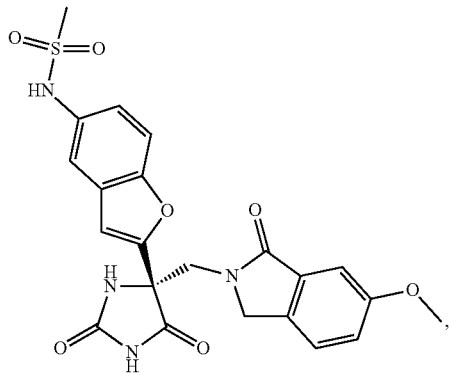
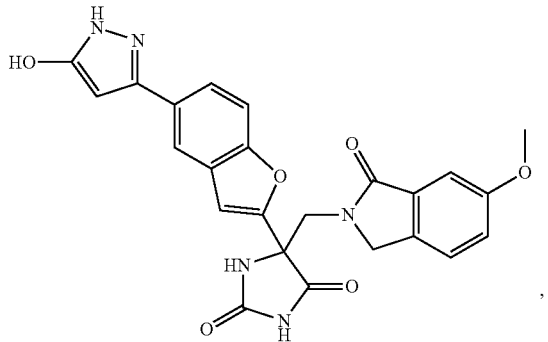
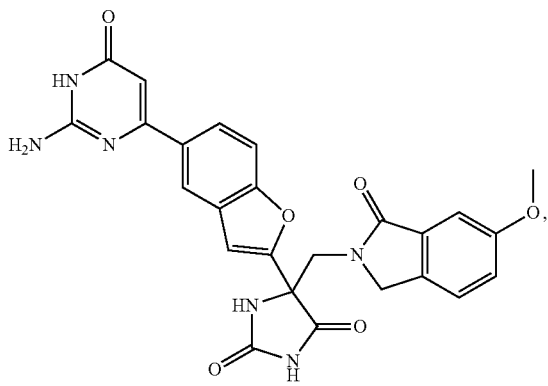
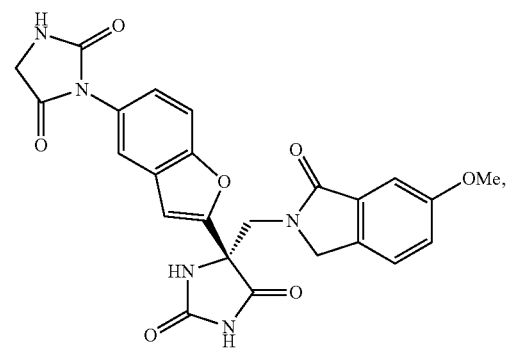

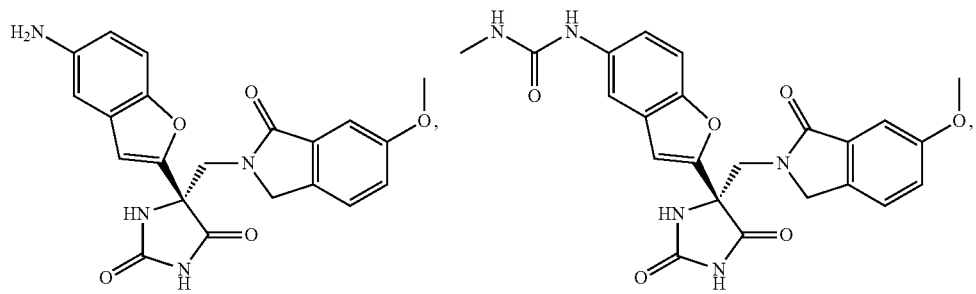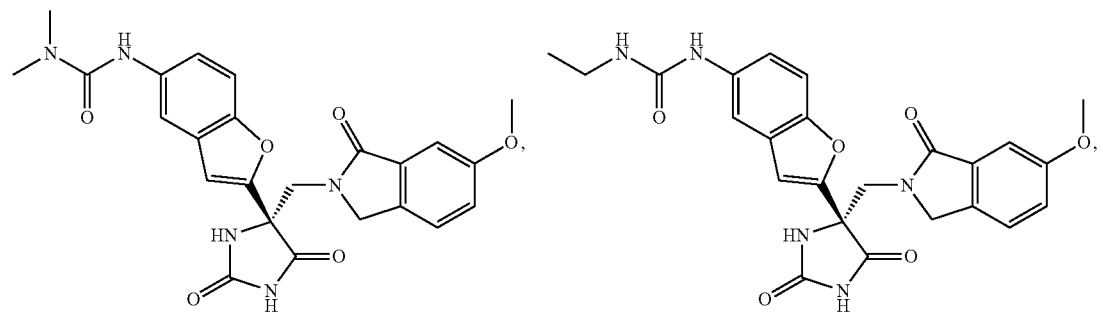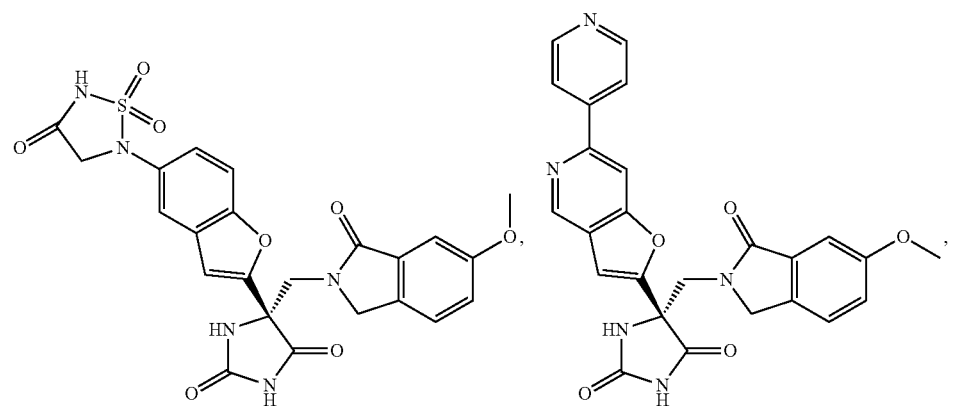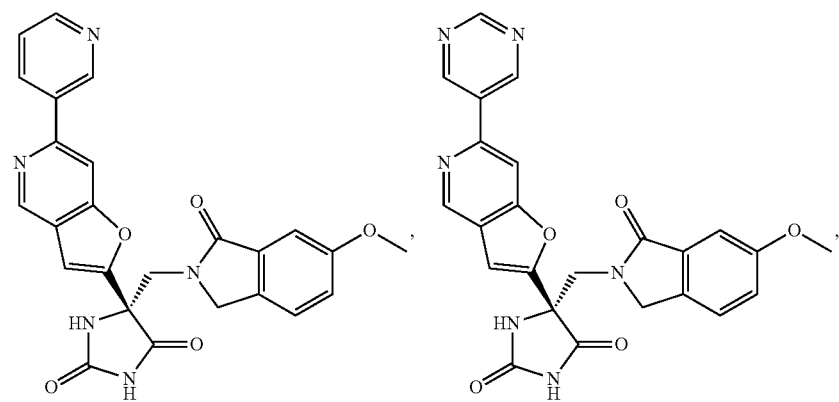

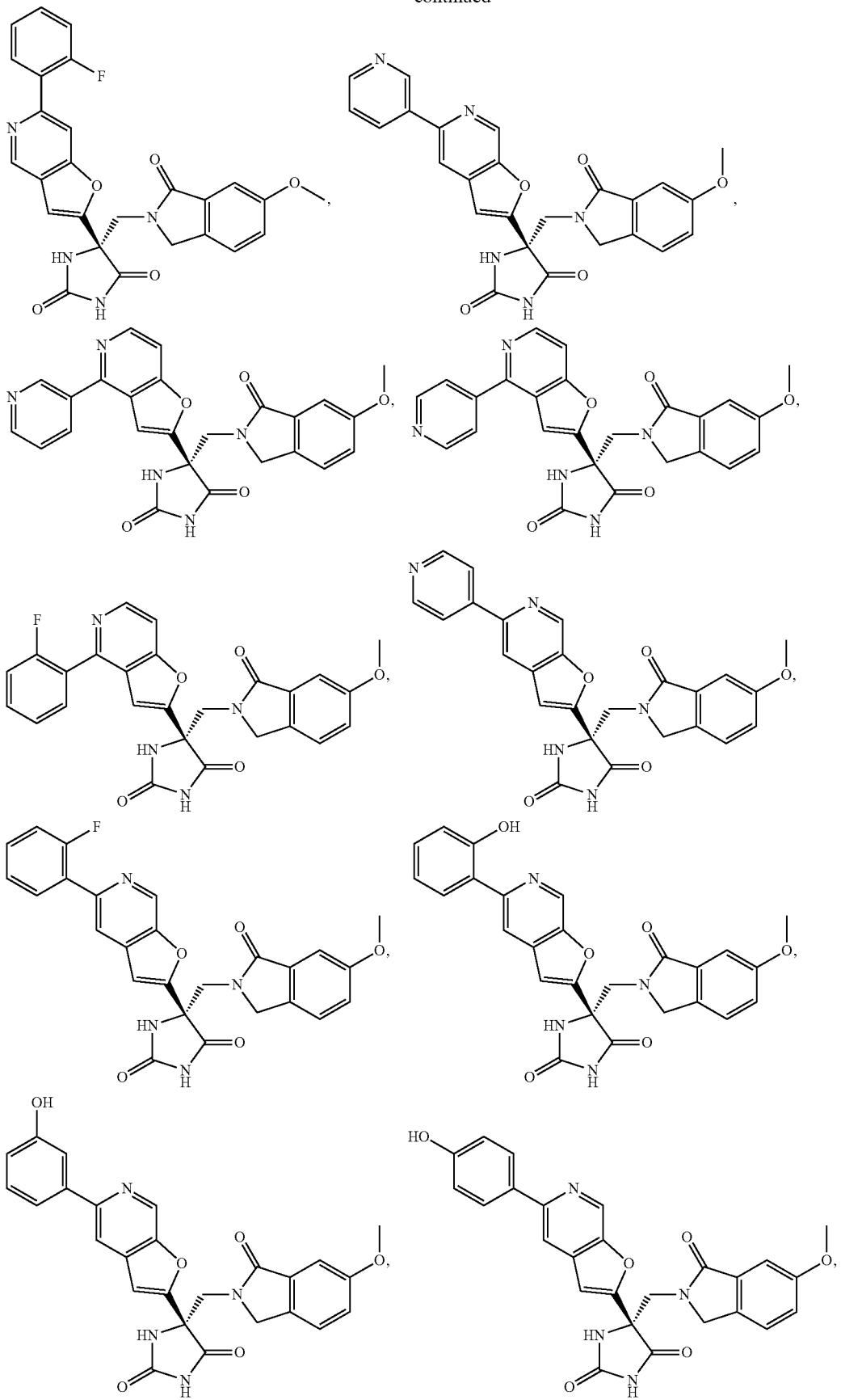

-continued
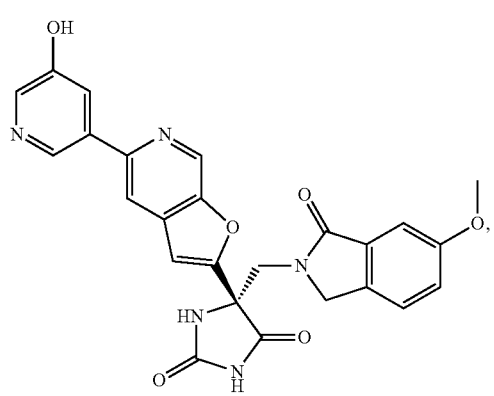
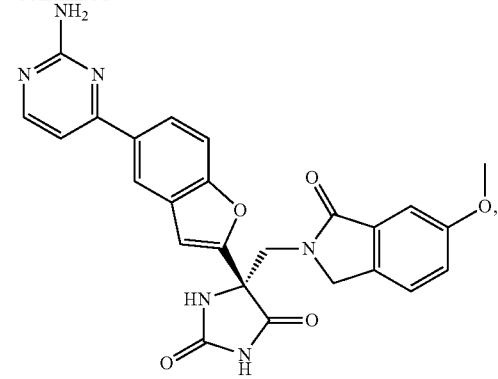
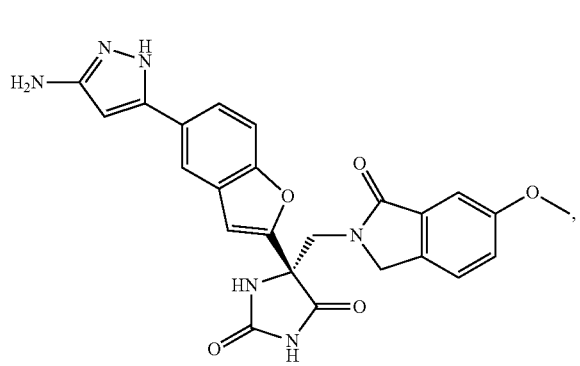
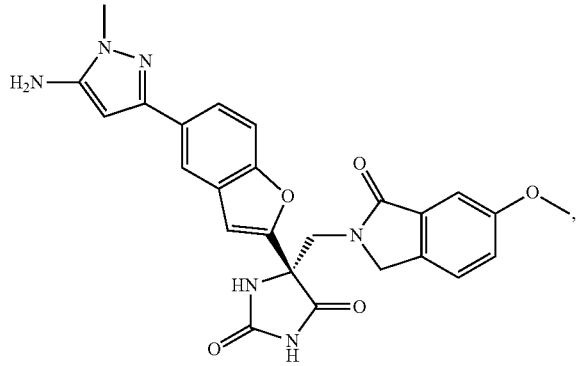
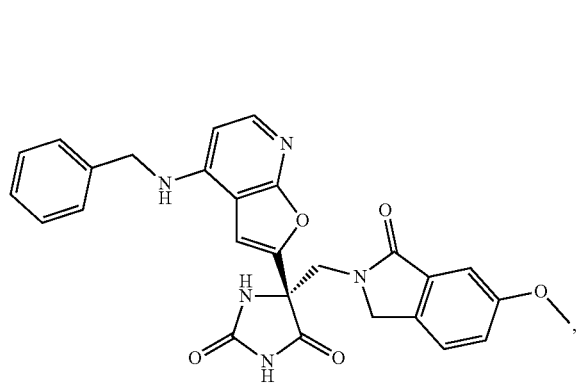
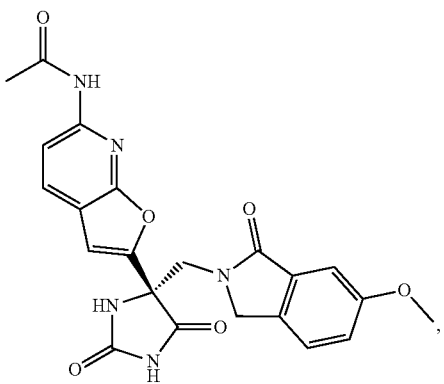
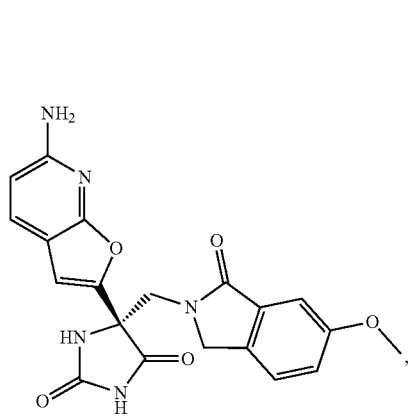
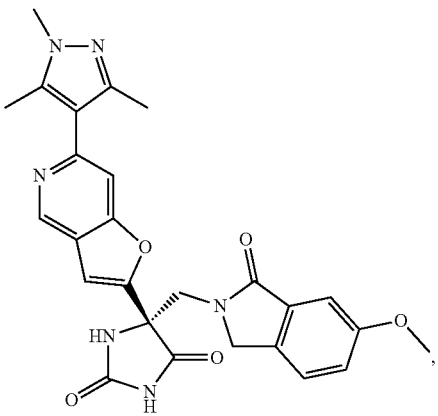

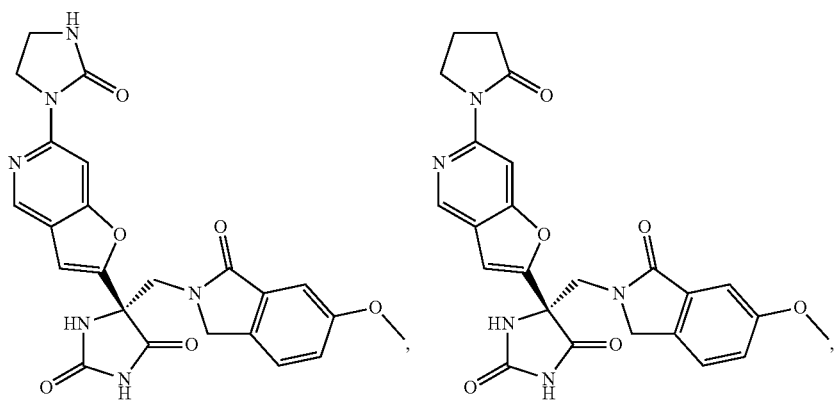
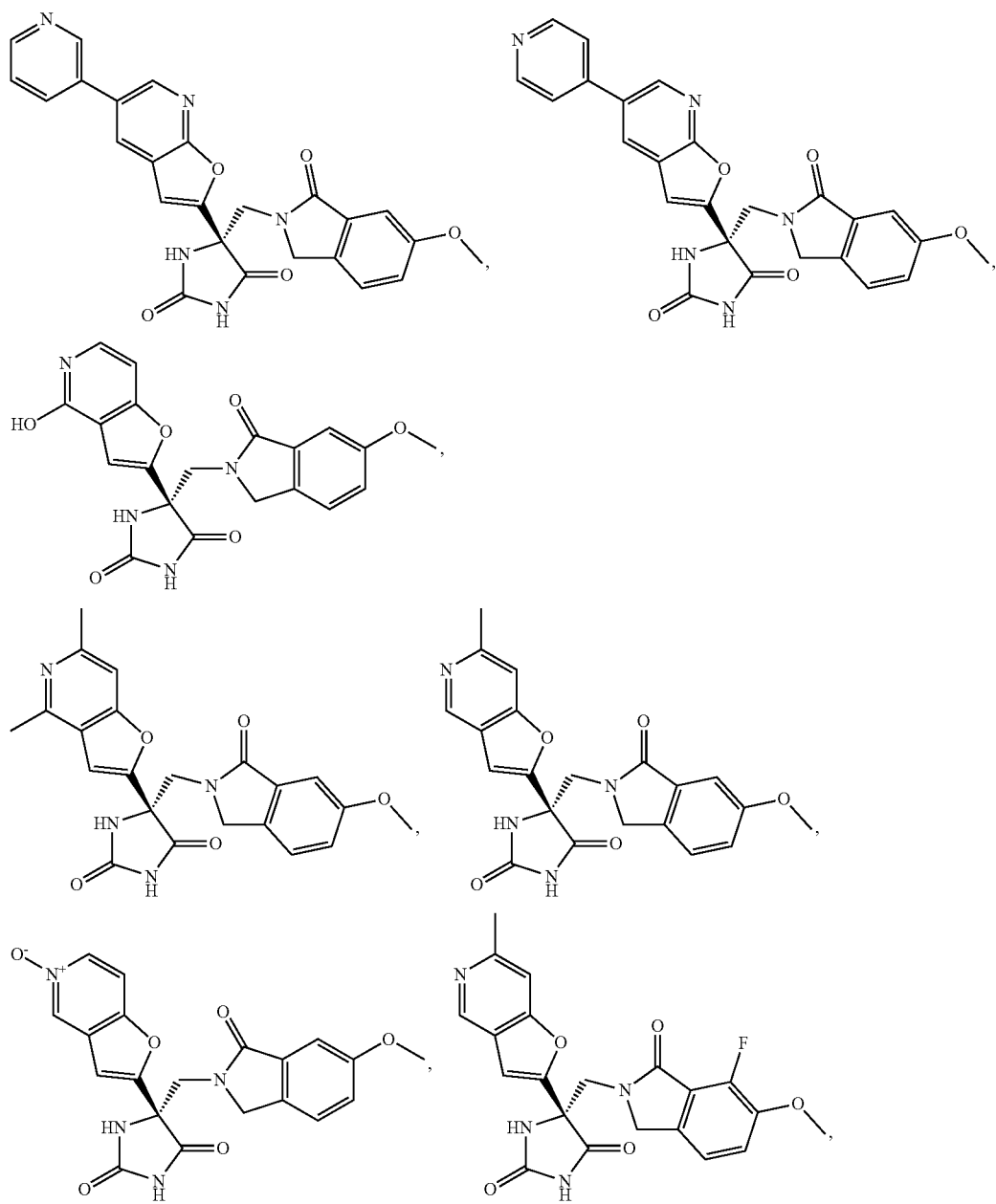

101 102
-continued
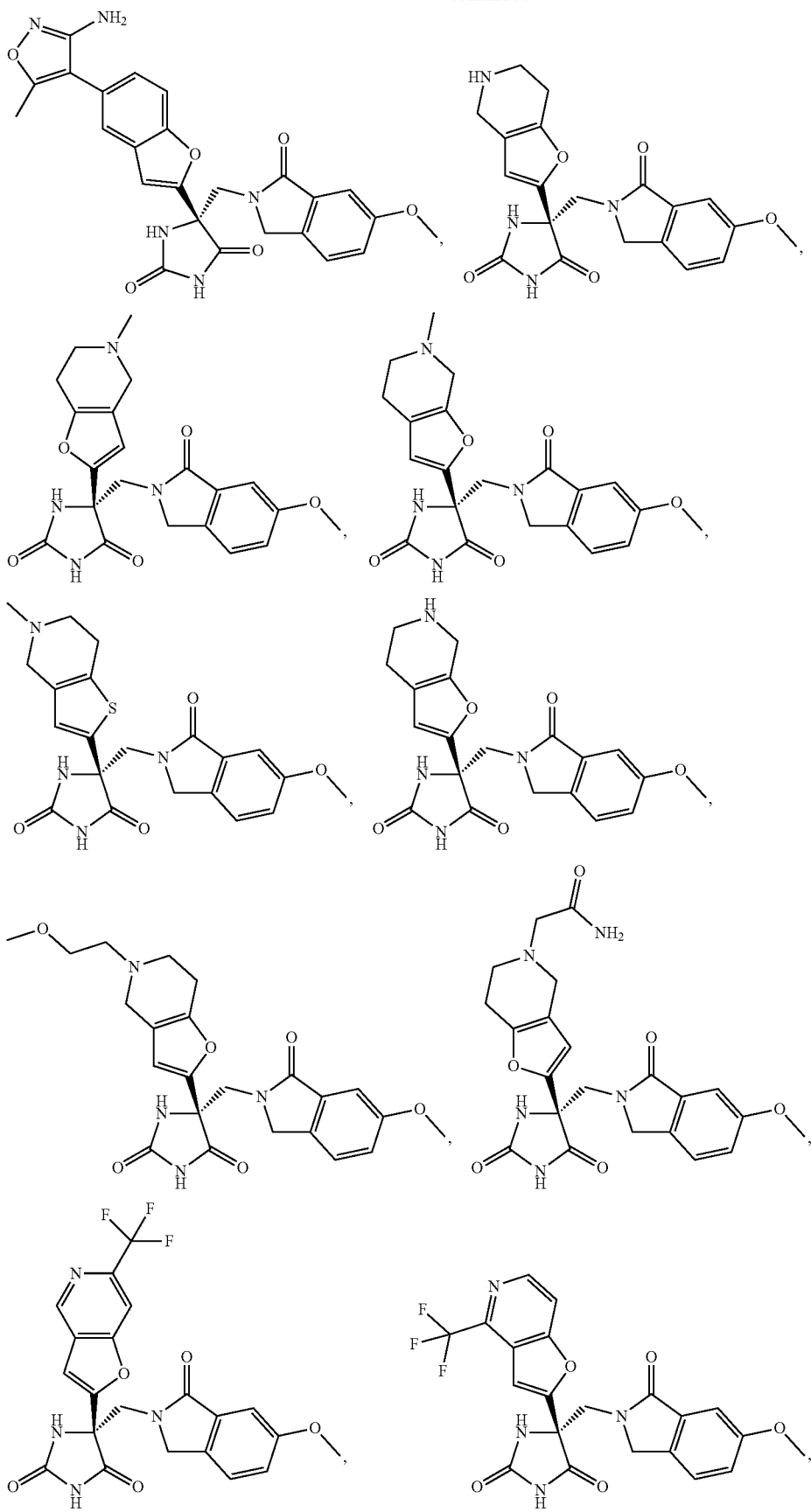

-continued
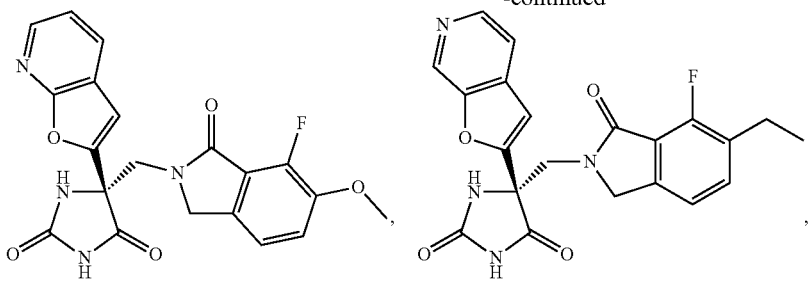
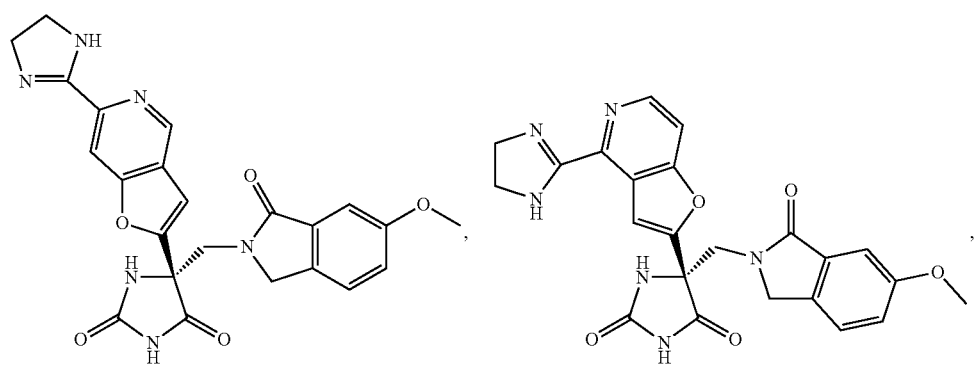
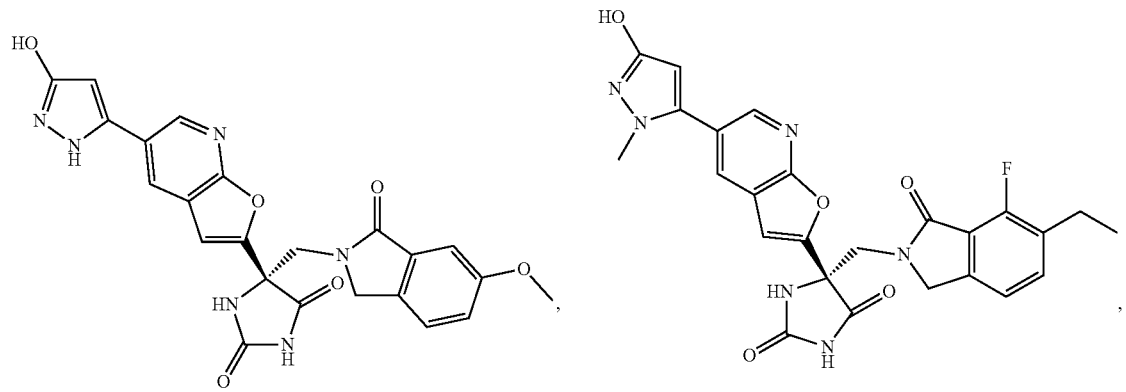
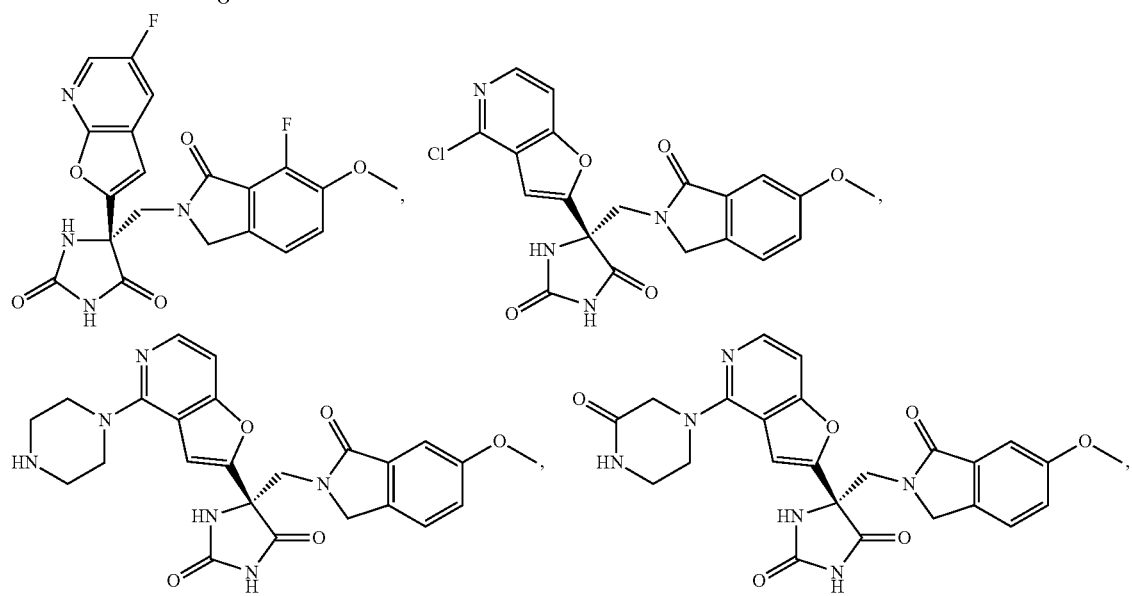

-continued
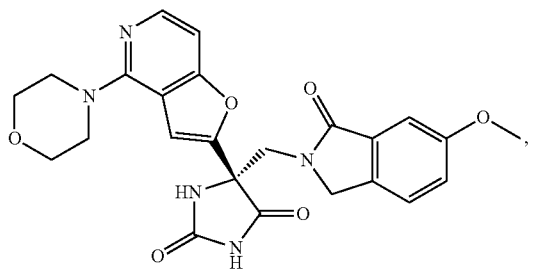
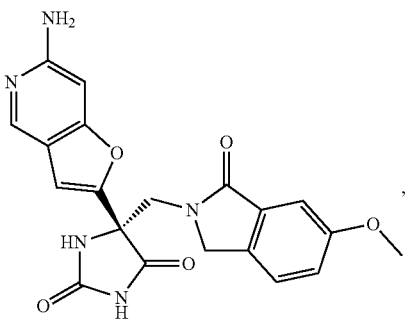
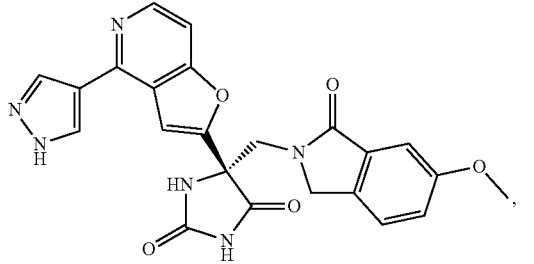
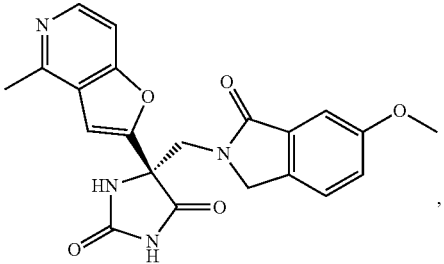
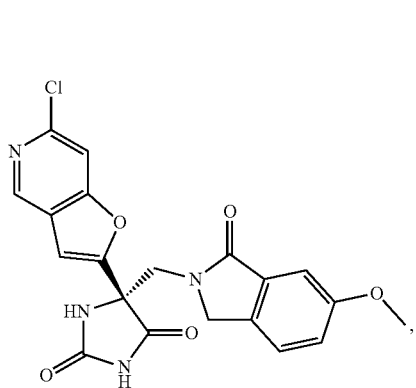
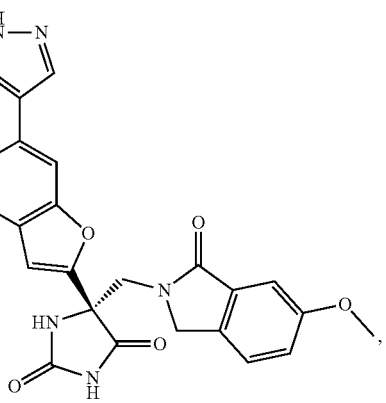
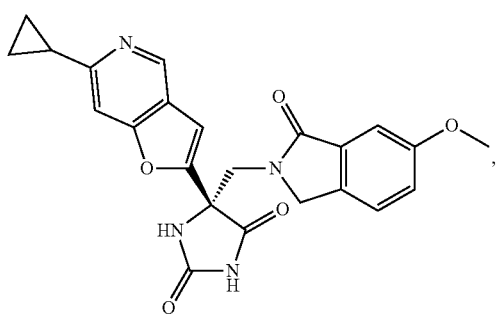
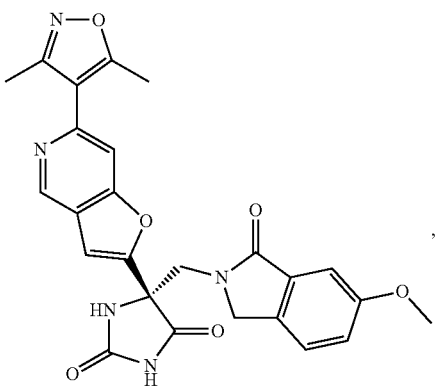
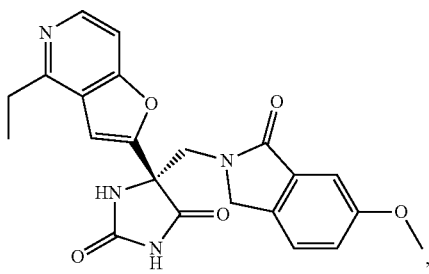
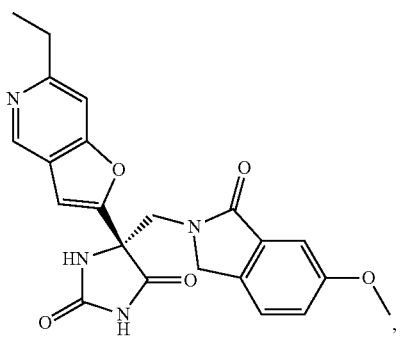

-continued
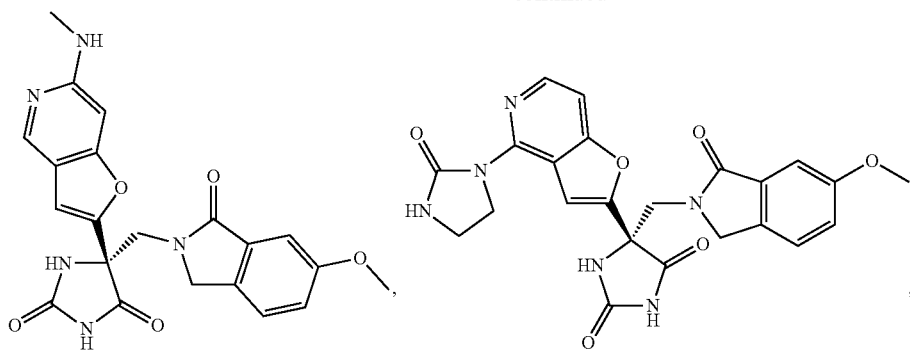
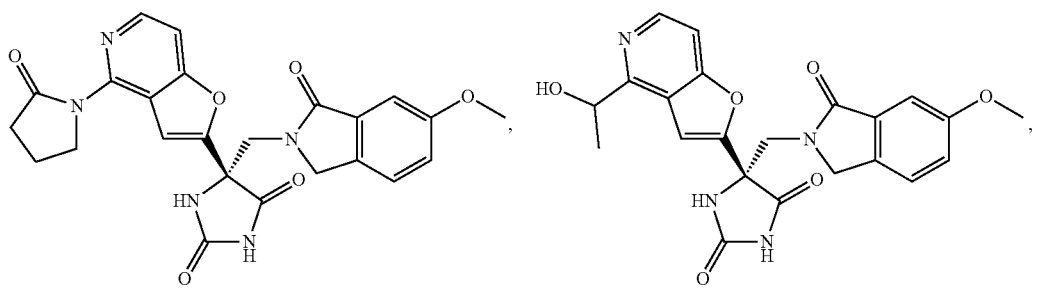
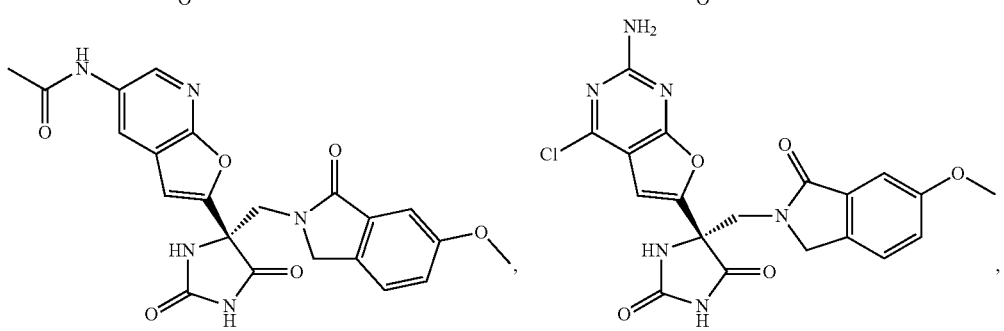
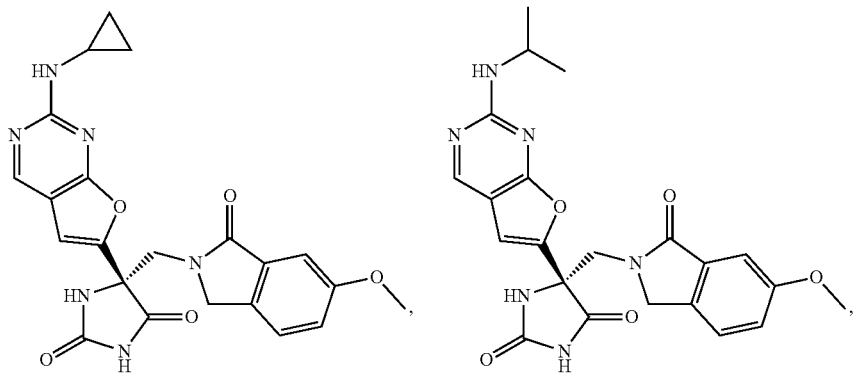
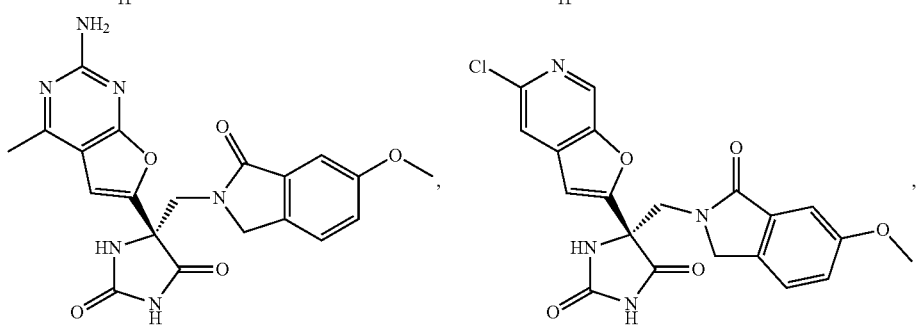

-continued
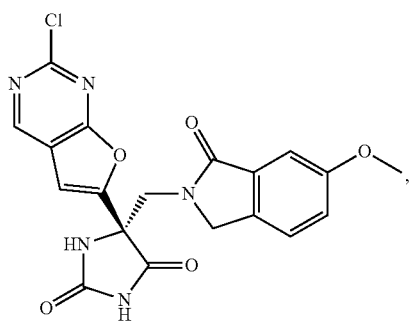 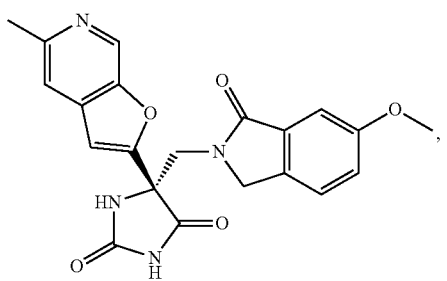
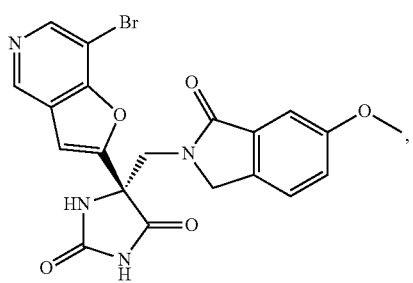 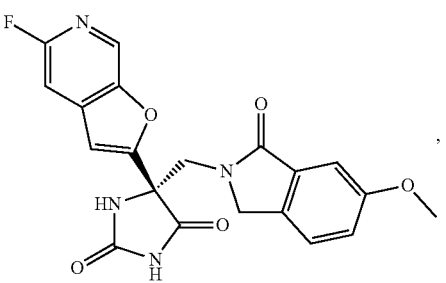
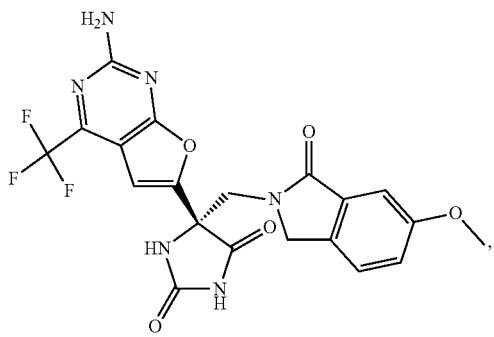 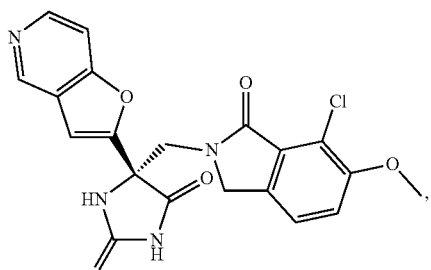
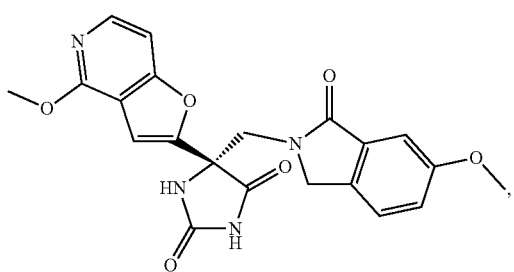 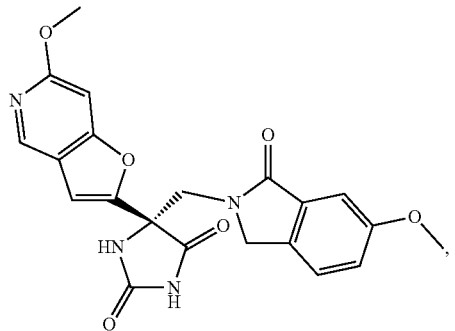
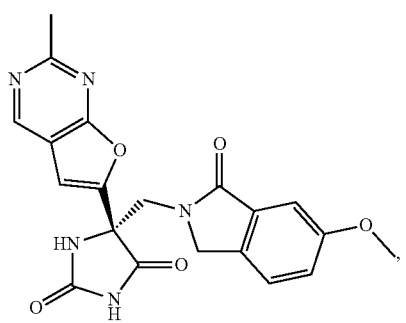 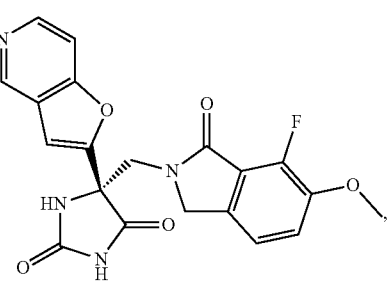

111
-continued
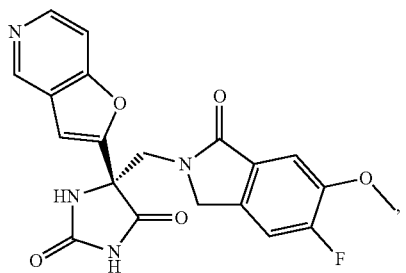
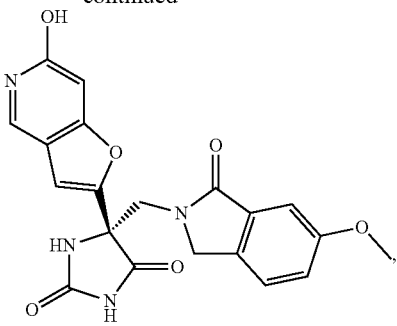
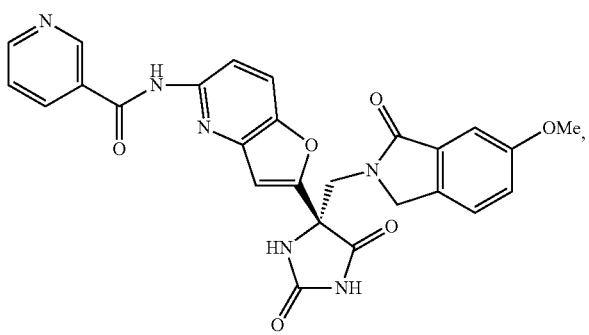
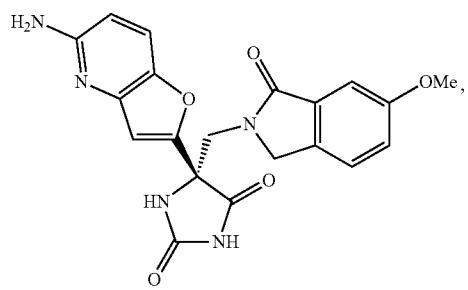
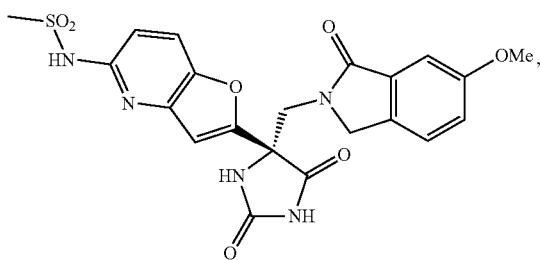
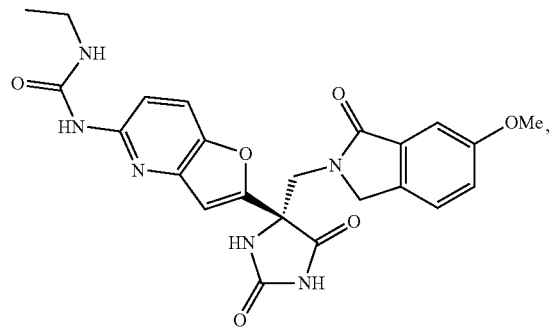
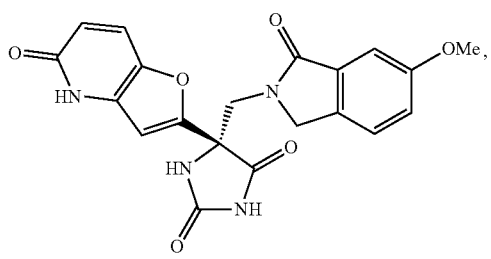
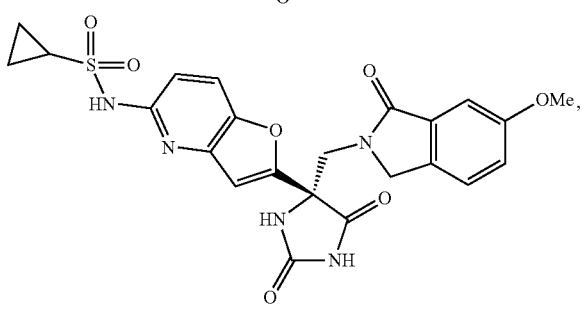
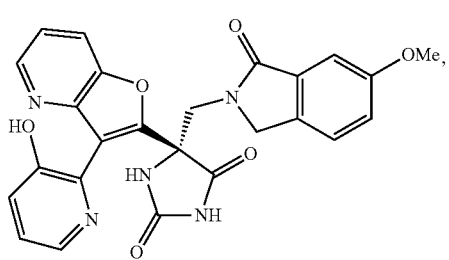
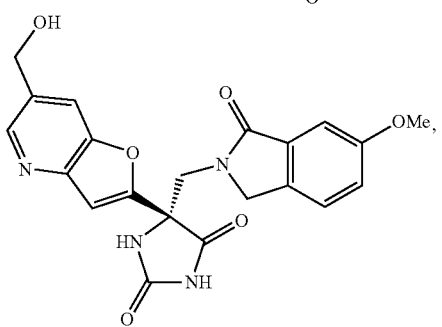

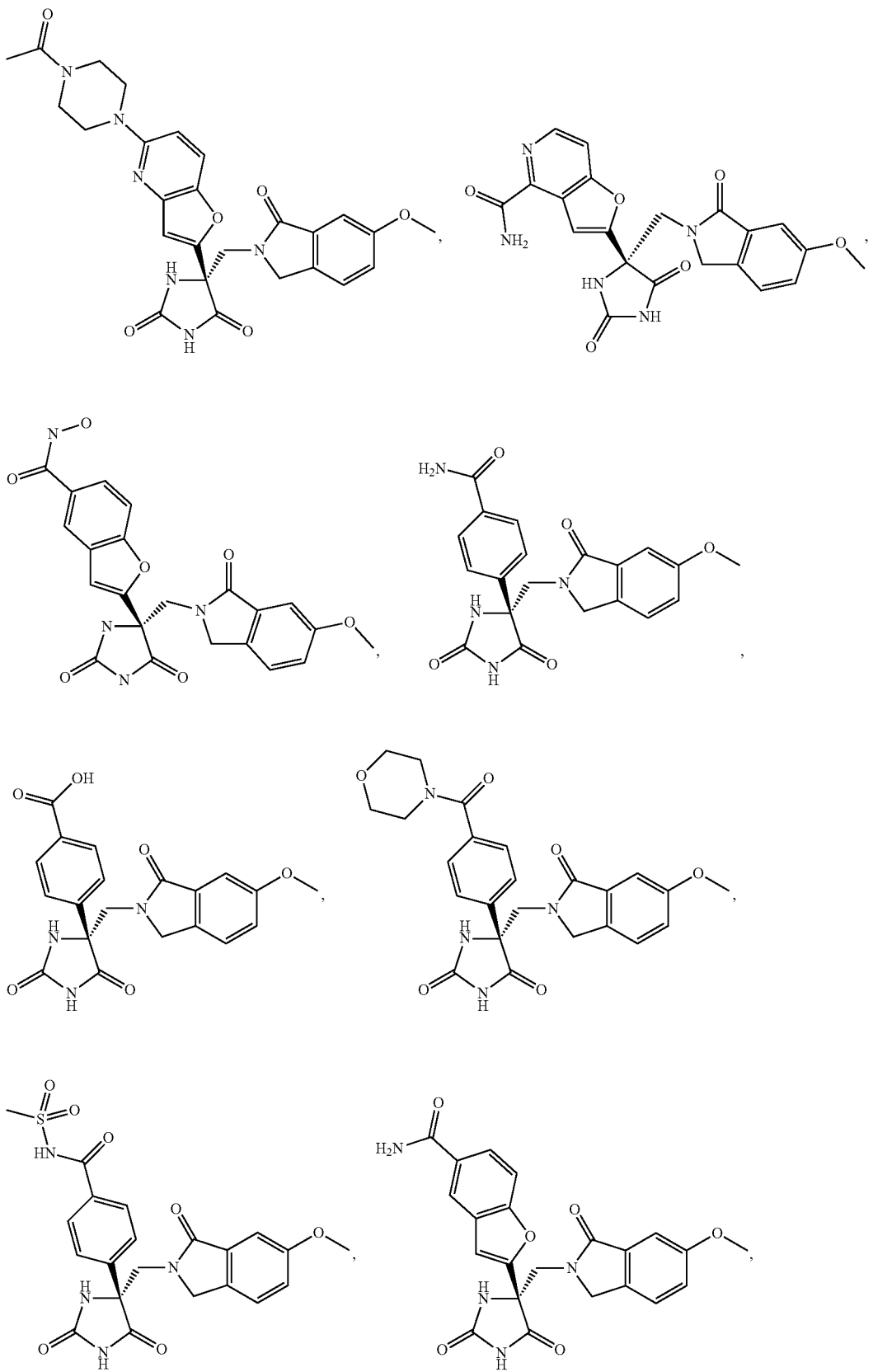

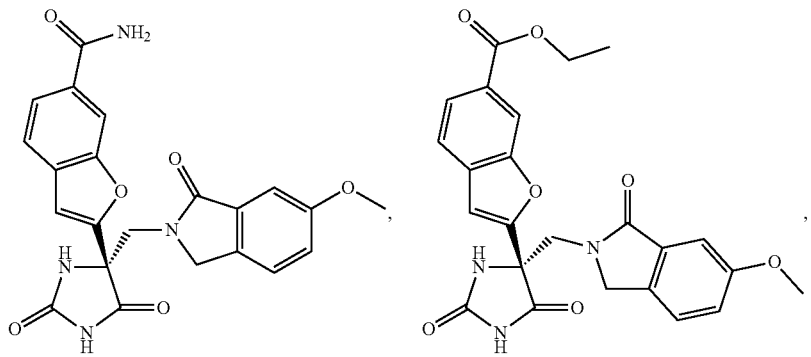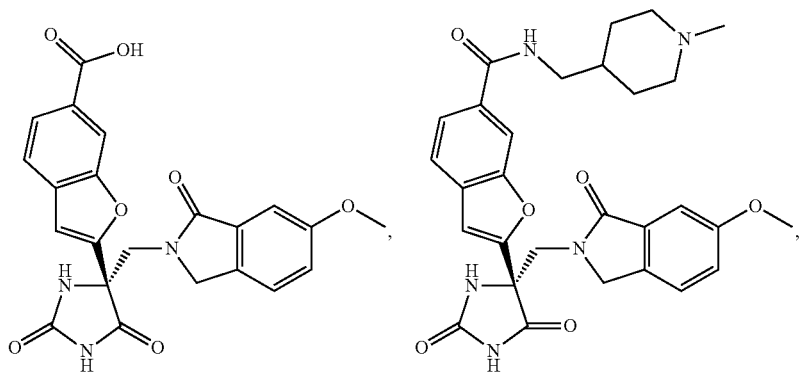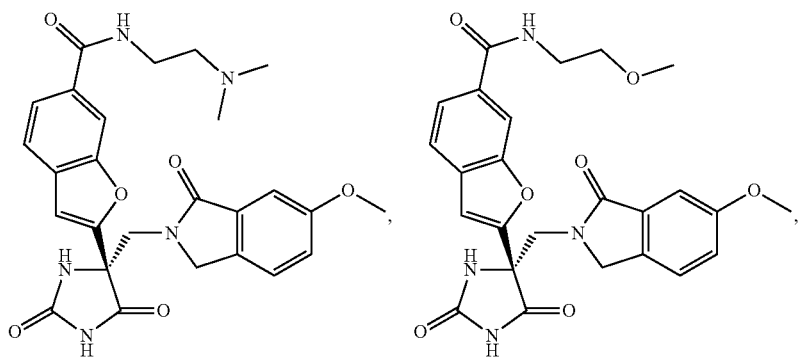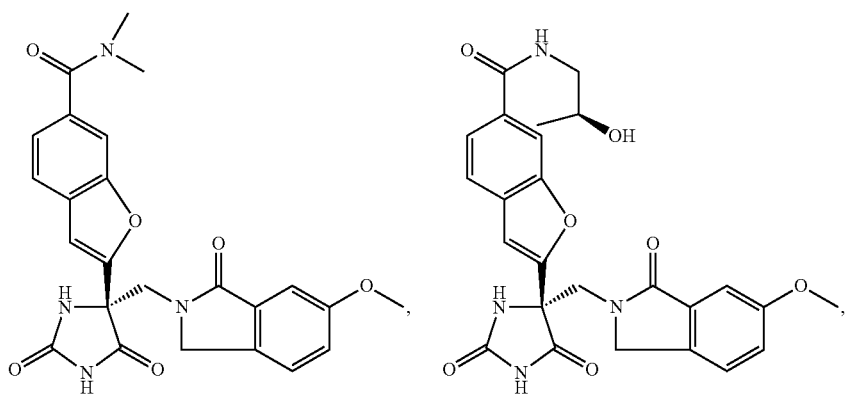

-continued
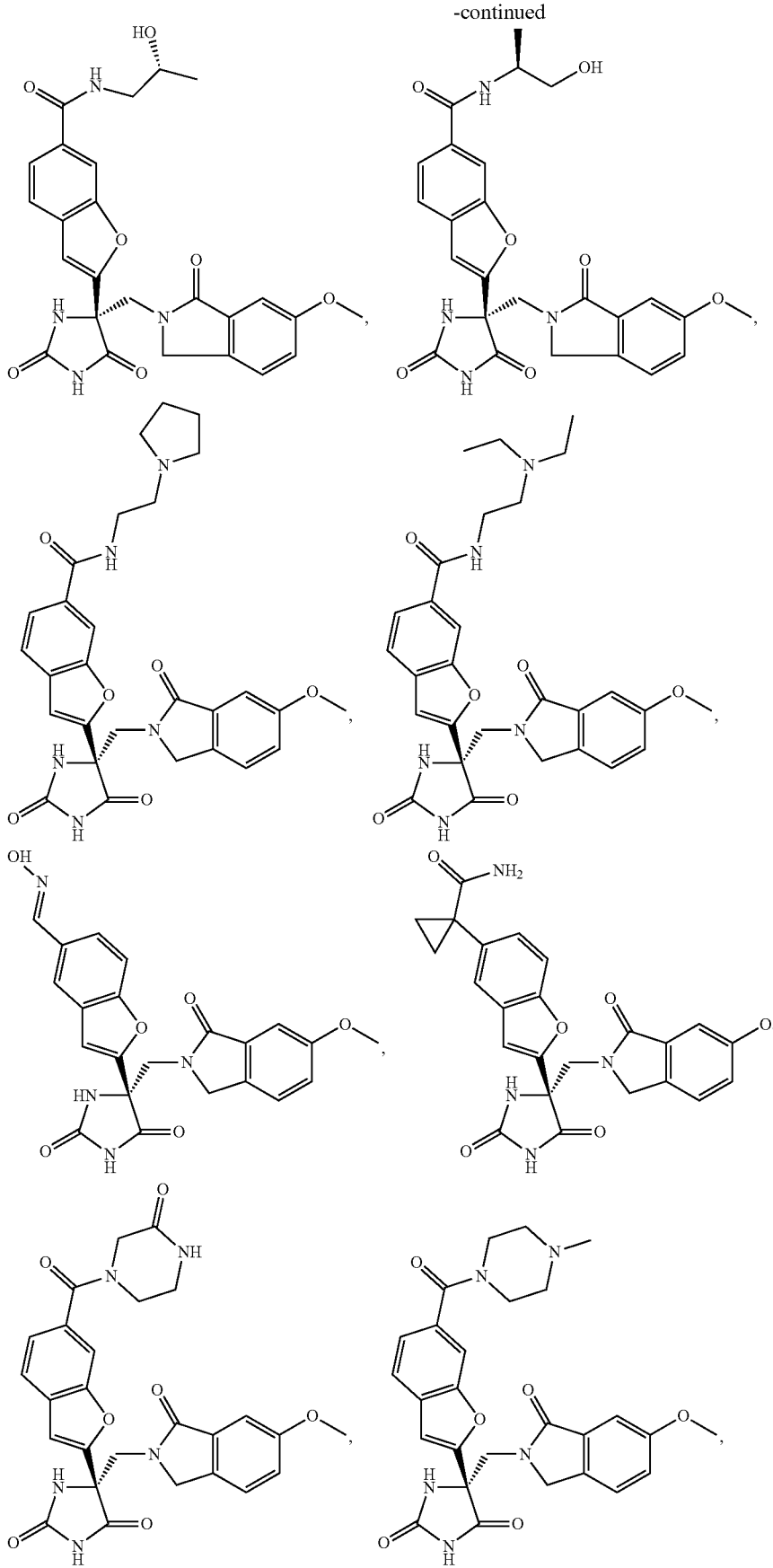

-continued
119
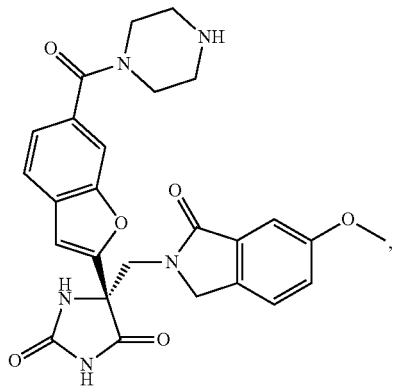
120
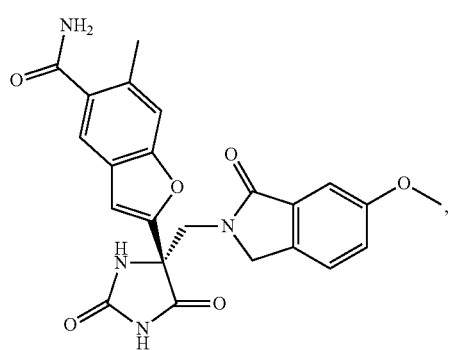
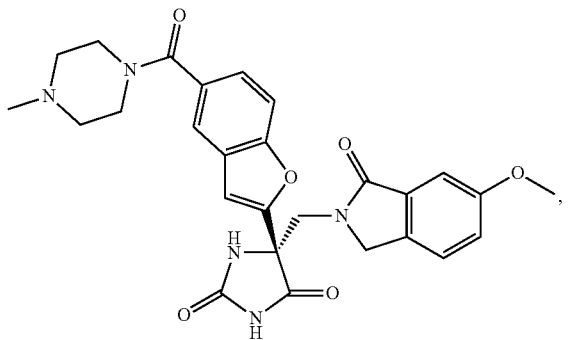
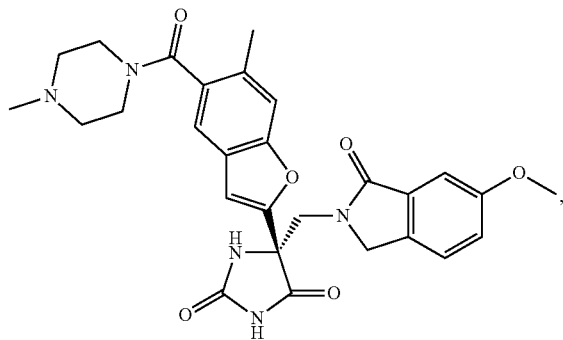
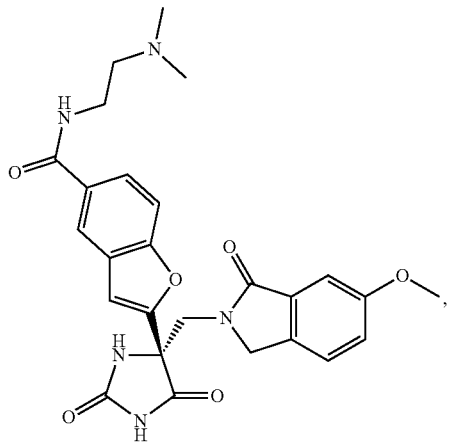
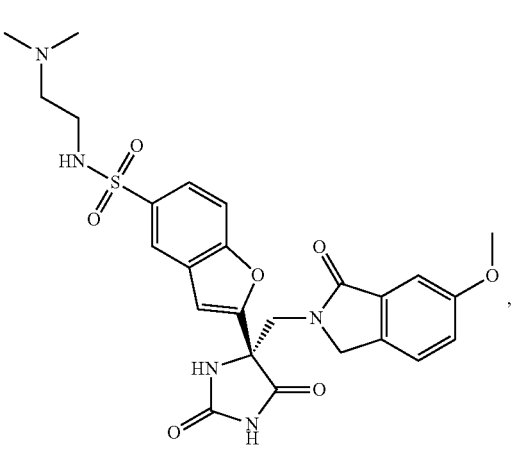
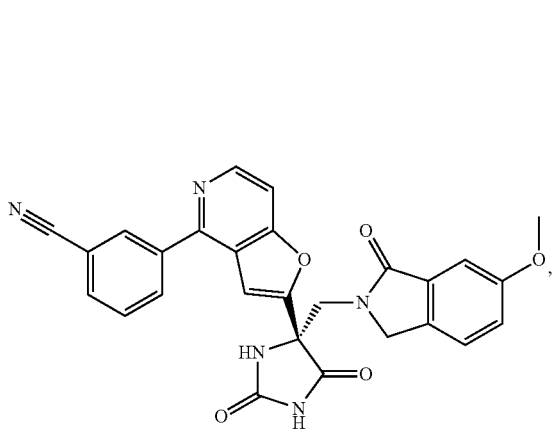
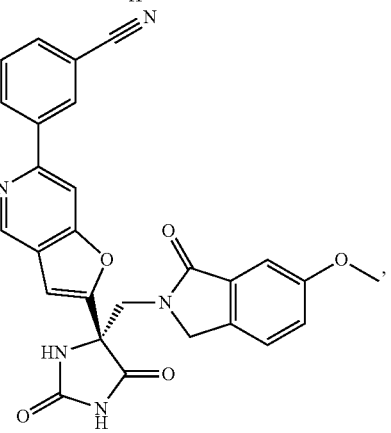

121 122
-continued
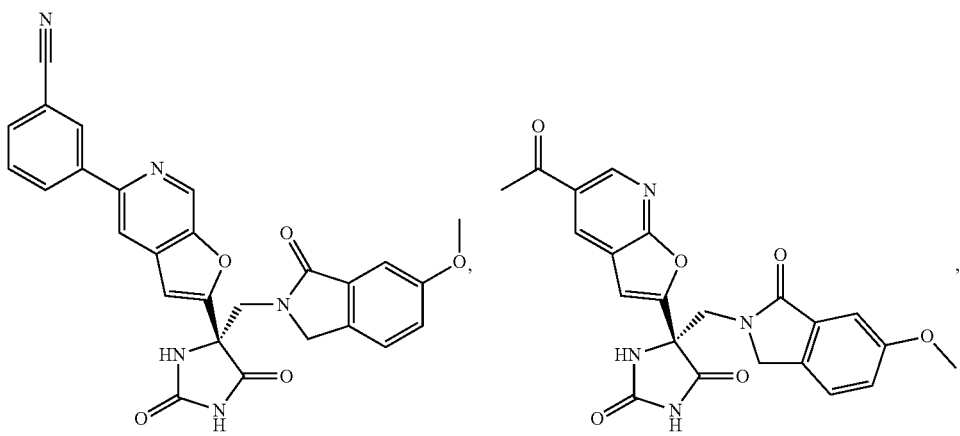
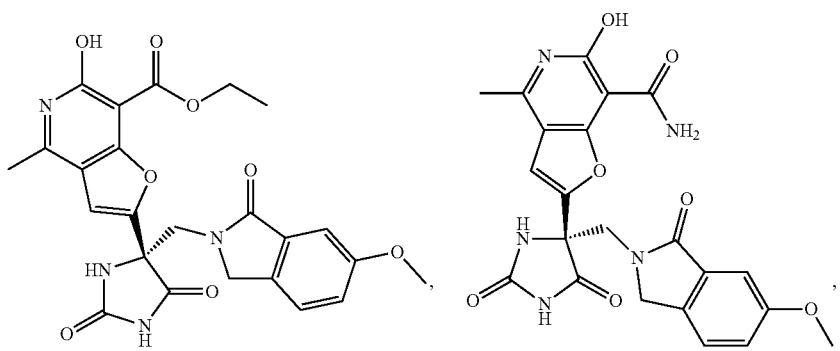
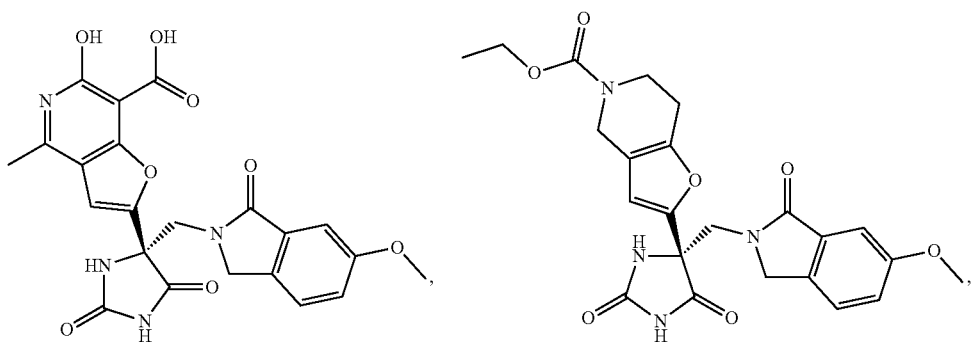
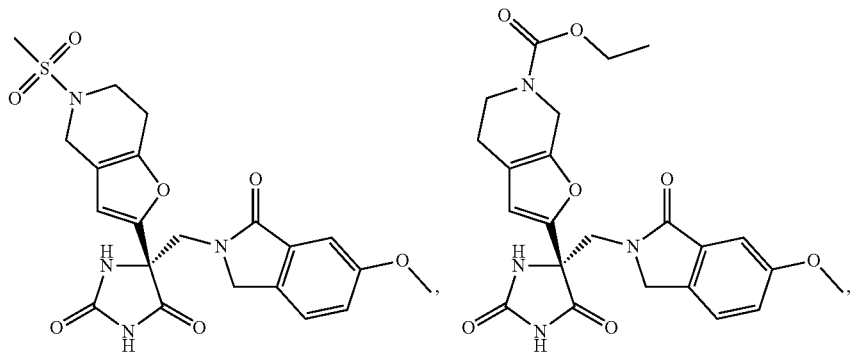

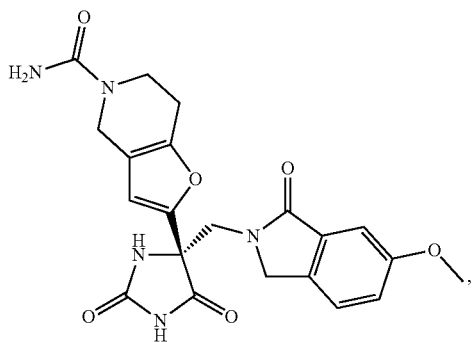
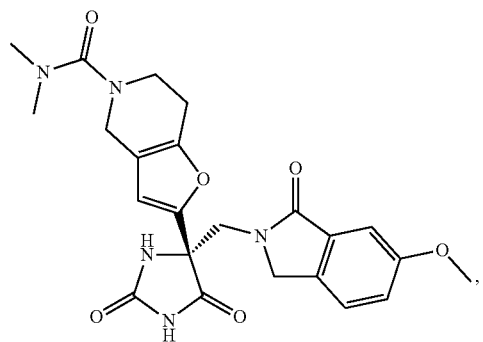
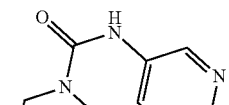
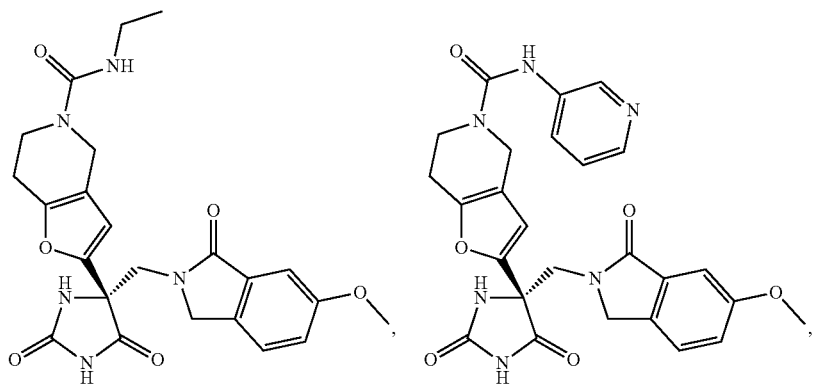
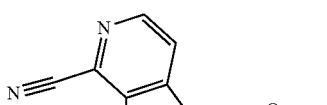
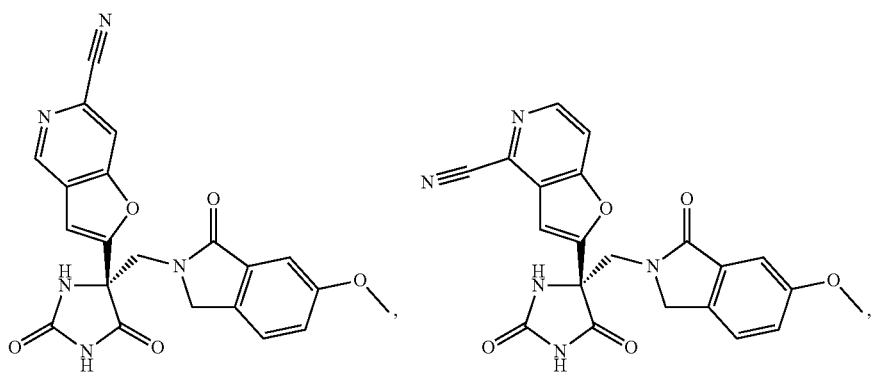
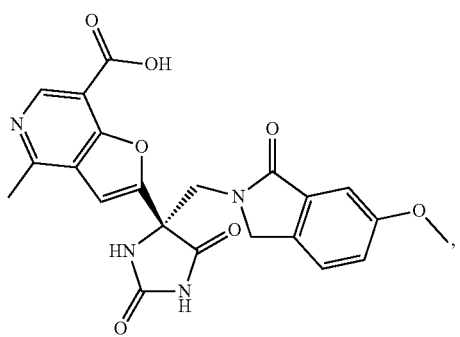
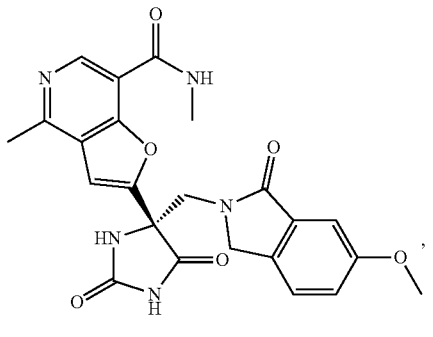

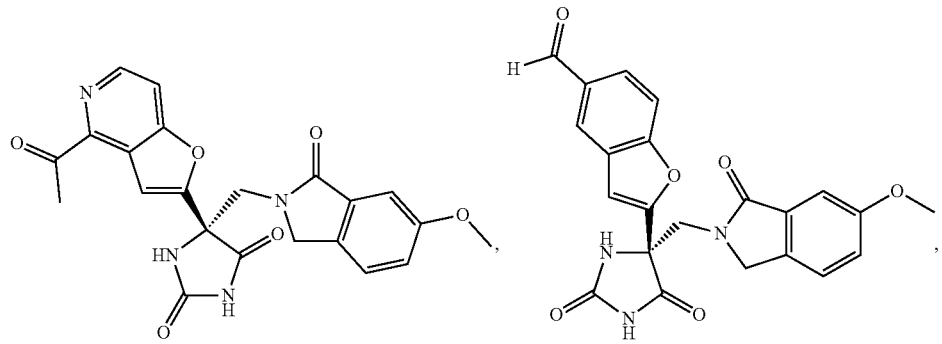
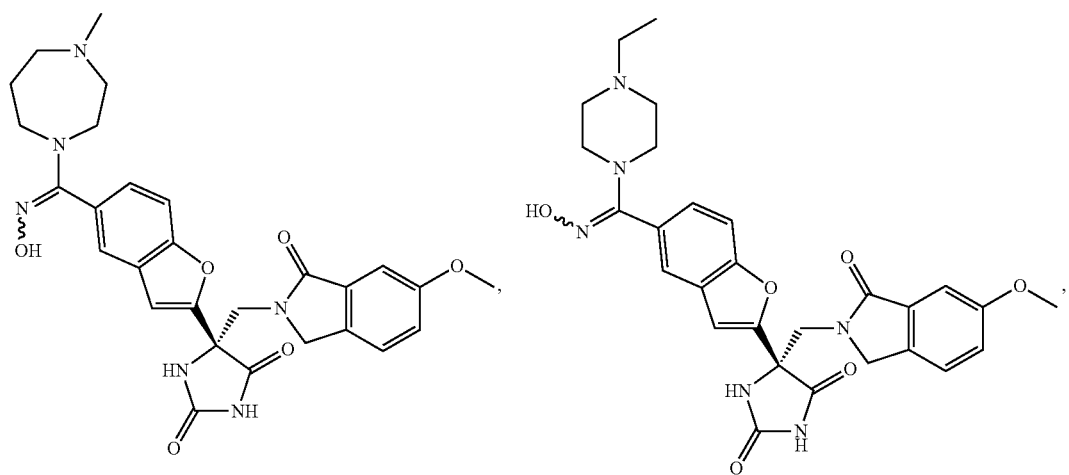
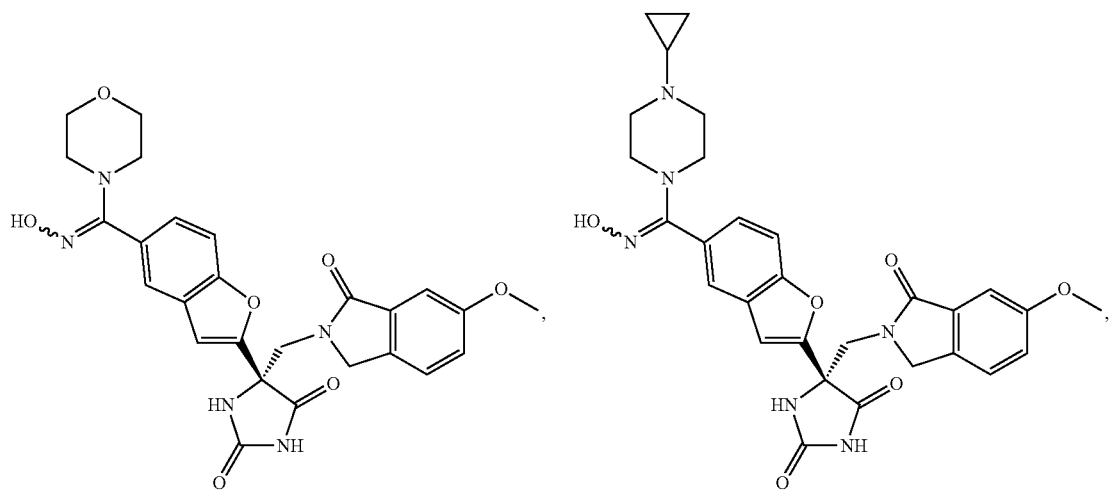

127
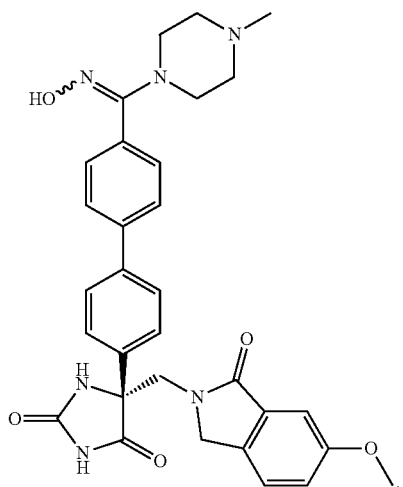
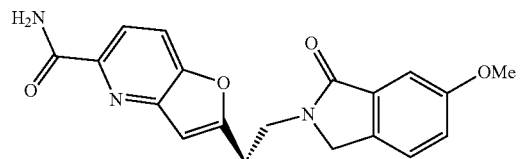
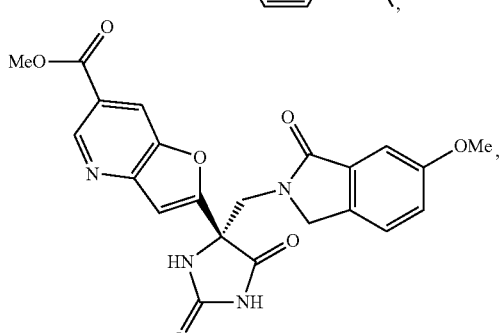
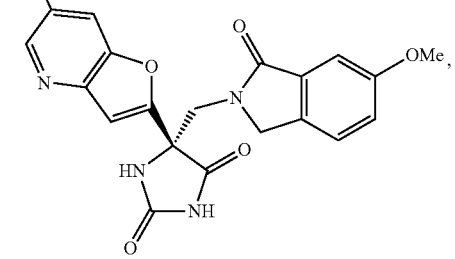
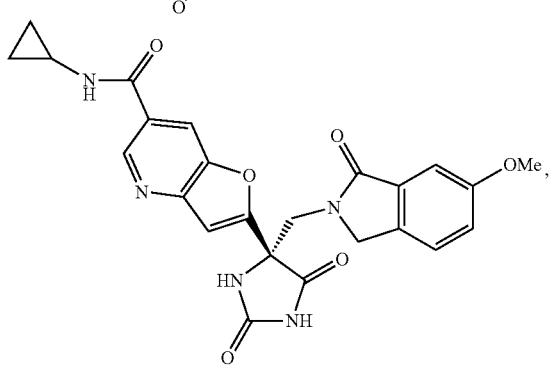
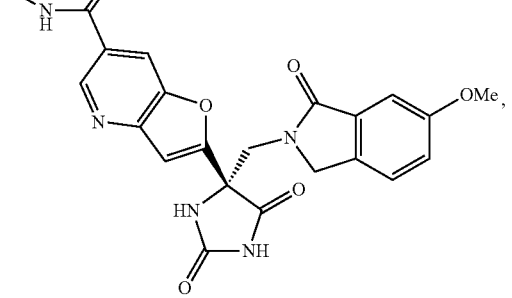
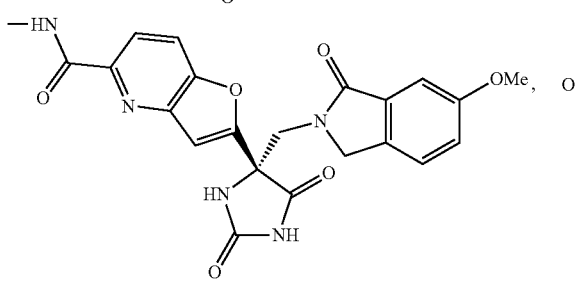
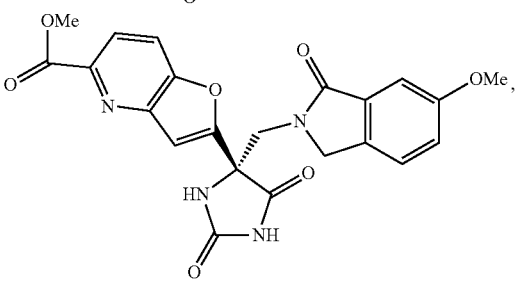
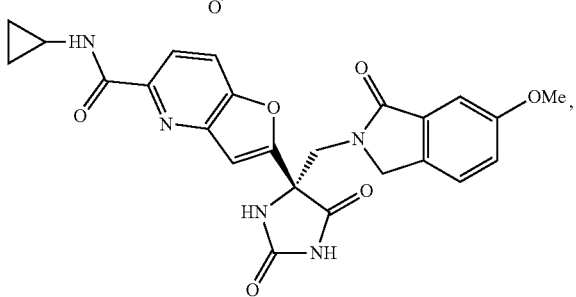
128
-continued

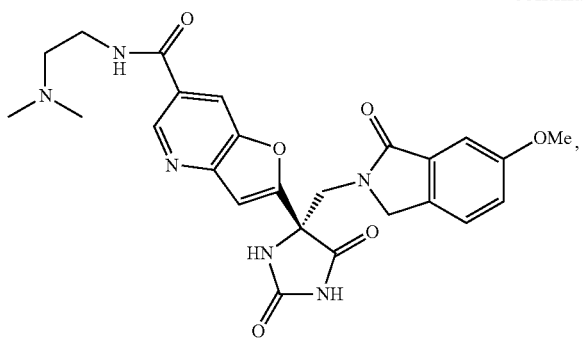
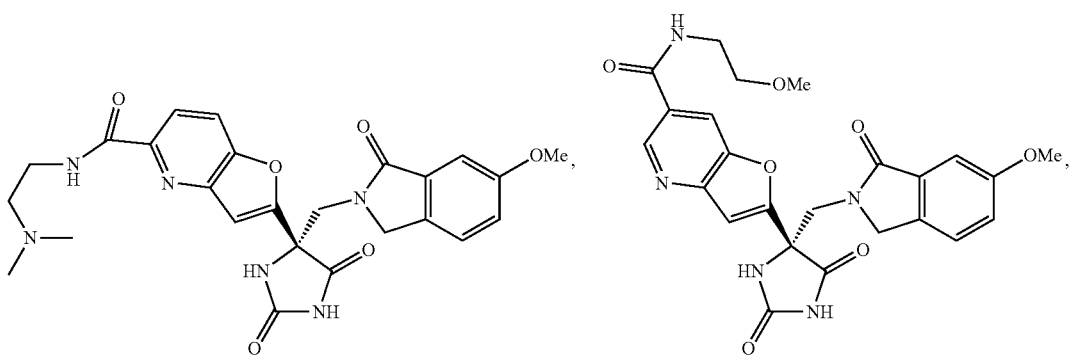
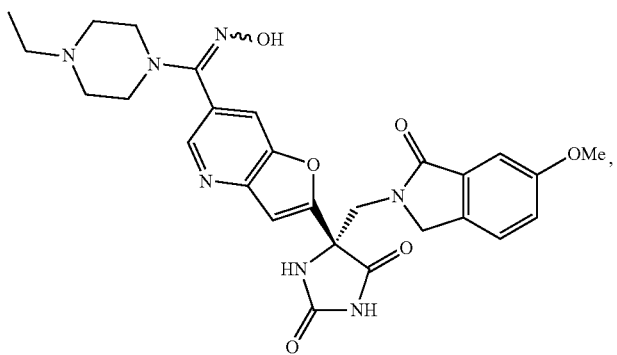
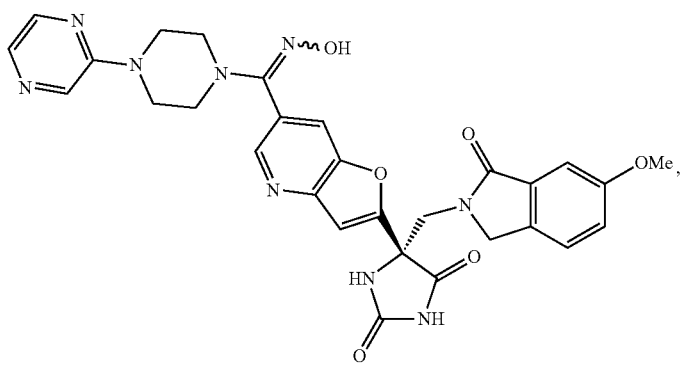

-continued
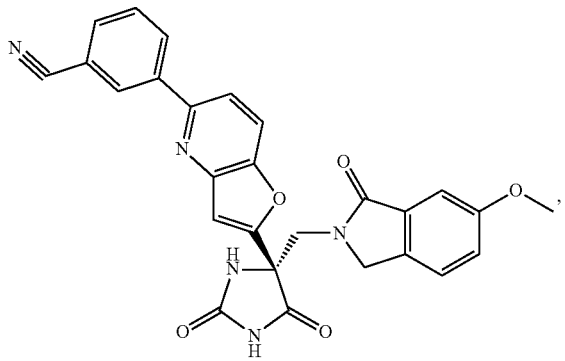
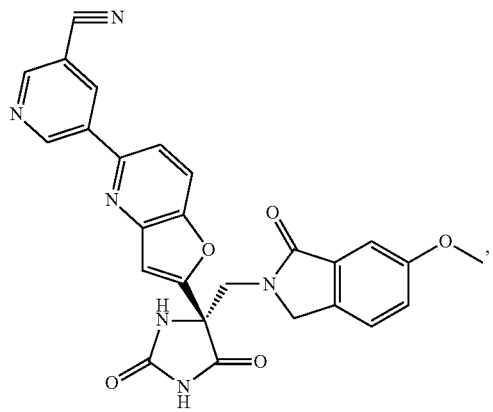
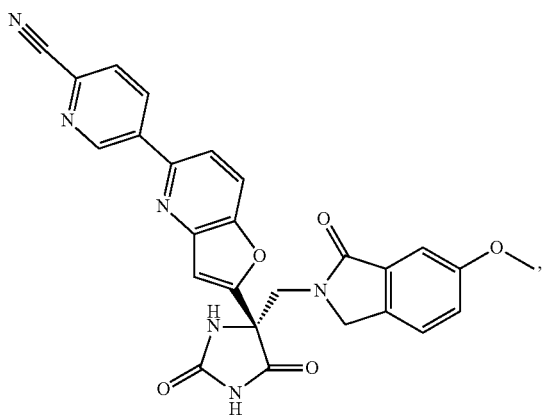
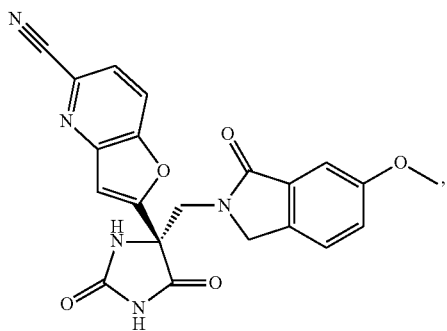
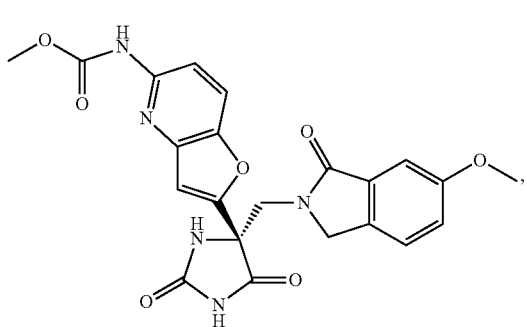
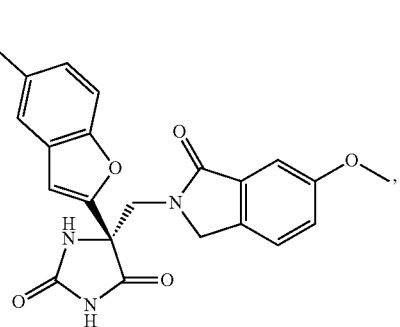
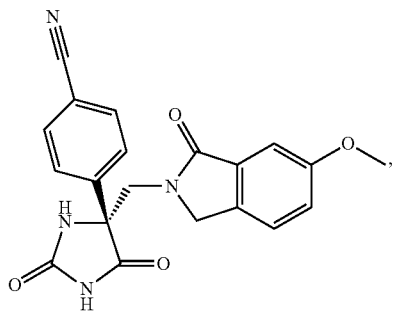
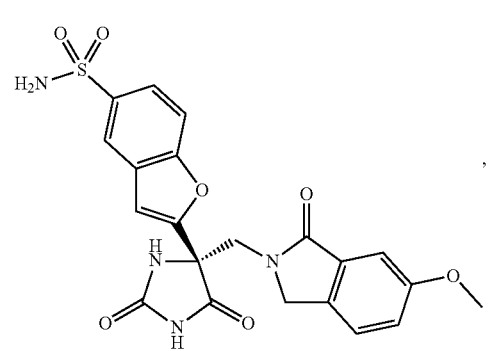

133
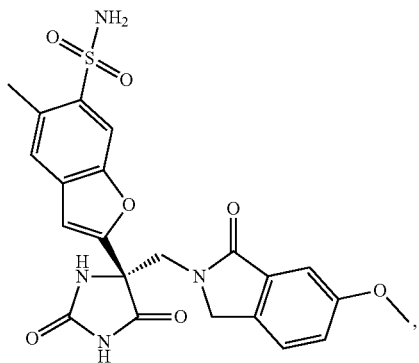
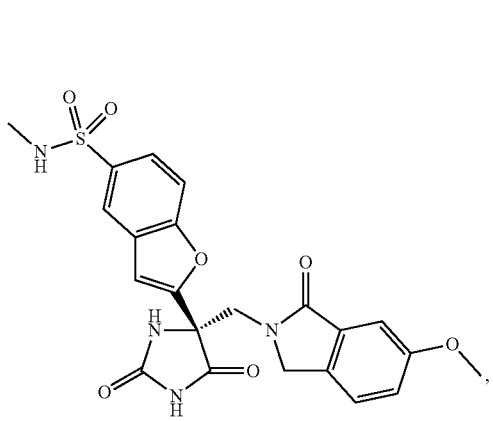
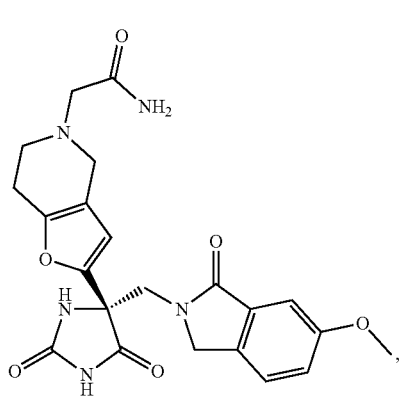
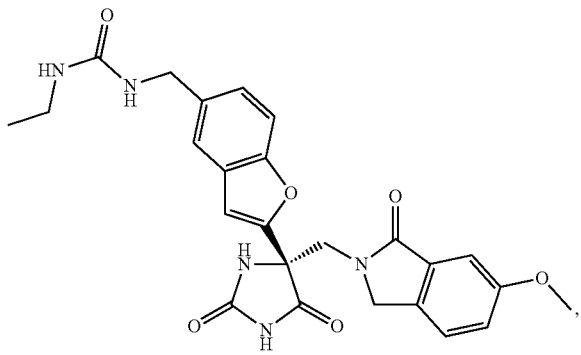
134
-continued
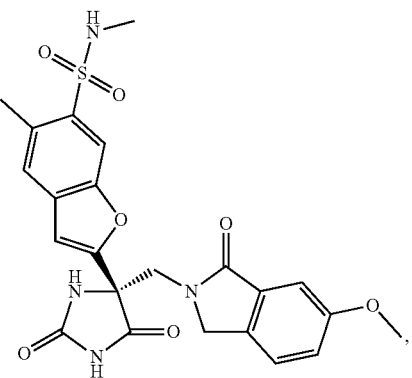
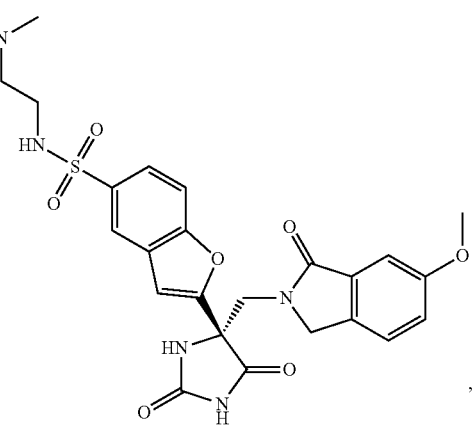
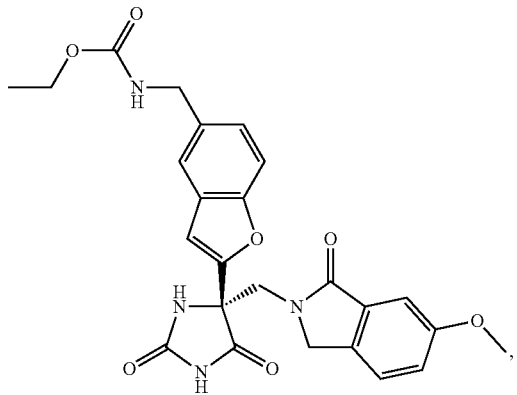
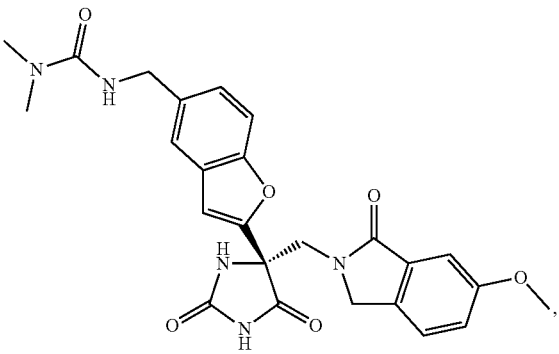

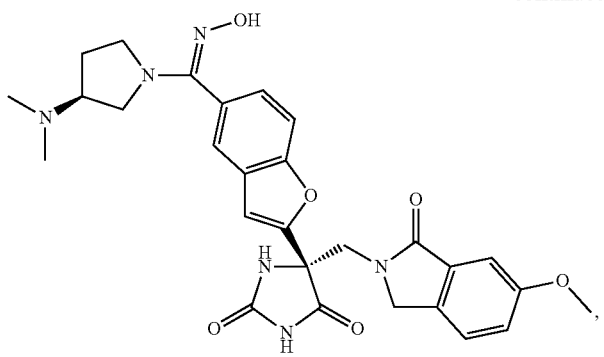
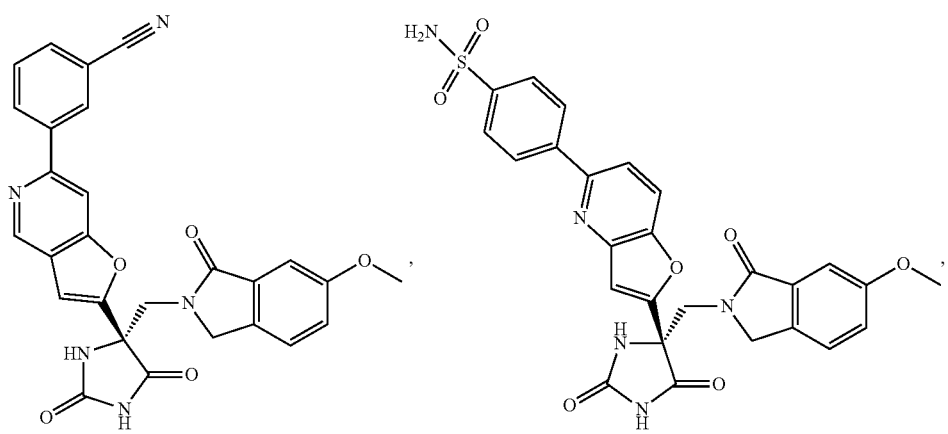
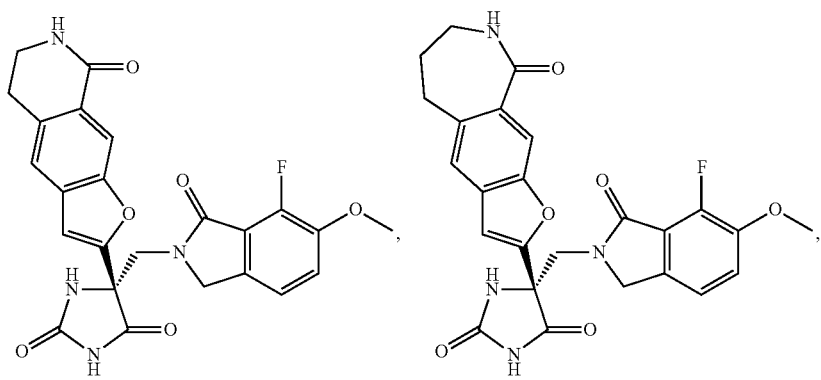
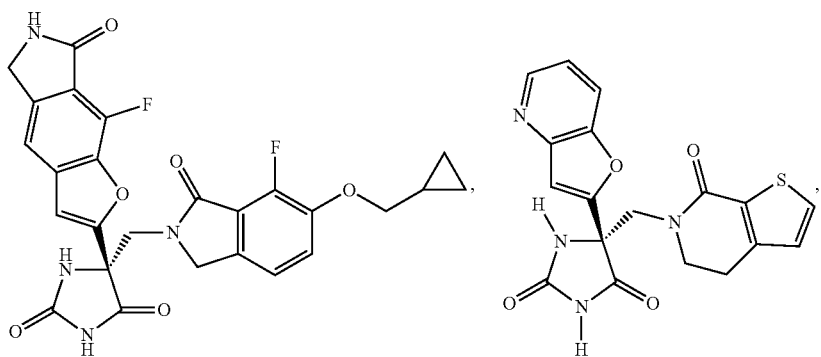

137
-continued
138
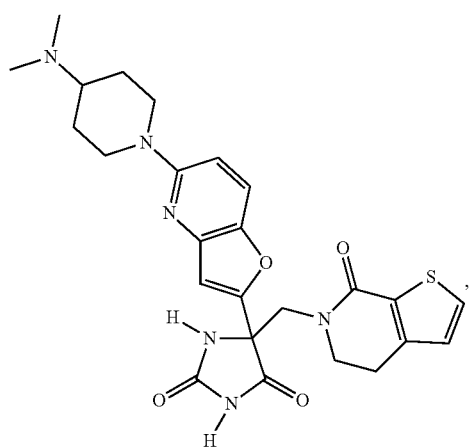
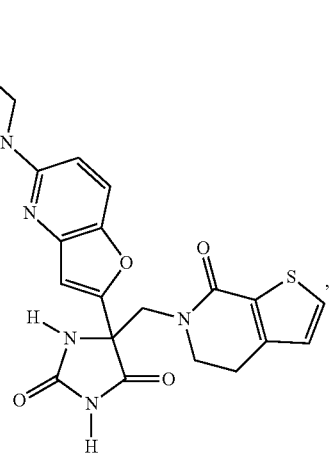
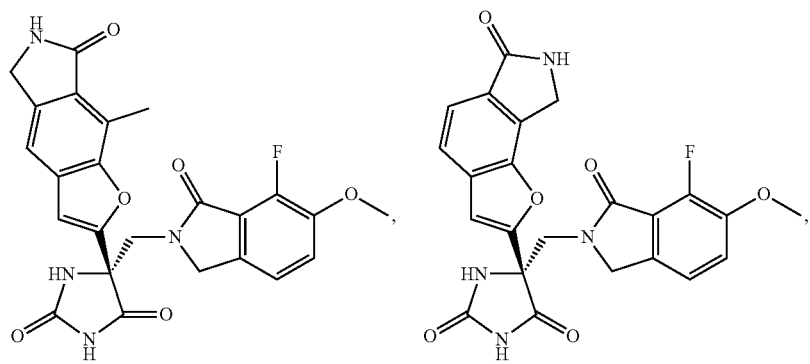
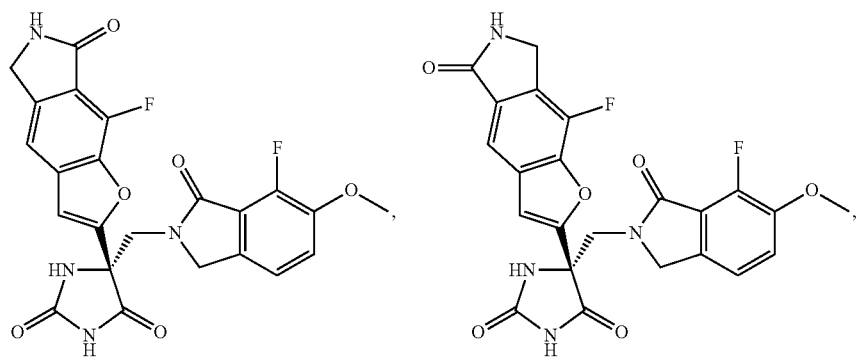
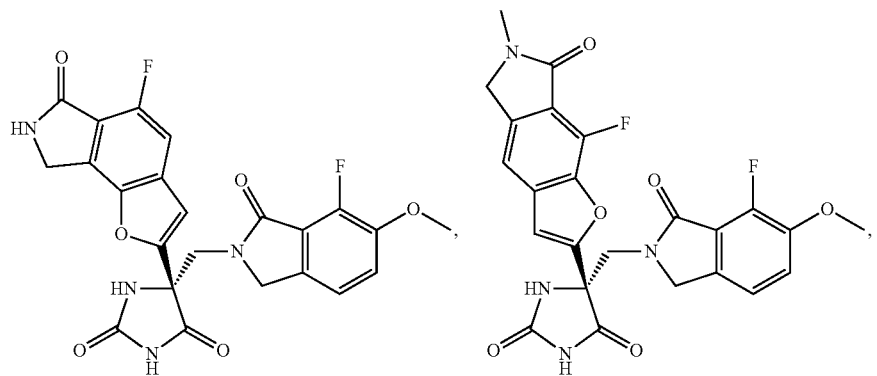

-continued

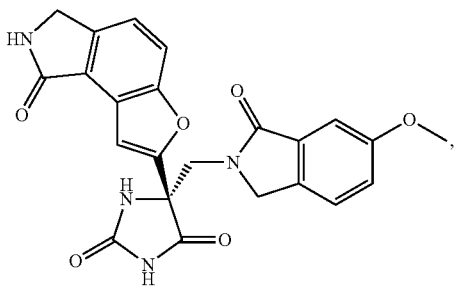
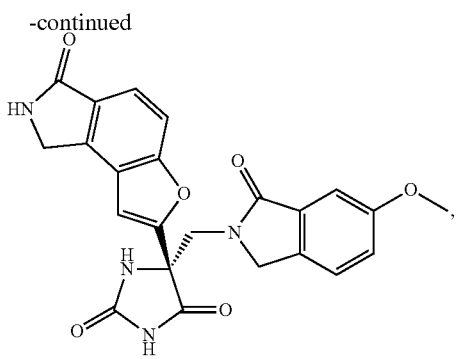

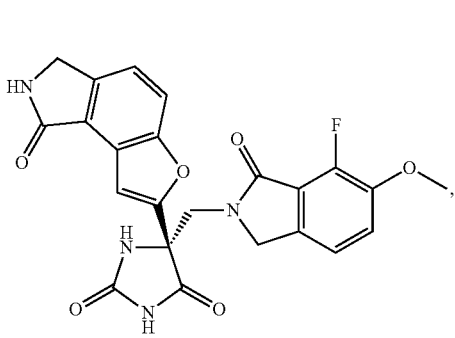
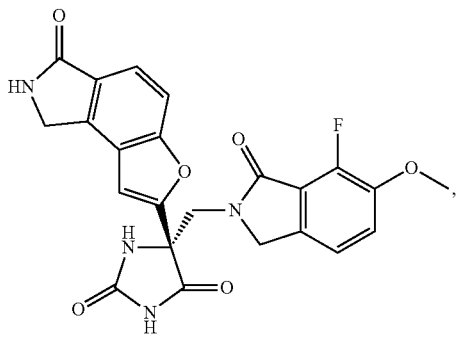

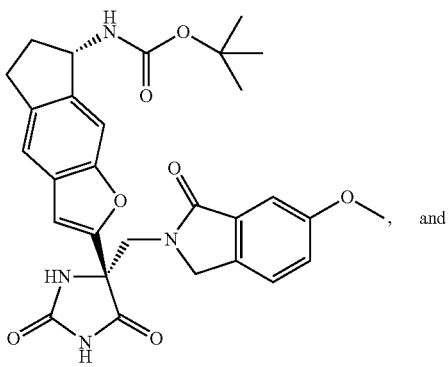
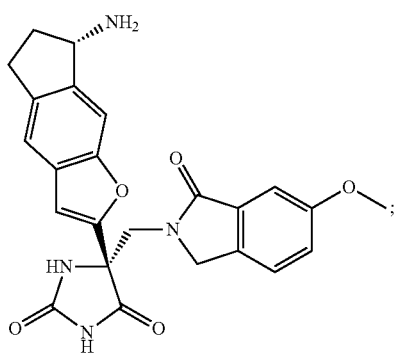

or a pharmaceutically acceptable salt thereof. These compounds are also referred to herein as "the above identified compounds" or "the compounds of the invention."

The above identified compounds can be useful as inhibitors of TACE and may be useful in the treatment and prevention of diseases associated with TACE, TNF-α, MMPs, ADAMs or any combination thereof.

DETAILED DESCRIPTION OF THE INVENTION

In its several embodiments, the present invention provides compounds as disclosed herein which are inhibitors of TACE, the production of TNF-α, MMPs, ADAMs or any combination thereof, pharmaceutical compositions containing one or more of the compounds, methods of preparing pharmaceutical formulations comprising one or more such compounds, and methods of treatment, prevention or amelioration of one or more of the symptoms of inflammation.

In another embodiment, the compounds of the present invention are selected from the group consisting of:

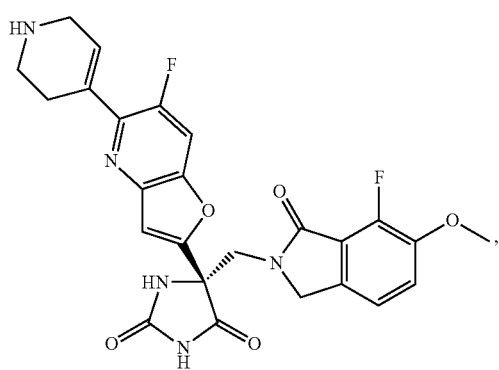

141
-continued
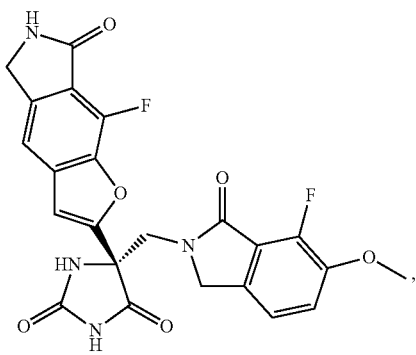
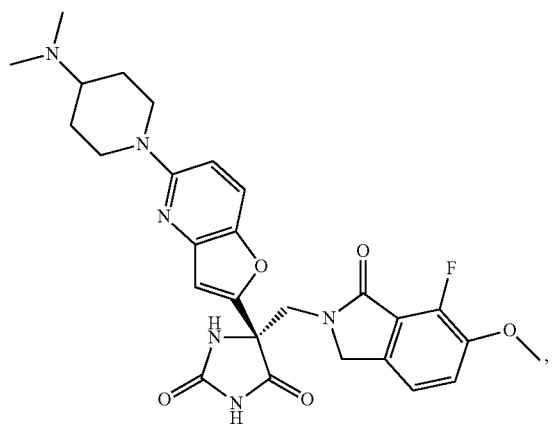
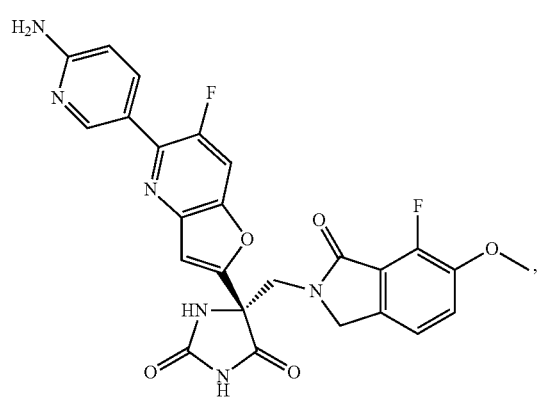
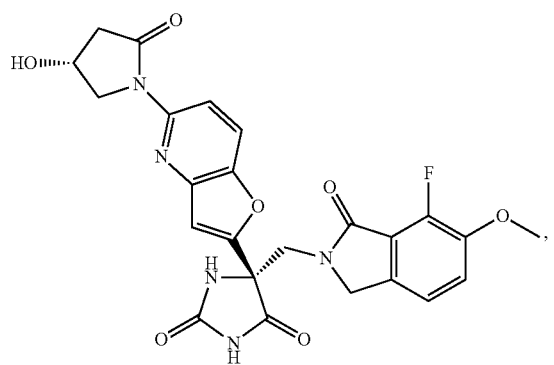
142
-continued
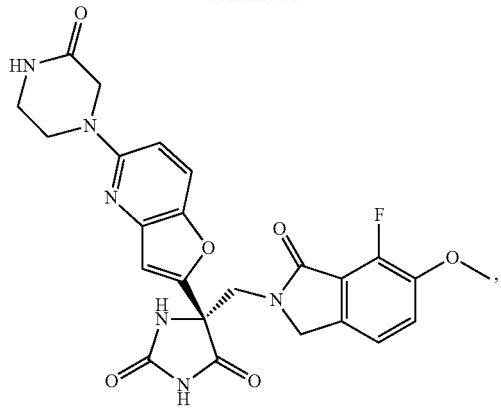
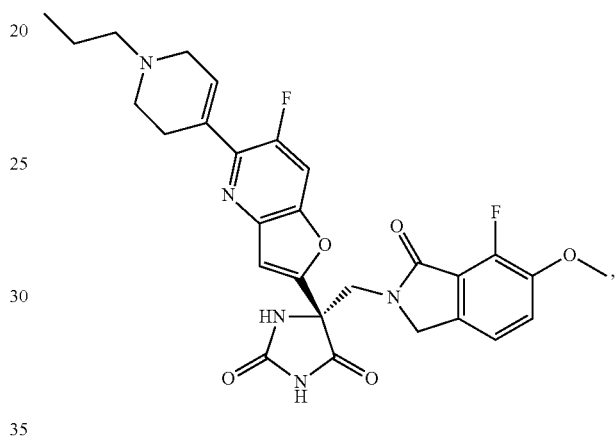
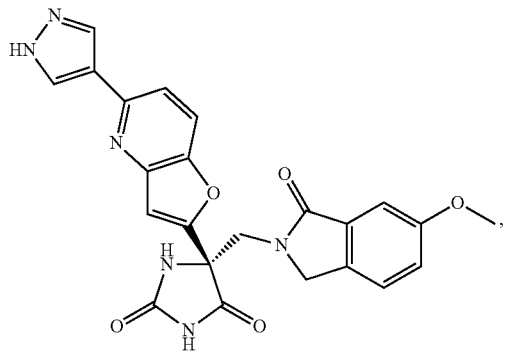
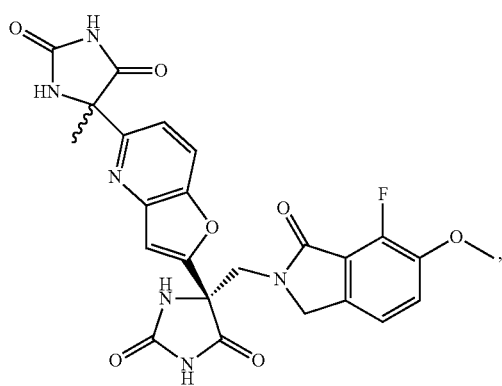

143
-continued
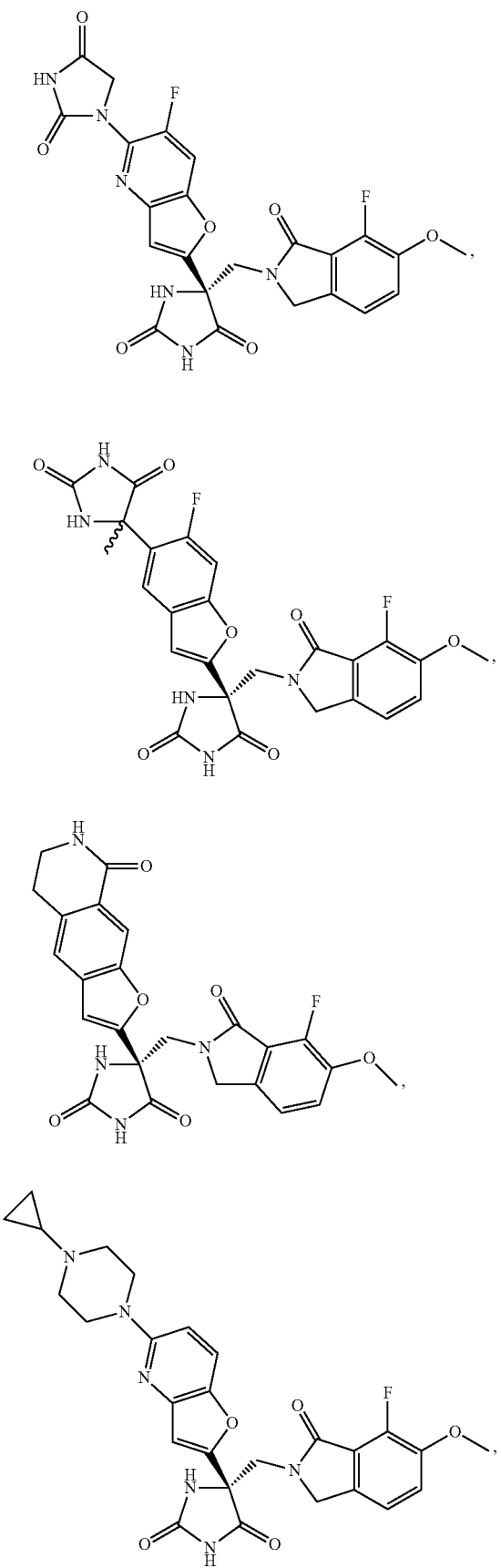
144
-continued
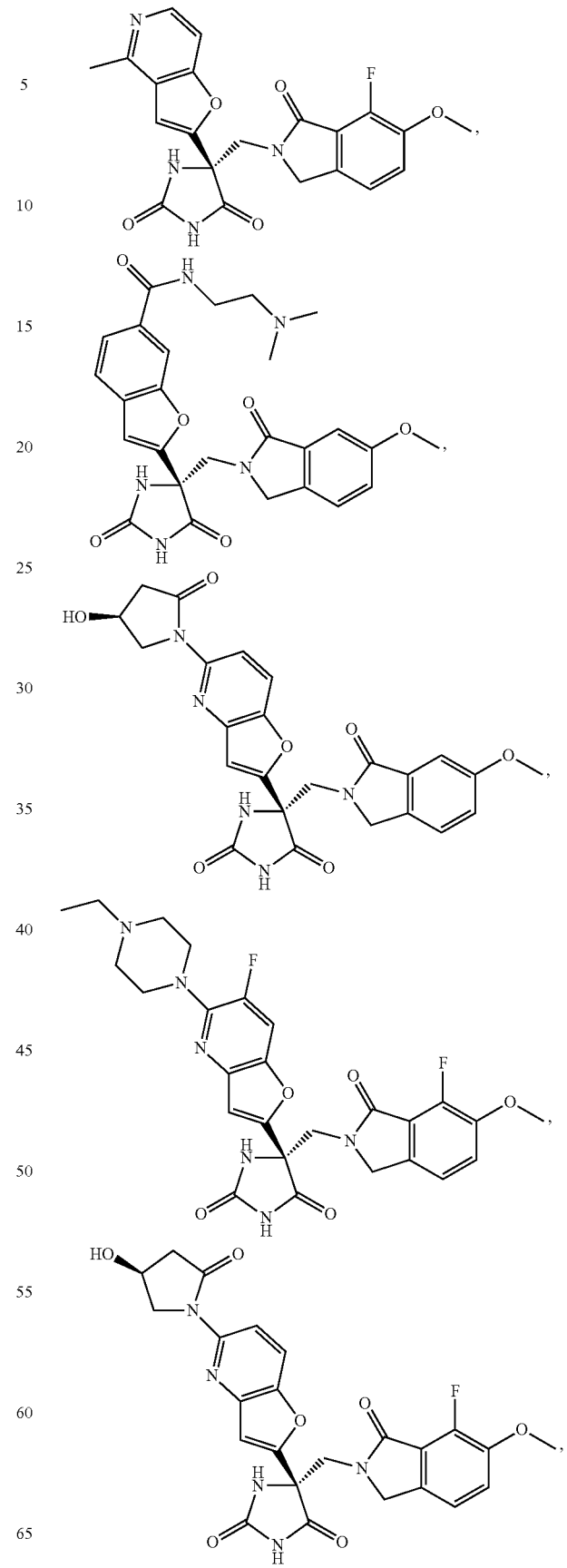

145
-continued
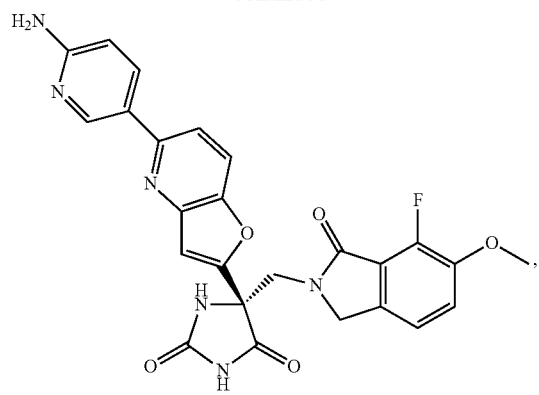
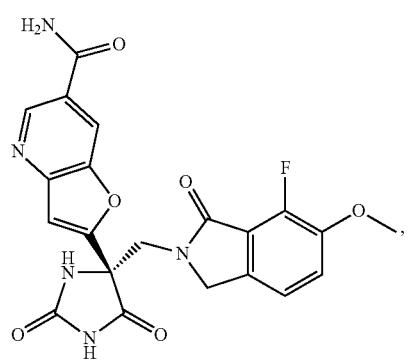
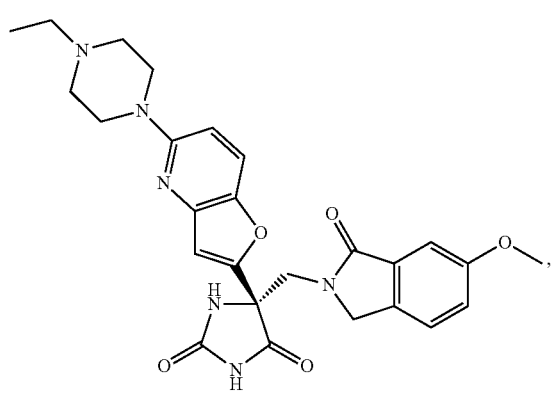
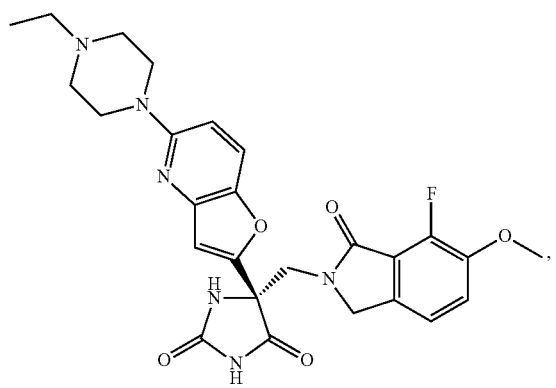
146
-continued
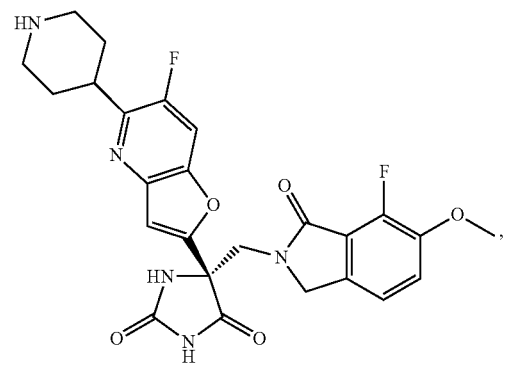
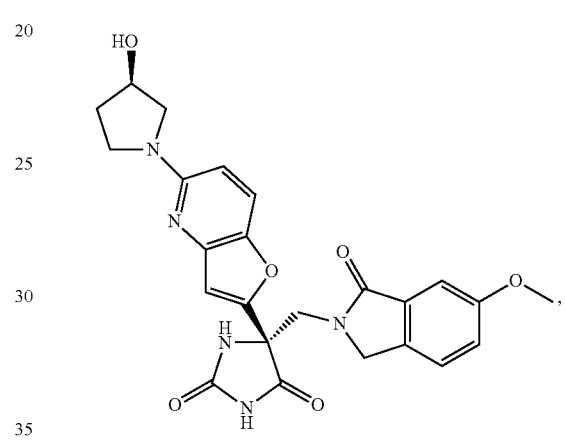
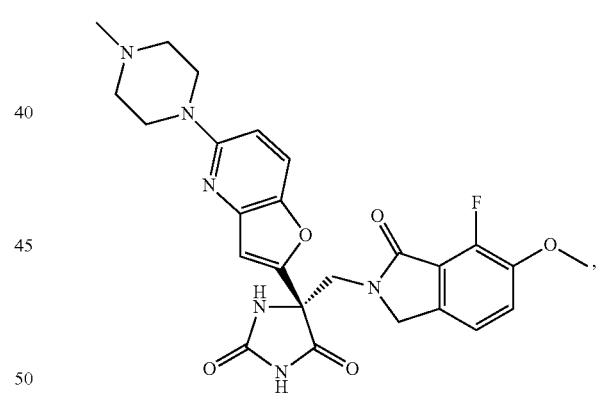
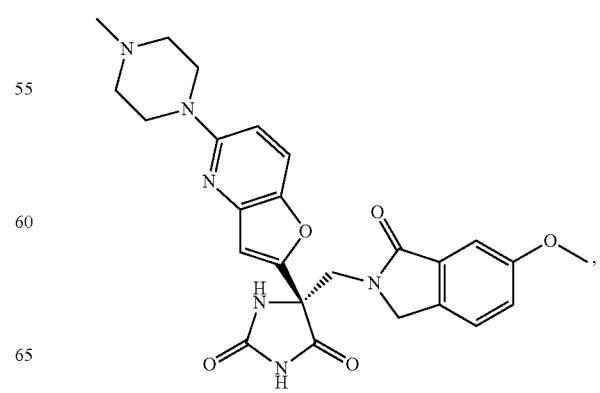

147
-continued
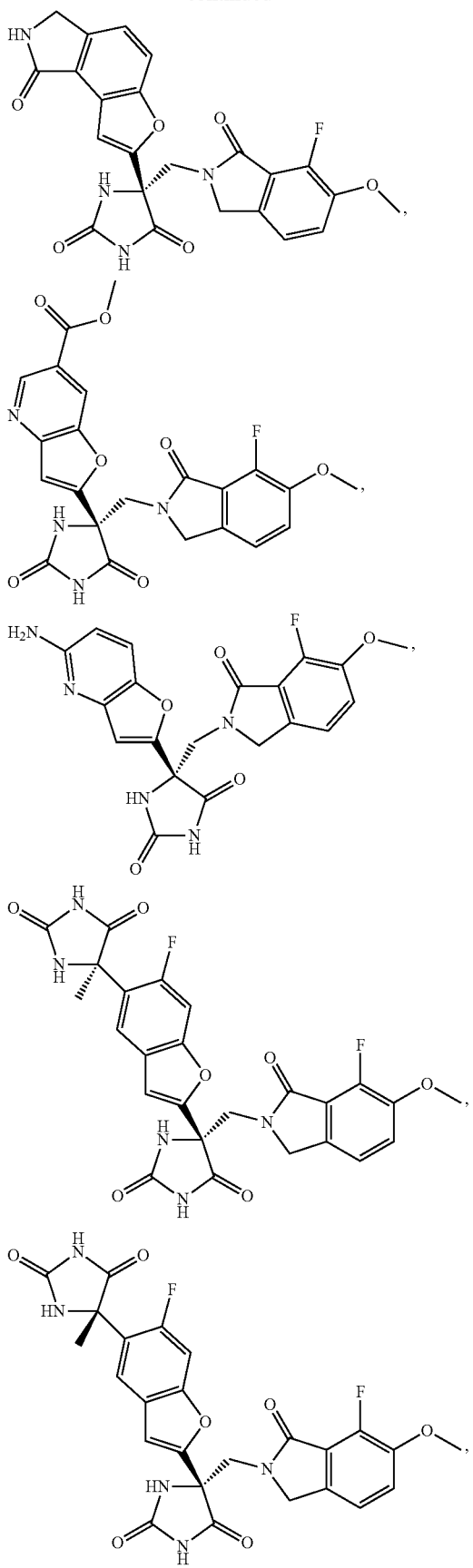
148
-continued
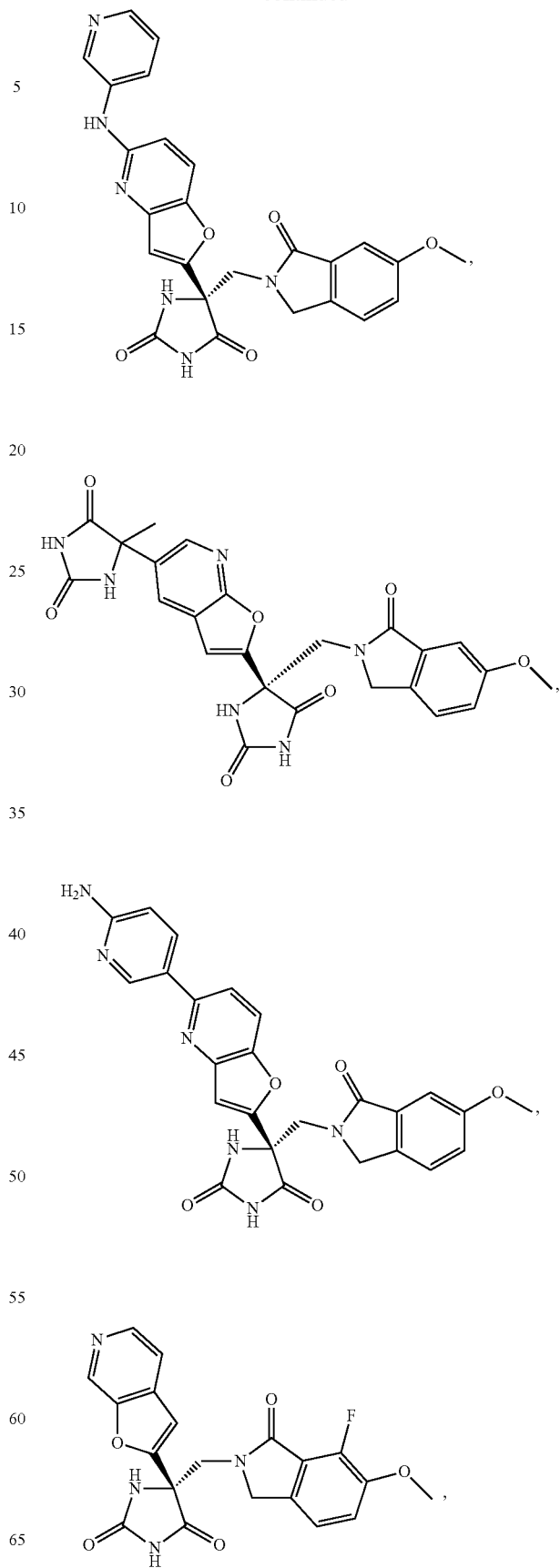

149
-continued
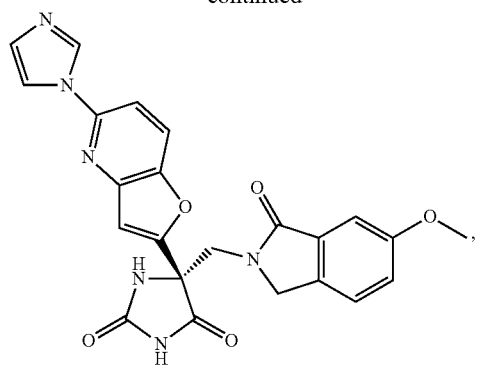
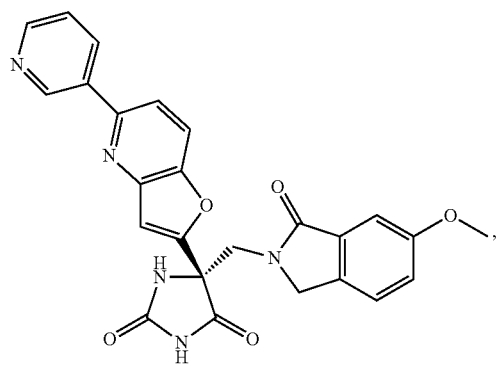
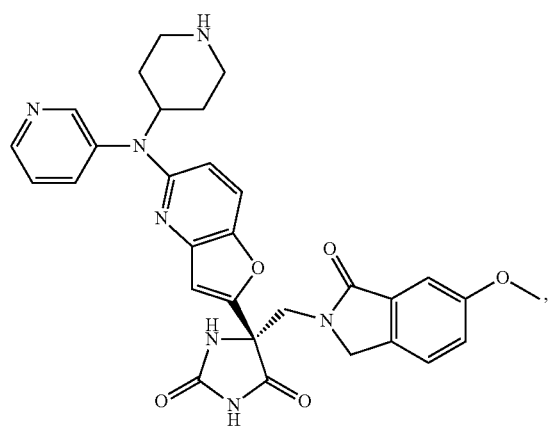
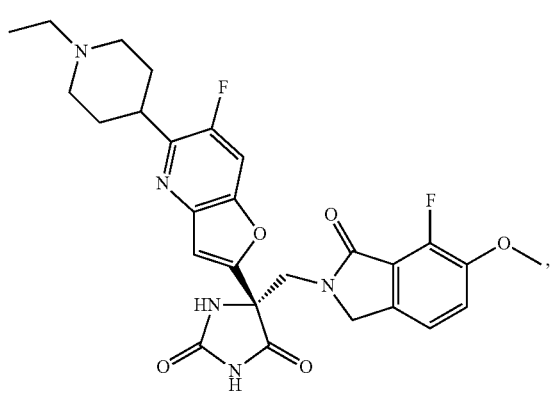
150
-continued
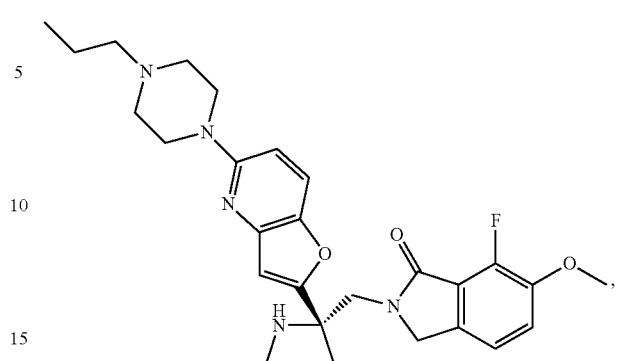
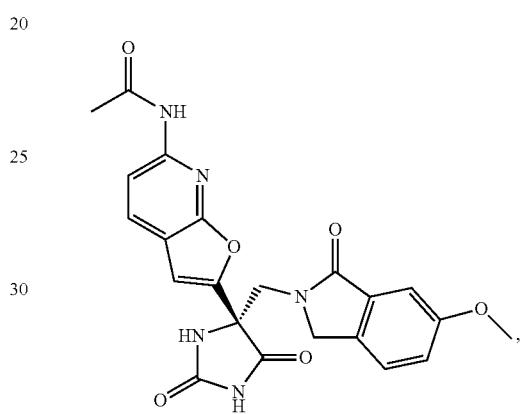
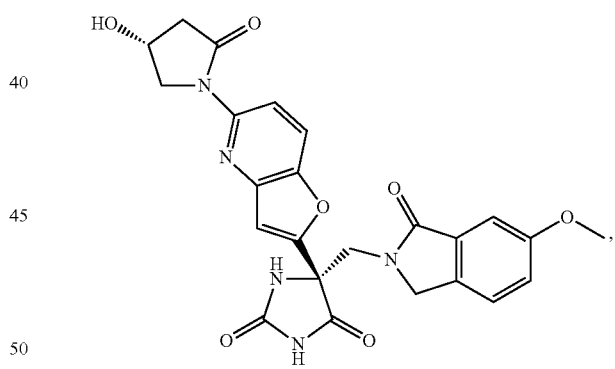
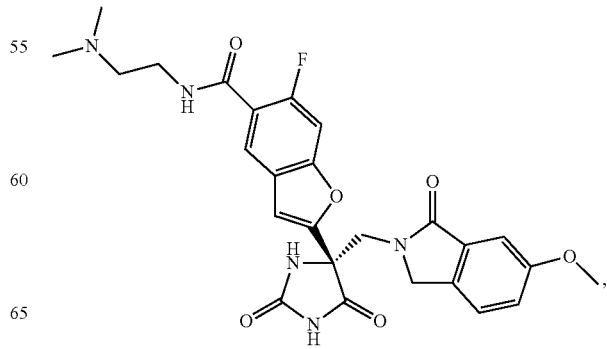

151
-continued
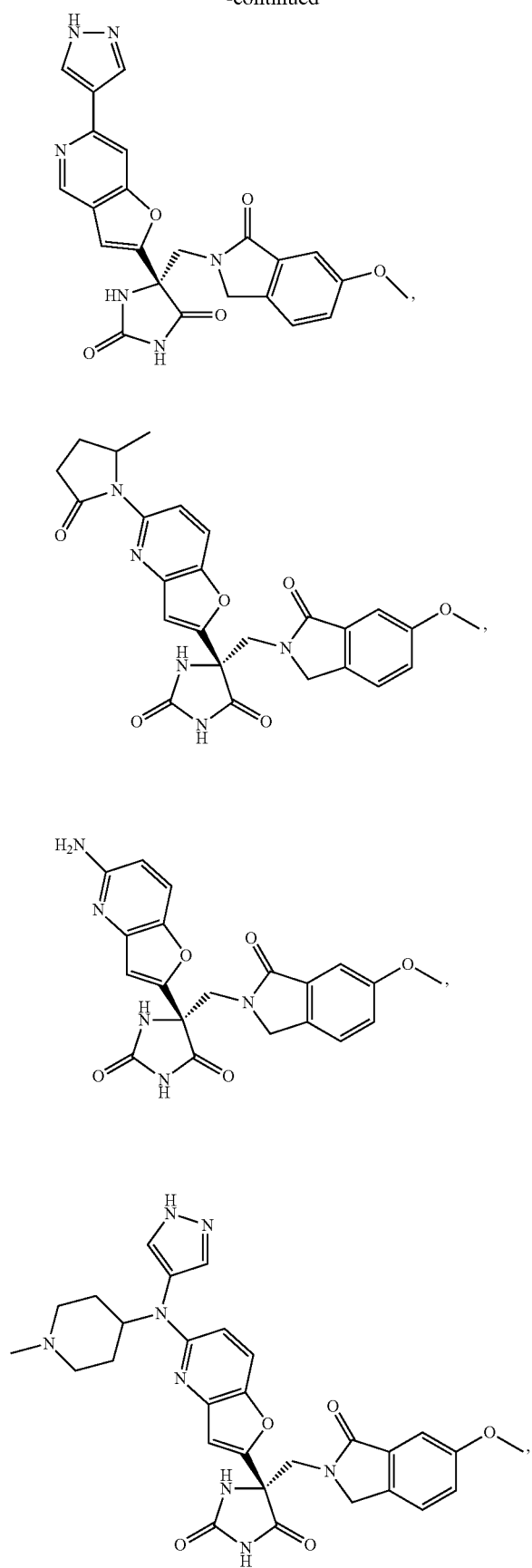
152
-continued
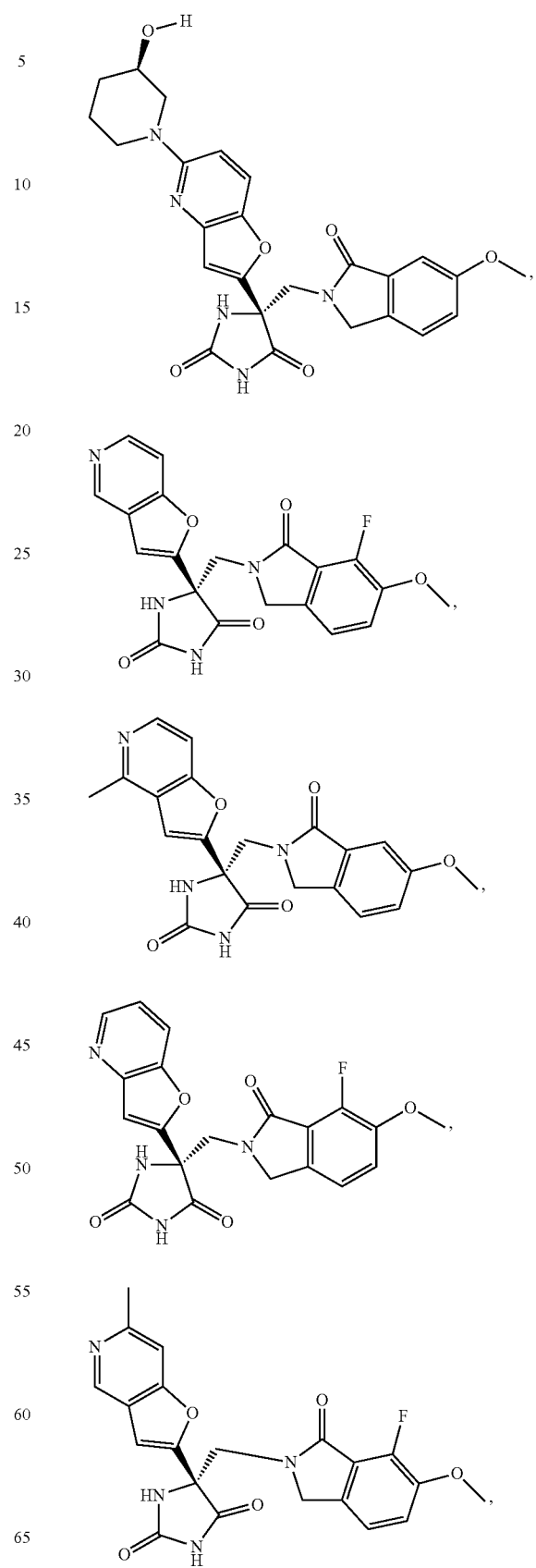

153
-continued
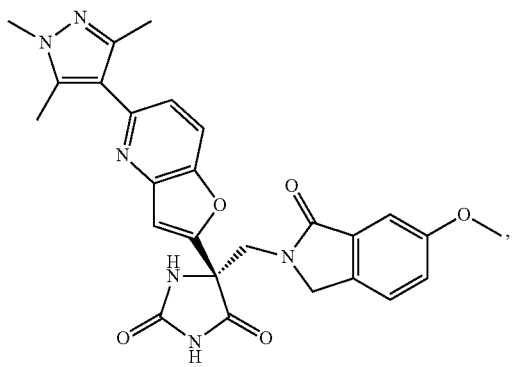
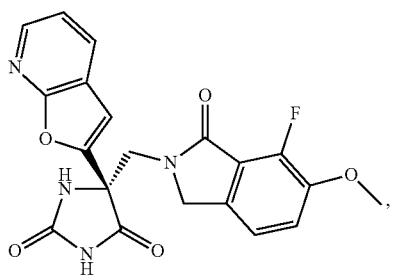
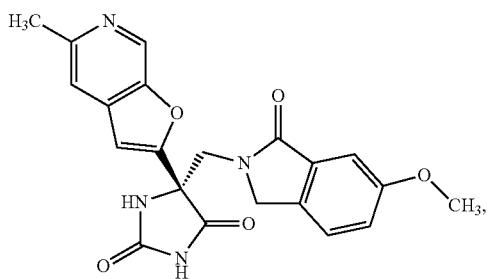
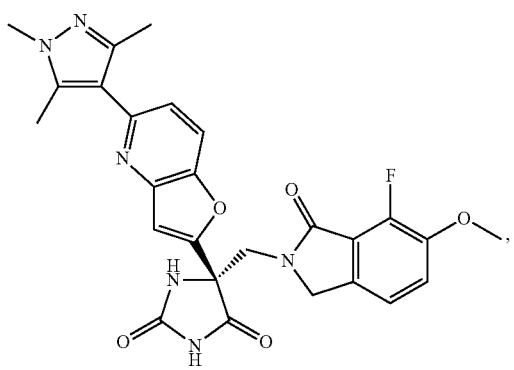
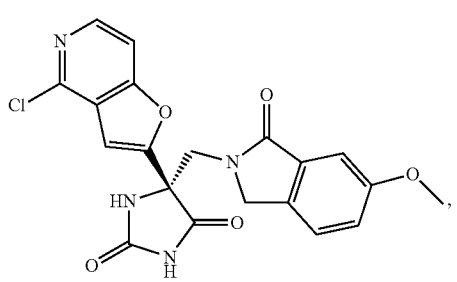
154
-continued
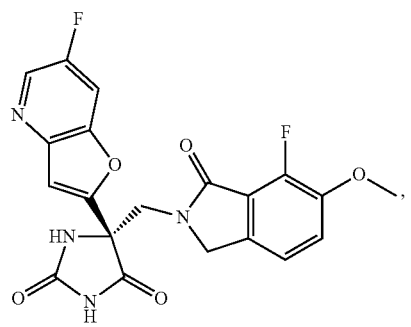
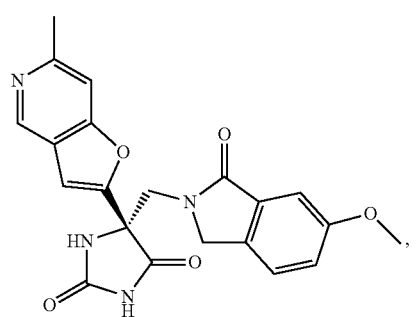
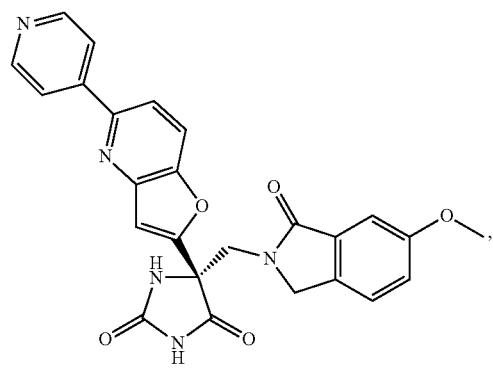
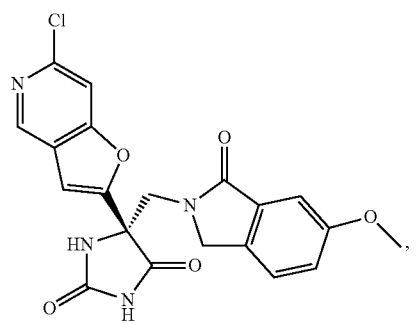
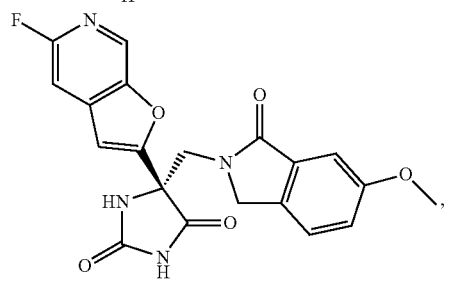

155
-continued
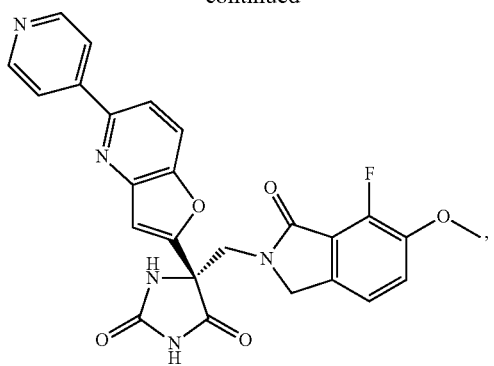
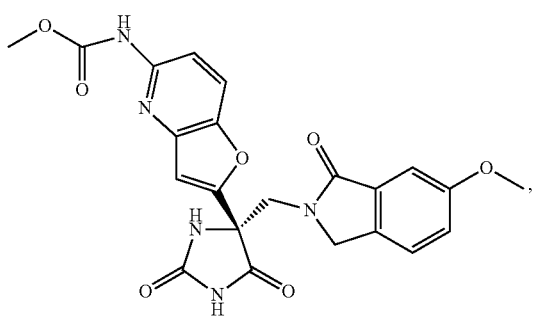
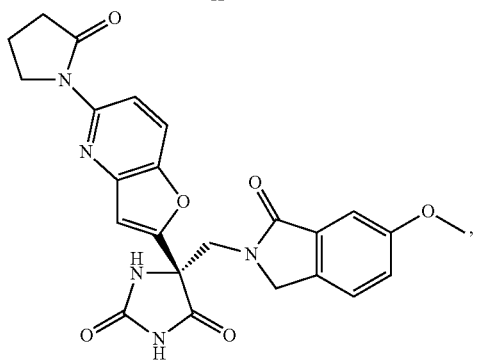
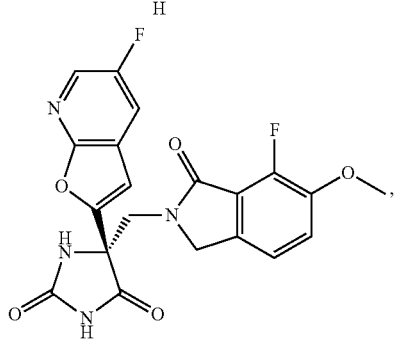
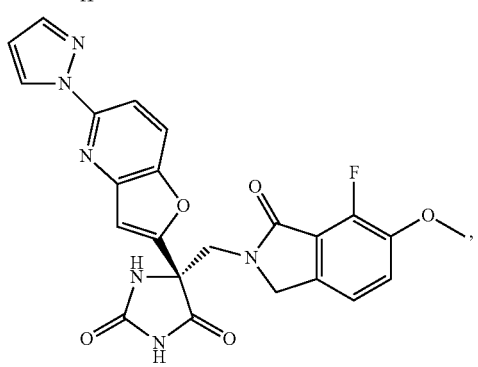
156
-continued
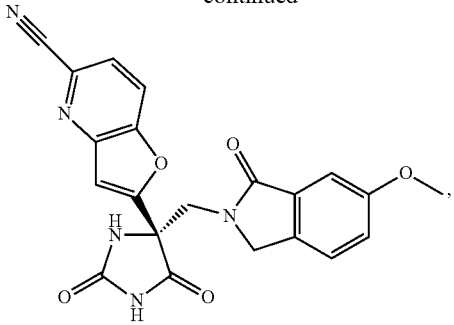
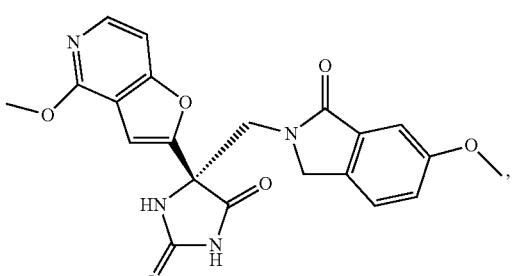
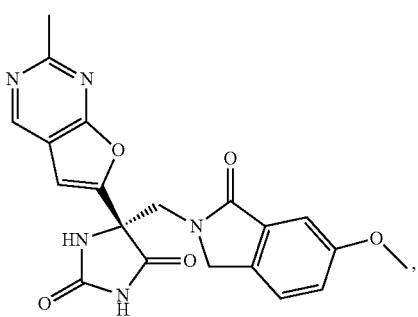
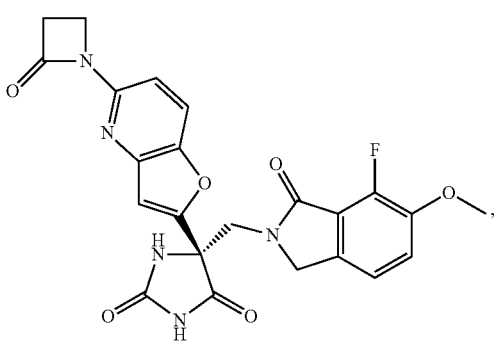
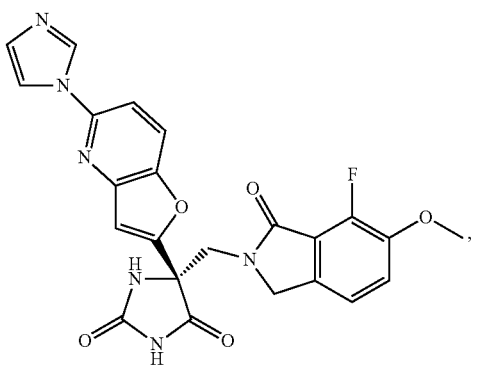

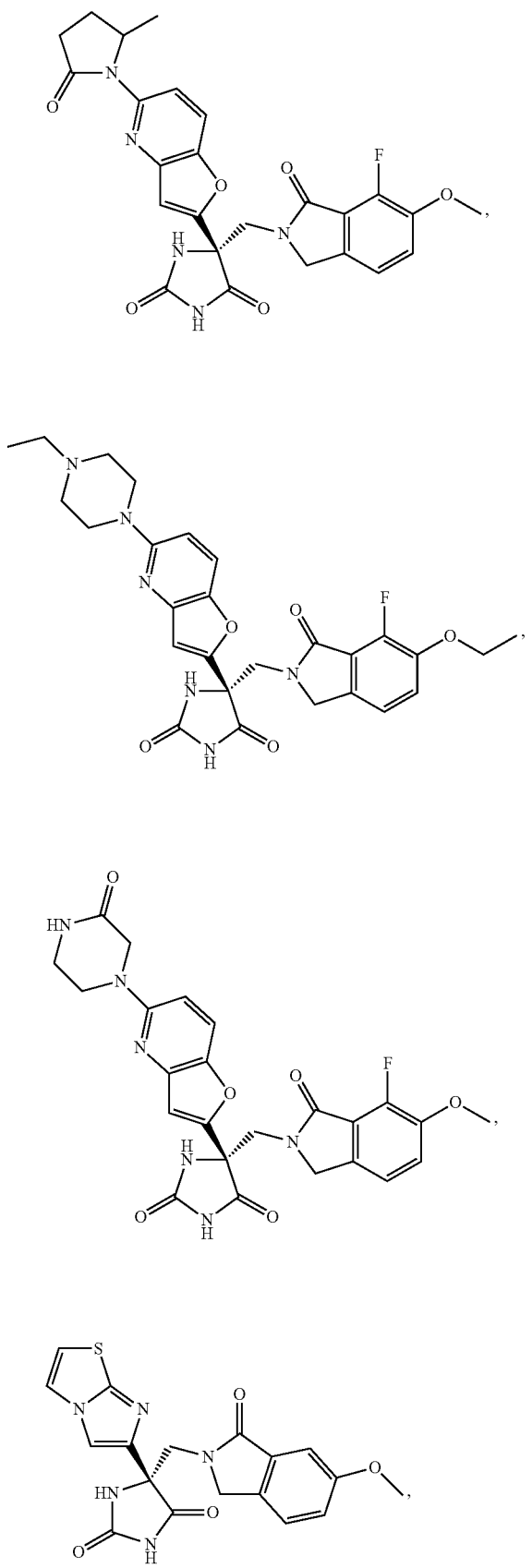
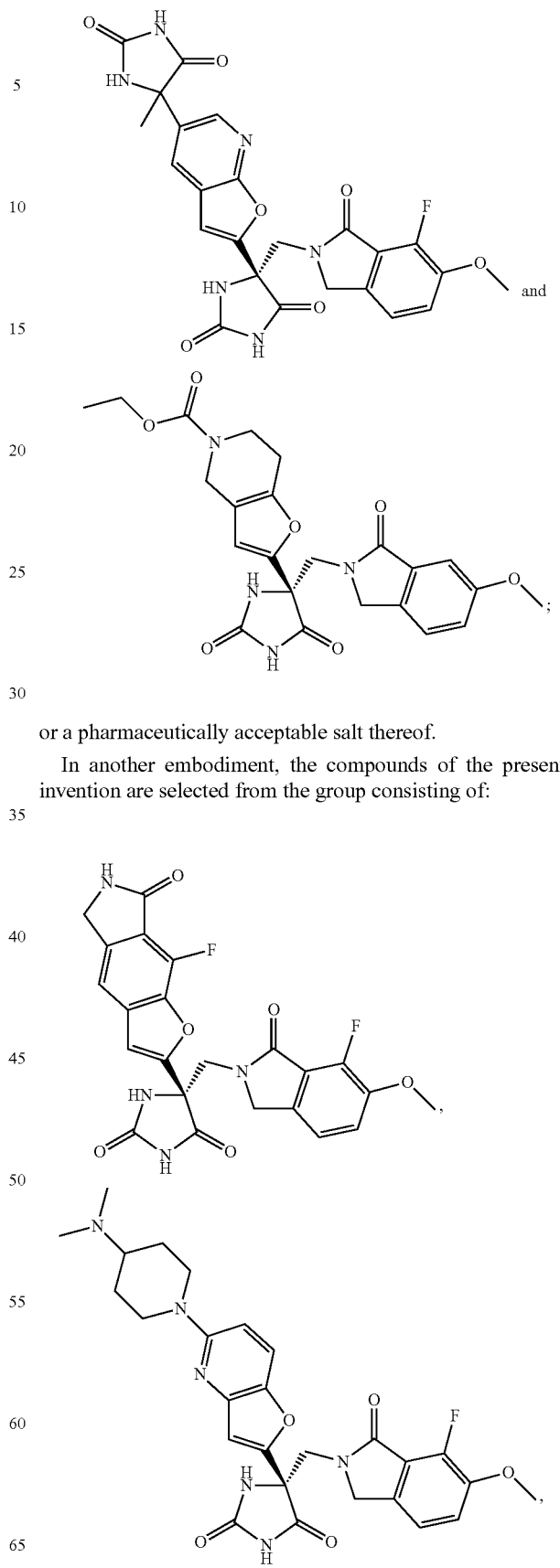
or a pharmaceutically acceptable salt thereof.
In another embodiment, the compounds of the present invention are selected from the group consisting of:

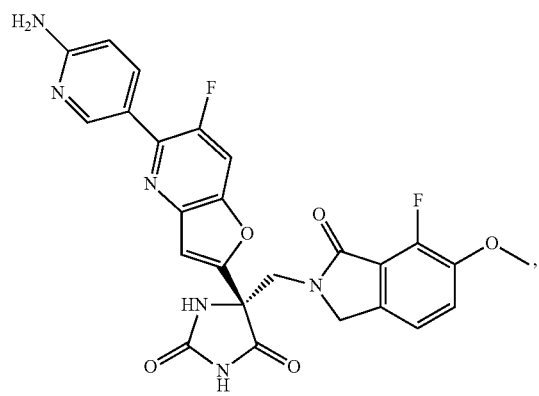
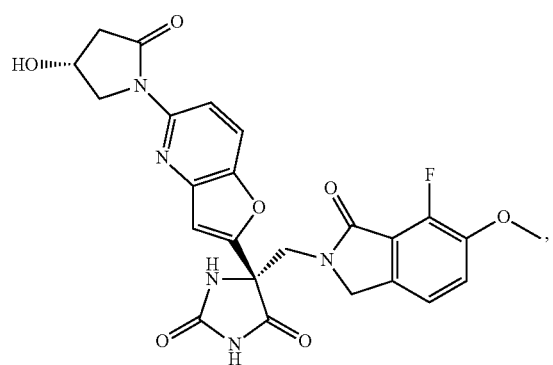
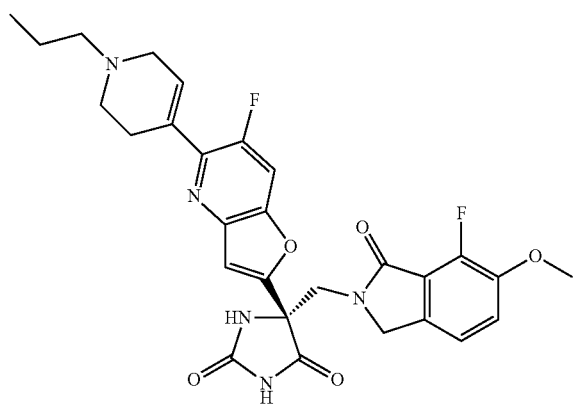
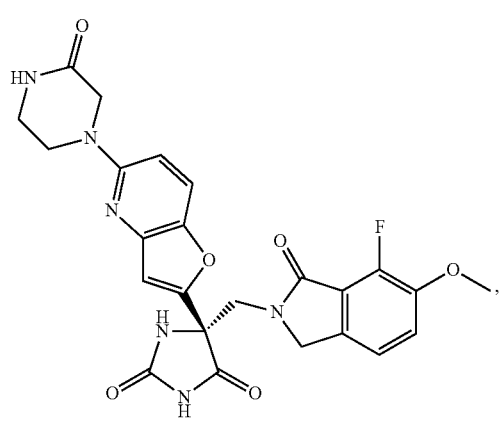
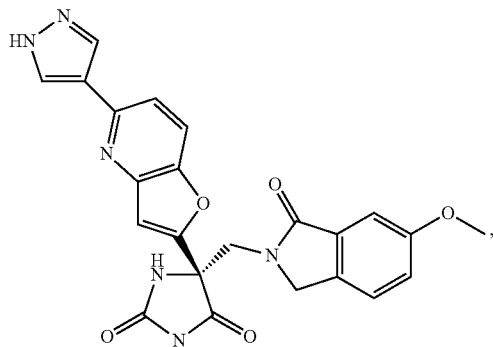
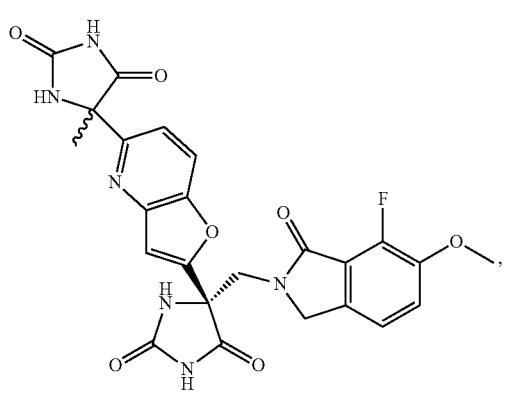
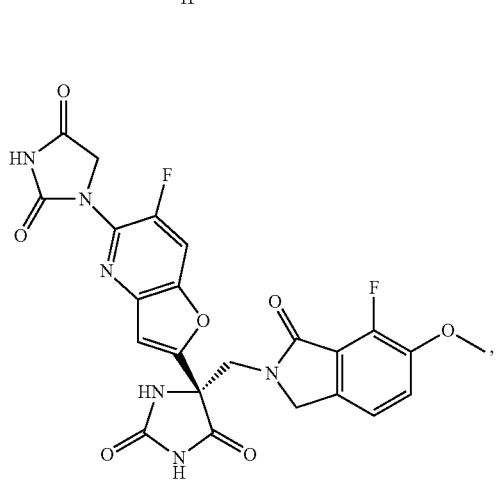
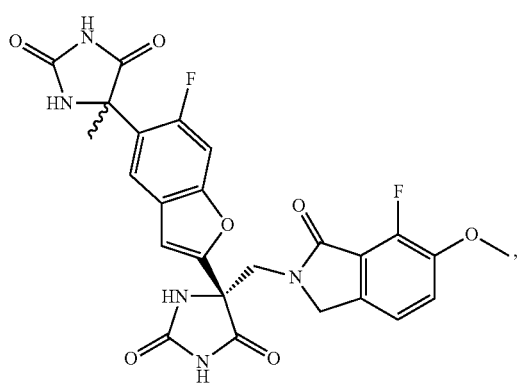

161
-continued
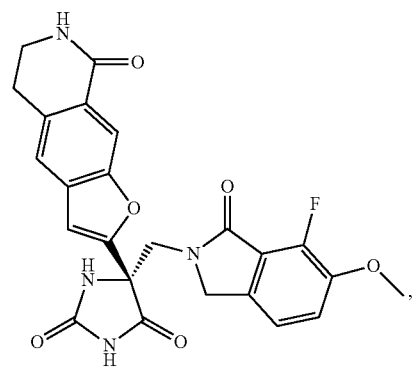
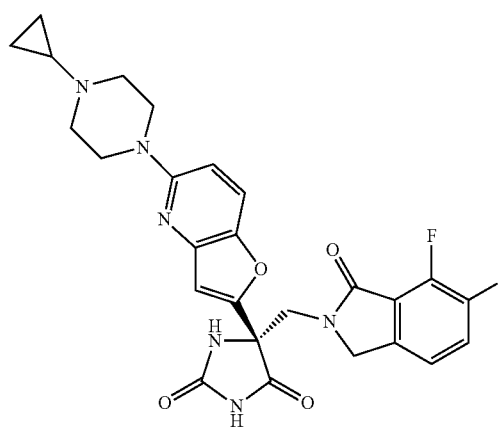
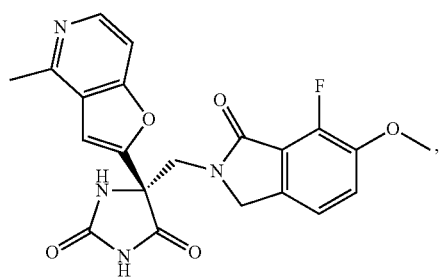
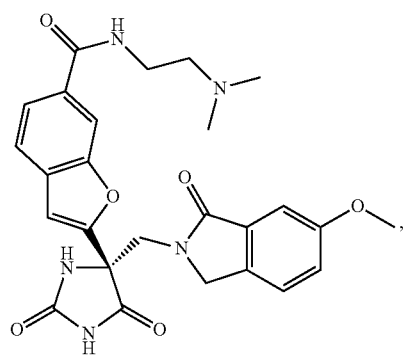
162
-continued
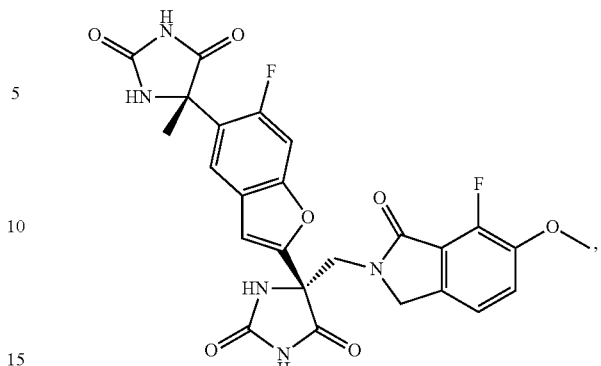
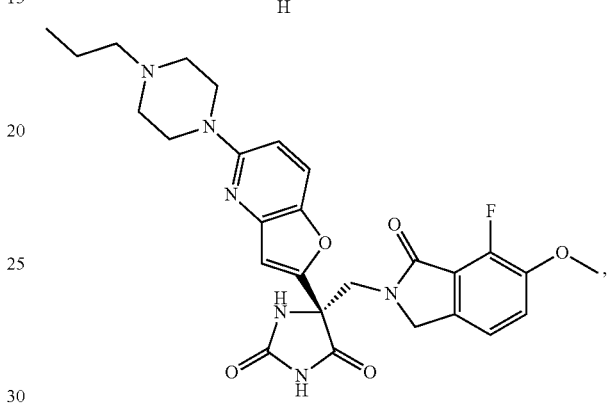
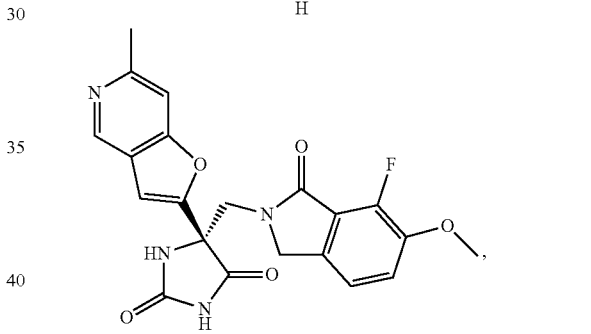
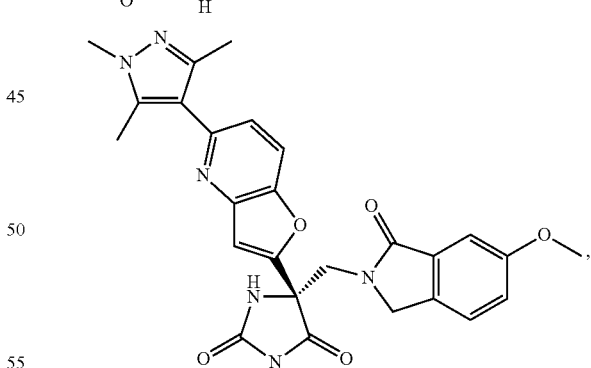
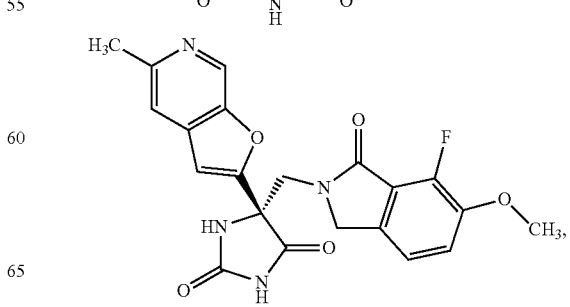

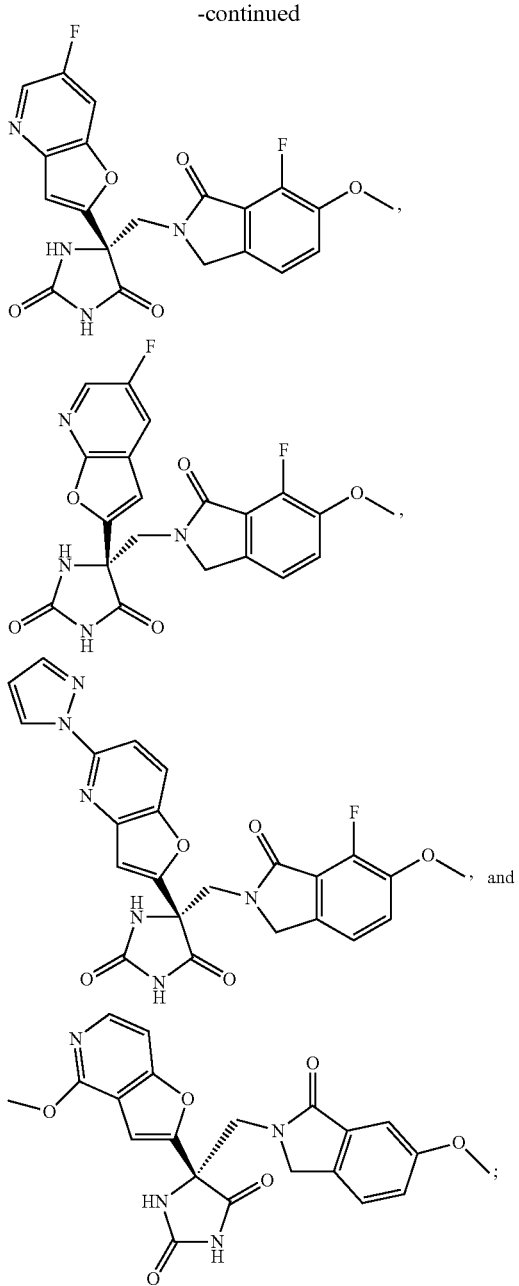

or a pharmaceutically acceptable salt thereof.

As used above, and throughout this disclosure, the following terms, unless otherwise indicated, shall be understood to have the following meanings:

"Patient," which is used interchangeably with "subject," includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)₂, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. A non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" means fluorine, chlorine, bromine, or iodine. Preferred halogens are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), G$_1$G$_2$N—, G$_1$G$_2$N-alkyl-, G$_1$G$_2$NC(O)—, G$_1$G$_2$NSO$_2$— and —SO$_2$NG$_1$G$_2$, wherein G$_1$ and G$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such a moiety are methylene dioxy, ethylenedioxy, —C(CH$_3$)$_2$— and the like which form moieties such as, for example:

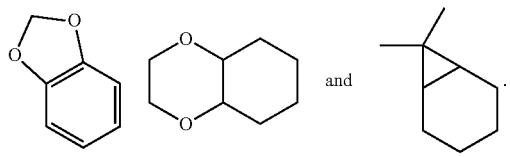

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes a ring system wherein a single moiety (e.g., carbonyl) simultaneously replaces two available hydrogens on the same carbon atom on the ring system. Examples of such moieties are pyrrolidone:

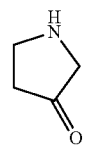

and thiomorpholinone:

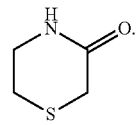

It should be noted that tautomeric forms such as, for example, the moieties:

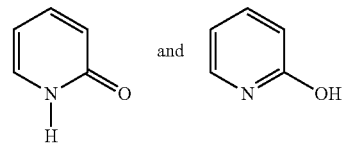 [SMILES: O=c1cccc[nH]1 ; Oc1ccccn1]

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well-known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or the above identified compounds, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield the above identified compounds or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto. The term "prodrug" means a compound (e.g, a drug precursor) that is transformed in vivo to yield the above identified compounds or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if any one of the above identified compounds or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-(C1-C2)alkyl and piperidino-, pyrrolidino- or morpholino($C_2$-$C_3$) alkyl, and the like.

Similarly, if anyone of the above identified compounds contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)$ alkyl$)_2$ or glycosyl (the radical resulting from the removal of a hydroxyl group of the hemiacetal form of a carbohydrate), and the like.

If anyone of the above identified compounds incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$) alkyl, ($C_3$-$C_7$) cycloalkyl, benzyl, or R-carbonyl is a natural α-aminoacyl or natural α-aminoacyl, —$C(OH)C(O)OY^1$ wherein $Y^1$ is H, ($C_1$-$C_6$)alkyl or benzyl, —$C(OY^2)Y^3$ wherein $Y^2$ is ($C_1$-$C_4$) alkyl and $Y^3$ is ($C_1$-$C_6$)alkyl, carboxy ($C_1$-$C_6$)alkyl, amino($C_1$-$C_4$)alkyl or mono-N— or di-N,N—($C_1$-$C_6$)alkylaminoalkyl, —$C(Y^4)Y^5$ wherein $Y^4$ is H or methyl and $Y^5$ is mono-N— or di-N,N—($C_1$-$C_6$)alkylamino morpholino, piperidin-1-yl or pyrrolidin-1-yl, and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting TACE, the production of TNF-α, MMPs, ADAMS or any combination thereof and thus producing the desired therapeutic, ameliorative, inhibitory or preventative effect.

The above identified compounds can form salts which are also within the scope of this invention. Reference to anyone of the above identified compounds herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when anyone of the above identified compounds contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the above identified compounds may be formed, for example, by reacting anyone of the above identified compounds with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

The above identified compounds, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Certain isotopically-labelled compounds of Formula (I) can be useful for medical imaging purposes. For instance, those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula (I), in particular those containing isotopes with longer half lives (T1/2>1 day), can generally be prepared by following procedures analogous to those disclosed in the Schemes and/or in the Examples herein below, by substituting an appropriate isotopically labeled reagent for a non-isotopically labeled reagent.

Polymorphic forms of the above identified compounds, and of the salts, solvates and prodrugs of the above identified compounds, are intended to be included in the present invention.

The present invention further includes the above identified compounds in all their isolated forms. Thus, the present invention encompasses all forms of the above identified compounds such as, for example, any solvates, hydrates, stereoisomers, and tautomers.

The above identified compounds have pharmacological properties; in particular, the above identified compounds can be inhibitors of TACE, TNF-α and/or MMP activity.

In one embodiment, the invention provides a pharmaceutical composition comprising as an active ingredient at least one of the above identified compounds.

In another embodiment, the invention provides a pharmaceutical composition of the above identified compounds additionally comprising at least one pharmaceutically acceptable carrier.

In another aspect, the invention provides a method of treating disorders associated with TACE, TNF-α, MMPs, ADAMs or any combination thereof, said method comprising administering to a patient in need of such treatment a pharmaceutical composition which comprises therapeutically effective amounts of at least one of the above identified compounds.

In another embodiment, the invention provides a use of any one of the above identified compounds for the manufacture of a medicament to treat disorders associated with TACE, TNF-α, MMPs, ADAMs or any combination thereof.

The above identified compounds can have anti-inflammatory activity and/or immunomodulatory activity and can be useful in the treatment of diseases including but not limited to septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, OA and RA, ankylosing spondylitis, psoriatic arthritis, adult Still's disease, ureitis, Wegener's granulomatosis, Behcet's disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and/or bronchitis. It is contemplated that a compound of this invention may be useful in treating one or more of the diseases listed.

In another embodiment, the invention provides a method of preparing a pharmaceutical composition for treating the disorders associated with TACE, TNF-α, MMPs, ADAMs or any combination thereof, said method comprising bringing into intimate contact at least one of the above identified compounds and at least one pharmaceutically acceptable carrier.

In another embodiment, the invention provides at least one of the above identified compounds exhibiting TACE, TNF-α, MMPs, ADAMs or any combination thereof inhibitory activity, including enantiomers, stereoisomers and tautomers of said compound, and pharmaceutically acceptable salts, esters, or solvates of said compound, said compound being selected from the compounds of structures listed as set forth above.

In another embodiment, the invention provides a pharmaceutical composition for treating disorders associated with TACE, TNF-α, MMP, ADAM or any combination thereof in a subject comprising, administering to the subject in need of such treatment a therapeutically effective amount of at least one of the above identified compounds or a pharmaceutically acceptable salt thereof.

In another embodiment, the invention provides the above identified compounds in purified form.

In another aspect, the invention provides a method of treating a condition or disease mediated by TACE, MMPs, TNF-α, aggrecanase, or any combination thereof in a subject comprising: administering to the subject in need of such treatment a therapeutically effective amount of at least one of the above identified compounds or a pharmaceutically acceptable salt thereof.

In another embodiment, the invention provides a method of treating a condition or disease selected from the group consisting of rheumatoid arthritis, osteoarthritis, periodontitis, gingivitis, corneal ulceration, solid tumor growth and tumor invasion by secondary metastases, neovascular glaucoma, inflammatory bowel disease, multiple sclerosis and psoriasis in a subject, comprising: administering to the subject in need of such treatment a therapeutically effective amount of at least one of the above identified compounds or a pharmaceutically acceptable salt thereof.

In another embodiment, the invention provides a method of treating a condition or disease selected from the group consisting of fever, cardiovascular conditions, hemorrhage, coagulation, cachexia, anorexia, alcoholism, acute phase response, acute infection, shock, graft versus host reaction, autoimmune disease and HIV infection in a subject comprising administering to the subject in need of such treatment a therapeutically effective amount of at least one of the above identified compounds or a pharmaceutically acceptable salt thereof.

In another embodiment, the invention provides a method of treating a condition or disease selected from the group consisting of septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcet's disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and bronchitis in a subject comprising administering to the subject in need of such treatment a therapeutically effective amount of at least one of the above identified compounds or a pharmaceutically acceptable salt thereof.

In another embodiment, the invention provides a method of treating a condition or disease associated with COPD, comprising: administering to the subject in need of such treatment a therapeutically effective amount of at least one of the above identified compounds or a pharmaceutically acceptable salt thereof.

In another embodiment, the invention provides a method of treating a condition or disease associated with rheumatoid arthritis, comprising: administering to the subject in need of such treatment a therapeutically effective amount of at least one of the above identified compounds or a pharmaceutically acceptable salt thereof.

In another aspect, the invention provides a method of treating a condition or disease associated with Crohn's disease, comprising: administering to the subject in need of such treatment a therapeutically effective amount of at least one of the above identified compounds or a pharmaceutically acceptable salt thereof.

In another embodiment, the invention provides a method of treating a condition or disease associated with psoriasis, comprising: administering to the subject in need of such treatment a therapeutically effective amount of at least one of the above identified compounds or a pharmaceutically acceptable salt thereof. In specific instances, the compound is administered topically to the subject.

In another embodiment, the invention provides a method of treating a condition or disease associated with ankylosing spondylitis, comprising: administering to the subject in need of such treatment a therapeutically effective amount of at least one of the above identified compounds or a pharmaceutically acceptable salt thereof.

In another embodiment, the invention provides a method of treating a condition or disease associated with sciatica, comprising: administering to the subject in need of such treatment a therapeutically effective amount of at least one of the above identified compounds or a pharmaceutically acceptable salt thereof.

In another embodiment, the invention provides a method of treating a condition or disease associated with complex regional pain syndrome, comprising: administering to the subject in need of such treatment a therapeutically effective amount of at least one of the above identified compounds or a pharmaceutically acceptable salt thereof.

In another embodiment, the invention provides a method of treating a condition or disease associated with psoriatic arthritis, comprising: administering to the subject in need of such treatment a therapeutically effective amount of at least one of the above identified compounds or a pharmaceutically acceptable salt thereof.

In another embodiment, the invention provides a method of treating a condition or disease associated with multiple sclerosis, comprising: administering to the subject in need of such treatment a therapeutically effective amount of at least one of the above identified compounds or a pharmaceutically acceptable salt thereof, in combination with a compound selected from the group consisting of Avonex®, Betaseron, Copaxone or other compounds indicated for the treatment of multiple sclerosis.

Additionally, a compound of the present invention may be co-administered or used in combination with disease-modifying antirheumatic drugs (DMARDS) such as methotrexate, azathioprine, leflunomide, pencillinamine, gold salts, mycophenolate mofetil, cyclophosphamide and other similar drugs. They may also be co-administered with or used in combination with non-steroidal anti-inflammatory drugs (NSAIDs) such as piroxicam, naproxen, indomethacin, ibuprofen and the like; cycloxygenase-2 selective (COX-2) inhibitors such as Vioxx® and Celebrex®; immunosuppressives such as steroids, cyclosporin, Tacrolimus, rapamycin and the like; biological response modifiers (BRMs) such as Enbrel®, Remicade®, IL-1 antagonists, anti-CD40, anti-CD28, IL-10, anti-adhesion molecules and the like; and other anti-inflammatory agents such as p38 kinase inhibitors, PDE4 inhibitors, other chemically different TACE inhibitors, chemokine receptor antagonists, Thalidomide and other small molecule inhibitors of pro-inflammatory cytokine production.

Also, a compound of the present invention may be co-administered or used in combination with an H1 antagonist for the treatment of seasonal allergic rhinitis and/or asthma. Suitable H1 antagonists may be, for example, Claritin®, Clarinex®, Allegra®, or Zyrtec®.

In another embodiment, the invention provides a method of treating a condition or disease mediated by TACE, MMPs, TNF-α, aggrecanase, or any combination thereof in a subject comprising: administering to the subject in need of such treatment a therapeutically effective amount of at least one of the above identified compounds or a pharmaceutically acceptable salt thereof in combination with a therapeutically effective amount of at least one medicament selected from the group consisting of disease modifying anti-rheumatic drugs (DMARDS), NSAIDs, COX-2 inhibitors, COX-1 inhibitors, immunosuppressives, biological response modifiers (BRMs), anti-inflammatory agents and H1 antagonists.

In another embodiment, the invention provides a method of treating a condition or disease selected from the group consisting of rheumatoid arthritis, osteoarthritis, periodontitis, gingivitis, corneal ulceration, solid tumor growth and tumor invasion by secondary metastases, neovascular glaucoma, inflammatory bowel disease, multiple sclerosis and psoriasis in a subject, comprising: administering to the subject in need of such treatment a therapeutically effective amount of at least one of the above identified compounds or a pharmaceutically acceptable salt thereof in combination with a therapeutically effective amount of at least one medicament selected from the group consisting of DMARDS, NSAIDs, COX-2 inhibitors, COX-1 inhibitors, immunosuppressives, BRMs, anti-inflammatory agents and H1 antagonists.

In another embodiment, the invention provides a method of treating a condition or disease selected from the group consisting of fever, cardiovascular conditions, hemorrhage, coagulation, cachexia, anorexia, alcoholism, acute phase response, acute infection, shock, graft versus host reaction, autoimmune disease and HIV infection in a subject, comprising: administering to the subject in need of such treatment a therapeutically effective amount of at least one of the above identified compounds or a pharmaceutically acceptable salt thereof in combination with a therapeutically effective amount of at least one medicament selected from the group consisting of DMARDS, NSAIDs, COX-2 inhibitors, COX-1 inhibitors, immunosuppressives, BRMs, anti-inflammatory agents and H1 antagonists.

In another embodiment, the invention provides a method of treating a condition or disease selected from the group consisting of septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcet's disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and bronchitis in a subject comprising administering to the subject in need of such treatment a therapeutically effective amount of at least one of the above identified compounds or a pharmaceutically acceptable salt thereof in combination with a therapeutically effective amount of at least one medicament selected from the group consisting of DMARDS, NSAIDs, COX-2 inhibitors, COX-1 inhibitors, immunosuppressives, BRMs, anti-inflammatory agents and H1 antagonists.

In another embodiment, the invention provides a method for treating RA comprising administering the above identified compounds in combination with compound selected from the class consisting of a COX-2 inhibitor e.g. Celebrex® or Vioxx®; a COX-1 inhibitor e.g. Feldene®; an immunosuppressive e.g. methotrexate or cyclosporin; a steroid e.g. 3-methasone; and anti-TNF-α compound, e.g. Enbrel® or Remicade®; a PDE IV inhibitor, or other classes of compounds indicated for the treatment of RA.

In another embodiment, the invention provides a method for treating multiple sclerosis comprising administering the above identified compounds in combination with a compound selected from the group consisting of Avonex®, Betaseron, Copaxone or other compounds indicated for the treatment of multiple sclerosis.

TACE activity can be determined by a kinetic assay measuring the rate of increase in fluorescent intensity generated by TACE catalyzed cleavage of an internally quenched peptide substrate (TNF-FRET 2). The purified catalytic domain of recombinant human TACE (rhTACEc, Residue 215 to 477 with two mutations (S266A and N452Q) and a 6×His tail) is used in the assay. It is purified from the baculovirus/Hi5 cells expression system using affinity chromatography. The substrate TNF-FRET 2 is an internally quenched peptide (MCA-Pro-Leu-Ala-Gln-Ala-Val-Arg-Ser-Ser-Ser-Dpa-Arg-NH$_2$). MCA is (7-Methoxycoumarin-4-yl)acetyl. Dpa is N-3-(2,4-Dinitrophenyl)-L-2,3-diaminopropionyl.

A 50 µl assay mixture contains 20 mM HEPES, pH 7.3, 5 mM CaCl$_2$, 100 µM ZnCl$_2$, 2% DMSO, 0.04% Methylcellulose, 30 µM SPDL-3, 70 pM rhTACEc and a test compound. RhTACEc is pre-incubated with the test compound for 90 min at 25° C. in the absence of substrate. The reaction was started by addition of the substrate TNF-FRET 2. The fluorescent intensity (excitation at 320 nm, emission at 405 nm) was measured every 45 seconds for 30 min using a fluorospectrometer (GEMINI XS, Molecular Devices).

K$_i$ values were derived using non-linear regression fitting to the modified Morrison's equation. See $v_i/v_o = 1 - \{(E_o + I_o + K_i^{app}) - [(E_o + I_o + K_i^{app})^2 - 4E_o I_o]^{1/2}\}/2E_o$, where $v_i$ is the measured initial velocity of substrate turnover at any given inhibitor concentration $I_o$, and $v_o$ is the initial velocity when $I_o = 0$. Apparent inhibitor dissociation constants K$_i^{app}$ were derived by curve fitting at different initial concentrations of TACE (E$_o$). The Ki values of representative compounds of the invention for this TACE assay are shown below in Table A.

The compounds' ability to inhibit TACE activity can also be determined in human whole blood using the assay conditions described in Example 204 below.

The pharmaceutical compositions containing the active ingredient may be in a form suitable for oral use, for example, as tablets, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for controlled release.

The term pharmaceutical composition is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

Formulations for oral use may also be presented as hard gelatin capsules wherein the active ingredients is mixed with an inert solid diluent, for example, calcium carbonate, calcium phosphate or kaolin, or a soft gelatin capsules where in the active ingredient is mixed with water or an oil medium, for example peanut oil, liquid paraffin or olive oil.

Aqueous suspensions contain the active material in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, e.g., sweetening, flavoring and coloring agents, may also be present.

The pharmaceutical compositions of the invention may also be in the form of an oil-in-water emulsion. The oily phase may be a vegetable oil, e.g., olive oil or arachis oil, or a mineral oil, e.g., liquid paraffin or mixtures of these. Suitable emulsifying agents may be naturally-occurring phosphatides, e.g., soy beans, lecithin, and esters or partial esters derived from fatty acids and hexitol anhydrides, for example, sorbitan monooleate, and condensation products of the said partial esters with ethylene oxide, e.g., polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, e.g., as a solution in 1,3-butane diol. Among the acceptable vehicles and solvents that may be employed are water, Ringer's solution and isotonic sodium chloride solution. In addition, sterile fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of suppositories for rectal administration of the drug. The compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the invention are employed. (For purposes of this application, topical application shall include mouthwashes and gargles.)

The compounds for the present invention can be administered in the intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the above identified compounds useful in the method of the present invention range from 0.01 to 1000 mg per day. More preferably, dosages range from 0.1 to 1000 mg/day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four time daily.

The amount of active ingredient that may be combined with the carrier materials to produce single dosage form will vary depending upon the host treated and the particular mode of administration.

It will be understood, however, that the specific dose level for any particular patient will depend upon a variety of factors including the age, body weight, general health, sex, diet, time of administration, route or administration, rate of excretion, drug combination and the severity of the particular disease undergoing therapy.

The compounds of the invention may be produced by processes known to those skilled in the art and as shown in the following reaction schemes and in the preparations and examples described below.

EXAMPLES

The following abbreviations may be used in the procedures and schemes:
ACN Acetonitrile
AcOH Acetic acid
Aq Aqueous
BOC tert-Butoxycarbonyl
BOC$_2$O BOC Anhydride
C degrees Celsius
CBZCl Benzyl chloroformate
DBU 1,8-Diazabicyclo[5.4.0]undec-7-ene
DCM Dichloromethane
DEAD Diethyl azodicarboxylate
(DHQ)2PHAL Hydroquinine 1,4-phthalazinediyldiether
DIAD Diisopropylazodicarboxylate
DIPEA Diisopropylethylamine
DMA N,N-Dimethylacetamide
DMAP 4-Dimethylaminopyridine
DME Dimethoxyethane
DMF Dimethylformamide
DMPU 1,3-Dimethyl-3,4,5,6-tetrahydro-2(1h)-pyrimidinone
DMSO Dimethyl sulfoxide
EDCl 1-(3-Dimethylaminopropyl)-3-ethylcarbodiimide hydrochloride
EI Electron ionization
Eq Equivalents
EtOAc Ethyl acetate
EtOH Ethanol
g grams
h hours
hr hours
$^1$H proton
HATU N,N,N',N'-Tetramethyl-O-(7-Azabenzotriazol-1-yl) Uronium hexafluorophosphate
Hex hexanes
HOBT 1-Hydroxybenzotriazole
HPLC High pressure liquid chromatography
LAH Lithium aluminum hydride
LDA Lithium diisopropylamide
M Molar
mmol milimolar
mCPBA meta-Chloroperoxybenzoic acid
Me Methyl
MeCN Acetonitrile
MeOH Methanol
min Minutes
mg Milligrams
MHZ Megahertz
mL Milliliter
MPLC Medium Pressure Liquid Chromatography
NMR Nuclear Magnetic Resonance
MS Mass Spectroscopy
NBS N-Bromosuccinimide
NMM N-Methylmorpholine
NMP 1-methyl-2-pyrrolidone
ON Overnight
PCC Pyridinium Chlorochromate
PTLC Preparative thin layer chromatography
PyBrOP Bromo-tris-pyrrolidino-phosphonium hexafluorophosphate
Pyr Pyridine
RT Room temperature
sgc Silica gel 60 chromatography
tBOC tert-Butoxycarbonyl
TACE TNF-alpha converting enzyme
TEA Triethylamine
TFA Trifluoroacetic acid
THF Tetrahydrofuran
TLC Thin layer chromatography NMR spectra were acquired on the following instruments: 400 MHZ NMR (Bruker), 500 MHZ NMR (Bruker), 400 MHz NMR (Varian), 300 MHZ NMR (Varian) using CD$_3$OD, CDCl$_3$ or DMSO-d$_6$ as solvents. LC-MS data were obtained using a PESciex API 150EX quadropole mass spectrometer using electroscopy ionization.

Purification via reverse phase chromatography (Gilson) was accomplished using a C18 reverse phase column with a gradient of (0.1% formic acid) 5:95 to 90:10 acetonitrile:water, at a flow rate of 14 mL/min. Samples were collected using UV detection. Alternatively an ISCO Companion with (0.1% formic acid) 5:95 to 95:5 acetonitrile:water, at a flow rate=10-55 mL/min.

Normal phase silica gel chromatography was either accomplished on a Biotage instrument using a 60 Å 12/M, 25/M, or 40/M flash cartridges, or on a Jones Flash Master Personal instrument using Isolute flash SI 5 g, 10 g, 20 g, 50 g, or 70 g cartridges.

The above identified compounds may be produced by processes known to those skilled in the art and as shown in the following reaction schemes and in the preparations and examples described below. These preparations and examples should not be construed to limit the scope of the disclosure. Alternate mechanistic pathways and analogous structures may be apparent to those skilled in the art. Some of the compounds made by these processes are listed in the tables below. All kinds of isomeric forms of the compounds are considered to be within the scope of this invention.

SYNTHETIC ROUTES AND EXAMPLES
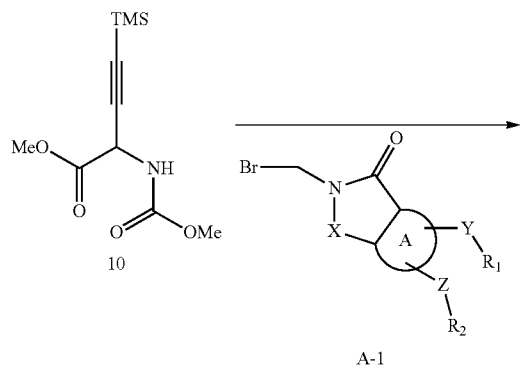
A-1
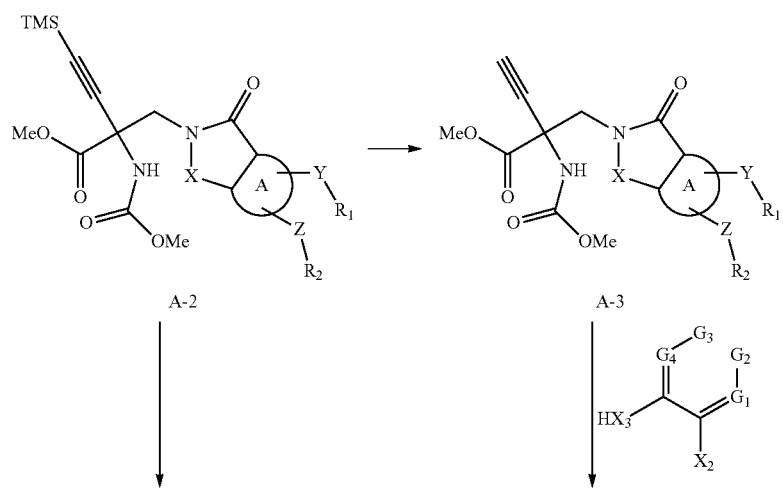
A-2    A-3
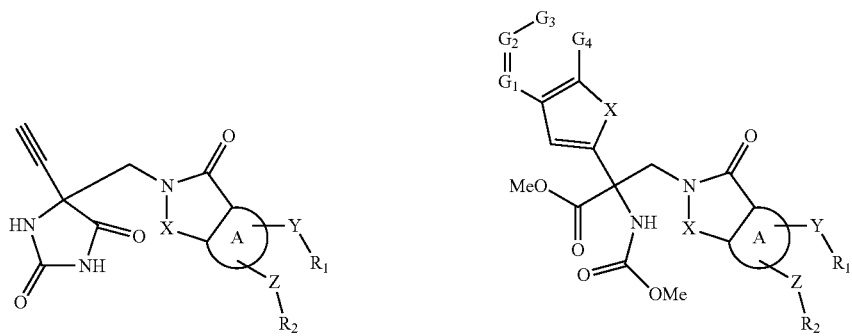
A-4    A-5

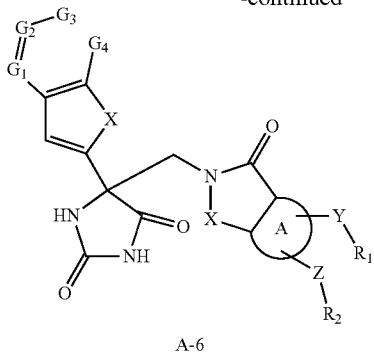

A-6

Alkylation of acetylene 10 with a suitable A-1 compound yields the quaternary protected amino acid derivative A-2. Compound A-2 may be either cyclized into hydantoin A-4 or deprotected to acetylene A-3. Conversion of the acetylene moiety to a fused biaryl ring is readily accomplished via a Sonogashira reaction with a (hetero)arylhalide to afford intermediates A-5 or A-6. Compound A-5 is converted to A-6 by treatment with 7M ammonia in methanol solution at 80° C. in a sealed bottle.

Example 1

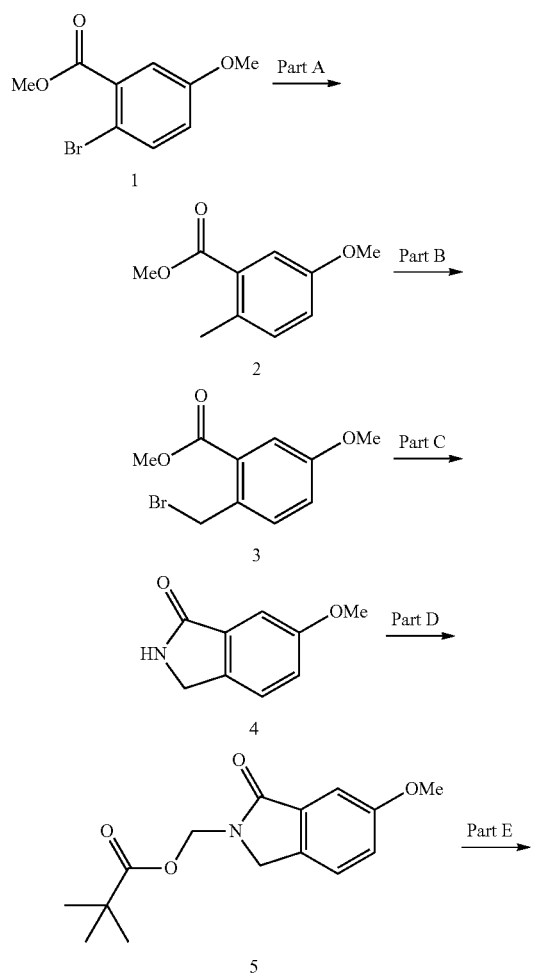

-continued

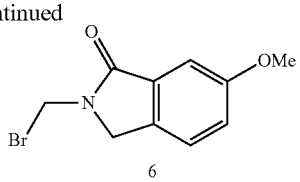

6

Part A:

Compound 1 (20.0 g, 81.61 mmol), trimethylboroxine (13.36 mL, 97.93 mmol), Pd(dppf)Cl$_2$ (1.0 g, 1.36 mmol), dioxane (350 mL), water (50 mL), and cesium carbonate (22.5 g, 163 mmol) were stirred at 110° C. (oil bath) under nitrogen for 16 hours. After cooling, the solid was removed by filtration. The solution was concentrated and purified by sgc (10:1 EtOAc/hexanes) to give 2 (12.1 g, 80%).

Part B:

Compound 2 (4.4 g, 24.2 mmol) was dissolved in carbon tetrachloride (80 mL) and N-bromosuccinimide (4.48 g, 24.2 mmol) and benzoyl peroxide (276 mg, 1.13 mmol) were added. The reaction mixture was stirred at reflux for 3 hours and then solids were filtered and washed with ether. The combined organic layers were washed with water, dried over sodium sulfate, and concentrated to provide the desired product 3 (6.1 g, 98%).

Part C:

Compound 3 (32.0 g, 124.0 mmol) was dissolved in 7 M ammonia in MeOH (150 mL) and stirred in a sealed pressure flask at 60° C. overnight. The reaction mixture was cooled and the solvent was removed under reduced pressure. The residue was suspended in ethyl acetate and stirred for 30 minutes. The solids were filtered and dissolved in methylene chloride. The methylene chloride solution was washed with water, dried over sodium sulfate, and concentrated to provide the desired product 4 (13.5 g, 67%).

Part D:

Compound 4 (2.2 g, 13.4 mmol) was dissolved in THF (250 mL) and DMPU (40 mL). Sodium t-butoxide (1.55 g, 16.13 mmol) was added and stirred for 5 hours. Chloromethylpivalate (3.0 mL, 20.1 mmol) was added dropwise and stirred overnight. The reaction was quenched with saturated ammonium chloride and extracted with ethyl acetate. The combined ethyl acetate layers were washed with water, brine, dried over sodium sulfate and concentrated. Purification by column chromatography (SiO$_2$, 25% ethyl acetate/hexanes) afforded the desired product 5 (2.5 g, 67%).

Part E:

Compound 5 (288 mg, 1.04 mmol) was dissolved in methylene chloride (5 mL) and cooled in an ice bath. Bromotrimethylsilane (0.3 mL, 2.08 mmol) was added dropwise and stirred in the ice bath for 30 minutes followed by 2 hours at room temperature. The reaction mixture was concentrated and re-dissolved in methylene chloride (2 mL). Hexanes (8 mL) was added and the solids were filtered to provide the desired product 6 (218 mg, 83%).

Example 2

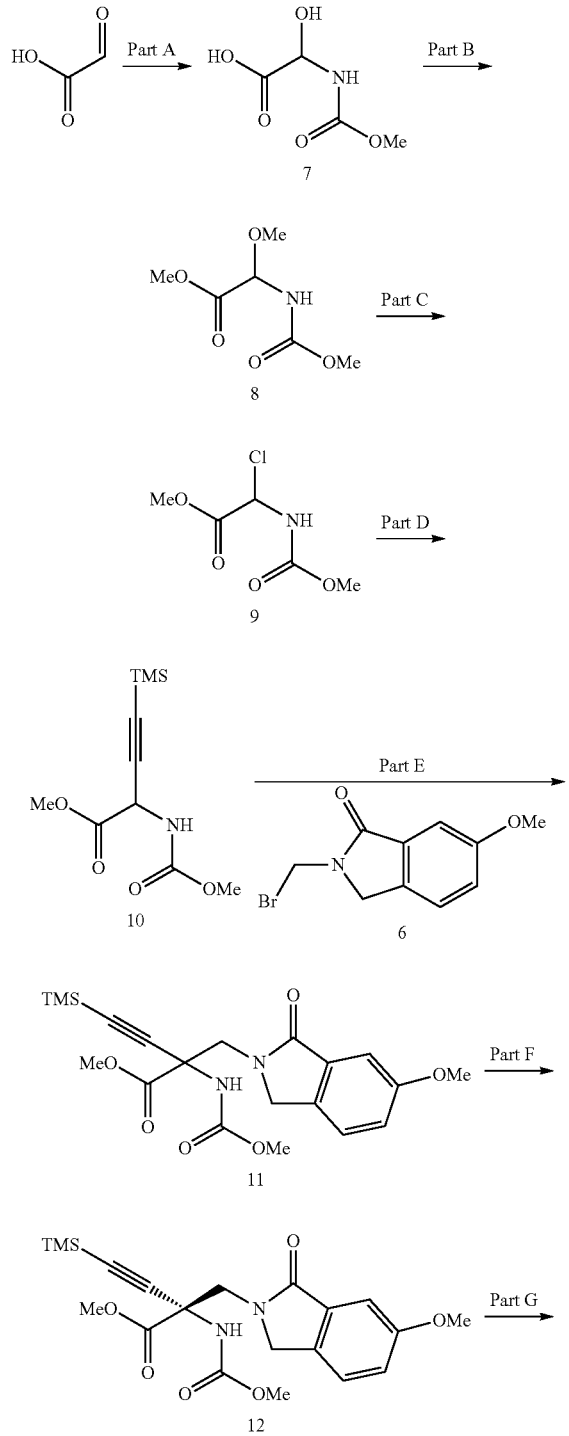

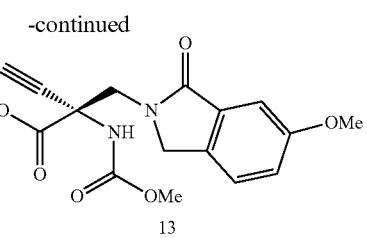

Part A:
Glyoxylic acid monohydrate (20.0 g, 218 mmol) and methyl carbamate (16.3 g, 218 mmol) were dissolved in diethyl ether (200 mL) and stirred overnight. The solids were filtered to provide the desired product 7 (32.0 g, 98%).

Part B:
Compound 7 (32.0 g, 214 mmol) was dissolved in MeOH (200 mL) and cooled in an ice bath. Concentrated sulfuric acid (8 mL) was added dropwise and the reaction was stirred overnight. The reaction mixture was diluted with ethyl acetate and water. The organic layer was washed with brine, dried over sodium sulfate, and concentrated to provide compound 8 that was used without purification (27.0 g, 71%).

Part C:
Compound 8 (27.0 g, 152 mmol) was dissolved in carbon tetrachloride (700 mL). Phosphorus pentachloride (50 g, 240 mmol) was added and the suspension was stirred for 18 hours (solution became clear over time). The solvent was removed under reduced pressure and the residue was stirred in petroleum ether (500 mL) overnight. The solids were filtered to provide compound 9 with no need for purification (26.5 g, 96%). Trituration step was repeated if mass yield was too high.

Part D:
Compound 9 (15.0 g, 82.7 mmol) was dissolved in methylene chloride (140 mL) and cooled in an ice bath. Bis(trimethylsilyl)acetylene (15.0 g, 88.2 mmol) was added in methylene chloride (20 mL). Freshly crushed aluminum chloride (11.0 g, 82.7 mmol) was added in portions over 20 minutes. The reaction mixture was allowed to slowly warm to room temperature and stirred overnight. The reaction was cooled in an ice bath and slowly quenched with water. The organic layer was washed several times with water, dried over sodium sulfate, and concentrated. The residue was triturated/recrystallized from hexanes to provide the desired product 10 (14.8 g, 69%). HPLC-MS $t_R$=1.84 min (ELSD); mass calculated for formula $C_{10}H_{17}NO_4Si$ 243.09, observed LCMS m/z 244.1 (M+H).

Part E:
Compound 10 (24.0 g, 98.7 mmol) and compound 6 (25.1 g, 99.0 mmol) were dissolved in THF (300 mL) and cooled to −78° C. A 1M solution of LiHMDS (198 mL, 198 mmol) was added dropwise over 30 minutes and the reaction mixture was stirred for 2 hours. Saturated ammonium chloride solution was added slowly and the reaction was allowed to warm to room temperature. The aqueous layer was extracted with ethyl acetate. The combined organic layers were washed with water, brine, dried over sodium sulfate, and concentrated. Purification by column chromatography ($SiO_2$, 33% ethyl acetate/hexanes to 50% ethyl acetate/hexanes) afforded the desired product 11 (26.0 g, 63%). HPLC-MS $t_R$=1.90 min ($UV_{254\ nm}$); mass calculated for formula $C_{20}H_{26}N_2O_6Si$ 418.15, observed LCMS m/z 419.2 (M+H).

Part F:
The two isomers were separated using a chiral OD column. One gram of material was injected into the column and the two peaks were separated by using a solvent mixture of 85% hexanes/ethanol. The second isomer was the desired compound 12 (400 mg, 80%).

Part G:

Compound 12 (8.0 g, 19.1 mmol) was dissolved in THF (250 mL) and cooled to 0° C. Tetrabutylammonium fluoride (1 M in THF, 22.9 mL, 22.9 mmol) was added dropwise and the reaction was stirred for 1 hour at room temperature. The reaction mixture was diluted with ethyl acetate and water. The organic layer was washed with water, saturated sodium bicarbonate, brine, dried over sodium sulfate and concentrated to provide compound 13 (5.8 g, 88%). The product was used without purification.

Example 3

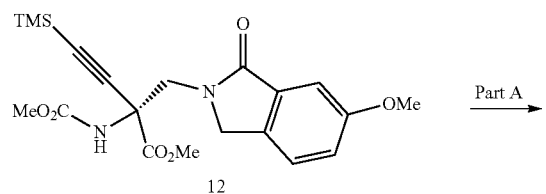

12

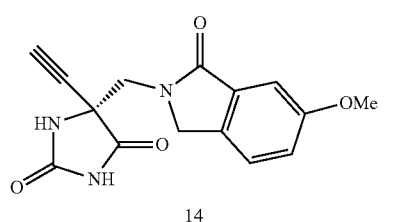

14

Part A:

Compound 12 (1.26 g, 3.0 mmol) in 7 M ammonia in methanol (20 mL) was heated to 85° C. in a pressure bottle overnight. The reaction mixture was concentrated to afford 14 (900 mg, 100%) which was used without further purification. HPLC-MS $t_R$=1.00 min (UV$_{254\,nm}$); mass calculated for formula $C_{15}H_{13}N_3O_4$ 299.09, observed LCMS m/z 300.1 (M+H).

Example 4

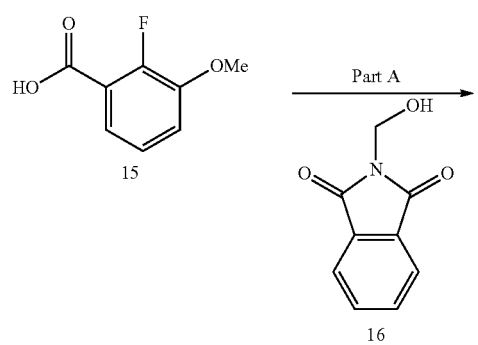

15

16

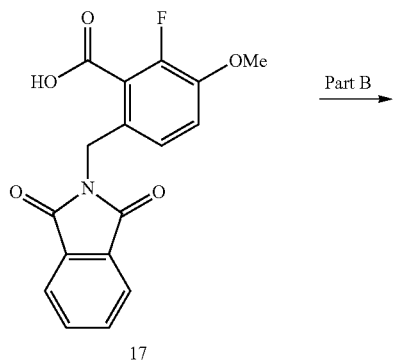

17

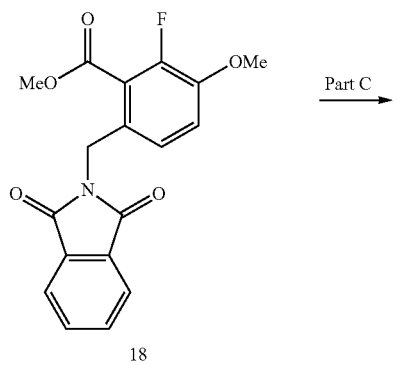

18

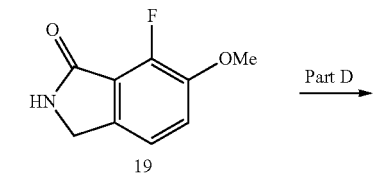

19

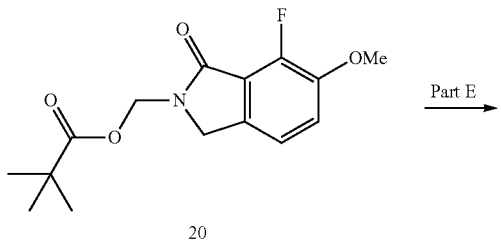

20

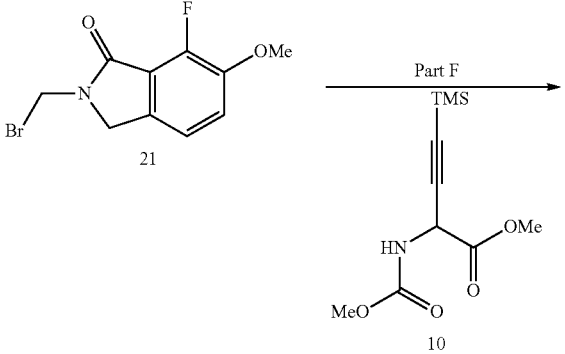

21

10

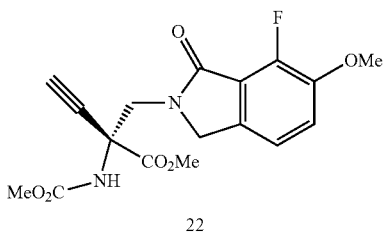

22

Part A:

Compound 15 (50.8 g, 298.65 mmol) and 16 (55.55 g, 313.58 mmol) were pre-mixed as solids and added to a concentrated sulfuric acid (150 mL) at 10° C. The reaction mixture was stirred at 10-15° C. for 2-3 hours. The reaction mixture was slowly added to ice water (800 mL) with good stirring. The reaction flask was rinsed with concentrated sulfuric acid and wash was added to the ice water. The solid was collected by filtration, washed with water (2×) and dried at 50° C. under vacuum to afford compound 17 (>100% by weight).

Part B:

To a solution of compound 17 (298.65 mmol) in DMF (1 L) was added sequentially cesium carbonate (127 g, 388.24 mmol) and methyl iodide (22.3 mL, 358.38 mmol). The reaction was stirred overnight at room temperature. The reaction mixture was diluted with water (800 ml) and ethyl acetate (800 mL) and the layers were separated. The aqueous layer was extracted with ethyl acetate (500 mL). The combined organic layers were washed with brine, dried over sodium sulfate and concentrated in vacuum. The crude reaction product was used without further purification.

Part C:

The crude product 18 was dissolved in methanol (1 L) and hydrazine hydrate (29 ml, 597.3 mmol) was added. The reaction mixture was stirred with a mechanical stirrer and heated to reflux for 3 hours. The reaction mixture was initially a suspension which cleared upon heating. As the reaction progressed a precipitate formed. The reaction mixture was cooled and the precipitate was collected by filtration. The solids were washed with methanol and the combined filtrate was reduced in volume to approximately 300 mL. The additional precipitate was collected by filtration and combined with the above solids. The solids were stirred with potassium carbonate solution (1 M, 200 mL) for 15 minutes and filtered. This washing process was repeated with another portion of potassium carbonate solution (1M, 150 ml). The solids were then washed with hydrochloric acid (2 M, 150 ml) for 15 minutes and filtered. This washing process was repeated with another portion of hydrochloric acid (1M, 150 ml) and the solid was rinsed with water. The potassium carbonate solution was extracted with ethyl acetate twice. The ethyl acetate washes were combined with the methanol filtrate, washed with brine, dried over sodium sulfate, and concentrated. The residue was washed with potassium carbonate solution (1 M, 20 mL) and hydrochloric acid (2 M, 20 mL). The additional solid was rinsed with water and combined with above solid. It was dried under vacuum at 50° C. for overnight to give compound 19 (47.87 g, 88.5% from compound 15).

Part D:

To a 3 L three neck flask was added compound 19 (61.07 g, 337.11 mmol) and DMPU (1500 mL). The suspension was stirred with a mechanic stirrer and gently warmed with a heat gun until a clear solution appeared. The solution was cooled to 0° C. and chloromethyl pivalate was added slowly with a syringe. The reaction mixture was stirred at 0° C. for three hours, diluted with $H_2O$ (1.5 L) and EtOAc (1.5 L), and the layers were separated. The organic layer was washed with $H_2O$ (500 mL×4), brine (500 mL), dried over sodium sulfate, and concentrated in vacuum. The product was purified by silica gel chromatography (Hexane/EtOAc: 2:1 to 1:1 to 0:1) to afford compound 20 (77.98 g, 78.3%)

Part E:

Compound 20 (70.97 g, 240.32 mmol) was dissolved in anhydrous $CH_2Cl_2$ (1 L). The solution was cooled to 0° C. and TMSBr (37.3 mL, 288.39 mmol) was added via syringe. The reaction mixture was stirred at 0° C. for two hours and concentrated in vacuum at 25° C. The residue was stirred with Hexane (500 mL) for 15 min, filtered, and rinsed with hexane (60 mL×2). The Hexane filtrate was concentrated in volume to approximately 100 mL and the additional solid was filtered, rinsed with hexane (10 mL×2), and combined with above solid. The solid was dried under vacuum for overnight to give compound 21 (64.81 g, 98.4%).

Part F:

To a flamed dried flask was added compound 21 (1.13 g, 4.11 mmol), compound 10 (1.0 g, 4.11 mmol), and anhydrous THF (25 mL). The solution was cooled to −78° C. and LiH-MDS (8.63 mL, 8.63 mmol) was added via syringe. The reaction mixture was stirred at −78° C. for two hours, diluted with saturated $NH_4Cl$ solution (30 mL) and EtOAc (50 mL). After warming up to room temperature, the aqueous layer was separated and extracted with EtOAc (20 mL) once. The organic layers were combined and TBAF (1 M in THF, 7 mL, 7 mmol) was added. The solution was stirred at 25° C. for 10 min, washed with water (50 mL), brine (50 mL), dried over sodium sulfate, and concentrated in vacuum. The product was purified by silica gel chromatography (Hexane/EtOAc: 2:1 to 1:1 to 0:1) to afford the racemate of compound 22 (891 mg, 59.5%)

The racemic mixture was separated using SFC conditions (20% MeOH/$CO_2$, 180 mL/min, back pressure of 225 bar, run time 9 minutes, OD-H chiral column). The racemate was dissolved in 1:1 acetonitrile/isopropyl alcohol (250 mg/mL). Compound 22 was isolated as the first peak. HPLC-MS $t_R$=1.26 min (UV 254 nm); mass calculated for formula $C_{17}H_{17}FN_2O_6$ 364.11, observed LCMS m/z 365.0 (M+H).

Example 4B

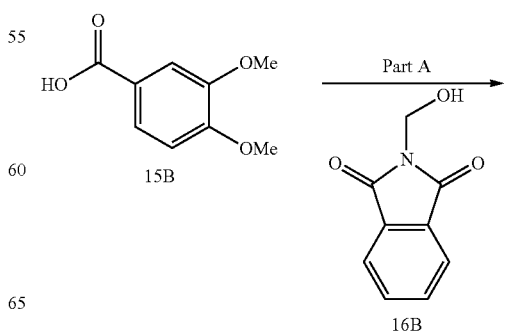

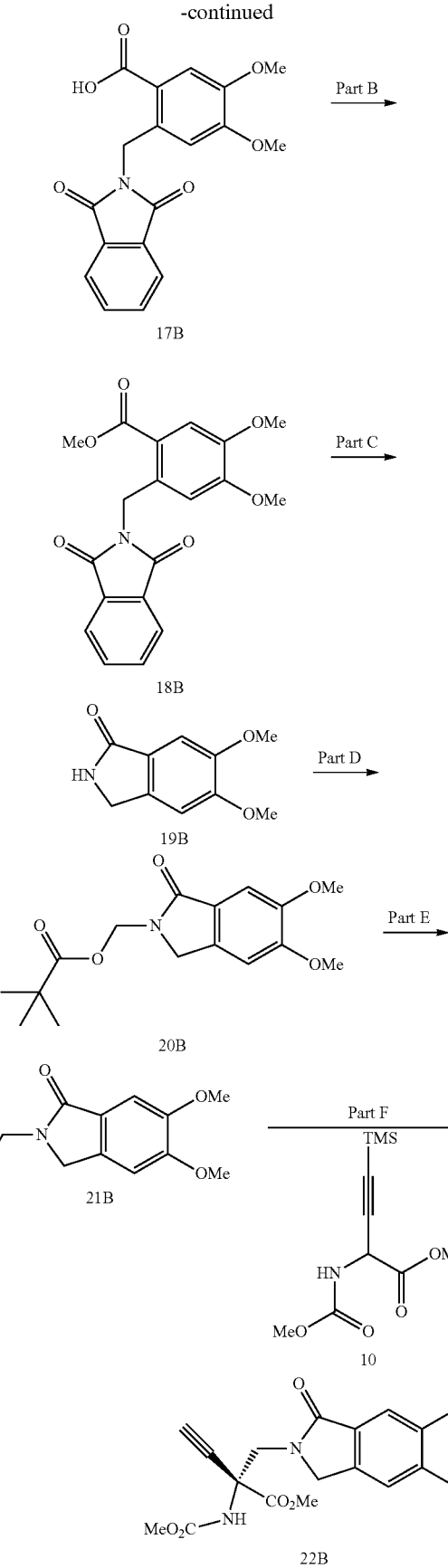

Part A:

Example 4, Part A Used for Preparation:

Yielded 17B (3.44 g, 92%). HPLC-MS $t_R$=1.60 min (ELSD); mass calculated for formula $C_{18}H_{15}NO_6$ 341.1, observed LCMS m/z 342.1 (M+H).

Part B:

Example 4, Part B Used for Preparation:

Yielded 18B (3.38 g, 95%). HPLC-MS $t_R$=1.69 min (ELSD); mass calculated for formula $C_{19}H_{17}NO_6$ 355.1, observed LCMS m/z 356.1 (M+H).

Part C:

Example 4, Part C Used for Preparation:

Yielded 19B (754 mg, 42%). $^1$H NMR (400 MHz, DMSO-$d_6$) δ 8.29 (s, 1H), 7.14 (d, 2H), 4.25 (s, 2H), 3.82 (s, 3H), 3.81 (s, 3H).

Part D:

Example 4, Part D Used for Preparation:

Yielded 20B (1.02 g, 80%). HPLC-MS $t_R$=1.61 min (ELSD); mass calculated for formula $C_{16}H_{21}NO_5$ 307.1, observed LCMS m/z 637.3 (2M+Na).

Part E:

Example 4, Part E Used for Preparation:

Yielded 21B (880 mg, 93%). $^1$H NMR (400 MHz, DMSO-$d_6$) δ 7.22 (s, 1H), 7.18 (s, 1H), 4.98 (s, 2H), 4.48 (s, 2H), 3.84 (s, 3H), 3.82 (s, 3H).

Part F:

Example 4, Part F Used for Preparation:

Yielded 22B (145 mg, 21%). The racemic mixture was separated using conditions (40% 2-propanol/60% hexanes, 70 mL/min, run time 40 minutes, OD-H chiral column). Compound 22B was isolated as the first peak (21.5 min, UV 254 nm). HPLC-MS $t_R$=1.74 min (ELSD); mass calculated for formula $C_{18}H_{20}N_2O_7$ 448.2, observed LCMS m/z 449.2 (M+H).

Example 5

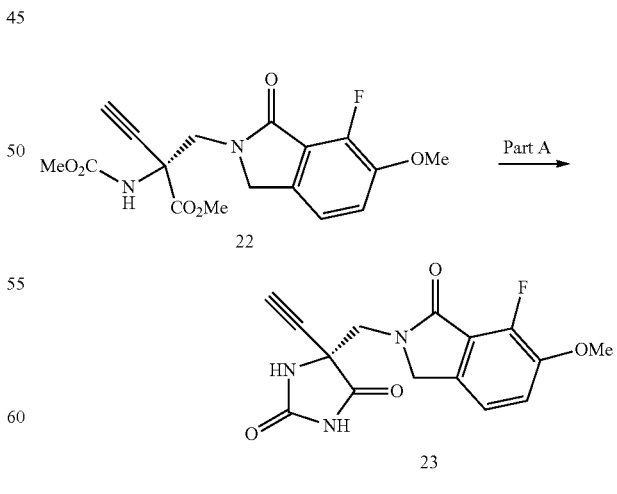

Part A:

Using the procedures described in Example 3, compound 22 (8.69 g, 23.8 mmol) was converted to 23 in quantitative yield. HPLC-MS $t_R$=0.93 min (UV 254 nm); mass calculated for formula $C_{15}H_{12}FN_3O_4$ 317.08, observed LCMS m/z 318.1 (M+H).

Example 6

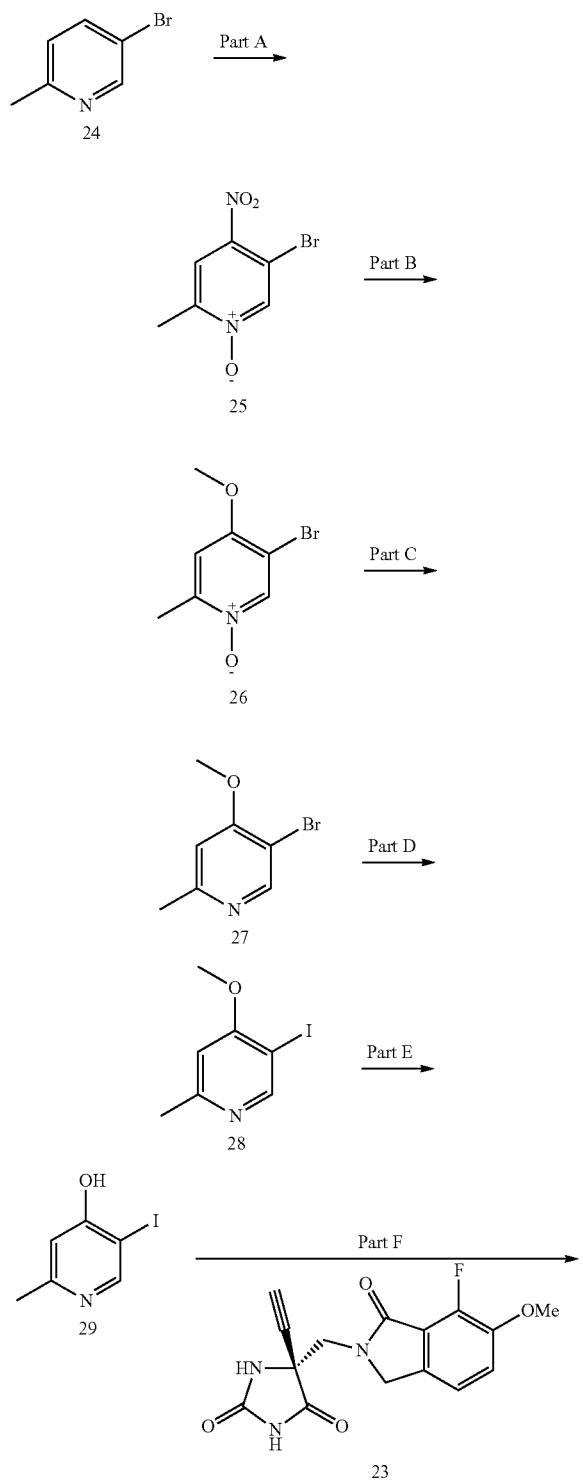

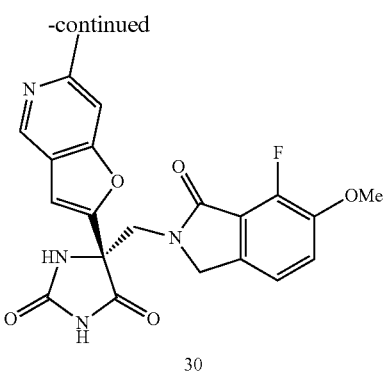

Part A:

A mixture of 2-methyl-5-bromopyridine (24) (3.00 g, 17.4 mmol), hydrogen peroxide (50%, 5 mL), glacial acetic acid (10 mL) and benzene (7 mL) was heated at reflux overnight. The reaction mixture was cooled and concentrated in vacuo. Water (5 mL) was added to the residue and the mixture was concentrated in vacuo to a yellow solid. The resulting solid was dissolved in concentrated sulfuric acid (5 mL) and to this was added slowly a mixture of concentrated sulfuric acid (5 mL) and concentrated nitric acid (7 mL). The reaction mixture was heated at 90-100° C. for 2.25 hours. After cooling to room temperature the mixture was poured over ice and treated with ammonium carbonate until the pH was 8-9. The resulting yellow solid was collected by filtration and washed with water to afford 25 (3.03 g, 75%). HPLC-MS $t_R$=0.96 min (UV 254 nm); mass calculated for formula $C_6H_5BrN_2O_3$ 231.95, observed LCMS m/z 234.9 (M+H).

Part B:

To compound 25 (1.36 g, 5.8 mmol) was added 0.5 M sodium methoxide solution (11.6 mL, 5.8 mmol) and the mixture was heated to reflux for 4 hours. After cooling the mixture was concentrated in vacuo. The residue was dissolved in chloroform and filtered to remove the solids. The filtrate was concentrated to afford 26 as a pale yellow solid (1.20 g, 95%). HPLC-MS $t_R$=0.58-0.72 min (UV 254 nm); mass calculated for formula $C_7H_8BrNO_2$ 216.97, observed LCMS m/z 218.1 (M+H).

Part C:

A mixture of compound 26 (1.20 g, 5.5 mmol), $MoO_2Cl_2$ $(dmf)_2$ (prepared as described in Synthesis 2004, 1629) (97 mg, 0.28 mmol) and triphenylphosphine (1.57 g, 6.0 mmol) in tetrahydrofuran (10 mL) was heated to reflux overnight. After cooling the mixture was concentrated in vacuo. The majority of the triphenylphosphine oxide was removed by suspending the residue in 1:1 diethyl ether:petroleum ether (30 ml) and ethyl acetate (3 mL). The mixture was stirred overnight and filtered. The filtrate was concentrated and the residue was purified by silica gel chromatography (10% ethyl acetate/hexanes to 80% ethyl acetate/hexanes) to afford 27 (0.89 g, 80%) as a pale yellow oil which solidified to an off-white solid upon standing. HPLC-MS $t_R$=0.62 min (UV 254 nm); mass calculated for formula $C_7H_8BrNO$ 200.98, observed LCMS m/z 202.0 (M+H).

Part D:

To isopropylmagnesium chloride (2.0 M, 0.84 mL, 1.67 mmol) in THF (6 mL) at 0° C. was added n-butyl lithium (2.5 M, 1.5 mL, 3.33 mmol). The reaction mixture was stirred for 15 minutes at 0° C. and then cooled to −10° C. A solution of 27 (672 mg, 3.33 mmol) in THF (4 mL) was added to the reaction mixture. After stirring for 30 minutes at −10° C. a solution of iodine (1.52 g, 6 mmol) in THF (5 mL) was added.

The reaction mixture was warmed to 0° C. and then allowed to warm to room temperature while stirring for 2.5 hours. The reaction mixture was quenched with acetic acid (0.3 mL) and diluted with ethyl acetate and water. The organic layer was separated and washed with sodium thiosulfate solution and brine, dried over sodium sulfate and concentrated. The residue was purified by silica gel chromatography (10% ethyl acetate/hexanes to 80% ethyl acetate hexanes) to afford 28 (554 mg, 67%) as an off white solid. HPLC-MS $t_R$=0.68 min (ELSD); mass calculated for formula $C_7H_8INO$ 248.97, observed LCMS m/z 250.0 (M+H).

Part E:

Treatment of 28 (320 mg, 1.28 mmol) with 1M aluminum bromide solution in dibromomethane (1.3 mL, 1.3 mmol) in the microwave at 85° C. for 10 minutes afforded a mixture of product and starting material. An additional equivalent of aluminum bromide solution was added and the reaction mixture was heated for 10 minutes at 85° C. in the microwave. The reaction mixture was diluted with water (2 mL) and dichloromethane. The solids were collected by filtration and washed with the following solvent sequence: dichloromethane, toluene with a minimum amount of water, toluene and dichloromethane. This afforded 29 (248 mg) as a beige solid which was used without additional purification. HPLC-MS $t_R$=0.52 min ($UV_{254\ nm}$); mass calculated for formula $C_6H_6INO$ 234.85, observed LCMS m/z 236.1 (M+H).

Part F:

A mixture of 29 (150 mg, 0.64 mmol), 23 (136 mg, 0.43 mmol), copper iodide (3 mg, 0.017 mmol), $Pd(PPh_3)_2Cl_2$ (6 mg, 0.009 mmol) and triethylamine (0.120 mL, 0.86 mmol) in DMF (2 mL) was heated at 110° C. in the microwave for 15 minutes. The reaction mixture was concentrated and purified by reverse phase chromatography using a 0.1% trifluoracetic acid in the aqueous mobile phase. The purified material was concentrated and converted to an HCl salt. A second purification by reverse phase chromatography with formic acid (0.2%) in the mobile phase was required to remove residual DMSO. The isolated fractions were concentrated and converted to the HCl salt to afford 30 (86 mg) as a pale yellow powder after lyophilization.

HPLC-MS $t_R$=0.72 min ($UV_{254\ nm}$); mass calculated for formula $C_{21}H_{17}FN_4O_5$ 424.12, observed LCMS m/z 425.0 (M+H).

Compound 30. $^1$H NMR (400 Hz, DMSO-$d_6$) δ 11.40 (s, 1H), 9.28 (s, 1H), 9.14 (s, 1H), 8.24 (s, 1H), 7.47-7.34 (m, 3H), 4.45 (m, 2H), 4.29 (m, 2H), 3.87 (s, 3H), 2.77 (s, 3H).

Compounds 200 and 201 were prepared using procedures similar to those described in Example 5, Part A and Example 6.

Compounds 202-204 were prepared using procedures similar to those described in Example 6.

Example 7

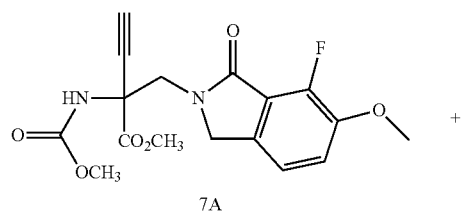

7A

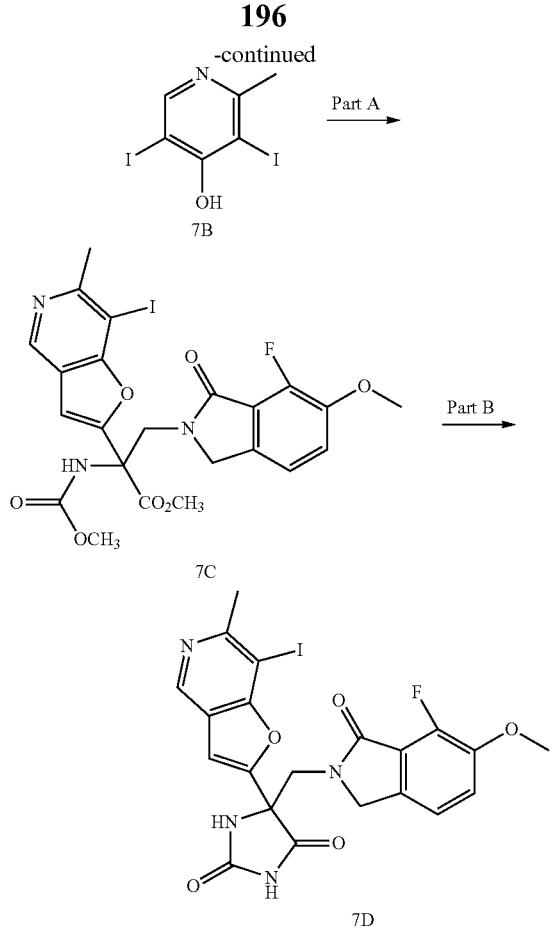

Part A

Compound 7A (4.14 g, 11.36 mmol), 7B (3.73 g, 10.33 mmol), $Pd(PPh_3)_2Cl_2$ (145 mg, 0.21 mmol), and CuI (40 mg, 0.21 mmol) were placed in a 250 mL flask. The flask was vacuumed and flushed nitrogen for three times. DMF (100 mL) were added. The solution was stirred at 40° C. for 18 h. DMF was removed under vacuum and the product was purified by sgc (MeOH/DCM: 1% to 5%) to give compound 7C (3.54 g, 52.2%).

Part B

Compound 7C (100 mg, 0.167 mmol) was dissolved in $NH_3$/MeOH (3 m) in a 15 mL pressure tube. The tube was capped and the solution was stirred at 80° C. for overnight. After cooling down, the solvent was removed under vacuum and the product was purified by C18 chromatography ($CH_3CN/H_2O$, 5% to 90%, with 0.1% $HCO_2H$) to give compound 7D (67 mg, 72.9%).

Example 8

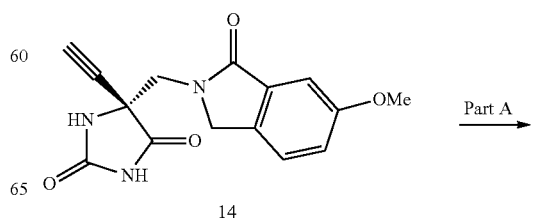

14

-continued

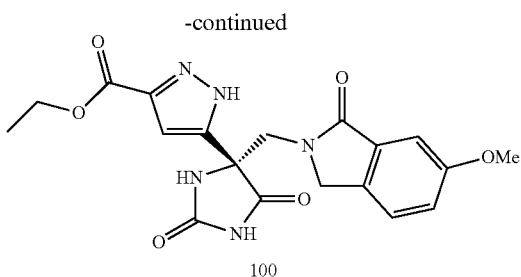

100

To compound 14 (81 mg, 0.23 mmol) in DMF (0.5 mL) was added ethyldiazoacetate (0.048 mL, 0.46 mmol) and the mixture was heated to 50° C. for 18 days. The reaction mixture was concentrated and purified by column chromatography (SiO$_2$, 50% ethyl acetate/hexane of 100% ethyl acetate) to obtain compound 100 (29 mg). HPLC-MS $t_R$=1.14 min (UV$_{254\ nm}$); mass calculated for formula C$_{19}$H$_{19}$FN$_5$O$_6$ 413.13, observed LCMS m/z 414.1 (M+H).

Example 9

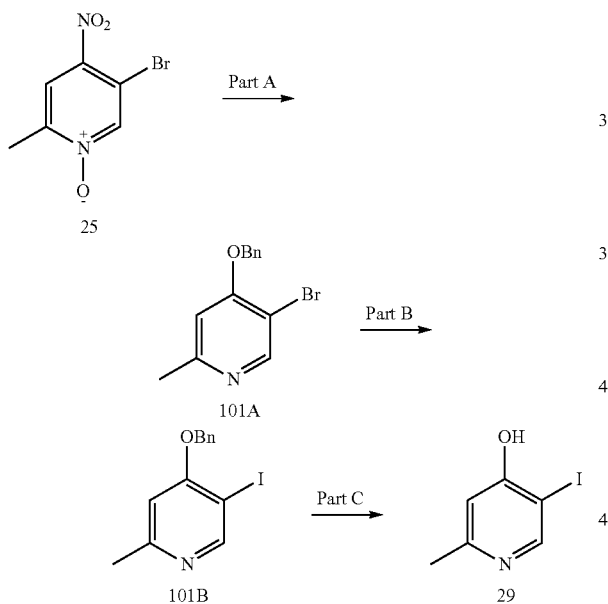

Part A:

To benzyl alcohol (10.3 mL) was added sodium hydride (95%, 260 mg, 10.3 mmol) and the mixture was stirred for 30 minutes at room temperature. Compound 25 was added to the mixture. The reaction mixture was heated at 50° C. for 3.75 hours. Upon cooling the mixture was diluted with dichloromethane and filtered. The filtrate was concentrated. The residue was dissolved in THF (50 ml) and treated with triphenylphosphine (2.62 g, 10 mmol) and MoO$_2$Cl$_2$(dmf)$_2$ (172 mg, 5 mol %). The mixture was heated at reflux for 24 hours. Upon cooling the mixture was filtered to remove the solids and the filtrate was concentrated. Purification by column chromatography (SiO$_2$, 10% ethyl acetate/hexanes to 80% ethyl acetate/hexanes) afforded 101A (1.37 g, 49%) as an off white solid. HPLC-MS $t_R$=1.22 min (UV$_{254\ nm}$); mass calculated for formula C$_{13}$H$_{12}$BrNO 277.01, observed LCMS m/z 278.0 (M+H).

Part B:
Compound 101B (1.0 g, 62%) was prepared using the procedure described in Example 6 Part D. HPLC-MS $t_R$=1.23 min (UV$_{254\ nm}$); mass calculated for formula C$_{13}$H$_{12}$INO 325.00, observed LCMS m/z 326.0.0 (M+H).

Part C:
To compound 101B (1.0 g, 3.07 mmol) in DCM (20 mL) was added BBr$_3$ solution (1 M, 8 mL). A precipitate formed immediately and the reaction was complete after 1 hour. The reaction mixture was quenched with ice water and adjusted to pH 7. The solids were collected by filtration, washed with water and dissolved in methanol. The organic filtrate was concentrated to afford 29 (429 mg, 60%). HPLC-MS $t_R$=0.22 min (UV$_{254\ nm}$); mass calculated for formula C$_6$H$_6$INO 234.95, observed LCMS m/z 236.1 (M+H).

Example 10

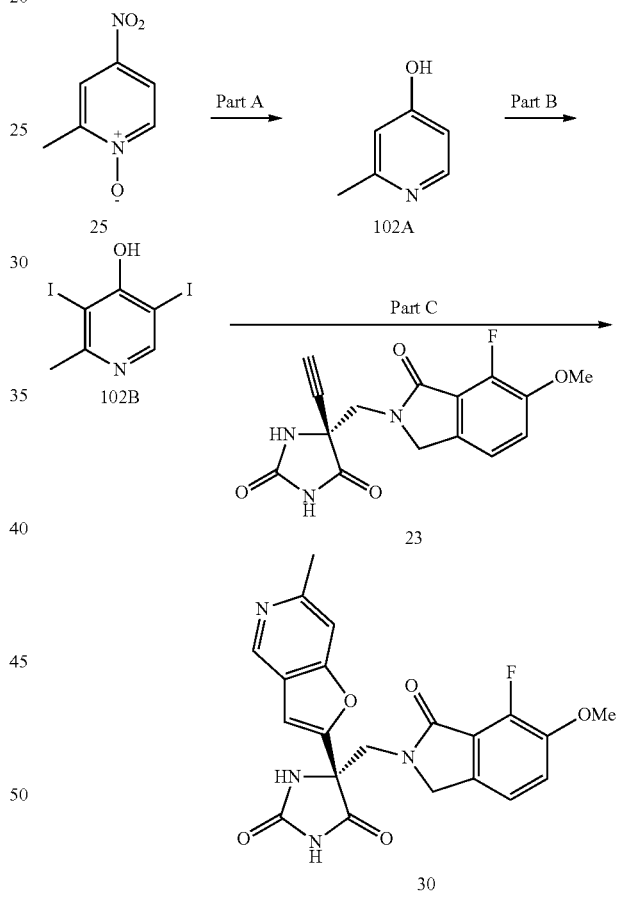

Part A:
A round bottom flask was charged with sodium hydride (95%, 1.14 g, 45.1 mmol) and cooled to 0° C. To the flask was added benzyl alcohol (50 mL, 500 mmol) and the mixture was stirred at 0° C. for 30 minutes. Compound 25 (6.84 g, 44.4 mmol) was added in several portions with stirring at 0° C. After 30 minutes the reaction was warmed to room temperature. The reaction was incomplete so the mixture was warmed to 60° C. for 1 hour. The reaction mixture was quenched with water and partitioned between water and ethyl acetate. The organic layer was separated, washed with brine, dried over sodium sulfate and concentrated to afford a brown oil (49.4 g). The resulting oil was dissolved in methanol (20 mL) and Raney Ni slurry (3 ml) was added under argon atmosphere. The flask was charged with hydrogen via a balloon and the mixture was stirred at room temperature overnight. The reaction mixture was diluted with methanol, filtered through celite and concentrated to afford a colorless oil. The oil was triturated with diethyl ether (200 ml) and compound 102A (1.04 g, 61% overall) was collected as a white solid by filtration. HPLC-MS $t_R$=0.20 min ($UV_{254\,nm}$); mass calculated for formula $C_6H_7NO$ 109.05, observed LCMS m/z 110.1 (M+H).

Part B:

A mixture of compound 102A (1.78 g, 16.35 mmol) and N-iodosuccinimide (7.36 g, 32.7 mmol) in acetonitrile (60 mL) was heated at reflux overnight. After cooling the solid was collected by filtration and washed with acetonitrile to afford compound 102B (5.29 g, 90%). HPLC-MS $t_R$=0.78 min ($UV_{254\,nm}$); mass calculated for formula $C_6H_6I_2NO$ 360.85, observed LCMS m/z 361.9 (M+H).

Part C:

A mixture of 102B (1.80 g, 5 mmol), 23 (1.59 g, 5 mmol), $Pd(PPh_3)_2Cl_2$ (70 mg, 0.10 mmol), CuI (38 mg, 0.2 mmol) and triethylamine (0.74 mL, 10 mmol) in DMF (25 mL) was stirred for 72 hours in a 150-mL pressure bottle under an argon atmosphere at room temperature. Sodium formate (680 mg, 10 mmol) and $Pd(PPh_3)_2Cl_2$ (70 mg, 0.10 mmol) was added to the reaction mixture. The mixture was stirred at 80° C. for 5 hours. An additional portion of sodium formate (340 mg, 5 mmol) and $Pd(PPh_3)_2Cl_2$ (70 mg, 0.10 mmol) was added. The reaction was stirred for 1.5 hours. The mixture was cooled, filtered through celite and the celite pad was washed with methanol. The combined filtrate was concentrated. The residue was suspended in 1% aq. acetonitrile (25 mL) and filtered to remove a gray precipitate. The filtrate was concentrated. The crude product was isolated by trituration with acetonitrile. The material was combined with previous batches and purified by column chromatography ($SiO_2$, dichloromethane to 10% ethanol/dichloromethane) to afford 30 (1.57 g).

Example 11

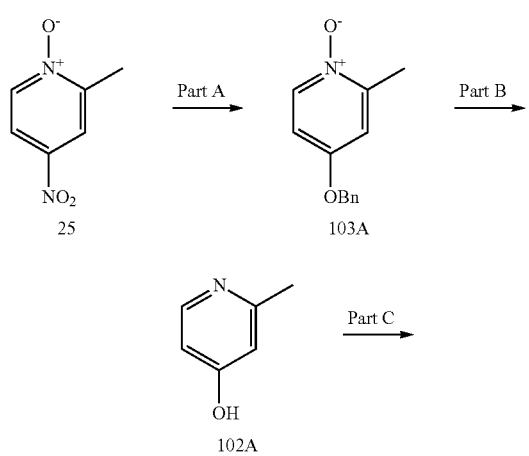

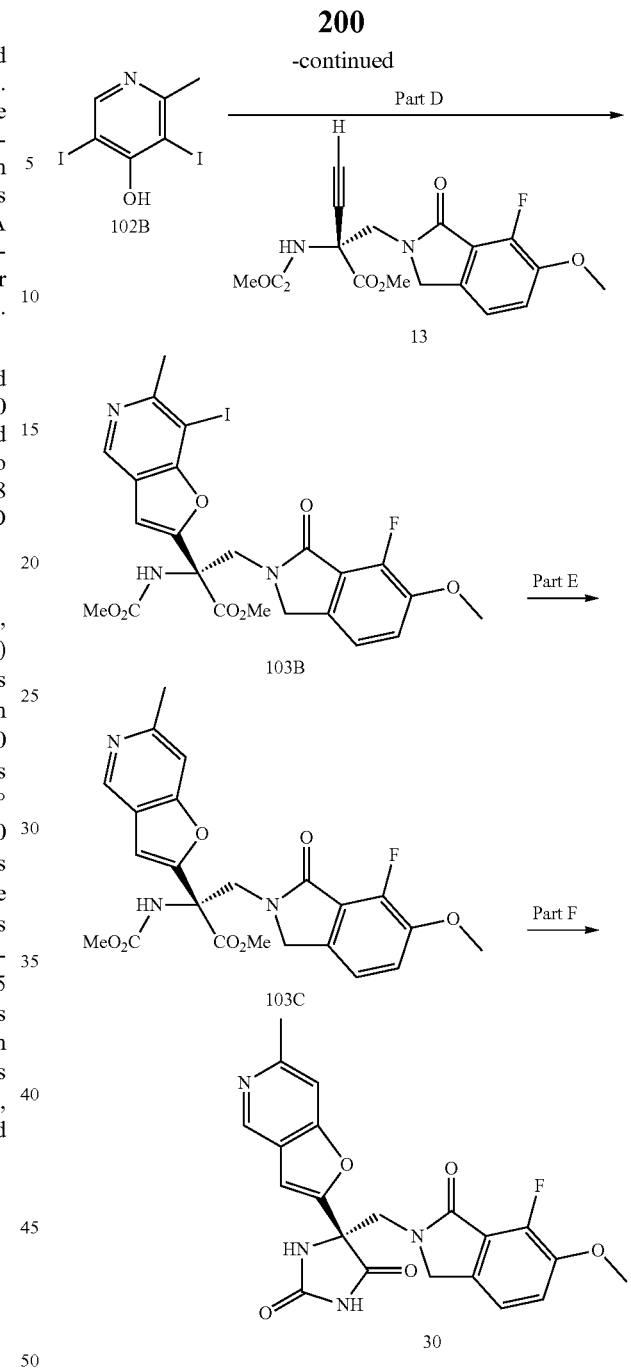

Part A

Potassium hydroxide (17.54 g, 321.7 mmol), tetra-n-butyl ammonium bromide (6.57 g, 20.3 mmol), and toluene were added to a 1 L 3 necked round bottomed flask equipped with a large stir bar. Benzyl alcohol (16 mL) was added and the flask was placed in an oil bath. The flask was placed under $N_2$ blanket and heated to 45° C. with rapid stirring. After about 1 h and 20 min, air that had been passed over a column of Drierite and activated 3 angstrom molecular sieves was bubbled through the reaction mixture. Ten minutes later, 4-nitro-2-picoline-N-oxide (Compound 25, 20.01 g, 129.9 mmol) was added in portions over 1 h. The reaction mixture was stirred quickly at 45 C with air bubbling through it continuously for 2 h during which time most of the starting material disappeared as determined by TLC. The reaction mixture was removed from the heat and dry ice was added. Brine (80 mL)

and EtOAc (400 mL) were added. The reaction mixture was transferred to a 2 L separatory funnel. Water (100 mL) and EtOAc (200 mL) were used to wash the residual black solid out of the reaction flask into the separatory funnel. A phase line could not be discerned. Liquid (200 mL) was drained from the sep funnel. Additional brine (160 mL) was added. No phase separation line could be seen. Additional liquid (160 mL) was drained from the sep funnel. Water was added (100 mL) to the sep funnel and additional liquid (100 mL) was drained from it—again without a phase separation line. The liquid that had been drained from the sep funnel was left standing in one flask over the weekend. The organic layer that remained in the sep funnel after the aqueous washes was left standing in another flask over the weekend. The liquid that had originally been drained from the separatory funnel was filtered through a pad of Celite and activated charcoal. Two distinct layers were obtained. The layers were separated and the aqueous layer was extracted with 4×250 mL of EtOAc. The combined organic layer was filtered and concentrated to dryness to give 18.2 g of brown solid. The crude product was suspended in diethyl ether. The flask was placed on the rotovap and spun in a 34° C. water bath without vacuum for about 20 min. The mixture was filtered. The retained solid was washed with diethyl ether to give 11.57 g (41%) of 103AA. TLC of the solid and the mother liquor indicated that the solid was almost all product while the mother liquor was a mix of product and other materials. The solid was purified further by sgc using 231 g of silica gel and eluting the column using 2 L of 5% MeOH in DCM and 2 L of 10% MeOH in DCM as the mobile phase. Compound 103A (10.9 g, 40% yield) was obtained as a brown solid. Mass calculated for formula $C_{13}H_{13}NO_2$ 215.09, observed LCMS m/z 216.2 (M+H).

Part B

Compound 103A (60.88 g, 283.0 mmol) was dissolved in MeOH (1 L) and Raney Ni (18 g) was added. The solution was shaken under $H_2$ at 40 psi for overnight. The catalyst was removed by filtration. The filtrate was concentrated and triturated with EtOAc. The resulting solid was filtered, washed with EtOAc, and dried under vacuum to give the first batch of compound 102A (20.01 g). The filtrate was concentrated and purified by sgc (5% MeOH in DCM, with 0.5% $NH_4OH$) to give the second batch of compound 102A (5.16 g). Both batches were combined to give compound 102A (25.17 g, 81.5%).

Part C

Compound 102A (30.0 g, 274.9 mmol) was grounded into fine powder and was suspended in $CH_3CN$ (600 mL) in a 2 L flask. NIS (123.7 g, 549.8 mmol) was added and the suspension was stirred at reflux temperature overnight. After cooling, the solid was filtered, washed with $CH_3CN$ three times, and dried under vacuum at 50° C. to give compound 102B (87.59 g, 88.3%).

Part D

Compound 102B (44.6 g, 123.5 mmol), compound 13 (50.0 g, 137.2 mmol), CuI (522 mg, 2.74 mmol), and $Pd(PPh_3)_2Cl_2$ (1.9 g, 2.74 mmol) were placed in a 3 L flask and degassed by repeated vacuuming and flushing with $N_2$. DMF (1 L) and disopropyl amine (25.0 mL, 178.4 mmol) were added. The solution was stirred at 25° C. for 48 hours under $N_2$. DMF was removed under vacuum at 60° C. The residue was dissolved in DCM (600 mL) and water (300 mL). The organic layer was separated and washed with 150 mL water. The aqueous layers were combined and extracted with EtOAc (200 mL, twice). All the organic layers were combined, washed with brine (~300 mL), dried over $Na_2SO_4$, and concentrated under vacuum. The product was purified by sgc (1.5 kg, EtOAc/DCM 1:1 to 9:1) to give the first batch of compound 103B (56.1 g). The overlap fraction was purified again with sgc to give the second batch of compound 103B (6.6 g). Both batches were combined to give compound 103B (62.7 g, 76.5%). Mass calculated for formula $C_{23}H_{21}FlN_3O_7$ 597.04, observed LCMS m/z 598.3 (M+H).

Part E

Compound 103B (17.49 g, 29.3 mmol), sodium formate (9.96 g, 146.4 mmol), and $Pd(PPh_3)_2Cl_2$ (1.03 g, 1.46 mmol) were placed in a 350 mL pressure bottle. The system was degassed by blowing $N_2$ gas into the bottle for about 5 minutes. The MeOH (117 mL) was added. The pressure bottle was sealed and the solution was stirred in a 85° C. oil bath overnight. After cooling, the solid was removed by filtration through a pad of celite. The filtrate was concentrated and dissolved in EtOAc (1200 mL) and water (60 mL). The aqueous layer was separated and extracted with EtOAc (120 mL×2). The organic layers were combined and washed with brine, dried over $Na_2SO_4$, concentrated under vacuum, and purified by sgc (EtOAc/DCM 1:1 to 1:0) to give compound 103C (13.42 g)

Compound 103C that had been purified via sgc (1.26 g) was dissolved in 75 mL of methanol. Activated charcoal (40 mg/3 weight %-Darco 12-20 mesh, granular-purchased from Aldrich Chemical Company) was added. The flask was placed in a 50° C. water bath and stirred at 50° C. for 3.5 h under a drying tube. The mixture was filtered through a pad of Celite which was rinsed with methanol. The filtrate was concentrated to a white solid (1.251 g). Methanol (63 mL) was added. The flask was equipped with a drying tube and was placed in a 50° C. water bath. The mixture was stirred until it became a clear solution, then it was removed from the bath. The solution was stirred at 25° C. for 1.5 h during which time a white solid precipitated from solution. The mixture was stirred at 0° C. in an ice-water bath for 1.5 h then filtered to give a white solid. The solid was rinsed with cold methanol then isolated to give 0.78 g of white first crop crystals. (Recovery=62%). The filtrate was partially concentrated on the rotovap at 40° C. A few seed crystals were added. The flask was equipped with a drying tube and left stirring ON at 25° C. The flask was placed in an ice water bath and left stirring at 0° C. for 1 h. The mixture was filtered to give a white solid. The solid was rinsed with cold methanol then isolated to give 149 mg of second crop crystals. Total recovery=74%. LCMS of both the first and second crop crystals at indicated that they were >99% pure ($UV_{254\ nm}$). $^1H$ NMR in $CDCl_3$ also indicated a high degree of purity. Mass calculated for formula $C_{23}H_{22}FN_3O_7$ 471.14, observed LCMS m/z 472.17 (M+H).

Part F

Compound 103C (1.0 g, 2.12 mmol) was suspended in $NH_3$ (7N in MeOH, 100 mL) in a pressure tube and it was sealed. The solution was stirred at 60° C. oil bath for 24 h. After cooling, the solvent was removed and the residue was stirred in DCM/MeOH (1:1, 10 mL) for overnight. The solid was filtered, and then was stirred with another 10 mL DCM/MeOH (1:1) for another overnight. The solid was filtered, washed with MeOH, dried under vacuum to give compound 30 (675.0 mg, 75.0%). All the filtrates were combined, concentrated, and saved for future further purification.

Example 12

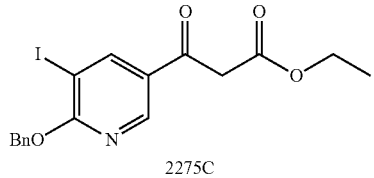

2275C

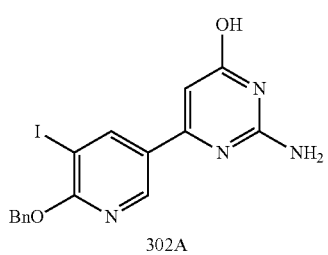

302A

Part A

Compound 2275C (425 mg, 1.0 mmol), guanidine acetate (179 mg, 1.5 mmol) and potassium carbonate (123 mg, 1.5 mmol) were heated at 80° C. in ethanol (5 mL) overnight. The reaction mixture was concentrated and purified by reverse phase chromatography to give 302A (67 mg). HPLC-MS $t_R$=1.87 min (UV$_{254\ nm}$); mass calculated for formula $C_{16}H_{13}IN_4O_2$ 420.01, observed LCMS m/z 421.0 (M+H).

Compound 302 was prepared from 302A using procedures described in Example 12 followed by standard debenzylation condition using Pd on carbon and Sonogashira conditions similar to those described in Example 52, Part D. Compound 300 was prepared from 2275C using procedures similar to those described in Example 12.

Example 13

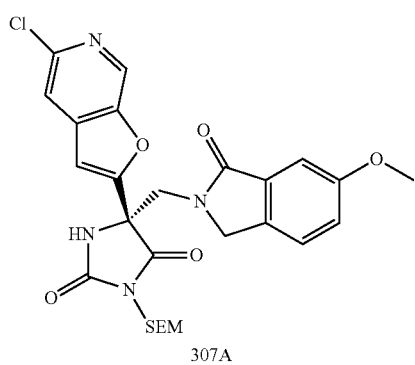

307A

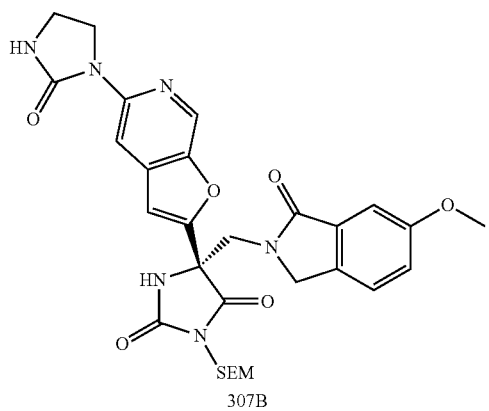

307B

Part A

To a mixture of compound 307A (50 mg, 0.091 mmol), bis(dibenzylideneacetone) palladium [Pd(dba)$_2$, 4.1 mg, 0.0045 mmol], 9,9-dimethyl-4,5-bis(diphenylphosphino) xanthene (Xantphos, 3.0 mg, 0.0055 mmol), and cesium carbonate (94 mg, 0.29 mmol) were added 2-imidazolinone (16.3 mg, 0.19 mmol) and dioxane (0.5 mL). The vial was sealed and stirred overnight at 100° C. After removal of solvent, the residue was purified by column chromatography (0 to 10% MeOH in CH$_2$Cl$_2$) to give 307B (40 mg). HPLC-MS $t_R$=1.84 min (UV$_{254\ nm}$); mass calculated for formula $C_{29}H_{34}N_6O_7Si$ 606.23, observed LCMS m/z 607.2 (M+H).

Compound 306 was prepared from 307A using procedures similar to those described in Example 33, Part D. Compounds 307 and 308 were prepared from 307A using procedures similar to those described in Example 13.

Example 14

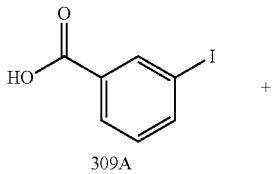

309A

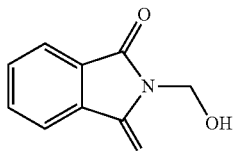

309B

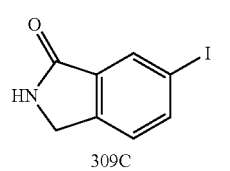

309C

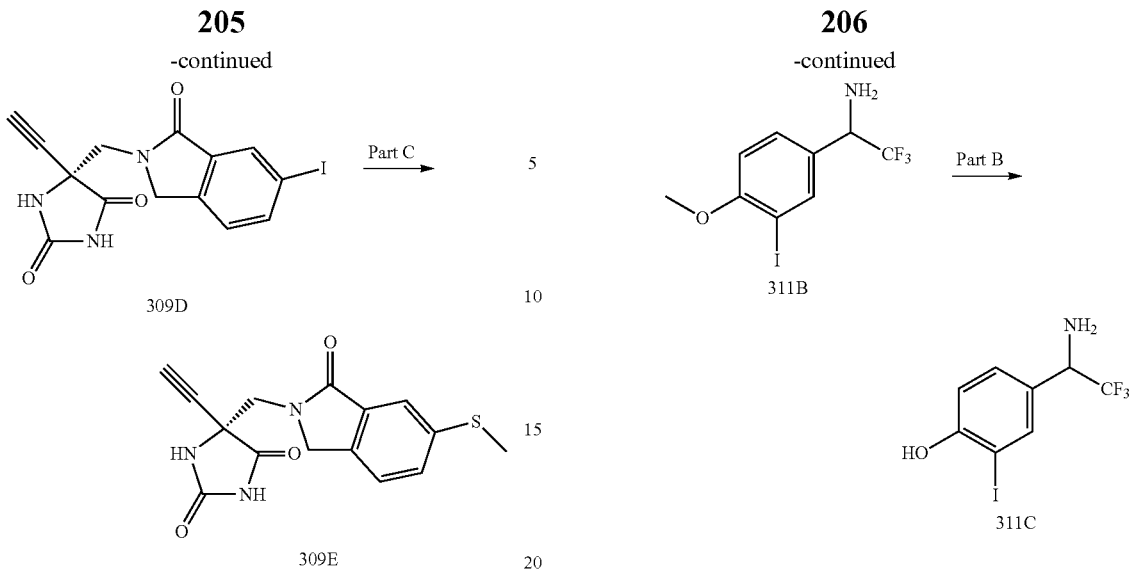

Part A

Compound 309A (4.96 g, 20 mmol) and compound 309B (3.72 g, 21 mmol) were suspended in concentrated sulfuric acid (20 mL) and heated at 55° C. for 3 hours, then at 90° C. for 3 hours. The reaction mixture was cooled to room temperature, poured into ice-water (150 mL), and filtered. The solid was washed with water, 3% ammonium hydroxide, dried, and heated in EtOH (30 mL) at 70° C. for 1 hour. The mixture was cooled to room temperature, filtered and a yellow solid 309C (2.87 g, 55%) was obtained. HPLC-MS $t_R$=1.39 min (UV 254 nm); mass calculated for formula $C_8H_6INO$ 258.95, observed LCMS m/z 260.0 (M+H).

Part B

Compound 309D was prepared according to the procedures described in Example 1 part D and part E, and Example 2 part E, part F and part G. HPLC-MS $t_R$=1.39 min (UV$_{254\ nm}$); mass calculated for formula $C_{14}H_{10}IN_3O_3$ 394.98, observed LCMS m/z 396.0 (M+H).

Part C

A mixture of 309D (100 mg, 0.25 mmol), Pd(dppf)$_2$Cl$_2$ (11 mg) and methyl tributylstannyl sulfide (94 mg, 0.28 mmol) was heated at 130° C. in the microwave for 15 minutes. The reaction mixture was concentrated and purified by reverse phase chromatography to afford 309E (55 mg) as a pale yellow powder after lyophilization. HPLC-MS $t_R$=1.17 min (UV$_{254\ nm}$); mass calculated for formula $C_{15}H_{13}N_3O_3S$ 315.07, observed LCMS m/z 316.1 (M+H).

Example 15

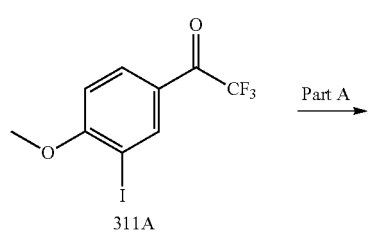

Part A

To 311A (356 mg, 1.08 mmol) in toluene (6 mL) was added LiHMDS (1.2 mL, 1.2 mmol) dropwise. After 15 min, borane-THF (2.2 mL, 2.2 mmol) was added. The resulting mixture was stirred for 20 min, cooled to 0° C., 2N NaOH solution (3 mL) was added. After 90 min at room temperature, the mixture was diluted with EtOAc, separated and the organic layer was washed with 2N NaOH, water, brine, dried and concentrated to give a crude oil which was purified by column chromatography (10% to 50% EtOAc in hexane) to give 311B (328 mg).

Part B

To compound 311B (328 mg, 0.99 mmol) in dichloromethane (5 mL) was added boron tribromide (3.5 mL) and the mixture was stirred at room temperature overnight. The reaction mixture was diluted with ethyl acetate, washed with water, brine, dried and concentrated to give 311C (77 mg). HPLC-MS $t_R$=0.85 min (UV$_{254\ nm}$); mass calculated for formula $C_8H_7F_3INO$ 316.97, observed LCMS m/z 318.0 (M+H).

Compound 311 was prepared from 311C using procedures similar to those described in Example 6.

Example 16

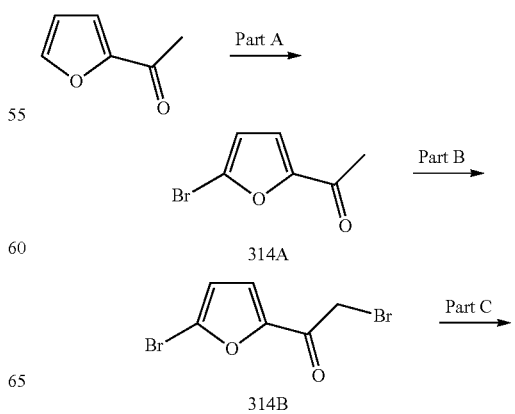

-continued

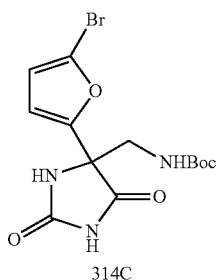

314C

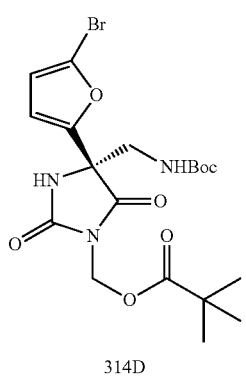

314D

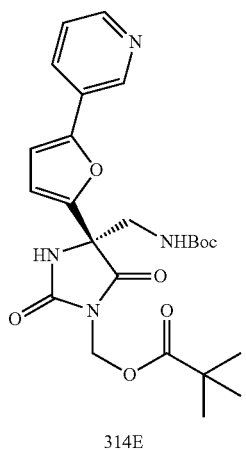

314E

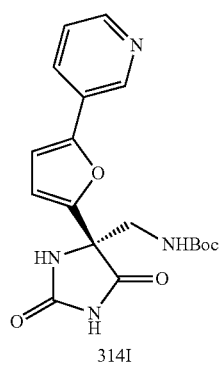

314I

Part D →

Part E →

Part H →

Part I
314H →

-continued

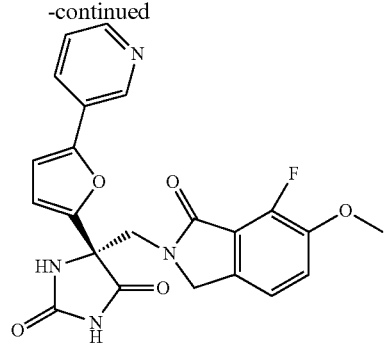

314

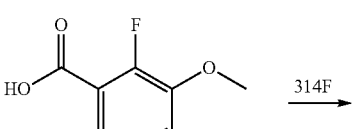

314F

314F →

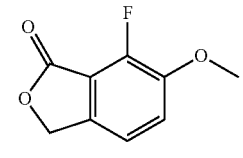

314G

314G →

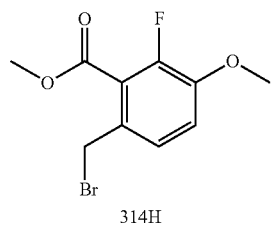

314H

Part A

A mixture of 2-acetylfuran (2.5 g, 22.7 mmol) and N-bromosuccinimide (4.45 g, 25 mmol) in DMF (15 mL) was stirred at room temperature overnight, poured into ice and extracted with ether (×3). The combined organic layers were washed with water, brine, dried and concentrated to give 314A (3.36 g).

Part B

Compound 314A (6.4 g, 34 mmol) was dissolved in 1,4-dioxane (12 mL) and ether (24 mL), cooled to 0° C., and bromine (1.75 mL, 34 mmol) was added slowly over 45 minutes. The resulting mixture was warmed to room temperature and saturated ammonium chloride was added after 2 hours. The aqueous layer was extracted with $CH_2Cl_2$ (×3), and the combined organic layers were washed with brine, dried and concentrated to give a brown oil 314B (11 g), which was used directly in the next step without purification.

Part C

Compound 314C was prepared in a similar manner as described in Yu, W. et. al (WO2007/084415 A2). HPLC-MS $t_R$=1.55 min ($UV_{254\ nm}$); mass calculated for formula $C_{13}H_{16}BrN_3O_5$ 373.03, observed LCMS m/z 396.0 (M+Na).

Part D

Compound 314C (3.26 g, 8.74 mmol), chloromethyl pivalate (1.31 g, 9.18 mmol) and potassium carbonate (1.45 g, 10.5 mmol) were stirred in DMF (5 mL) at room temperature overnight. The mixture was diluted with ethyl acetate, washed with water (×3), brine, dried, concentrated and purified by column chromatography (0 to 50% EtOAc in hexane)

to give the racemate of 314D (2.5 g). The two isomers were separated using a chiral OD column. One gram of material was injected into the column and the two peaks were separated by using a solvent mixture of 85% hexanes/ethanol. The second isomer was the desired compound 314D (440 mg, 88%).

Part E

Compound 314E was prepared according to the procedures described in Yu, W. et. al (WO2007/084415 A2). HPLC-MS $t_R$=1.76 min (UV$_{254\ nm}$); mass calculated for formula $C_{24}H_{30}N_4O_7$ 486.21, observed LCMS m/z 487.1 (M+H).

Part F

Compound 314F (500 mg, 2.94 mmol) and paraformaldehyde (1.6 g) were heated at 100° C. in acetic acid (5 mL) for 3 days. After removal of the acetic acid, the residue was dissolved in ethyl acetate, washed with saturated NaHCO$_3$, water, brine, dried and concentrated to give 314G (285 mg) as a white solid. $^1$H NMR (400 MHz, CD$_3$OD): δ 7.53 (m, 1H), 7.32 (m, 1H), 5.29 (s, 2H), 3.94 (s, 3H).

Part G

Compound 314H was prepared according to the procedures described in Yu, W. et. al (WO2007/084415 A2). $^1$H NMR (400 MHz, CDCl$_3$): δ 7.26 (m, 1H), 6.97 (m, 1H), 4.62 (s, 2H), 3.90 (s, 3H).

Part H

Compound 314E (112 mg, 0.23 mmol) in methanol (3 mL) and saturated ammonium hydroxide solution (3 mL) was stirred at room temperature overnight. The solvent was removed to give a crude 314I. HPLC-MS $t_R$=1.11 min (UV$_{254\ nm}$); mass calculated for formula $C_{18}H_{20}N_4O_5$ 372.14, observed LCMS m/z 373.1 (M+H).

Part I

Compound 314 was prepared from 314I and 314H according to the procedures described in Yu, W. et. al (WO2007/084415 A2). HPLC-MS $t_R$=0.92 min (UV$_{254\ nm}$); mass calculated for formula $C_{22}H_{17}FN_4O_5$ 436.12, observed LCMS m/z 437.1 (M+H).

Compound 310 was prepared using procedures similar to those described in Example 16.

Compounds 312 and 313 were prepared from 314D and 314H using procedures similar to those described in Example 16, followed by hydrogenation to remove the bromine.

Example 17

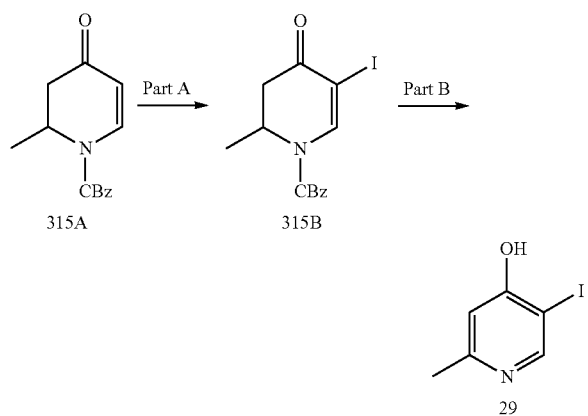

Part A

Compound 315A (245 mg, 1.0 mmol) (Kitagawa, H. et al. *Bioorg. Chem. Lett.*, 2007, 15, 1106-1116) and N-iodosuccinimide (225 mg, 1.0 mmol) were stirred in acetonitrile (5 mL) at room temperature overnight. After the removal of solvent, the crude was purified by column chromatography (0 to 50% EtOAc in hexane) to give 315B (320 mg). $^1$H NMR (400 MHz, CDCl$_3$): δ 8.25 (bs, 1H), 7.40 (m, 5H), 5.30 (m, 2H), 4.78 (m, 1H), 2.93 (dd, J=16.4 Hz, 6.8 Hz, 1H), 2.64 (d, J=16.4 Hz, 1H), 1.26 (d, J=6.8 Hz, 3H).

Part B

Compound 29 was prepared from compound 315B according to the procedures described in Kitagawa. H. et al. (*Bioorg. Chem. Lett.*, 2007, 15, 1106-1116). HPLC-MS $t_R$=0.43 min (UV$_{254\ nm}$); mass calculated for formula $C_6H_6INO$ 234.95, observed LCMS m/z 236.1 (M+H). $^1$H NMR (400 MHz, CD$_3$OD): δ 8.17 (s, 1H), 6.26 (s, 1H), 2.29 (s, 3H).

Compound 2258 was prepared from compound 29 using a procedure similar to that described in Example 6, Part F.

Example 18

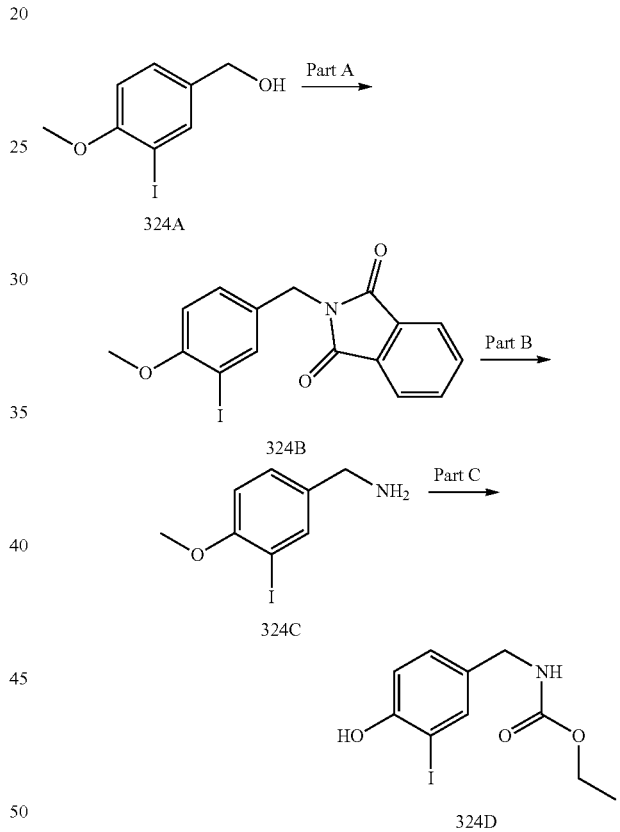

Part A

To compound 324A (1 g, 4.06 mmol), triphenylphosphine (2.0 g, 7.72 mmol), and phthalimide (657 mg, 4.47 mmol) in THF (30 mL) was added DIAD (1.56 g, 732 mmol) and the resulting mixture was stirred at room temperature overnight. The solvent was removed and the residue was diluted with Et$_2$O, filtered and filtrate was concentrated to give a crude oil, which was purified by column chromatography to give 324B (521 mg).

Part B

Compound 324B (515 mg, 1.31 mmol) was stirred in hydrazine monohydrate (5 mL) at room temperature overnight. After removal of the hydrazine, the residue was suspended in Et$_2$O, filtered, washed with Et$_2$O, and the filtrate concentrated to give 324C (372 mg). $^1$H NMR (400 MHz, CD₃OD): δ 7.78 (d, J=2.4 Hz, 1H), 7.33 (dd, J=8.4, 2.4 Hz, 1H), 6.91 (d, J=8.4 Hz, 1H), 3.84 (s, 3H), 3.74 (s, 2H).

Part C

To compound 324C (190 mg, 0.722 mmol) in dichloromethane (2 mL) were added triethylamine (0.2 mL) and ethyl chloroformate (0.1 mL). The resulting mixture was stirred at room temperature for 30 minutes, diluted with EtOAc, washed with brine, dried and concentrated. The residue was purified by column chromatography (30% to 50% EtOAc in hexane) to give the methyl ether of 324D (119 mg).

The compound obtained above was suspended in dichloromethane (3 mL) at 0° C. and BBr₃ (0.8 mL) was added. The reaction mixture was stirred at room temperature overnight, diluted with dichloromethane, washed with water, brine, dried and concentrated to give 324D (90 mg). HPLC-MS $t_R$=1.56 min (UV$_{254\ nm}$); mass calculated for formula $C_{10}H_{12}INO_3$ 320.99, observed LCMS m/z 322.0 (M+H).

Compound 324 was prepared from compound 324D using procedures similar to those described in Example 6.

Compounds 325 and 326 were prepared from compound 324 using standard protecting group chemistry followed by treatment with the appropriate isocyanates.

Example 19

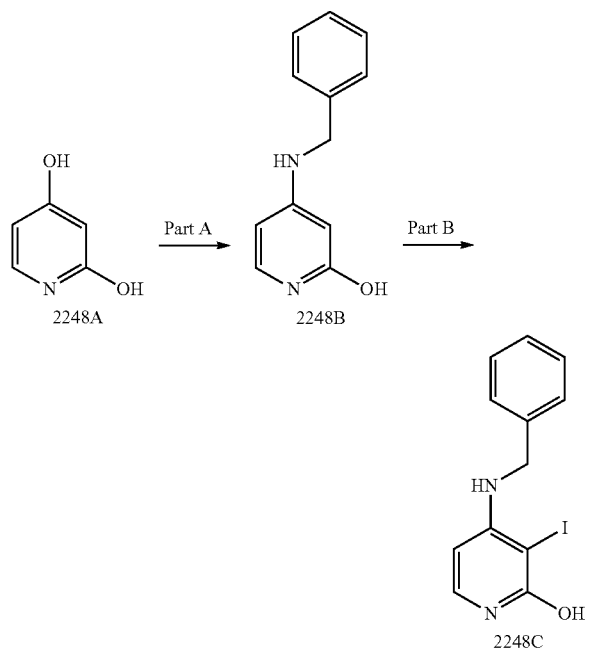

Part A:

Compound 2248B was prepared from commercially available 2248A as described in *Synthesis* 1984, 765-766, as a white solid (77%); HPLC-MS $t_R$=0.98 min (UV$_{254\ nm}$); mass calculated for formula $C_{12}H_{12}N_2O$ 200.09, observed LCMS m/z 201.1 (M+H).

Part B:

Compound 2248C was prepared from 2248B and NIS via a previously described procedure (Yu, W. et al WO2007084415(A2)); HPLC-MS $t_R$=1.27 min (UV$_{254\ nm}$); mass calculated for formula $C_{12}H_{11}IN_2O$ 325.99, observed LCMS m/z 327.0 (M+H).

Compound 2248 was prepared using the procedures described in Example 19 and procedures similar to those described in Example 52, Part D.

Example 20

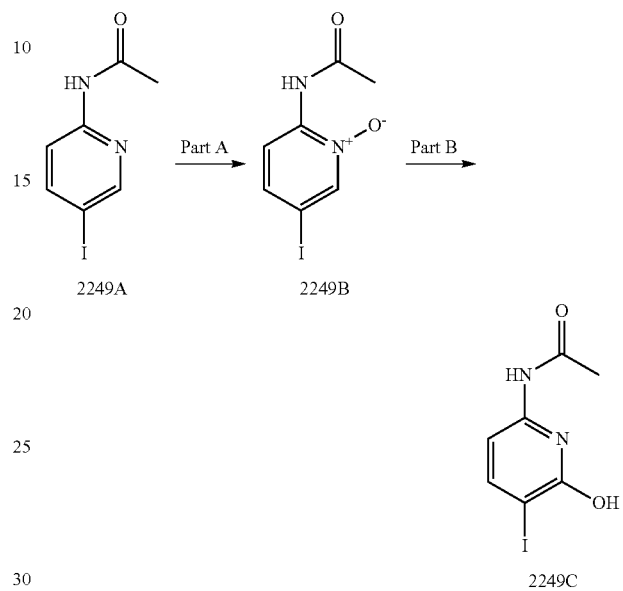

Part A:

Compound 2249B was prepared from commercially available 2249A as described in *Tetrahedron Lett.* 2002, 3121-3123; HPLC-MS $t_R$=0.87 min (UV$_{254\ nm}$); mass calculated for formula $C_7H_7IN_2O_2$ 277.96, observed LCMS m/z 279.0 (M+H).

Part B:

Compound 2249C was prepared from 2249B via a previously described procedure (*Tetrahedron Lett.* 2002, 3121-3123); HPLC-MS $t_R$=0.80 min (UV$_{254\ nm}$); mass calculated for formula $C_7H_7IN_2O_2$ 277.96, observed LCMS m/z 279.0 (M+H).

Compound 2249 was prepared using the procedures described in Example 20 and procedures similar to those described in Example 52, Part D.

Example 21

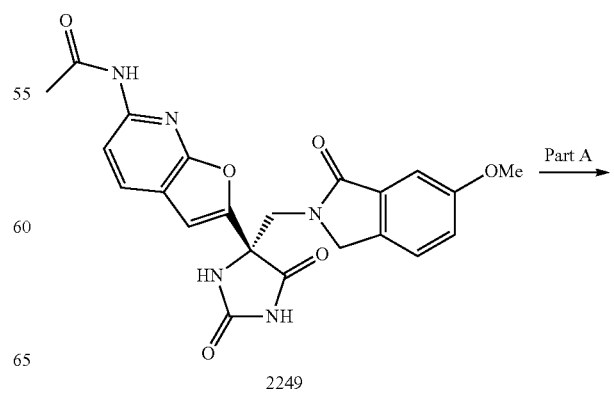

-continued

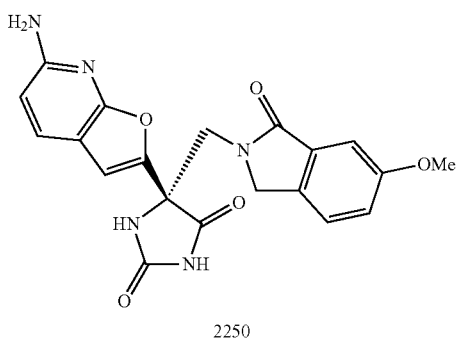

2250

Part A:

Into an ACE epoxy-coated pressure bottle was added 2249 (37 mg, 0.082 mmol), 4M HCl in 1,4-Dioxane (1.5 mL, 6 mmol) and MeOH (1.5 mL) and the mixture was heated at 80° C. overnight. The reaction mixture was concentrated and purified by reverse phase chromatography, followed by lyophilization and salt exchange (HCl) to afford 2250 (26 mg) as a beige solid; HPLC-MS $t_R$=1.04 min (UV$_{254\ nm}$); mass calculated for formula $C_{20}H_{17}N_5O_5$ 407.12, observed LCMS m/z 408.1 (M+H).

Example 22

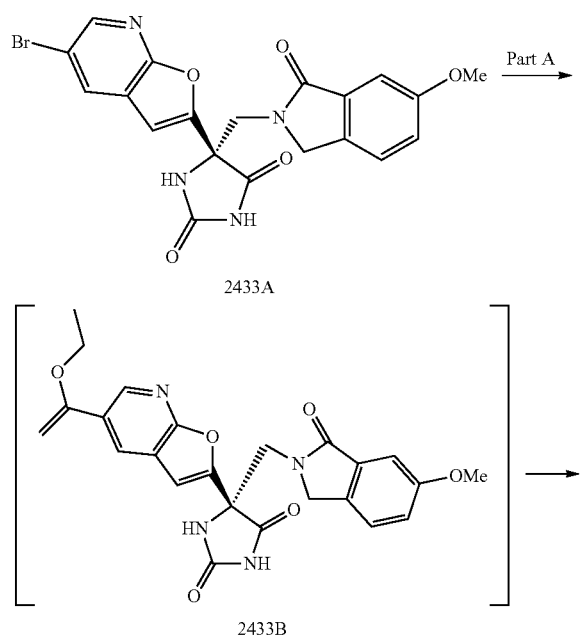

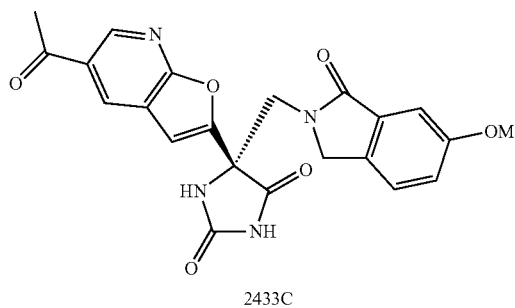

Part A:

In a Biotage microwave vial was added 2433 A (WO2007084415(A2)) (200 mg, 0.42 mmol), tributyl(1-ethoxyvinyl)tin (0.29 mL, 0.85 mmol), Pd(dppf)Cl$_2$ (34 mg, 0.042 mmoL) and DMF (5 mL) and the mixture was heated at 140° C. in the microwave for 20 min when LC-MS showed intermediate 2433B. Then 6M HCl (3 mL) was added and the mixture was stirred at rt for 1 h. The reaction mixture was concentrated and purified by reverse phase chromatography, followed by lyophilization and salt exchange (HCl) to afford 2433C (80 mg) as a beige solid; HPLC-MS $t_R$=1.19 min (UV$_{254\ nm}$); mass calculated for formula $C_{22}H_{18}N_4O_6$ 434.12, observed LCMS m/z 435.1 (M+H).

Compounds 2254-2255 were prepared from 2433A using procedures that were similar to those described in Example 35, Part D.

Example 23

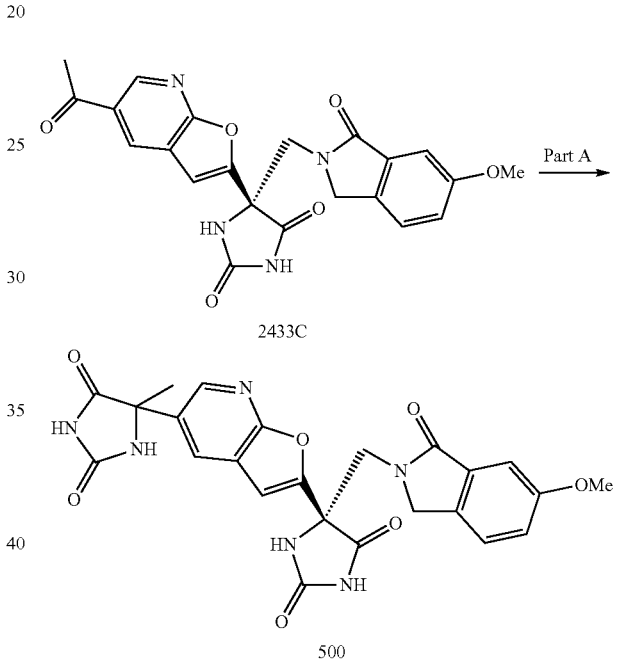

Compound 500 was prepared from 2433C via a previously described procedure (Lavey, B. J. et al WO2007084451 (A1)); HPLC-MS $t_R$=1.15 min (UV$_{254\ nm}$); mass calculated for formula $C_{24}H_{20}N_6O_7$ 504.14, observed LCMS m/z 505.1 (M+H).

Example 24

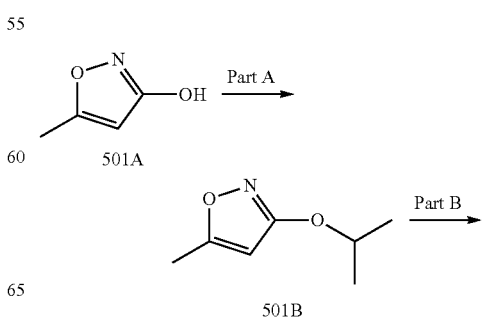

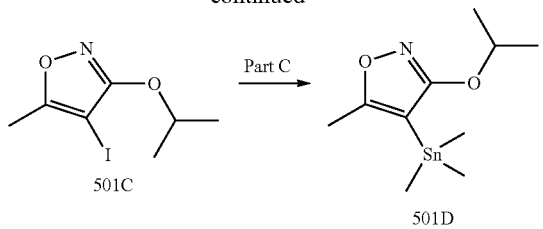

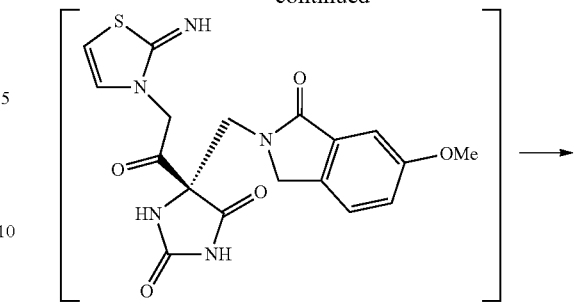

Part A:

In a round bottom flask was added 501A (5.0 g, 50 mmol), K$_2$CO$_3$ (9.1 g, 66 mmol) and DMF (60 mL) and the mixture was stirred at rt for 20 min. Then 2-iodopropane was added (6.0 mL, 60 mmol) and mixture was heated at 75° C. overnight. The reaction mixture was concentrated, extracted with ethyl acetate, washed with water, brine and concentrated to an oil, which was purified by column chromatography (SiO$_2$, ethyl acetate/hexanes) to afford 501B as an oil (1.43 g; 20%); HPLC-MS t$_R$=1.16 min (UV$_{254\ nm}$); mass calculated for formula C$_7$H$_{11}$NO$_2$ 141.08, observed LCMS m/z 142.1 (M+H).

Part B:

In a round bottom flask was added 501B (1.42 g, 10 mmol), acetic acid (20 mL), followed by NIS (2.26 g, 10 mmol) and sulfuric acid (0.25 mL) and the mixture was stirred at rt overnight. The reaction mixture was concentrated, taken in ethyl acetate, washed with saturated sodium bicarbonate solution, 5% sodium thiosulfate solution, brine and concentrated to an oil, which was purified by column chromatography (SiO$_2$, 30-70% ethyl acetate/hexanes) to afford 501C as an oil (2.12 g; 79%); HPLC-MS t$_R$=1.51 min (UV$_{254\ nm}$); mass calculated for formula C$_7$H$_{10}$INO$_2$ 266.97, observed LCMS m/z 268.0 (M+H).

Part C:

In a Biotage microwave vial was added 501C (0.6 g, 2.0 mmol), hexamethylditin (2.9 g, 9 mmol), Pd(PPh$_3$)$_4$ (290 mg, 0.25 mmol) and 1,2-dimethoxyethane (9 mL) and the mixture was heated at 120° C. in the microwave for 20 min. The reaction mixture was partitioned between ethyl acetate and water. The combined organics were passed through a pad of Celite and concentrated to an oil, which was purified by column chromatography (SiO$_2$, 10-50% ethyl acetate/hexanes) to afford 501D as an oil (0.46 g; 60%); HPLC-MS t$_R$=1.91 min (UV$_{254\ nm}$); mass calculated for formula C$_{10}$H$_{19}$NO$_2$Sn 305.04, observed LCMS m/z 306.1 (M+H).

Compound 501 was prepared via Stille coupling of compound 501D to compound 2433A.

Example 25

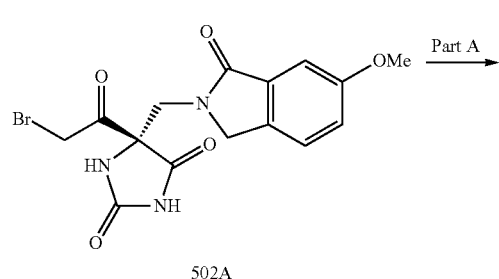

Part A:

Compound 502A was prepared according to procedures previously described ((Yu, W. et al WO2007084415(A2)). In a 40 mL vial was added 502A (406 mg, 0.51 mmol), 2-aminothiazole (67 mg, 0.66 mmol) and acetone (7 mL) and the mixture was heated at 65° C. for 1 h when LC-MS indicated the presence of 502B and traces of 502C. The mixture was concentrated to a solid residue, taken in ethanol (9 mL) and treated with 2 M HCl solution (4.5 mL) and then heated at 80° C. for 1 h, when LC-MS showed only 502C. The mixture was concentrated and purified by column chromatography (SiO$_2$, 3-20% methanol/DCM), followed by reverse phase chromatography, and lyophilization/salt exchange (HCl) to afford 502C (42 mg, 21%) as a solid; HPLC-MS t$_R$=2.14 min (UV$_{254\ nm}$; 10 min); mass calculated for formula C$_{18}$H$_{15}$N$_5$O$_4$S 397.08, observed LCMS m/z 398.0 (M+H).

Compound 503 was prepared using procedures similar to those described in Example 25.

Example 26

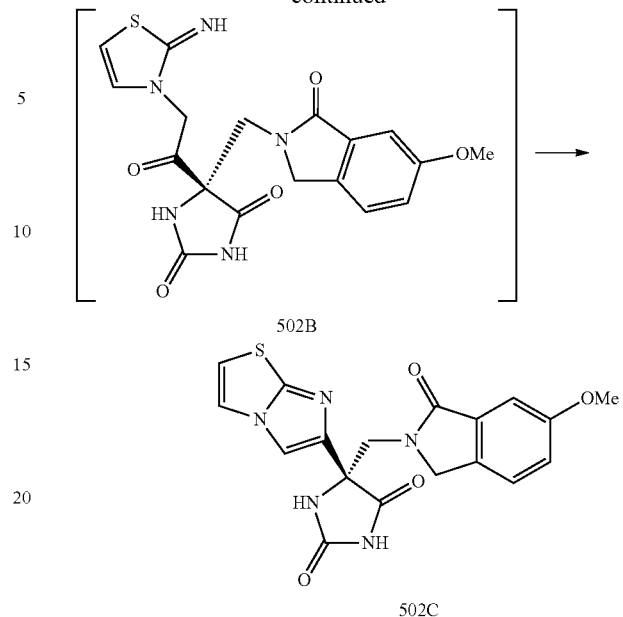

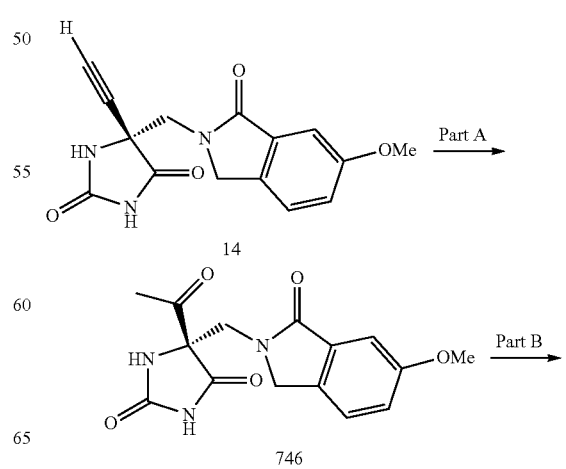

-continued

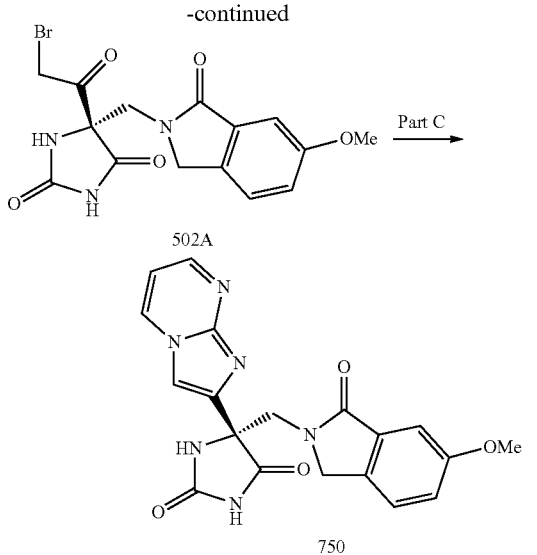

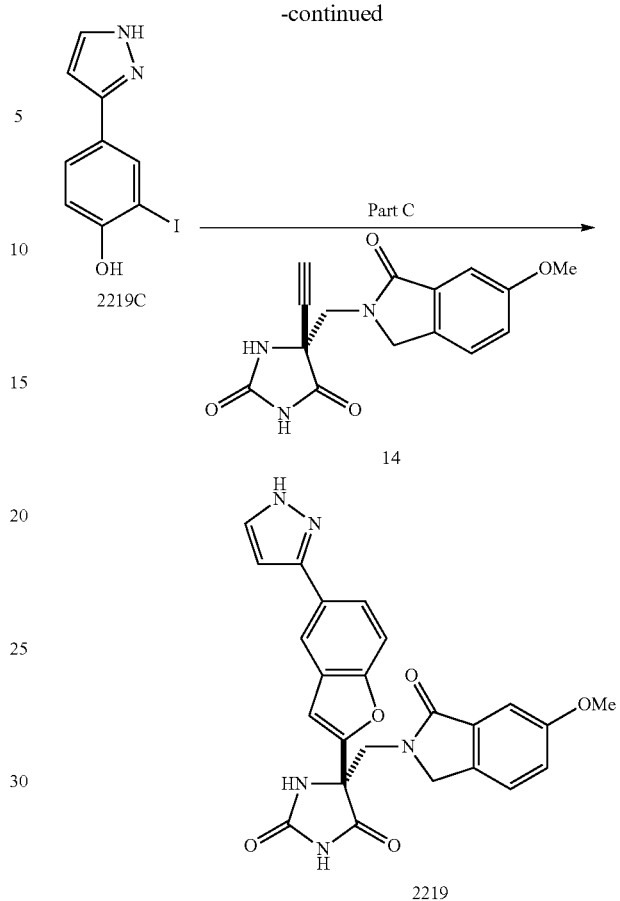

Part A:

Compound 14 (900 mg, 3.33 mmol), and HgO (200 mg) were dissolved in a solution of sulfuric acid (0.4 mL), methanol (5 mL) and water (3 mL) and stirred at 80° C. for 3 hours. The solids were filtered and discarded. The solution was diluted with water and ethyl acetate. The organic layer was dried over sodium sulfate and concentrated to provide compound 746 (750 mg).

Part B:

Compound 746 (306 mg, 0.96 mmol) and bromine (153 mg, 0.96 mmol) were dissolved in acetic acid (5 mL) and stirred for 2 hours at 50° C. The solvent was evaporated to provide compound 502A (380 mg). HPLC-MS $t_R$=1.11 min (UV$_{254\,nm}$); mass calculated for formula C15H14BrN3O5 395.0, observed LCMS m/z 396.0 (M+H).

Part C:

Compound 502A (198 mg, 0.5 mmol) and 2-aminopyrimidine (71 mg, 0.75 mmol) were dissolved in ethanol (5 mL) and refluxed for 2 hours. The solvent was evaporated and the residue was purified by reverse phase chromatography to provide compound 750 (62 mg). HPLC-MS $t_R$=0.87 min (UV$_{254\,nm}$); mass calculated for formula $C_{19}H_{16}N_6O_4$ 392.1, observed LCMS m/z 393.1 (M+H). $^1$H NMR (400 MHz, DMSO): δ 11.1 (s, 1H), 9.1 (m, 1H), 8.95 (m, 1H), 8.75 (m, 1H), 8.1 (m, 1H), 7.5 (m, 1H), 7.23 (m, 1H), 7.2 (m, 3H), 4.3 (m, 4H), 3.8 (s, 3H).

Example 27

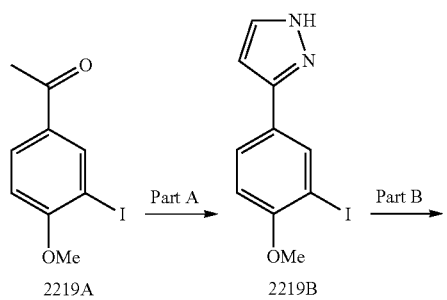

Part A:

Compound 2219A (1.5 g, 5.43 mmol) and 1-tert-butoxy-N,N,N',N'-tetramethylmethanediamine (2 mL) were dissolved in 1,2-dimethoxyethane (10 mL) and stirred at 80° C. for 4 hours. The solvent was removed under reduced pressure. The residue was dissolved in ethanol (20 mL) and treated with sodium carbonate (1 g) and hydrazine monohydrate (2 mL). The resulting mixture was stirred at 80° C. for 2 hours and then quenched with water and extracted with ethyl acetate. The combined organic layers were dried over sodium sulfate and concentrated under reduced pressure to provide compound 2219B (1.5 g).

Part B:

Compound 2219B (500 mg, 1.66 mmol) was dissolved in methylene chloride (5 mL) and treated with 1M BBr$_3$ (5 mL). The reaction was stirred overnight at room temperature and then quenched with water and extracted with ethyl acetate. The combined organic layers were dried over sodium sulfate and concentrated to provide compound 2218C (400 mg). $^1$H NMR (400 MHz, DMSO): δ 10.4 (bs, 1H), 8.0 (s, 1H), 7.8 (m, 2H), 6.9 (m, 1H), 6.6 (m, 1H).

Part C:

The reaction was performed in a similar manner to Example 6, Part F. HPLC-MS $t_R$=1.40 min (UV$_{254\,nm}$); mass calculated for formula C24H19N5O5 457.2, observed LCMS m/z 458.2 (M+H). $^1$H NMR (400 MHz, DMSO): δ 11.2 (s, 1H), 8.8 (m, 1H), 8.0 (m, 1H), 7.9-7.5 (m, 4H), 7.5-7.4 (m, 1H), 7.2 (m, 2H), 6.75 (m, 1H), 4.5-4.25 (m, 4H), 3.8 (s, 3H).

Example 28

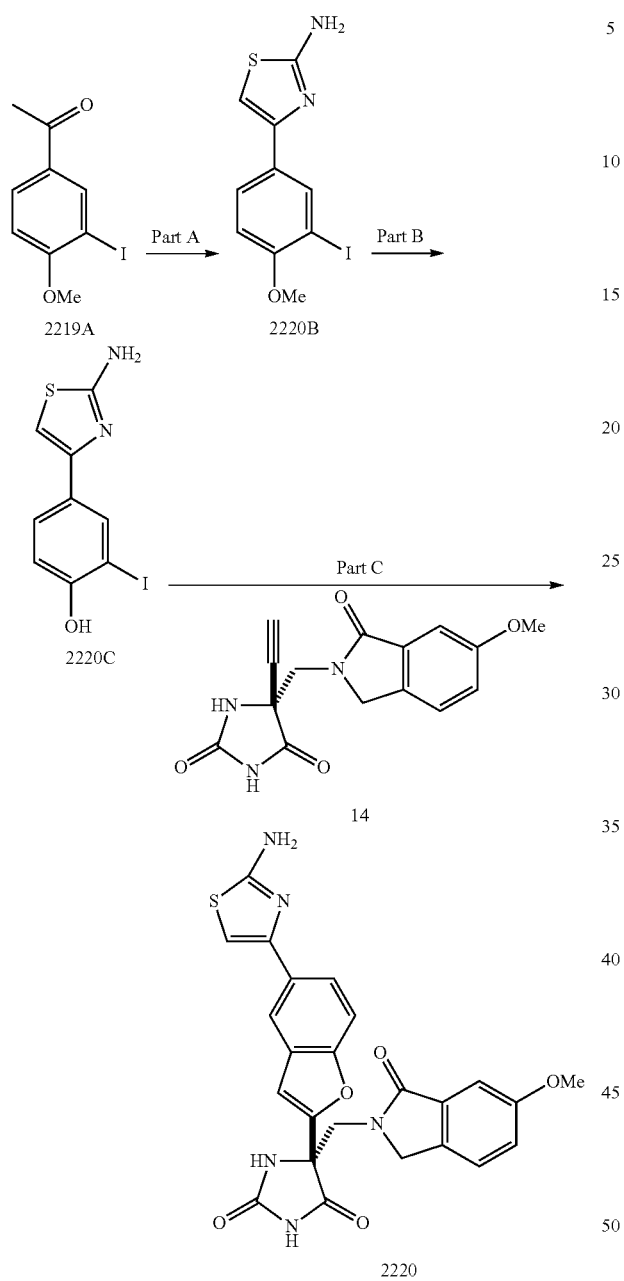

Part A:
Compound 2219A (2.0 g, 7.2 mmol) was dissolved in chloroform (100 mL) and bromine (1.16 g, 7.2 mmol). The reaction was stirred at room temperature overnight and then quenched with water. The organic layer was dried over sodium sulfate and concentrated to provide 2.4 g of the bromomethylketone. The bromomethylketone (1.0 g, 2.8 mmol) was dissolved in DMF (15 mL) and treated with thiourea (214 mg, 2.8 mmol). The reaction was stirred at 70° C. for 3 hours and then quenched with water and extracted with ethyl acetate. The combined organic layers were dried over sodium sulfate and concentrated to provide compound 2220B (830 mg).

Part B:
Compound 2220B (400 mg, 1.2 mmol) was dissolved in methylene chloride (5 mL) and treated with 1M BBr$_3$ (5 mL). The reaction was stirred overnight at room temperature and then quenched with water and extracted with ethyl acetate. The combined organic layers were dried over sodium sulfate and concentrated to provide compound 2219C (200 mg).

Part C:
The reaction was performed in a similar manner to Example 6, Part F. HPLC-MS $t_R$=1.26 min (UV$_{254\,nm}$); mass calculated for formula C$_{24}$H$_{19}$N$_5$O$_5$S 489.1, observed LCMS m/z 490.1 (M+H). $^1$H NMR (400 MHz, DMSO): δ 11.2 (s, 1H), 8.8 (s, 1H), 8.1 (s, 1H), 7.75 (m, 2H), 7.5 (m, 1H), 7.2 (m, 3H), 4.5-4.3 (m, 4H), 3.8 (s, 3H).

Example 29

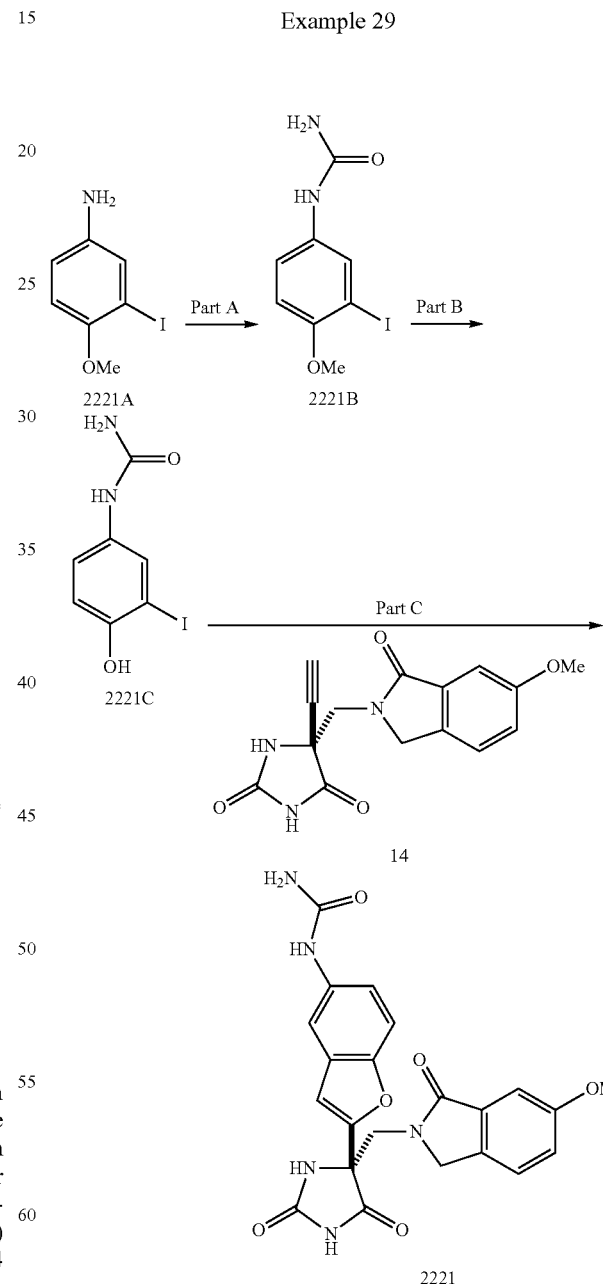

Part A:
Compound 2221A (250 mg, 1.07 mmol) and TMS-CNO (0.5 mL) were dissolved in pyridine (1 mL) and methylene chloride (10 mL) and stirred overnight. The reaction was quenched with water and extracted with ethyl acetate. The organic layer was dried over sodium sulfate and concentrated. The residue was purified by column chromatography (2% MeOH/ethyl acetate) to provide compound 2221B (85 mg).

Part B:

Compound 2221B (75 mg, 0.26 mmol) was dissolved in methylene chloride (5 mL) and treated with 1M BBr$_3$ (5 mL). The reaction was stirred overnight at room temperature and then quenched with water and extracted with ethyl acetate. The combined organic layers were dried over sodium sulfate and concentrated to provide compound 2221C (70 mg).

Part C:

The reaction was performed in a similar manner to Example 6, Part F. HPLC-MS $t_R$=1.17 min (UV$_{254\ nm}$); mass calculated for formula C22H19N5O6 449.1, observed LCMS m/z 450.2 (M+H). $^1$H NMR (400 MHz, DMSO): δ 11.2 (s, 1H), 8.8 (s, 1H), 8.5 (s, 1H), 7.8 (m, 1H), 7.4-7.3 (m, 2H), 7.2 (m, 3H), 7.0 (m, 1H), 5.8 (bs, 2H), 4.4-4.2 (m, 4H), 3.8 (s, 3H).

Compound 2226 was prepared from 2221 using procedures similar to those described in Example 31, Part C. Compounds 2227-2229 were prepared from compound 2226 via treatment with the corresponding isocyanates.

Example 30

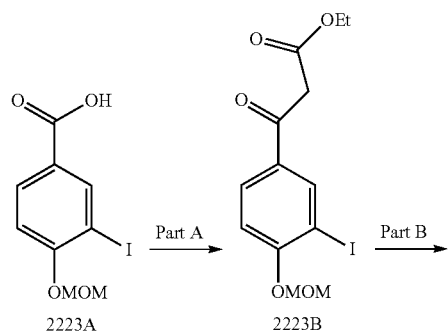

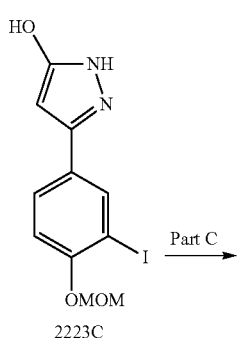

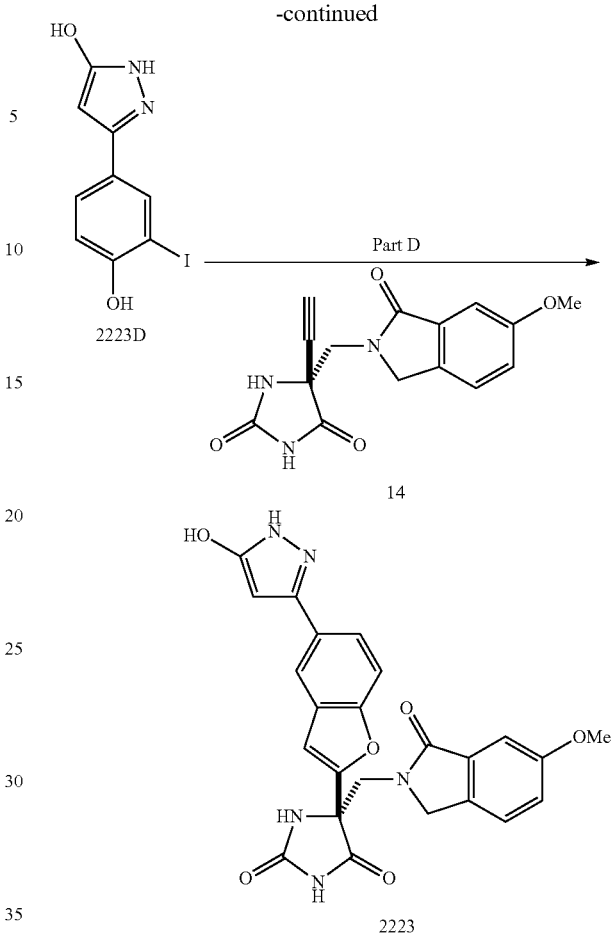

Part A:

Compound 2223A (1.5 g, 4.91 mmol) was dissolved in acetonitrile (30 mL) and CDI (800 mg, 4.91 mmol) was added. In a separate flask potassium ethyl malonate (1.67 g, 9.8 mmol) was suspended in a solution of THF (30 mL) and triethylamine (2.03 mL, 14.7 mmol). The suspension was treated with magnesium chloride (1.16 g, 12.28 mmol) and stirred at 40° C. for 4 hours. The first solution was added dropwise to the suspension at 0° C. and then the reaction was stirred at 40° C. overnight. The reaction was treated with 3 N HCl and extracted with ethyl acetate. The combined organic layers were dried over sodium sulfate and concentrated to provide compound 2223B (1.0 g).

Part B:

Compound 2223B (450 mg, 1.29 mmol), hydrazine monohydrate (0.5 mL), and sodium carbonate (0.5 g) were suspended in ethanol (5 mL) and stirred at 80° C. overnight. The reaction was quenched with 1 N HCl and extracted with ethyl acetate. The combined organic layers were dried over sodium sulfate and concentrated to provide compound 2223C (410 mg).

Part C:

Compound 2223C (85 mg, 0.24 mmol) was dissolved in methanol (7 mL) and concentrated HCl (0.2 mL) and stirred at 70° C. for 2 hours. The solvent was removed under reduced pressure and the residue lyophilized to provide compound 2223D (80 mg). HPLC-MS $t_R$=0.93 min (UV$_{254\ nm}$); mass calculated for formula C9H7N2O2I 302.0, observed LCMS m/z 303.0 (M+H).

Part D:

The reaction was performed in a similar manner to Example 6, Part F. HPLC-MS $t_R$=1.23 min (UV$_{254\,nm}$); mass calculated for formula C24H19N5O6 473.1, observed LCMS m/z 474.2 (M+H). $^1$H NMR (400 MHz, DMSO): δ 11.2 (s, 1H), 8.8 (s, 1H), 7.9 (s, 1H), 7.6 (m, 1H), 7.4 (m, 1H), 7.2 (m, 2H), 5.9 (m, 1H), 4.4-4.2 (m, 4H), 3.8 (s, 3H).

Example 31

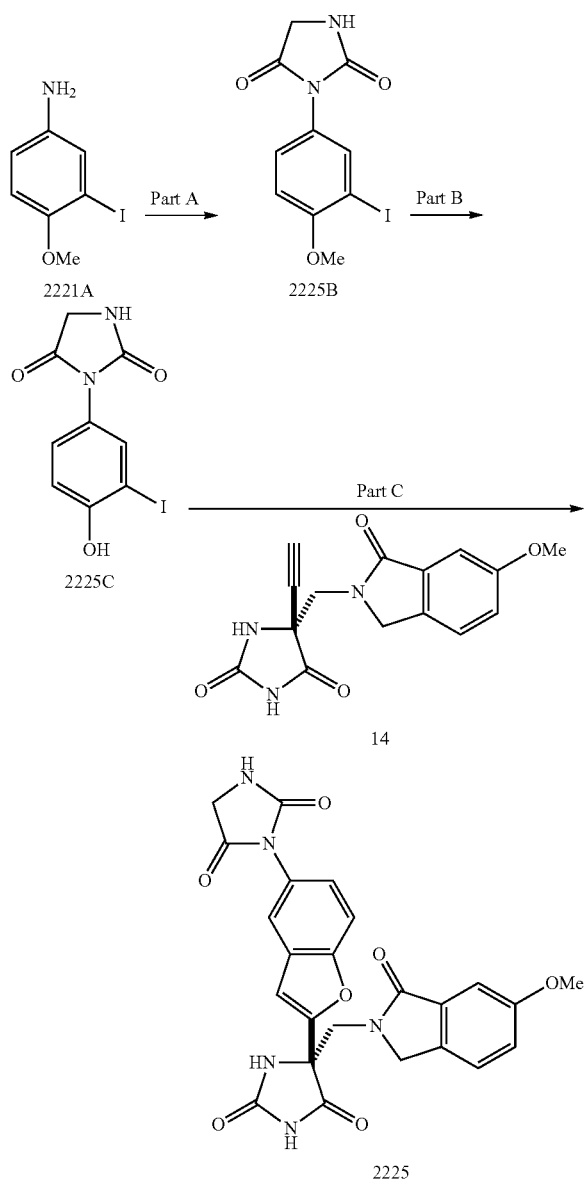

Part A:

Compound 2221A (400 mg, 1.62 mmol) was dissolved in chloroform (15 mL) and ethyl carbonisocyanatidate (222 mg, 1.7 mmol) was added and the reaction was stirred overnight at room temperature. The solvent was removed under reduced pressure and HCl (10 mL) and ethanol (10 mL) were added and the reaction was stirred at 90° C. for 4 hours. The solvent was removed and ethyl acetate and water were added. (Some solids did not dissolve and these were filtered and found to be the product.) The organic layer was dried over sodium sulfate and concentrated to provide 2225B (275 mg).

Part B:

Compound 2225B (275 mg, 0.82 mmol) was dissolved in methylene chloride (5 mL) and treated with 1M BBr$_3$ (5 mL). The reaction was stirred overnight at room temperature and then quenched with water and extracted with ethyl acetate. The combined organic layers were dried over sodium sulfate and concentrated to provide compound 2225C (200 mg).

Part C:

The reaction was performed in a similar manner to Example 6, Part F. HPLC-MS $t_R$=1.05 min (UV$_{254\,nm}$); mass calculated for formula $C_{24}H_{13}N_5O_7$ 489.1, observed LCMS m/z 490.1 (M+H). $^1$H NMR (400 MHz, DMSO): δ 11.2 (s, 1H), 8.8 (s, 1H), 8.3 (s, 1H), 7.7 (m, 1H), 7.6 (m, 1H), 7.5 (m, 1H), 7.25 (m, 1H), 7.2-7.1 (m, 3H), 4.4-4.2 (m, 4H), 3.8 (s, 3H).

Example 32

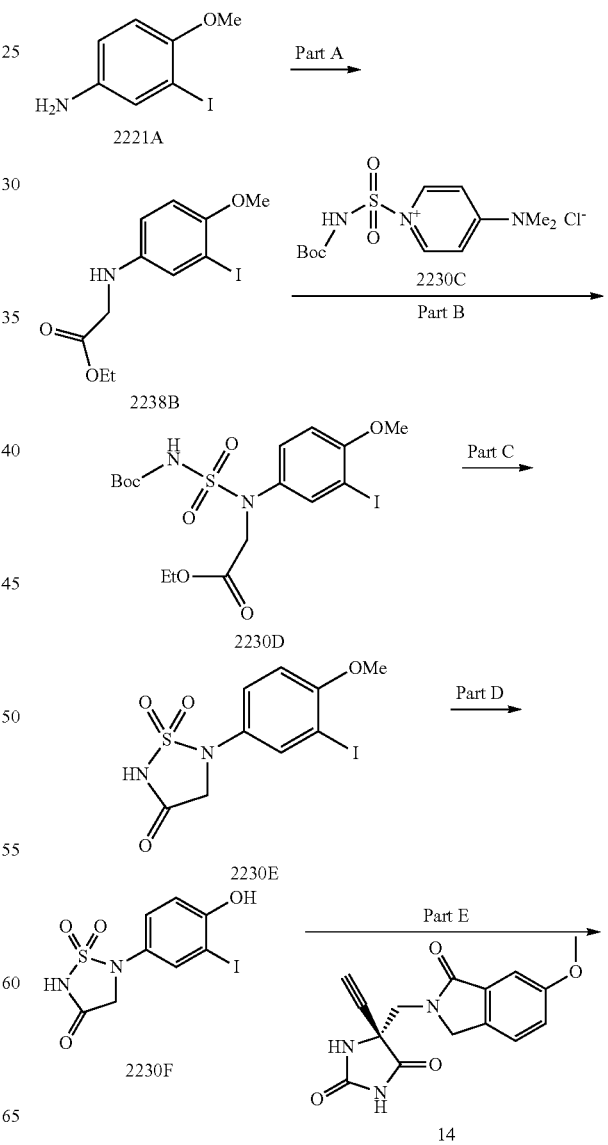

Example 33

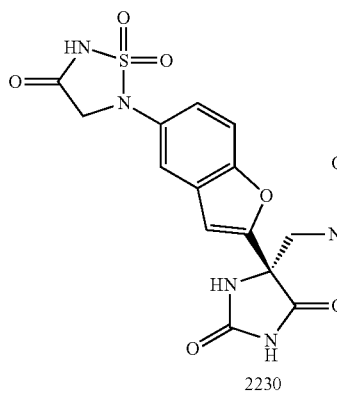
2230

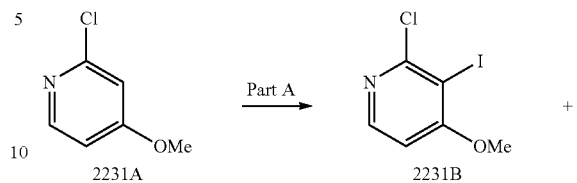
2231A  2231B

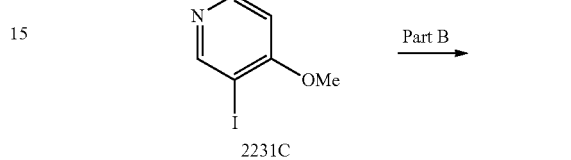
2231C

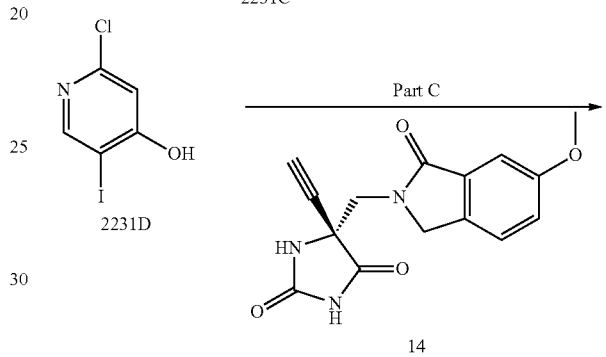
2231D

14

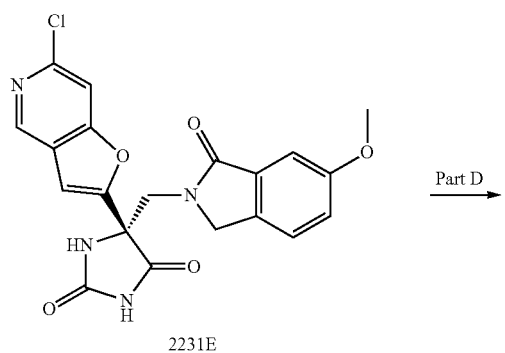
2231E

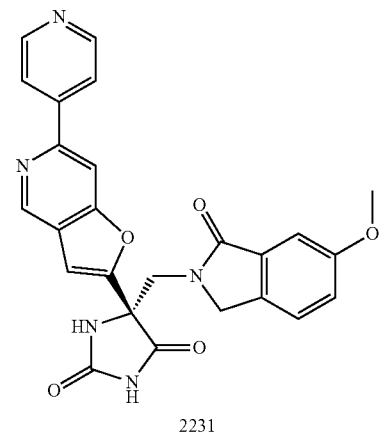
2231

Part A:

Compound 2221A (500 mg, 2.01 mmol) and bromomethyl acetate (305 mg, 2.01 mmol) were dissolved in DMF (5 mL) and diisopropylethylamine (0/2 mL, 4.01 mmol) and stirred at 70° C. overnight. The reaction was quenched with water and extracted with ethyl acetate. The organic layers were dried over sodium sulfate and concentrated to provide compound 2230B (600 mg).

Part B:

Compound 2230B (600 mg, 1.86 mmol) and compound 2230C (628 mg, 1.86 mmol) were dissolved in methylene chloride (5 mL) and pyridine (5 mL) and stirred overnight. The reaction was quenched with 1N HCl and extracted with ethyl acetate. The combined organic layers were dried over sodium sulfate and concentrated to provide 2230D (900 mg).

Part C:

Compound 2230D (462 mg, 0.92 mmol) was dissolved in TFA (3 mL) and methylene chloride (3 mL) and stirred for 2 hours. The solvent was removed under reduced pressure and the residue was dissolved in water and ethyl acetate. The organic layer was dried over sodium sulfate and the concentrated under reduced pressure. The residue was dissolved in THF (6 mL) and treated with 60% NaH (150 mg). The reaction was stirred for 2 hours and then quenched with 1N HCl solution and extracted with ethyl acetate. The organic layer was dried over sodium sulfate and concentrated to provide 2230E (250 mg).

Part D:

Compound 2230E (250 mg, 0.67 mmol) was dissolved in methylene chloride (5 mL) and treated with 1M BBr3 (2 mL). The reaction was stirred overnight at room temperature and then quenched with water and extracted with ethyl acetate. The combined organic layers were dried over sodium sulfate and concentrated to provide compound 2230F (220 mg). $^1$H NMR (400 MHz, DMSO): δ 7.5 (m, 1H), 7.1-7.0 (m, 1H), 6.8 (m, 1H), 4.25 (s, 2H).

Part E:

The reaction was performed in a similar manner to Example 6, Part F. HPLC-MS 10 min $t_R$=2.5 min (UV$_{254\ nm}$); mass calculated for formula $C_{23}H_{19}N_5O_8S$ 525.1, observed LCMS m/z 526.2 (M+H). $^1$H NMR (400 MHz, DMSO): δ 11.2 (s, 1H), 8.8 (s, 1H), 7.5 (m, 1H), 7.4 (m, 1H), 7.3 (m, 1H), 7.2 (m, 1H), 7.2-7.1 (m, 3H), 4.4-4.2 (m, 4H), 3.8 (s, 3H).

Part A:

Compound 2231A (3.15 g, 22.1 mmol), NIS (5.5 g, 24.4 mmol) and triflic acid (25 mL) were stirred for 48 hours. The reaction mixture was added slowly to ice water and then extracted with ethyl acetate. The organic later was washed with brine, dried over sodium sulfate and concentrated. Column chromatography (85:15 hexanes/ethyl acetate) provided compounds 2231B (1.5 g) and 2231C (1.5 g).

Part B:

Compound 2231C (420 mg, 1.56 mmol) was dissolved in methylene chloride (5 mL) and 1 M AlBr$_3$ in dibromomethane (3.0 mL) and stirred at 85° C. in a microwave for 15 minutes. The reaction was quenched slowly with water and the solids were filtered to provide compound 2231D (360 mg). $^1$H NMR (400 MHz, DMSO): δ 8.5 (s, 1H), 6.85 (s, 1H).

Part C:

The reaction was performed in a similar manner to Example 6, Part F. HPLC-MS 10 min $t_R$=3.05 min (UV$_{254\,nm}$); mass calculated for formula $C_{20}H_{15}N_4O_5$ 426.0, observed LCMS m/z 427.0 (M+H).

Part D:

Compound 2231E (80 mg, 0.187 mmol), 4-pyridylboronic acid (48 mg, 0.39 mmol), Pd(dppf)Cl2 (10 mg), and potassium phosphate (110 mg, 0.52 mmol) were dissolved in DMF (3 mL) and stirred at 100° C. for 2 hours. The solvent was removed and the residue was purified by reverse phase chromatography to provide compound 2231 (30 mg). HPLC-MS $t_R$=0.91 min (UV$_{254\,nm}$); mass calculated for formula $C_{25}H_{19}N_5O_5$ 469.1, observed LCMS m/z 470.1 (M+H). $^1$H NMR (400 MHz, DMSO): δ 11.2 (s, 1H), 9.2 (s, 1H), 9.0 (s, 1H), 8.9 (m, 1H), 8.8 (m, 1H), 8.5 (m, 1H), 7.5 (m, 1H), 7.4 (m, 1H), 7.2-7.1 (m, 2H), 4.4-4.2 (m, 4H), 3.8 (s, 3H).

Compounds 2236-2237 were prepared from 2231E using a procedure similar to that described in Example 34, Part D.

Example 34

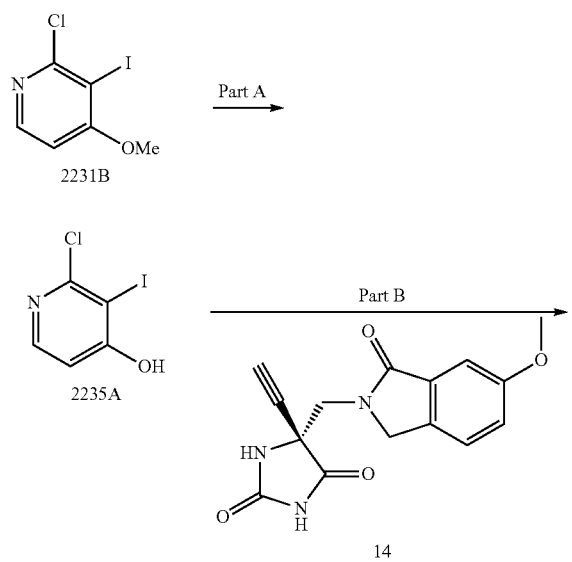

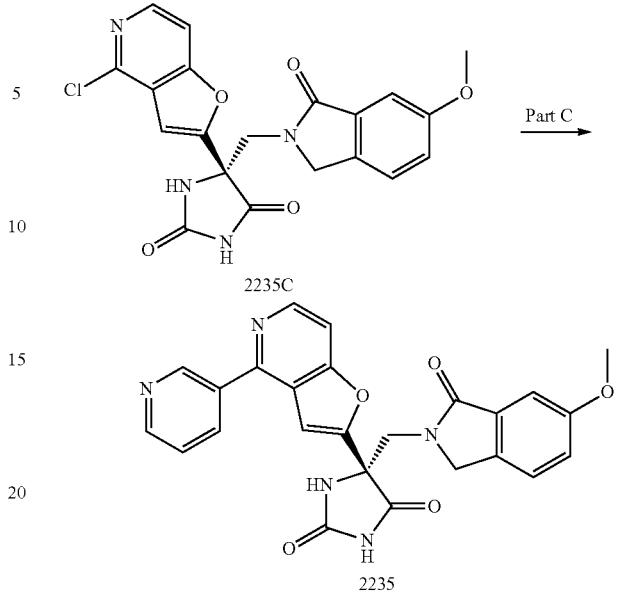

Part A:

Compound 2231B (1.5 g, 5.5 mmol) was dissolved in methylene chloride (5 mL) and 1 M AlBr$_3$ in dibromomethane (10.0 mL) and stirred at 85° C. in a microwave for 15 minutes. The reaction was quenched slowly with water and the solids were filtered to provide compound 2235A (1.25 g).

Part B:

The reaction was performed in a similar manner to Example 6, Part F. HPLC-MS $t_R$=1.42 min (UV$_{254\,nm}$); mass calculated for formula $C_{20}H_{15}N_4O_5$ 426.0, observed LCMS m/z 427.0 (M+H).

Part C:

Compound 2235C (80 mg, 0.187 mmol), 3-pyridylboronic acid pinacol ester (205 mg, 1.0 mmol), Pd(PtBu$_3$)$_2$ (20 mg), and potassium phosphate (400 mg) were dissolved in DMF (3 mL) water (0.5 mL) and stirred at 150° C. for 15 minutes in a microwave. The solvent was removed and the residue was purified by reverse phase chromatography to provide compound 2235 (30 mg). HPLC-MS $t_R$=0.96 min (UV$_{254\,nm}$); mass calculated for formula $C_{25}H_{19}N_5O_5$ 469.1, observed LCMS m/z 470.1 (M+H). $^1$H NMR (400 MHz, DMSO): δ 11.2 (s, 1H), 9.4 (bs, 1H), 9.0 (s, 1H), 8.9 (m, 2H), 8.8 (m, 1H), 8.1 (m, 1H), 8.0 (m, 1H), 7.8 (m, 1H), 7.5 (m, 1H), 7.2-7.1 (m, 2H), 4.4-4.2 (m, 4H), 3.8 (s, 3H).

Compounds 2232-2234 and 2251 were prepared from 2235C using procedures similar to those described in Example 33, Part D.

Compounds 2252-2253 were prepared from 2235C using procedures similar to those described in Example 55.

Example 35

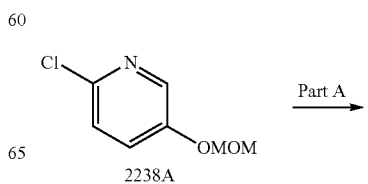

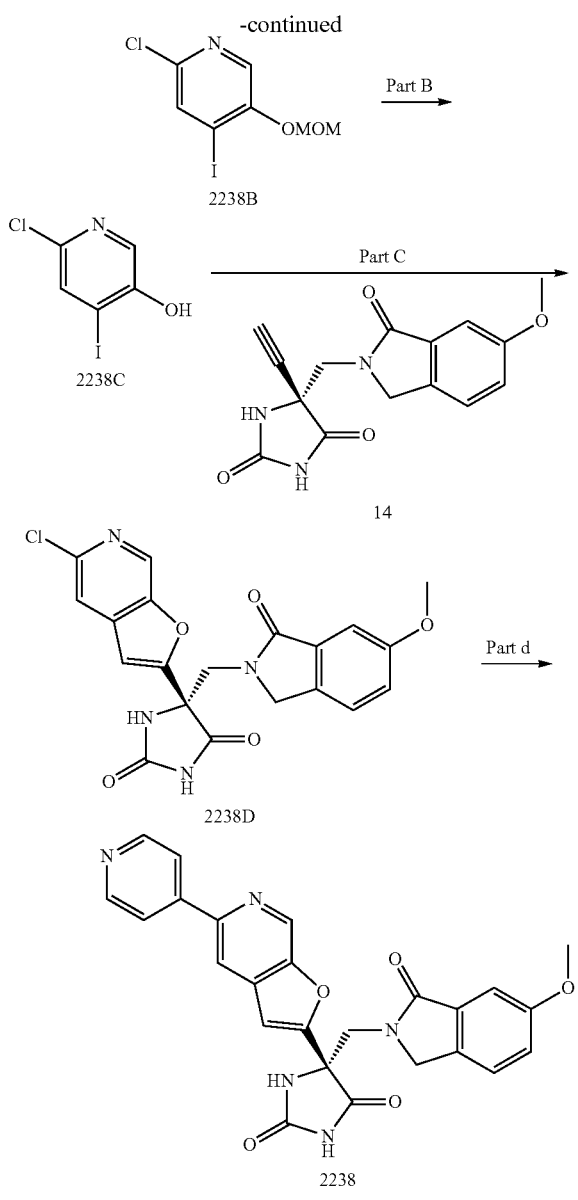

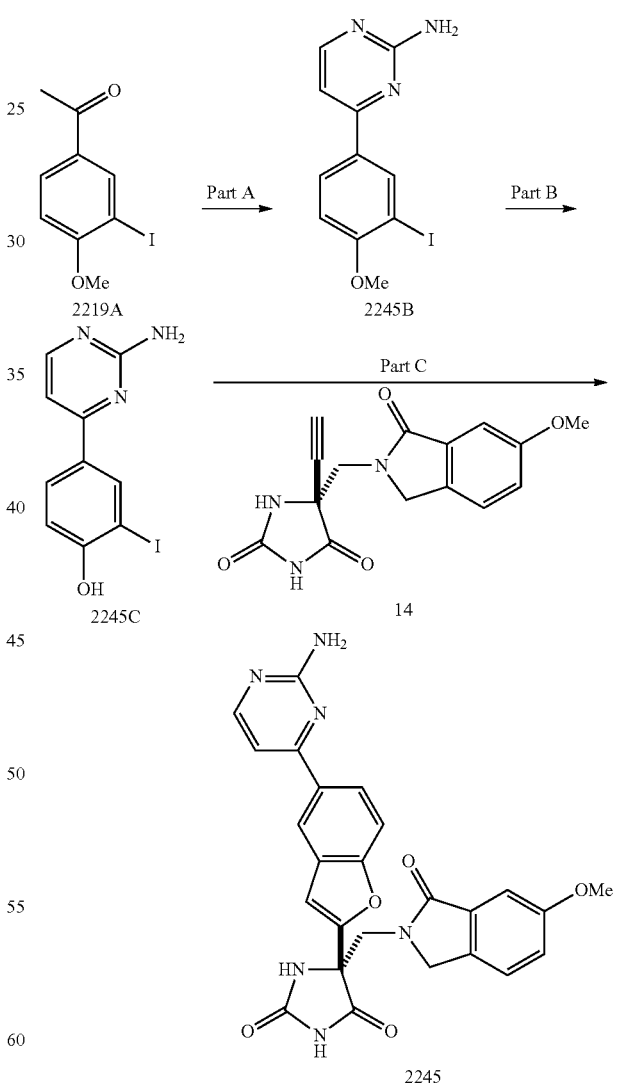

Part D:

Compound 2238D (80 mg, 0.187 mmol), 4-pyridylboronic acid (48 mg, 0.39 mmol), Pd(tBu₃)₂ (15 mg), and potassium phosphate (300 mg) were dissolved in DMF (3 mL) and water (0.5 mL) and stirred at 150° C. for 15 minutes in a microwave. The solvent was removed and the residue was purified by reverse phase chromatography to provide compound 2238 (9.0 mg). HPLC-MS $t_R$=0.88 min (UV$_{254\,nm}$); mass calculated for formula $C_{25}H_{19}N_5O_5$ 469.1, observed LCMS m/z 470.1 (M+H). ¹H NMR (400 MHz, DMSO): δ 11.3 (s, 1H), 9.3 (s, 1H), 9.1 (s, 1H), 9.0 (m, 2H), 8.8 (m, 1H), 8/5 (m, 2H), 7.5 (m, 1H), 7.3 (m, 1H), 7.2-7.1 (m, 2H), 4.4-4.2 (m, 4H), 3.8 (s, 3H).

Compounds 2239-2244 were prepared from 2238D using procedures that were similar to that described in Example 35, Part D.

Example 36

Part A:

Compound 2238A (1.1 g, 6.39 mmol) was dissolved in THF (15 mL) and cooled to −78° C. A solution of 2.5M n-BuLi (2.8 mL, 7.03 mmol) was added dropwise and stirred for 1 hour. A solution of iodine (1.89 g, 7.5 mmol) in THF (10 mL) was added dropwise and stirred for 30 minutes. The reaction was quenched with water and extracted with ethyl acetate. The organic layer was washed with sodium thiosulfate, brine, dried over sodium sulfate and concentrated. The residue was recrystallized from ethyl acetate/hexanes to provide compound 2238B (1.1 g).

Part B:

Compound 2238B (800 mg, 2.6 mmol) was dissolved in methanol (7 mL) and concentrated HCl (0.2 mL) and stirred at 70° C. for 2 hours. The solvent was removed under reduced pressure and the residue lyophilized to provide compound 2238C (500 mg).

Part C:

The reaction was performed in a similar manner to Example 6, Part F. HPLC-MS $t_R$=1.42 min (UV$_{254\,nm}$); mass calculated for formula C20H15N4O5 426.0, observed LCMS m/z 427.0 (M+H).

Part A:

Compound 2219A (1.0 g, 3.63 mmol) was dissolved in 1,2-dimethoxyethane (10 mL) and treated with 1-tert-butoxy-N,N,N',N'-tetramethylmethanediamine (2 mL). After stirring at 90° C. for 3 hours the solvent was removed. The residue was dissolved in ethanol (15 mL) and guanidine carbonate (3.2 g, 18 mmol) was added. The reaction was stirred at 90° C. overnight and then quenched with water and extracted with ethyl acetate. The combined organic layers were dried over sodium sulfate and concentrated to provide compound 2245B that was used without purification (1.1 g).

Part B:

Compound 2245B (550 mg, 1.7 mmol) was dissolved in methylene chloride (10 mL) and 1 M $AlBr_3$ in dibromomethane (4.0 mL) and stirred at 85° C. in a microwave for 30 minutes. The reaction was quenched slowly with water and the solids were filtered to provide compound 2245C (475 mg).

Part C:

The reaction was performed in a similar manner to Example 6, Part F. HPLC-MS $t_R$=1.00 min ($UV_{254\ nm}$); mass calculated for formula $C_{25}H_{20}N_6O_5$ 484.1, observed LCMS m/z 485.0 (M+H). $^1$H NMR (400 MHz, DMSO): δ 11.2 (s, 1H), 8.9 (m, 1H), 8.5 (m, 1H), 8.1 (m, 1H), 7.8 (m, 1H), 7.5 (m, 1H), 7.25 (s, 1H), 7.1 (m, 1H), 4.4-4.2 (m, 4H), 3.8 (s, 3H).

Compound 2247 was prepared using procedures that were similar to those described in Example 36.

Example 37

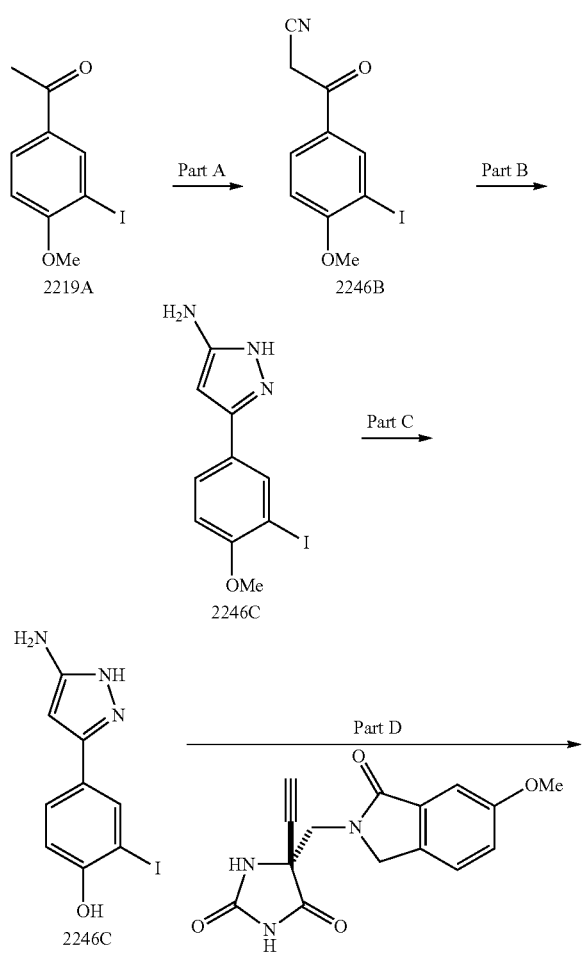

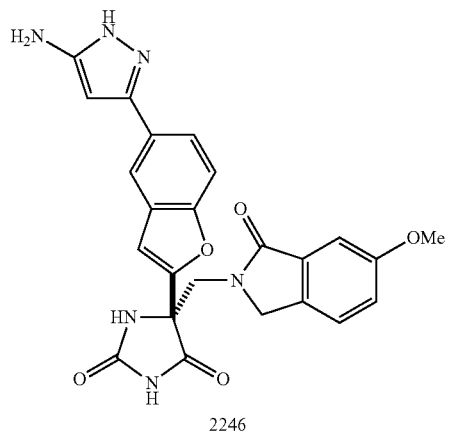

Part A:

Compound 2219A (2.0 g, 7.2 mmol) was dissolved in chloroform (100 mL) and bromine (1.16 g, 7.2 mmol). The reaction was stirred at room temperature overnight and then quenched with water. The organic layer was dried over sodium sulfate and concentrated to provide 2.4 g of the bromomethylketone. The bromomethylketone (575 mg, 1.6 mmol) was dissolved in ethanol (20 mL) and water (3 mL) and treated with potassium cyanide (218 mg, 3.25 mmol). The reaction was stirred at rt for 1 hour and then quenched with water (10 mL) and 1N HCl (30 mL). The solids were filtered and washed with 5% ethyl acetate/hexanes to provide compound 2246B (225 mg) along with 150 mg slightly impure material.

Part B:

Compound 2246B (500 mg, 1.66 mmol) was dissolved in ethanol (10 ml) and hydrazine (0.5 mL). The reaction was stirred at 90° C. overnight and then quenched with water and extracted with ethyl acetate. The combined organic layers were dried over sodium sulfate and concentrated. The resulting residue was triturated with ethyl acetate/hexanes to provide compound 2246C (300 mg). $^1$H NMR (400 MHz, $CDCl_3$): δ 7.95 (m, 1H), 7.5 (m, 1H), 7.1 (m, 1H), 5.8 (s, 1H), 5.3 (s, 2H), 3.5 (s, 3H).

Part C:

Compound 2246C (3000 mg, 0.94 mmol) was dissolved in methylene chloride (10 mL) and 1 M $AlBr_3$ in dibromomethane (4.0 mL) and stirred at 85° C. in a microwave for 30 minutes. The reaction was quenched slowly with water and extracted with ethyl acetate. The organic layer was dried over sodium sulfate and concentrated. The residue was purified using reverse phase chromatography to provide compound 2246D (70 mg).

Part D:

The reaction was performed in a similar manner to Example 6, Part F. HPLC-MS $t_R$=0.975 min ($UV_{254\ nm}$); mass calculated for formula $C_{24}H_{20}N_6O_5$ 472.1, observed LCMS m/z 473.0 (M+H). $^1$H NMR (400 MHz, DMSO): δ 11.2 (s, 1H), 8.9 (m, 1H), 8.1 (m, 1H), 7.75 (m, 1H), 7.5 (m, 1H), 7.2-7.1 (m, 3H), 6.25 (m, 1H), 4.4-4.2 (m, 4H), 3.8 (s, 3H).

Example 38

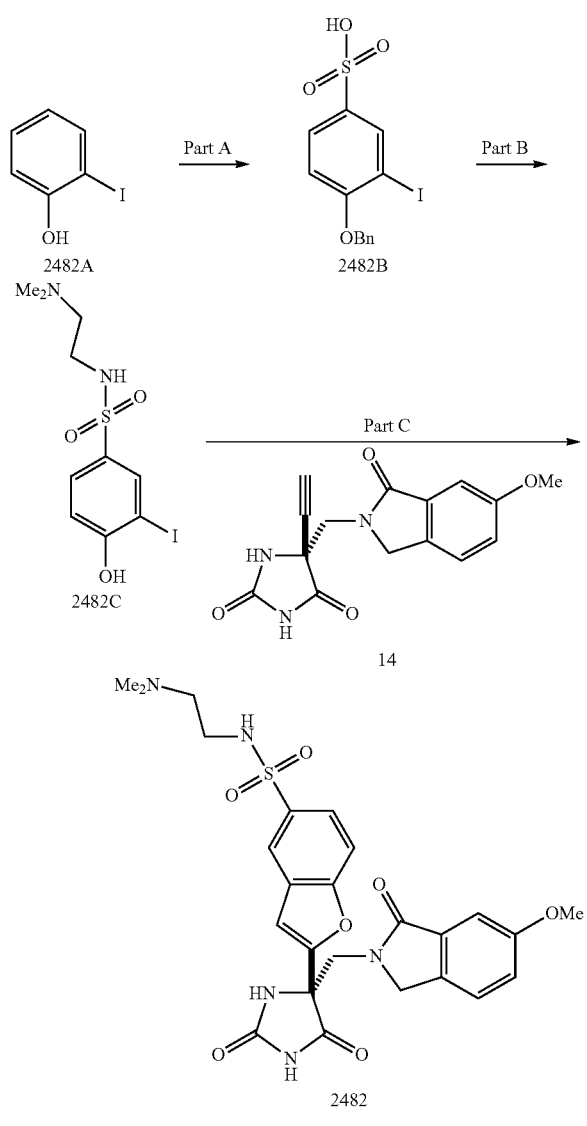

Part A:
Compound 2482A (6.5 g, 29.8 mmol) was dissolved in nitromethane (33 mL) and cooled in an ice bath. Fuming sulfuric acid (5.4 mL) was added dropwise and the reaction was stirred at room temperature for 2 hours. The reaction was poured into water and washed with ethyl acetate. The aqueous layer was neutralized with 5 M NaOH and some of the water was removed under reduced pressure. Sodium hydroxide (2.4 g, 60 mmol), benzyl bromide (11.2 g, 60 mmol) and ethanol (80 mL) were added and the solution was refluxed overnight. The reaction was quenched with water and extracted with ethyl acetate. The combined organic layers were dried over sodium sulfate and concentrated. The residue was triturated with diethylether to provide compound 2482B (7.5 g).

Part B:
Compound 2482B (500 mg, 1.28 mmol) was suspended in methylene chloride (20 mL) and PCl₅ (530 mg) was added and stirred at 40° C. for 2 hours. A solution of saturated sodium bicarbonate was added and the organic layer was dried over sodium sulfate and concentrated. The residue was dissolved in THF (10 mL) and treated with N,N-dimethylethane-1,2-diamine (3 mL) and triethylamine (0.5 mL) and stirred overnight. The reaction was quenched with water and extracted with ethyl acetate. The organic layer was dried over sodium sulfate and concentrated. The residue was dissolved in methylene chloride (10 mL) and 1 M AlBr₃ in dibromomethane (4.0 mL) and stirred at 85° C. in a microwave for 30 minutes. The reaction was quenched slowly with water and extracted with ethyl acetate. The organic layer was dried over sodium sulfate and concentrated to provide compound 2482C (150 mg). HPLC-MS $t_R$=0.99 min (UV$_{254\ nm}$); mass calculated for formula $C_{24}H_{20}N_6O_5$ 370.1, observed LCMS m/z 371.0 (M+H).

Part C:
The reaction was performed in a similar manner to Example 6, Part F. HPLC-MS10 min $t_R$=2.248 min (UV$_{254\ nm}$); mass calculated for formula C25H27N5O7S 541.1, observed LCMS m/z 542.1 (M+H). ¹H NMR (400 MHz, DMSO): δ 11.2 (s, 1H), 10.0 (bs, 1H), 8.9 (m, 1H), 8.2 (m, 1H), 8.0 (m, 1H), 7.8 (m, 2H), 7.5 (m, 1H), 7.25 (s, 1H), 7.1 (m, 2H), 4.4-4.2 (m, 4H), 3.8 (s, 3H), 3.0 (m, 4H), 2.75 (m, 6H).

Example 39

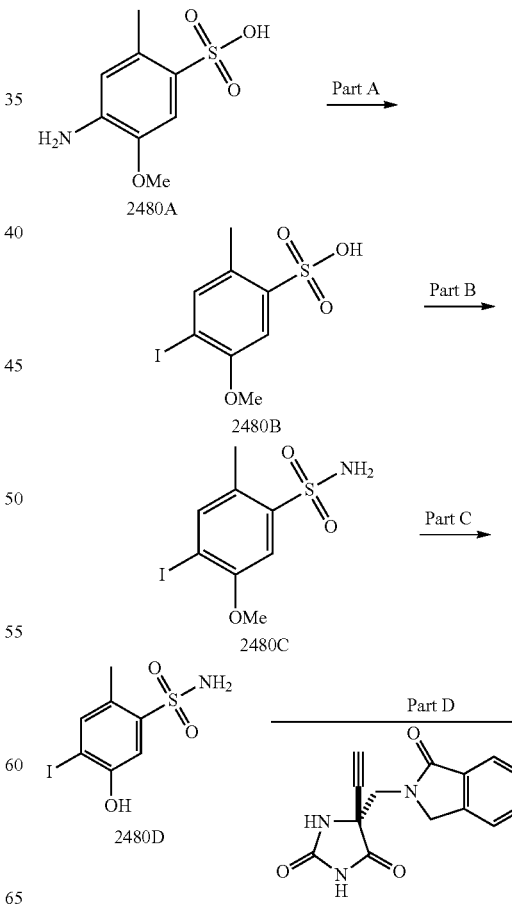

-continued

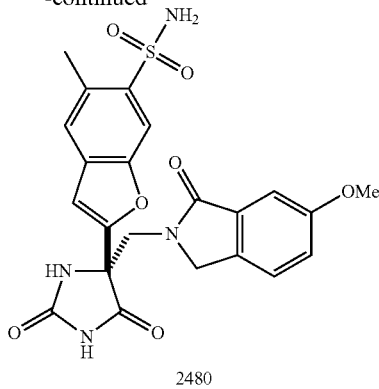

2480

Part A:

Compound 2480A (480 mg, 2.2 mmol) was suspended in ice and sulfuric acid (3 mL). A solution of sodium nitrite (185 mg, 2.64 mmol) in water (2 mL) was added dropwise and stirred for 20 minutes. This solution was added dropwise to a solution of KI (1.09 g, 6.6 mmol) in water (15 mL) in an ice bath. The reaction was stirred overnight and then extracted with ethyl acetate. The combined organic layers were dried over sodium sulfate and concentrated to provide compound 2480B (80 mg).

Part B:

Compound 2480B (80 mg, 0.243 mmol) was dissolved in thionyl chloride (4 mL) and DMF (0.2 mL) and stirred at reflux for 4 hours. The solvents were removed and the residue was dissolved in THF (3 mL) and ammonium hydroxide (1 mL) and stirred overnight. The reaction was quenched with water and extracted with ethyl acetate. The combined organic layers were dried over sodium sulfate and concentrated to provide compound 2480C (80 mg). $^1$H NMR (400 MHz, DMSO): δ 7.8 (m, 1H), 7.3 (m, 1H), 3.8 (s, 3H), 2.4 (s, 3H).

Part C:

Compound 2280C (200 mg, 0.61 mmol) was dissolved in methylene chloride (10 mL) and treated with 1M BBr$_3$ (2 mL). The reaction was stirred overnight at room temperature and then quenched with water and extracted with ethyl acetate. The combined organic layers were dried over sodium sulfate and concentrated to provide compound 2280D (180 mg).

Part D:

The reaction was performed in a similar manner to Example 6, Part F. HPLC-MS t$_R$=1.17 min (UV$_{254\ nm}$); mass calculated for formula C$_{22}$H$_{20}$N$_4$O$_7$S 484.1, observed LCMS m/z 485.0 (M+H). $^1$H NMR (400 MHz, DMSO): δ 11.2 (s, 1H), 8.9 (m, 1H), 8.1 (m, 1H), 7.6 (m, 1H), 7.5 (m, 2H), 7.15 (m, 2H), 7.05 (m, 1H), 6.95 (s, 1H), 4.4-4.2 (m, 4H), 3.8 (s, 3H), 2.65 (s, 3H).

Example 40

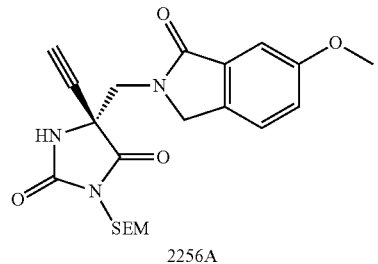 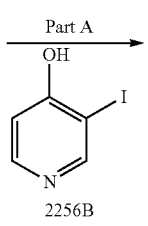

2256A    2256B

Part A

-continued

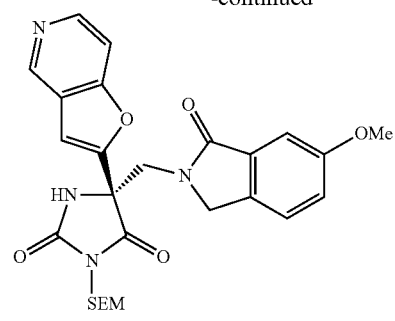

2256C

Part B

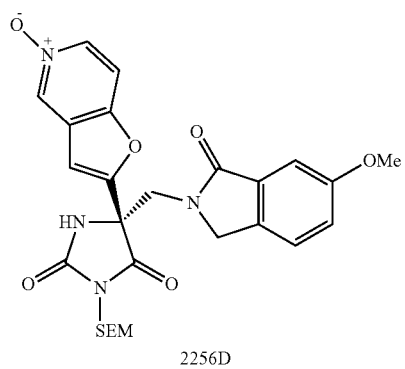

2256D

Part C

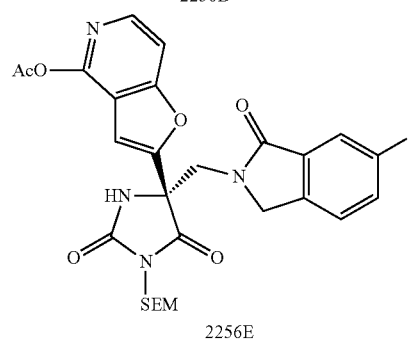

2256E

+

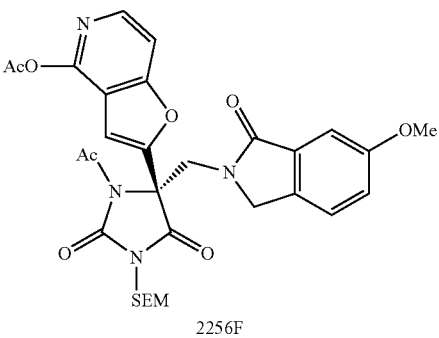

2256F

Part D

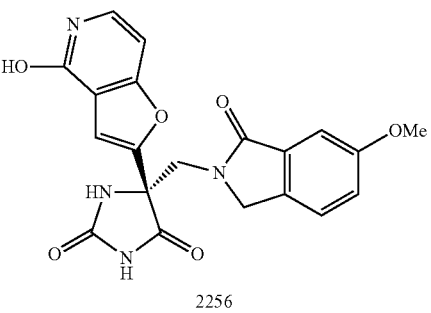 [SMILES: COc1ccc2c(c1)C(=O)N(C[C@@]1(c3cc4c(O)nccc4o3)NC(=O)NC1=O)C2]

2256

Part A:

Compounds 2256A and 2256B were prepared using the procedures described in Yu, W. et. al. WO2007/084415A2.

Compound 2256C was prepared using the procedure described in Example 6, Part F. HPLC-MS $t_R$=1.49 min (UV$_{254\ nm}$); mass calculated for formula $C_{26}H_{30}N_4O_6Si$ 522.19, observed LCMS m/z 523.2 (M+H).

Part B:

To compound 2256C (408 mg, 0.78 mmol) in dichloromethane (10 mL) was added m-CPBA (77%, 220 mg, 0.98 mmol) and the reaction mixture was stirred overnight. Additional m-CPBA (220 mg, 0.98 mmol) was added to the mixture and the mixture was stirred overnight. The reaction was judged to be 80% complete by HPLC-MS and additional m-CPBA (120 mg) was added. Stirring was continued for 3 days. The mixture was poured into saturated sodium bicarbonate solution and the layers were separated. The organic layer was washed with brine, dried and concentrated. Purification by column chromatography (SiO$_2$, 10% methanol/dichloromethane) afforded compound 2256D (127 mg, 30%). HPLC-MS $t_R$=1.60 min (UV$_{254\ nm}$); mass calculated for formula $C_{26}H_{30}N_4O_7Si$ 538.19, observed LCMS m/z 539.1 (M+H).

Part C:

A mixture of 2256D (126 mg, 0.23 mmol) was heated in acetic anhydride (4 mL) at 120° C. overnight. The reaction mixture was concentrated and purified by column chromatography (SiO$_2$, DCM to 5% methanol/DCM) to afford 2256E (50 mg, 37%) and 2256F (74 mg, 52%).

2256E: HPLC-MS $t_R$=1.89 min (UV$_{254\ nm}$); mass calculated for formula $C_{28}H_{32}N_4O_8Si$ 580.22, observed LCMS m/z 553.2 (M−28+H).

2256F: HPLC-MS $t_R$=2.32 min (UV$_{254\ nm}$); mass calculated for formula $C_{30}H_{34}N_4O_9Si$ 622.21, observed LCMS m/z 623.2 (M+H).

Part D:

A mixture of 2256E (50 mg) and 2256F (74 mg) was treated with 4 M HCl in dioxane (4 mL) at 90° C. overnight. The reaction mixture was concentrated. The residue was dissolved in 1.0 N NaOH (1 mL) and acetonitrile (1 mL) and stirred for 24 hours at room temperature. The mixture was neutralized and purified by reverse phase HPLC to afford 2256 (21 mg). HPLC-MS $t_R$=2.20 min (10 min, UV$_{254\ nm}$); mass calculated for formula $C_{20}H_{16}N_4O_6$ 408.11, observed LCMS m/z 409.1 (M+H).

Example 41

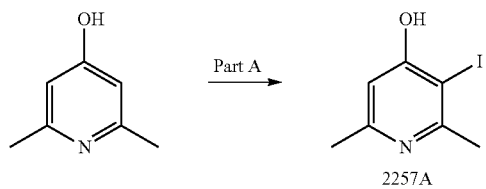

Part A:

A mixture of 2,6-dimethyl-4-hydroxypyridine (1.23 g, 10 mmol), sodium carbonate (2.12 g, 20 mmol) and iodine (2.54 g, 10 mmol) in water (20 mL) were stirred at room temperature overnight. The mixture was acidified to pH 4 with conc. HCl and the percipitate was collected by filtration. The crude solid was suspended in methanol (50 mL) and heated to dissolve the mono-iodo product. The diiodo product (773 mg) was removed by hot filtration and the filtrate was cooled to afford 2257A (792 mg, 32%) as a solid. $^1$H NMR (400 MHz, DMSO-d$_6$) δ 11.59 (s, 1H), 5.85 (s, 1H) 2.44 (s, 3H), 2.17 (s, 3H).

Compound 2257 was prepared using the procedures described in Example 41 and procedures similar to those described in Example 52, Part D.

Example 42

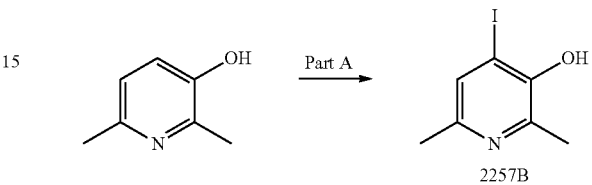

Part A:

Compound 2257B (167 mg, 32%) was made from 2,6-dimethyl-3-hydroxypyridine (503 mg, 4.08 mmol) using the procedure described in Example 42. $^1$H NMR (400 MHz, CDCl$_3$) δ 7.30 (s, 1H) 2.52 (s, 3H), 2.41 (s, 3H).

Example 43

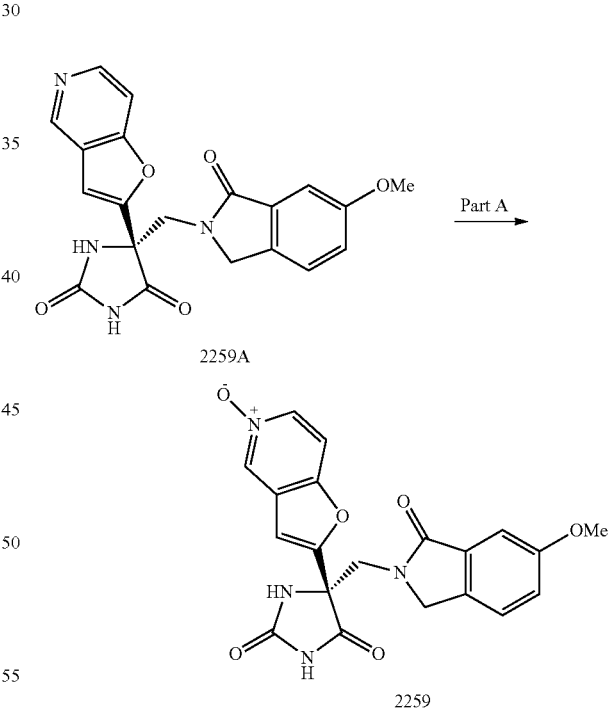

Part A:

To compound 2259A (prepared as described in Yu, W. et. al. WO2007/084415A2) (50 mg, 0.13 mmol) in dichloromethane (2 mL) was added m-CPBA (75%, 37 mg, 0.16 mmol). The resulting slurry was stirred overnight at room temperature. Additional m-CPBA (50 mg) and water (2 mL) was added to the mixture. After stirring overnight the mixture was concentrated and 2259 was isolated by reverse phase HPLC to afford a white solid (20 mg). HPLC-MS $t_R$=0.8 min (UV$_{254\,nm}$); mass calculated for formula C$_{20}$H$_{16}$N$_4$O$_6$ 408.11, observed LCMS m/z 409.1 (M+H).

Example 44

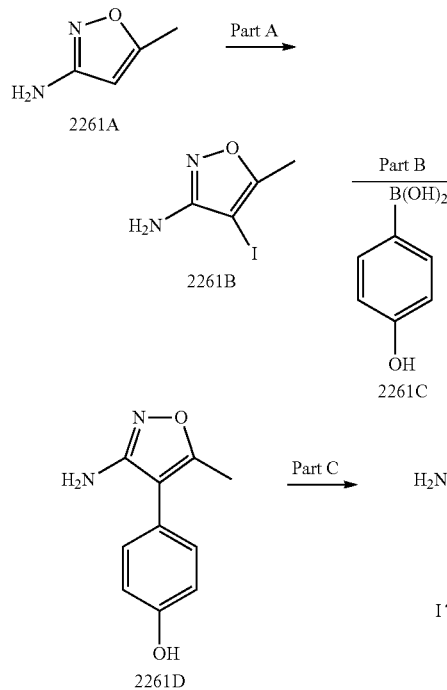

Part A:

A mixture of compound 2261A (98 mg, 1 mmol) and NIS (225 mg, 1 mmol) in HOAc (2 mL) and conc. H$_2$SO$_4$ (0.025 mL) was stirred at room temperature overnight. The reaction mixture was diluted with ethyl acetate and water and the organic layer was separated. The organic layer was washed with water, sodium thiosulfate and brine, dried over sodium sulfate and concentrated. Purification by column chromatography (SiO$_2$, 10% ethyl acetate/hexane to 80% ethyl acetate/hexane) afforded 2261B (140 mg, 62%). HPLC-MS t$_R$=1.18 min (UV$_{254\,nm}$); mass calculated for formula C$_4$H$_5$IN$_2$O 223.94, observed LCMS m/z 224.9 (M+H).

Part B:

A mixture of 2261B (140 mg, 0.62 mmol), 2261C (128 mg, 0.93 mmol) Pd(t-Bu$_3$P)$_2$ (31 mg, 0.06 mmol) and potassium phosphate-hydrate (428 mg, 1.86 mmol) in DMF (5 mL) was heated in a Biotage microwave reactor at 150° C. for 15 minutes. The reaction mixture was filtered through a celite plug and the filtrate was concentrated. Purification by column chromatography (SiO$_2$, 20% ethyl acetate/hexane to 100% ethyl acetate) afforded 2261D (85 mg, 72%). HPLC-MS t$_R$=0.92 min (UV$_{254\,nm}$); mass calculated for formula C$_{10}$H$_{10}$N$_2$O$_2$ 190.07, observed LCMS m/z 191.1 (M+H).

Part C:

The iodination of 2261D (85 mg, 0.45 mmol) was accomplished using the procedure described in Example 44, Part A to afford 2261E (100 mg, 70%) as an off-white solid. HPLC-MS t$_R$=1.45 min (UV$_{254\,nm}$); mass calculated for formula C$_{10}$H$_9$IN$_2$O$_2$ 315.97, observed LCMS m/z 317.0 (M+H).

Example 45

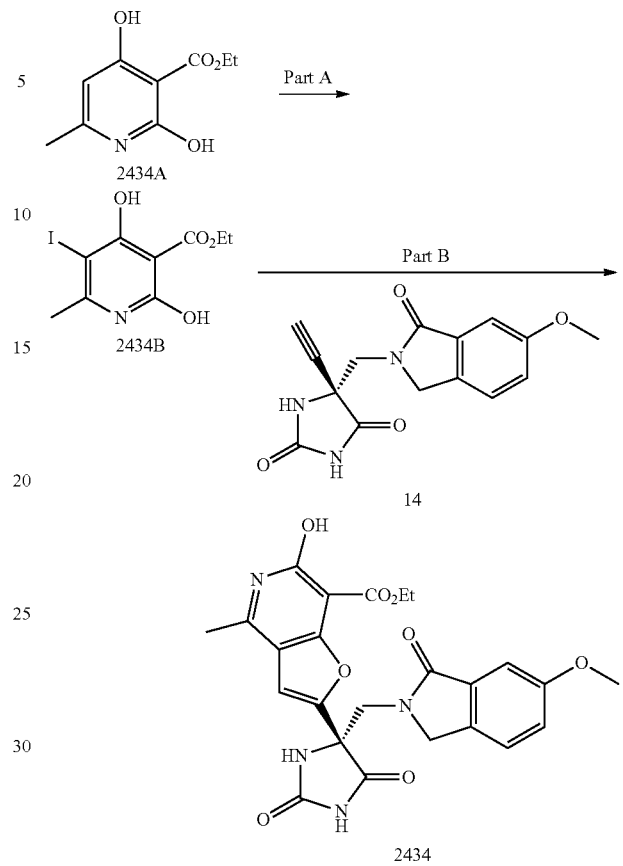

Part A:

A mixture of compound 2434A (1.07 g, 5.42 mmol), sodium carbonate (1.73 g, 16.3 mmol) and iodine (1.38 g, 5.42 mmol) in water (20 mL) was stirred overnight at room temperature. The reaction mixture was acidified with conc. HCl and 2434B (1.68 g, 96%) was collected by filtration. HPLC-MS t$_R$=1.34 min (UV$_{254\,nm}$); mass calculated for formula C$_9$H$_{10}$INO$_4$ 322.97, observed LCMS m/z 324.0 (M+H).

Part B:

Compound 2434 was prepared using the procedure described in Example 6, Part F. HPLC-MS t$_R$=1.34 min (UV$_{254\,nm}$); mass calculated for formula C$_{24}$H$_{22}$N$_4$O$_8$ 494.14, observed LCMS m/z 495.0 (M+H).

Example 46

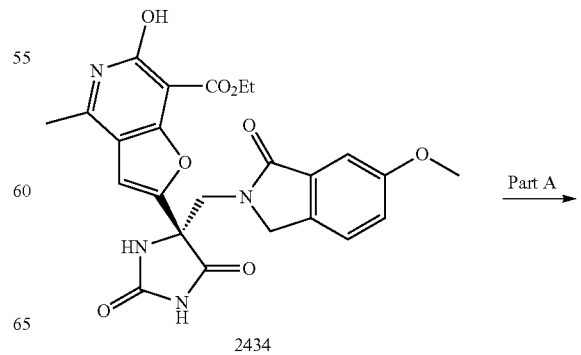

241

-continued

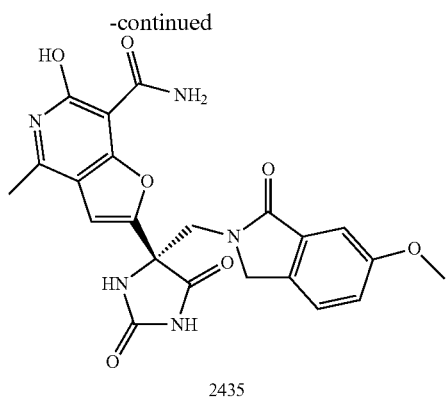

2435

Part A:

Compound 2434 (44 mg, 0.09 mmol) in 7 M ammonia/methanol solution (4 mL) was heated at 90° C. overnight in a pressure bottle. The reaction mixture was concentrated and purified by reverse phase HPLC to afford 2435 (17 mg). HPLC-MS $t_R$=2.23 min (10 min, $UV_{254\,nm}$); mass calculated for formula $C_{22}H_{19}N_5O_7$ 465.13, observed LCMS m/z 466.0 (M+H).

Example 47

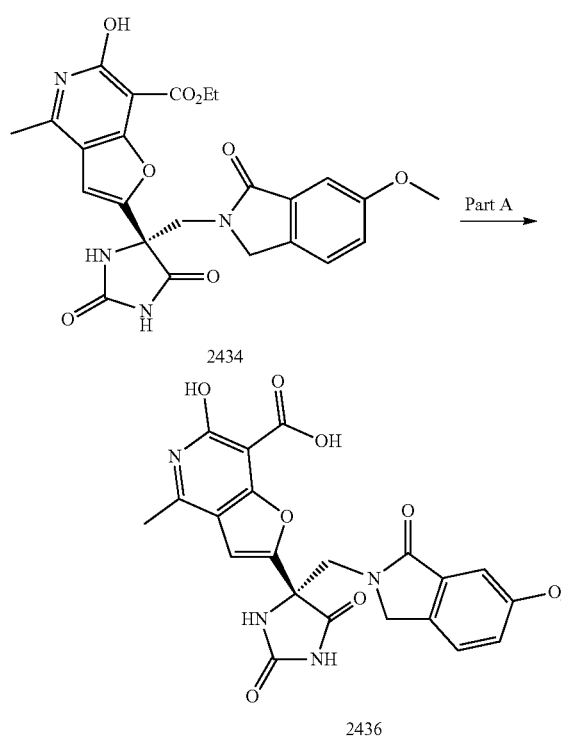

2434

2436

Part A:

A mixture of compound 2434 (43 mg, 0.087 mmol) and 1 N sodium hydroxide (0.174 mL) in THF (1 mL) and water (0.5 mL) was heated at 120° C. for 40 minutes in a Biotage microwave. The reaction mixture was acidified to pH 3 and concentrated. The residue was suspended in water and 2436 was collected by filtration. HPLC-MS $t_R$=0.95 min ($UV_{254\,nm}$); mass calculated for formula $C_{22}H_{18}N_4O_8$ 466.11, observed LCMS m/z 467.0 (M+H).

242

Example 48

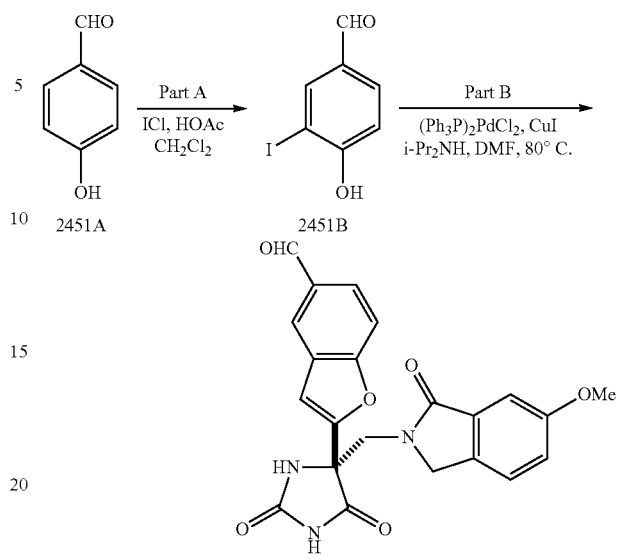

2451A     2451B

2451

Part A

Compound 2451B was prepared via a modification of the procedure reported by Azoulay, M. et al. in *Bioorg. Med. Chem. Lett.* 2006, 16, 3147-3149. Thus, to a stirred suspension of Compound 2451A (4.07 g, 33.3 mmol) in $CH_2Cl_2$ (67 mL), a solution of iodine monochloride (6.50 g, 40.0 mmol) in glacial acetic acid (6 mL) was added dropwise over ~15 min. The darkened reaction mixture was stirred for 21 h at rt. The reaction had not proceeded to completion by this time but satisfactory conversion had been achieved to allow continuation of the procedure. The reaction mixture was washed with 10% aq $Na_2S_2O_3$ (2×100 mL) until the dark red-orange color discharged to pale yellow. The organic phase was washed with brine (~100 mL), dried over anhydrous $MgSO_4$, filtered and concentrated under reduced pressure to afford a beige solid. Purification by sgc (3-10% MeOH/$NH_3$—$CH_2Cl_2$) gave two fractions. The first fraction (2.44 g) contained a mixture of Compounds 2451A and 2451B while the second fraction contained pure Compound 2451B (1.39 g).

Part B

Aryl iodide 2451B was converted into Compound 2451 by following the procedures given in Lavey, B. J. et al. PCT Appl. WO2007084455 (A1), p. 130 for Example 44, Part B.

Example 49

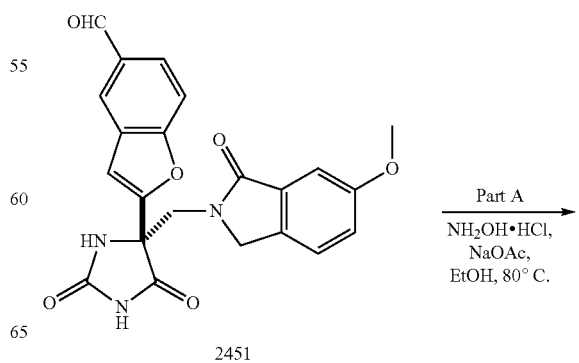

2451

Example 50

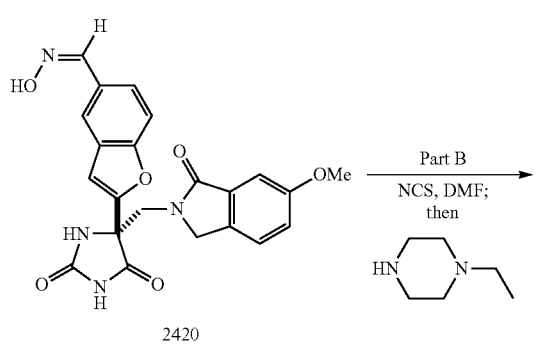
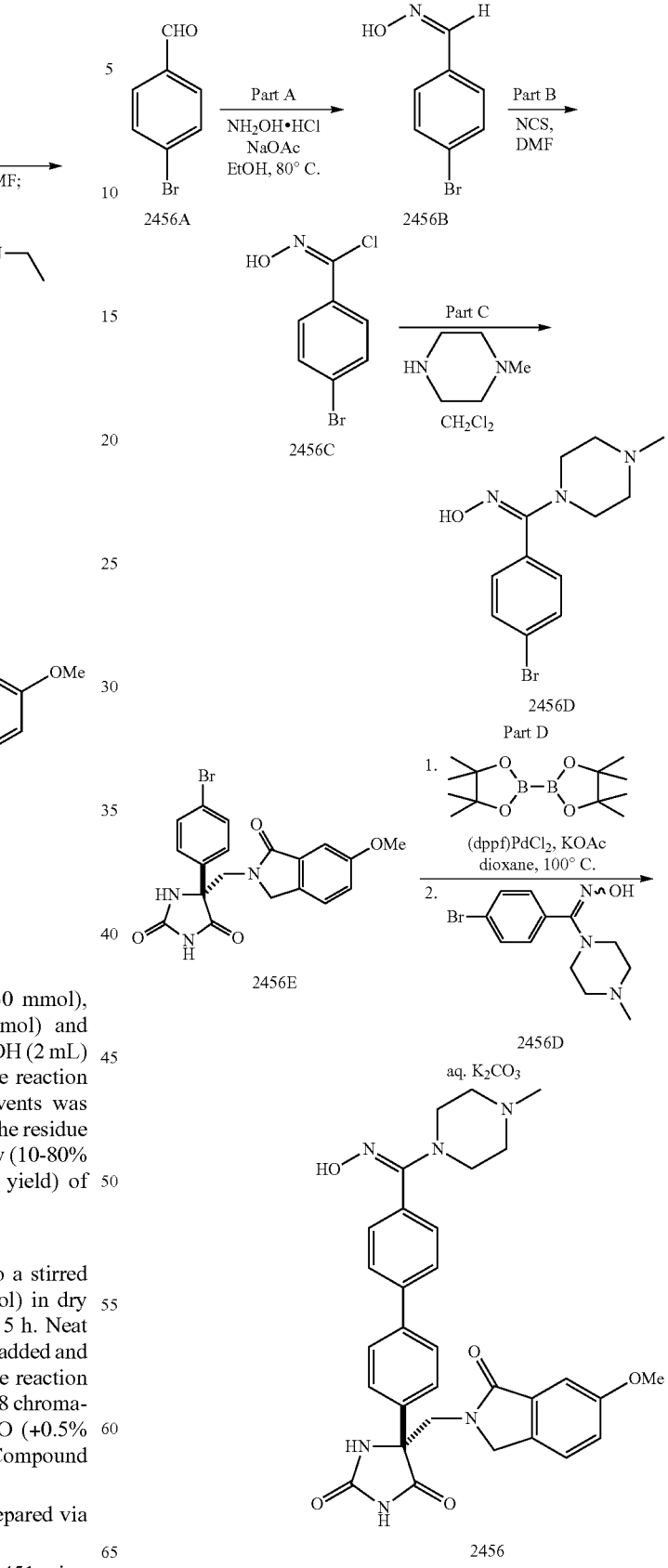

Part A

A mixture of Compound 2451 (222 mg, 0.530 mmol), hydroxylamine hydrochloride (73 mg, 1.06 mmol) and sodium acetate (87 mg, 1.06 mmol) in absolute EtOH (2 mL) was stirred at 80° C. in a sealed tube for 2 d. The reaction mixture was allowed to cool to rt and the solvents was removed by evaporation under reduced pressure. The residue was purified by reverse-phase C18 chromatography (10-80% MeCN—H₂O gradient) to afford 144 mg (63% yield) of Compound 2420 as a white solid.

Part B

Solid NCS (14 mg, 0.104 mmol) was added to a stirred solution of Compound 2420 (45 mg, 0.104 mmol) in dry DMF (1.0 mL). The mixture was stirred at rt for 5 h. Neat N-ethylpiperazine (29 µL, 26 mg, 0.23 mmol) was added and the reaction mixture was stirred at rt for 18 h. The reaction mixture was subjected directly to reverse-phase C18 chromatography [10-50% MeCN (+0.5% NH₄OH)—H₂O (+0.5% NH₄OH) gradient] to give 25 mg (45% yield) of Compound 2453 as a beige solid.

The compounds 2452, 2454 and 2455 were prepared via analogous procedures.

Compound 2488 was prepared from compound 2451 using procedures similar to those described in Example 49.

Part A

A mixture of p-bromobenzaldehyde (Compound 2456A; 5.00 g, 27.0 mmol), hydroxylamine hydrochloride (3/3 g, 54.1 mmol) and anhydrous sodium acetate (4.43 g, 54.1 mmol) in absolute ethanol (100 mL) was stirred at reflux (80° C. external oil bath temperature) in a pressure vessel for 24 h. The solvent was removed under reduced pressure. The remaining solid was dissolved in Et$_2$O (~250 mL) and the resulting solution was washed sequentially with water (2×~100 mL) and brine (~100 mL). The organic layer was dried over anhydrous MgSO$_4$, filtered and concentrated under reduced pressure to afford 2456B as a white solid (5.23 g, 97% yield).

Part B

Solid N-chlorosuccinimide (0/22 g, 5.39 mmol) was added to a stirred solution of oxime 2456B (1.072 g, 5.39 mmol) in dry DMF (15 mL). The reaction mixture was stirred at rt for 18 h. The reaction mixture was diluted with Et$_2$O (150 mL) and was washed sequentially with water (3×50 mL) and brine (~50 mL). The organic layer was dried over anhydrous MgSO$_4$, filtered and concentrated under reduced pressure to give a pale yellow solid. Purification of the solid by sgc (40 g silica gel cartridge; 5-25% EtOAc-hexanes gradient) gave 973 mg (77% yield) of the desired product 2456C as a white solid.

Part C

N-Methylpiperazine (208 µL, 187 mg, 1.87 mmol) was added to a solution of oximyl chloride 2456C (200 mg, 0.85 mmol) in CH$_2$Cl$_2$ (5 mL) and the resulting mixture was stirred overnight at rt. Evaporation of the solvent gave a residue that was purified by sgc (1-10% MeOH/NH$_3$ in CH$_2$Cl$_2$ gradient) to afford 202 mg (80% yield) of the desired product 2456D as a white solid.

Part D

Compounds 2456D and 2456E were combined to afford Compound 2456 according to the procedure given in Lavey, B. J. et al. PCT Appl. WO2007084455 (A1), p. 112 for Example 10.

Example 51

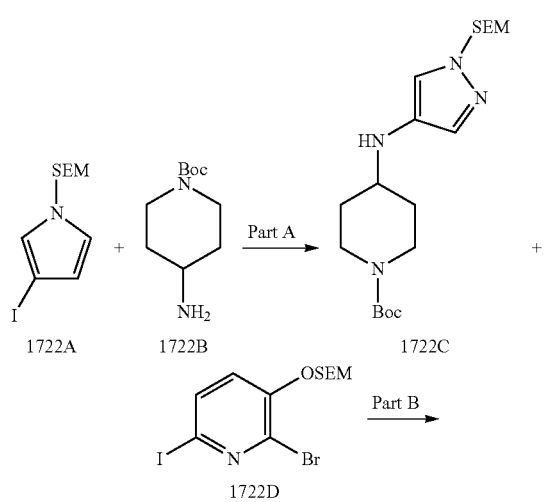

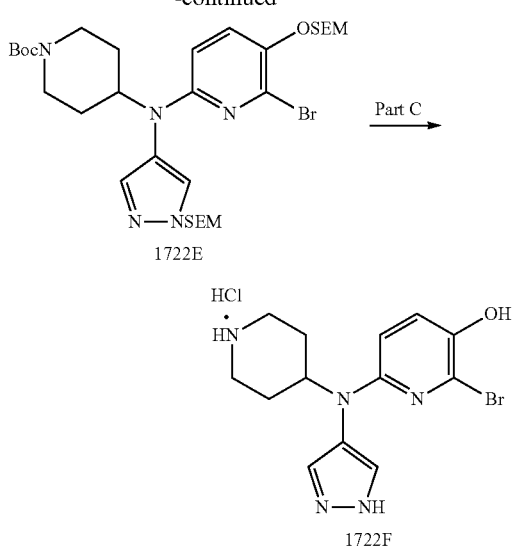

Part A:

A mixture of 1722A (700 mg, 2.16 mmol), 1722B (433 mg, 2.16 mmol), copper iodide (41 mg, 0.22 mmol), L-proline (50 mg, 0.43 mmol) and K$_2$CO$_3$ (600 mg, 4.3 mmol) in DMSO (3 mL) was stirred at 100° C. overnight. After cooling, the reaction mixture was diluted with ethyl acetate (20 mL) and Brine (20 mL). The layers were separated. The organic layer was dried with Na$_2$SO$_4$ and then concentrated to dryness. The crude material was purified by silica gel chromatography (Hexane/EtOAc:1:1) to afford compound 1722C (250 mg, 29%).

Part B:

A mixture of 1722C (250 mg, 0.63 mmol), 1722D (325 mg, 0.76 mmol), Pd(OAc)$_2$ (16 mg, 0.024 mmol), Xantphos (16 mg, 0.049 mmol) and sodium t-butoxide (97 mg, 1.0 mmol) in dioxane (3 mL) was stirred in a sealed tube at 100° C. overnight. After cooling, the reaction mixture was diluted with ethyl acetate (10 mL) and H$_2$O (10 mL). The layers were separated. The organic layer was dried with Na$_2$SO$_4$ and then concentrated to dryness. The crude material was purified by silica gel chromatography (Hexane/EtOAc: 2:1) to afford product 1722E (190 mg, 43%).

Part C:

Compound 1722E (190 mg, 0.27 mmol) was then dissolved in methanol (5 mL) and HCl (10 mL, 4N in dioxane) was added. The reaction was stirred at room temperature overnight. Solvent was removed and the material was dried under vacuum to afford 1722F (90 mg, 99%).

Example 52

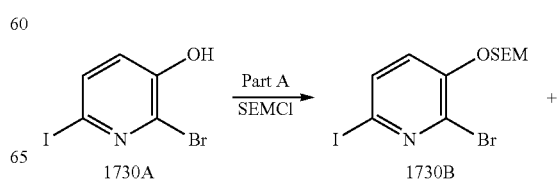

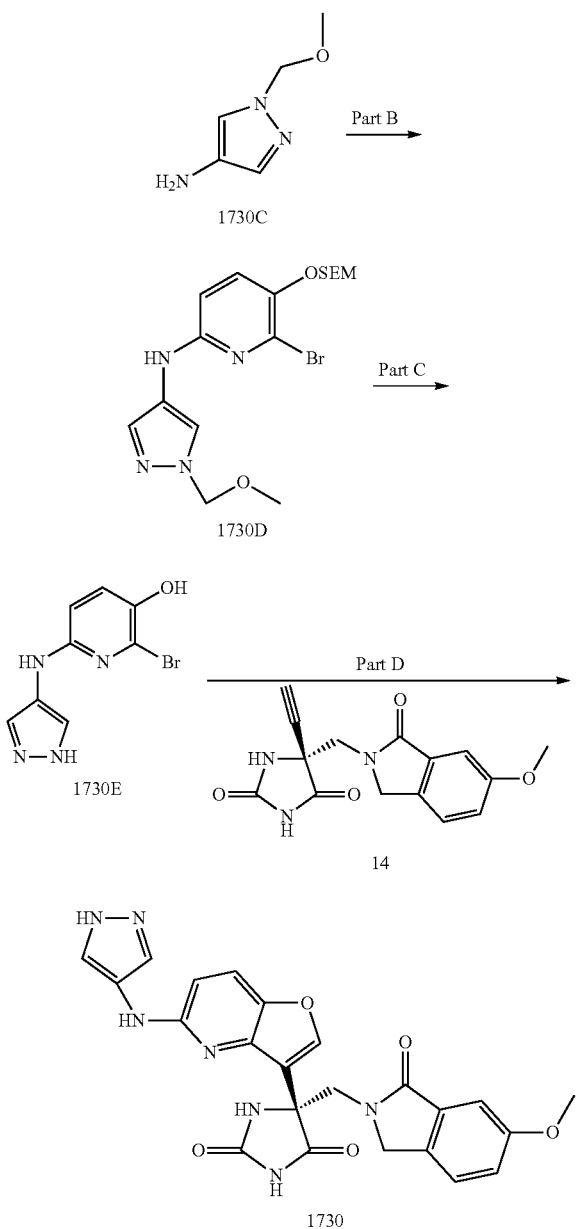

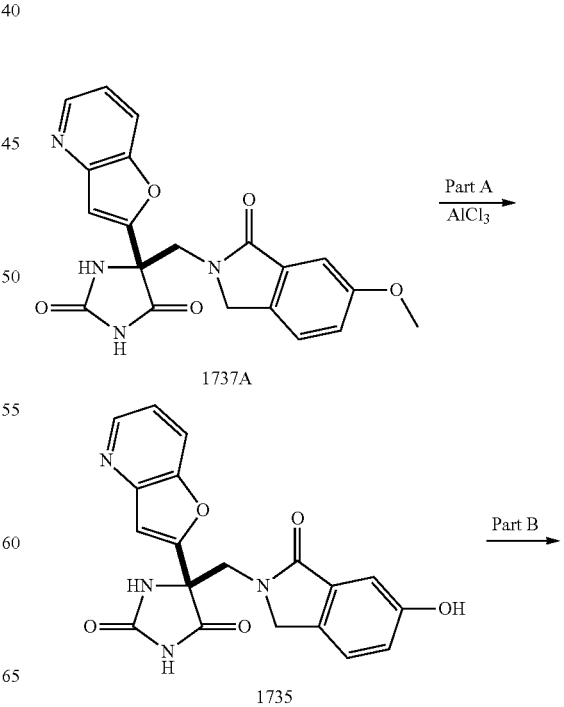

C. overnight. After cooling, the reaction mixture was diluted with ethyl acetate (100 mL) and H$_2$O (100 mL). The layers were separated. The organic layer was dried with Na$_2$SO$_4$ and then concentrated to dryness. The crude material was purified by silica gel chromatography (Hexane/EtOAc: 1:1) to afford compound 1730D (240 mg, 48%).

Part C:

Compound 1730D (240 gm, 0.56 mmol) was dissolved in methanol (10 mL) and HCl (20 mL, 4N in dioxane) was added and the reaction mixture was stirred at room temperature two and half days. The mass spectrum of the reaction mixture still showed the presence of starting material. Solvents were removed and HCl (50 mL, 6N in H$_2$O) and methanol (10 mL) were added and the mixture was stirred at room temperature overnight. Solvents were removed to afford compound 1730E (140 mg, 99%) which was used without further purification.

Part D:

A mixture of 1730E (72 mg, 0.28 mmol), compound 14 (93 mg, 0.31 mmol), copper iodide (5 mg, 0.028 mmol), Pd(PPh$_3$)$_2$Cl$_2$ (5 mg, 0.008 mmol) and diisopropylamine (0.40 mL, 2.85 mmol) in DMF (1 mL) was stirred at 85° C. overnight. The reaction mixture was purified by Gilson reserve phase HPLC using a 0.1% formic acid in the acetonitrile-water mobile phase. The fractions which contained 1730 were concentrated to a light yellow solid (25 mg, 19%). HPLC-MS t$_R$=1.94 min (UV$_{254\,nm}$); mass calculated for formula C$_{23}$H$_{19}$N$_7$O$_5$ 473.44, observed LCMS m/z 474.3 (M+H).

Compounds 1700-1704, 1714, 1721, 1728-1734 were prepared using procedures similar to those described in Example 52.

Compounds 1717, 1722, and 1734 were prepared using procedures similar to those described in Examples 51 and 52.

Example 53

Part A:

A mixture of compound 1730A (6.2 g, 20.67 mmol) which was made according to the literature procedures (*Synthesis*, 1990, 497-498) and triethyl amine (8.7 mL, 62.41 mmol) was stirred in methylene chloride (100 mL) at room temperature. SEMCl (4.4 mL, 24.94 mmol) was added dropwise and the reaction mixture was stirred at room temperature overnight. The reaction mixture was extracted with H$_2$O (100 mL) and layers were separated. The organic layer was dried and concentrated to dryness. The crude material was purified by silica gel chromatography (Hexane/EtOAc: 4:1) to afford compound 17308 (5 g, 56%).

Part B:

A mixture of 17308 (500 mg, 1.16 mmol), 1730C (148 mg, 1.16 mmol), Pd(OAc)$_2$ (23 mg, 0.10 mmol), Xantphos (40 mg, 0.069 mmol) and sodium t-butoxide (138 mg, 1.43 mmol) in dioxane (3 mL) was stirred in a sealed tube at 100°

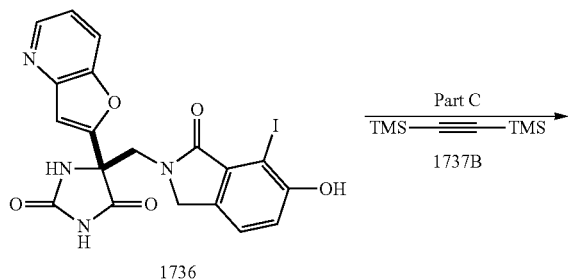

1736

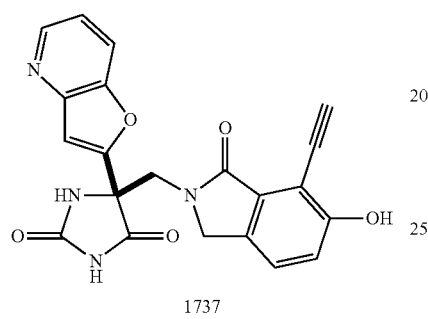

1737

Part A:

Compound 1737A (1.8 g, 4.59 mmol) and AlCl₃ (1.8 g, 13.50 mmol) were stirred in methylene chloride in a sealed tube at 75° C. overnight. After cooling, the reaction mixture was taken up in ethyl acetate and extracted with water. The aqueous layer was extracted with ethyl acetate 3 times. The combined organic layers were dried with Na₂SO₄ and then concentrated to dryness. The crude material which was 1735 (1.6 g, 92%) was used without further purification. HPLC-MS $t_R$=1.57 min (UV$_{254\ nm}$); mass calculated for formula $C_{19}H_{14}N_4O_5$ 378.10, observed LCMS m/z 379.2 (M+H).

Part B:

Compound 1735 (300 mg, 0.79 mmol) was dissolved in NH₃·H₂O (9 mL) and stirred in ice bath to make mixture 1. Iodine (180 mg, 0.63 mmol) and KI (421 mg, 2.54 mmol) were dissolved in H₂O (3 mL) and this mixture was added dropwise to mixture 1. After addition, the ice bath was removed and the reaction mixture was stirred at room temperature for 2 h. After the reaction was terminated, the solvent was removed. The crude material was purified with ISCO reverse phase column and eluted with actonitrile-water to give 1736 (100 mg, 25%). HPLC-MS $t_R$=1.92 min (UV$_{254\ nm}$); mass calculated for formula $C_{19}H_{13}IN_4O_5$ 503.99, observed LCMS m/z 505.3 (M+H).

Part C:

A mixture of 1736 (60 mg, 0.12 mmol), 1737B (25.6 mg, 0.24 mmol), copper iodide (5 mg, 0.028 mmol), Pd(PPh₃)₂Cl₂ (5 mg, 0.008 mmol) and diisopropylamine (0.10 mL, 0.72 mmol) in DMF (1 mL) was stirred at 85° C. overnight. The reaction mixture was purified by Gilson reverse phase HPLC using a 0.1% formic acid in the acetonitrile-water mobile phase. The isolated fractions were concentrated to afford 1737 (1 mg, 2%)) as white solid. HPLC-MS $t_R$=1.80 min (UV$_{254\ nm}$); mass calculated for formula $C_{21}H_{14}N_4O_5$ 402.10, observed LCMS m/z 403.2 (M+H).

Example 53.1

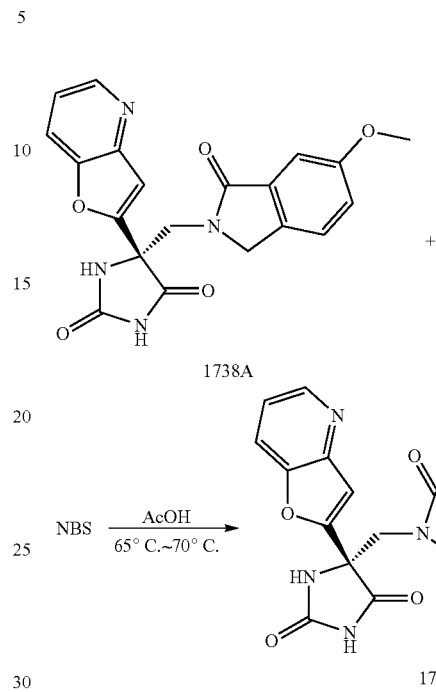

1738A

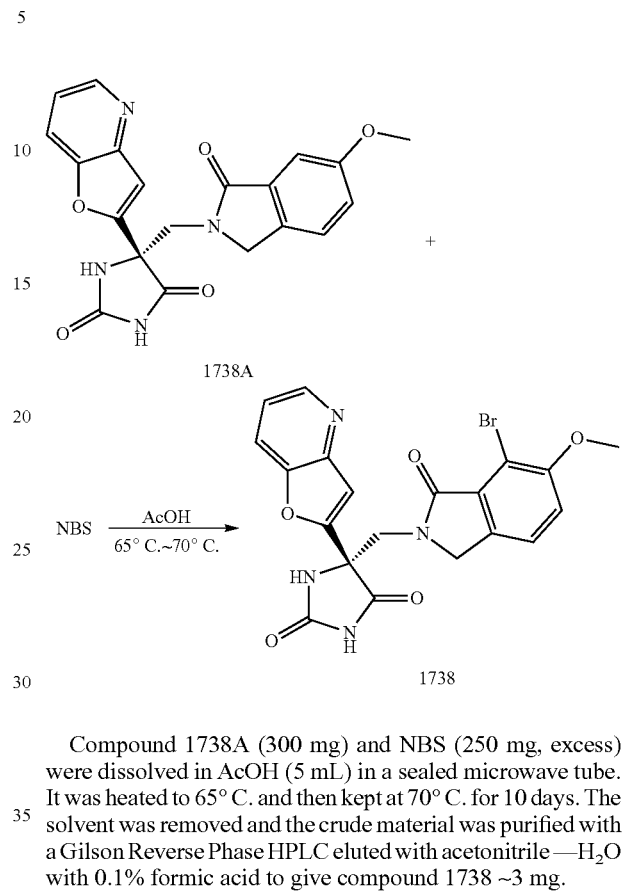

1738

Compound 1738A (300 mg) and NBS (250 mg, excess) were dissolved in AcOH (5 mL) in a sealed microwave tube. It was heated to 65° C. and then kept at 70° C. for 10 days. The solvent was removed and the crude material was purified with a Gilson Reverse Phase HPLC eluted with acetonitrile—H₂O with 0.1% formic acid to give compound 1738 ~3 mg.

Example 53.2

Compounds 1741 and 1743 were prepared from compounds 1741B and 1741C (below) using chemistry similar to that described in Example 52, Part D.

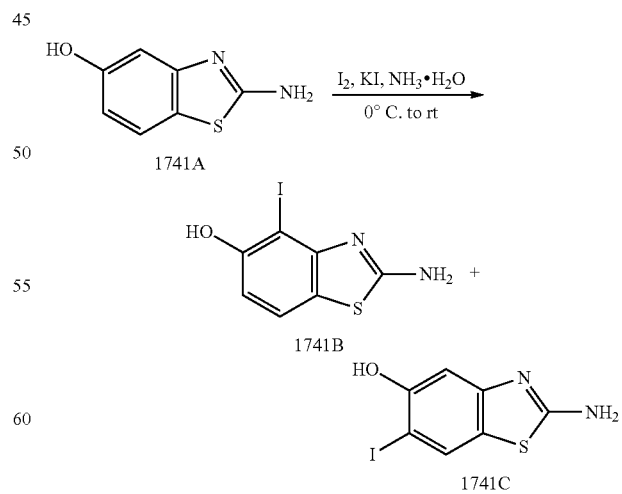

1741A

1741B

1741C

Compound 1741A (190 mg, 1.14 mmol) was dissolved in NH₃·H₂O (16 mL) and stirred in ice bath to make mixture 1. Iodine (260 mg, 0.92 mmol) and KI (608 mg, 3.67 mmol)

were dissolved in H$_2$O (4 mL) and this mixture was added dropwise to mixture 1. After addition, the ice bath was removed and the reaction mixture was stirred at room temperature for 2 h. After the reaction was terminated, the solvent was removed. The crude material was purified with prepative plates eluted with 10% NH$_3$.MeOH in MeCl$_2$ to give compound 1741A (25 mg) and compound 1741B (15 mg).

Similarly, compound 1739 was prepared from the corresponding iodo intermediate using procedures similar to those described in Example 53.2 and Example 52, Part D.

Example 54 added dropwise and the reaction mixture was stirred at room temperature overnight. The reaction mixture was diluted with methylene chloride (20 mL) and extracted with H$_2$O (20 mL) and layers were separated. The organic layer was dried and concentrated to dryness. The crude material was purified by silica gel chromatography (5% 7N Ammonia MeOH solution in CH$_2$Cl$_2$)) to afford compound 1740A (360 mg, 27%).

Part B:

A mixture of 1740A (160 mg, 0.31 mmol) and Hunig's base (0.082 mL, 0.47 mmol) were stirred in methylene chloride (10 mL) at −78° C. Compound 1740B (0.06 mL, 0.37 mL) was added dropwise. The reaction mixture was stirred at

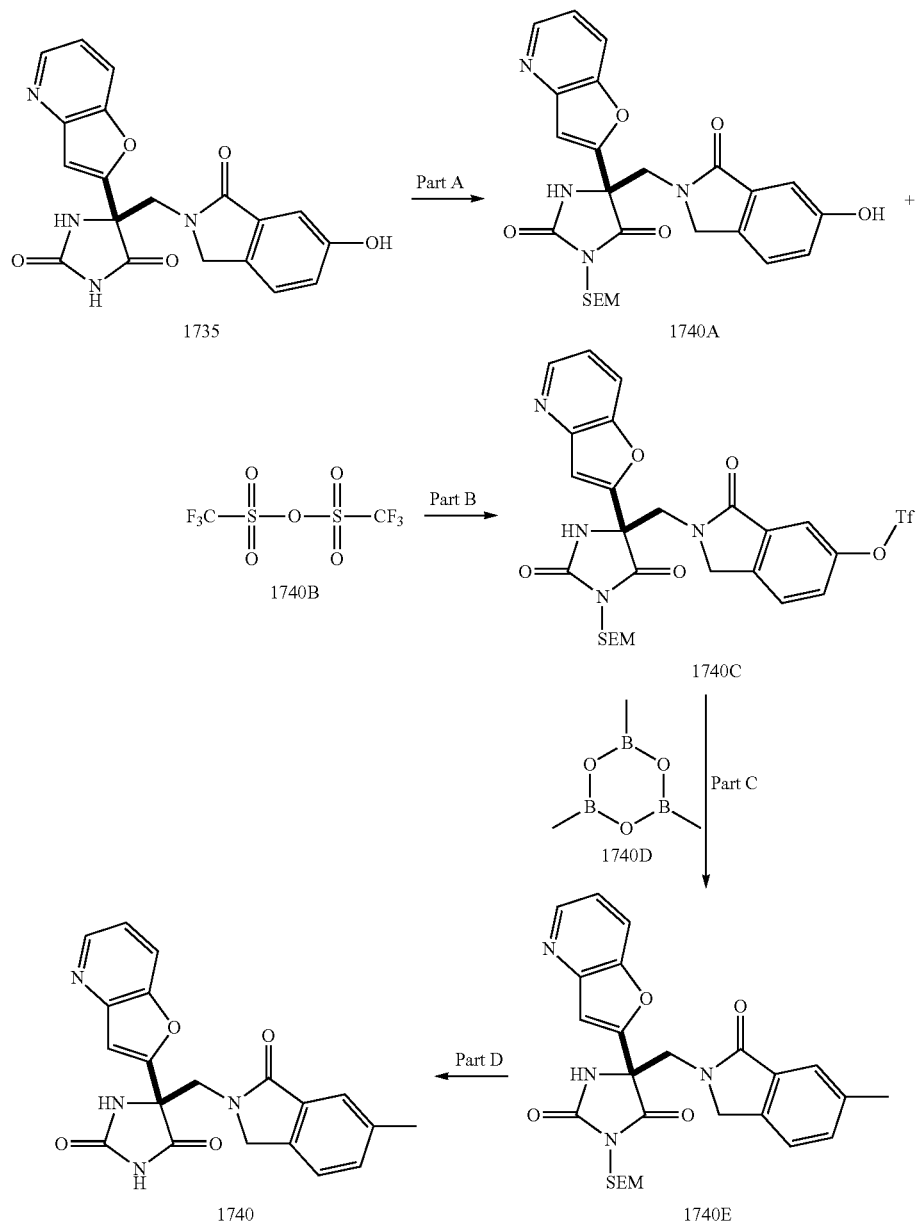

Part A:

A mixture of compound 1735 (1.0 g, 2.65 mmol) and Hunig's base (1.38 mL, 7.93 mmol) was stirred in DMF (10 mL) at room temperature. SEMCI (0.7 mL, 3.97 mmol) was −78° C. for 1 hr. The reaction mixture was extracted with brine (10 mL). The organic layer was dried and concentrated to dryness. The crude material was purified by silica gel chromatography (5% 7N Ammonia MeOH solution in CH$_2$Cl$_2$) to afford compound 1740C (68 mg, 34%).

Part C:

To a pressure bottle was added compound 1740C (68 mg, 0.11 mmol), compound 1740D (20 mg, 0.16 mmol), Pd(PPh$_3$)$_4$ (4 mg, 0.0033 mmol), dioxane (2 mL) and potassium phosphate (45 mg, 0.21 mmol). The reaction mixture was vacuumed and purged with nitrogen for three times and stirred at 100° C. overnight. The reaction mixture was diluted with water (20 mL) and extracted with EtOAc (20 mL×3). The organic layers were combined and washed with brine, dried over sodium sulfate and concentrated to dryness. The residue was purified by silica gel chromatography (5% 7N Ammonia MeOH solution in CH$_2$Cl$_2$) to afford 1740E (40 mg, 74%).

Part D:

Compound 1740E (40 mg, 0.079 mmol) was stirred in methylene chloride (10 mL) at −78° C. BF$_3$.EtOEt (0.075 mL, 0.59 mmol) was added dropwise. The reaction mixture was warmed up to room temperature and stirred for 1 hr. Excess of triethylamine was added and the solvent was removed. The crude material was dissolved in methanol (3 mL) and NaOH (1 mL, 1 N in water) was added and the reaction mixture was stirred for 30 min. Solvent was removed and water was added. The solid was collected with suction filtration to afford 1740 (20 mg, 67%) as white solid. HPLC-MS t$_R$=2.52 min (UV$_{254\ nm}$); mass calculated for formula C$_{20}$H$_{16}$N$_4$O$_5$ 376.12, observed LCMS m/z 377.2 (M+H).

Compound 1742 was prepared from 1740C using procedures similar to those described in Example 54.

Example 55

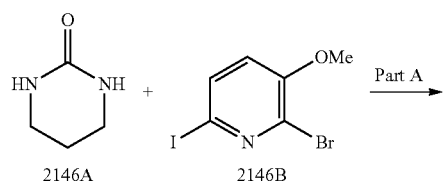

2146A  2146B

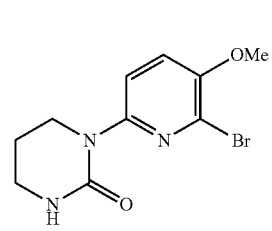

2146C

Part A:

A mixture of 2146A (319 mg, 3.19 mmol), 2146B (500 mg, 1.59 mmol), Pd(OAc)$_2$ (25 mg, 0.038 mmol), Xantphos (45 mg, 0.14 mmol) and sodium t-butoxide (153 mg, 1.59 mmol) in dioxane (3 mL) was stirred in a sealed tube at 60° C. overnight. After cooling, the reaction mixture was diluted with ethyl acetate (10 mL) and H$_2$O (10 mL). The layers were separated. The organic layer was dried with Na$_2$SO$_4$ and then concentrated to dryness. The crude material was purified by silica gel chromatography (100% ethyl acetate) to afford product 2146C (130 mg, 29%).

Example 56

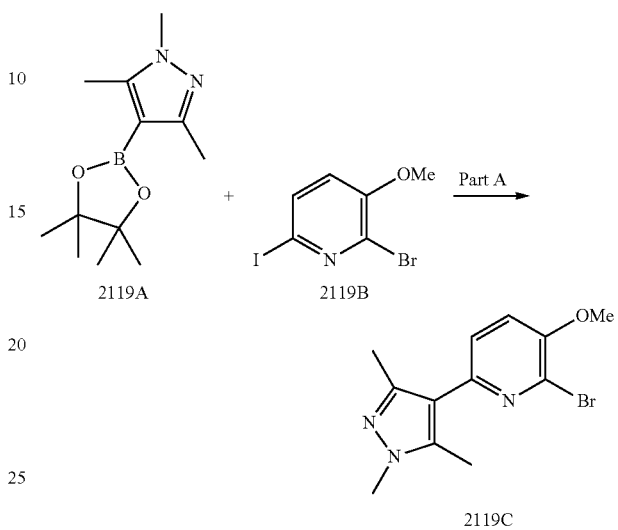

2119A  2119B

2119C

To a pressure bottle, was added compound 2119B (314 mg, 1.0 mmol), compound 2119A (236 mg, 1.0 mmol), Pd(PPh$_3$)$_4$ (58 mg, 0.05 mmol), acetonitrile (5 mL), potassium carbonate (5 mL, 1N aq.). The reaction mixture was vacuumed and purged with Nitrogen for three times and stirred at 80° C. overnight. The reaction mixture was diluted with water (30 mL), extracted with EtOAc (20 mL×3), the organic layers were combined and washed with brine, dried over sodium sulfate and concentrated to dryness. The residue was purified by column chromatography (SiO$_2$, 25% Hexane in EtOAc) to afford 2119C, (0.25 g, 84%).

Example 57

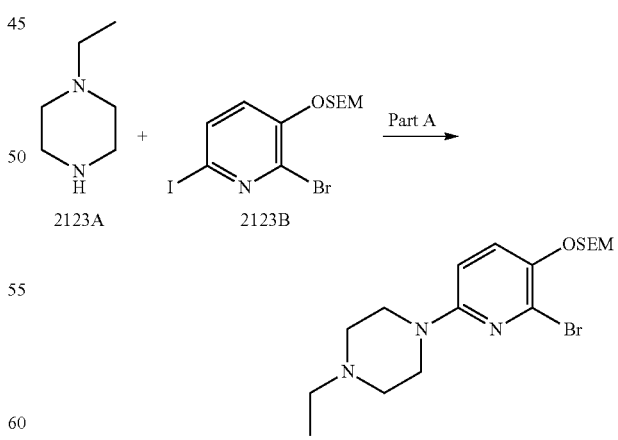

2123A  2123B

2123C

A mixture of 2123A (0.127 mL, 1.0 mmol), 2123B (430 mg, 1.0 mmol), copper iodide (19.5 mg, 0.1 mmol), L-proline (43 mg, 0.2 mmol) and K$_2$CO$_3$ (276 mg, 2.0 mmol) in DMSO (3 mL) was stirred at 70° C. overnight. After cooling, the reaction mixture was diluted with ethyl acetate (20 mL) and Brine (20 mL). The layers were separated. The organic layer was dried with Na$_2$SO$_4$ and then concentrated to dryness. The crude material was purified by silica gel chromatography (Hexane/EtOAc 5:1) to afford compound 2123C (133 mg, 33%).

Compounds 1291-1294, 1298, 1705-1713, 1715, 1723, and 1725-1727 were prepared using procedures similar to that described in Example 57 and Example 51, Parts C and D.

Compounds 2123 and 2400 were prepared using procedures similar to those described in Example 57 and Example 52, Parts C and D.

Compounds 2495 and 2496 were prepared from compound 2494C using procedures similar to those described in Example 57 and Example 52, Parts C and D.

Example 58

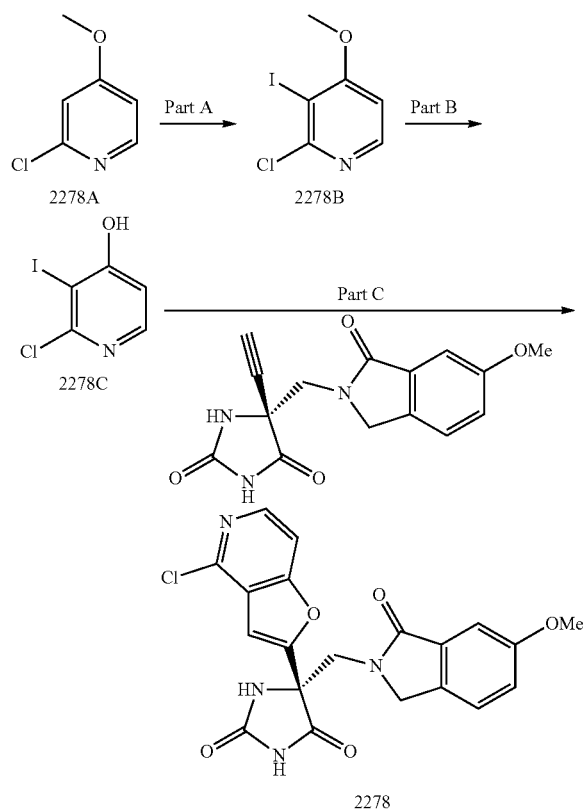

Part A:
Compound 2278A (1.0 g, 6.9 mmol) was dissolved in THF (20 mL) and cooled to −78° C. A 1.6 M solution of n-BuLi (5.2 mL, 8.3 mmol) was added dropwise over 10 minutes. After stirring for one hour at −78° C. a solution of iodine (2.1 g, 8.3 mmol) in THF (10 mL) was added. The reaction mixture was stirring for 2 hours. The reaction mixture was quenched with ethyl acetate and water. The organic layer was separated and washed with sodium thiosulfate solution and brine, dired over sodium sulfate and concentrated. The residue was purified by silica gel chromatography (20% ethyl acetate/hexanes to 40% ethyl acetate hexanes) to afford 2278 B (1.72 g, 73%) as a white solid. HPLC-MS $t_R$=1.60 min; mass calculated for formula C$_6$H$_5$ClINO 268.91, observed LCMS m/z 269.9 (M+H).

Part B:
Treatment of 2278 B (300 mg, 1.1 mmol) with 1M aluminum bromide solution in dibromomethane (5.6 mL, 5.6 mmol) and dichloromethane (0.5 mL) in the microwave at 100° C. for 15 minutes. The reaction mixture was adjusted pH to 5-6 and then diluted with water (2 mL) and dichloromethane. The solids were collected by filtration and washed with the following solvent sequence: dichloromethane, toluene with a minimum amount of water, toluene and dichloromethane. This afforded 2278 C as beige solid which was used without additional purification. HPLC-MS $t_R$=1.20 min (UV$_{254\ nm}$); mass calculated for formula C$_5$H$_3$ClINO 254.89, observed LCMS m/z 255.9 (M+H).

Part C:
A mixture of 2278 C (380.0 mg, 1.27 mmol), 14 (from example 3) (360.0 mg, 1.41 mmol), copper iodide (48.3 mg, 0.25 mmol), Pd(PPh$_3$)$_4$ (150 mg, 0.13 mmol) and triethylamine (0.88 mL, 8.35 mmol) in DMF (3 mL) was heated at 100° C. in the microwave for 10 minutes. The reaction mixture was concentrated and purified by HPLC to afford 2278 (200 mg, 37%) as a pale yellow powder.

HPLC-MS $t_R$=1.48 min (UV$_{254\ nm}$); mass calculated for formula C$_{20}$H$_{15}$ClN$_4$O$_5$ 426.07, observed LCMS m/z 427.2 (M+H).

Compound 1716 was prepared using procedures similar to those described in Example 56 and Example 58, Parts C and D.

Compounds 1329-1331 and 2123 were prepared using procedures similar to those described in Examples 55 and 58.

Example 59

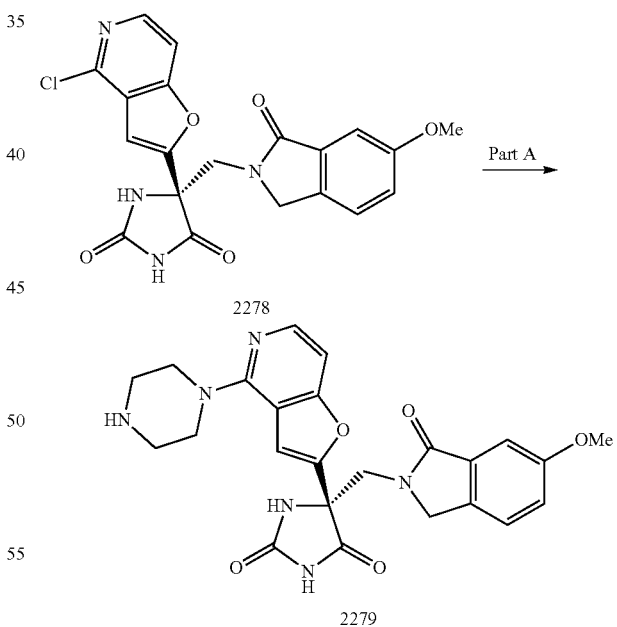

Part A:
A mixture of 2278 (50 mg, 0.12 mmol) and piperazine (41.2 mg, 0.5 mmol) in NMP (1 mL) was heated at 200° C. in the microwave for 30 minutes. The reaction mixture was concentrated and purified by HPLC to afford 2279 (26.2 mg, 48%) as a white solid. HPLC-MS $t_R$=1.75 min (UV$_{254\ nm}$); mass calculated for formula C$_{24}$H$_{24}$N$_6$O$_5$ 476.18, observed LCMS m/z 477.2 (M+H).

Compounds 2280 and 2281 were prepared analogously using the previously-described procedure for 2279.

Example 60

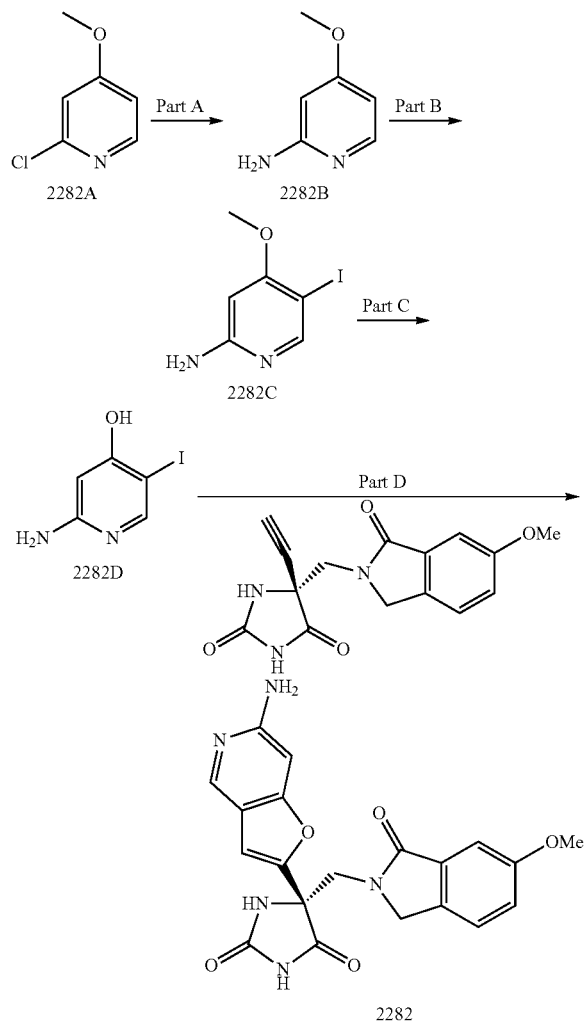

Part A:
A dried resealable tube was charged with compound 2282 A (2.0 g, 13.9 mmol), 1 M LiHMDS solution in THF (16.7 mL, 16.7 mmol) Pd$_2$(dba)$_3$ (0.127 mL, 0.139 mmol) and x-Phos (133.0 mg, 0.28 mmol). The reaction mixture was stirred at 69° C. overnight. After filtered solids, the solution was added 1 M HCl (30 mL) and then stirred 5 minutes. The solution was neutralized to be basic and extracted with ethyl acetate. The combined ethyl acetated layers were dried over sodium sulfate and concentrated to afford the desired product 2282 B (1.3 g, 75%).

Part B:
Compound 2282 B (200 mg, 1.61 mmol) and 1 M iodine monochloride solution in dichloromethane (3.22 mL, 3.22 mmol) in dichloromethane (2 mL) were stirred at room temperature overnight. A lot of solids precipitated. The solids were collected by filtration and washed with dichloromethane. This afforded 2282 C as beige solid (330.0 mg, 80%) which was used without additional purification.

Part C:
Compound 2282 C was prepared using the procedure described in Example 58 part B. HPLC-MS $t_R$=0.47 min (UV$_{254\ nm}$); mass calculated for formula C$_5$H$_5$IN$_2$O 235.94, observed LCMS m/z 237.0 (M+H).

Part D:
Compound 2282 D was prepared using the procedure described in Example 58 part C. HPLC-MS $t_R$=2.37 min (UV$_{254\ nm}$); mass calculated for formula C$_{20}$H$_{17}$N$_5$O$_5$ 407.12, observed LCMS m/z 408.1 (M+H).

Example 61

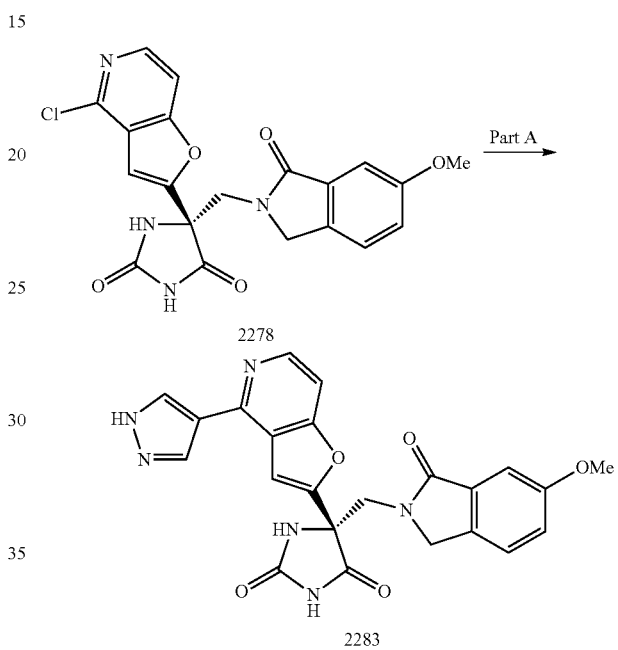

Part A:
A mixture of 2278 (60.0 mg, 0.14 mmol), pyrazole-4-boronic acid pinacol ester (81.5, 0.42 mmol), Pd(PtBu$_3$)$_2$ (14.4 mg, 0.028 mmol) and K$_3$PO$_4$.H$_2$O (64.4 mg, 0.28 mmol) in DMF (2 mL) was heated at 150° C. in the microwave for 30 min. The reaction mixture was concentrated and purified by HPLC to afford 2283 (16.4 mg, 26%). HPLC-MS $t_R$=2.34 min (UV$_{254\ nm}$); mass calculated for formula C$_{23}$H$_{15}$N$_6$O$_5$ 458.13, observed LCMS m/z 459.2 (M+H).

Compound 2284 was prepared using the procedure described in Example 61 HPLC-MS $t_R$=1.76 min (UV$_{254\ nm}$); mass calculated for formula C$_{21}$H$_{18}$N$_4$O$_5$ 406.13, observed LCMS m/z 407.2 (M+H).

Example 62

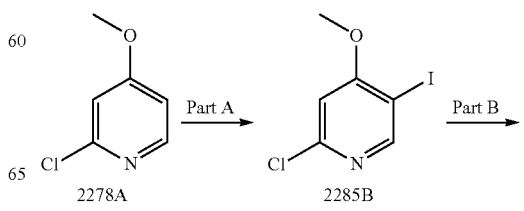

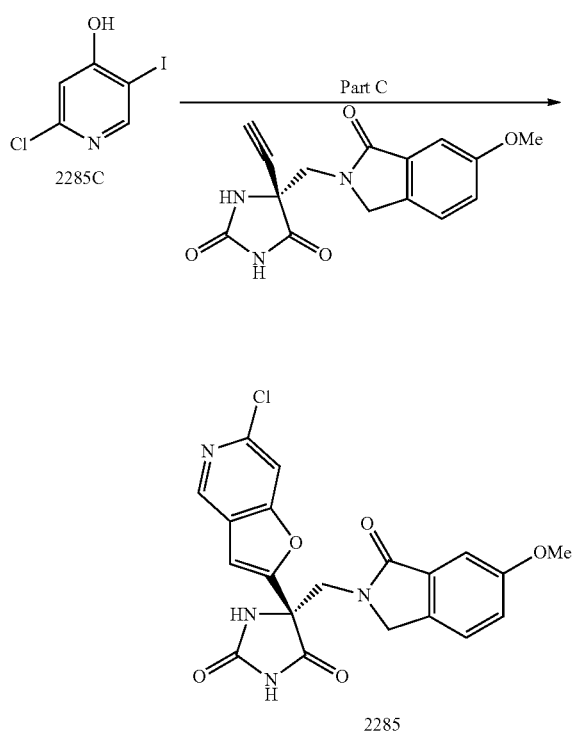

Part A:

Compound 2278 A (2.5 g, 17.4 mmol) was dissolved in $CF_3SO_3H$ (15 g) at 0° C. NIS (4.5 g, 19.2 mmol) was added in small portions to the well-stirred solution. The reaction mixture stirred at RT 2 days and then poured to icy water and neutratized with $NaHCO_3$ to pH 8. A lot of solids precipitated which was collected and then dissolved in DCM. The organic solution was washed with 10% sodium thiosulfate solution and brine, dired over sodium sulfate and concentrated. The residue was purified by silica gel chromatography (10% ethyl acetate/hexanes to 20% ethyl acetate hexanes) to afford 2285 B (1.5 g, 32%) as a white solid. HPLC-MS $t_R$=1.85 min; mass calculated for formula $C_6H_5ClINO$ 268.91, observed LCMS m/z 270.0 (M+H).

Part B:

Compound 2285 C was prepared using the procedure described in Example 58 part B. HPLC-MS $t_R$=1.29 min ($UV_{254\,nm}$); mass calculated for formula $C_5H_3ClINO$ 254.89, observed LCMS m/z 255.9 (M+H).

Part C:

Compound 2285 was prepared using the procedure described in Example 58 part C. HPLC-MS $t_R$=2.79 min ($UV_{254\,nm}$); mass calculated for formula $C_{20}H_{15}ClN_4O_5$ 426.07, observed LCMS m/z 427.2 (M+H).

Compounds 2444-2445 were prepared from compounds 2285 and 2278 using Pd-catalyzed cyanation reaction described in *Tetrahedron Letters*, 1999, 40, 8193-8195.

Compound 2489 was prepared from compound 2285 using a procedure similar to that described in Example 63.

Example 63

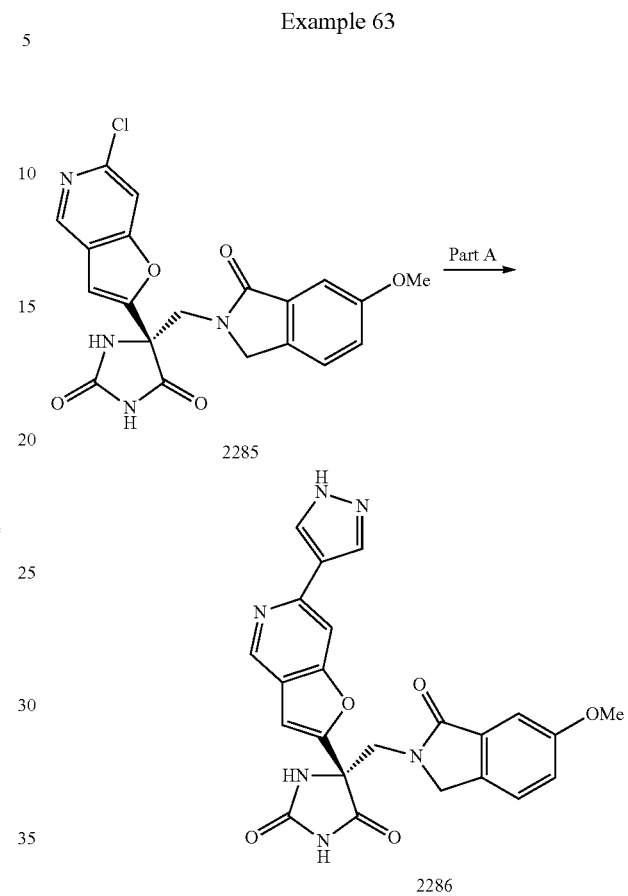

Compound 2286 was prepared with compound 2285 and pyrazole-4-boronic acid pinacol ester using the procedure described in Example 61. HPLC-MS $t_R$=2.28 min ($UV_{254\,nm}$); mass calculated for formula $C_{23}H_{18}N_6O_5$ 458.13, observed LCMS m/z 459.1 (M+H).

Compounds 2287 and 2288 were prepared using described procedure for 2286.

Compounds 2430-2432 were prepared from compounds 2285 and 2278 using procedures similar to that described in Example 63.

Example 64

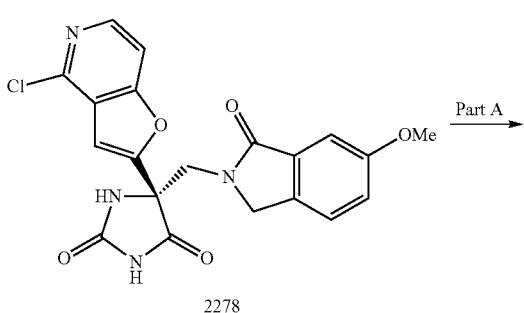

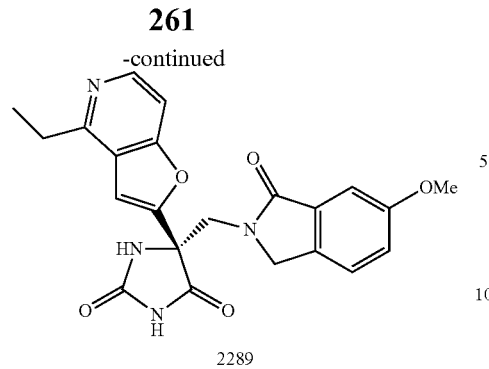

2289

Part A:

A mixture of 2278 (100.0 mg, 0.23 mmol), 1 M Zn(Et)₂ solution in hexane (0.70 mL, 0.70 mmol), Pd(dppf)₂Cl₂ (19.0 mg, 0.023 mmol) and K₂CO₃ (65.0 mg, 0.47 mmol) in DMF (2 mL) was heated at 150° C. in the microwave for 15 min. The reaction mixture was concentrated and purified by HPLC to afford 2289 (53.0 mg, 55%). HPLC-MS $t_R$=1.75 min (UV$_{254\ nm}$); mass calculated for formula $C_{22}H_{20}N_4O_5$ 420.14, observed LCMS m/z 421.2 (M+H).

Compound 2290 was prepared with the compound 2285 and Zn(Et)₂ using the procedure described in Example 64. HPLC-MS $t_R$=2.25 min (UV$_{254\ nm}$); mass calculated for formula $C_{22}H_{20}N_4O_5$ 420.14, observed LCMS m/z 421.1 (M+H).

Compound 2448 was prepared with the compound 2278 and Tributyl(1-ethoxyvinyl)tin using the procedure described in Example 64. HPLC-MS $t_R$=2.60 min (UV$_{254\ nm}$); mass calculated for formula $C_{22}H_{18}N_4O_6$ 434.12, observed LCMS m/z 435.2 (M+H).

Example 65

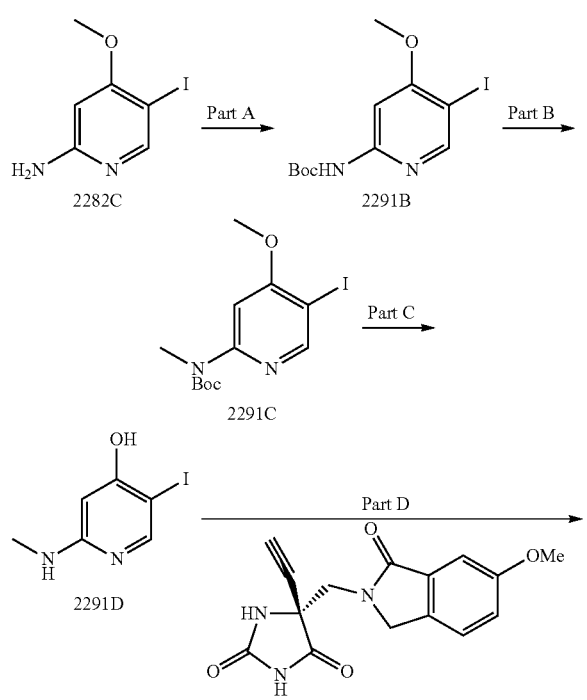

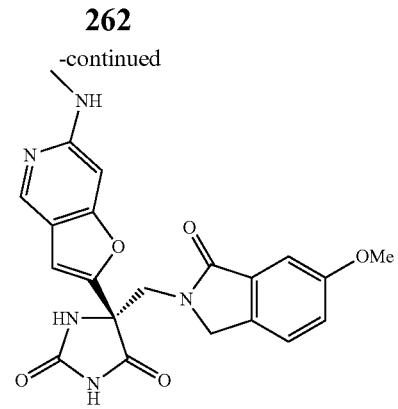

2291

Part A:

Compound 2282 C HCl salt (600.0 mg, 2.1 mmol) and TEA (0.73 mL, 5.3 mmol) were dissolved in methylene chloride (15 mL). (Boc)₂O (502.0 mg, 2.3 mmol) was added and followed by adding small amount of DMAP. The reaction mixture stirred at RT over night. The reaction mixture was concentrated and purified with column chromatography (SiO₂, 20% ethyl acetate/hexanes) to afford desired product 2291 B (190 mg, 25%).

Part B:

To compound 2291 B (190 mg, 0.54 mmol) in THF (6 mL) was added sodium hydride (60%, 28.0 mg, 0.71 mmol). After the reaction mixture was stirred at R$_T$ 40 min, iodide methane (0.28 mL, 4.5 mmol) was added sequentially and then let the reaction mixture stirred over night. The mixture was filtered to remove solids and the filtrate was concentrated. Purification by column chromatogryphy to afford product (160.0 mg, 81%) which was then redissolved in DCM (5 mL). 4 M HCl in dioxane (1 mL) was added to solution. The reaction mixture stirred at RT 4 h to give compound 2291 C.

Part C:

Compound 2291D was prepared using the procedure described in Example 58 part B. HPLC-MS $t_R$=0.39 min (UV$_{254\ nm}$); mass calculated for formula $C_6H_7IN_2O$ 249.96, observed LCMS m/z 250.9 (M+H).

Part D:

Compound 2291 was prepared using the procedure described in Example 58 part C. HPLC-MS $t_R$=1.89 min (UV$_{254\ nm}$); mass calculated for formula $C_{20}H_{15}ClN_4O_5$ 421.13, observed LCMS m/z 422.3 (M+H).

Example 66

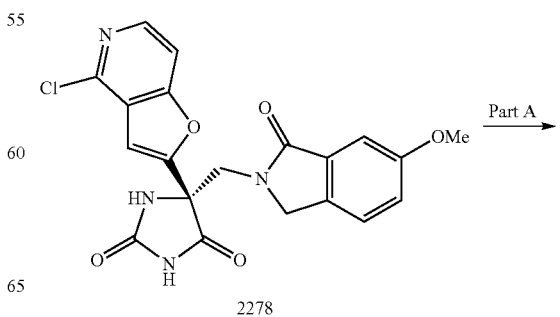

2278

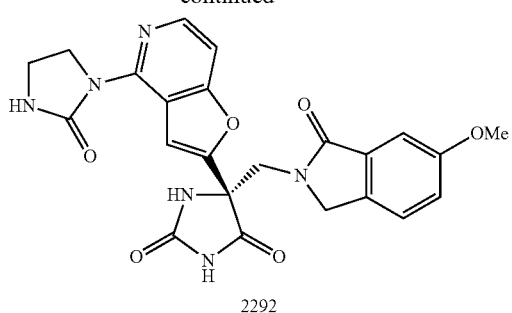

2292

Part A:

A mixture of 2278 (100.0 mg, 0.23 mmol), 2-imidazolidone (60.0 mg, 0.70 mmol), $Pd_2(dba)_3$ (21.0 mg, 0.023 mmol), Xantphos (27.0 mg, 0.047 mmol) and $Ce_2CO_3$ (152.0 mg, 0.47 mmol) in 1,4-dioxane (5 mL) was heated at 120° C. in the microwave for 30 min. The reaction mixture was concentrated and purified by HPLC to afford 2292 (10.1 mg, 9%). HPLC-MS $t_R$=0.89 min ($UV_{254\ nm}$); mass calculated for formula $C_{23}H_{20}N_6O_6$ 476.14, observed LCMS m/z 477.1 (M+H).

Compound 2293 was prepared using the procedure described in Example 66 HPLC-MS $t_R$=2.32 min ($UV_{254\ nm}$); mass calculated for formula $C_{24}H_{21}N_6O_6$ 475.15, observed LCMS m/z 476.2 (M+H).

Example 67

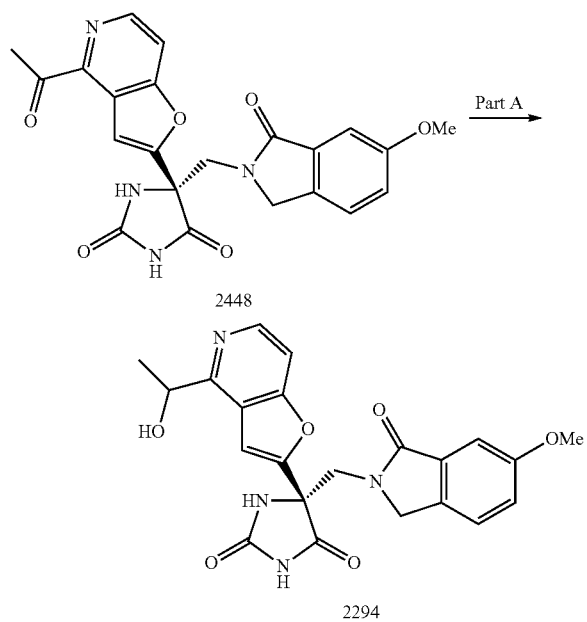

To compound 2448 (70.0 mg, 0.16 mmol) in MeOH (10 mL) was added $NaBH_4$ (50 mg, 1.3 mmol). The reaction mixture was stirred at RT overnight and then concentrated and purified by HPLC to afford 2294 (58.5 mg, 84%). HPLC-MS $t_R$=1.72 min ($UV_{254\ nm}$); mass calculated for formula $C_{22}H_{20}N_4O_6$ 436.14, observed LCMS m/z 437.2 (M+H).

Example 68

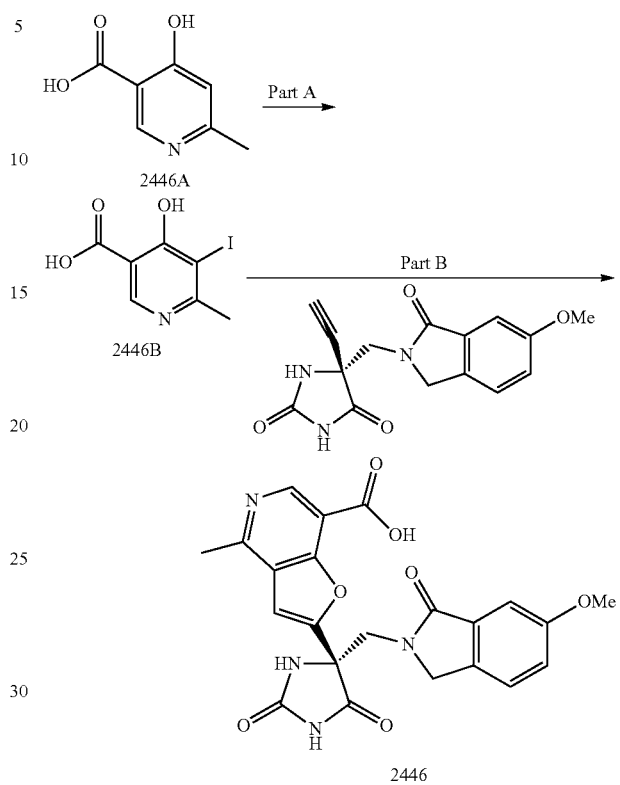

Part A:

To compound 2446 A (0.2 g, 1.31 mmol) and $CaCO_3$ (262.0 mg, 2.6 mmol) in DMF (5 mL) was added 1 M ICl in DCM (1.97 mL, 1.97 mmol). The reaction mixture stirred at RT 1 h to give 2446 B. HPLC-MS $t_R$=0.90 min; mass calculated for formula $C_7H_6INO_3$ 278.94, observed LCMS m/z 280.0 (M+H).

Part B:

Compound 2446 was prepared using the procedure described in Example 58 part C. HPLC-MS $t_R$=1.89 min ($UV_{254\ nm}$); mass calculated for formula $C_{22}H_{18}N_4O_7$ 450.12, observed LCMS m/z 422.3 (M+H).

Example 69

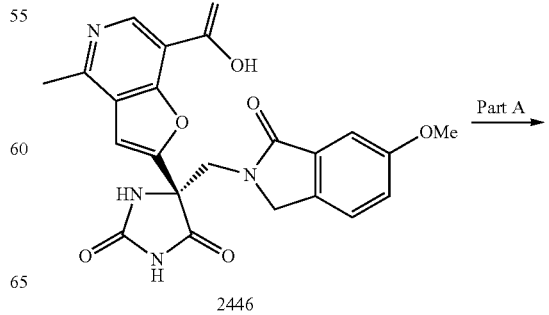

2446

-continued

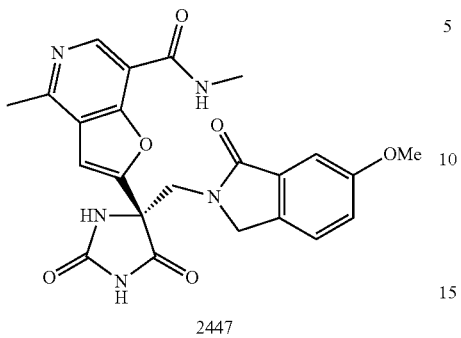
2447

Part A:

A 100 round bottom flask was charged with 2446 (130 mg, 0.29 mmol) and HATU (121.2 mg, 0.32 mmol) in DMF (5 mL). After the reaction mixture was stirred at RT for 30 min, 2 M MeNH$_2$ in THF (0.17 mL, 0.35 mmol) and followed with DIPEA (0.061 mL, 0.35 mmol) were added. The reaction mixture stirred overnight. Concentrated and purified by HPLC to afford 2447 (25.3 mg, 19%). HPLC-MS $t_R$=1.72 min (UV$_{254\ nm}$); mass calculated for formula C$_{22}$H$_{20}$N$_4$O$_6$ 436.14, observed LCMS m/z 437.2 (M+H).

Example 70

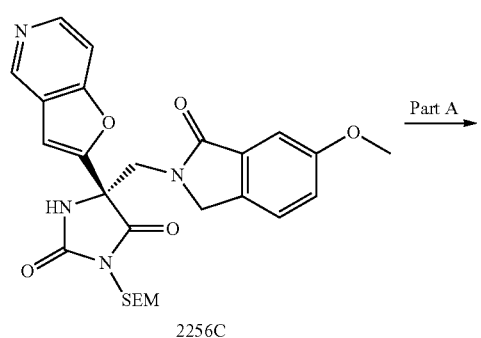
2256C

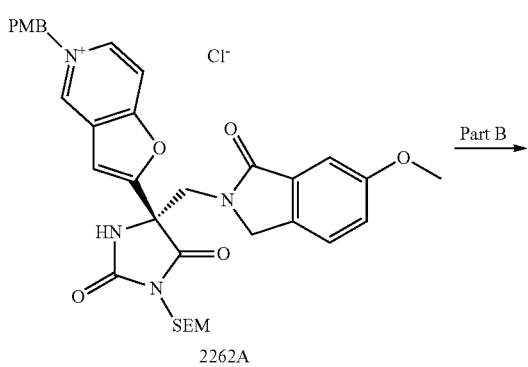
2262A

-continued

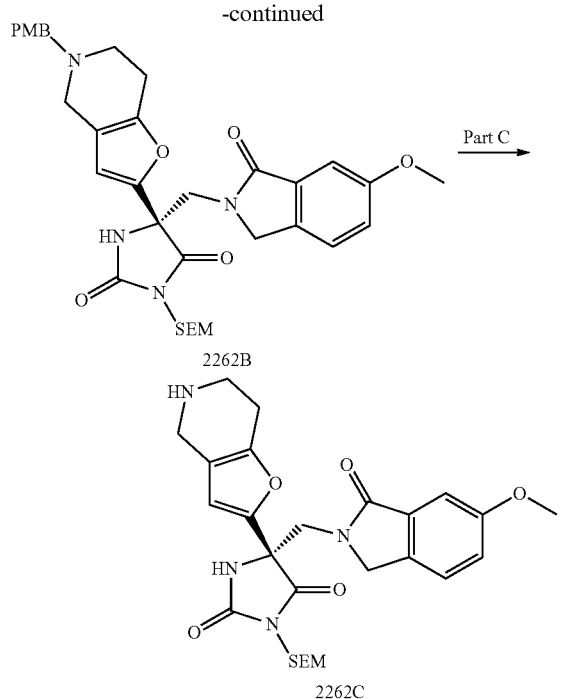
2262B

2262C

Part A

Compound 2256C (142 mg, 0.27 mmol) and 4-methoxybenzyl chloride (78 mg, 0.50 mmol) were refluxed in acetonitrile (5 mL) overnight, concentrated and the residue was washed with ether (×3) to give a yellow solid 2262A (160 mg). HPLC-MS $t_R$=1.43 min (UV 254 nm); mass calculated for formula C$_{34}$H$_{39}$N$_4$O$_7$Si 643.26, observed LCMS m/z 644.2 (M+H).

Part B

To compound 2262A (160 mg, 0.25 mmol) in dichloromethane (3 mL) and methanol (3 mL) at −78° C. was added LiBH$_4$ (11 mg, 0.50 mmol). After 2 hours, the reaction was quenched with water, warmed up to room temperature and evaporated. The residue was dissolved in ethyl acetate, washed with brine, dried and concentrated to give 2262B (160 mg), which was used directly in the next step without purification.

Part C

To compound 2262B (400 mg, 0.62 mmol) in dichloroethane (10 mL) at 0° C. was added 1-chloroethyl chloroformate (0.087 mL, 0.81 mmol). The mixture was stirred at room temperature overnight, concentrated and the residue was refluxed in methanol (10 mL) for 1 hour. After removal of solvent, the solid was washed with ether to give the HCl salt of 2262C (352 mg). HPLC-MS $t_R$=1.38 min (UV 254 nm); mass calculated for formula C$_{26}$H$_{34}$N$_4$O$_6$Si 526.22, observed LCMS m/z 527.3 (M+H).

Compounds 315-321 were prepared using procedures similar to those described in Example 70 followed by functionalization of the piperidine nitrogen and removal of the SEM group using chemistry similar to that described in Example 54, Part D.

Compounds 2263-2268 were prepared using procedures similar to those described in Example 70.

Compounds 2437-2443 were prepared from compound 2262C by treatment of the piperidine with standard electrophilic reagents.

Compound 2483 was prepared from compound 2262C using procedures similar to those described in Example 70.

Example 71

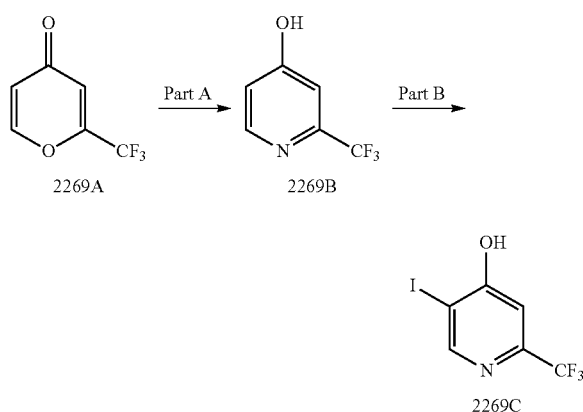

Part A

Compound 2269A (473 mg, 2.88 mmol), prepared according to a procedure as described by Tyvorskii, V. I. et. al (*Tetrahedron*, 1998, 54, 2819-2826), in 7 M ammonia in methanol (5 mL) was heated to 70° C. in a pressure bottle overnight. The reaction mixture was concentrated and purified by column chromatography to give 2269B (273 mg). HPLC-MS $t_R$=1.11 min (UV 254 nm); mass calculated for formula $C_6H_4F_6NO$ 163.02, observed LCMS m/z 164.1 (M+H).

Part B

Compound 2269B (180 mg, 1.10 mmol) and N-iodosuccinimide (260 mg, 1.16 mmol) in dichloromethane (10 mL) were stirred at room temperature overnight. The mixture was diluted with ethyl acetate, washed with 5% $Na_2S_3O_3$ solution, brine, dried, concentrated and the residue purified by column chromatography (20% EtOAc in hexane) to give 2269C (219 mg). HPLC-MS $t_R$=1.39 min (UV 254 nm); mass calculated for formula $C_6H_3F_6INO$ 288.92, observed LCMS m/z 290.0 (M+H).

Compound 2269 was prepared using the procedures described in Example 71 and procedures similar to those described in Example 52, Part D.

Example 72

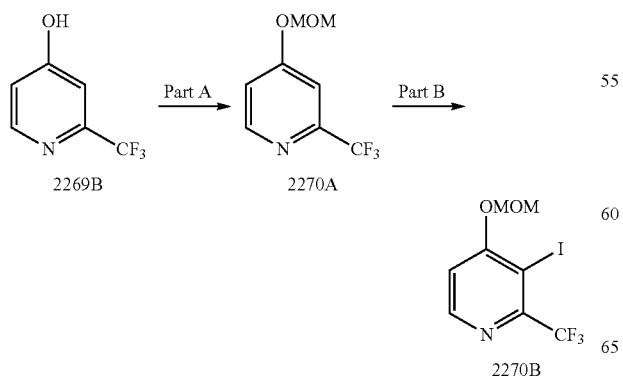

Part A

A mixture of compound 2269B (800 mg, 4.91 mmol), chloromethyl methyl ether (711 mg, 8.83 mmol) and silver carbonate (2.03 g, 7.37 mmol) in ethyl acetate (15 mL) was heated at 50° C. overnight, and filtered. The filtrate was concentrated and the resulting crude was purified by column chromatography (15% to 50% EtOAc in hexane) to give 2270A (158 mg).

Part B

Compound 2270A (158 mg, 0.76 mmol) was dissolved in THF (5 mL) and cooled to −78° C. A solution of 2.5M n-BuLi (0.37 mL, 0.91 mmol) was added dropwise and stirred for 1 hour. Chloroiodoethane (174 mg, 0.91 mmol) was added dropwise and stirred for 1 hour. The reaction was quenched with saturated ammonium chloride and extracted with ethyl acetate. The organic layers were washed with water, brine, dried and concentrated. The residue was purified by column chromatography to provide compound 2270B (25 mg) $^1$H NMR (400 MHz, $CDCl_3$): δ 8.42 (d, J=4.2 Hz, 1H), 7.11 9d, j=4.3 Hz, 1H), 5.38 (s, 2H), 3.52 (s, 3H).

Compound 2270 was prepared using the procedures described in Example 72 and procedures similar to those described in Example 52, Part D.

Example 73

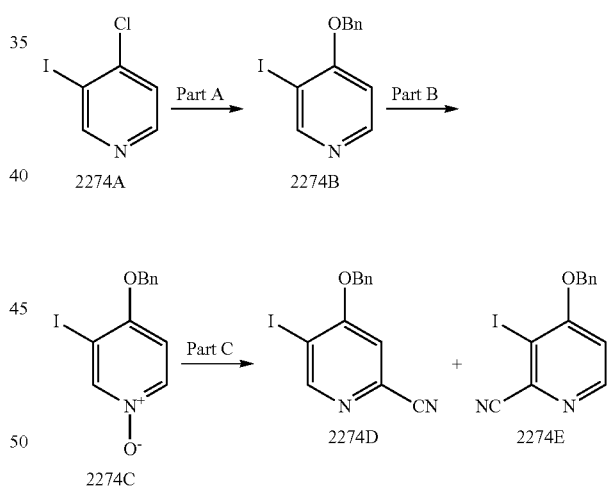

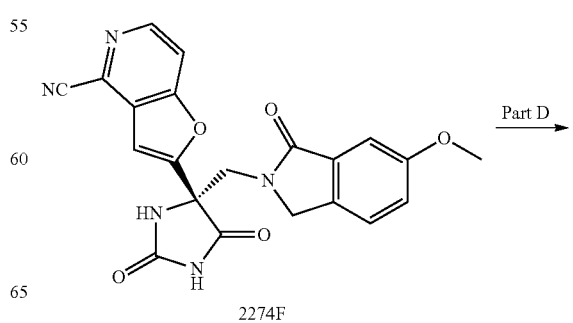

Compound 2273 was prepared using procedures similar to those described in Example 73.

Example 74

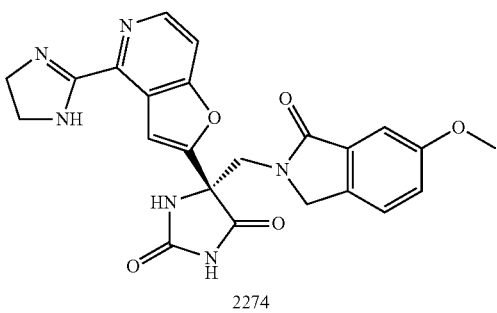

2274

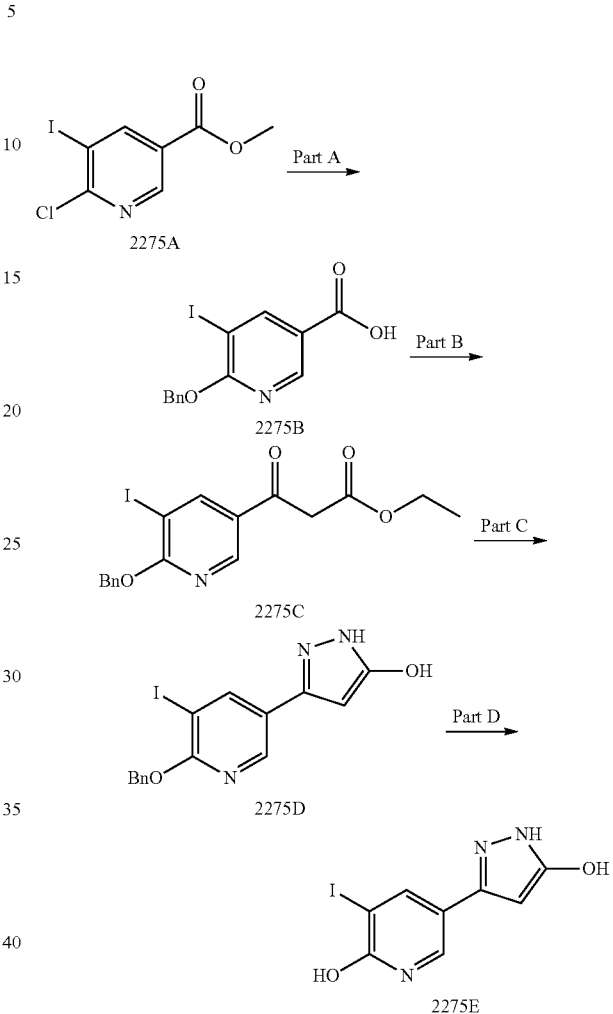

Part A

To benzyl alcohol (828 mg, 7.66 mmol) was added sodium hydride (60%, 306 mg, 7.66 mmol) at 0° C. and the mixture was stirred for 30 minutes at room temperature. Compound 2274A (1.22 g, 5.11 mmol) was added to the mixture. The reaction mixture was stirred at room temperature for 6 hours. The reaction mixture was quenched with water and partitioned between water and ethyl acetate. The organic layer was washed with water, brine, dried and concentrated. The crude was purified by column chromatography (0 to 10% EtOAc in hexane) to give 2274B (186 mg).

Part B

To compound 2274B (196 mg, 0.60 mmol) in dichloromethane (2 mL) at 0° C. was added mCPBA (70%, 165 mg, 0.67 mmol). The mixture was stirred at room temperature overnight, diluted with ethyl acetate and the organic layer was washed with saturated $NaHCO_3$, water, brine, dried and concentrated. The crude was purified by column chromatography (5 to 10% MeOH in $CH_2Cl_2$) to give 2274C (220 mg), which was used directly in next step.

Part C

To compound 2274C (220 mg) in triethylamine (5 mL) was added TMSCN (1.5 mL). The mixture was heated at 90° C. for 4 hours and concentrated. The residue was partitioned between dichloromethane and brine. The aqueous layer was extracted with $CH_2Cl_2$ (2×). The combined organic layers were dried, concentrated and purified by column chromatography (20% EtOAc in hexane) to give 2274D (85 mg) and 2274E (87 mg). 2274D: $^1$H NMR (400 MHz, $CDCl_3$): δ 8.56 (s, 1H), 7.43 (m, 5H), 7.11 (s, 1H), 5.21 (s, 2H). 2274E: $^1$H NMR (400 MHz, $CDCl_3$): δ 8.42 (d, J=5.6 Hz, 1H), 7.43 (m, 5H), 6.99 (d, J=5.6 Hz, 1H), 5.21 (s, 2H).

Part D

A mixture of compound 2274F (60 mg, 0.144 mmol) and sulfur (5 mg) in ethylenediamine (2 mL) was heated at 100° C. in a microwave for 7 minutes. The reaction mixture was concentrated and purified by reverse phase chromatography to give 2274 (27 mg). HPLC-MS $t_R$=0.97 min (UV 254 nm); mass calculated for formula $C_{23}H_{20}N_6O_5$ 460.15, observed LCMS m/z 461.1 (M+H).

Compounds 322 and 323 were prepared from 2274D and 2274E using procedures described in Example 73 and procedures similar to those described in Example 58, Part C.

Part A

To benzyl alcohol (2 mL) was added sodium hydride (60%, 340 mg, 8.5 mmol) at 0° C. and the mixture was stirred for 30 minutes at room temperature. Compound 2275A (1.68 g, 5.7 mmol) was added to the mixture. The reaction mixture was stirred at room temperature overnight. The reaction mixture was quenched with water and partitioned between water and ether. The aqueous layer was acidified to pH ~2, filtered and the solid washed with water, and dried afford a white solid 2275B (790 mg). HPLC-MS $t_R$=2.06 min (UV 254 nm); mass calculated for formula $C_{13}H_8INO_3$ 354.97, observed LCMS m/z 356.0 (M+H).

Part B

Compound 2275B (267 mg, 0.75 mmol) was dissolved in acetonitrile (5 mL) and CDI (123 mg, 0.75 mmol) was added. In a separate flask potassium ethyl malonate (255 g, 1.5 mmol) was suspended in a solution of THF (5 mL) and triethylamine (0.31 mL, 2.25 mmol). The suspension was treated with magnesium chloride (178 mg, 1.88 mmol) and stirred at 40° C. for 4 hours. The first solution was added dropwise to the suspension at 0° C. and then the reaction was stirred at 40° C. overnight. The reaction was treated with 3 N HCl and extracted with ethyl acetate. The combined organic layers were dried over sodium sulfate and concentrated to provide compound 2275C (218 mg).

Part C

Compound 2275C (300 mg, 0.71 mmol) and hydrazine monohydrate (3 mL) were suspended in methanol (5 mL) and stirred at 60° C. overnight. The reaction was concentrated and purified by reverse chromatography using a 0.1% trifluoroacetic acid in the aqueous mobile phase. The isolated fractions were concentrated to afford 2275D (145 mg) as a white powder after lyophilization. HPLC-MS $t_R$=1.90 min (UV$_{254\,nm}$); mass calculated for formula $C_{15}H_{12}IN_3O_2$ 393.00, observed LCMS m/z 394.0 (M+H).

Part D

Compound 2275D (60 mg, 0.15 mmol) was stirred in dichloromethane (3 mL) and TFA (1 mL) for 90 minutes. The mixture was concentrated to give a brown residue 2275E. HPLC-MS $t_R$=0.80 min (UV$_{254\,nm}$); mass calculated for formula $C_8H_6IN_3O_2$ 302.95, observed LCMS m/z 304.0 (M+H).

Compounds 2275-2276 were prepared using the procedures described in Example 74 and procedures similar to those described in Example 52, Part D.

Example 75

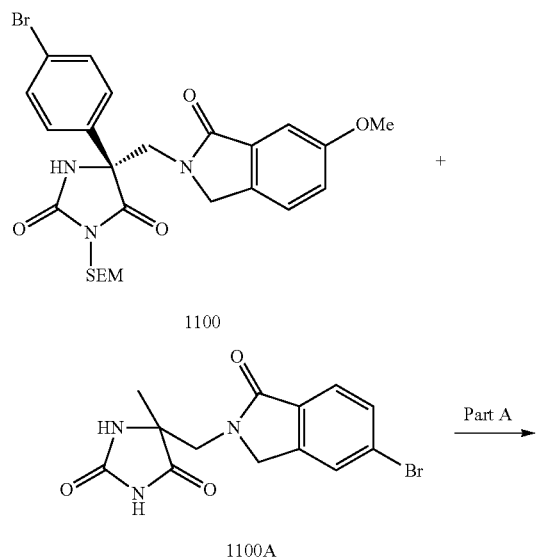

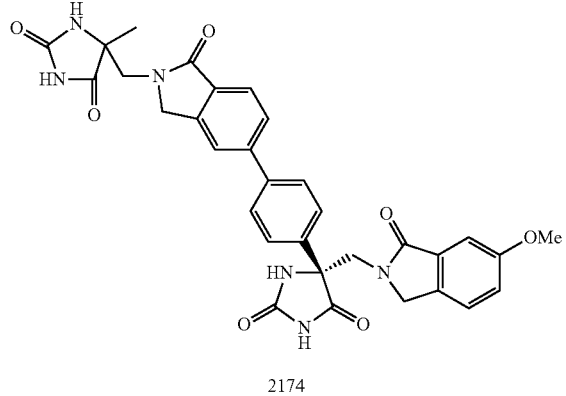

2174

Part A

Compounds 1100 and 1100A were obtained using procedures described in Yu, W.; Tong, L. et al Compounds for the treatment of inflammatory disorders US 2007/0219218 and/or Yu, W.; Tong, L. et al PCT Int. Appl. (2006), WO2006019768.

Compound 1100 (0.1 g, 0.18 mmol), pinacolatodiboron (55 mg, 0.21 mmol), Pd(dppf)Cl$_2$ (15 mg, 0.022 mmol) and potassium acetate (55 mg, 0.56 mmol) were added to a flask and placed under a blanket of N$_2$. Dioxane (2 mL) was added and the reaction mixture was heated at 100° C. for 1 h under N$_2$. The reaction mixture was allowed to cool to rt. Compound 1100A (0.12 g) was added as a suspension in 1.5 mL of acetonitrile. Aq 1M K$_2$CO$_3$ (1.5 mL) was added. The flask was heated to 100° C. for 5 h. The reaction mixture was diluted with EtOAc, washed with saturated aq NaHCO$_3$, and water. The resulting organic layer was concentrated to dryness. The crude product was purified via sgc using a 10%-100% gradient of (10% MeOH in EtOAc)/hexanes as the mobile phase to give 33 mg of 1100B. LCMS calcd 738.20 obsd M+H=739.3.

Part B

Compound 1100B was converted to 2174 using procedures similar to those described in Example 92 Part A. LCMS calcd 608.20 obsd M+H=609.3.

Example 76

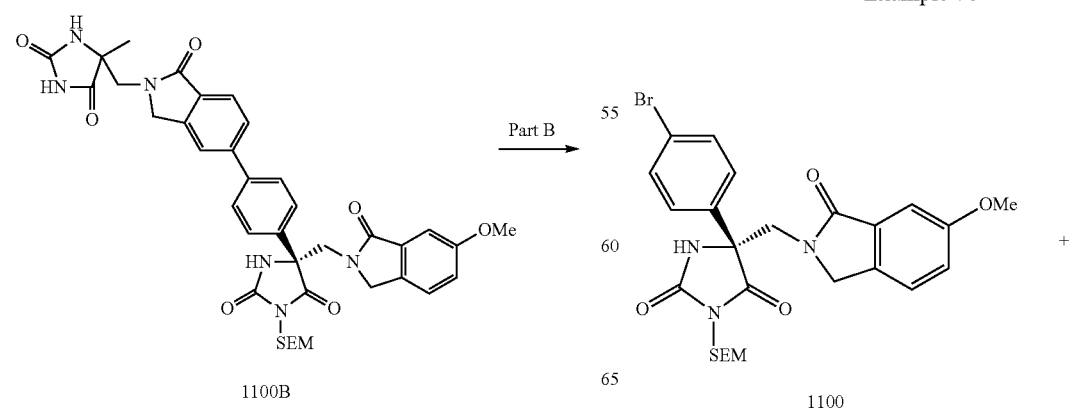

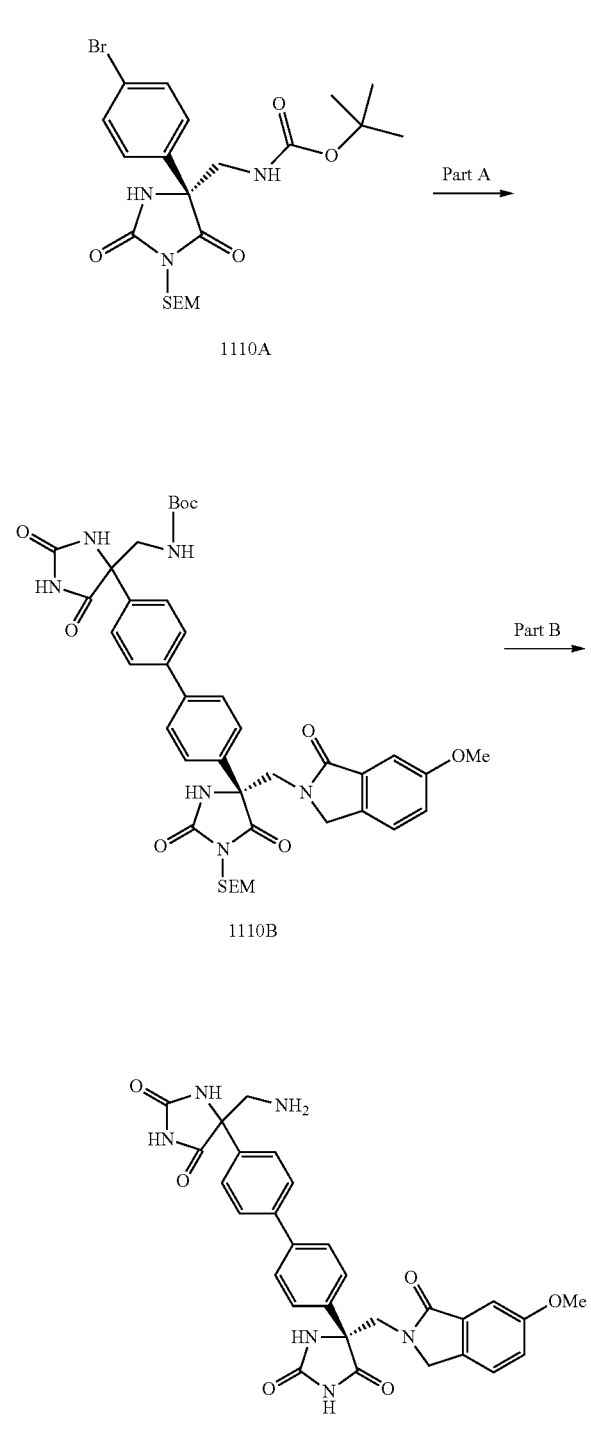

1110A

1110B

2175

Part A

Compounds 1100 and 1110A were obtained using procedures described in Yu, W.; Tong, L. et al Compounds for the treatment of inflammatory disorders US 2007/0219218 and/or Yu, W.; Tong, L. et al PCT Int. Appl. (2006), WO 2006019768.

Compound 2175 was prepared using procedures similar to those described in Example 75.

Example 77

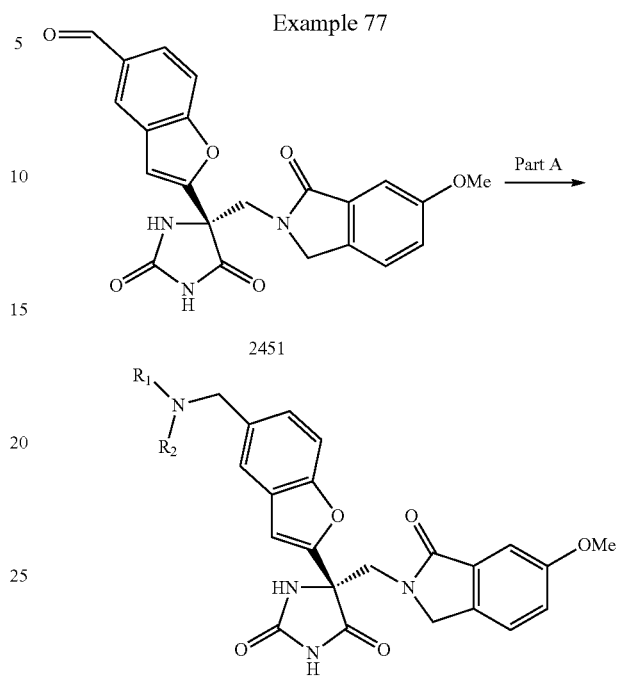

2451

Part A

Compound 2451 was prepared using chemistry described in Example 48. It was converted to a variety of benzylic amines using chemistry similar to that described below for compound 2177.

Compound 2451 (72 mg, 0.17 mmol), N,N-dimethyl ethylenediamine (CAS #108-00-9, 18 mg, 20 mmol), $CH_2Cl_2$ (5 mL), acetic acid (12 mg, 20 mmol), and sodium triacetoxyborohydride (54 mg, 0.25 mmol) were added to a rb flask and stirred overnight at rt. Aq 1M HCl was added and the reaction mixture was concentrated. The crude product was purified via reverse phase chromatography using a 5%-90% $CH_3CN/H_2O$ gradient as the mobile phase with 0.1% formic acid added to each component of the mobile phase. The major peak was isolated to give 33 mg of compound 2177. LRMS calcd 491.22 obsd M+H=492.3.

Compounds 2176, 2179-2181, 2183, 2185, 2186, and 2484-2486 were prepared using procedures similar to those described in Example 77.

Example 78

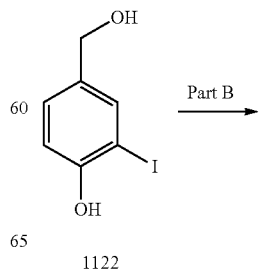

1122

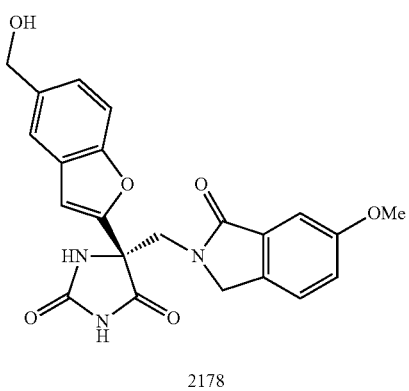

2178

Part A

Compound 1122 is known (Grzegorz M. Salamonczyk, Vibha B. Oza, Charles J. Sih *Tetrahedron Letters* 1997, 38, 6965.) and is also commercially available. Compound 1122 may be converted to 2178 using chemistry similar to that described in Example 81. LCMS Calcd 421.1 Obsd M+H=422.2

Example 79

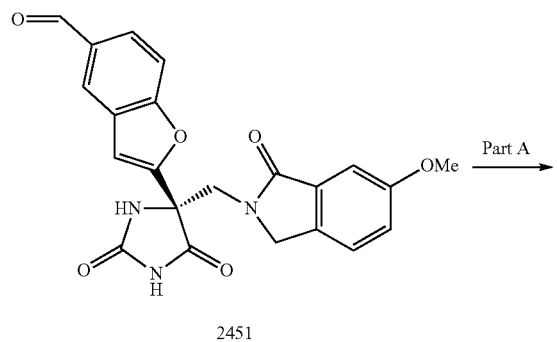

2451

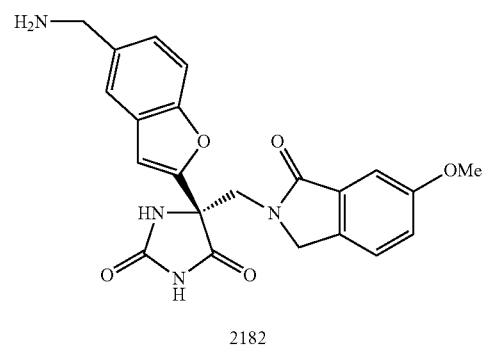

2182

Part A

Compound 2451 (75 mg, 0.18 mmol), absolute ethanol (10 mL), hydroxylamine hydrochloride (37 mg, 0.53 mmol), and sodium acetate (44 mg, 0.53 mmol) were added to a rb flask equipped with a stir bar. The flask was heated to 80° C. and left stirring overnight. The reaction mixture was concentrated to dryness. The crude product was purified via sgc using 100:10:1 $CH_2Cl_2$:MeOH:$NH_4OH$ as the mobile phase to give 32 mg of compound 2420. LCMS Calcd 434.1 Obsd M+H=435.2

Part B

Compound 2420 (30 mg, 0.069 mmol) was dissolved in methanol (5 mL) and TFA (0.1 mL). The solution was placed in a Parr bottle. Platinum dioxide (5 mg) was added and the reaction mixture was shaken under 50 psi of hydrogen overnight. The reaction mixture was filtered and the filtrate was concentrated to dryness. The resulting material was diluted with methanol and triethylamine (02 mL) was added. The solution was concentrated to dryness. The crude product was purified via prep TLC using 100:10:1 $CH_2Cl_2$:MeOH:$NH_4OH$ as the mobile phase. The main product was dissolved in methanol and HCl in $Et_2O$ was added until the pH was less than 1. The solution was concentrated to dryness to give 9 mg of compound 2182-HCl salt. HRMS $C_{22}H_{21}N_4O_5$ calcd 420.1434 obsd M+H=421.1506 Δm/m=1.2 ppm.

Example 80

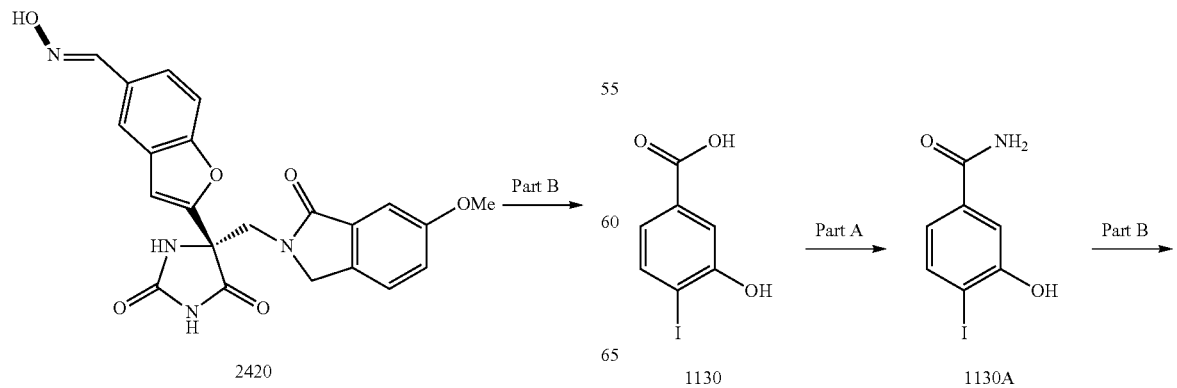

2420

1130

1130A

-continued

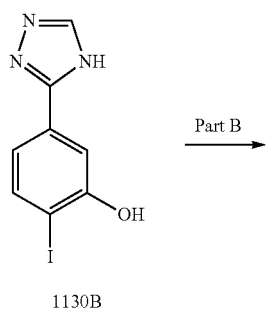

1130B

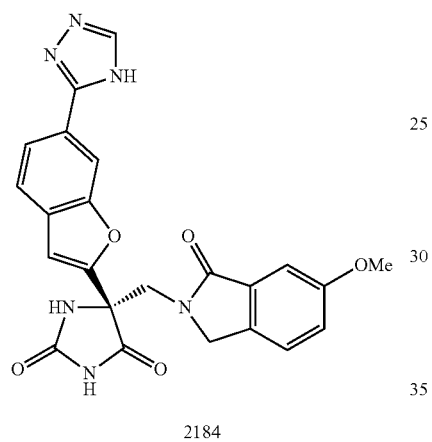

2184

Part A

Compound 1130 (1.0 g, 3.79 mmol) was dissolved in DMF (15 mL). Carbonyl diimidazole (0.74 g, 4.56 mmol) was added and the reaction mixture was stirred at rt for 2 h. The reaction mixture was added dropwise into 10 mL of concentrated ammonium hydroxide. The reaction mixture was stirred at rt overnight. The reaction mixture was diluted with EtOAc and washed with aq NH$_4$Cl and water. The organic layer was concentrated to dryness to give 0.96 g of 1130A. $^1$HNMR (DMSO) d 10.5 (s, 1H), 7.92 (br s, 1H), 7.73 (d, 8 Hz, 1H), 7.35 (br s, 1H) 7.33 (d, 2 Hz, 1H), 7.07 (d of d, 8 Hz, 2 Hz, 1H), 3.35 (s, HOD peak), 2.50 (s, DMSO peak).

Part B

Compound 1130A (0.23 g, 0.76 mmol) and N,N-dimethylformamide dimethyl acetal (4 mL) were heated in a sealed tube for 3 h at 110° C. The resulting solution was concentrated to dryness. Acetic acid (3 mL) and hydrazine (0.3 mL) were added and the reaction mixture was heated in a sealed tube for 2 h at 90° C. The reaction mixture was partitioned between EtOAc and aq NaHCO$_3$. The organic layer was concentrated to dryness. The crude product was purified via sgc using a gradient of 0%-100% (100:10:1 CH$_2$Cl$_2$:MeOH:NH$_4$OH): CH$_2$Cl$_2$ as the mobile phase to give 0.14 g of 1130B. LRMS calcd 286.96 obsd M+H=287.88.

Part C

Compound 1130B was converted to compound 2184 using Sonogashira conditions similar to those described in Example 81. LCMS calcd 458.13 obsd M+H=459.3.

Example 81

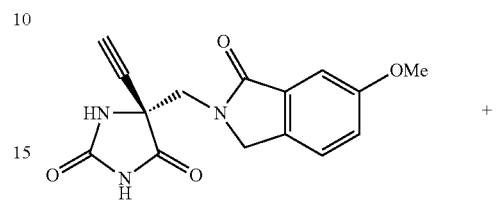

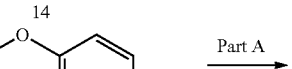

2187

Part A

Compound 14 (90 mg, 0.30 mmol), copper (I) iodide (3.6 mg, 0.019 mmol), 2-bromo-5-methoxyphenol (88 mg, 0.36 mmol). and dichlorobis(triphenyl phosphine)palladium(II) (27 mg, 0.038 mmol) were added to a 25 mL Schlenck tube equipped with a stir bar. The tube was capped with a septum and cycled between vacuum and nitrogen four times. DMF (1.5 mL, Aldrich sure seal) was added via syringe and the tube was cycled between vacuum and nitrogen three times. Diisopropylamine (0.25 mL) was added via syringe. The tube was placed in an 80° C. oil bath and left stirring for 18 h under nitrogen. The reaction mixture was removed from the bath and diluted with EtOAc and 1.0 M aq pH 5.5 sodium phosphate buffer. The layers were separated. The organic layer was washed with pH 5.5 sodium phosphate buffer, water, and brine. The resulting organic layer was concentrated to dryness. The crude product was purified via sgc using a 0.5%-7% ethanol/CH$_2$Cl$_2$ gradient as the mobile phase to give impure compound 2187. The impure product was repurified via prep TLC using 95:5 CH$_2$Cl$_2$:MeOH as the mobile phase to give 3 mg of 2187. %). HPLC-MS t$_R$=3.20 min (UV 254 nm); mass calculated 421.1, observed (M+H) LCMS m/z 422.2.

Compound 2214 was prepared from 2-iodophenol using procedures similar to those described in Example 81.

Compound 2222 was prepared from the corresponding 2-iodophenol using procedures similar to those described in Example 81.

Example 82

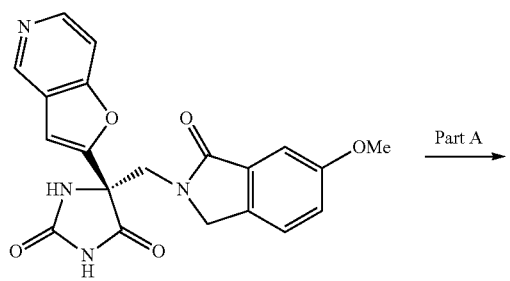

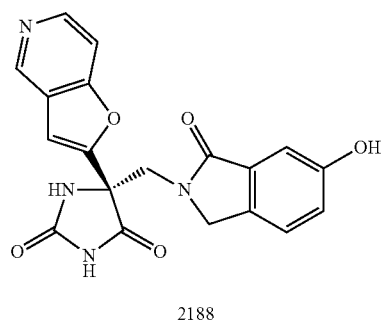

Part A

Compound 2259A (10.9 mg, 0.028 mmol) and pyridine hydrochloride were added to a microwave tube equipped with a stir bar. The tube was heated in the microwave at 180° C. for 1 h. The resulting solid was diluted with 1.5 mL of methanol and 30 mL of water. Sodium carbonate was added to neutralize the HCl. The resulting solution was concentrated to dryness on the rotovap. The crude product was partially purified via reverse phase chromatography using an Isco C-18 Cartridge and a 20%-90% $CH_3CN/H_2O$ gradient as the mobile phase. Formic acid (0.1% by volume) was added to each component of the mobile phase. The main peak was isolated as product mixed with pyridine-HCl. The sample was concentrated to dryness and re-columned using a 15%-50% $CH_3CN/H_2O$ gradient with 0.1% formic acid added. Compound 2188 was obtained as product (8 mg). HPLC-MS $t_R$=1.39 min (UV 254 nm); mass calculated 378.1, observed (M+H) LCMS m/z 379.2

Example 83

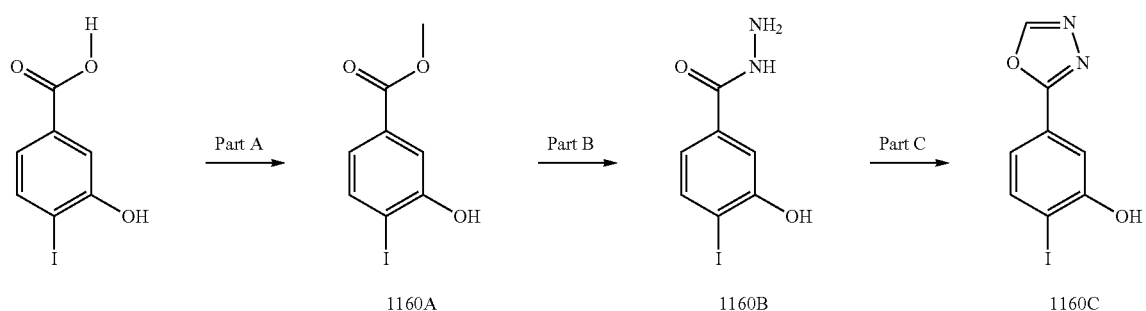

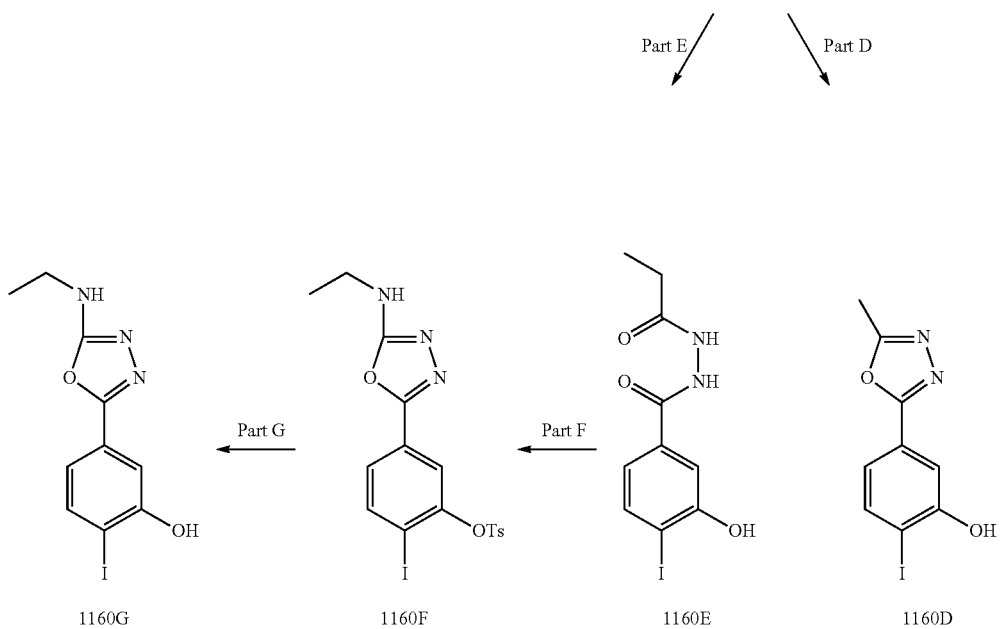

Part A

3-Hydroxy-4-Iodobenzoic acid (1.15 g, 4.36 mmol) was dissolved in 10 mL of MeOH. Thionyl chloride was added and the flask was placed under $N_2$. After stirring for 5 m at rt, the flask was placed in a 50° C. oil bath and stirred for 2 h. The reaction mixture was concentrated to dryness. The crude product was purified via sgc using a 10%-30% (5% MeOH in EtOAc)/hexanes gradient as the mobile phase. Compound 1160A was isolated as a white solid (1.08 g, 89% yield). HPLC-MS $t_R$=3.72 min (UV 254 nm); mass calculated 277.9, observed (M+H) LCMS m/z 279.2.

Part B

Compound 1160A (0.57 g, 2.05 mmol) was dissolved in 6 mL of absolute ethanol. The flask was placed under $N_2$ blanket. Hydrazine monohydrate (1 mL, 20.4 mmol) was added and the flask was placed in a 60° C. oil bath. The flask was placed behind a blast shield and stirred at 60° C. under nitrogen for 27 h. The flask was allowed to cool to rt and partially concentrated on the rotovap. Water and ethyl acetate were added. The layers were separated. The organic layer was washed twice with water, then once with brine. The resulting solution was concentrated to give 1160B as a white solid (261 mg/46% yield). LRMS calcd 277.96 obsd M+H=278.92.

Part C

Compound 1160B (544 mg, 1.95 mmol), absolute ethanol (10 mL), and triethylorthoformate (3 mL) were added to a flask, placed under $N_2$, and heated to 70° C. The reaction was stirred for 2 h, then allowed to cool to rt. Pyridinium paratoluene sulfonate was added (24 mg) and the reaction mixture was left stirring over the weekend at rt. The reaction mixture was heated to 70° C. under $N_2$ for 7 h, then left stirring ON at rt. The reaction mixture was concentrated to dryness on the rotovap. The crude product was purified via sgc using a 1%-4% EtOH/$CH_2Cl_2$ gradient as the mobile phase to give 1160C as a white solid (0.13 g/23% yield) LRMS Calcd 287.9 Obsd M+H 289.1.

Compound 2189 was prepared from 1160 C using a procedure similar to that described in Example 84 part B.

Part D

Compound 1160B (536 mg, 1.93 mmol), absolute ethanol (10 mL), and triethyl orthoacetate (3 mL) were added to a flask and converted to 1160D using a procedure similar to that used to prepare 1160C. LRMS Calcd 301.96 Obsd M+H 302.92.

Compound 2190 was prepared from 1160D using a procedure similar to that described in Example 84 part B. HPLC-MS $t_R$=2.95 min (UV 254 nm); mass calcd 473.1, obsd (M+H) LCMS m/z 474.3.

Part E

Compound 1160B (576 mg, 2.07 mmol) was suspended in EtOAc (10 mL), and ethyl isocyanate (0.2 mL) was added. The reaction mixture was stirred at rt over the weekend, then concentrated to dryness. The crude product was purified via sgc using a 2%-10% EtOH/$CH_2Cl_2$ gradient as the mobile phase. Compound 1160E was collected as a white solid to give 458 mg in 63% yield. LRMS Calcd 348.9 LRMS obsd M+H 349.9.

Part F

Compound 1160E (458 mg, 1.31 mmol), $CH_2Cl_2$, triethylamine (1.5 mL), and para toluene sulfonyl chloride (545 mg, 2.85 mmol) were added to a flask and left stirring at rt for 3.5 days. The reaction mixture was concentrated to dryness to remove the excess triethylamine. $CH_2Cl_2$ and aq 1.0 M pH 7.0 sodium phosphate buffer were added. The layers were separated. The organic layer was washed with water and brine. The resulting solution was dried with $MgSO_4$, filtered, and concentrated to dryness. The crude product was purified via sgc using a 1%-5% EtOH/$CH_2Cl_2$ gradient as the mobile phase to give 0.52 g of 1160F as a white solid. LRMS calcd 484.99 obsd M+H=486.0.

Part G

Compound 1160F (0.51 g, 1.05 mmol) was partially dissolved in dioxane (6 mL) and absolute ethanol (1.0 mL). Aq. 1.0 M LiOH was added (1.5 mL) and the reaction mixture was stirred at rt for 5 h. Additional aq LiOH (1.5 mL) was added and the reaction mixture was stirred overnight at rt. The reaction mixture was concentrated to dryness. EtOAc and aq 1.0 M $NaH_2PO_4$ were added. The layers were separated. The aq layer was extracted with EtOAc. The combined organic layer was washed with brine, filtered, and concentrated to an off white solid. (0.50 g). The crude product was purified via sgc using a 2%-3.5% EtOH/$CH_2Cl_2$ gradient as the mobile phase to give 0.12 g of 1160G as a white solid. LRMS calcd 330.98 obsd M+H 332.02

Compound 2193 was prepared from 1160G using a procedure similar to that described in Example 84 part B. LCMS calcd 502.16 obsd M+H=503.04.

Example 84

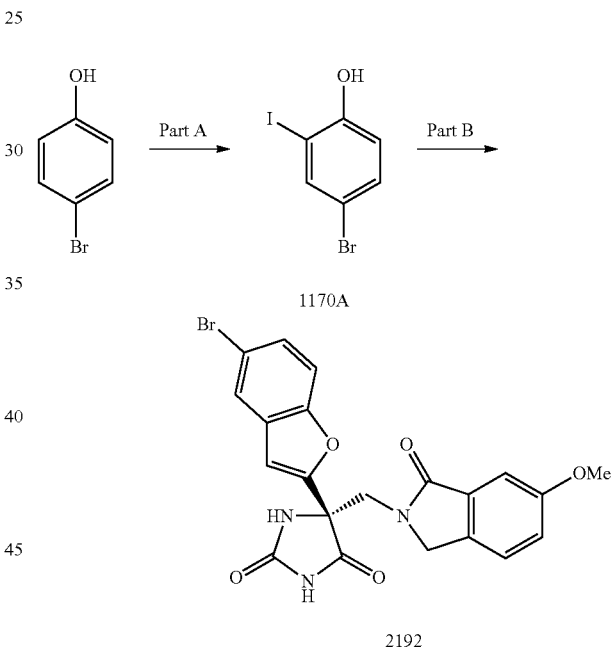

Part A

4-Bromophenol (8.65 g, 50 mmol), sodium iodide (7.52 g, 50 mmol), and sodium hydroxide (2.0 g, 50 mmol) were added to a 250 mL flask equipped with a stir bar. Methanol (100 mL) was added. The reaction mixture was stirred at rt until most of the starting materials had dissolved. The flask was cooled in an ice water bath and aqueous sodium hypochlorite (72 mL of commercial 5.25% Clorox bleach) was added dropwise over 1 h. The reaction mixture was stirred for 35 min at 0° C. A 10% aq soln of sodium thiosulfate was added and the reaction mixture was stirred overnight. The reaction mixture was diluted with water (75 mL), then acidified to pH 6.5 with satd aq $NaH_2PO_4$. Brine (15 mL) was added. The resulting mixture was extracted with 2×100 mL of an 80:20 mixture of EtOAc:Hexanes. The combined organic layer was concentrated to give 10.77 grams of a clear oil. The crude product was purified via sgc using a Supelco 90 g $SiO_2$ cartridge and a $CH_2Cl_2$/hexanes gradient (15%-40%) as the mobile phase. The first major peak was collected as product to give 1170A as a white solid (3.52 g, 24% yield). The $^1$HNMR spectral data matched that reported in *J. Med. Chem.* 2005, 48, p. 52.

Part B

Compound 1170A (206 mg, 0.689 mmol), compound 14 (205 mg, 0.685 mmol), dichlorobis(triphenylphosphine)palladium(II) (31 mg, 0.044 mmol), and copper (I) iodide (4 mg) were added to a 25 mL Schlenck tube equipped with a stir bar. The tube was capped with a septum and cycled between vacuum and nitrogen four times. DMF was added via syringe and the tube was cycled between vacuum and nitrogen three times. Triethylamine (0.2 mL) was added via syringe and the tube was placed in a 75° C. oil bath. The reaction mixture was stirred for 20 h, then partially concentrated. Diethyl ether was added, causing an off white ppt to form. The solution was concentrated to dryness. The crude product was purified via sgc using a 1%-4% EtOH/$CH_2Cl_2$ gradient as the mobile phase to give 2192 as a white solid (0.17 g/53% yield). LRMS calcd 469.03 obsd M+H=470.9 and 472.3-(bromine isotope pattern).

Compounds 2224 and 2476 was prepared using procedures similar to those described in Example 84.

Example 85

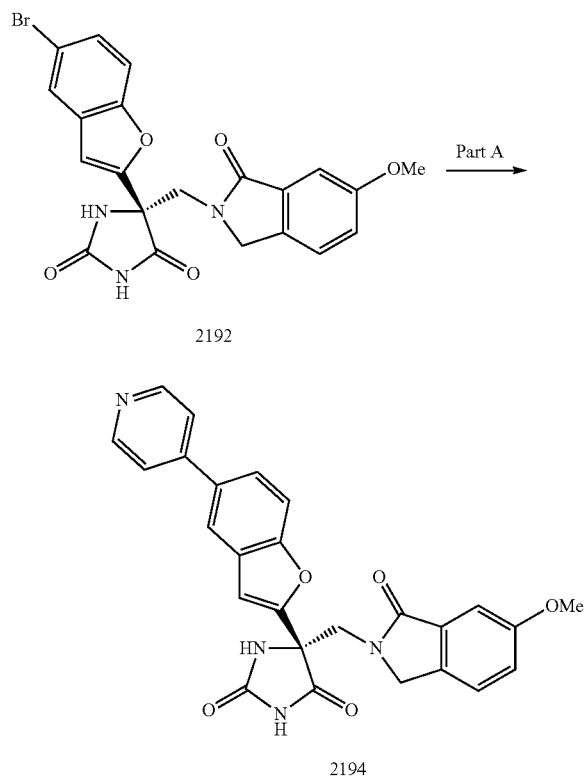

Part A

Pyridine 4-boronic acid (95 mg, 0.202 mmol), tripotassium phosphate (133 mg, 0.626 mmol), and Bis(tri-tert-butylphosphine)palladium(0) (6 mg, 0.012 mmol) were added to a microwave tube equipped with a stir bar. The tube was capped, connected to a vacuum manifold via syringe, then cycled between vacuum and nitrogen five times. A solution of compound 2192 dissolved in DMF (0.856 mL) and water (0.145 mL) was added via syringe using a small guage needle. The tube was cycled between vacuum and $N_2$ four times. The reaction mixture was stirred in the microwave at rt for 5 min, then heated to 150° C. for 30 min. The crude reaction mixture was injected directly onto an Isco C-18 cartridge and eluted using a 20%-80% $CH_3CN$/water gradient as the mobile phase with 0.1% formic acid added to each component of the mobile phase. Compound 2194 was isolated as a yellow oil (23 mg/24% yield). LCMS calcd 468.14 obsd M+H=469.3.

Compounds 2195, 2197, and 2198 were prepared from compound 2192 using procedures similar to that described in Part A of Example 85. —(See tables for mass spectral data.)

Example 86

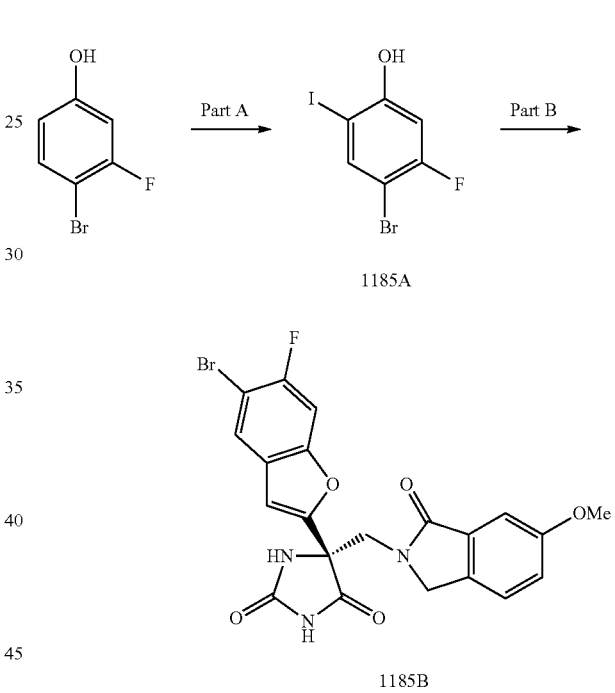

Part A

3-Fluoro-4-bromophenol was converted to compound 1185A using a procedure similar to that described in Example 84 Part A. $^1$HNMR CDCl$_3$ δ 7.80 (d, 7.5 Hz-meta H—F coupling, 1H), 6.82 (d, 9.4 Hz-ortho H—F coupling, 1H), 5.40 (s, 1H, OH peak-disappears on addition of $D_2O$).

Part B

Compound 1185A was converted to 1185B using a procedure similar to that described in Example 84 Part B. LRMS calcd 487.02 obsd M+H=488.0 and 489.9-bromine isotope pattern.

Compounds 1181-1183 were prepared from compounds 1185A and 23 using procedures similar to those described in Example 86.

Compounds 1184-1188 were prepared from compound 1185B using procedures similar to those described in Example 85, Part A.

Example 87

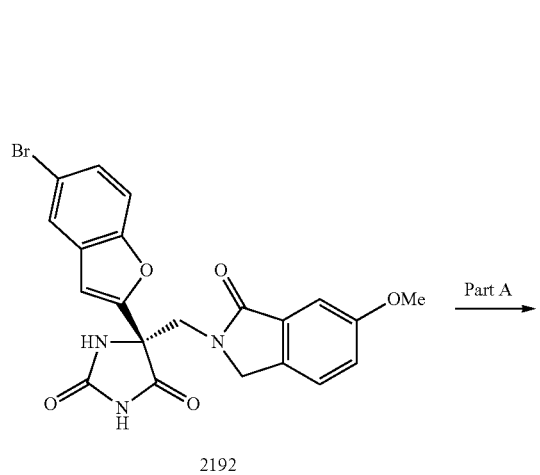

Part A

Compound 2192 (83 mg, 0.17 mmol), 1,2,4-triazole (83 mg, 1.20 mmol), copper (I) iodide (5 mg, 0.026 mmol), 8-hydroxyquinoline (6 mg, 0.041 mmol), and cesium carbonate (118 mg, 0.041 mmol) were added to a Schlenck tube equipped with a stir bar. The tube was capped with a septum and cycled between vacuum and nitrogen four times. DMF (1 mL) was added and the reaction mixture was cycled between vacuum and nitrogen four times. The tube was placed in an oil bath and heated to 120° C. The reaction mixture was stirred at 120° C. under $N_2$ for 24 h then partially concentrated on the rotovap. EtOAc and 1.0 M aq pH 5.5 sodium phosphate buffer were added. The layers were separated. The organic layer was washed with water and brine, dried with $MgSO_4$, filtered, and concentrated to a yellow solid. The crude product was purified via sgc using a 2%-9% 2-propanol/$CH_2Cl_2$ gradient as the mobile phase. The second peak off the column was isolated to give 62 mg of 2196. LCMS calcd 458.13 obsd M+H=459.3.

Example 88

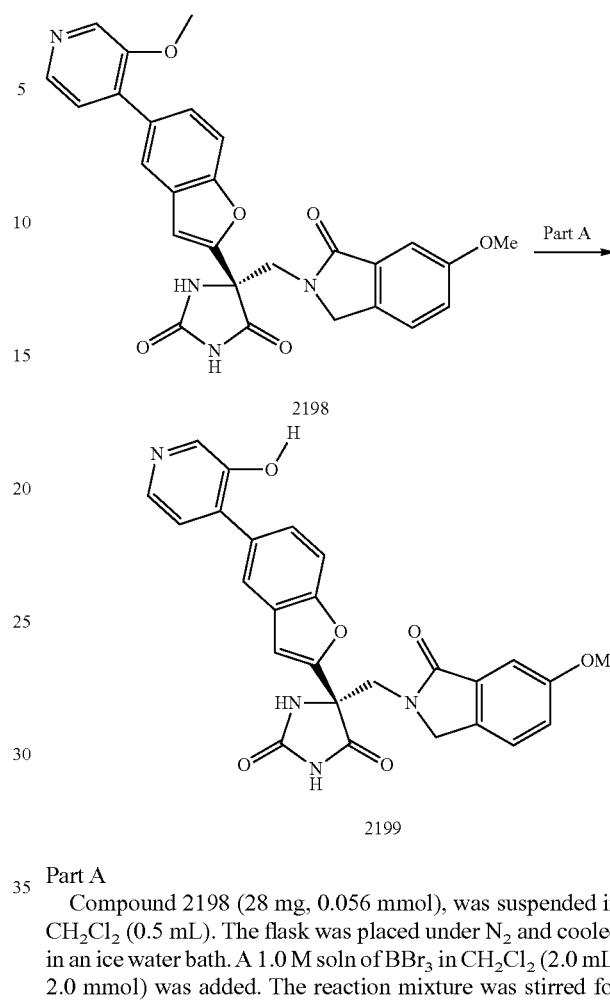

Part A

Compound 2198 (28 mg, 0.056 mmol), was suspended in $CH_2Cl_2$ (0.5 mL). The flask was placed under $N_2$ and cooled in an ice water bath. A 1.0 M soln of $BBr_3$ in $CH_2Cl_2$ (2.0 mL, 2.0 mmol) was added. The reaction mixture was stirred for approximately 1 h and 45 min. Aqueous 1.0 M pH 5.5 sodium phosphate buffer was added. The reaction mixture was left stirring over the weekend. Aq NaOH was added until the reaction mixture was weakly acidic. $CH_2Cl_2$ was added and the layers were separated. The aq layer was extracted with EtOAc. The organic layers were dried with $MgSO_4$, filtered, and concentrated. The aqueous layer was also filtered, giving a white solid. Analysis of the solid by $^1$HNMR and LCMS indicates that it is a 90:10 mixture of product: starting material. LCMS calcd 484.1 obsd M+H=485.3.

Example 89

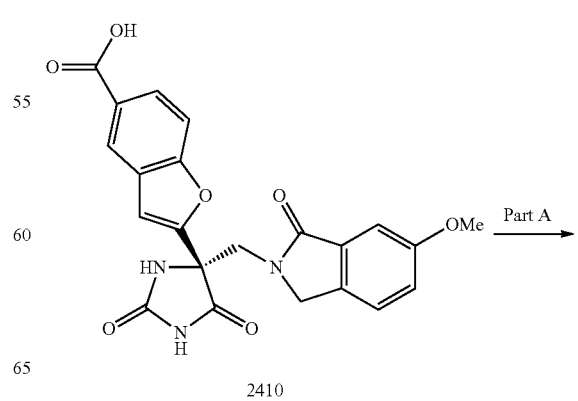

287

-continued

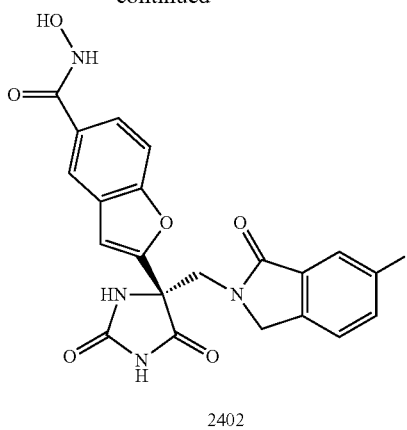
2402

Part A

Compound 2410 was prepared using chemistry described in Example 96. Compound 2410 (0.13 g, 0.30 mmol), HOBT (40 mg, 0.30 mmol), and EDCl (0.115 g, 0.60 mmol) were added to 3 mL of DMF and stirred for 2 h. The reaction mixture was added to a mixture of hydroxylamine hydrochloride (0.1 g, 1.4 mmol) and triethylamine (0.15 g, 1.48 mmol) in 0.5 mL of DMF. The resulting reaction mixture was stirred overnight at rt. EtOAc was added and the reaction mixture was washed with water. The organic layer was dried with $Na_2SO_4$. The crude product was purified via sgc using a gradient of 1-100% (10% MeOH in $CH_2Cl_2$ with 0.2% added formic acid): $CH_2Cl_2$ giving 28 mg of impure product. The product was purified via prep TLC using 10:1 $CH_2Cl_2$:MeOH with 0.2% added formic acid as the mobile phase to give 10 mg of 2402. LCMS calcd 451.2 obsd M+H=450.4.

Example 90

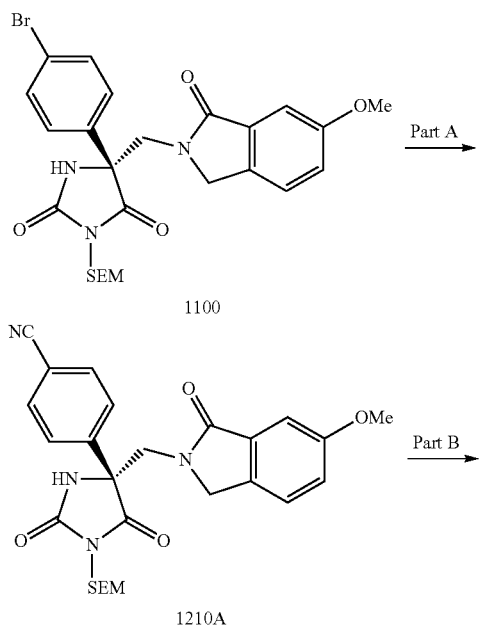

288

-continued

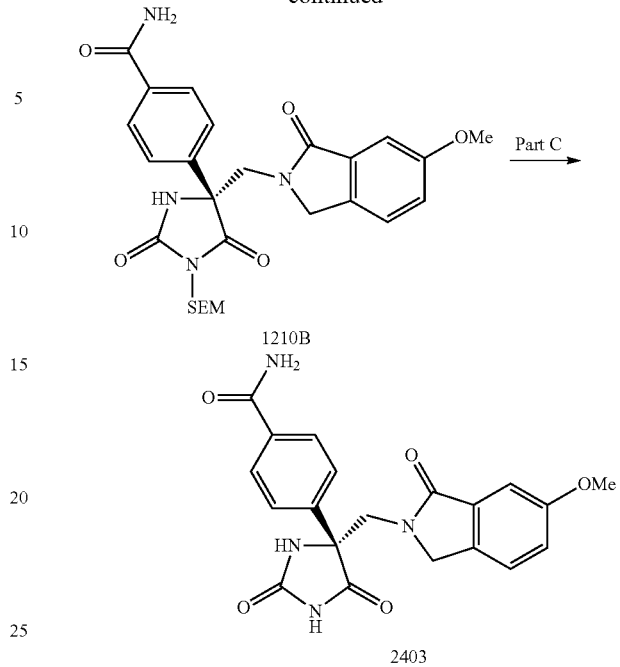
2403

Part A

Compound 1100 was obtained using procedures described in Yu, W.; Tong, L. et al Hydantoin derivatives as matrix metalloprotease inhibitors and their preparation, pharmaceutical compositions, and use for the treatment of inflammatory disorders. PCT Int. Appl. (2006), WO 2006019768 and/or Yu, W.; Tong, L. et al Compounds for the treatment of inflammatory disorders US 2007/0219218.

The procedure in part A follows that described in S. A. Weissman *J. Org. Chem.* 2005, 70, 1508-1510.

Compound 1100 (258 mg, 0.472 mmol) potassium ferrocyanide (II) trihydrate (56 mg, 0.133 mmol), tris(dibenzylidineacetone)dipalladium(0) (14 mg, 0.015 mmol), and sodium carbonate (50 mg, 0.47 mmol) were added to a 25 mL Schlenck tube equipped with a stir bar. The tube was capped with a septum and cycled between vacuum and nitrogen twice. Dimethyl acetamide was added via syringe. The tube was cycled between vacuum and nitrogen three times, then placed in a 85° C. oil bath. The bath was heated to 120° C. and the reaction mixture was stirred for 17 h. The reaction mixture was allowed to cool to rt then diluted with EtOAc and filtered. The filtrate was washed with water, aq 5% ammonium hydroxide, water, and brine. The resulting organic solution. was dried with $MgSO_4$, filtered, and concentrated to dryness. The crude product was partially purified via sgc using a 5%-60% (5% MeOH in EtOAc)/hexanes gradient on a 40 g $SiO_2$ cartridge. The resulting mixture of starting material and product was purified via prep TLC using 25% (5% MeOH in EtOAc)/hexanes as the mobile phase. Compound 1210A was isolated as a clear oil (85 mg) LRMS calcd 506.2 obsd M+Na 529.1.

Part B

The procedure in part B is based on that described in S. I. Maffioli et al *Org. Lett* 2005, 7, 5237-5239. Compound 1210A (69 mg, 0.136 mmol), palladium(II)acetate (10 mg, 0.044 mmol), and acetamide (48 mg, 0.81 mmol) were added to a microwave tube equipped with a stir bar. THF (0.40 mL) and water (0.125 mL) were added. The tube was capped, and the reaction mixture was stirred at rt overnight. The reaction mixture was diluted with EtOAc, washed with 1M aq NaHCO₃, water, and brine. The organic layer was dried with MgSO₄, filtered, and concentrated to dryness. The crude product was purified via prep TLC using 95:5 CH₂Cl₂:MeOH as the mobile phase. The major UV active band was isolated to give compound 1210B as product. LRMS calcd 524.21 obsd M+Na at 547.25

Part C

Compound 1210B was deprotected to give 2403 using procedures similar to those described in Yu, W.; Tong, L. et al Hydantoin derivatives as matrix metalloprotease inhibitors and their preparation, pharmaceutical compositions, and use for the treatment of inflammatory disorders. PCT Int. Appl. (2006), WO 2006019768.

Example 91

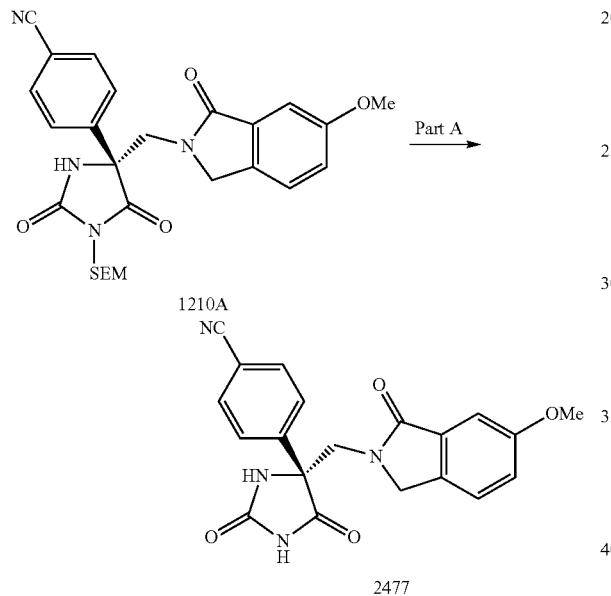

Part A

Compound 1210A (130 mg, 0.256 mmol) was dissolved in 20 mL of anhydrous acetonitrile and concentrated to dryness. Additional anhydrous acetonitrile (2.5 mL) was added and the flask was placed under N₂ blanket. The solution was cooled in an ice-water bath causing material to precipitate. After about 10 min stirring, BF₃-etherate (0.165 mL) was added, causing 1210A to redissolve. The reaction mixture was stirred at 0° C. for 1.5 h. The reaction mixture was concentrated to dryness then placed back in the ice-bath. Triethylamine (1.5 mL) was added followed by methanol (6 mL). The reaction was stirred at 0° C. for 5 min, then stirred at rt for 2 h. The resulting soln was concentrated to dryness. The reaction mixture was purified via reverse phase chromatography using a 15%-70% CH₃CN/H₂O gradient with 0.1% formic acid added to each component of the mobile phase. The main peak was isolated to give impure 2477. LRMS and ¹HNMR appeared to indicate that the product was mixed with the partially deprotected hydroxymethyl compound. The sample was dissolved in methanol (8 mL) and triethylamine (3 mL) was added. The reaction mixture was stirred for 3 h at rt then concentrated to dryness. The crude product was purified via reverse phase chromatography using a 25%-80% CH₃CN/H₂O gradient with 0.1% formic acid added to each component of the mobile phase. The main peak was isolated to give 66 mg of 2477 as a white solid. LCMS calcd 376.1 obsd M+H=377.2.

Example 92

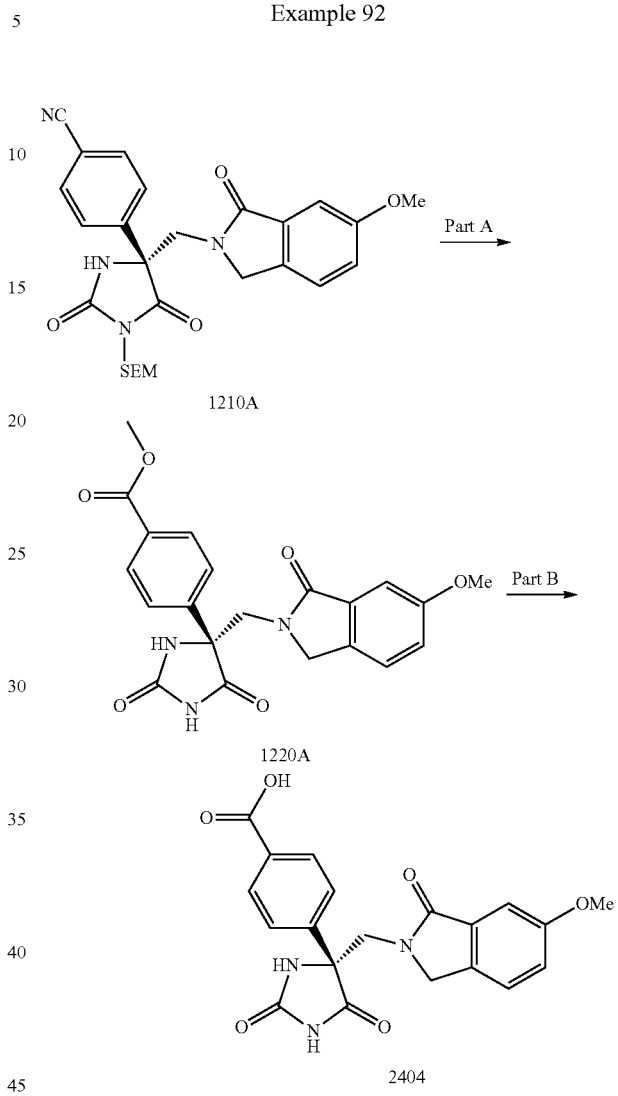

Part A

Compound 1210A (0.51 g, 1.0 mmol) was dissolved in 4 M HCl in dioxane (20 mL, Aldrich) and added to a 75 mL pressure tube equipped with a stir bar. Methanol was added (7 mL). The tube was capped and placed in a 75° C. oil bath. The bath was heated to 80° C. and the reaction mixture was stirred for 15 h. The reaction mixture was allowed to cool to rt and the solution was concentrated to dryness. Methanol was added and the reaction mixture was reconcentrated. The resulting yellow solid was dissolved in methanol (22 mL) and triethylamine (5 mL) was added. The reaction mixture was stirred at rt for 4.5 h. The solution was concentrated to dryness. EtOAc and 1.0 M pH 5.5 sodium phosphate buffer were added. The layers were separated. The organic layer was washed with additional sodium phosphate buffer (pH=5.5), water, and brine. The resulting organic solution was dried with MgSO₄, filtered, and concentrated to dryness giving a brown foam. The crude product was purified via sgc using 1.5% absolute ethanol/CH₂Cl₂ as the mobile phase. Impure compound 1220A was obtained as a white solid (292 mg) and used in the next step without additional purification.

Part B

Compound 1220A (310 mg, 0.75 mmol) was dissolved in 3 mL of dioxane and 0.3 mL of methanol. Water (2 mL) was added, followed by lithium hydroxide monohydrate (47 mg, 1.1 mmol). The reaction mixture was left stirring overnight at rt under $N_2$. After approximately 12 h, additional LiOH (1.5 mL of 1.0 M aq) was added. Three hours later, additional aq LiOH (1.5 mL) was added. About 19 h after the reaction had started, it was concentrated to near dryness. Aq 1.0 M pH 5.5 buffer was added, followed by DMF. The resulting mixture was injected directly onto an Isco C-18 cartridge which was eluted with a 25%-80% $CH_3CN/H_2O$ gradient with 0.1% formic acid added to each component of the mobile phase. Impure compound 2404 was isolated as a white solid. This material was purified further via prep TLC using 5% MeOH in $CH_2Cl_2$ with 1% added formic acid as the mobile phase. LCMS calcd 395.3 obsd M+H 396.2

Example 93

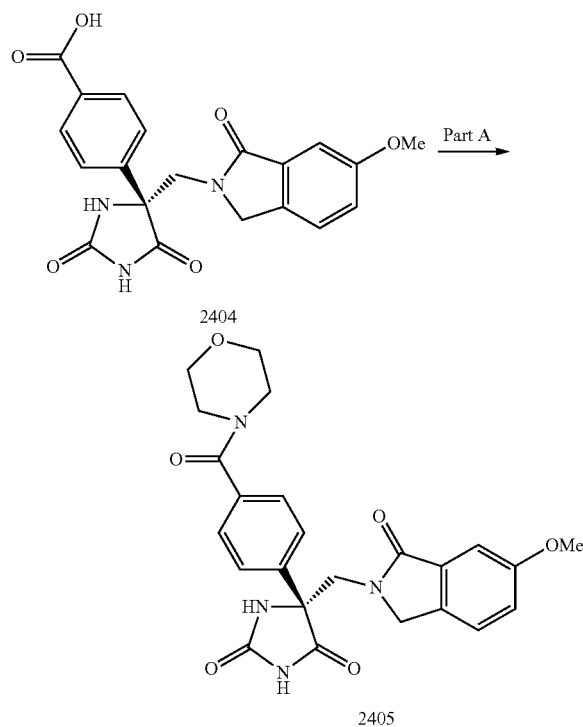 [SMILES: COc1ccc2c(c1)C(=O)N(C[C@@]1(c3ccc(C(=O)O)cc3)NC(=O)NC1=O)C2 ; COc1ccc2c(c1)C(=O)N(C[C@@]1(c3ccc(C(=O)N4CCOCC4)cc3)NC(=O)NC1=O)C2]

Part A

Compound 2404 (111 mg, 0.28 mmol), dioxane (2 mL), and carbonyl diimidazole (50 mg, 0.31 mmol) were mixed in a flask. The starting material did not dissolve completely, so DMF (0.5 mL) was added. The reaction mixture was warmed for about 1 min with a heat gun and stirred for 15 min. About one third of the reaction mixture was added to a vial containing morpholine (about 0.025 mL). The reaction mixture was stirred at rt overnight. The reaction mixture was partitioned between EtOAc and pH 5.5 sodium phosphate buffer. The organic layer was washed with pH 5.5 sodium phosphate buffer, water, and brine. The resulting organic solution was dried with $MgSO_4$, filtered, and concentrated to dryness. The crude product was purified via prep TLC using 5% MeOH/ $CH_2Cl_2$ as the mobile phase. Compound 2405 was isolated as a white solid. LCMS calcd 464.17 obsd M+H 465.3.

Example 94

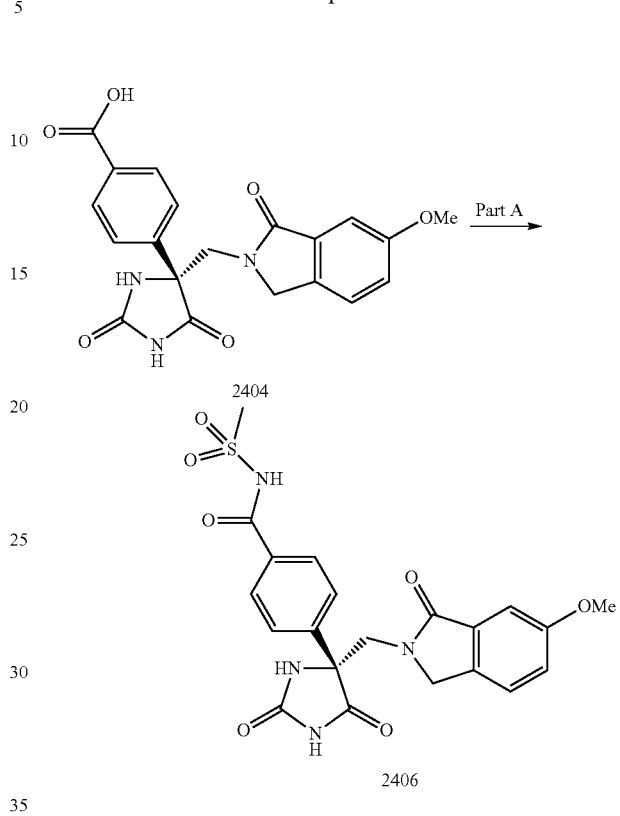

Part A

Compound 2404 (52 mg, 0.13 mmol) was dissolved in 2 mL of THF. Carbonyl diimidazole (48 mg, 0.30 mmol) was added and the reaction mixture was left stirred at rt for 18 h under $N_2$. Methanesulfonamide (24 mg, 0.25 mmol) was added, followed by DBU (78 microliters). The reaction mixture was stirred at rt for 24 h. $CH_2Cl_2$ and 0.2 M aq HCl were added. The layers were separated. The organic layer was washed with 0.2 M HCl and a 2:1 mixture of brine and 0.2 M HCl. The resulting organic solution was gravity filtered, then concentrated to dryness on the rotovap. The crude product was purified via prep TLC using 1:1 (5% MeOH in EtOAc): hexanes with 0.5% (vol) added formic acid as the mobile phase. Compound 2406 was obtained as a white solid. LCMS calcd 472.1 obsd M+H=473.3.

Example 95

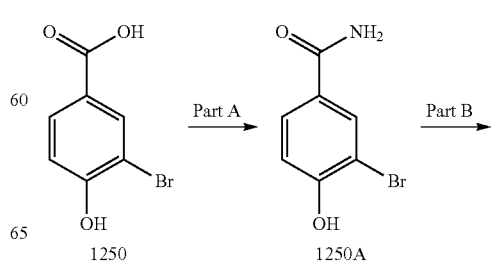

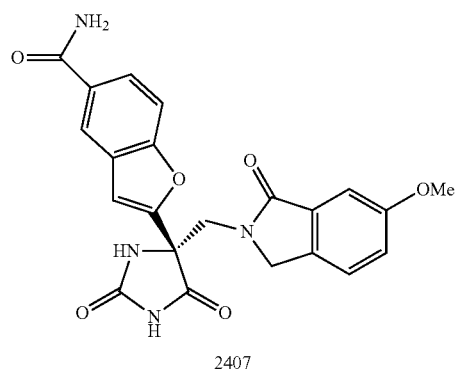

2407

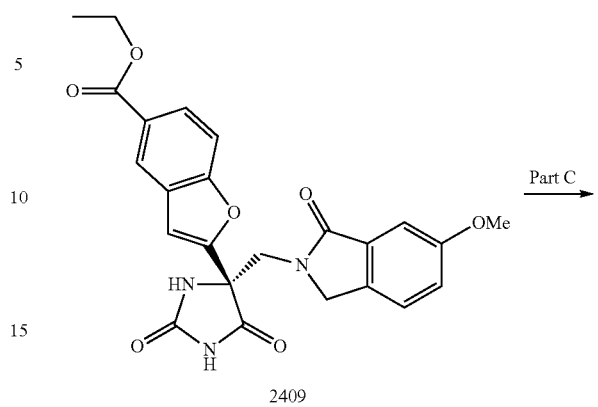

2409

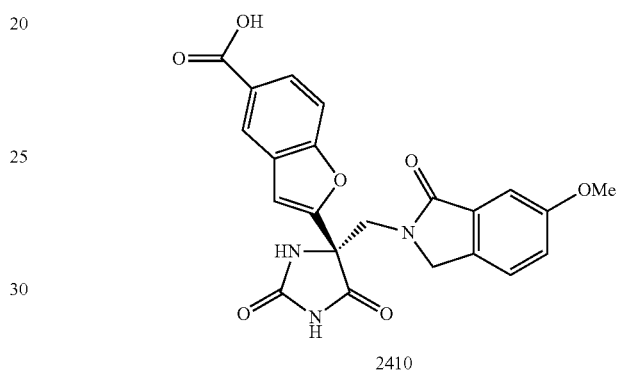

2410

Part A

3-Bromo-4-hydroxybenzoic acid (1.00 g, 4.60 mmol) was dissolved in 20 mL of THF. Carbonyl diimidazole was added and the reaction mixture was stirred at rt for 1 h and 20 min forming a white precipitate. Methanolic ammonia (25 mL, Aldrich 7 N) was added and the reaction mixture was stirred at rt ON. The reaction mixture was concentrated to dryness. The reaction mixture was partitioned between EtOAc and pH 5.5 sodium phosphate buffer. The organic layer was washed with pH 5.5 sodium phosphate buffer, water, and brine. The resulting organic solution was dried with $MgSO_4$, filtered, and concentrated to dryness. The crude product was purified via sgc using a 50%-100% (5% MeOH in EtOAc)/hexanes gradient. The second major peak was collected as product to give 0.32 g of 1250A. LRMS calcd 214.9 obsd M+H 215.9, 217.9—(bromine isotope pattern).

Part B

Compound 1250A was converted to 2407 using procedures similar to those described in Example 81. —See table for analytical data.

Compound 2408 was prepared using procedures similar to those described in Example 95. —See table for analytical data.

Example 96

Part A

Compound 1130 was converted to 1260A using a procedure similar to that described in Example 83 Part A, but using absolute ethanol as the solvent. Yield=96%, LRMS calcd 291.96 obsd M+H=292.9

Part B

Compound 1260A was converted to 2409 using procedures similar to those described in Example 81. LRMS calcd 463.13 obsd M+H 463.99.

Part C

Compound 2409 was converted to 2410 using procedures similar to those described in Example 92. LCMS calcd 435.1 obsd M+H 436.2.

Example 97

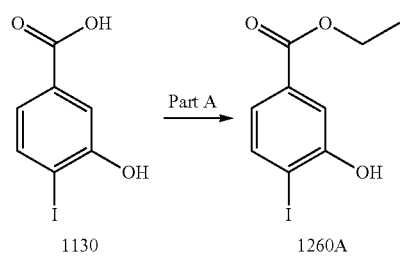

1130     1260A

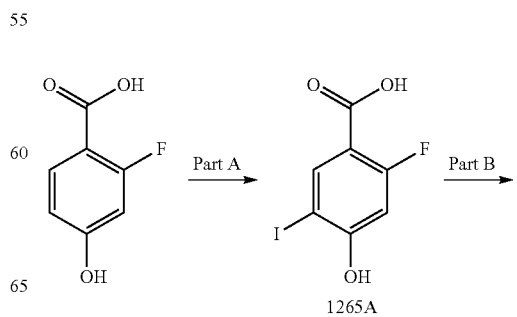

1265A

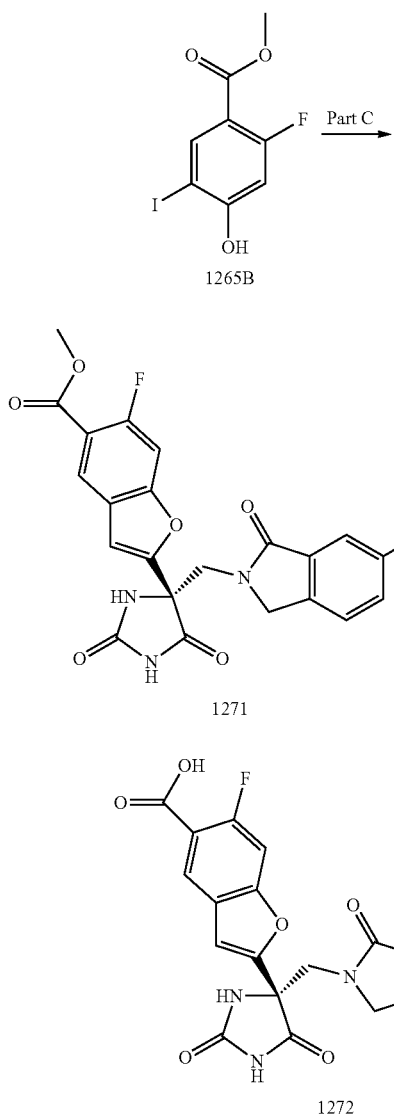

Part A

Potassium iodide (6.38 g, 38.4 mmol) was dissolved in 5 mL of water. Iodine (3.26 g, 12.8 mmol) was added followed by 5 mL of water. The reaction mixture was stirred until it became a solution. The iodine/KI solution was added dropwise to a solution of 2-fluoro-4-hydroxybenzoic acid (2.0 g, 12.8 mmol) in aq $NH_4OH$ (80 mL). The reaction mixture was stirred for 1 h. The reaction mixture was partially concentrated on the rotary evaporator to remove excess $NH_3$. (Caution: These reaction conditions are believed to form $NI_3$ which is explosive and shock sensitive when it is a dry solid. Do not evaporate the reaction mixture to dryness.) Concentrated aq HCl was added to adjust the pH to 1. The resulting solution was extracted with EtOAc. The organic layer was concentrated to dryness. The crude product was purified via sgc using $CH_2Cl_2$:MeOH 20:1 with 0.5% added formic acid as the mobile phase. Compound 1265A was obtained as the product (3.16 g). $^1$HNMR $CD_3OD$ δ 8.2 (d, 8.2 Hz-meta H—F coupling, 1H), 6.56 (d, 12.3 Hz-ortho H—F coupling, 1H).

Part B

Compound 1265A was converted to 1265B using a procedure similar to that described in Example 83 Part A. The crude product was partially purified via sgc using a 1%-4% MeOH/$CH_2Cl_2$ gradient as the mobile phase. The resulting white solid was purified a second time via sgc using a 10%-40% (5% MeOH in EtOAc)/hexanes gradient as the mobile phase. LRMS calcd 295.9 obsd M+H 297.0.

Part C

Compound 1265B was converted to 1271 using procedures similar to those described in Example 81. LCMS calcd 467.1 obsd M+H 468.3.

Part D

Compound 1271 was converted to 1272 using procedures similar to those described in Example 92. LCMS calcd 453.1 obsd M+H 454.2.

Example 98

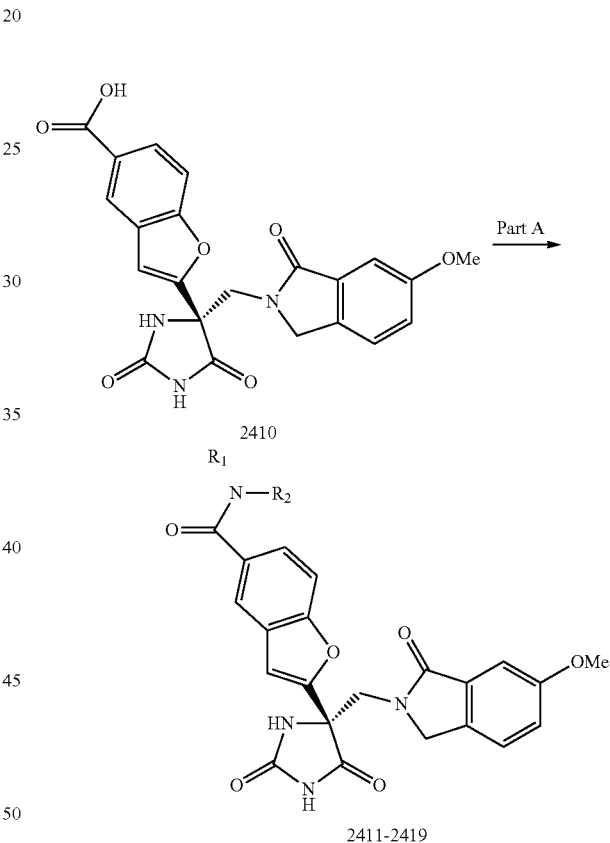

Part A

Compound 2410 (24 mg, 0.055 mmol) and carbonyl diimidazole (10 mg, 0.062 mmol) were added to a 2 dram vial equipped with a stir bar. DMF (250 microliters) was added. The reaction mixture was stirred at rt for 1 h. N,N-dimethylethylene diamine (100 microliters) was added and the reaction mixture was stirred at rt overnight. Aqueous $NH_4Cl$ (4 drops, 2 M) was added to the vial and the reaction mixture was stirred for 30 min. The crude reaction mixture was purified via reverse phase HPLC to give 6 mg of the product-(2412) LCMS calcd 505.2 obsd M+H 506.3

Compounds 1273-1279, 1281-1283, and 2411-2419 were prepared using the chemistry described in Example 98. —Please see table for the analytical data.

Example 99

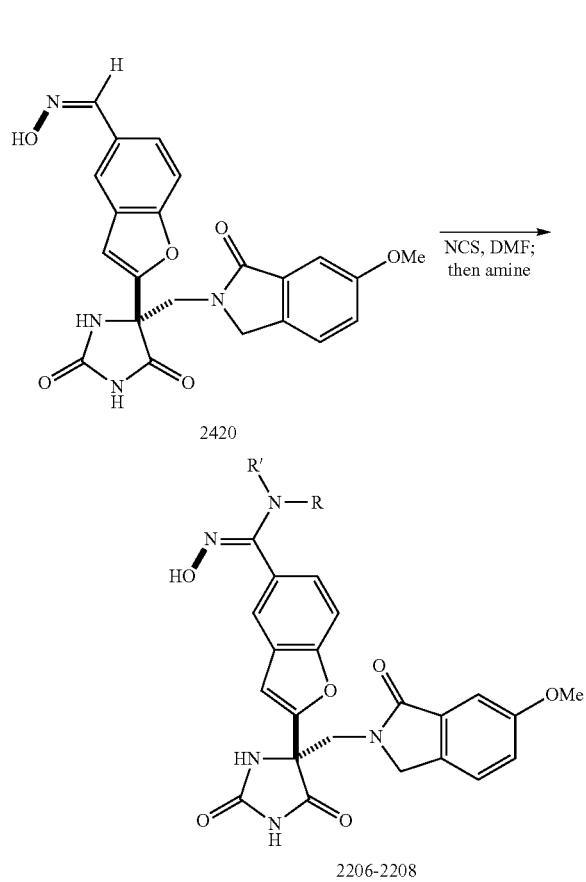

Compounds 2206, 2207, and 2208 were prepared from compound 2420 using chemistry described in Example 49. Please see table for the analytical data.

Example 100

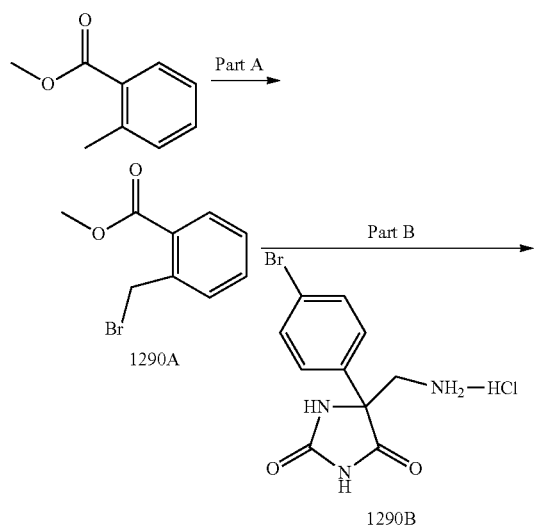

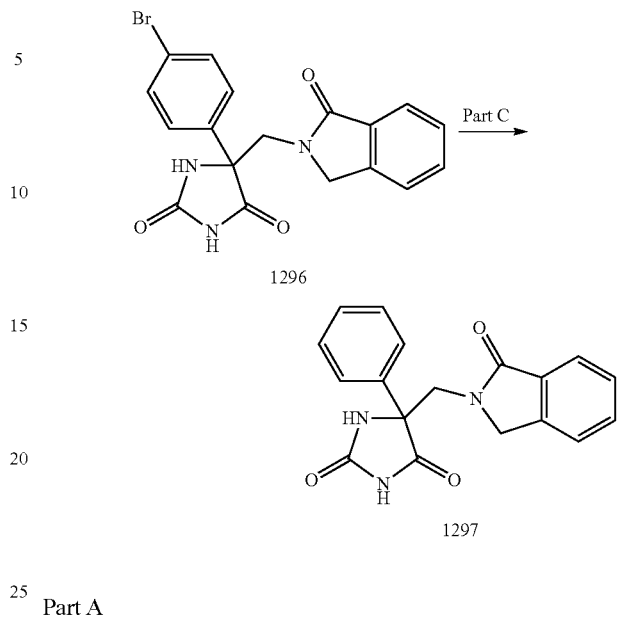

Part A

Methyl o-toluate was converted to the known compound 1290A using procedures described in Yu, W.; Tong, L. et al Compounds for the treatment of inflammatory disorders US 2007/0219218 and/or Yu, W.; Tong, L. et al PCT Int. Appl. (2006), WO2006019768. Analytical data matched that reported in the literature.

Part B

Compound 1290B was obtained using procedures described in Yu, W.; Tong, L. et al Compounds for the treatment of inflammatory disorders US 2007/0219218 and/or Yu, W.; Tong, L. et al PCT Int. Appl. (2006), WO2006019768. Compound 1290A was converted to 1296 using procedures similar to those described in Yu, W.; Tong, L. et al Compounds for the treatment of inflammatory disorders US 2007/ 0219218 and/or Yu, W.; Tong, L. et al PCT Int. Appl. (2006), WO2006019768. LCMS calcd 399.0 obsd M+H 400.2.

Part C

Compound 1296 (0.11 g, 0.27 mmol) was dissolved in 30 mL of methanol and the solution was added to a Parr hydrogenation bottle. Palladium on carbon (20 mg of 10% Pd on C from Aldrich Chemical) was added and the bottle was shaken under $H_2$ at 45 psi for 2 h. The catalyst was removed via filtration and the filtrate was concentrated to dryness. The resulting solid was triturated in MeOH. The solid was isolated to give 56 mg of 1297. LCMS calcd 321.1 obsd M+H 322.2.

Example 101

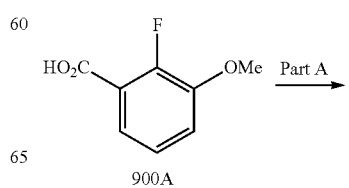

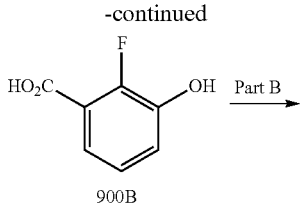

900B

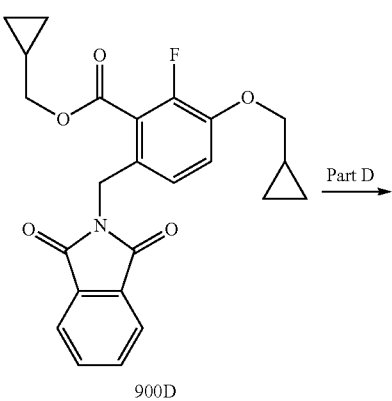

900C

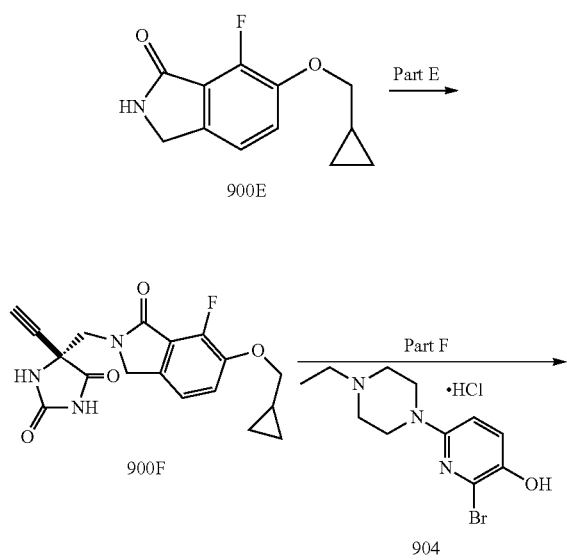

900D

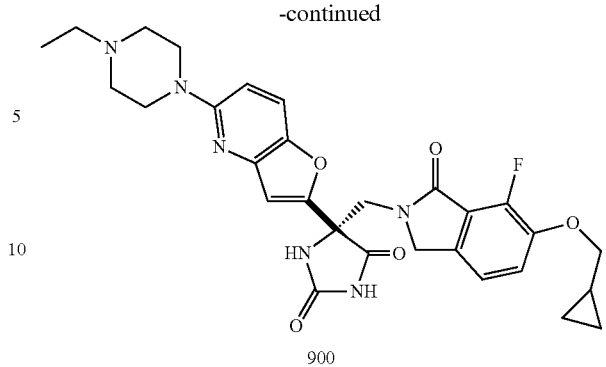

900

Part A:

Commercially available 2-fluoro-3-methoxybenzoic acid 900A (2.0 g, 12 mmol) and solid pyridine hydrochloride (8.0 g, 71 mmol) were admixed in a 15-mL pressure tube. The tube was flushed with nitrogen, capped and lowered completely into a preheated 170° C. oil bath to prevent potential sublimation of pyridine hydrochloride into the headspace above the reaction mixture. The reaction was allowed to proceed at 170° C. for 3 days. The mixture was allowed to cool, but before the contents started to solidify again, DMF (~5 mL) was added. The resulting brown solution was allowed to cool to rt and was then injected onto a 130 g Teledyne-ISCO RediSep® C18 cartridge. Elution using a 0-95% [MeCN+1% $HCO_2H$]/[$H_2O$+1% $HCO_2H$] gradient gave the desired product 900B as a beige solid (1.78 g, 99% yield).

Part B:

An admixture of 900B (1.06 g, 6.76 mmol) and N-hydroxyphthalimide (1.26 g, 7.11 mmol) was added in portions to conc. sulfuric acid that had been precooled to 0° C. The solution was stirred at 0° C. for 3 h, and then poured into an ice-water mixture. The mixture was stirred for 15 min. The precipitated solid was collected by filtration, washed with water, and dried in vacuo to give the hydroxyacid 900C as an off-white solid (2.13 g) which was used without further purification.

Part C:

Solid cesium carbonate (8.83 g, 27.2 mmol) was added to a stirred solution of hydroxyacid 900C (2.14 g, 6.79 mmol) in DMF (20 mL) and the suspension was stirred at rt for 15 min. Bromomethylcyclopropane (2.7 mL, 3.7 g, 27 mmol) was added and the reaction mixture was stirred overnight at rt. The reaction mixture was filtered through a Celite® pad and then purified directly by reverse-phase chromatography (Teledyne-ISCO RediSep® C18 cartridge; 10-90% acetonitrile-water gradient, followed by normal phase sgc (0-10% MeOH—$CH_2Cl_2$ gradient) to give 1.42 g (49% yield) of Compound 900D.

Part D:

In a pressure vessel, hydrazine hydrate (0.33 mL, 334 mg, 6.68 mmol) was added to a stirred solution of Compound 900D (1.42 g, 3.34 mmol) in methanol (15 mL). The vessel was sealed and immersed in a preheated 70° C. oil bath. The reaction mixture was stirred at 70° C. for 1 h. The solvent was removed by evaporation under reduced pressure. The resulting solid was suspended in 1 M aq. potassium carbonate (20 mL) and stirred for 1 h. The solid was collected by filtration and dried overnight under vacuum (<1 mmHg). Compound 900E was obtained in 683 mg, 92% yield.

Part E:

Compound 900E was elaborated to Compound 900F by sequential application of procedures described in Example 1, Parts D and E; then Example 2, Parts E-G; and finally Example 3.

Part F:

Compound 900F was converted to the target Compound 900 by reaction with the bromohydroxypyridine derivative 904 (prepared according to Example 102) following the procedure given in Example 6. HPLC-MS $t_R$=2.73 min (UV$_{254\ nm}$); mass calculated for formula $C_{29}H_{31}FN_6O_5$: 562.2, observed LCMS m/z 563.3 [M+H]$^+$.

Example 102

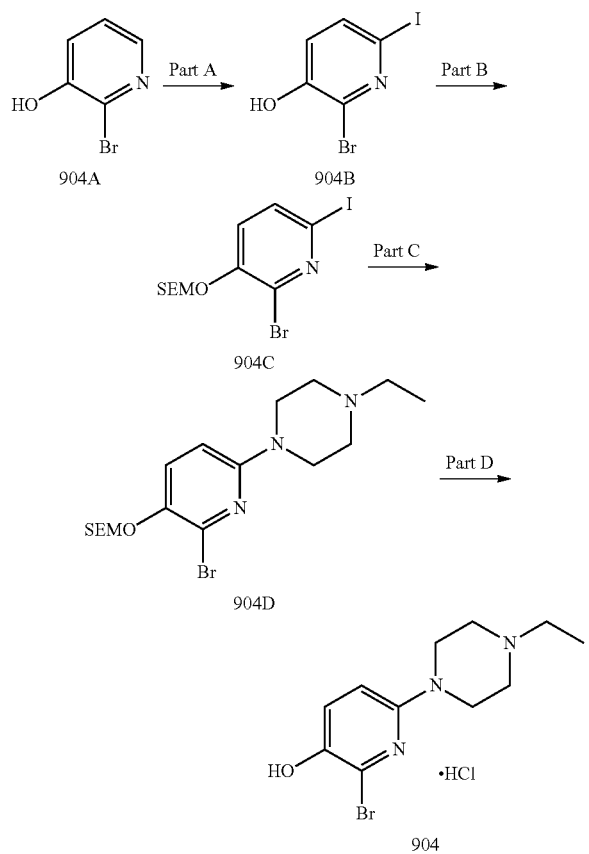

Part A:

Iodine (30 g, 118 mmol) was added portionwise to a stirred solution of 2-bromo-3-hydroxypyridine 904A (20 g, 115 mmol) and potassium carbonate (32 g, 230 mmol) in water (265 mL). The reaction mixture was stirred overnight at rt. Solid sodium bisulfite was added to quench excess iodine. Acetic acid was added until pH 5-6 was attained. The precipitated solid was collected by filtration and was dried in vacuo. The desired product 904B was obtained in 25 g, 73% yield.

Part B:

SEM-Cl (23 mL, 33 g, 109 mmol) was added to a stirred, ice-cooled solution of 2-iodophenol 904B (1.0 g, 4.6 mmol) and DIPEA (29 mL, 21 g, 164 mmol) in dichloromethane (550 mL). The solution was allowed to warm to rt and was stirred overnight at rt. The solvent was evaporated and the crude residue was purified directly by sgc (0-50% EtOAc-hexanes gradient) to give 45 g of the desired product 904C as a clear colorless oil (95% yield).

Part C:

Solid copper(I) iodide (221 mg, 1.16 mmol), L-proline (267 mg, 2.32 mmol) and potassium carbonate (3.2 g, 23 mmol) were added sequentially to a stirred solution of Compound 904C (5.0 g, 12 mmol) in dry DMSO (29 mL). The reaction mixture was stirred, under nitrogen atmosphere, at 75° C. for 36 h. The reaction mixture was allowed to cool to rt and was filtered. The filtrate was diluted with EtOAc (~100 mL), and was washed sequentially with water (2×~100 mL) and brine (~100 mL). The organic layer was dried over anhydrous MgSO$_4$, filtered, and concentrated. The crude product was purified by sgc (0-10% MeOH/CH$_2$Cl$_2$ containing 1% NH$_4$OH) to afford 2.5 g (51% yield) of the desired Compound 904D.

Part D:

Hydrogen chloride solution (9 mL, 4 M in dioxane, 36 mmol) was added to a stirred solution of Compound 904D (2.50 g, 6.00 mmol) in CH$_2$Cl$_2$ (10 mL) at rt. The reaction mixture was stirred at rt for 18 h. Diethyl ether (~25 mL) was added and the suspension was stirred at rt for 10 min. The solid was collected by filtration, washed with a small amount of diethyl ether (~5-10 mL) and dried. Compound 904 was obtained as a hydrochloride salt in 1.93 g, 100% yield. Mass calculated for formula $C_{11}H_{16}^{79}BrN_3O$: 285.1, observed m/z 286.2 [M+H]$^+$.

Example 103

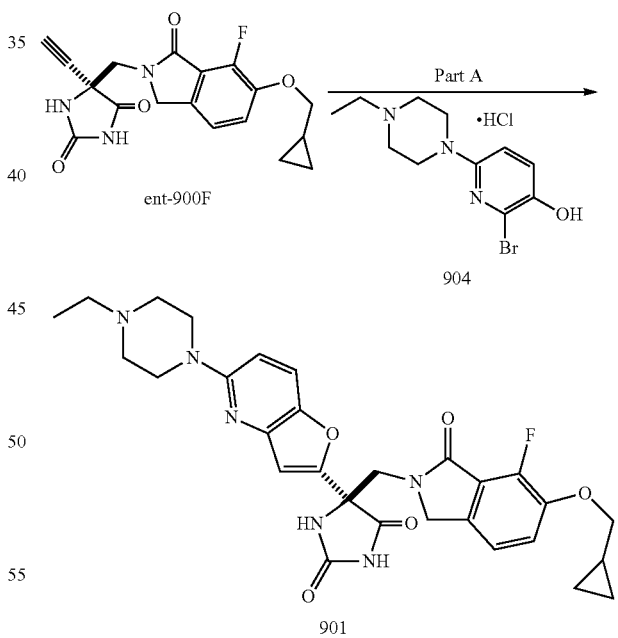

Part A:

Compound ent-900F, which is the enantiomer of Compound 900F, was obtained from HPLC resolution procedure described in Example 900, Part E or Example 2, Part F. Compound ent-900F was combined with Compound 900G according to the procedure described in Example 6. HPLC-MS $t_R$=2.72 min (UV$_{254\ nm}$); mass calculated for formula $C_{29}H_{31}FN_6O_5$: 562.2, observed LCMS m/z 563.3 [M+H]$^+$.

Example 104

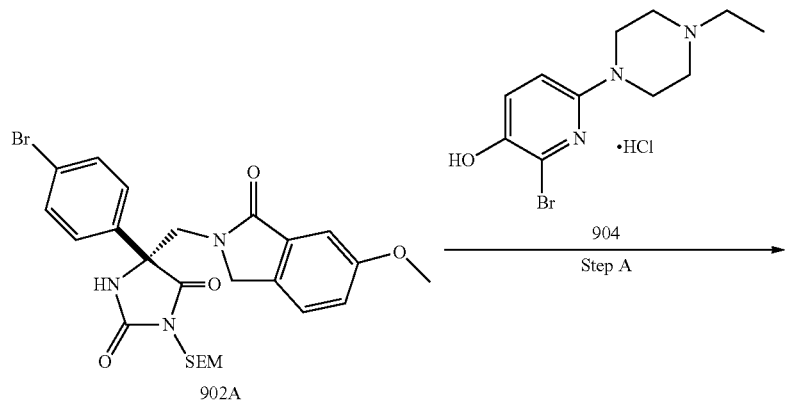

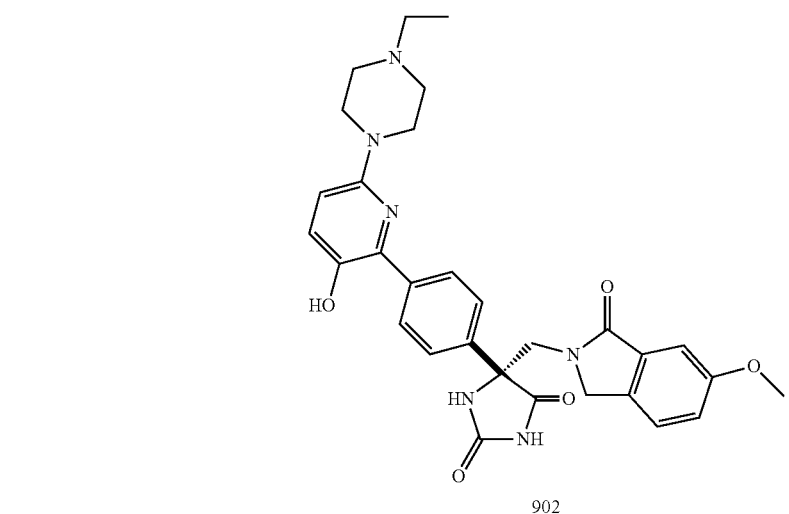

Part A:

Compound 902A was prepared by the method given in Lavey, B. et al. WO 2007/084455 A1, Example 8. A flame-dried microwave tube was charged with Compound 902A (200 mg, 0.356 mmol), bis(pinacolato)diboron (136 mg, 0.535 mmol), (dppf)PdCl$_2$.CH$_2$Cl$_2$ (88 mg, 0.11 mmol), and potassium acetate (105 mg, 1.07 mmol). The tube was stoppered, evacuated and placed under nitrogen atmosphere. Dry, degassed dioxane (3.2 mL) was added. The reaction mixture was stirred at 120° C. for 2 h. The reaction mixture was allowed to cool to rt. A solution of Compound 904 (287 mg, 0.89 mmol) in acetonitrile (0.9 mL), followed by 1 M aq. potassium carbonate (4 mL) were added. The reaction mixture was stirred at 120° C. for 2 d. The mixture was filtered and the aqueous layer was extracted with EtOAc (3×25 mL). The combined organic layers were washed with brine (~50 mL), dried over anhydrous MgSO$_4$, filtered, and concentrated under reduced pressure. The residue was purified by reverse-phase C18 chromatography to give 19 mg of a product whose structure was confirmed as that of Compound 902. HPLC-MS $t_R$=2.73 min (UV$_{254\ nm}$); mass calculated for formula C$_{30}$H$_{32}$N$_6$O$_5$: 556.2, observed LCMS m/z 557.3 [M+H]$^+$.

Example 105

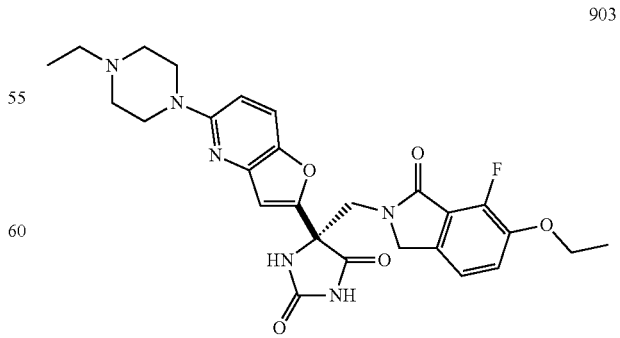

Compound 903 was prepared via a sequence analogous to that described in Example 101. HPLC-MS $t_R$=3.50 min (UV$_{254\ nm}$); mass calculated for formula C$_{27}$H$_{29}$FN$_6$O$_5$: 536.2, observed LCMS m/z 537.3 [M+H]$^+$.

Example 106

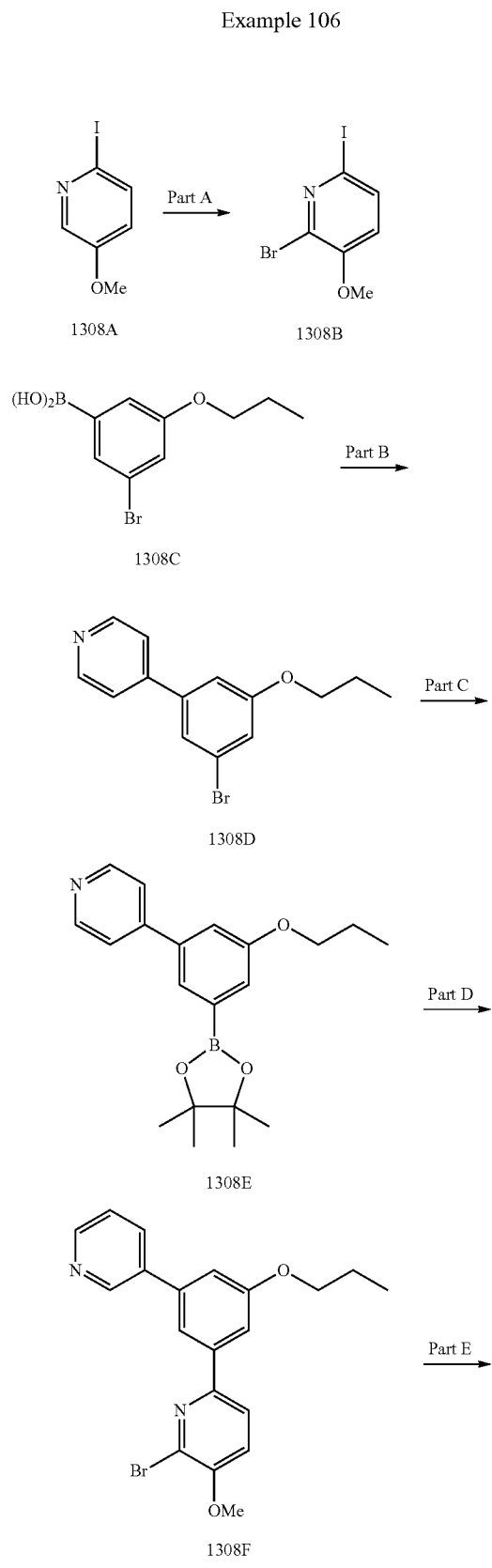

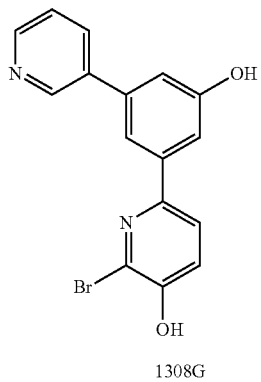

Part A

Compound 1308A (1.0 g, 4.52 mmol) was dissolved in TfOH (10 g) at 0° C. NBS (881 mg, 4.97 mmol) was added. The solution was stirred at RT for three hours. It was poured into ice-water. The solid was collected and dissolved in DCM, washed with brine, dried over Na$_2$SO$_4$, concentrated and dried under vacuum to give compound 1308B (1.62 g) which was used without further purification.

Part B

Compound 1308C (755 mg, 2.93 mmol), 4-Iodopyridine (500 mg, 2.44 mmol), Pd(dppf)$_2$Cl$_2$ (178 mg, 0.244 mmol) were added into a 50 mL flask. The flask was vacuumed and flushed nitrogen for three times. CH$_3$CN (3 mL) and K$_2$CO$_3$ (1M, 3 mL) were added. The solution was stirred at 80° C. for 18 h. After cooling down, water and EtOAc were added. The organic layer was separated, washed with brine, dried over Na$_2$SO$_4$, and concentrated. The product was purified by sgc (EtOAc/Hexane: 0% to 50%) to give compound 1308C (619 mg, 72.6%).

Part C

Compound 1308D (619 mg, 2.13 mmol), bis(pinacolato) diboron (810 mg, 3.19 mmol), Pd(dppf)Cl$_2$ (80 mg, 0.11 mmol), and KOAc (626 mg, 6.38 mmol) were placed into a 50 mL flask. The flask was vacuumed and flushed nitrogen for three times. Dioxane (12 mL) was added. The solution was stirred at 90° C. for 24 h. After cooling down, the solution was passed through a short celite pad, and concentrated. The product was purified by sgc (EtOAc/Hexane: 25% to 80%) to give compound 1308E (784 mg).

Part D

Compound 1308F was prepared by the same method as described in part B.

Part E

Compound 1308F (484 mg, 1.21 mmol) was suspended in Dichloroethane. AlCl$_3$ (486 mg, 3.64 mmol) was added at 0° C. The solution was stirred at 65° C. for 18 h. More AlCl$_3$ (486 mg, 3.64 mmol) was added and the solution was stirred at 65° C. for additional 18 h. After cooling down, water and EtOAc were added. The organic layer was separated, washed with brine, dried over Na$_2$SO$_4$, and concentrated. The product was purified by sgc (MeOH/DCM: 10%) to give compound 1308G (75 mg, 18.3%).

Example 107

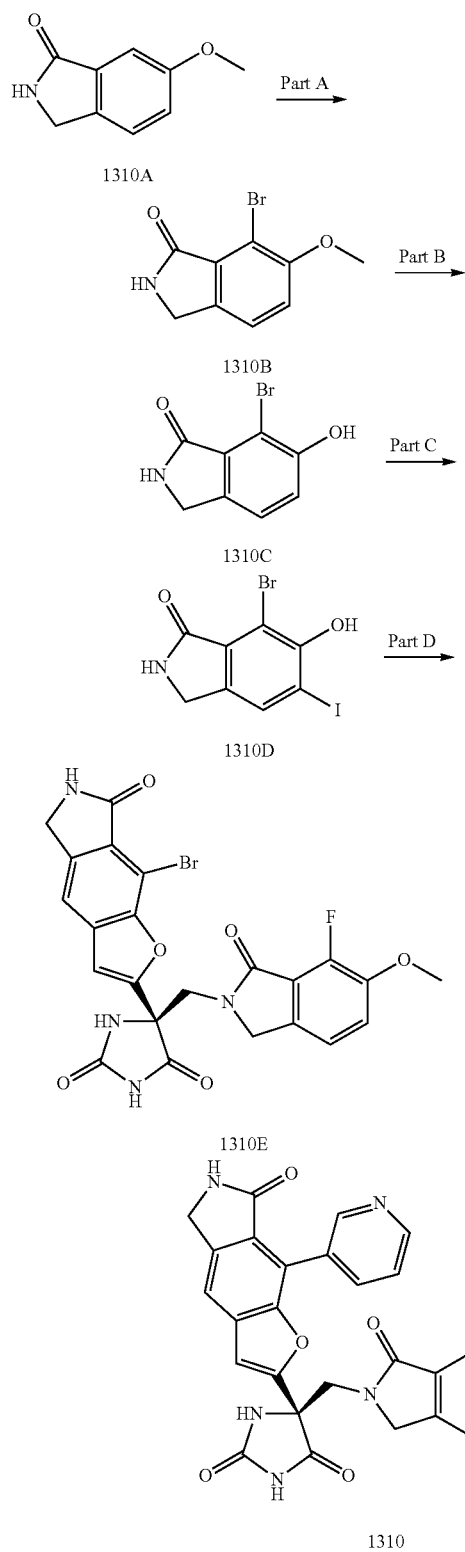

Part A

KBr (9.51 g, 79.8 mmol) was dissolved in water (100 mL) and Bromine (1.32 mL, 257 mmol) was added and stirred at RT for 10 min. Compound 1310A (4.0 g, 24.5 mmol) was added slowly into this solution portion wise. The solution was stirred in dark for three days. The solid was collected by filtration, washed with water, dried under vacuum at 40° C. for 18 hours to give compound 1310B (5.67 g, 96.0%).

Part B

Compound 1310B (1.0 g, 4.15 mmol) was suspended in DCM. BBr$_3$ (1M in DCM, 12.4 mL, 12.4 mmol) was added at 0° C. The solution was then stirred at RT for two hours. Solvent was removed and DCM and MeOH were added. The solid was collected and air dried to give compound 1310C (976 mg).

Part C

Compound 1310D was prepared by the same method as described in part B of Example 117.

Part D

Compound 1310E was prepared by the same method as described in Example 6.

Part E

Compound 1310 was prepared by the same method as described part B of Example 106.

Compound 1308 was prepared using procedures similar to those described in Example 106 and Example 107, Part E.

Compounds 2500-2502 were prepared using procedures similar to those described in Example 107.

Example 108

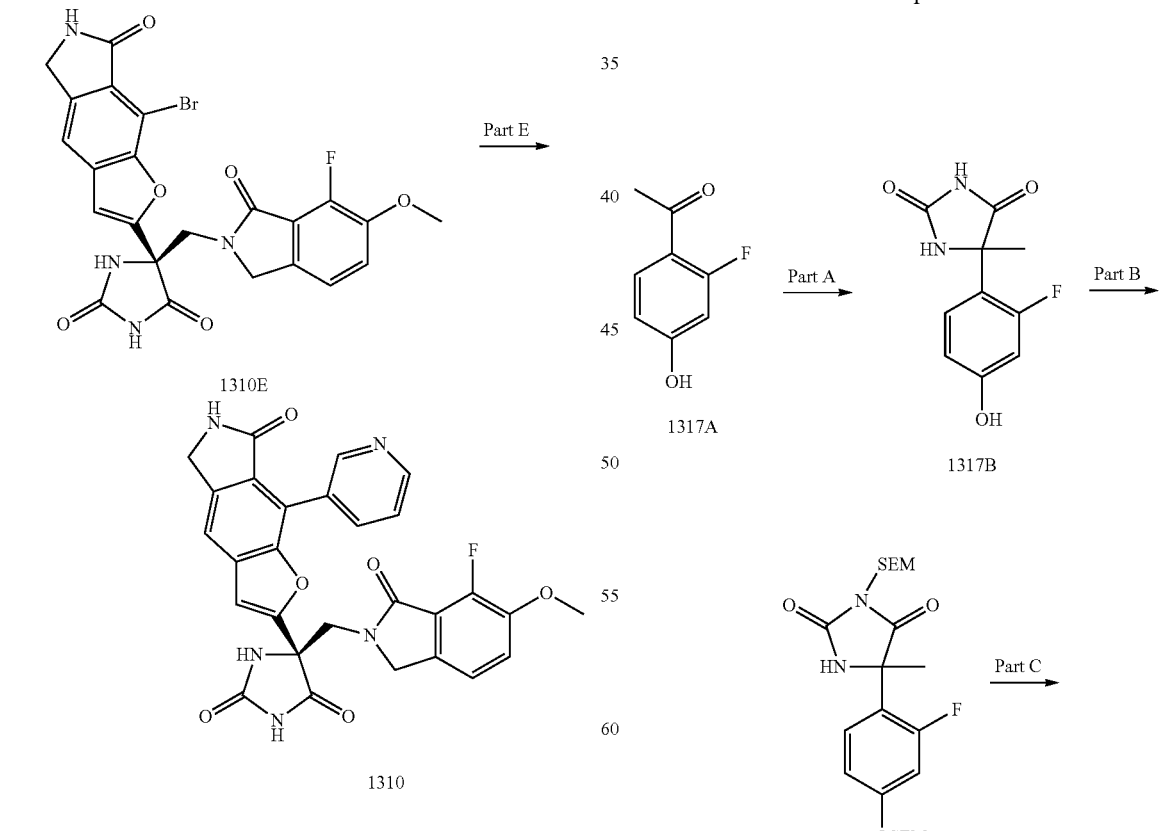

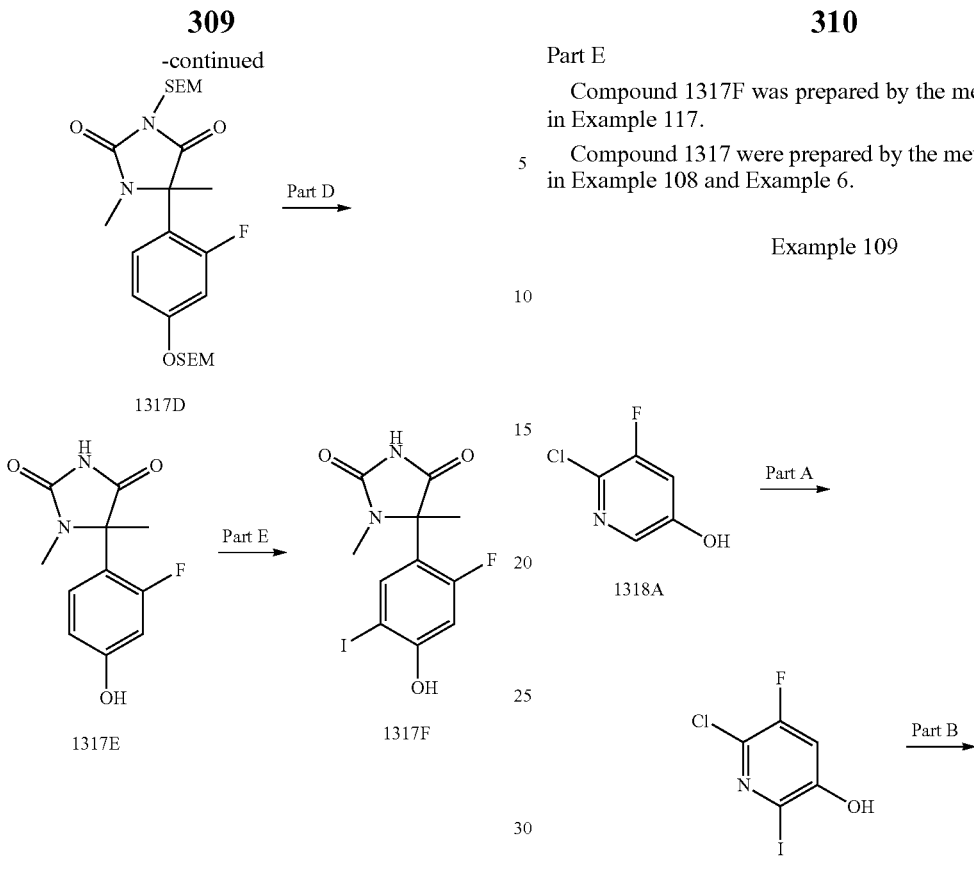

1317D 1317E 1317F

Part A
Compound 1317B was prepared by the same method as described in part A of Example 115.

Part B
Compound 1317B (2.0 g, 8.92 mmol), SEMCI (3.46 mL, 19.63 mmol), and DIPEA (3.82 mL, 22.3 mmol) were stirred in DMF (50 mL) at RT for overnight. DMF was removed by rotary evaporator at 60° C. water bath. The product was purified by sgc (MeOH/DCM, 0% to 5%) to give compound 1317C (2.13 g, 48.9%) and mono protected product (370 mg).

Part C
Compound 1317C (142 mg, 0.293 mmol) was dissolved in DMF (2 mL) and cooled to 0° C. NaH (15.0 mg, 0.586 mmol) was added followed by MeI (83 mg, 0.586 mmol). The solution was stirred at RT for 2 h, quenched with HCl (1N) and added EtOAc. The organic layer was separated, washed with brine, dried over $Na_2SO_4$, and concentrated to give compound 1317D which was used without further purification.

Part D
Compound 1317D was dissolved in MeOH (2 mL) in a 15 mL pressure tube. HCl (4M in dioxane, 2 mL) was added. The pressure tube was capped and stirred at 90° C. for overnight. After cooling down, the solvent was removed under vacuum. The residue was dissolved in MeOH (3 mL) and Triethyl amine (0.5 mL) was added. The solution was stirred at RT for three hours. The solvent was removed and the product was purified by C18 chromatography ($CH_3CN/H_2O$, 5% to 90%, with 0.1% $HCO_2H$) to give compound 1317E (63.2 mg, 70.3% from compound 1317C).

Part E
Compound 1317F was prepared by the method described in Example 117.

Compound 1317 were prepared by the methods described in Example 108 and Example 6.

Example 109

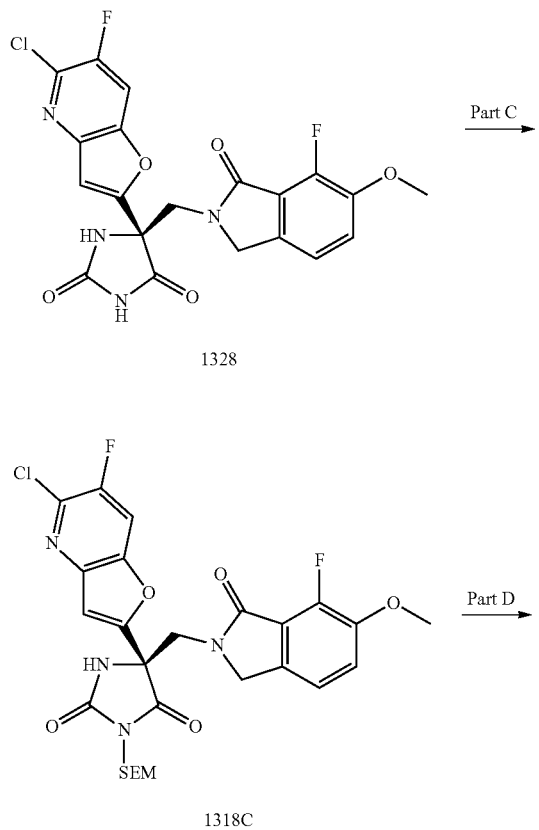

1318A

1318B

1328

1318C

-continued

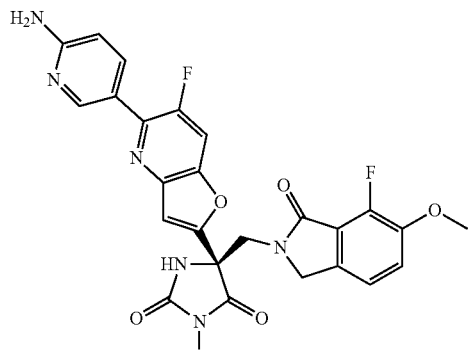

1318D

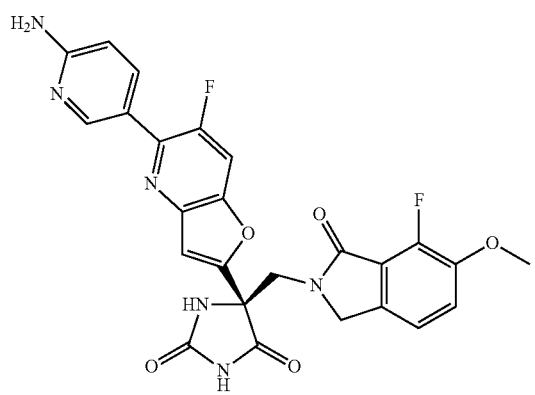

1318

Part A

Compound 1318B was prepared by the same method described in Example 117.

Part B

Compound 1328 was prepared by the same method described in Example 6.

Part C

Compound 1328 (380 mg, 0.82 mmol) was dissolved in DMF (5 mL). DIPEA (0.28 mL, 1.64 mmol) and SEMCl (0.173 mL, 0.985 mmol) were added. The solution was stirred at RT for overnight. DMF was removed by rotary evaporator. The product was purified by sgc (EtOAc/Hexane: 20% to 100%) to give compound 1318C (441 mg, 90.7%).

Part D

To a 5 mL flask was added compound 1318C (65 mg, 0.11 mmol), 2-amino-5-(4,4,5,5-tetramethyl-1,3,2-dioxaborolan-2-yl)pyridine (35 mg, 0.16 mmol), Pd(dppf)Cl$_2$ ((5 mg). The flask was vacuumed and flushed with N$_2$ for three times. K$_2$CO$_3$ (1M, 0.5 mL, 0.5 mmol) and CH$_3$CN were added. The solution was stirred at 80° C. for overnight. After cooling down, water and EtOAc were added. The organic layer was separated, washed with brine, dried over Na$_2$SO$_4$, and concentrated. The product was purified by SiO$_2$ chromatography (MeOH/DCM: 1% to 5%) to give compound 1318D.

Part E

Compound 1318D obtained in Part D was dissolved in MeOH (2 mL) in a 15 mL pressure tube. HCl (4M in dioxane, 2 mL) was added. The tube was capped and stirred at 90° C. for overnight. After cooling down, the solvent was removed and the residue was dissolved in MeOH (3 ml) and DIPEA (0.5 mL) was added. The solution was stirred at RT for three hours. The solvent was removed and the product was purified by C18 chromatography (CH$_3$CN/H$_2$O, 5% to 90%, with 0.1% HCO$_2$H) to give compound 1318 (18.9 mg, 33.0% from compound 1318C).

Compounds 1315 and 1318 were prepared by the methods described in Example 109.

Example 110

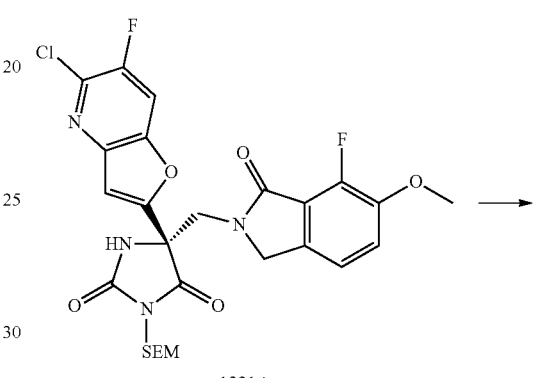

1321A

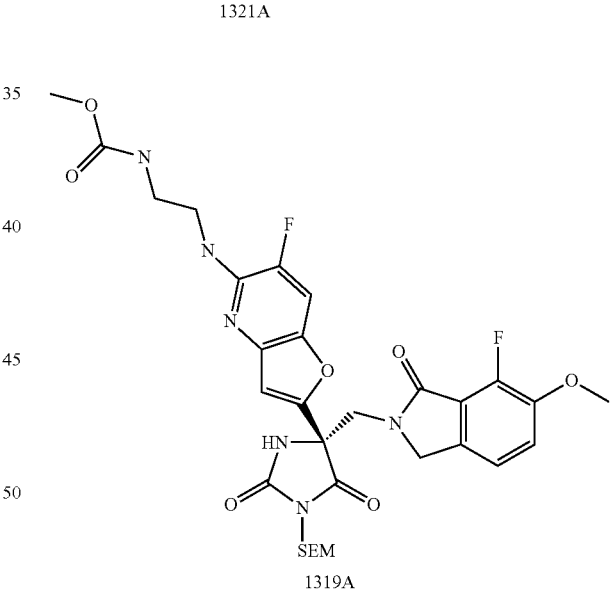

1319A

Compound 1321A (65 mg, 0.11 mmol), 2-imidazolidone (11.4 mg, 0.132 mmol), Pd(OAc)$_2$ (3 mg, 0.013 mmol), Xantphos (15.6 mg, 0.027 mmol), and t-BuONa (16 mg, 0.164 mmol) were placed in a 10 mL flask. The flask was vacuumed and flushed N$_2$ three times. Dioxane (1 mL) and water (2.95 mg, 0.164 mmol) were added. The solution was stirred at 100° C. for eight hours. The solvent was removed under vacuum and the product was purified by sgc (MeOH/DCM 1% to 5%) to give compound 1319A which was used in the next step.

Compound 1319 was prepared by the methods described in Example 110 and Part E of Example 109.
Example 111
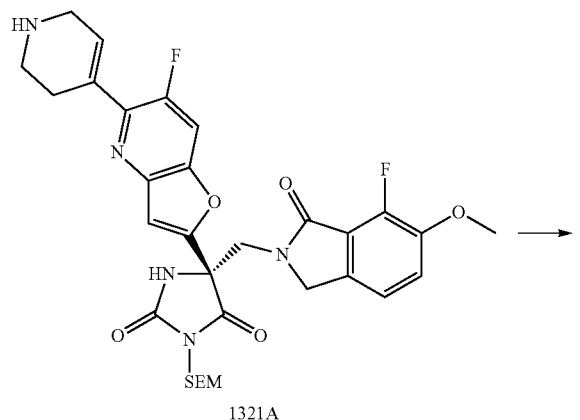
1321A
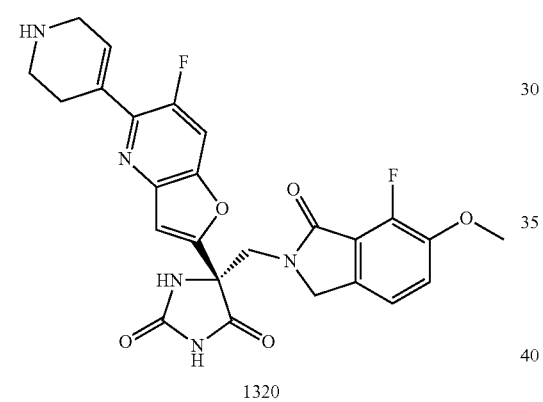
1320
Compound 1320 was prepared by the method described in Part E of Example 109
Example 112
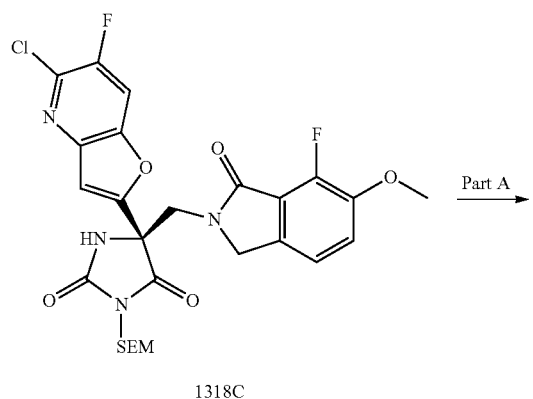
1318C
-continued
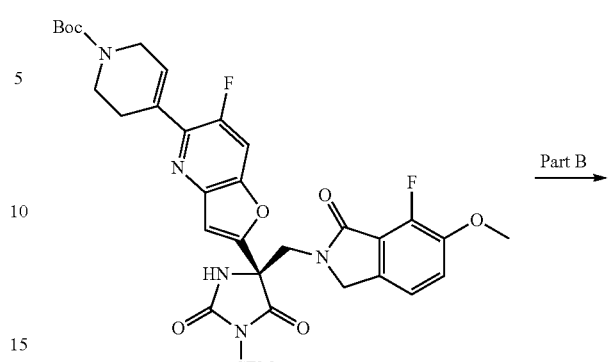
1321A
Part B →
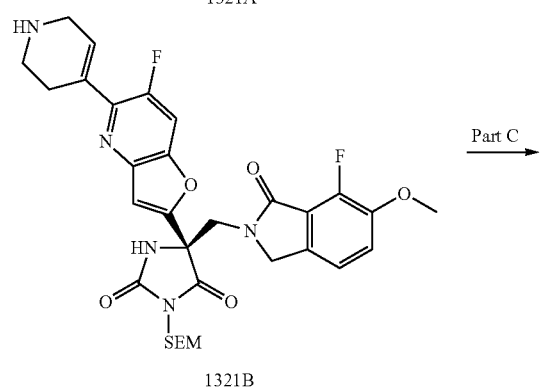
1321B
Part C →
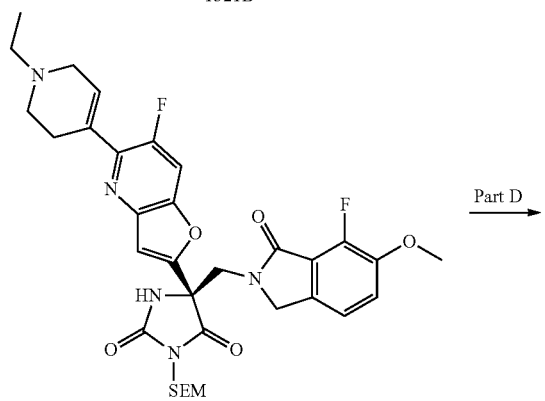
1321C
Part D →
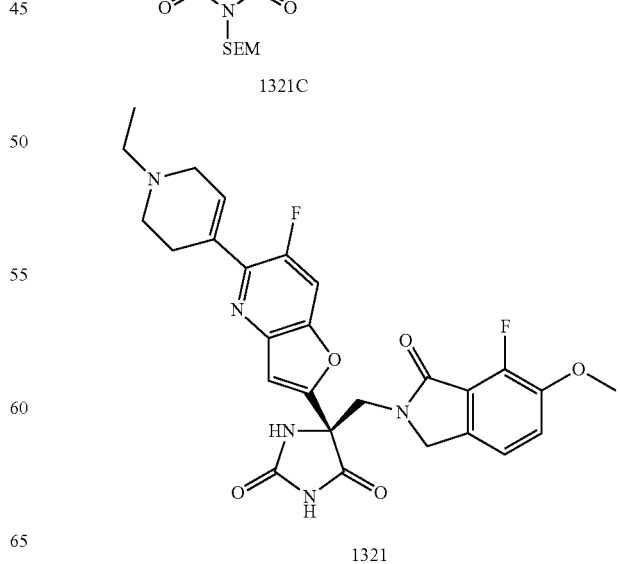
1321
Part A →

Part A

Compound 1321A was prepared by the method described in Part D of Example 109.

Part B

Compound 1321A (432 mg) was dissolved in MeOH (50 mL). HCl (4M in Dioxane, 10 mL) was added. The solution was stirred at RT for overnight, concentrated, and dried under vacuum to give compound 1321B which was used without further purification.

Part C

Compound 1321C was prepared by the method described in Part C of Example 109.

Part D

Compound 1321 was prepared by the method described in Part E of Example 109.

Compounds 1321 and 1322 were prepared by the methods described in Example 112.

Example 113

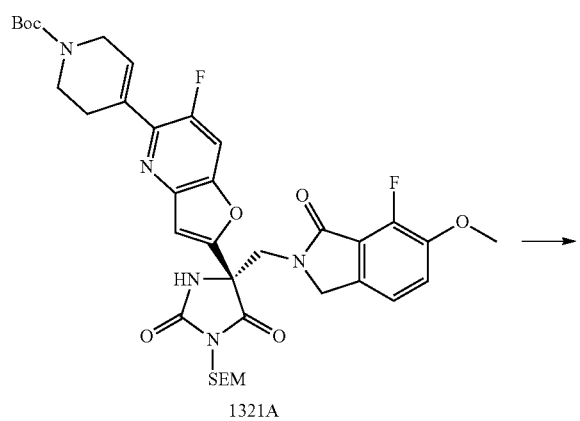

Compound 1321A (320 mg, 0.43 mmol) was dissolved in EtOH (15 mL). Pd/C (10%) was added. The solution was stirred under H$_2$ (1 atm) for overnight. The solid was removed by filtration, and the EtOH was removed under vacuum. The residue was separated by sgc (EtOAc) to give compound 1323A (325 mg, 100%).

Compound 1323 were prepared by the methods described in Example 113 and Example 111.

Compounds 1324 and 1325 were prepared by the methods described in Example 113 and Example 112.

Example 114

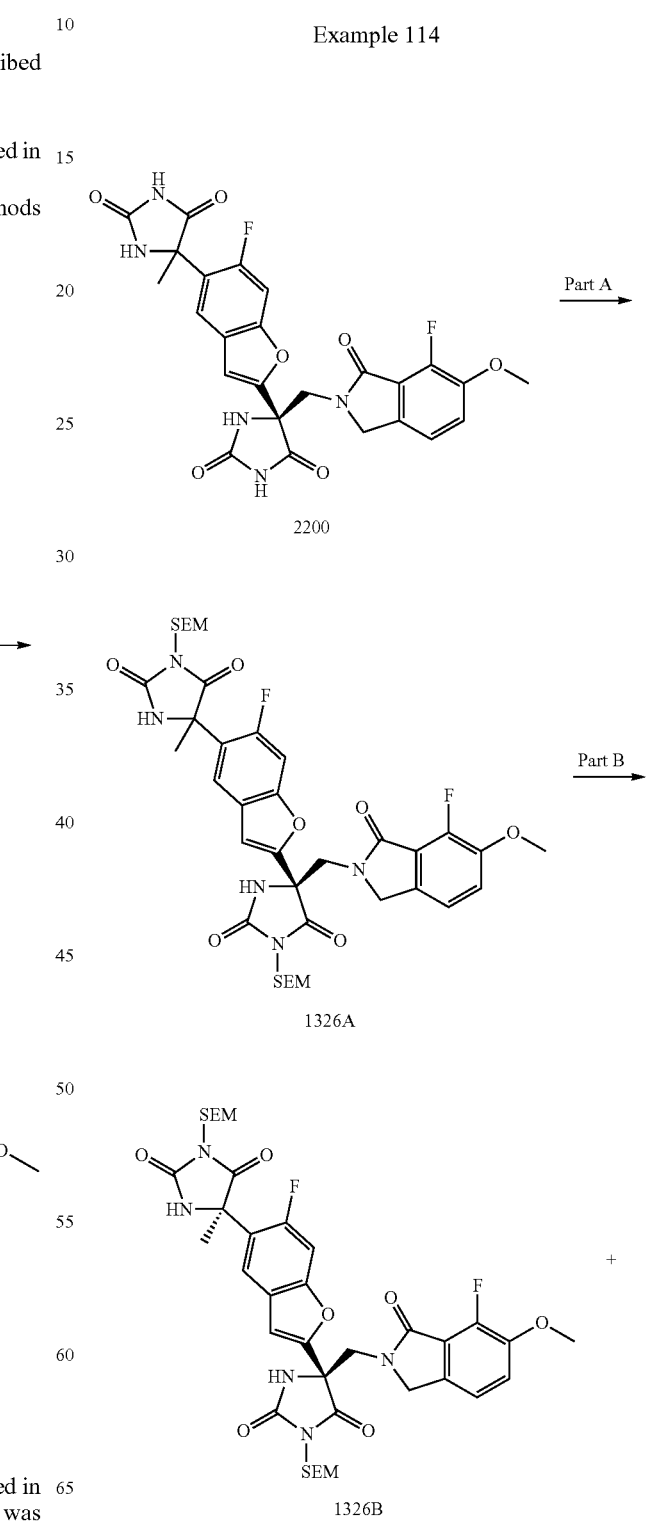

-continued

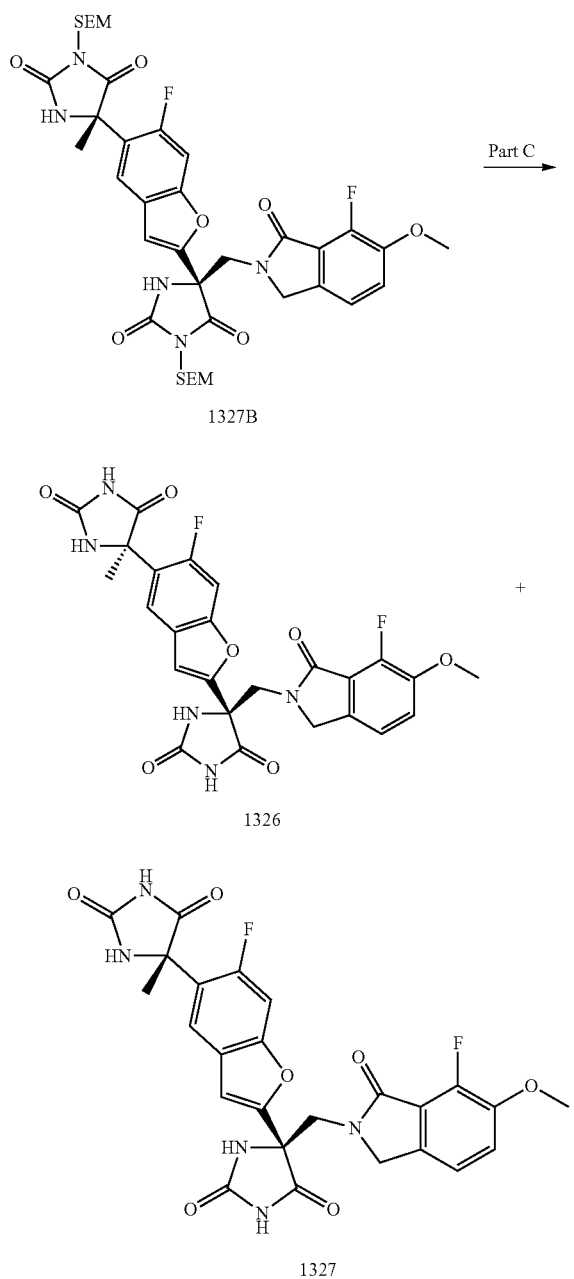

Part A

Compound 1326A was prepared by the method described in Part C of Example 109.

Part B

Compound 1326A (320 mg) was dissolved in EtOH (10 ml) and it was injected into an OD chiral column eluted by Hexane/EtOH (1:1, flow rate 40 mL/min). The first peak was collected and concentrated to give compound 1326B (90 mg). The second peak was collected and concentrated to give compound 1327B (93 mg).

Part C

Compound 1326B (90 mg) was dissolved in CH$_3$CN (3 ml) and cooled to 0° C. BF$_3$.Et$_2$O (0.07 mL, 0.56 mmol) was added. The solvent was stirred at RT for three hours. Triethylamine (0.5 mL) was added. The solution was stirred at RT for overnight. The solvent was removed and the product was purified by C18 chromatography (CH$_3$CN/H$_2$O, 5% to 90%, with 0.1% HCO$_2$H) to give compound 1326 (39.0 mg, 64.6%).

Compound 1327 was prepared by the same method.

Example 115

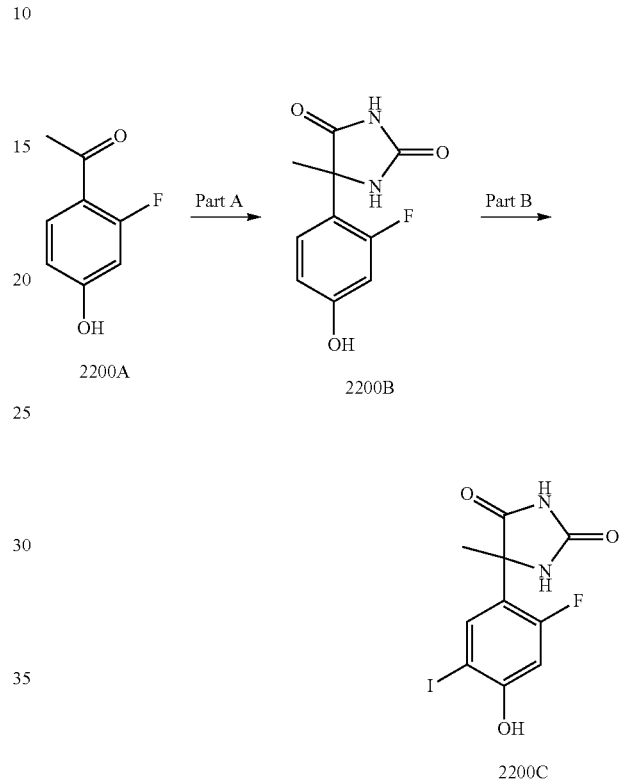

Part A

Compound 2200A (2.0 g, 13.0 mmol) was suspended in NH$_3$—H$_2$O (37%, 13 mL) in a 150 mL pressure bottle. KCN (845 mg, 13.0 mmol), (NH$_4$)$_2$CO$_3$ (5.0 g, 52.0 mmol), and MeOH (13 mL) were added. The pressure bottle was capped and stirred at 80~90° C. for 16 h, then at 100° C. for two days. After cooling down, the solution was concentrated to half of its original volume, adjusting the pH to 6~7 with HCl (2N). The solid was collected, dissolved in DMF (10 mL) and purified by C18 chromatography (CH$_3$CN/H$_2$O, 5% to 90%) to give compound 2200B (1.28 g, 44.0%)

Part B

To a solution of compound 2200B (1.22 g, 5.66 mmol) in NH$_3$—H$_2$O (37%, 40 mL) was added a solution of I$_2$ (1.29 g, 5.1 mmol) and KI (2.54 g, 15.3 mmol) in water (10 mL) dropwise. The solution was stirred at 25° C. for 1 hour. The solution was concentrated to half of its original volume, adjusting the pH to 6~7 with HCl (2N). The solid was collected by filtration, washed with water, dried under vacuum for overnight to give compound 2200C (1.65 g, 83.3.0%)

Compounds 1305, 1306, 1307, 1316, 2200, 2205, 2206, 2207, 2208, 2210, and 2211 were prepared by the methods described in Example 115 and Example 6.

Example 116

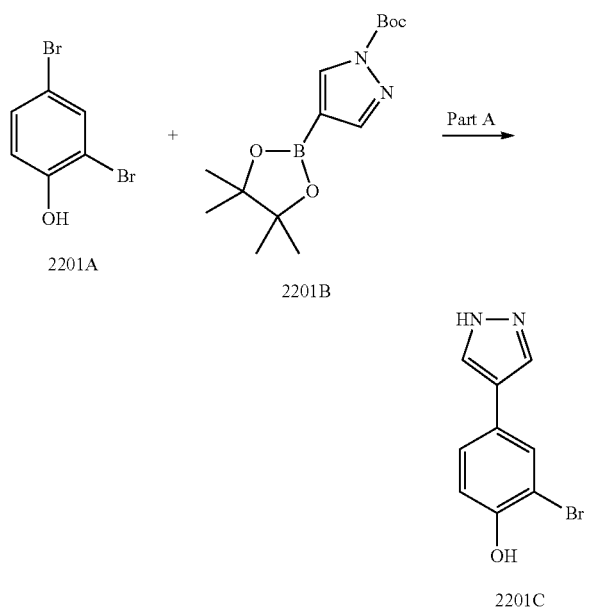

Part A

To a 25 mL flask was added compound 2201A (220.0 mg, 0.87 mmol), compound 2201B (233 mg, 0.792 mmol), and Pd(dppf)Cl$_2$ (59 mg, 0.08 mmol). The flask was degassed under vacuum and refilled with N$_2$. K$_2$CO$_3$ (1M in water, 3 mL, 3 mmol) and CH$_3$CN (5 mL) were added and the solution was stirred at 80° C. for overnight. After cooling down, EtOAc (10 mL) was added and the aqueous layer was separated and washed with EtOAc (5 mL) once. The organic layers were combined and dried over Na$_2$SO$_4$, concentrated, and purified by C18 chromatography (CH$_3$CN/H$_2$O, 5% to 90%) to give compound 2201C (>85 mg).

Compounds 2201, 2202, 2213 and 2218 were prepared by the methods described in Example 116 and Example 6.

Example 117

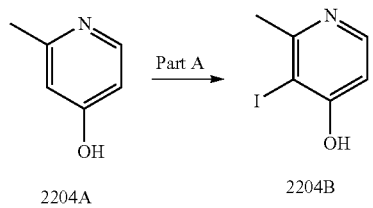

Compound 2204B was prepared by the same method as described in Part B of Example 115.

Compounds 1311, 1312, 1313, 2204, 2216, and 2217 were prepared by the methods described in Example 117 and Example 6.

Compound 2401 was prepared by the methods described in Example 117 and Example 52.

Compound 1314 were prepared by the method described in Example 116, Example 117, and Example 6.

Example 118

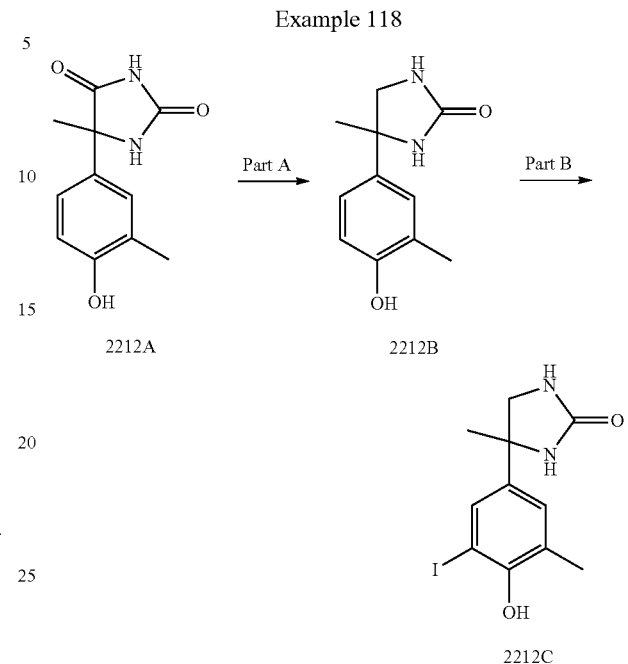

Part A

Compound 2212A (1.0 g, 4.54 mmol) was suspended in anhydrous THF (20 mL) and cooled to 0° C. Red-Al (3.2 M, 14.2 mL, 45.4 mmol) was added dropwise. After the addition was completed, the solution was heated to 85° C. for 4 hours. It was then cooled to 0° C. and quenched with water. Organic solvent was removed by rotary evaporator. NaOH (1M) and EtOAc were added and the organic layer was separated. The aqueous layer was extracted with EtOAc twice. The EtOAc layers were combined, concentrated, and purified by C18 chromatography (CH$_3$CN/H$_2$O, 5% to 90%, with 0.1% HCO$_2$H) to give compound 2212B (305 mg, 32.6%)

Part B

Compound 2212C was prepared by the same method as described in Part B of Example 115.

Compound 2212 were prepared by the methods described in Example 118 and Example 6.

Example 119

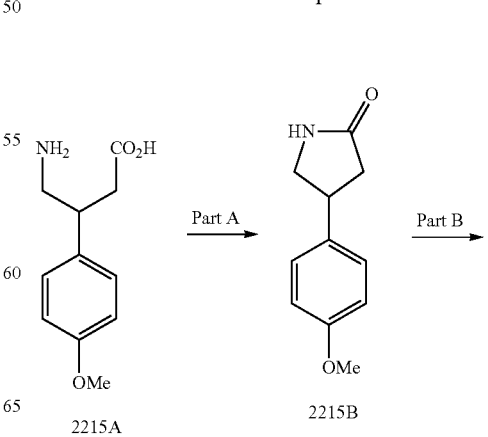

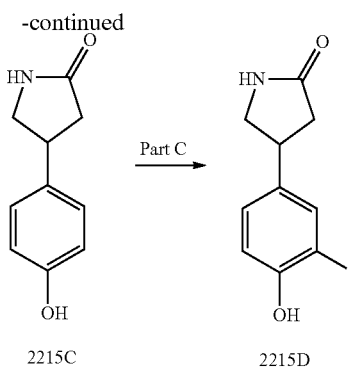

2215C → 2215D (Part C)

Part A

Compound 2215A (2.0 g, 9.5 mmol), EDCl (2.74 g, 14.3 mmol), and HOBT (1.93 g, 14.3 mmol) were placed in a 25 mL flask and DMF (45 mL) and DIPEA (6.64 mL, 38.0 mmol) were added. The solution was stirred at 25° C. for overnight. Water and EtOAc were added. The organic layer was separated, washed with brine, dried over $Na_2SO_4$, and concentrated. The residue was suspended in water, stirred for 30 min, the solid was collected by filtration, washed with water, dried at 50° C. for 2 hours to give compound 2215B (414 mg, 22.8%).

Part B

Compound 2215C was prepared by the same method as described in Part B in Example 120.

Part C

Compound 2215D was prepared by the same method as described in Part B of Example 115.

Compound 2215 were prepared by the methods described in Example 119 and Example 6.

Example 120

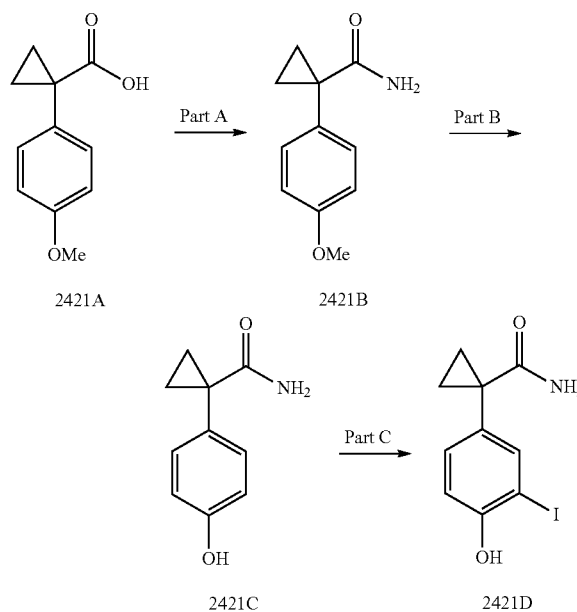

Part A

Compound 2421A (3 g) was dissolved in $SOCl_2$ (15 mL) and the solution was heated to reflux temperature for two hours. $SOCl_2$ was removed by rotary evaporator. The residue was dissolved in $CH_2Cl_2$ and added into a cold mixture of $NH_3$—$H_2O$ (37%) and ice with good stirring. After the addition was completed, the solution was stirred at 25° C. for 20 min. The organic layer was separated and washed with brine, dried over $Na_2SO_4$, and concentrated with rotary evaporator to give 2421B which was used without further purification.

Part B

Compound 2421B (1.0 g, 5.23 mmol) and pyridine HCl (3.6 g, 31.3 mmol) were placed in a 5 mL microwave reaction tube and sealed. The tube was heated to 200° C. for one hour. After cooling down, the residue was dissolved in DMF and purified by C18 chromatography ($CH_3CN/H_2O$, 5% to 90%, with 0.1% $HCO_2H$) to give compound 2421C (886 mg, 95.6%)

Part C

Compound 2421C (500 mg, 2.82 mmol) was dissolved in $NH_3$—$H_2O$ (37%, 15 mL). A solution of $I_2$ (644 mg, 2.54 mmol) and KI (1.6 g, 10.2 mmol) in water (5 mL) was added dropwise. After the addition was completed, the solution was stirred at 25° C. for 1 h, The solution was concentrated to about 10 mL, adjusting the pH to 2~4 with HCl (2N). The solution was purified by C18 chromatography ($CH_3CN/H_2O$, 5% to 90%, with 0.1% $HCO_2H$) to give compound 2421D (712 mg, 83%)

Compounds 2209, 2421 and 2425 were prepared by the methods described in Example 120 and Example 6.

Example 121

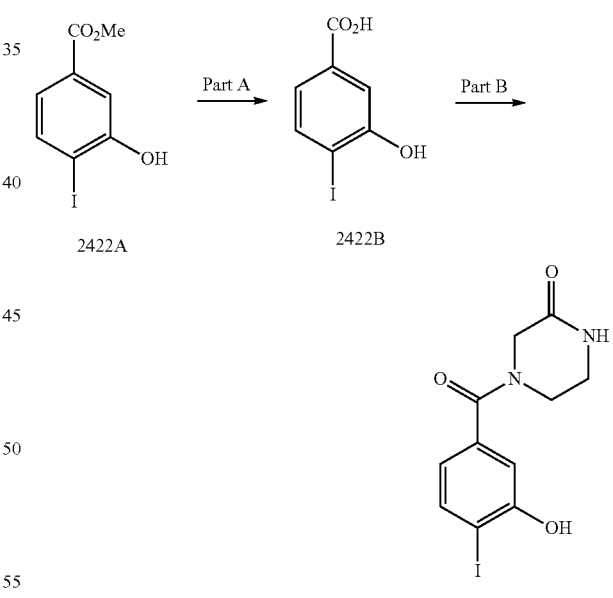

Part A

Compound 2422A (3.0 g, 10.8 mmol) was dissolved in a mixture solution of THF (40 mL) and water (920 mL). LiOH (905 mg, 21.6 mmol) was added and the solution was stirred at 65° C. for overnight. After cooling down, HCl (2N) and EtOAc were added and the organic layer was separated, washed with brine, dried over $Na_2SO_4$, concentrated and dried under vacuum to give compound 2422B (2.51 g, 88.1%).

Part B

Compound 2422B (300 mg, 1.14 mmol) and piperazine-2-one (170 mg, 1.70 mmol) were dissolved in DMF (6 mL). HATU (480 mg, 1.26 mmol) and DIPEA (0.6 mL, 3.4 mmol) were added. The solution was stirred at 25° C. for overnight. Water and EtOAc were added and the organic layer was separated, washed with brine, dried over Na₂SO₄, and concentrated. The product was purified by SiO₂ chromatography to give pure compound 2422C (352 mg, 89.2%).

Compounds 2422, 2423, 2424, 2426, 2427 and 2428 were prepared by the methods described in Example 121 and Example 6.

Example 122

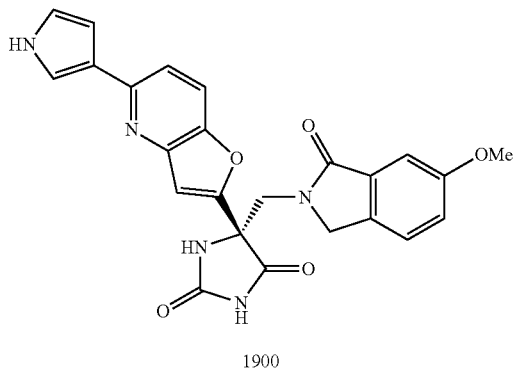

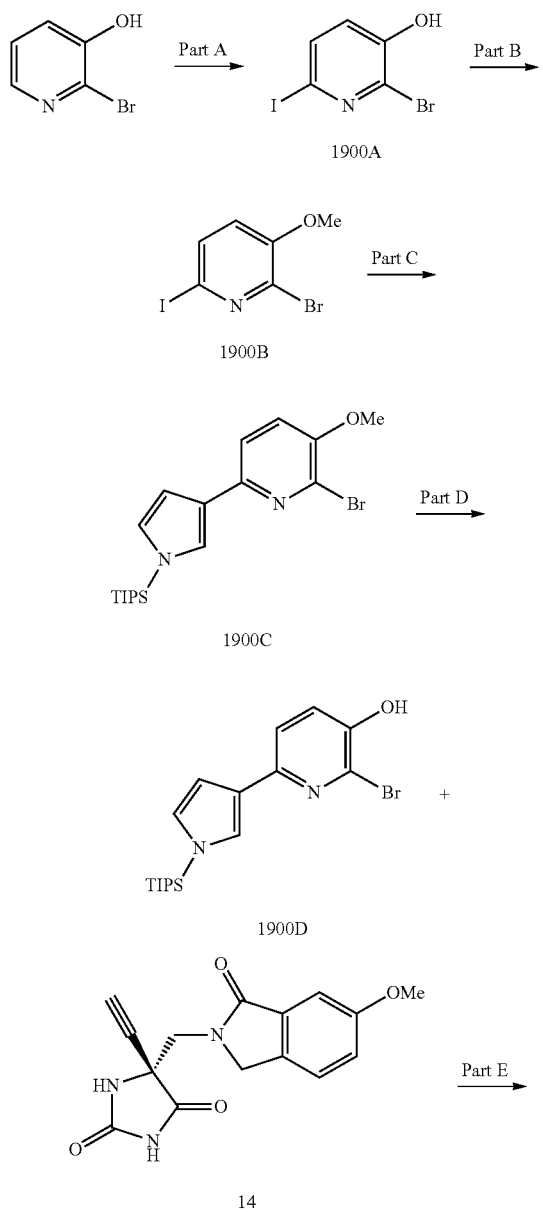

Part A:

A suspension of 2-bromo-3-hydroxypyridine (6 g, 34.4 mmol) in water (140 mL) was treated with potassium carbonate (9.52 g, 69.0 mmol) and iodine (9.6 g, 38.0 mmol) at 25° C. The mixture was stirred for 3 h and the solid was filtered and washed with water to provide the desired product 1900A (6.5 g, 63%).

Part B:

A solution of compound 1900A (6.5 g, 21.7 mmol) in DMF was treated with potassium carbonate (8.9 g, 65.0 mmol) and iodomethane (5.4 mL, 86.7 mmol) at 25° C. The mixture was stirred for 3 h and added to water. The solid was filtered and washed with water to provide the desired product 1900B (6.7 g, 99%).

Part C:

Compound 1900B (189 mg, 0.60 mmol), N-triisopropylsilylpyrrol-3-boronic acid (241 mg, 0.90 mmol), Pd(dppf)Cl₂ (49 mg, 0.06 mmol), acetonitrile (5 mL), and potassium carbonate (1N aq. solution, 1.5 mL, 1.5 mmol) were stirred at 80° C. (oil bath) under nitrogen for 18 h. After cooling, the mixture was diluted in EtOAc and the solid was removed by filtration. The solution was concentrated and purified by SiO₂ column chromatography (1:3 EtOAc/hexanes) to give 1900C (66 mg, 27%).

Part D:

Compound 1900C (66 mg, 0.16 mmol) was dissolved in 1,2-dichloroethane (2 mL) and aluminum chloride (65 mg, 0.48 mmol) was added. The reaction mixture was stirred at 40° C. for 6 h. After cooled to 25° C., the mixture was added to aq. Na₂CO₃ solution and the organic layers were extracted with EtOAc. The combined organic layers were washed with brine solution, dried (Na₂SO₄), and concentrated in vacuo to provide the crude product 1900D (60 mg, 95%).

Part E:

Compound 14 (42 mg, 0.14 mmol), compound 1900D (60 mg, 0.15 mmol), Pd(PPh₃)₂Cl₂ (2.1 mg, 0.003 mmol), CuI (0.6 mg, 0.003 mmol), and N,N-diisopropylethylamine (60 µL, 0.35 mmol) in DMF (1 mL) was stirred at 80° C. for 18 h. After cooled to 25° C., the solid was removed by filtration and the filtrate was purified by HPLC (water-acetonitrile) to provide the desired product 1900 (18 mg, 28%).

Example 123

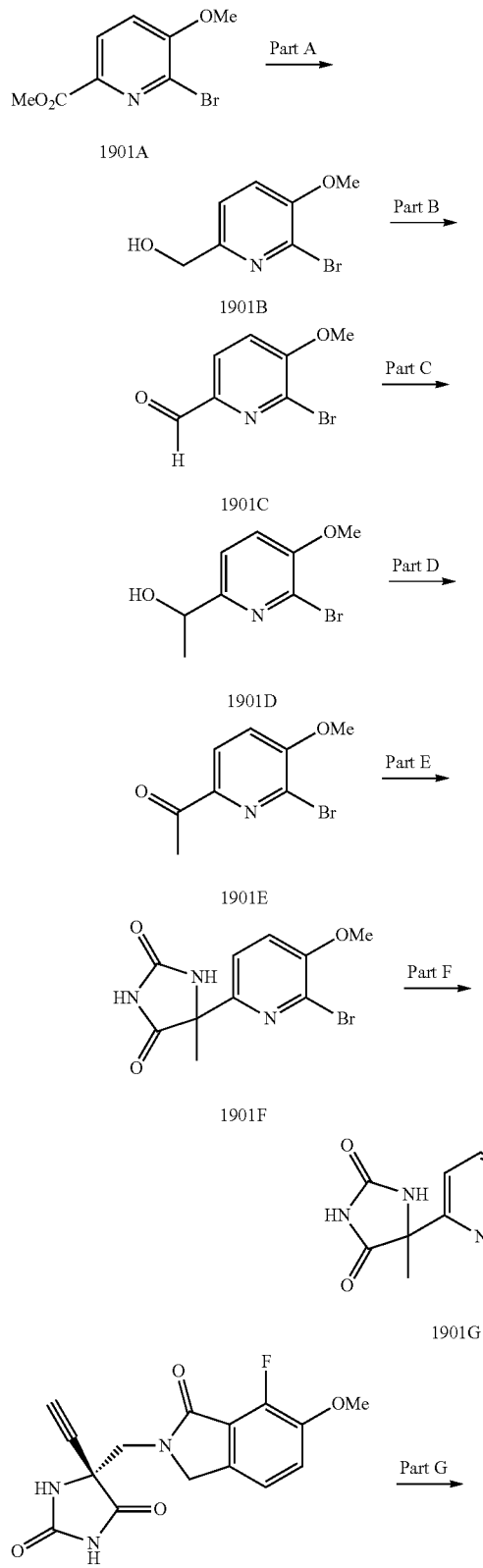

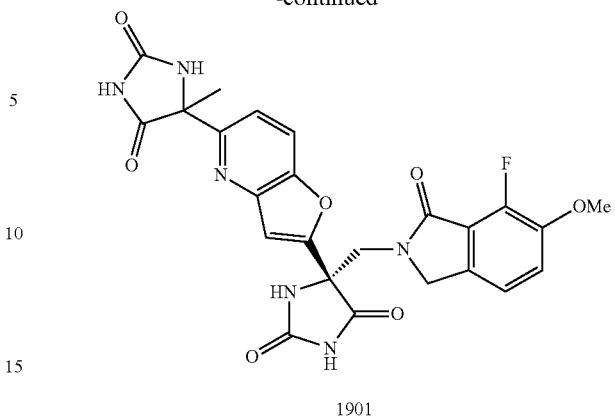

1901

Part A:
Compound 1901A (971 mg, 3.95 mmol) was suspended in $CH_2Cl_2$ (70 mL) and cooled in dry ice-acetone bath. Diisopropylaluminum hydride (1M in hexane, 9.88 mL, 9.88 mmol) was added slowly and the temperature was allowed to warm to 0° C. for 2 h. The reaction was quenched by 10% aq. citric acid and the mixture was stirred at 25° C. for 1 h. The organic layers were extracted with $CH_2Cl_2$ and the combined organic solution was washed with brine solution, dried ($Na_2SO_4$), and concentrated in vacuo to provide crude product 1901B (758 mg, 87%).

Part B:
Compound 1901B (748 mg, 3.43 mmol) was dissolved in $CHCl_3$ (40 mL) and $MnO_2$ (1.8 g) was added at 25° C. After stirring for 1 days at 40° C., the solid was removed by filtration and the filtrate was concentrated in vacuo to provide the desired product 1901C (569 mg, 77%).

Part C:
Compound 1901C (255 mg, 1.18 mmol) was dissolved in THF (5 mL) and cooled in dry ice-acetone bath. MeMgCl (3M in THF, 0.47 mL, 1.41 mmol) was added dropwisely and the reaction was allowed to warm to 0° C. for 2 h. After quenching with small amount of MeOH, the mixture was added to cold water. The organic layers were extracted with EtOAc and the combined organic solution was washed with brine solution, dried ($Na_2SO_4$), and concentrated in vacuo to provide the desired product 1901D (269 mg, 98%).

Part D:
Compound 1901D (269 mg, 1.16 mmol) was dissolved in $CH_2Cl_2$ (4 mL) and cooled in dry ice-acetone bath. DMSO (0.2 mL, 2/8 mmol) and oxalyl chloride (0.15 mL, 1.74 mmol) were added and the mixture was stirred for 10 min at the temperature. After cessation of gas released, triethylamine (0.8 mL, 5.8 mmol) was added. The mixture was stirred at −70 to −78° C. for 1 h and added to cold mixture of aq. $NaHCO_3$ solution and $CH_2Cl_2$. After stirring for 10 min at 0° C., the organic layers were extracted with $CH_2Cl_2$ and the combined organic solution was washed with brine solution, dried ($Na_2SO_4$), and concentrated in vacuo to provide the desired product 1901E (256 mg, 96%).

Part E:
Compound 1901E (254 mg, 1.1 mmol), potassium cyanide (143 mg, 2.2 mmol), and ammonium carbonate (423 mg, 4.4 mmol) were dissolved in EtOH (10 mL) and water (4 mL). The mixture was stirred at 60° C. in a pressure vessel for 15 h. After cooled to 25° C., the mixture was concentrated and the residue was dissolved in EtOAc. The organic solution was washed with water, brine solution, dried ($Na_2SO_4$), and concentrated in vacuo. The residue was purified by SiO₂ column (MeOH/CH₂Cl₂ gradient from 0% to 10% MeOH) to provide desired product 1901F as a 1:1 mixture of diastereomers (227 mg, 69%).

Part F:

Compound 1901F (226 mg, 0.75 mmol) was dissolved in 1,2-dichloroethane (10 mL) and aluminum chloride (399 mg, 3.0 mmol) was added. The reaction mixture was stirred at 40° C. for 18 h. After cooling, the mixture was added to aq. Na₂CO₃ solution and the organic layers were extracted with EtOAc. The combined organic layers were washed with brine solution, dried (Na₂SO₄), and concentrated in vacuo to provide the crude product 1901G (196 mg, 91%).

Part G:

Compound 23 (106 mg, 0.33 mmol), compound 1901G (124 mg, 0.43 mmol), Pd(PPh₃)₂Cl₂ (5.0 mg, 0.007 mmol), CuI (1.3 mg, 0.010 mmol), and N,N-diisopropylethylamine (0.11 mL, 0.66 mmol) in DMF (2 mL) was stirred at 80° C. for 18 h. After cooled to 25° C., the solid was removed by filtration and the filtrate was purified by HPLC (water-acetonitrile) to provide the desired product 1901 as a 1:1 mixture of diastereomers (98 mg, 57%).

Compound 2203 was prepared from compound 23 using procedures similar to those described in Example 52, Part D.

Compounds 303, 304, 2271-2272 and 2277 were prepared from compound 23 and the corresponding ortho iodophenols using procedures similar to those described in Example 6, Part F.

Compound 504 was prepared from compound 23 using procedures similar to those described in Example 23.

Example 124

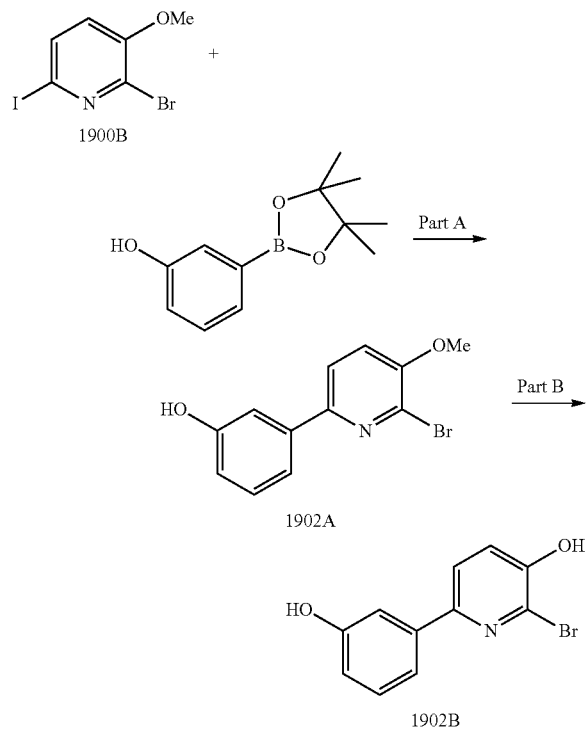

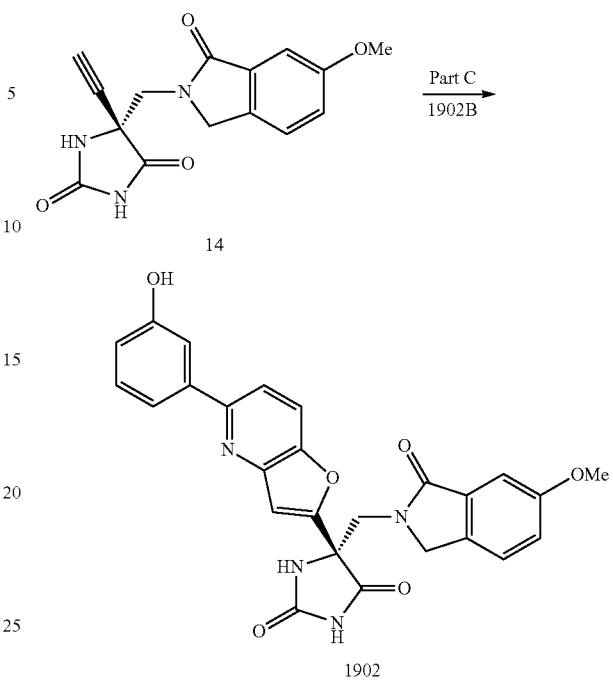

Part A:

Compound 1900B (550 mg, 1.75 mmol), 2-(3-Hydroxyphenyl)-4,4,5,5-tetramethyl-1,3,2-dioxaborolane (425 mg, 1.93 mmol), Pd(PPh₃)₄ (100 mg, 0.087 mmol), and potassium carbonate (1M aq. solution, 10 mL, 10 mmol) were dissolved in acetonitrile (70 mL). The mixture was degassed and heated to 90° C. for 29 h. After cooling to 25° C., the mixture was concentrated and the residue was purified by SiO₂ column chromatography (MeOH/CH₂Cl₂ gradient from 0% to 10% MeOH) to provide 1902A (430 mg, 88%).

Part B:

Compound 1902B was prepared using a procedure found in Part D of Example 122.

Part C:

Compound 1902 was prepared from compounds 14 and 1902B by using a procedure found in Part E of Example 122.

Compounds 2100, 2470-2472, and 2490 were prepared using procedures similar to those described in Example 124.

Compound 2473 was prepared from 1900B and compound 14 using the Pd-catalyzed cyanation reaction described in *Tetrahedron Letters*, 1999, 40, 8193-8195 followed by a Sonogashira coupling procedure similar to that described in Example 124.

Example 125

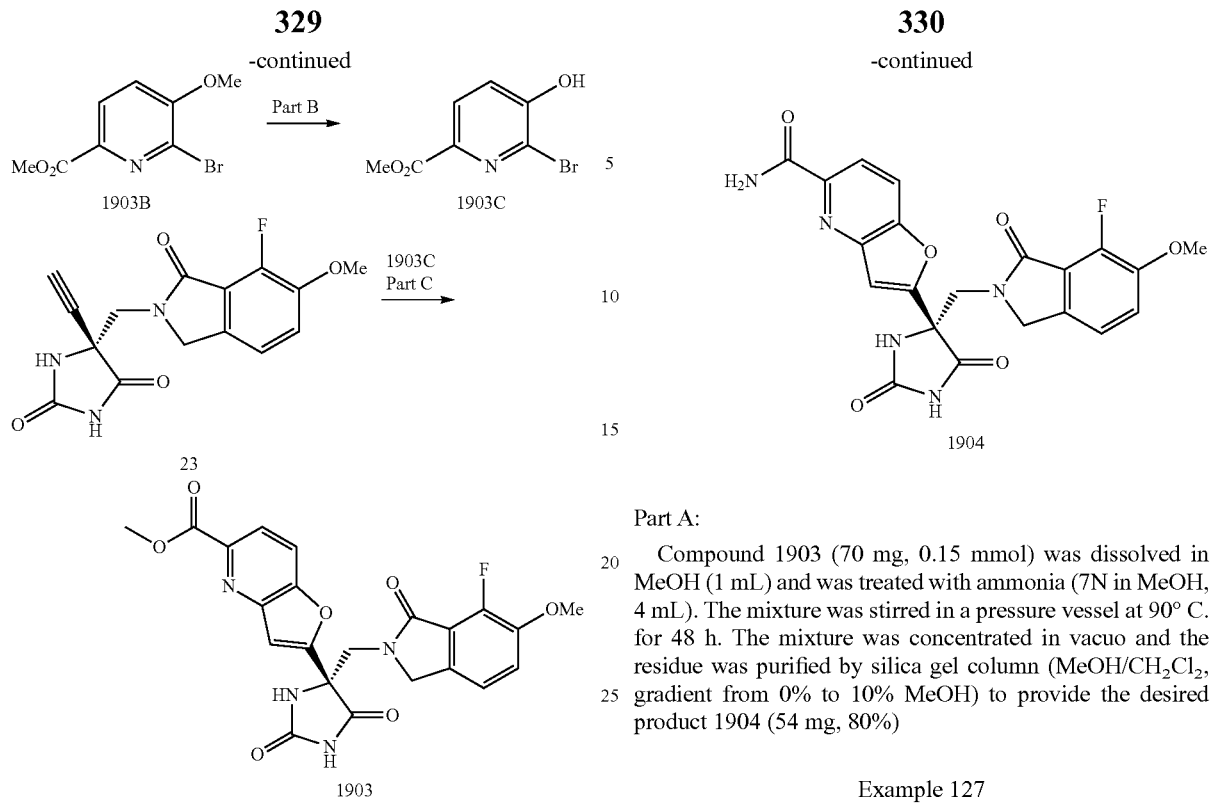

Part A:

Compound 1903A (450 mg, 1.94 mmol, prepared by a procedure similar to that described by T. Ross Kelly and F. Lang, *J. Org. Chem.* 1996, 61, 4623-4633) was suspended in $CH_2Cl_2$-MeOH and cooled to 0° C. The mixture was stirred for 15 min and treated with trimethylsilyl diazomethane (2 M in hexane, 1.95 mL, 3.9 mmol). After stirred for 3 h at 25° C., the reaction mixture was flushed with $N_2$ stream for 20 min. Filtration through silica gel provided the desired product 1903B (380 mg, 80%)

Part B:

Compound 1903C was prepared using a procedure found in Part D of Example 122.

Part C:

Compound 1903 was prepared from compound 23 using a procedure found in Part E of Example 122.

Example 126

Part A:

Compound 1903 (70 mg, 0.15 mmol) was dissolved in MeOH (1 mL) and was treated with ammonia (7N in MeOH, 4 mL). The mixture was stirred in a pressure vessel at 90° C. for 48 h. The mixture was concentrated in vacuo and the residue was purified by silica gel column (MeOH/$CH_2Cl_2$, gradient from 0% to 10% MeOH) to provide the desired product 1904 (54 mg, 80%)

Example 127

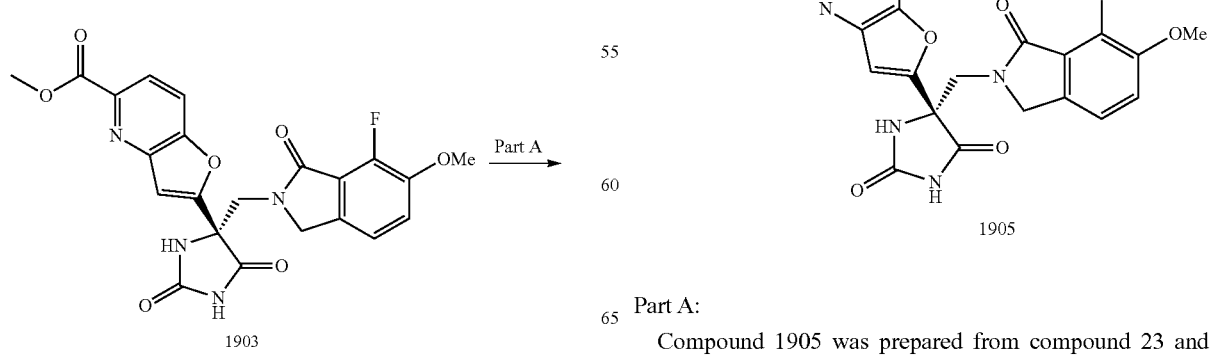

Part A:

Compound 1905 was prepared from compound 23 and 1905A (prepared by a procedure similar to that described by T. Ross Kelly and F. Lang, *J. Org. Chem.* 1996, 61, 4623-4633) using a procedure found in Part E of Example 122.

Example 128

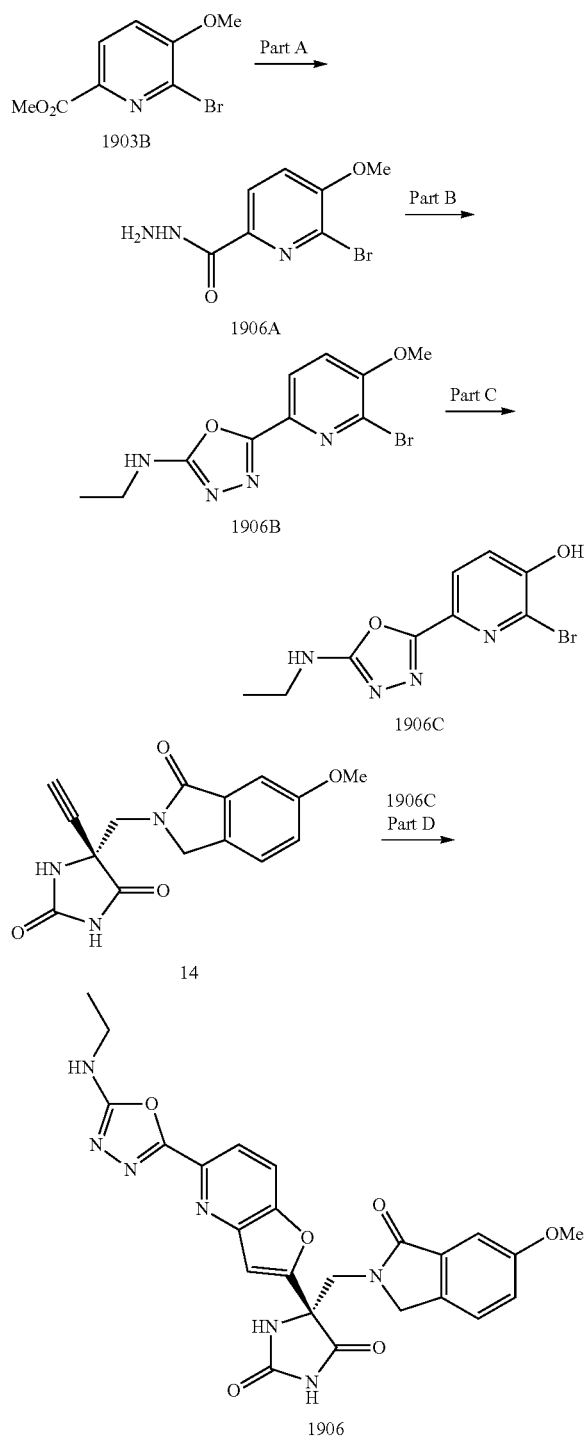

Part A:
Compound 1903B (380 mg, 1.55 mmol) and hydrazine (0.15 mL, 4.6 mmol) were dissolved in EtOH (30 mL). The reaction mixture was stirred at 100° C. for 19 h. The mixture was cooled to 25° C. and the precipitates were filtered and washed with cold EtOH to provide the desired product 1906A (380 mg, quant.).

Part B:
Compound 1906A (400 mg, 1.62 mmol) and ethyl isocyanate (0.13 mL, 1.62 mmol) was dissolved in acetonitrile (3 mL). The mixture was stirred at 25° C. for 1 h followed by addition of p-toluenesulfonyl chloride (618 mg, 3.25 mmol) and triethylamine (0.65 mL, 4.88 mmol). The mixture was stirred at 25° C. for 20 h and concentrated in vacuo. The residue was purified by silica gel column (MeOH/CH$_2$Cl$_2$, gradient from 0% to 10% MeOH) to provide the desired product 1906B (260 mg, 54%).

Part C:
Compound 1906C was prepared using a procedure found in Part D of Example 122.

Part D:
Compound 1906 was prepared from compounds 14 and 1906C using a procedure found in Part E of Example 122.

Example 129

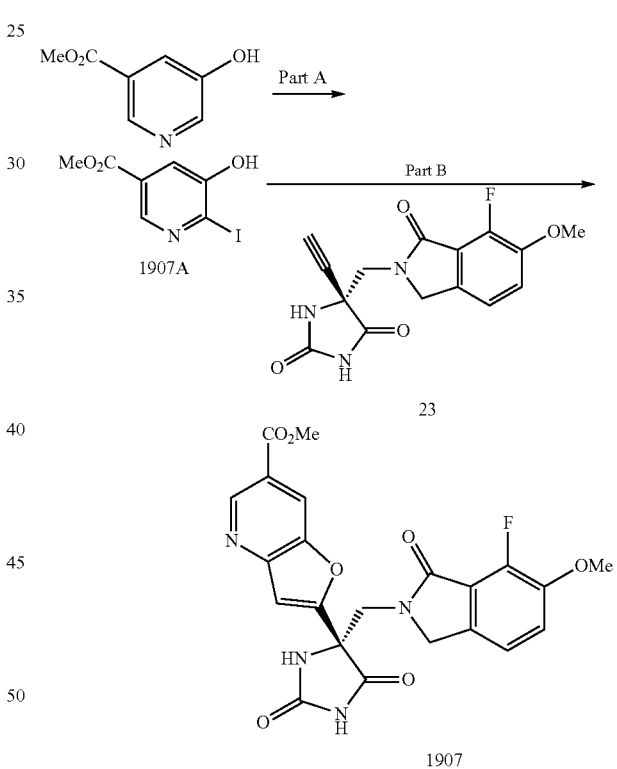

Part A:
Methyl 5-hydroxynicotinate (1 g, 6.54 mmol), sodium carbonate (1.39 g, 13.1 mmol), and iodine (1.6 g, 6.54 mmol) were suspended in water (100 mL) and stirred at 25° C. for 1.5 h. The mixture was acidified with aq. 1N HCl and the resulting solid was filtered to provide the desired product 1907A (1.62 g, 89%).

Part B:
Compound 1907 was prepared from compounds 23 and 1907A by using a procedure found in Part E of Example 122.

Compound 2458 was prepared from compound 14 using a procedure similar to that described in Example 129.

333

Compound 2459 was prepared from compound 2458 using a procedure similar to that described in Example 130.

Example 130

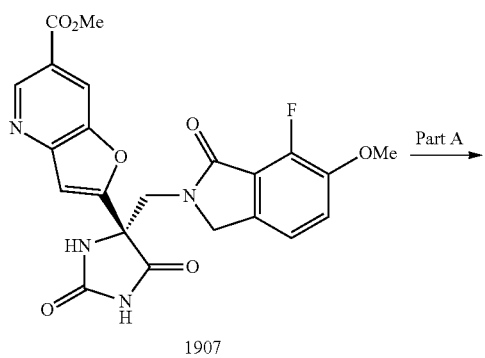
1907

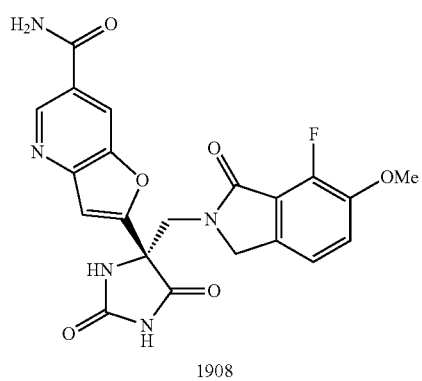
1908

Part A:

Compound 1908 was prepared from compound 1907 by using a procedure found in Part A of Example 126.

Compound 2457 was prepared using a procedure similar to that described in Example 130.

Example 131

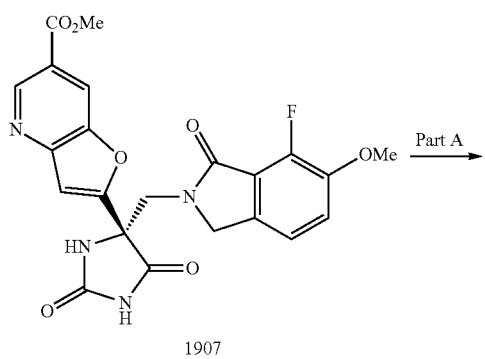
1907

334

-continued

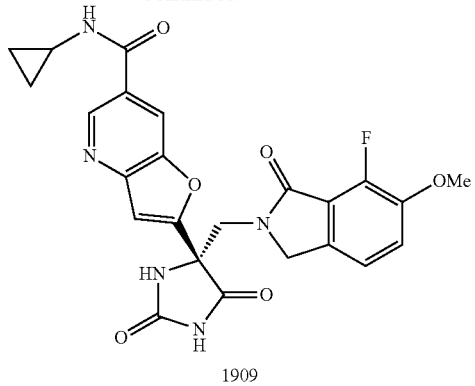
1909

Part A:

Compound 1909 was prepared from compound 1907 by using a procedure found in Part A of Example 126.

Compounds 2460-2462 and 2467 were prepared using procedures similar to that described in Example 131.

Example 132

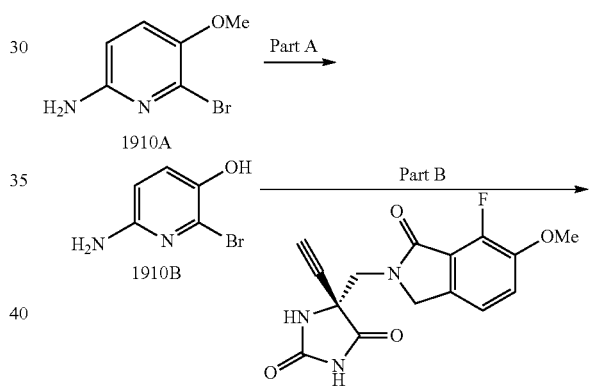

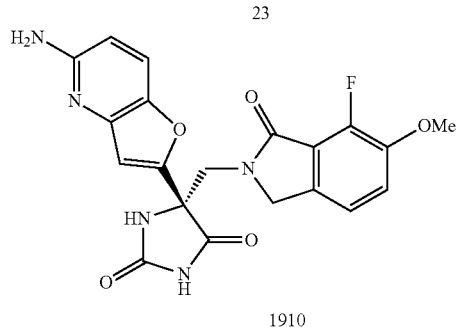
1910

Part A:

Compound 1910B was prepared from compound 1910A (prepared by a procedure similar to that described by Gary J. Clark and Leslie W. Deady, *Australian Journal of Chemistry* 1981, 34, 927-32) by using a procedure found in Part D of Example 122.

Part B:

Compound 1910 was prepared from compounds 1910B and 23 by using a procedure found in Part E of Example 122.

Compound 2314 was prepared from compound 14 using procedures similar to those described in Example 132. Compound 2474 was prepared from compound 2314 by treatment with methyl chloroformate.

Example 133

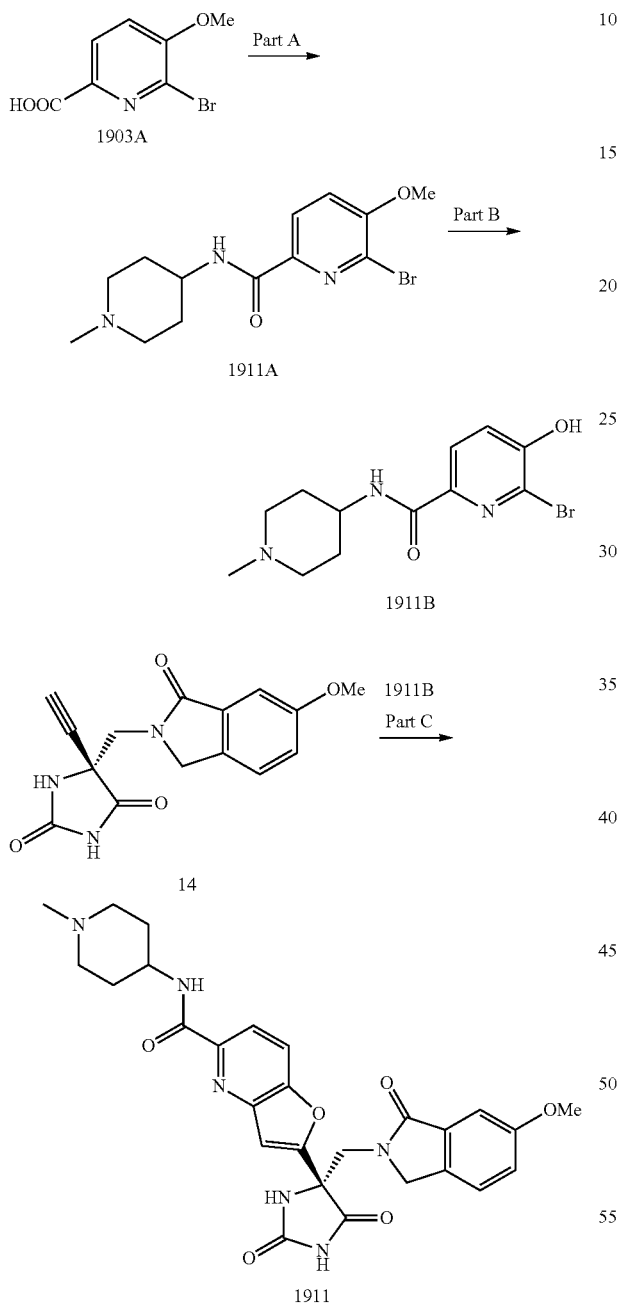

Part A:
Compound 1903A (500 mg, 2.17 mmol), N-methyl-4-aminopiperidine (297 mg, 2.60 mmol), PyBop (1.35 g, 2.60 mmol), and N,N-diisopropylethylamine (0.46 mL, 2.60 mmol) were dissolved in CH$_2$Cl$_2$ (50 mL). The solution was stirred at 25° C. for 18 h and added to aq. NaHCO$_3$ solution. The organic layers were extracted with CH$_2$Cl$_2$ and the combined organic solution was washed with brine solution, dried (Na$_2$SO$_4$), and concentrated in vacuo. The residue was purified by silica gel column (MeOH/CH$_2$Cl$_2$, gradient from 0% to 10% MeOH) to provide the desired product 1911A (602 mg, 85%).

Part B:
Compound 1911B was prepared from compound 1911A by using a procedure found in Part D of Example 122.

Part C:
Compound 1911 was prepared from compounds 14 and 1911B by using a procedure found in Part E of Example 122.

Compounds 2463-2466 were prepared using procedures similar to those described in Example 133.

Example 134

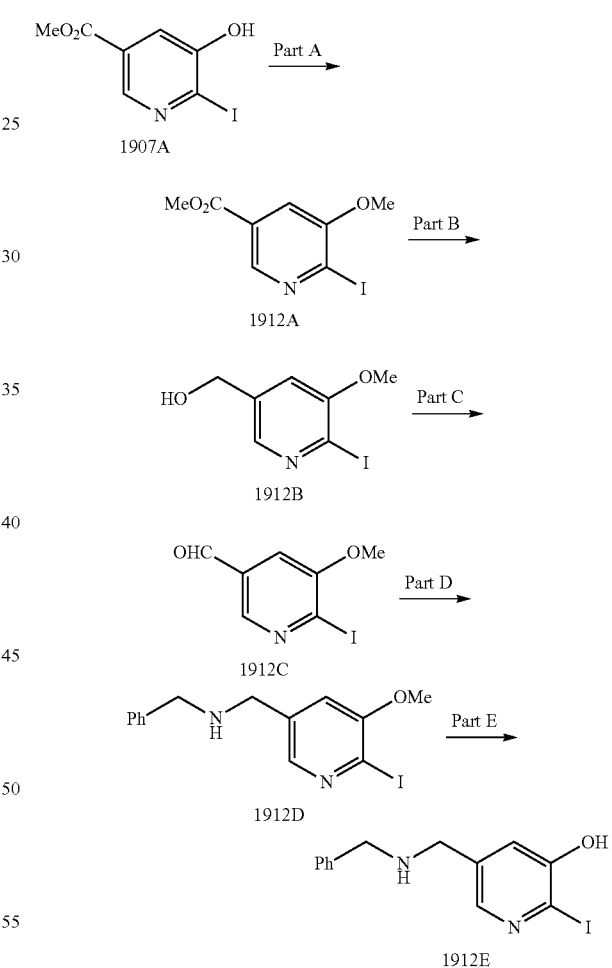

-continued

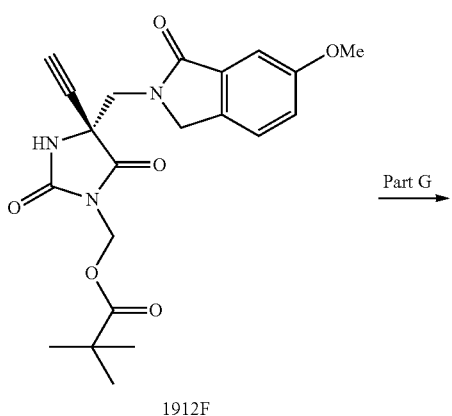

1912F

1912G

1912

Part A:

To a solution of compound 1907A (635 mg, 2.28 mmol) in DMF (2 mL) were added iodomethane (0.42 mL, 6.84 mmol) and sodium hydride (60% dispersion in oil, 136 mg, 3.42 mmol) at 0° C. The mixture was stirred for 2 h at 0° C. to 25° C. and added to cold water. The organic layers were extracted with EtOAc and the combined organic solution was washed with brine solution, dried (Na$_2$SO$_4$), and concentrated in vacuo. The residue was purified by silica gel column chromatography (CH$_2$Cl$_2$) to provide the desired product 1912A (630 mg, 94%).

Part B:

To a solution of compound 1912A (510 mg, 0.35 mmol) in CH$_2$Cl$_2$ (10 mL) was added diisobutylaluminum hydride (1 M in THF, 3.65 mL, 3.65 mmol) at −78° C. The reaction mixture was stirred for 18 h at −78° C. to 25° C. The reaction was quenched by MeOH and added to water. After stirred for 1 h, insoluble material was removed by filtration through celite pad and the filtrate was concentrated in vacuo. The residue was purified by silica gel column (MeOH/CH$_2$Cl$_2$, gradient from 0% to 4% MeOH) to provide the desired product 1912B (398 mg, 72%).

Part C:

To a solution of compound 1912B (356 mg, 1.34 mmol) in CHCl$_3$ (20 mL) was added manganese dioxide (500 mg). The mixture was stirred at 25° C. for 3 days. The solid was removed by filtration through celite pad and the filtrate was concentrated in vacuo to provide the desired product 1912C (301 mg, 86%).

Part D:

A mixture of compound 1912C (231 mg, 0.88 mmol) and benzylamine (0.11 mL, 0.97 mmol) in 1,2-dichloroethane (6 mL) was stirred at 60° C. for 5 h. To this was added sodium triacetoxyborohydride (280 mg, 1.32 mmol) and the mixture was stirred for 18 h. After cooled to 25° C., the mixture was added to aq. NaHCO$_3$ solution and the organic layers were extracted with CH$_2$Cl$_2$. The combined organic solution was washed with brine solution, dried (Na$_2$SO$_4$), and concentrated in vacuo. The residue was purified by silica gel column (MeOH/CH$_2$Cl$_2$, gradient from 0% to 10% MeOH) to provide the desired product 1912D (185 mg, 60%).

Part E:

Compound 1912E was prepared from compound 1912D by using a procedure found in Part D of Example 122.

Part F:

To a suspension of compound 14 (574 mg, 1.92 mmol) and potassium carbonate (265 mg, 1.92 mmol) in DMF (4 mL) was added chloromethyl pivalate (0.30 mL, 2.02 mmol) at 25° C. After stirred for 18 h, the mixture was added to cold water and the organic layers were extracted with EtOAc. The combined organic solution was washed with brine solution, dried (Na$_2$SO$_4$), and concentrated in vacuo. The residue was purified by silica gel column (MeOH/CH$_2$Cl$_2$, gradient from 0% to 10% MeOH) to provide the desired product 1912F (568 mg, 72%).

Part G:

Compound 1912G was prepared from compounds 1912E and 1912F by using a procedure found in Part E of Example 122.

Part H:

A mixture of compound 1912G (8 mg, 0.013 mmol) and ammonium hydroxide (0.5 mL) in MeOH (0.5 mL) was stirred at 25° C. for 18 h. After concentration, the residue was purified by preparative TLC (10% MeOH in CH$_2$Cl$_2$) to provide the desired product 1912 (3 mg, 45%).

Compounds 2468-2469 were prepared from compounds 1912C and 14 using procedures similar to those described in Example 49.

Example 135

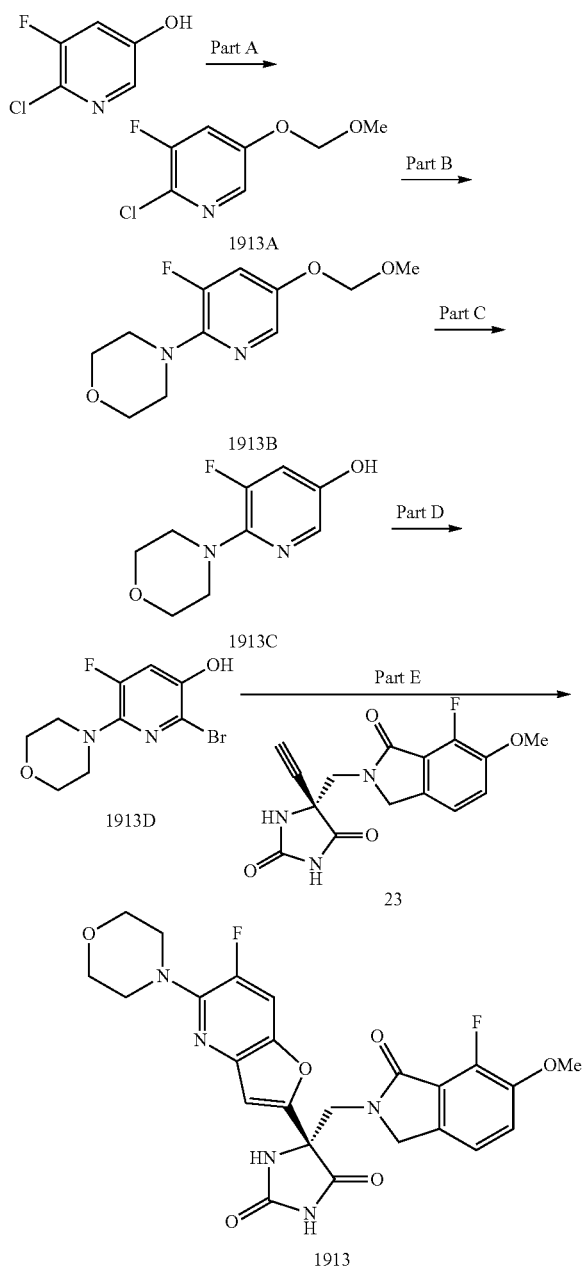

Part A:

A mixture of 2-chloro-3-fluoro-5-hydroxypyridine (400 mg, 2.7 mmol), and methoxymethyl chloride (0.3 mL, 4.0 mmol), and potassium carbonate (746 mg, 5.4 mmol) in DMF (2 mL) was stirred at 25° C. for 3 days and added to water. The organic layers were extracted with EtOAc and the combined organic solution was washed with brine solution, dried ($Na_2SO_4$), and concentrated in vacuo. The residue was purified by silica gel column ($CH_2Cl_2$) to provide the desired product 1913A (474 mg, 92%).

Part B:

To a flame dried 2-neck flask were added $Pd(OAc)_2$ (3.4 mg, 0.015 mmol), rac-BINAP (11.2 mg, 0.018 mmol), and toluene (0.7 mL). Triethylamine (0.0045 mL, 0.032 mmol) was added and the mixture was stirred at 25° C. for 1 h before adding morpholine (91 µL, 0.63 mmol) and compound 1913A (142 mg, 0.74 mmol) in toluene (1.0 mL). After stirred for 10 min., sodium t-butoxide (100 mg, 1.04 mmol) was added. The reaction mixture was stirred for 18 h and added to brine solution. The organic layers were extracted with EtOAc and the combined organic solution was dried ($Na_2SO_4$) and concentrated in vacuo. The residue was purified by silica gel column ($MeOH/CH_2Cl_2$, gradient from 0% to 10% MeOH) to provide the desired product 1913B (104 mg, 58%).

Part C:

A mixture of compound 1913B (75 mg, 0.31 mmol) and aq. 2 M HCl (0.5 mL) in THF (1 mL) was stirred at 50° C. for 20 h. The mixture was diluted in EtOAc and washed with aq. $NaHCO_3$ solution. The organic solution was dried ($Na_2SO_4$) and concentrated in vacuo to provide the desired product 1913C (62 mg, quant).

Part D:

To a solution of compound 1913C (79 mg, 0.4 mmol) in acetic acid (2 mL) was added bromine (10% solution in acetic acid, 29 µL, 0.56 mmol). The mixture was stirred at 50° C. for 20 h and concentrated in vacuo. The residue was dissolved in EtOAc and washed with aq. $NaHCO_3$ solution. After drying over $Na_2SO_4$, the solution was concentrated in vacuo and the residue was purified by silica gel column ($MeOH/CH_2Cl_2$, gradient from 0% to 10% MeOH) to provide the desired product 1913D (15 mg, 14%).

Part E:

Compound 191E was prepared from compounds 23 and 1913D by using a procedure found in Part E of Example 122.

Example 136

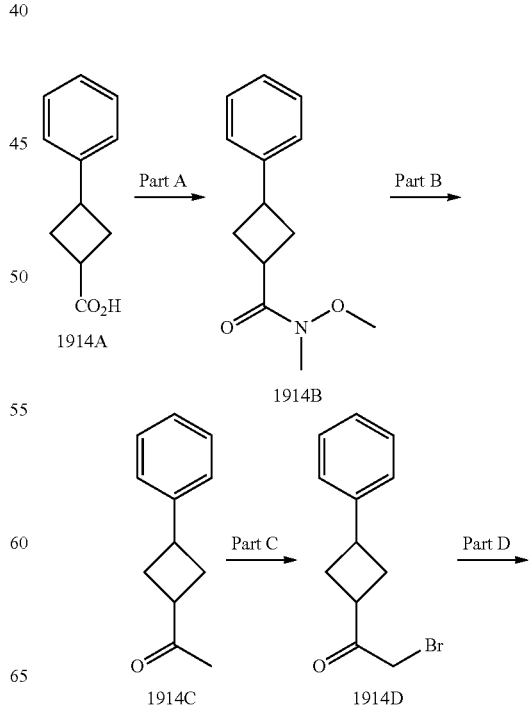

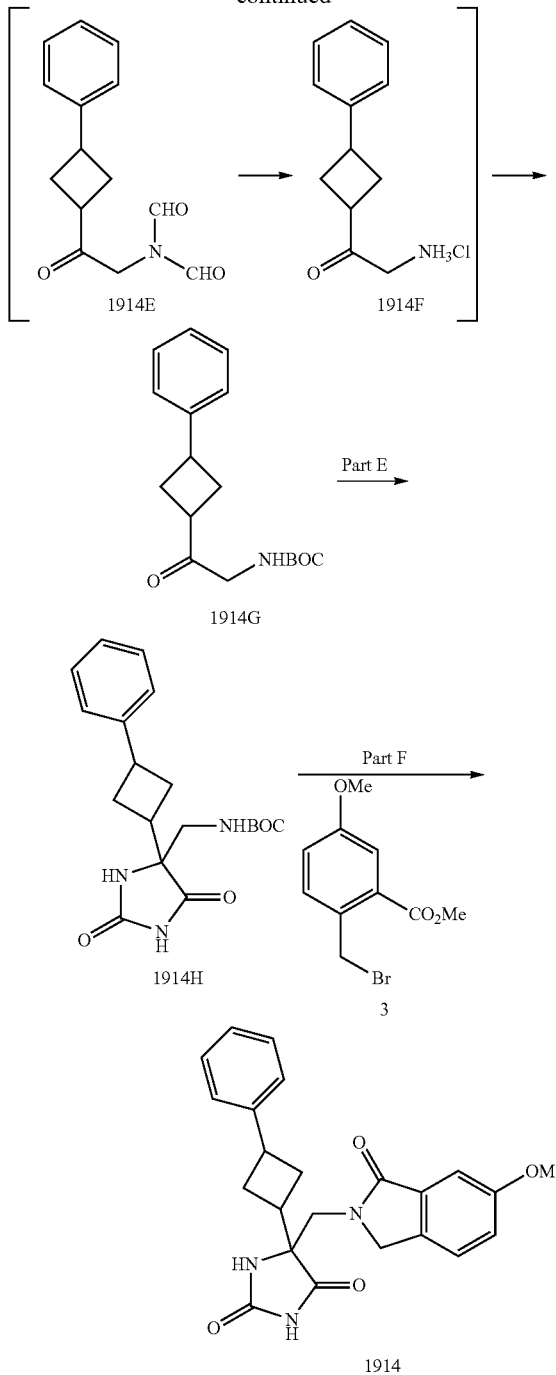

Part B:

Compound 1914B (340 mg, 1.55 mmol) in THF (5 mL) was treated with MeMgCl (3 M in THF, 0.78 mL, 2.33 mmol) at 0° C. After stirred for 2.5 h at the temperature, the reaction was quenched by aq. $NH_4Cl$ solution and the organic layers were extracted with $CH_2Cl_2$. The combined organic solution was washed with brine solution, dried ($Na_2SO_4$), and concentrated in vacuo to afford a crude compound 1914C (270 mg, quant.) which was used in the next step without further purification.

Part C:

Compound 1914C (270 mg, 1.55 mmol) in MeOH (4 mL) was treated with 10 drops of HBr in MeOH (prepared by adding 2 drops of aq. HBr in 1 mL MeOH). To this was added bromine in MeOH (4 mL) slowly for 1 h at 25° C., and the mixture was stirred for 12 h. The mixture was added to ice-water and the organic layers were extracted with $CH_2Cl_2$. The combined organic solution was washed with brine solution, dried ($Na_2SO_4$), and concentrated in vacuo to afford a crude compound which was purified by $SiO_2$ column to provide each stereoisomers of compound 1914D (350 mg, 89%, cis:trans=1:1).

Part D:

Compound 1914D (cis isomer, 62 mg, 0.25 mmol) in MeCN (2 mL) was treated with sodium diformylamide (28 mg, 0.29 mmol) at 25° C. After stirring for 18 h, the mixture was filtered and the filtrate was concentrated in vacuo to afford a crude compound 1914E. Compound 1914E was dissolved in EtOH (4 mL) and treated with 4 N HCl in dioxane (1 mL) at 25° C. for 16 h. The mixture was concentrated in vacuo to afford a crude compound 1914F. Compound 1914F was dissolved in 1,4-dioxane (3 mL) and water (1 mL) and treated with $BOC_2O$ (70 mg, 0.32 mmol) and $NaHCO_3$ (200 mg, 2.34 mmol) at 25° C. for 18 h. The mixture was added to cold water and the organic layers were extracted with $CH_2Cl_2$. The combined organic solution was washed with brine solution, dried ($Na_2SO_4$), and concentrated in vacuo. The residue was purified by $SiO_2$ column to provide compound 1914G (44 mg, 61%).

Part E:

A mixture of compound 1914G (44 mg, 0.15 mmol), KCN (50 mg, 0.76 mmol), and ammonium carbonate (132 mg, 1.36 mmol) was dissolved in EtOH (2 mL)—water (1 mL) and stirred at 60° C. for 18 h in a pressure vessel. The mixture was cooled and concentrated in vacuo. Purification by preparative TLC of the residue provided the desired product 1914H (42 mg, 78%).

Part F:

Compound 1914H (42 mg, 0.12 mmol) was dissolved in MeOH (1.5 mL) and treated with HCl (4 N in dioxane, 1.0 mL) for 18 h at 25° C. The mixture was concentrated in vacuo and the residue was dissolved in DMF (1 mL). To this were added compound 3 (31 mg, 0.12 mmol) and N,N-diisopropylethylamine (63 μL, 0.36 mmol). After stirred for 18 h at 60° C., the mixture was cooled and purified by C-18 reverse phase column (water/acetonitrile, gradient from 0% to 90% acetonitrile) to provide the desired product 1914 (41 mg, 86%).

Compound 1915 was prepared using the methods described in Part A to F in Example 136.

Part A:

Compound 1914A (prepared using a procedure described by Colin Beard and Alfred Burger, *Journal of Organic Chemistry* 1962, 27, 1647, 480 mg, 2.7 mmol) was dissolved in DMF (4 mL) and treated with methoxymethylamine hydrochloride (395 mg, 4.04 mmol), EDCl (778 mg, 4.05 mmol), HOBt (656 mg, 4.86 mmol), and triethylamine (1.13 mL, 8.1 mmol). The mixture was stirred at 25° C. for 14 h and diluted in EtOAc followed by washing with aq. $NaHCO_3$ solution, brine solution, dried on $Na_2SO_4$, and concentrated in vacuo. The residue was purified by $SiO_2$ column to afford compound 1914B (340 mg, 58%).

Compound 1916 was prepared using the methods described in Example 128.

Example 137

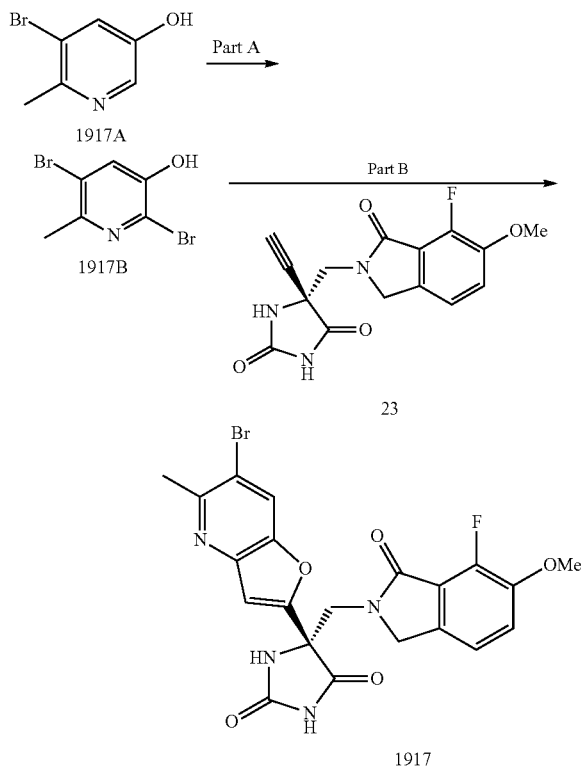

Part A:

Compound 1917A (prepared using a similar procedure described by Holladay, Mark W., et al., PCT Int. Appl. (1999), 392 pp. WO 9932480 A1 19990701, 100 mg, 0.53 mmol) was dissolved in $CH_2Cl_2$ (2 mL) and pyridine (0.2 mL). Pyridium perbromide (189 mg, 0.53 mmol) was added and the mixture was stirred at 0° C. for 1 h. After concentrated in vacuo, the residue was purified by silica gel column (MeOH/$CH_2Cl_2$, gradient from 3% to 7% MeOH) to provide the desired product 1917B (75 mg, 54%).

Part B:

Compound 1917 was prepared using the procedure described in Part E of Example 122.

Example 138

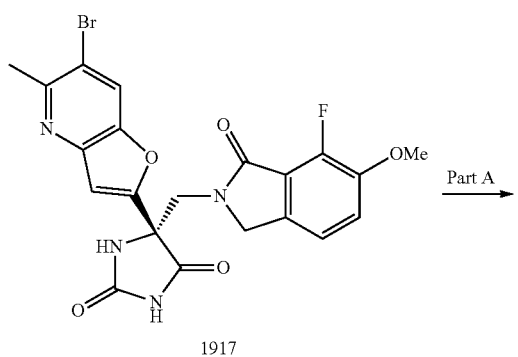

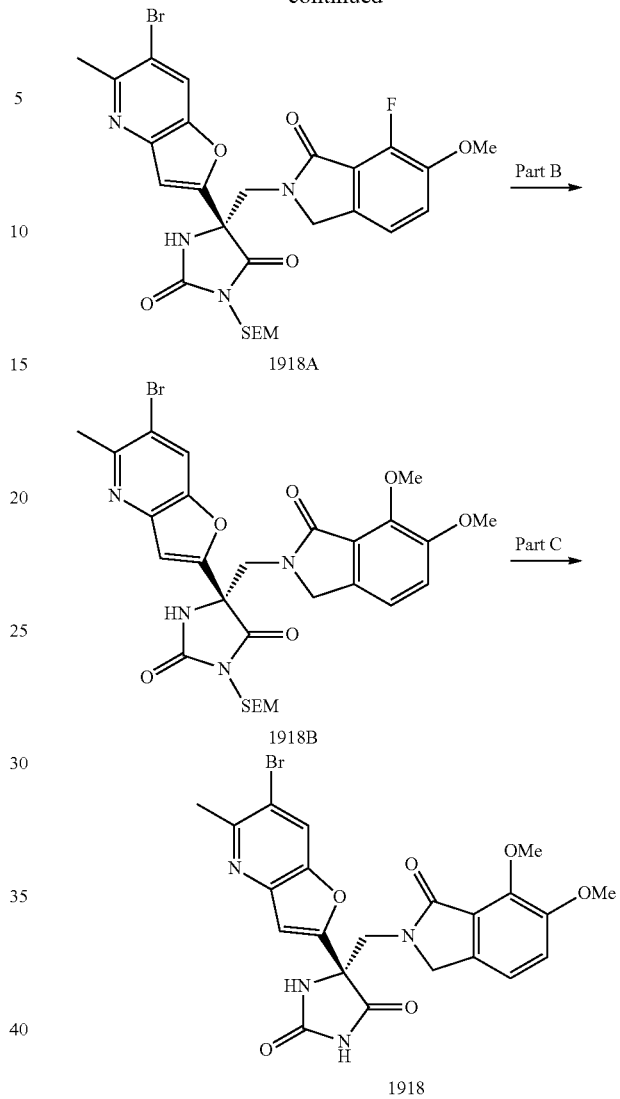

Part A:

A mixture of compound 1917 (62 mg, 0.12 mmol), SEM chloride (26 μL, 0.15 mmol), and N,N-diisopropylethylamine (28 μL, 0.16 mmol) in DMF (1 mL) was stirred at 25° C. for 18 h. The mixture was added to cold water and the organic layers were extracted with EtOAc. The combined organic solution was washed with brine solution, dried ($Na_2SO_4$), and concentrated in vacuo. Purification of the residue by silica gel column (MeOH/$CH_2Cl_2$, gradient from 0% to 10% MeOH) provided the desired product 1918A (64 mg, 83%).

Part B:

A mixture of compound 1918A (64 mg, 0.10 mmol), piperazine (13.0 mg, 0.15 mmol), rac-BINAP (2.5 mg, 4.0 μmol), $Pd_2(dba)_3$ (1.9 mg, 2 μmol), and sodium t-butoxide (15 mg, 0.15 mmol) in toluene (2 mL) was degassed and stirred at 80° C. for 24 h. After cooled to 25° C., the mixture was diluted in EtOAc and filtered through celite pad. The filtrate was concentrated in vacuo and the residue was purified by preparative TLC (5% MeOH in $CH_2Cl_2$) to provide compound 1918B (10 mg, 15%).

Part C:

Compound 1918B (10 mg, 0.015 mmol) was dissolved in MeOH (3 mL) and treated with HCl (4 N in dioxane, 1 mL).

The mixture was stirred at 90° C. for 18 h in a pressure vessel. After cooling to 25° C., the mixture was concentrated in vacuo and the residue was purified by preparative TLC (10% MeOH in CH$_2$Cl$_2$) to provide desired product 1918 (7 mg, 90%).

Example 139

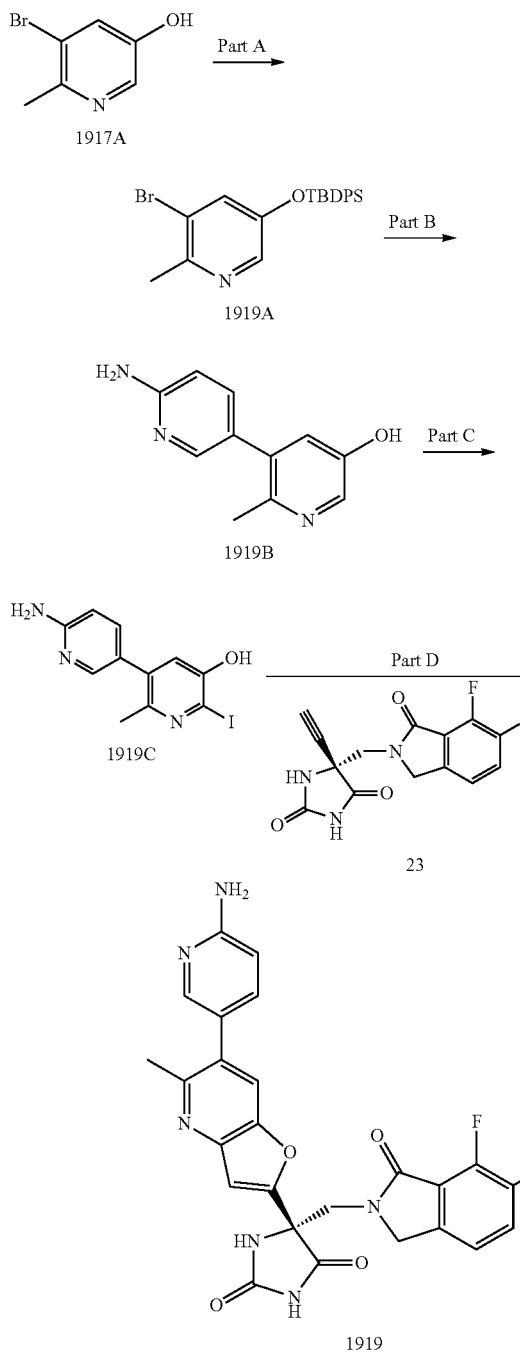

Part A:
A mixture of compound 1917A (1.63 g, 8.67 mmol), t-butyldiphenylsilyl chloride (2.37 mL, 9.10 mmol), and imidazole (767 mg, 11.27 mmol) in DMF (10 mL) was stirred at 25° C. for 18 h. The mixture was added to water and the organic layers were extracted with EtOAc. The combined organic solution was washed with brine solution, dried (Na$_2$SO$_4$), and concentrated in vacuo. The residue was purified by silica gel column (CH$_2$Cl$_2$) to provide the desired product 1919A (2.95 g, 80%).

Part B:
A mixture of compound 1919A (221 mg, 0.52 mmol), 2-amino-5-(4,4,5,5-tetramethyl-1,3,2-dioxaborolan-2-yl) pyridine (141 mg, 0.62 mmol), [PdCl$_2$(dppf)]CH$_2$Cl$_2$ (17 mg, 0.021 mmol), and potassium carbonate (1 M aq. solution, 0.68 mL, 0.68 mmol) in acetonitrile (5 mL) was degassed and stirred at 80° C. for 5 h. After cooled to 25° C., the mixture was diluted in EtOAc and filtered through celite pad. The filtrate was concentrated in vacuo and the residue was purified by silica gel column (MeOH/CH$_2$Cl$_2$, pradient from 0% to 10% MeOH) to provide the desired product 1919B (99 mg, 94%).

Part C:
A solution of KI (154 mg, 0.93 mmol) and iodine (71 mg, 0.28 mmol) in water (3 mL) was stirred at 25° C. for 10 min. and added to a stirred mixture of compound 1919B (63 mg, 0.31 mmol) in ammonium hydroxide (2.5 mL). The reaction mixture was stirred for 5 h and concentrated in vacuo. The residue was treated with water to give precipitates, which was filtered off and washed with water to provide the desired product 1919C (101 mg, quant.).

Part D:
Compound 1919 was prepared from compounds 23 and 1919C by using the procedure described in Part E of Example 122.

Example 140

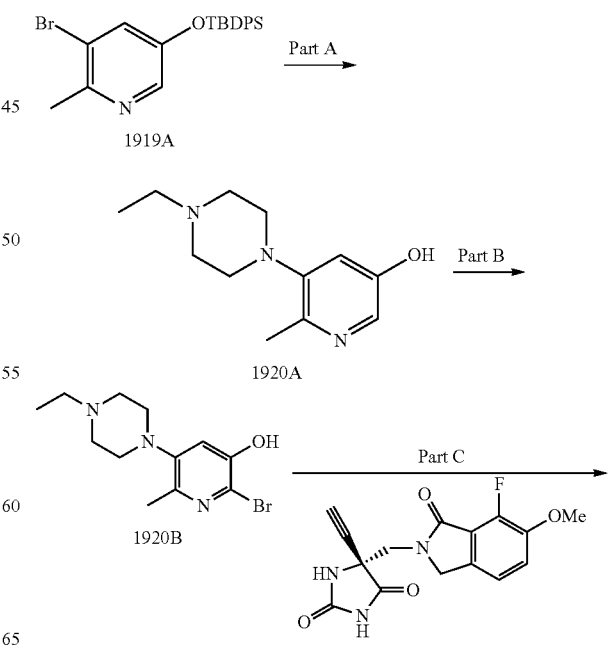

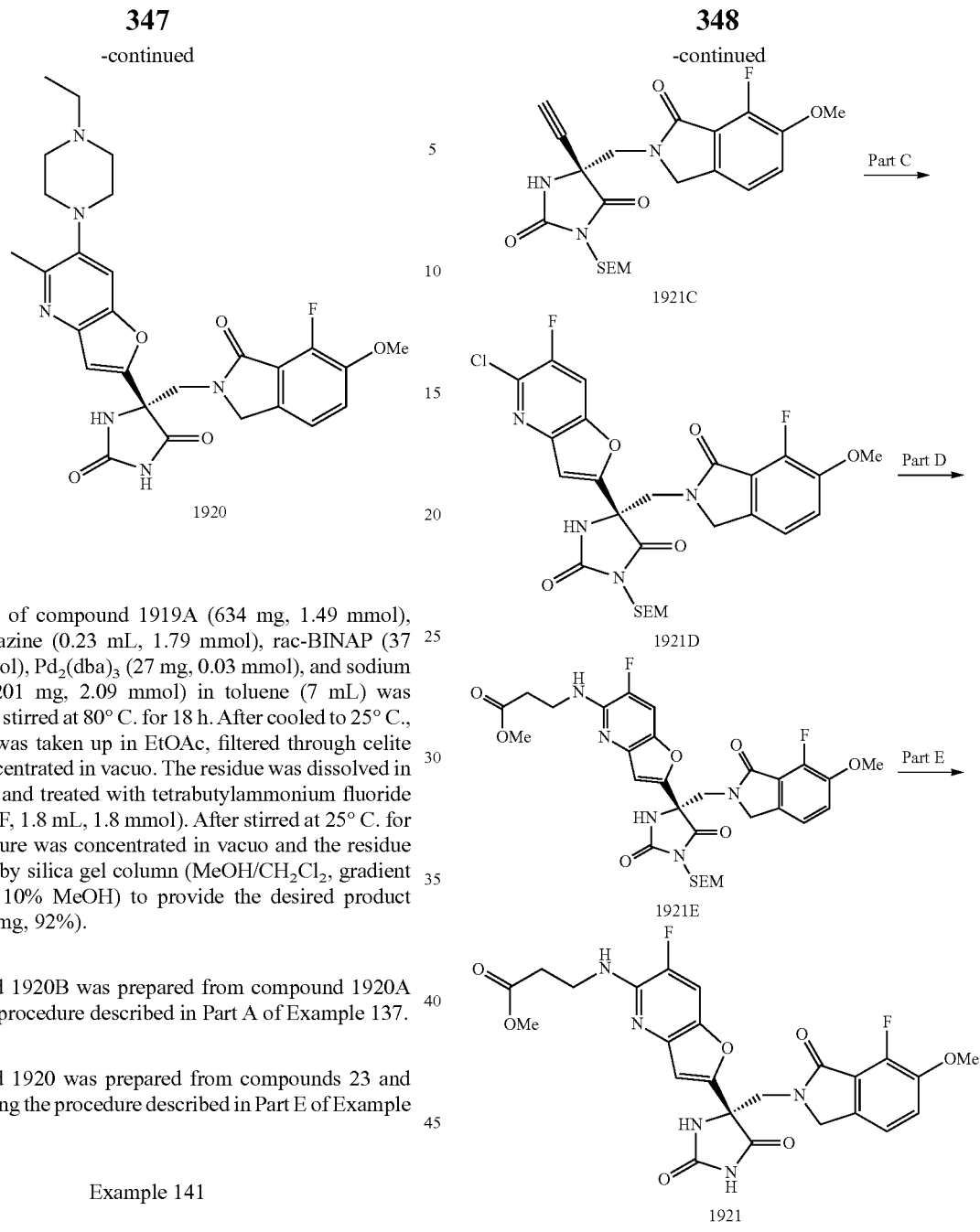

Part A:

A mixture of compound 1919A (634 mg, 1.49 mmol), N-ethylpiperazine (0.23 mL, 1.79 mmol), rac-BINAP (37 mg, 0.06 mmol), Pd$_2$(dba)$_3$ (27 mg, 0.03 mmol), and sodium t-butoxide (201 mg, 2.09 mmol) in toluene (7 mL) was degassed and stirred at 80° C. for 18 h. After cooled to 25° C., the mixture was taken up in EtOAc, filtered through celite pad, and concentrated in vacuo. The residue was dissolved in THF (8 mL) and treated with tetrabutylammonium fluoride (1.0 M in THF, 1.8 mL, 1.8 mmol). After stirred at 25° C. for 4 h, the mixture was concentrated in vacuo and the residue was purified by silica gel column (MeOH/CH$_2$Cl$_2$, gradient from 0% to 10% MeOH) to provide the desired product 1920A (293 mg, 92%).

Part B:

Compound 1920B was prepared from compound 1920A by using the procedure described in Part A of Example 137.

Part C:

Compound 1920 was prepared from compounds 23 and 1920B by using the procedure described in Part E of Example 122.

Example 141

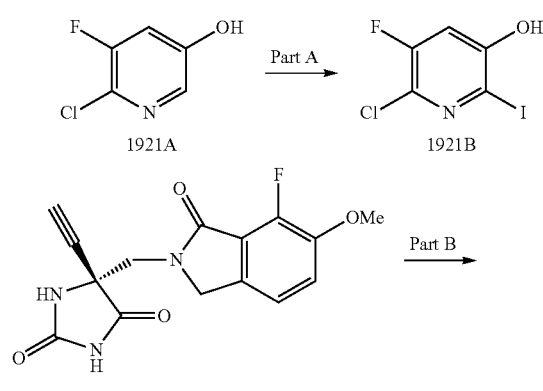

Part A:

Compound 1921B was prepared from compound 1921A by using a procedure described in Part C of Example 139.

Part B:

Compound 1921C was prepared from compound 23 by using a procedure described in Part A of Example 138.

Part C:

Compound 1921D was prepared from compounds 1921C and 1921B by using a procedure described in Part E of Example 122.

Part D:

A mixture of compound 1921D (80 mg, 0.14 mmol), 2-azetidinone (14 mg, 0.20 mmol), Xantphos (3 mg, 0.005 mmol), Pd(OAc)$_2$ (0.6 mg, 0.003 mmol), and cesium carbonate (78 mg, 0.24 mmol) in 1,4-dioxane (2 mL) was degassed and stirred at 100° C. for 18 h. After cooled to 25° C., reaction mixture was diluted in EtOAc and washed with water, brine solution, dried (Na$_2$SO$_4$), and concentrated in vacuo. The residue was purified by silica gel column (MeOH/CH$_2$Cl$_2$, gradient from 2% to 10% MeOH) to provide the product 1921E (20 mg, 25%).

Part E:

Compound 1921 was prepared from compound 1921E by using a procedure found in Part C of Example 138.

Example 142

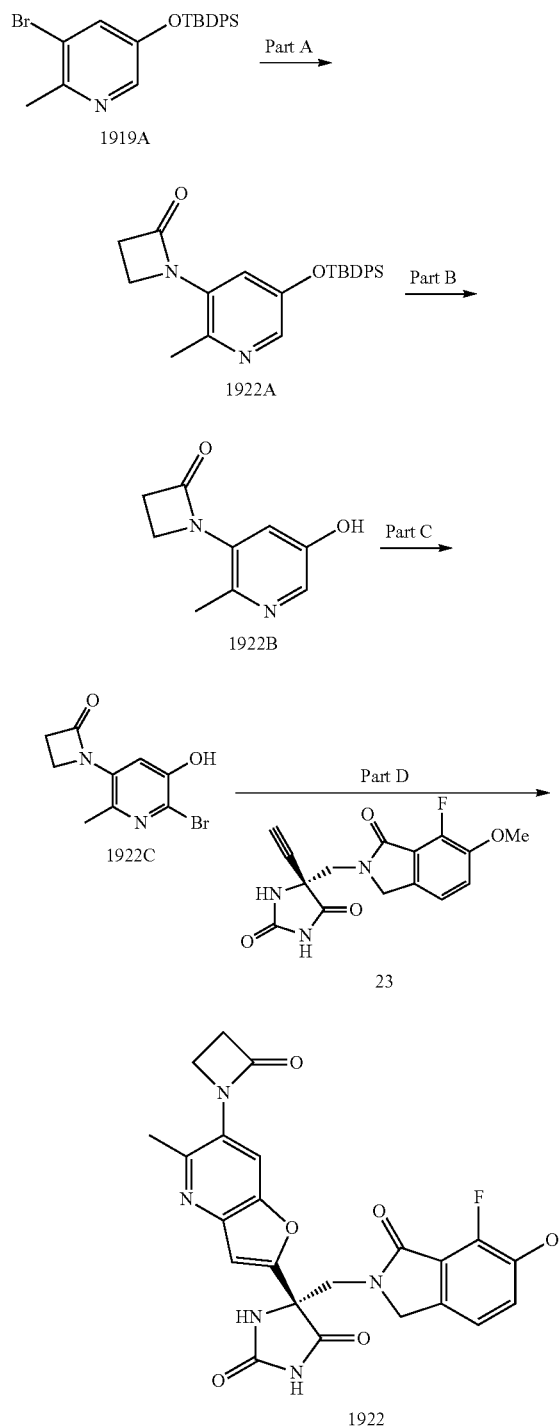

Part A:

A mixture of compound 1919A (154 mg, 0.36 mmol), 2-azetidinone (31 mg, 0.43 mmol), CuI (1.4 mg, 0.007 mmol), trans-N,N'-dimethylcyclohexane-1,2-diamine (6 mL, 0.04 mmol), and potassium carbonate (100 mg, 0.72 mmol) in 1,4-dioxane (2 mL) was degassed and stirred at 110° C. for 24 h. After cooled to 25° C., reaction mixture was diluted in EtOAc, filtered through celite pad, and concentrated in vacuo. The residue was purified by silica gel column (MeOH/CH$_2$Cl$_2$, gradient from 0% to 10% MeOH) to provide the product 1922A (45 mg, 31%).

Part B:

Compound 1922A (190 mg, 0.46 mmol) was dissolved in THF (3 mL) and treated with tetrabutylammonium fluoride (1.0 M in THF, 0.55 mL, 0.55 mmol). After stirred at 25° C. for 4 h, the mixture was concentrated in vacuo and the residue was purified by silica gel column (MeOH/CH$_2$Cl$_2$, gradient from 0% to 10% MeOH) to provide the desired product 1922B (69 mg, 84%).

Part C:

Compound 1922C was prepared from compound 1922B by using a procedure described in Part A of Example 137.

Part D:

Compound 1922 was prepared from compounds 23 and 1922C by using a procedure described in Part E of Example 122.

Example 143

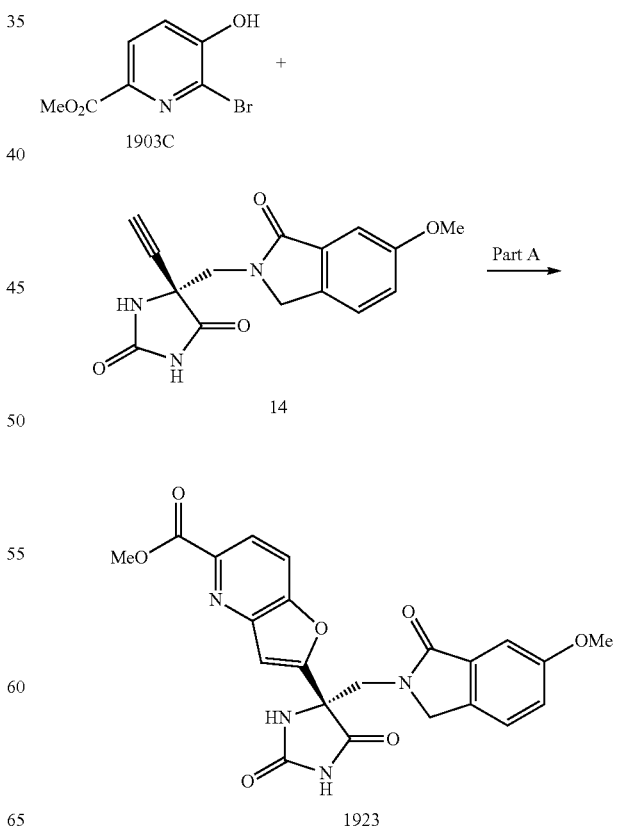

Part A:
Compound 1923 was prepared from compounds 14 and 1903C by using a procedure described in Part E of Example 122.

Example 144

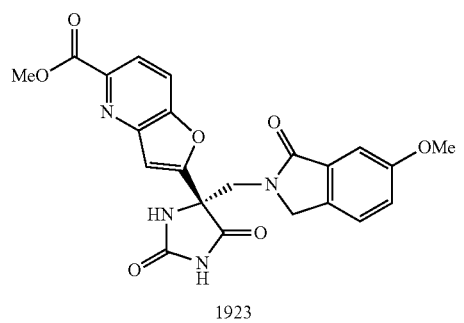
1923

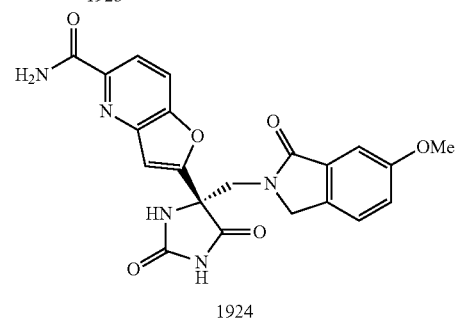
1924

Part A:
Compound 1924 was prepared from compound 1923 by using a procedure described in Part A of Example 126.

Example 145

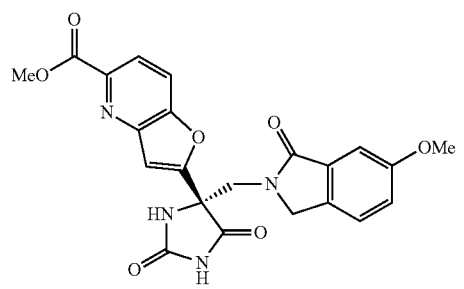
1923

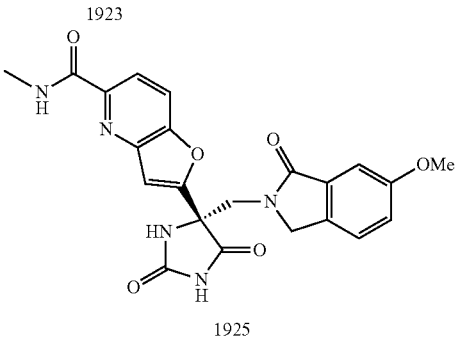
1925

Part A:
Compound 1925 was prepared from compounds 1923 and methylamine by using a procedure described in Part A of Example 126.

Example 146

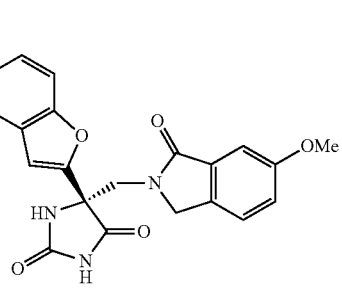
1923

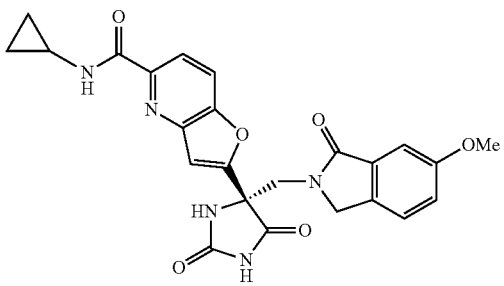
1926

Part A:
Compound 1926 was prepared from compounds 1923 and cyclopropylamine by using a procedure described in Part A of Example 126.

Example 147

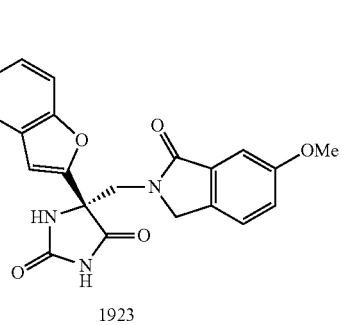
1923

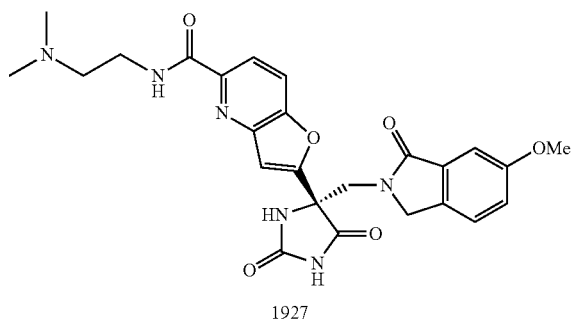

1927

Part A:

Compound 1927 was prepared from compounds 1923 and 2-(N,N-dimethylamino)ethylamine by using a procedure described in Part A of Example 126.

Example 148

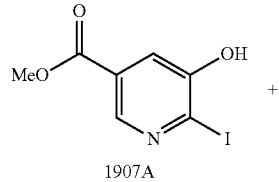

1907A

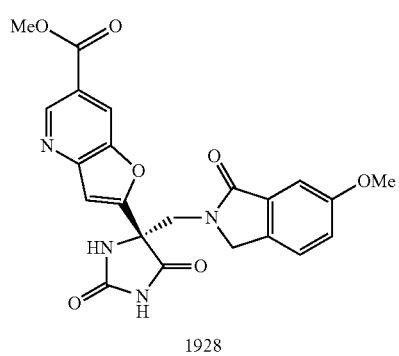

14

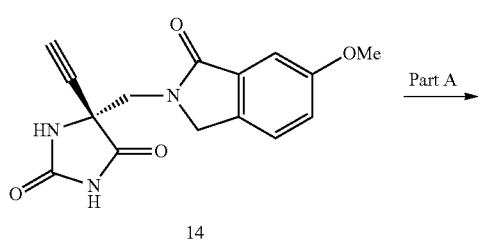

1928

Part A:

Compound 1928 was prepared from compounds 14 and 1907A by using a procedure described in Part E of Example 122.

Example 149

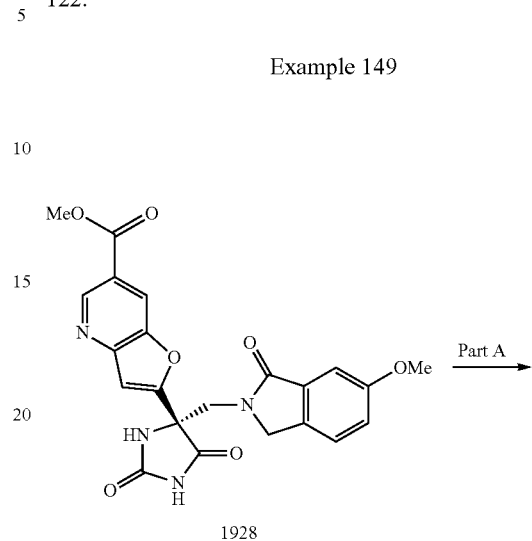

1928

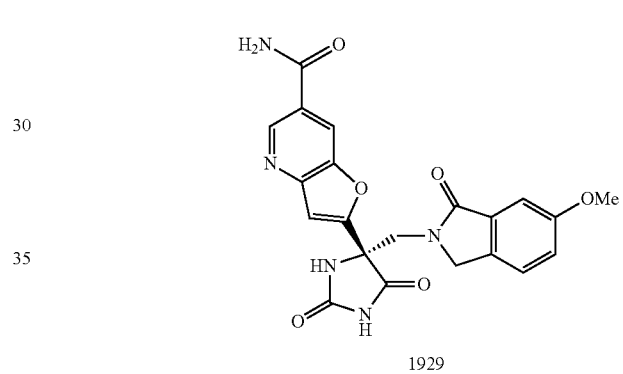

1929

Part A:

Compound 1929 was prepared from compounds 1928 and ammonia by using a procedure described in Part A of Example 126.

Example 150

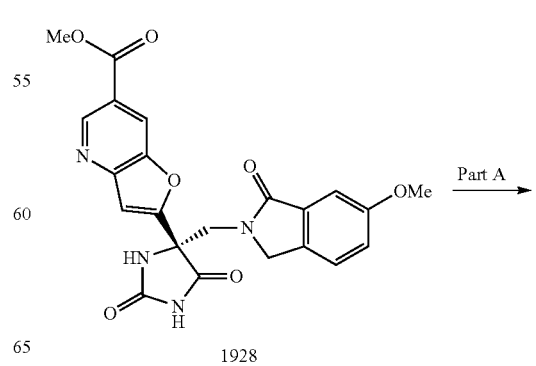

1928

-continued

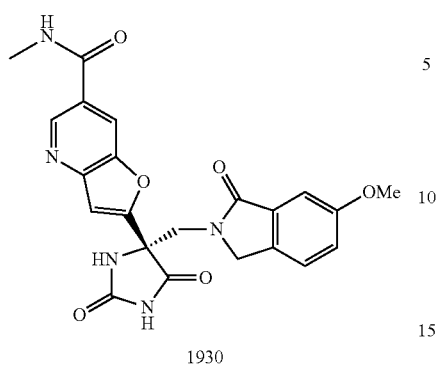

1930

Part A:

Compound 1930 was prepared from compounds 1928 and methylamine by using a procedure described in Part A of Example 126.

Example 151

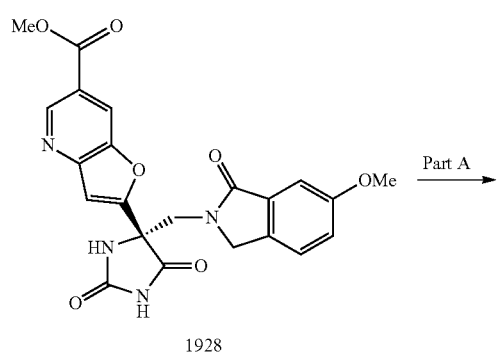

1928

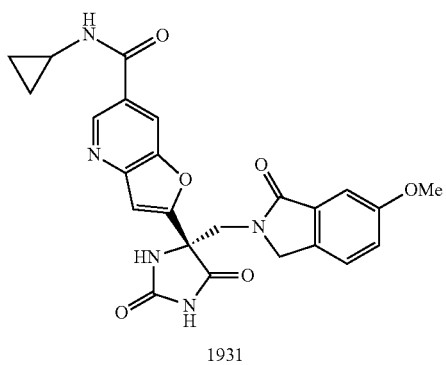

1931

Part A:

Compound 1931 was prepared from compounds 1928 and cyclopropylamine by using a procedure described in Part A of Example 126.

Example 152

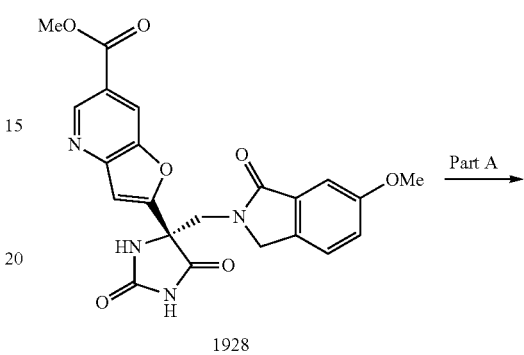

1928

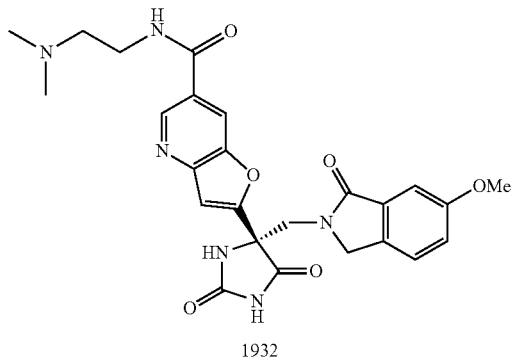

1932

Part A:

Compound 1932 was prepared from compounds 1928 and 2-(N,N-dimethylamino)ethylamine by using a procedure described in Part A of Example 126.

Example 153

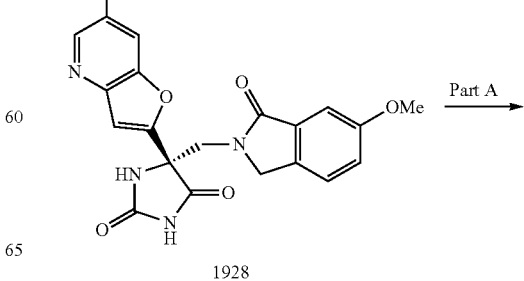

1928

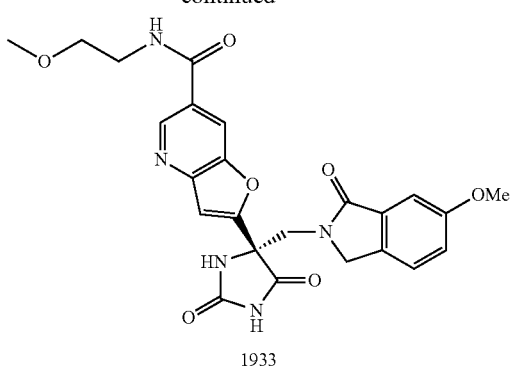

1933

Part A:
Compound 1933 was prepared from compounds 1928 and 2-methoxyethylamine by using a procedure described in Part A of Example 126.

Example 154

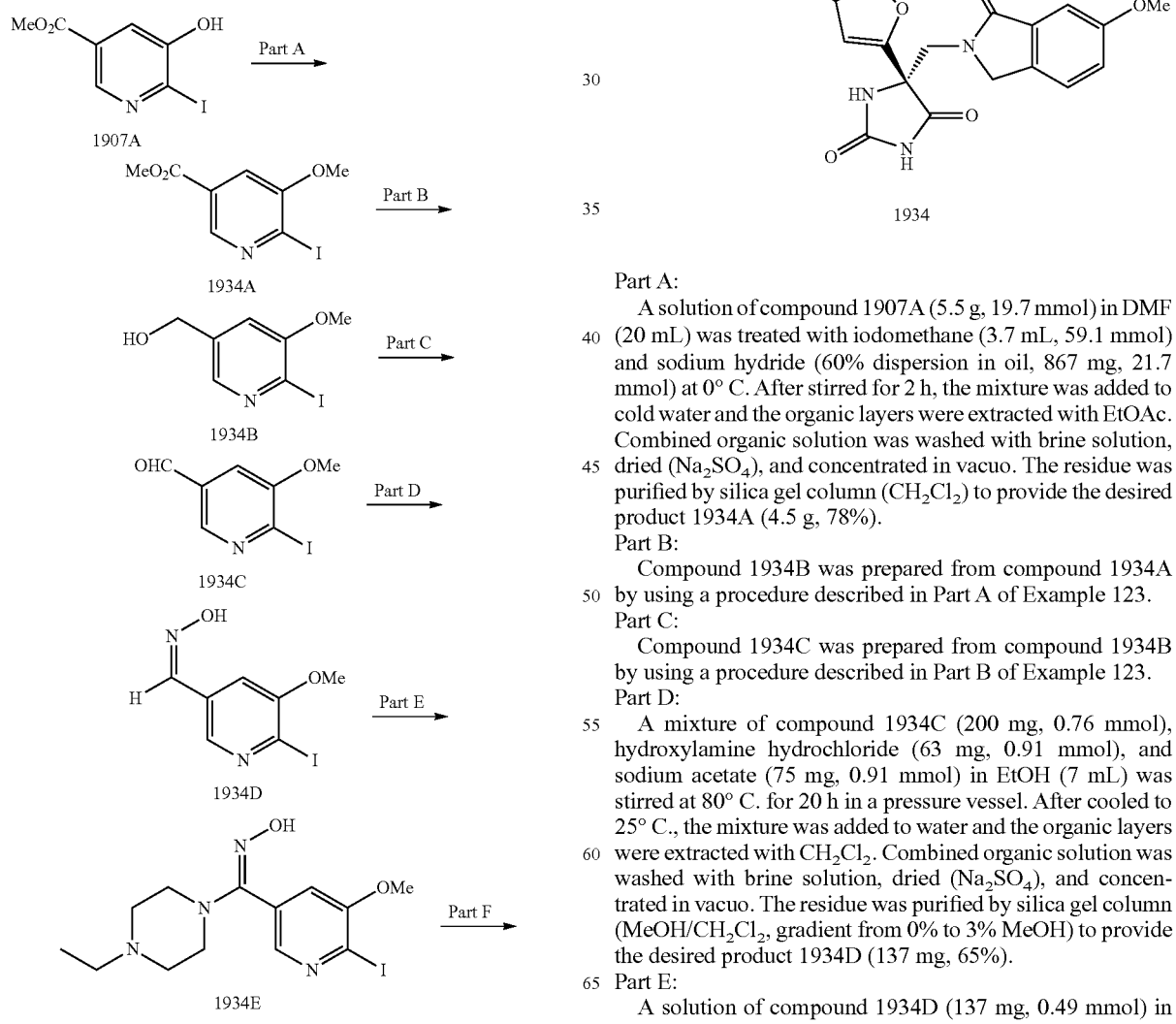

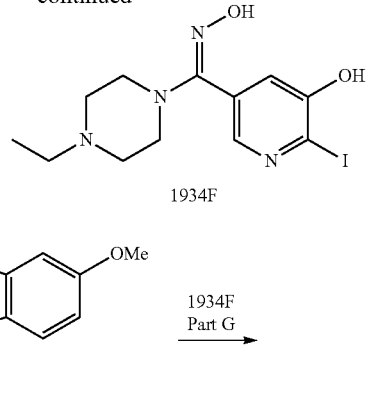

Part A:
A solution of compound 1907A (5.5 g, 19.7 mmol) in DMF (20 mL) was treated with iodomethane (3.7 mL, 59.1 mmol) and sodium hydride (60% dispersion in oil, 867 mg, 21.7 mmol) at 0° C. After stirred for 2 h, the mixture was added to cold water and the organic layers were extracted with EtOAc. Combined organic solution was washed with brine solution, dried ($Na_2SO_4$), and concentrated in vacuo. The residue was purified by silica gel column ($CH_2Cl_2$) to provide the desired product 1934A (4.5 g, 78%).

Part B:
Compound 1934B was prepared from compound 1934A by using a procedure described in Part A of Example 123.

Part C:
Compound 1934C was prepared from compound 1934B by using a procedure described in Part B of Example 123.

Part D:
A mixture of compound 1934C (200 mg, 0.76 mmol), hydroxylamine hydrochloride (63 mg, 0.91 mmol), and sodium acetate (75 mg, 0.91 mmol) in EtOH (7 mL) was stirred at 80° C. for 20 h in a pressure vessel. After cooled to 25° C., the mixture was added to water and the organic layers were extracted with $CH_2Cl_2$. Combined organic solution was washed with brine solution, dried ($Na_2SO_4$), and concentrated in vacuo. The residue was purified by silica gel column (MeOH/$CH_2Cl_2$, gradient from 0% to 3% MeOH) to provide the desired product 1934D (137 mg, 65%).

Part E:
A solution of compound 1934D (137 mg, 0.49 mmol) in DMF (1 mL) was treated with N-chlorosuccinimide (72 mg, 0.54 mmol) at 25° C. After stirred for 3 h, the mixture was treated with ethylpiperazine (0.13 mL, 0.99 mmol) and stirred for 2 h. The mixture was added to water and the organic layers were extracted with EtOAc. Combined organic solution was washed with brine solution, dried (Na₂SO₄), and concentrated in vacuo. The residue was purified by silica gel column (MeOH/CH₂Cl₂, gradient from 0% to 4% MeOH) to provide the desired product 1934E (133 mg, 70%).

Part F:

Compound 1934F was prepared from compound 1934E by using a procedure described in Part D of Example 122.

Part G:

Compound 1934 was prepared from compounds 14 and 1934F by using a procedure described in Part E of Example 122.

Compound 2320 was prepared from 1934B using chemistry similar to that described in Example 165.

Example 155

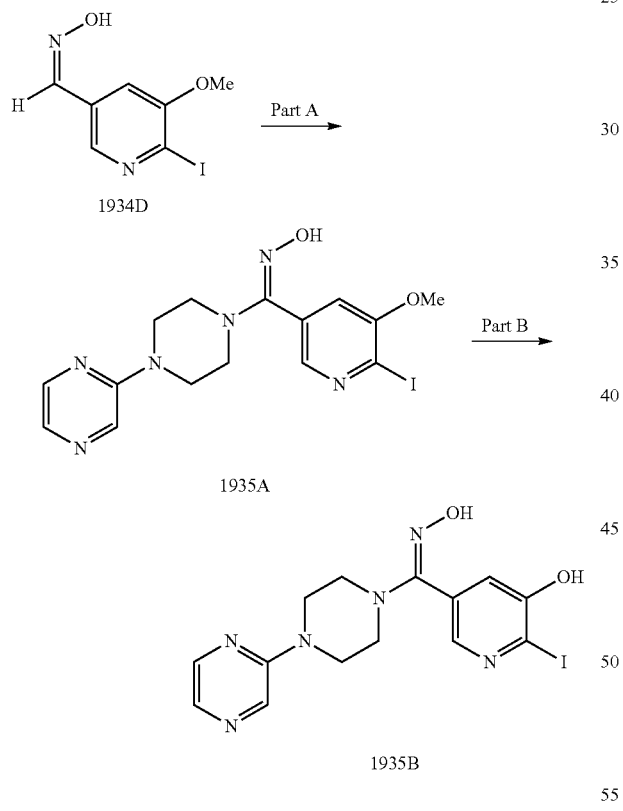

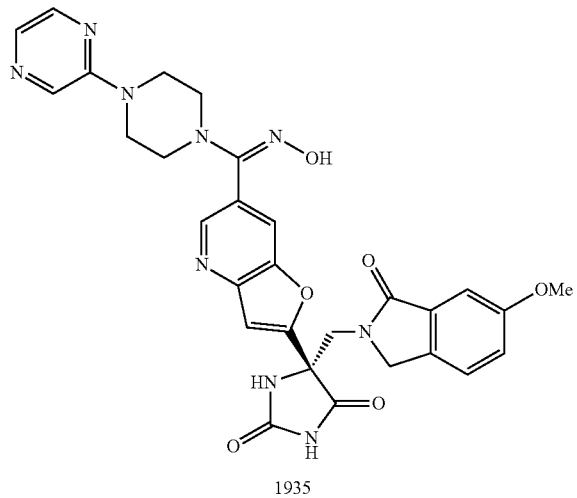

Part A:

Compound 1935A was prepared from compounds 1934D and N-(2-pyrazine)-piperazine by using a procedure described in Part D of Example 154.

Part B:

Compound 1935B was prepared from compound 1935A by using a procedure described in Part D of Example 122.

Part C:

Compound 1935 was prepared from compounds 14 and 1935B by using a procedure described in Part E of Example 122.

Example 156

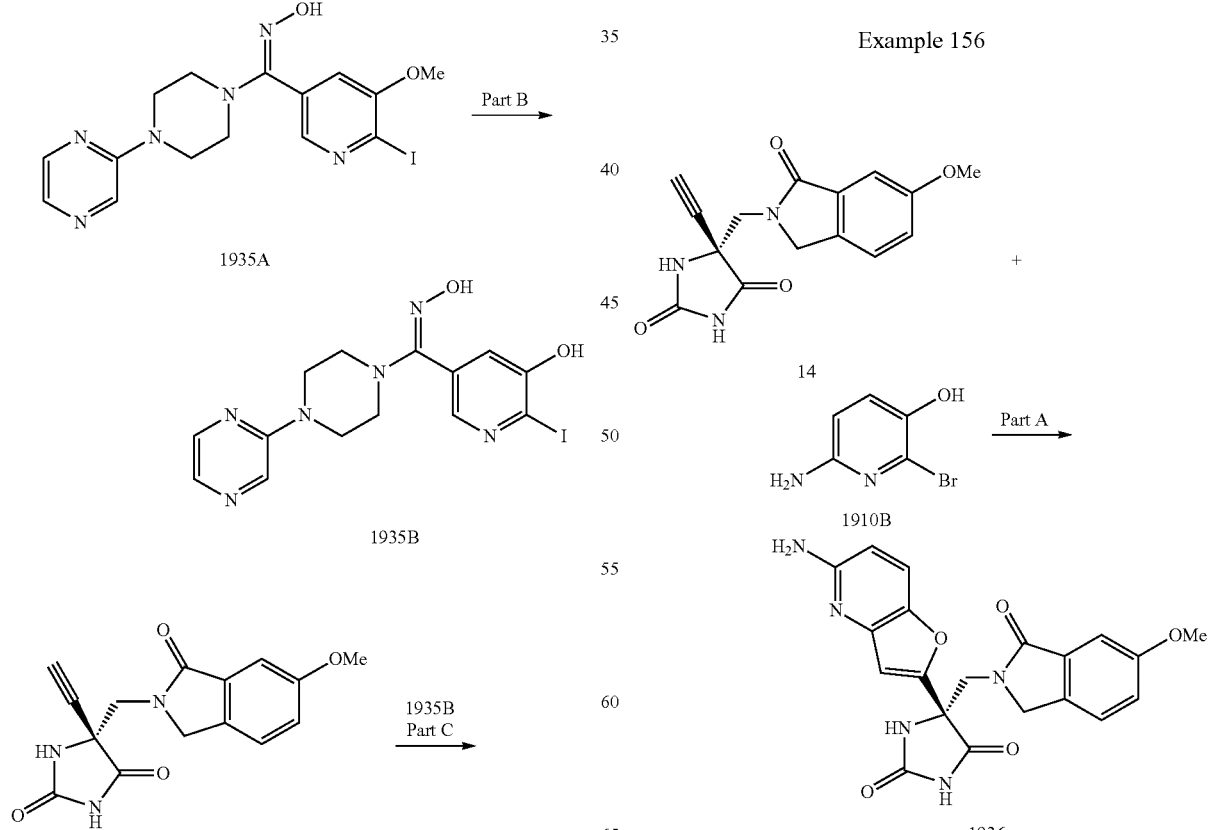

Part A:

Compound 1936 was prepared from compounds 14 and 1910B by using a procedure described in Part E of Example 122.

Example 157

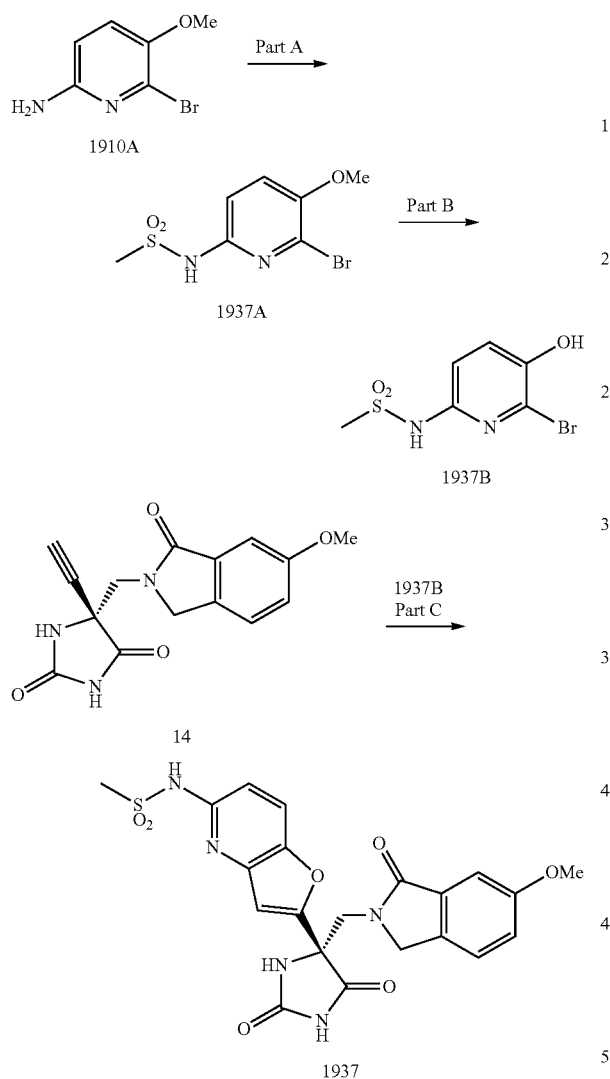

Part A:

A solution of compound 1910A (46 mg, 0.23 mmol) in pyridine (1 mL) was treated with methanesulfonyl chloride (20 μL, 0.26 mmol). After stirred at 40° C. for 18 h, the mixture was added to water and the organic layers were extracted with EtOAc. Combined organic solution was washed with brine solution, dried ($Na_2SO_4$), and concentrated in vacuo. The residue was purified by preparative TLC (5% MeOH in $CH_2Cl_2$) to provide the desired product 1937A (54 mg, 84%).

Part B:

Compound 1937B was prepared from compound 1937A by using a procedure described in Part D of Example 122.

Part C:

Compound 1937 was prepared from compounds 14 and 1937B by using a procedure described in Part E of Example 122.

Example 158

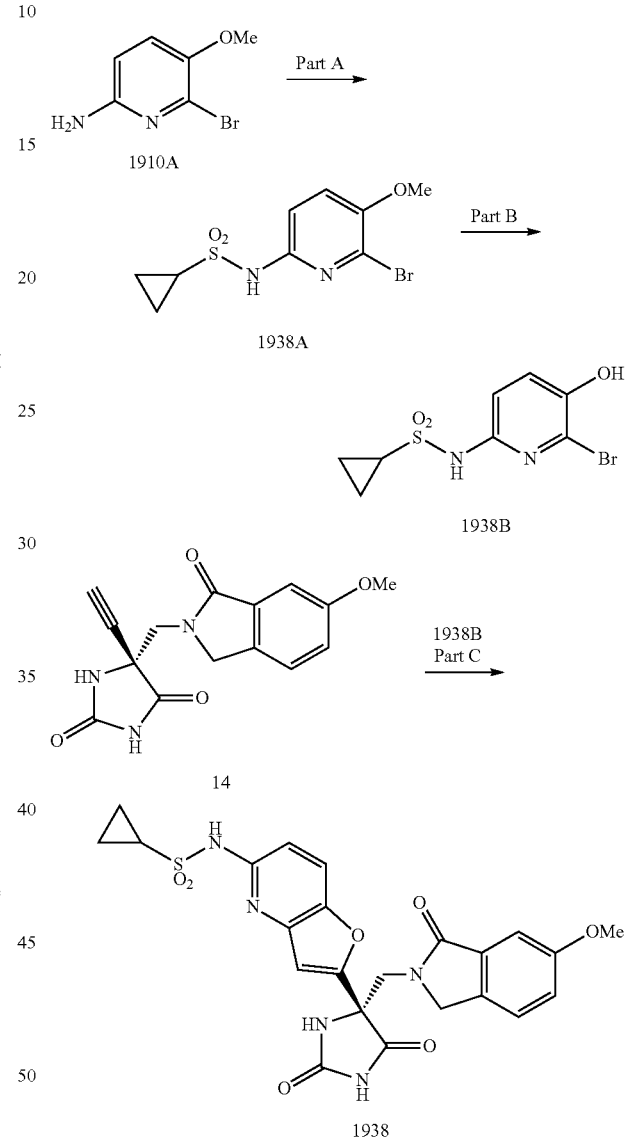

Part A:

Compound 1938A was prepared from compound 1910A and cyclopropylsulfonyl chloride by using a procedure described in Part A of Example 157.

Part B:

Compound 1938B was prepared from compound 1938A by using a procedure described in Part D of Example 122.

Part C:

Compound 1938 was prepared from compounds 14 and 1938B by using a procedure described in Part E of Example 122.

Compounds 2313, 2315, 2316, and 2318 were prepared using procedures similar to those described in Example 158.

Example 159

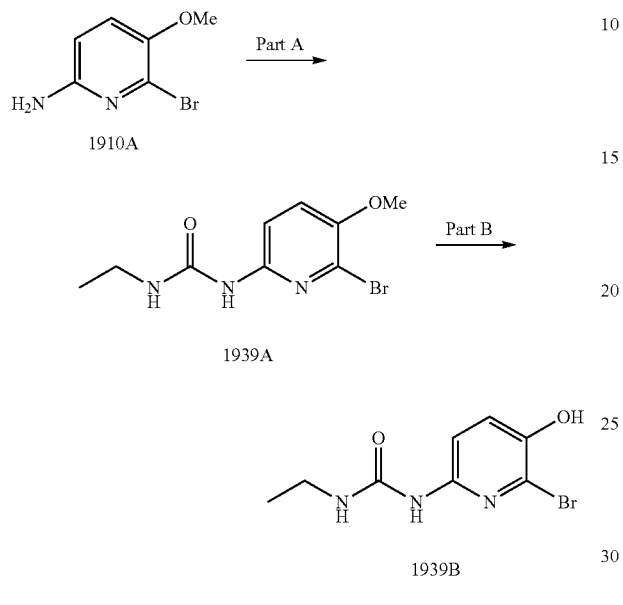

Part A:

A mixture of compound 1910A (80 mg, 0.40 mmol) and ethyl isocyanate (35 μL, 0.44 mmol) in CHCl₃ (3 mL) was stirred at 70° C. for 36 h. The mixture was concentrated in vacuo and the residue was purified by silica gel column (MeOH/CH₂Cl₂, gradient from 0% to 4% MeOH) to provide the desired product 1939A (94 mg, 86%).

Part B:

Compound 1939B was prepared from compound 1939A by using a procedure described in Part D of Example 122.

Part C:

Compound 1939 was prepared from compounds 14 and 1939B by using a procedure described in Part E of Example 122.

Example 160

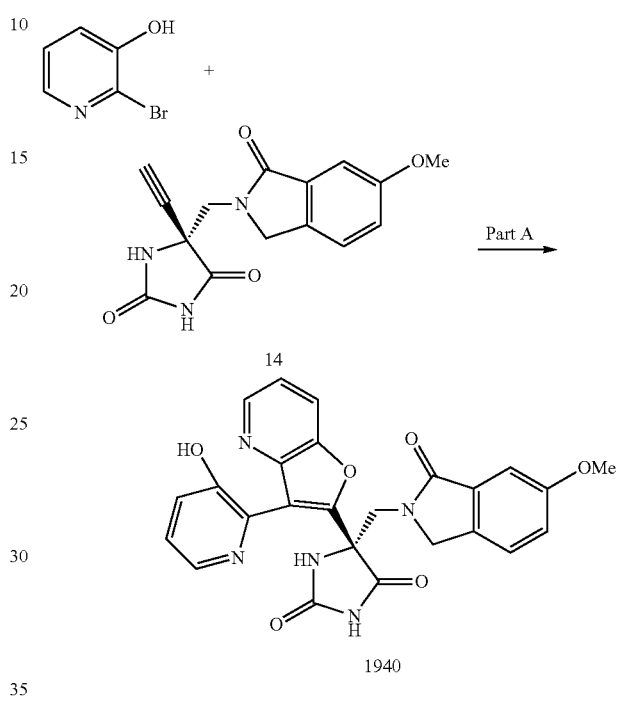

Part A:

Compound 1940 was prepared as a byproduct from compounds 14 and 2-bromo-3-hydroxypyridine by using a procedure described in Part E of Example 122.

Example 161

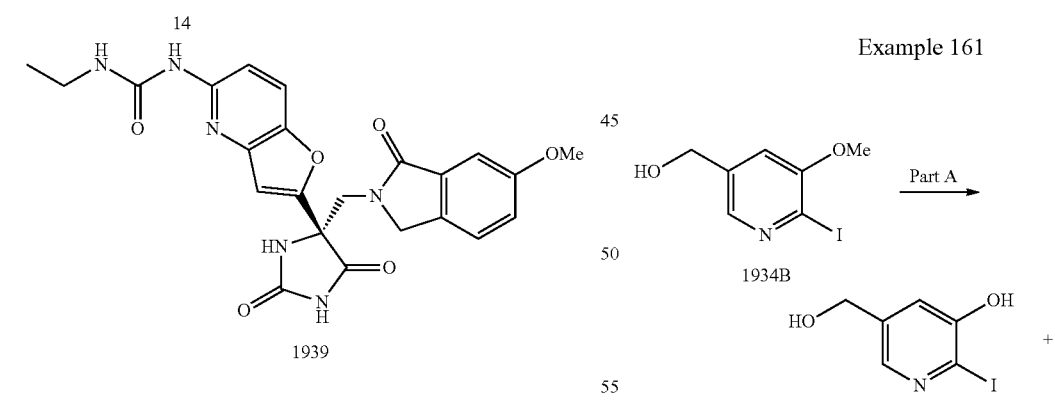

365
-continued

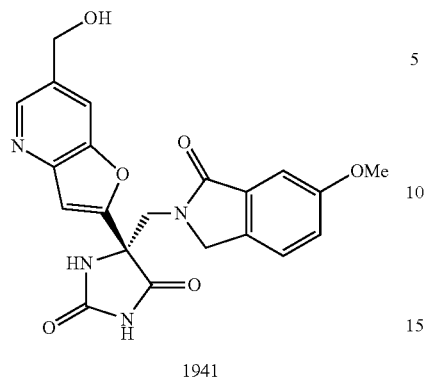

1941

Part A:

Compound 1941A was prepared from compound 1934B by using a procedure described in Part D of Example 122.

Part B:

Compound 1941 was prepared from compounds 14 and 1941A by using a procedure described in Part E of Example 122.

Example 162

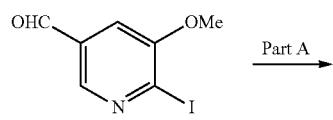

1934C

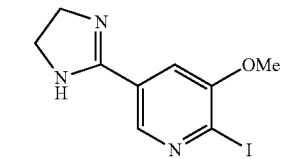

1942A

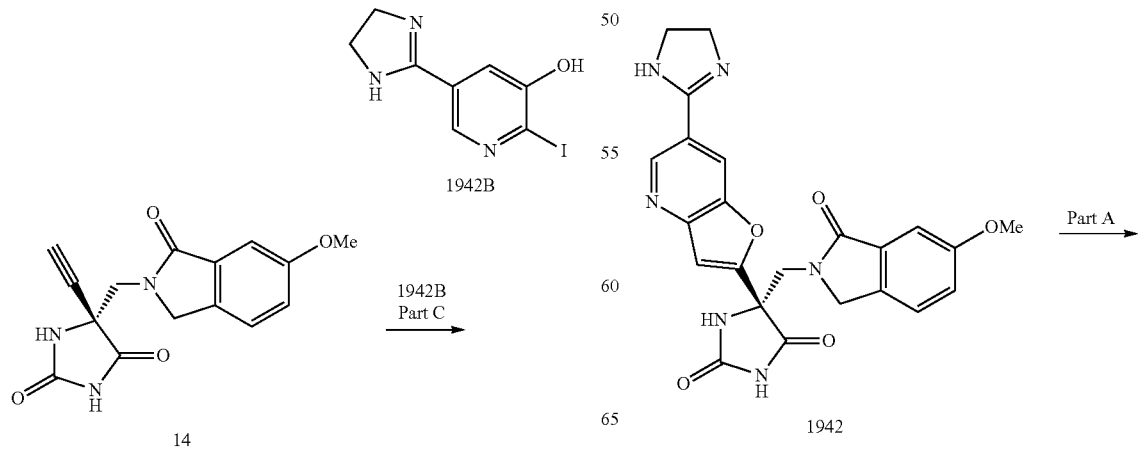

366
-continued

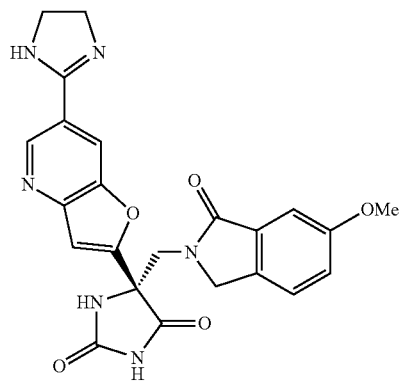

1942

Part A:

A mixture of compound 1934C (98 mg, 0.37 mmol) and ethylene diamine (0.03 μL, 0.41 mmol) in t-butanol (3.5 mL) was stirred at 25° C. for 0.5 h. To this solution were added potassium carbonate (153 mg, 1.11 mmol) and iodine (117 mg, 0.46 mmol) and the mixture was stirred at 70° C. for 2 h. After cooled to 25° C., the mixture was diluted in EtOAc and iodine was quenched by 10% aq. sodium sulfite. The solid was filtered and washed with water to provide the desired product 1942A (90 mg, 80%).

Part B:

Compound 1942B was prepared from compound 1942A by using a procedure described in Part D of Example 122.

Part C:

Compound 1942 was prepared from compounds 14 and 1942B by using a procedure described in Part E of Example 122.

Example 163

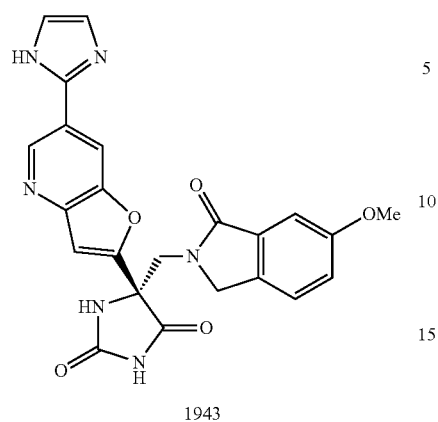

Part A:

A solution of compound 1942 (9 mg, 0.02 mmol) in DMSO (0.5 mL) was treated with iodobenzene diacetate (20 mg, 0.06 mmol) and potassium carbonate (9.2 mg, 0.07 mmol) at 25° C. After stirred for 20 h, the mixture purified by C-18 reverse phase column (0.1% TFA in acetonitrile—0.1% TFA in water) to provide the desired product 1943 (3.4 mg, 38%).

Part A:

A mixture of compound 1934B (61 mg, 0.23 mmol), ethyl isocyanate (22 μL, 0.28 mmol), and triethylamine (48 μL, 0.34 mmol) was stirred at 40° C. for 3 days. After cooled to 25° C., the mixture was concentrated in vacuo and the residue was purified by silica gel column (MeOH/CH$_2$Cl$_2$, gradient from 0% to 3% MeOH) to provide the desired product 1944A (55 mg, 72%).

Part B:

Compound 1944B was prepared from compound 1944A by using a procedure described in Part D of Example 122.

Part C:

Compound 1944 was prepared from compounds 14 and 1944B by using a procedure described in Part E of Example 122.

Example 164

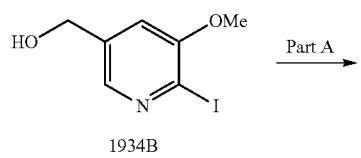

1934B

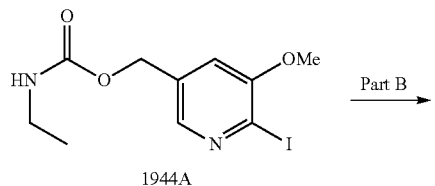

1944A

Example 165

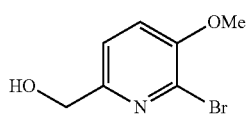

1901B

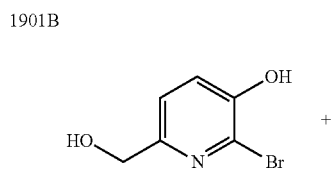

1945A

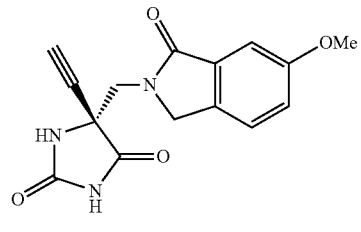

14

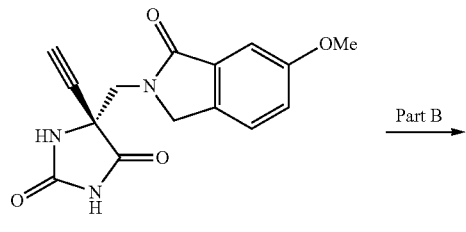

14

Example 167

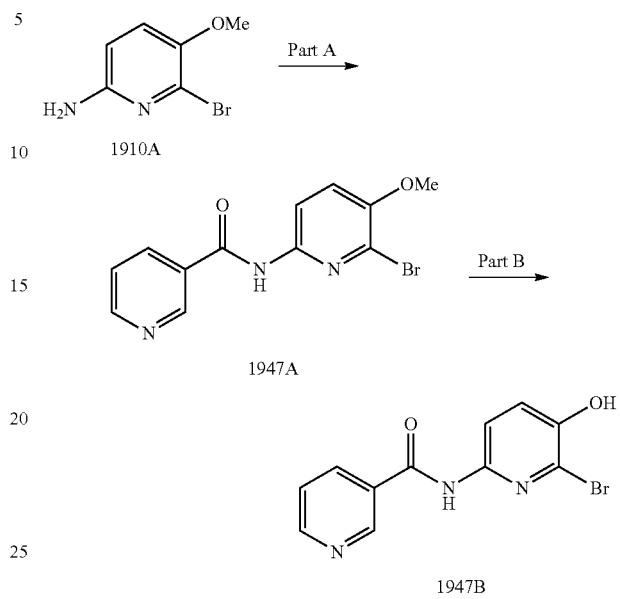

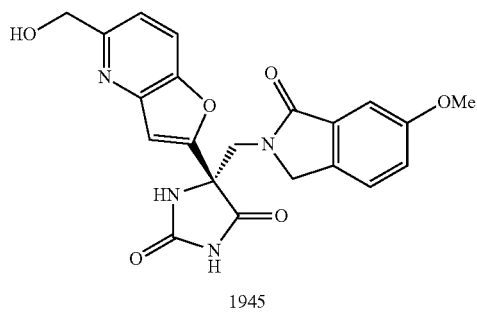

Part A:

Compound 1945A was prepared from compound 1901B by using a procedure described in Part D of Example 122.

Part B:

Compound 1945 was prepared from compounds 14 and 1945A by using a procedure described in Part E of Example 122.

Example 166

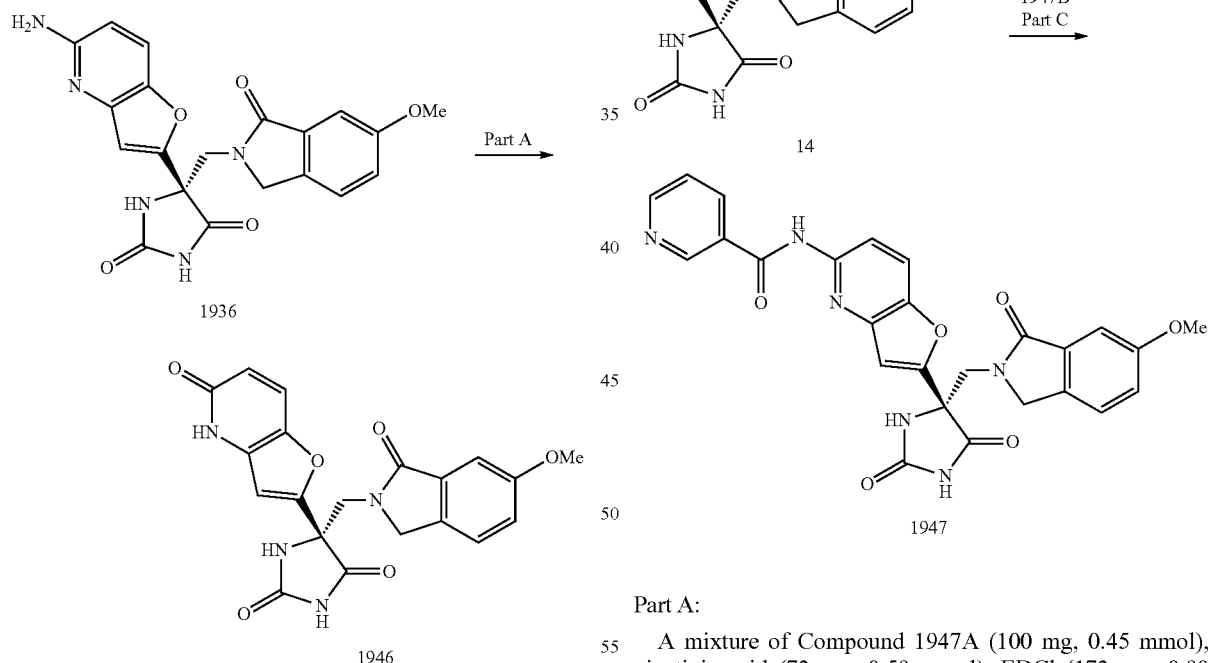

Part A:

A solution of compound 1936 (9 mg, 0.022 mmol) in conc. sulfuric acid (0.5 mL) was treated with sodium nitrite (16 mg, 0.28 mmol) at −10° C. The mixture was stirred at 25° C. for 2 h and added to cold water. After pH adjustment with 10% sodium carbonate solution, the organic layers were extracted with EtOAc. Combined organic solution was washed with brine solution, dried ($Na_2SO_4$), and concentrated in vacuo to provide the desired product 1946 (8 mg, 89%).

Part A:

A mixture of Compound 1947A (100 mg, 0.45 mmol), nicotinic acid (73 mg, 0.59 mmol), EDCl (173 mg, 0.90 mmol), HOBt (183 mg, 1.35 mmol), and triethylamine (0.13 mL, 0.90 mmol) in THF (20 mL) was stirred at 25° C. for 20 h. After diluted in $CH_2Cl_2$, the mixture was washed with aq. $NaHCO_3$ solution, dried ($Na_2SO_4$), and concentrated in vacuo. The residue was purified by silica gel column (MeOH/$CH_2Cl_2$, gradient from 0% to 5% MeOH) to provide the desired product 1947A (110 mg, 79%).

Part B:

Compound 1947B was prepared from compound 1947A by using a procedure described in Part D of Example 122.

Part C:

Compound 1947 was prepared from compounds 14 and 1947B by using a procedure described in Part E of Example 122.

Example 168

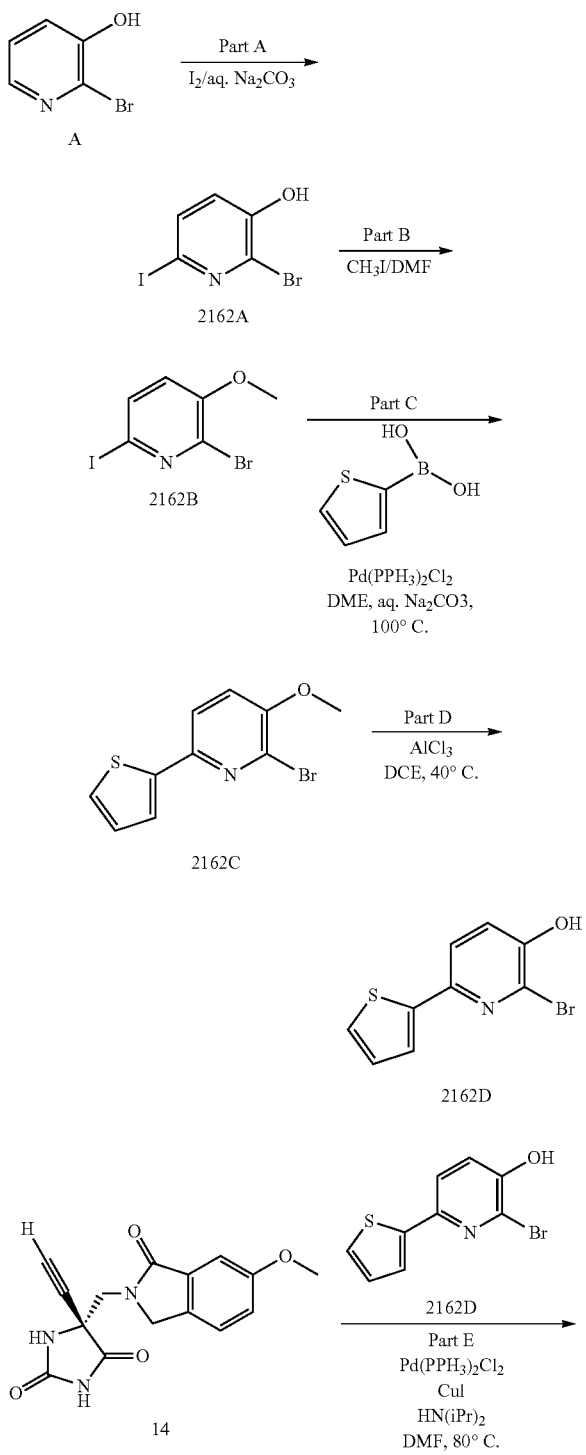

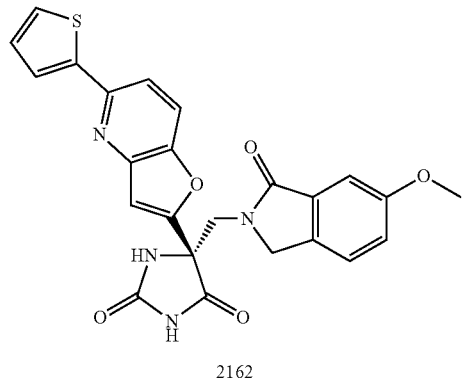 [SMILES: COc1ccc2c(c1)C(=O)N(C[C@@]1(c3cc4nc(-c5cccs5)ccc4o3)NC(=O)NC1=O)C2]

2162

Part A and Part B:

Intermediate 2162 B was prepared following the literature procedures.[1,2]

1. Koch, V.; Schnatterer, S. *Synthesis,* 497, 1990.
2. Chapman, G. M.; Stanforth, S. P.; Tarbit, B; Watson, M. D. *Journal of the Chemical Society, Perkin Transactions* 1, 581, 2002.

Part C:

Intermediate 2162B (0.3 g, 0.95 mmol), 2-thiophene boronic acid (0.3 g, 2.3 mmol), Pd(PPh$_3$)$_2$Cl$_2$ (0.06 g, 0.008 mmol), aq. Na$_2$CO$_3$ (2 mL), dimethoxyethane (DME) were stirred at 110° C. under nitrogen for 10 hours. After cooling, the reaction was diluted with EtOAc (100 mL) the organics were washed with water (2×50 mL) and brine (1×50 mL). The organics were dried over MgSO$_4$ and the crude was purified by flash column chromatography (ISCO CombiFlash Rf, SiO$_2$, 4 g cartridge (Hexanes to 20% EtOAc/hexanes) to give 2162 C (0.23 g).

Part D:

Compound 2162C (0.23 g, 0.85 mmol) was dissolved in dichloroethane (DCE) (5 mL) and aluminum chloride (0.1 g, 0.85 mmol) was added. The reaction mixture was stirred at 40° C. for 10 hours. The reaction was cooled and diluted with EtOAc (50 mL) and washed 2×25 mL water, and brine (1×25 mL) and then dried over sodium sulfate, and concentrated to provide a crude which was purified by flash column chromatography (ISCO CombiFlash Rf, SiO$_2$, 4 g cartridge (Hexanes to 25% EtOAc/hexanes) to yield compound 2162 D (0.16 g).

Part E:

A mixture of 14 (0.05 g, 0.16 mmol), 2162D (0.05 g, 0.5 mmol), copper iodide (8 mg, 0.045 mmol), Pd(PPh$_3$)$_2$Cl$_2$ (5 mg, 0.008 mmol) and diisopropylethylamine (0.1 mL, 0.86 mmol) in DMF (3 mL) was charged into a sealed tube and purged with nitrogen (3×). The mixture was heated at 80° C. for 12 h. The reaction mixture was filtered and the filtrate was concentrated and purified by reverse phase chromatography using a 0.1% trifluoracetic acid in the aqueous mobile phase (100% water to 50% acetonotrile/water) to provide 0.014 g of pure product 2162. MS m/z 474.99. (M+H).

The following compounds were made using the procedure described in Example 168, using corresponding boronic acid/ester in step Part C and compound 14 or 23 in step Part E.

| ID | STRUCTURE | (M + 1)+ | LC MS* t_R |
|---|---|---|---|
| 2147 | 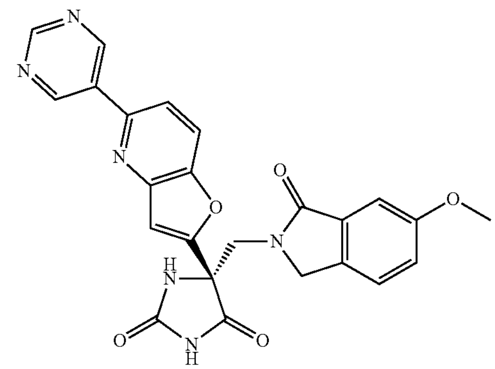 [SMILES: COc1ccc2c(c1)C(=O)N(C[C@@]1(c3cc4nc(-c5cncnc5)ccc4o3)NC(=O)NC1=O)C2] | 471.3 | 4.14 |
| 2149 | 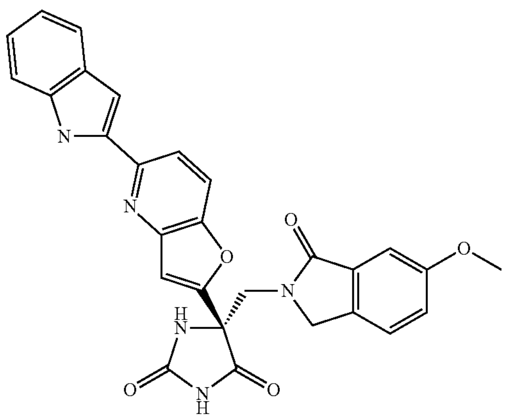 [SMILES: COc1ccc2c(c1)C(=O)N(C[C@@]1(c3cc4nc(-c5cc6ccccc6[nH]5)ccc4o3)NC(=O)NC1=O)C2] | 508.3 | 2.62 |
| 2150 | 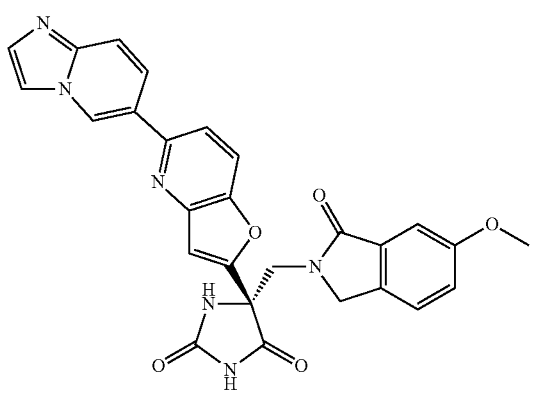 [SMILES: COc1ccc2c(c1)C(=O)N(C[C@@]1(c3cc4nc(-c5ccc6nccn6c5)ccc4o3)NC(=O)NC1=O)C2] | 509.3 | 2.04 |
| 2151 | 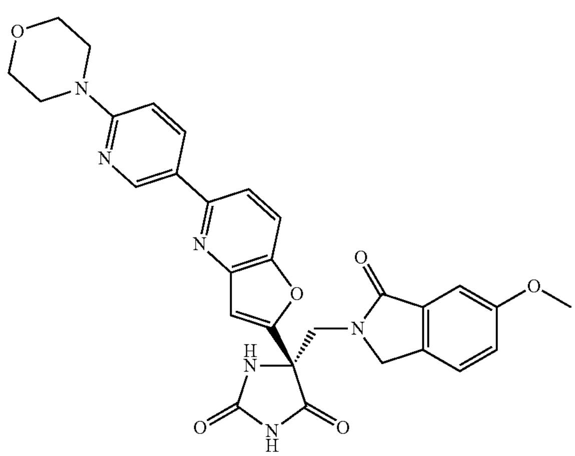 [SMILES: COc1ccc2c(c1)C(=O)N(C[C@@]1(c3cc4nc(-c5ccc(N6CCOCC6)nc5)ccc4o3)NC(=O)NC1=O)C2] | 555.3 | 2.20 |

-continued
| ID | STRUCTURE | (M + 1)+ | LC MS* t_R |
|---|---|---|---|
| 2152 | 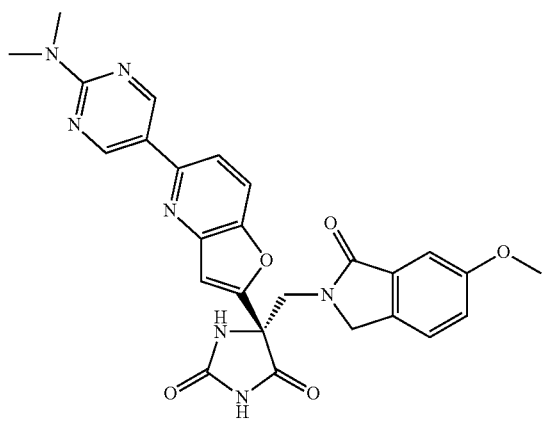 | 514.3 | 2.63 |
| 1527 | 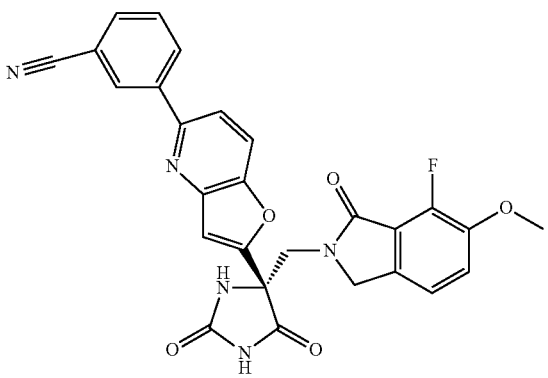 [SMILES: COc1ccc2c(c1F)C(=O)N(C[C@@]1(c3cc4nc(-c5cccc(C#N)c5)ccc4o3)NC(=O)NC1=O)C2] | 512.3 | 3.56 |
| 1528 | 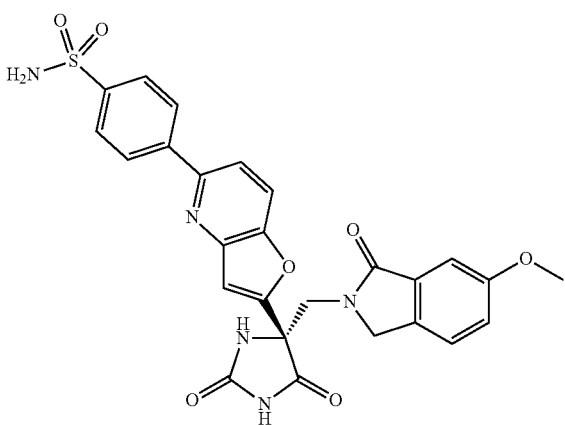 [SMILES: COc1ccc2c(c1)C(=O)N(C[C@@]1(c3cc4nc(-c5ccc(S(N)(=O)=O)cc5)ccc4o3)NC(=O)NC1=O)C2] | 548.3 | 2.91 |

-continued
| ID | STRUCTURE | (M + 1)+ | LC MS* t$_R$ |
|----|-----------|----------|--------------|
| 1529 | 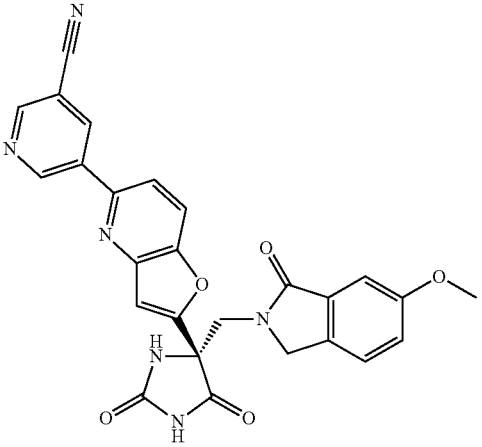 [SMILES: COc1ccc2c(c1)C(=O)N(C[C@@]1(c3cc4nc(-c5cncc(C#N)c5)ccc4o3)NC(=O)NC1=O)C2] | 495.11 | 3.56 |
| 1530 | 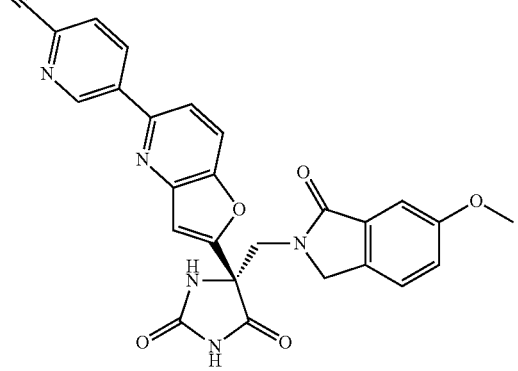 | 495.3 | 3.13 |
Example 169
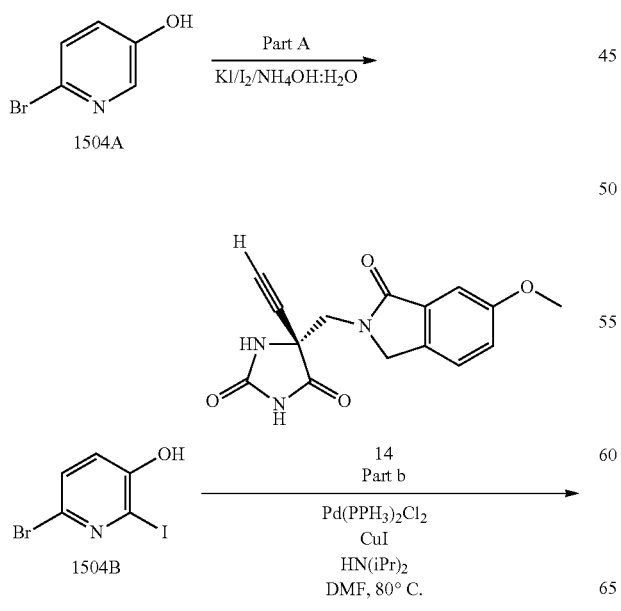
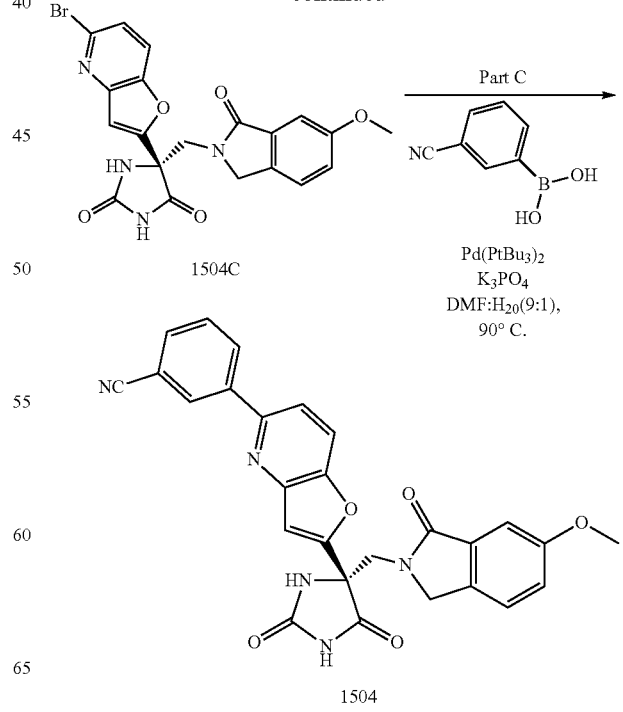

Part A:

Compound 1504A (commercially available) (2 g, 11.5 mmol) was dissolved in NH$_4$OH (32 mL). The solution was cooled to 0° C. and then aqueous solution (8 mL) containing KI (5.71 g, 34.5 mmol) and I$_2$ (2.6 g, 10 mmol) was added drop wise and stirred for 15 hours. The solvent was removed and the resulting solid was redissolved in CH$_2$Cl$_2$ (50 mL) and the solution was treated with 10 g silica gel. After 10 min. the silica gel was filtered off and washed with CH$_2$Cl$_2$ (2×50 mL). The filtrate was concentrated to provide pure product 1504B (1.8 g, 52%).

Part B:

A mixture of 14 (0.52 g, 1.6 mmol), 1504B (0.52 g, 1.7 mmol), copper iodide (8 mg, 0.045 mmol), Pd(PPh$_3$)$_2$Cl$_2$ (5 mg, 0.008 mmol) and diisopropylethylamine (0.48 mL, 4 mmol) in DMF (5 mL) was charged into a sealed tube and purged with nitrogen (3×). The mixture was heated at 40° C. for 12 h. The reaction mixture was filtered and the filtrate was concentrated and purified by flash column chromatography (ISCO CombiFlash Rf, SiO$_2$, 12 g cartridge (CH$_2$Cl$_2$ to 5% CH$_3$OH/CH$_2$Cl$_2$) to yield pure product 1504C (0.7 g, 90%).

Part C:

A mixture of 1504C (0.05 g, 0.1 mmol), 3-cyanophenylboronic acid (0.075 g, 0.5 mmol), Pd(P$^t$Bu$_3$)$_2$ (5 mg, 0.009 mmol) and K$_3$PO$_4$ (0.065 g, 0.3 mmol), and DMF:H$_2$O (10:1; 1.4 mL) was charged into a sealed tube and purged with nitrogen (3×). The mixture was heated at 90° C. for 20 h. The reaction mixture was filtered and the filtrate was concentrated and purified by reverse phase chromatography using a 0.1% trifluoracetic acid in the aqueous mobile phase (100% water to 50% acetonotrile/water) to provide 0.025 g (48%) of pure product 1504. LC-MS* t$_R$=3.56 min; observed LCMS m/z 512.3 (M+H).

The following compounds were made from 1504C using the procedure described in Example 169, using corresponding boronic acid/ester in Part C and 14 or 23 in Part B.

| ID | STRUCTURE | (M + 1)$^+$ | LC MS* t$_R$ |
|---|---|---|---|
| 1505 | 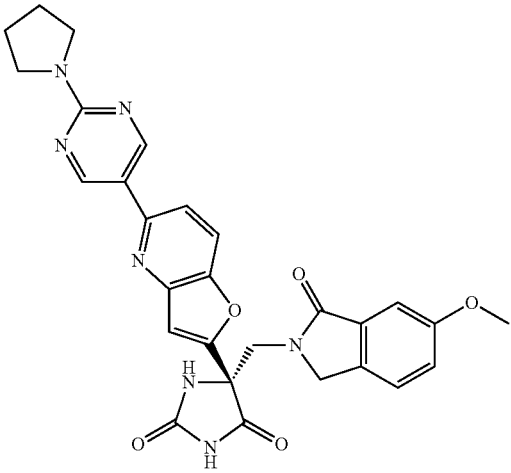 [SMILES: COc1ccc2c(c1)C(=O)N(C[C@@]1(c3cc4nc(-c5cnc(N6CCCC6)nc5)ccc4o3)NC(=O)NC1=O)C2] | 540.3 | 2.82 |
| 1507 | 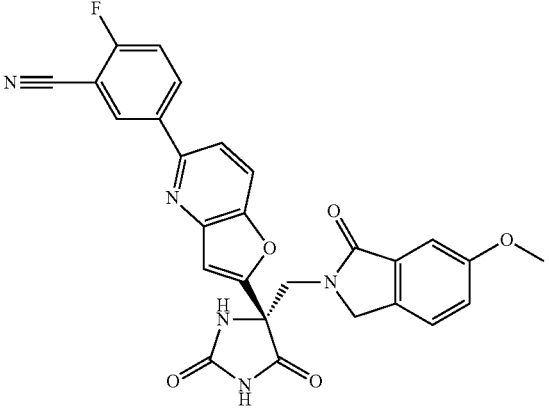 [SMILES: COc1ccc2c(c1)C(=O)N(C[C@@]1(c3cc4nc(-c5ccc(F)c(C#N)c5)ccc4o3)NC(=O)NC1=O)C2] | 512.3 | 3.65 |

-continued

| ID | STRUCTURE | (M + 1)+ | LC MS* t_R |
|---|---|---|---|
| 1508 | 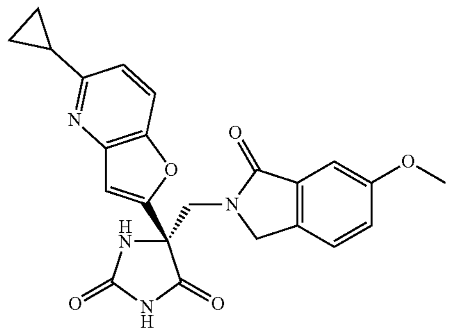 [SMILES: COc1ccc2c(c1)C(=O)N(C[C@@]1(c3cc4nc(C5CC5)ccc4o3)NC(=O)NC1=O)C2] | 433.2 | 2.44 |
| 1509 | 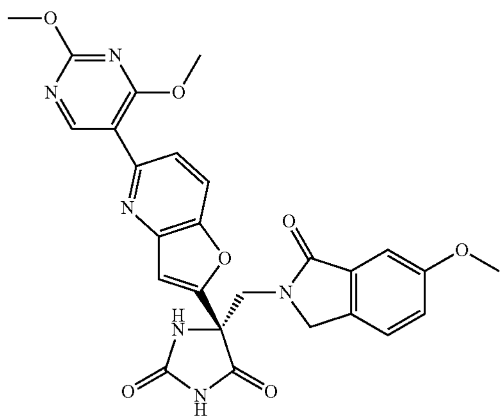 | 531.3 | 3.35 |
| 1518 | 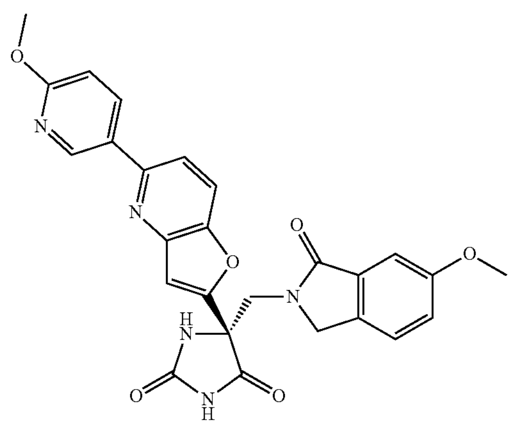 [SMILES: COc1ccc2c(c1)C(=O)N(C[C@@]1(c3cc4nc(-c5ccc(OC)nc5)ccc4o3)NC(=O)NC1=O)C2] | 500.3 | 3.18 |
| 1519 | 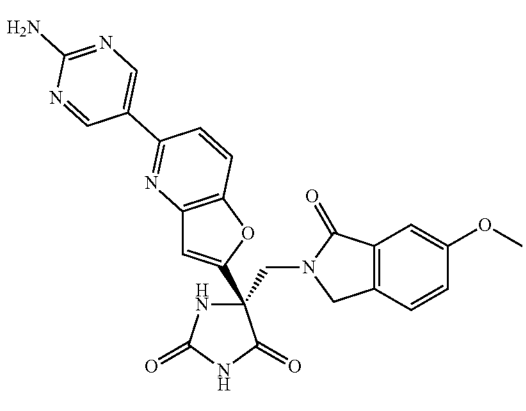 [SMILES: COc1ccc2c(c1)C(=O)N(C[C@@]1(c3cc4nc(-c5cnc(N)nc5)ccc4o3)NC(=O)NC1=O)C2] | 486.3 | 2.42 |

| ID | STRUCTURE | (M + 1)+ | LC MS* $t_R$ |
|---|---|---|---|
| 1520 | 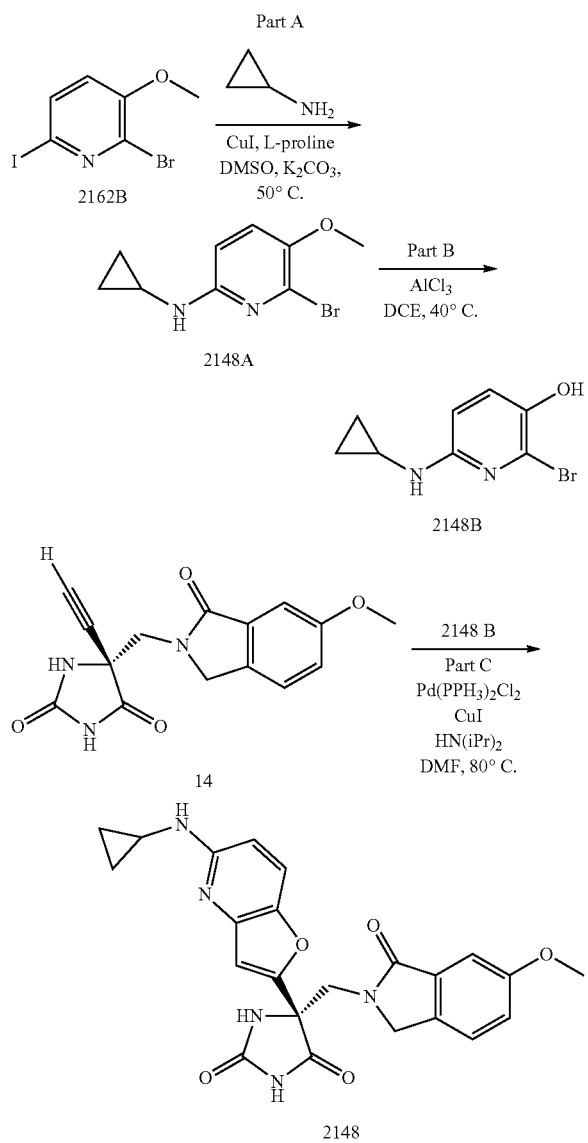 | 488.3 | 3.21 |

Example 170

Part A:

A mixture of 2162 B (0.25 g, 0.8 mmol), CuI (0.015 g, 0.07 mmol), L-proline (0.018 g, 0.4 mmol), $K_2CO_3$ (0.22 g, 1.6 mmol) in DMSO (3 mL) was charged into a sealed tube and purged with nitrogen (3×). Cyclopropylamine (0.11 mL, 1.6 mmol) was injected and the mixture was heated at 50° C. for 10 h. The reaction was cooled and diluted with EtOAc (50 mL) and washed 2×25 mL water, and brine (1×25 mL) and then dried over sodium sulfate, and concentrated to provide a crude which was purified by flash column chromatography (ISCO CombiFlash Rf, $SiO_2$, 12 g cartridge (Hexanes to 25% EtOAc/hexanes) to yield compound 2148A (0.1 g, 53%).

Part B:

Compound 2148A (0.1 g, 0.4 mmol) was dissolved in dichloroethane (DCE) (15 mL) and aluminum chloride (0.14 g, 1 mmol) was added. The reaction mixture was stirred at 45° C. for 10 hours. The reaction was cooled and diluted with EtOAc (50 mL) and washed 2×25 mL water, and brine (1×25 mL) and then dried over sodium sulfate, and concentrated to provide a crude which was purified by flash column chromatography (ISCO CombiFlash Rf, $SiO_2$, 4 g cartridge (Hexanes to 25% EtOAc/hexanes) to yield compound 2148B (0.05 g, 50%).

Part C:

A mixture of 14 (0.05 g, 0.16 mmol), 2148B (0.04 g, 0.018 mmol), copper iodide (8 mg, 0.045 mmol), $Pd(PPh_3)_2Cl_2$ (5 mg, 0.008 mmol) and diisopropylethylamine (0.047 mL, 0.33 mmol) in DMF (3 mL) was charged into a sealed tube and purged with nitrogen (3×). The mixture was heated at 80° C. for 12 h. The reaction mixture was filtered and the filtrate was concentrated and purified by reverse phase chromatography using a 0.1% trifluoracetic acid in the aqueous mobile phase (100% water to 50% acetonotrile/water) to provide 0.019 g of pure product 2148. LC-MS* $t_R$=2.07 min (ELSD); observed LCMS m/z 448.2 (M+H).

The following compounds were made from 2162B using the procedure described in Example 170, using corresponding amines in Part A and compound 14 or 23 in Part C.

| ID | STRUCTURE | (M + 1)+ | LC MS* $t_R$ |
|---|---|---|---|
| 2160 | 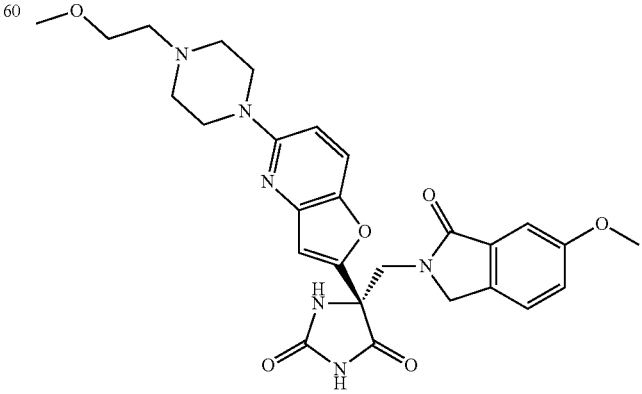 | 535.3 | 1.99 |
| 2163 | 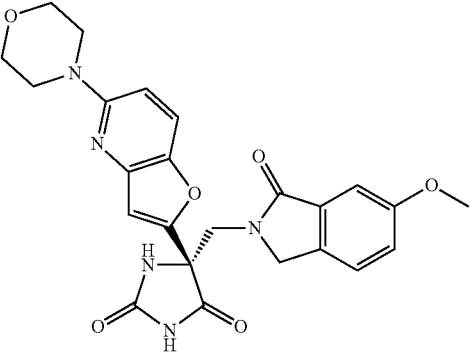 | 478.3 | 2.21 |
| 2164 | 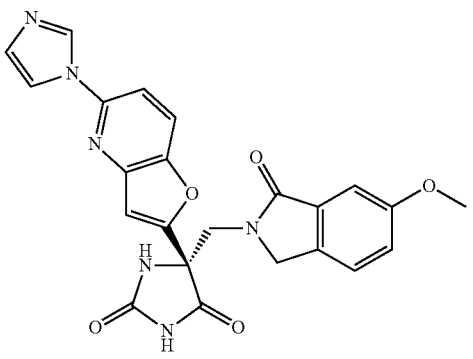 [SMILES: COc1ccc2c(c1)C(=O)N(C[C@@]1(c3cc4nc(-n5ccnc5)ccc4o3)NC(=O)NC1=O)C2] | 459.3 | 2.06 |
| 2165 | 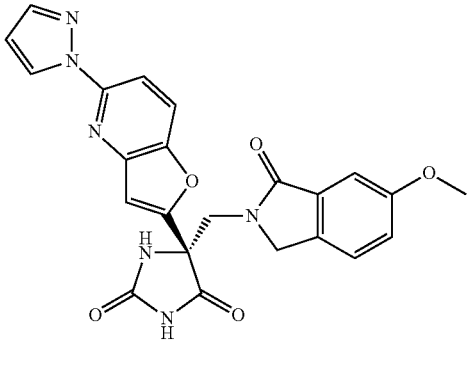 [SMILES: COc1ccc2c(c1)C(=O)N(C[C@@]1(c3cc4nc(-n5cccn5)ccc4o3)NC(=O)NC1=O)C2] | 459.3 | 3.28 |

-continued

| ID | STRUCTURE | (M + 1)+ | LC MS* t_R |
|---|---|---|---|
| 2166 | 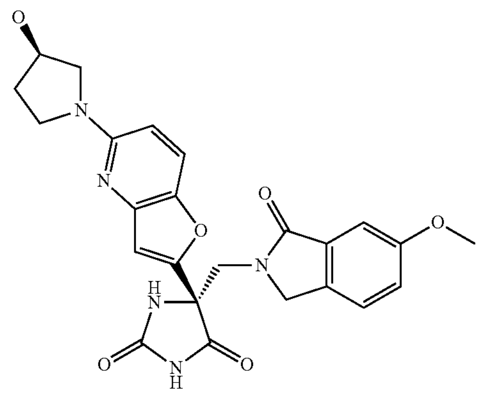 [SMILES: COc1ccc2c(c1)C(=O)N(C[C@@]1(c3cc4nc(N5CC[C@@H](O)C5)ccc4o3)NC(=O)NC1=O)C2] | 478.3 | 2.02 |
| 2168 | 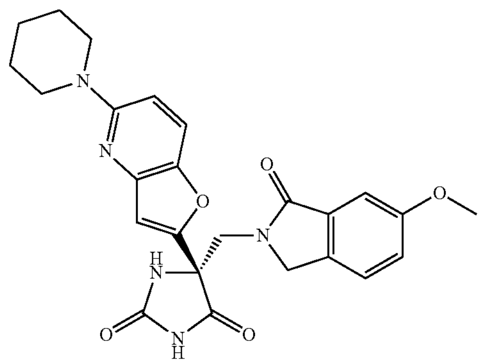 | 476.3 | 2.26 |
| 2170 | 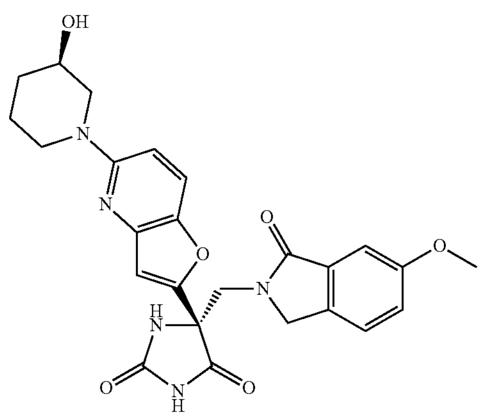 [SMILES: COc1ccc2c(c1)C(=O)N(C[C@@]1(c3cc4nc(N5CCC[C@@H](O)C5)ccc4o3)NC(=O)NC1=O)C2] | 492.3 | 2.03 |
| 2172 | 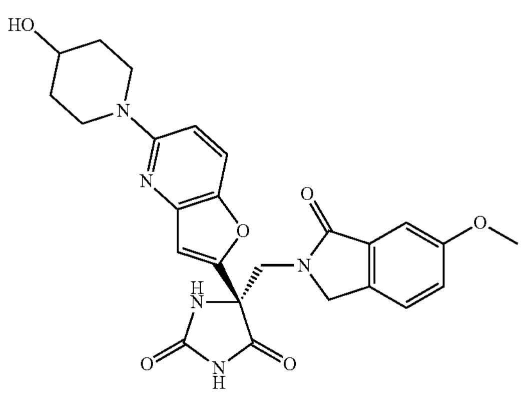 [SMILES: COc1ccc2c(c1)C(=O)N(C[C@@]1(c3cc4nc(N5CCC(O)CC5)ccc4o3)NC(=O)NC1=O)C2] | 492.3 | 1.97 |

-continued

| ID | STRUCTURE | (M + 1)+ | LC MS* t_R |
|---|---|---|---|
| 1513 | 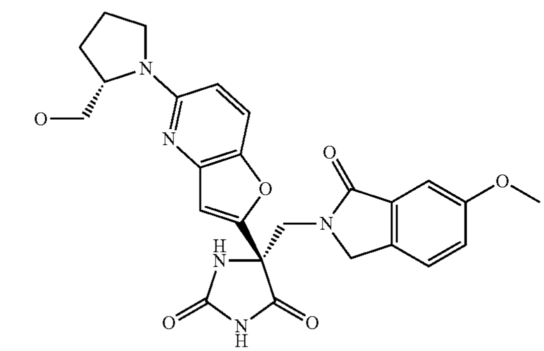 [SMILES: COc1ccc2c(c1)C(=O)N(C[C@@]1(c3cc4nc(N5CCC[C@H]5CO)ccc4o3)NC(=O)NC1=O)C2] | 492.3 | 2.01 |
| 1515 | 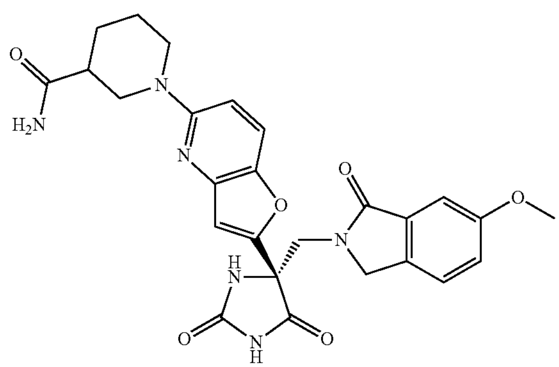 [SMILES: COc1ccc2c(c1)C(=O)N(C[C@@]1(c3cc4nc(N5CCCC(C(N)=O)C5)ccc4o3)NC(=O)NC1=O)C2] | 519.3 | 1.92 |
| 1516 | 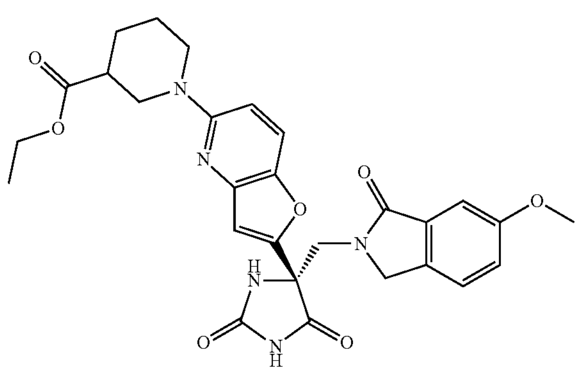 [SMILES: CCOC(=O)C1CCCN(c2ccc3oc([C@]4(CN5Cc6ccc(OC)cc6C5=O)NC(=O)NC4=O)cc3n2)C1] | 548.3 | 2.57 |
| 1517 | 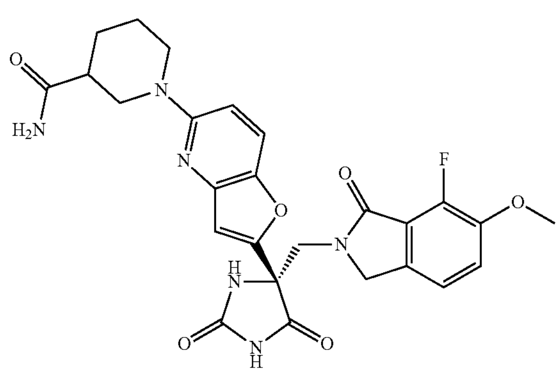 [SMILES: COc1ccc2c(c1F)C(=O)N(C[C@@]1(c3cc4nc(N5CCCC(C(N)=O)C5)ccc4o3)NC(=O)NC1=O)C2] | 537.3 | 2.05 |

| ID | STRUCTURE | (M + 1)⁺ | LC MS* t_R |
|---|---|---|---|
| 1521 | 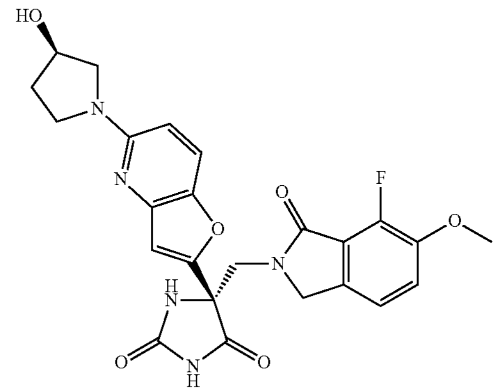 [SMILES: COc1ccc2c(c1F)C(=O)N(C[C@@]1(c3cc4nc(N5CC[C@@H](O)C5)ccc4o3)NC(=O)NC1=O)C2] | 496.3 | 2.01 |
| 1523 | 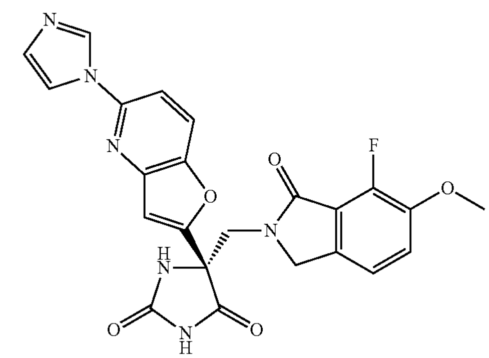 [SMILES: COc1ccc2c(c1F)C(=O)N(C[C@@]1(c3cc4nc(-n5ccnc5)ccc4o3)NC(=O)NC1=O)C2] | 477.3 | 2.12 |
| 1524 | 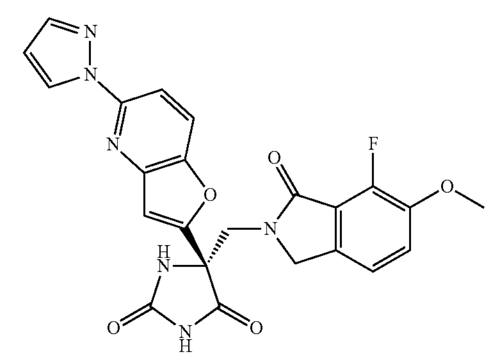 [SMILES: COc1ccc2c(c1F)C(=O)N(C[C@@]1(c3cc4nc(-n5cccn5)ccc4o3)NC(=O)NC1=O)C2] | 477.3 | 3.06 |
| 1531 | 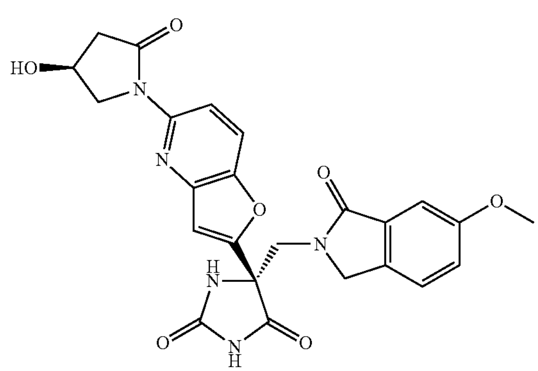 [SMILES: COc1ccc2c(c1)C(=O)N(C[C@@]1(c3cc4nc(N5C[C@@H](O)CC5=O)ccc4o3)NC(=O)NC1=O)C2] | 492.3 | 2.46 |

393

In addition, compound 1500 was prepared using procedures similar to those described in Example 170.

Example 171

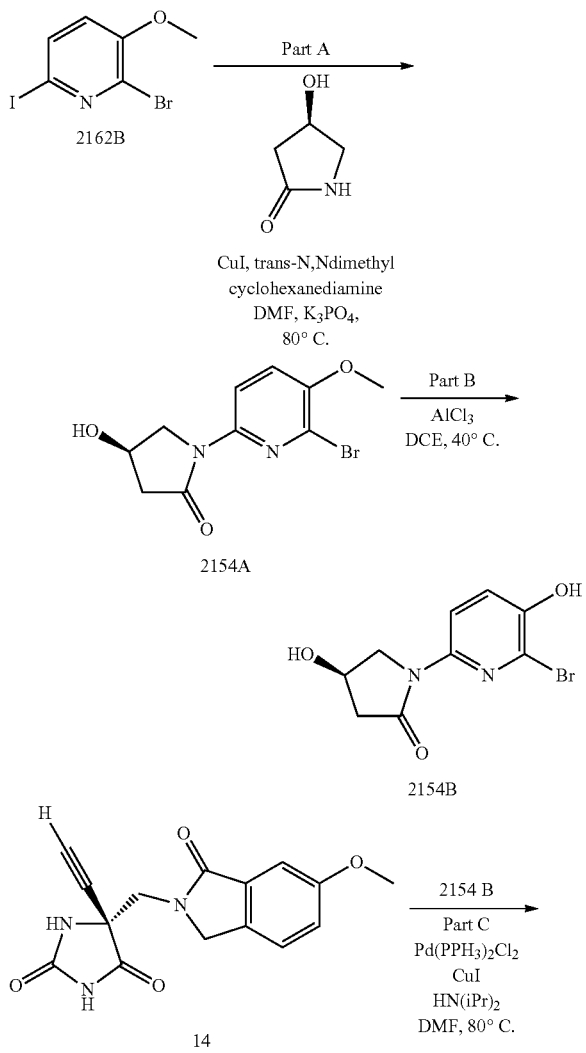

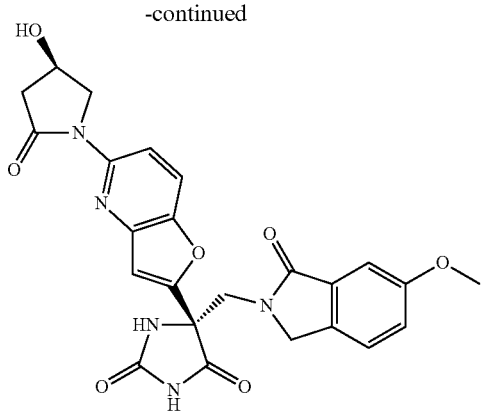

Part A:

A mixture of 2-Bromo-5-iodo-3-methoxy pyridine 2162 B (0.5 g, 1.59 mmol), (S)-(−)-4-hydroxy-2-pyrrolidinone (commercially available, 0.16 g, 1.59 mmoles), Potassium phosphate, 0.68 g, 3.2 mmol), CuI (0.015 g, 0.079 mmol) and DMF (4 ml) was charged into a sealed tube and purged with nitrogen (3×). trans-N,N-Dimethyl-1,2-cyclohexanediamine (0.01 g, 0.07 mmol) was added under $N_2$ through the seal. The reaction was heated at 80° C. for 16 h. After cooling to room temperature the reaction was diluted with EtOAc (20 ml), washed with water (3×20 ml), dried ($Na_2SO_4$), filtered, concentrated to give a crude which was purified by by flash column chromatography (ISCO CombiFlash Rf, $SiO_2$, 12 g cartridge (Hexanes to 50% EtOAc/hexanes) to yield compound 2154 A (0.16 g, 35%).

Part B:

The procedure from Example 168 Part D was repeated on 2154A (0.12 g, 0.42 mmol) to provide 2154B (0.08 g, 70%).

Part C:

The procedure from Example 170 Part C was repeated on 2154B (0.08 g, 0.3 mmol) and 14 (0.09 g, 0.3 mmol) to provide 2154 (0.06 g, 41%). LC-MS* $t_R$=2.43 min observed LCMS m/z 492.3 (M+H).

The following compounds were made from 2162B using the procedure described in Example 171, using corresponding amides in step Part A and compound 14 or 23 in step Part C.

| ID | STRUCTURE | (M + 1)⁺ | LC MS* $t_R$ |
|---|---|---|---|
| 2156 | 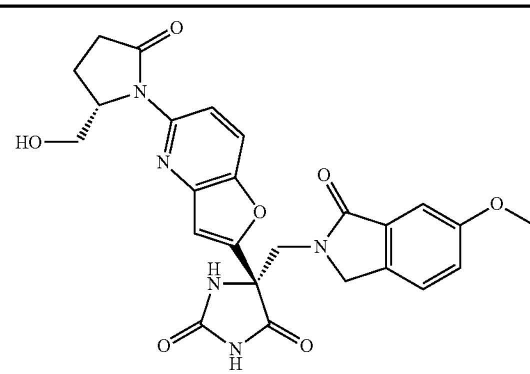 | 506.3 | 2.38 |

| ID | STRUCTURE | (M + 1)+ | LC MS* t_R |
|---|---|---|---|
| 2157 | 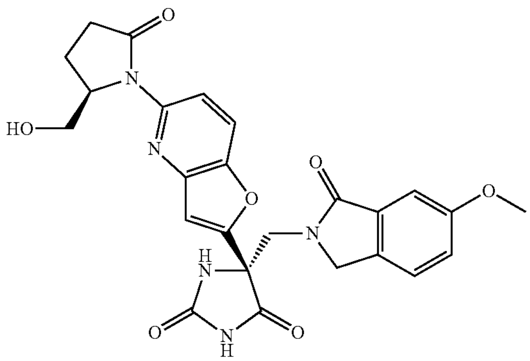 [SMILES: COc1ccc2c(c1)C(=O)N(C[C@@]1(c3cc4nc(N5C(=O)CC[C@@H]5CO)ccc4o3)NC(=O)NC1=O)C2] | 506.3 | 2.50 |
| 2158 | 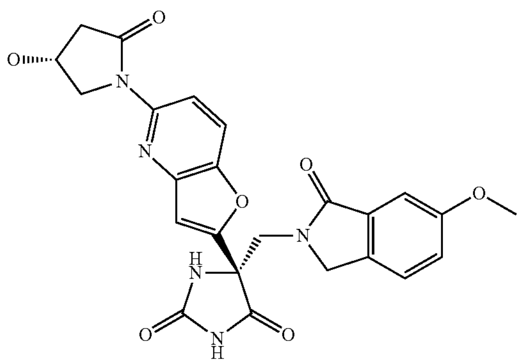 [SMILES: COc1ccc2c(c1)C(=O)N(C[C@@]1(c3cc4nc(N5C[C@H](O)CC5=O)ccc4o3)NC(=O)NC1=O)C2] | 492.3 | 2.35 |
| 2159 | 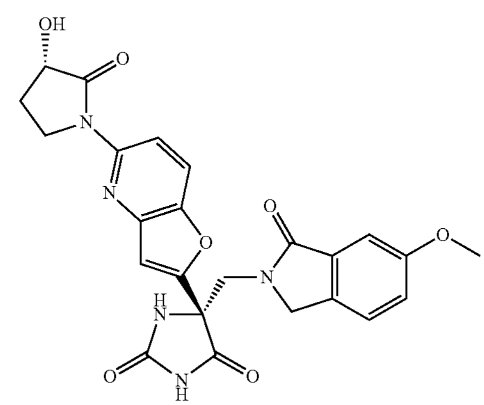 [SMILES: COc1ccc2c(c1)C(=O)N(C[C@@]1(c3cc4nc(N5CC[C@H](O)C5=O)ccc4o3)NC(=O)NC1=O)C2] | 535.3 | 1.99 |
| 2161 | 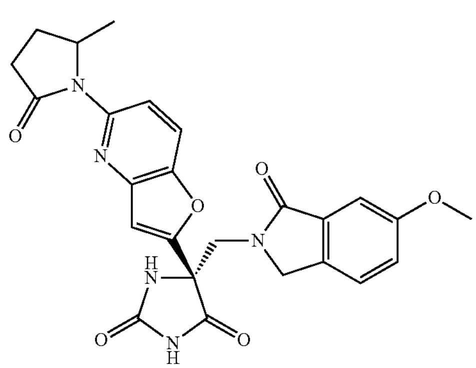 [SMILES: COc1ccc2c(c1)C(=O)N(C[C@@]1(c3cc4nc(N5C(=O)CCC5C)ccc4o3)NC(=O)NC1=O)C2] | 490.3 | 2.82 |

-continued

| ID | STRUCTURE | (M + 1)⁺ | LC MS* t_R |
|---|---|---|---|
| 2173 | 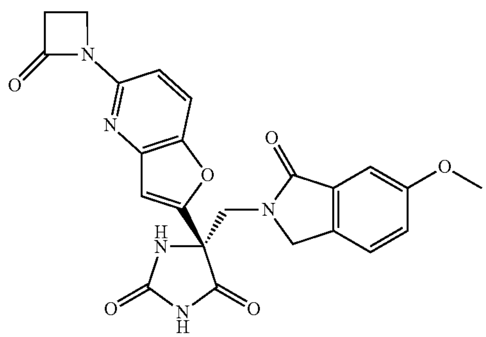 [SMILES: COc1ccc2c(c1)C(=O)N(C[C@@]1(c3cc4nc(N5CCC5=O)ccc4o3)NC(=O)NC1=O)C2] | 462.3 | 2.72 |
| 1501 | 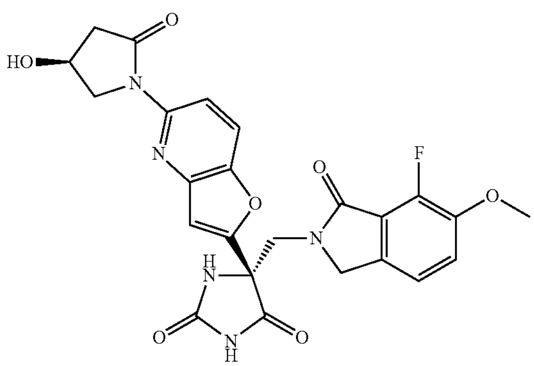 [SMILES: COc1ccc2c(c1F)C(=O)N(C[C@@]1(c3cc4nc(N5C[C@@H](O)CC5=O)ccc4o3)NC(=O)NC1=O)C2] | 510.3 | 2.56 |
| 1510 | 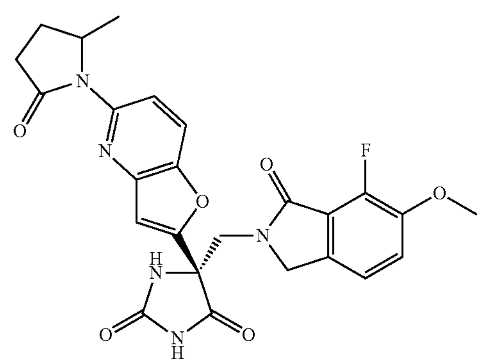 [SMILES: COc1ccc2c(c1F)C(=O)N(C[C@@]1(c3cc4nc(N5C(=O)CCC5C)ccc4o3)NC(=O)NC1=O)C2] | 508.3 | 3.20 |
| 1511 | 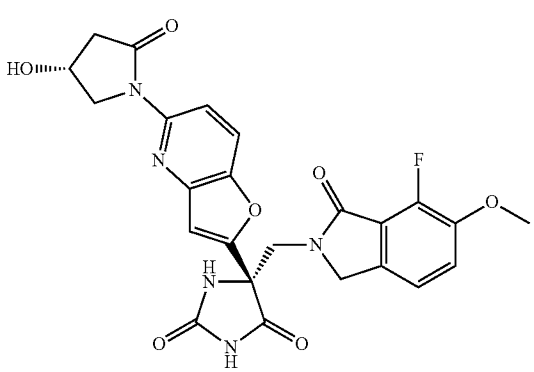 [SMILES: COc1ccc2c(c1F)C(=O)N(C[C@@]1(c3cc4nc(N5C[C@H](O)CC5=O)ccc4o3)NC(=O)NC1=O)C2] | 510.3 | 2.32 |

-continued

| ID | STRUCTURE | (M + 1)⁺ | LC MS* t_R |
|---|---|---|---|
| 1512 | 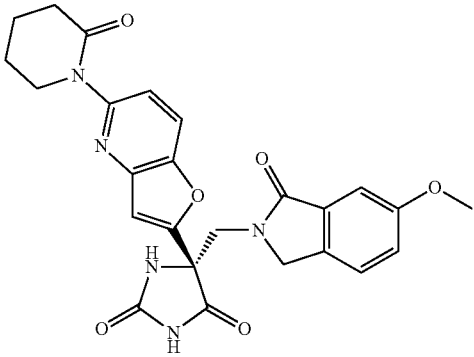 [SMILES: COc1ccc2c(c1)C(=O)N(C[C@@]1(c3cc4nc(N5CCCCC5=O)ccc4o3)NC(=O)NC1=O)C2] | 490.3 | 2.54 |
| 1522 | 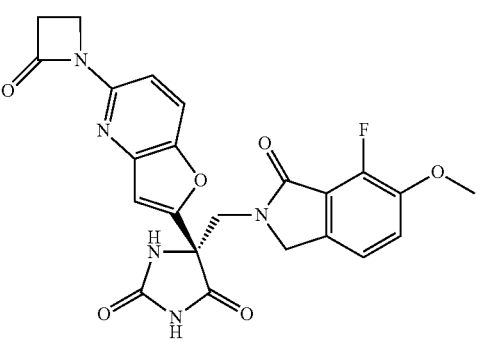 [SMILES: COc1ccc2c(c1F)C(=O)N(C[C@@]1(c3cc4nc(N5CCC5=O)ccc4o3)NC(=O)NC1=O)C2] | 480.3 | 2.79 |

In addition, compound 1502 was prepared using procedures similar to those described in Example 171.

Example 172

Part A

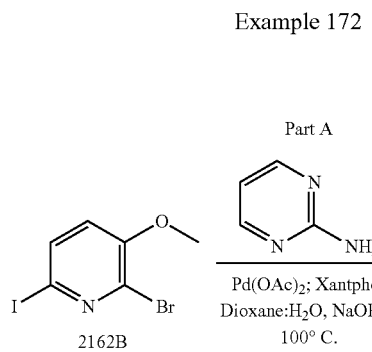

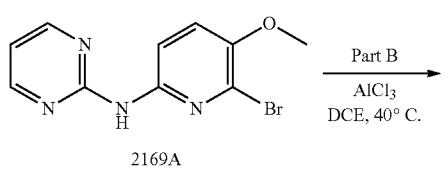

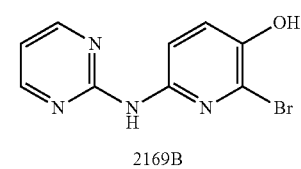

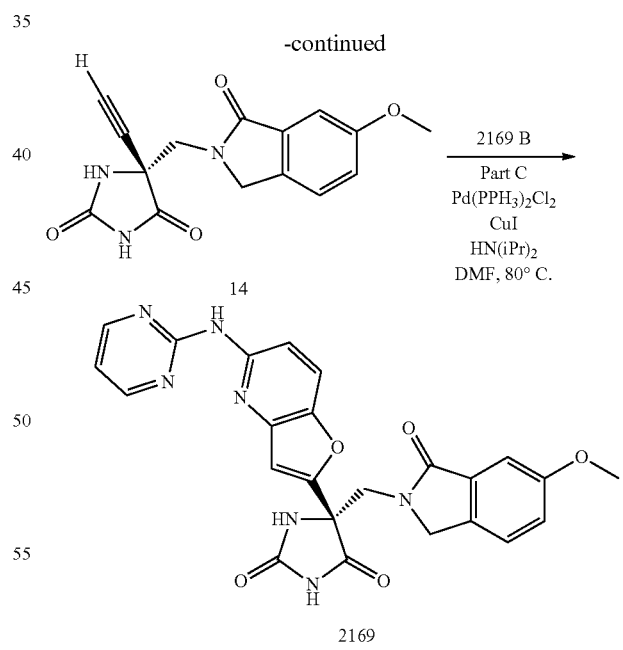

Part A:

A mixture of 2-bromo-5-iodo-3-methoxypyridine 2162 B (0.5 g, 1.6 mmol), 2-aminopyrimidine (0.14 g, 1.4 mmol), Palladium acetate (0.033 g, 0.15 mmol), Xanthphos (0.058 g, 0.1 mmol) sodium t-butoxide (0.24 g, 2.5 mmol) and Dioxane:H₂O (10:1; 5 mL) was charged into a sealed tube and purged with nitrogen (3×). The reaction was heated at 100° C. for 10 h. After cooling to room temperature the reaction was diluted with CH₂Cl₂ (150 ml), washed with water (2×50 ml) and brine (1×50 mL), dried (Na₂SO₄), filtered and concentrated to give a crude product which was purified by by flash column chromatography (ISCO CombiFlash Rf, SiO₂, 12 g cartridge (CH₂Cl₂ to 5% CH₃OH/CH₂Cl₂) to yield compound 2169A (0.28 g, 62%).

Part B:

The procedure from Example 168 part D was repeated on 2169A (0.13 g, 0.46 mmol) to provide 2169B (0.092 g, 77%).

Part C:

The procedure from Example 170 Part C was repeated on 2169B (0.1 g, 0.3 mmol) and 14 (0.09 g, 0.3 mmol) to provide 2169 (0.07 g, 45%). LC-MS $t_R$=2.12 min observed LCMS m/z 486.3 (M+H).

Similarly compound 2171 was made from 2162B using the procedure described in Example 172, using the corresponding amide in step Part A and compound 14 in step Part C.

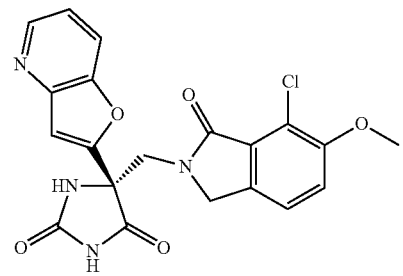

2153

| ID | STRUCTURE | (M + 1)⁺ | LC MS* $t_R$ |
|---|---|---|---|
| 2171 | 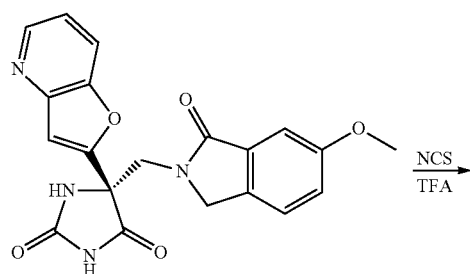 | 476.3 | 2.80 |

Example 173

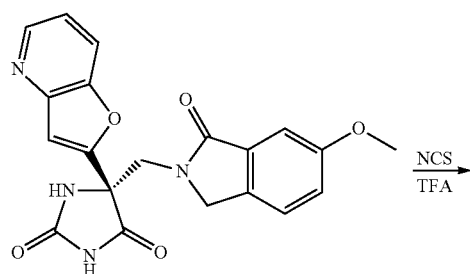

2153A

To a solution of compound 2153A (Sodium salt) (0.07 g, 0.17 mmol) in Trifluoroacetic acid (TFA, 8 mL), N-chlorosuccinimide (0.044 g, 0.32 mmol) was added in portions. The mixture was stirred for 3 days. The solvent was removed and the resulting semisolid material was dissolved in CH₂Cl₂: CH₃OH (75:25 mL) and treated with a 2 g of silica gel. The mixture was filtered and the mother liquor was concentrated then triturated with CH₂Cl₂. The supernatant was decanted. The insoluble residue was dried in high vacuum to yield 2153 (0.068 g, 89%). HPLC-MS $t_R$=2.17 min; observed LCMS m/z 427.3 (M+H).

Example 174

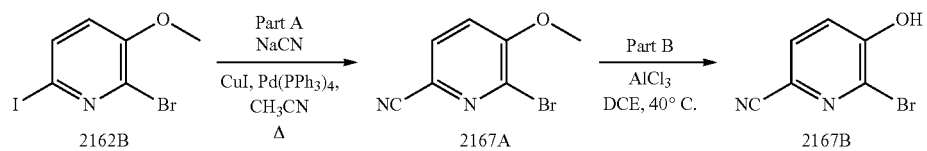

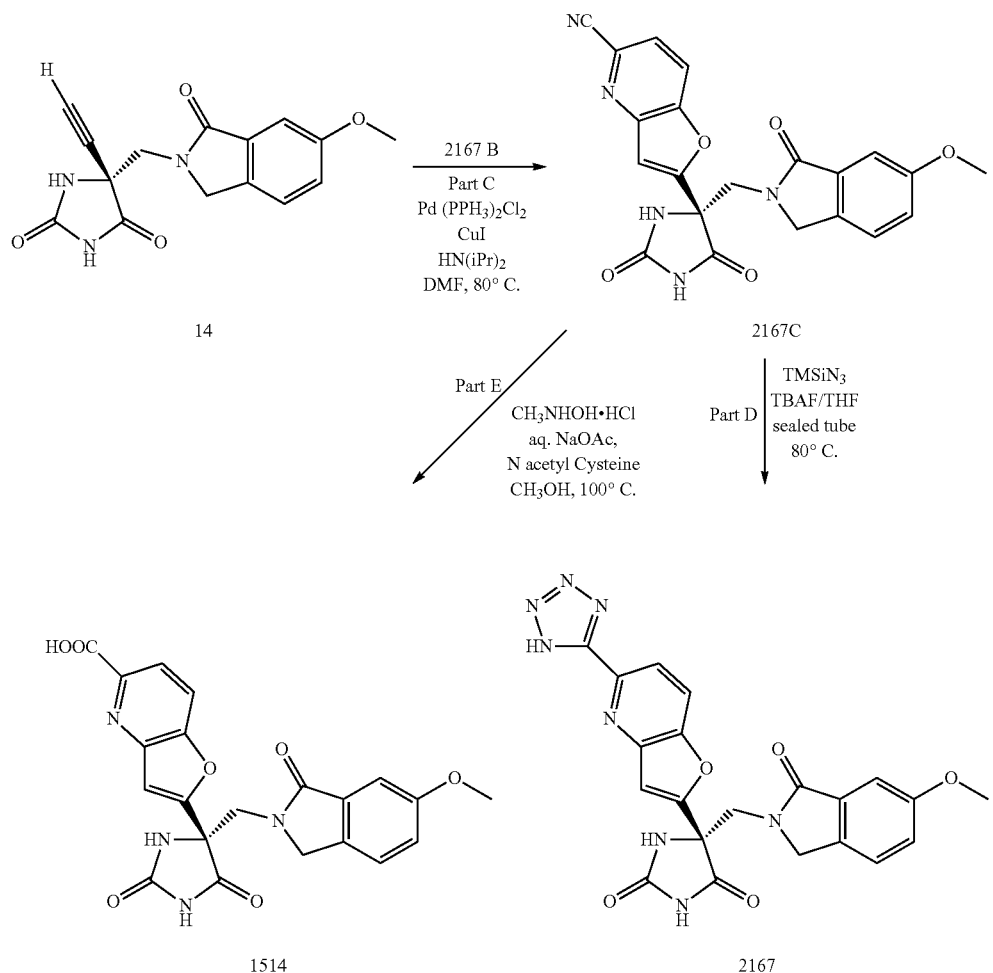

Part A:

A mixture of 2-bromo-5-iodo-3-methoxypyridine 2162 B (0.95 g, 3.0 mmol), NaCN (0.176 g, 3.6 mmol), (tetrakistriphenylphospine)palladium (0.2 g, 1.8 mmol), CuI (0.07 g, 0.4 mmol) and acetonitrile (10 mL) was charged into a sealed tube and purged with nitrogen (3×). The reaction was heated at 80° C. for 10 h. After cooling to room temperature the reaction was diluted with EtOAc (100 ml), washed with water (2×50 ml) and brine (1×50 mL), dried (Na$_2$SO$_4$), filtered, concentrated to give a crude which was purified by flash column chromatography (ISCO CombiFlash Rf, SiO$_2$, 12 g cartridge (hexanes to 35% EtOAc/hexanes) to yield compound 2167A (0.25 g, 30%).

Part B:

Procedure from Example 168 part D was repeated on 2167A (0.2 g, 0.93 mmol) to provide 2167B (0.11 g, 60%).

Part C:

Procedure from Example 170 part C was repeated on 2167B (0.12 g, 0.3 mmol) and 14 (0.11 g, 0.3 mmol) to provide 2167 C (0.09 g, 45%).

Part D:

A mixture of 2167C (0.01 g 0.025 mmol), TMSiN$_3$ (2 mL, excess), tetrabutylammonium fluoride (1M TBAF in THF, 0.1 mL) was charged into a sealed tube and purged with nitrogen (3×). The reaction was heated at 80° C. for 10 h. After cooling to room temperature the solvent was removed and the crude was subjected to reverse phase using 0% acetonitrile to 30% acetonitrile/water, to provide pure 2167 (0.0072 g, 70%). LC-MS* t$_R$=2.58 observed LCMS m/z 461.3 (M+H).

Example 175

2167C (0.015 g 0.025 mmol) was hydrolyzed under acidic conditions to provide 1514 (0.009 g, 60%). HPLC-MS t$_R$=2.52 min; observed LCMS m/z 436.2 (M+H).

Example 176

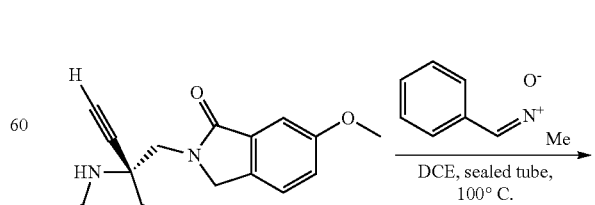

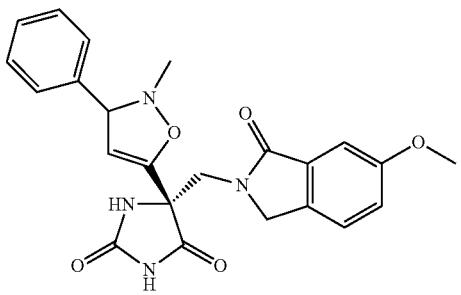

1526

A mixture of 14 (0.01 g), N-methylbenznitrone (0.005 g) in dichloroethane (1 mL) was charged into a sealed tube and the reaction was heated at 100° C. for 24 h. The reaction was cooled and the solvent was removed to yield crude product which was purified by reverse phase column chromatography water to 50% acetonotrile/water eluting system. Yield of 1526 (0.001 g, 10%) HPLC-MS $t_R$=3.35 min observed LCMS m/z 435.2 (M+H).

Example 177

1525 was prepared using the procedure described for Example 176, using 23. HPLC-MS $t_R$=3.31 min; observed LCMS m/z 453.2 (M+H).

Example 178

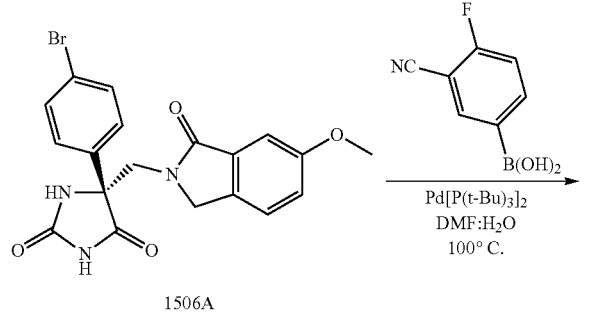

1506A

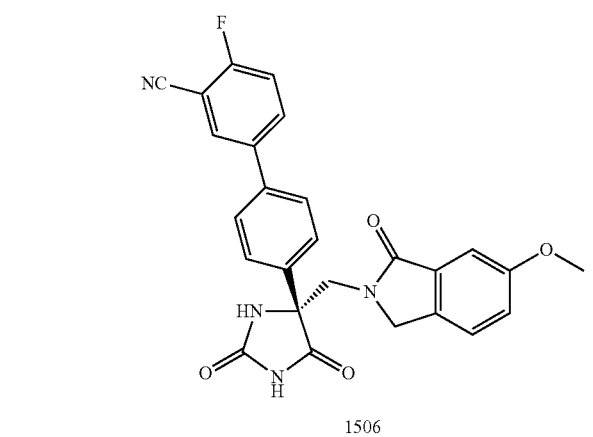

1506

A mixture compound 1506A (0.07 g, 0.16 mmol), 3-cyano-4-fluoro phenyl boronic acid (0.024 g, 0.12 mmol), Palladium bist-butylphospine (0.005 g), in DMF:H$_2$O (9:1, 2 mL) was charged into a sealed tube and purged with nitrogen (3×). The reaction was heated at 90° C. for 18 h. After cooling to room temperature the solvent was removed and the crude was subjected to reverse phase chromatography using a 0.1% formic acid in the aqueous mobile phase (100% water to 50% acetonotrile/water) to provide 0.048 g of pure product 1506. LC-MS $t_R$=3.9 min; observed LCMS m/z 471.3 (M+H).

Example 179

1503 was prepared using the procedure described for Example 178, using pyrrolidinopyrimidine boronic acid (commercially available). LC-MS* $t_R$=2.87 min; observed LCMS m/z 499.3 (M+H).

The HPLC conditions used to purify compound 153 are set forth below:

*Instrument (MS) name: PE Sciex API 150-EX single stage quadrupole

Solvent pumps: Shimadzu LC-10AD

Column: Phenomenex (Gemini, 5 micron, C18, 4.6 i.d.)

Solvent A: Water w/0.05% TFA (v/v)

Solvent B: Acetonitrile w/0.05% TFA (v/v)

Flow rate: 1 ml/min

Starting B conc: 10%

Gradient B 10%-95% in 5 mins, hold 2 mins, 95%-10% in 1 min

Example 180

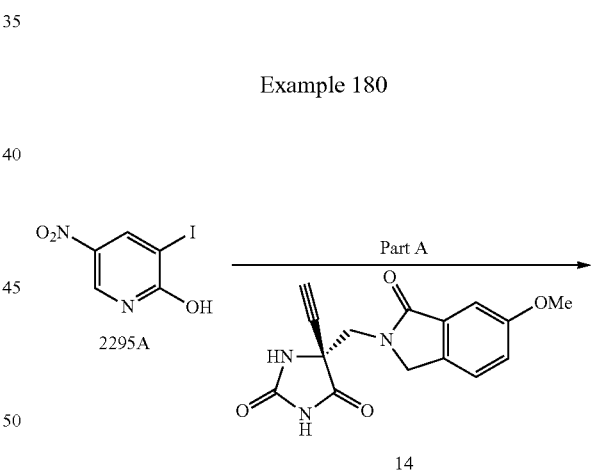

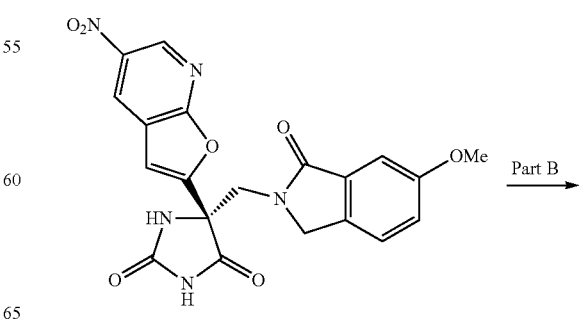

2295B

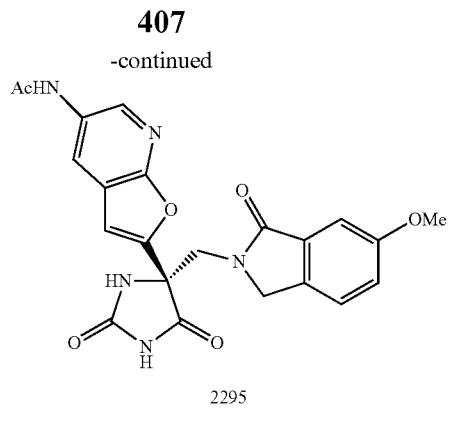

2295

Part A:

A mixture of 2295A (638 mg, 2.4 mmol), 14 (600 mg, 2 mmol), Pd$_2$(dba)$_3$ (36.6 mg, 0.04 mmol), dppf (44.3 mg, 0.08 mmol), CuI (15.2 mg, 0.08 mmol), and DIEA (1.05 mL, 6 mmol) in DMF (5 mL) was heated at 100° C. for 12 h. The reaction mixture was concentrated and purified by HPLC to afford 2295B (440 mg, 51%) as a pale yellow powder. HPLC-MS $t_R$=1.31 min (UV$_{254\ nm}$); mass calculated for formula C$_{20}$H$_{15}$N$_5$O$_7$ 437.10, observed LCMS m/z 438.1 (M+H).

Part B:

A mixture of 2295B (437 mg, 1.0 mmol) and iron granules (400 mg, 7.14 mmol) in acetic acid (5 mL) was heated at 100° C. for 5 h. The reaction mixture was concentrated and purified by HPLC to afford a white solid of 2295B (25.1 mg, 5.6%) as a byproduct. HPLC-MS $t_R$=2.48 min (UV$_{254\ nm}$); mass calculated for formula C$_{22}$H$_{19}$N$_5$O$_6$ 449.10, observed LCMS m/z 450.1 (M+H).

Compound 505 was prepared from compound 23 and the corresponding iodophenol using procedures similar to that described in Example 180.

Example 181

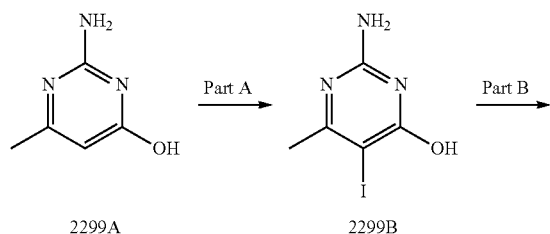

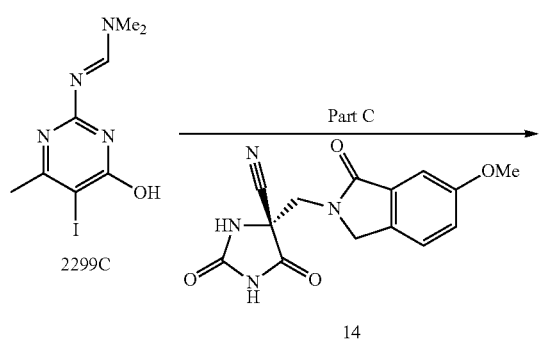

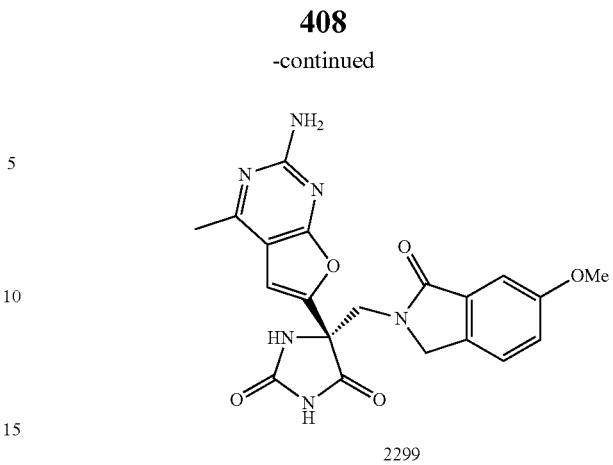

2299

Part A:

Compound 2299A (1.25 g, 10 mmol) and NIS (2.25 g, 10 mmol) in acetonitrile (30 mL) was heated at 80° C. for 12 h. After cooling to room temperature, the precipitate was collected by filtration, affording 2299B (2.41 g, 96%) as an off-white solid. HPLC-MS $t_R$=0.58 min (UV$_{254\ nm}$); mass calculated for formula C$_5$H$_6$IN$_3$O 250.96, observed LCMS m/z 252.0 (M+H).

Part B:

Compound 2299B (2.0 g, 8.0 mmol) and N,N-dimethylformamide dimethyl acetal (2 mL) in DMF (10 mL) were stirred at room temperature for 2 h. The precipitate was collected by filtration, affording 2299C (1.02 g, 42%) as a white solid. $^1$H NMR (DMSO-d$_6$), δ (ppm): 11.7 (s, 1H), 8.53 (s, 1H), 3.13 (s, 3H), 3.00 (s, 3H), 2.35 (s, 3H).

Part C:

A mixture of 2299C (110 mg, 0.36 mmol), 14 (90 mg, 0.3 mmol), Pd$_2$(dba)$_3$ (27.5 mg, 0.03 mmol), CuI (5.7 mg, 0.03 mmol), and DIEA (0.125 mL, 0.72 mmol) in DMSO (5 mL) was heated at 100° C. under microwave irradiation for 20 min. Ammonium hydrate (30%, 0.5 mL) was added, and the mixture was again heated at 100° C. under microwave irradiation for 10 min. The reaction mixture was concentrated and purified by HPLC to afford 2299 (5.7 mg, 4.5%) as an off-white solid. HPLC-MS $t_R$=1.12 min (UV$_{254\ nm}$); mass calculated for formula C$_{20}$H$_{18}$N$_6$O$_5$ 422.13, observed LCMS m/z 423.1 (M+H).

Compounds 2296 and 2305 were prepared using the above described procedures in Example 181.

Example 182

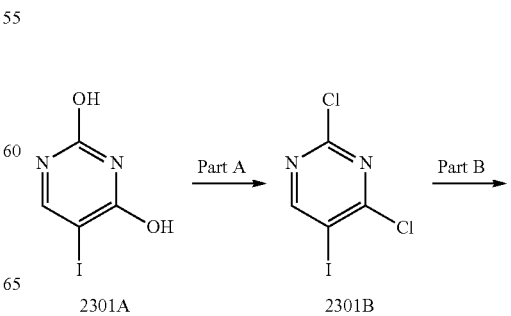

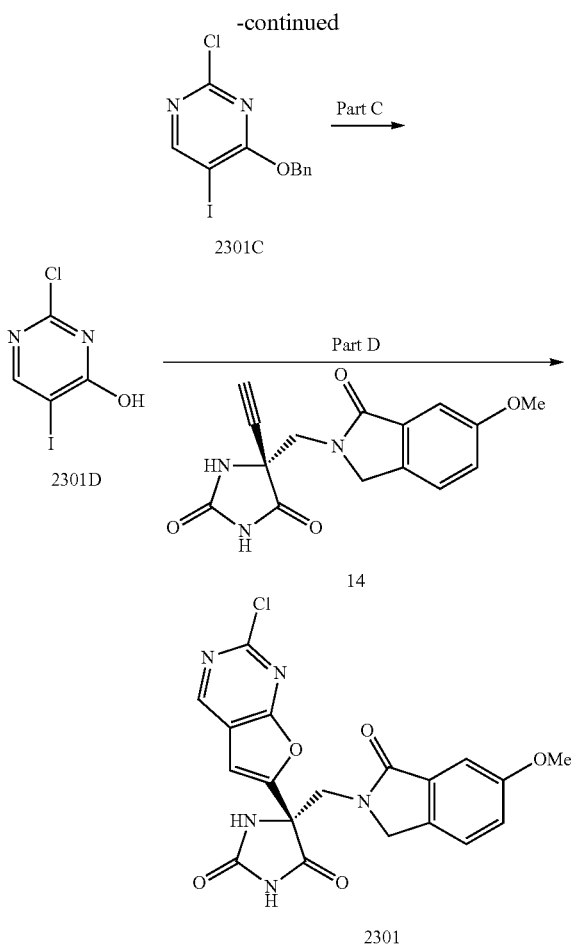

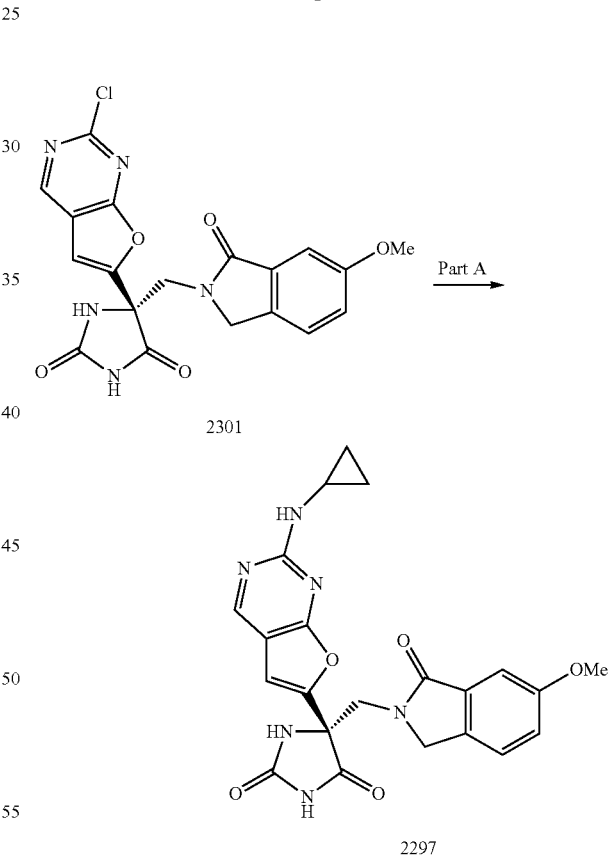

was stirred at −78° C. for 1 h then was allowed to warm to room temperature. LC-MS indicated that the reaction was completed. The solution was cooled to −78° C. again, and water (20 mL) was slowly added. Upon warming to room temperature, DCM was evaporated by rotary evaporation. The solid was collected by filtration and dried in vacuo to afford the crude product of 2301D (500 mg, 85%) as a yellow solid which was used for the subsequent reaction without purification. HPLC-MS $t_R$=0.819 min ($UV_{254\ nm}$); mass calculated for formula $C_4H_2ClIN_2O$ 255.89, observed LCMS m/z 256.9 (M+H).

Part D:

A mixture of 2301D (400 mg, 1.56 mmol), 14 (200 mg, 0.66 mmol), $Pd(PPh_3)_4$ (76 mg, 0.066 mmol), CuI (12.6 mg, 0.066 mmol), and DIEA (0.280 mL, 3.2 mmol) in DMSO (10 mL) was heated at 100° C. under microwave irradiation for 10 min. The reaction mixture was purified by HPLC to afford 2301 (115 mg, 41%) as a white solid. HPLC-MS $t_R$=2.58 min ($UV_{254\ nm}$); mass calculated for formula $C_{19}H_{14}ClN_5O_5$ 427.07, observed LCMS m/z 428.1 (M+H).

Example 183

Part A:

5-Iodouracil (10 g, 42 mmol) in $POCl_3$ (35 mL) was added with 0.1 mL of DMF. The mixture was stirred at 80° C. for 12 h, and concentrated to dryness. Crushed ice (~100 mL) was carefully added into the flask, and the mixture was allowed to stir for 30 min. Solid was collected by filtration, washed with water, and dried in vacuo, affording off-white solid 4.83 g. The filtrate was adjusted to pH ~3 with 1N NaOH, more precipitate was formed, which was also collected by filtration and dried. Total solid amount of 2301B was 6.09 g (53%). $^1$H NMR (DMSO-$d_6$), δ (ppm): 9.10 (s, 1H).

Part B:

Benzyl alcohol (1.24 mL) was added dropwise into a suspension of NaH (60% with mineral oil, 0.52 g) in dry DMF (30 mL) at 0° C., then stirred at room temperature for 1 h. Compound 2301B (2.75 g, 10 mmol) in dry DMF (10 mL) was added slowly via syringe. The reaction mixture was heated at 60° C. for 12 h and cooled to room temperature, $H_2O$ (40 mL) was added, the solution was extracted with EtOAc (30 mL×3). Organic extract was washed with 1N HCl, saturated $NaHCO_3$, brine, dried over $Na_2SO_4$, and concentrated. Flash column chromatography in $SiO_2$ (EtOAc/hexanes 20:80) afforded compound 2301C (2.5 g, 72%) HPLC-MS $t_R$=1.165 min ($UV_{254\ nm}$); mass calculated for formula $C_{11}H_8ClIN_2O$ 345.94, observed LCMS m/z 346.9 (M+H).

Part C:

Aluminum tribromide (1M solution in DCM, 6 mL) was added dropwise into a solution of compound 2301C (800 mg, 2.3 mmol) in DCM (15 mL) at −78° C. The reaction mixture Part A:

A mixture of 2301 (50 mg, 0.12 mmol) and cyclopropylamine (0.5 mL) in NMP (0.2 mL) was heated at 120° C. in the microwave for 15 minutes. The reaction mixture was concentrated and purified by HPLC to afford 2297 (23.2 mg, 37%) as a white solid. HPLC-MS $t_R$=2.798 min ($UV_{254\ nm}$); mass calculated for formula $C_{22}H_{20}N_6O_5$ 448.15, observed LCMS m/z 449.1 (M+H).

Compound 2298 was prepared in the same method.

Example 184

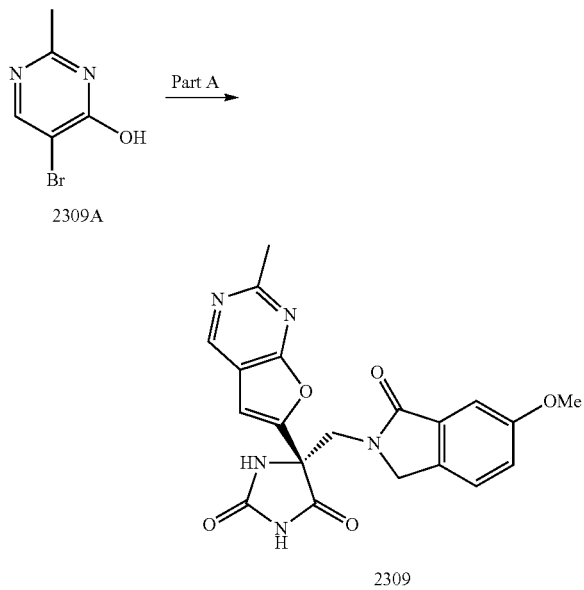

2309

Part A:

A mixture of 2309A (83 mg, 0.44 mmol), 14 (from Example 3) (120 mg, 0.4 mmol), Pd$_2$(dba)$_3$ (18.3 mg, 0.02 mmol), dppf (22 mg, 0.04 mmol), CuI (7.6 mg, 0.04 mmol), and DIEA (0.28 mL, 1.6 mmol) in DMF (2 mL) was heated at 150° C. under microwave irradiation for 10 min. The reaction mixture was concentrated and purified by HPLC to afford 2309 (60 mg, 37%) as a white solid. HPLC-MS $t_R$=2.22 min (UV$_{254\ nm}$); mass calculated for formula C$_{20}$H$_{17}$N$_5$O$_5$ 407.12, observed LCMS m/z 408 (M+H).

Example 185

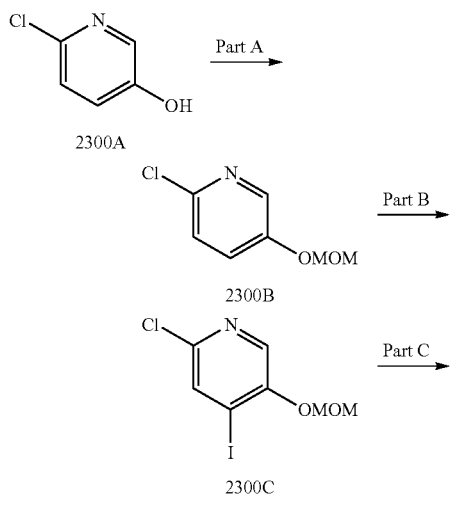

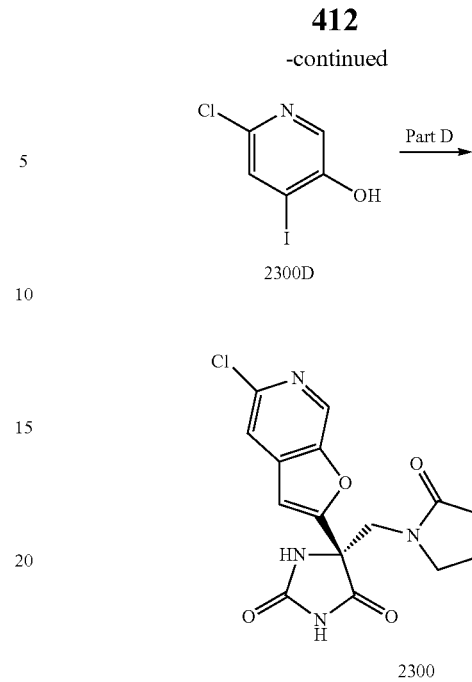

2300

Part A:

Chloromethyl methyl ether (3.42 mL, 45 mmol) was added dropwise into the mixture of compound 2300A (3.89 g, 30 mmol) and K$_2$CO$_3$ (8.29 g) in DMF (40 mL) at 0° C. The reaction mixture was stirred at 0° C. for 30 min then at room temperature overnight, diluted with EtOAc (100 mL) and H$_2$O (60 mL). The organic layer was separated, washed with Brine, dried over Na$_2$SO$_4$, and concentrated. Flash column chromatography on SiO$_2$ (EtOAc/hexanes 20:80) afforded compound 2300B (3.45 g, 66%) as a colorless liquid.

Part B:

n-BuLi (2.5 M solution in hexanes, 4.4 mL, 11 mmol) was added dropwise into a solution of compound 2300B (1.73 g, 10 mmol) in THF (40 mL) at −78° C. After stirring at this temperature for 1 h, iodine (3.05 g, 12 mmol) in THF (15 mL) was added dropwise during 30 min. The reaction mixture was allowed to stir at −78° C. for 30 min and quenched with 1N NH$_4$Cl aqueous solution, and diluted with EtOAc (60 mL) and H$_2$O (40 mL). The organic layer was separated, washed with Brine, dried over Na$_2$SO$_4$, and concentrated, giving rise to a white solid (2.8 g). Recrystallization in EtOAc/hexanes afforded compound 2230C (2.34 g, 78%).

Part C:

Compound 2300C (1.34 g, 4.47 mmol) in DCM (10 mL) was treated with trifluoroacetic acid (3 mL) for 1.5 h at room temperature to afford compound 2300D (1.02 g, 85%).

Part D:

A mixture of compound 2300D (175 mg, 0.6 mmol), 14 (150 mg, 0.5 mmol), Pd (PPh$_3$)$_4$ (29 mg, 0.025 mmol), CuI (4.8 mg, 0.025 mmol), and DIEA (0.35 mL, 2 mmol) in DMF (2 mL) was heated at 100° C. under microwave irradiation for 15 min. The reaction mixture was concentrated and purified by HPLC to afford 2300 (60 mg, 40%) as a white solid. HPLC-MS $t_R$=2.77 min (UV$_{254\ nm}$); mass calculated for formula C$_{20}$H$_{15}$ClN$_4$O$_5$ 426.07, observed LCMS m/z 427 (M+H).

Compound 2304 was prepared by the same procedure described above.

Example 186

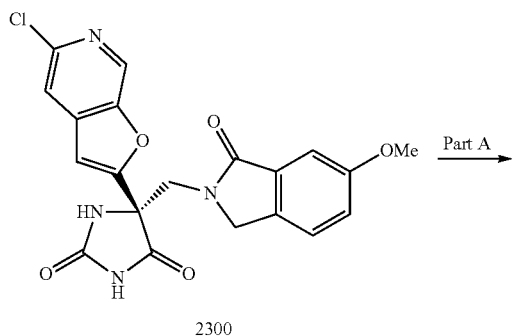
2300

2302

Part A:

A mixture of 2300 (30 mg, 0.07 mmol), trimethylboroxine (50% solution in THF, 35 mg, 0.14 mmol), bis(tri-t-butylphosphine)palladium (3.5 mg, 0.007 mmol), and potassium phosphate monohydrate (80 mg, 0.35 mmol) in DMF (1 mL) was heated at 150° C. under microwave irradiation for 10 minutes. The reaction mixture was purified by HPLC to afford 2302 (9.2 mg, 32%) as a white solid. HPLC-MS $t_R$=1.78 min (UV$_{254\ nm}$); mass calculated for formula $C_{21}H_{18}N_4O_5$ 406.13, observed LCMS m/z 407 (M+H).

Example 187

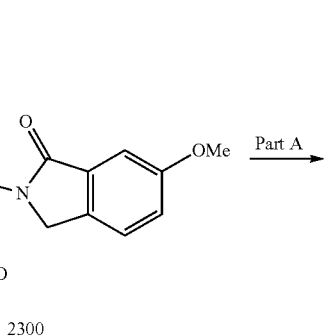
2303A       2303B

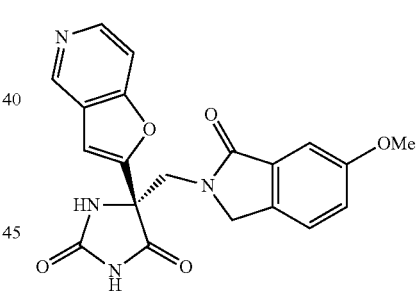
2303

Part A:

Compound 2303A (2.5 g, 14.36 mmol) and NIS in acetonitrile (40 mL) were heated at 80° C. overnight. After cooling to room temperature, the precipitate was collected by filtration to afford compound 2303B (2.06 g, 48%).

Part B:

A mixture of 2303B (108 mg, 0.36 mmol), 14 (from example 3) (90 mg, 0.3 mmol), Pd$_2$(dba)$_3$ (6.9 mg, 0.0075 mmol), dppf (8.3 mg, 0.015 mmol), CuI (2.9 mg, 0.015 mmol), and DIEA (157 µL, 0.9 mmol) in DMF (1 mL) was heated at 100° C. under microwave irradiation for 15 min. The reaction mixture was concentrated and purified by HPLC to afford 2303 (150 mg, 99%) as a white solid. HPLC-MS $t_R$=2.934 min (UV$_{254\ nm}$); mass calculated for formula $C_{20}H_{15}BrN_4O_5$ 470.02, observed LCMS m/z 471.0 (M+H).

Example 188

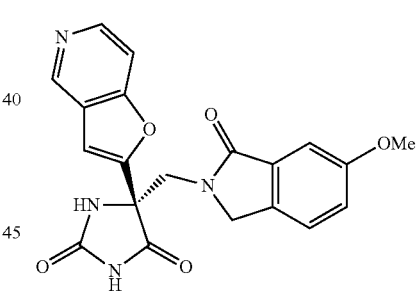
2259A

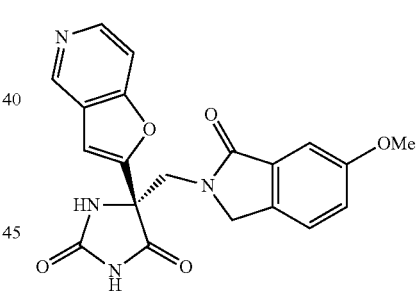
2306

Part A:

Compound 2259A (60 mg, 0.18 mmol) and NCS (24.3 mg, 0.18 mmol) in trifluoroacetic acid (0.5 mL) were stirred at room temperature for 3 days. The HPLC purification afforded compound 2306 (19.6 mg, 26%) as a white solid. HPLC-MS $t_R$=2.887 min (UV$_{254\ nm}$); mass calculated for formula $C_{20}H_{15}ClN_4O_5$ 426.07, observed LCMS m/z 427.1 (M+H).

Examples 189 and 190

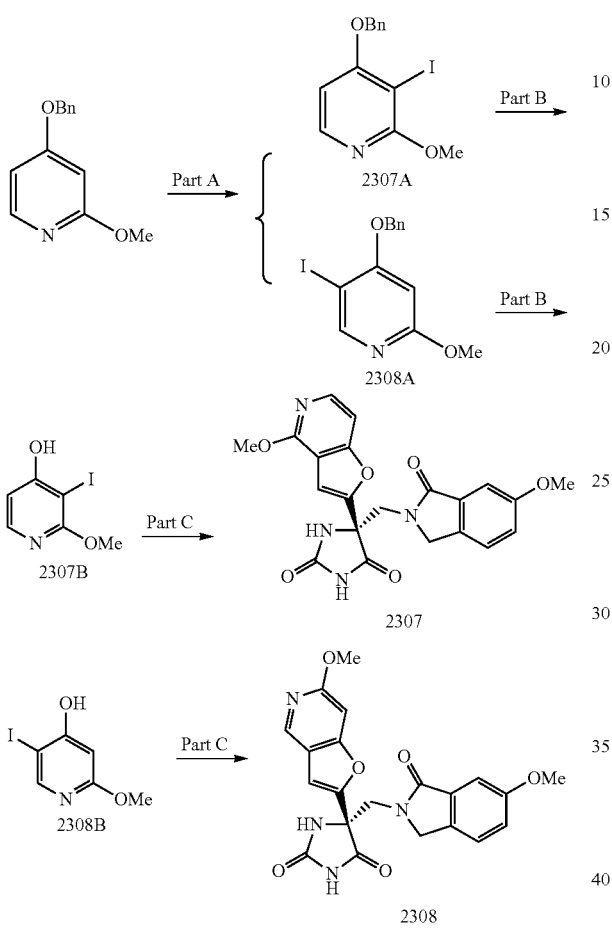

Part A:
4-benzyloxy-2-hydroxypyridine (2.0 g, 10 mmol) and NIS (2.25 g, 10 mmol) in acetonitrile (25 mL) were stirred at 80° C. overnight. After cooling to room temperature, the precipitate was collected by filtration, resulting in 1.7 g of solid, which was then dissolved in 20 mL of DMF, Ag$_2$CO$_3$ (4.0 g, 14.5 mmol) was added, followed by dropwise addition methyl iodide (1.5 mL). The reaction mixture was stirred at 50° C. overnight. The solid was filtered off; the solution was concentrated to dryness. Column chromatography in silica gel (EtOAc/hexane 20:80) afforded compound 2307A (2$^{nd}$ fraction, 900 mg, 26.4%) as a colorless oil and 2308A (1$^{st}$ fraction, 320 mg, 9.3%) as a white solid. $^1$H NMR (CDCl$_3$), 2307A: δ (ppm): 7.93 (d, J=5.93 Hz, 1H), 7.47-7.33 (m, 5H), 6.44 (d, J=5.83 Hz, 1H), 5.23 (s, 2H), 3.99 (s, 3H); 2308A: δ (ppm): 8.30 (s, 1H), 7.47-7.33 (m, 5H), 6.22 (s, 1H), 5.15 (s, 2H), 3.89 (s, 3H).

Part B:
Compound 2308A (300 mg, 0.88 mmol) in DCM (10 mL) was added dropwise with trifluoromethane sulfonic acid (0.5 mL) at −20° C., then stirred at room temperature for 30 min. Water (20 mL) was added slowly and 1N NaOH was added to adjust pH ~7. the mixture was extracted with DCM, dried over Na$_2$SO$_4$, concentrated, affording compound 2308B (150 mg, 68%) as a off-white solid. HPLC-MS $t_R$=0.702 min (UV$_{254\ nm}$); mass calculated for formula $C_6H_6INO_2$ 250.94, observed LCMS m/z 251.9 (M+H).

Part C:
A mixture of 2308B (138 mg, 0.55 mmol), 14 (150 mg, 0.5 mmol), Pd$_2$(dba)$_3$ (23 mg, 0.025 mmol), dppf (28 mg, 0.05 mmol), CuI (9.5 mg, 0.05 mmol), and DIEA (0.60 mL, 3 mmol) in DMF (2 mL) was heated at 150° C. under microwave irradiation for 15 min. The reaction mixture was concentrated and purified by HPLC to afford 2308 (72 mg, 49%) as a white solid. HPLC-MS $t_R$=2.31 min (UV$_{254\ nm}$); mass calculated for formula $C_{21}H_{18}N_4O_6$ 422.12, observed LCMS m/z 423.1 (M+H).

Compound 2307 was prepared in the same procedure.

Example 191

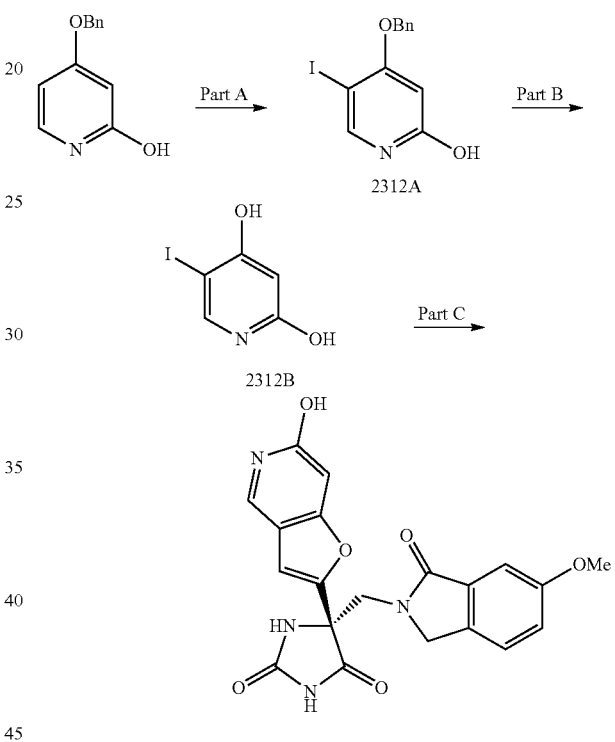

Part A:
4-benzyloxy-2-hydroxypyridine (4.0 g, 20 mmol) and NIS (4.5 g, 20 mmol) in acetonitrile (120 mL) were stirred at 80° C. overnight. After cooling to room temperature, the precipitate was collected by filtration, resulting in 1.5 g of solid. Recrystallization from acetonitrile afforded compound 2312A as an off-white solid (1.1 g). HPLC-MS $t_R$=1.530 min (UV$_{254\ nm}$); mass calculated for formula $C_{12}H_{10}INO$ 326.98, observed LCMS m/z 328.0 (M+H).

Part B:
To a suspension of compound 2312A (500 mg, 1.53 mmol) in DCM (8 mL) was added dropwise with trifluoromethane sulfonic acid (0.5 mL) at −20° C. The solid was gradually dissolved. The solution was allowed to stir at room temperature for 2 h and a precipitate formed. The solid was collected by filtration and dried in vacuo, affording compound 2312B (150 mg, 41%) as a off-white solid. HPLC-MS $t_R$=0.702 min (UV$_{254\ nm}$); mass calculated for formula $C_5H_4INO_2$ 236.93, observed LCMS m/z 238.0 (M+H).

Part C:

A mixture of 2312B (120 mg, 0.5 mmol), 14 (150 mg, 0.5 mmol), Pd$_2$(dba)$_3$ (23 mg, 0.025 mmol), dppf (28 mg, 0.05 mmol), CuI (9.5 mg, 0.05 mmol), and DIEA (0.348 mL, 2 mmol) in DMF (2 mL) was heated at 150° C. under microwave irradiation for 15 min. The reaction mixture was concentrated and purified by HPLC to afford 2312 (43 mg, 21%) as a white solid. HPLC-MS $t_R$=1.88 min (UV$_{254\ nm}$); mass calculated for formula C$_{20}$H$_{16}$N$_4$O$_6$ 408.11, observed LCMS m/z 409 (M+H).

Example 192 and 193

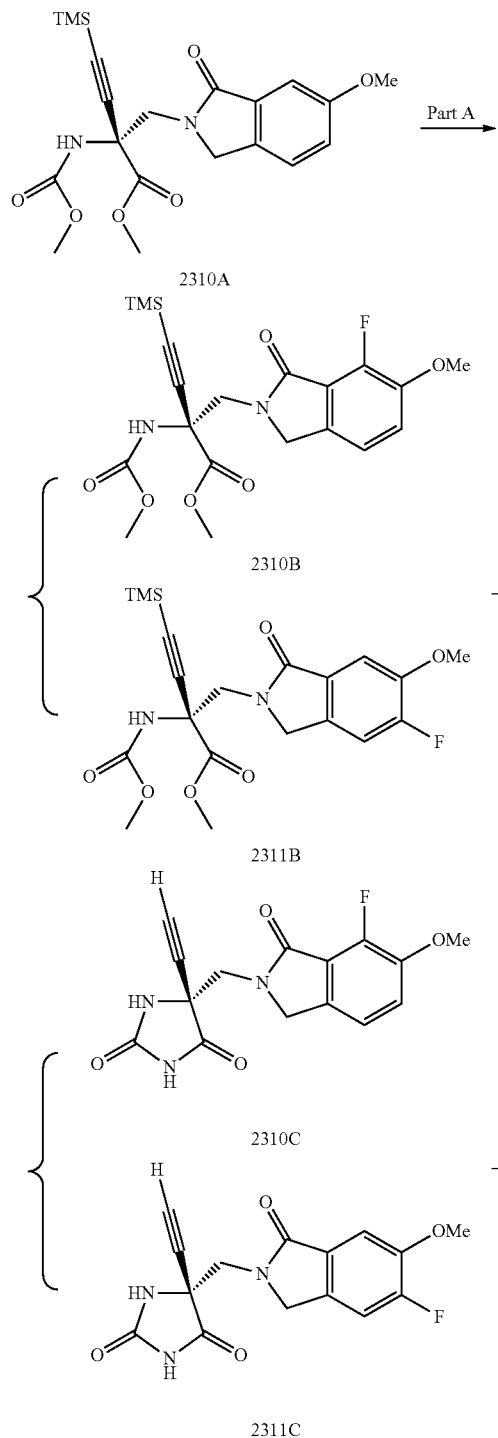

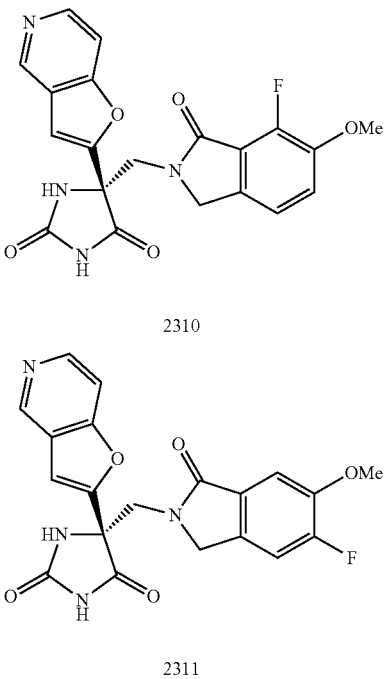

Part A:

A mixture of Compound 2310A (418 mg, 1 mmol) and F-TEDA (Selectofluor, 705 mg, 2 mmol) in acetonitrile (6 mL) was stirred at 80° C. for 1.5 h. The solvent vas removed by rotary evaporation, the residue was dissolved in EtOAc, washed with water, brine, dried over Na$_2$SO$_4$, and concentrated. Flash column chromatography on SiO$_2$ (EtOAc/hexanes 60:40) afforded a mixture (240 mg, 55%) of compounds 2310B and 2311B. HPLC-MS $t_R$=1.867 min (UV$_{254\ nm}$); mass calculated for formula C$_{20}$H$_{25}$FN$_2$O$_6$Si 436.15, observed LCMS m/z 437.1 (M+H).

Part B:

The above mixture of compounds 2310B and 2311B was added with 5 mL of 7 N ammonia in methanol and heated at 80° C. for 2 h. Rotary evaporation afforded a mixture (160 mg, 92%) of compounds 2310C and 2311C. HPLC-MS $t_R$=0.940 min (UV$_{254\ nm}$); mass calculated for formula C$_{15}$H$_{12}$FN$_3$O$_4$ 317.08, observed LCMS m/z 318.1 (M+H).

Part C:

A mixture of 2310B and 2311B (160 mg, 0.5 mmol), 2256B (110.5 mg, 0.5 mmol), Pd$_2$(dba)$_3$ (23 mg, 0.025 mmol), dppf (28 mg, 0.05 mmol), CuI (9.5 mg, 0.05 mmol), and DIEA (0.348 mL, 2 mmol) in DMF (2 mL) was heated at 100° C. under microwave irradiation for 20 min. The reaction mixture was concentrated and purified by HPLC to afford compounds 2310 (35 mg, 17%, HPLC-MS $t_R$=2.135 min (UV$_{254\ nm}$) and 2311 (7 mg, 3.5%, HPLC-MS $t_R$=2.234 min (UV$_{254\ nm}$); mass calculated for formula C$_{20}$H$_{15}$FN$_4$O$_5$ 410.10, observed LCMS m/z 411.1 (M+H).

Example 194

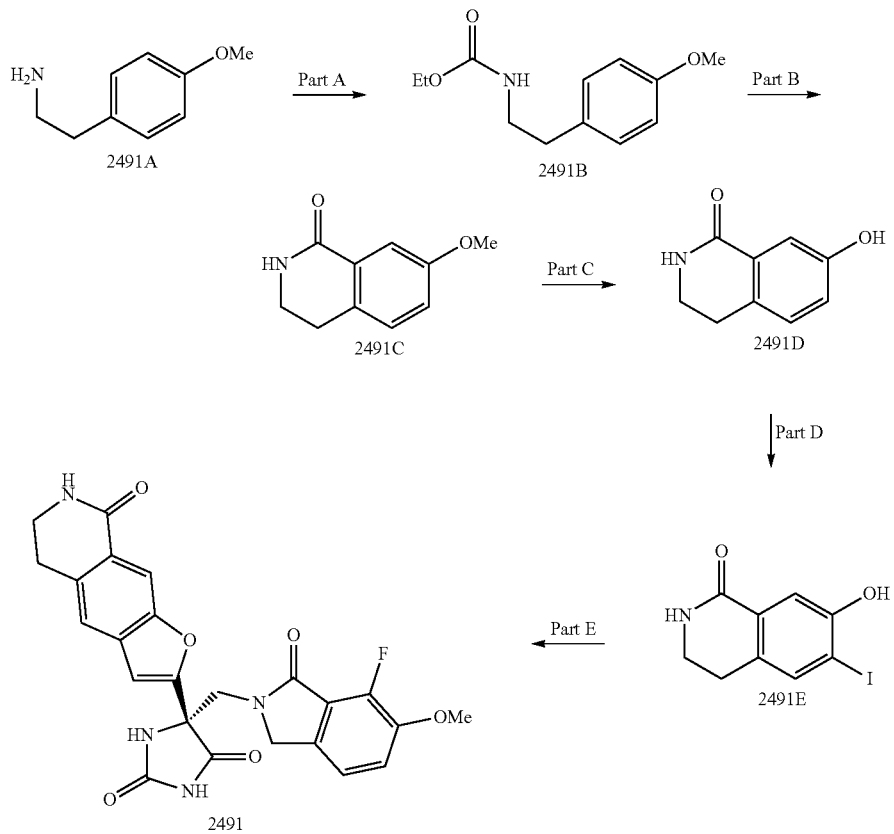

Part A:

Neat ethyl chloroformate (4.4 mL, 5.0 g, 46 mmol) was added dropwise over 10 min to a stirred, ice-cold solution of 1-aminoethyl-4-methoxybenzene 2491A (6.3 g, 42 mmol) and triethylamine (6.3 mL, 4.6 g, 46 mmol) in dry dichloromethane (125 mL). The reaction was allowed to proceed at 0° C. for 45 min. The reaction mixture was washed sequentially with water (2×~100 mL) and brine (~100 mL). The organic layer was dried over anhydrous MgSO$_4$, filtered and concentrated to give intermediate 2491B as a pale yellow liquid (9.03 g, 97% yield), which was used without further purification.

Part B:

Polyphosphoric acid (21 g) was weighed into a 100-mL round bottom flask. The flask was lowered into a preheated 120° C. oil bath and was heated for ~20-30 min until magnetic stirring of the viscous liquid at ~200-400 rpm became possible. At this point, the carbamate 2491B (4.92 g, 22.1 mmol) was added in portions. The dark reaction mixture was stirred at 120° C. for 2 h. The temperature of the reaction mixture was allowed to cool below 100° C. Water (10 mL) was added slowly and cautiously to the stirred reaction mixture, which was then allowed to cool to rt. The mixture was extracted with EtOAc (2×250 mL). The combined organic extracts were washed with saturated aq NaHCO$_3$ (~300 mL) and brine (~300 mL), dried over anhydrous MgSO$_4$, filtered and concentrated. The residue was purified by reverse-phase chromatography (130 g Teledyne-ISCO RediSep® C18 cartridge; 10-90% acetonitrile-water gradient. The bicyclic lactam 2491C was obtained as a beige solid (751 mg, 19% yield).

Part C:

Solid benzolactam 2491C (1.02 g, 5.76 mmol) and pyridinium chloride (4.00 g, 34.8 mmol) were admixed in a 15-mL pressure tube. The tube was flushed with nitrogen, capped and lowered completely into a preheated 170° C. oil bath to prevent potential sublimation of pyridinium chloride into the headspace above the reaction mixture. The reaction was allowed to proceed at 170° C. for 4 days. The mixture was allowed to cool, but before the contents started to solidify again, DMF (~7 mL) was added. The resulting brown solution was allowed to cool to rt and was then injected onto a 130 g Teledyne-ISCO RediSep® C18 cartridge. Elution using a 0-95% [MeCN+1% HCO$_2$H]/[H$_2$O+1% HCO$_2$H] gradient gave the desired product 2491D as a beige solid (920 mg, 98% yield).

Part D:

A solution of potassium iodide (433 mg, 2.61 mmol) and iodine (199 mg, 0.784 mmol) in water (0.65 mL) was added dropwise over ~5 min to a stirred solution of hydroxybenzolactam 2491D (142 mg, 0.871 mmol) in concentrated ammonium hydroxide (2.0 mL). The dark yellow-brown reaction mixture was stirred at rt for 24 h, and was then concentrated under reduced pressure to afford a brown residue. The residue was suspended in water (~5 mL). 1 M aq. HCl (~1 mL) was added, and the resulting tan precipitate was collected by filtration. The collected solid was dried in a vacuum oven (~20 mmHg, 45° C.) for 24 h. The desired product 2491E was obtained as a tan solid (159 mg, 63% yield). $^1$H NMR (500 MHz, CD$_3$OD): δ (ppm)=7.69 (s, 1H), 7.37 (s, 1H), 3.47 (t, J=7 Hz, 2H), 2.88 (t, J=7 Hz, 2H). Mass calcd for formula C$_9$H$_8$INO$_2$ 288.96, observed m/z 290.3 [M+H]$^+$.

Part E:

The hydroxyiodobenzolactam 2491E was converted to the target compound 2491 using the procedure given in Example 6. HPLC-MS $t_R$=2.83 min (UV$_{254\ nm}$); mass calculated for formula $C_{24}H_{19}FN_4O_6$ 478.13, observed LCMS m/z 479.3 [M+H]$^+$.

Example 195

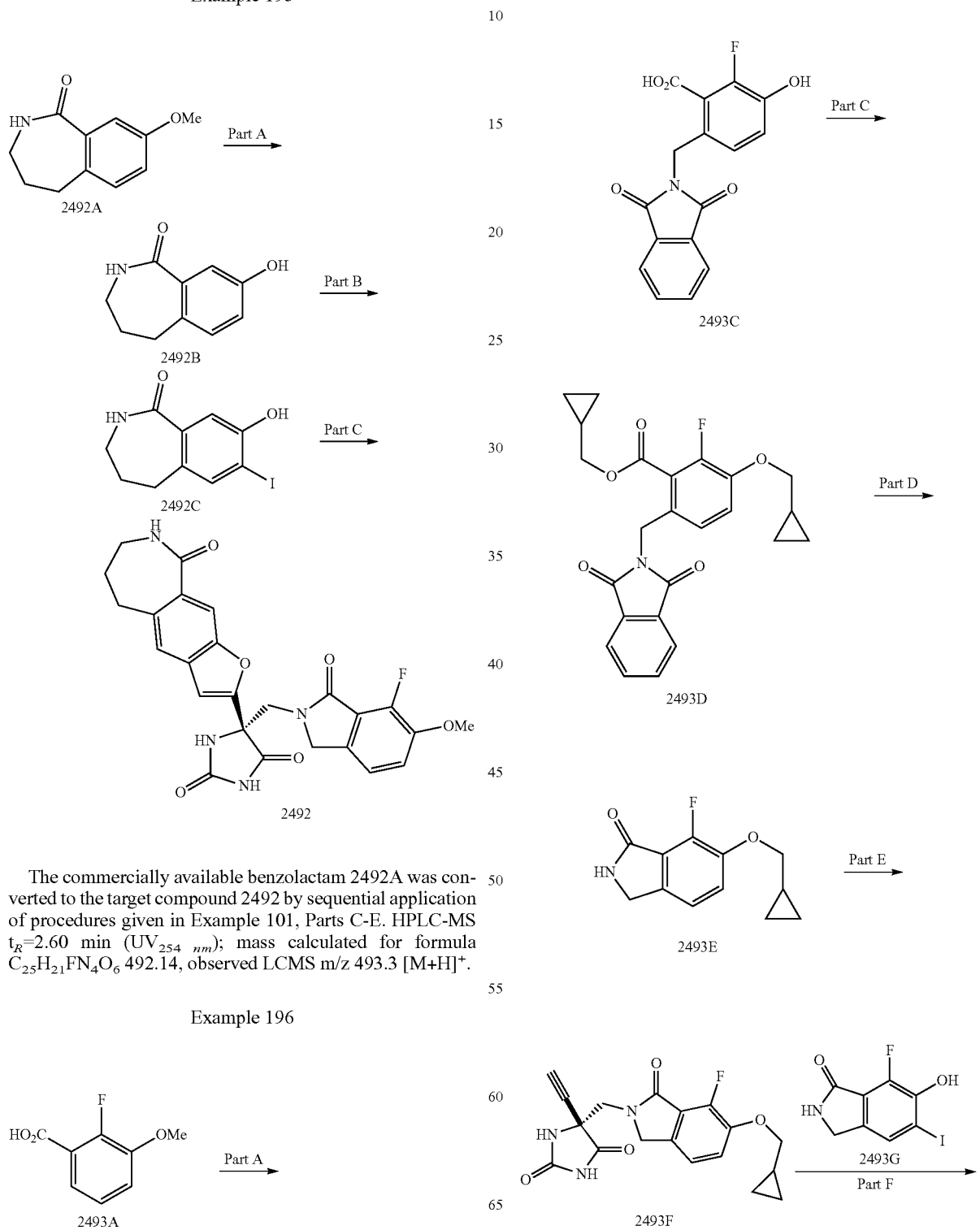

The commercially available benzolactam 2492A was converted to the target compound 2492 by sequential application of procedures given in Example 101, Parts C-E. HPLC-MS $t_R$=2.60 min (UV$_{254\ nm}$); mass calculated for formula $C_{25}H_{21}FN_4O_6$ 492.14, observed LCMS m/z 493.3 [M+H]$^+$.

Example 196

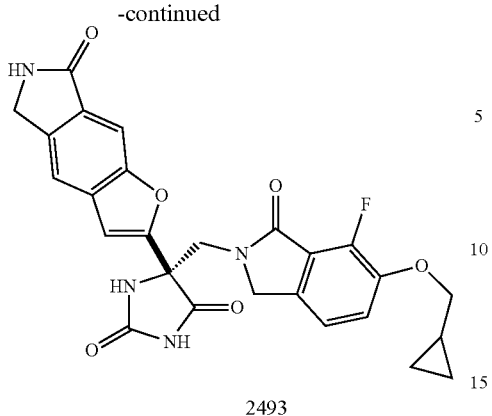

2493

Part A:

Commercially available 2-fluoro-3-methoxybenzoic acid 2493A was converted to the hydroxy derivative 2493B using the procedure given in Example 195, Part A.

Part B:

A mixture of 2493B (1.06 g, 6.76 mmol) and N-hydroxyphthalimide (1.26 g, 7.11 mmol) was added in portions to conc. sulfuric acid that had been precooled to 0° C. The solution was stirred at 0° C. for 3 h, and then poured into an ice-water mixture. The mixture was stirred for 15 min. The precipitated solid was collected by filtration, washed with water, and dried in vacuo to give the hydroxyacid 2493C as an off-white solid (2.13 g) which was used without further purification.

Part C:

Solid cesium carbonate (8.83 g, 27.2 mmol) was added to a stirred solution of hydroxyacid 2493C (2.14 g, 6.79 mmol) in DMF (20 mL) and the suspension was stirred at rt for 15 min. Bromomethylcyclopropane (2.7 mL, 3.7 g, 27 mmol) was added and the reaction mixture was stirred overnight at rt. The reaction mixture was filtered through a Celite® pad and then purified directly by reverse-phase chromatography (Teledyne-ISCO RediSep® C18 cartridge; 10-90% acetonitrile-water gradient, followed by normal phase sgc (0-10% MeOH—CH$_2$Cl$_2$ gradient) to give 1.42 g (49% yield) of Compound 2493D.

Part D:

In a pressure vessel, hydrazine hydrate (0.33 mL, 334 mg, 6.68 mmol) was added to a stirred solution of Compound 2493D (1.42 g, 3.34 mmol) in methanol (15 mL). The vessel was sealed and immersed in a preheated 70° C. oil bath. The reaction mixture was stirred at 70° C. for 1 h. The solvent was removed by evaporation under reduced pressure. The resulting solid was suspended in 1 M aq. potassium carbonate (20 mL) and stirred for 1 h. The solid was collected by filtration and dried overnight under vacuum (<1 mmHg). Compound 2493E was obtained in 683 mg, 92% yield.

Part E:

Compound 2493E was elaborated to Compound 2493F by sequential application of procedures described in Example 1, Parts D and E; then Example 2, Parts E-G; and finally Example 3.

Part F:

Compound 2493F was converted to the target Compound 2493 by reaction with hydroxyiodobenzolactam 2493G (see Example 197) following the procedure given in Example 6.

Compound HPLC-MS $t_R$=2.93 min (UV$_{254\ nm}$); mass calculated for formula $C_{26}H_{20}F_2N_4O_6$ 522.14, observed LCMS m/z 523.3 [M+H]$^+$.

Example 197

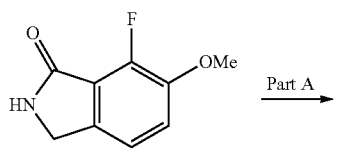

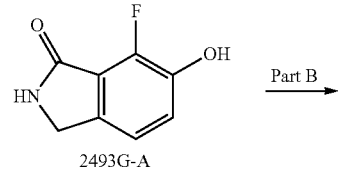

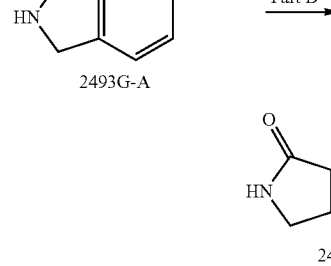

Compound 2493G was prepared from Compound 19 (Example 4) following the procedures described in Example 103 or in Example 101, Parts C-D. Mass calculated for formula $C_8H_5FINO_2$ 292.9, observed m/z 294.0 [M+H]$^+$.

Example 198

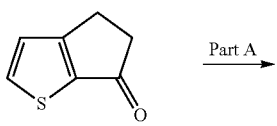

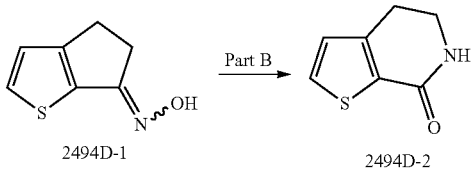

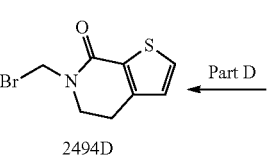

Part A 4,5-Dihydro-6H-cyclopenta[b]thiophen-6-one was prepared according to the procedure described in: Bonini, B. F. et al *Eur. J. Org. Chem.* 2004, 4442-4451. It was converted to 2494D-1 using procedures described in WO2007/146758 (pp 32-33).

Part B

Compound 2494D-1 was converted to 2494D-2 using procedures described in WO2007/146758 (pp 32-33).

Part C

Compound 2494D-2 (0.16 g, 1.0 mmol) was dissolved in THF (7 mL, Aldrich anhydrous) and DMPU (1 mL). Sodium tert butoxide (0.12 g, 1.25 mmol) was added in several portions. The reaction mixture was stirred at rt for 1 h. Chloromethyl pivalate (0.20 g, 1.49 mmol) was added dropwise. The reaction mixture was capped with a septum and stirred overnight at rt. The reaction mixture was diluted with EtOAc and washed with water. The organic layer was concentrated to dryness. The crude product was purified via sgc using a 20%-80% EtOAc/hexanes gradient as the mobile phase. The major product was isolated to give 0.25 g of 2494D-3. $^1$HNMR (CDCl$_3$) δ 7.57 (d, 5 Hz, 1H), 6.97 (d, 5 Hz, 1H), 5.62 (d, 1H), 3.75-3.84 (m, 2H), 3.03-2.94 (m, 2H), 1.25 (s, 9H).

Part D

Compound 2494D-3 (0.25 g, 0.94 mmol) was dissolved in 5 mL of CH$_2$Cl$_2$. The flask was placed under N$_2$ and cooled in an ice-water bath. Trimethylsilyl bromide (0.29 g, 1.89 mmol) was added dropwise. The reaction mixture was stirred for 1 h at 0° C. The ice bath was removed and the reaction mixture was stirred at rt on. The reaction mixture was partially concentrated to remove about 2 mL of CH$_2$Cl$_2$. Hexanes (10 mL) were added causing the product to precipitate. The solid was filtered off, then washed with hexanes. The resulting solid was dried under vacuum to give 0.19 g of 2494D. $^1$HNMR (CD$_3$OD) δ 7.73 (d, J=5 Hz, 1H), 7.05 (d, J=5 Hz, 1H), 4.93-4.91 (m, 4H), 3.79-3.69 (m, 2H), 3.06-2.97 (m, 2H).

Example 199

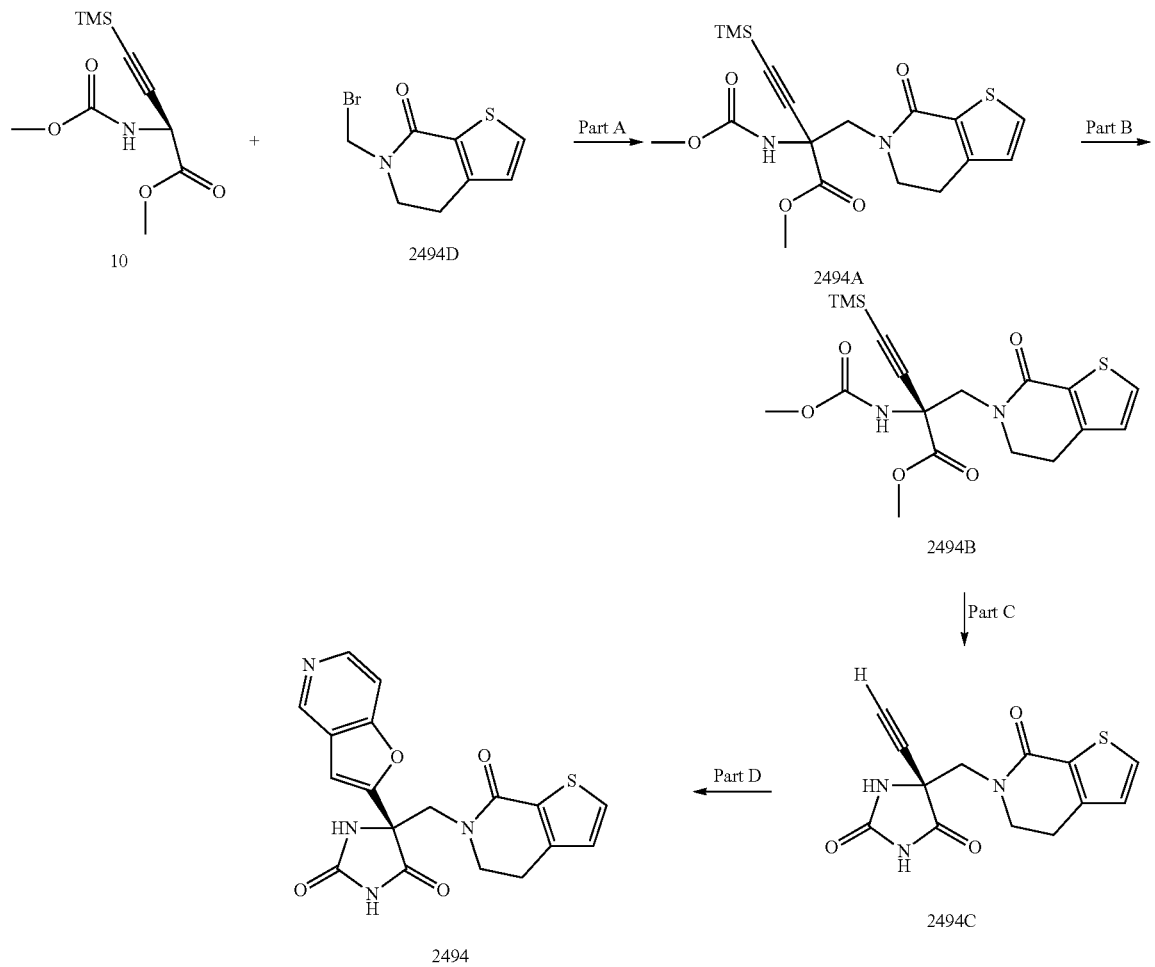

Part A

Compound 10 (0.19 g, 0/8 mmol) and compound 2494D (0.19 g, 77 mmol) were dissolved in 5 mL of THF (Aldrich anhydrous). The flask was capped with a septum, placed under N$_2$, and cooled in a dry-ice/acetone bath. Lithium bis(trimethylsilyl)amide solution (1.54 mL of 1M LiHMDS in THF) was added dropwise via syringe. The reaction mixture was stirred for 2 h then quenched with aq NH$_4$Cl solution. The reaction mixture was diluted with EtOAc and washed with aq NH$_4$Cl solution and water. The organic layer was concentrated to dryness. The crude product was purified via flash sgc using a 20%-100% EtOAc/hexanes gradient as the mobile phase to give 0.24 g of 2494A. $^1$HNMR CDCl$_3$ δ 7.53 (d, 5 Hz, 1H), 6.93 (d, 5 Hz, 1H), 4.34-4.25 (m, 1H), 3.98-3.88 (m, 1H), 3.88 (s, 3H), 3.80-3.70 (m, 2H), 3.68 (s, 3H), 3.06-2.83 (m, 2H), 0.20 (s, 9H).

Part B

Compound 2494A was separated into its enantiomers via chiral HPLC on a Chiral Technologies preparative Chiralpak OD column. Absolute ethanol/hexanes (10:90) were used as the mobile phase at a flow rate of 40 mL/min. The detector was set at 266 nm. The second peak off the column gave the biologically active enantiomer.

Part C

Compound 2494B was converted into 2494C using a procedure similar to that described in Example 3. $^1$HNMR (CD$_3$OD) δ 7.69 (d, 5 Hz, 1H), 6.93 (d, 5 Hz, 1H), 4.17 (d, 6 Hz, 1H), 3.96 (d, 6 Hz, 1H), 3.85-3.67 (m, 2H), 3.26 (s, 1H), 3.03-2.85 (m, 2H).

Part D

Copper (I) iodide (2 mg, 0.01 mmol), 3-iodo-4-hydroxypyridine (66 mg, 0.29 mmol), Pd(PPh$_3$)$_2$Cl$_2$ (1 mg, 0.001 mmol) were added to a rb flask equipped with a stir bar and placed under N$_2$ blanket via vacuum evacuation and N$_2$ backfill. Compound 2494C (43 mg, 0.15 mmol) and diisopropyl amine (50 microliters) were dissolved in DMF and added via syringe. The reaction mixture was heated at 80° C. for 24 h. The reaction mixture was diluted with EtOAc and washed with water. The organic layer was concentrated to dryness. The crude product was purified via prep TLC using CH$_2$Cl$_2$/MeOH/NH$_4$OH 100/10/1 as the mobile phase. The major band was isolated as product. The resulting material was dissolved in methanol. HCl in diethyl ether was added until the pH was about 1. The resulting solution was concentrated to dryness. The product was dried under vacuum to give 29 mg of 2494. LCMS calcd 382.07 obsd 383.2

Example 200

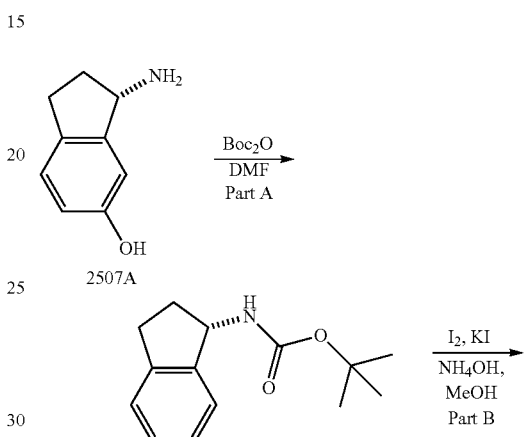

Part A

Compound 2504A (460 mg, 2.82 mmol) and pyridine HCl (1.95 g, 16.9 mmol) were placed in a 5 mL microwave reaction tube and sealed. The tube was heated to 200° C. for one hour. After cooling down, the residue was dissolved in DMF and purified by C18 chromatography (CH$_3$CN/H$_2$O, 5% to 90%, with 0.1% HCO$_2$H) to give compound 2504B (270 mg, 64.2%)

Part B

Compound 2504B (270 mg, 1.81 mmol) was dissolved in NH$_3$—H$_2$O (37%, 7 mL). A solution of I$_2$ (307 mg, 1.21 mmol) and KI (803 mg, 4.84 mmol) in water (2 mL) was added dropwise. After the addition was completed, the solution was stirred at 25° C. for 1 h, The solution was concentrated to about one fourth of its original volume. The pH value was adjusted to 2~4 with HCl (2N). The solid was collected by filtration, washed with water, and dried under vacuum for overnight to give compound 2504C (347 mg, 70.0%)

Compounds 2498, 2503, 2504, 2505, and 2506 were prepared by the methods described in Part A to C of Example 1, Example 200, and Example 6.

Compound 2497 and 2499 were prepared by the methods described in Part A to C of Example 4, Example 200, and Example 6.

Example 201

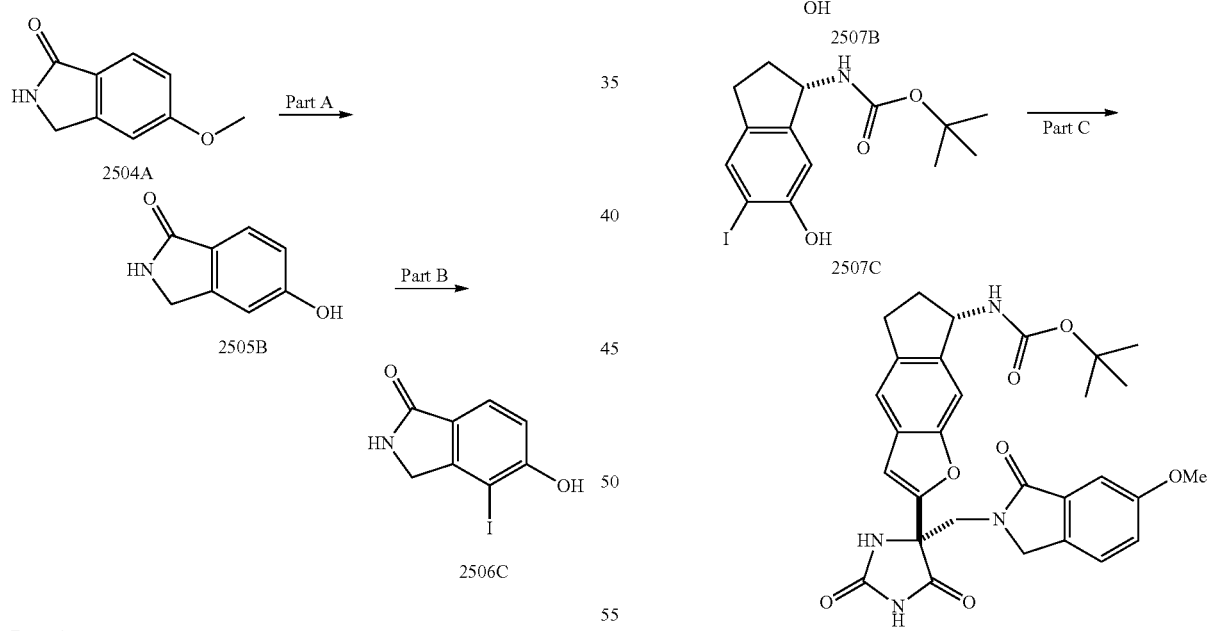

Part A

Solid di-t-butyl dicarbonate (439 mg, 2.01 mmol) was added to a solution of the hydroxyamine 2507A (300 mg, 2.01 mmol; Aldrich) in dry DMF (10 mL) and the reaction was stirred overnight at rt. The reaction mixture was diluted with EtOAc (100 mL) and washed with water (3×~25 mL). The organic layer was washed with brine (~25 mL), dried over anhydrous MgSO$_4$, filtered and concentrated to afford 0.530 g of Compound 2507B as a colorless oil (72% yield).

Part B

The alcohol 2507B (239 mg, 0.96 mmol) was suspended in conc. ammonium hydroxide (6 mL). Methanol was added dropwise until all of the solid 2507B was dissolved. A solution of iodine (194 mg, 0.77 mmol) and potassium iodide (518 mg, 3.1 mmol) in water (2 mL) was added dropwise at rt. The reaction mixture was stirred overnight at rt. The volatile solvent component was removed under reduced pressure. The pH of the resulting solution was adjusted to ~2 using 2 N HCl. EtOAc (~25 mL) was added. The aqueous layer was separated and extracted with EtOAc (2×~25 mL). The combined extracts were washed with water (~25 mL) and brine (~25 mL), then dried over anhydrous $MgSO_4$, filtered and concentrated to afford a crude solid. Sequential purification by sgc (0-100% EtOAc-hexanes gradient) and PTLC (20% EtOAc-hexanes) afforded 106 mg of the desired product, Compound 2507C, as an off-white solid (29% yield).

Part C

Iodo-alcohol 2507C was converted into Compound 2507 by following the procedure given in Yu, W. et al. PCT Appl. WO2007084455 (A1), p. 131 for Example 44, Part B.

Example 202

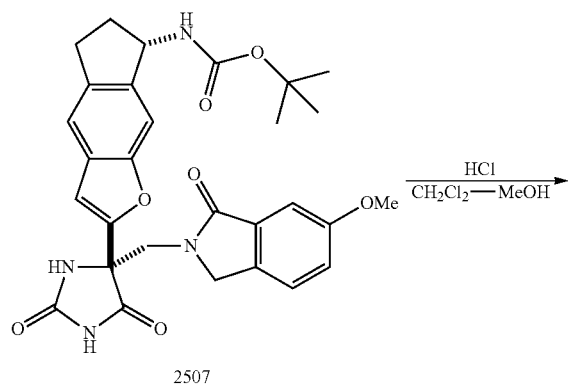

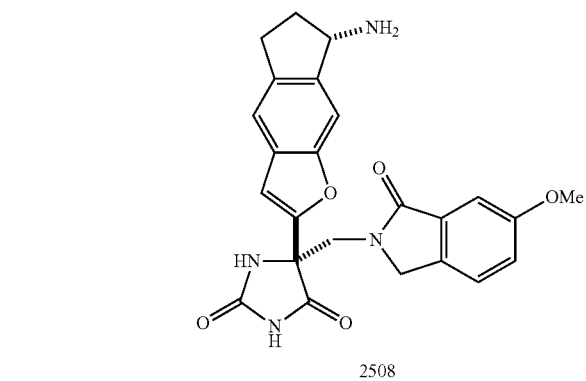

The substrate (Compound 2507; 37 mg, 0.068 mmol) was dissolved in $CH_2Cl_2$-MeOH (~9:1; 1.0 mL) and then treated with anhydrous HCl (1.75 mL; 4 M in dioxane). The reaction was allowed to proceed overnight at rt. Evaporation of the solvents provided 28 mg (85% yield) of the desired product, Compound 2508, as a yellow, solid hydrochloride salt.

Example 203

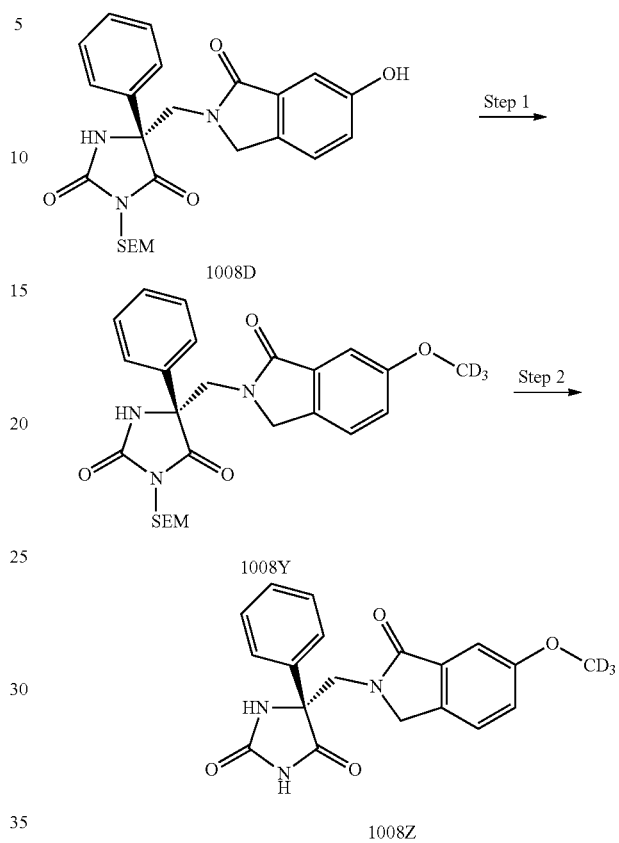

This example exemplifies the preparation of a deuterium-bearing compound of the invention. Skilled artisans will recognize that compounds of the invention, bearing deuterium at other sites can be similarly prepared by using commercially available, or other known deuterated reagents.

Part A:

Compound 1008D (100 mg, 0.214 mmol), iodomethane-$D_3$ (37 mg, 0.257 mmol, 1.2 eq), and $Cs_2CO_3$ (140 mg, 0.428 mmol) are stirred in DMF (2 mL) at 0° C. for 2 hours, then at 25° C. overnight. Water (5 mL) is added and the aqueous solution is extracted with EtOAc (10 mL) three times. The organic phases are combined and concentrated. The product is purified by SGC (Hexane/EtOAc: 3:1) to give compound 1008Y.

Part B:

The SEM protecting group of Compound 1008Y is removed using chemistry similar to that described previously in Example 109 Part E to give compound 1008Z.

Example 204

Assay for Inhibition of TNF-α Production from Human Whole Blood (hWBA)

Human whole blood was diluted 1:1 with serum free medium (RPMI, L-glutamine, Pen-Strep, HEPES) and incubated with a test compound in a final volume of 360 μL for 1 h at 37° C. Forty microliters of LPS (10 μg/mL) was then added. Supernatant was collected after 3.5 h incubation and the concentration of TNF-α was determined by ELISA (R&D Systems). The concentration of the test compound which inhibits 50% of the amount of TNF-α from the untreated control was determined. The $IC_{50}$ values for representative compounds of the invention are shown below in Table A.

Example 205

Area Under the Curve Determinations of Plasma Levels in Rats (rrAUC)

To gain insight into the pharmacokinetic properties of the compounds of the invention, plasma levels of the compounds in rats were determined according to the protocol described in Korfmacher, W. A.; Cox, K. A.; Ng, K. J.; Veals, J.; Hsieh, Y.; Wainhaus, S.; Broske, L.; Prelusky, D.; Nomeir, A.; White, R. E. *Rapid Commun. Mass Spectrom.* 2001, 15, 335. Briefly, rats, after an overnight fast, were dosed orally with the test compound at a dose of 10 mg/kg in a 5 mL/kg dose volume. Blood was collected at 0.5, 1, 2, 3, 4, and 6 h post-dosing. Mass spectrometry using high performance liquid chromatography was used to identify and measure the concentrations of the test compounds in the plasma at the various time points. The HPLC retention time and parent ion of each test compound was used to identify and quantitate the compounds in plasma. The area under the curve (AUC) data for representative compounds of the invention is shown below in Table A.

The present invention provides compounds which are selected from the group consisting of compounds listed in Table A below, or a pharmaceutically acceptable salt thereof. Table A also lists the mass spectroscopy data.

TABLE A

| ID | STRUCTURE | EXACT MASS | MASS OBSVD | Ki (nM) | hWBA ($IC_{50}$) | RR[1] AUC (nM · h) |
|---|---|---|---|---|---|---|
| 100 | 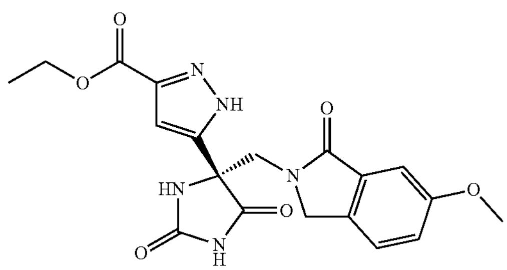 [SMILES: CCOC(=O)c1cc([C@]2(CN3Cc4ccc(OC)cc4C3=O)NC(=O)NC2=O)[nH]n1] | 562.3 | 563.3 | 0.99 | 2221 | 358 |
| 200 | 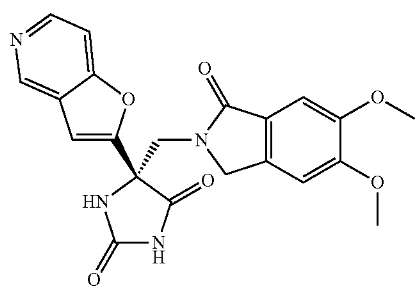 [SMILES: COc1cc2c(cc1OC)C(=O)N(C[C@@]1(c3cc4cnccc4o3)NC(=O)NC1=O)C2] | 422.1 | 423.1 | 7.23 | 10001 | |
| 201 | 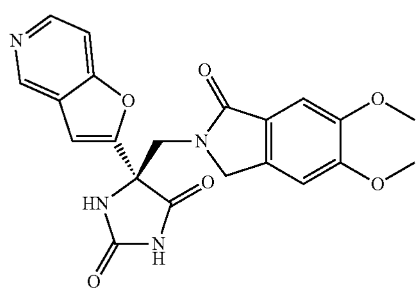 [SMILES: COc1cc2c(cc1OC)C(=O)N(C[C@]1(c3cc4cnccc4o3)NC(=O)NC1=O)C2] | 422.1 | 423.1 | 149 | 6656 | |
| 202 | 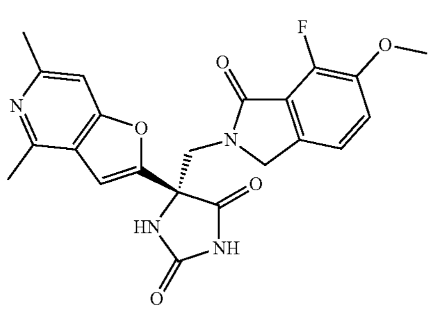 | 438.1 | 439.1 | 0.568 | 552.7 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 203 | 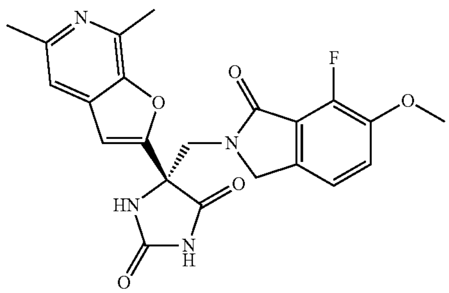 | 438.1 | 439.1 | 0.0608 | 943 | |
| 204 | 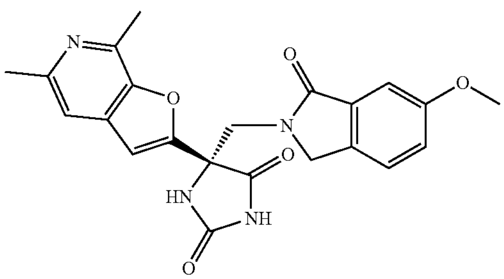 | 420.1 | 421.1 | 0.667 | 4094 | |
| 300 | 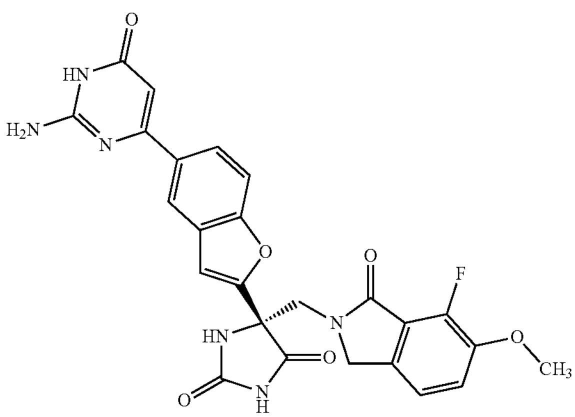 [SMILES: COc1ccc2c(c1F)C(=O)N(C[C@@]1(c3cc4cc(-c5cc(=O)[nH]c(N)n5)ccc4o3)NC(=O)NC1=O)C2] | 518.14 | 519.1 | 0.538 | 364.35 | |
| 301 | 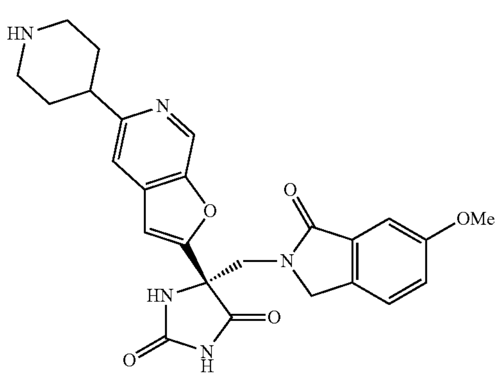 [SMILES: COc1ccc2c(c1)C(=O)N(C[C@@]1(c3cc4cc(C5CCNCC5)ncc4o3)NC(=O)NC1=O)C2] | 475.19 | 476.2 | 1.04 | 162.45 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 302 | 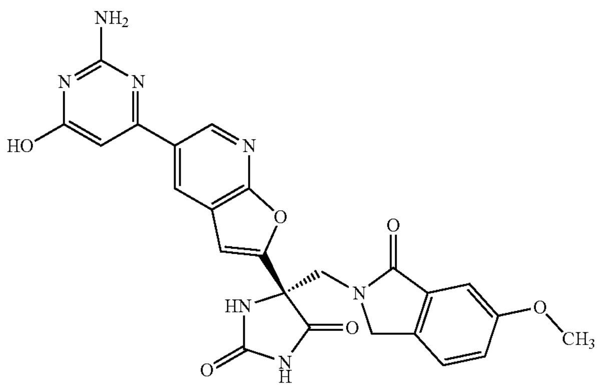 [SMILES: COc1ccc2c(c1)C(=O)N(C[C@@]1(c3cc4cc(-c5cc(O)nc(N)n5)cnc4o3)NC(=O)NC1=O)C2] | 501.14 | 502.1 | 0.53 | 151 | 0 |
| 303 | 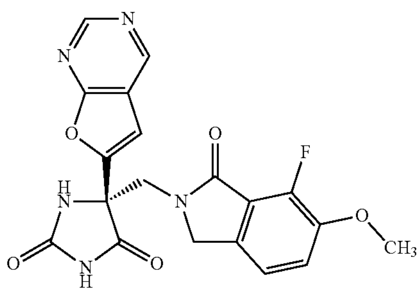 [SMILES: COc1ccc2c(c1F)C(=O)N(C[C@@]1(c3cc4cncnc4o3)NC(=O)NC1=O)C2] | 411.10 | 412.1 | 1.57 | 197.8 | |
| | | 425.11 | 426.1 | 1.23 | 299.8 | |
| 304 | 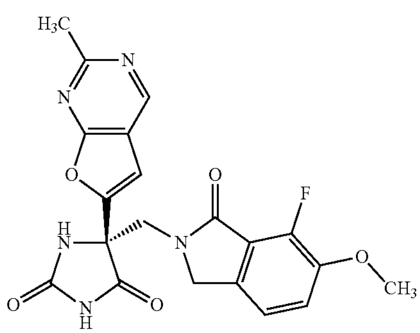 [SMILES: COc1ccc2c(c1F)C(=O)N(C[C@@]1(c3cc4cnc(C)nc4o3)NC(=O)NC1=O)C2] | | | | | |
| 305 | 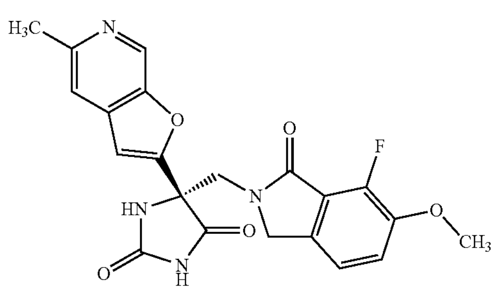 | 424.12 | 425.1 | 0.64 | 241.02 | 19112 |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 306 | 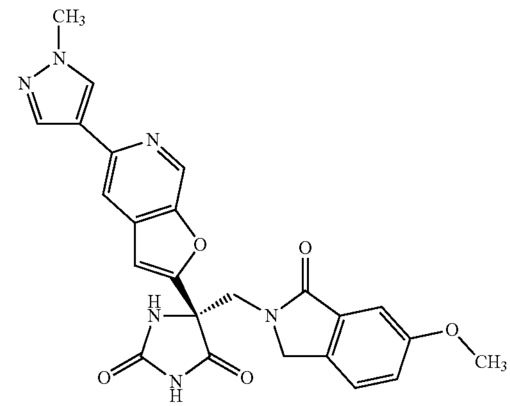 [SMILES: COc1ccc2c(c1)C(=O)N(C[C@@]1(c3cc4cc(-c5cnn(C)c5)ncc4o3)NC(=O)NC1=O)C2] | 472.15 | 473.2 | 0.661 | 658.15 | |
| 307 | 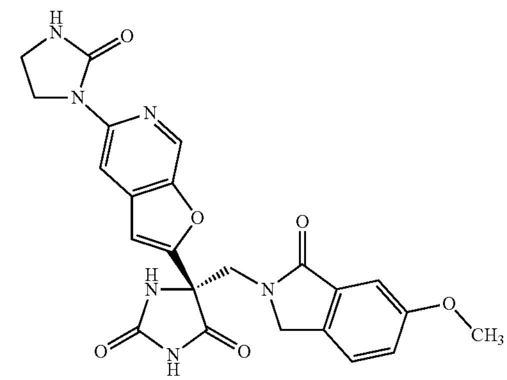 [SMILES: COc1ccc2c(c1)C(=O)N(C[C@@]1(c3cc4cc(N5CCNC5=O)ncc4o3)NC(=O)NC1=O)C2] | 476.14 | 477.1 | | 529 | |
| 308 | 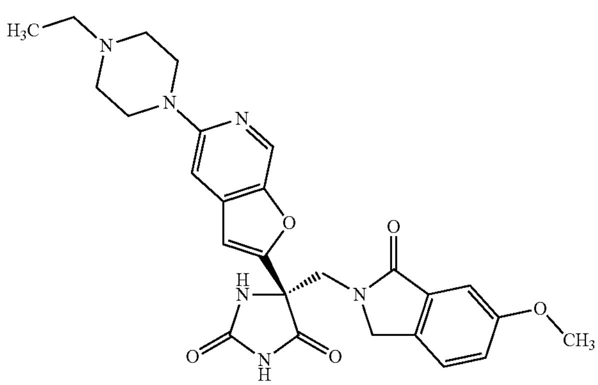 [SMILES: CCN1CCN(c2cc3cc([C@]4(CN5Cc6ccc(OC)cc6C5=O)NC(=O)NC4=O)oc3cn2)CC1] | 504.21 | 505.1 | | 343 | |
| 309 | 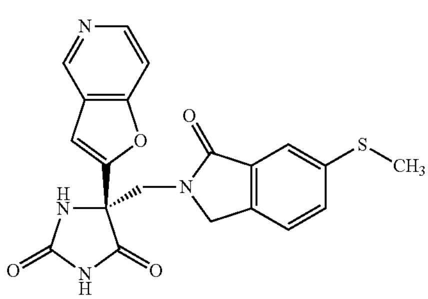 [SMILES: CSc1ccc2c(c1)C(=O)N(C[C@@]1(c3cc4cnccc4o3)NC(=O)NC1=O)C2] | 408.09 | 409.1 | 0.377 | 661.8 | |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 310 | 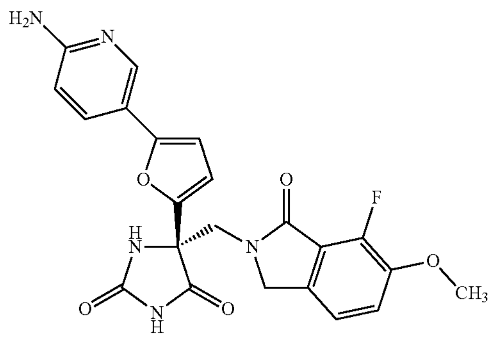 [SMILES: COc1ccc2c(c1F)C(=O)N(C[C@@]1(c3ccc(-c4ccc(N)nc4)o3)NC(=O)NC1=O)C2] | 451.13 | 452.0 | 0.0208 | 243.7 | |
| 311 | 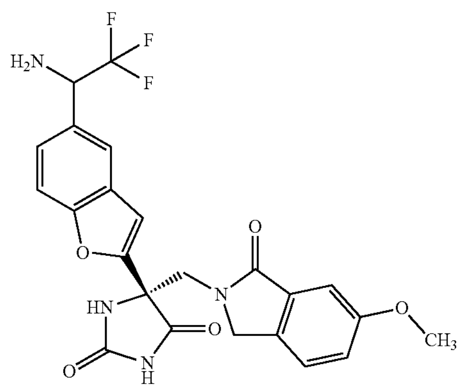 [SMILES: COc1ccc2c(c1)C(=O)N(C[C@@]1(c3cc4cc(C(N)C(F)(F)F)ccc4o3)NC(=O)NC1=O)C2] | 488.13 | 489.1 | 0.594 | 783.7 | |
| 312 | 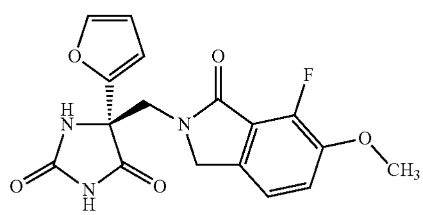 [SMILES: COc1ccc2c(c1F)C(=O)N(C[C@]1(c3ccco3)NC(=O)NC1=O)C2] | 359.09 | 360.1 | 501 | 10000001 | |
| 313 | 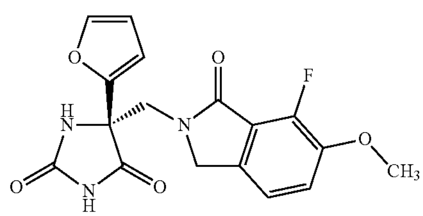 [SMILES: COc1ccc2c(c1F)C(=O)N(C[C@@]1(c3ccco3)NC(=O)NC1=O)C2] | 359.09 | 360.1 | 0.736 | 1794 | |
| 314 | 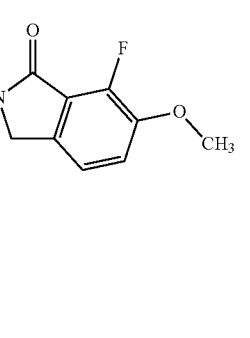 | 436.12 | 437.1 | 0.444 | 536.5 | |

TABLE A-continued

| ID | STRUCTURE | EXACT MASS | MASS OBSVD | Ki (nM) | hWBA (IC$_{50}$) | RR$^1$ AUC (nM · h) |
|---|---|---|---|---|---|---|
| 315 | 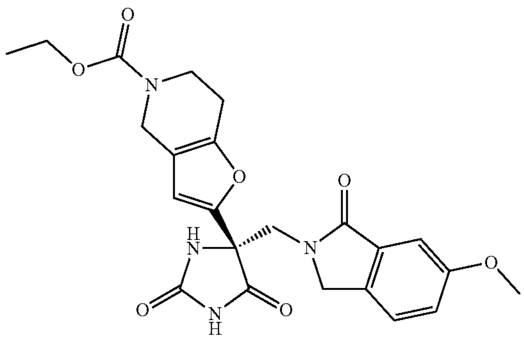 [SMILES: CCOC(=O)N1CCc2oc([C@]3(CN4Cc5ccc(OC)cc5C4=O)NC(=O)NC3=O)cc2C1] | 468.16 | 469.1 | 0.93 | 654 | 4026 |
| 316 | 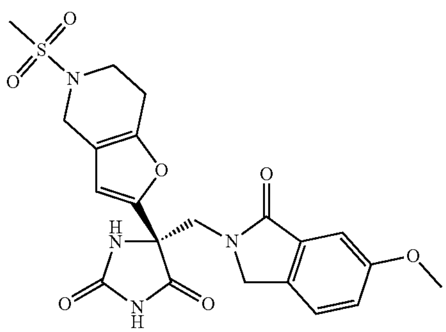 | 474.12 | 475.1 | 0.82 | 497 | |
| 317 | 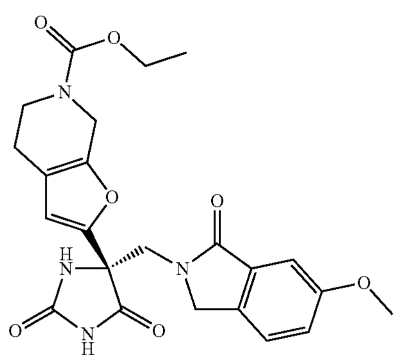 [SMILES: CCOC(=O)N1CCc2cc([C@]3(CN4Cc5ccc(OC)cc5C4=O)NC(=O)NC3=O)oc2C1] | 468.16 | 469.1 | 2.13 | 704 | |
| 318 | 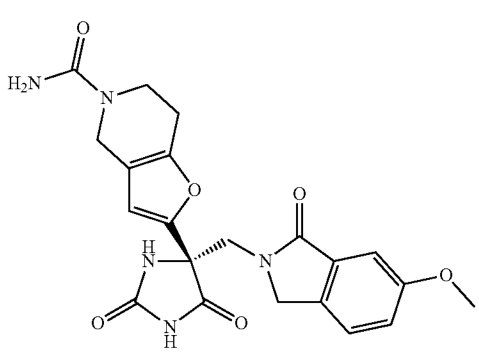 [SMILES: COc1ccc2c(c1)C(=O)N(C[C@@]1(c3cc4c(o3)CCN(C(N)=O)C4)NC(=O)NC1=O)C2] | 439.15 | 440.1 | 5.62 | 646 | |

TABLE A-continued

| ID | STRUCTURE | EXACT MASS | MASS OBSVD | Ki (nM) | hWBA (IC$_{50}$) | RR$^1$ AUC (nM · h) |
|---|---|---|---|---|---|---|
| 319 | 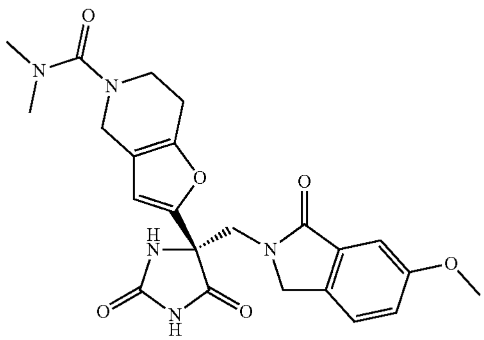 | 467.18 | 468.2 | 1.83 | 501 | |
| 320 | 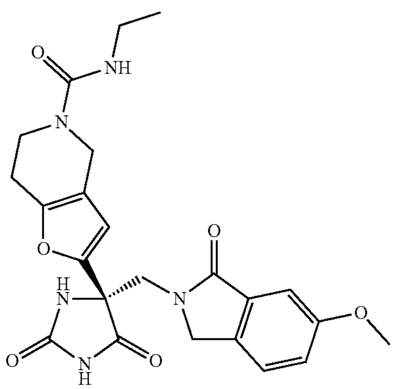 [SMILES: CCNC(=O)N1CCc2oc([C@]3(CN4Cc5ccc(OC)cc5C4=O)NC(=O)NC3=O)cc2C1] | 467.18 | 468.1 | 0.40 | 309 | 11 |
| 321 | 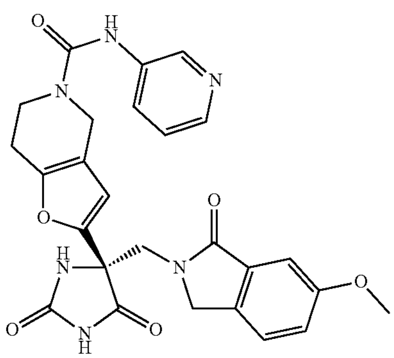 [SMILES: COc1ccc2c(c1)C(=O)N(C[C@@]1(c3cc4c(o3)CCN(C(=O)Nc3cccnc3)C4)NC(=O)NC1=O)C2] | 516.18 | 517.2 | 701 | 1000001 | |
| 322 | 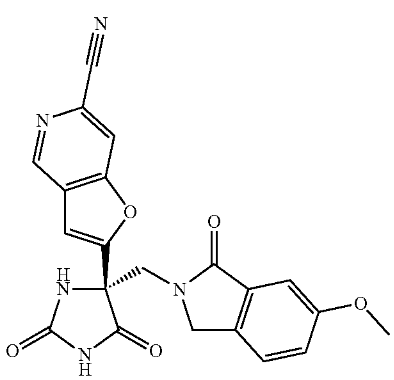 [SMILES: COc1ccc2c(c1)C(=O)N(C[C@@]1(c3cc4cnc(C#N)cc4o3)NC(=O)NC1=O)C2] | 417.11 | 418.1 | 0.67 | 759 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 323 | 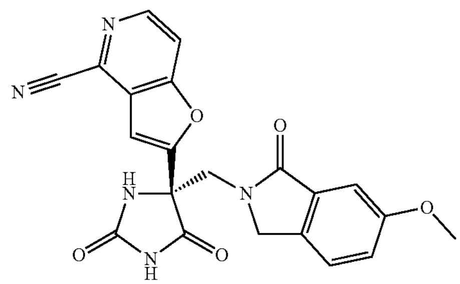 [SMILES: COc1ccc2c(c1)C(=O)N(C[C@@]1(c3cc4c(C#N)nccc4o3)NC(=O)NC1=O)C2] | 417.11 | 418.1 | 0.70 | 1238 | 485 |
| 324 | 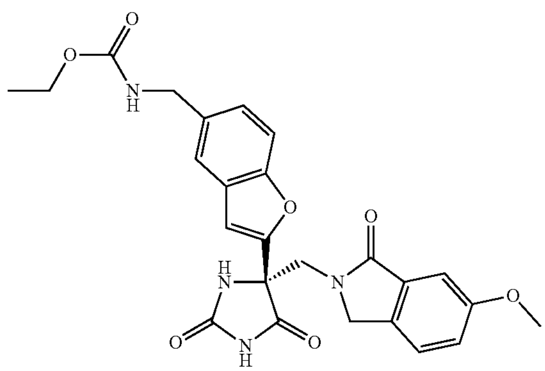 [SMILES: CCOC(=O)NCc1ccc2oc([C@]3(CN4Cc5ccc(OC)cc5C4=O)NC(=O)NC3=O)cc2c1] | 492.16 | 493.1 | 0.49 | 1691 | |
| 325 | 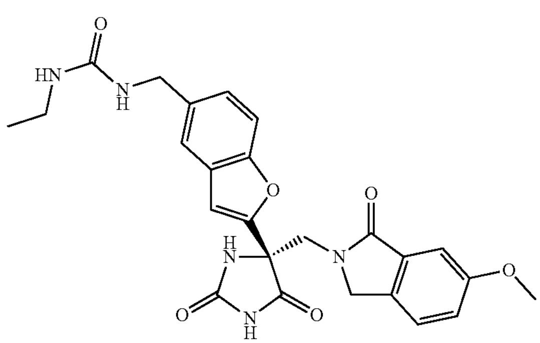 [SMILES: CCNC(=O)NCc1ccc2oc([C@]3(CN4Cc5ccc(OC)cc5C4=O)NC(=O)NC3=O)cc2c1] | 491.18 | 492.3 | 0.76 | 1989 | |
| 326 | 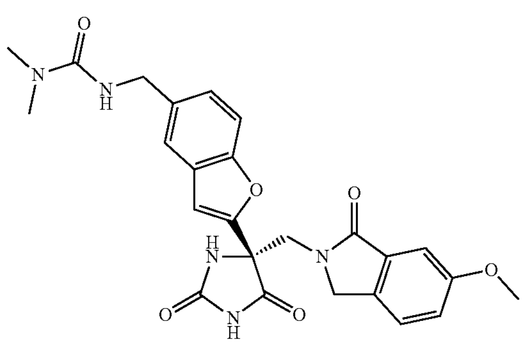 | 491.18 | 492.3 | 0.49 | 1226 | |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 750 | 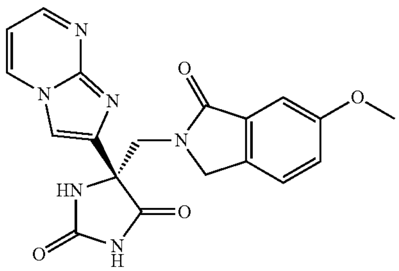 [SMILES: COc1ccc2c(c1)C(=O)N(C[C@@]1(c3cn4cccnc4n3)NC(=O)NC1=O)C2] | 392.1 | 393.1 | 1.91 | 705.1 | 320 |
| 500 | 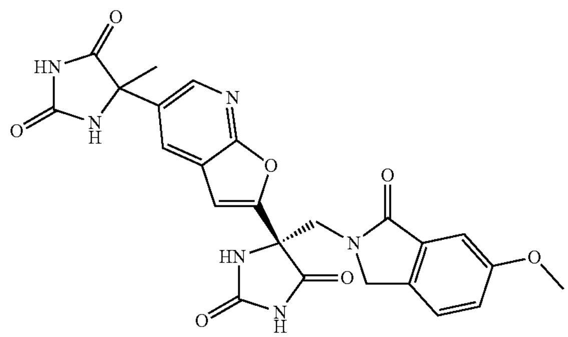 [SMILES: COc1ccc2c(c1)C(=O)N(C[C@@]1(c3cc4cc(C5(C)NC(=O)NC5=O)cnc4o3)NC(=O)NC1=O)C2] | 504.14 | 505.1 | 0.695 | 163 | 1099 |
| 501 | 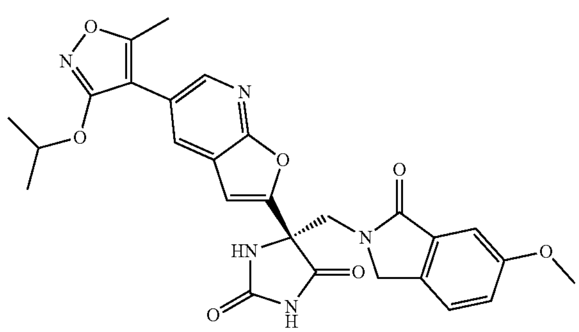 [SMILES: COc1ccc2c(c1)C(=O)N(C[C@@]1(c3cc4cc(-c5c(OC(C)C)noc5C)cnc4o3)NC(=O)NC1=O)C2] | 531.17 | 532.2 | 0.844 | 1589 | |
| 502C | 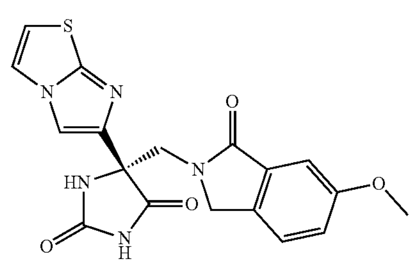 [SMILES: COc1ccc2c(c1)C(=O)N(C[C@@]1(c3cn4ccsc4n3)NC(=O)NC1=O)C2] | 397.08 | 398.0 | 1.26 | 538.2 | 2216 |
| 503 | 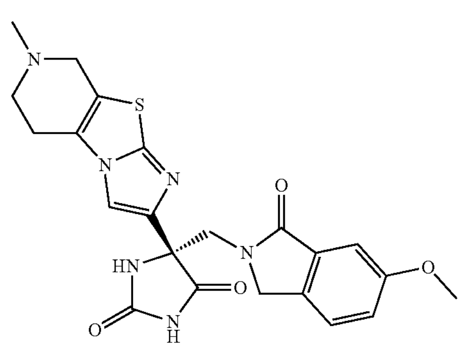 | 466.14 | 467.1 | 4.23 | 1833.5 | |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 504 | 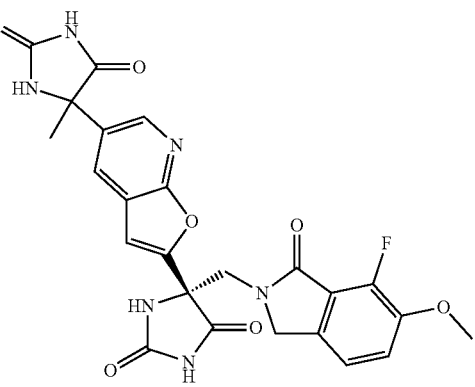 | 522.13 | 523.2 | 0.758 | 239 | 3662 |
| 505 | 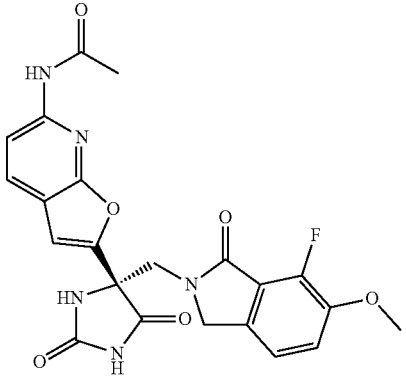 [SMILES: COc1ccc2c(c1F)C(=O)N(C[C@@]1(c3cc4ccc(NC(C)=O)nc4o3)NC(=O)NC1=O)C2] | 467.12 | 468.1 | 0.558 | 251.7 | |
| 1700 | 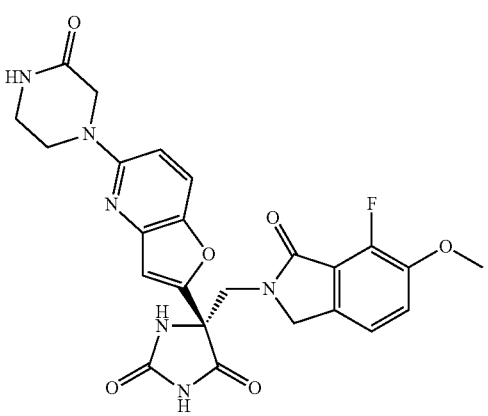 [SMILES: COc1ccc2c(c1F)C(=O)N(C[C@@]1(c3cc4nc(N5CCNC(=O)C5)ccc4o3)NC(=O)NC1=O)C2] | 508.2 | 509.3 | 0.60 | 95 | 105 |

TABLE A-continued

| ID | STRUCTURE | EXACT MASS | MASS OBSVD | Ki (nM) | hWBA (IC$_{50}$) | RR$^1$ AUC (nM · h) |
|---|---|---|---|---|---|---|
| 1701 | 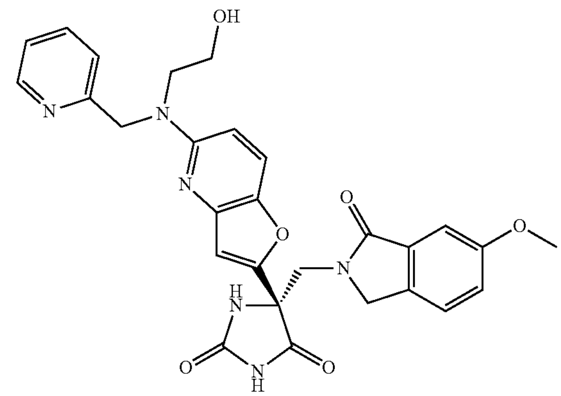 [SMILES: COc1ccc2c(c1)C(=O)N(C[C@@]1(c3cc4nc(N(CCO)Cc5ccccn5)ccc4o3)NC(=O)NC1=O)C2] | 542.2 | 543.3 | 2.49 | 2214 | |
| 1702 | 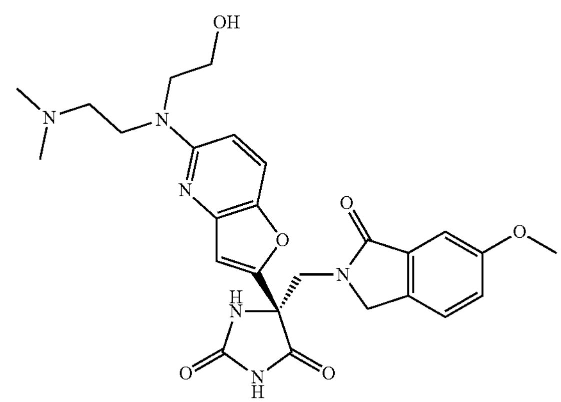 | 522.2 | 523.3 | 3.96 | 1767 | |
| 1703 | 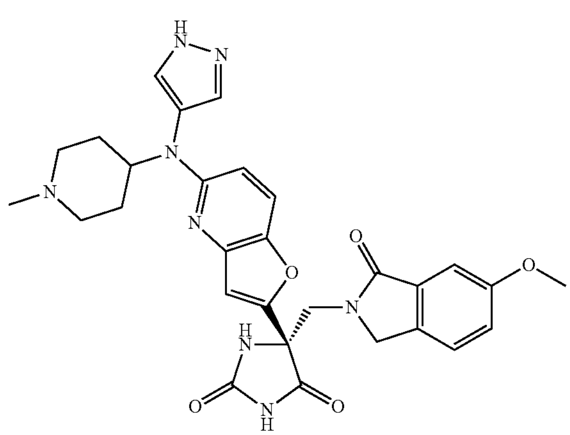 | 570.2 | 571.3 | 1.00 | 187 | 64 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 1704 | 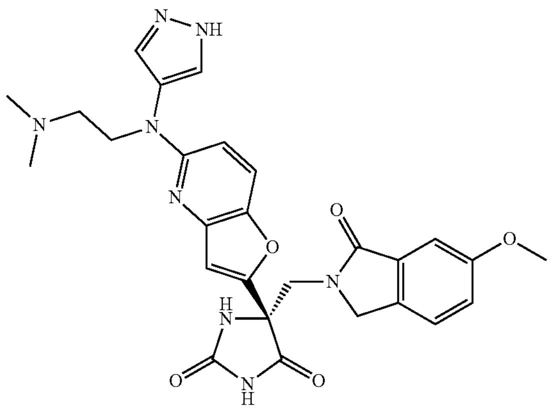 | 544.2 | 545.3 | 0.86 | 274 | |
| 1705 | 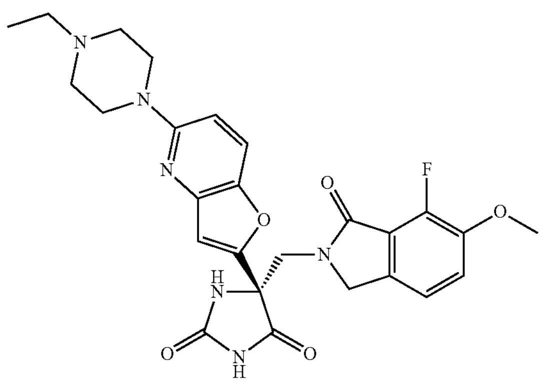 [SMILES: CCN1CCN(c2ccc3oc([C@]4(CN5Cc6ccc(OC)c(F)c6C5=O)NC(=O)NC4=O)cc3n2)CC1] | 522.2 | 523.3 | 0.82 | 137 | 1200 |
| 1706 | 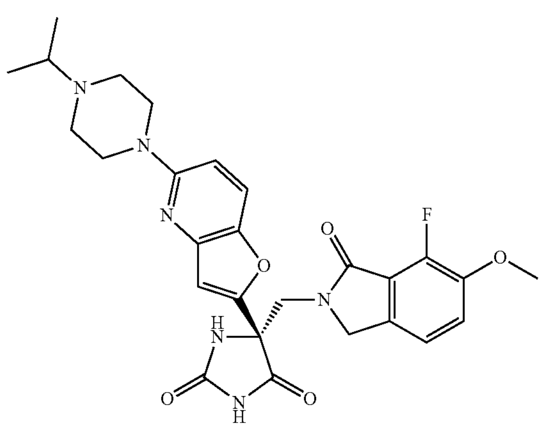 [SMILES: COc1ccc2c(c1F)C(=O)N(C[C@@]1(c3cc4nc(N5CCN(C(C)C)CC5)ccc4o3)NC(=O)NC1=O)C2] | 536.2 | 537.3 | 0.50 | 224 | 273 |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 1707 | 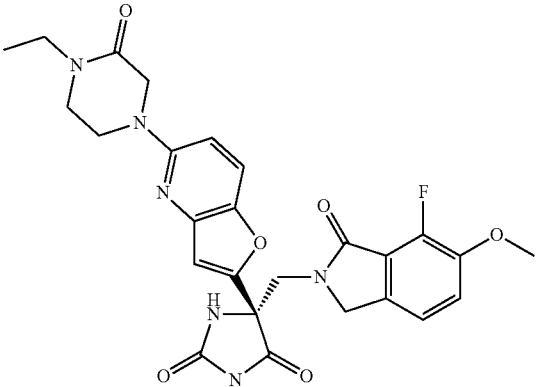 | 536.2 | 537.3 | 0.50 | 235 | 650 |
| 1708 | 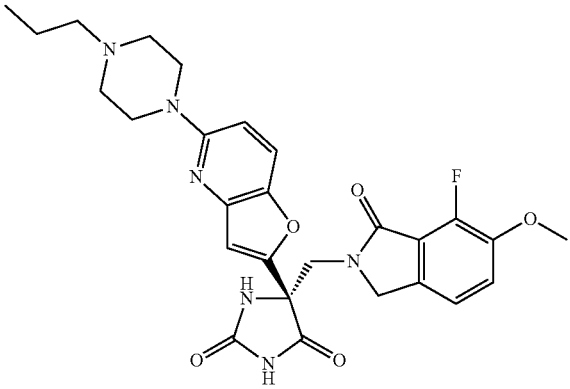 [SMILES: CCCN1CCN(c2ccc3oc([C@]4(CN5Cc6ccc(OC)c(F)c6C5=O)NC(=O)NC4=O)cc3n2)CC1] | 536.2 | 537.3 | | 175 | 10387 |
| 1709 | 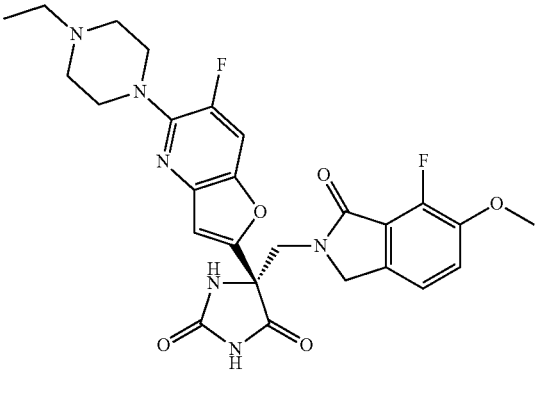 [SMILES: CCN1CCN(c2nc3cc([C@]4(CN5Cc6ccc(OC)c(F)c6C5=O)NC(=O)NC4=O)oc3cc2F)CC1] | 540.2 | 541.3 | 0.70 | 131 | 623 |
| 1710 | 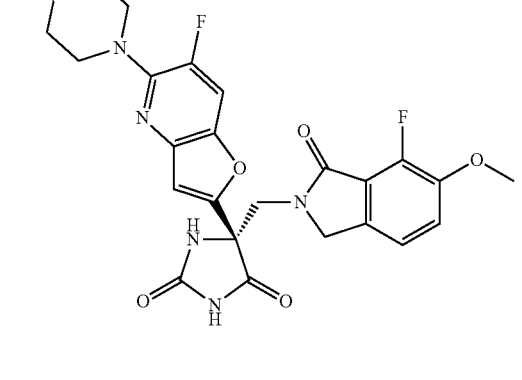 | 526.2 | 527.3 | 1.08 | 218 | |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 1711 | 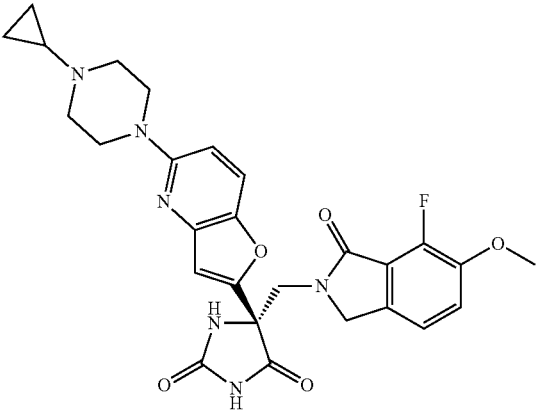 [SMILES: COc1ccc2c(c1F)C(=O)N(C[C@@]1(c3cc4nc(N5CCN(C6CC6)CC5)ccc4o3)NC(=O)NC1=O)C2] | 534.2 | 535.3 | 0.5 | 113 | 5090 |
| 1712 | 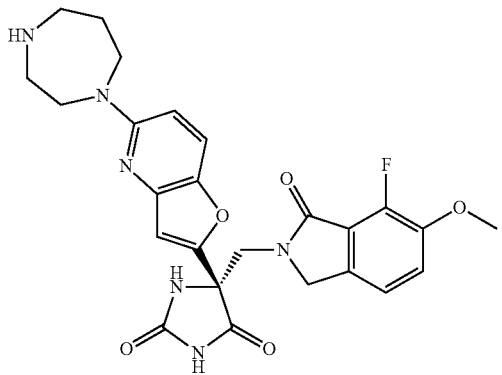 [SMILES: COc1ccc2c(c1F)C(=O)N(C[C@@]1(c3cc4nc(N5CCCNCC5)ccc4o3)NC(=O)NC1=O)C2] | 508.2 | 509.3 | 0.83 | 189 | |
| 1713 | 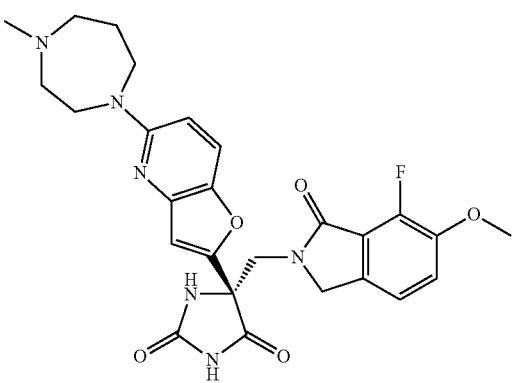 | 522.2 | 523.3 | 0.76 | 153 | |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 1714 | 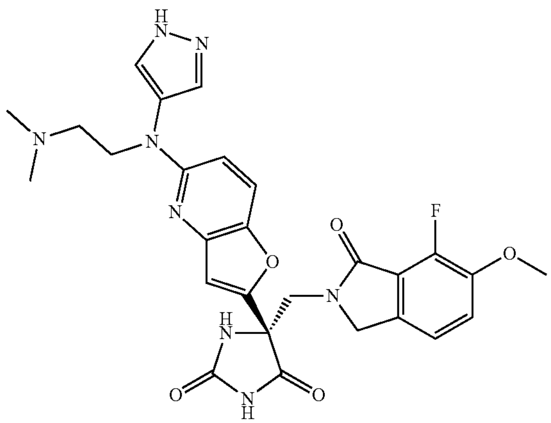 | 562.2 | 563.3 | 0.85 | 271 | |
| 1715 | 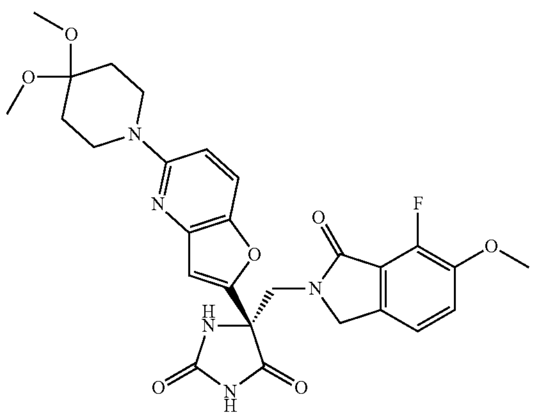 | 553.2 | 554.3 | 2.79 | 480 | 199 |
| 1716 | 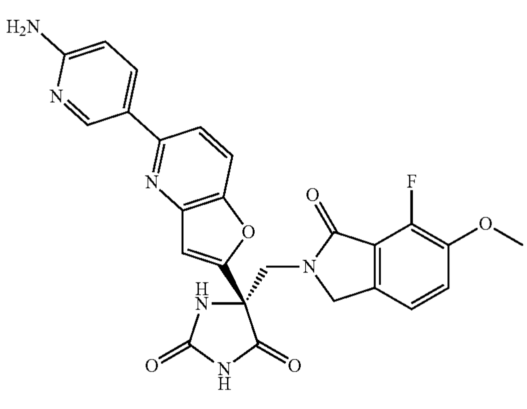 [SMILES: COc1ccc2c(c1F)C(=O)N(C[C@@]1(c3cc4nc(-c5ccc(N)nc5)ccc4o3)NC(=O)NC1=O)C2] | 502.1 | 503.3 | 0.48 | 132 | 393 |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 1717 | 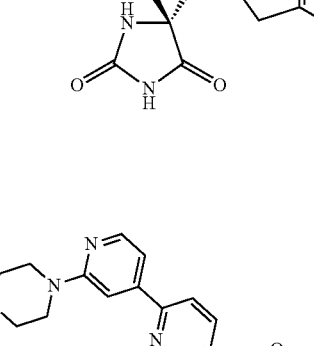 | 588.2 | 589.3 | 0.62 | 183 | 0 |
| 1718 | 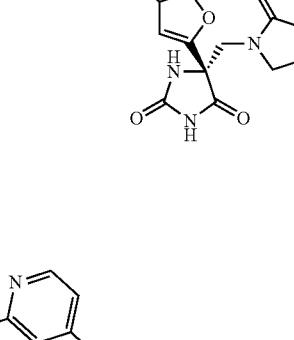 | 667.2 | 668.4 | 0.48 | 299 | |
| 1719 | 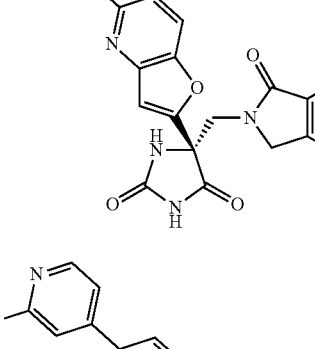 | 571.2 | 572.3 | 0.24 | 148 | |
| 1720 | 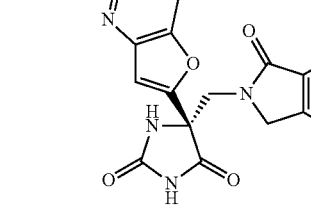 | 553.2 | 554.3 | 0.31 | 224 | |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 1721 | 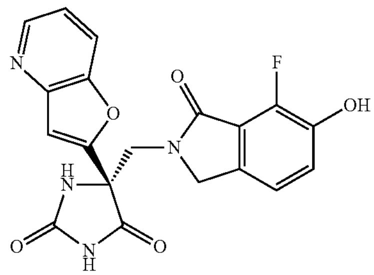 [SMILES: O=C1NC(=O)[C@](CN2Cc3ccc(O)c(F)c3C2=O)(c2cc3ncccc3o2)N1] | 396.1 | 397.2 | 1.64 | >10000 | |
| 1722 | 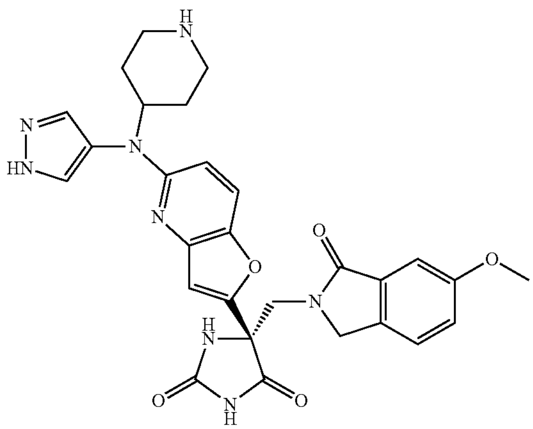 [SMILES: COc1ccc2c(c1)C(=O)N(C[C@@]1(c3cc4nc(N(c5cn[nH]c5)C5CCNCC5)ccc4o3)NC(=O)NC1=O)C2] | 556.2 | 557.3 | 0.39 | 93 | |
| 1723 | 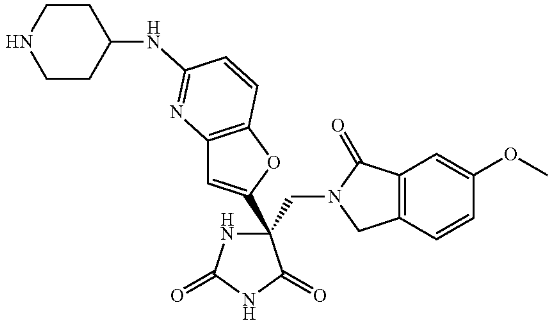 [SMILES: COc1ccc2c(c1)C(=O)N(C[C@@]1(c3cc4nc(NC5CCNCC5)ccc4o3)NC(=O)NC1=O)C2] | 490.2 | 491.3 | 2.66 | 560 | |
| 1724 | 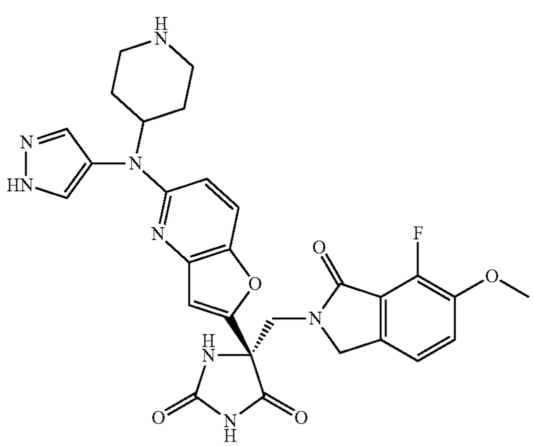 [SMILES: COc1ccc2c(c1F)C(=O)N(C[C@@]1(c3cc4nc(N(c5cn[nH]c5)C5CCNCC5)ccc4o3)NC(=O)NC1=O)C2] | 574.2 | 575.3 | 1.31 | 185 | 0 |

TABLE A-continued

| ID | STRUCTURE | EXACT MASS | MASS OBSVD | Ki (nM) | hWBA (IC$_{50}$) | RR$^1$ AUC (nM·h) |
|---|---|---|---|---|---|---|
| 1725 | 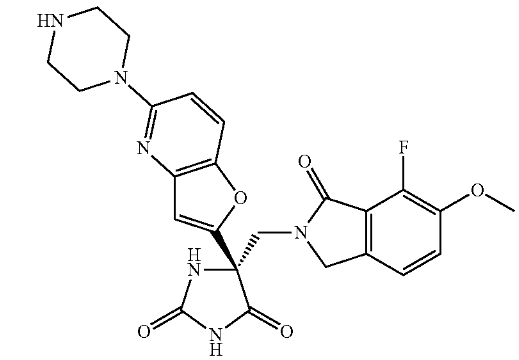 | 494.2 | 495.3 | 0.60 | 97 | |
| 1726 | 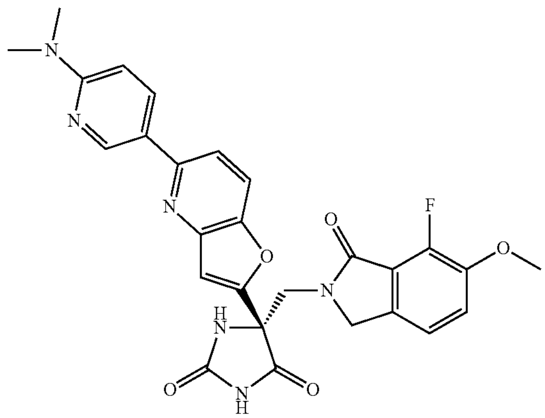 | 530.2 | 531.3 | 1.49 | >10000 | |
| 1727 | 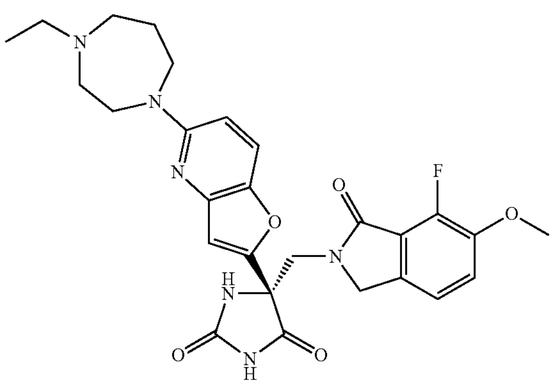 [SMILES: CCN1CCCN(c2ccc3oc([C@]4(CN5Cc6ccc(OC)c(F)c6C5=O)NC(=O)NC4=O)cc3n2)CC1] | 536.2 | 537.3 | 0.048 | 154 | |
| 1728 | 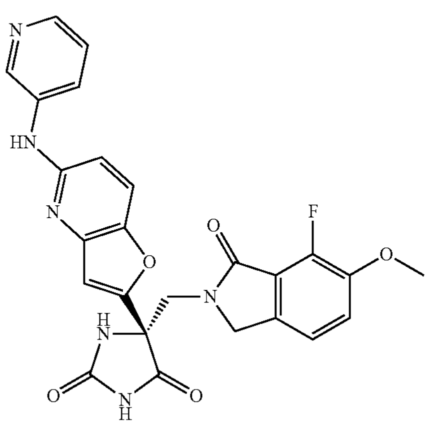 [SMILES: COc1ccc2c(c1F)C(=O)N(C[C@@]1(c3cc4nc(Nc5cccnc5)ccc4o3)NC(=O)NC1=O)C2] | 502.1 | 503.3 | 0.47 | 280 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 1729 | 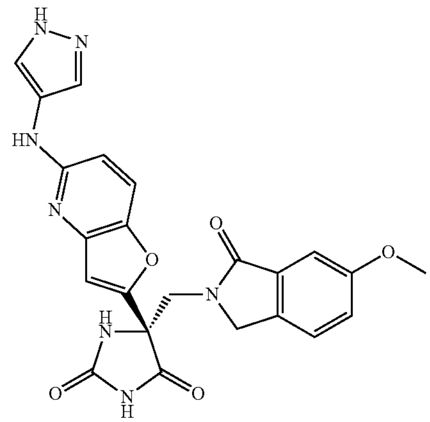 [SMILES: COc1ccc2c(c1)C(=O)N(C[C@@]1(c3cc4nc(Nc5cn[nH]c5)ccc4o3)NC(=O)NC1=O)C2] | 473.1 | 474.3 | 0.43 | 211 | |
| 1730 | 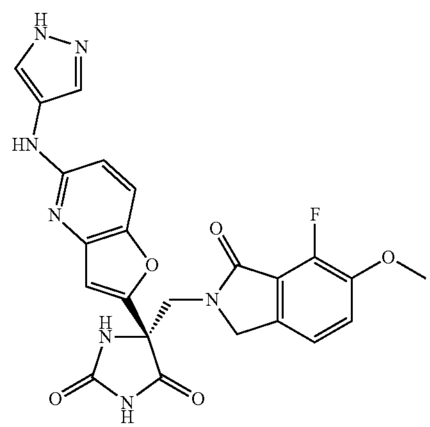 [SMILES: COc1ccc2c(c1F)C(=O)N(C[C@@]1(c3cc4nc(Nc5cn[nH]c5)ccc4o3)NC(=O)NC1=O)C2] | 491.1 | 492.3 | 0.60 | 175 | |
| 1731 | 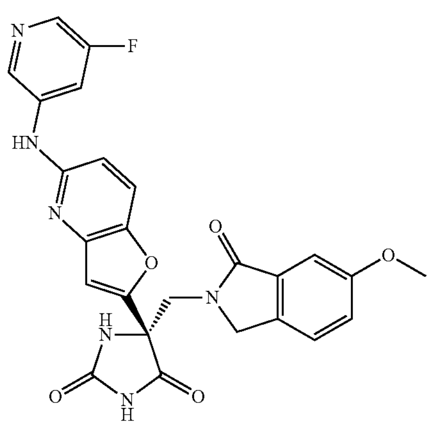 [SMILES: COc1ccc2c(c1)C(=O)N(C[C@@]1(c3cc4nc(Nc5cncc(F)c5)ccc4o3)NC(=O)NC1=O)C2] | 502.1 | 503.3 | 1.32 | 4135 | |
| 1732 | 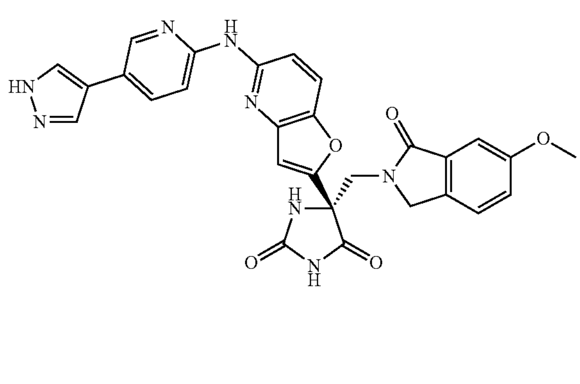 [SMILES: COc1ccc2c(c1)C(=O)N(C[C@@]1(c3cc4nc(Nc5ccc(-c6cn[nH]c6)cn5)ccc4o3)NC(=O)NC1=O)C2] | 550.2 | 551.3 | 1.91 | 333 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 1733 | 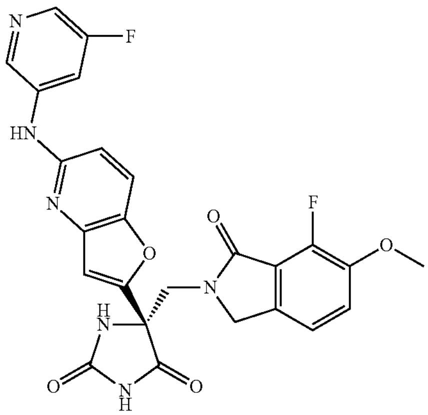 [SMILES: COc1ccc2c(c1F)C(=O)N(C[C@@]1(c3cc4nc(Nc5cncc(F)c5)ccc4o3)NC(=O)NC1=O)C2] | 520.1 | 521.3 | 0.71 | 454 | 904 |
| 1734 | 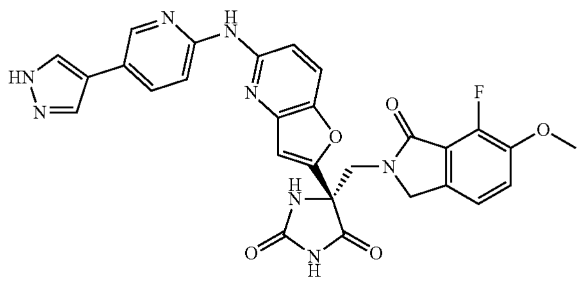 [SMILES: COc1ccc2c(c1F)C(=O)N(C[C@@]1(c3cc4nc(Nc5ccc(-c6cn[nH]c6)cn5)ccc4o3)NC(=O)NC1=O)C2] | 568.2 | 569.3 | 1.92 | 289 | 68 |
| 1735 | 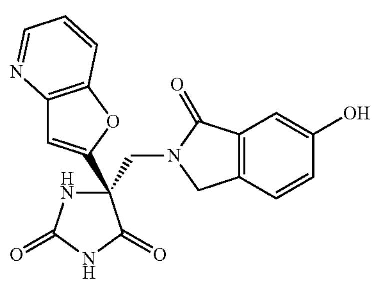 | 378.1 | 399.2 | 1.52 | 3830 | |
| 1736 | 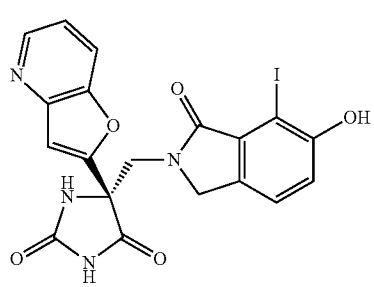 | 504.0 | 505.3 | 53.5 | >10000 | |
| 1737 | 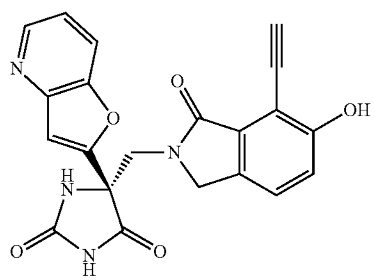 [SMILES: C#Cc1c(O)ccc2c1C(=O)N(C[C@@]1(c3cc4ncccc4o3)NC(=O)NC1=O)C2] | 402.1 | 403.2 | 5.8 | >10000 | |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 1738 | 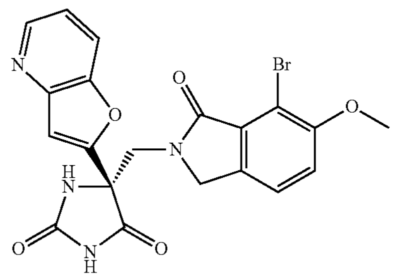 [SMILES: COc1ccc2c(c1Br)C(=O)N(C[C@@]1(c3cc4ncccc4o3)NC(=O)NC1=O)C2] | 470.0 | 471.3 | 1.4 | >10000 | |
| 1739 | 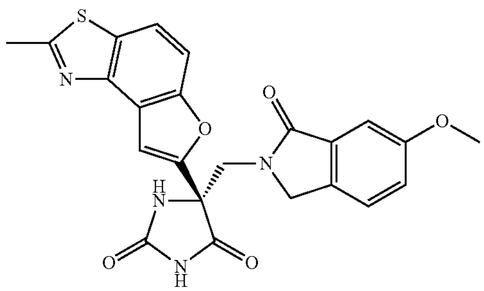 | 462.1 | 463.3 | 0.071 | | 4528 |
| 1740 | 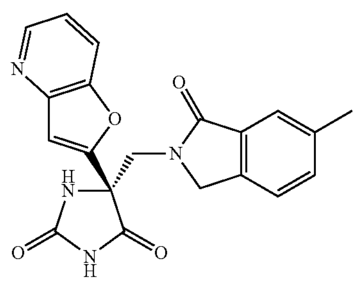 [SMILES: Cc1ccc2c(c1)C(=O)N(C[C@@]1(c3cc4ncccc4o3)NC(=O)NC1=O)C2] | 376.1 | 377.2 | 2.91 | >10000 | |
| 1741 | 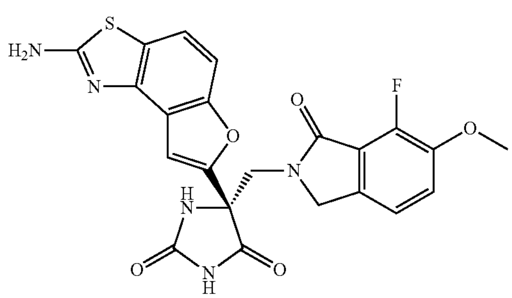 [SMILES: COc1ccc2c(c1F)C(=O)N(C[C@@]1(c3cc4c(ccc5sc(N)nc54)o3)NC(=O)NC1=O)C2] | 481.1 | 482.3 | 0.22 | | 231 |
| 1742 | 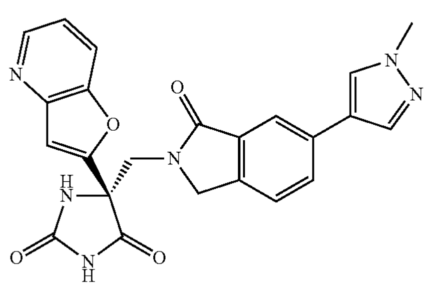 [SMILES: Cn1cc(-c2ccc3c(c2)C(=O)N(C[C@@]2(c4cc5ncccc5o4)NC(=O)NC2=O)C3)cn1] | 442.1 | 443.2 | 3.63 | | 3722 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 1743 | 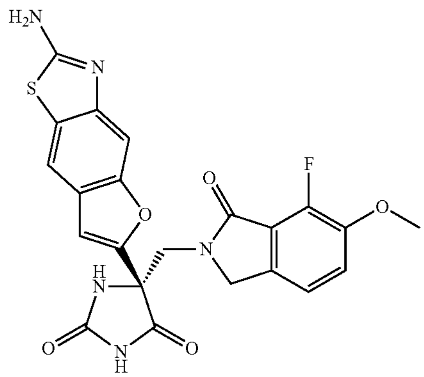 [SMILES: COc1ccc2c(c1F)C(=O)N(C[C@@]1(c3cc4cc5sc(N)nc5cc4o3)NC(=O)NC1=O)C2] | 481.1 | 482.3 | 0.14 | 236 | |
| 900 | 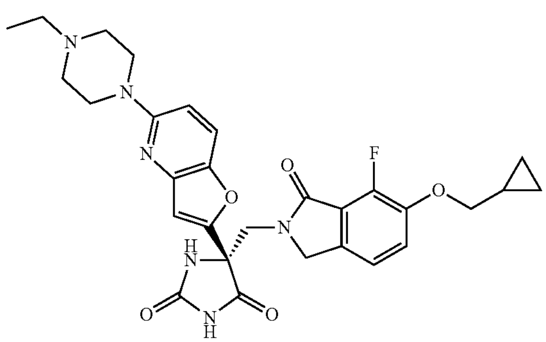 [SMILES: CCN1CCN(c2ccc3oc([C@]4(CN5Cc6ccc(OCC7CC7)c(F)c6C5=O)NC(=O)NC4=O)cc3n2)CC1] | 562.2 | 563.3 | 0.52 | 289.9 | 24 |
| 901 | 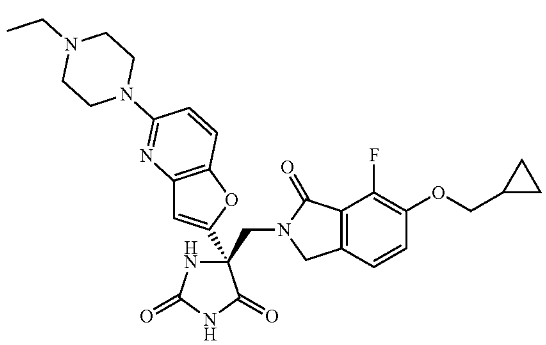 [SMILES: CCN1CCN(c2ccc3oc([C@@]4(CN5Cc6ccc(OCC7CC7)c(F)c6C5=O)NC(=O)NC4=O)cc3n2)CC1] | 562.2 | 563.3 | 501 | 10000001 | |
| 902 | 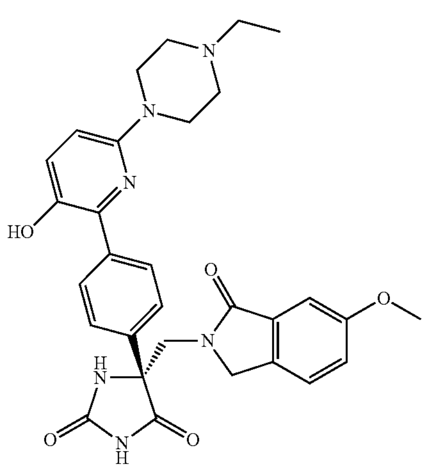 [SMILES: CCN1CCN(c2ccc(O)c(-c3ccc([C@]4(CN5Cc6ccc(OC)cc6C5=O)NC(=O)NC4=O)cc3)n2)CC1] | 556.2 | 557.3 | | 1510 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 903 | 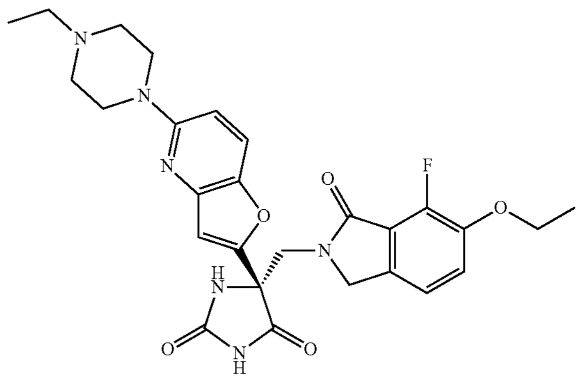 [SMILES: CCOc1ccc2c(c1F)C(=O)N(C[C@@]1(c3cc4nc(N5CCN(CC)CC5)ccc4o3)NC(=O)NC1=O)C2] | 536.2 | 537.3 | 0.557 | 193.05 | 1000 |
| 1900 | 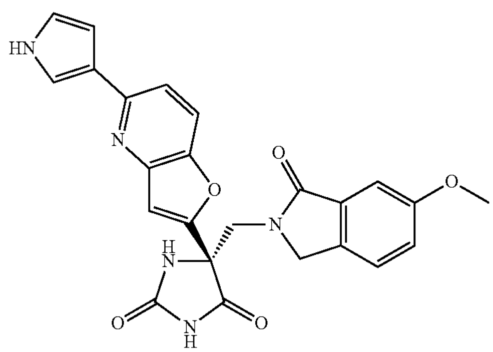 [SMILES: COc1ccc2c(c1)C(=O)N(C[C@@]1(c3cc4nc(-c5cc[nH]c5)ccc4o3)NC(=O)NC1=O)C2] | 457.1 | 458.3 | 0.57 | 459 | |
| 1901 | 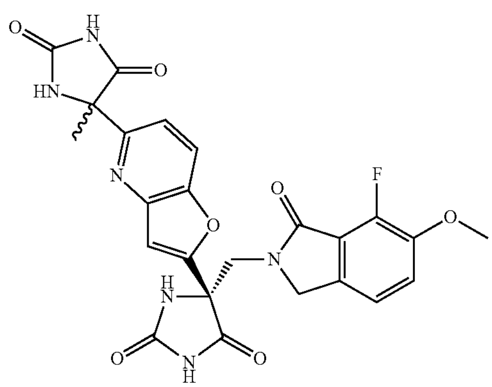 [SMILES: COc1ccc2c(c1F)C(=O)N(C[C@@]1(c3cc4nc(C5(C)NC(=O)NC5=O)ccc4o3)NC(=O)NC1=O)C2] | 522.1 | 523.2 | 0.49 | 100 | 1072 |
| 1902 | 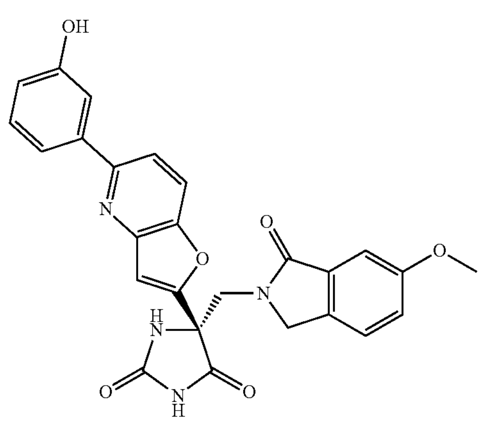 [SMILES: COc1ccc2c(c1)C(=O)N(C[C@@]1(c3cc4nc(-c5cccc(O)c5)ccc4o3)NC(=O)NC1=O)C2] | 484.1 | 485.3 | 0.28 | 998 | |

TABLE A-continued

| ID | STRUCTURE | EXACT MASS | MASS OBSVD | Ki (nM) | hWBA (IC$_{50}$) | RR$^1$ AUC (nM · h) |
|---|---|---|---|---|---|---|
| 1903 | 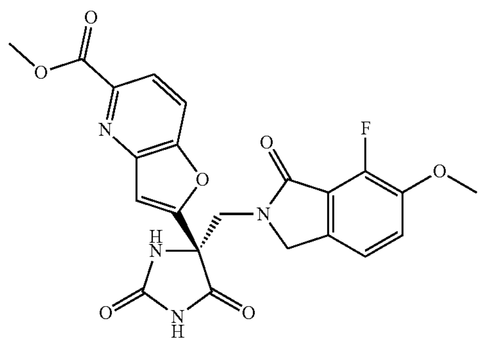 | 468.1 | 469.3 | 0.48 | 248 | |
| 1904 | 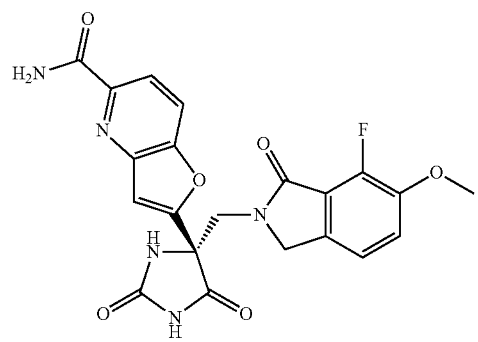 [SMILES: COc1ccc2c(c1F)C(=O)N(C[C@@]1(c3cc4nc(C(N)=O)ccc4o3)NC(=O)NC1=O)C2] | 453.1 | 454.2 | 0.61 | 132 | |
| 1905 | 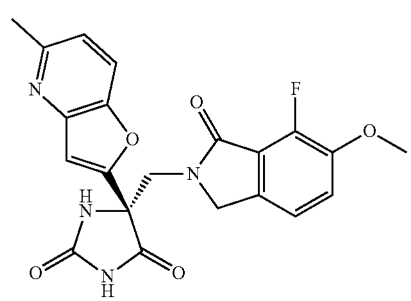 | 576.3 | 577.3 | 0.27 | 346 | |
| 1906 | 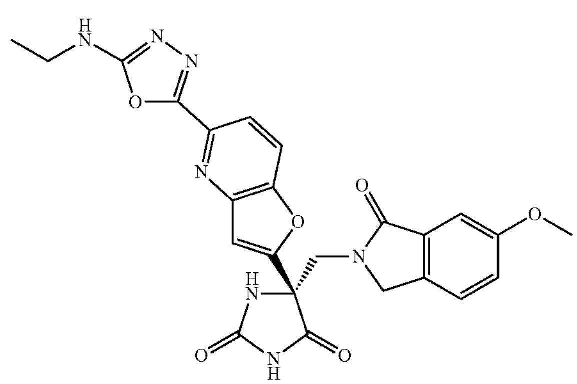 [SMILES: CCNc1nnc(-c2ccc3oc([C@]4(CN5Cc6ccc(OC)cc6C5=O)NC(=O)NC4=O)cc3n2)o1] | 503.2 | 504.2 | 0.77 | 606 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 1907 | 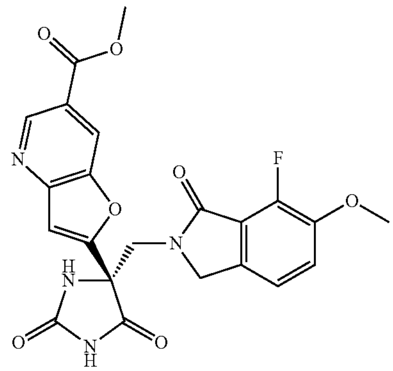 [SMILES: COC(=O)c1cnc2cc([C@]3(CN4Cc5ccc(OC)c(F)c5C4=O)NC(=O)NC3=O)oc2c1] | 546.2 | 547.3 | 0.88 | 152 | 496 |
| 1908 | 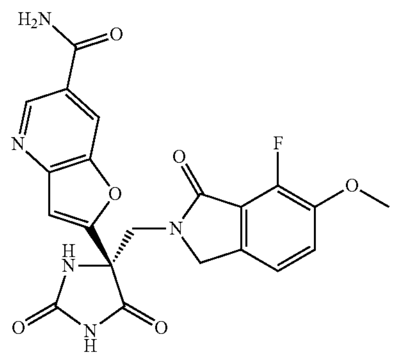 [SMILES: COc1ccc2c(c1F)C(=O)N(C[C@@]1(c3cc4ncc(C(N)=O)cc4o3)NC(=O)NC1=O)C2] | 453.1 | 454.2 | 0.42 | 136 | 94 |
| 1909 | 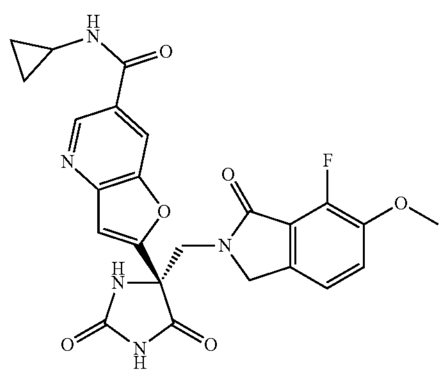 [SMILES: COc1ccc2c(c1F)C(=O)N(C[C@@]1(c3cc4ncc(C(=O)NC5CC5)cc4o3)NC(=O)NC1=O)C2] | 493.1 | 494.3 | 1.15 | 585 | 66 |
| 1910 | 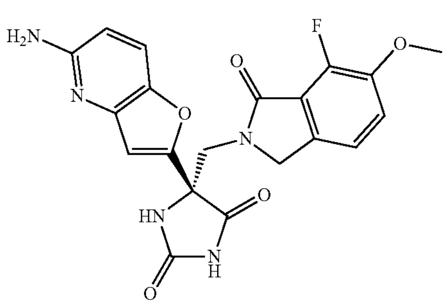 [SMILES: COc1ccc2c(c1F)C(=O)N(C[C@@]1(c3cc4nc(N)ccc4o3)NC(=O)NC1=O)C2] | 425.1 | 426.3 | 0.34 | 153 | 351 |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 1911 | 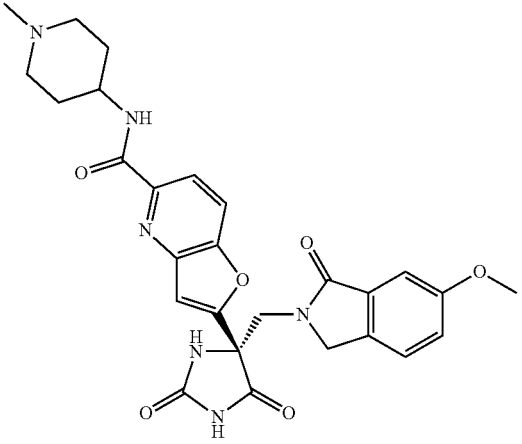 | 532.2 | 533.3 | 1.32 | 317 | |
| 1912 | 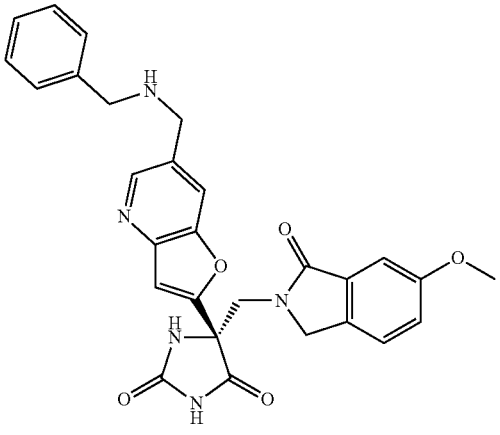 [SMILES: COc1ccc2c(c1)C(=O)N(C[C@@]1(c3cc4ncc(CNCc5ccccc5)cc4o3)NC(=O)NC1=O)C2] | 511.2 | 512.3 | 2.24 | 3205 | |
| 1913 | 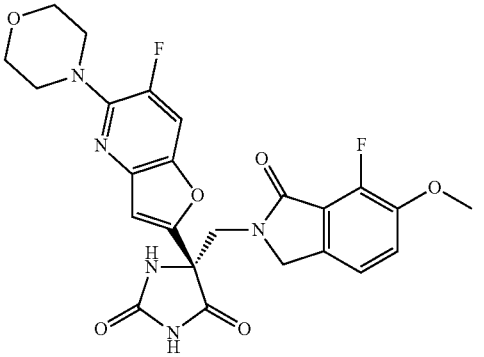 [SMILES: COc1ccc2c(c1F)C(=O)N(C[C@@]1(c3cc4nc(N5CCOCC5)c(F)cc4o3)NC(=O)NC1=O)C2] | 513.2 | 514.3 | 0.53 | 657 | |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 1914 | 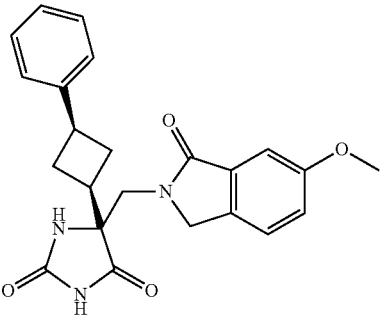 [SMILES: COc1ccc2c(c1)C(=O)N(CC1([C@H]3C[C@@H](c4ccccc4)C3)NC(=O)NC1=O)C2] | 405.2 | 406.2 | 26.1 | 100000 | |
| 1915 | 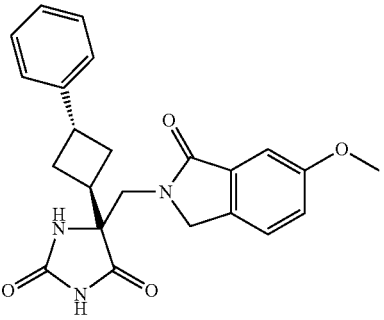 [SMILES: COc1ccc2c(c1)C(=O)N(CC1([C@H]3C[C@H](c4ccccc4)C3)NC(=O)NC1=O)C2] | 405.2 | 406.2 | 9.99 | 100000 | |
| 1916 | 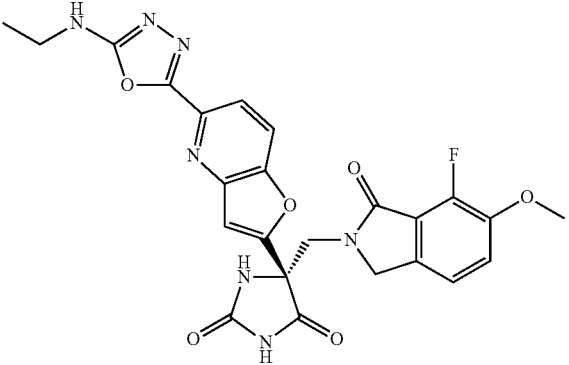 [SMILES: CCNc1nnc(-c2ccc3oc([C@]4(CN5Cc6ccc(OC)c(F)c6C5=O)NC(=O)NC4=O)cc3n2)o1] | 521.2 | 522.3 | 0.81 | 308 | |
| 1917 | 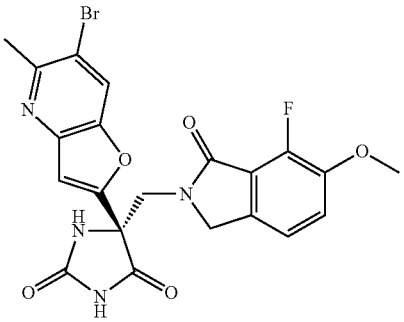 | 502.0 | 503.2 | 0.50 | 1339 | |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 1918 | 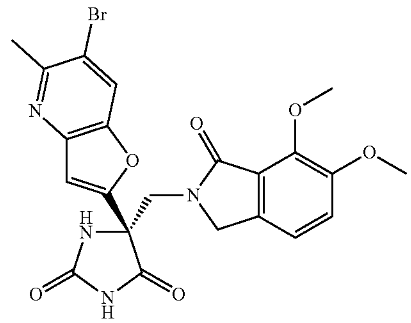 | 514.1 | 515.1 | 2.48 | | 34150 |
| 1919 | 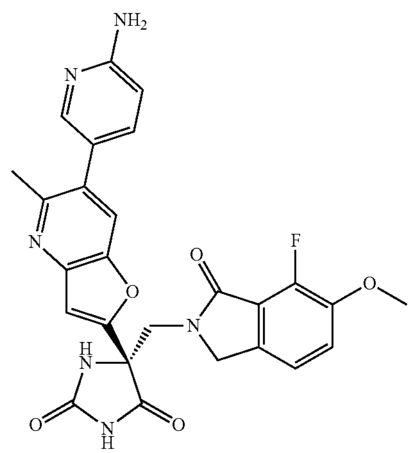 | 516.2 | 517.3 | NA | | 308 |
| 1920 | 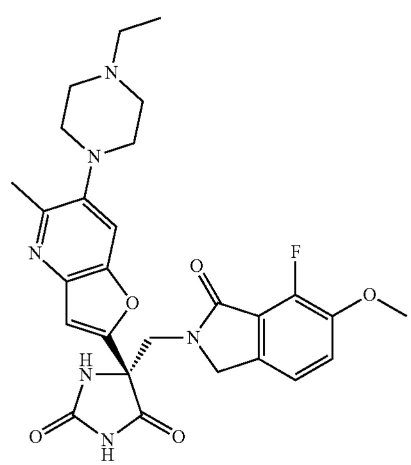 | 536.2 | 537.3 | 2.16 | | 674 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 1921 | 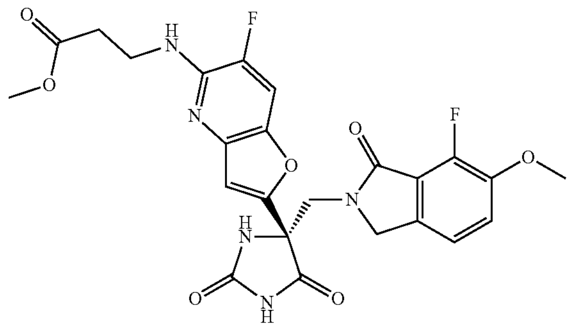 | 529.1 | 530.2 | NA | 239 | |
| 1922 | 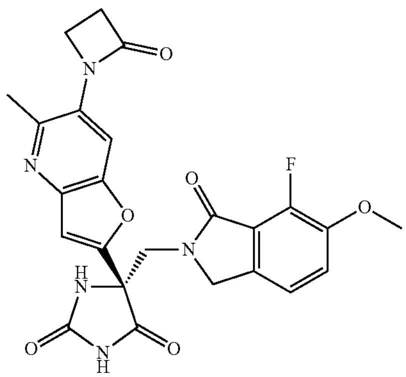 | 493.1 | 494.2 | 1.25 | 281 | 88 |
| 1923 | 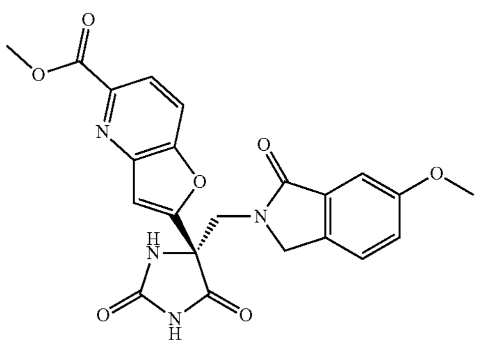 | 450.1 | 451.2 | 0.13 | 339 | |
| 1924 | 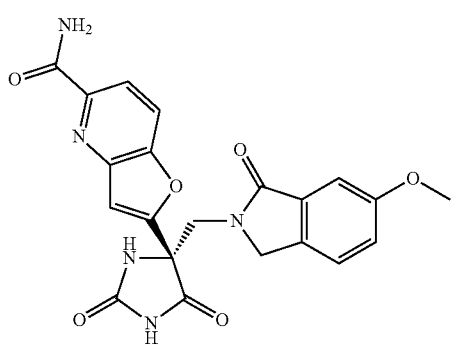 [SMILES: COc1ccc2c(c1)C(=O)N(C[C@@]1(c3cc4nc(C(N)=O)ccc4o3)NC(=O)NC1=O)C2] | 435.1 | 436.2 | 0.55 | 200 | 113 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 1925 | 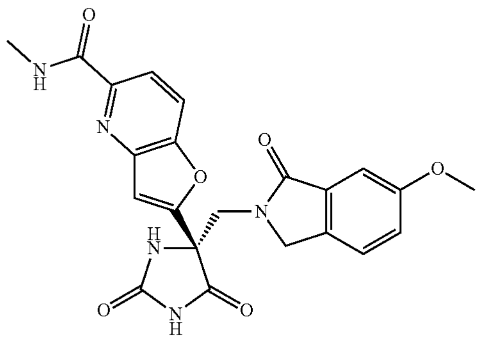 | 449.1 | 450.2 | 0.86 | 280 | 1070 |
| 1926 | 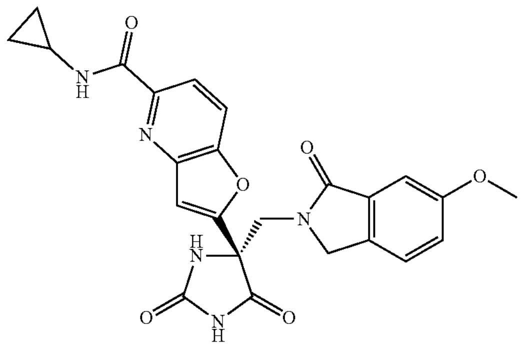 [SMILES: COc1ccc2c(c1)C(=O)N(C[C@@]1(c3cc4nc(C(=O)NC5CC5)ccc4o3)NC(=O)NC1=O)C2] | 475.2 | 476.3 | 0.12 | 367 | |
| 1927 | 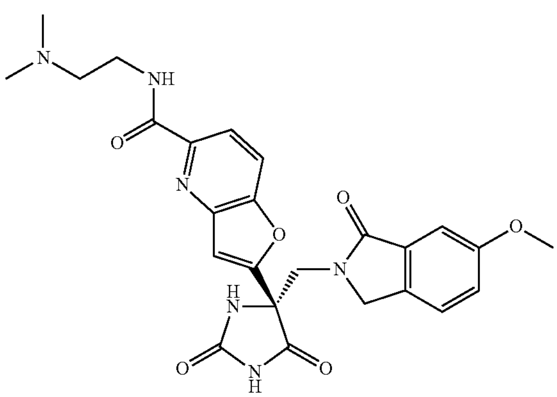 | 506.2 | 507.3 | 0.87 | 567 | 0 |
| 1928 | 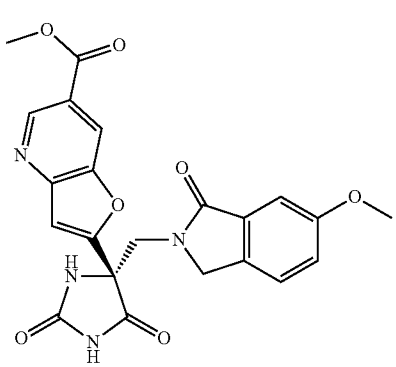 | 450.1 | 451.2 | 0.52 | 841 | |

TABLE A-continued
| ID | STRUCTURE | EXACT MASS | MASS OBSVD | Ki (nM) | hWBA (IC$_{50}$) | RR[1] AUC (nM·h) |
|---|---|---|---|---|---|---|
| 1929 | 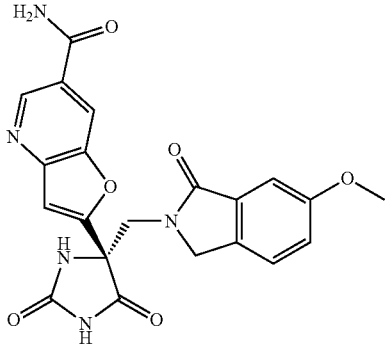 [SMILES: COc1ccc2c(c1)C(=O)N(C[C@@]1(c3cc4ncc(C(N)=O)cc4o3)NC(=O)NC1=O)C2] | 435.1 | 436.2 | 0.37 | 173 | |
| 1930 | 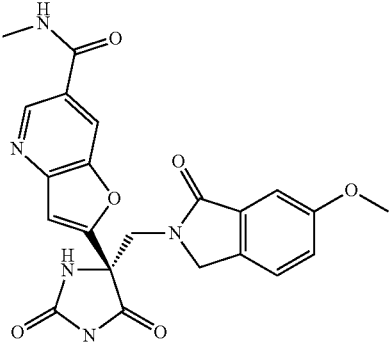 | 449.1 | 450.2 | 0.87 | 351 | 0 |
| 1931 | 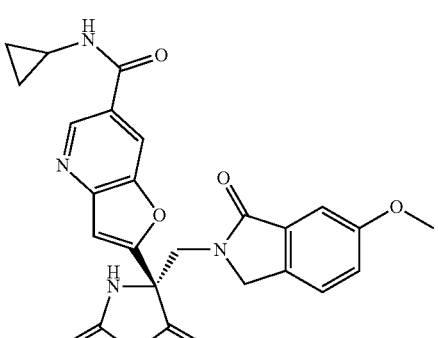 | 475.2 | 476.3 | 0.56 | 321 | |
| 1932 | 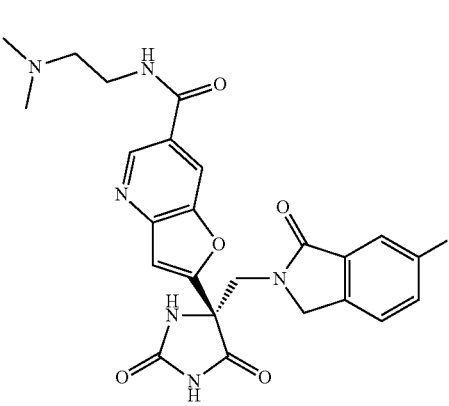 | 506.2 | 507.3 | | 800 | 0 |

TABLE A-continued

| ID | STRUCTURE | EXACT MASS | MASS OBSVD | Ki (nM) | hWBA (IC$_{50}$) | RR$^1$ AUC (nM · h) |
|----|-----------|------------|------------|---------|------------------|---------------------|
| 1933 | 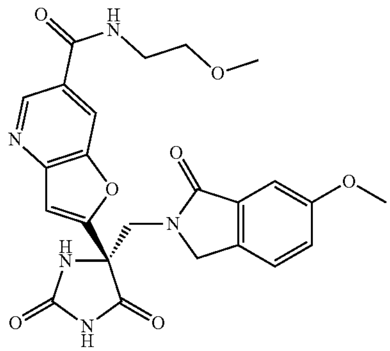 [SMILES: COCCNC(=O)c1cnc2cc([C@]3(CN4Cc5ccc(OC)cc5C4=O)NC(=O)NC3=O)oc2c1] | 493.2 | 494.3 | 0.72 | 657 | |
| 1934 | 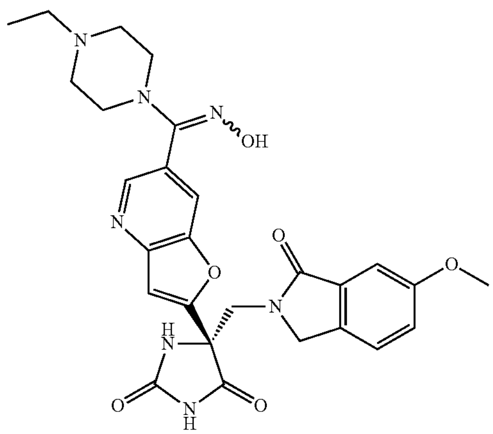 [SMILES: CCN1CCN(C(=NO)c2cnc3cc([C@]4(CN5Cc6ccc(OC)cc6C5=O)NC(=O)NC4=O)oc3c2)CC1] | 547.2 | 548.3 | 1.44 | 342 | |
| 1935 | 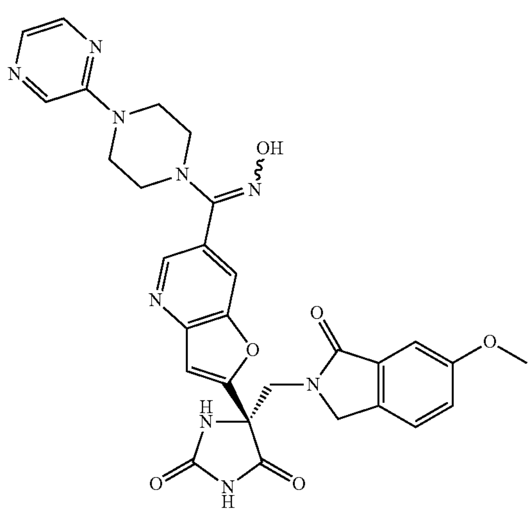 [SMILES: COc1ccc2c(c1)C(=O)N(C[C@@]1(c3cc4ncc(C(=NO)N5CCN(c6cnccn6)CC5)cc4o3)NC(=O)NC1=O)C2] | 597.2 | 598.3 | 0.59 | 546 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 1936 | 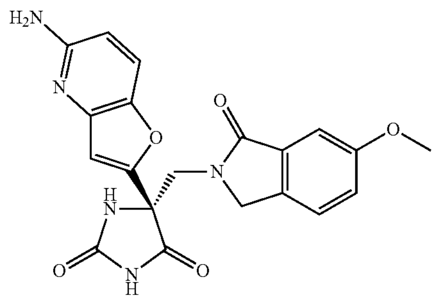 [SMILES: COc1ccc2c(c1)C(=O)N(C[C@@]1(c3cc4nc(N)ccc4o3)NC(=O)NC1=O)C2] | 407.1 | 408.2 | 0.51 | 187 | 424 |
| 1937 | 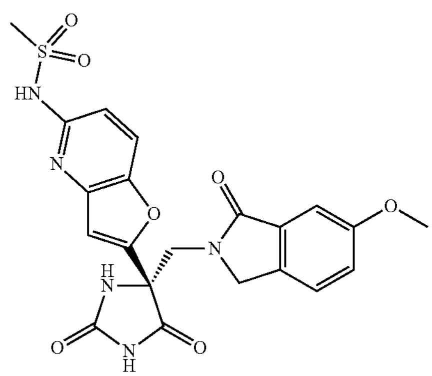 | 485.1 | 486.3 | 2.17 | 189 | 0 |
| 1938 | 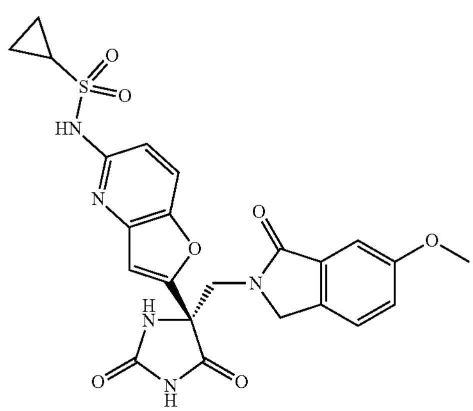 [SMILES: COc1ccc2c(c1)C(=O)N(C[C@@]1(c3cc4nc(NS(=O)(=O)C5CC5)ccc4o3)NC(=O)NC1=O)C2] | 511.1 | 512.3 | 0.58 | 518 | 15 |
| 1939 | 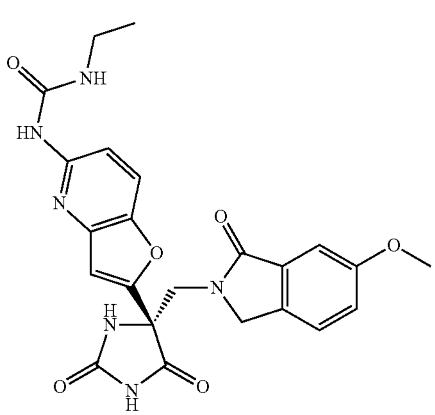 [SMILES: CCNC(=O)Nc1ccc2oc([C@]3(CN4Cc5ccc(OC)cc5C4=O)NC(=O)NC3=O)cc2n1] | 478.2 | 479.3 | 1.12 | 671 | |

TABLE A-continued

| ID | STRUCTURE | EXACT MASS | MASS OBSVD | Ki (nM) | hWBA (IC$_{50}$) | RR$^1$ AUC (nM·h) |
|---|---|---|---|---|---|---|
| 1940 | 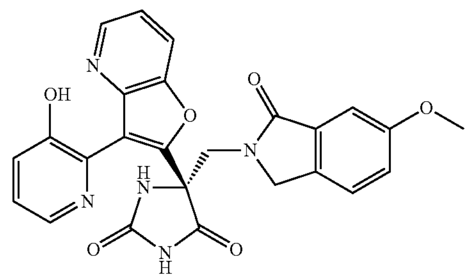 [SMILES: COc1ccc2c(c1)C(=O)N(C[C@@]1(c3oc4cccnc4c3-c3ncccc3O)NC(=O)NC1=O)C2] | 485.1 | 486.1 | 0.75 | 659 | |
| 1941 | 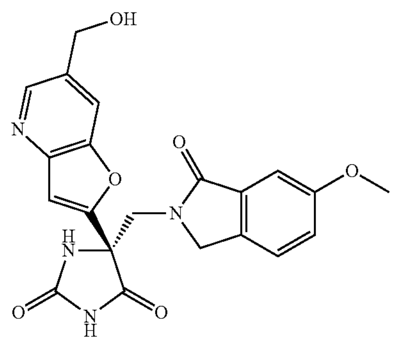 [SMILES: COc1ccc2c(c1)C(=O)N(C[C@@]1(c3cc4ncc(CO)cc4o3)NC(=O)NC1=O)C2] | 422.1 | 423.2 | 0.59 | 609 | |
| 1942 | 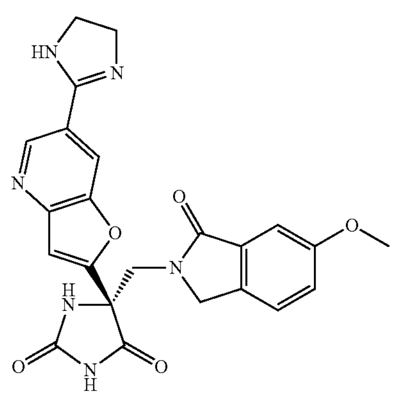 [SMILES: COc1ccc2c(c1)C(=O)N(C[C@@]1(c3cc4ncc(C5=NCCN5)cc4o3)NC(=O)NC1=O)C2] | 460.2 | 461.2 | 2.09 | 3879 | |
| 1943 | 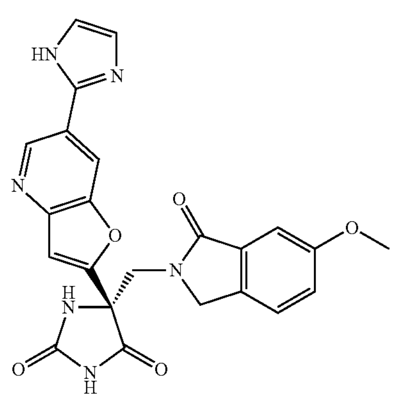 [SMILES: COc1ccc2c(c1)C(=O)N(C[C@@]1(c3cc4ncc(-c5ncc[nH]5)cc4o3)NC(=O)NC1=O)C2] | 458.1 | 459.2 | 0.54 | 742 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 1944 | 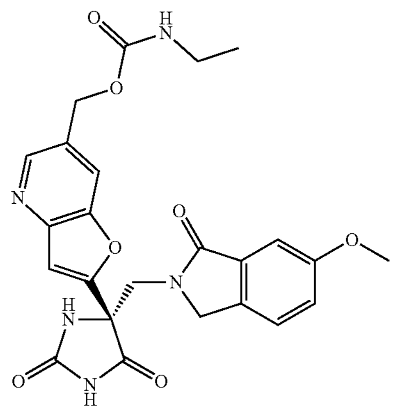 [SMILES: CCNC(=O)OCc1cnc2cc([C@]3(CN4Cc5ccc(OC)cc5C4=O)NC(=O)NC3=O)oc2c1] | 493.2 | 494.1 | 0.69 | | 2252 |
| 1945 | 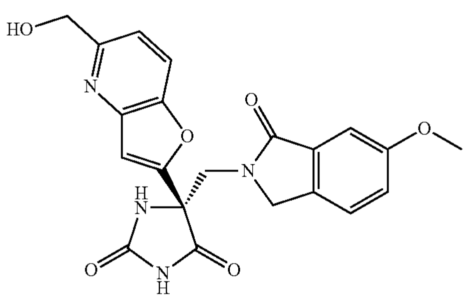 [SMILES: COc1ccc2c(c1)C(=O)N(C[C@@]1(c3cc4nc(CO)ccc4o3)NC(=O)NC1=O)C2] | 422.1 | 423.1 | 0.69 | | 728 |
| 1946 | 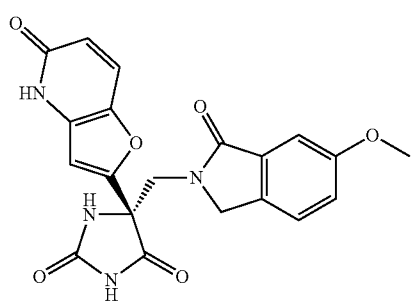 [SMILES: COc1ccc2c(c1)C(=O)N(C[C@@]1(c3cc4[nH]c(=O)ccc4o3)NC(=O)NC1=O)C2] | 408.1 | 409.2 | 0.37 | | 542 |
| 1947 | 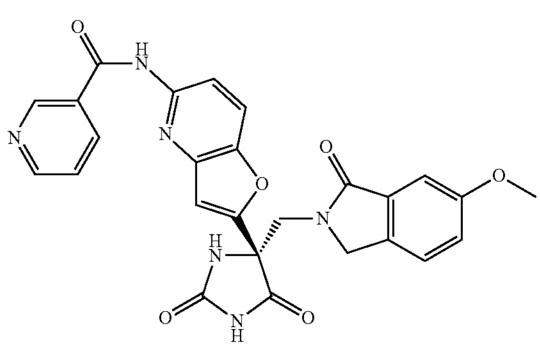 [SMILES: COc1ccc2c(c1)C(=O)N(C[C@@]1(c3cc4nc(NC(=O)c5cccnc5)ccc4o3)NC(=O)NC1=O)C2] | 512.1 | 513.2 | | | 537 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 1500 | 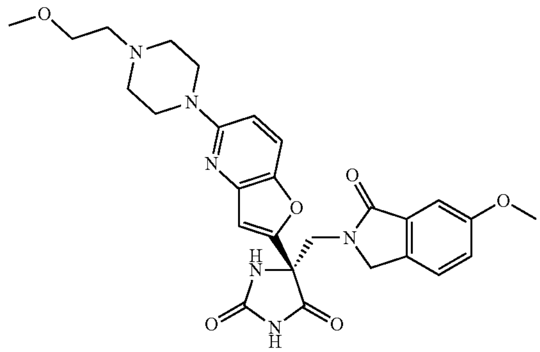 | 534.6 | 535.3 | 1.1 | 332.7 | |
| 1501 | 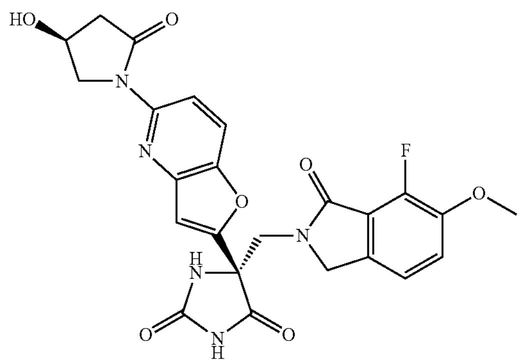 [SMILES: COc1ccc2c(c1F)C(=O)N(C[C@@]1(c3cc4nc(N5C[C@@H](O)CC5=O)ccc4o3)NC(=O)NC1=O)C2] | 509.4 | 510.3 | 0.5 | 131.45 | 667 |
| 1502 | 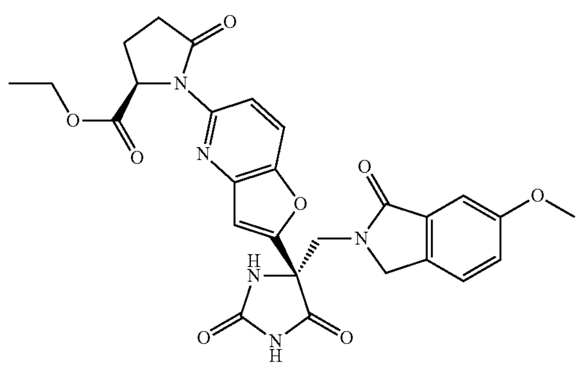 [SMILES: CCOC(=O)[C@H]1CCC(=O)N1c1ccc2oc([C@]3(CN4Cc5ccc(OC)cc5C4=O)NC(=O)NC3=O)cc2n1] | 547.5 | 548.3 | | 1383 | |
| 1503 | 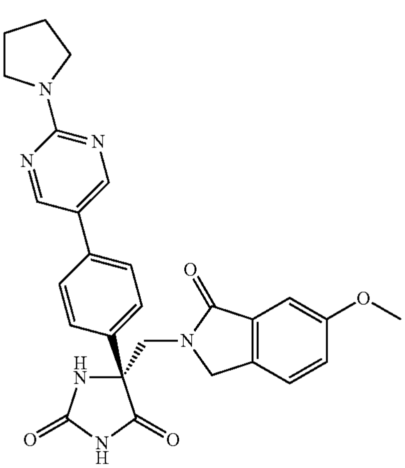 [SMILES: COc1ccc2c(c1)C(=O)N(C[C@@]1(c3ccc(-c4cnc(N5CCCC5)nc4)cc3)NC(=O)NC1=O)C2] | 498.5 | 499.3 | 2.4 | 7094 | |

TABLE A-continued

| ID | STRUCTURE | EXACT MASS | MASS OBSVD | Ki (nM) | hWBA (IC$_{50}$) | RR$^1$ AUC (nM·h) |
|---|---|---|---|---|---|---|
| 1504 | 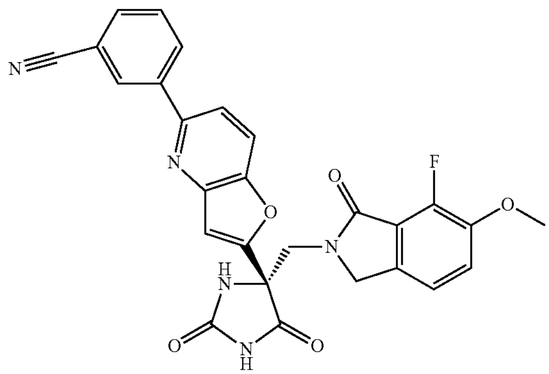 [SMILES: COc1ccc2c(c1F)C(=O)N(C[C@@]1(c3cc4nc(-c5cccc(C#N)c5)ccc4o3)NC(=O)NC1=O)C2] | 511.5 | 512.3 | 0.4 | | 578.6 |
| 1505 | 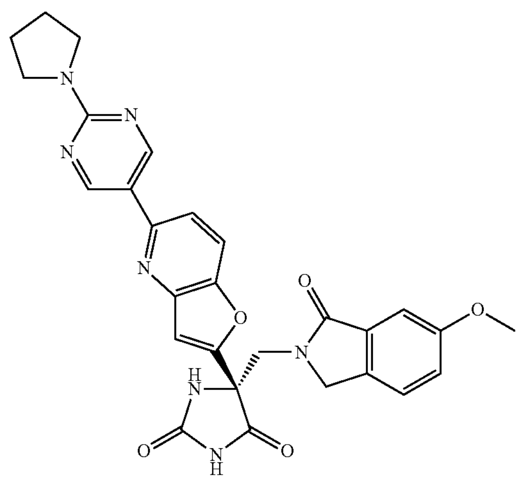 [SMILES: COc1ccc2c(c1)C(=O)N(C[C@@]1(c3cc4nc(-c5cnc(N6CCCC6)nc5)ccc4o3)NC(=O)NC1=O)C2] | 539.5 | 540.3 | 0.6 | | 1292 |
| 1506 | 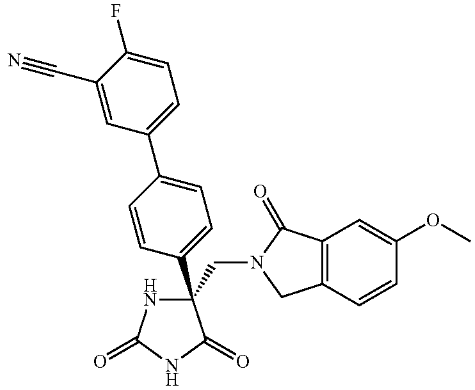 [SMILES: COc1ccc2c(c1)C(=O)N(C[C@@]1(c3ccc(-c4ccc(F)c(C#N)c4)cc3)NC(=O)NC1=O)C2] | 470.5 | 471.3 | 6.4 | | 10000001 |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 1507 | 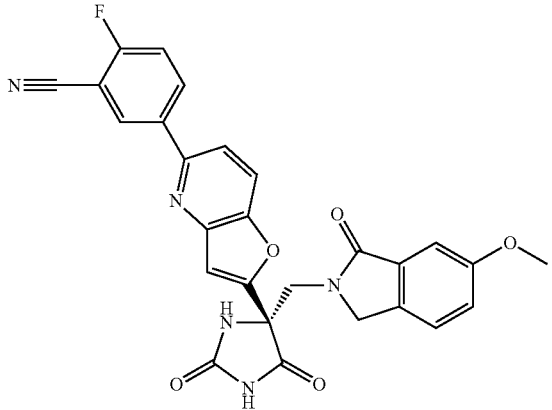 [SMILES: COc1ccc2c(c1)C(=O)N(C[C@@]1(c3cc4nc(-c5ccc(F)c(C#N)c5)ccc4o3)NC(=O)NC1=O)C2] | 511.5 | 512.3 | 0.7 | 4119 | |
| 1508 | 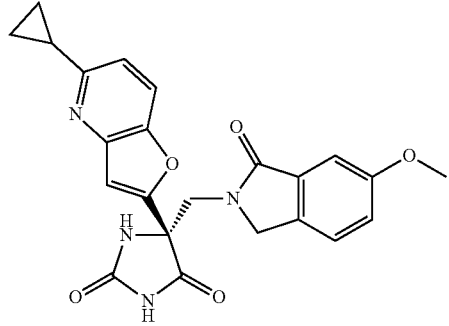 [SMILES: COc1ccc2c(c1)C(=O)N(C[C@@]1(c3cc4nc(C5CC5)ccc4o3)NC(=O)NC1=O)C2] | 432.4 | 433.2 | 0.9 | 2431 | |
| 1509 | 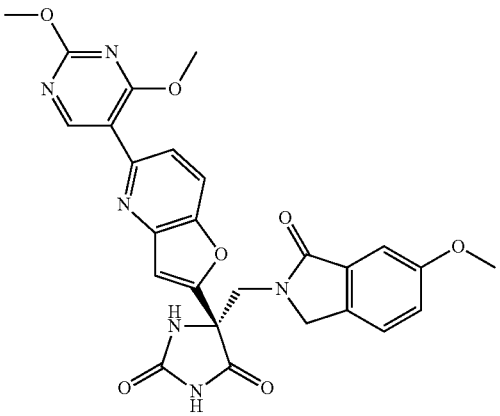 | 530.5 | 531.3 | 0.5 | 2922 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 1510 | 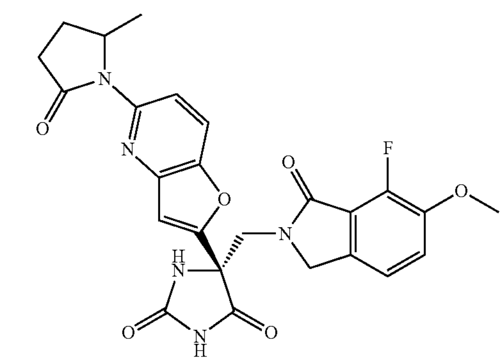 [SMILES: COc1ccc2c(c1F)C(=O)N(C[C@@]1(c3cc4nc(N5C(=O)CCC5C)ccc4o3)NC(=O)NC1=O)C2] | 507.5 | 508.3 | 0.4 | 263 | 5187 |
| 1511 | 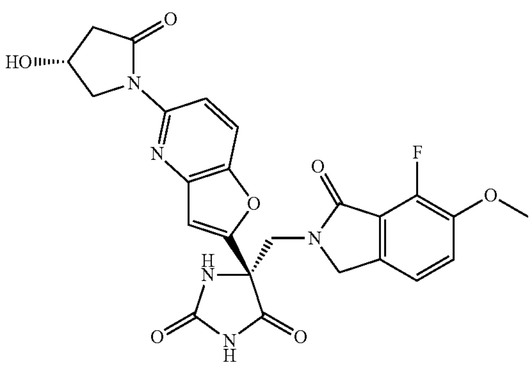 [SMILES: COc1ccc2c(c1F)C(=O)N(C[C@@]1(c3cc4nc(N5C[C@H](O)CC5=O)ccc4o3)NC(=O)NC1=O)C2] | 509.4 | 510.3 | 0.4 | 93.35 | 4009 |
| 1512 | 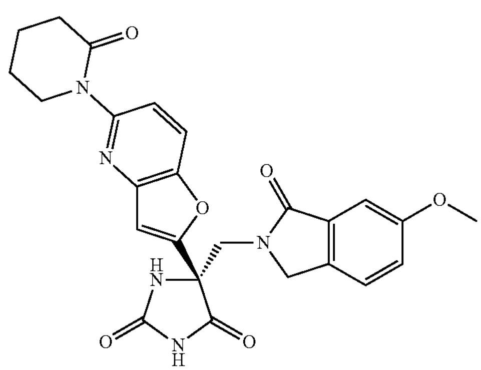 [SMILES: COc1ccc2c(c1)C(=O)N(C[C@@]1(c3cc4nc(N5CCCCC5=O)ccc4o3)NC(=O)NC1=O)C2] | 489.5 | 490.3 | 1.3 | 1546.8 | 303 |
| 1513 | 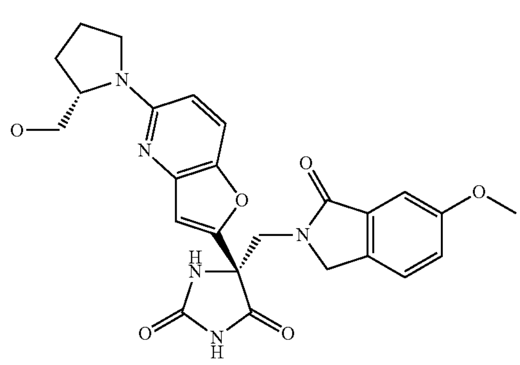 [SMILES: COc1ccc2c(c1)C(=O)N(C[C@@]1(c3cc4nc(N5CCC[C@H]5CO)ccc4o3)NC(=O)NC1=O)C2] | 491.5 | 492.3 | 0.7 | 526.1 | 524 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 1514 | 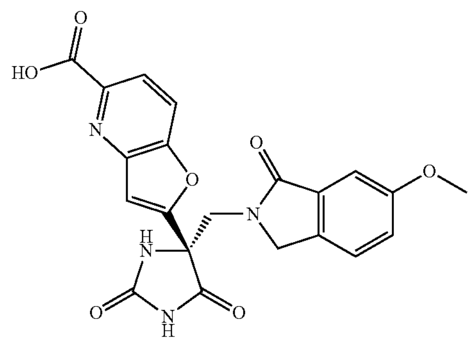 [SMILES: COc1ccc2c(c1)C(=O)N(C[C@@]1(c3cc4nc(C(=O)O)ccc4o3)NC(=O)NC1=O)C2] | 436.4 | 436.2 | 0.7 | 194.85 | |
| 1515 | 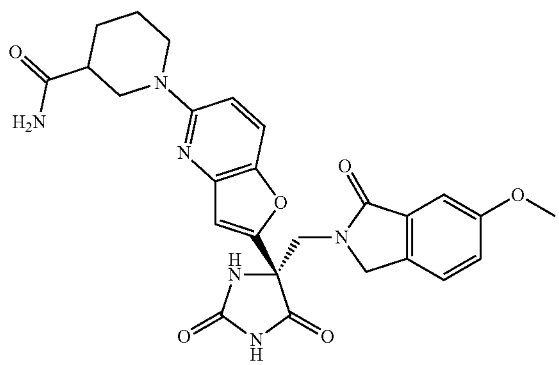 [SMILES: COc1ccc2c(c1)C(=O)N(C[C@@]1(c3cc4nc(N5CCCC(C(N)=O)C5)ccc4o3)NC(=O)NC1=O)C2] | 518.5 | 519.3 | 0.7 | 245.2 | 145 |
| 1516 | 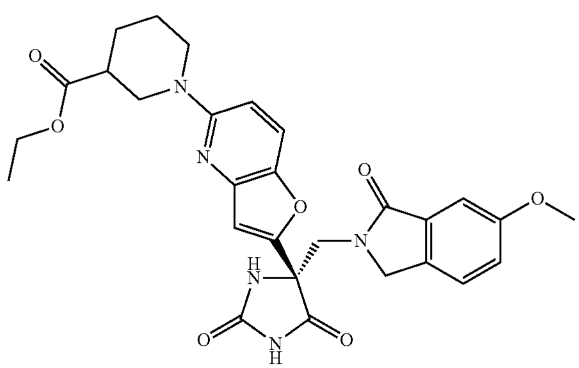 [SMILES: CCOC(=O)C1CCCN(c2ccc3oc([C@]4(CN5Cc6ccc(OC)cc6C5=O)NC(=O)NC4=O)cc3n2)C1] | 547.6 | 548.3 | 0.5 | 1738 | 41 |
| 1517 | 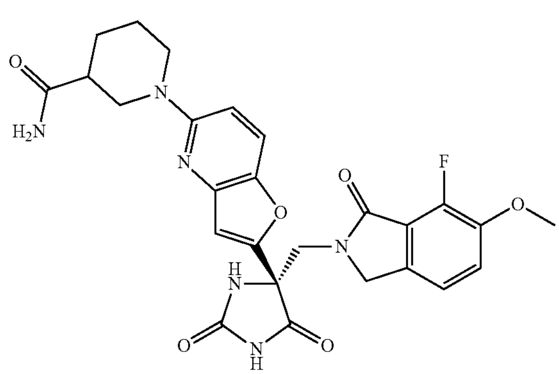 [SMILES: COc1ccc2c(c1F)C(=O)N(C[C@@]1(c3cc4nc(N5CCCC(C(N)=O)C5)ccc4o3)NC(=O)NC1=O)C2] | 536.5 | 537.3 | 0.5 | 259.9 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 1518 | 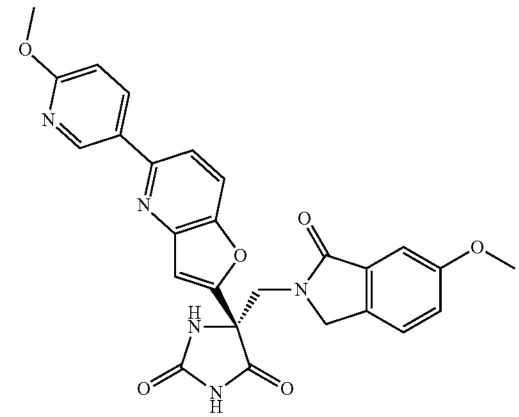 [SMILES: COc1ccc2c(c1)C(=O)N(C[C@@]1(c3cc4nc(-c5ccc(OC)nc5)ccc4o3)NC(=O)NC1=O)C2] | 499.5 | 500.3 | 0.9 | 1507 | |
| 1519 | 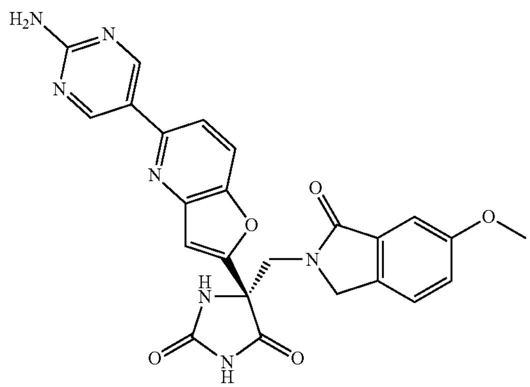 [SMILES: COc1ccc2c(c1)C(=O)N(C[C@@]1(c3cc4nc(-c5cnc(N)nc5)ccc4o3)NC(=O)NC1=O)C2] | 485.5 | 486.3 | 0.4 | 142 | |
| 1520 | 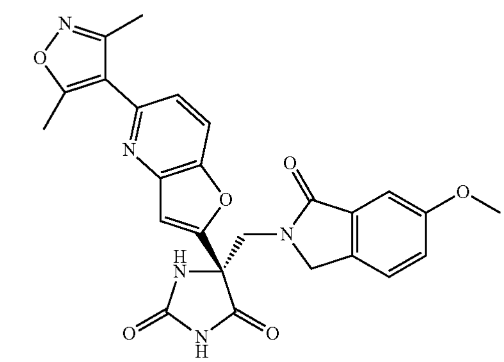 [SMILES: COc1ccc2c(c1)C(=O)N(C[C@@]1(c3cc4nc(-c5c(C)noc5C)ccc4o3)NC(=O)NC1=O)C2] | 487.5 | 488.3 | 0.5 | 1188 | |
| 1521 | 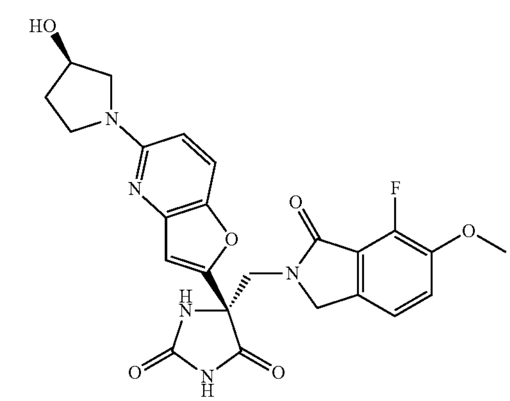 [SMILES: COc1ccc2c(c1F)C(=O)N(C[C@@]1(c3cc4nc(N5CC[C@@H](O)C5)ccc4o3)NC(=O)NC1=O)C2] | 495.5 | 496.3 | 0.3 | 168.8 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 1522 | 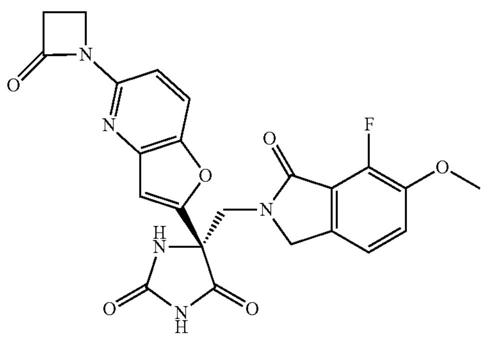 | 479.4 | 480.3 | 0.3 | 211.43 | 4633 |
| 1523 | 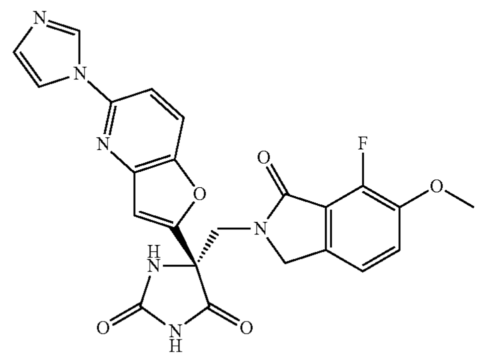 | 476.4 | 477.3 | 0.6 | 289.4 | 4294 |
| 1524 | 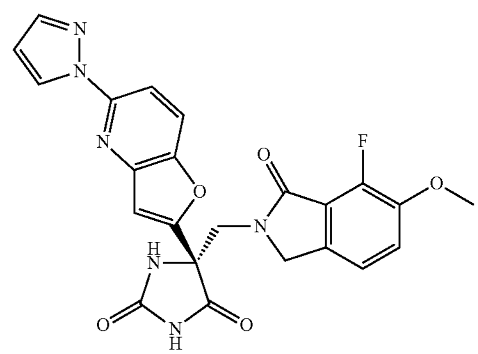 [SMILES: COc1ccc2c(c1F)C(=O)N(C[C@@]1(c3cc4nc(-n5cccn5)ccc4o3)NC(=O)NC1=O)C2] | 476.4 | 477.3 | 0.3 | 557.1 | 7995 |
| 1525 | 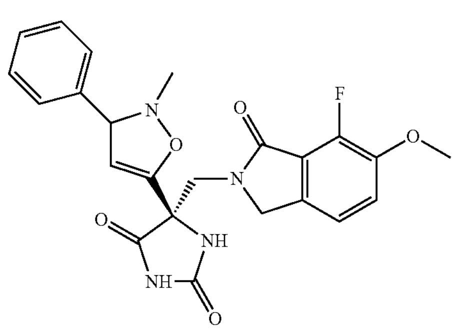 [SMILES: COc1ccc2c(c1F)C(=O)N(C[C@]1(C3=CC(c4ccccc4)N(C)O3)NC(=O)NC1=O)C2] | 452.4 | 453.2 | 3.2 | 100001 | |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 1526 | 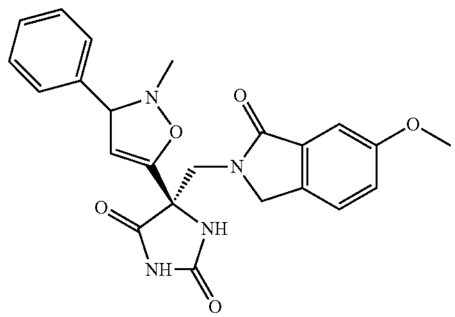 [SMILES: COc1ccc2c(c1)C(=O)N(C[C@]1(C3=CC(c4ccccc4)N(C)O3)NC(=O)NC1=O)C2] | 434.4 | 435.2 | 2.5 | | 100001 |
| 1527 | 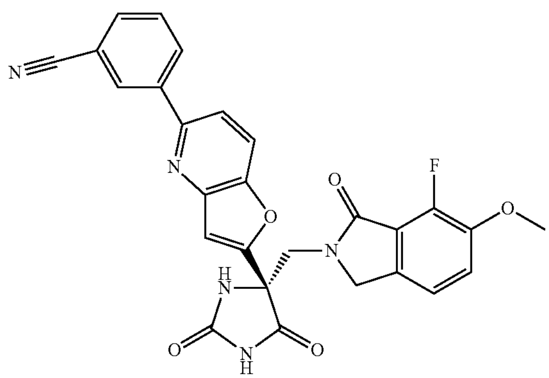 [SMILES: COc1ccc2c(c1F)C(=O)N(C[C@@]1(c3cc4nc(-c5cccc(C#N)c5)ccc4o3)NC(=O)NC1=O)C2] | 511.5 | 512.3 | 0.4 | | 578.6 |
| 1528 | 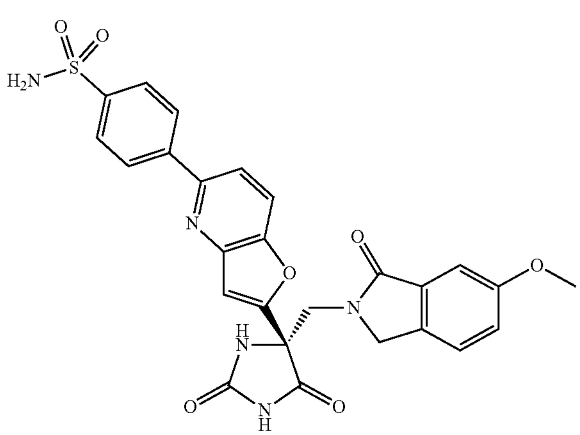 [SMILES: COc1ccc2c(c1)C(=O)N(C[C@@]1(c3cc4nc(-c5ccc(S(N)(=O)=O)cc5)ccc4o3)NC(=O)NC1=O)C2] | 547.5 | 548.3 | | | 2687 |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 1529 | 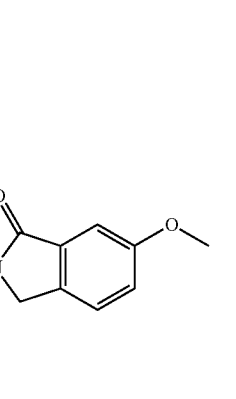 | 494.5 | 495.11 | 0.8 | 3658 | |
| 1530 | 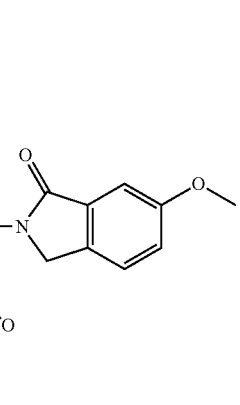 | 494.5 | 495.3 | 0.7 | 1612 | 536 |
| 1531 | 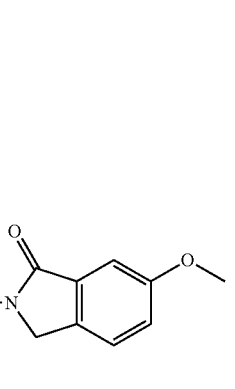 | | | 0.65 | 125 | |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 1305 | 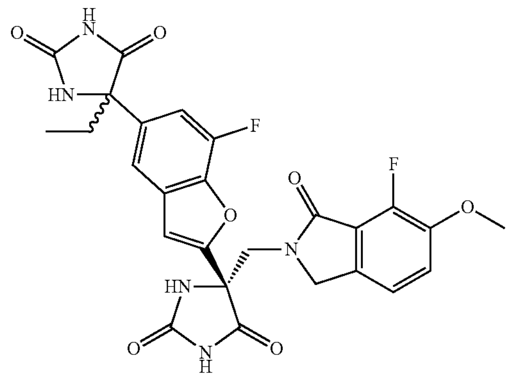 [SMILES: CCC1(c2cc(F)c3oc([C@]4(CN5Cc6ccc(OC)c(F)c6C5=O)NC(=O)NC4=O)cc3c2)NC(=O)NC1=O] | 533.14 | 554.3 | 0.77 | 239 | 1868 |
| 1306 | 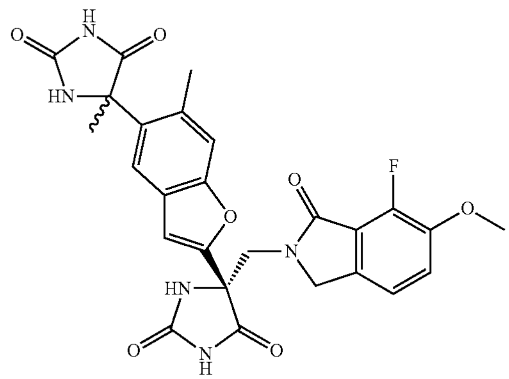 [SMILES: COc1ccc2c(c1F)C(=O)N(C[C@@]1(c3cc4cc(C5(C)NC(=O)NC5=O)c(C)cc4o3)NC(=O)NC1=O)C2] | 535.15 | 536.3 | 1.42 | 414 | 0 |
| 1307 | 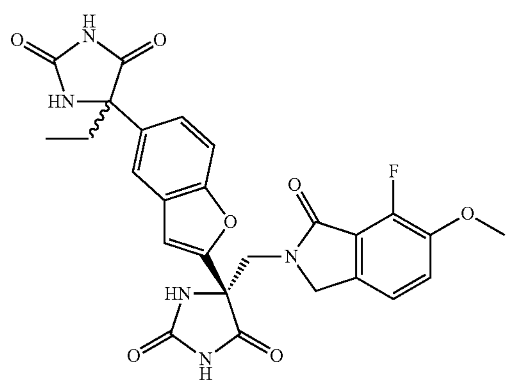 [SMILES: CCC1(c2ccc3oc([C@]4(CN5Cc6ccc(OC)c(F)c6C5=O)NC(=O)NC4=O)cc3c2)NC(=O)NC1=O] | 535.15 | 536.3 | 0.81 | 204 | 2011 |
| 1308 | 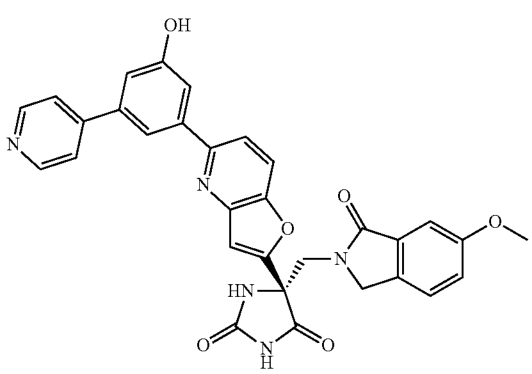 [SMILES: COc1ccc2c(c1)C(=O)N(C[C@@]1(c3cc4nc(-c5cc(O)cc(-c6ccncc6)c5)ccc4o3)NC(=O)NC1=O)C2] | 561.16 | 562.3 | 1.39 | 2946 | 0 |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 1310 | 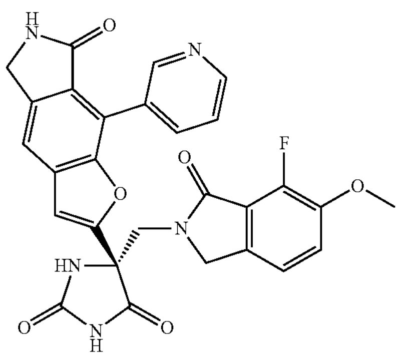 [SMILES: COc1ccc2c(c1F)C(=O)N(C[C@@]1(c3cc4cc5c(c(-c6cccnc6)c4o3)C(=O)NC5)NC(=O)NC1=O)C2] | | | | 404 | 614 |
| 1311 | 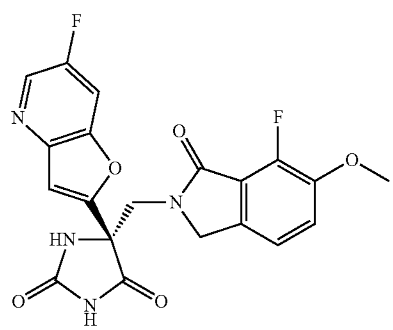 [SMILES: COc1ccc2c(c1F)C(=O)N(C[C@@]1(c3cc4ncc(F)cc4o3)NC(=O)NC1=O)C2] | 428.09 | 429.2 | 1.18 | 297 | 14640 |
| 1312 | 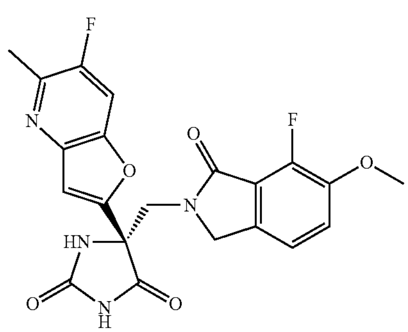 | 442.11 | 443.3 | 0.74 | 911 | 38339 |
| 1313 | 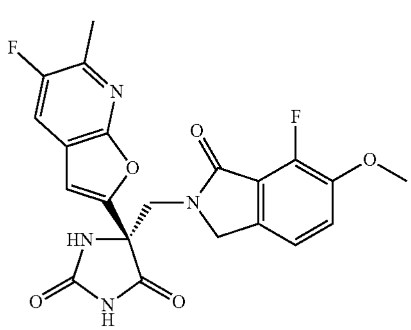 [SMILES: COc1ccc2c(c1F)C(=O)N(C[C@@]1(c3cc4cc(F)c(C)nc4o3)NC(=O)NC1=O)C2] | 442.11 | 443.2 | 0.83 | 686 | |

TABLE A-continued
| ID | STRUCTURE | EXACT MASS | MASS OBSVD | Ki (nM) | hWBA (IC$_{50}$) | RR[1] AUC (nM·h) |
|---|---|---|---|---|---|---|
| 1314 | 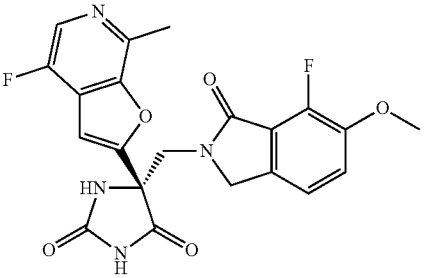 [SMILES: COc1ccc2c(c1F)C(=O)N(C[C@@]1(c3cc4c(F)cnc(C)c4o3)NC(=O)NC1=O)C2] | 442.11 | 443.2 | 1.20 | 727 | |
| 1315 | 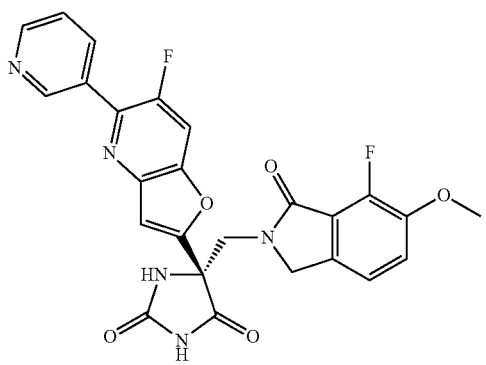 [SMILES: COc1ccc2c(c1F)C(=O)N(C[C@@]1(c3cc4nc(-c5cccnc5)c(F)cc4o3)NC(=O)NC1=O)C2] | 505.12 | 506.3 | 0.09 | 1115 | |
| 1316 | 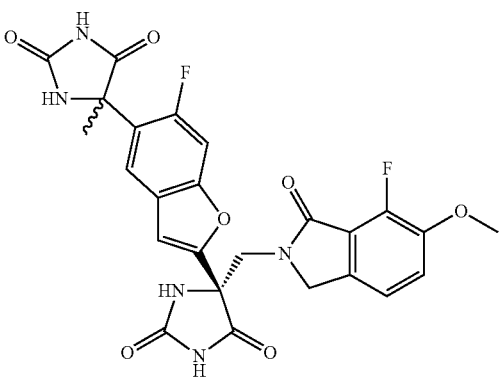 [SMILES: COc1ccc2c(c1F)C(=O)N(C[C@@]1(c3cc4cc(C5(C)NC(=O)NC5=O)c(F)cc4o3)NC(=O)NC1=O)C2] | 539.12 | 540.3 | 1.02 | 104 | 45700 |
| 1317 | 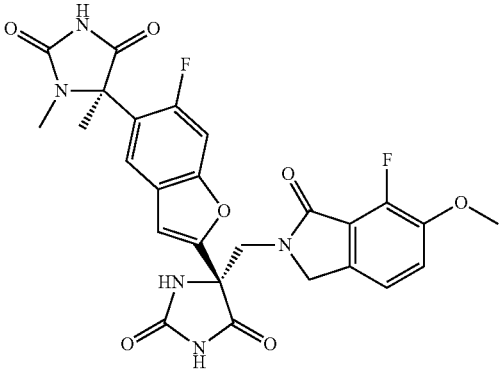 [SMILES: COc1ccc2c(c1F)C(=O)N(C[C@@]1(c3cc4cc([C@]5(C)C(=O)NC(=O)N5C)c(F)cc4o3)NC(=O)NC1=O)C2] | 553.14 | 554.3 | 0.47 | 234 | 0 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 1318 | 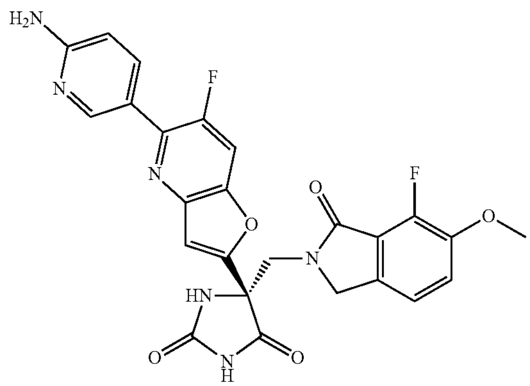 [SMILES: COc1ccc2c(c1F)C(=O)N(C[C@@]1(c3cc4nc(-c5ccc(N)nc5)c(F)cc4o3)NC(=O)NC1=O)C2] | 520.13 | 521.3 | 0.36 | 87 | 863 |
| 1319 | 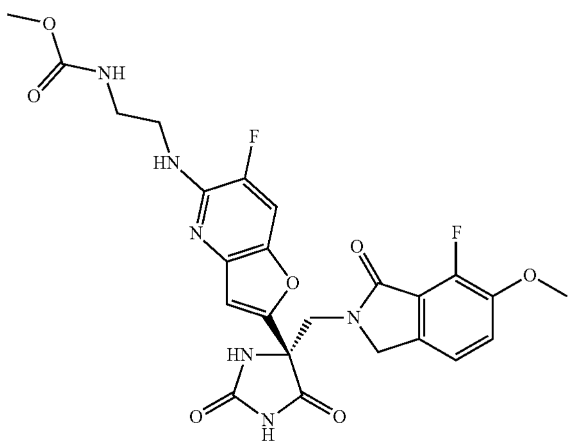 | 544.15 | 545.3 | | 252 | |
| 1320 | 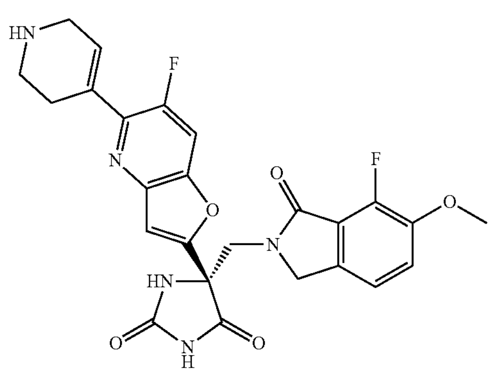 [SMILES: COc1ccc2c(c1F)C(=O)N(C[C@@]1(c3cc4nc(C5=CCNCC5)c(F)cc4o3)NC(=O)NC1=O)C2] | 509.15 | 510.3 | 0.37 | 55 | 101 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 1321 | 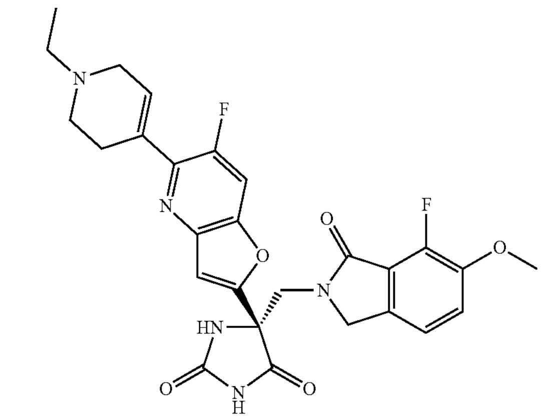 [SMILES: CCN1CC=C(c2nc3cc([C@]4(CN5Cc6ccc(OC)c(F)c6C5=O)NC(=O)NC4=O)oc3cc2F)CC1] | 537.18 | 538.3 | 0.64 | 184 | |
| 1322 | 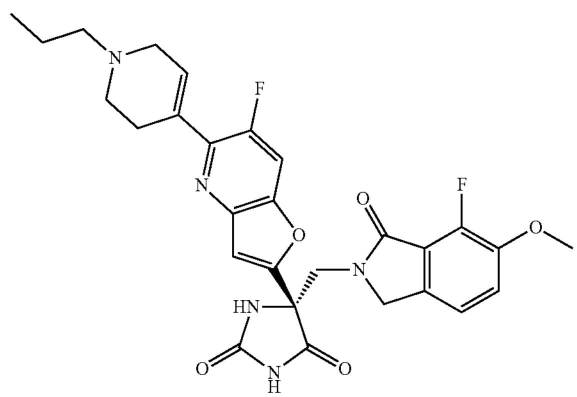 [SMILES: CCCN1CC=C(c2nc3cc([C@]4(CN5Cc6ccc(OC)c(F)c6C5=O)NC(=O)NC4=O)oc3cc2F)CC1] | 551.20 | 552.3 | 0.51 | 96 | |
| 1323 | 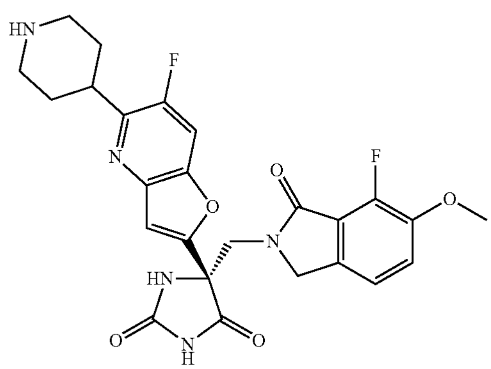 [SMILES: COc1ccc2c(c1F)C(=O)N(C[C@@]1(c3cc4nc(C5CCNCC5)c(F)cc4o3)NC(=O)NC1=O)C2] | 511.17 | 512.3 | 0.08 | 140 | |
| 1324 | 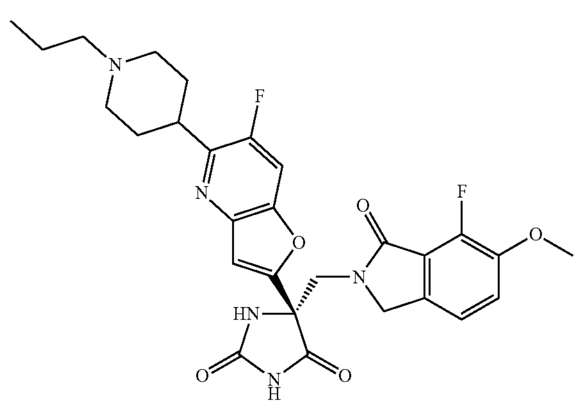 [SMILES: CCCN1CCC(c2nc3cc([C@]4(CN5Cc6ccc(OC)c(F)c6C5=O)NC(=O)NC4=O)oc3cc2F)CC1] | 553.21 | 554.3 | 0.58 | 248 | |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 1325 | 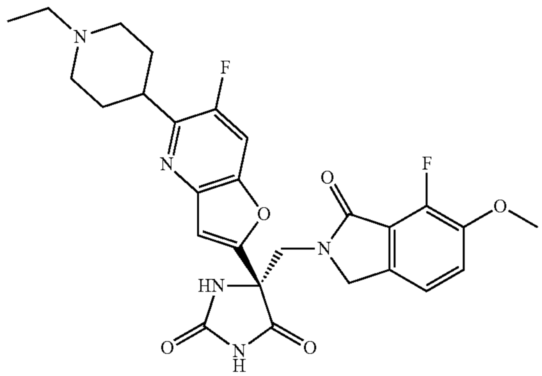 [SMILES: CCN1CCC(c2nc3cc([C@]4(CN5Cc6ccc(OC)c(F)c6C5=O)NC(=O)NC4=O)oc3cc2F)CC1] | 539.20 | 540.3 | 1.00 | 175 | 9 |
| 1326 | 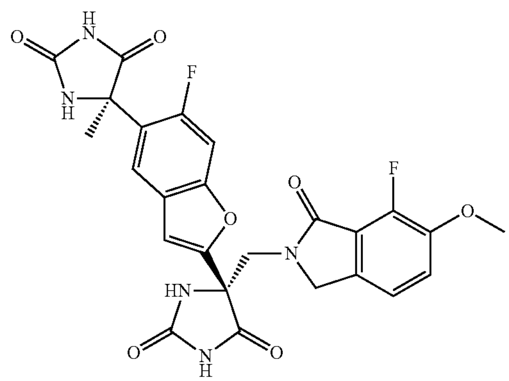 [SMILES: COc1ccc2c(c1F)C(=O)N(C[C@@]1(c3cc4cc([C@@]5(C)NC(=O)NC5=O)c(F)cc4o3)NC(=O)NC1=O)C2] | 539.13 | 540.3 | 0.63 | 156 | 1037 |
| 1327 | 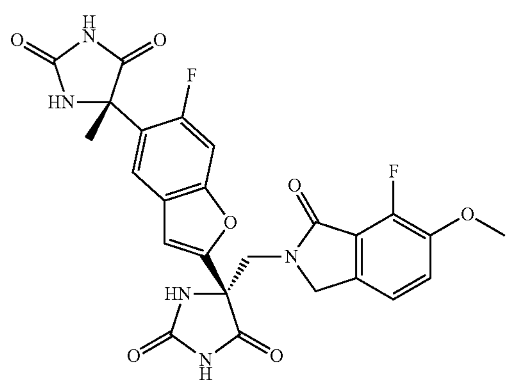 [SMILES: COc1ccc2c(c1F)C(=O)N(C[C@@]1(c3cc4cc([C@]5(C)NC(=O)NC5=O)c(F)cc4o3)NC(=O)NC1=O)C2] | 539.13 | 540.3 | 0.47 | 161 | 2968 |
| 1328 | 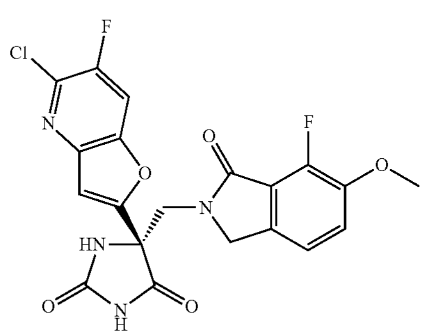 [SMILES: COc1ccc2c(c1F)C(=O)N(C[C@@]1(c3cc4nc(Cl)c(F)cc4o3)NC(=O)NC1=O)C2] | 462.05 | 463.3 | 0.49 | 2676 | 5610 |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 1329 | 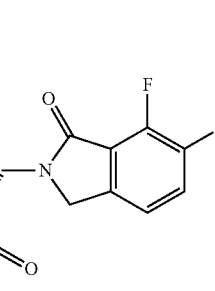 | 526.14 | | 0.59 | 234 | 226 |
| 1330 | 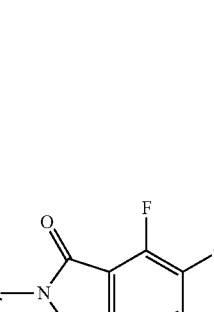 | 526.10 | 527.3 | 0.39 | 101 | 3186 |
| 1331 | 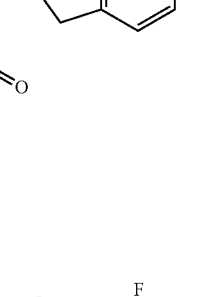 | 512.13 | 545.3 | 0.66 | 310 | 670 |
| 1181 | 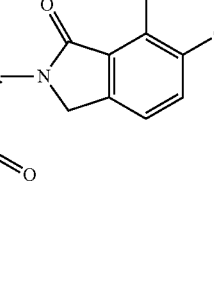 | 535.2 | 536.3 | 0.41 | 354 | |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 1182 | 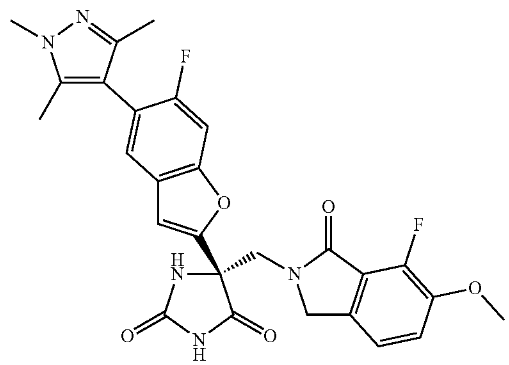 | 535.17 | 536.3 | 0.41 | 354 | |
| 1183 | 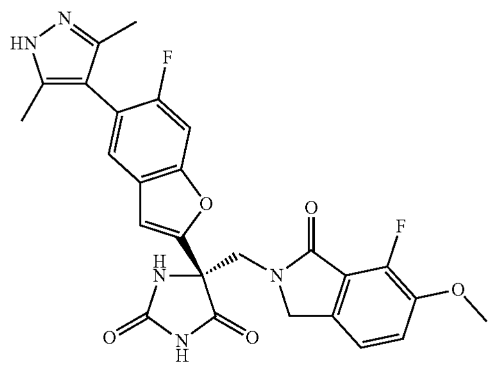 | 521.15 | 522.3 | 0.14 | 232 | |
| 1184 | 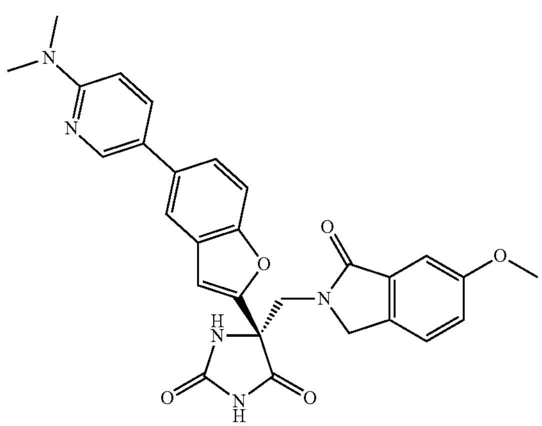 | 511.2 | 512.3 | 0.85 | 2709 | |
| 1186 | 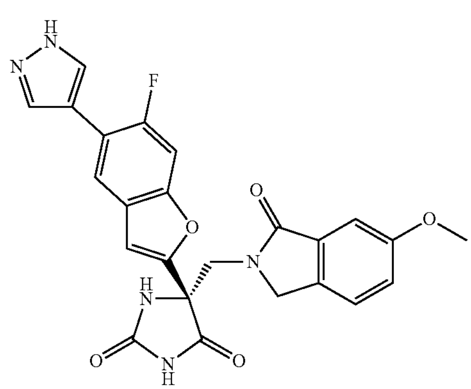 [SMILES: COc1ccc2c(c1)C(=O)N(C[C@@]1(c3cc4cc(-c5cn[nH]c5)c(F)cc4o3)NC(=O)NC1=O)C2] | 475.1 | 476.3 | 0.56 | 550 | 285 |

TABLE A-continued

| ID | STRUCTURE | EXACT MASS | MASS OBSVD | Ki (nM) | hWBA (IC$_{50}$) | RR$^1$ AUC (nM · h) |
|---|---|---|---|---|---|---|
| 1187 | 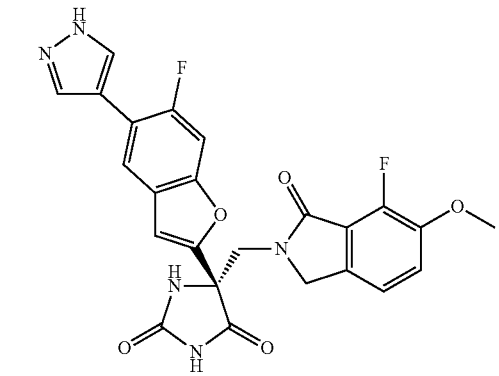 [SMILES: COc1ccc2c(c1F)C(=O)N(C[C@@]1(c3cc4cc(-c5cn[nH]c5)c(F)cc4o3)NC(=O)NC1=O)C2] | 493.1 | 494.3 | 0.23 | 286 | 1073 |
| 1188 | 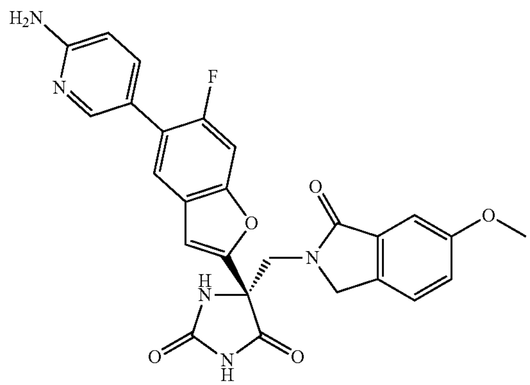 [SMILES: COc1ccc2c(c1)C(=O)N(C[C@@]1(c3cc4cc(-c5ccc(N)nc5)c(F)cc4o3)NC(=O)NC1=O)C2] | 501.1 | 502.3 | 0.51 | 720 | 355 |
| 1271 | 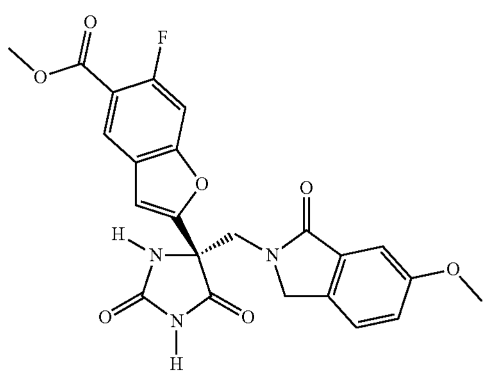 | 467.1 | 468.3 | 0.45 | 1054 | |
| 1272 | 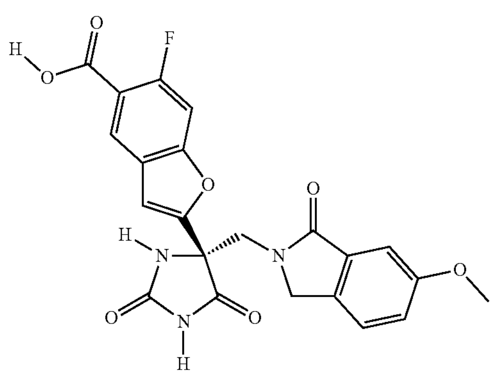 [SMILES: COc1ccc2c(c1)C(=O)N(C[C@@]1(c3cc4cc(C(=O)O)c(F)cc4o3)NC(=O)NC1=O)C2] | 453.1 | 454.2 | 0.51 | 667 | |

TABLE A-continued

| ID | STRUCTURE | EXACT MASS | MASS OBSVD | Ki (nM) | hWBA (IC$_{50}$) | RR$^1$ AUC (nM · h) |
| --- | --- | --- | --- | --- | --- | --- |
| 1273 | 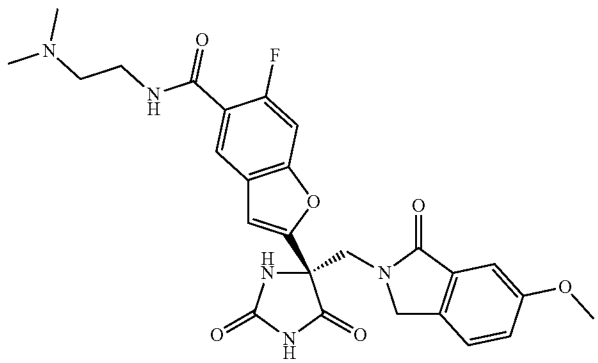 | 523.2 | 524.3 | 0.59 | 181 | 37 |
| 1274 | 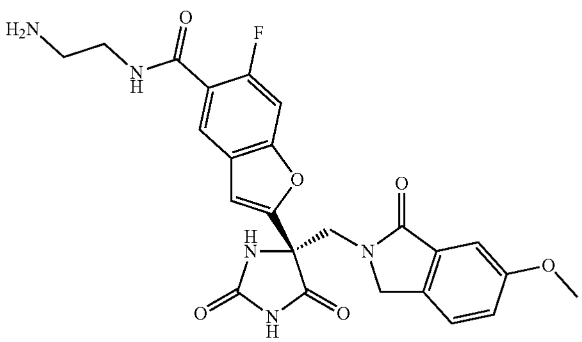 [SMILES: COc1ccc2c(c1)C(=O)N(C[C@@]1(c3cc4cc(C(=O)NCCN)c(F)cc4o3)NC(=O)NC1=O)C2] | 495.2 | 496.3 | 0.50 | 142 | 0 |
| 1275 | 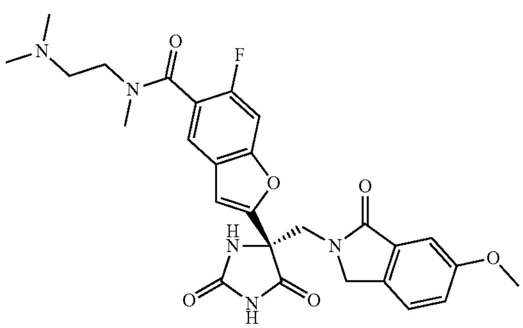 | 537.2 | 538.3 | 0.88 | 441 | |
| 1276 | 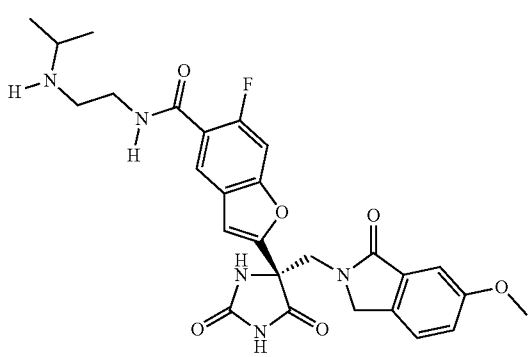 [SMILES: COc1ccc2c(c1)C(=O)N(C[C@@]1(c3cc4cc(C(=O)NCCNC(C)C)c(F)cc4o3)NC(=O)NC1=O)C2] | 537.2 | 538.3 | 1.2 | 251 | |

TABLE A-continued
| ID | STRUCTURE | EXACT MASS | MASS OBSVD | Ki (nM) | hWBA (IC$_{50}$) | RR[1] AUC (nM·h) |
|---|---|---|---|---|---|---|
| 1277 | 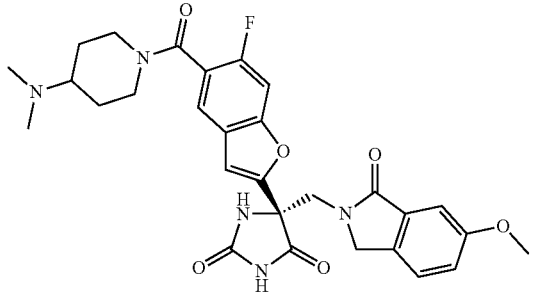 | 563.2 | 564.3 | 0.62 | 471 | |
| 1278 | 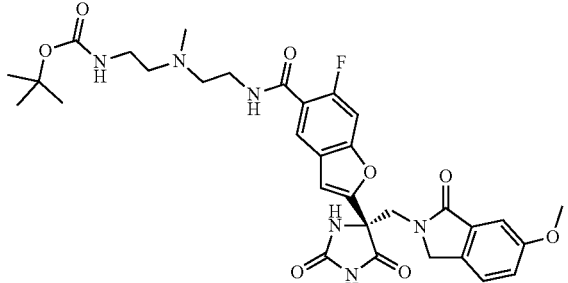 | 652.3 | 653.4 | 1.8 | 3261 | |
| 1279 | 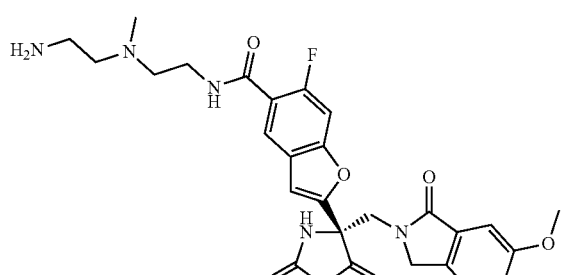 | 552.2 | 553.3 | 1.0 | 504 | |
| 1281 | 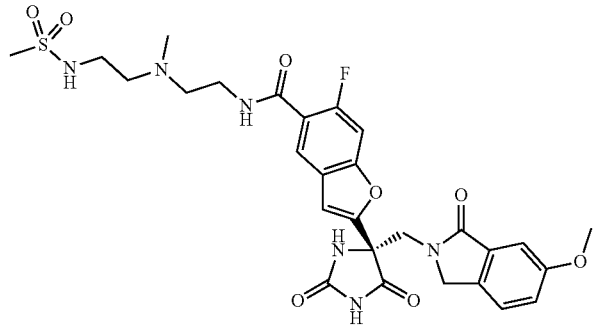 | 630.2 | 631.3 | 0.83 | 1104 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 1282 | 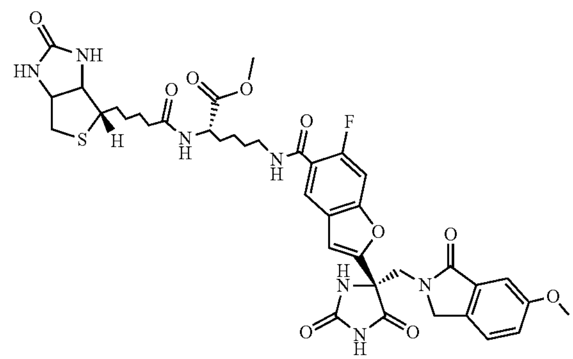 [SMILES: COC(=O)[C@H](CCCCNC(=O)c1cc2cc([C@]3(CN4Cc5ccc(OC)cc5C4=O)NC(=O)NC3=O)oc2cc1F)NC(=O)CCCC[C@@H]1SCC2NC(=O)NC21] | 821.3 | 822.5 | 0.48 | 407 | |
| 1283 | 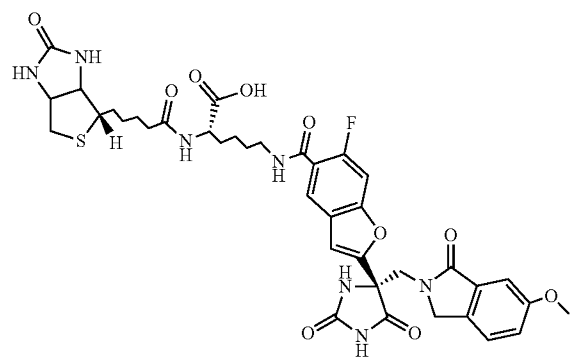 [SMILES: COc1ccc2c(c1)C(=O)N(C[C@@]1(c3cc4cc(C(=O)NCCCC[C@H](NC(=O)CCCC[C@@H]5SCC6NC(=O)NC65)C(=O)O)c(F)cc4o3)NC(=O)NC1=O)C2] | 807.3 | 808.4 | 0.39 | 3296 | |
| 1291 | 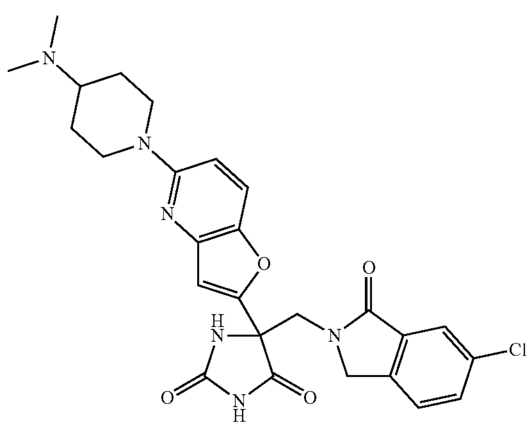 [SMILES: CN(C)C1CCN(c2ccc3oc(C4(CN5Cc6ccc(Cl)cc6C5=O)NC(=O)NC4=O)cc3n2)CC1] | 522.2 | 523.3 | 1.33 | 1399 | |
| 1292 | 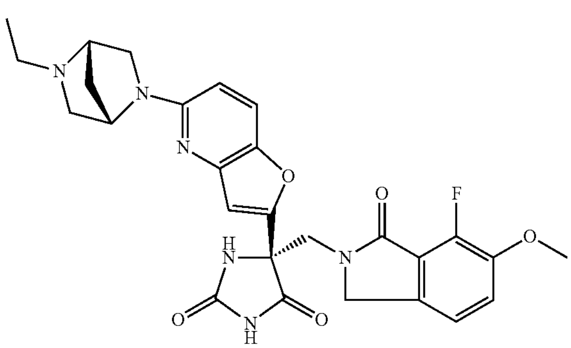 [SMILES: CCN1C[C@@H]2C[C@H]1CN2c1ccc2oc([C@]3(CN4Cc5ccc(OC)c(F)c5C4=O)NC(=O)NC3=O)cc2n1] | 534.2 | 535.3 | 0.86 | 177 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 1293 | 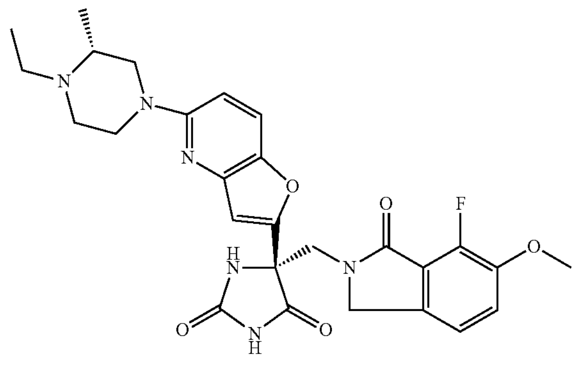 [SMILES: CCN1CCN(c2ccc3oc([C@]4(CN5Cc6ccc(OC)c(F)c6C5=O)NC(=O)NC4=O)cc3n2)C[C@H]1C] | 536.2 | 537.3 | 0.79 | 112 | |
| 1294 | 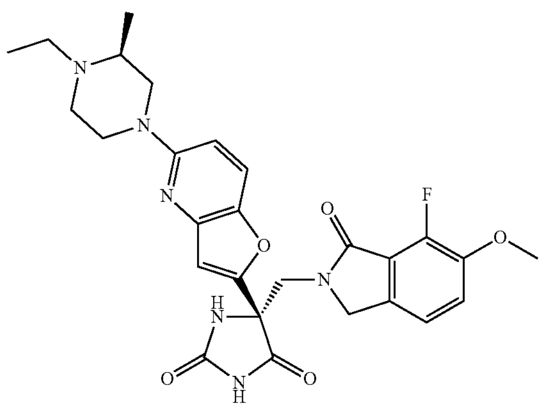 [SMILES: CCN1CCN(c2ccc3oc([C@]4(CN5Cc6ccc(OC)c(F)c6C5=O)NC(=O)NC4=O)cc3n2)C[C@@H]1C] | 536.2 | 537.3 | 1.1 | 275 | |
| 1296 | 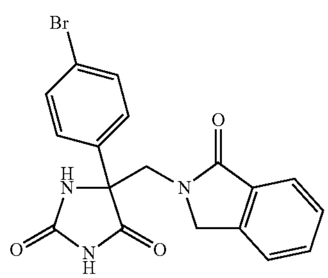 [SMILES: O=C1NC(=O)C(CN2Cc3ccccc3C2=O)(c2ccc(Br)cc2)N1] | 399.0 | 400.2 | 7.0 | >10000 | |
| 1297 | 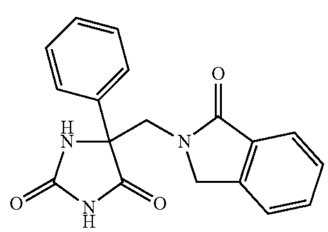 [SMILES: O=C1NC(=O)C(CN2Cc3ccccc3C2=O)(c2ccccc2)N1] | 321.1 | 322.2 | 16.4 | | |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 1298 | 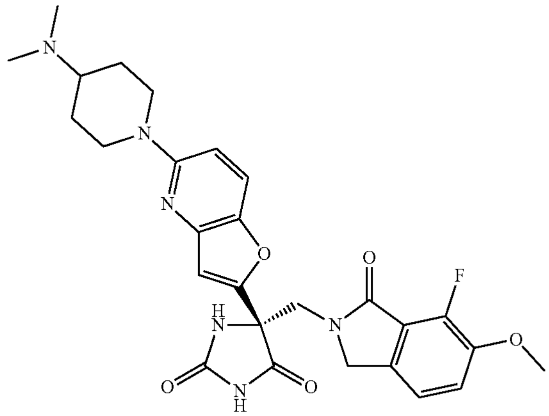 | 536.22 | 537.3 | | 79 | 37 |
| 2100 | 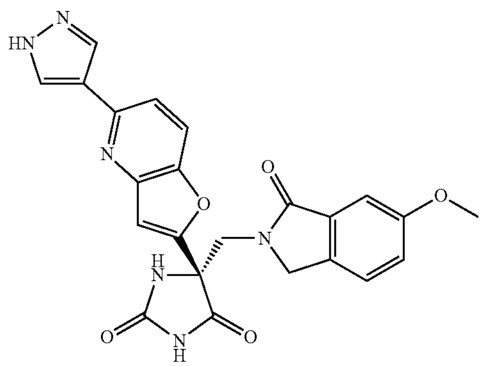 [SMILES: COc1ccc2c(c1)C(=O)N(C[C@@]1(c3cc4nc(-c5cn[nH]c5)ccc4o3)NC(=O)NC1=O)C2] | 458.13 | 459.3 | 0.197 | 99.4 | 104 |
| 2101 | 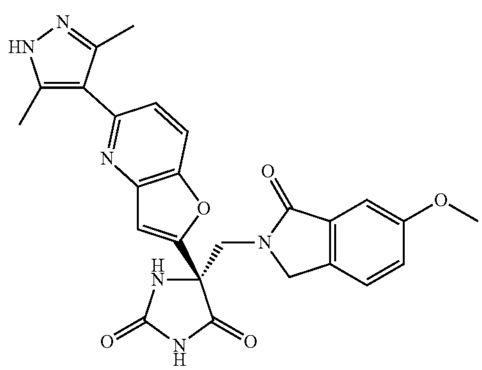 | 486.17 | 487.3 | 0.14 | 203.4 | 0 |
| 2102 | 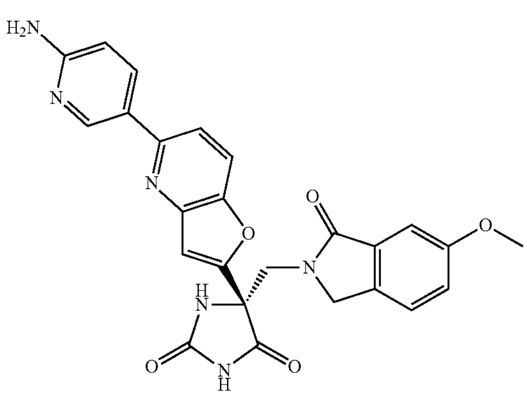 | 484.15 | 485.3 | 0.328 | 163.9 | 92 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2103 | 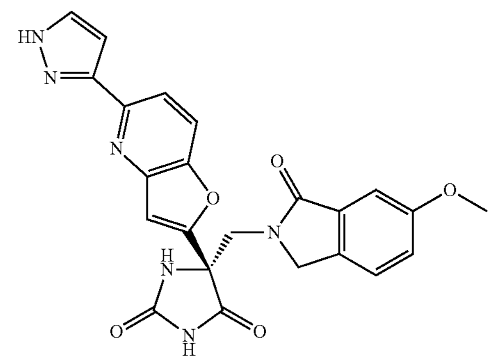 [SMILES: COc1ccc2c(c1)C(=O)N(C[C@@]1(c3cc4nc(-c5cc[nH]n5)ccc4o3)NC(=O)NC1=O)C2] | 458.43 | 459.3 | 0.342 | 375.2 | 0 |
| 2104 | 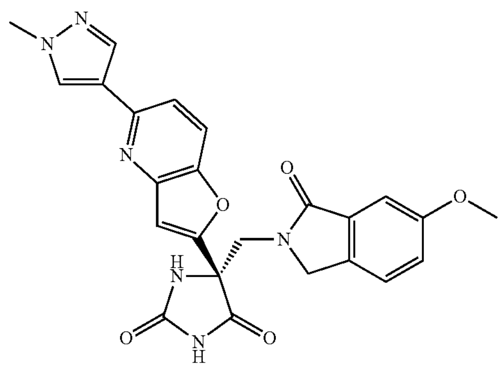 | 472.15 | 473.3 | 0.191 | 284.9 | 369 |
| 2105 | 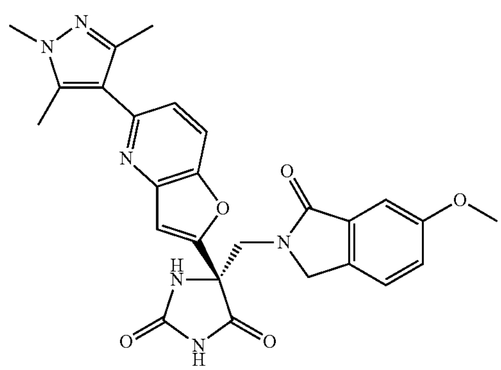 | 500.18 | 501.3 | 0.155 | 216.2 | 7544 |
| 2106 | 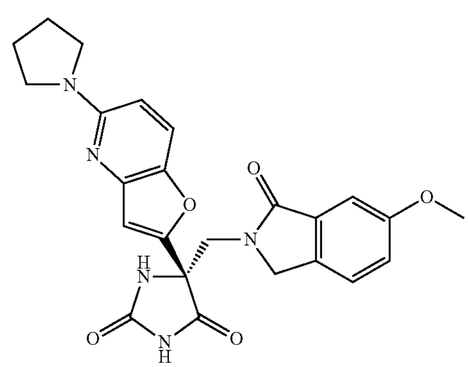 [SMILES: COc1ccc2c(c1)C(=O)N(C[C@@]1(c3cc4nc(N5CCCC5)ccc4o3)NC(=O)NC1=O)C2] | 461.17 | 462.3 | 0.422 | 668.9 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2107 | 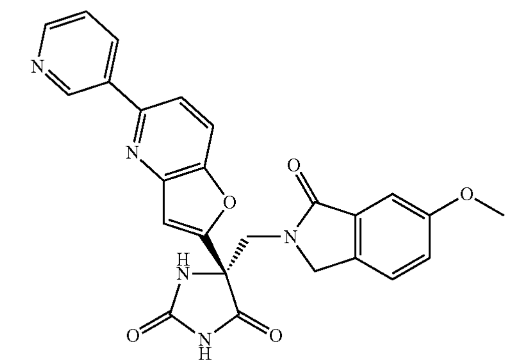 [SMILES: COc1ccc2c(c1)C(=O)N(C[C@@]1(c3cc4nc(-c5cccnc5)ccc4o3)NC(=O)NC1=O)C2] | 469.14 | 470.3 | 0.902 | 171.4 | 3082 |
| 2108 | 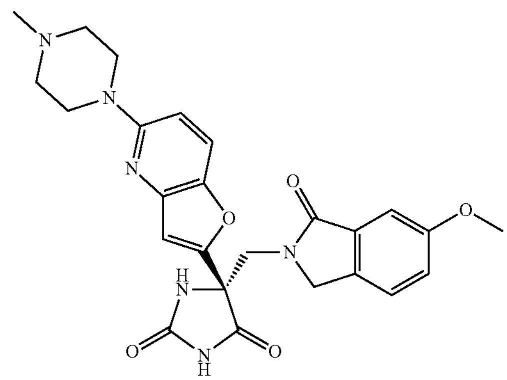 | 490.20 | 491.3 | 0.613 | 150.4 | 430 |
| 2109 | 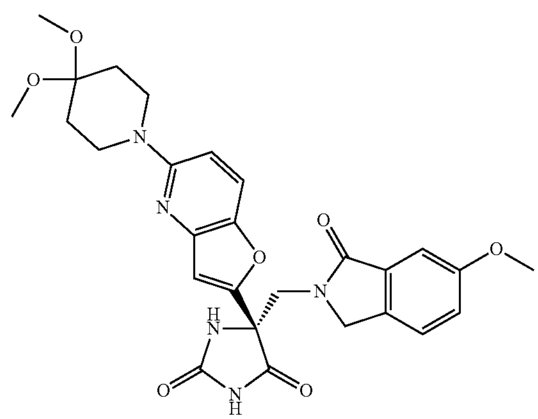 | 535.21 | 536.3 | 0.75 | 160.8 | |
| 2110 | 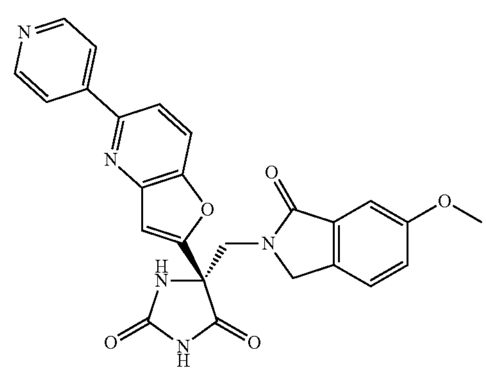 | 469.14 | 470.3 | 0.62 | 351 | 10547 |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 2111 | 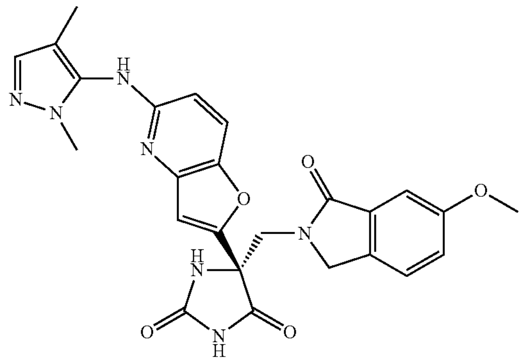 [SMILES: COc1ccc2c(c1)C(=O)N(C[C@@]1(c3cc4nc(Nc5c(C)cnn5C)ccc4o3)NC(=O)NC1=O)C2] | 501.49 | 502.3 | 0.762 | 1132 | |
| 2112 | 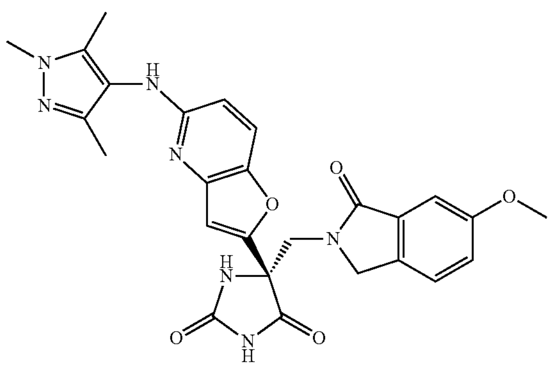 | 515.19 | 516.3 | 0.385 | 532.6 | 19 |
| 2113 | 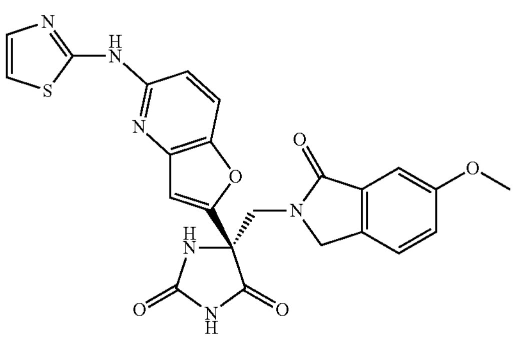 [SMILES: COc1ccc2c(c1)C(=O)N(C[C@@]1(c3cc4nc(Nc5nccs5)ccc4o3)NC(=O)NC1=O)C2] | 490.11 | 491.3 | 0.62 | 1404 | |
| 2114 | 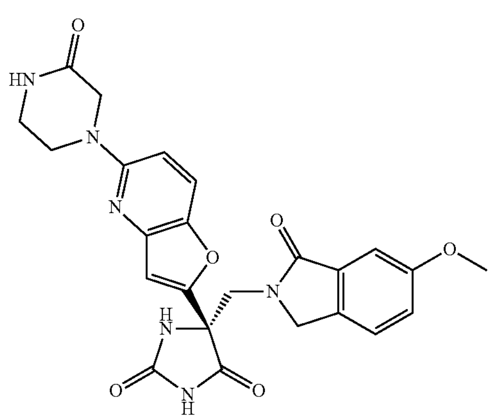 [SMILES: COc1ccc2c(c1)C(=O)N(C[C@@]1(c3cc4nc(N5CCNC(=O)C5)ccc4o3)NC(=O)NC1=O)C2] | 490.16 | 491.3 | 0.306 | 192.6 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2115 | 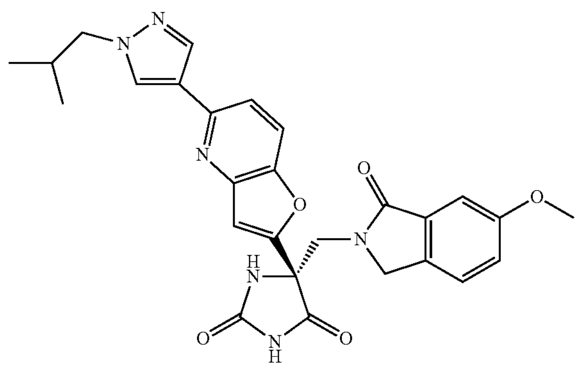 [SMILES: COc1ccc2c(c1)C(=O)N(C[C@@]1(c3cc4nc(-c5cnn(CC(C)C)c5)ccc4o3)NC(=O)NC1=O)C2] | 514.20 | 515.3 | 0.193 | 967.9 | 349 |
| 2116 | 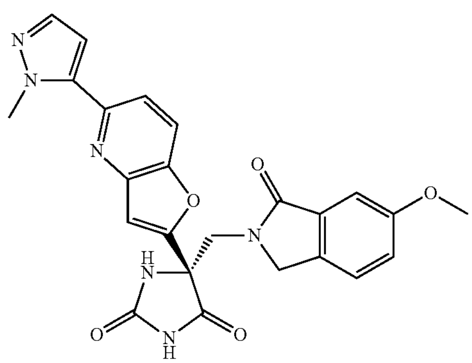 | 472.15 | 473.3 | | 1205 | 5191 |
| 2117 | 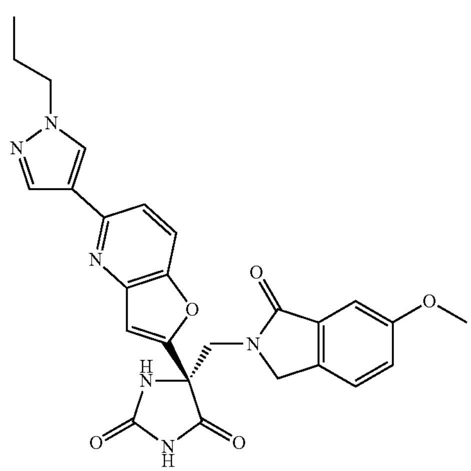 [SMILES: CCCn1cc(-c2ccc3oc([C@]4(CN5Cc6ccc(OC)cc6C5=O)NC(=O)NC4=O)cc3n2)cn1] | 500.18 | 501.3 | 0.408 | 1013 | 320 |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 2118 | 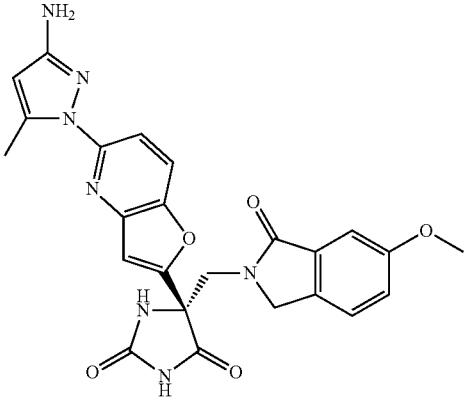 | 487.16 | 488.3 | 0.6 | 3793.9 | 527 |
| 2119 | 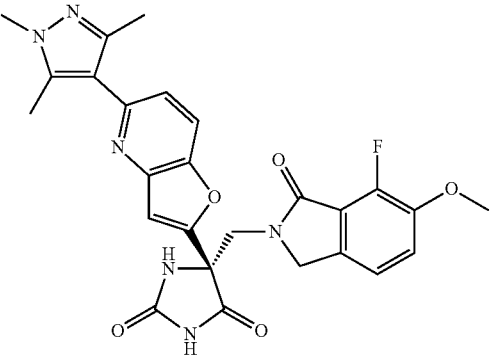 | 518.17 | 519.3 | 0.39 | 243 | 7004 |
| 2120 | 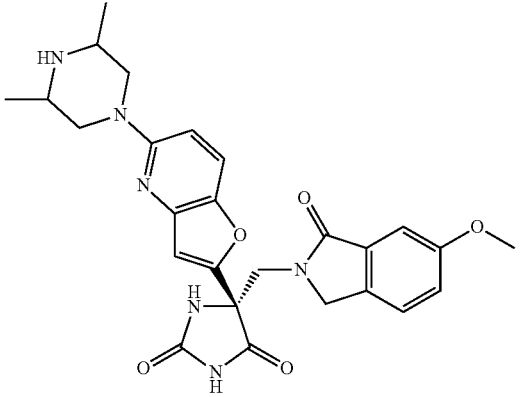 | 504.21 | 505.3 |  | 1205 | 5191 |
| 2121 | 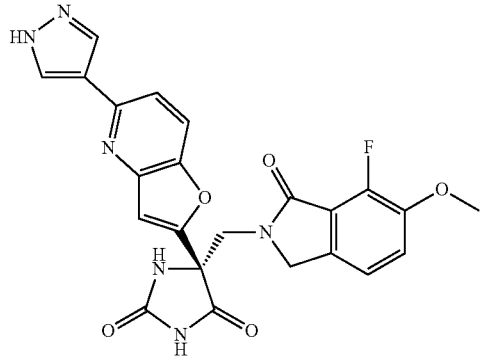 [SMILES: COc1ccc2c(c1F)C(=O)N(C[C@@]1(c3cc4nc(-c5cn[nH]c5)ccc4o3)NC(=O)NC1=O)C2] | 476.12 | 477.3 | 0.263 | 102 | 0 |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 2122 | 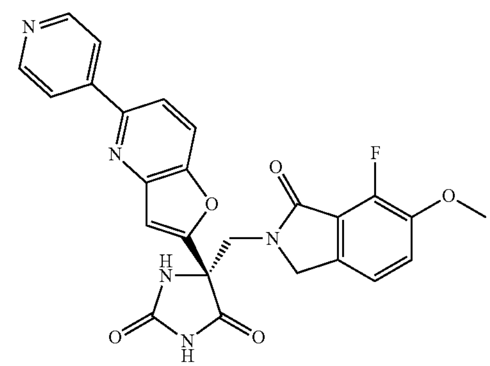 | 487.13 | 488.3 | 0.58 | 425.85 | 8179 |
| 2123 | 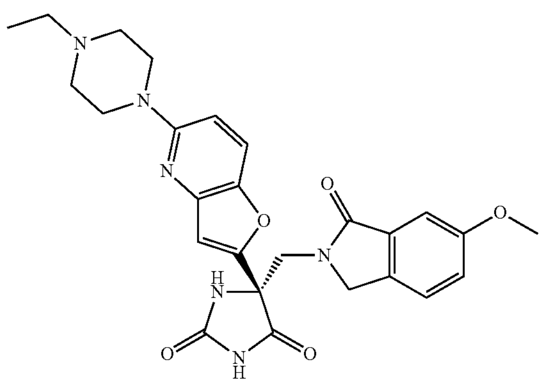 [SMILES: CCN1CCN(c2ccc3oc([C@]4(CN5Cc6ccc(OC)cc6C5=O)NC(=O)NC4=O)cc3n2)CC1] | 504.21 | 505.3 | 0.807 | 135.95 | 727 |
| 2124 | 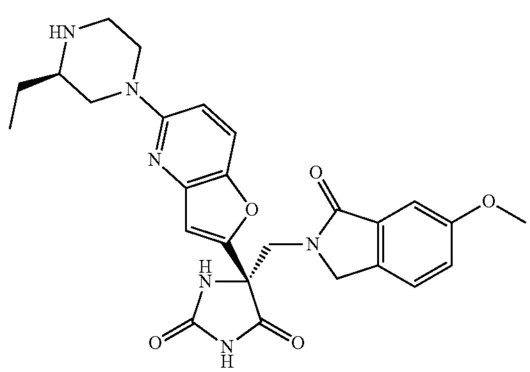 [SMILES: CC[C@@H]1CN(c2ccc3oc([C@]4(CN5Cc6ccc(OC)cc6C5=O)NC(=O)NC4=O)cc3n2)CCN1] | 504.21 | 505.3 | 1.09 | 270 | 14 |
| 2125 | 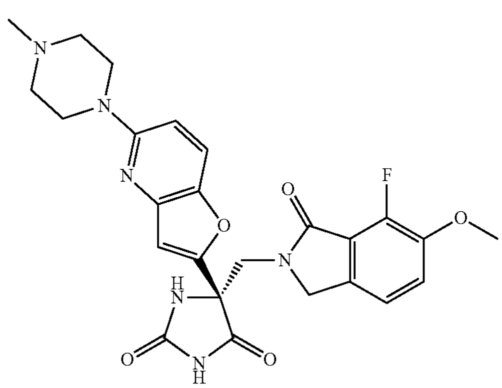 | 508.19 | 509.3 | 0.5 | 143.66 | 1516 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2126 | 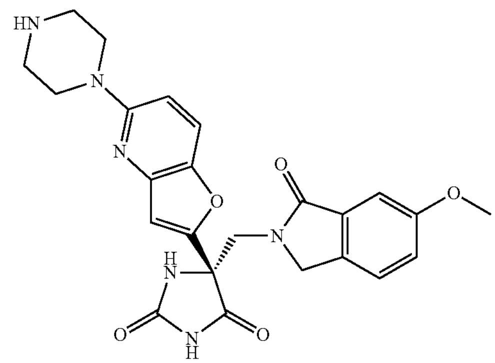 [SMILES: COc1ccc2c(c1)C(=O)N(C[C@@]1(c3cc4nc(N5CCNCC5)ccc4o3)NC(=O)NC1=O)C2] | 476.18 | 477.3 | 0.661 | 193.85 | |
| 2127 | 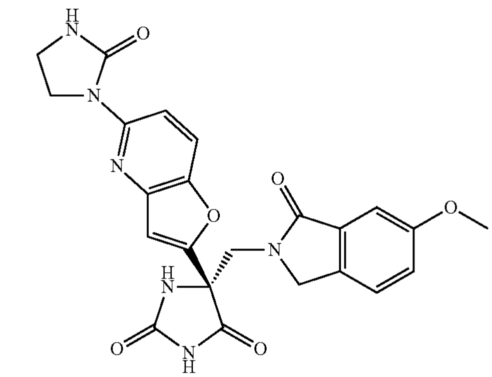 [SMILES: COc1ccc2c(c1)C(=O)N(C[C@@]1(c3cc4nc(N5CCNC5=O)ccc4o3)NC(=O)NC1=O)C2] | 476.14 | 477.3 | 0.435 | 221.45 | |
| 2128 | 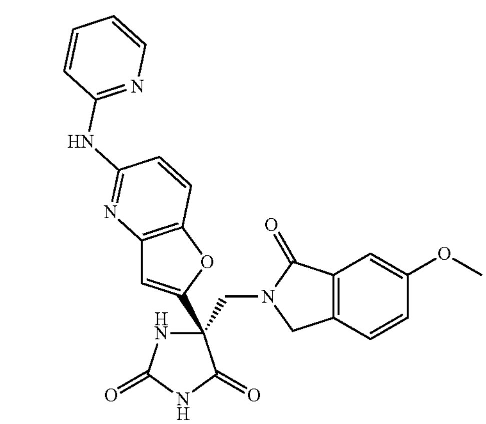 [SMILES: COc1ccc2c(c1)C(=O)N(C[C@@]1(c3cc4nc(Nc5ccccn5)ccc4o3)NC(=O)NC1=O)C2] | 484.15 | 485.3 | 0.888 | 1913 | |
| 2129 | 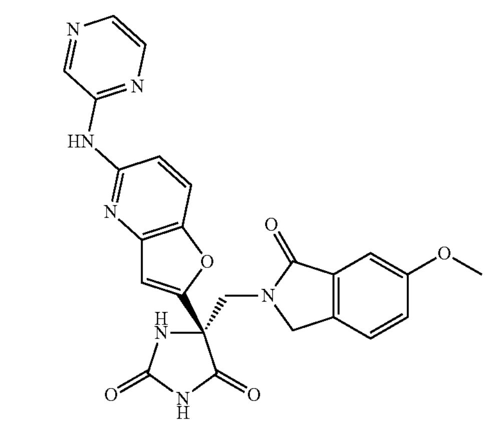 [SMILES: COc1ccc2c(c1)C(=O)N(C[C@@]1(c3cc4nc(Nc5cnccn5)ccc4o3)NC(=O)NC1=O)C2] | 485.14 | 486.3 | 0.395 | 750 | 1326 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2130 | 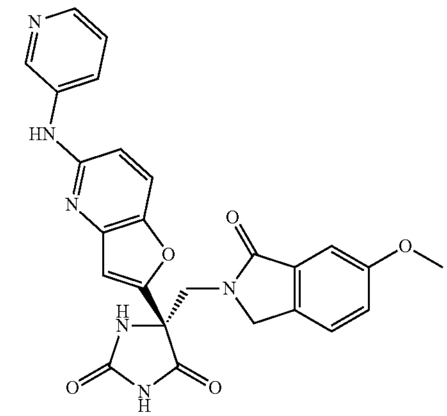 [SMILES: COc1ccc2c(c1)C(=O)N(C[C@@]1(c3cc4nc(Nc5cccnc5)ccc4o3)NC(=O)NC1=O)C2] | 484.15 | 485.3 | 0.629 | 162.8 | 72 |
| 2131 | 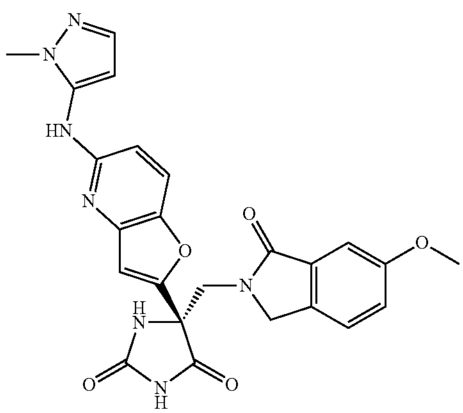 | 487.16 | 488.3 | 0.418 | 637.2 | 257 |
| 2132 | 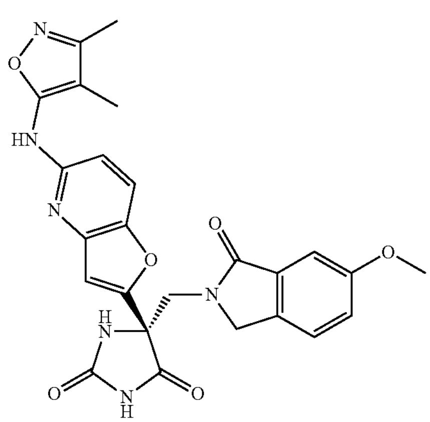 [SMILES: COc1ccc2c(c1)C(=O)N(C[C@@]1(c3cc4nc(Nc5onc(C)c5C)ccc4o3)NC(=O)NC1=O)C2] | 502.16 | 503.3 | 0.593 | 3132.8 | 145 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2133 | 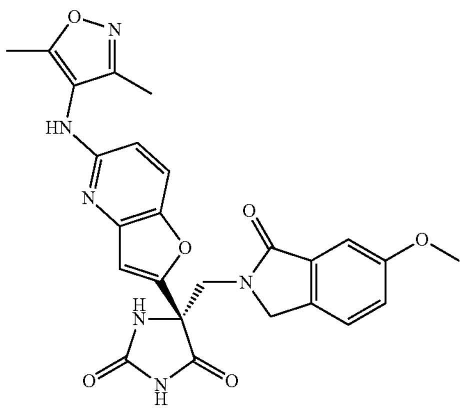 | 502.16 | 503.3 | 0.635 | 460.3 | 0 |
| 2134 | 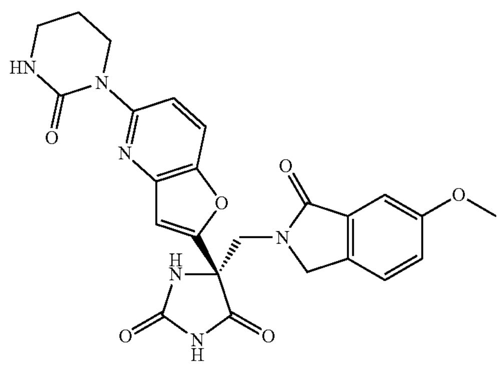 [SMILES: COc1ccc2c(c1)C(=O)N(C[C@@]1(c3cc4nc(N5CCCNC5=O)ccc4o3)NC(=O)NC1=O)C2] | 490.16 | 491.3 | 0.467 | 114.95 | |
| 2135 | 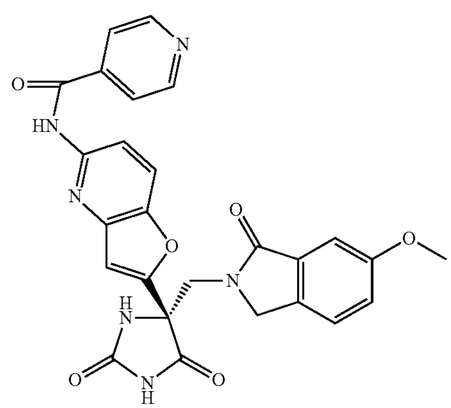 [SMILES: COc1ccc2c(c1)C(=O)N(C[C@@]1(c3cc4nc(NC(=O)c5ccncc5)ccc4o3)NC(=O)NC1=O)C2] | 512.14 | 513.3 | 1.2 | 2781 | 560 |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 2136 | 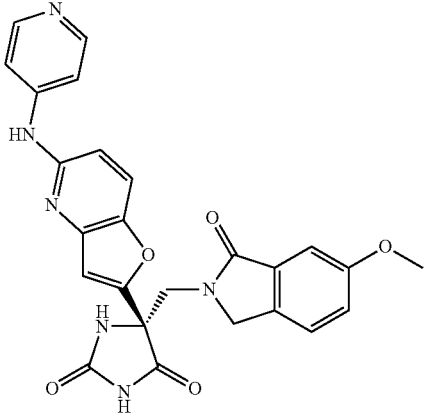 [SMILES: COc1ccc2c(c1)C(=O)N(C[C@@]1(c3cc4nc(Nc5ccncc5)ccc4o3)NC(=O)NC1=O)C2] | 484.15 | 485.3 | 0.427 | 246.9 | 0 |
| 2137 | 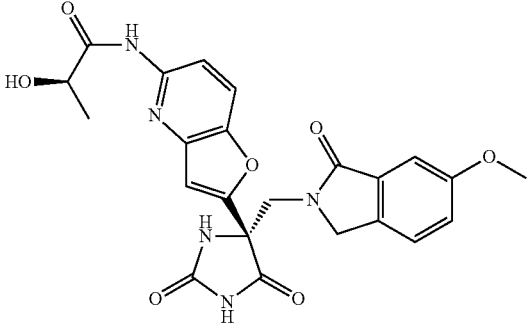 [SMILES: COc1ccc2c(c1)C(=O)N(C[C@@]1(c3cc4nc(NC(=O)[C@@H](C)O)ccc4o3)NC(=O)NC1=O)C2] | 479.14 | 480.3 | 0.36 | 310 | |
| 2138 | 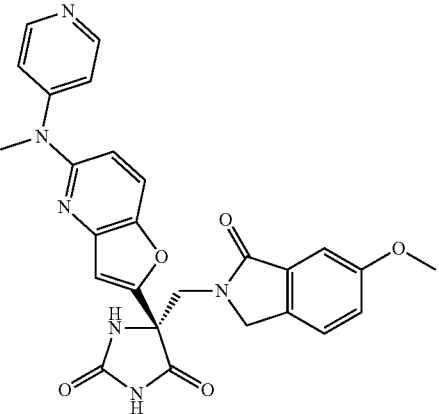 | 498.17 | 499.3 | 0.881 | 524 | |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 2139 | 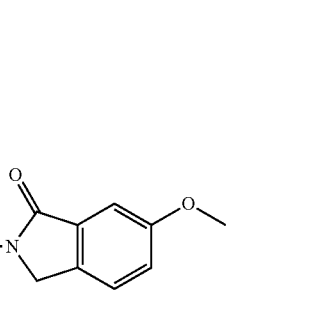 | 504.21 | 505.3 | 1.44 | 387.5 | |
| 2141 | 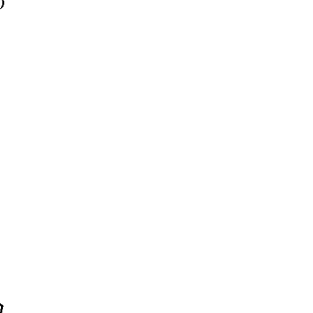 | 504.21 | 505.3 | 0.599 | 381.05 | 2709 |
| 2142 | 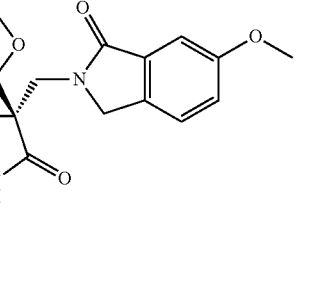 | 547.25 | 548.3 | 0.875 | 463.45 | 60 |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 2143 | 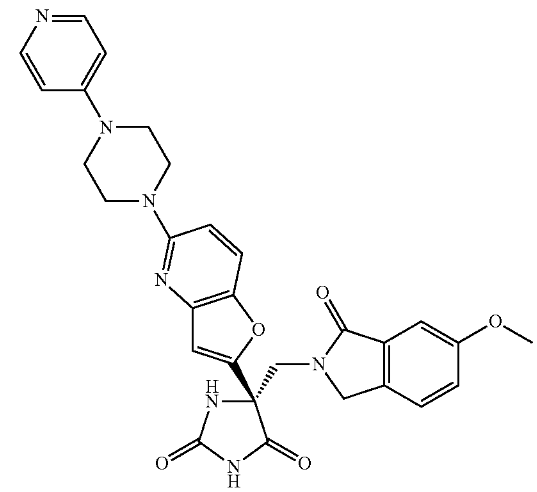 [SMILES: COc1ccc2c(c1)C(=O)N(C[C@@]1(c3cc4nc(N5CCN(c6ccncc6)CC5)ccc4o3)NC(=O)NC1=O)C2] | 553.21 | 554.3 | 0.976 | 551.05 | 0 |
| 2144 | 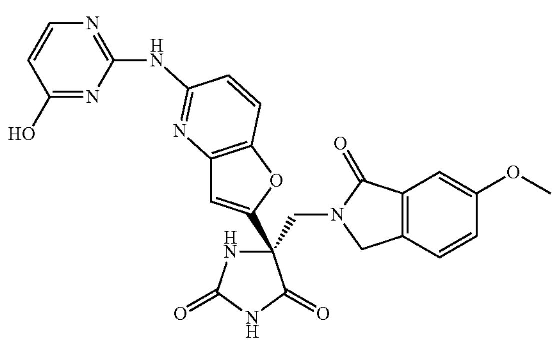 [SMILES: COc1ccc2c(c1)C(=O)N(C[C@@]1(c3cc4nc(Nc5nccc(O)n5)ccc4o3)NC(=O)NC1=O)C2] | 501.14 | 502.3 | 0.194 | 266.85 | |
| 2145 | 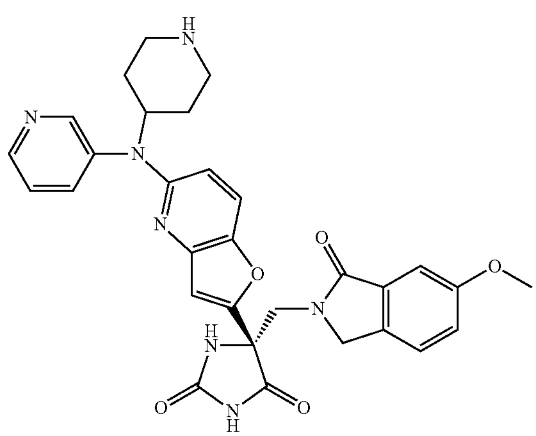 [SMILES: COc1ccc2c(c1)C(=O)N(C[C@@]1(c3cc4nc(N(c5cccnc5)C5CCNCC5)ccc4o3)NC(=O)NC1=O)C2] | 567.22 | 568.3 | 0.547 | 174.4 | 86 |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 2146 | 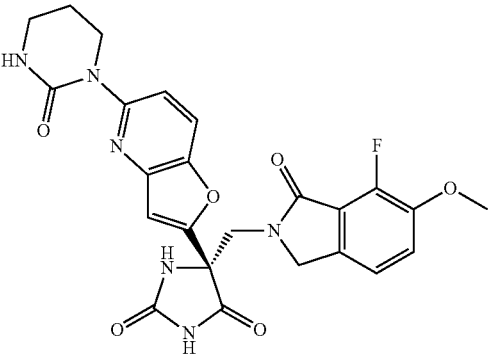 [SMILES: COc1ccc2c(c1F)C(=O)N(C[C@@]1(c3cc4nc(N5CCCNC5=O)ccc4o3)NC(=O)NC1=O)C2] | 508.15 | 509.3 | 0.974 | 506.7 | 522 |
| 2147 | 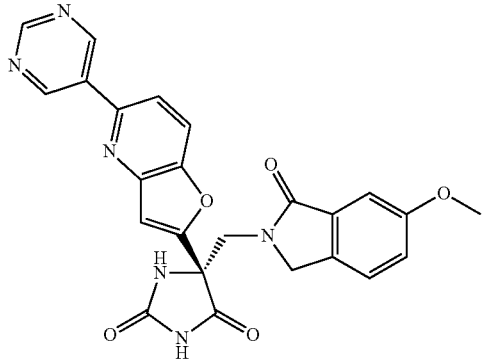 | 470.43 | 471.3 | 0.299 | 1081 | 2194 |
| 2148 | 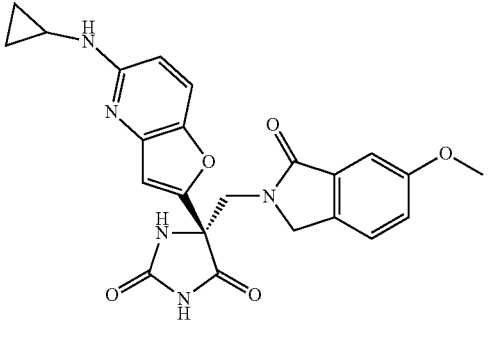 [SMILES: COc1ccc2c(c1)C(=O)N(C[C@@]1(c3cc4nc(NC5CC5)ccc4o3)NC(=O)NC1=O)C2] | 483.90 | 448.2 | 0.179 | 624.2 | 9341 |
| 2149 | 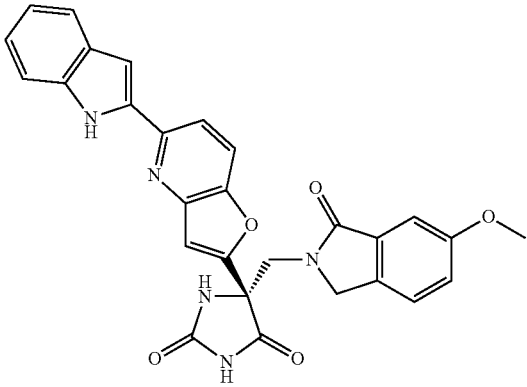 [SMILES: COc1ccc2c(c1)C(=O)N(C[C@@]1(c3cc4nc(-c5cc6ccccc6[nH]5)ccc4o3)NC(=O)NC1=O)C2] | 507.49 | 508.3 | 0.286 | 533.8 | |

TABLE A-continued

| ID | STRUCTURE | EXACT MASS | MASS OBSVD | Ki (nM) | hWBA (IC$_{50}$) | RR$^1$ AUC (nM · h) |
|---|---|---|---|---|---|---|
| 2150 | 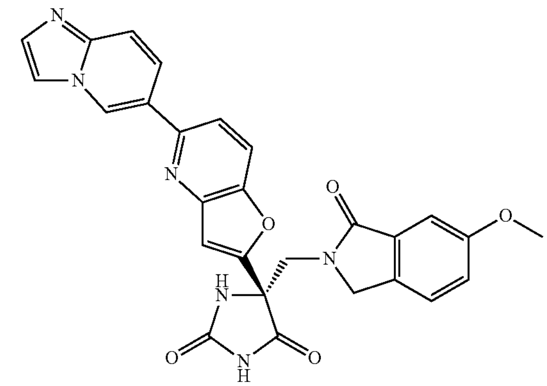 [SMILES: COc1ccc2c(c1)C(=O)N(C[C@@]1(c3cc4nc(-c5ccc6nccn6c5)ccc4o3)NC(=O)NC1=O)C2] | 508.48 | 509.3 | 0.806 | 828.3 | |
| 2151 | 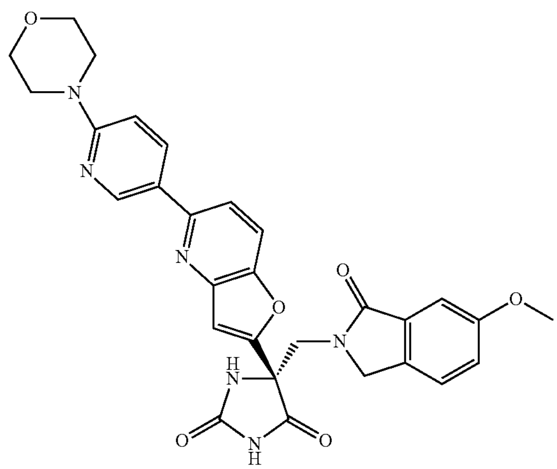 [SMILES: COc1ccc2c(c1)C(=O)N(C[C@@]1(c3cc4nc(-c5ccc(N6CCOCC6)nc5)ccc4o3)NC(=O)NC1=O)C2] | 554.55 | 555.3 | | 799.8 | 692 |
| 2152 | 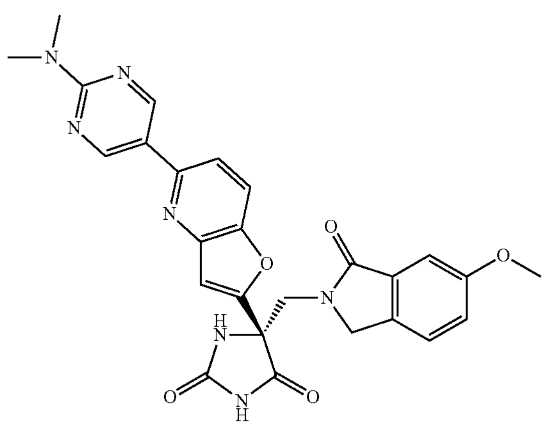 | 513.50 | 514.3 | 0.374 | 675.4 | |
| 2153 | 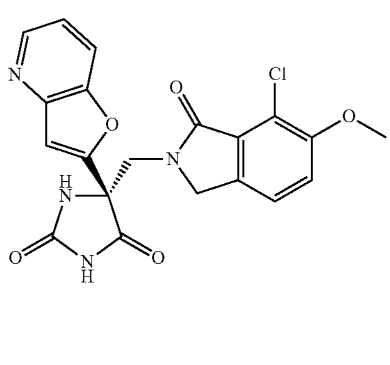 [SMILES: COc1ccc2c(c1Cl)C(=O)N(C[C@@]1(c3cc4ncccc4o3)NC(=O)NC1=O)C2] | 426.80 | 427.2 | 1.1 | 2653 | 1755 |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 2154 | 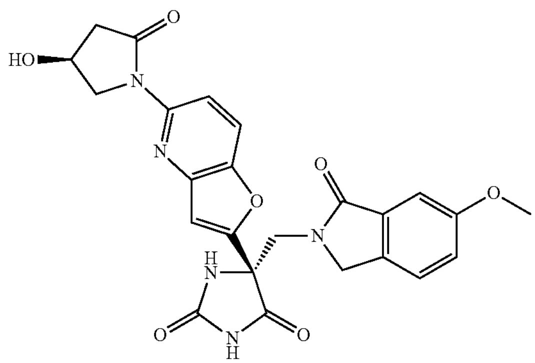 | 491.45 | 492.3 | 0.645 | 124.7 | 393 |
| 2156 | 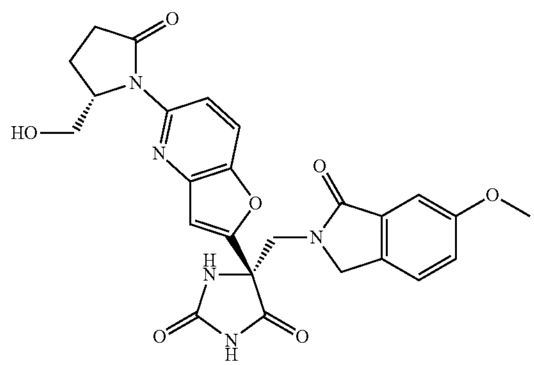 [SMILES: COc1ccc2c(c1)C(=O)N(C[C@@]1(c3cc4nc(N5C(=O)CC[C@H]5CO)ccc4o3)NC(=O)NC1=O)C2] | 505.47 | 506.3 | 0.976 | 324.7 | 33 |
| 2157 | 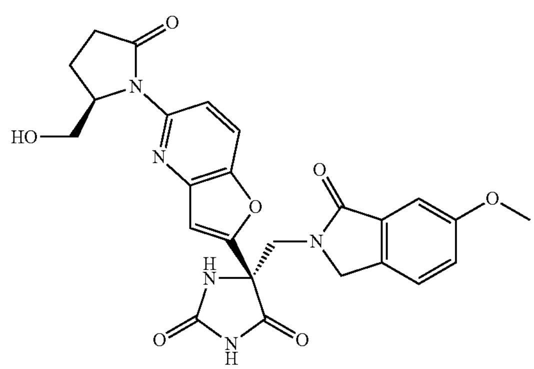 [SMILES: COc1ccc2c(c1)C(=O)N(C[C@@]1(c3cc4nc(N5C(=O)CC[C@@H]5CO)ccc4o3)NC(=O)NC1=O)C2] | 505.47 | 506.3 | 0.731 | 382 | 0 |
| 2158 | 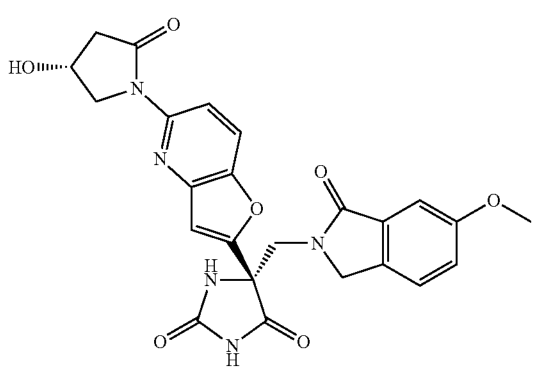 [SMILES: COc1ccc2c(c1)C(=O)N(C[C@@]1(c3cc4nc(N5C[C@H](O)CC5=O)ccc4o3)NC(=O)NC1=O)C2] | 491.45 | 492.3 | 0.545 | 179.7 | 1189 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2159 | 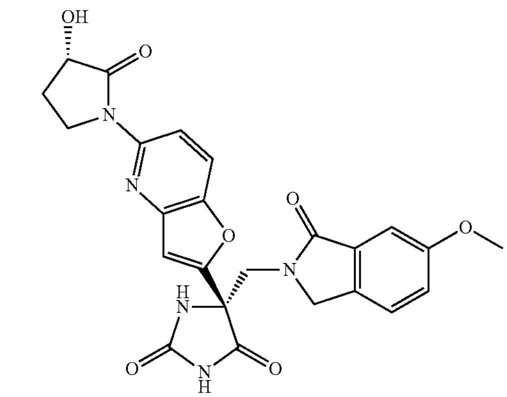 [SMILES: COc1ccc2c(c1)C(=O)N(C[C@@]1(c3cc4nc(N5CC[C@H](O)C5=O)ccc4o3)NC(=O)NC1=O)C2] | 491.45 | 492.3 | 0.935 | 331.4 | 527 |
| 2160 | 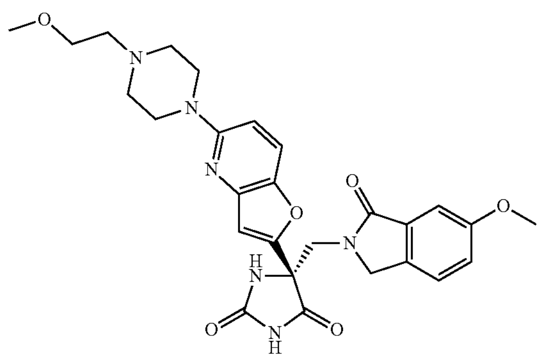 | 534.56 | 535.3 | 1.1 | 332.7 | |
| 2161 | 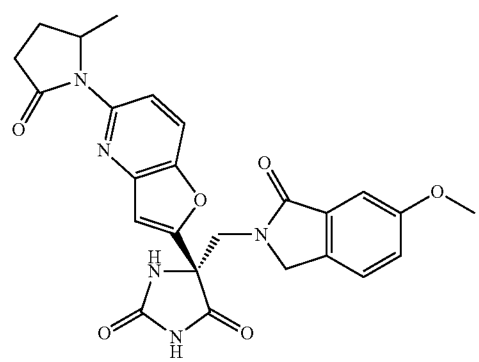 [SMILES: COc1ccc2c(c1)C(=O)N(C[C@@]1(c3cc4nc(N5C(=O)CCC5C)ccc4o3)NC(=O)NC1=O)C2] | 489.48 | 490.3 | 0.54 | 186.1 | 4789 |
| 2162 | 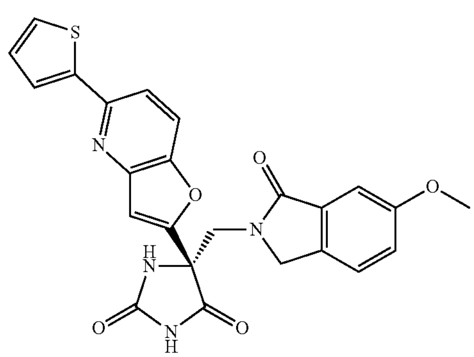 [SMILES: COc1ccc2c(c1)C(=O)N(C[C@@]1(c3cc4nc(-c5cccs5)ccc4o3)NC(=O)NC1=O)C2] | 474.5 | 474.9 | 0.125 | 1410 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2163 | 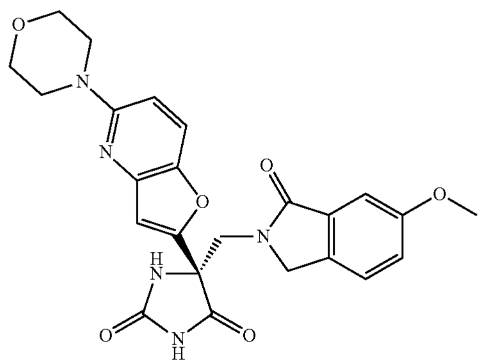 | 477.5 | 478.3 | 0.563 | 1116 | 3642 |
| 2164 | 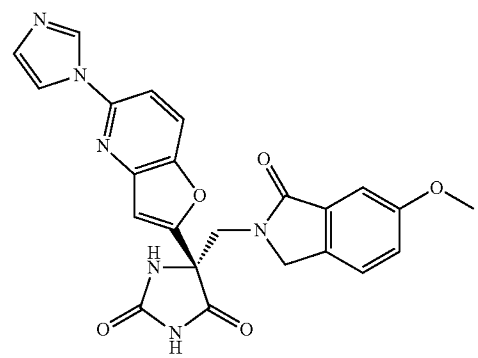 [SMILES: COc1ccc2c(c1)C(=O)N(C[C@@]1(c3cc4nc(-n5ccnc5)ccc4o3)NC(=O)NC1=O)C2] | 458.4 | 459.3 | 0.557 | 168 | 534 |
| 2165 | 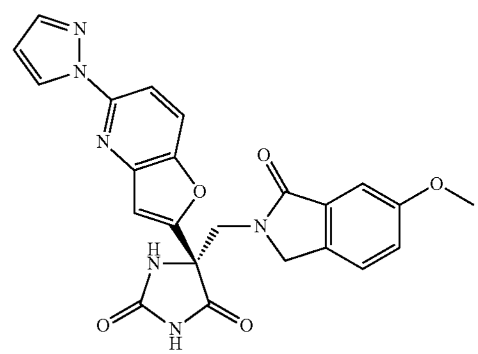 [SMILES: COc1ccc2c(c1)C(=O)N(C[C@@]1(c3cc4nc(-n5cccn5)ccc4o3)NC(=O)NC1=O)C2] | 458.4 | 459.3 | 0.405 | 1371 | 21023 |
| 2166 | 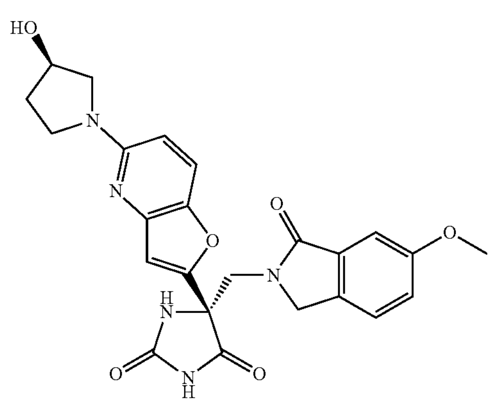 [SMILES: COc1ccc2c(c1)C(=O)N(C[C@@]1(c3cc4nc(N5CC[C@@H](O)C5)ccc4o3)NC(=O)NC1=O)C2] | 477.5 | 478.3 | 0.276 | 140.6 | 600 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2167 | 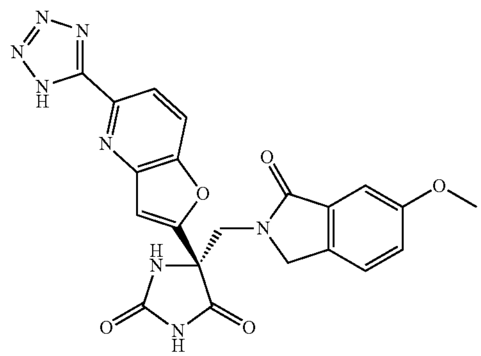 [SMILES: COc1ccc2c(c1)C(=O)N(C[C@@]1(c3cc4nc(-c5nnn[nH]5)ccc4o3)NC(=O)NC1=O)C2] | 460.4 | 461.3 | 0.351 | 289.3 | |
| 2168 | 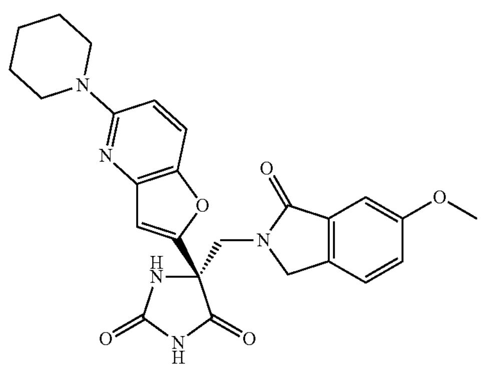 | 475.5 | 476.3 | 0.34 | 885.1 | 3526 |
| 2169 | 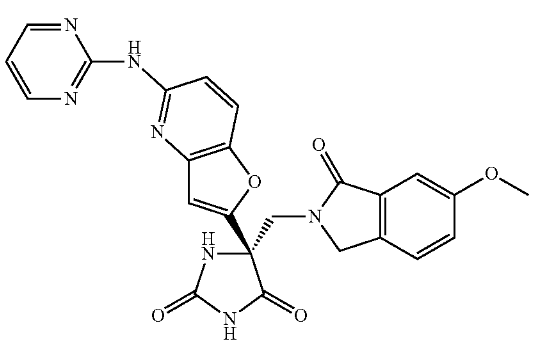 [SMILES: COc1ccc2c(c1)C(=O)N(C[C@@]1(c3cc4nc(Nc5ncccn5)ccc4o3)NC(=O)NC1=O)C2] | 485.5 | 486.3 | 0.576 | 919.8 | 4835 |
| 2170 | 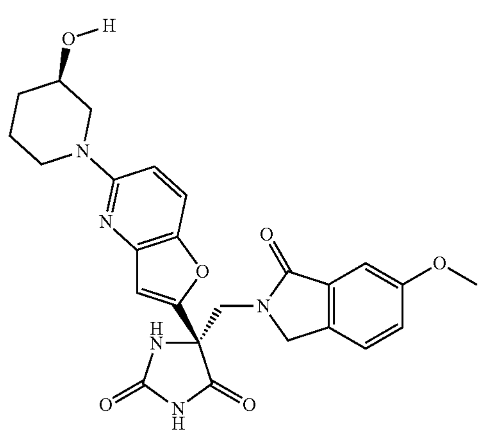 [SMILES: COc1ccc2c(c1)C(=O)N(C[C@@]1(c3cc4nc(N5CCC[C@@H](O)C5)ccc4o3)NC(=O)NC1=O)C2] | 491.5 | 492.3 | 0.415 | 188.7 | 414 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2171 | 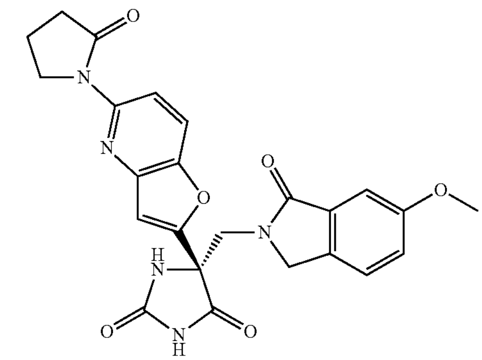 [SMILES: COc1ccc2c(c1)C(=O)N(C[C@@]1(c3cc4nc(N5CCCC5=O)ccc4o3)NC(=O)NC1=O)C2] | 475.5 | 476.3 | 0.67 | 487 | 9095 |
| 2172 | 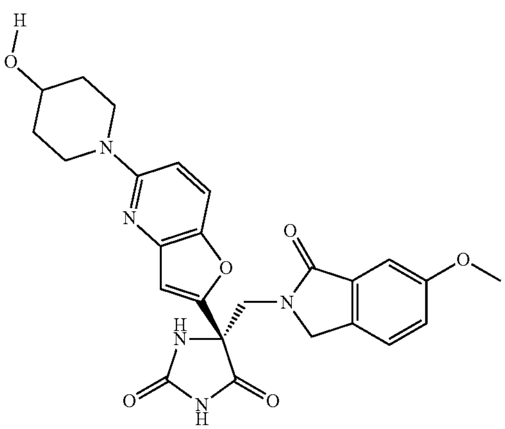 [SMILES: COc1ccc2c(c1)C(=O)N(C[C@@]1(c3cc4nc(N5CCC(O)CC5)ccc4o3)NC(=O)NC1=O)C2] | 491.5 | 492.3 | 0.577 | 210.25 | |
| 2173 | 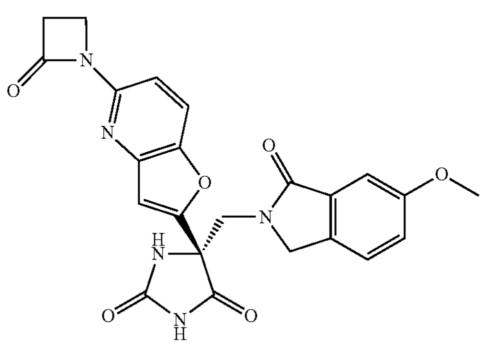 [SMILES: COc1ccc2c(c1)C(=O)N(C[C@@]1(c3cc4nc(N5CCC5=O)ccc4o3)NC(=O)NC1=O)C2] | 461.4 | 462.3 | 0.955 | 243.2 | 2541 |

TABLE A-continued
| ID | STRUCTURE | EXACT MASS | MASS OBSVD | Ki (nM) | hWBA (IC$_{50}$) | RR$^1$ AUC (nM · h) |
|---|---|---|---|---|---|---|
| 2174 | 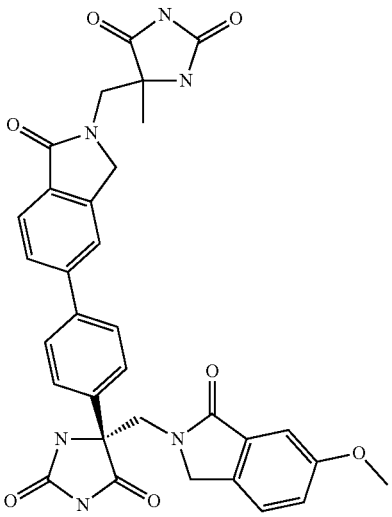 [SMILES: COc1ccc2c(c1)C(=O)N(C[C@@]1(c3ccc(-c4ccc5c(c4)CN(CC4(C)NC(=O)NC4=O)C5=O)cc3)NC(=O)NC1=O)C2] | 608.20 | 609.3 | 1.88 | 617.3 | |
| 2175 | 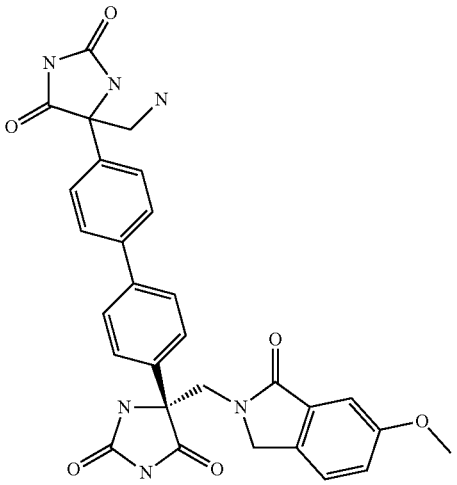 [SMILES: COc1ccc2c(c1)C(=O)N(C[C@@]1(c3ccc(-c4ccc(C5(CN)NC(=O)NC5=O)cc4)cc3)NC(=O)NC1=O)C2] | 554.2 | 555.3 | 2.08 | | 1763 |
| 2176 | 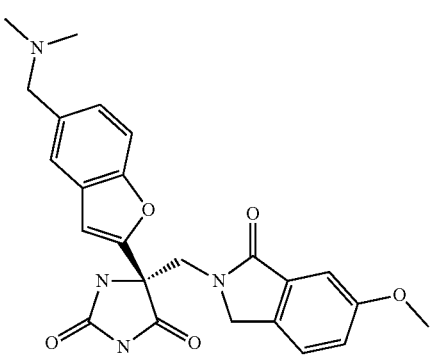 | 448.17 | 449.2 | 0.267 | | 1040 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2177 | 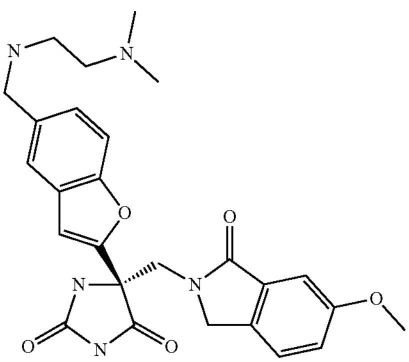 [SMILES: COc1ccc2c(c1)C(=O)N(C[C@@]1(c3cc4cc(CNCCN(C)C)ccc4o3)NC(=O)NC1=O)C2] | 491.22 | 492.3 | 0.711 | 278.3 | 69 |
| 2178 | 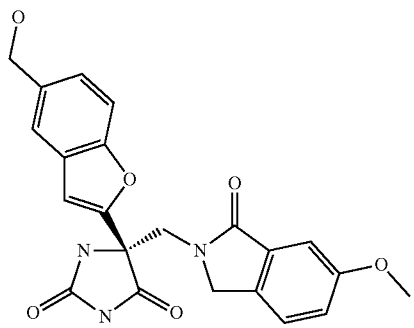 | 421.13 | 422.2 | 0.546 | 517.9 | |
| 2179 | 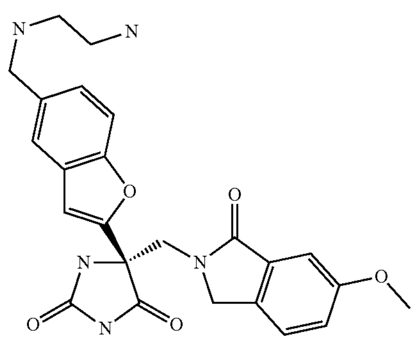 [SMILES: COc1ccc2c(c1)C(=O)N(C[C@@]1(c3cc4cc(CNCCN)ccc4o3)NC(=O)NC1=O)C2] | 463.19 | 464.3 | 0.713 | 376.1 | |
| 2180 | 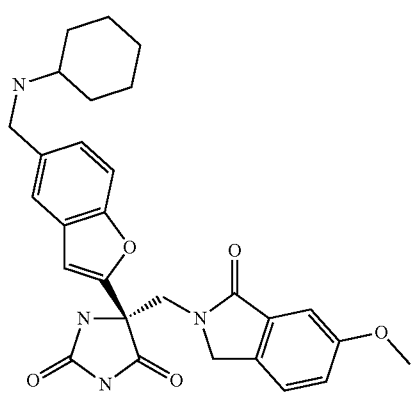 [SMILES: COc1ccc2c(c1)C(=O)N(C[C@@]1(c3cc4cc(CNC5CCCCC5)ccc4o3)NC(=O)NC1=O)C2] | 502.22 | 503.3 | 0.443 | 616.9 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2181 | 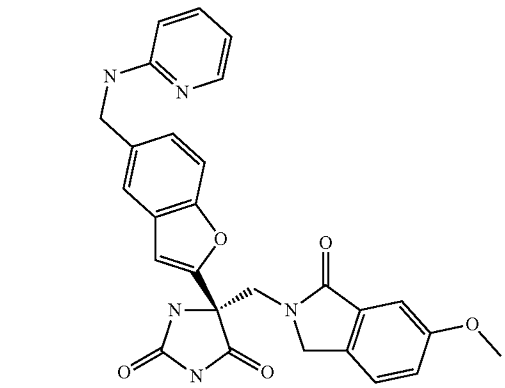 [SMILES: COc1ccc2c(c1)C(=O)N(C[C@@]1(c3cc4cc(CNc5ccccn5)ccc4o3)NC(=O)NC1=O)C2] | 497.17 | 498.3 | 0.343 | 1650 | |
| 2182 | 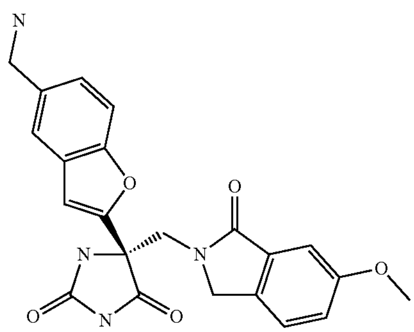 [SMILES: COc1ccc2c(c1)C(=O)N(C[C@@]1(c3cc4cc(CN)ccc4o3)NC(=O)NC1=O)C2] | 420.14 | 421.2 | 0.79 | 532 | |
| 2183 | 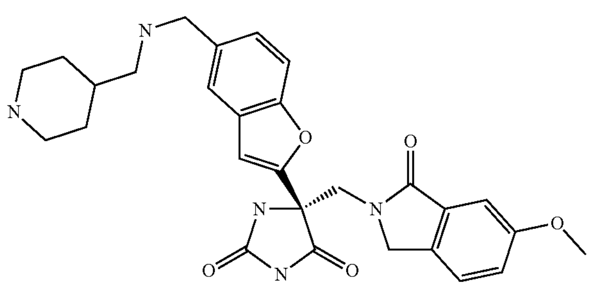 [SMILES: COc1ccc2c(c1)C(=O)N(C[C@@]1(c3cc4cc(CNCC5CCNCC5)ccc4o3)NC(=O)NC1=O)C2] | 517.23 | 518.3 | 1.02 | 526 | |
| 2184 | 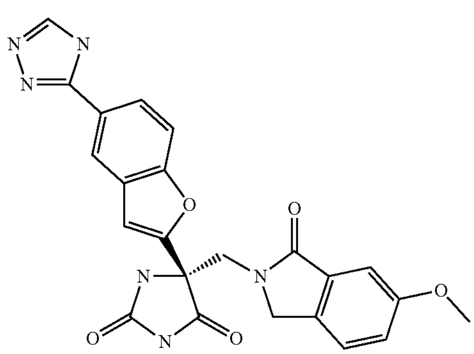 [SMILES: COc1ccc2c(c1)C(=O)N(C[C@@]1(c3cc4cc(-c5nnc[nH]5)ccc4o3)NC(=O)NC1=O)C2] | 458.13 | 459.2 | 0.355 | 347.15 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2185 | 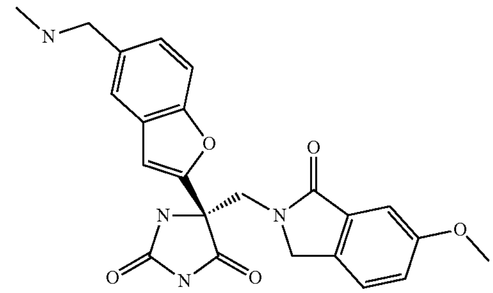 | 434.16 | 435.2 | 3.99 | 1038 | |
| 2186 | 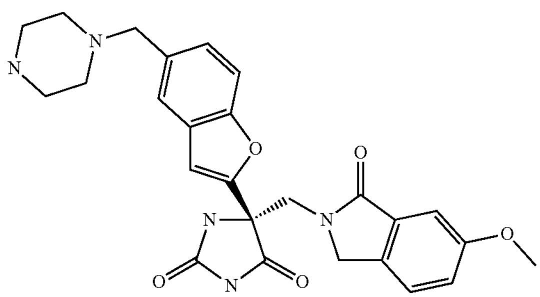 [SMILES: COc1ccc2c(c1)C(=O)N(C[C@@]1(c3cc4cc(CN5CCNCC5)ccc4o3)NC(=O)NC1=O)C2] | 489.20 | 490.3 | 0.539 | 344.7 | 0 |
| 2187 | 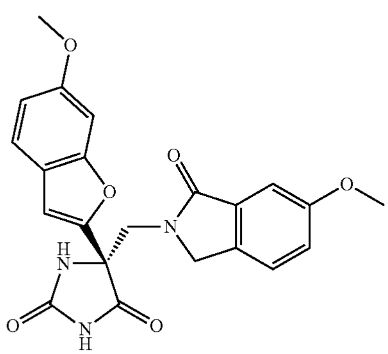 [SMILES: COc1ccc2c(c1)C(=O)N(C[C@@]1(c3cc4ccc(OC)cc4o3)NC(=O)NC1=O)C2] | 421.1 | 422.2 | 0.989 | 4026 | |
| 2188 | 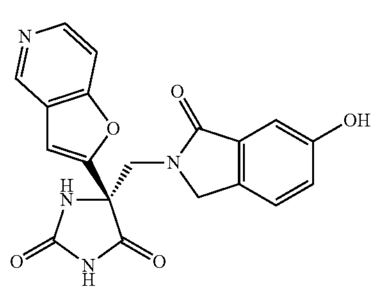 [SMILES: O=C1NC(=O)[C@](CN2Cc3ccc(O)cc3C2=O)(c2cc3cnccc3o2)N1] | 378.1 | 379.2 | 2.26 | 2987.5 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2189 | 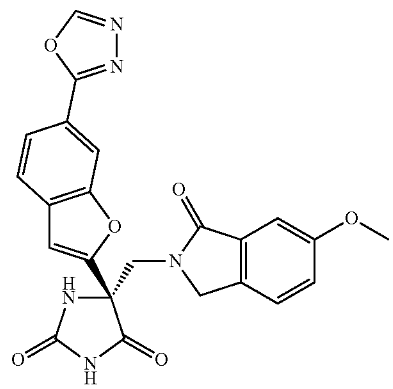 [SMILES: COc1ccc2c(c1)C(=O)N(C[C@@]1(c3cc4ccc(-c5nnco5)cc4o3)NC(=O)NC1=O)C2] | 459.12 | 460.3 | 0.536 | 672.25 | 988 |
| 2190 | 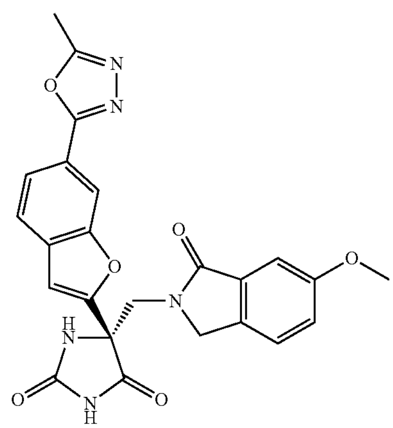 [SMILES: COc1ccc2c(c1)C(=O)N(C[C@@]1(c3cc4ccc(-c5nnc(C)o5)cc4o3)NC(=O)NC1=O)C2] | 473.1 | 474.3 | 0.515 | 958.4 | 414 |
| 2192 | 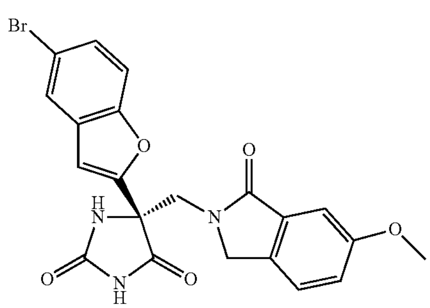 [SMILES: COc1ccc2c(c1)C(=O)N(C[C@@]1(c3cc4cc(Br)ccc4o3)NC(=O)NC1=O)C2] | 469.0 | 470, 472.3 | 0.491 | 3309 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2193 | 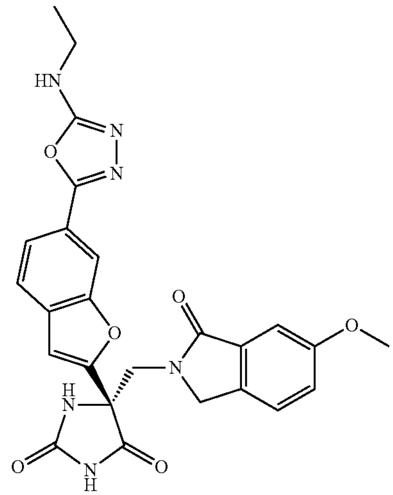 [SMILES: CCNc1nnc(-c2ccc3cc([C@]4(CN5Cc6ccc(OC)cc6C5=O)NC(=O)NC4=O)oc3c2)o1] | 502.2 | 503.3 | 0.253 | 170 | 0 |
| 2194 | 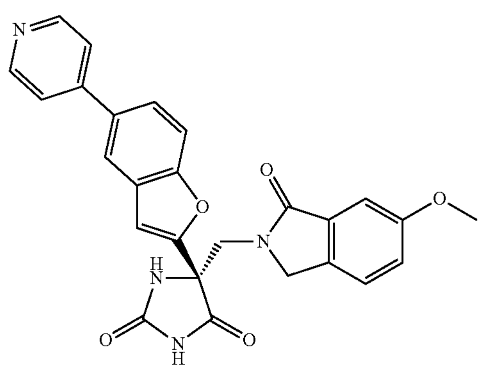 [SMILES: COc1ccc2c(c1)C(=O)N(C[C@@]1(c3cc4cc(-c5ccncc5)ccc4o3)NC(=O)NC1=O)C2] | 468.1 | 469.3 | 0.741 | 1167 | |
| 2195 | 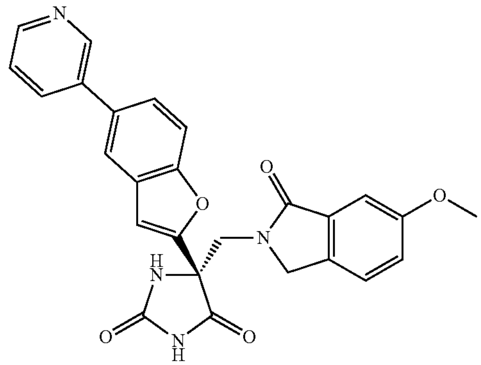 [SMILES: COc1ccc2c(c1)C(=O)N(C[C@@]1(c3cc4cc(-c5cccnc5)ccc4o3)NC(=O)NC1=O)C2] | 468.1 | 469.3 | 0.966 | 2118 | 1155 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2196 | 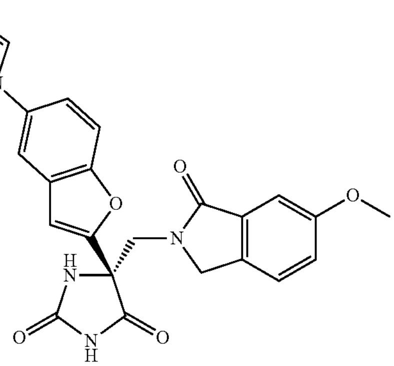 | 458.1 | 459.3 | 0.645 | 1545 | 7063 |
| 2197 | 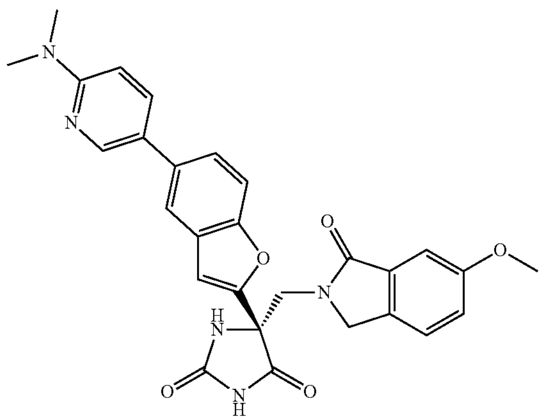 | 511.2 | 512.3 | 0.849 | 2709 | |
| 2198 | 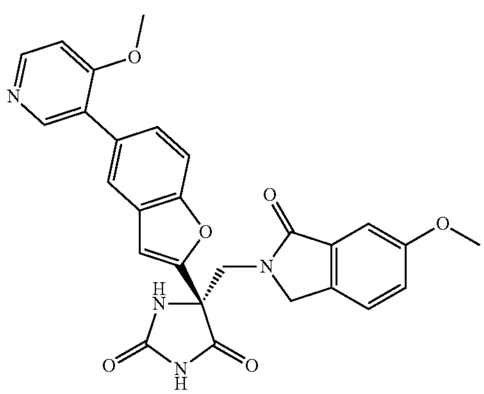 [SMILES: COc1ccc2c(c1)C(=O)N(C[C@@]1(c3cc4cc(-c5cnccc5OC)ccc4o3)NC(=O)NC1=O)C2] | 498.5 | 499.3 | 0.637 | 1892 | |
| 2199 | 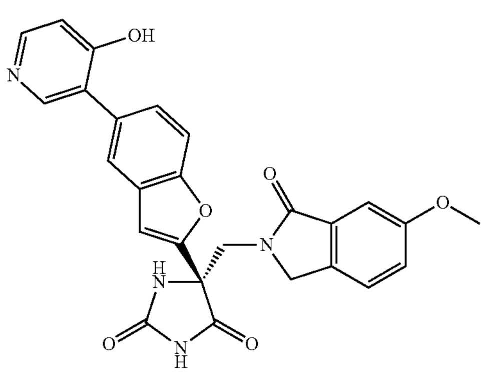 [SMILES: COc1ccc2c(c1)C(=O)N(C[C@@]1(c3cc4cc(-c5cnccc5O)ccc4o3)NC(=O)NC1=O)C2] | 484.1 | 485.3 | 1.96 | 7362 | |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 2200 | 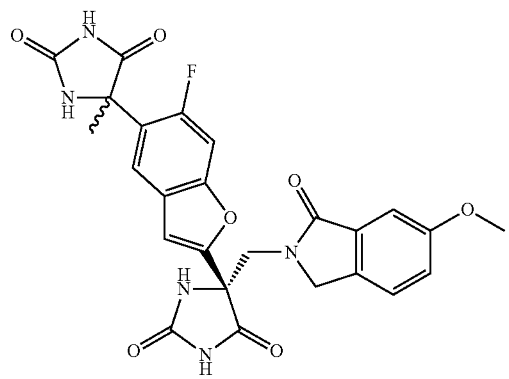 [SMILES: COc1ccc2c(c1)C(=O)N(C[C@@]1(c3cc4cc(C5(C)NC(=O)NC5=O)c(F)cc4o3)NC(=O)NC1=O)C2] | 521.13 | 522.3 | 1.85 | 216.6 | 177 |
| 2201 | 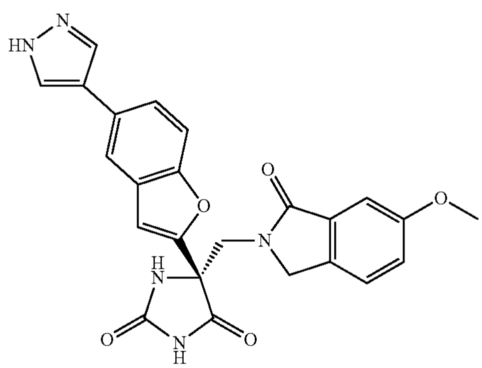 [SMILES: COc1ccc2c(c1)C(=O)N(C[C@@]1(c3cc4cc(-c5cn[nH]c5)ccc4o3)NC(=O)NC1=O)C2] | 457.14 | 458.3 | 0.345 | 293.85 | |
| 2202 | 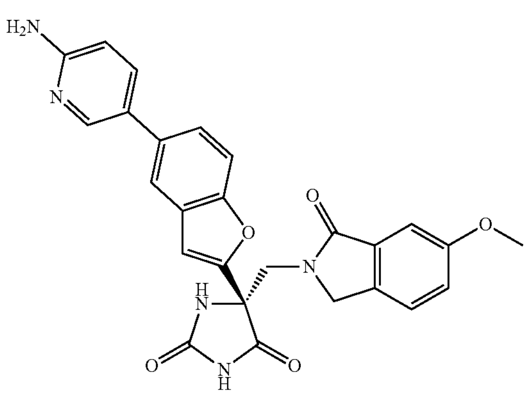 [SMILES: COc1ccc2c(c1)C(=O)N(C[C@@]1(c3cc4cc(-c5ccc(N)nc5)ccc4o3)NC(=O)NC1=O)C2] | 483.15 | 484.3 | 0.488 | 713 | |
| 2203 | 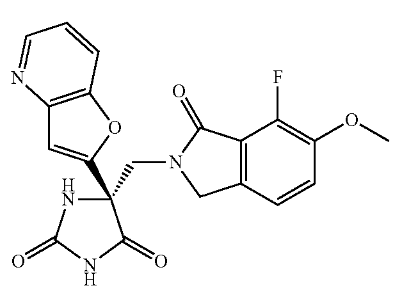 [SMILES: COc1ccc2c(c1F)C(=O)N(C[C@@]1(c3cc4ncccc4o3)NC(=O)NC1=O)C2] | 410.10 | 411.2 | 0.468 | 200 | 3922 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2204 | 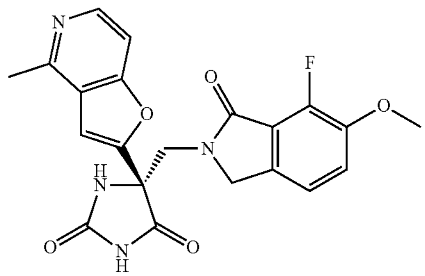 | 424.12 | 425.2 | 0.34 | 114.7 | 983 |
| 2205 | 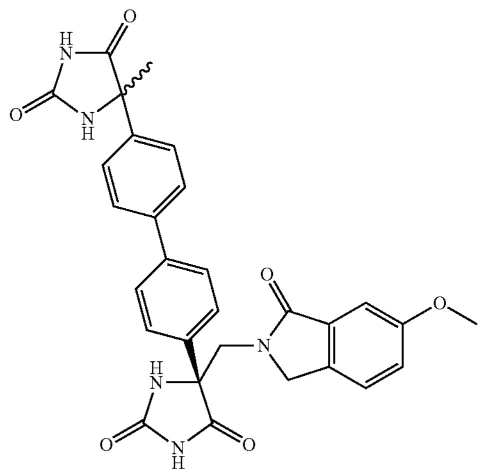 [SMILES: COc1ccc2c(c1)C(=O)N(C[C@@]1(c3ccc(-c4ccc(C5(C)NC(=O)NC5=O)cc4)cc3)NC(=O)NC1=O)C2] | 539.18 | 540.3 | 0.659 | 1001 | |
| 2206 | 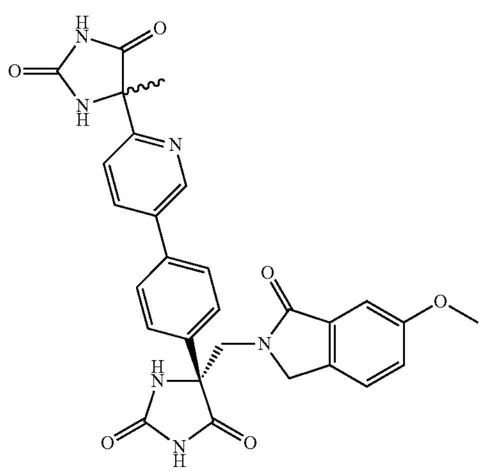 [SMILES: COc1ccc2c(c1)C(=O)N(C[C@@]1(c3ccc(-c4ccc(C5(C)NC(=O)NC5=O)nc4)cc3)NC(=O)NC1=O)C2] | 540.18 | 541.3 | 0.82 | 1785 | |
| 2207 | 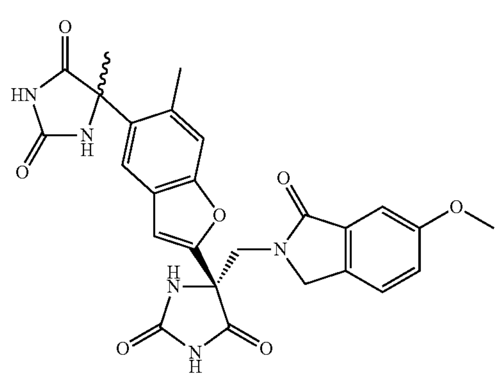 [SMILES: COc1ccc2c(c1)C(=O)N(C[C@@]1(c3cc4cc(C5(C)NC(=O)NC5=O)c(C)cc4o3)NC(=O)NC1=O)C2] | 517.16 | 518.3 | 0.813 | 310.2 | 63 |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 2208 | 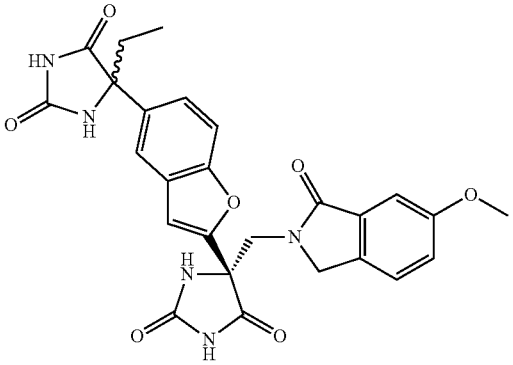 [SMILES: CCC1(c2ccc3oc([C@]4(CN5Cc6ccc(OC)cc6C5=O)NC(=O)NC4=O)cc3c2)NC(=O)NC1=O] | 517.16 | 518.3 | 0.249 | 220.3 | |
| 2209 | 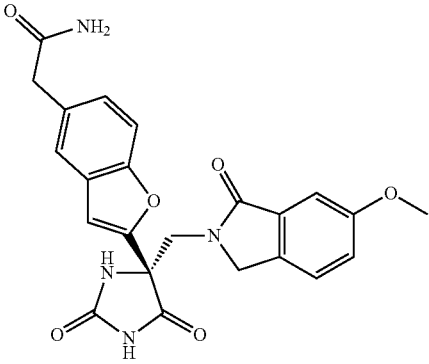 [SMILES: COc1ccc2c(c1)C(=O)N(C[C@@]1(c3cc4cc(CC(N)=O)ccc4o3)NC(=O)NC1=O)C2] | 448.14 | 449.2 | 2.51 | 542.3 | |
| 2210 | 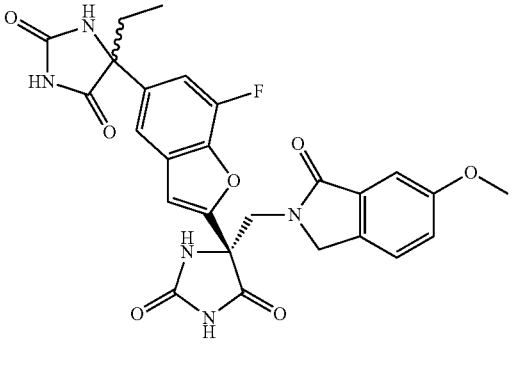 [SMILES: CCC1(c2cc(F)c3oc([C@]4(CN5Cc6ccc(OC)cc6C5=O)NC(=O)NC4=O)cc3c2)NC(=O)NC1=O] | 535.15 | 536.3 | 0.319 | 231.7 | 18 |
| 2211 | 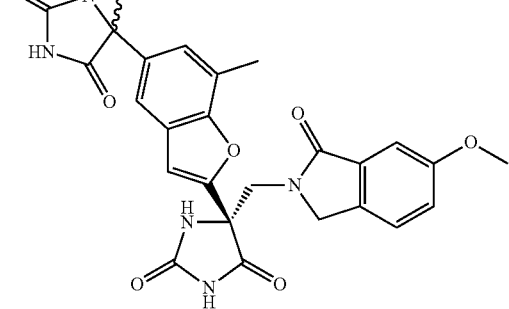 | 517.49 | 518.3 | 0.216 | 1552 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2212 | 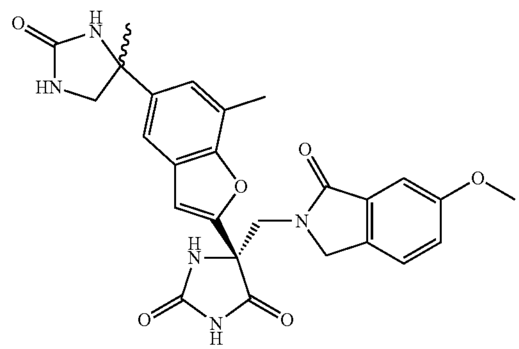 [SMILES: COc1ccc2c(c1)C(=O)N(C[C@@]1(c3cc4cc(C5(C)CNC(=O)N5)cc(C)c4o3)NC(=O)NC1=O)C2] | 503.18 | 504.3 | 0.095 | 2858 | |
| 2213 | 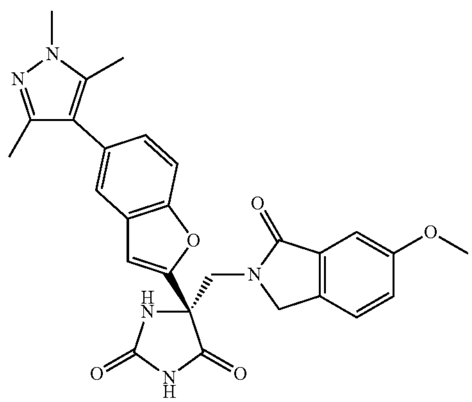 | 499.19 | 500.3 | 0.403 | 1509 | |
| 2214 | 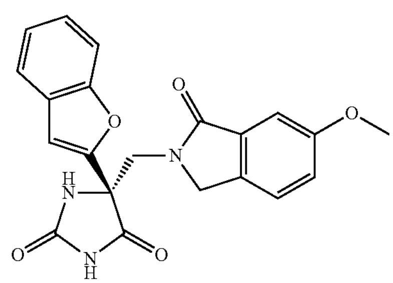 [SMILES: COc1ccc2c(c1)C(=O)N(C[C@@]1(c3cc4ccccc4o3)NC(=O)NC1=O)C2] | 391.12 | 392.2 | 0.274 | 2313.6 | 195 |
| 2215 | 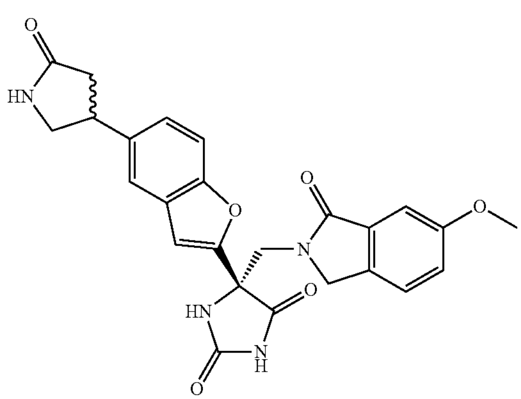 [SMILES: COc1ccc2c(c1)C(=O)N(C[C@@]1(c3cc4cc(C5CNC(=O)C5)ccc4o3)NC(=O)NC1=O)C2] | 474.15 | 485.3 | 0.524 | 380.8 | |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 2216 | 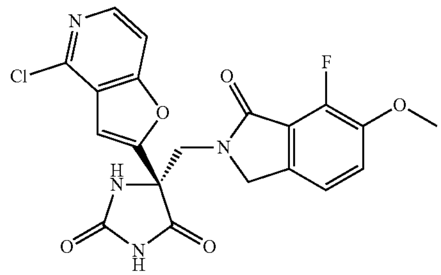 [SMILES: COc1ccc2c(c1F)C(=O)N(C[C@@]1(c3cc4c(Cl)nccc4o3)NC(=O)NC1=O)C2] | 444.06 | 445.2 | 0.41 | 312.6 | |
| 2217 | 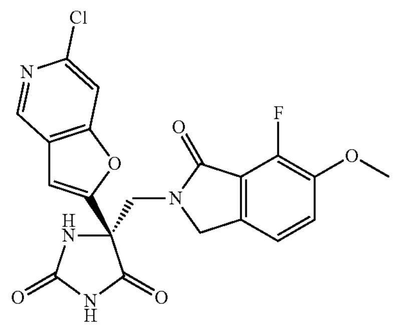 [SMILES: COc1ccc2c(c1F)C(=O)N(C[C@@]1(c3cc4cnc(Cl)cc4o3)NC(=O)NC1=O)C2] | 444.06 | 445.2 | 0.604 | 859.2 | |
| 2218 | 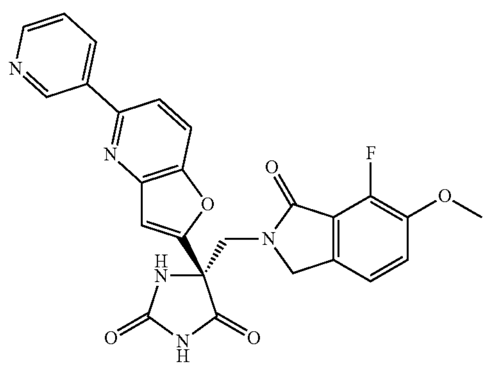 [SMILES: COc1ccc2c(c1F)C(=O)N(C[C@@]1(c3cc4nc(-c5cccnc5)ccc4o3)NC(=O)NC1=O)C2] | 487.13 | | 0.232 | 1000 | |
| 2219 | 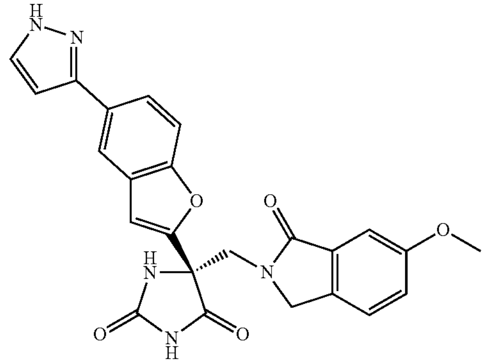 [SMILES: COc1ccc2c(c1)C(=O)N(C[C@@]1(c3cc4cc(-c5cc[nH]n5)ccc4o3)NC(=O)NC1=O)C2] | 457.14 | 458.2 | 0.682 | 1392 | 1015 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2220 | 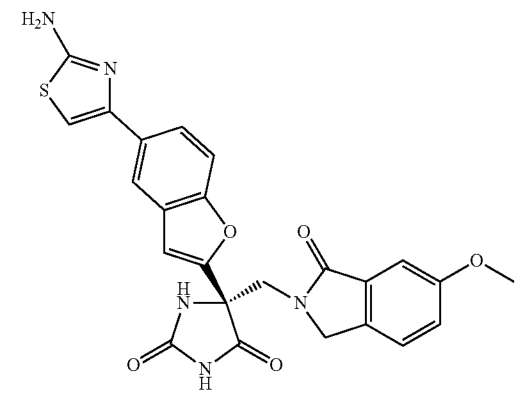 [SMILES: COc1ccc2c(c1)C(=O)N(C[C@@]1(c3cc4cc(-c5csc(N)n5)ccc4o3)NC(=O)NC1=O)C2] | 489.11 | 490.1 | 0.243 | 722 | 165 |
| 2221 | 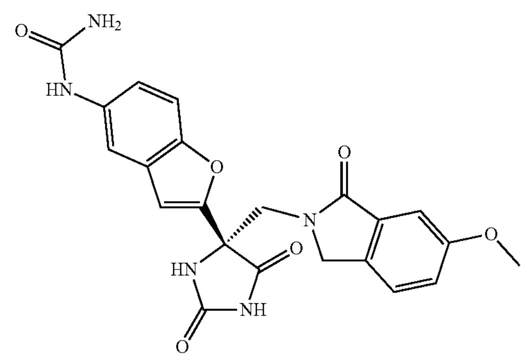 [SMILES: COc1ccc2c(c1)C(=O)N(C[C@@]1(c3cc4cc(NC(N)=O)ccc4o3)NC(=O)NC1=O)C2] | 449.13 | 450.2 | 0.099 | 142.6 | 0 |
| 2222 | 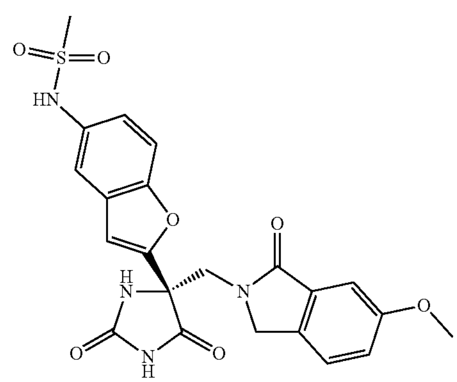 [SMILES: COc1ccc2c(c1)C(=O)N(C[C@@]1(c3cc4cc(NS(C)(=O)=O)ccc4o3)NC(=O)NC1=O)C2] | 484.11 | 485.0 | 0.701 | 342.6 | 0 |
| 2223 | 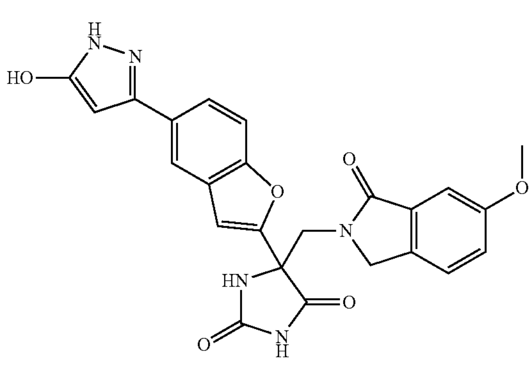 [SMILES: COc1ccc2c(c1)C(=O)N(CC1(c3cc4cc(-c5cc(O)[nH]n5)ccc4o3)NC(=O)NC1=O)C2] | 473.13 | 474.1 | 1.23 | 242.45 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2224 | 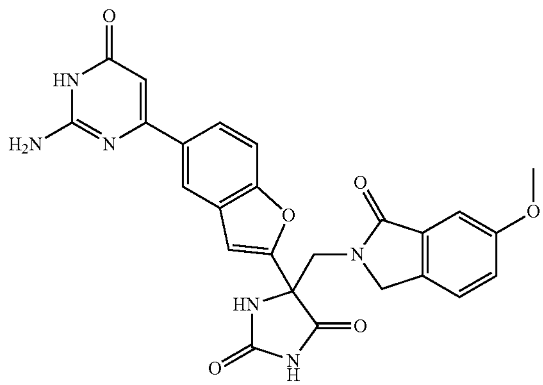 [SMILES: COc1ccc2c(c1)C(=O)N(CC1(c3cc4cc(-c5cc(=O)[nH]c(N)n5)ccc4o3)NC(=O)NC1=O)C2] | 500.14 | 501.2 | 0.313 | 139.45 | 0 |
| 2225 | 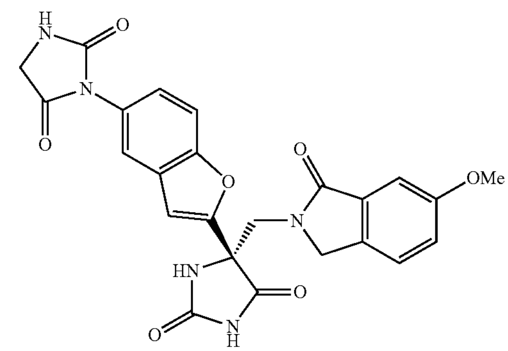 [SMILES: COc1ccc2c(c1)C(=O)N(C[C@@]1(c3cc4cc(N5C(=O)CNC5=O)ccc4o3)NC(=O)NC1=O)C2] | 489.13 | 490.1 | 0.564 | 677.1 | 0 |
| 2226 | 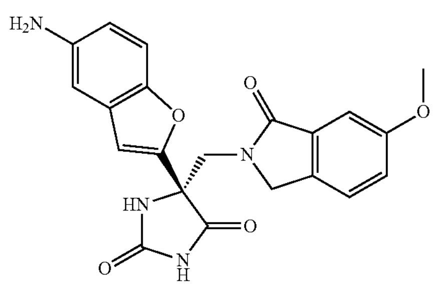 [SMILES: COc1ccc2c(c1)C(=O)N(C[C@@]1(c3cc4cc(N)ccc4o3)NC(=O)NC1=O)C2] | 406.13 | 40 | 0.807 | 573.45 | 467 |
| 2227 | 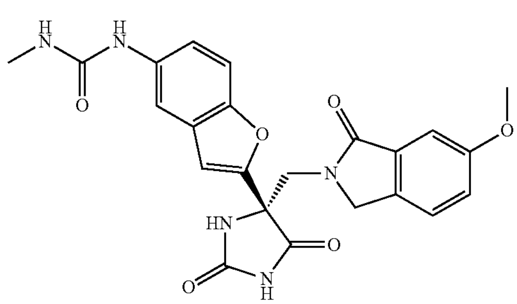 | 463.15 | 464.2 | 0.478 | 540.8 | 57 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2228 | 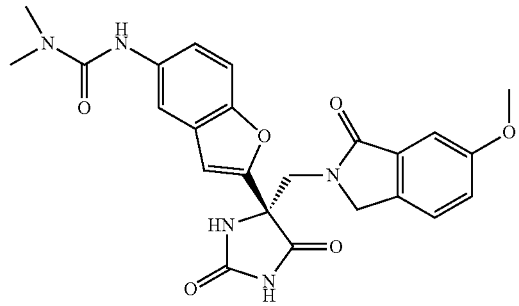 | 477.16 | 478.1 | 0.839 | 2374 | 129 |
| 2229 | 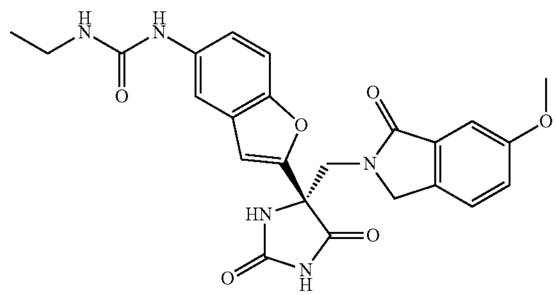 [SMILES: CCNC(=O)Nc1ccc2oc([C@]3(CN4Cc5ccc(OC)cc5C4=O)NC(=O)NC3=O)cc2c1] | 477.16 | 478.1 | 0.388 | 456.6 | 158 |
| 2230 | 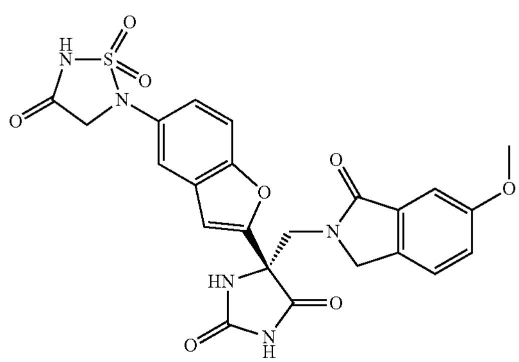 [SMILES: COc1ccc2c(c1)C(=O)N(C[C@@]1(c3cc4cc(N5CC(=O)NS5(=O)=O)ccc4o3)NC(=O)NC1=O)C2] | 525.10 | 526.0 | 0.781 | 4412.5 | |
| 2231 | 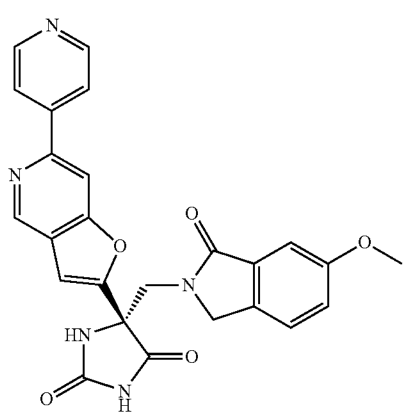 [SMILES: COc1ccc2c(c1)C(=O)N(C[C@@]1(c3cc4cnc(-c5ccncc5)cc4o3)NC(=O)NC1=O)C2] | 469.14 | 470.1 | 0.54 | 1422 | 2752 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2232 | 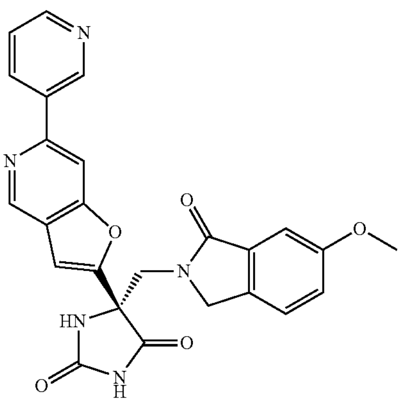 [SMILES: COc1ccc2c(c1)C(=O)N(C[C@@]1(c3cc4cnc(-c5cccnc5)cc4o3)NC(=O)NC1=O)C2] | 469.14 | 470.1 | 0.538 | 1099 | 2223 |
| 2233 | 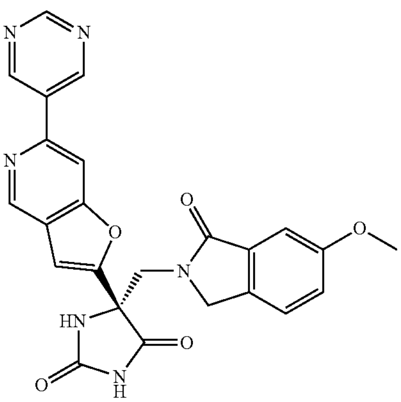 [SMILES: COc1ccc2c(c1)C(=O)N(C[C@@]1(c3cc4cnc(-c5cncnc5)cc4o3)NC(=O)NC1=O)C2] | 470.13 | 471.1 | 0.763 | 772 | 3809 |
| 2234 | 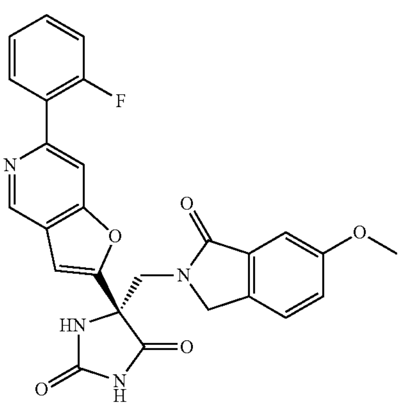 [SMILES: COc1ccc2c(c1)C(=O)N(C[C@@]1(c3cc4cnc(-c5ccccc5F)cc4o3)NC(=O)NC1=O)C2] | 486.13 | 487.1 | 0.527 | 14340 | 126641 |
| 2235 | 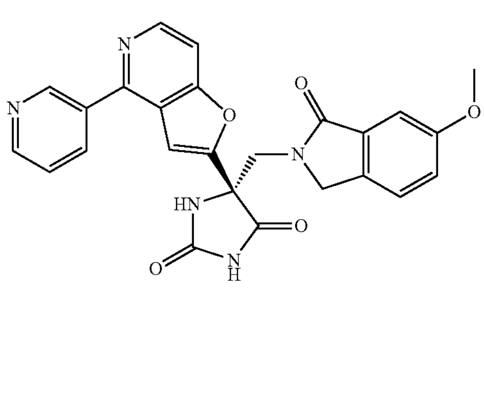 [SMILES: COc1ccc2c(c1)C(=O)N(C[C@@]1(c3cc4c(-c5cccnc5)nccc4o3)NC(=O)NC1=O)C2] | 469.14 | 470.1 | 0.384 | 553 | 18 |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 2236 | 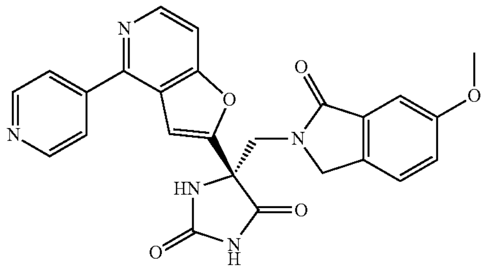 [SMILES: COc1ccc2c(c1)C(=O)N(C[C@@]1(c3cc4c(-c5ccncc5)nccc4o3)NC(=O)NC1=O)C2] | 469.14 | 470.2 | 0.54 | 948.75 | 20 |
| 2237 | 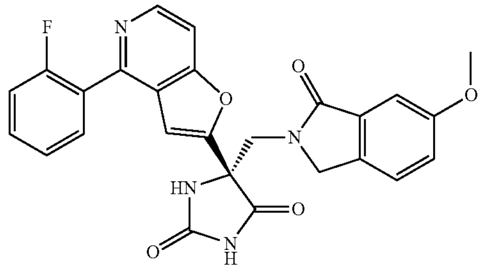 [SMILES: COc1ccc2c(c1)C(=O)N(C[C@@]1(c3cc4c(-c5ccccc5F)nccc4o3)NC(=O)NC1=O)C2] | 486.13 | 487.1 | 0.356 | 1146 | |
| 2238 | 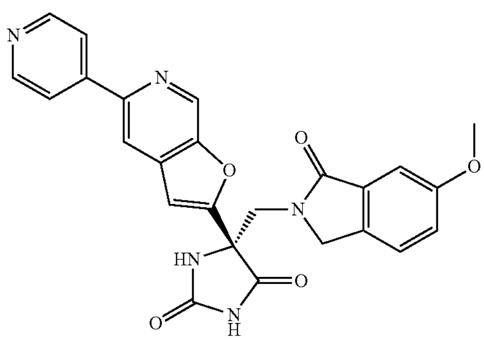 [SMILES: COc1ccc2c(c1)C(=O)N(C[C@@]1(c3cc4cc(-c5ccncc5)ncc4o3)NC(=O)NC1=O)C2] | 469.14 | 470.2 | 0.889 | 628 | 4855 |
| 2239 | 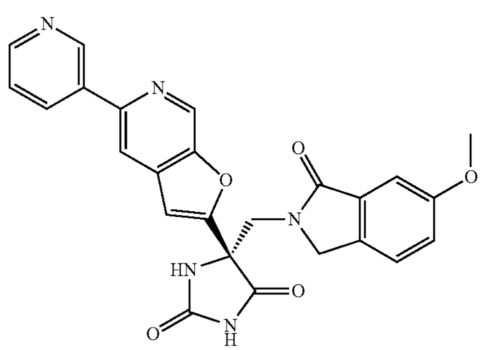 [SMILES: COc1ccc2c(c1)C(=O)N(C[C@@]1(c3cc4cc(-c5cccnc5)ncc4o3)NC(=O)NC1=O)C2] | 469.14 | 470.2 | 0.669 | 718.3 | 9837 |
| 2240 | 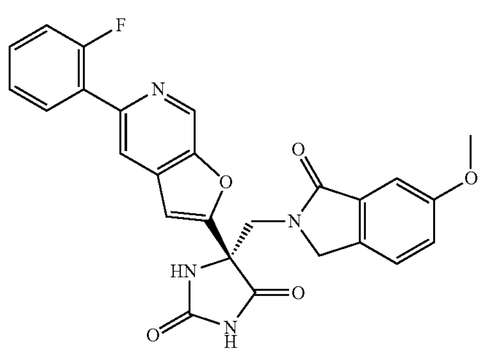 [SMILES: COc1ccc2c(c1)C(=O)N(C[C@@]1(c3cc4cc(-c5ccccc5F)ncc4o3)NC(=O)NC1=O)C2] | 486.13 | 487.1 | 0.714 | 3643.5 | 12775 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2241 | 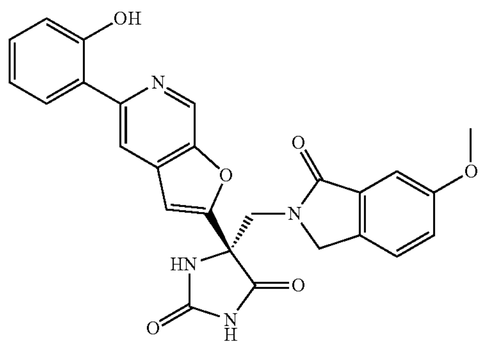 [SMILES: COc1ccc2c(c1)C(=O)N(C[C@@]1(c3cc4cc(-c5ccccc5O)ncc4o3)NC(=O)NC1=O)C2] | 484.14 | 485.2 | 1.19 | 10001 | 1393 |
| 2242 | 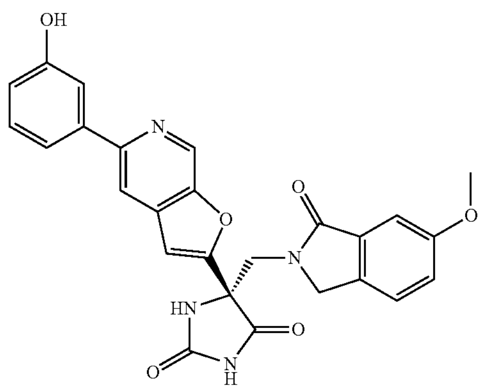 [SMILES: COc1ccc2c(c1)C(=O)N(C[C@@]1(c3cc4cc(-c5cccc(O)c5)ncc4o3)NC(=O)NC1=O)C2] | 484.14 | 485.2 | 0.566 | 3388 | 0 |
| 2243 | 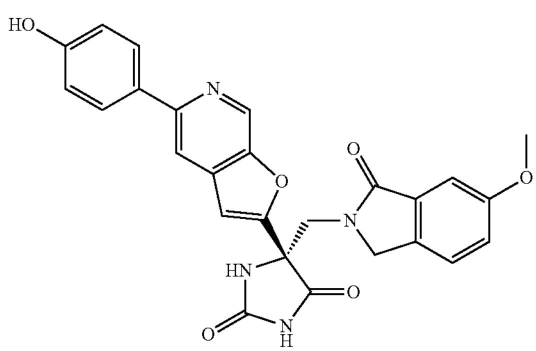 [SMILES: COc1ccc2c(c1)C(=O)N(C[C@@]1(c3cc4cc(-c5ccc(O)cc5)ncc4o3)NC(=O)NC1=O)C2] | 484.14 | 485.0 | 0.427 | 752.85 | 27 |
| 2244 | 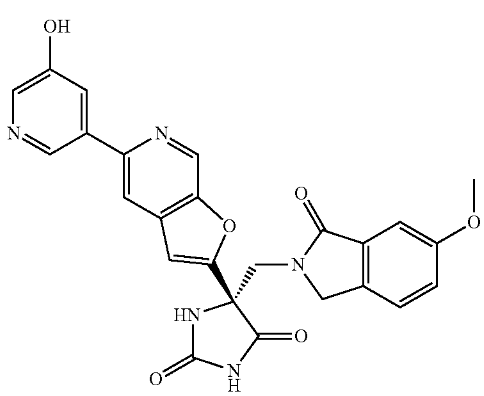 [SMILES: COc1ccc2c(c1)C(=O)N(C[C@@]1(c3cc4cc(-c5cncc(O)c5)ncc4o3)NC(=O)NC1=O)C2] | 485.13 | 486.1 | 0.35 | 365.1 | 0 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2245 | 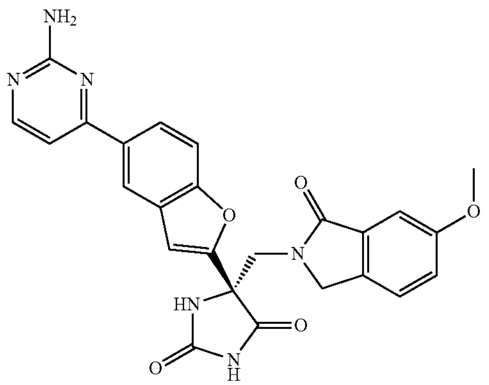 [SMILES: COc1ccc2c(c1)C(=O)N(C[C@@]1(c3cc4cc(-c5ccnc(N)n5)ccc4o3)NC(=O)NC1=O)C2] | 484.15 | 485.1 | 0.456 | 1056.4 | 6028 |
| 2246 | 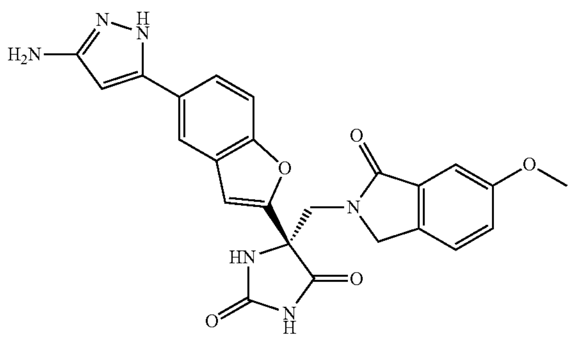 [SMILES: COc1ccc2c(c1)C(=O)N(C[C@@]1(c3cc4cc(-c5cc(N)n[nH]5)ccc4o3)NC(=O)NC1=O)C2] | 472.15 | 473.1 | 0.523 | 110.25 | |
| 2247 | 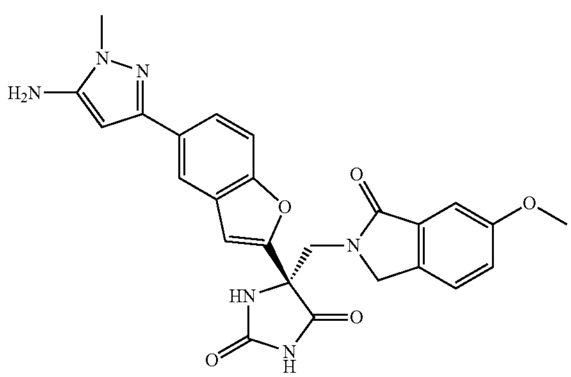 [SMILES: COc1ccc2c(c1)C(=O)N(C[C@@]1(c3cc4cc(-c5cc(N)n(C)n5)ccc4o3)NC(=O)NC1=O)C2] | 486.17 | 487.1 | 0.333 | 781.9 | 375 |
| 2248 | 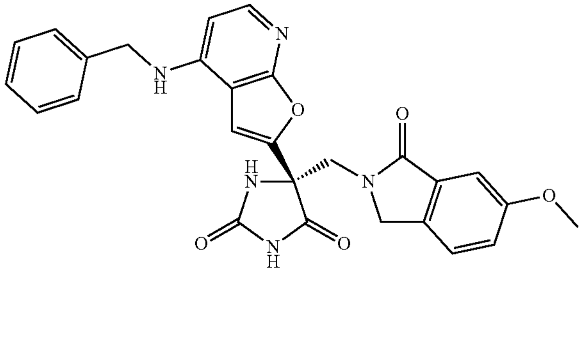 [SMILES: COc1ccc2c(c1)C(=O)N(C[C@@]1(c3cc4c(NCc5ccccc5)ccnc4o3)NC(=O)NC1=O)C2] | 497.17 | 498.2 | 1.61 | 233 | 0 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2249 | 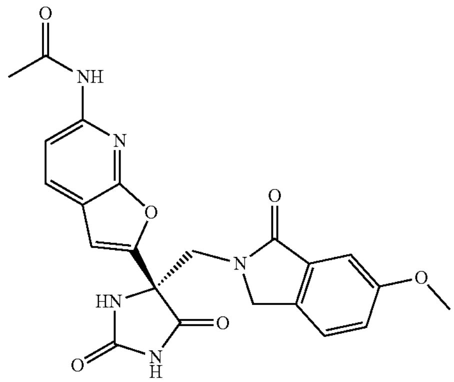 [SMILES: COc1ccc2c(c1)C(=O)N(C[C@@]1(c3cc4ccc(NC(C)=O)nc4o3)NC(=O)NC1=O)C2] | 449.13 | 450.2 | 0.65 | 178.2 | 974 |
| 2250 | 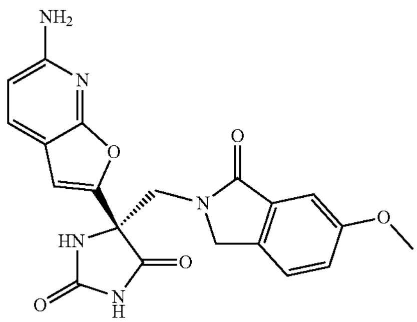 [SMILES: COc1ccc2c(c1)C(=O)N(C[C@@]1(c3cc4ccc(N)nc4o3)NC(=O)NC1=O)C2] | 407.2 | 408.2 | 0.433 | 217.6 | 391 |
| 2251 | 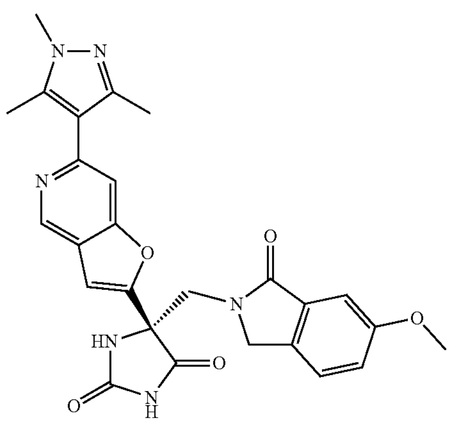 | 500.18 | 501.2 | 0.746 | | 2488 |
| 2252 | 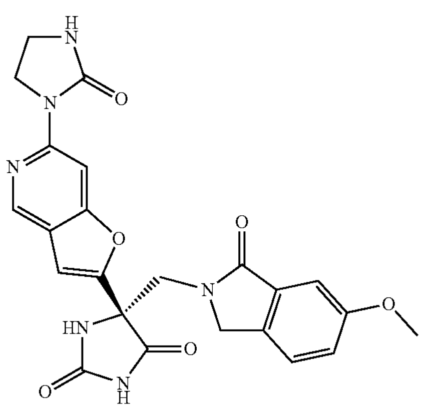 [SMILES: COc1ccc2c(c1)C(=O)N(C[C@@]1(c3cc4cnc(N5CCNC5=O)cc4o3)NC(=O)NC1=O)C2] | 476.14 | 477.1 | 1.79 | 206 | 1184 |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 2253 | 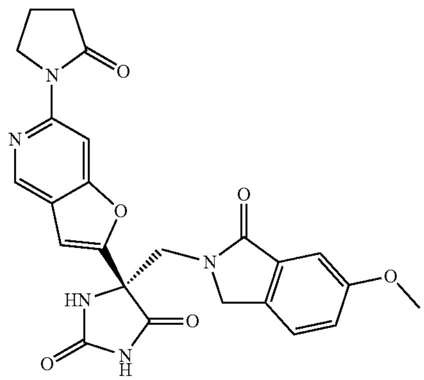 [SMILES: COc1ccc2c(c1)C(=O)N(C[C@@]1(c3cc4cnc(N5CCCC5=O)cc4o3)NC(=O)NC1=O)C2] | 475.15 | 476.2 | 0.972 | 2672 | |
| 2254 | 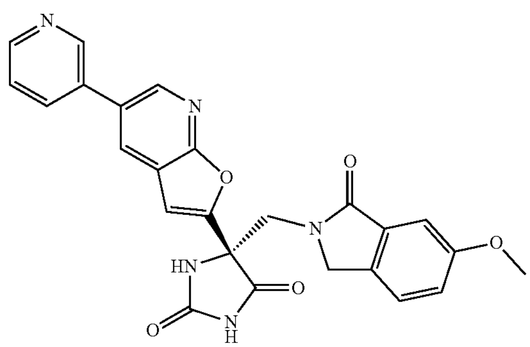 [SMILES: COc1ccc2c(c1)C(=O)N(C[C@@]1(c3cc4cc(-c5cccnc5)cnc4o3)NC(=O)NC1=O)C2] | 469.14 | 470.2 | 0.599 | 1669 | 1768 |
| 2255 | 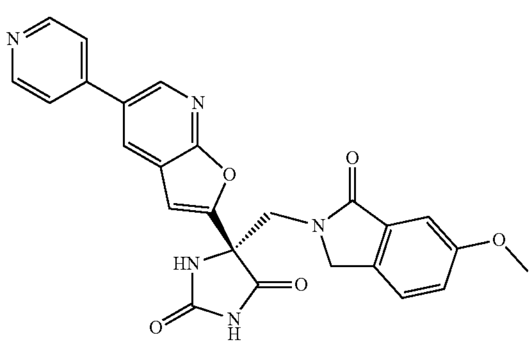 [SMILES: COc1ccc2c(c1)C(=O)N(C[C@@]1(c3cc4cc(-c5ccncc5)cnc4o3)NC(=O)NC1=O)C2] | 469.14 | 470.2 | 0.523 | 395.8 | 527 |
| 2256 | 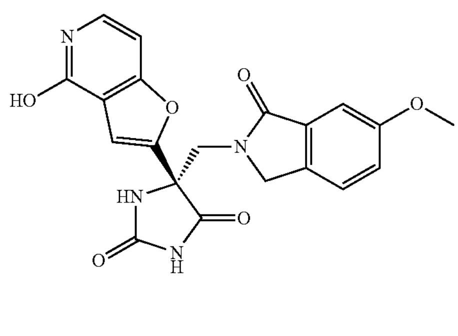 [SMILES: COc1ccc2c(c1)C(=O)N(C[C@@]1(c3cc4c(O)nccc4o3)NC(=O)NC1=O)C2] | 408.11 | 409.1 | 0.231 | 251.5 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2257 | 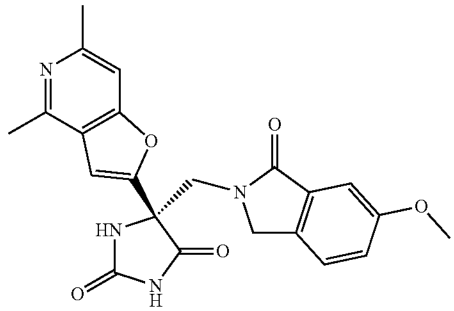 | 420.14 | 421.1 | 0.53 | 676 | 4228 |
| 2258 | 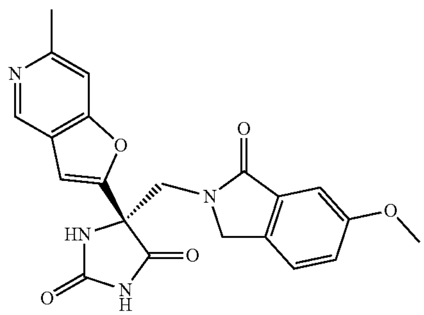 | 406.13 | 407.1 | 0.366 | 345.15 | 19089 |
| 2259 | 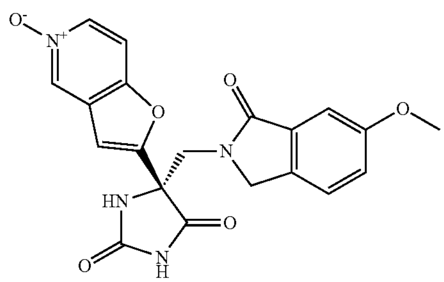 [SMILES: COc1ccc2c(c1)C(=O)N(C[C@@]1(c3cc4c[n+]([O-])ccc4o3)NC(=O)NC1=O)C2] | 408.11 | 409.1 | 1.08 | 509 | |
| 30 | 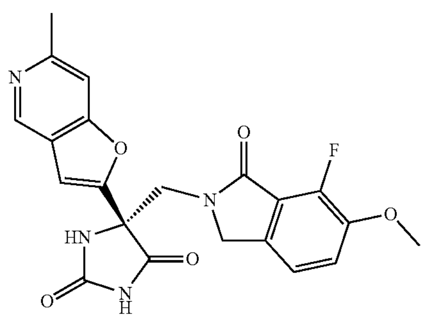 [SMILES: COc1ccc2c(c1F)C(=O)N(C[C@@]1(c3cc4cnc(C)cc4o3)NC(=O)NC1=O)C2] | 424.12 | 425.0 | 0.38 | 205 | 26338 |
| 2261 | 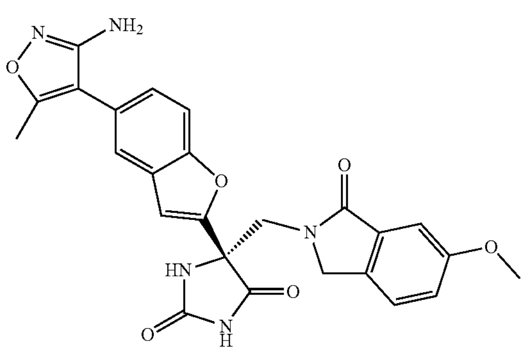 [SMILES: COc1ccc2c(c1)C(=O)N(C[C@@]1(c3cc4cc(-c5c(N)noc5C)ccc4o3)NC(=O)NC1=O)C2] | 487.15 | 448.2 | 0.347 | 515 | |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 2262 | 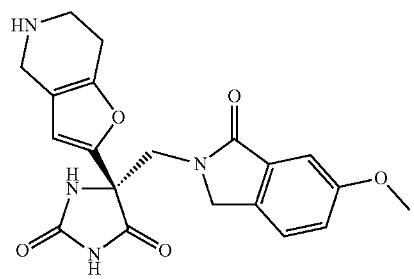 [SMILES: COc1ccc2c(c1)C(=O)N(C[C@@]1(c3cc4c(o3)CCNC4)NC(=O)NC1=O)C2] | 396.14 | 397.1 | 6.54 | 1001 | |
| 2263 | 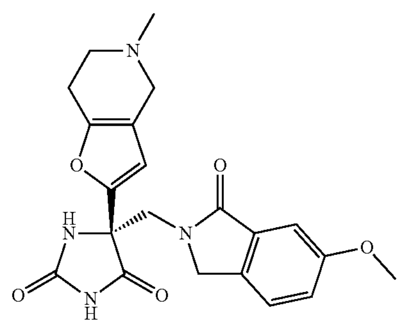 [SMILES: COc1ccc2c(c1)C(=O)N(C[C@@]1(c3cc4c(o3)CCN(C)C4)NC(=O)NC1=O)C2] | 410.16 | 409.1 | 7.71 | 1001 | 240 |
| 2264 | 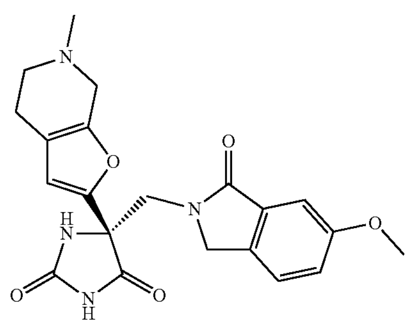 [SMILES: COc1ccc2c(c1)C(=O)N(C[C@@]1(c3cc4c(o3)CN(C)CC4)NC(=O)NC1=O)C2] | 410.16 | 411.2 | 0.417 | 1179 | 623 |
| 2265 | 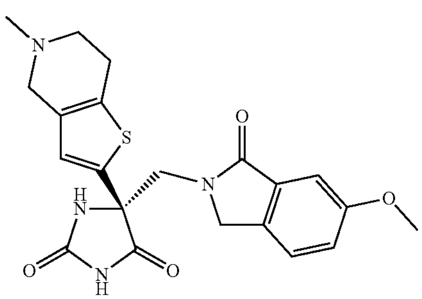 | 426.14 | 427.1 | 8.77 | 1444 | |
| 2266 | 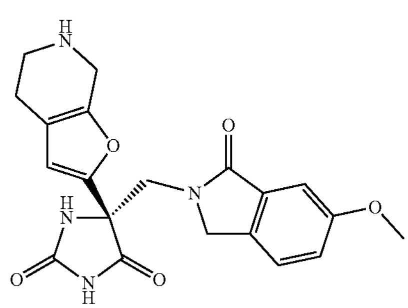 [SMILES: COc1ccc2c(c1)C(=O)N(C[C@@]1(c3cc4c(o3)CNCC4)NC(=O)NC1=O)C2] | 396.14 | 397.1 | 7.83 | 860.4 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2267 | 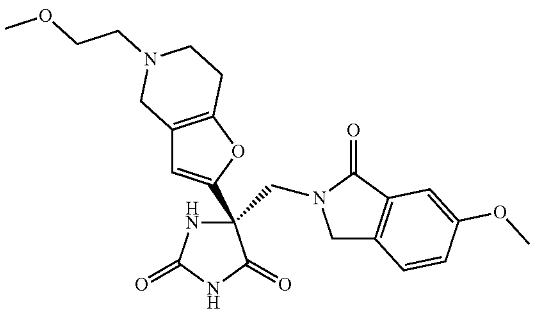 | 454.19 | 455.2 | 5.27 | 1037 | 278 |
| 2268 | 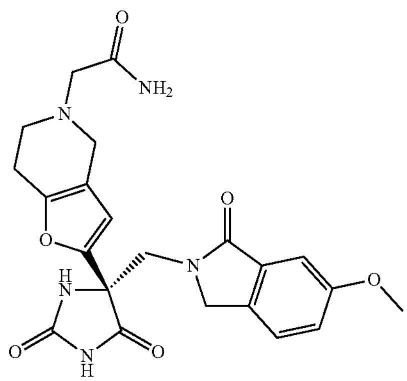 [SMILES: COc1ccc2c(c1)C(=O)N(C[C@@]1(c3cc4c(o3)CCN(CC(N)=O)C4)NC(=O)NC1=O)C2] | 453.16 | 454.1 | 0.702 | 251.7 | |
| 2269 | 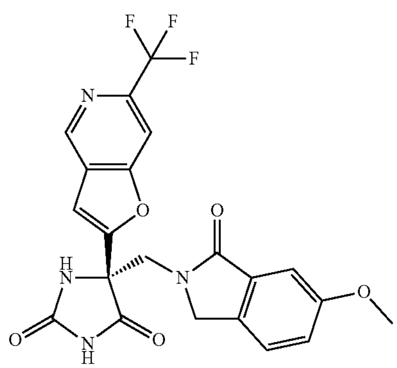 [SMILES: COc1ccc2c(c1)C(=O)N(C[C@@]1(c3cc4cnc(C(F)(F)F)cc4o3)NC(=O)NC1=O)C2] | 460.10 | 461.1 | 0.497 | 1623.2 | 19305 |
| 2270 | 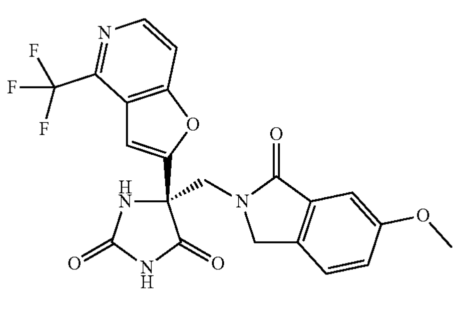 [SMILES: COc1ccc2c(c1)C(=O)N(C[C@@]1(c3cc4c(C(F)(F)F)nccc4o3)NC(=O)NC1=O)C2] | 460.10 | 461.2 | 0.441 | 1071.3 | |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 2271 | 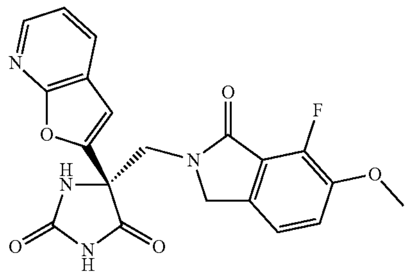 [SMILES: COc1ccc2c(c1F)C(=O)N(C[C@@]1(c3cc4cccnc4o3)NC(=O)NC1=O)C2] | 410.10 | 411.1 | 0.36 | 217.5 | 10584 |
| 2272 | 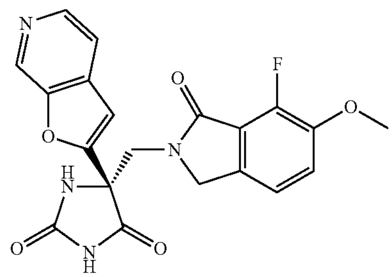 [SMILES: COc1ccc2c(c1F)C(=O)N(C[C@@]1(c3cc4ccncc4o3)NC(=O)NC1=O)C2] | 410.10 | 411.1 | 0.3 | 166.8 | 2790 |
| 2273 | 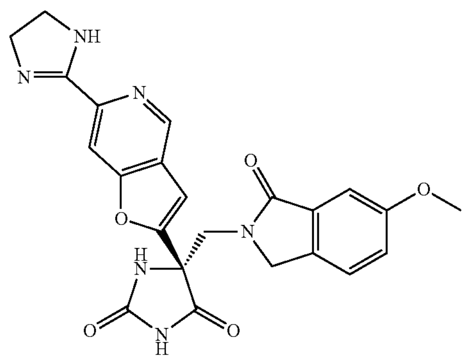 [SMILES: COc1ccc2c(c1)C(=O)N(C[C@@]1(c3cc4cnc(C5=NCCN5)cc4o3)NC(=O)NC1=O)C2] | 460.15 | 461.2 | 0.124 | 747.4 | |
| 2274 | 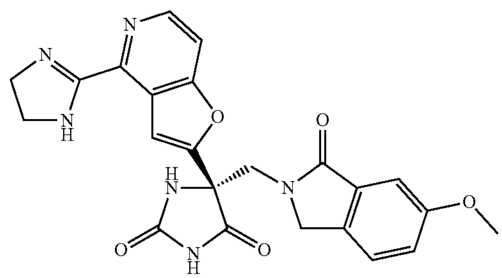 [SMILES: COc1ccc2c(c1)C(=O)N(C[C@@]1(c3cc4c(C5=NCCN5)nccc4o3)NC(=O)NC1=O)C2] | 460.15 | 461.1 | 2 | 2240 | 33 |
| 2275 | 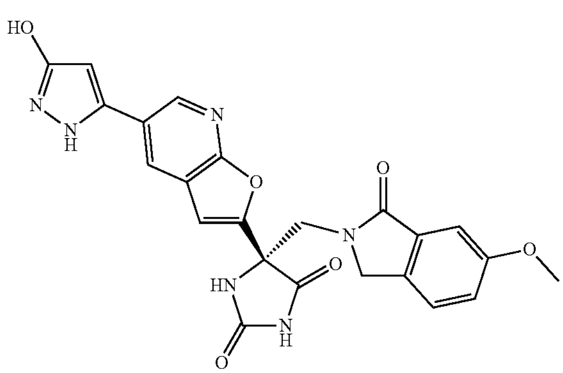 [SMILES: COc1ccc2c(c1)C(=O)N(C[C@@]1(c3cc4cc(-c5cc(O)n[nH]5)cnc4o3)NC(=O)NC1=O)C2] | 474.13 | 475.1 | 1.08 | 490.6 | 0 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2276 | 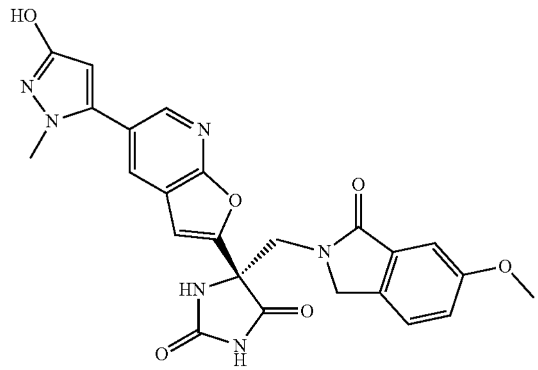 [SMILES: COc1ccc2c(c1)C(=O)N(C[C@@]1(c3cc4cc(-c5cc(O)nn5C)cnc4o3)NC(=O)NC1=O)C2] | 488.14 | 489.1 | 0.562 | 222 | 0 |
| 2277 | 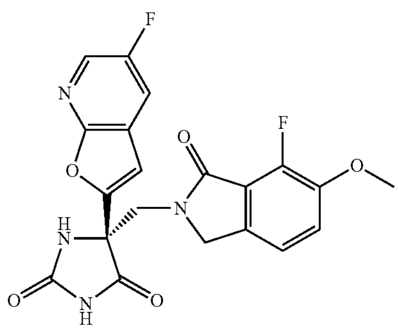 [SMILES: COc1ccc2c(c1F)C(=O)N(C[C@@]1(c3cc4cc(F)cnc4o3)NC(=O)NC1=O)C2] | 428.09 | 429.1 | 0.505 | 499.2 | 26234 |
| 2278 | 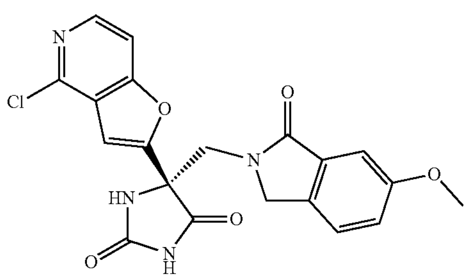 [SMILES: COc1ccc2c(c1)C(=O)N(C[C@@]1(c3cc4c(Cl)nccc4o3)NC(=O)NC1=O)C2] | 426.07 | 427.2 | 0.637 | 260.38 | 12133 |
| 2279 | 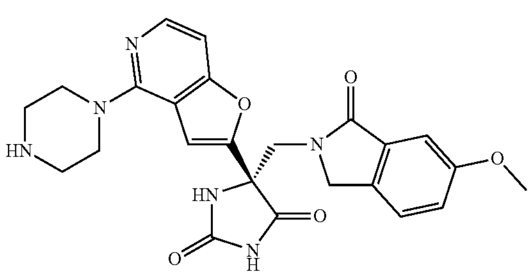 [SMILES: COc1ccc2c(c1)C(=O)N(C[C@@]1(c3cc4c(N5CCNCC5)nccc4o3)NC(=O)NC1=O)C2] | 476.18 | 477.2 | 2.55 | 233.5 | 0 |
| 2280 | 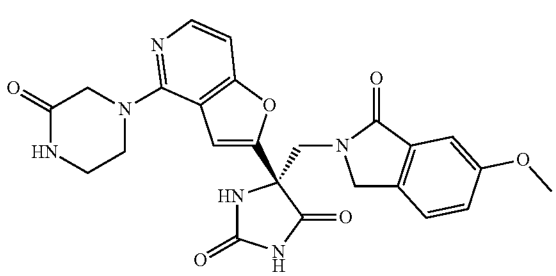 [SMILES: COc1ccc2c(c1)C(=O)N(C[C@@]1(c3cc4c(N5CCNC(=O)C5)nccc4o3)NC(=O)NC1=O)C2] | 490.16 | 491.1 | 1.1 | 340 | 0 |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 2281 | 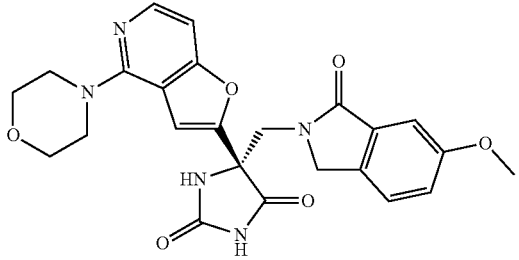 [SMILES: COc1ccc2c(c1)C(=O)N(C[C@@]1(c3cc4c(N5CCOCC5)nccc4o3)NC(=O)NC1=O)C2] | 477.16 | 478.2 | 0.458 | 509.7 | 749 |
| 2282 | 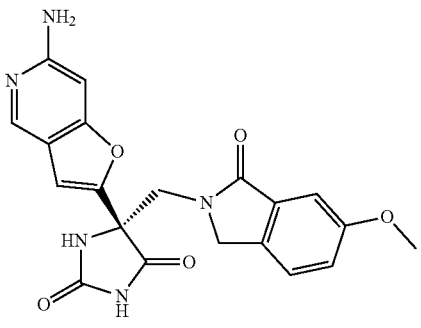 [SMILES: COc1ccc2c(c1)C(=O)N(C[C@@]1(c3cc4cnc(N)cc4o3)NC(=O)NC1=O)C2] | 407.12 | 408.1 | 0.422 | 267.8 | |
| 2283 | 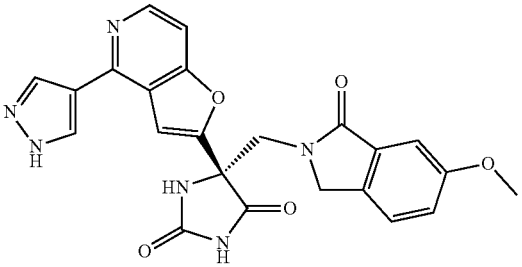 [SMILES: COc1ccc2c(c1)C(=O)N(C[C@@]1(c3cc4c(-c5cn[nH]c5)nccc4o3)NC(=O)NC1=O)C2] | 458.13 | 459.2 | 0.185 | 153.6 | |
| 2284 | 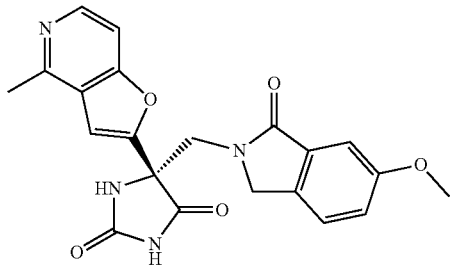 | 406.13 | 407.5 | 0.5 | 198 | 2801 |
| 2285 | 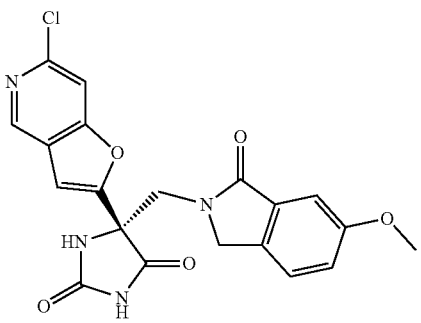 [SMILES: COc1ccc2c(c1)C(=O)N(C[C@@]1(c3cc4cnc(Cl)cc4o3)NC(=O)NC1=O)C2] | 426.07 | 427.4 | 0.44 | 368.4 | 22248 |

TABLE A-continued
| ID | STRUCTURE | EXACT MASS | MASS OBSVD | Ki (nM) | hWBA (IC$_{50}$) | RR$^1$ AUC (nM · h) |
|---|---|---|---|---|---|---|
| 2286 | 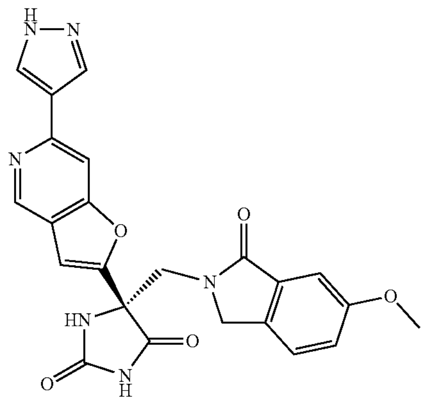 [SMILES: COc1ccc2c(c1)C(=O)N(C[C@@]1(c3cc4cnc(-c5cn[nH]c5)cc4o3)NC(=O)NC1=O)C2] | 458.13 | 459.1 | 0.566 | 183.88 | 46 |
| 2287 | 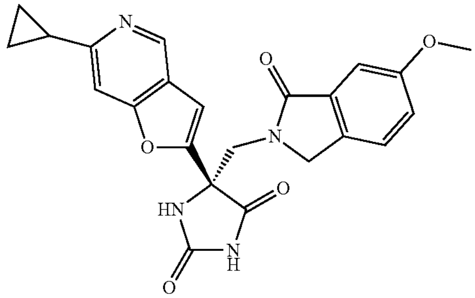 [SMILES: COc1ccc2c(c1)C(=O)N(C[C@@]1(c3cc4cnc(C5CC5)cc4o3)NC(=O)NC1=O)C2] | 432.14 | 433.2 | 0.429 | 575.15 | |
| 2288 | 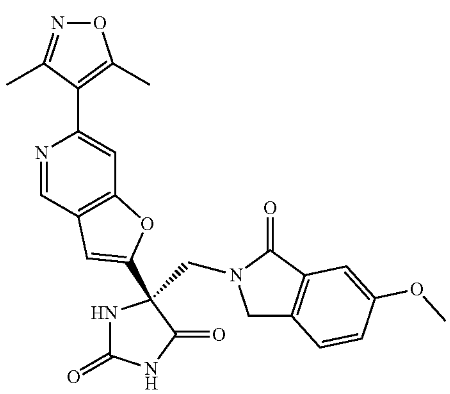 | 487.15 | 488.2 | 0.721 | 696.2 | |
| 2289 | 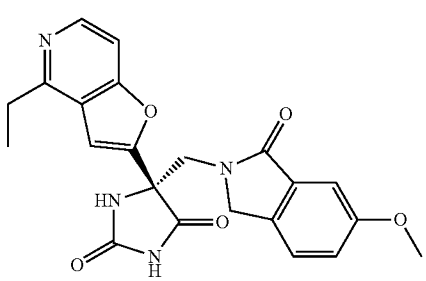 [SMILES: CCc1nccc2oc([C@]3(CN4Cc5ccc(OC)cc5C4=O)NC(=O)NC3=O)cc12] | 420.14 | 421.2 | 0.25 | 357.8 | 3559 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2290 | 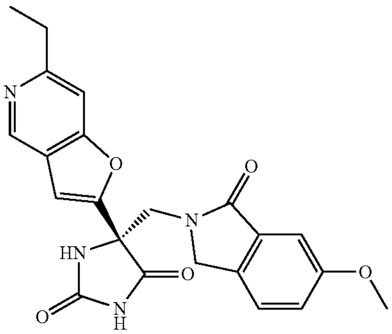 [SMILES: CCc1cc2oc([C@]3(CN4Cc5ccc(OC)cc5C4=O)NC(=O)NC3=O)cc2cn1] | 420.14 | 421.1 | 0.264 | 642.6 | 20322 |
| 2291 | 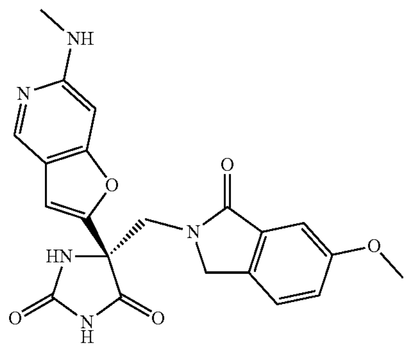 [SMILES: CNc1cc2oc([C@]3(CN4Cc5ccc(OC)cc5C4=O)NC(=O)NC3=O)cc2cn1] | 421.14 | 422.2 | 0.578 | 3422 | |
| 2292 | 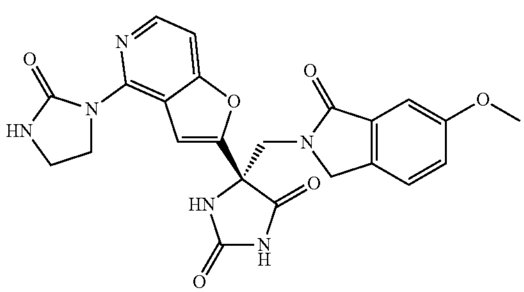 [SMILES: COc1ccc2c(c1)C(=O)N(C[C@@]1(c3cc4c(N5CCNC5=O)nccc4o3)NC(=O)NC1=O)C2] | 476.14 | 477.1 | 1.32 | 484.7 | |
| 2293 | 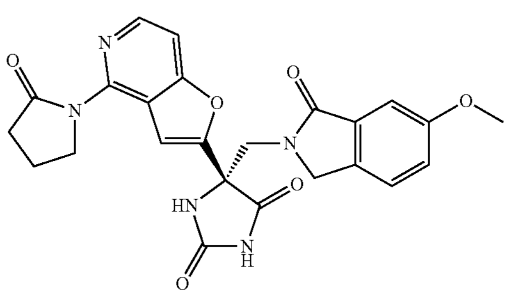 [SMILES: COc1ccc2c(c1)C(=O)N(C[C@@]1(c3cc4c(N5CCCC5=O)nccc4o3)NC(=O)NC1=O)C2] | 475.15 | 476.2 | 1.26 | 530.7 | 219 |
| 2294 | 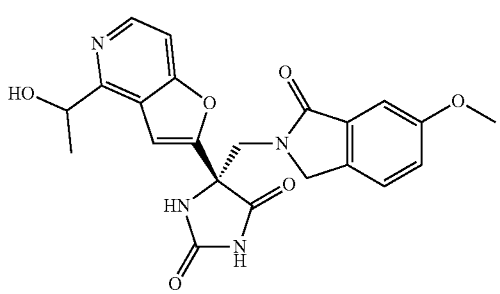 [SMILES: COc1ccc2c(c1)C(=O)N(C[C@@]1(c3cc4c(C(C)O)nccc4o3)NC(=O)NC1=O)C2] | 436.14 | 437.2 | 0.553 | 322.7 | 154 |

TABLE A-continued

| ID | STRUCTURE | EXACT MASS | MASS OBSVD | Ki (nM) | hWBA (IC$_{50}$) | RR$^1$ AUC (nM · h) |
|---|---|---|---|---|---|---|
| 2295 | 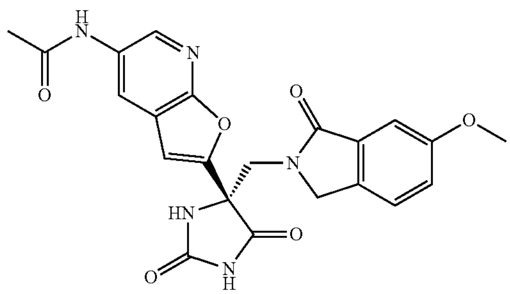 [SMILES: COc1ccc2c(c1)C(=O)N(C[C@@]1(c3cc4cc(NC(C)=O)cnc4o3)NC(=O)NC1=O)C2] | 449.13 | 450.1 | 1.31 | 222 | 44 |
| 2296 | 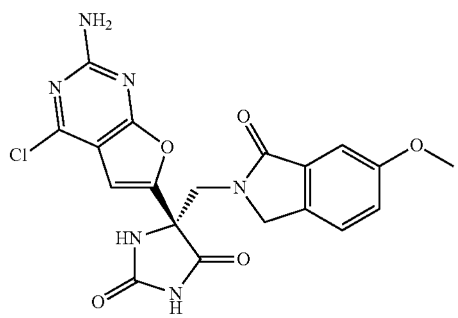 [SMILES: COc1ccc2c(c1)C(=O)N(C[C@@]1(c3cc4c(Cl)nc(N)nc4o3)NC(=O)NC1=O)C2] | 442.08 | 443.1 | 4.59 | 10001 | |
| 2297 | 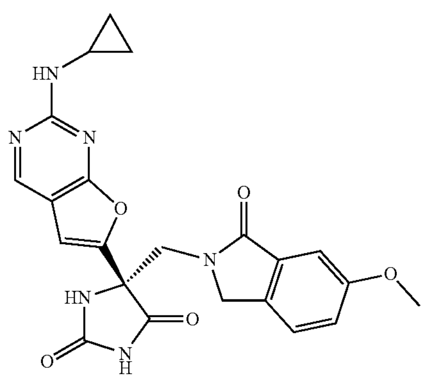 [SMILES: COc1ccc2c(c1)C(=O)N(C[C@@]1(c3cc4cnc(NC5CC5)nc4o3)NC(=O)NC1=O)C2] | 448.15 | 449.1 | 0.822 | 1001 | |
| 2298 | 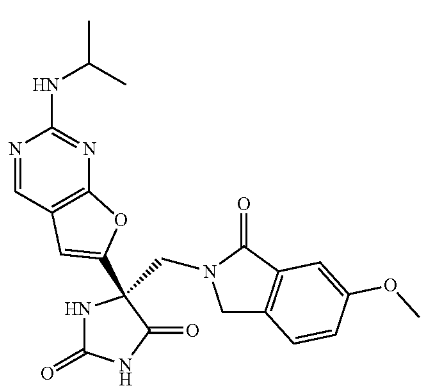 [SMILES: COc1ccc2c(c1)C(=O)N(C[C@@]1(c3cc4cnc(NC(C)C)nc4o3)NC(=O)NC1=O)C2] | 450.17 | 451.1 | 1.69 | 1001 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2299 | 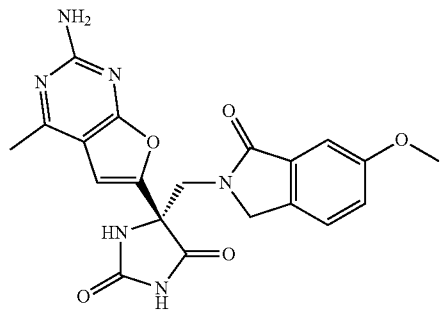 | 422.13 | 423.0 | 0.762 | 284 | |
| 2300 | 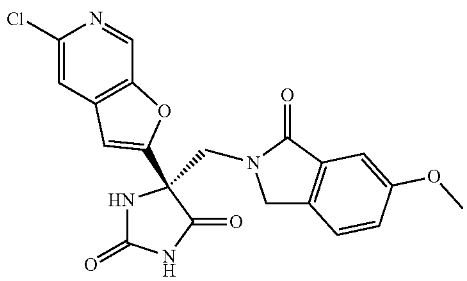 [SMILES: COc1ccc2c(c1)C(=O)N(C[C@@]1(c3cc4cc(Cl)ncc4o3)NC(=O)NC1=O)C2] | 426.07 | 427.1 | 0.49 | 902.3 | 22727 |
| 2301 | 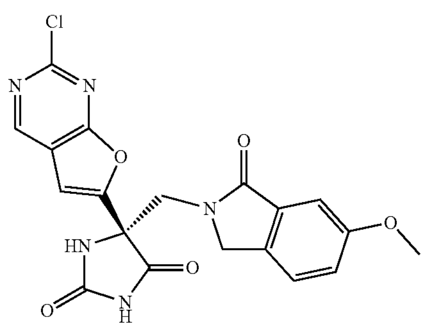 [SMILES: COc1ccc2c(c1)C(=O)N(C[C@@]1(c3cc4cnc(Cl)nc4o3)NC(=O)NC1=O)C2] | 427.07 | 428.1 | 0.36 | 531.8 | |
| 2302 | 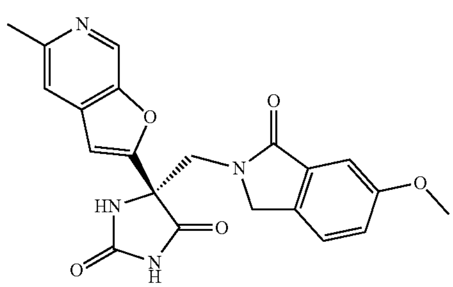 | 406.13 | 407.2 | 0.437 | 469.6 | |
| 2303 | 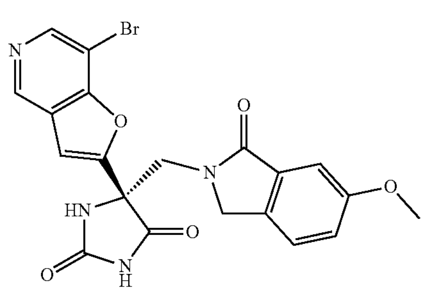 [SMILES: COc1ccc2c(c1)C(=O)N(C[C@@]1(c3cc4cncc(Br)c4o3)NC(=O)NC1=O)C2] | 470.02 | 471.0 | 0.312 | 630.5 | |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 2304 | 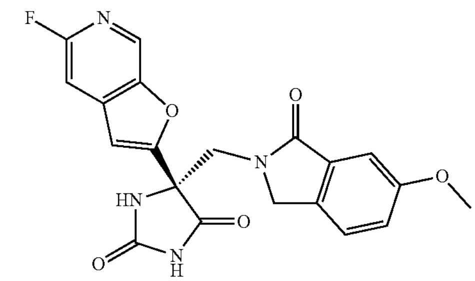 [SMILES: COc1ccc2c(c1)C(=O)N(C[C@@]1(c3cc4cc(F)ncc4o3)NC(=O)NC1=O)C2] | 410.10 | 411.1 | 0.276 | 418.7 | 9311 |
| 2305 | 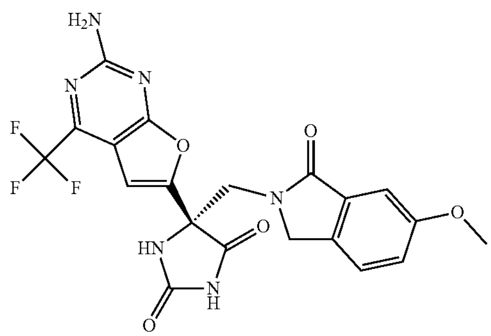 [SMILES: COc1ccc2c(c1)C(=O)N(C[C@@]1(c3cc4c(C(F)(F)F)nc(N)nc4o3)NC(=O)NC1=O)C2] | 476.11 | 477.1 | 0.568 | 1419.8 | |
| 2306 | 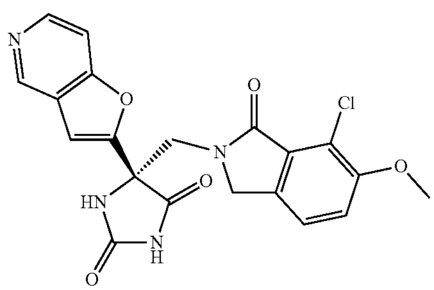 [SMILES: COc1ccc2c(c1Cl)C(=O)N(C[C@@]1(c3cc4cnccc4o3)NC(=O)NC1=O)C2] | 426.07 | 427.1 | 0.57 | 834 | |
| 2307 | 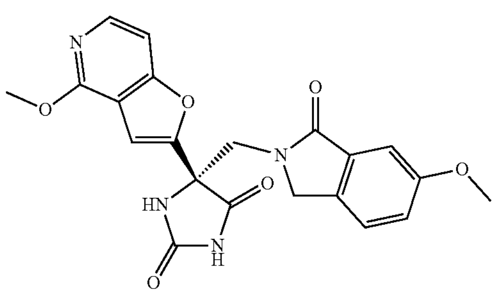 | 422.12 | 423.2 | 0.437 | 604 | 41403 |
| 2308 | 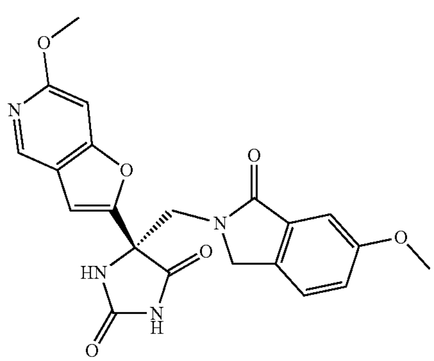 [SMILES: COc1ccc2c(c1)C(=O)N(C[C@@]1(c3cc4cnc(OC)cc4o3)NC(=O)NC1=O)C2] | 422.12 | 423.2 | 0.328 | 2111.9 | |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 2309 | 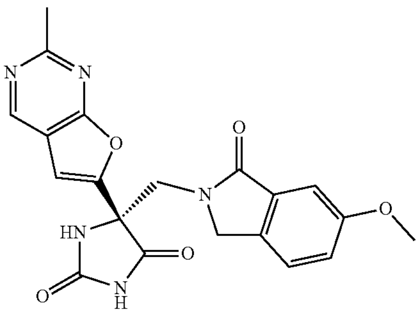 [SMILES: COc1ccc2c(c1)C(=O)N(C[C@@]1(c3cc4cnc(C)nc4o3)NC(=O)NC1=O)C2] | 407.12 | 408.2 | 0.594 | 624 | 18033 |
| 2310 | 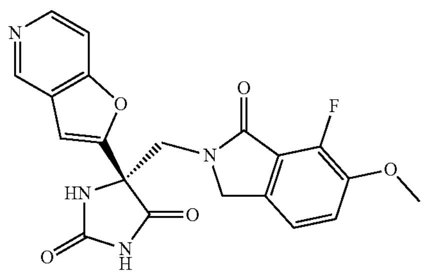 [SMILES: COc1ccc2c(c1F)C(=O)N(C[C@@]1(c3cc4cnccc4o3)NC(=O)NC1=O)C2] | 410.10 | 411.1 | 0.37 | 197 | 2309 |
| 2311 | 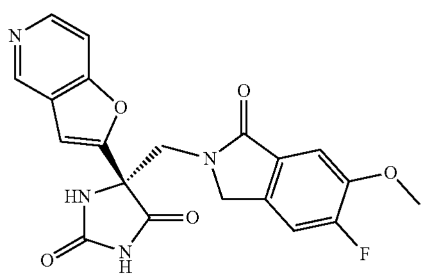 [SMILES: COc1cc2c(cc1F)CN(C[C@@]1(c3cc4cnccc4o3)NC(=O)NC1=O)C2=O] | 410.10 | 411.1 | 1.72 | 942 | |
| 2312 | 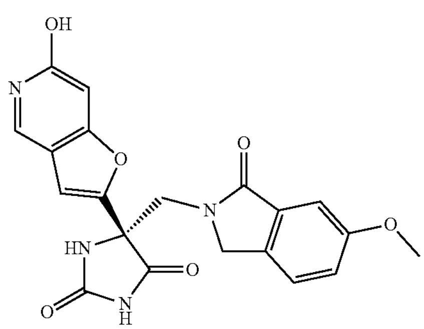 [SMILES: COc1ccc2c(c1)C(=O)N(C[C@@]1(c3cc4cnc(O)cc4o3)NC(=O)NC1=O)C2] | 408.11 | 409.2 | 1.06 | 218.2 | 0 |
| 2313 | 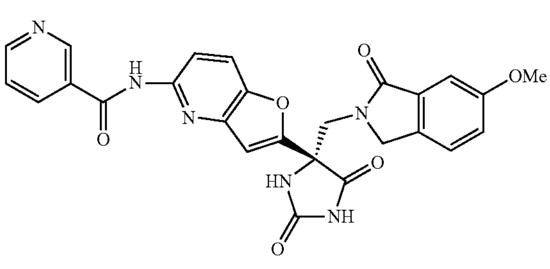 [SMILES: COc1ccc2c(c1)C(=O)N(C[C@@]1(c3cc4nc(NC(=O)c5cccnc5)ccc4o3)NC(=O)NC1=O)C2] | 512.47 | 513.3 | | 536.8 | |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 2314 | 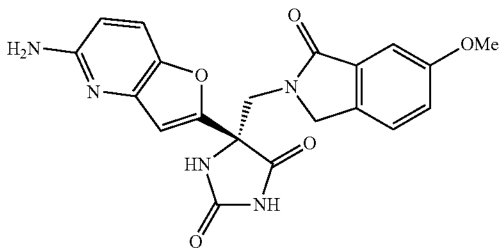 [SMILES: COc1ccc2c(c1)C(=O)N(C[C@@]1(c3cc4nc(N)ccc4o3)NC(=O)NC1=O)C2] | 407.37 | 408.2 | 0.511 | 187 | 424 |
| 2315 | 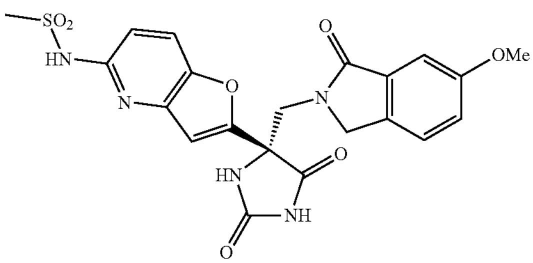 [SMILES: COc1ccc2c(c1)C(=O)N(C[C@@]1(c3cc4nc(NS(C)(=O)=O)ccc4o3)NC(=O)NC1=O)C2] | 485.46 | 486.3 | 2.17 | 188.8 | 0 |
| 2316 | 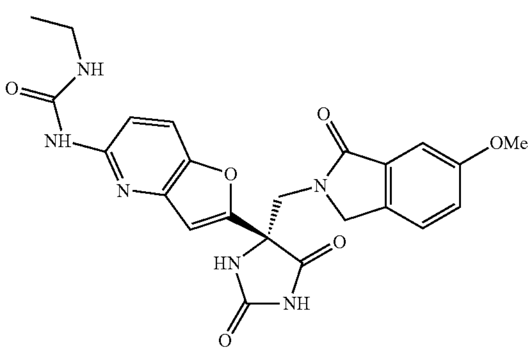 [SMILES: CCNC(=O)Nc1ccc2oc([C@]3(CN4Cc5ccc(OC)cc5C4=O)NC(=O)NC3=O)cc2n1] | 478.45 | 479.3 | 1.12 | 671.7 | |
| 2317 | 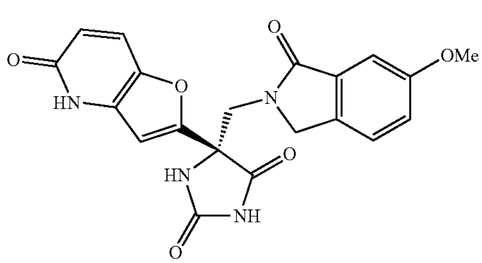 [SMILES: COc1ccc2c(c1)C(=O)N(C[C@@]1(c3cc4[nH]c(=O)ccc4o3)NC(=O)NC1=O)C2] | 408.36 | 409.2 | 0.375 | 542.3 | |
| 2318 | 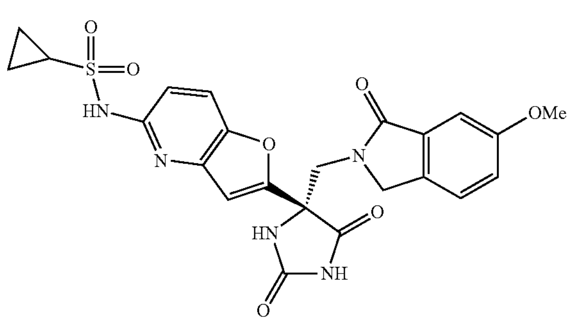 [SMILES: COc1ccc2c(c1)C(=O)N(C[C@@]1(c3cc4nc(NS(=O)(=O)C5CC5)ccc4o3)NC(=O)NC1=O)C2] | 511.50 | 512.3 | 0.579 | 518.1 | 15 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2320 | 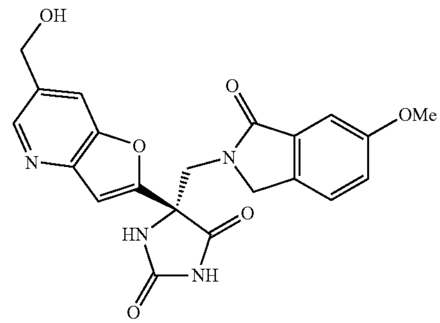 [SMILES: COc1ccc2c(c1)C(=O)N(C[C@@]1(c3cc4ncc(CO)cc4o3)NC(=O)NC1=O)C2] | 422.39 | 423.2 | 0.586 | 609 | |
| 2400 | 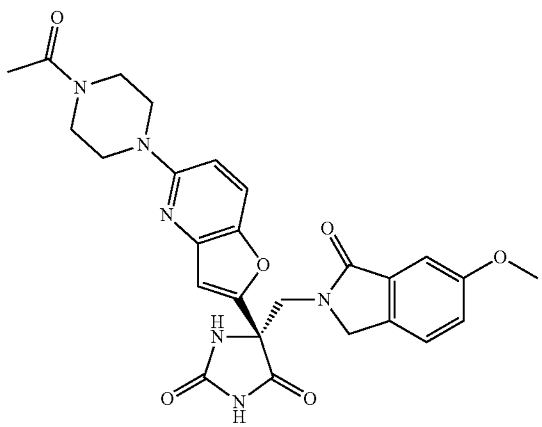 [SMILES: COc1ccc2c(c1)C(=O)N(C[C@@]1(c3cc4nc(N5CCN(C(C)=O)CC5)ccc4o3)NC(=O)NC1=O)C2] | 518.19 | 519.3 | 0.585 | 280.1 | 439 |
| 2401 | 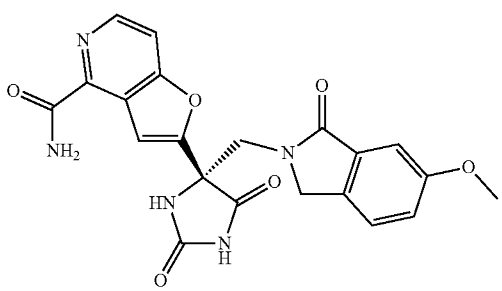 [SMILES: COc1ccc2c(c1)C(=O)N(C[C@@]1(c3cc4c(C(N)=O)nccc4o3)NC(=O)NC1=O)C2] | 435.12 | 436.1 | 0.58 | 270 | 1425 |
| 2402 | 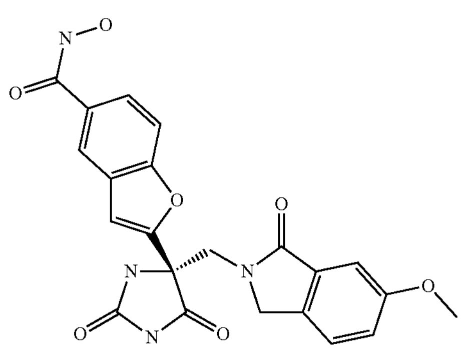 [SMILES: COc1ccc2c(c1)C(=O)N(C[C@@]1(c3cc4cc(C(=O)NO)ccc4o3)NC(=O)NC1=O)C2] | 450.12 | 451.2 | 0.50 | 256 | |

TABLE A-continued

| ID | STRUCTURE | EXACT MASS | MASS OBSVD | Ki (nM) | hWBA (IC$_{50}$) | RR$^1$ AUC (nM · h) |
|---|---|---|---|---|---|---|
| 2403 | 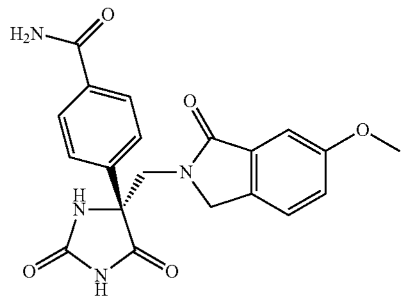 [SMILES: COc1ccc2c(c1)C(=O)N(C[C@@]1(c3ccc(C(N)=O)cc3)NC(=O)NC1=O)C2] | 394.1 | 395.2 | 1.3 | 1973 | |
| 2404 | 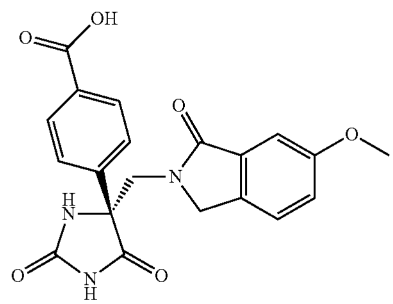 [SMILES: COc1ccc2c(c1)C(=O)N(C[C@@]1(c3ccc(C(=O)O)cc3)NC(=O)NC1=O)C2] | 395.11 | 396.2 | 3.15 | 1709 | |
| 2405 | 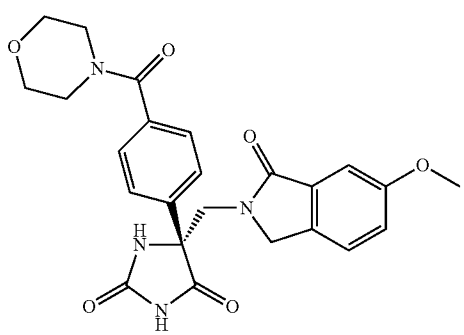 [SMILES: COc1ccc2c(c1)C(=O)N(C[C@@]1(c3ccc(C(=O)N4CCOCC4)cc3)NC(=O)NC1=O)C2] | 464.1 | 465.3 | 2.91 | 2708 | |
| 2406 | 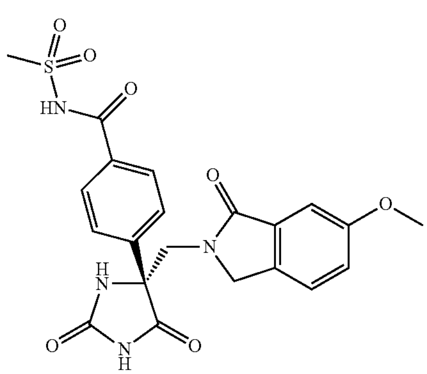 | 472.1 | 473.3 | 5.38 | 7108 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2407 | 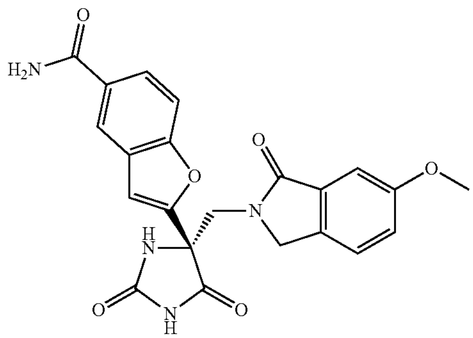 [SMILES: COc1ccc2c(c1)C(=O)N(C[C@@]1(c3cc4cc(C(N)=O)ccc4o3)NC(=O)NC1=O)C2] | 434.1 | 435.2 | 0.12 | 162 | |
| 2408 | 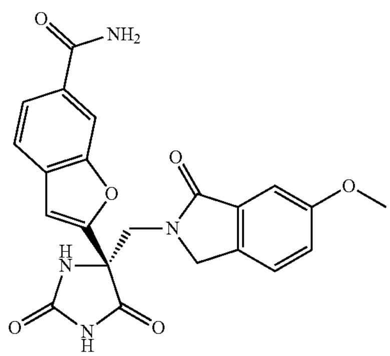 [SMILES: COc1ccc2c(c1)C(=O)N(C[C@@]1(c3cc4ccc(C(N)=O)cc4o3)NC(=O)NC1=O)C2] | 434.1 | 435.2 | 0.49 | 132 | 0 |
| 2409 | 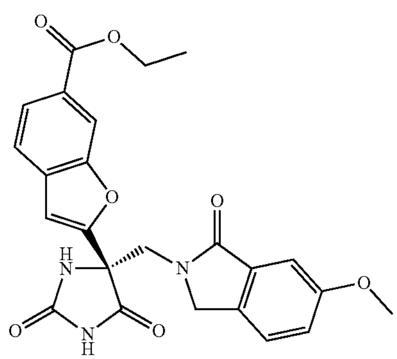 [SMILES: CCOC(=O)c1ccc2cc([C@]3(CN4Cc5ccc(OC)cc5C4=O)NC(=O)NC3=O)oc2c1] | 463.1 | 464.3 | 0.33 | 1867 | |
| 2410 | 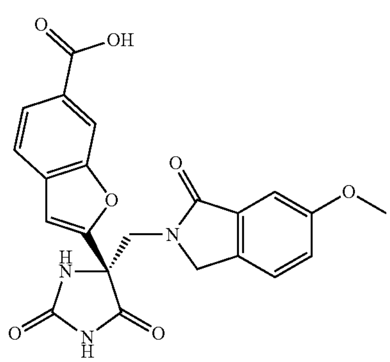 | 435.1 | 436.2 | 0.30 | 591 | |

TABLE A-continued
| ID | STRUCTURE | EXACT MASS | MASS OBSVD | Ki (nM) | hWBA (IC$_{50}$) | RR[1] AUC (nM·h) |
|---|---|---|---|---|---|---|
| 2411 | 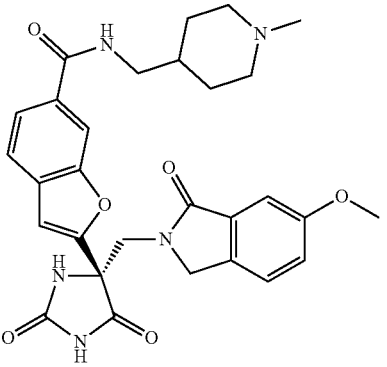 [SMILES: COc1ccc2c(c1)C(=O)N(C[C@@]1(c3cc4ccc(C(=O)NCC5CCN(C)CC5)cc4o3)NC(=O)NC1=O)C2] | 545.2 | 546.3 | 1.14 | 348 | |
| 2412 | 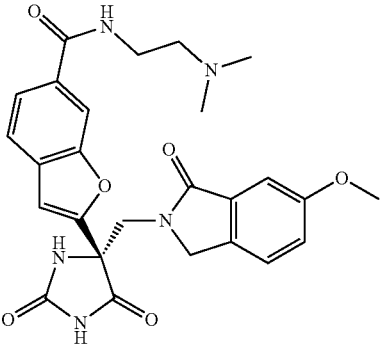 [SMILES: COc1ccc2c(c1)C(=O)N(C[C@@]1(c3cc4ccc(C(=O)NCCN(C)C)cc4o3)NC(=O)NC1=O)C2] | 505.2 | 506.3 | 0.32 | 115 | 104 |
| 2413 | 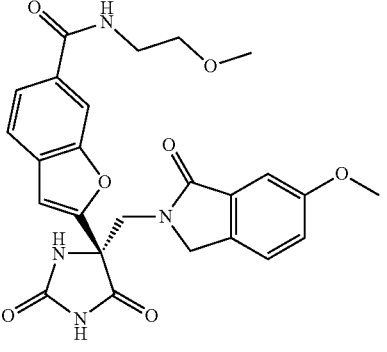 [SMILES: COCCNC(=O)c1ccc2cc([C@]3(CN4Cc5ccc(OC)cc5C4=O)NC(=O)NC3=O)oc2c1] | 492.2 | 493.3 | 0.60 | 300 | |
| 2414 | 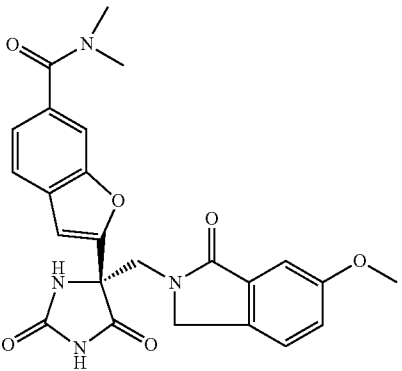 [SMILES: COc1ccc2c(c1)C(=O)N(C[C@@]1(c3cc4ccc(C(=O)N(C)C)cc4o3)NC(=O)NC1=O)C2] | 462.2 | 463.3 | 0.41 | 990 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2415 | 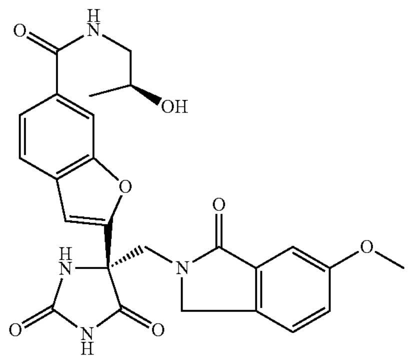 [SMILES: COc1ccc2c(c1)C(=O)N(C[C@@]1(c3cc4ccc(C(=O)NC[C@H](C)O)cc4o3)NC(=O)NC1=O)C2] | 492.2 | 493.3 | 0.51 | 452 | 0 |
| 2416 | 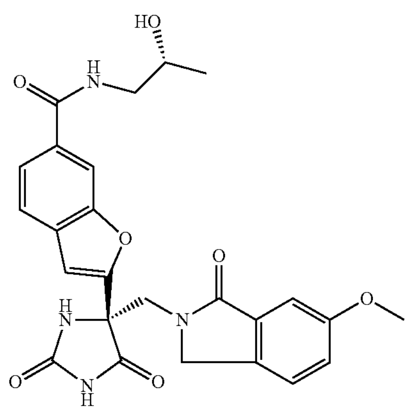 [SMILES: COc1ccc2c(c1)C(=O)N(C[C@@]1(c3cc4ccc(C(=O)NC[C@@H](C)O)cc4o3)NC(=O)NC1=O)C2] | 492.2 | 493.3 | 0.56 | 891 | |
| 2417 | 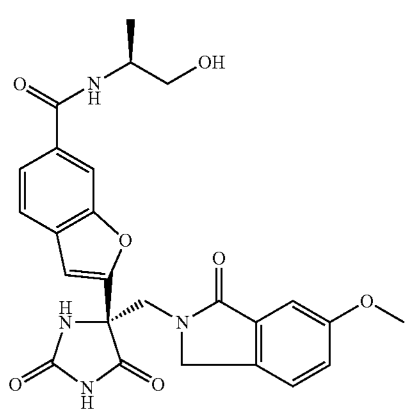 [SMILES: COc1ccc2c(c1)C(=O)N(C[C@@]1(c3cc4ccc(C(=O)N[C@@H](C)CO)cc4o3)NC(=O)NC1=O)C2] | 492.2 | 493.3 | 0.64 | 508 | 0 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2418 | 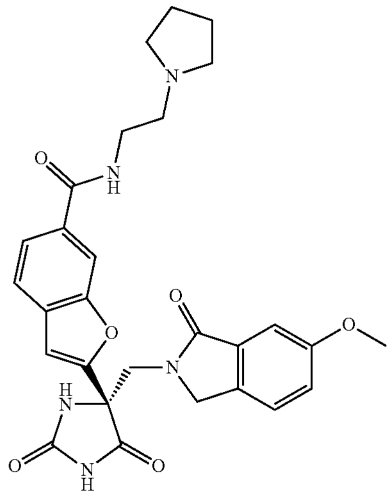 [SMILES: COc1ccc2c(c1)C(=O)N(C[C@@]1(c3cc4ccc(C(=O)NCCN5CCCC5)cc4o3)NC(=O)NC1=O)C2] | 531.2 | 532.3 | 0.76 | 265 | 0 |
| 2419 | 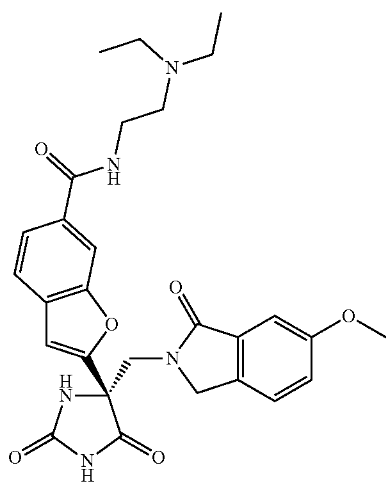 [SMILES: CCN(CC)CCNC(=O)c1ccc2cc([C@]3(CN4Cc5ccc(OC)cc5C4=O)NC(=O)NC3=O)oc2c1] | 533.2 | 534.3 | 0.79 | 332 | 0 |
| 2420 | 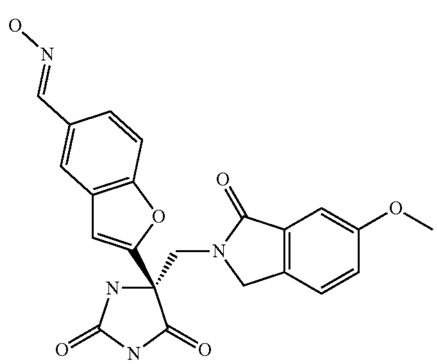 [SMILES: COc1ccc2c(c1)C(=O)N(C[C@@]1(c3cc4cc(/C=N/O)ccc4o3)NC(=O)NC1=O)C2] | 434.12 | | 0.40 | 328 | |

TABLE A-continued
| ID | STRUCTURE | EXACT MASS | MASS OBSVD | Ki (nM) | hWBA (IC$_{50}$) | RR[1] AUC (nM·h) |
|---|---|---|---|---|---|---|
| 2421 | 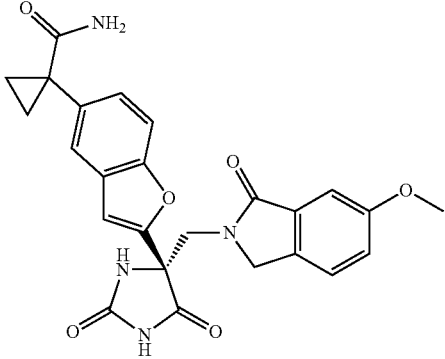 [SMILES: COc1ccc2c(c1)C(=O)N(C[C@@]1(c3cc4cc(C5(C(N)=O)CC5)ccc4o3)NC(=O)NC1=O)C2] | 474.15 | 475.3 | 0.38 | 886 | 37 |
| 2422 | 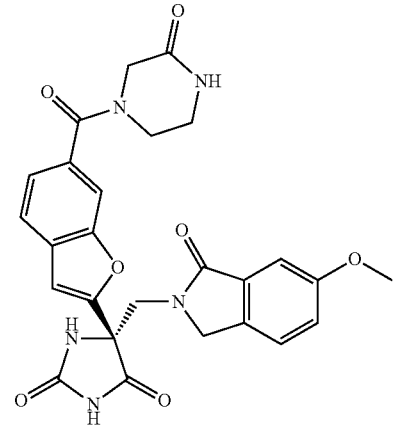 [SMILES: COc1ccc2c(c1)C(=O)N(C[C@@]1(c3cc4ccc(C(=O)N5CCNC(=O)C5)cc4o3)NC(=O)NC1=O)C2] | 517.16 | 518.3 | 0.68 | 519 | 0 |
| 2423 | 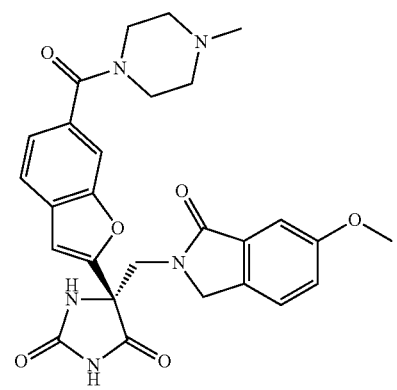 [SMILES: COc1ccc2c(c1)C(=O)N(C[C@@]1(c3cc4ccc(C(=O)N5CCN(C)CC5)cc4o3)NC(=O)NC1=O)C2] | 517.20 | 518.3 | 1.01 | 1088 | 0 |
| 2424 | 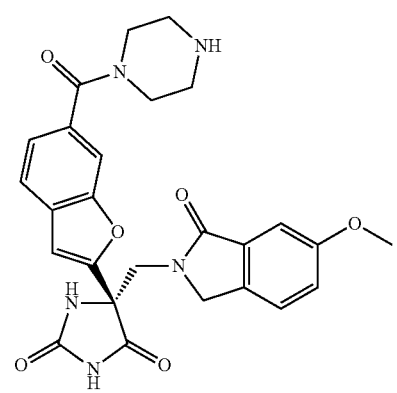 [SMILES: COc1ccc2c(c1)C(=O)N(C[C@@]1(c3cc4ccc(C(=O)N5CCNCC5)cc4o3)NC(=O)NC1=O)C2] | 503.18 | 504.3 | 0.98 | 702 | 13 |

TABLE A-continued

| ID | STRUCTURE | EXACT MASS | MASS OBSVD | Ki (nM) | hWBA (IC$_{50}$) | RR[1] AUC (nM·h) |
|---|---|---|---|---|---|---|
| 2425 | 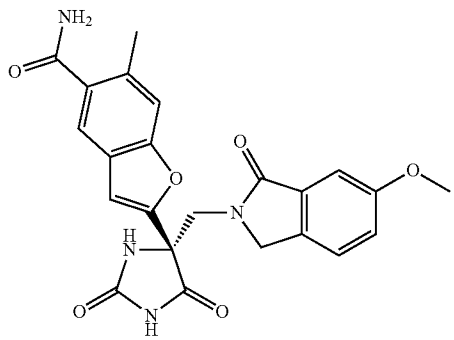 [SMILES: COc1ccc2c(c1)C(=O)N(C[C@@]1(c3cc4cc(C(N)=O)c(C)cc4o3)NC(=O)NC1=O)C2] | 448.14 | 449.2 | 0.51 | 992 | |
| 2426 | 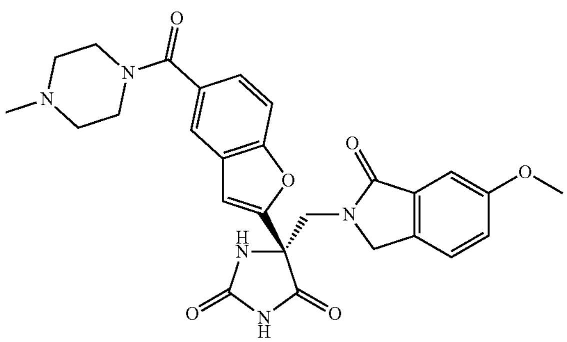 | 517.20 | 518.3 | 1.26 | 850 | 57 |
| 2427 | 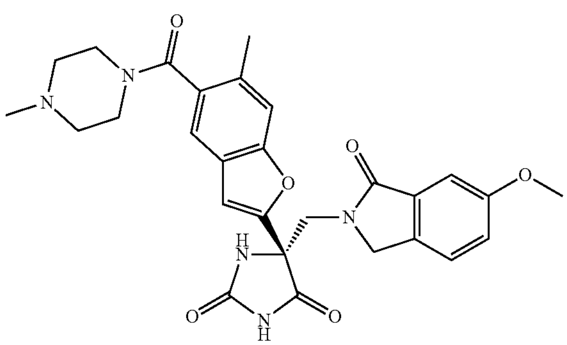 | 531.21 | 532.3 | 1.42 | 560 | |
| 2428 | 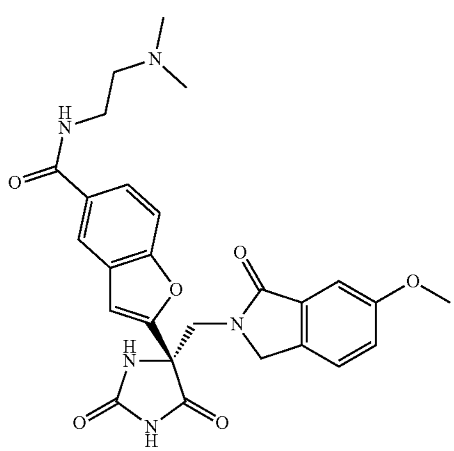 [SMILES: COc1ccc2c(c1)C(=O)N(C[C@@]1(c3cc4cc(C(=O)NCCN(C)C)ccc4o3)NC(=O)NC1=O)C2] | 505.20 | 506.3 | 0.75 | 115 | 0 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2429 | 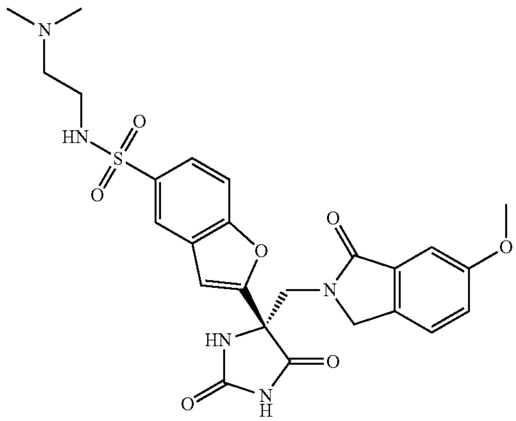 | 541.16 | 542.2 | 0.67 | 304 | 0 |
| 2430 | 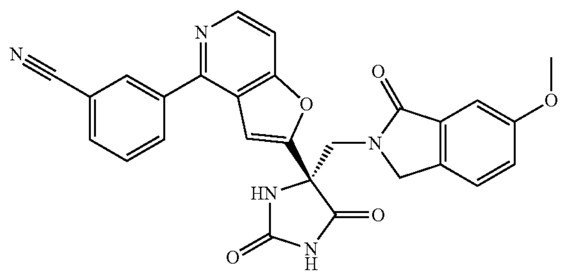 [SMILES: COc1ccc2c(c1)C(=O)N(C[C@@]1(c3cc4c(-c5cccc(C#N)c5)nccc4o3)NC(=O)NC1=O)C2] | 493.14 | 494.2 | 0.72 | 10000 | |
| 2431 | 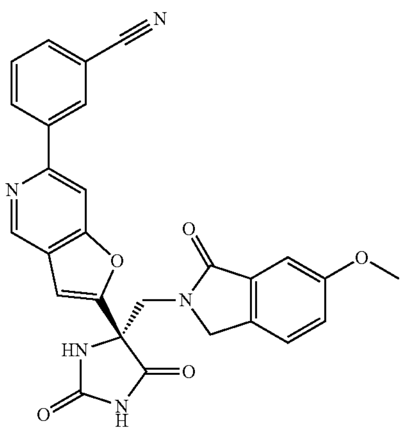 [SMILES: COc1ccc2c(c1)C(=O)N(C[C@@]1(c3cc4cnc(-c5cccc(C#N)c5)cc4o3)NC(=O)NC1=O)C2] | 493.14 | 494.2 | 0.80 | 8425 | 10648 |
| 2432 | 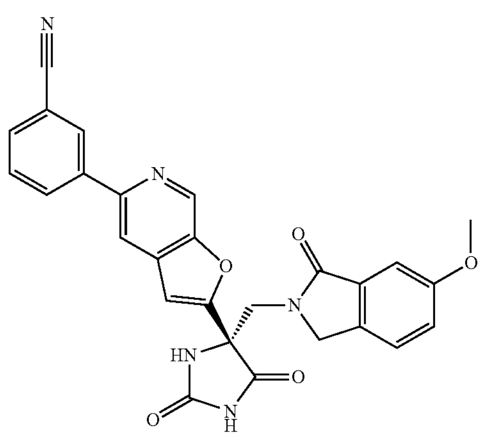 [SMILES: COc1ccc2c(c1)C(=O)N(C[C@@]1(c3cc4cc(-c5cccc(C#N)c5)ncc4o3)NC(=O)NC1=O)C2] | 493.13 | 494.0 | 0.92 | 1720 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2433 | 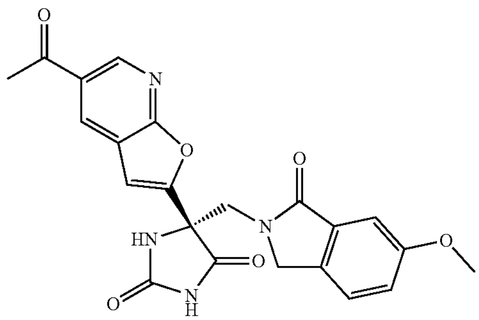 [SMILES: COc1ccc2c(c1)C(=O)N(C[C@@]1(c3cc4cc(C(C)=O)cnc4o3)NC(=O)NC1=O)C2] | 434.12 | 435.1 | 0.731 | 711.5 | |
| 2434 | 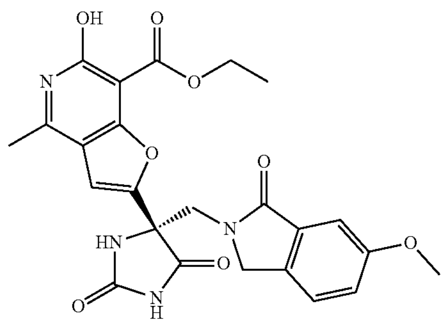 | 494.14 | 495.1 | 1.32 | 174 | 0 |
| 2435 | 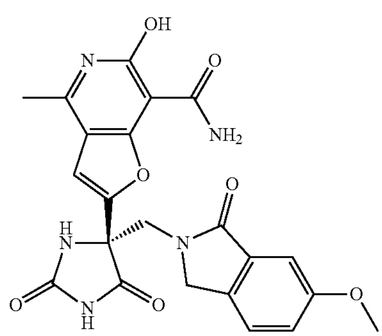 [SMILES: COc1ccc2c(c1)C(=O)N(C[C@@]1(c3cc4c(C)nc(O)c(C(N)=O)c4o3)NC(=O)NC1=O)C2] | 465.13 | 466.1 | 1.14 | 504 | 0 |
| 2436 | 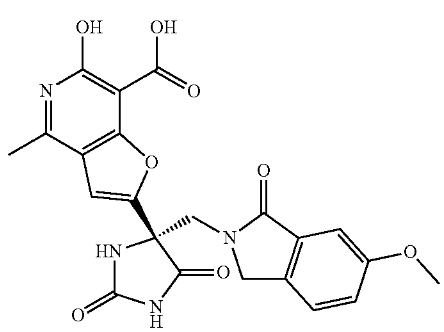 | 466.11 | 467.1 | 2.41 | 2388 | |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 2437 | 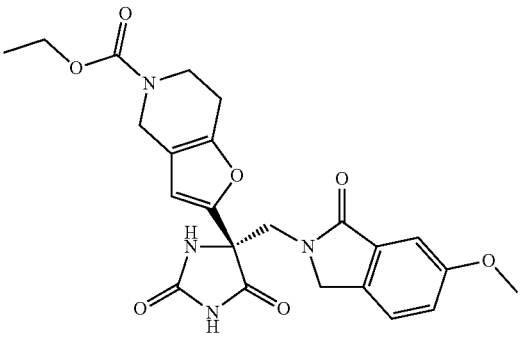 [SMILES: CCOC(=O)N1CCc2oc([C@]3(CN4Cc5ccc(OC)cc5C4=O)NC(=O)NC3=O)cc2C1] | 468.16 | 469.1 | 0.93 | 654 | 4026 |
| 2438 | 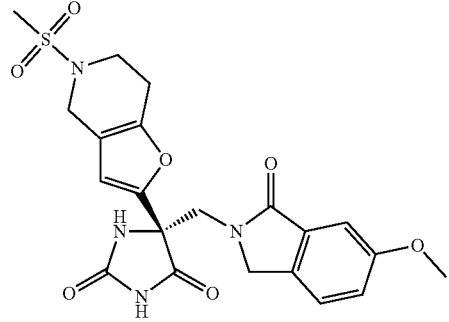 | 474.12 | 475.1 | 0.82 | 497 | |
| 2439 | 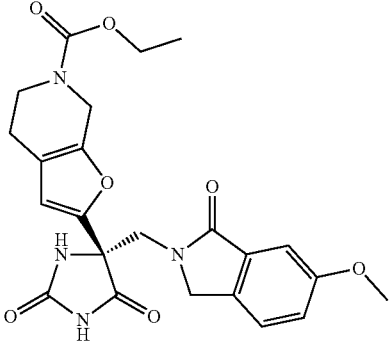 [SMILES: CCOC(=O)N1CCc2cc([C@]3(CN4Cc5ccc(OC)cc5C4=O)NC(=O)NC3=O)oc2C1] | 468.16 | 469.1 | 2.13 | 704 | |
| 2440 | 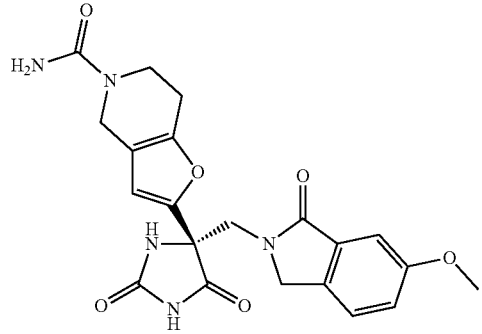 [SMILES: COc1ccc2c(c1)C(=O)N(C[C@@]1(c3cc4c(o3)CCN(C(N)=O)C4)NC(=O)NC1=O)C2] | 439.15 | 440.1 | 5.62 | 646 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2441 | 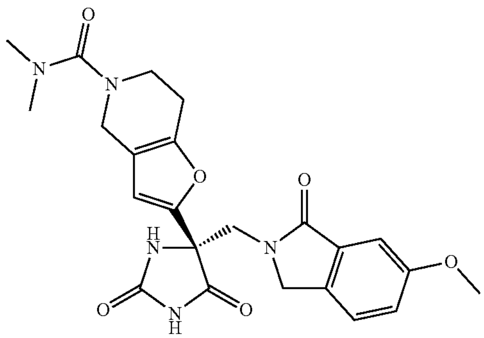 | 467.18 | 468.2 | 1.83 | 501 | |
| 2442 | 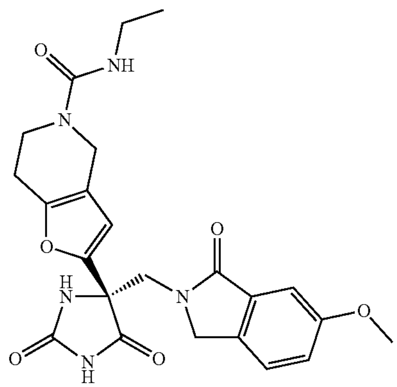 [SMILES: CCNC(=O)N1CCc2oc([C@]3(CN4Cc5ccc(OC)cc5C4=O)NC(=O)NC3=O)cc2C1] | 467.18 | 468.1 | 0.40 | 309 | |
| 2443 | 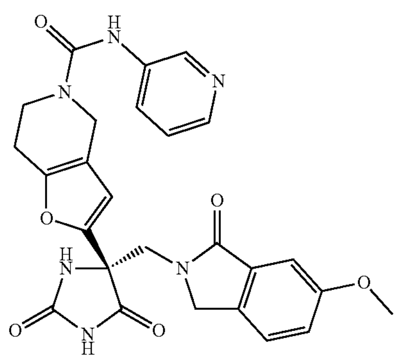 [SMILES: COc1ccc2c(c1)C(=O)N(C[C@@]1(c3cc4c(o3)CCN(C(=O)Nc3cccnc3)C4)NC(=O)NC1=O)C2] | 516.18 | 517.2 | 701 | 1000001 | |
| 2444 | 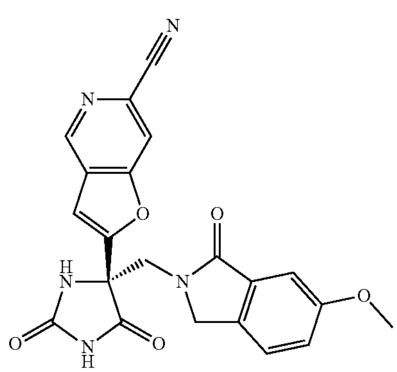 [SMILES: COc1ccc2c(c1)C(=O)N(C[C@@]1(c3cc4cnc(C#N)cc4o3)NC(=O)NC1=O)C2] | 417.11 | 418.1 | 0.67 | 759 | |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 2445 | 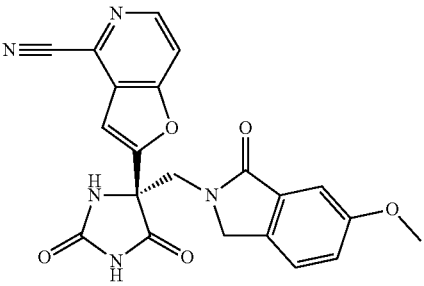 [SMILES: COc1ccc2c(c1)C(=O)N(C[C@@]1(c3cc4c(C#N)nccc4o3)NC(=O)NC1=O)C2] | 417.11 | 418.1 | 0.70 | 1238 | 485 |
| 2446 | 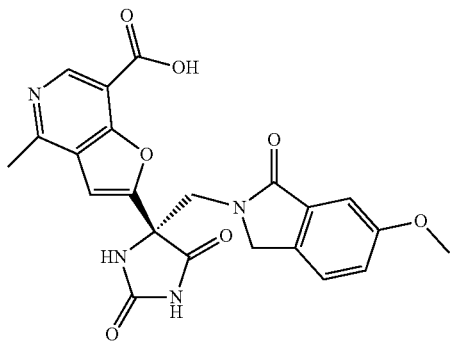 | 450.12 | 451.2 | 2.26 | 1601 | |
| 2447 | 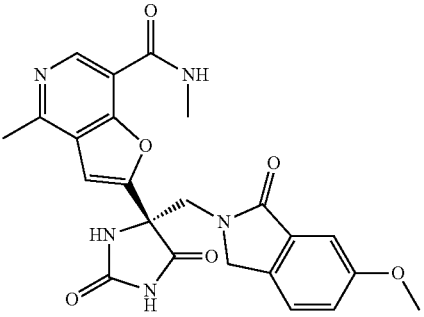 | 463.15 | 464.1 | 0.54 | 554 | 0 |
| 2448 | 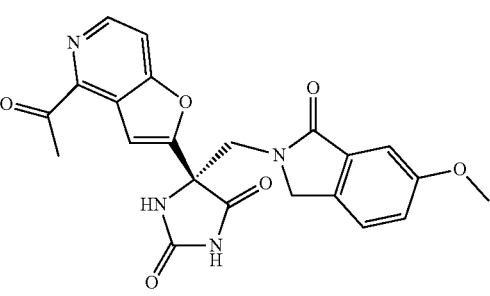 [SMILES: COc1ccc2c(c1)C(=O)N(C[C@@]1(c3cc4c(C(C)=O)nccc4o3)NC(=O)NC1=O)C2] | 434.12 | 435.2 | 0.80 | 839 | |

TABLE A-continued

| ID | STRUCTURE | EXACT MASS | MASS OBSVD | Ki (nM) | hWBA (IC$_{50}$) | RR$^1$ AUC (nM · h) |
|---|---|---|---|---|---|---|
| 2451 | 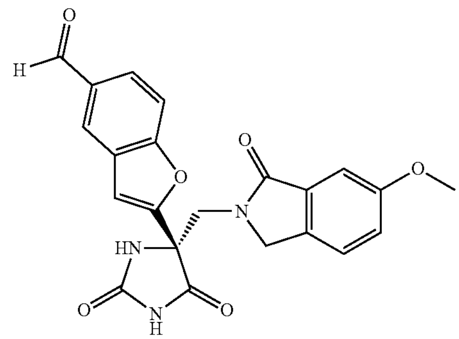 [SMILES: COc1ccc2c(c1)C(=O)N(C[C@@]1(c3cc4cc(C=O)ccc4o3)NC(=O)NC1=O)C2] | 419.1 | 420.2 | 0.41 | 987 | |
| 2452 | 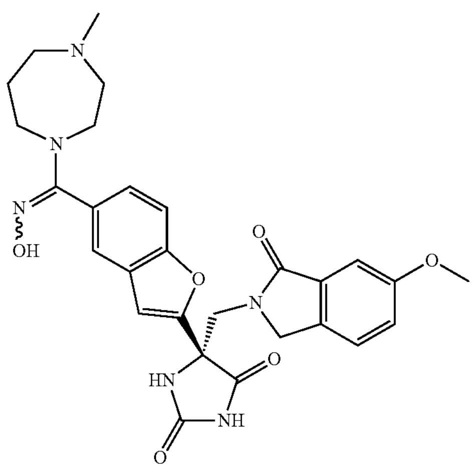 [SMILES: COc1ccc2c(c1)C(=O)N(C[C@@]1(c3cc4cc(C(=NO)N5CCCN(C)CC5)ccc4o3)NC(=O)NC1=O)C2] | 546.2 | 547.3 | 0.67 | 350 | |
| 2453 | 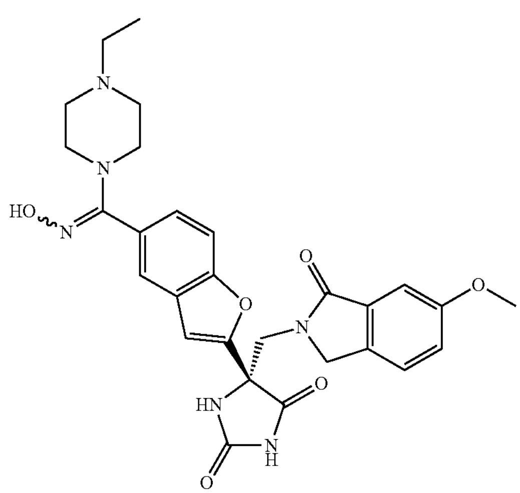 [SMILES: CCN1CCN(C(=NO)c2ccc3oc([C@]4(CN5Cc6ccc(OC)cc6C5=O)NC(=O)NC4=O)cc3c2)CC1] | 546.2 | 547.3 | 0.51 | 393 | 0 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2454 | 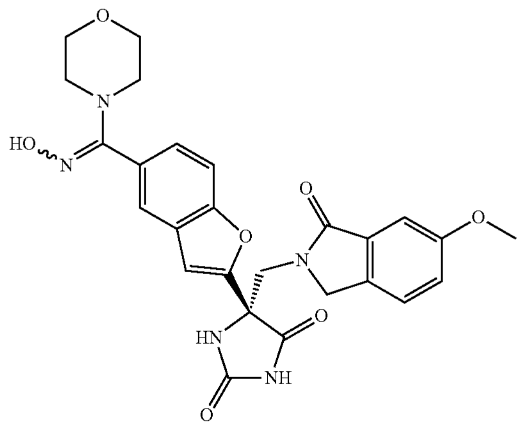 [SMILES: COc1ccc2c(c1)C(=O)N(C[C@@]1(c3cc4cc(C(=NO)N5CCOCC5)ccc4o3)NC(=O)NC1=O)C2] | 519.2 | 520.3 | 0.49 | 760 | |
| 2455 | 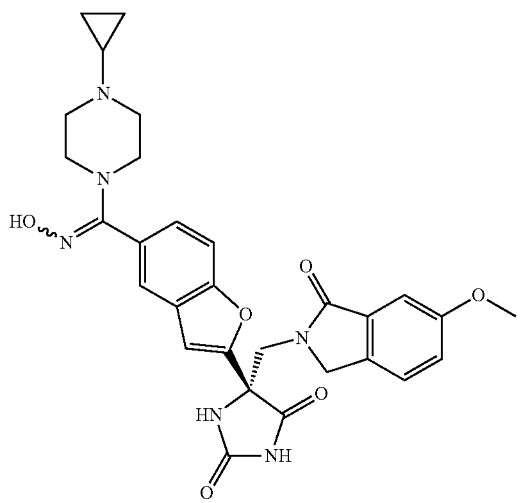 [SMILES: COc1ccc2c(c1)C(=O)N(C[C@@]1(c3cc4cc(C(=NO)N5CCN(C6CC6)CC5)ccc4o3)NC(=O)NC1=O)C2] | 558.2 | 559.3 | 0.58 | 885 | 13 |
| 2456 | 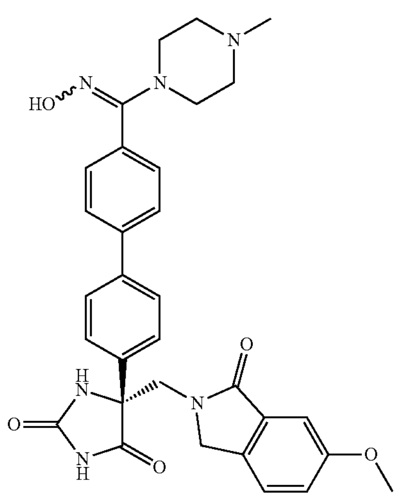 [SMILES: COc1ccc2c(c1)C(=O)N(C[C@@]1(c3ccc(-c4ccc(C(=NO)N5CCN(C)CC5)cc4)cc3)NC(=O)NC1=O)C2] | 568.2 | 569.3 | 0.76 | 1013 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2457 | 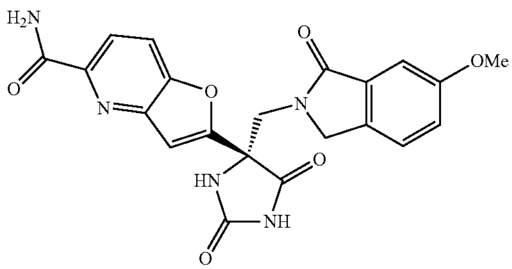 [SMILES: COc1ccc2c(c1)C(=O)N(C[C@@]1(c3cc4nc(C(N)=O)ccc4o3)NC(=O)NC1=O)C2] | 435.38 | 436.2 | 0.55 | 200 | 113 |
| 2458 | 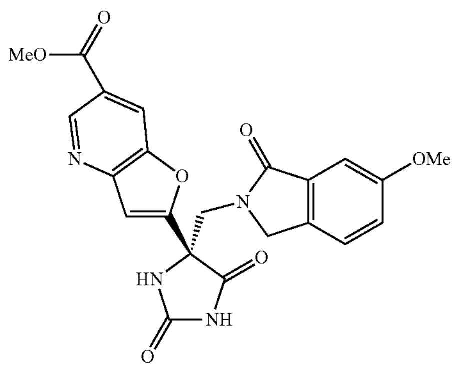 [SMILES: COC(=O)c1cnc2cc([C@]3(CN4Cc5ccc(OC)cc5C4=O)NC(=O)NC3=O)oc2c1] | 450.40 | 451.2 | 0.518 | 840.6 | |
| 2459 | 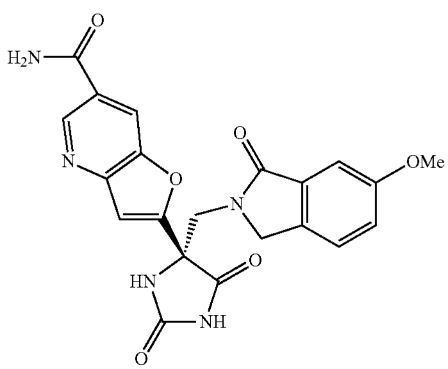 [SMILES: COc1ccc2c(c1)C(=O)N(C[C@@]1(c3cc4ncc(C(N)=O)cc4o3)NC(=O)NC1=O)C2] | 435.38 | 436.2 | 0.367 | 173.2 | |
| 2460 | 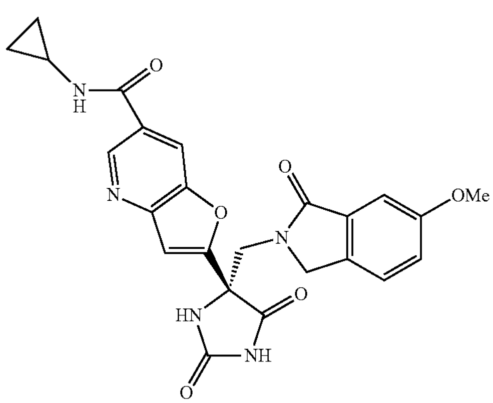 [SMILES: COc1ccc2c(c1)C(=O)N(C[C@@]1(c3cc4ncc(C(=O)NC5CC5)cc4o3)NC(=O)NC1=O)C2] | 475.45 | 476.3 | 0.556 | 321.25 | |

TABLE A-continued

| ID | STRUCTURE | EXACT MASS | MASS OBSVD | Ki (nM) | hWBA (IC$_{50}$) | RR$^1$ AUC (nM · h) |
|---|---|---|---|---|---|---|
| 2461 | 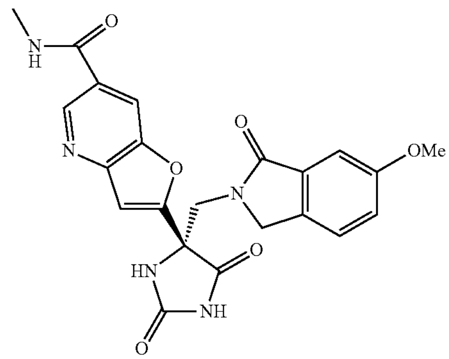 [SMILES: CNC(=O)c1cnc2cc([C@]3(CN4Cc5ccc(OC)cc5C4=O)NC(=O)NC3=O)oc2c1] | 449.41 | 450.2 | 0.871 | 350.65 | 0 |
| 2462 | 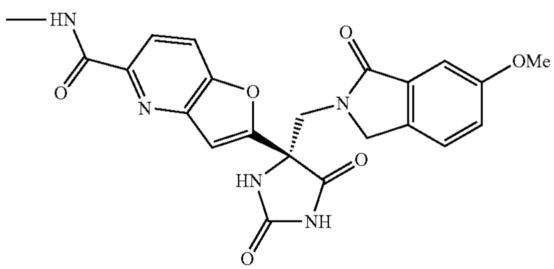 [SMILES: CNC(=O)c1ccc2oc([C@]3(CN4Cc5ccc(OC)cc5C4=O)NC(=O)NC3=O)cc2n1] | 449.41 | 450.2 | 0.859 | 279.8 | 1070 |
| 2463 | 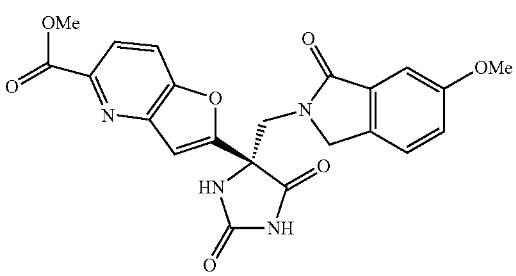 [SMILES: COC(=O)c1ccc2oc([C@]3(CN4Cc5ccc(OC)cc5C4=O)NC(=O)NC3=O)cc2n1] | 450.40 | 451.2 | 0.13 | 338.75 | |
| 2464 | 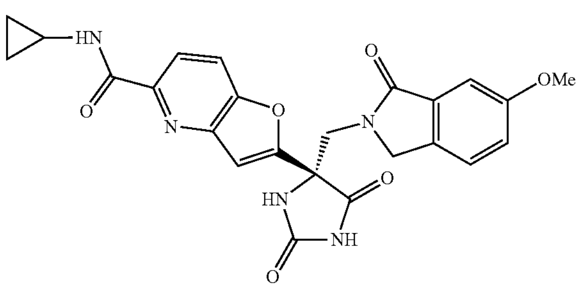 [SMILES: COc1ccc2c(c1)C(=O)N(C[C@@]1(c3cc4nc(C(=O)NC5CC5)ccc4o3)NC(=O)NC1=O)C2] | 475.45 | 476.3 | 0.115 | 366.9 | |
| 2465 | 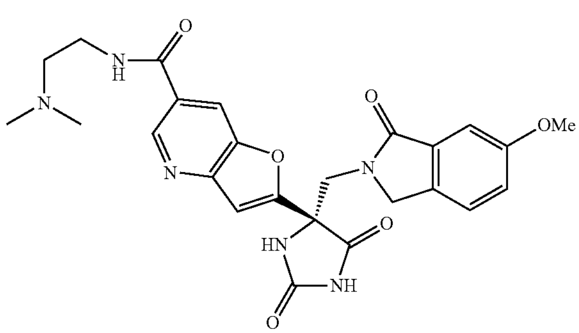 [SMILES: COc1ccc2c(c1)C(=O)N(C[C@@]1(c3cc4ncc(C(=O)NCCN(C)C)cc4o3)NC(=O)NC1=O)C2] | 506.51 | 507.3 | | 800 | 0 |

TABLE A-continued
| ID | STRUCTURE | EXACT MASS | MASS OBSVD | Ki (nM) | hWBA (IC$_{50}$) | RR[1] AUC (nM·h) |
|---|---|---|---|---|---|---|
| 2466 | 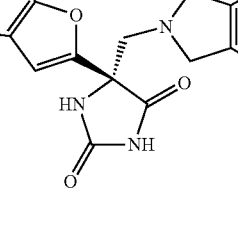 | 506.51 | | 0.867 | 566.9 | 0 |
| 2467 | 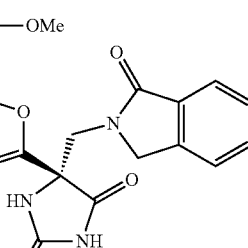 | 493.16 | 494.3 | 0.72 | 657 | |
| 2468 | 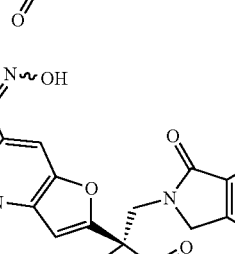 | 547.56 | 548.3 | 1.44 | 342 | |
| 2469 | 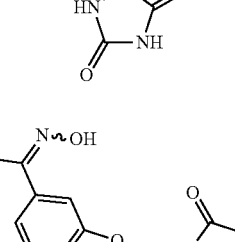 | 597.58 | 598.3 | 0.59 | 546 | |
| 2470 | 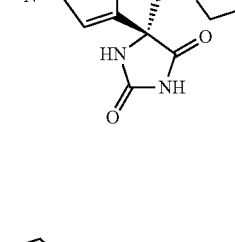 | 493.47 | 494.3 | 0.578 | 802.7 | 22065 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2471 | 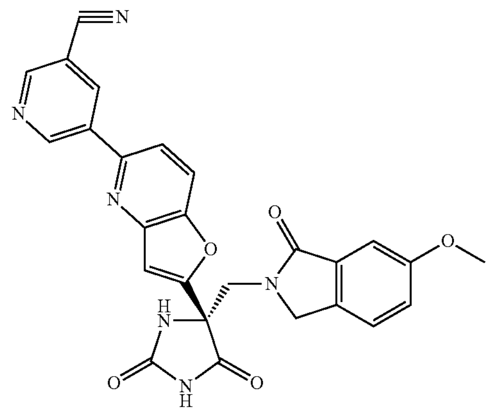 [SMILES: COc1ccc2c(c1)C(=O)N(C[C@@]1(c3cc4nc(-c5cncc(C#N)c5)ccc4o3)NC(=O)NC1=O)C2] | 494.45 | | 0.779 | 3658 | |
| 2472 | 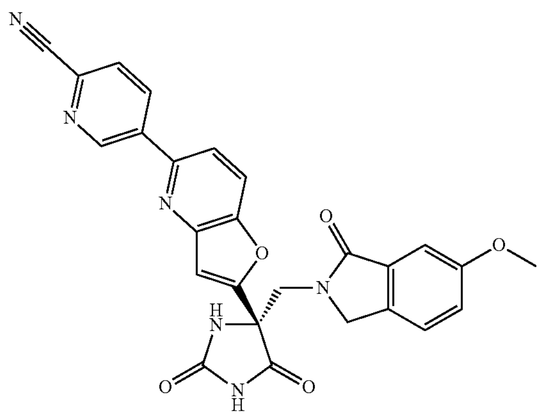 [SMILES: COc1ccc2c(c1)C(=O)N(C[C@@]1(c3cc4nc(-c5ccc(C#N)nc5)ccc4o3)NC(=O)NC1=O)C2] | 494.45 | 495.3 | 0.745 | 1612 | 536 |
| 2473 | 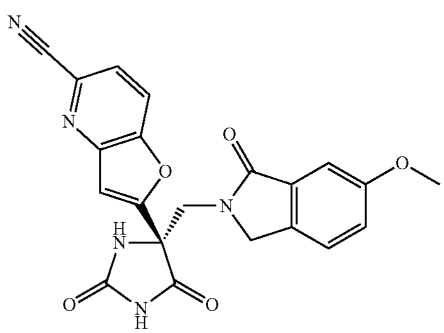 [SMILES: COc1ccc2c(c1)C(=O)N(C[C@@]1(c3cc4nc(C#N)ccc4o3)NC(=O)NC1=O)C2] | 417.4 | 418.2 | 0.32 | 564 | 5688 |
| 2474 | 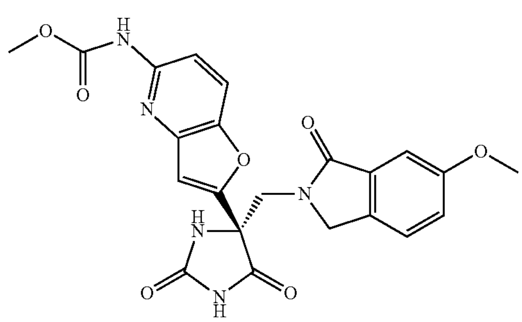 | 465.4 | 466.3 | 0.52 | 549 | 15484 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2476 | 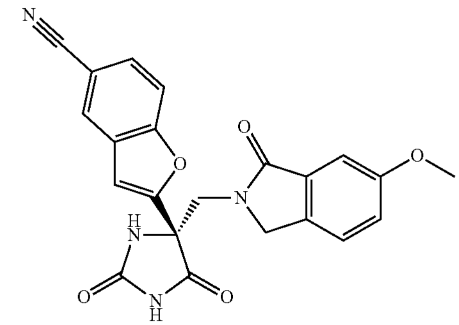 [SMILES: COc1ccc2c(c1)C(=O)N(C[C@@]1(c3cc4cc(C#N)ccc4o3)NC(=O)NC1=O)C2] | 416.11 | 417.2 | 0.37 | 848 | |
| 2477 | 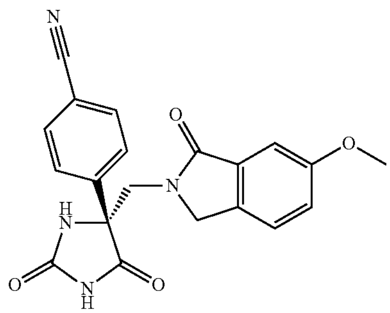 [SMILES: COc1ccc2c(c1)C(=O)N(C[C@@]1(c3ccc(C#N)cc3)NC(=O)NC1=O)C2] | 376.12 | 377.2 | 1.41 | 3484 | |
| 2478 | 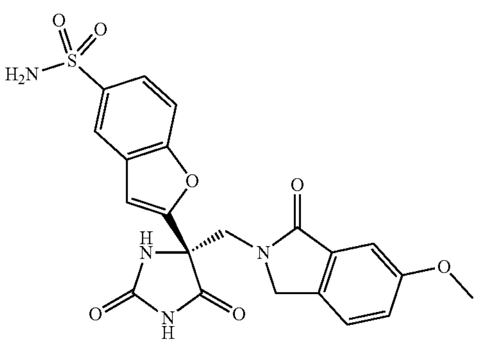 [SMILES: COc1ccc2c(c1)C(=O)N(C[C@@]1(c3cc4cc(S(N)(=O)=O)ccc4o3)NC(=O)NC1=O)C2] | 470.09 | 471.1 | 0.35 | 600 | |
| 2479 | 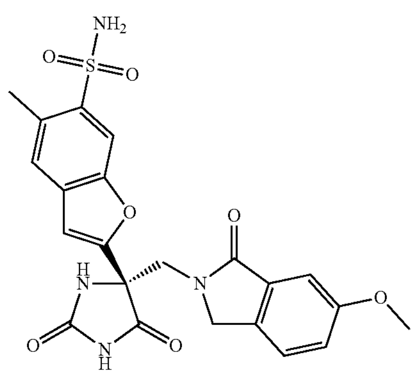 | 484.11 | 485.2 | 0.36 | 2077 | 0 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2480 | 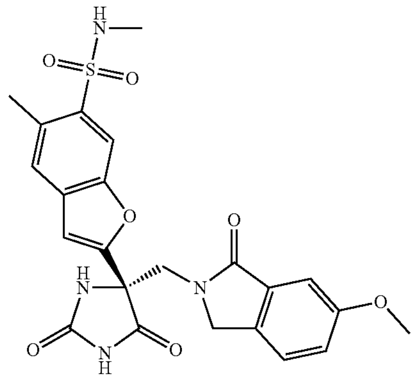 | 498.12 | 499.1 | 0.43 | 1392 | 212 |
| 2481 | 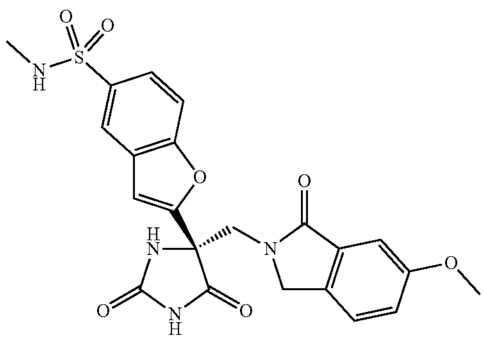 | 484.11 | 485.2 | 0.16 | 310 | 890 |
| 2482 | 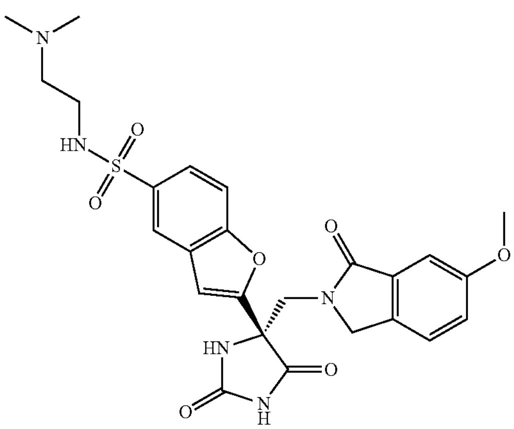 | 541.16 | 542.2 | 0.67 | 304 | 0 |
| 2483 | 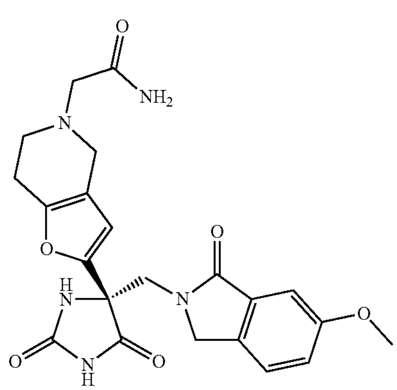 [SMILES: COc1ccc2c(c1)C(=O)N(C[C@@]1(c3cc4c(o3)CCN(CC(N)=O)C4)NC(=O)NC1=O)C2] | 453.16 | 454.1 | 0.70 | 252 | |

695
696
TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 2484 | 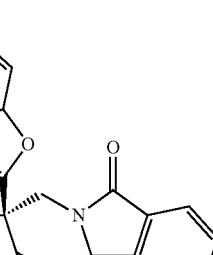 | 492.16 | 493.1 | 0.49 | 1691 | |
| 2485 | 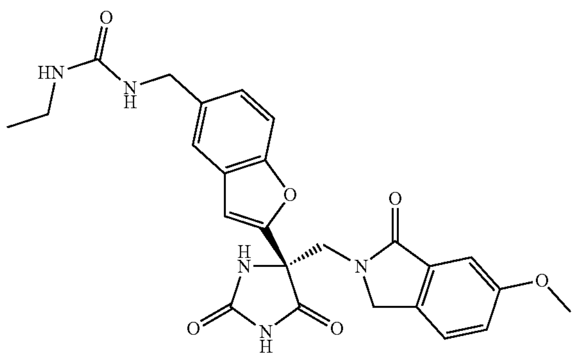 [SMILES: CCNC(=O)NCc1ccc2oc([C@]3(CN4Cc5ccc(OC)cc5C4=O)NC(=O)NC3=O)cc2c1] | 491.18 | 492.3 | 0.76 | 1989 | |
| 2486 | 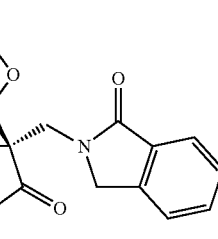 | 491.18 | 492.1 | 0.49 | 1226 | |
| 2488 | 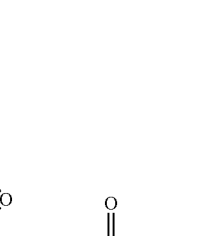 | 546.2 | 547.3 | 0.80 | 321 | |

TABLE A-continued
| ID | STRUCTURE | EXACT MASS | MASS OBSVD | Ki (nM) | hWBA (IC$_{50}$) | RR[1] AUC (nM · h) |
|---|---|---|---|---|---|---|
| 2489 | 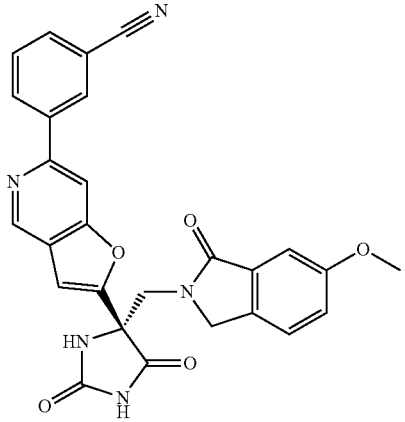 [SMILES: COc1ccc2c(c1)C(=O)N(C[C@@]1(c3cc4cnc(-c5cccc(C#N)c5)cc4o3)NC(=O)NC1=O)C2] | 493.14 | 494.2 | 0.799 | 8425 | 10648 |
| 2490 | 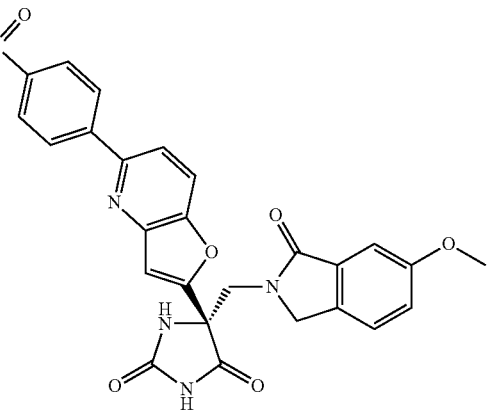 | 547.53 | 548.3 | | 2687 | |
| 2491 | 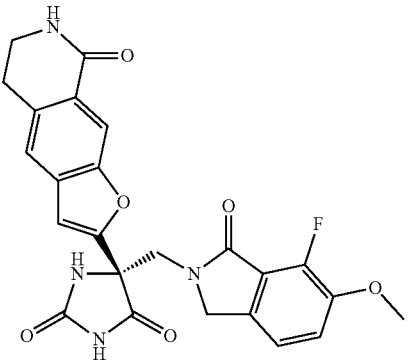 [SMILES: COc1ccc2c(c1F)C(=O)N(C[C@@]1(c3cc4cc5c(cc4o3)C(=O)NCC5)NC(=O)NC1=O)C2] | 478.1 | 479.3 | 0.195 | 108.75 | 972 |
| 2492 | 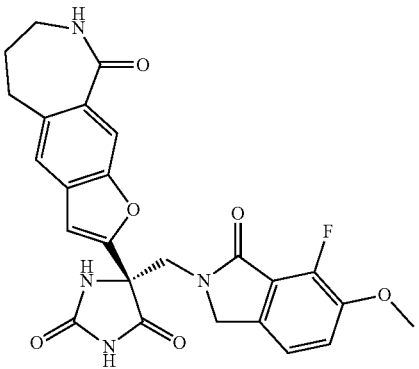 [SMILES: COc1ccc2c(c1F)C(=O)N(C[C@@]1(c3cc4cc5c(cc4o3)C(=O)NCCC5)NC(=O)NC1=O)C2] | 492.1 | 493.3 | | 321.7 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2493 | 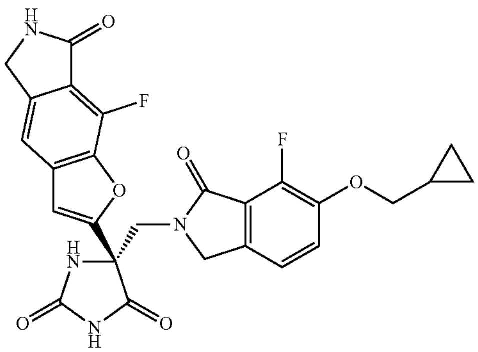 [SMILES: O=C1NC(=O)[C@](CN2Cc3ccc(OCC4CC4)c(F)c3C2=O)(c2cc3cc4c(c(F)c3o2)C(=O)NC4)N1] | 522.1 | 523.3 | 0.49 | 349.25 | |
| 2494 | 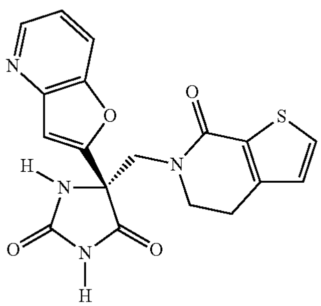 [SMILES: O=C1NC(=O)[C@](CN2CCc3ccsc3C2=O)(c2cc3ncccc3o2)N1] | 382.07 | 383.2 | 1.25 | 2248 | |
| 2495 | 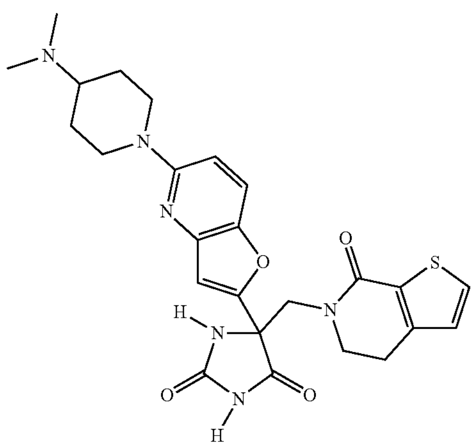 [SMILES: CN(C)C1CCN(c2ccc3oc(C4(CN5CCc6ccsc6C5=O)NC(=O)NC4=O)cc3n2)CC1] | 508.19 | 509.3 | 0.71 | 650 | |
| 2496 | 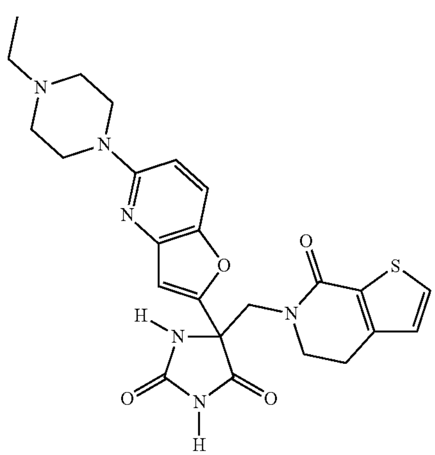 [SMILES: CCN1CCN(c2ccc3oc(C4(CN5CCc6ccsc6C5=O)NC(=O)NC4=O)cc3n2)CC1] | 494.17 | 495.3 | 0.66 | 314 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2497 | 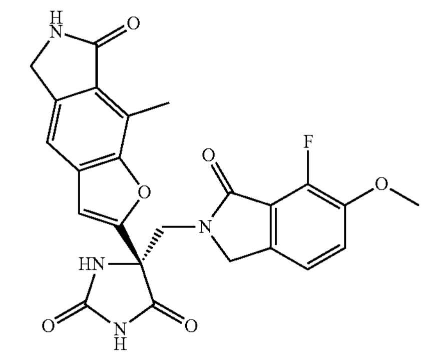 [SMILES: COc1ccc2c(c1F)C(=O)N(C[C@@]1(c3cc4cc5c(c(C)c4o3)C(=O)NC5)NC(=O)NC1=O)C2] | 478.13 | 479.3 | 0.29 | 673 | 1053 |
| 2498 | 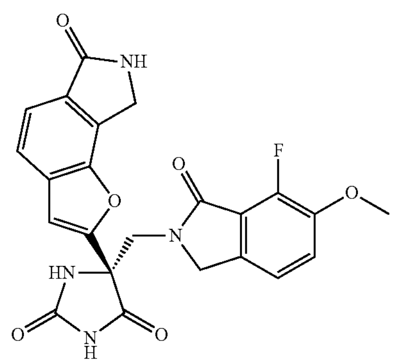 [SMILES: COc1ccc2c(c1F)C(=O)N(C[C@@]1(c3cc4ccc5c(c4o3)CNC5=O)NC(=O)NC1=O)C2] | 464.11 | 465.3 | 1.21 | 166 | 0 |
| 2499 | 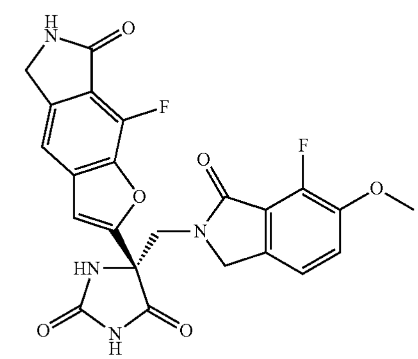 [SMILES: COc1ccc2c(c1F)C(=O)N(C[C@@]1(c3cc4cc5c(c(F)c4o3)C(=O)NC5)NC(=O)NC1=O)C2] | 482.10 | 483.3 | 0.33 | 72 | 1085 |
| 2500 | 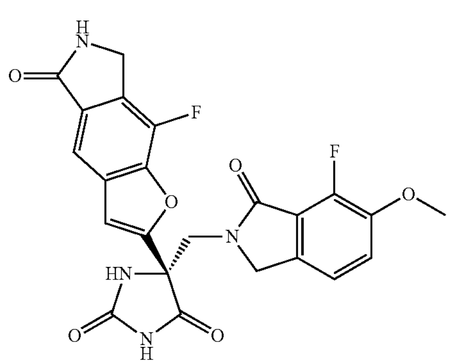 [SMILES: COc1ccc2c(c1F)C(=O)N(C[C@@]1(c3cc4cc5c(c(F)c4o3)CNC5=O)NC(=O)NC1=O)C2] | 482.10 | 483.3 | 0.52 | 282 | |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2501 | 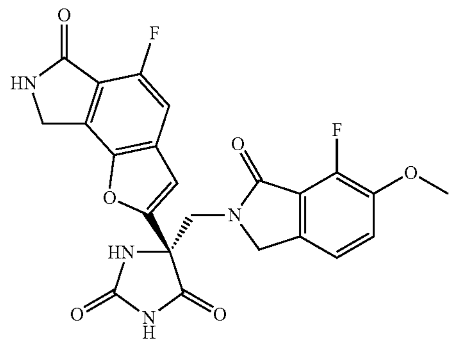 [SMILES: COc1ccc2c(c1F)C(=O)N(C[C@@]1(c3cc4cc(F)c5c(c4o3)CNC5=O)NC(=O)NC1=O)C2] | 482.10 | 483.3 | 0.86 | 148 | 448 |
| 2502 | 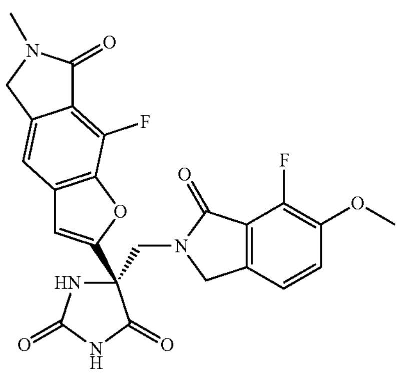 [SMILES: COc1ccc2c(c1F)C(=O)N(C[C@@]1(c3cc4cc5c(c(F)c4o3)C(=O)N(C)C5)NC(=O)NC1=O)C2] | 496.12 | 497.3 | 0.69 | 381 | 3117 |
| 2503 | 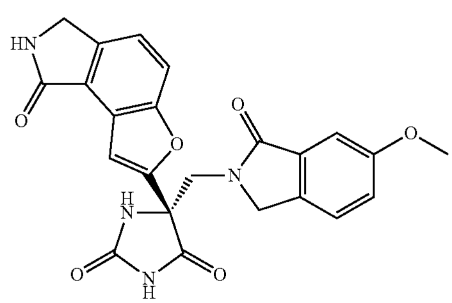 [SMILES: COc1ccc2c(c1)C(=O)N(C[C@@]1(c3cc4c5c(ccc4o3)CNC5=O)NC(=O)NC1=O)C2] | 446.12 | 447.2 | 0.36 | 170 | 304 |
| 2504 | 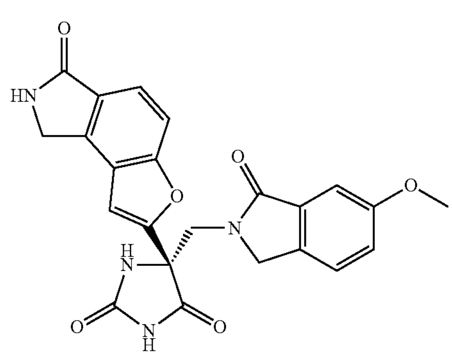 [SMILES: COc1ccc2c(c1)C(=O)N(C[C@@]1(c3cc4c5c(ccc4o3)C(=O)NC5)NC(=O)NC1=O)C2] | 446.12 | 447.2 | 0.45 | 189 | 181 |

TABLE A-continued

| ID | STRUCTURE | EXACT MASS | MASS OBSVD | Ki (nM) | hWBA (IC$_{50}$) | RR[1] AUC (nM · h) |
|---|---|---|---|---|---|---|
| 2505 | 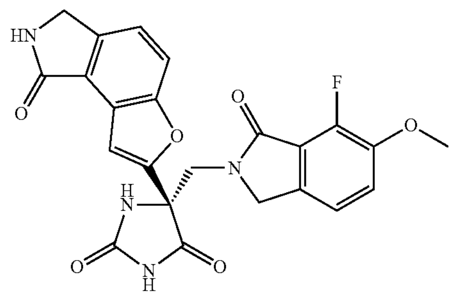 [SMILES: COc1ccc2c(c1F)C(=O)N(C[C@@]1(c3cc4c5c(ccc4o3)CNC5=O)NC(=O)NC1=O)C2] | 464.11 | 465.3 | 0.60 | 151 | 1122 |
| 2506 | 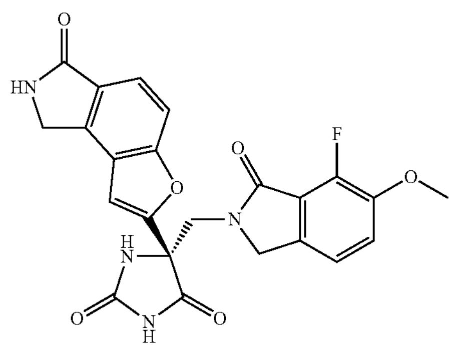 [SMILES: COc1ccc2c(c1F)C(=O)N(C[C@@]1(c3cc4c5c(ccc4o3)C(=O)NC5)NC(=O)NC1=O)C2] | 464.11 | 465.3 | 0.323 | 155.8 | 437 |
| 2507 | 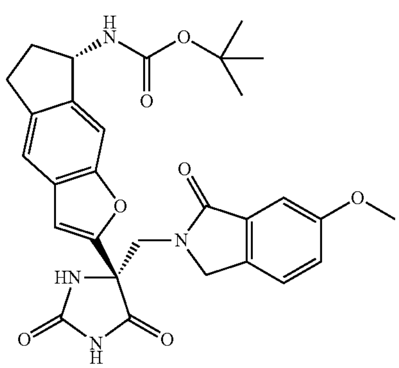 [SMILES: COc1ccc2c(c1)C(=O)N(C[C@@]1(c3cc4cc5c(cc4o3)[C@@H](NC(=O)OC(C)(C)C)CC5)NC(=O)NC1=O)C2] | 546.2 | 547.3 | 1.43 | 4164 | |
| 2508 | 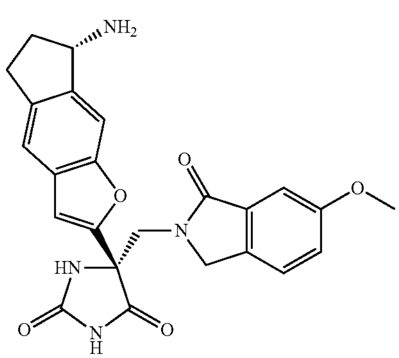 [SMILES: COc1ccc2c(c1)C(=O)N(C[C@@]1(c3cc4cc5c(cc4o3)[C@@H](N)CC5)NC(=O)NC1=O)C2] | 446.2 | 447.2 | 0.52 | 1016 | |

[1] rapid rat AUC (rrAUC) nM · h of the drug.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.
Each document referred to herein is incorporated by reference in its entirety for all purposes.
We claim:
1. A compound selected from the group consisting of:
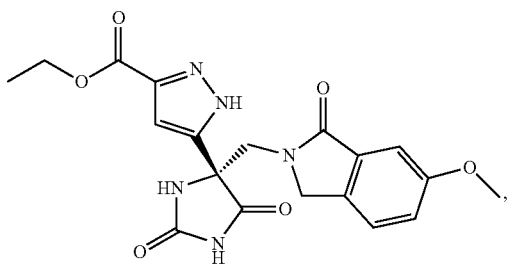
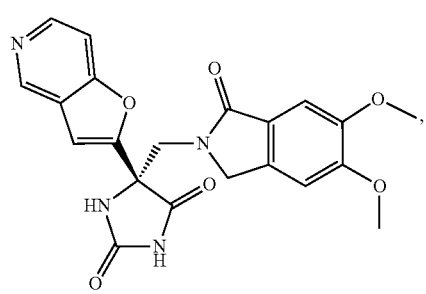
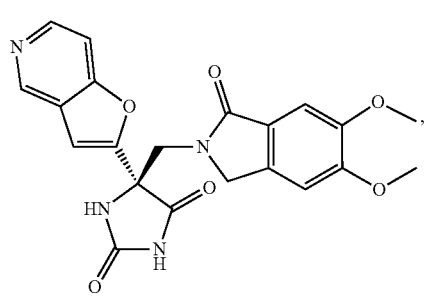
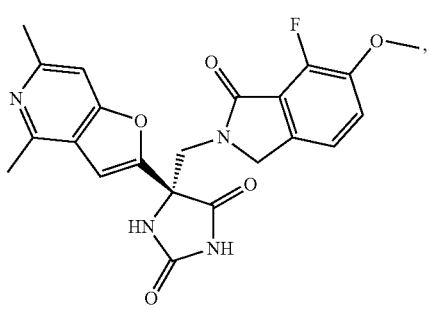
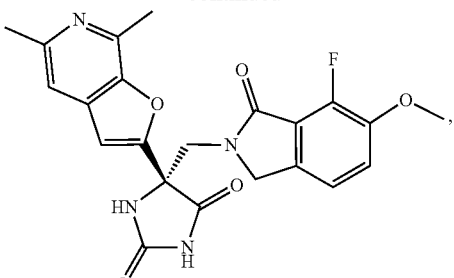
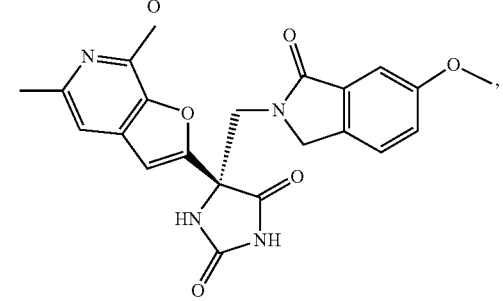
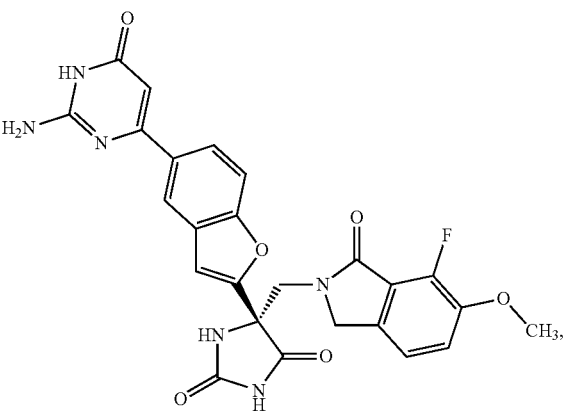
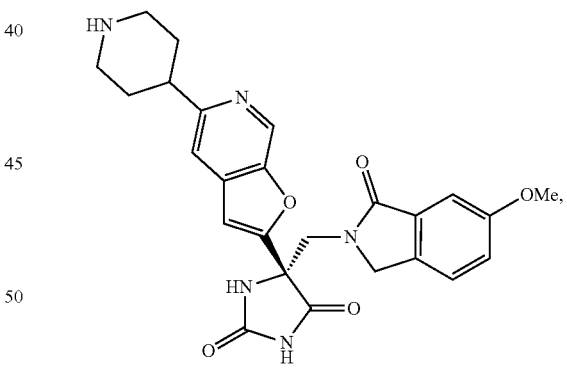
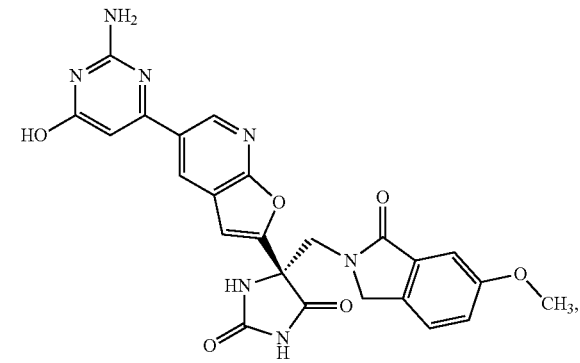

709
-continued
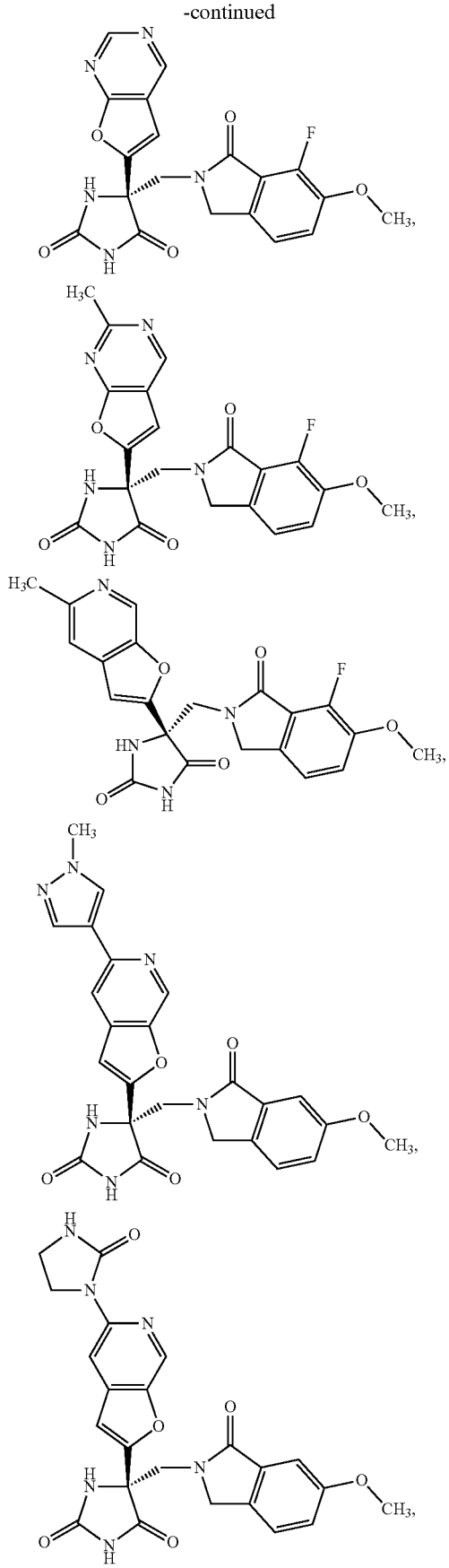
710
-continued
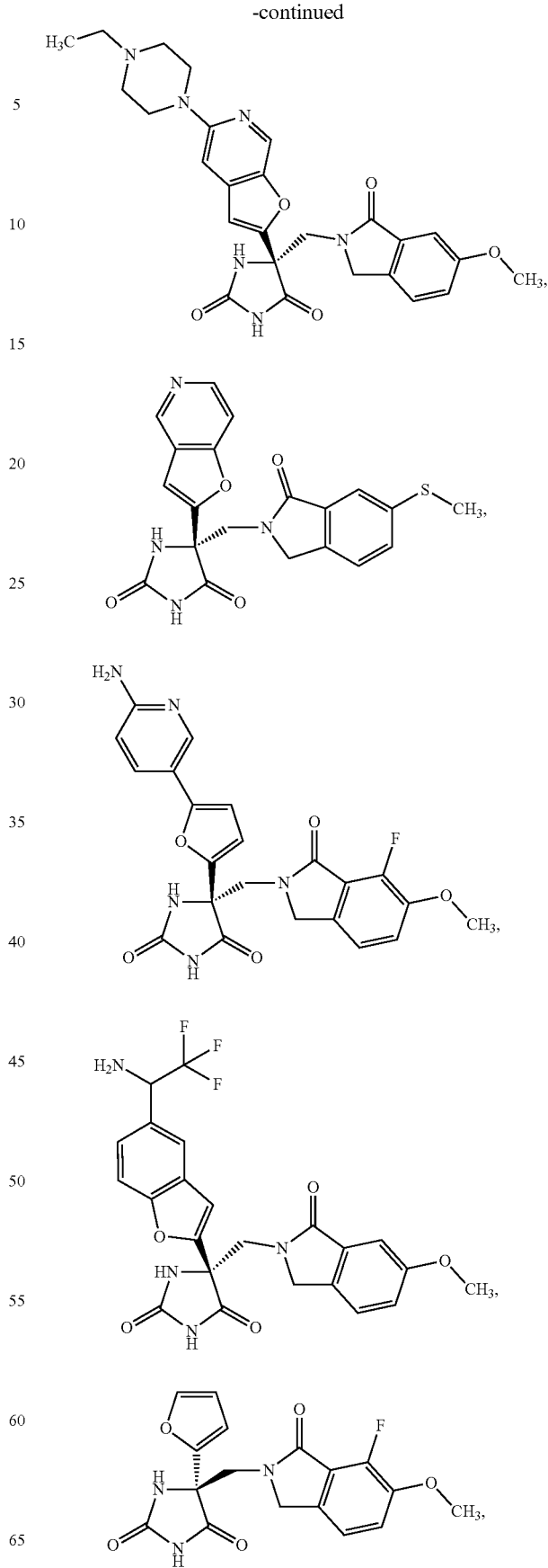

711
-continued
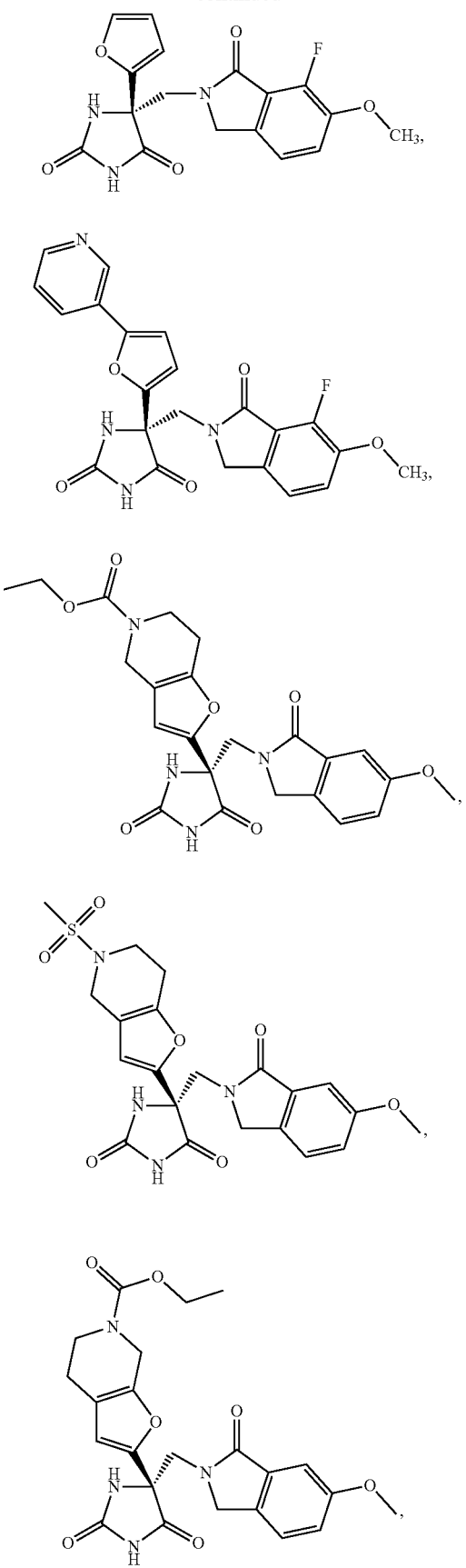
712
-continued
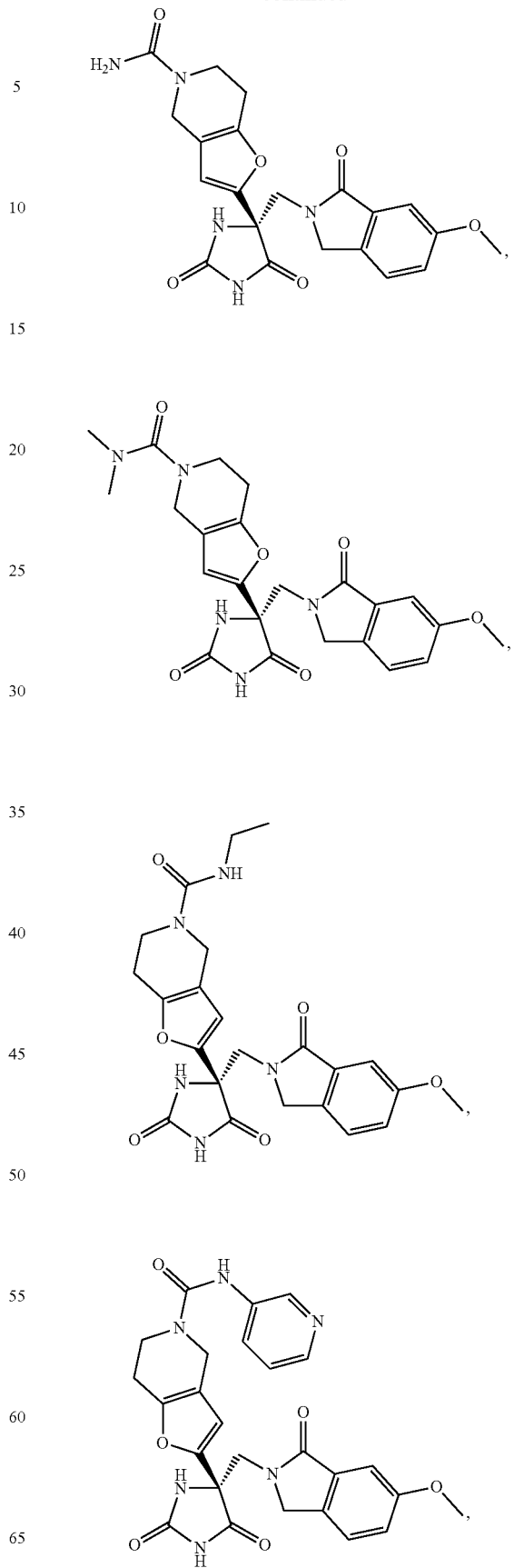

713
-continued
714
-continued
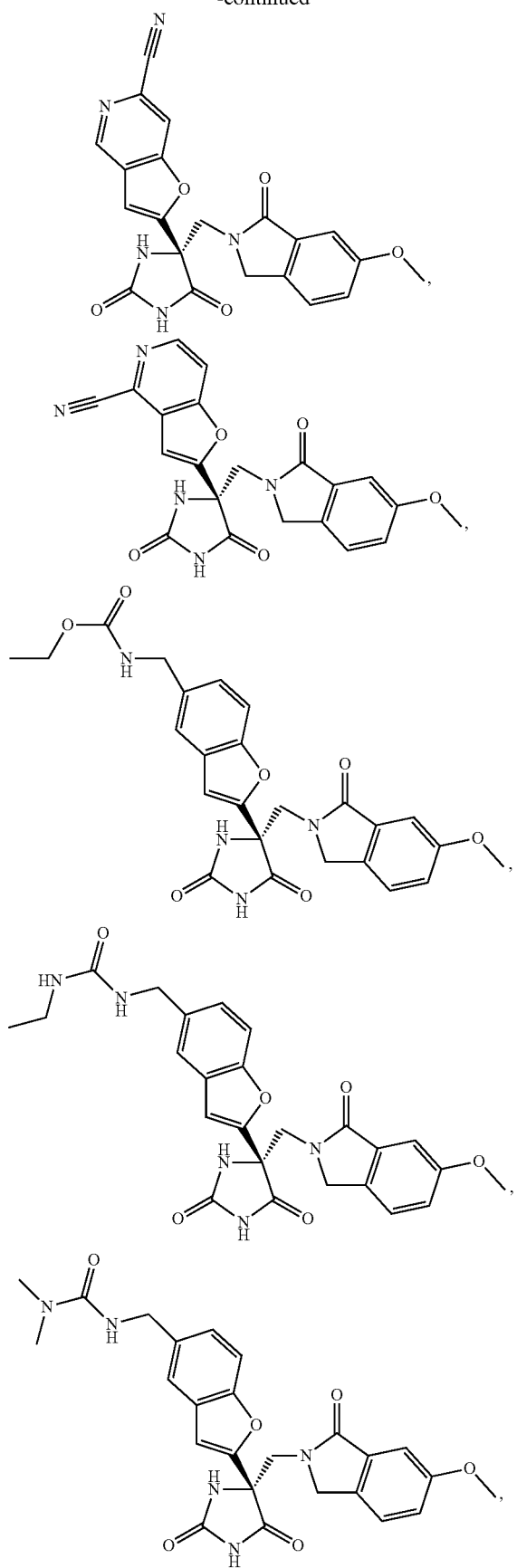
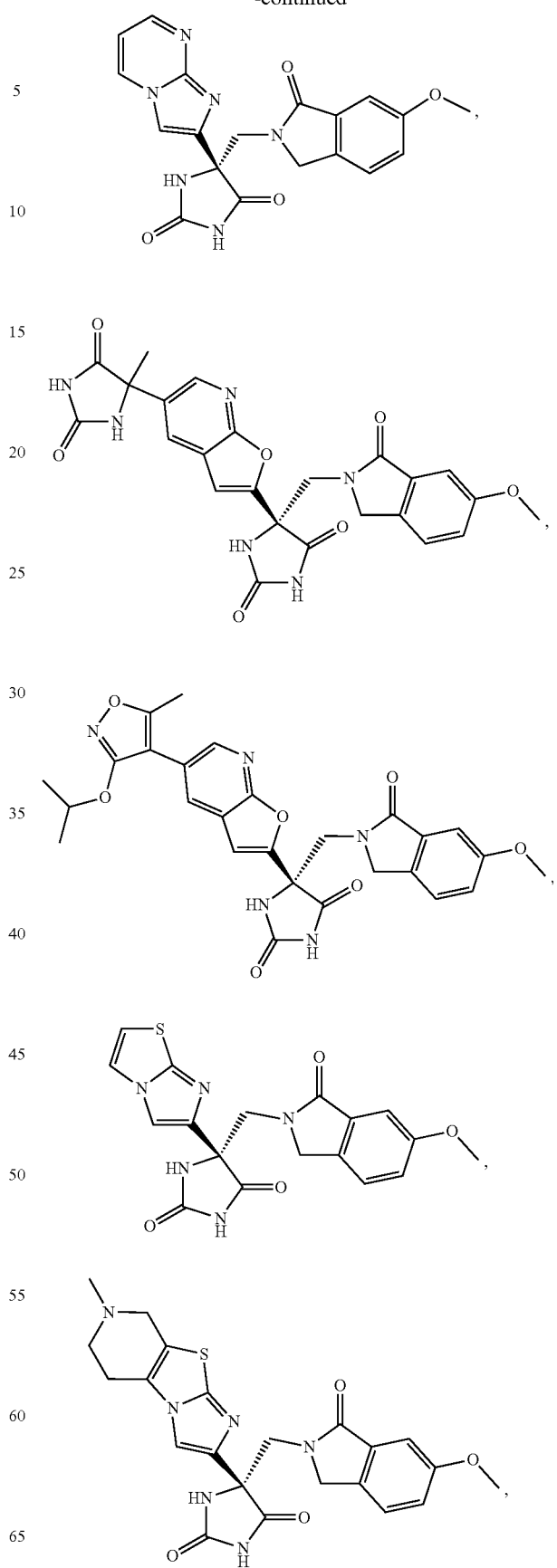

715
-continued
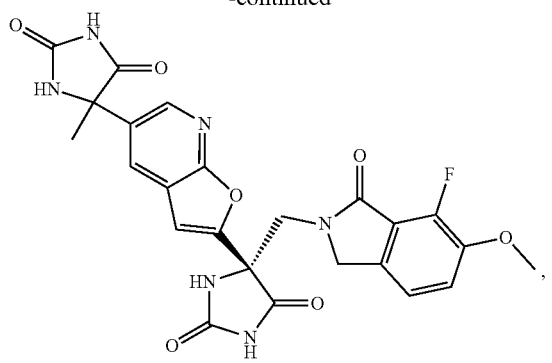
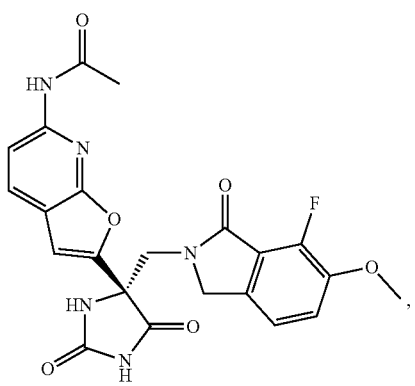
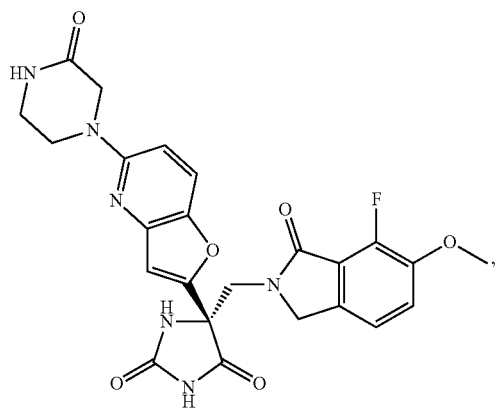
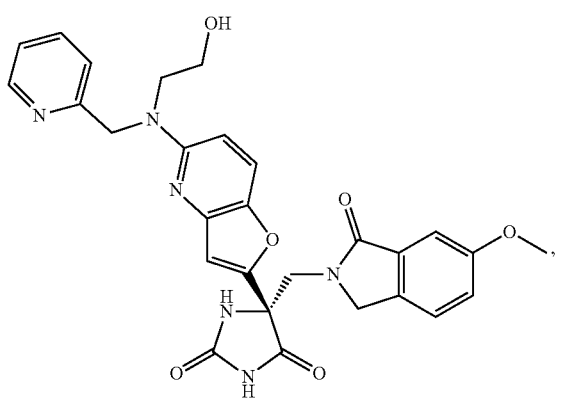
716
-continued
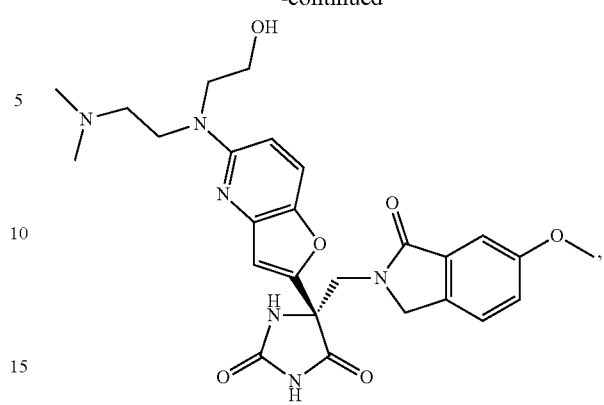
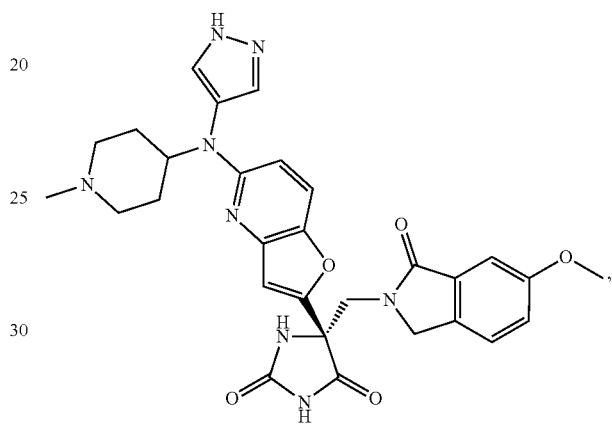
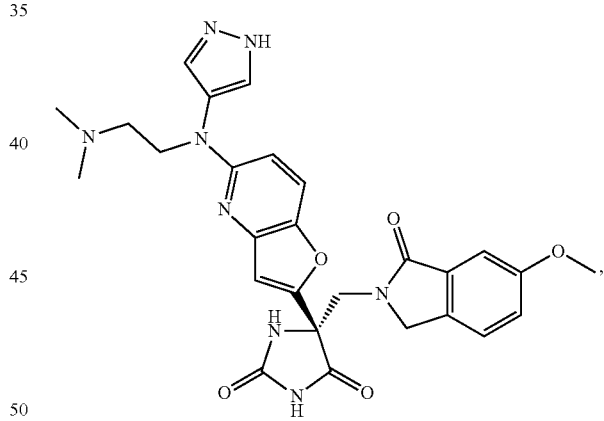
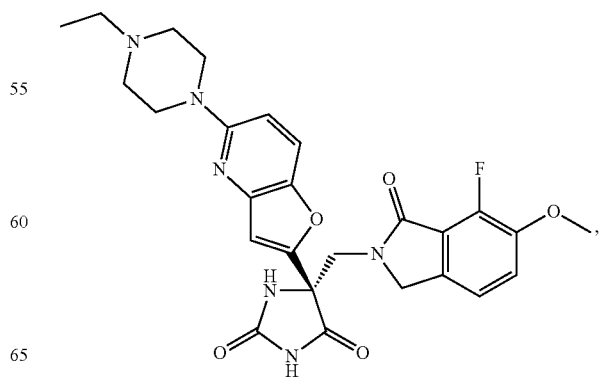

717
-continued
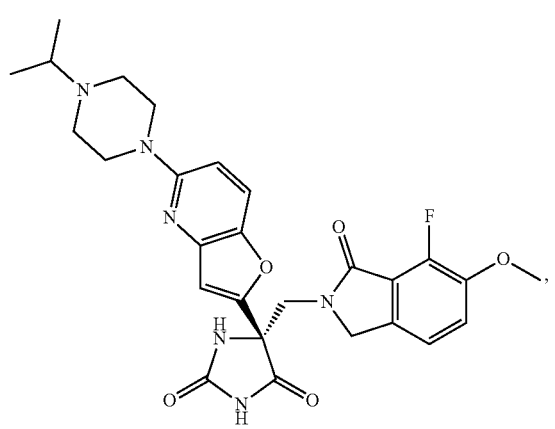
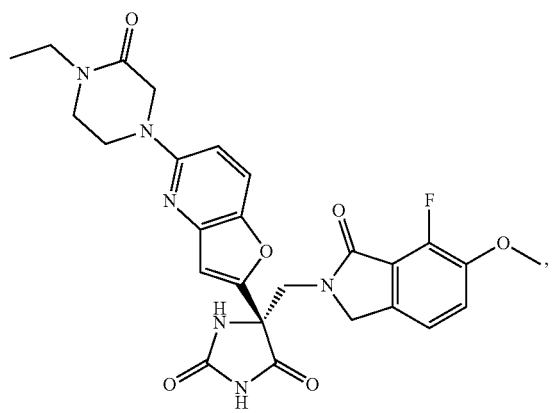
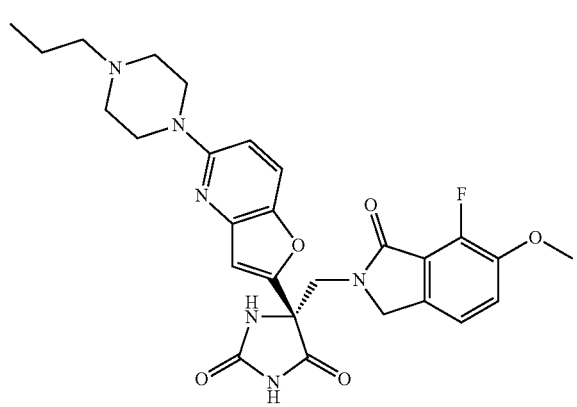
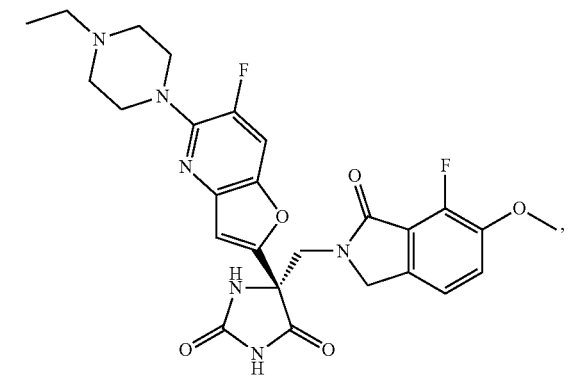
718
-continued
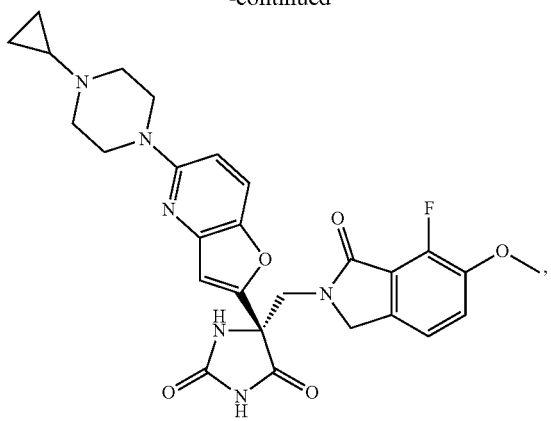
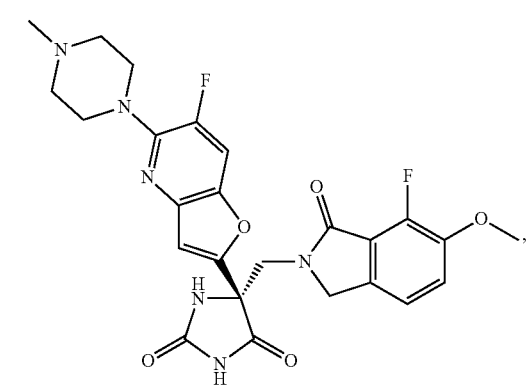
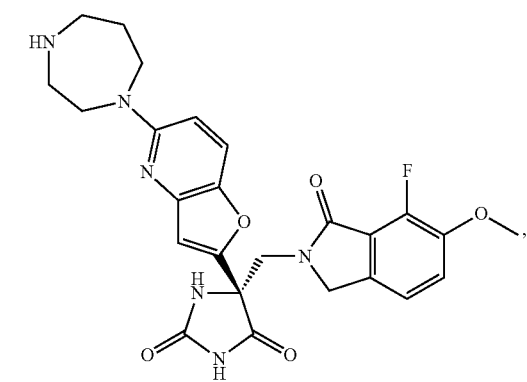
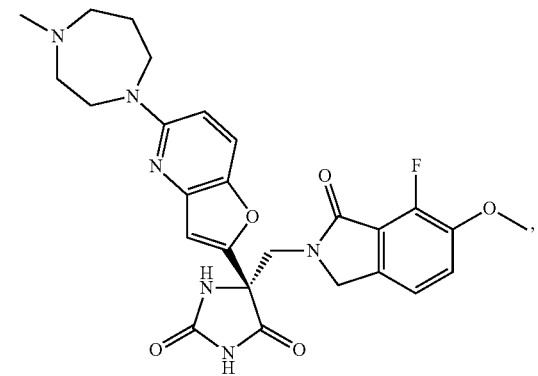

719
-continued
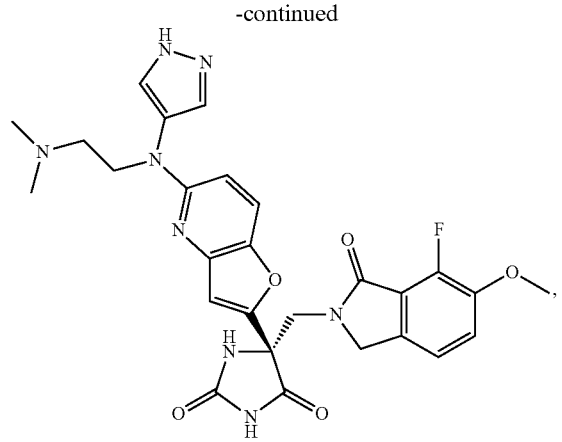
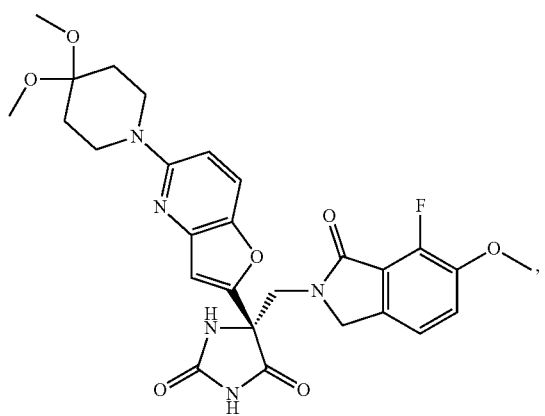
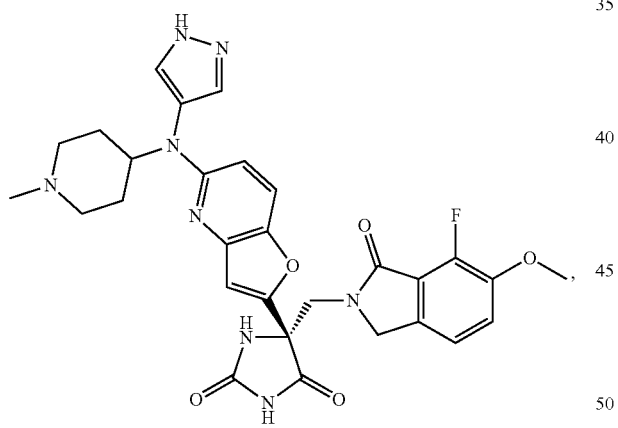
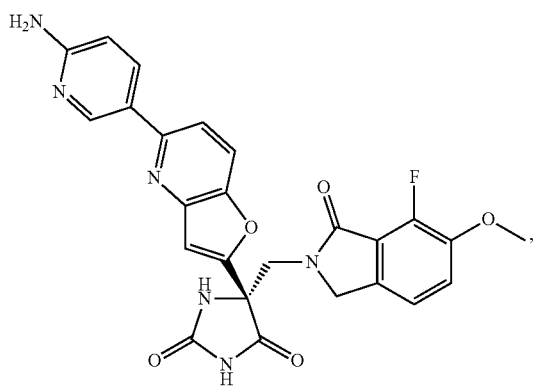
720
-continued
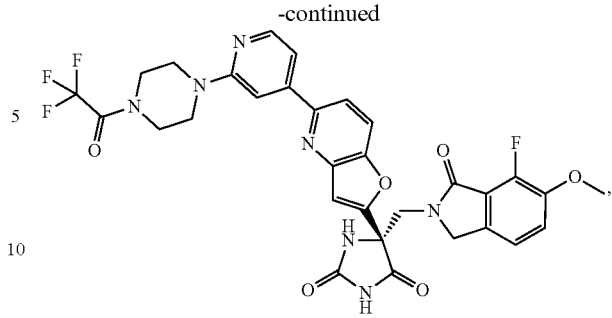
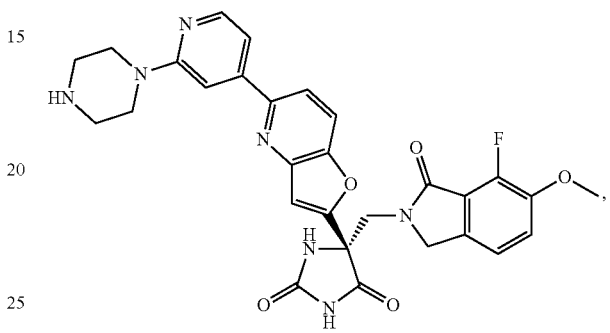
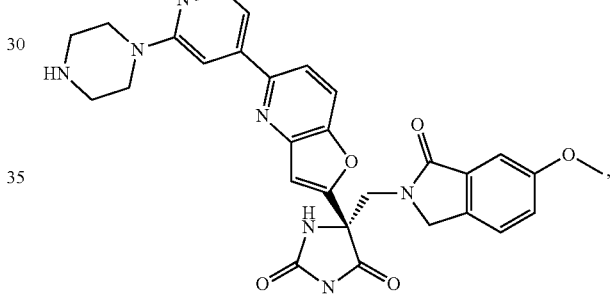
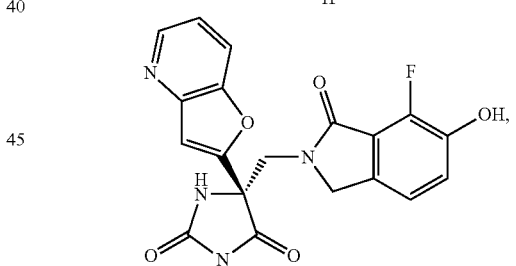
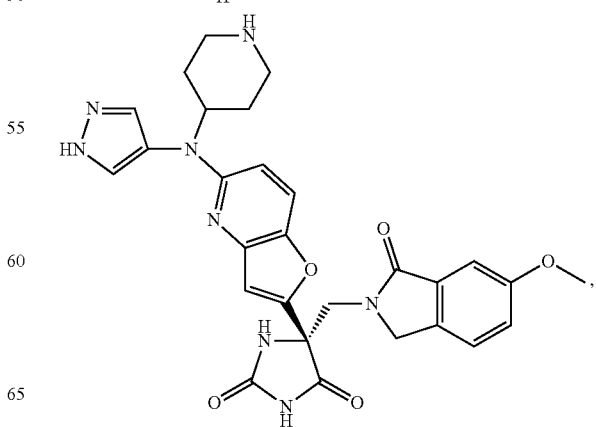

721
-continued
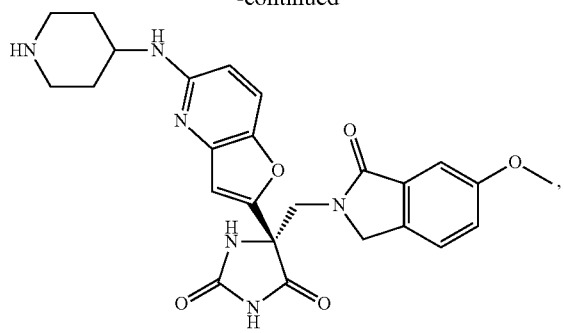
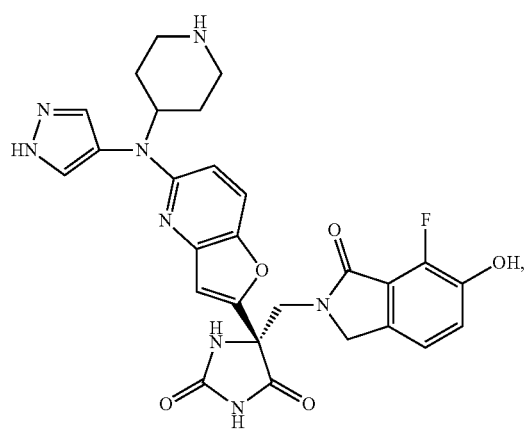
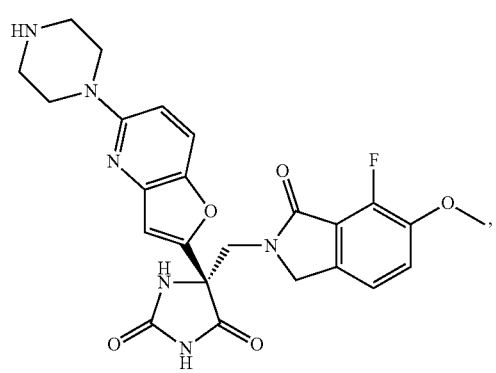
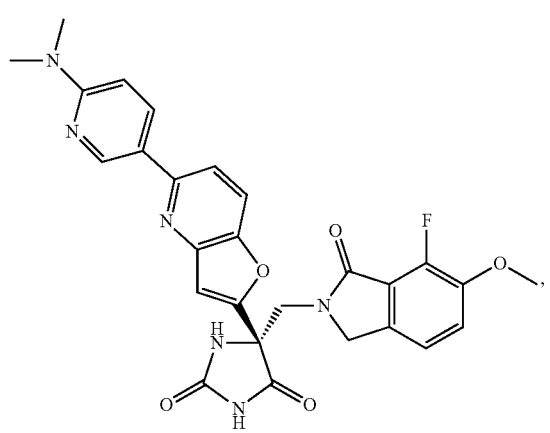
722
-continued
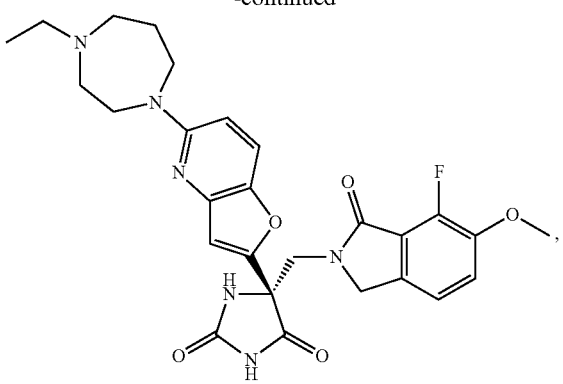
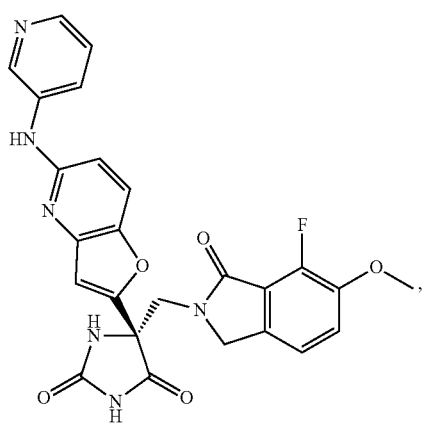
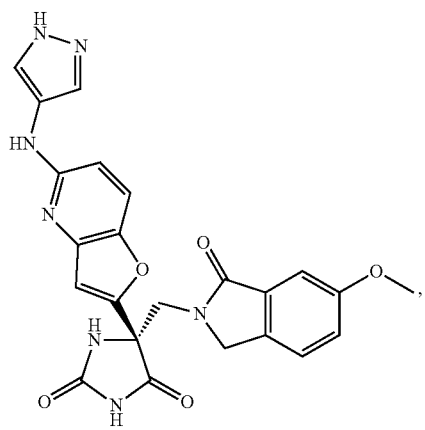
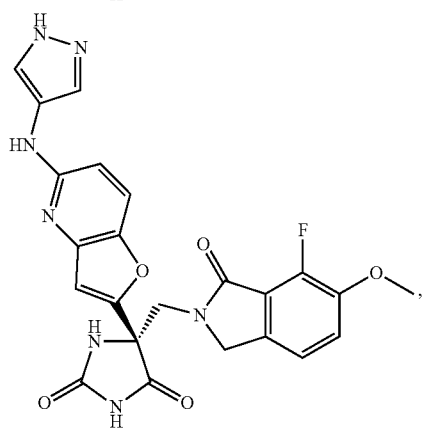

723
-continued
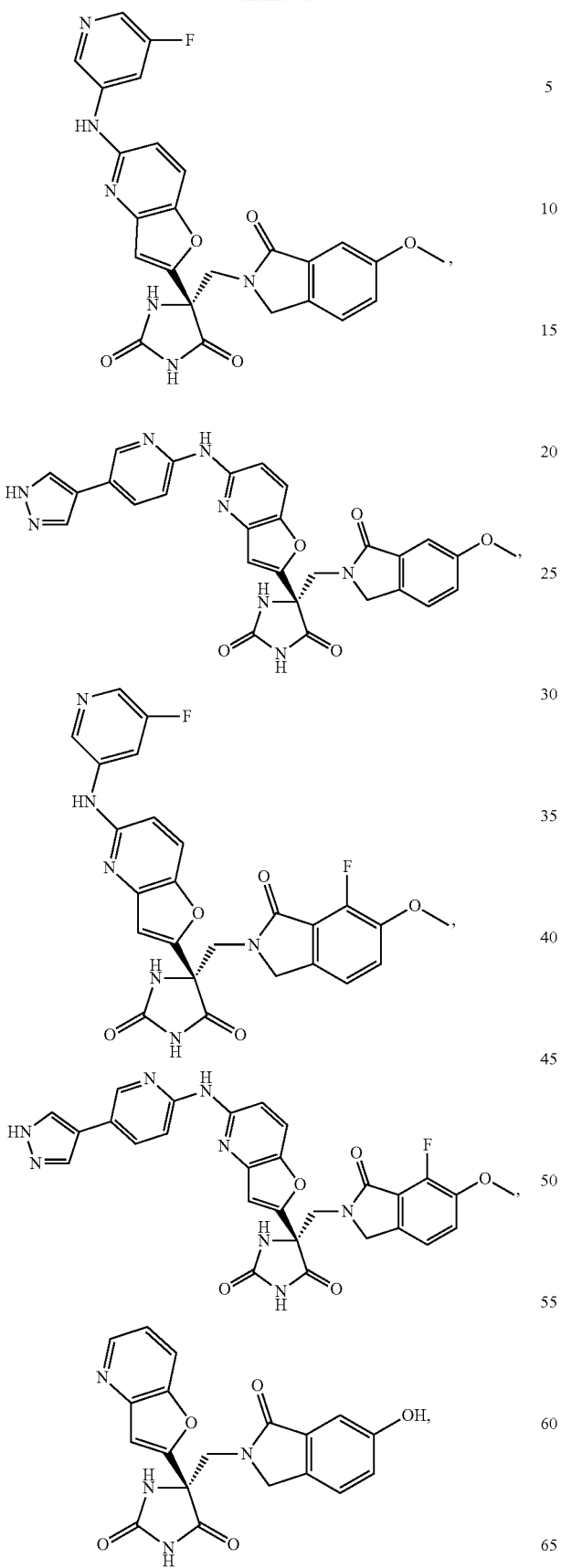
724
-continued
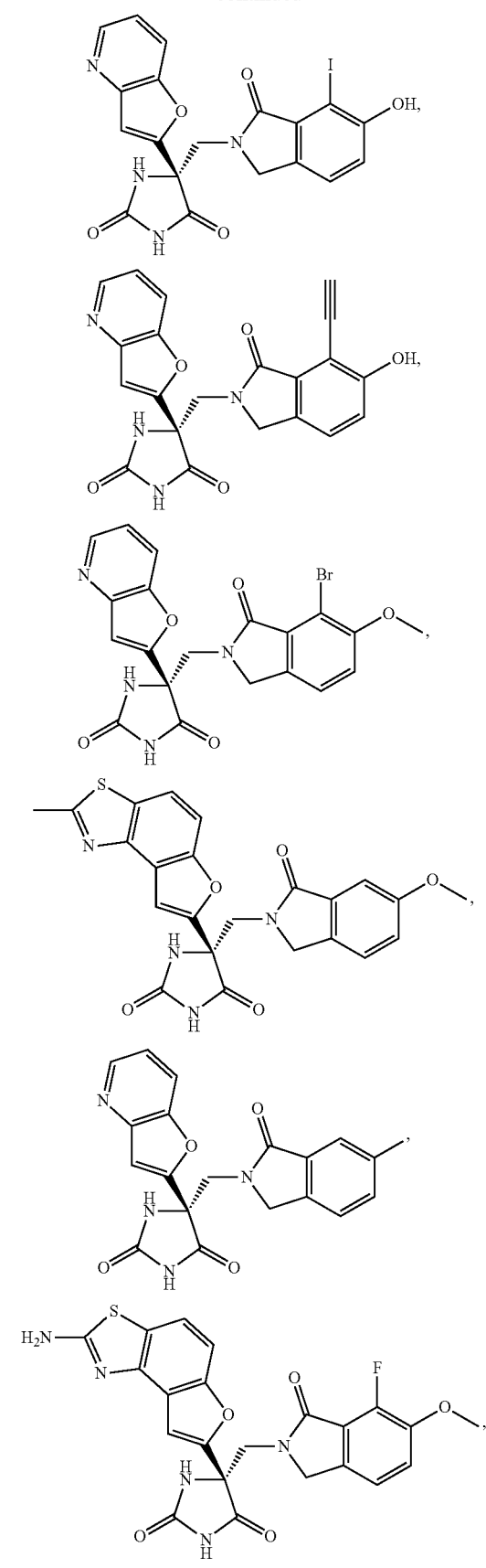

725
-continued
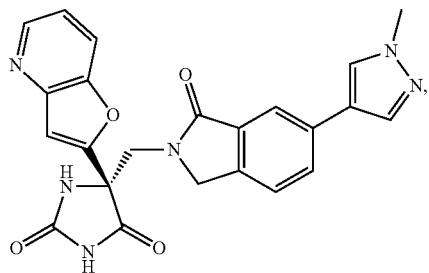
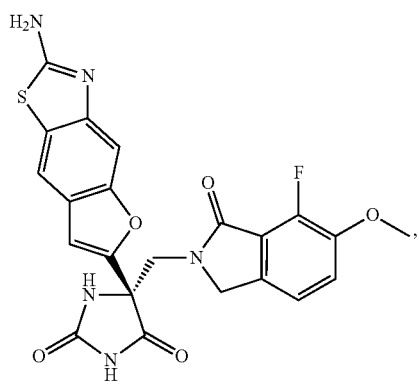
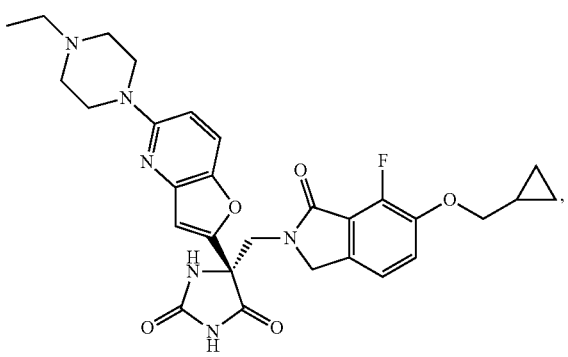
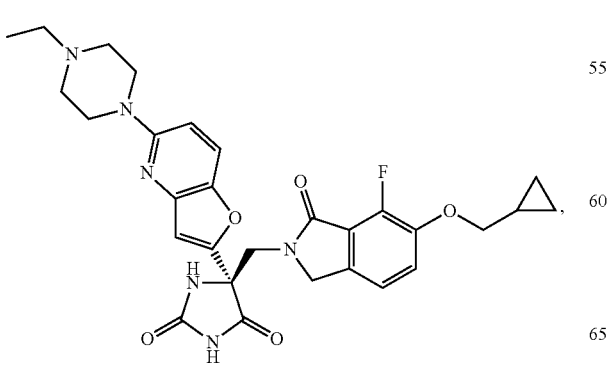
726
-continued
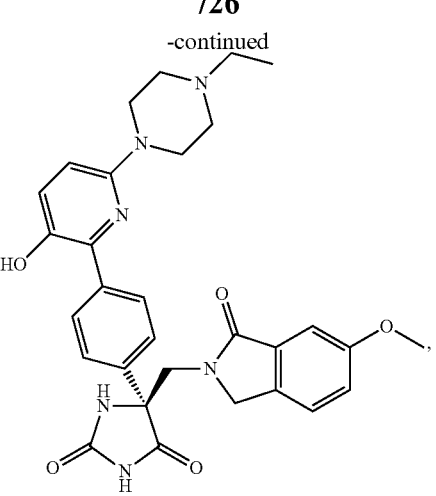
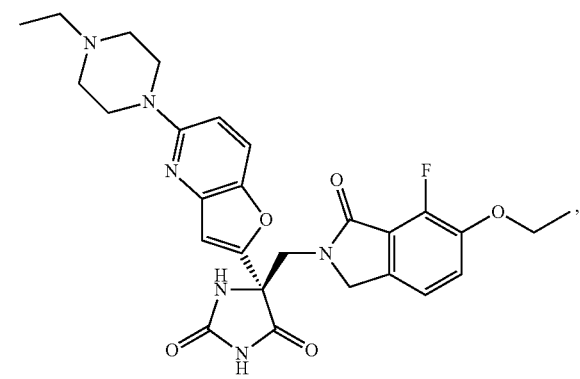
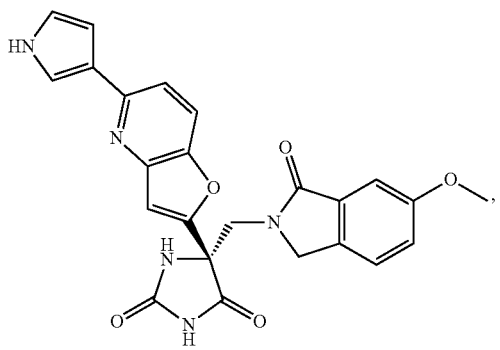
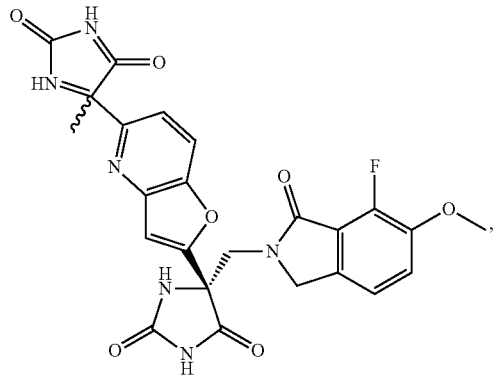

727
-continued
728
-continued
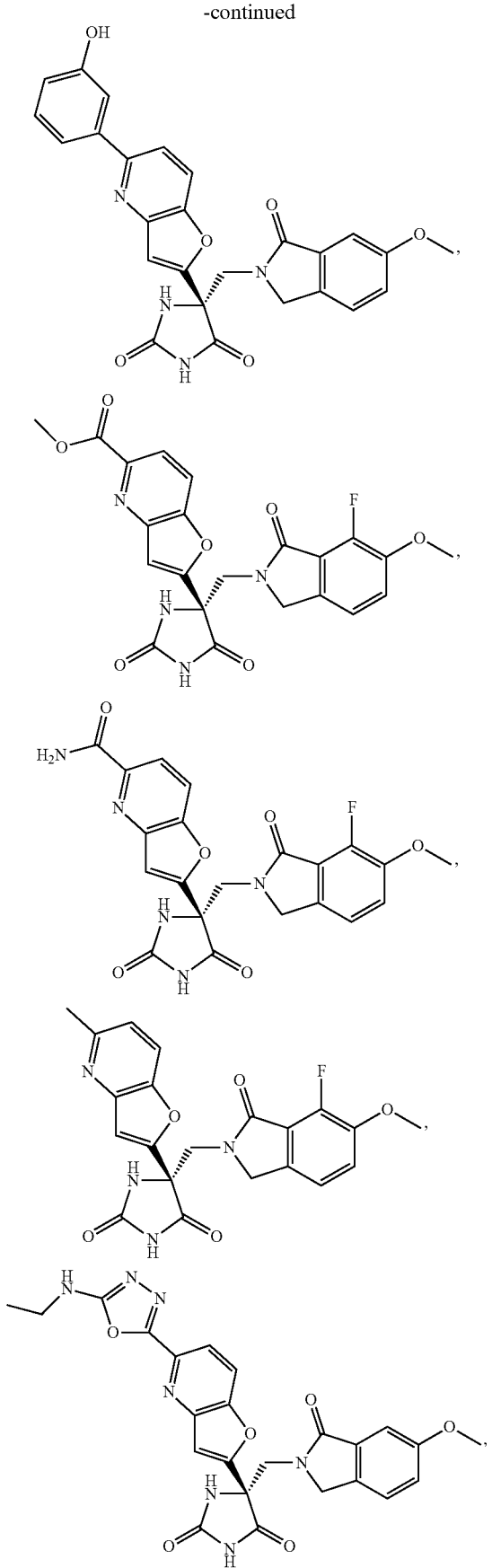
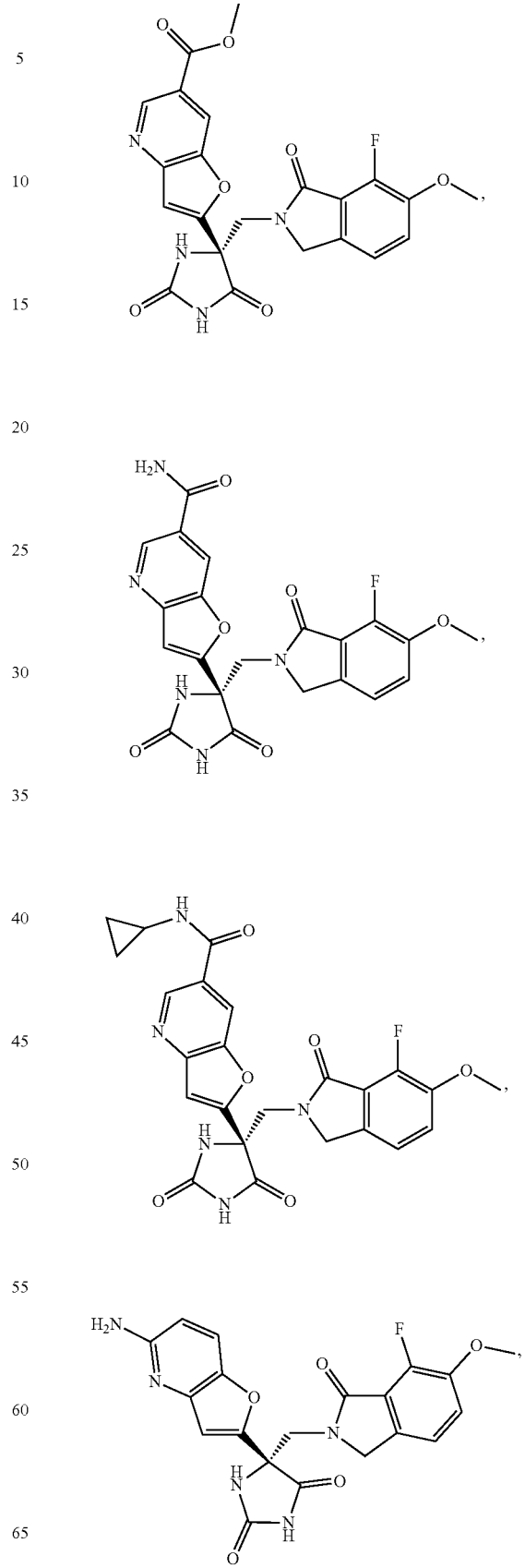

729
-continued
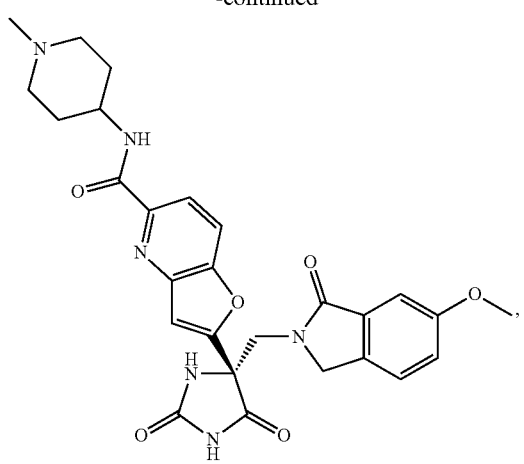
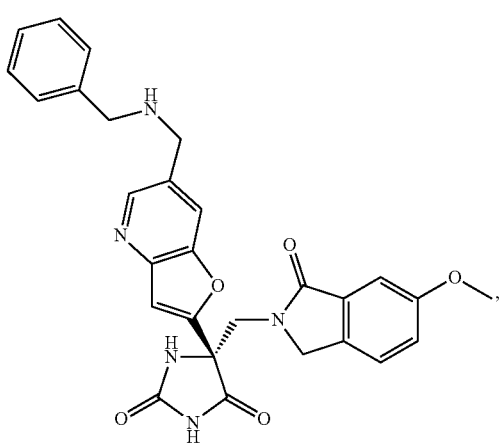
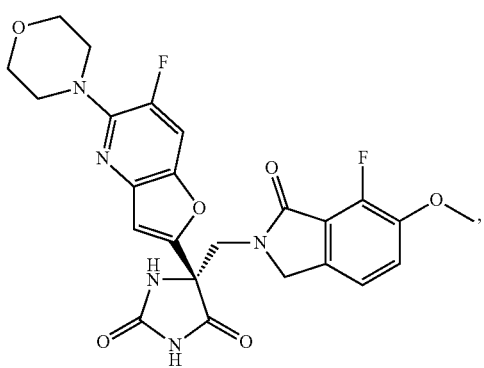
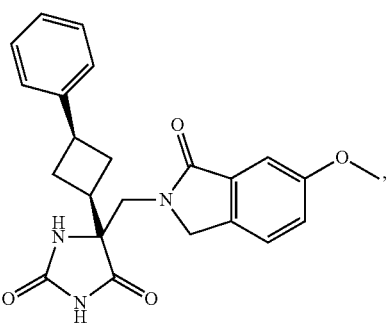
730
-continued
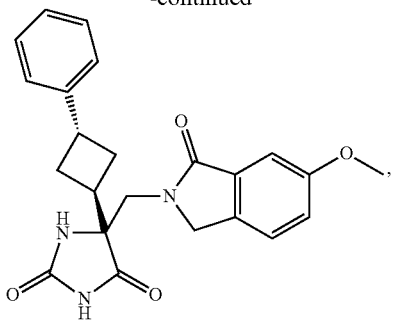
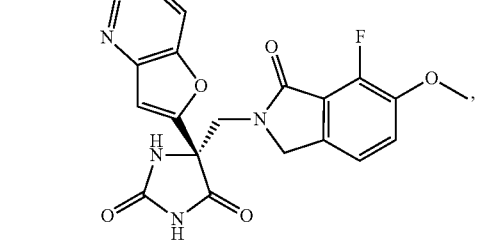
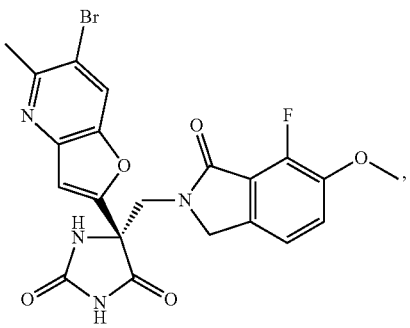
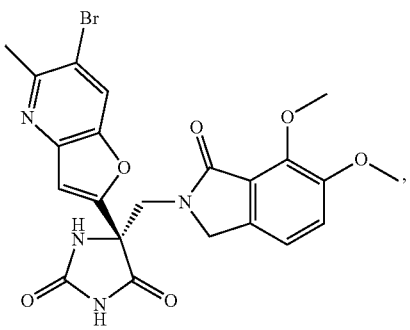

731
-continued
732
-continued
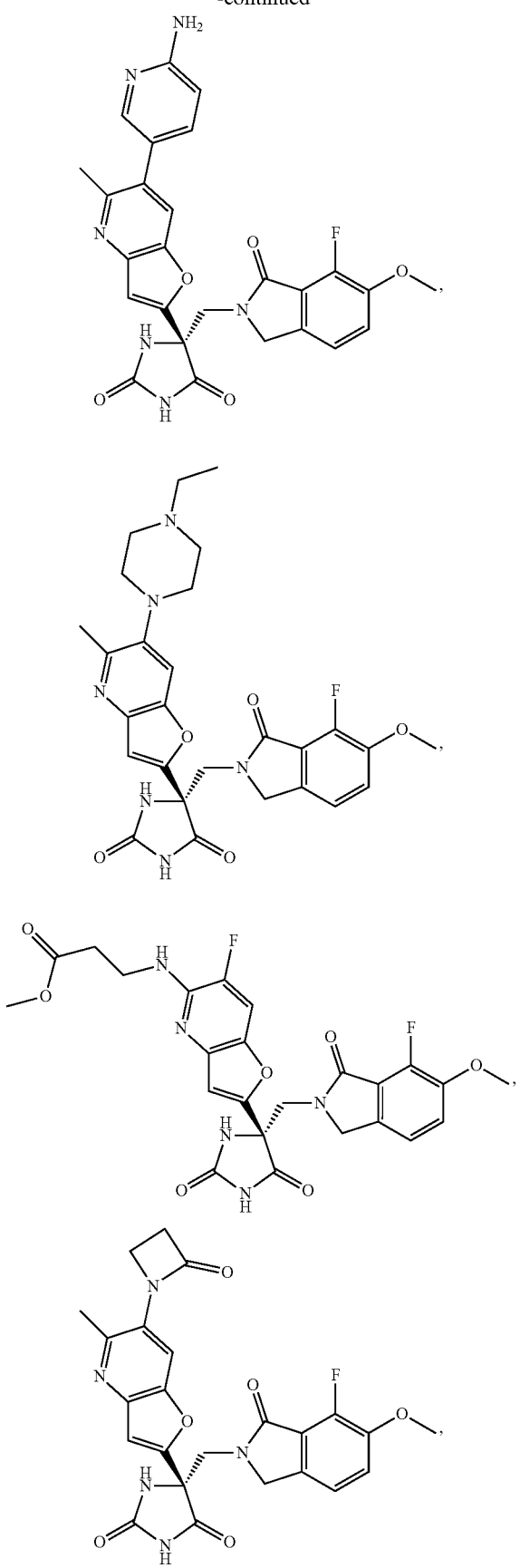
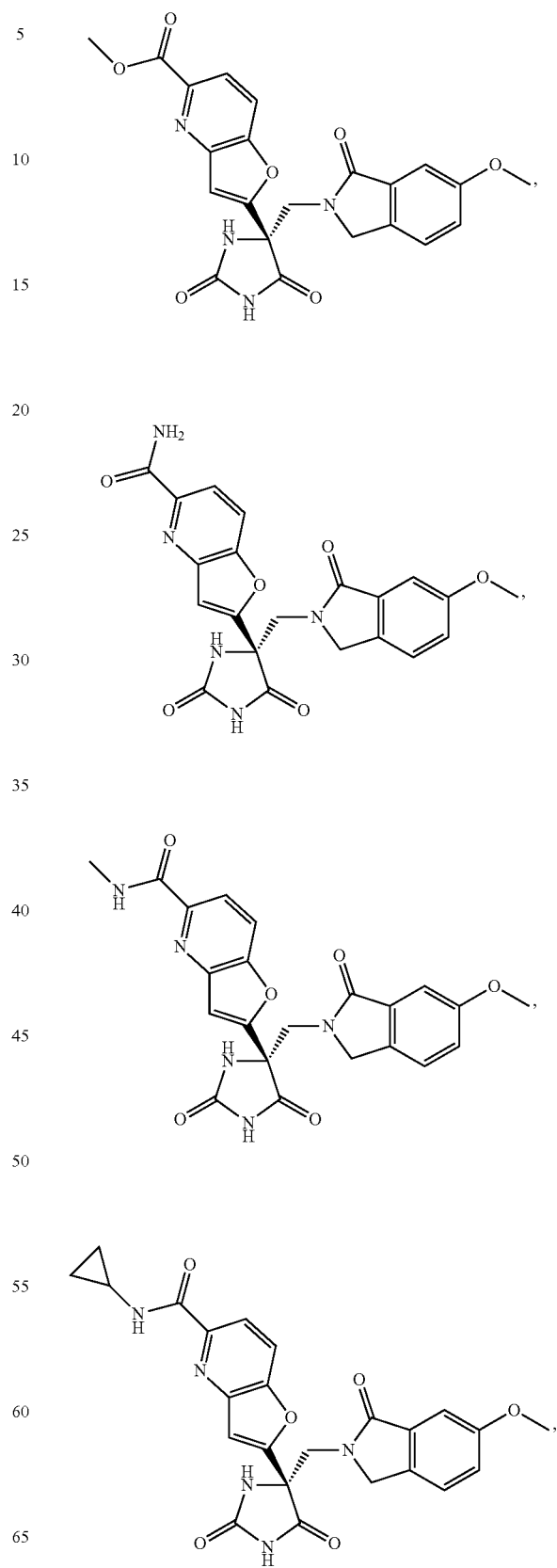

733
-continued
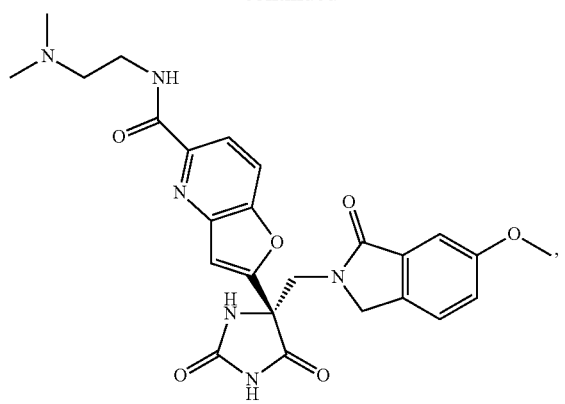
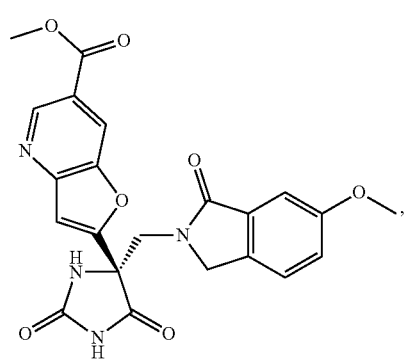
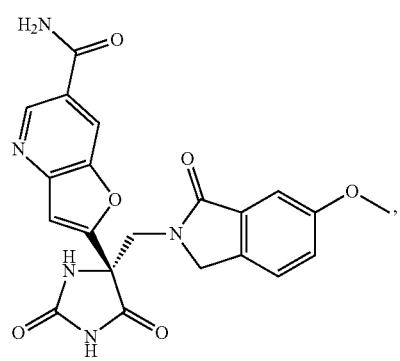
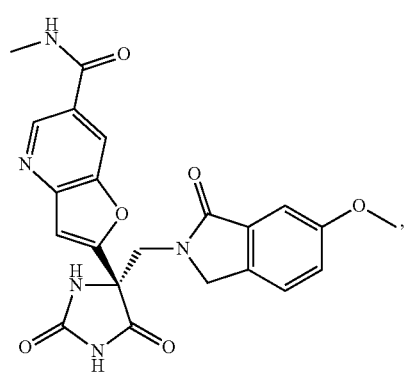
734
-continued
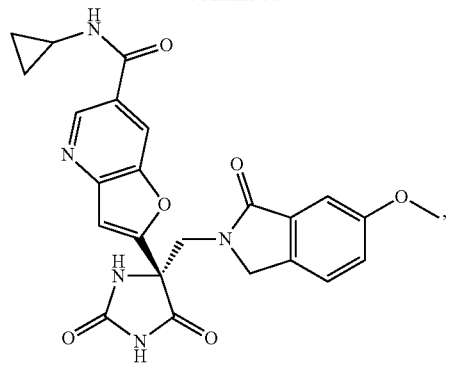
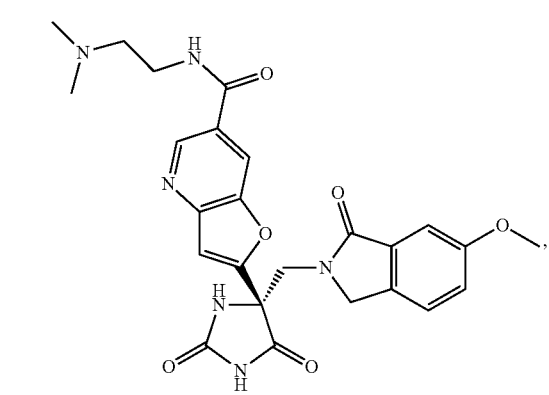
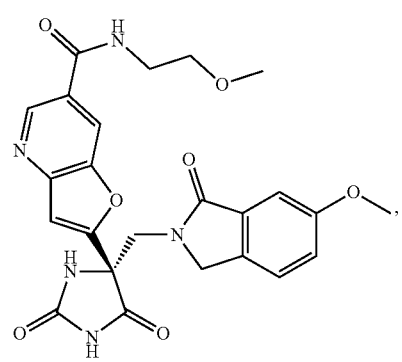
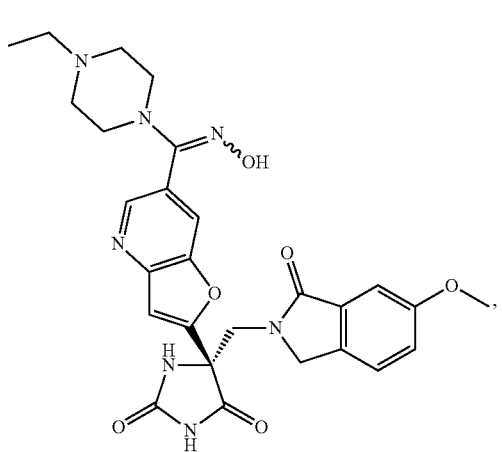

735
-continued
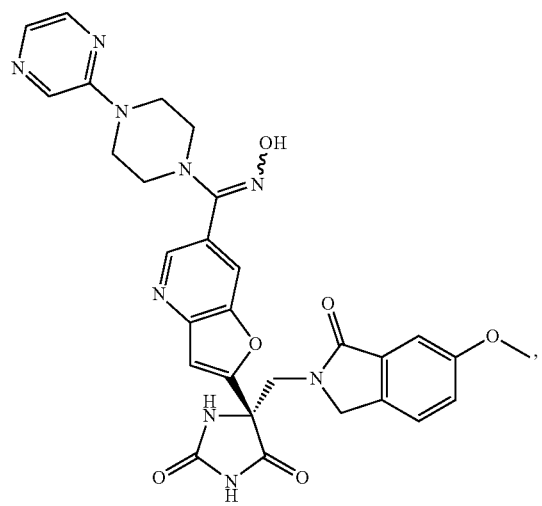
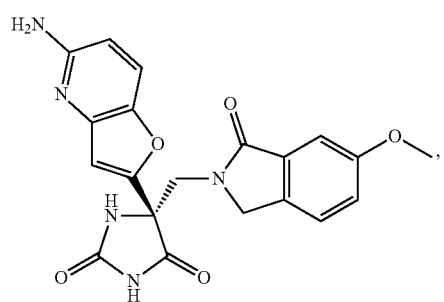
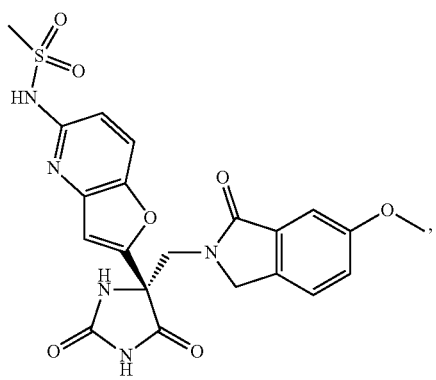
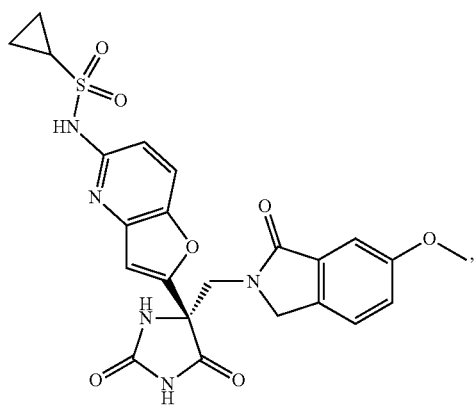
736
-continued
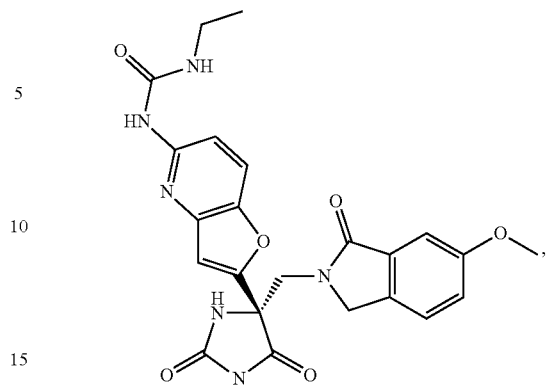
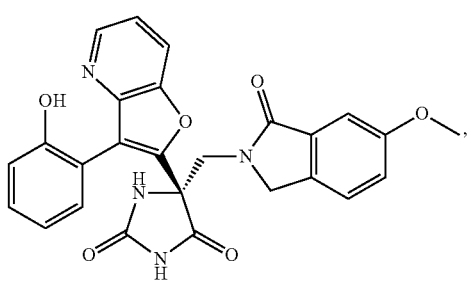
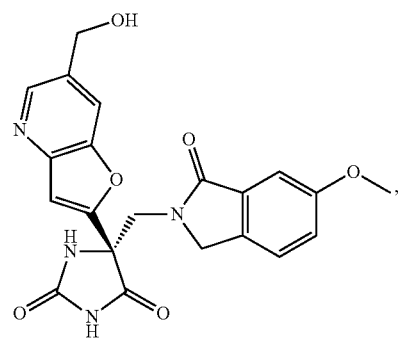
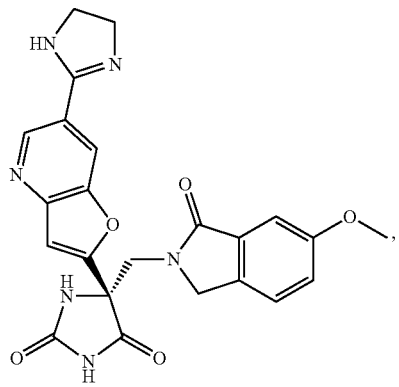

737
-continued
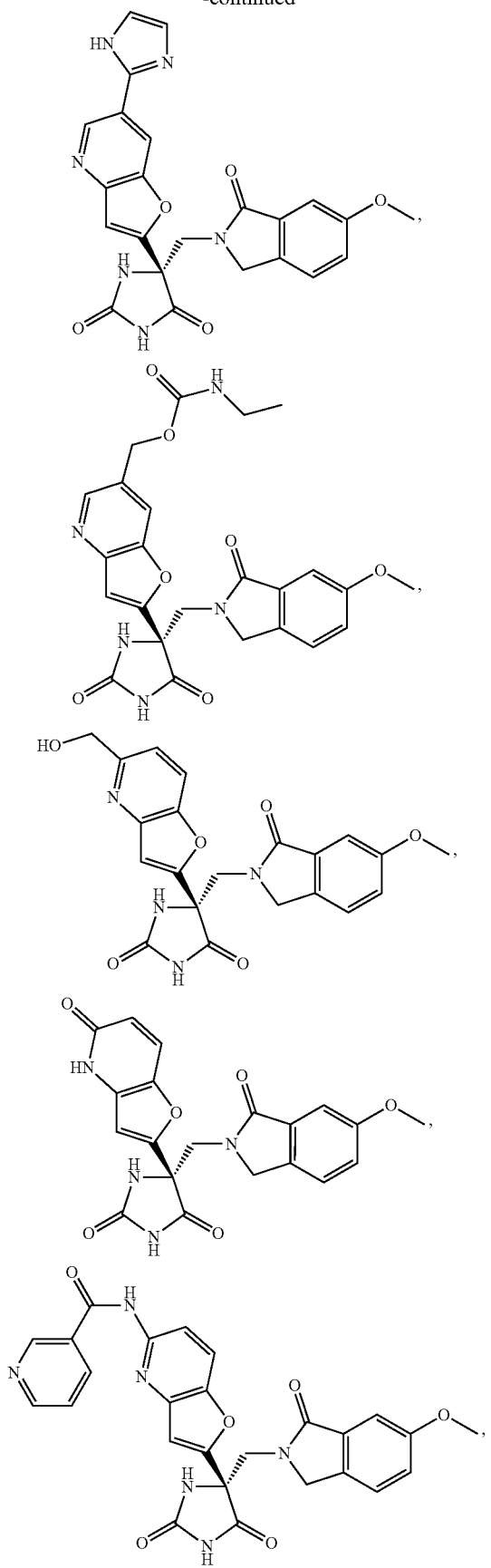
738
-continued
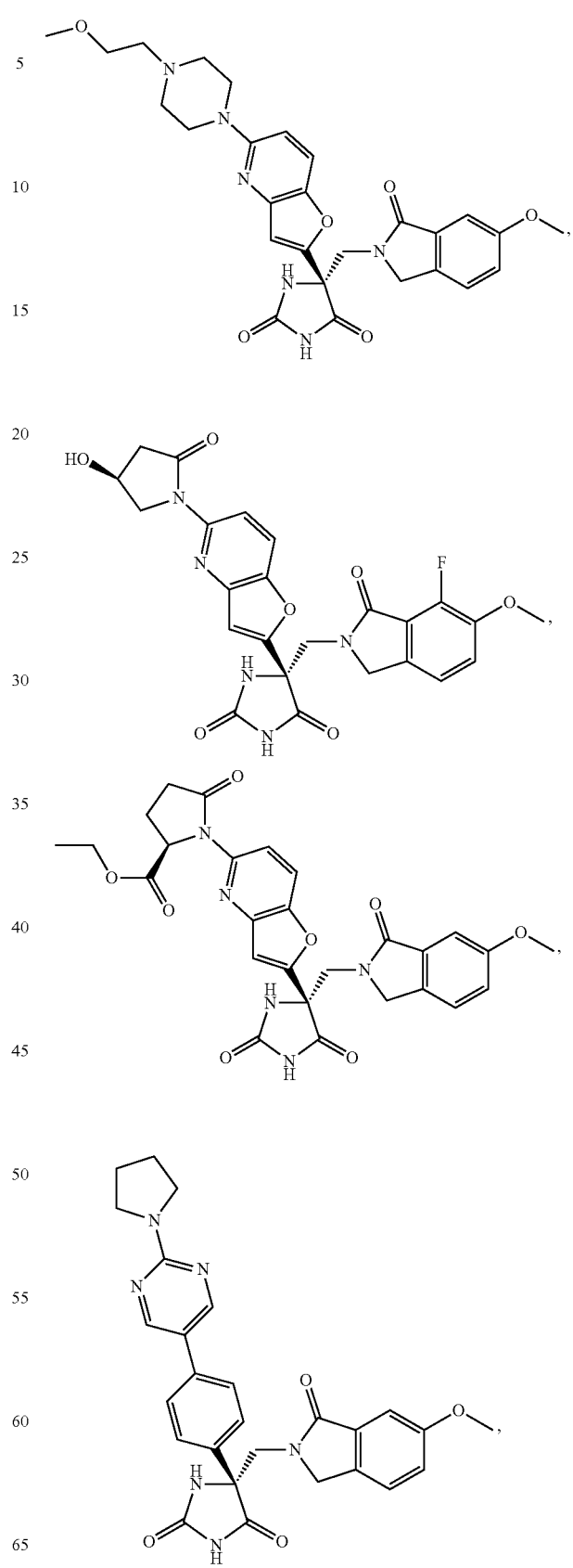

739
-continued
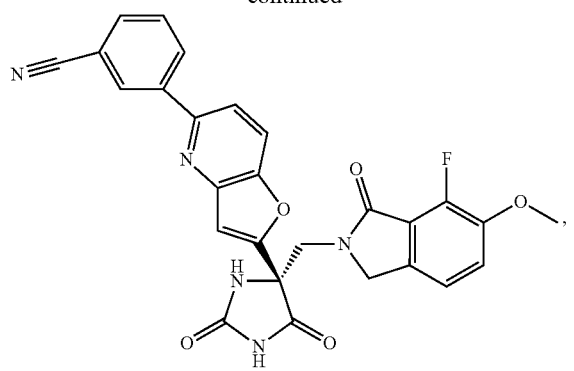
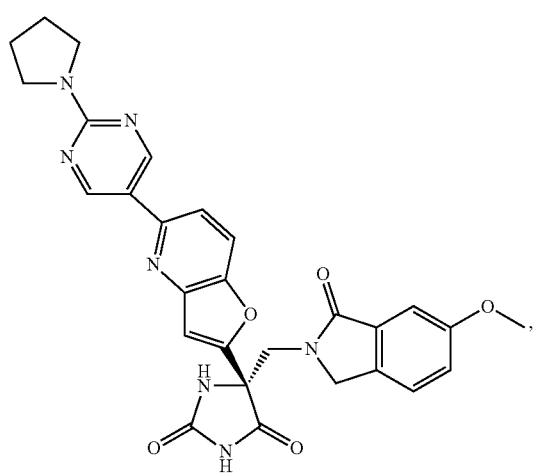
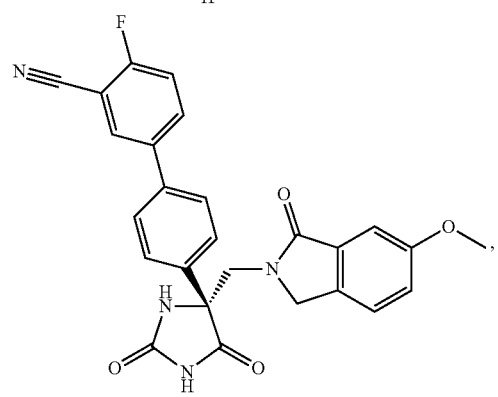
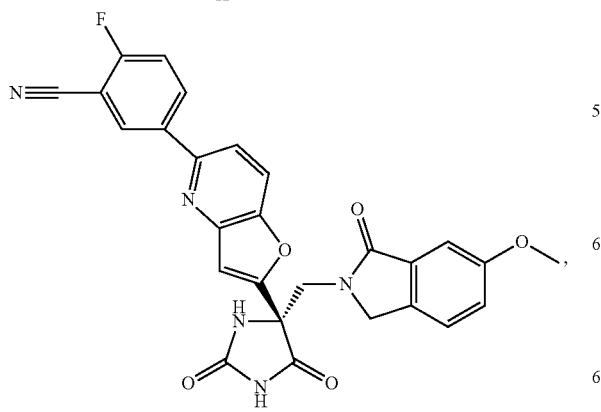
740
-continued
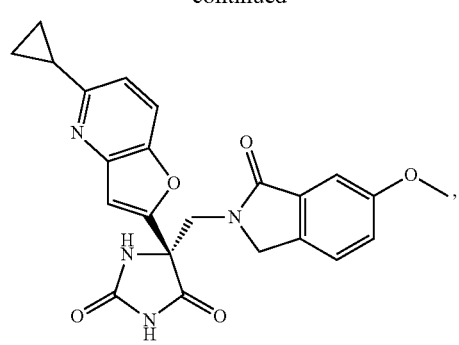
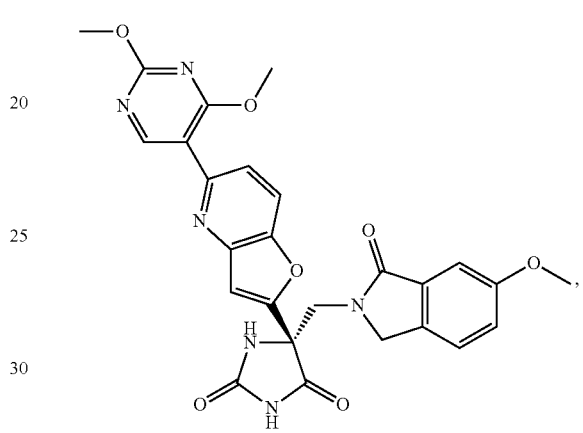
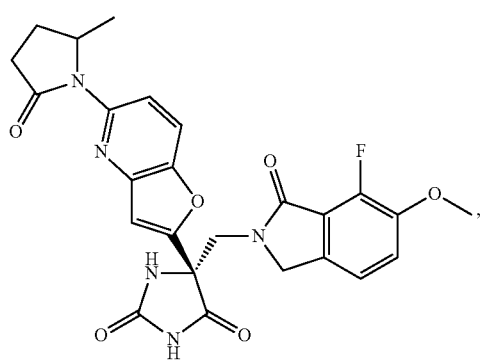
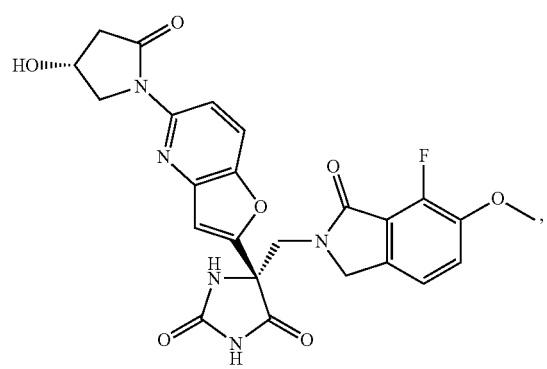

741
-continued
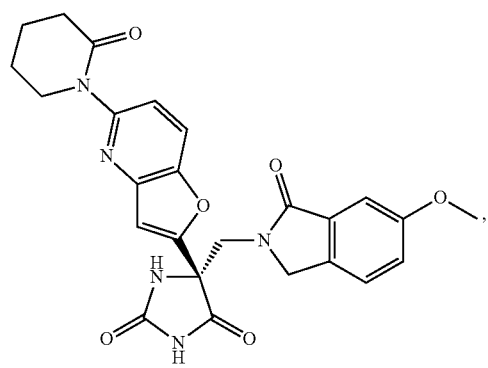
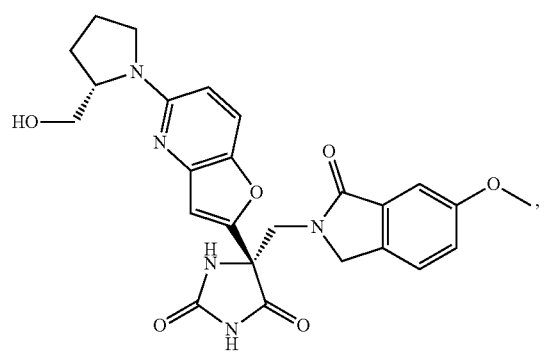
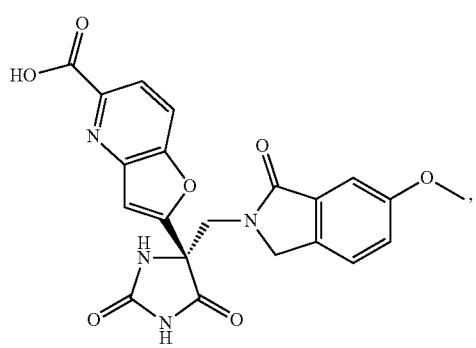
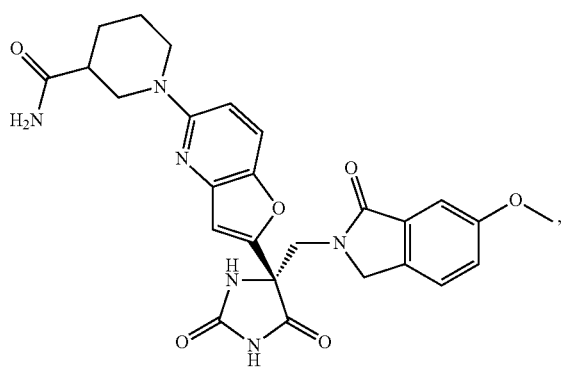
742
-continued
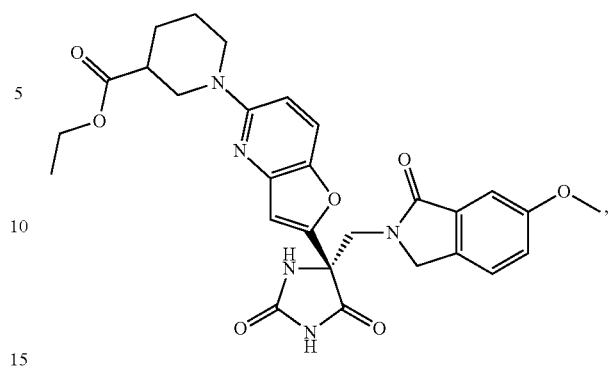
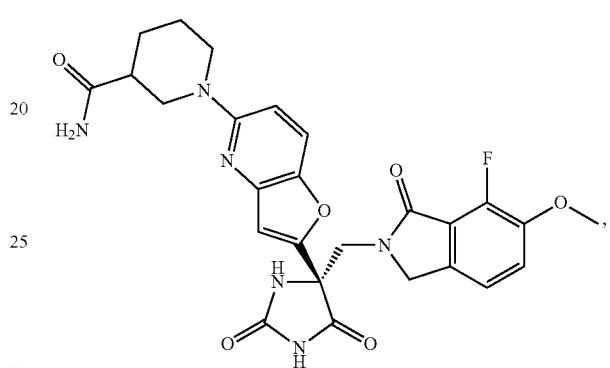
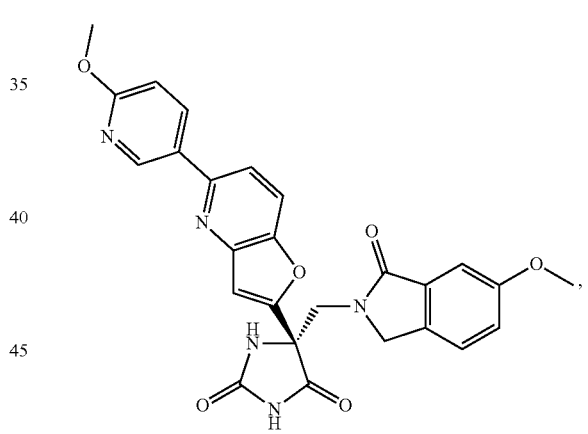
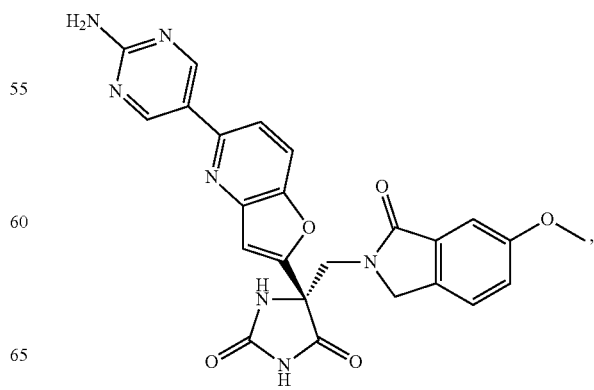

743
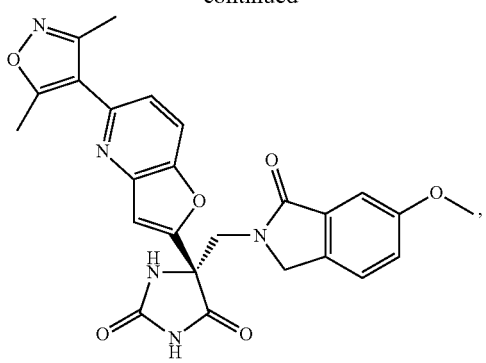
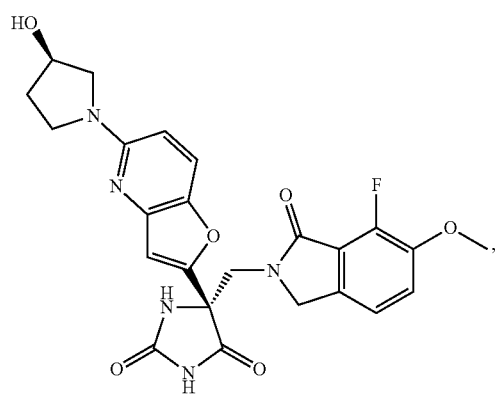
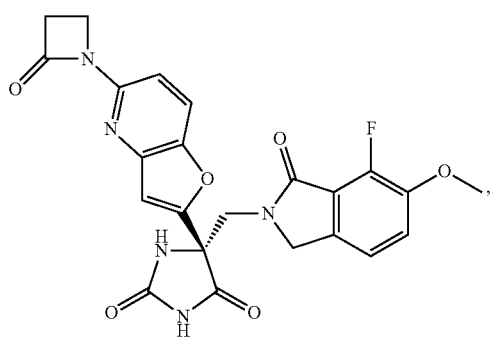
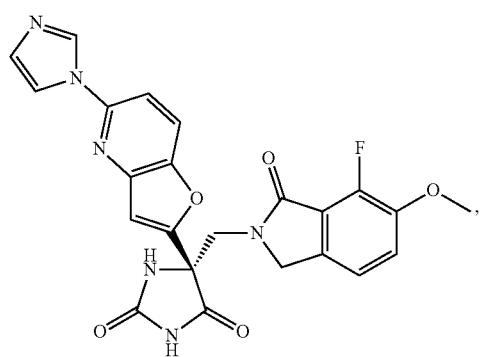
744
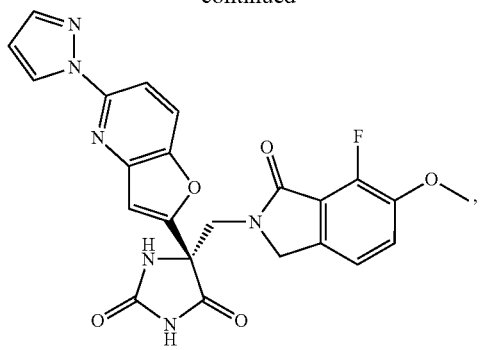
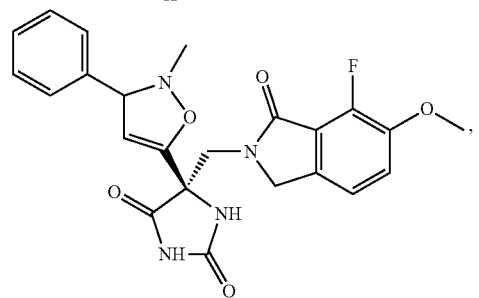
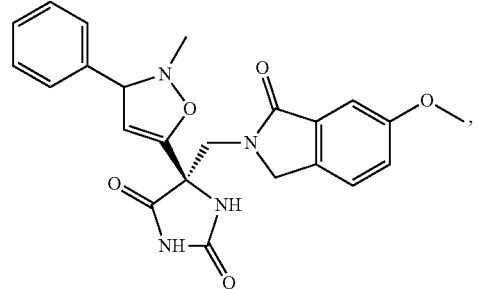
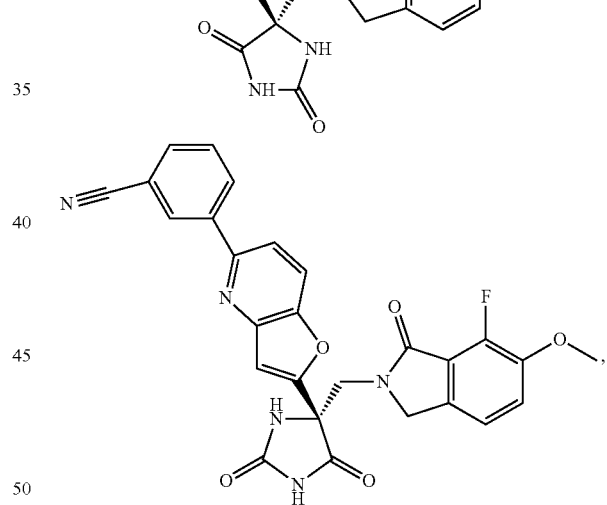
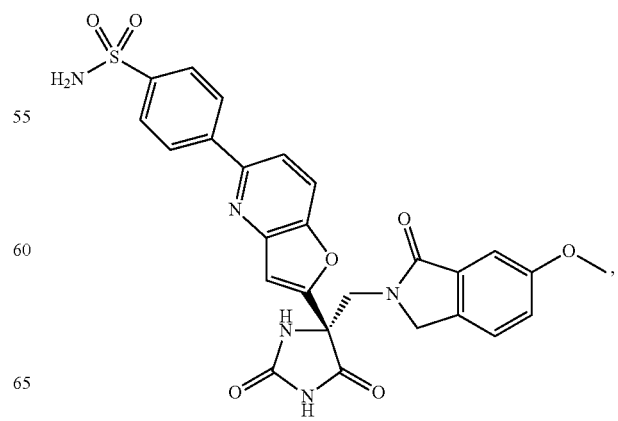

745
-continued
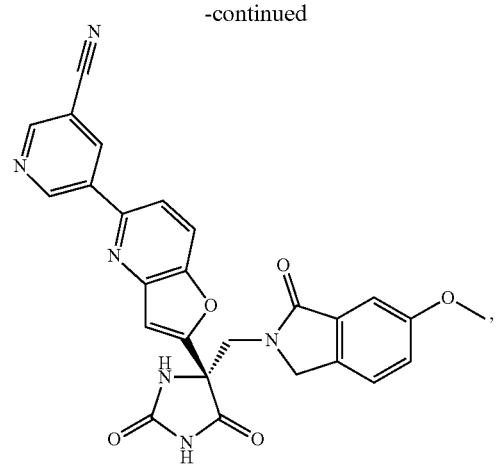
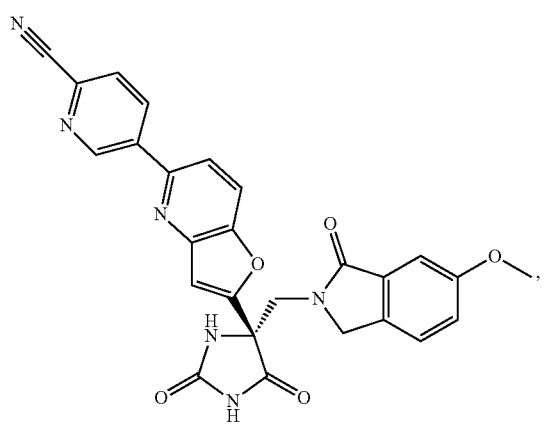
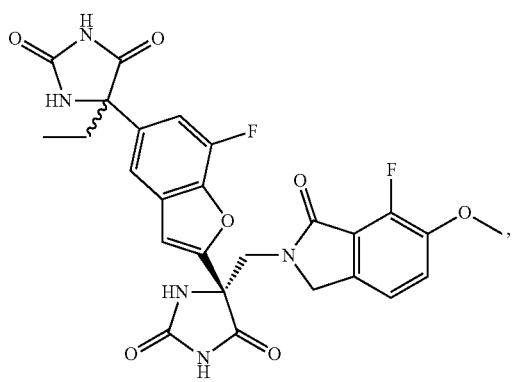
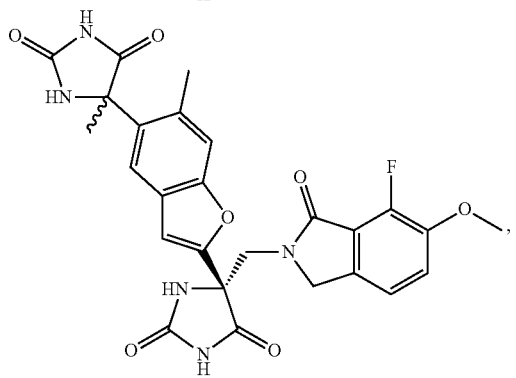
746
-continued
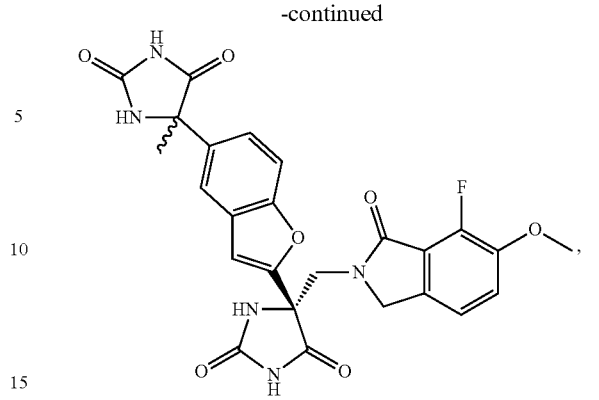
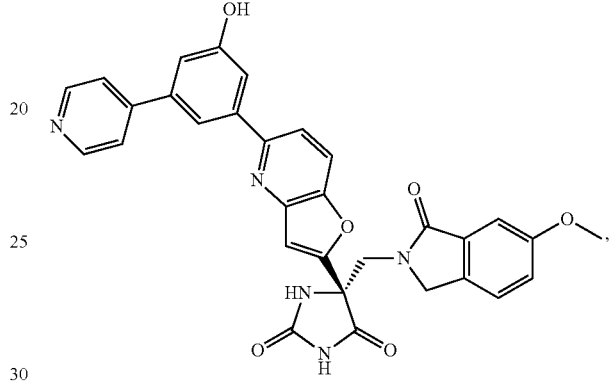
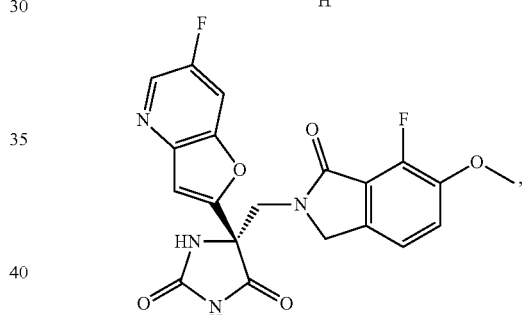
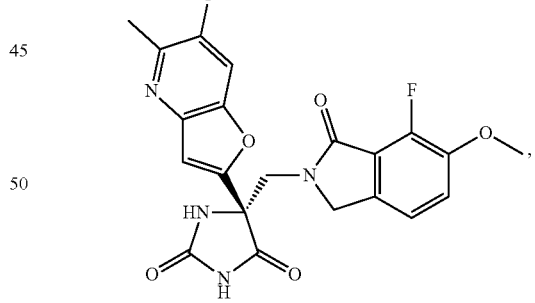
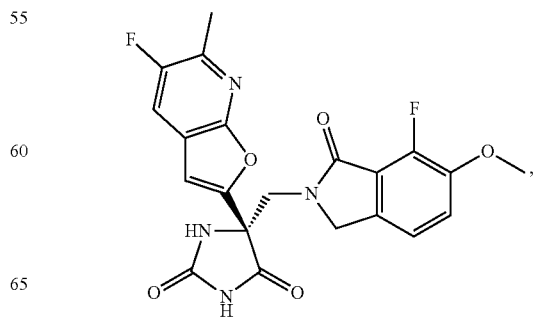

747
-continued
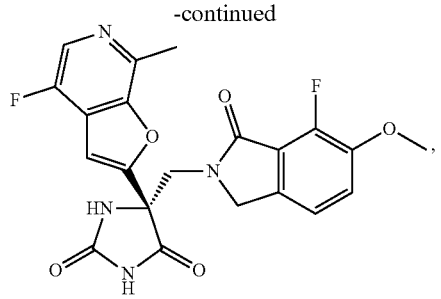
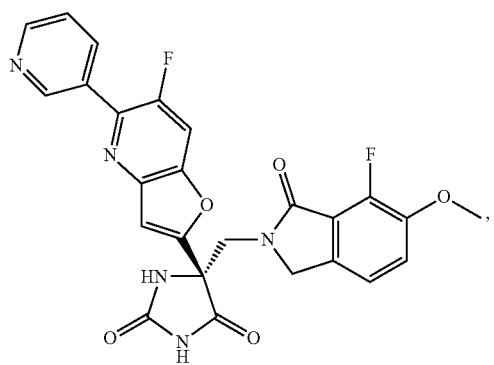
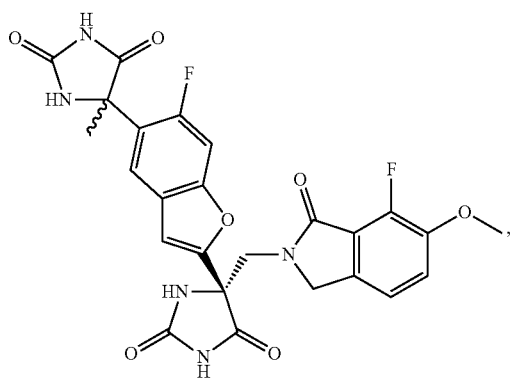
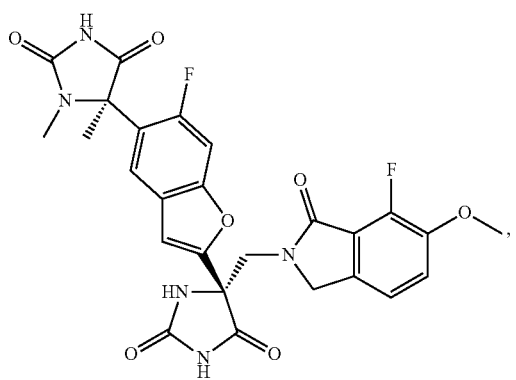
748
-continued
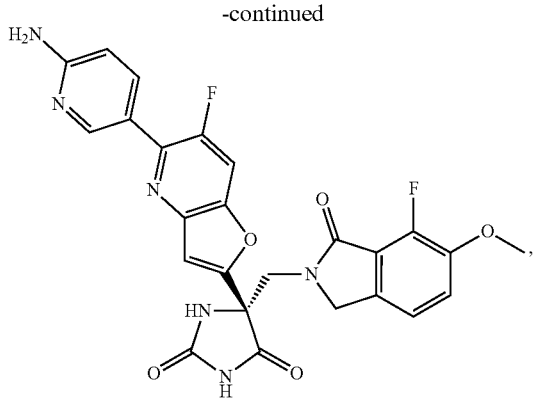
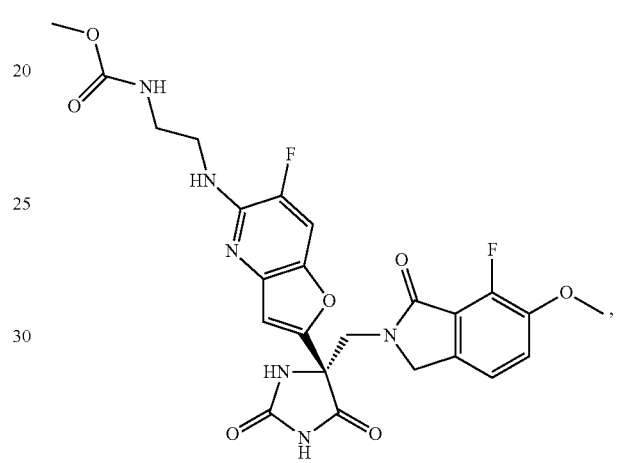
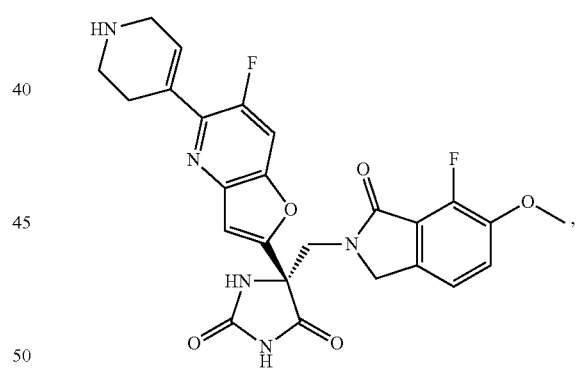
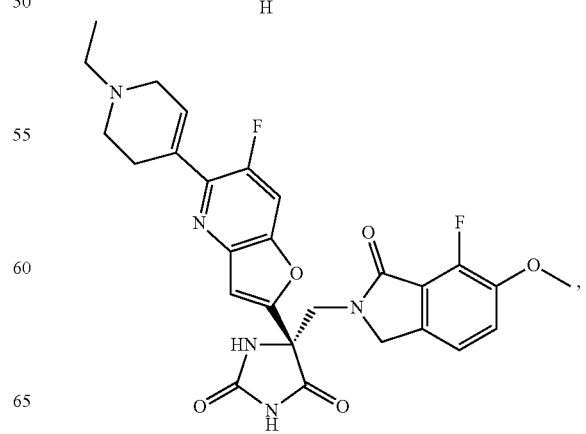

749
-continued
750
-continued
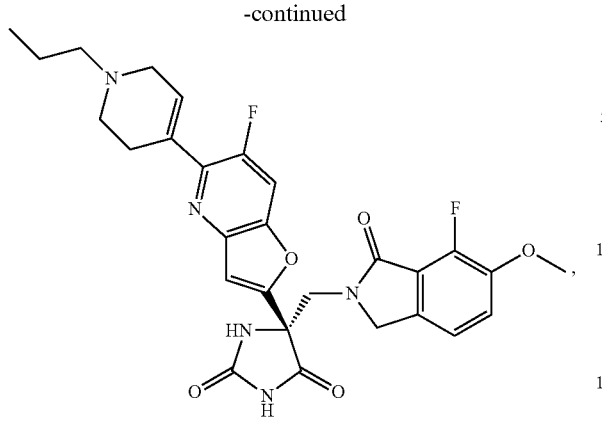
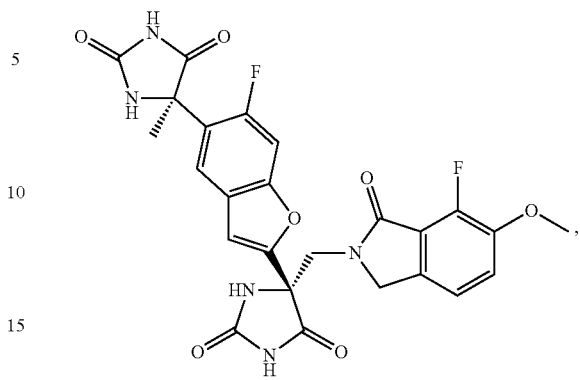
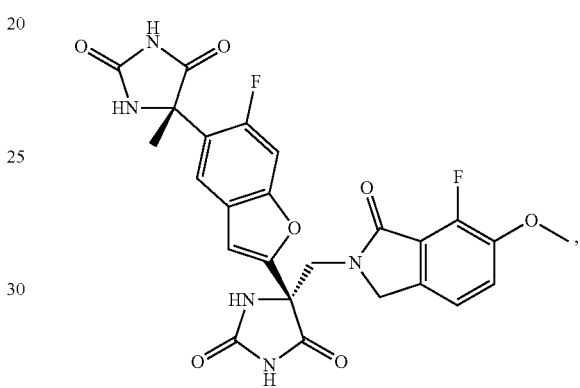
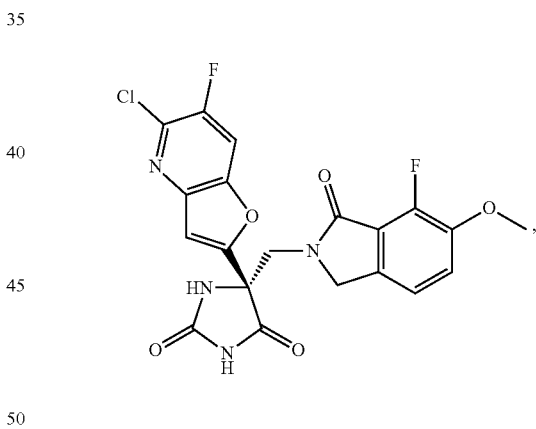
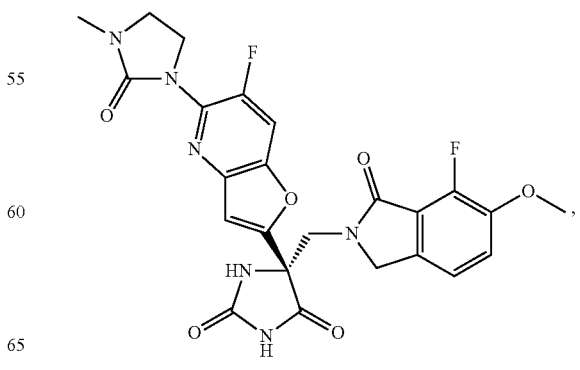

751
-continued
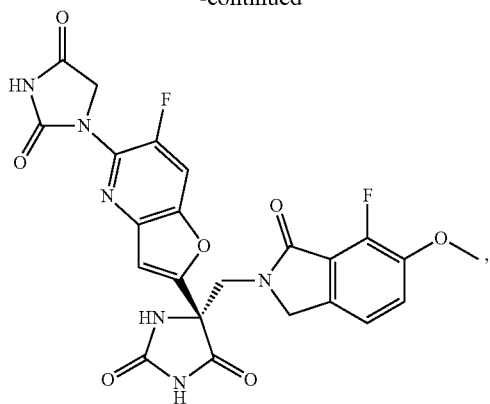
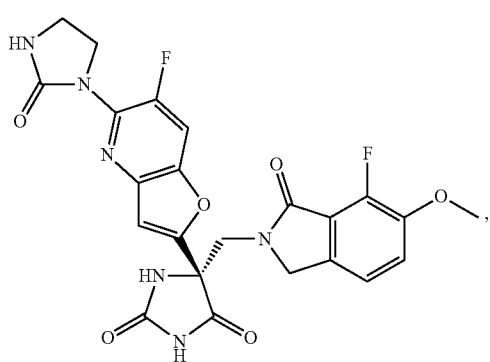
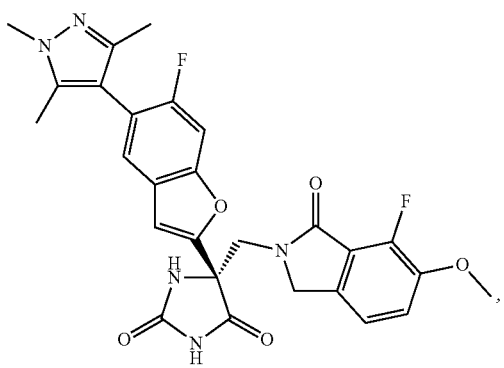
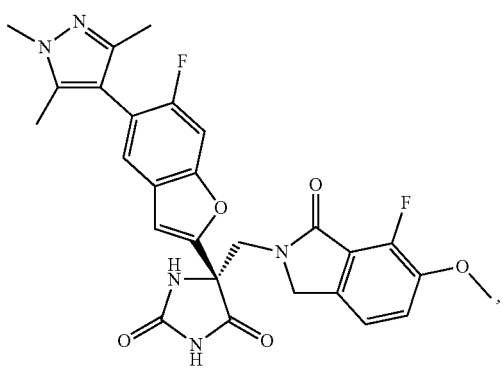
752
-continued
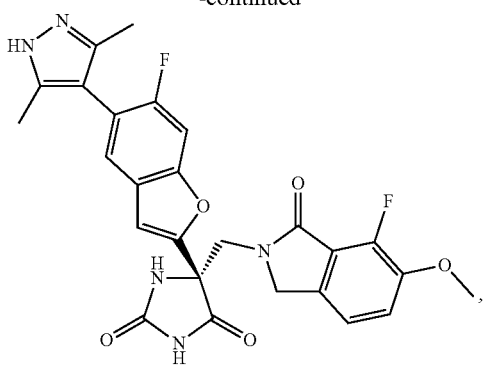
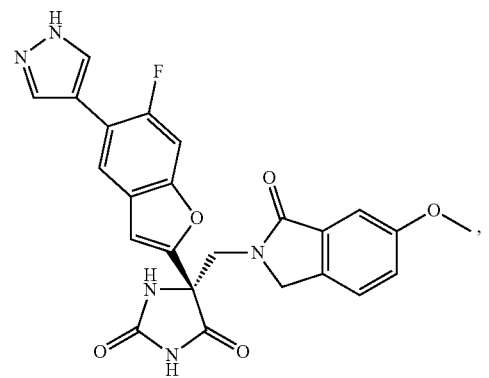
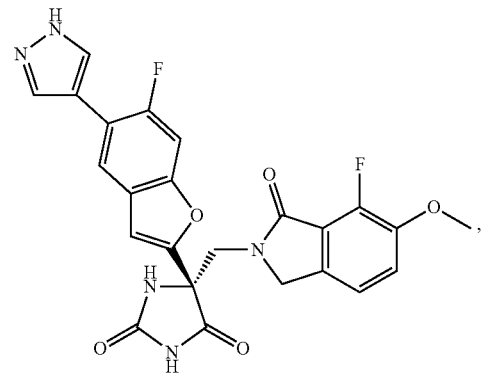

753
-continued
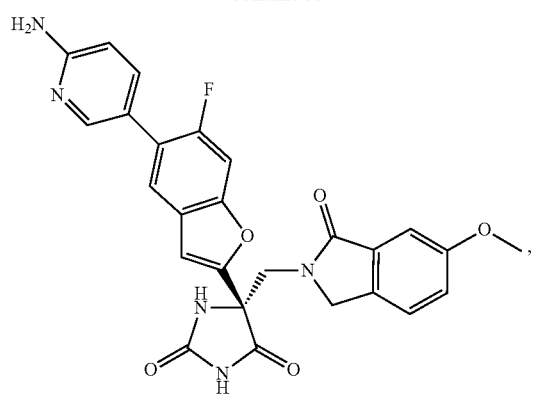
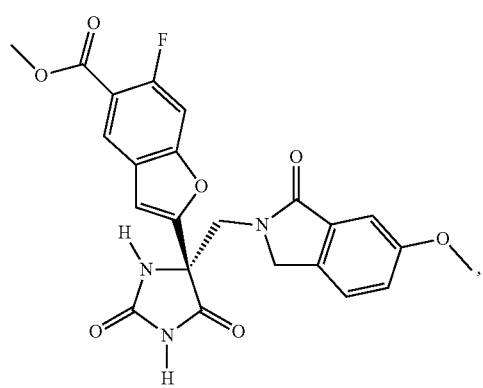
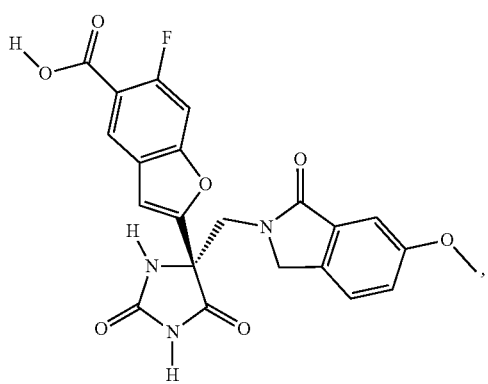
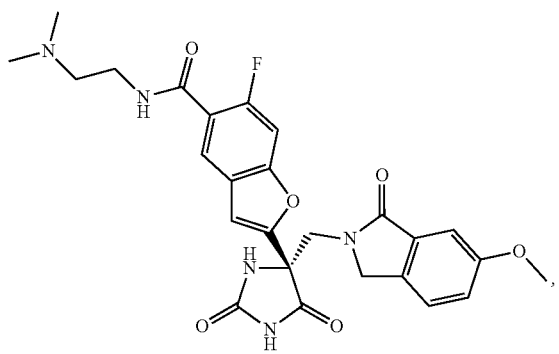
754
-continued
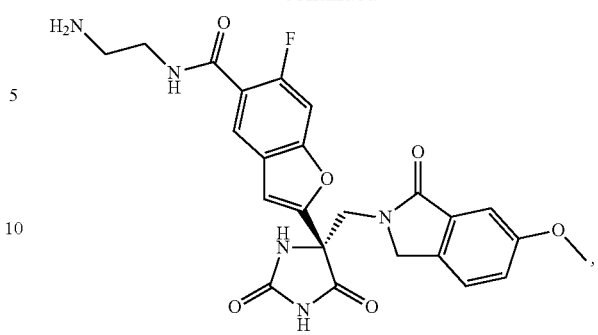
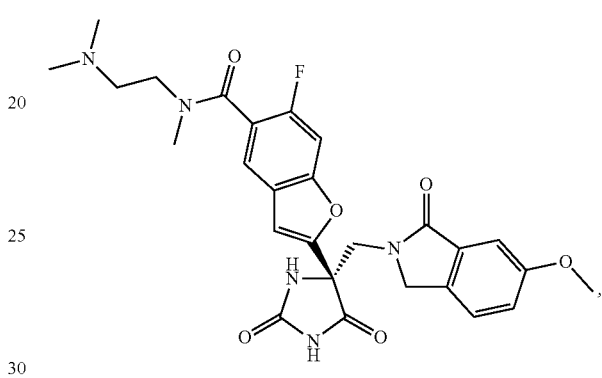
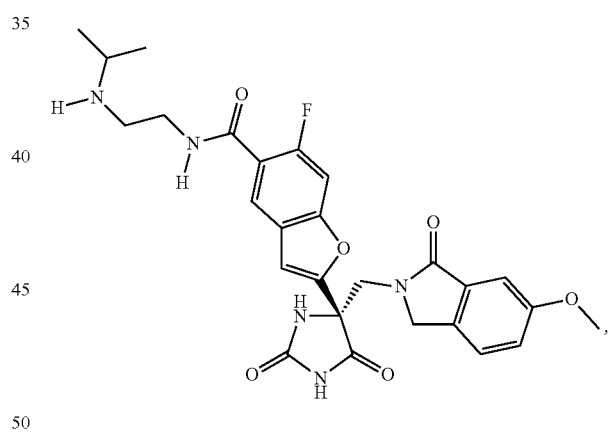
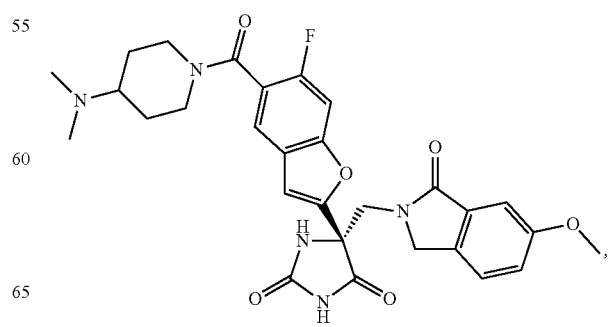

755
-continued
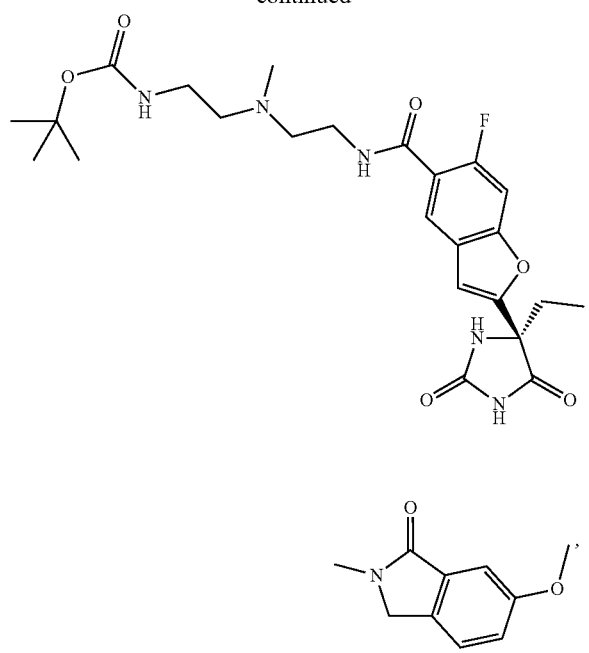
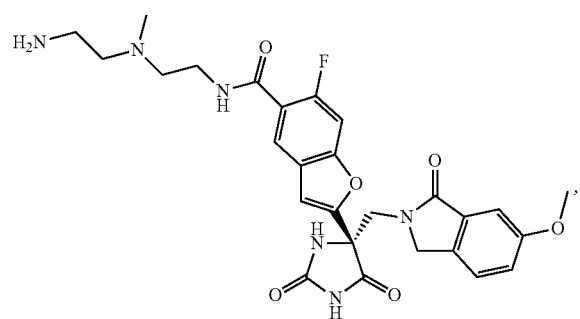
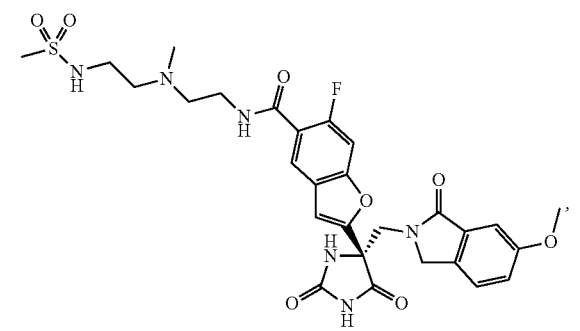
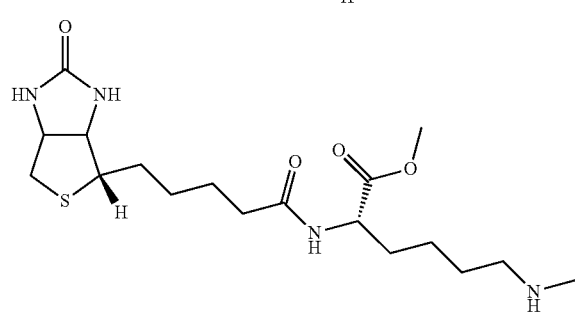
756
-continued
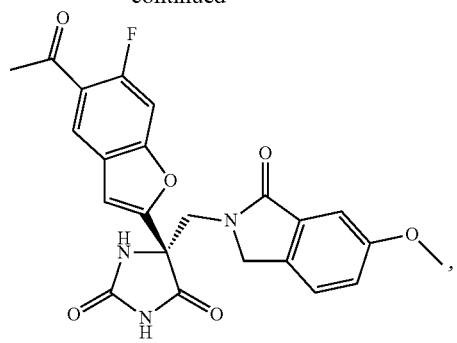
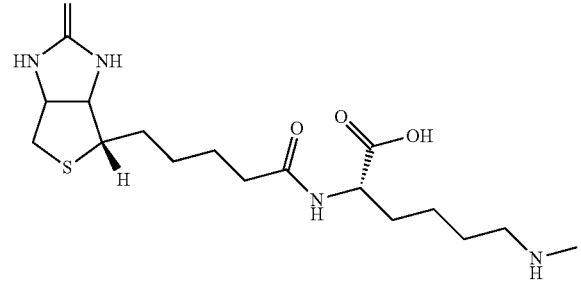
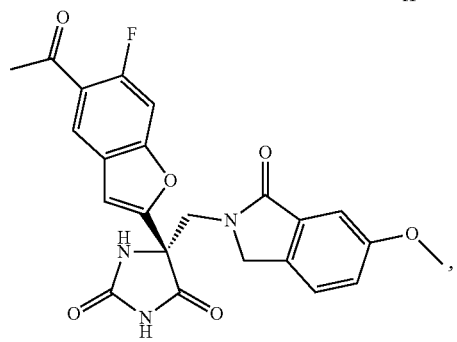
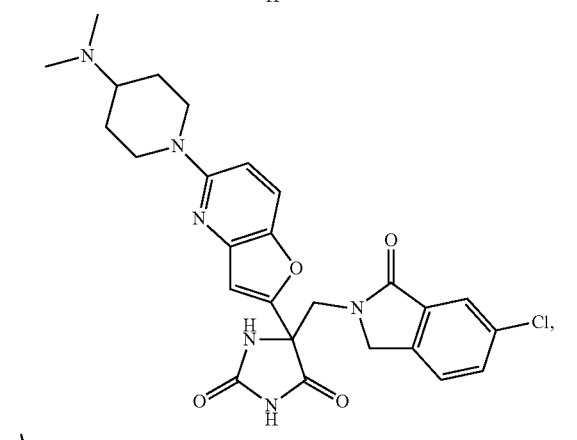
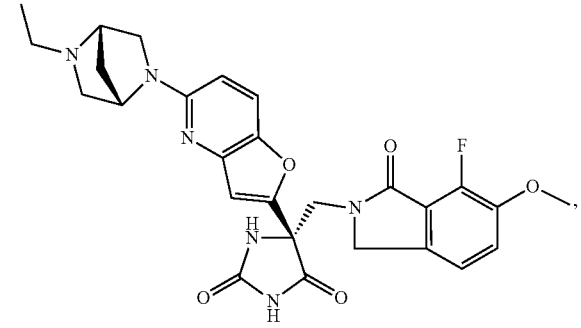

757
-continued
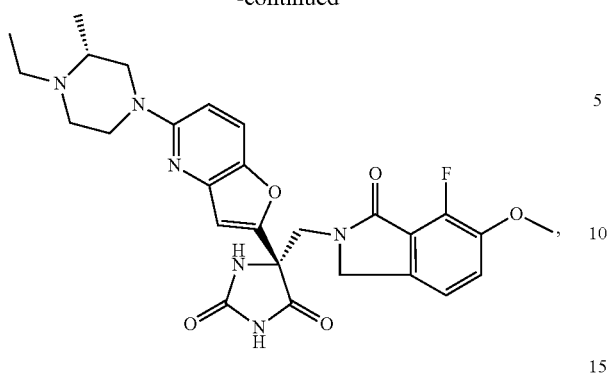
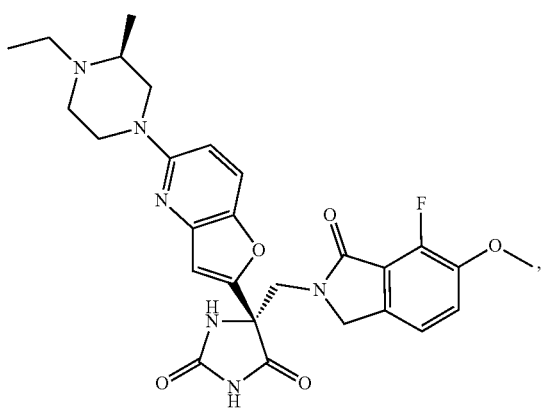
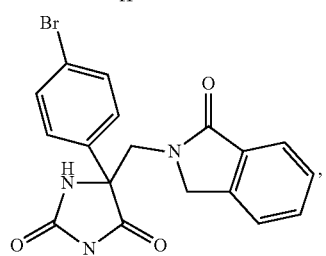
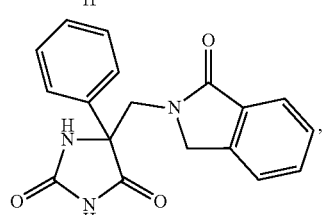
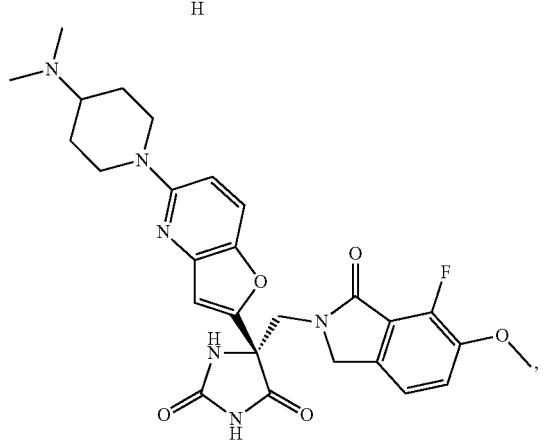
758
-continued
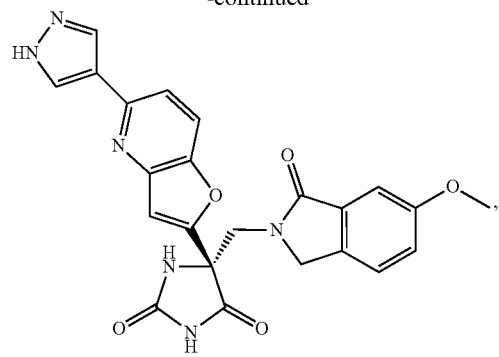
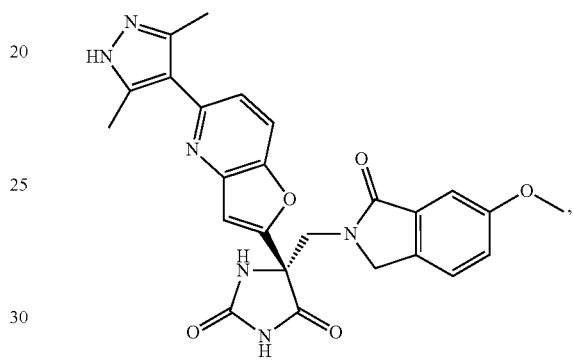
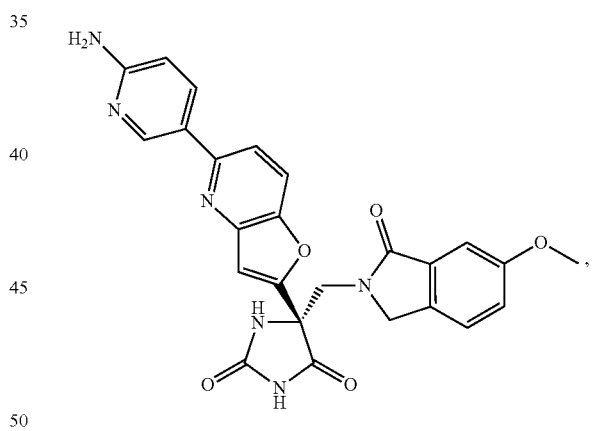
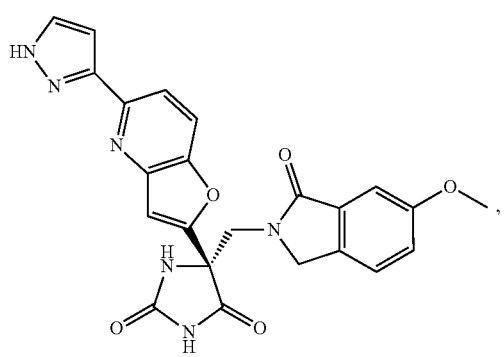

759
-continued
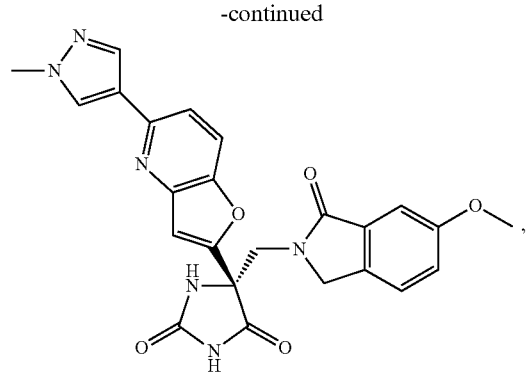
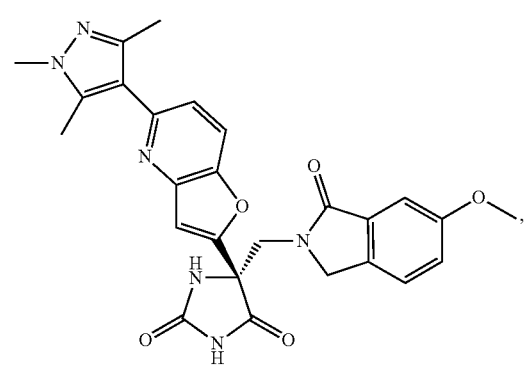
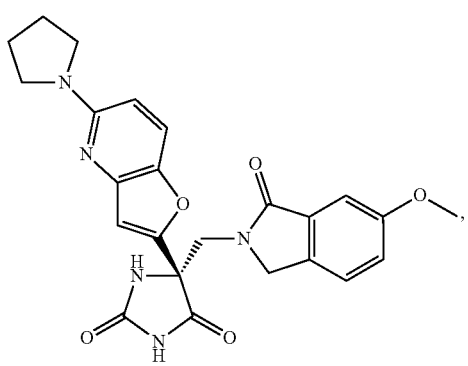
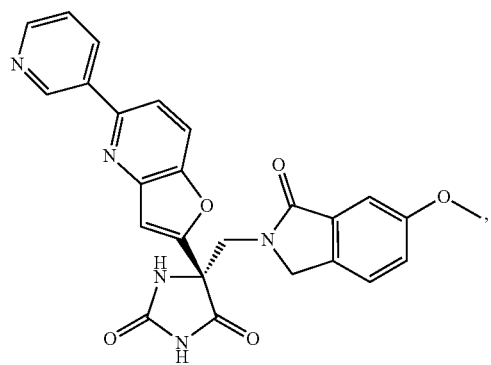
760
-continued
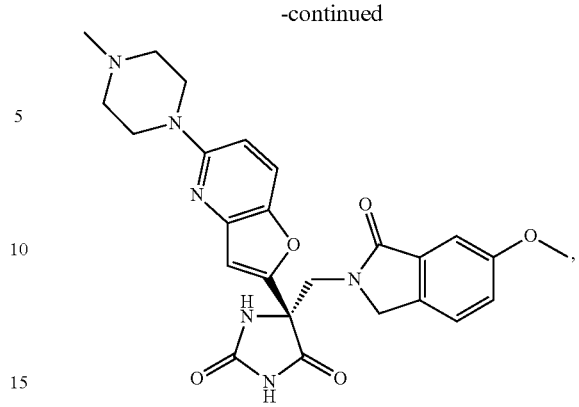
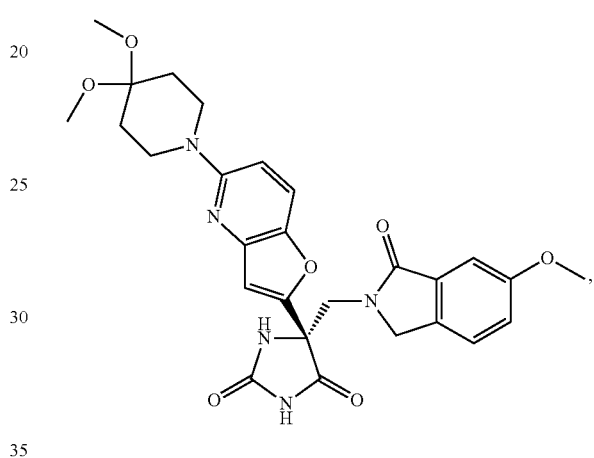
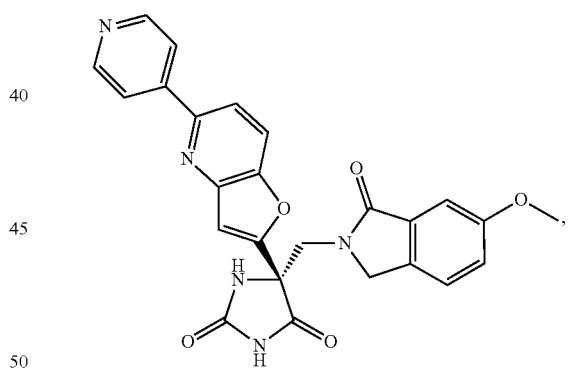
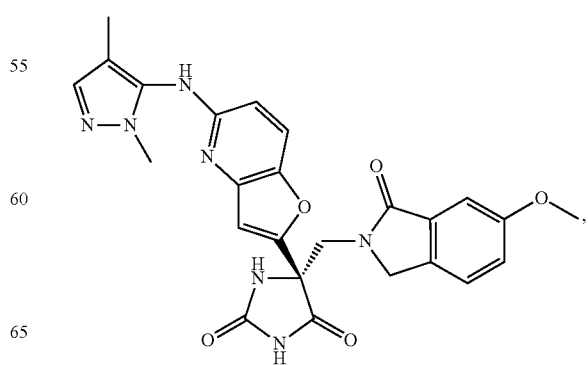

761
-continued
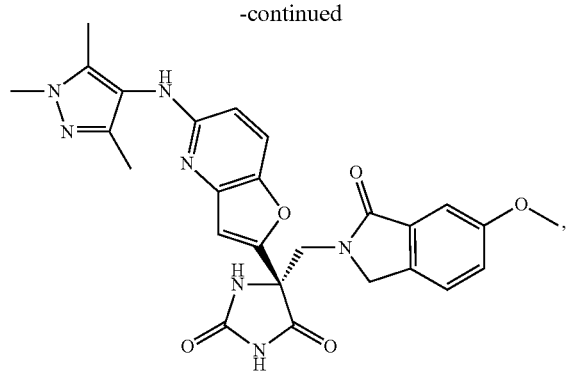
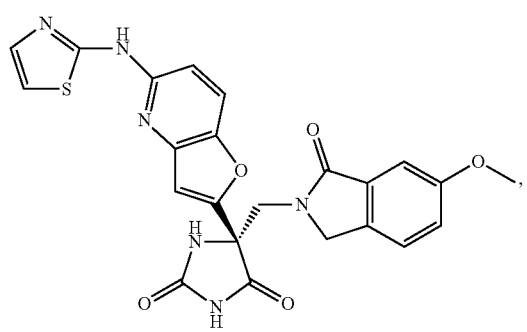
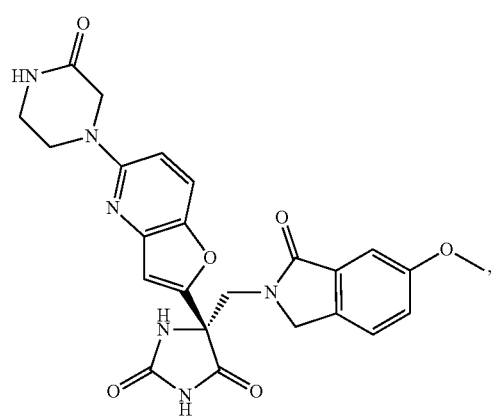
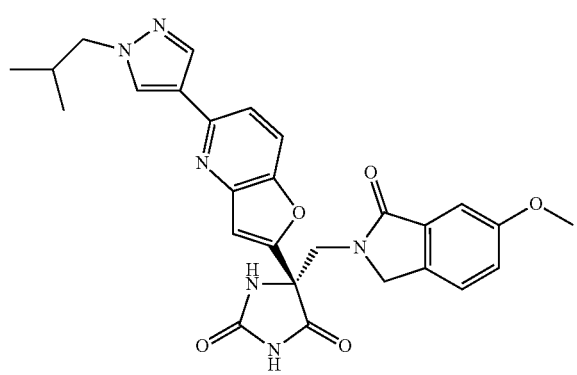
762
-continued
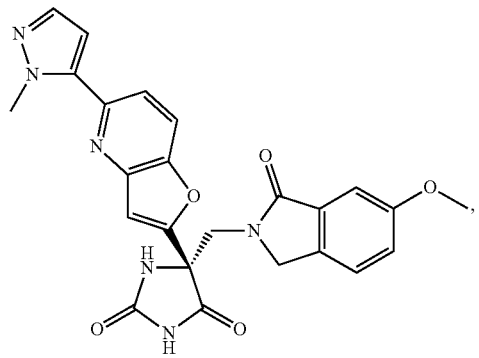
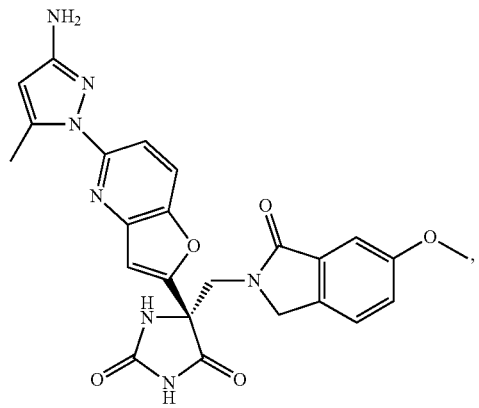
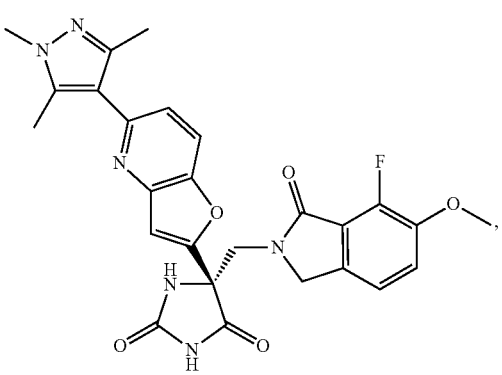

763
-continued
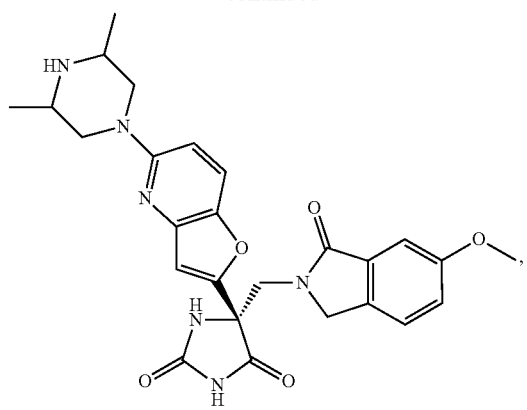
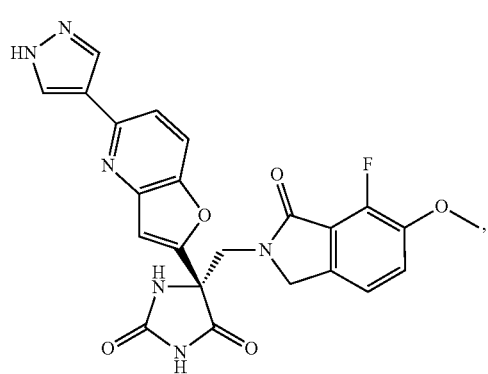
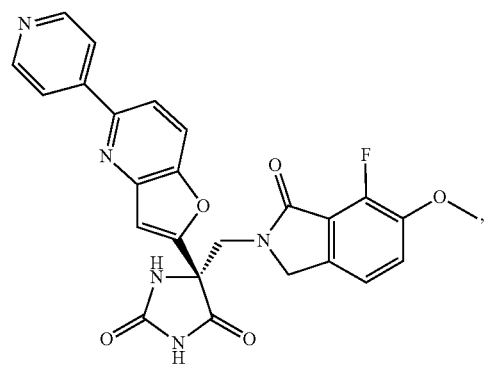
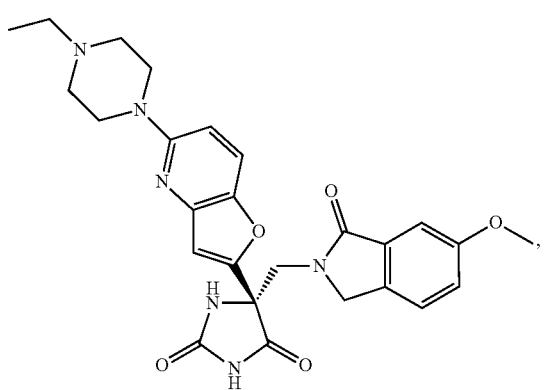
764
-continued
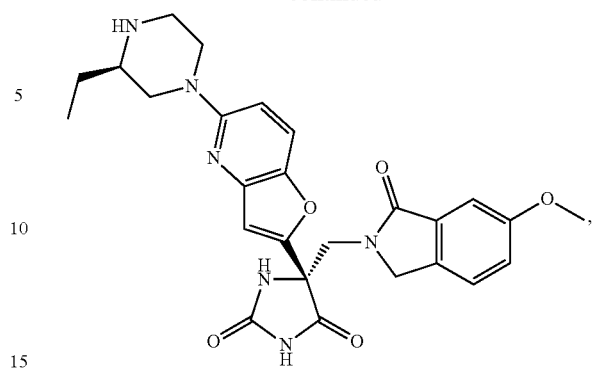
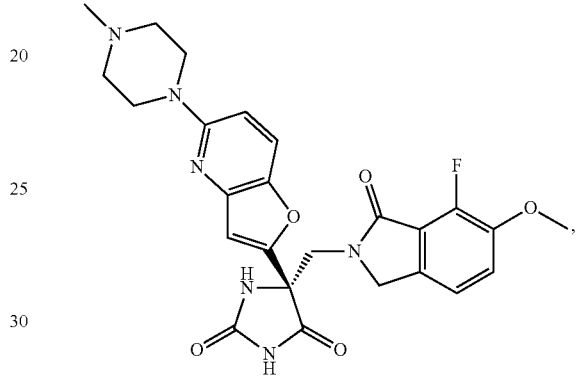
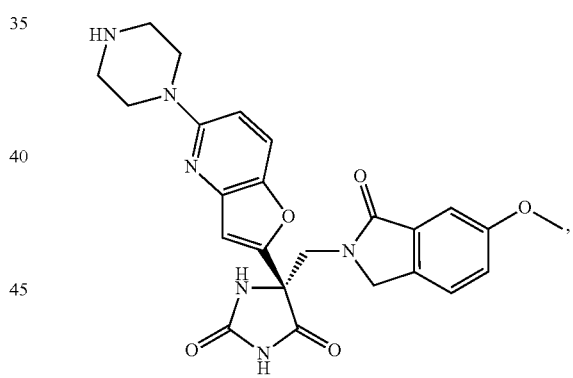
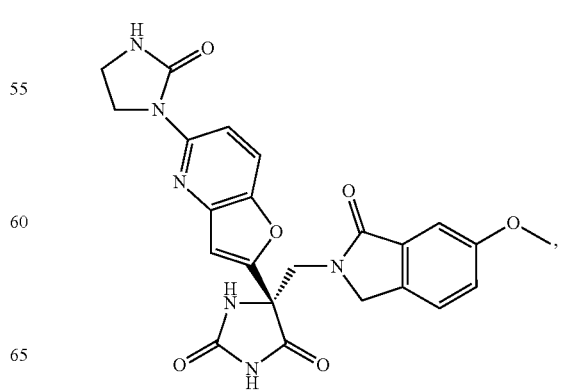

765
-continued
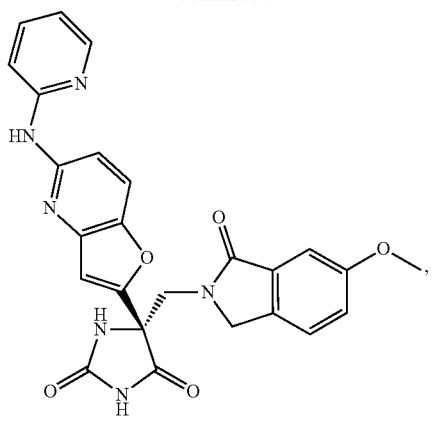
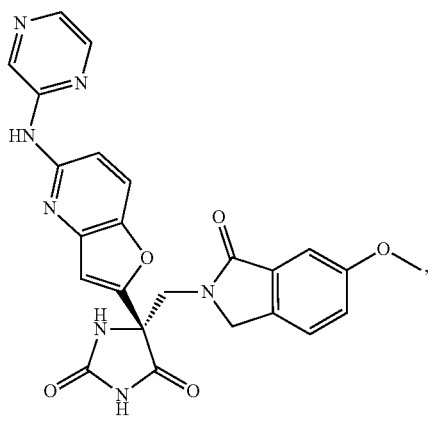
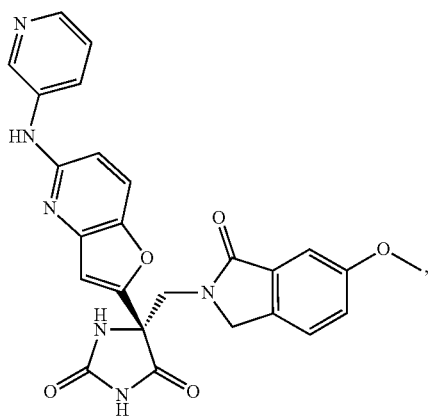
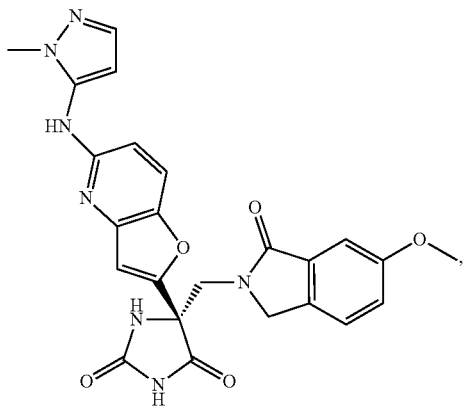
766
-continued
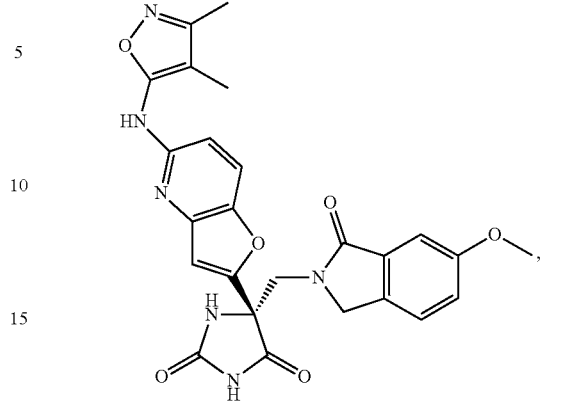
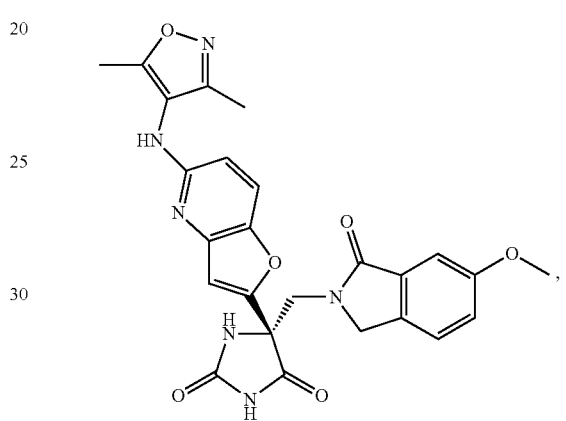
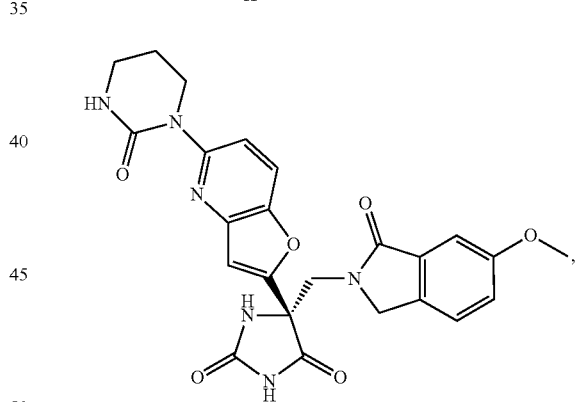
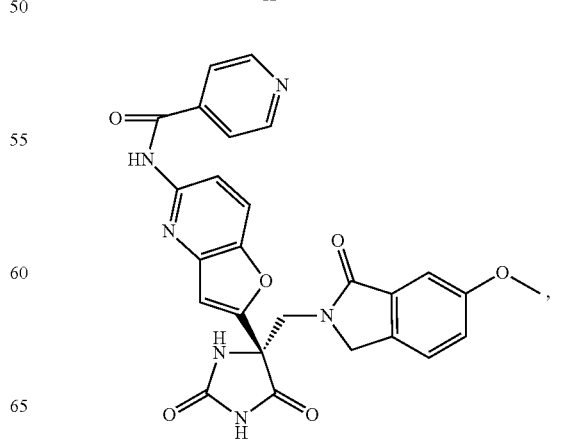

767
-continued
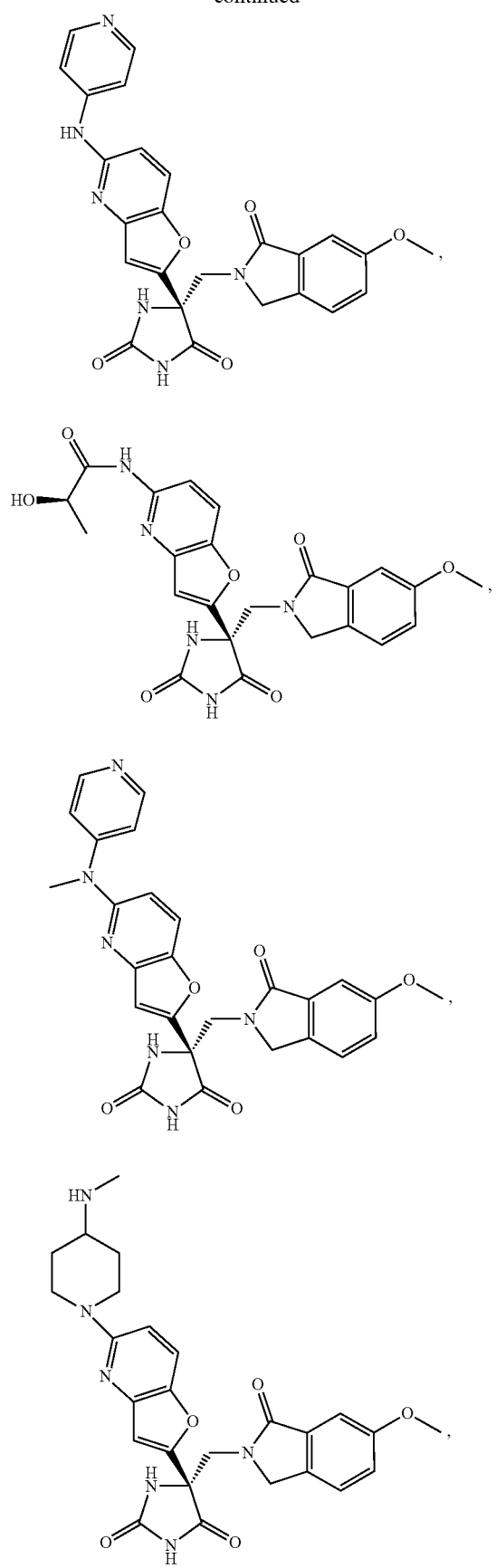
768
-continued
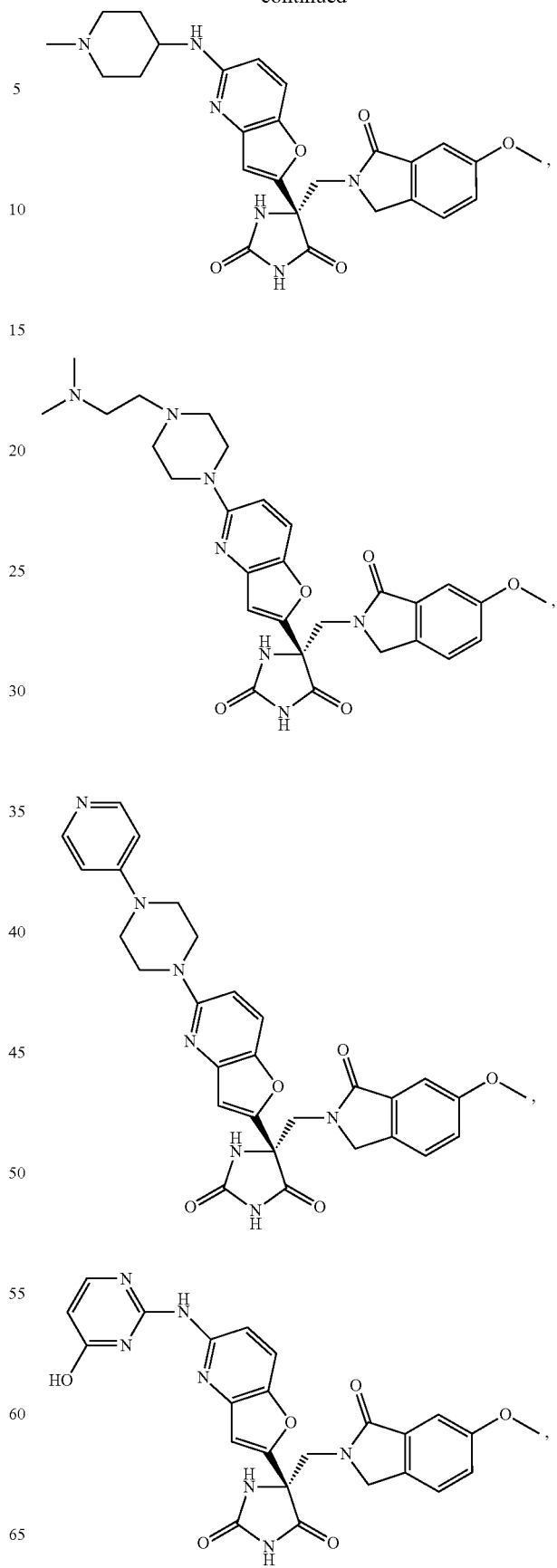

769
-continued
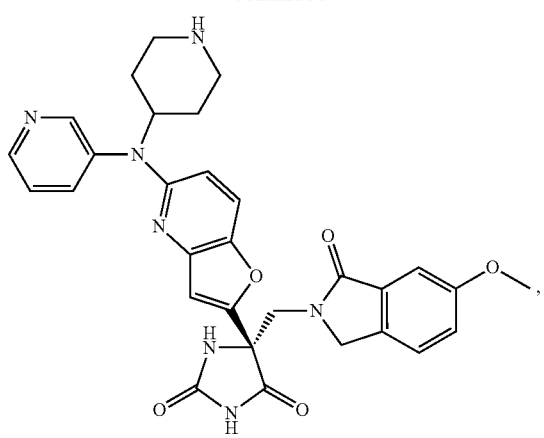
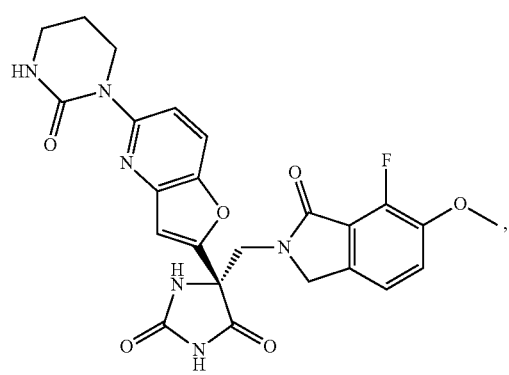
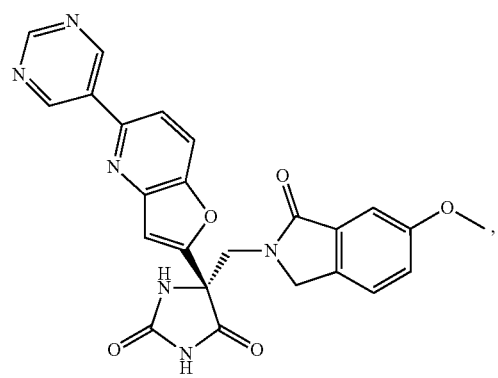
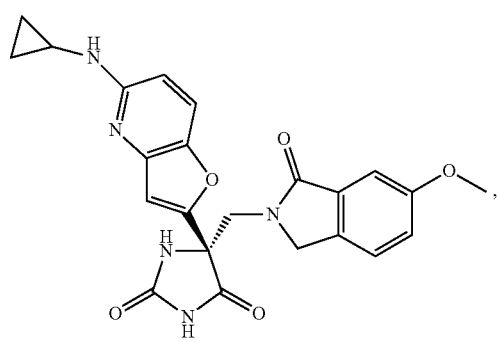
770
-continued
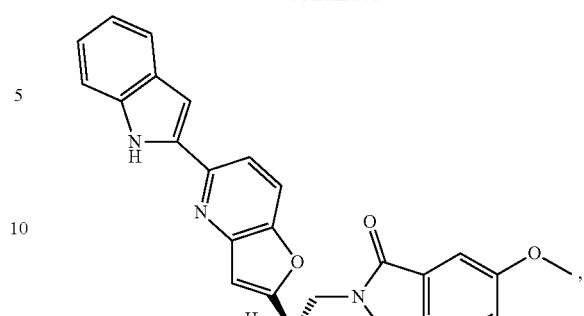
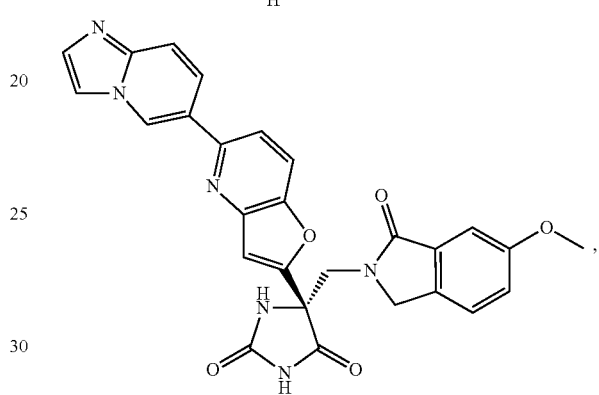
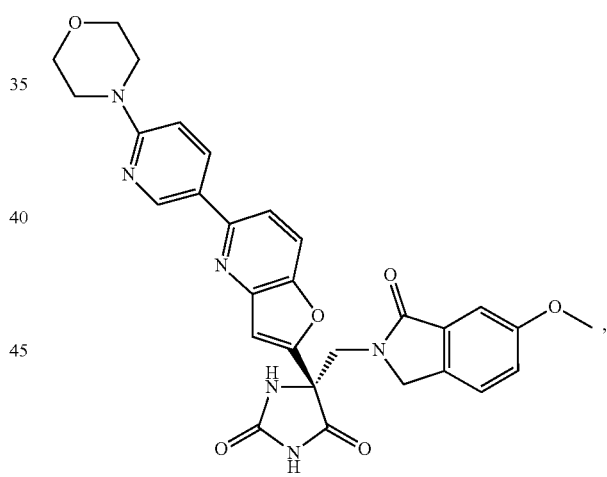
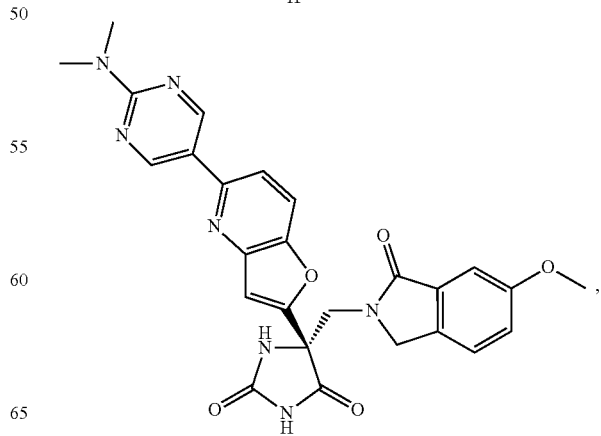

771
-continued
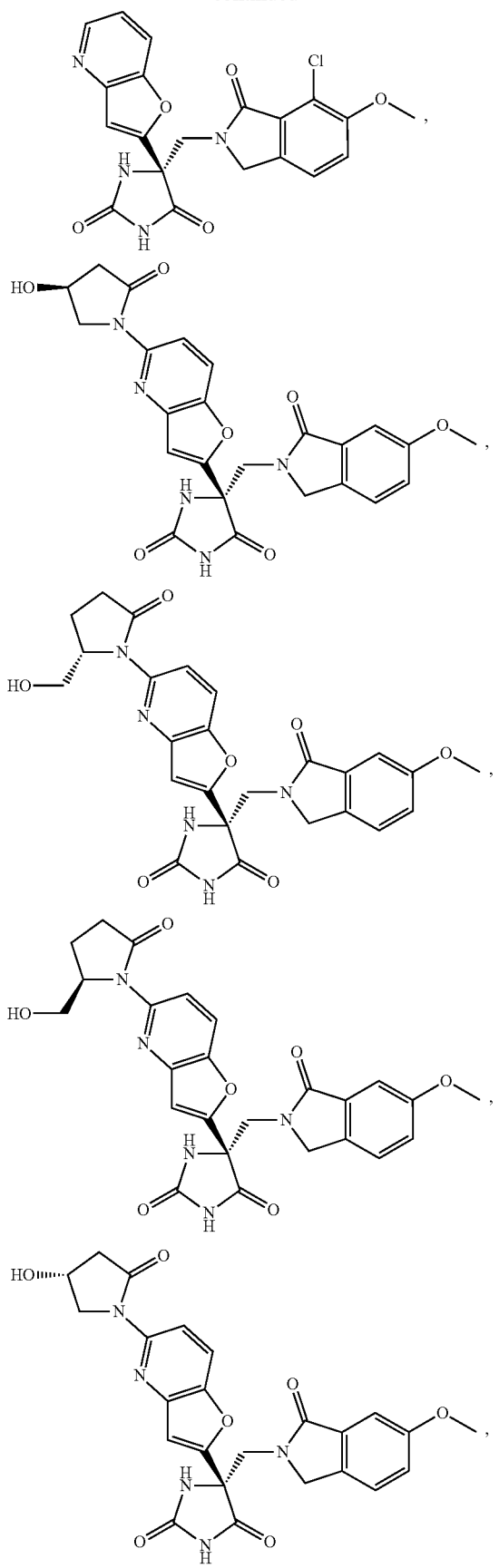
772
-continued
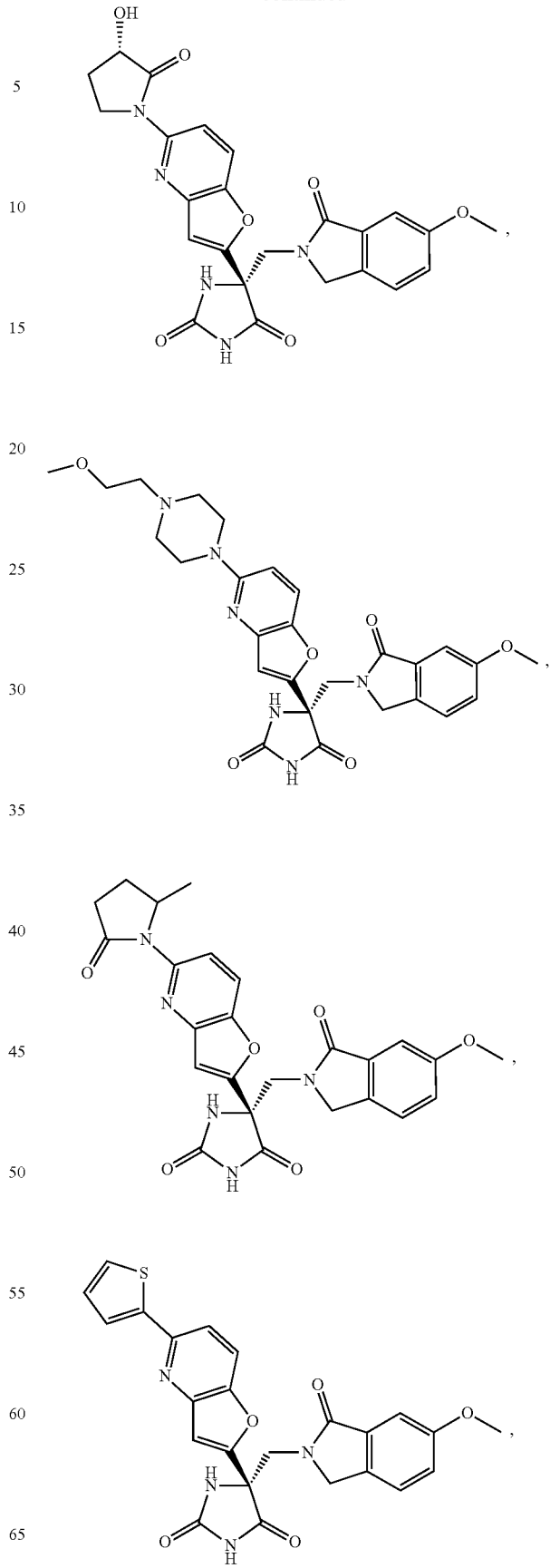

773
-continued
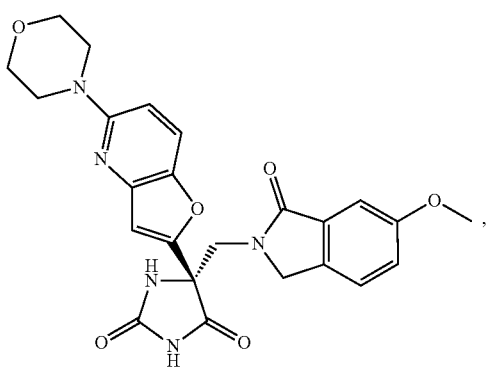
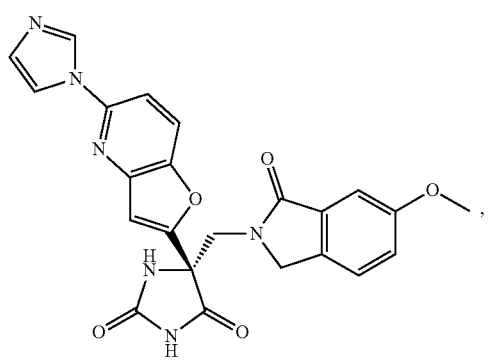
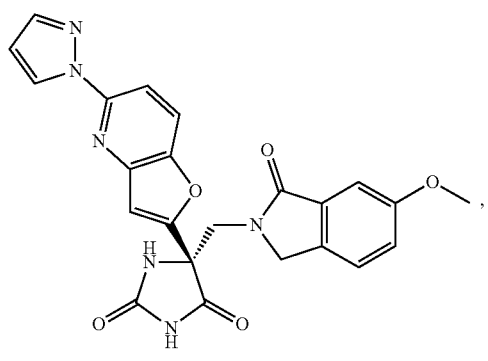
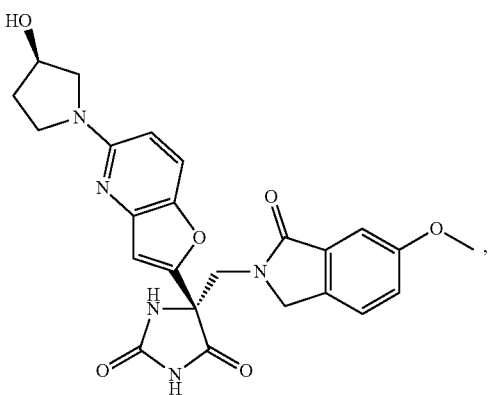
774
-continued
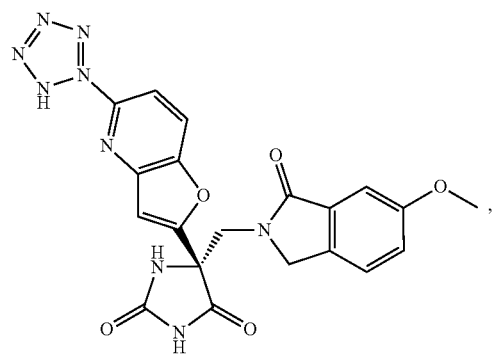
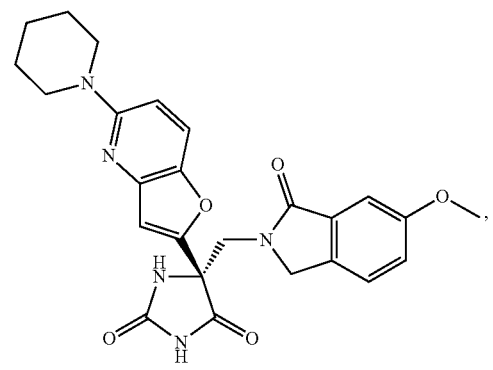
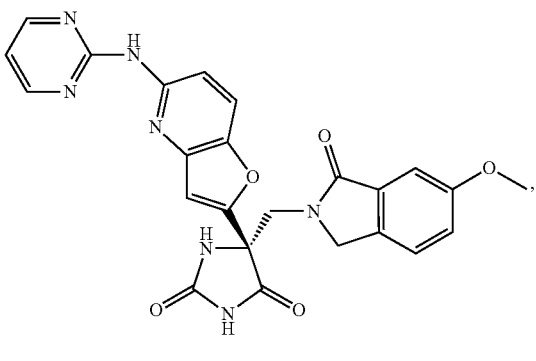
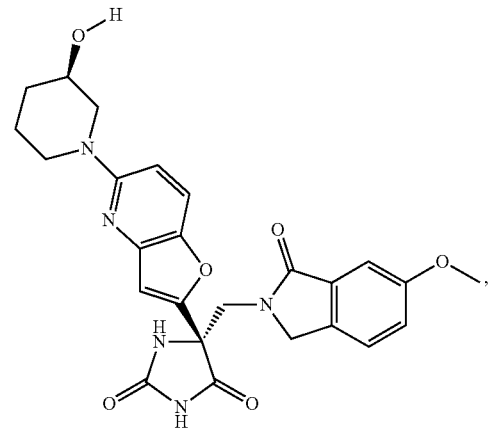

775
-continued
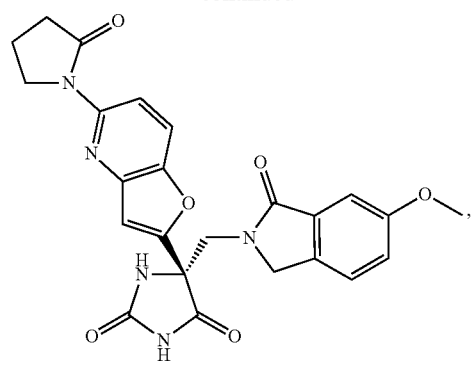
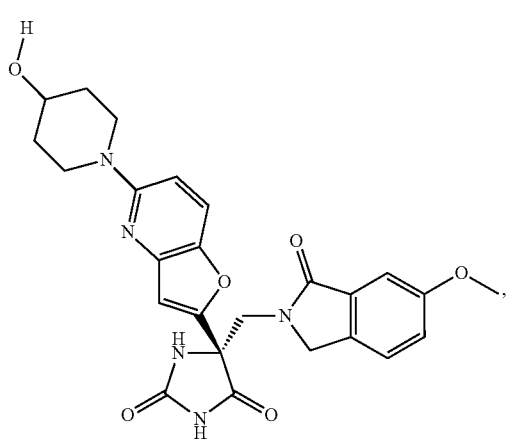
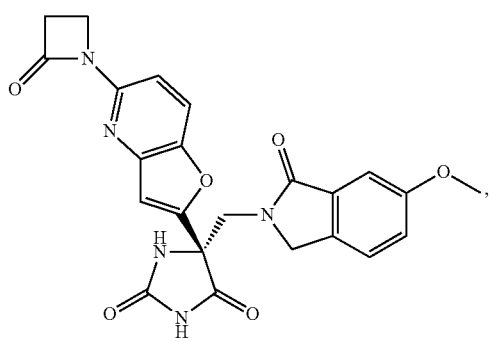
776
-continued
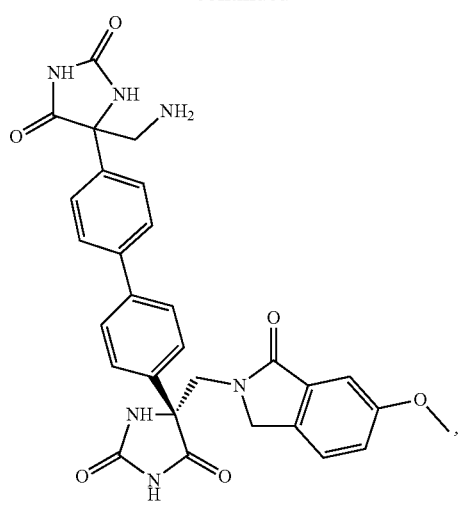
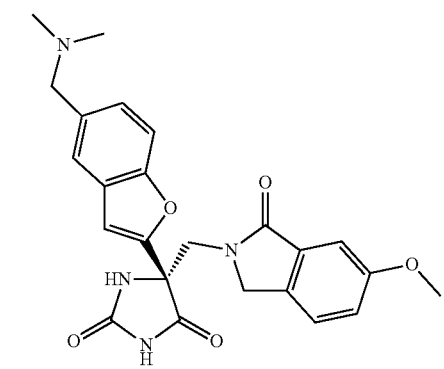
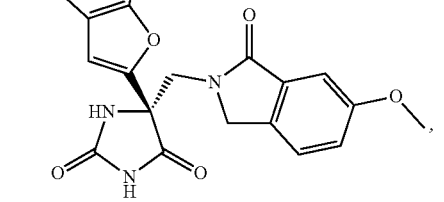

777
-continued
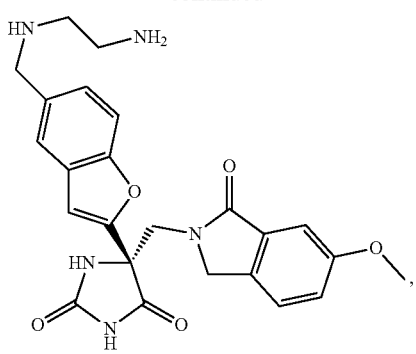
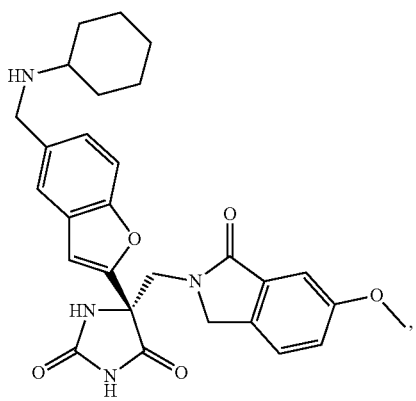
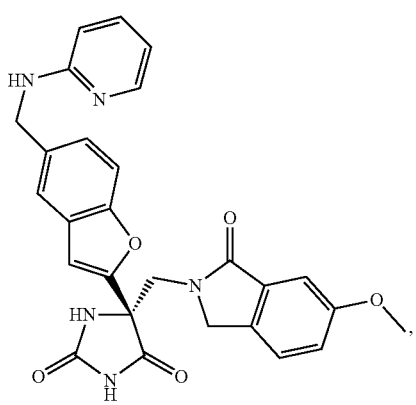
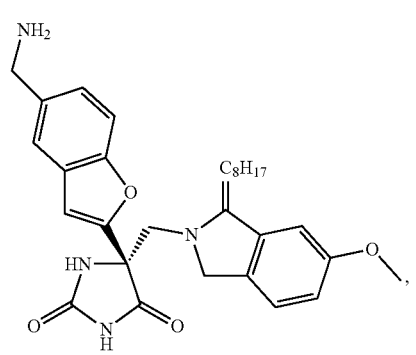
778
-continued
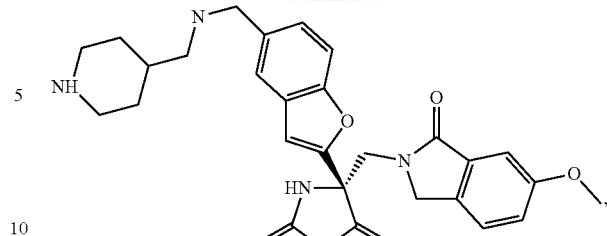
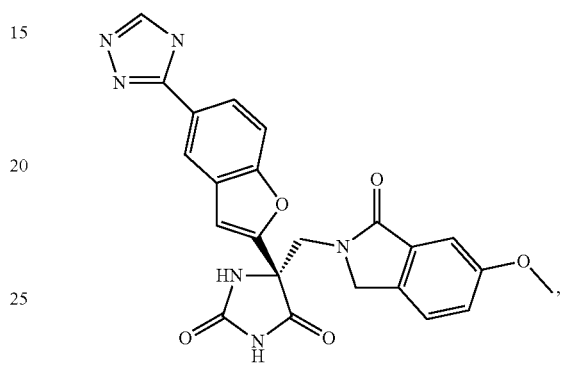
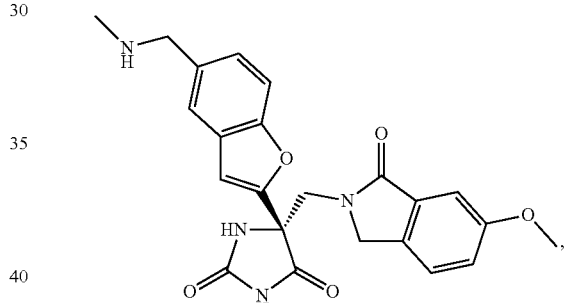
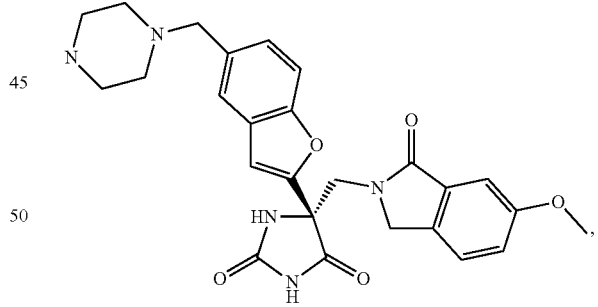
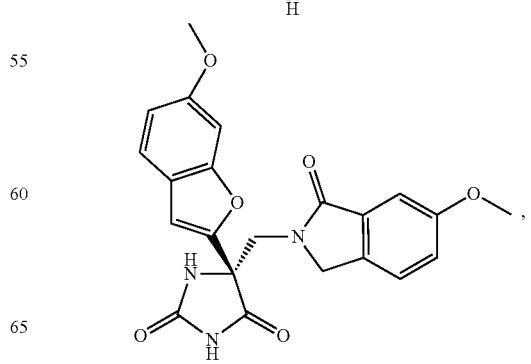

779
-continued
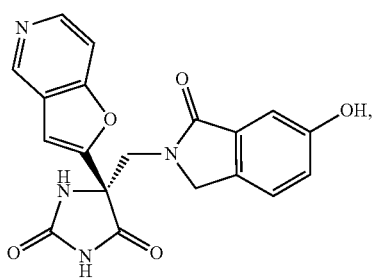
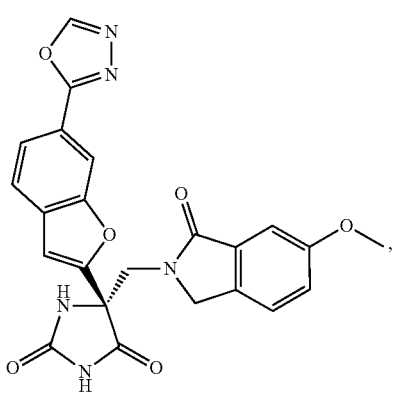
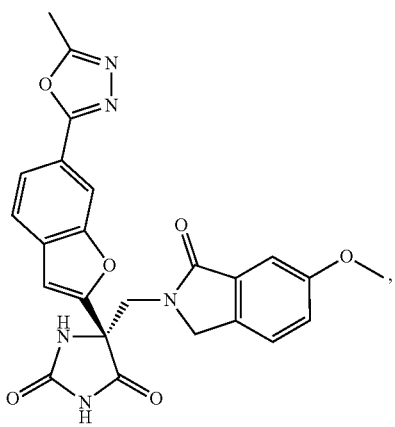
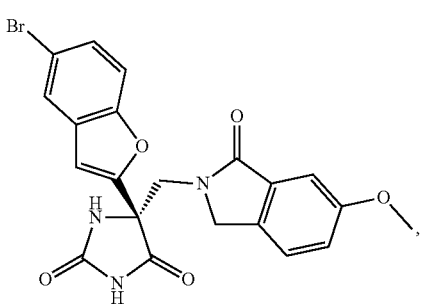
780
-continued
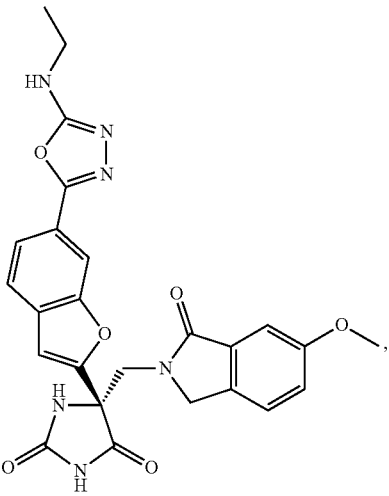
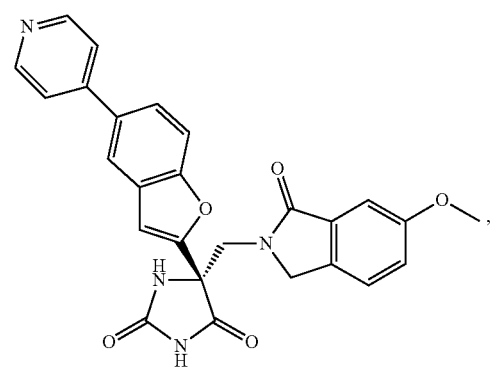
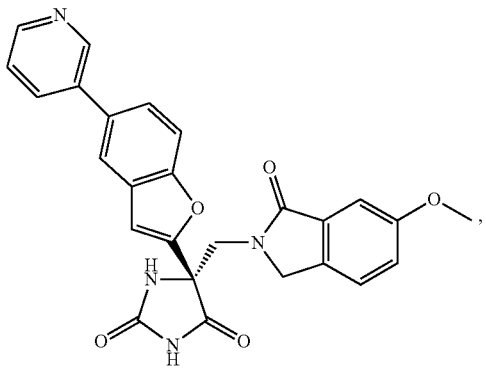
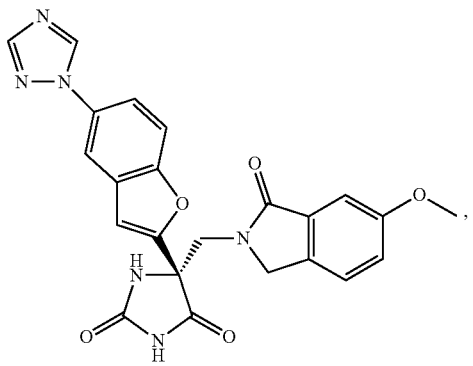

781
-continued
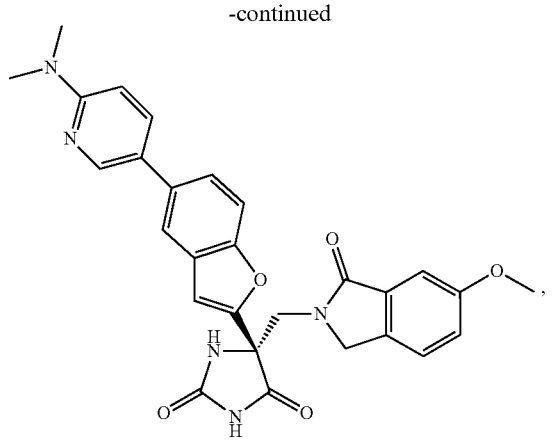
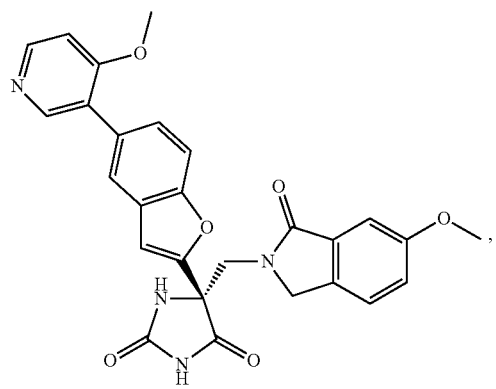
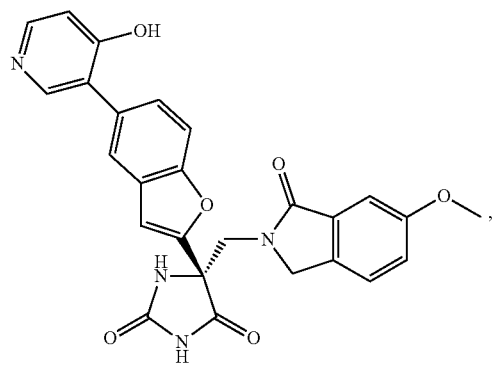
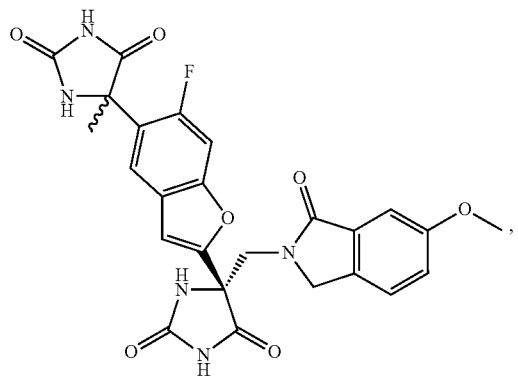
782
-continued
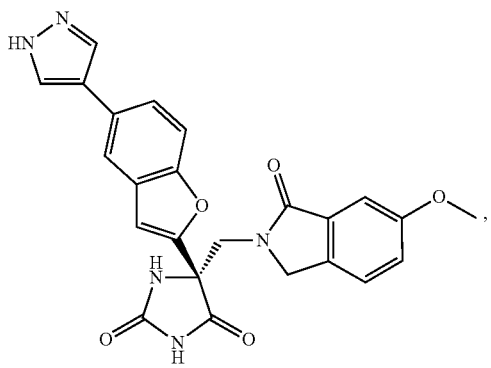
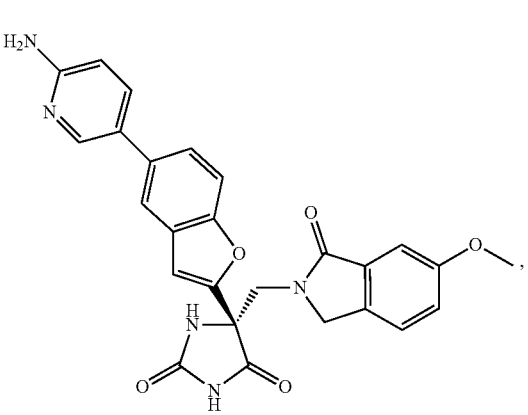
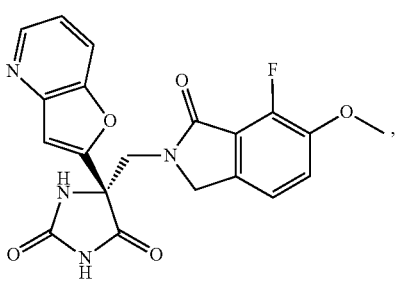
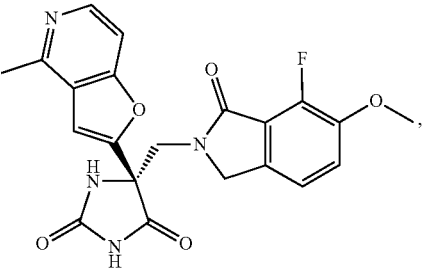

783
-continued
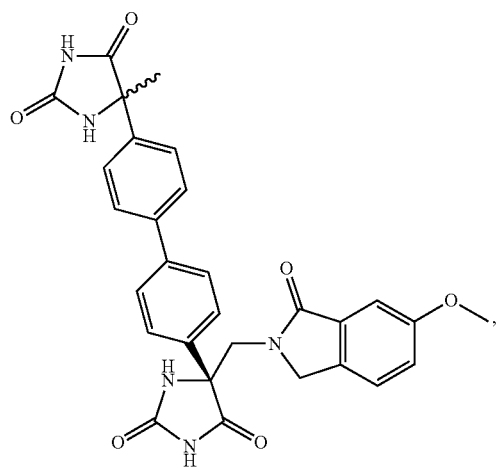
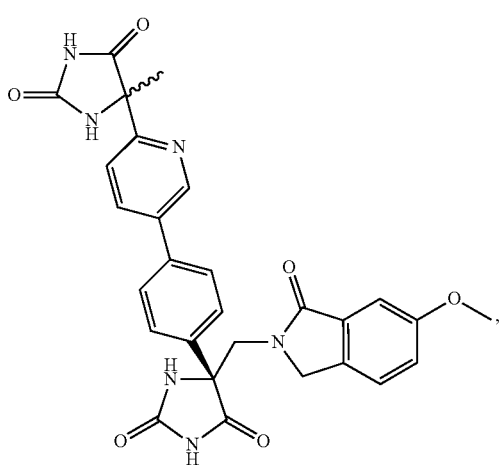
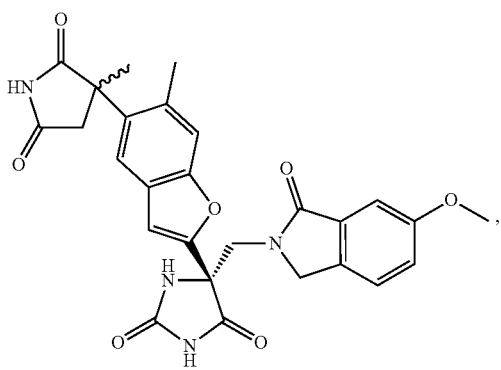
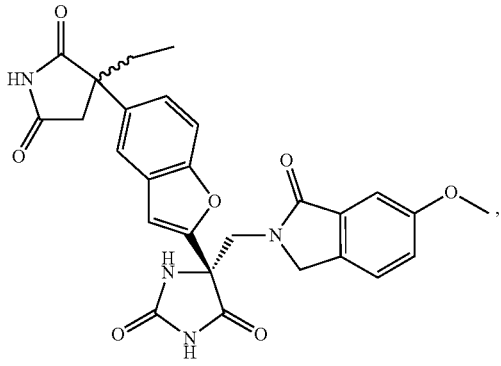
784
-continued
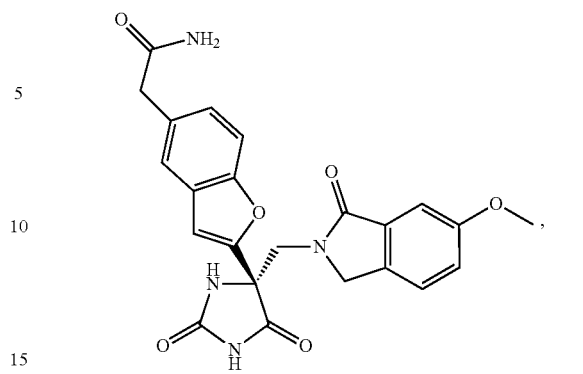
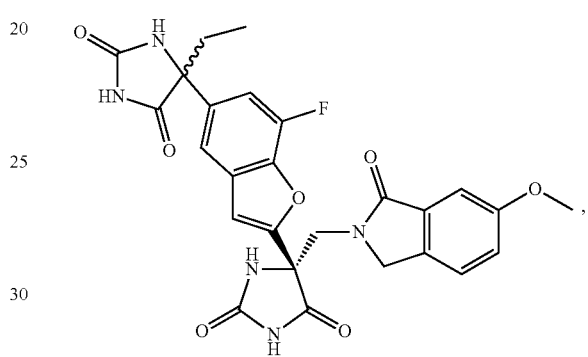
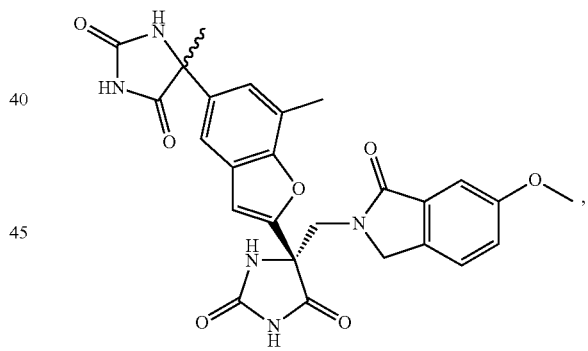
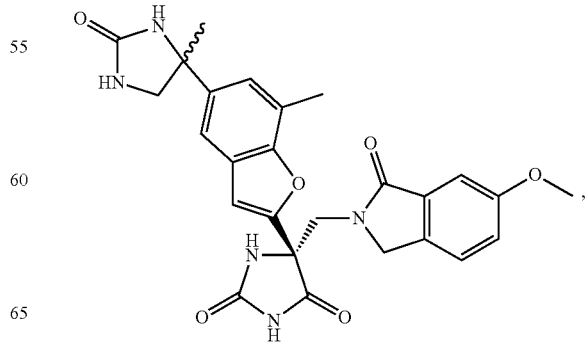

785
-continued
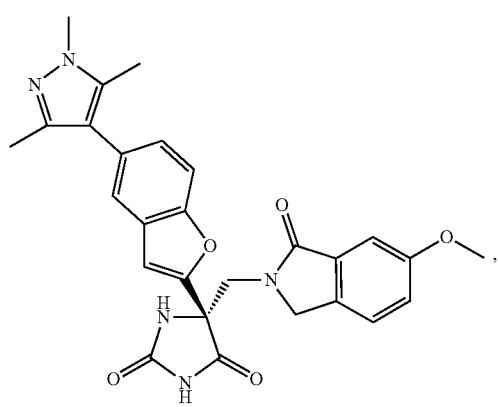
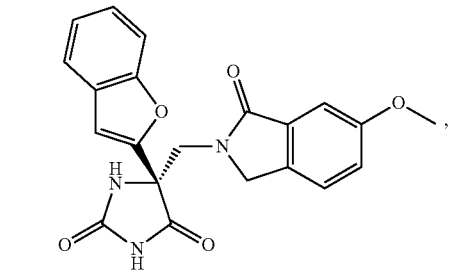
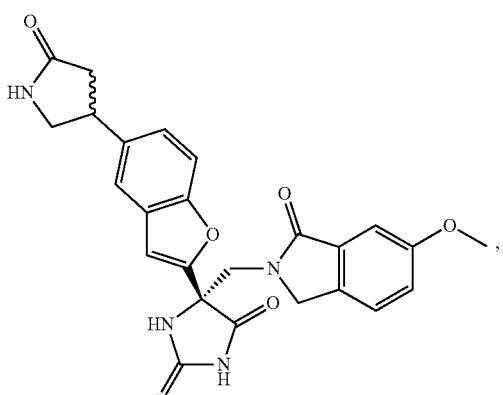
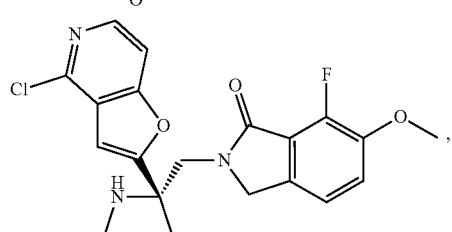
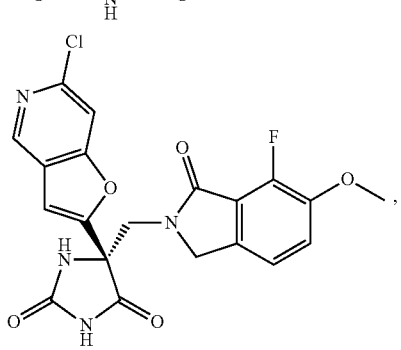
786
-continued
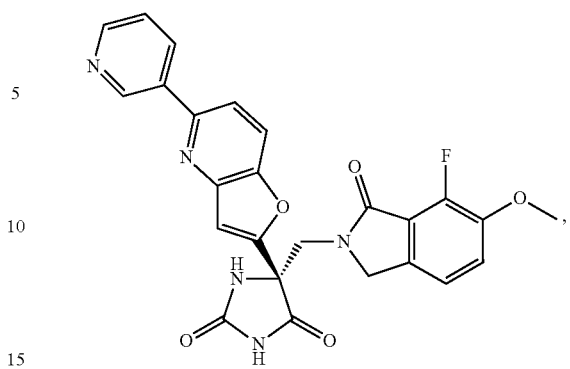
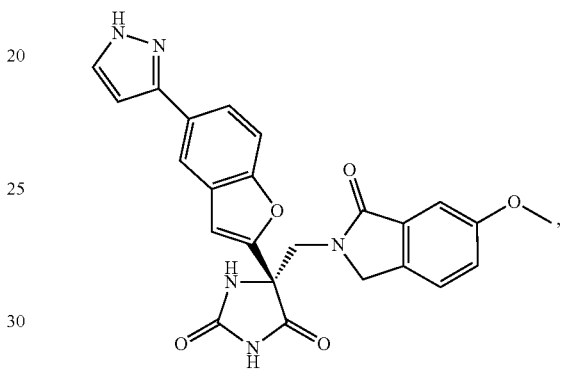
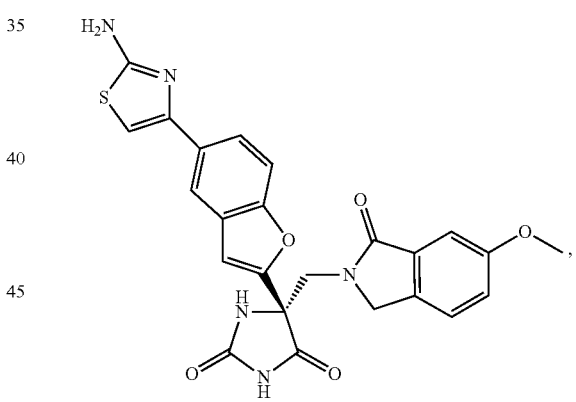
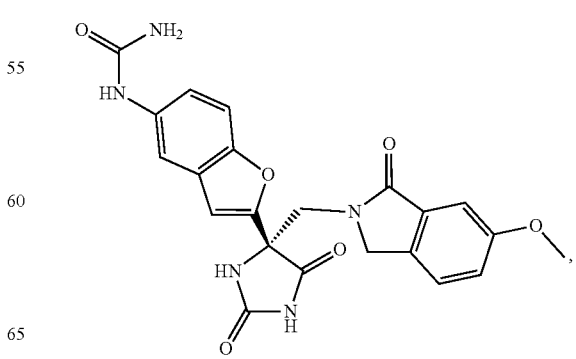

787
-continued
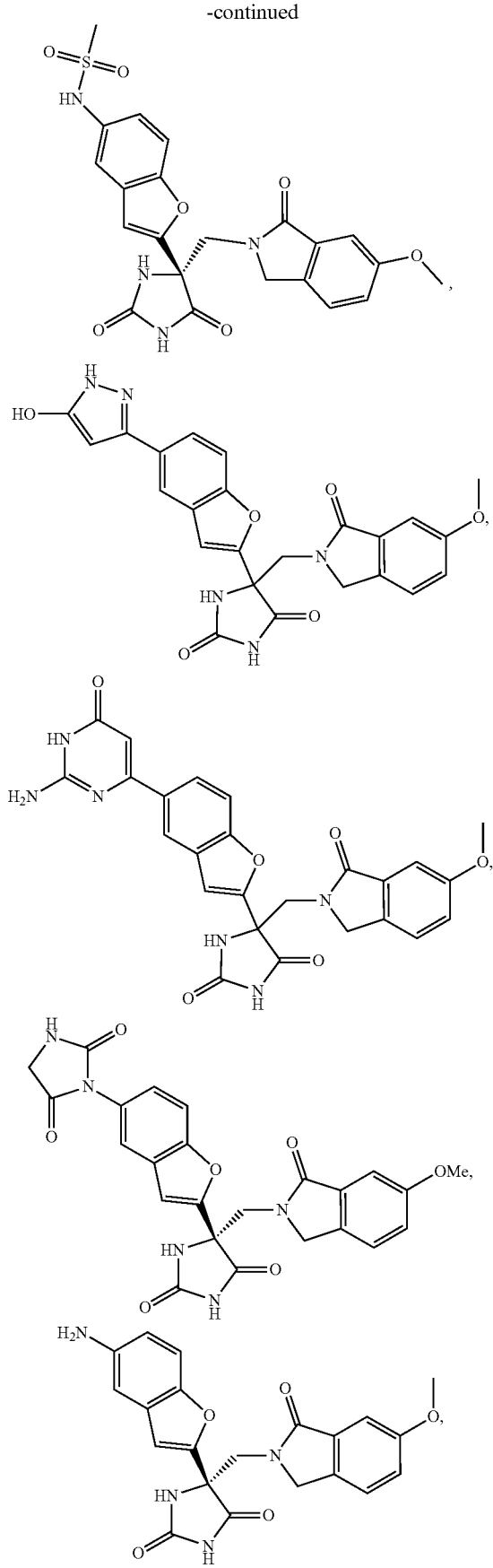
788
-continued
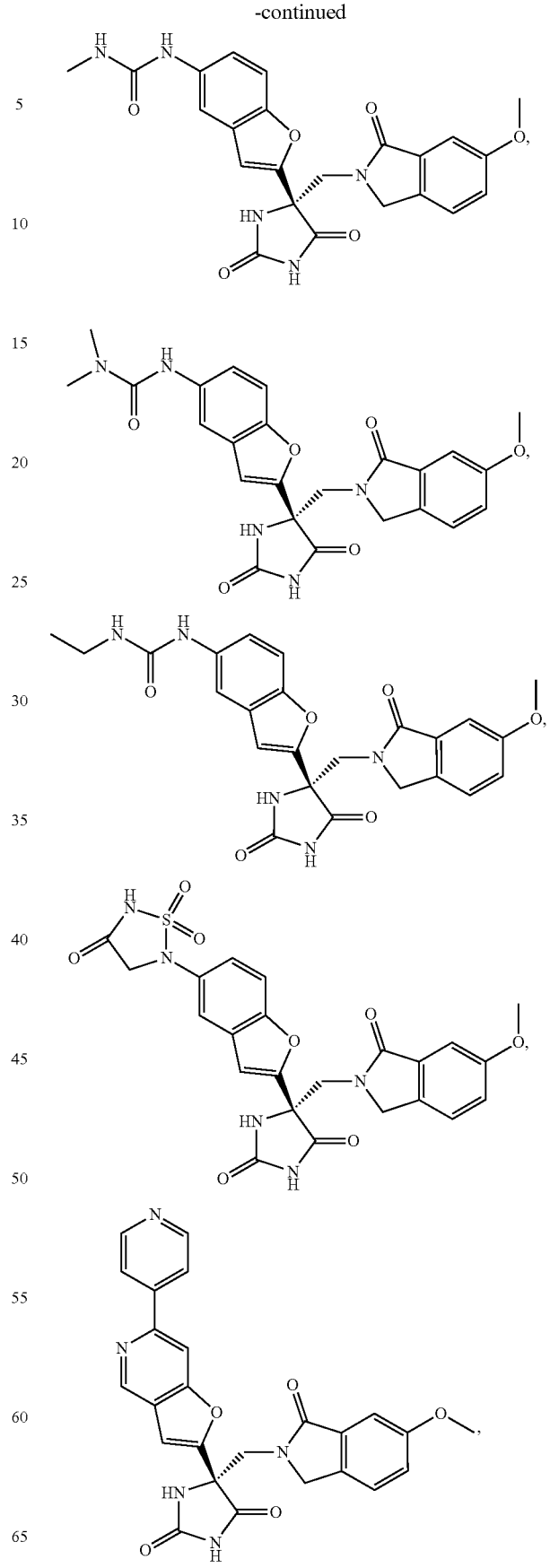

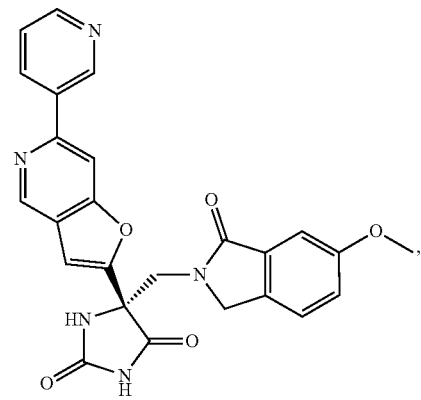
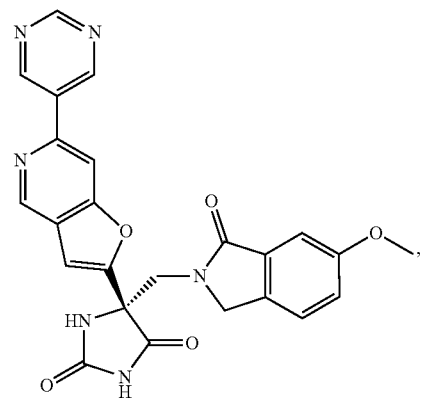
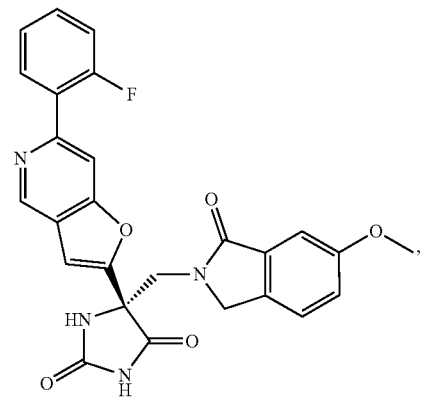
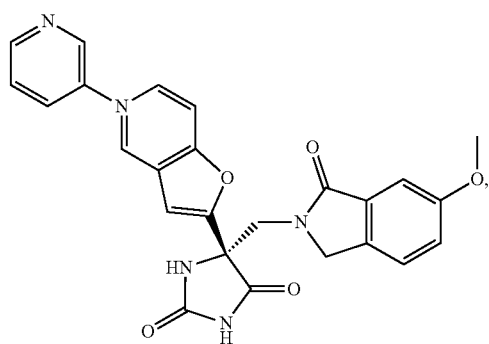
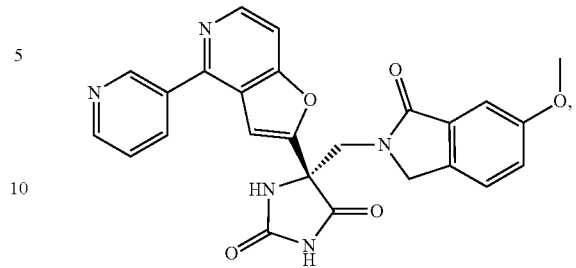
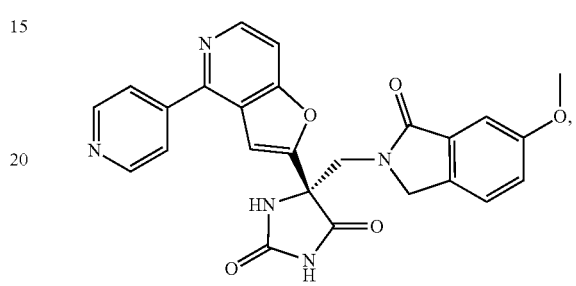
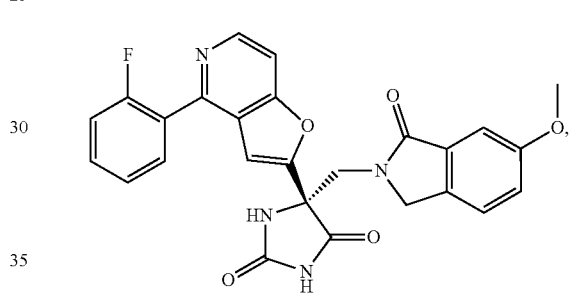
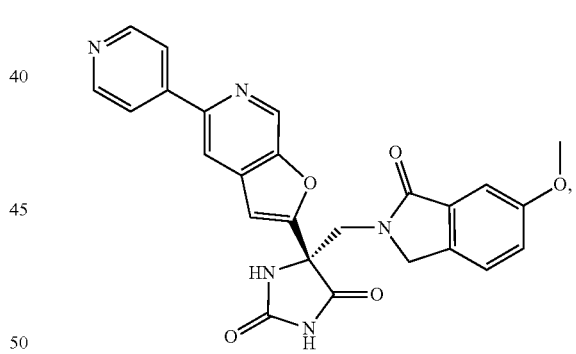
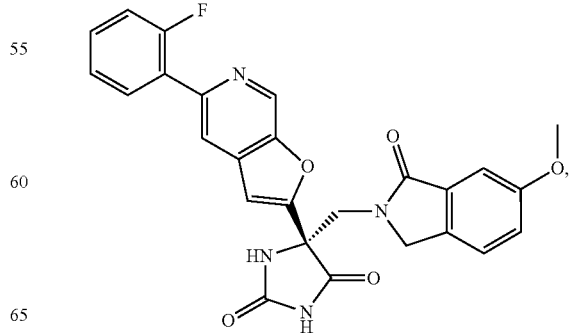

791
-continued
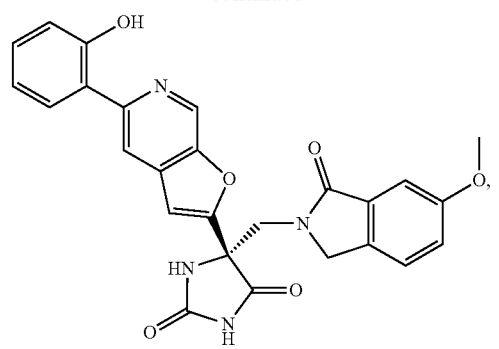
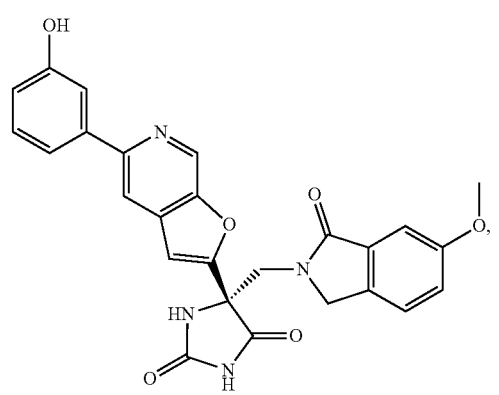
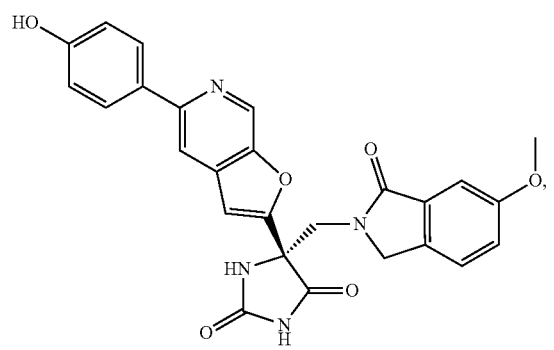
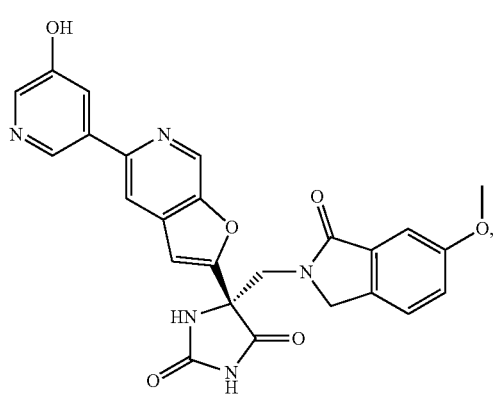
792
-continued
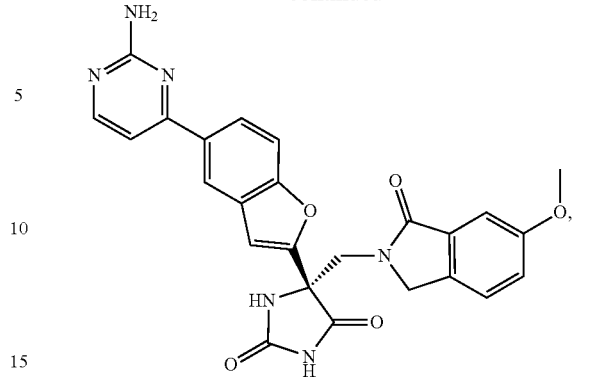
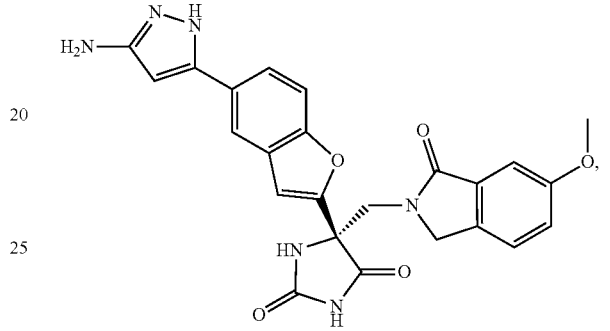
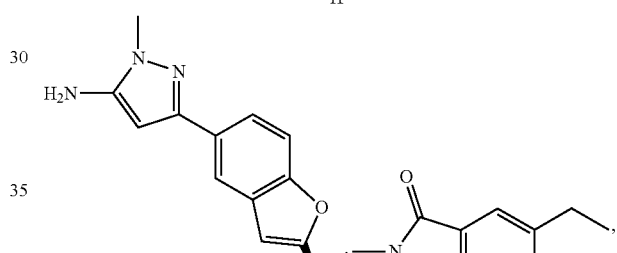
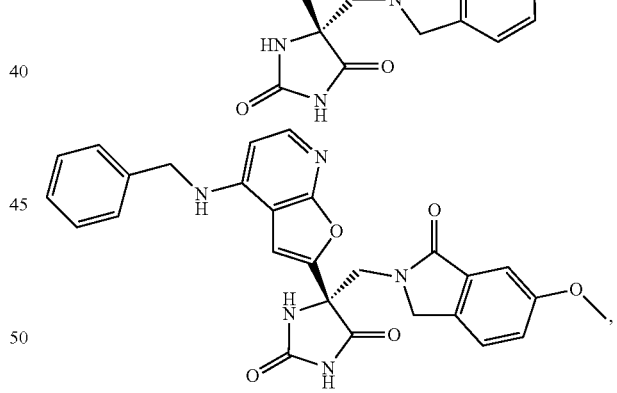

793
-continued
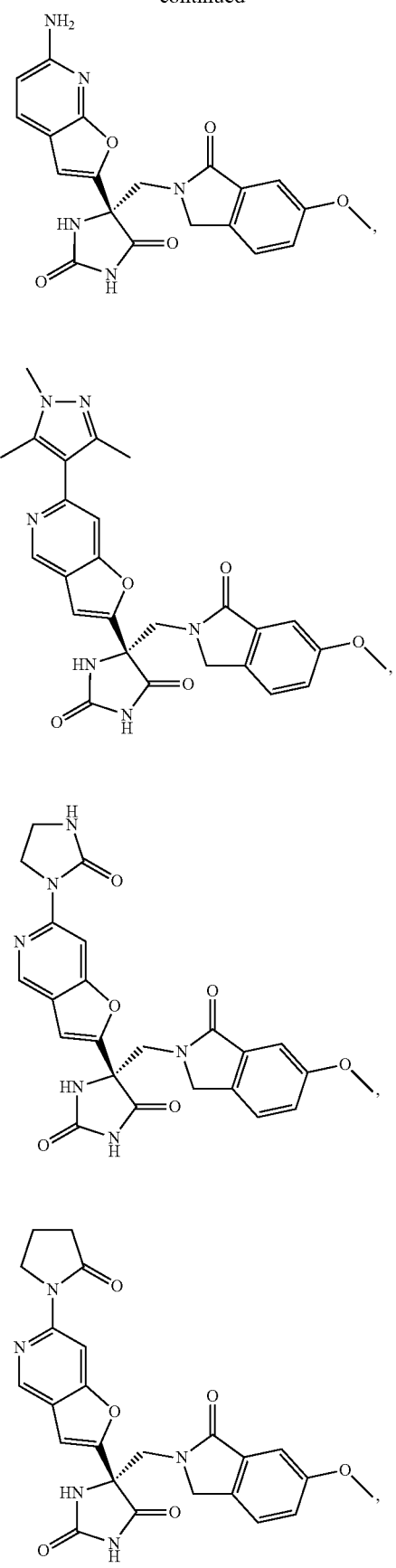
794
-continued
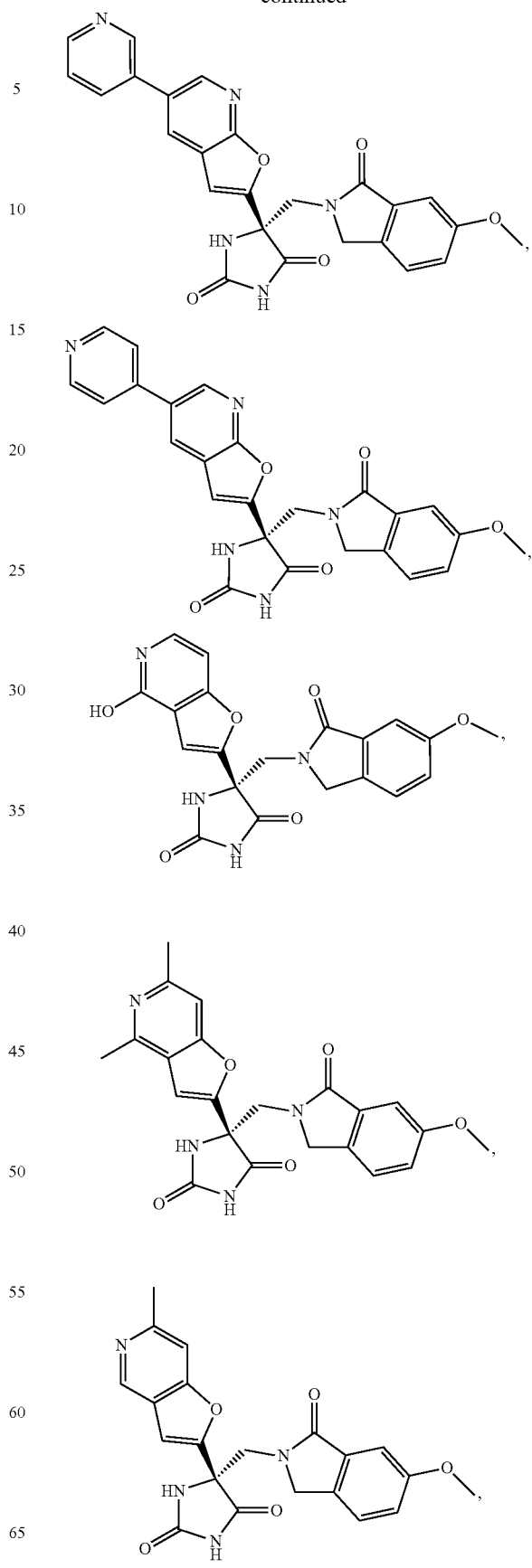

795
-continued
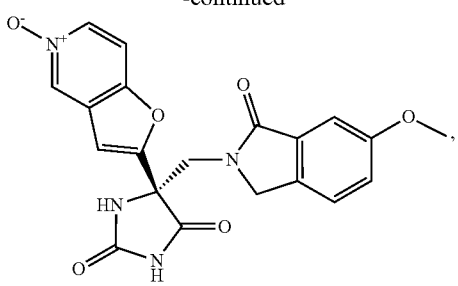
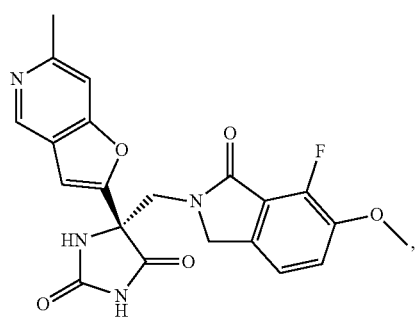
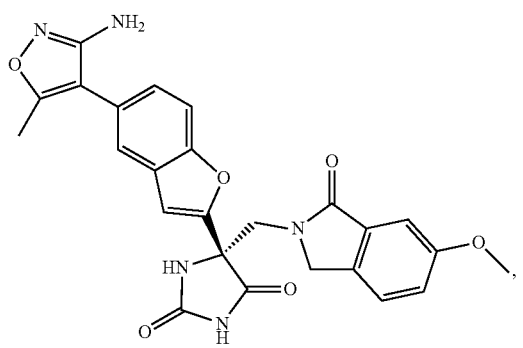
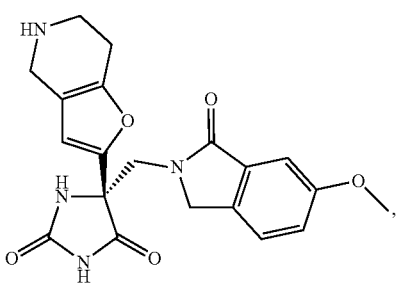
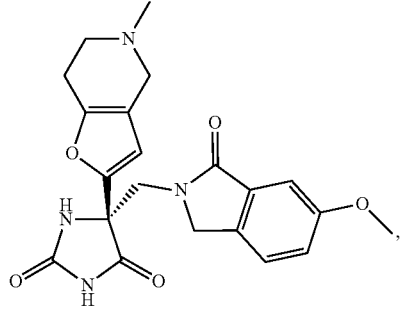
796
-continued
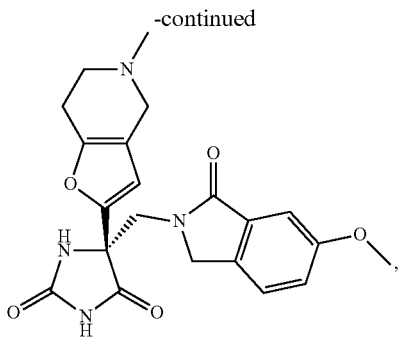
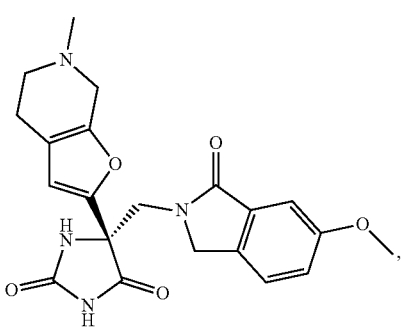
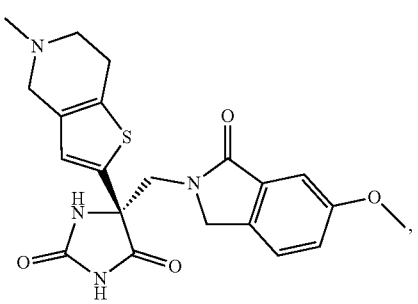
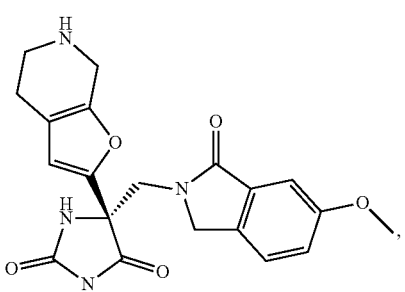
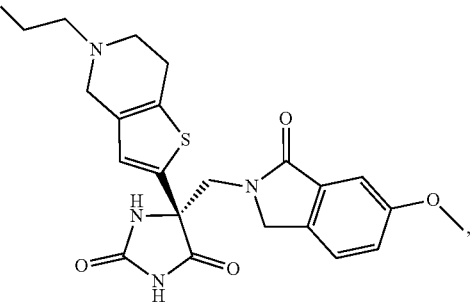

797
-continued
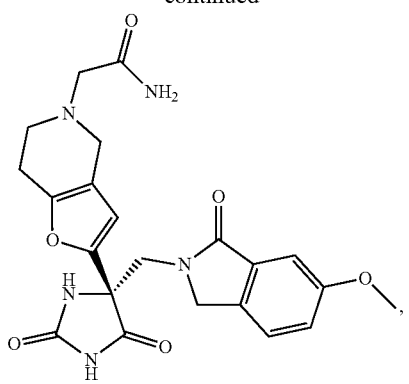
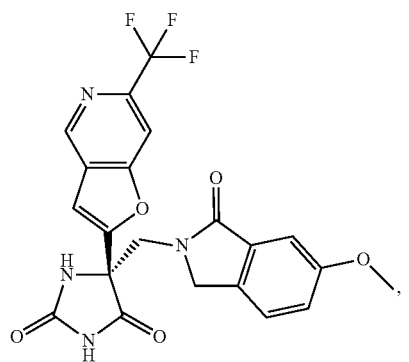
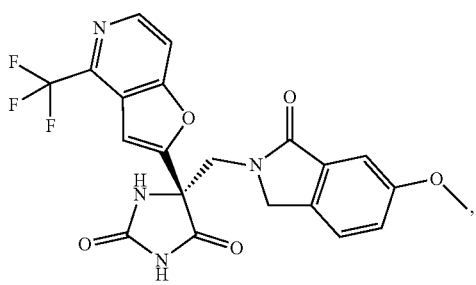
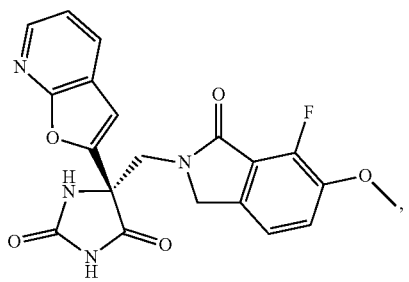
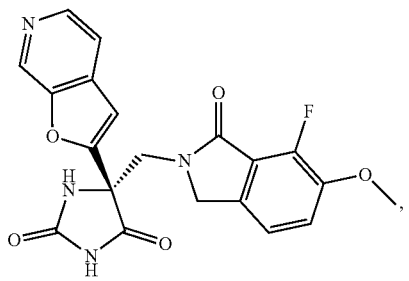
798
-continued
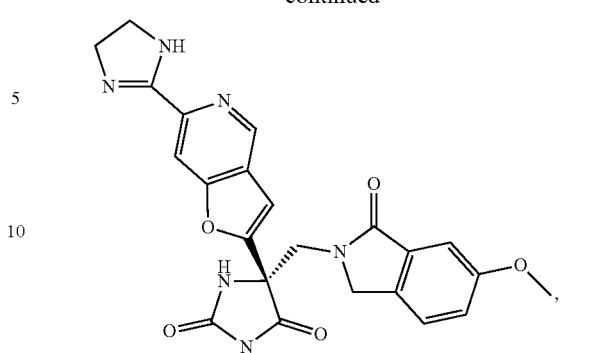
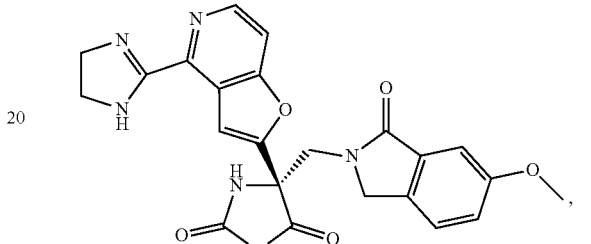
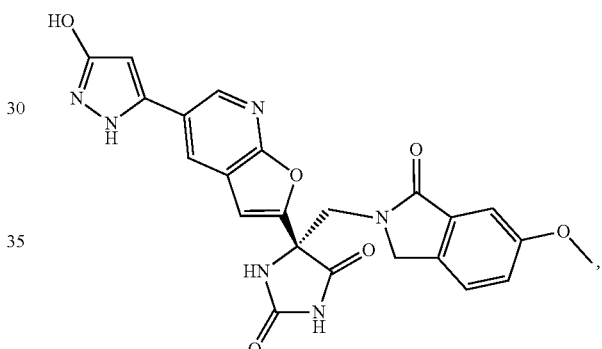
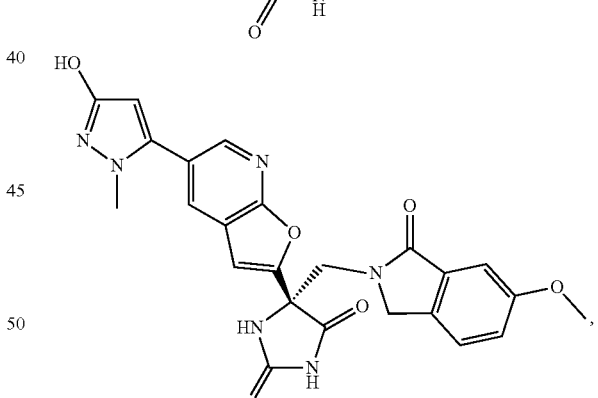
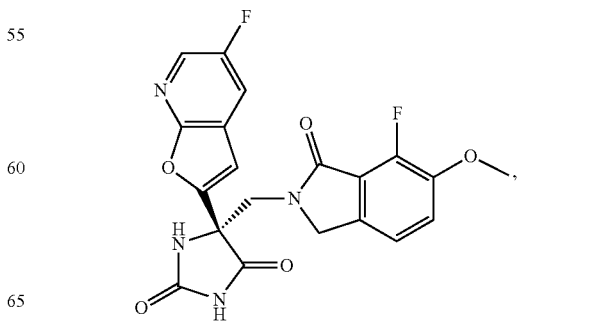

799
-continued
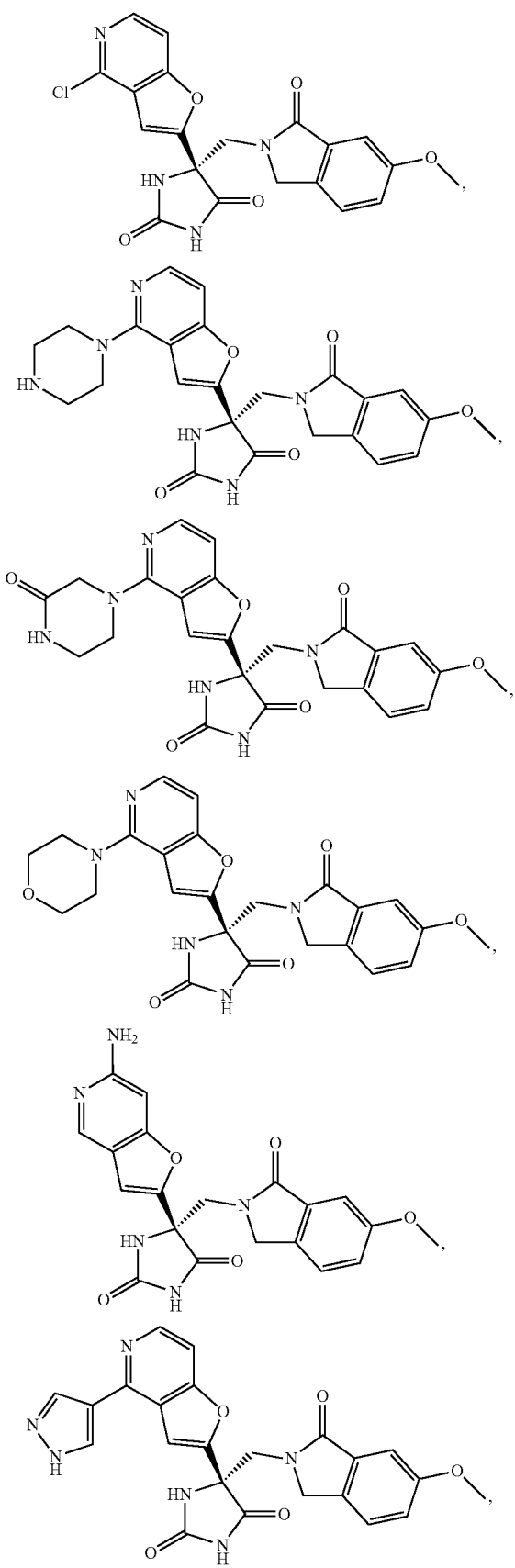
800
-continued
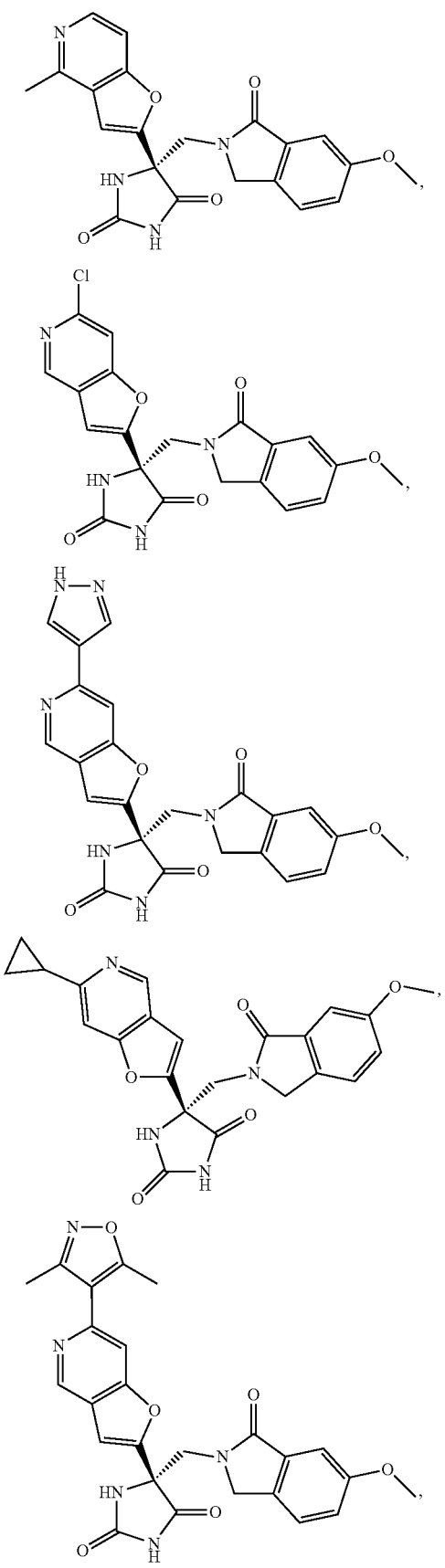

801
-continued
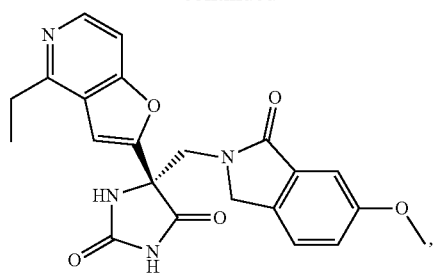
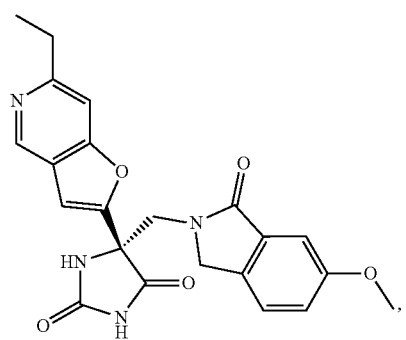
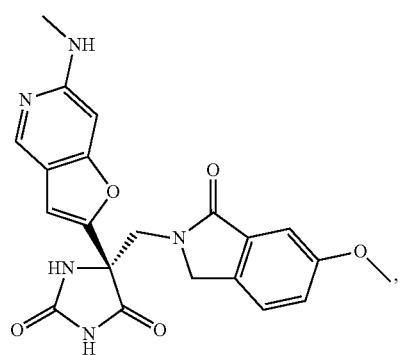
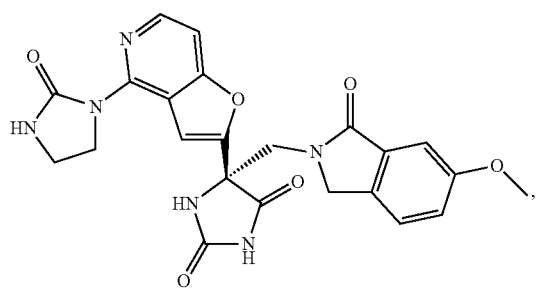
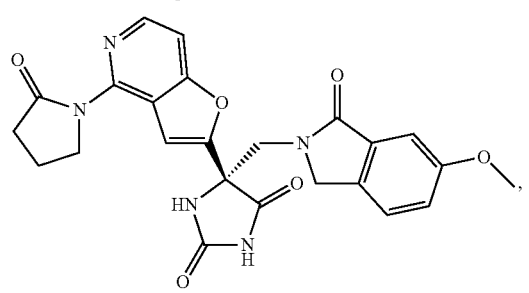
802
-continued
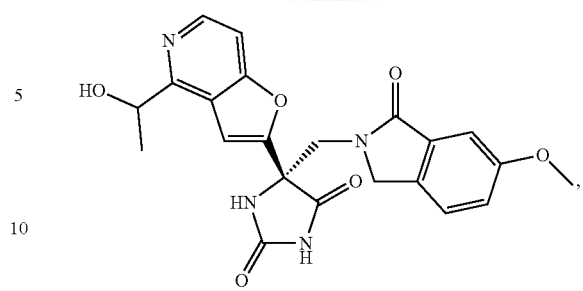
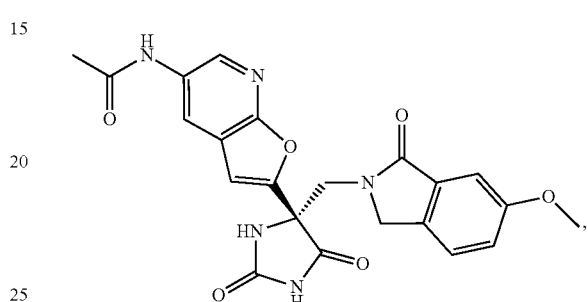
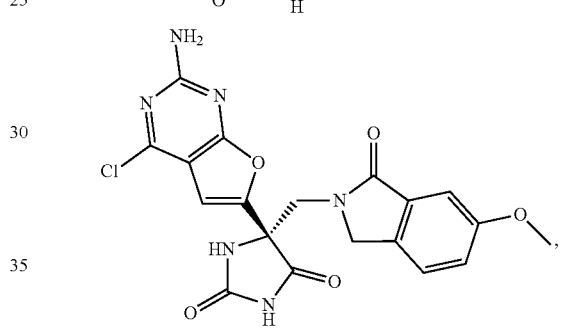
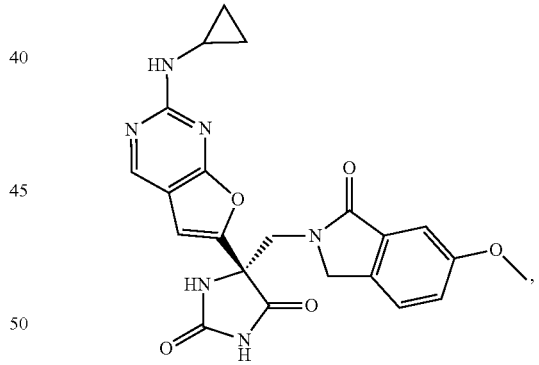
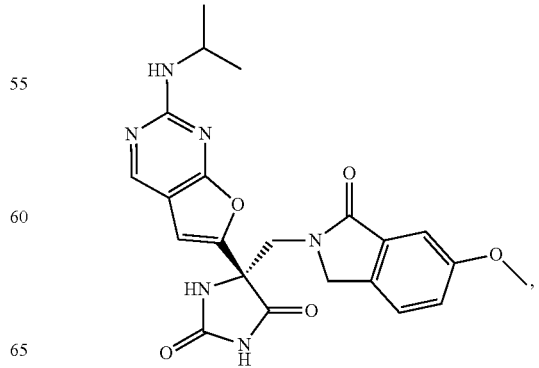

803
-continued
804
-continued
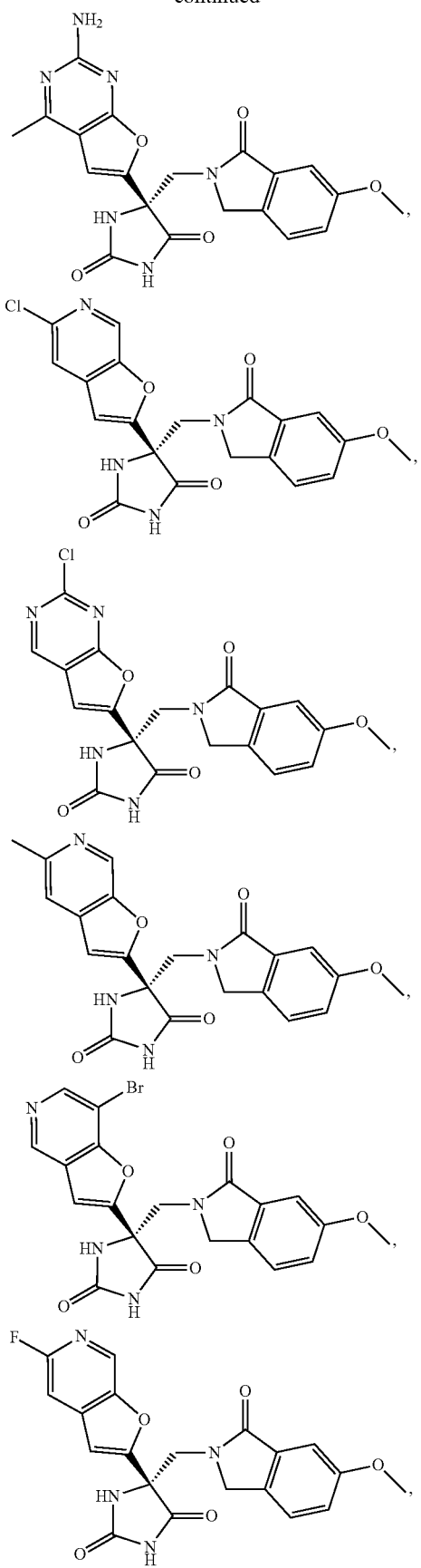
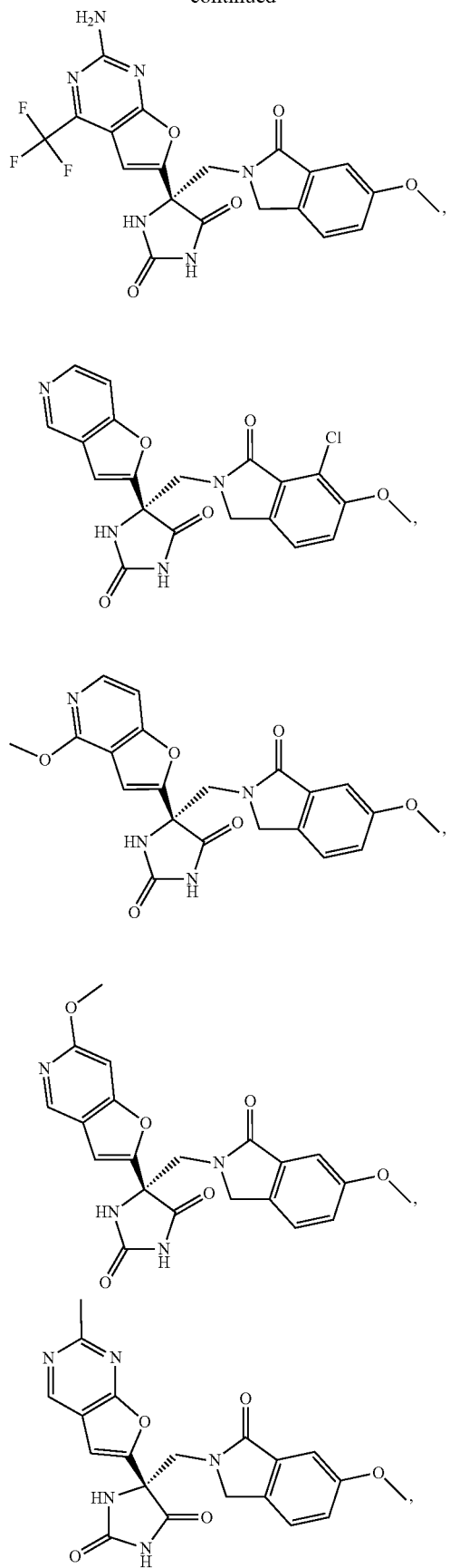

805
-continued
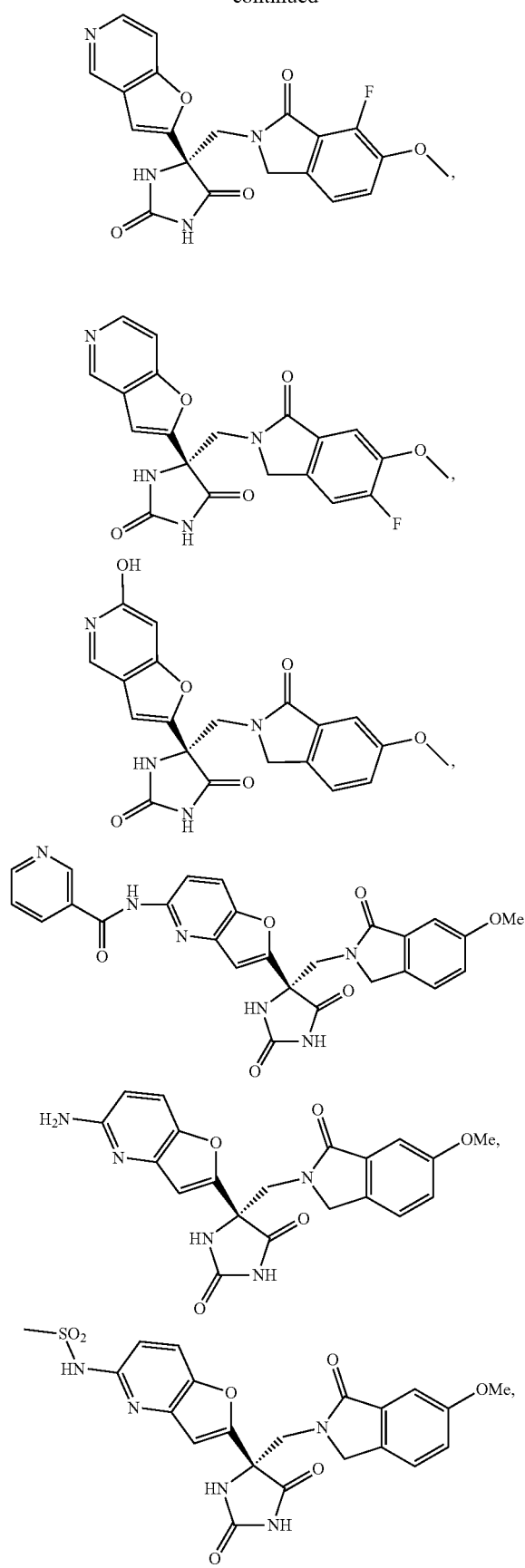
806
-continued
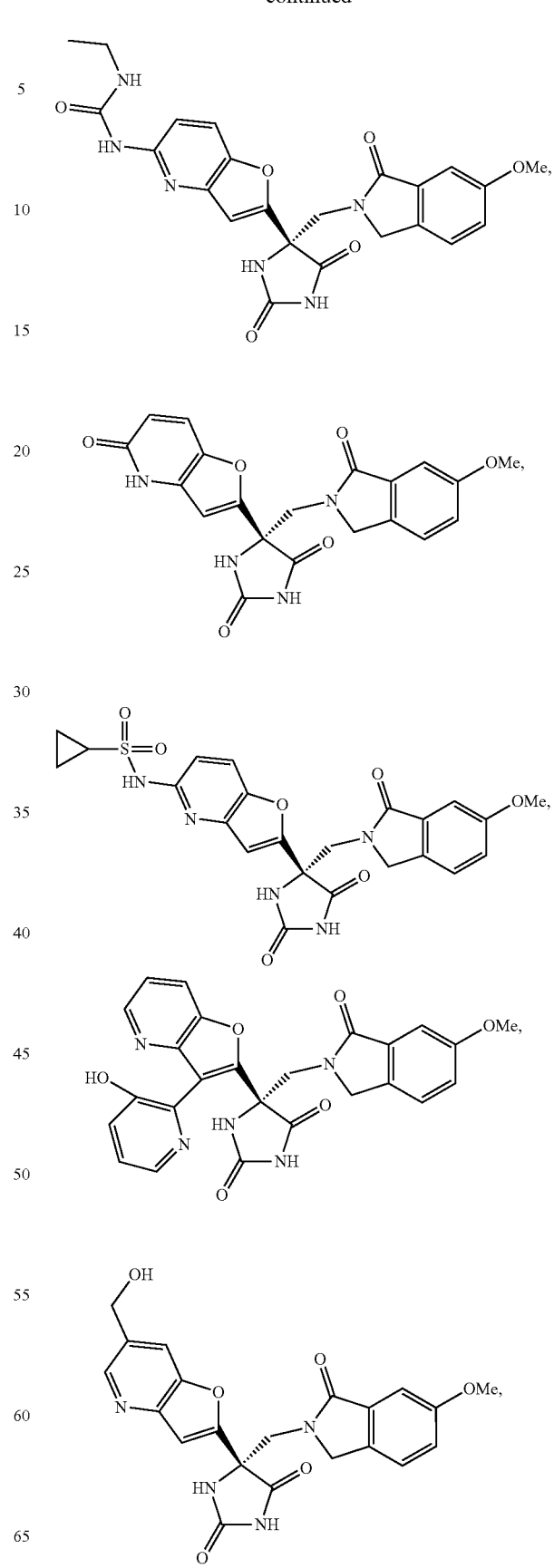

807
-continued
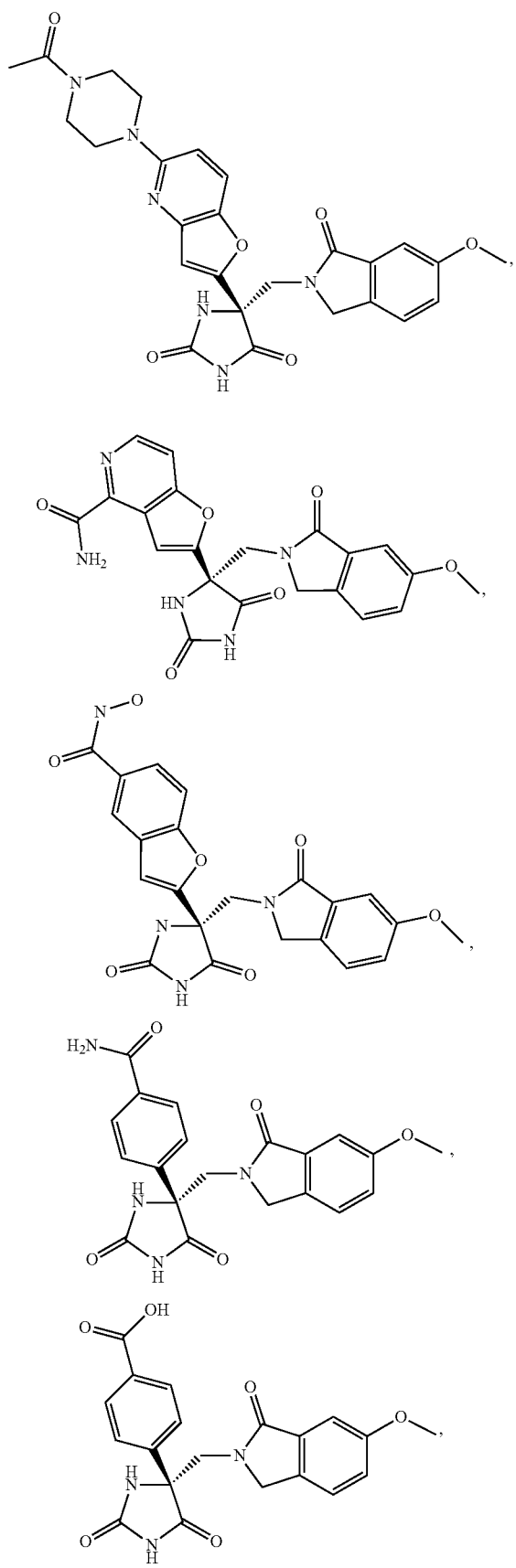
808
-continued
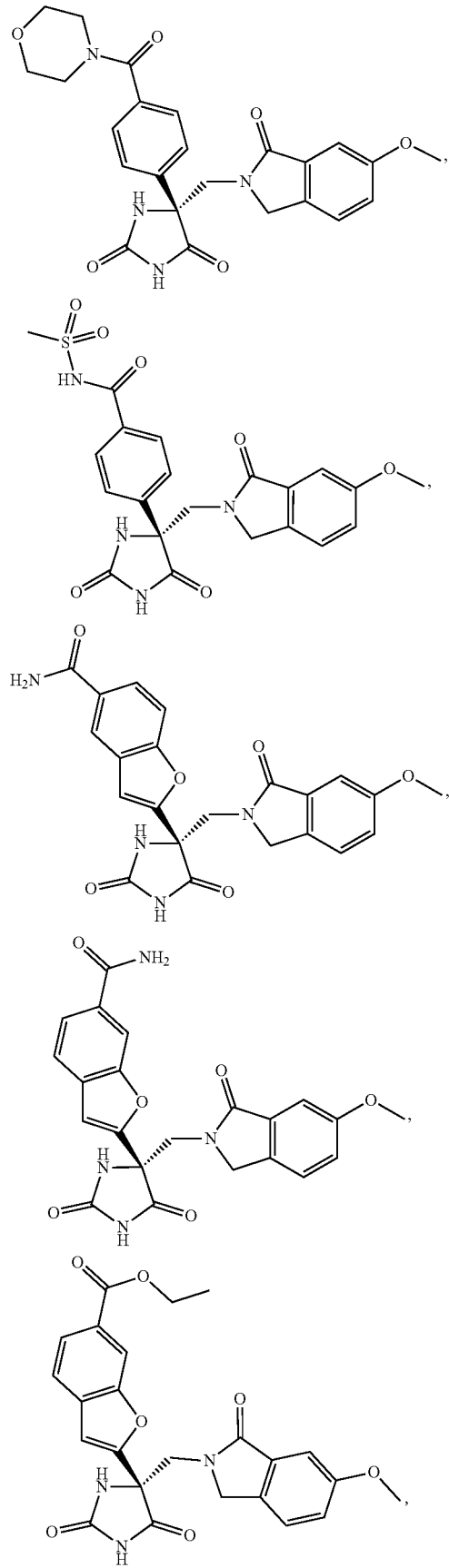

809
-continued
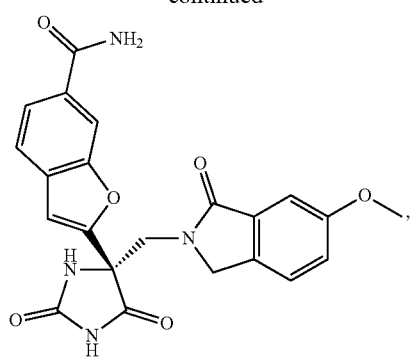
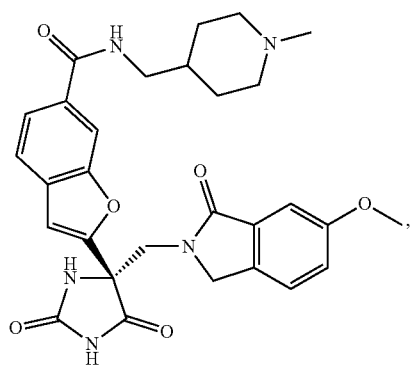
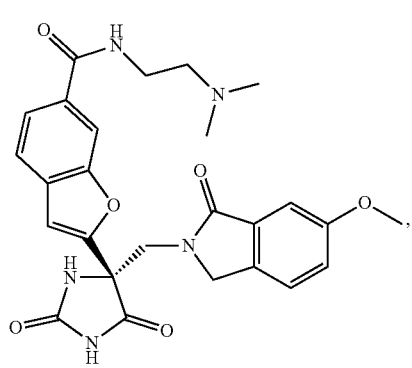
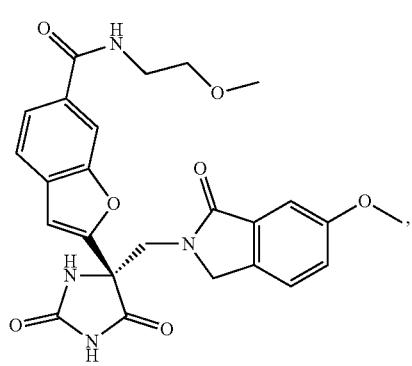
810
-continued
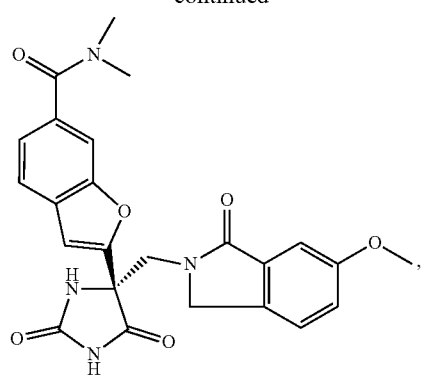
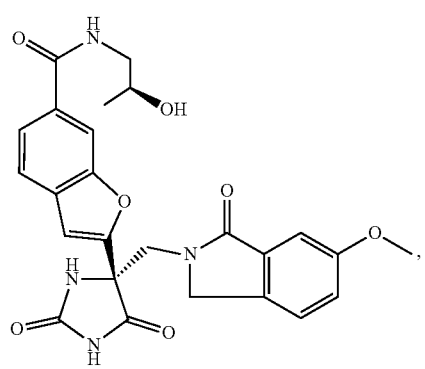
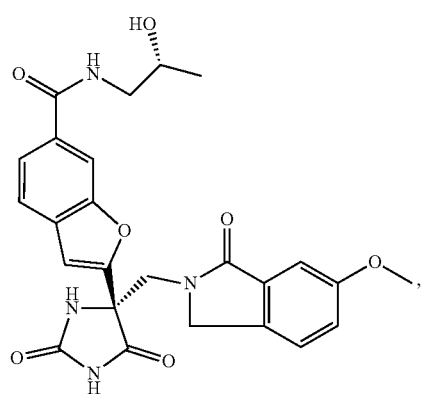
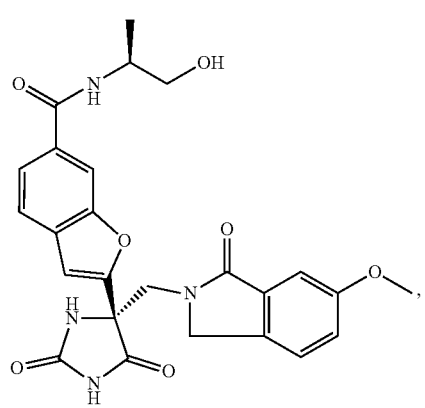

811
-continued
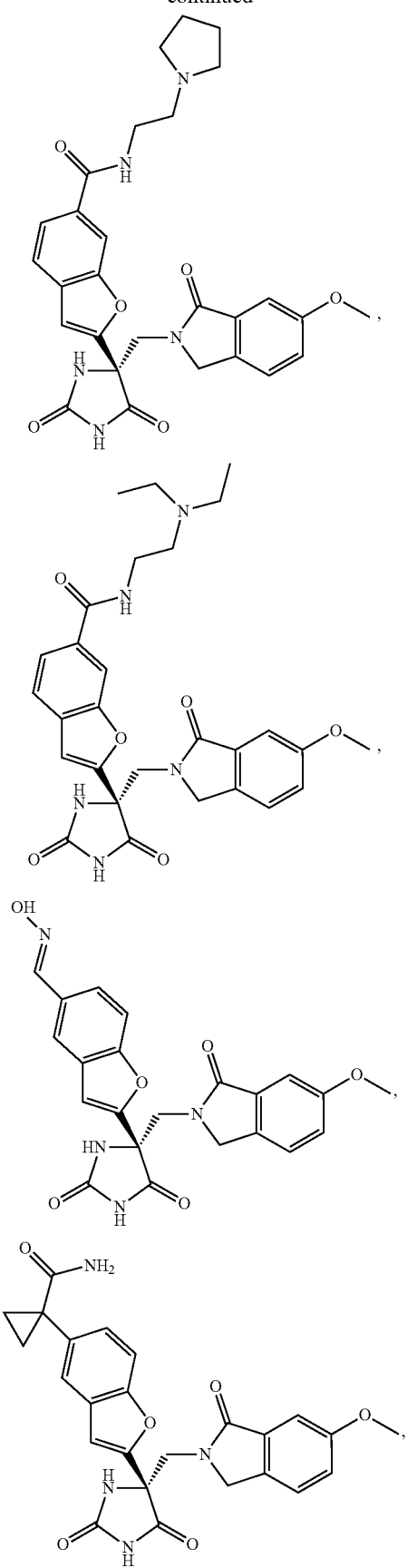
812
-continued
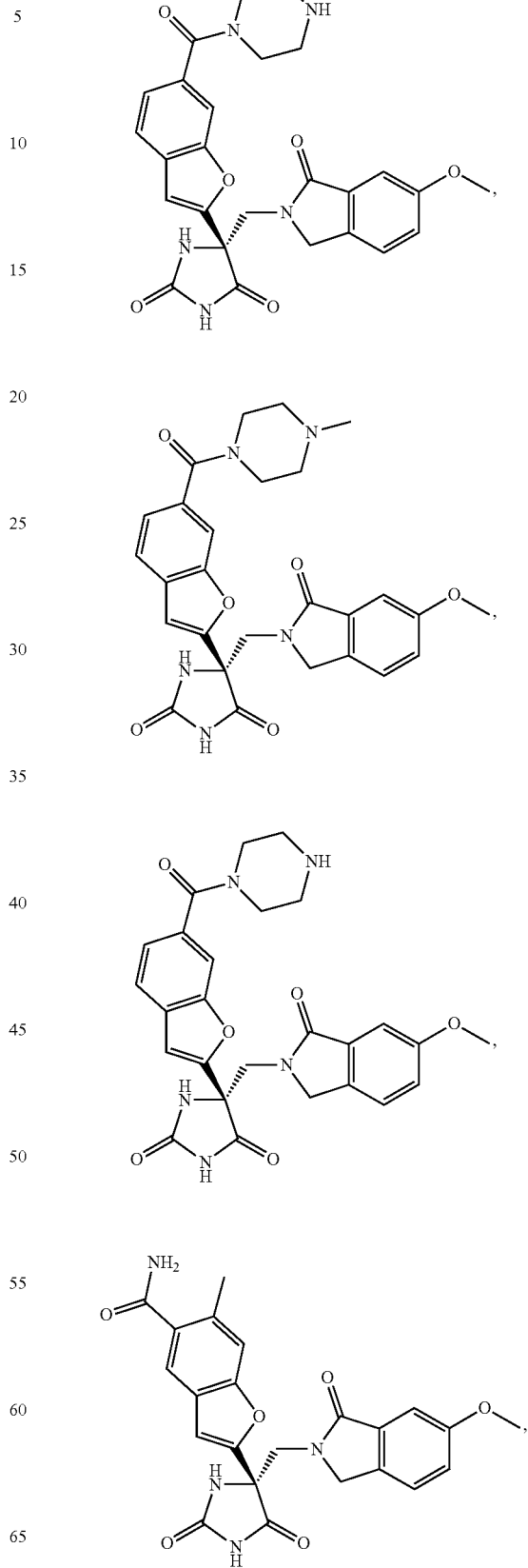

813
-continued
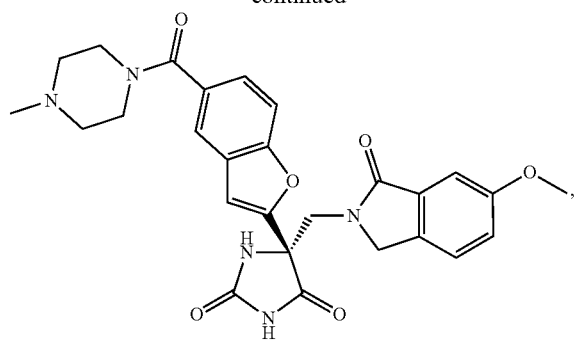
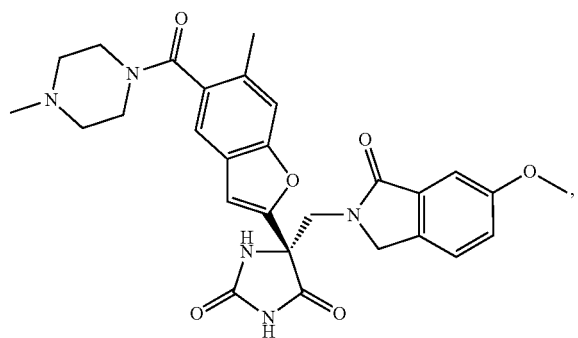
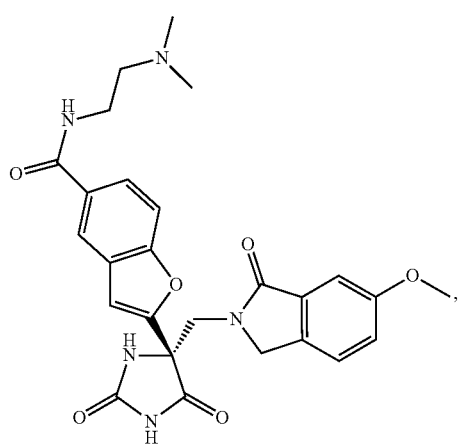
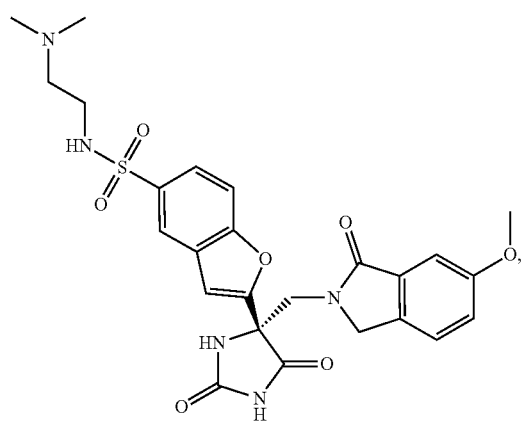
814
-continued
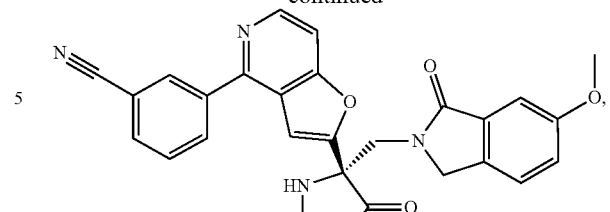
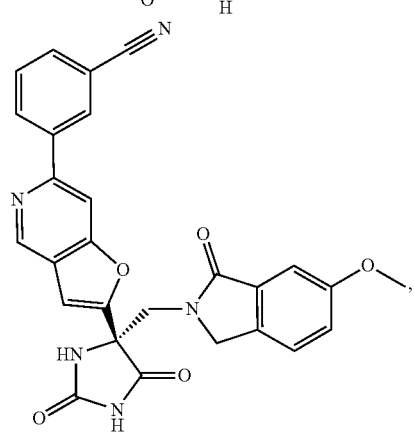
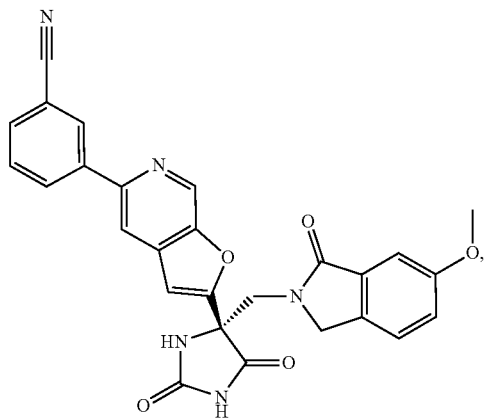
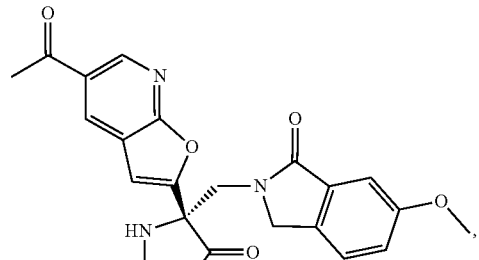
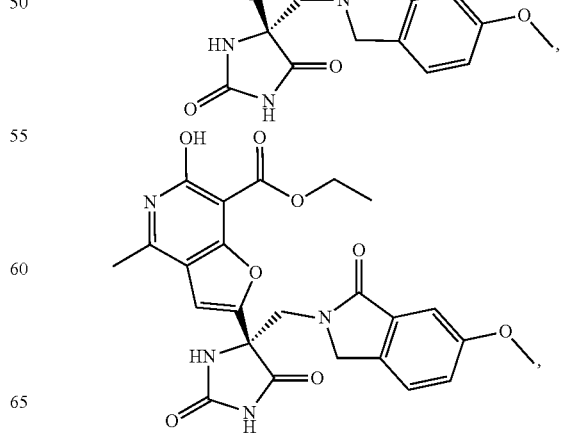

815
-continued
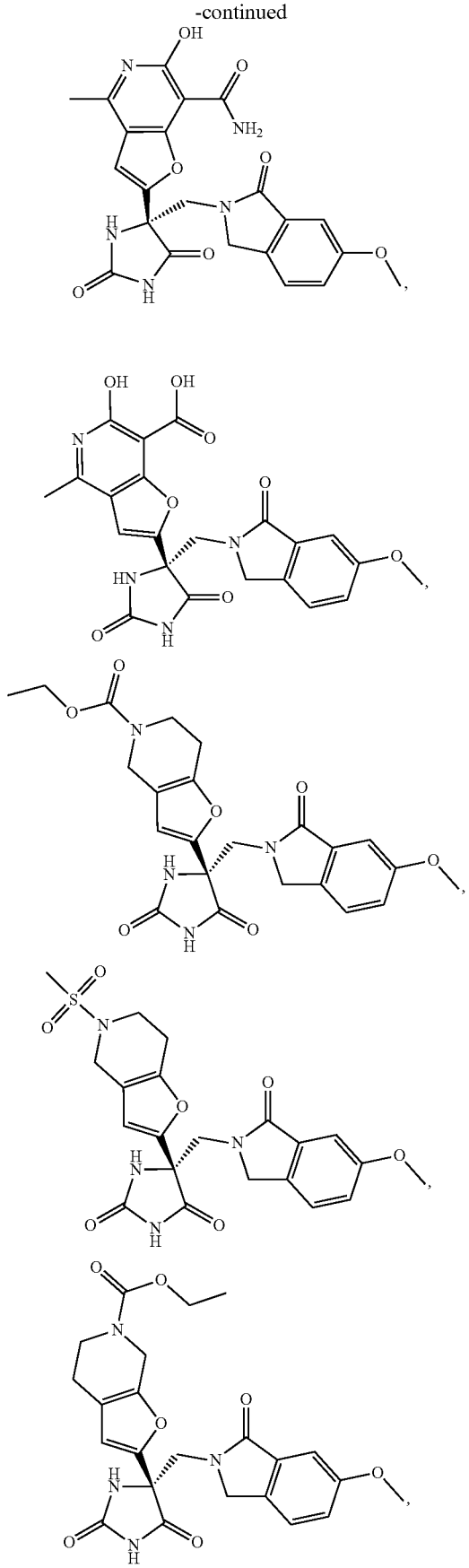
816
-continued
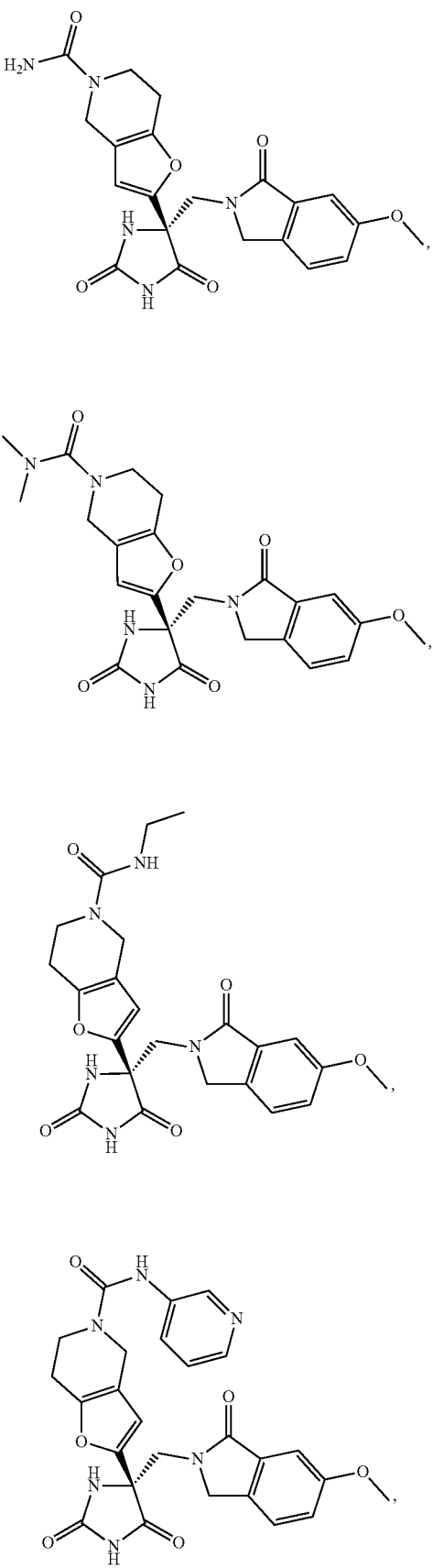

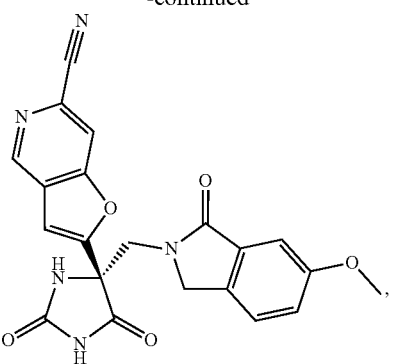
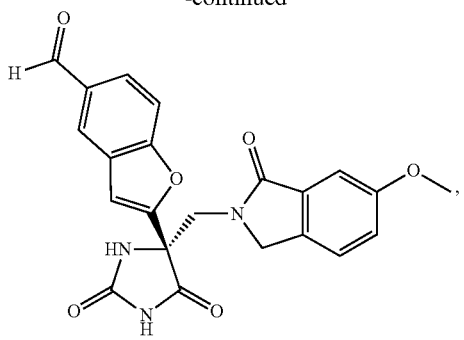
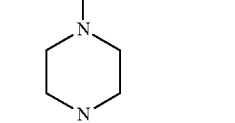

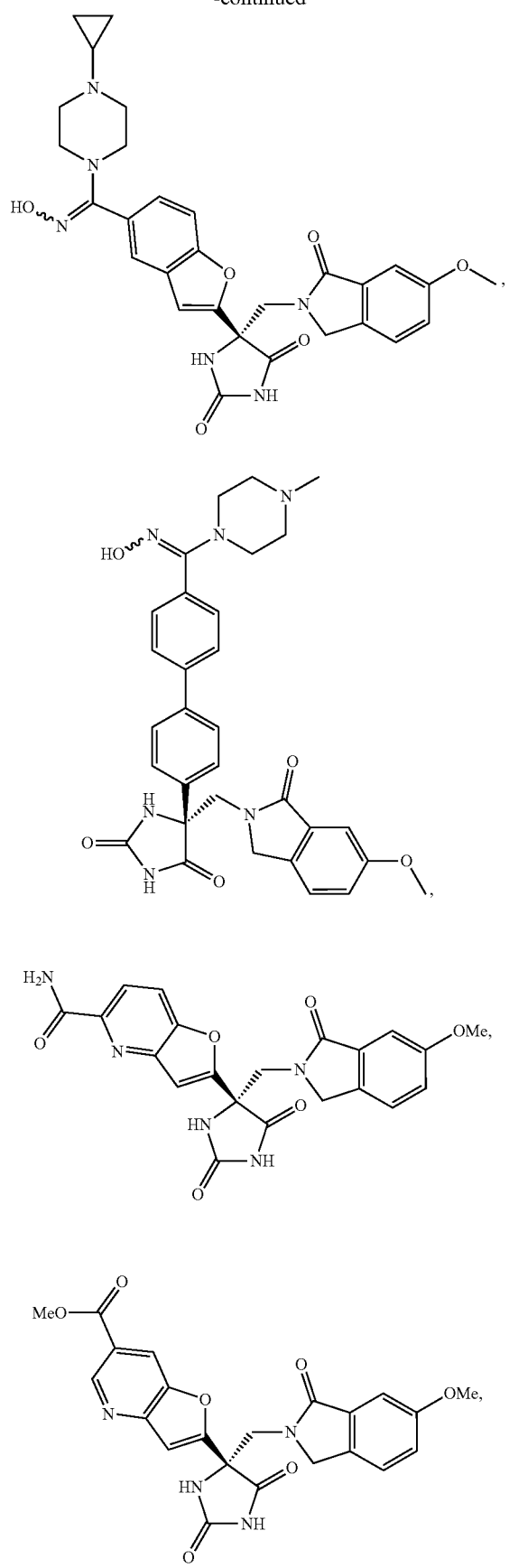
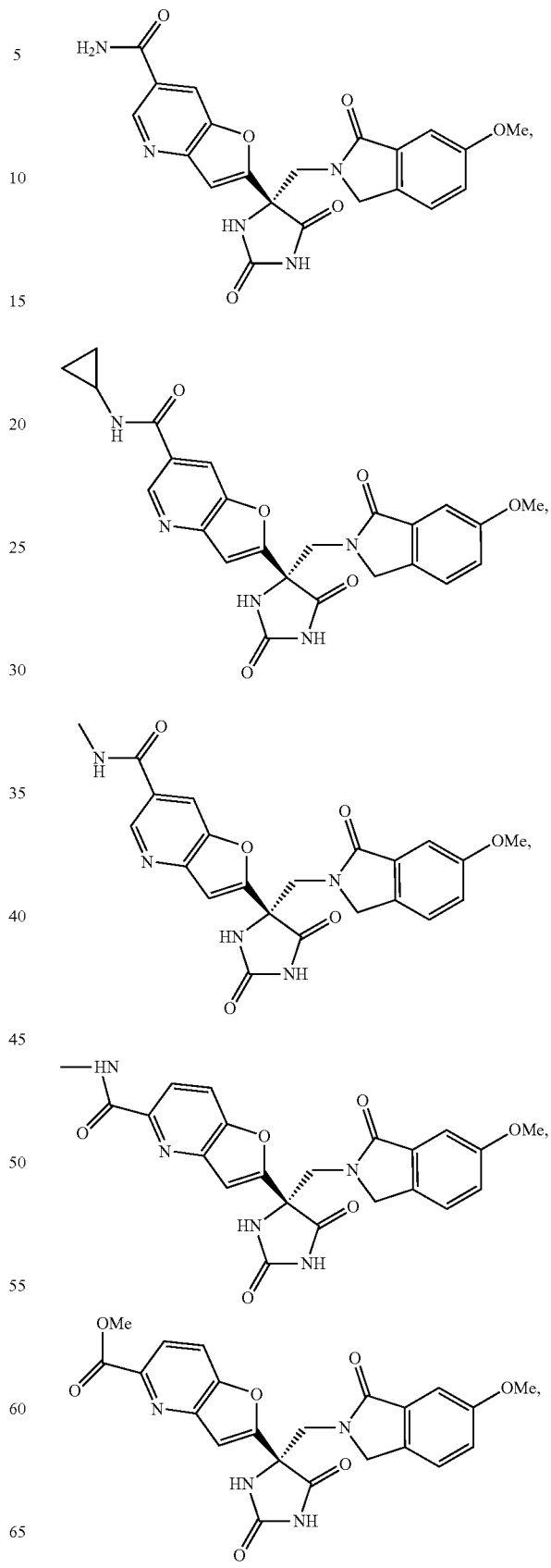

821
-continued
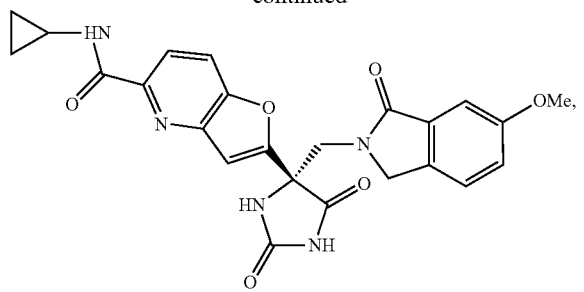
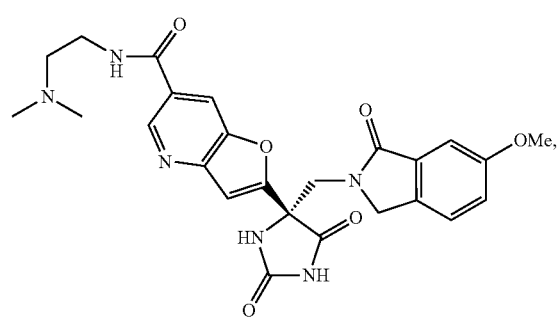
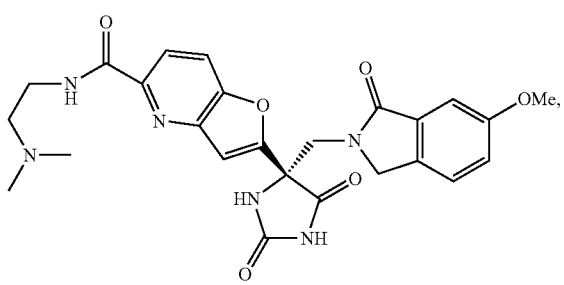
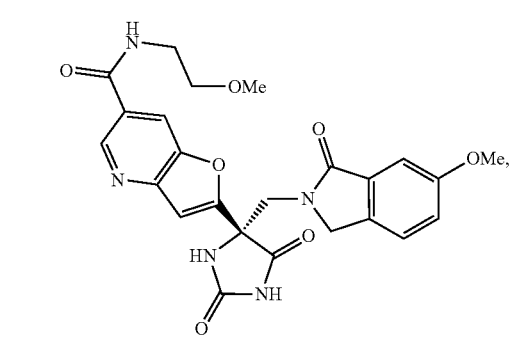
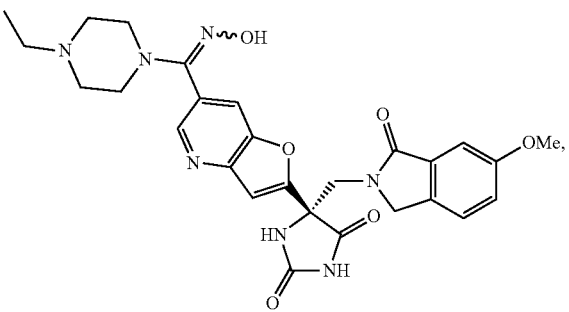
822
-continued
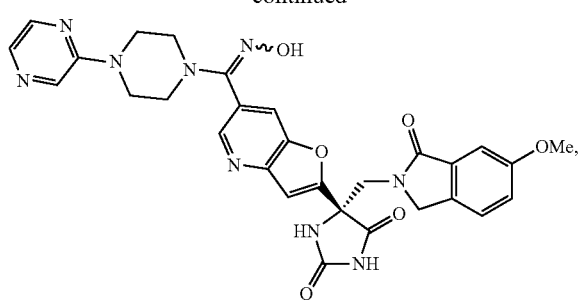
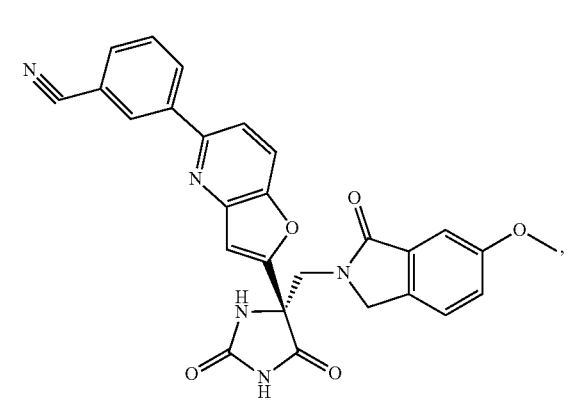
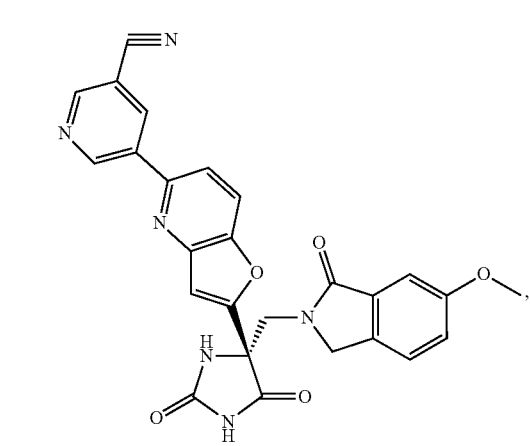
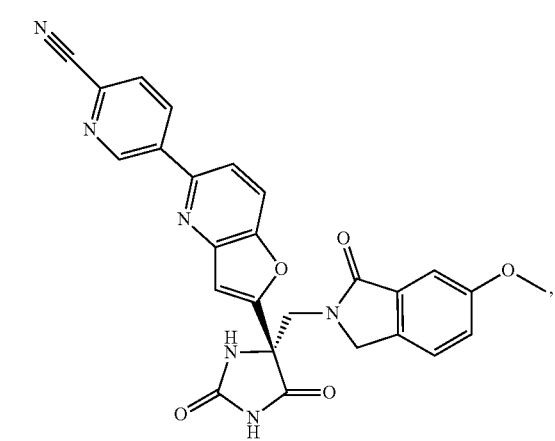

823
-continued
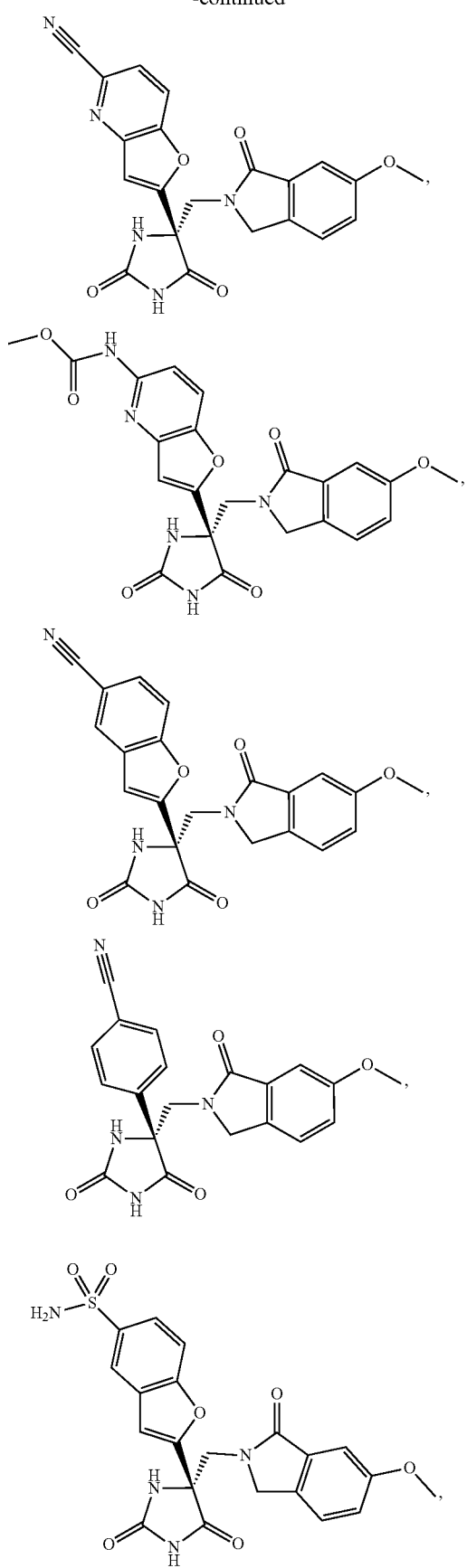
824
-continued
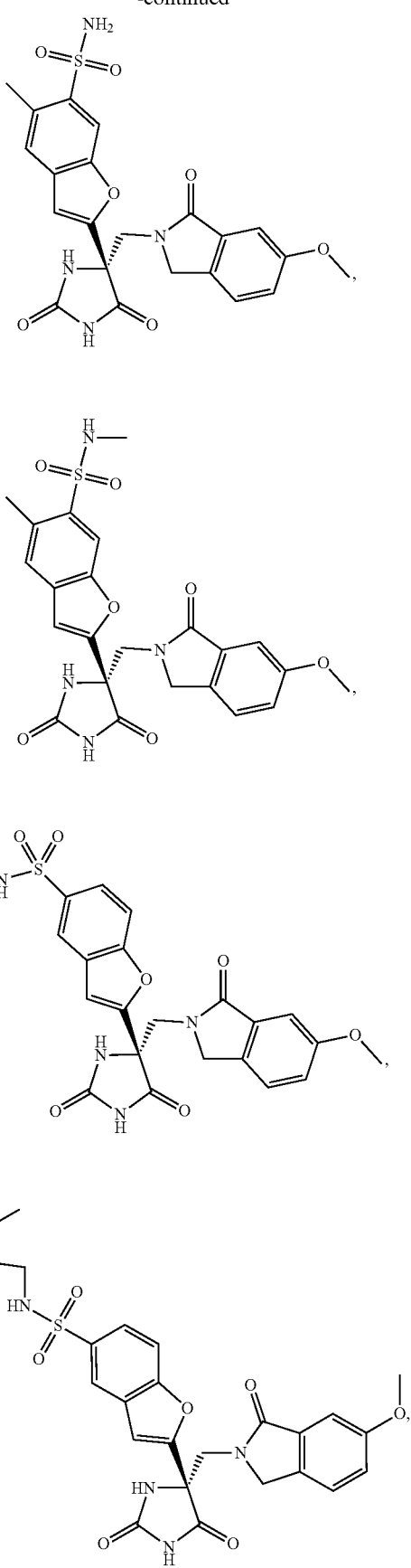

825
-continued
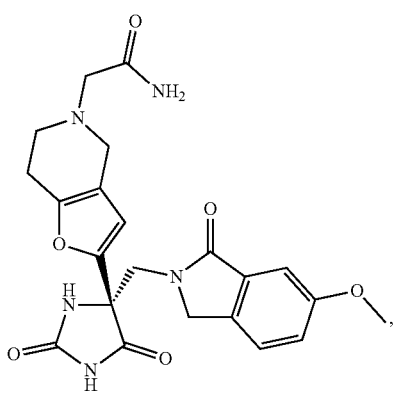
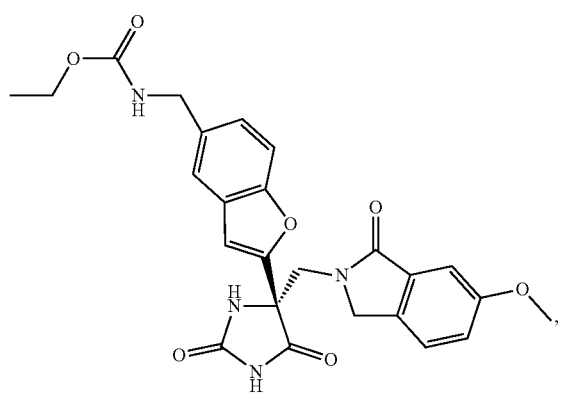
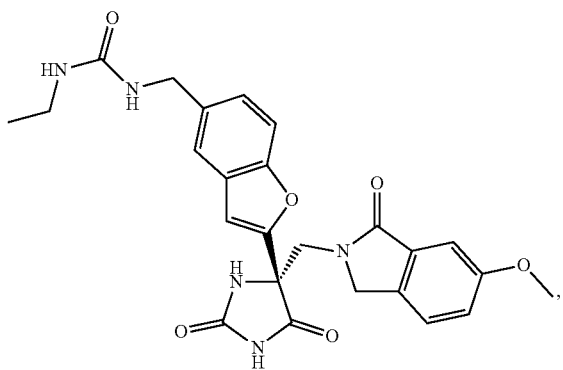
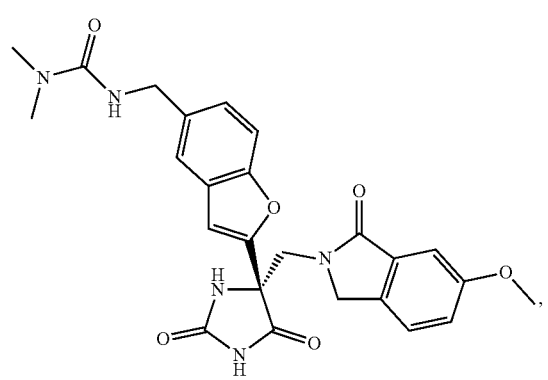
826
-continued
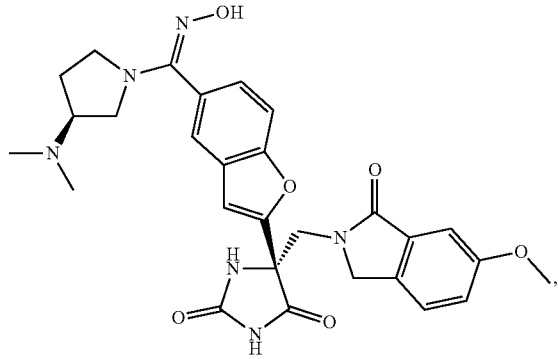
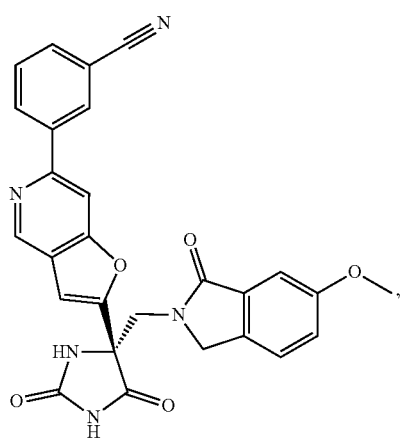
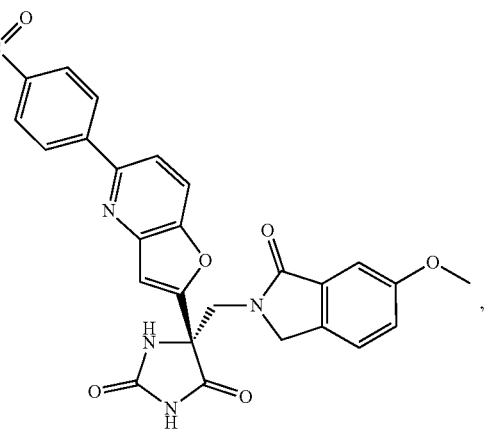
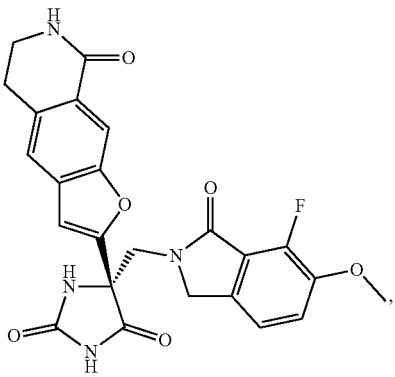

827
-continued
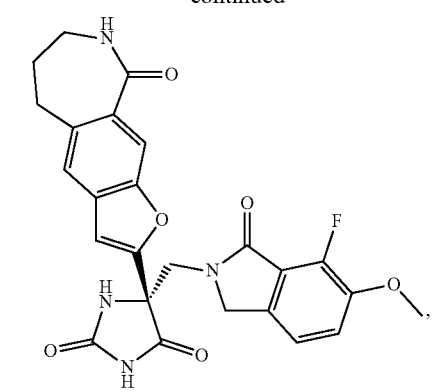
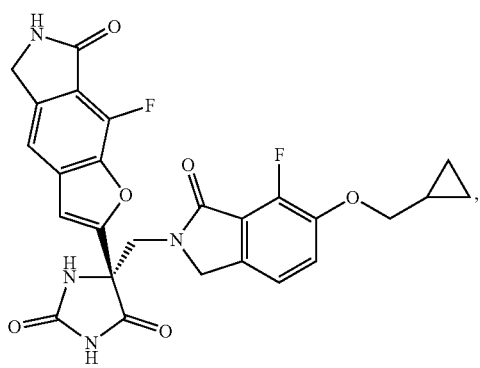
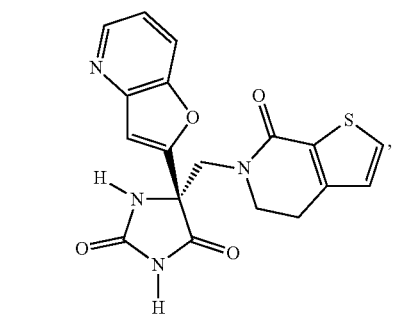
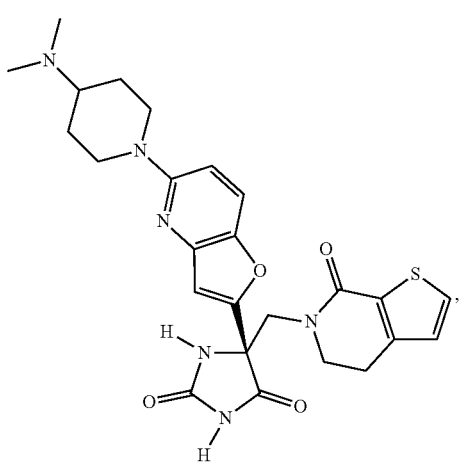
828
-continued
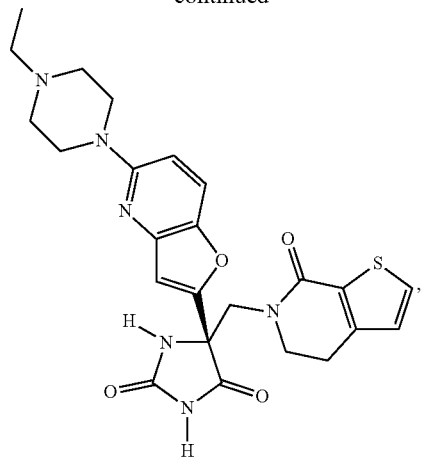
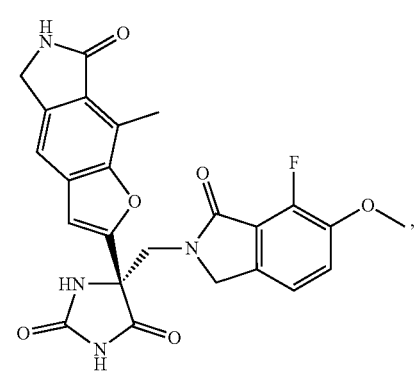
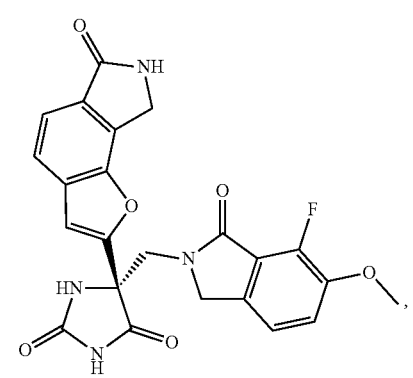
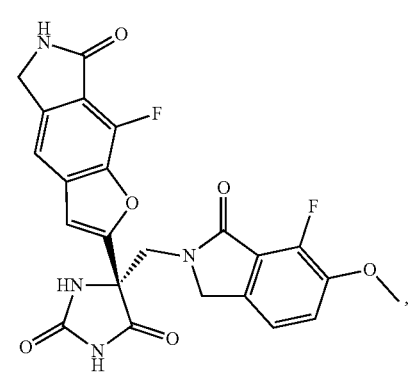

829
-continued
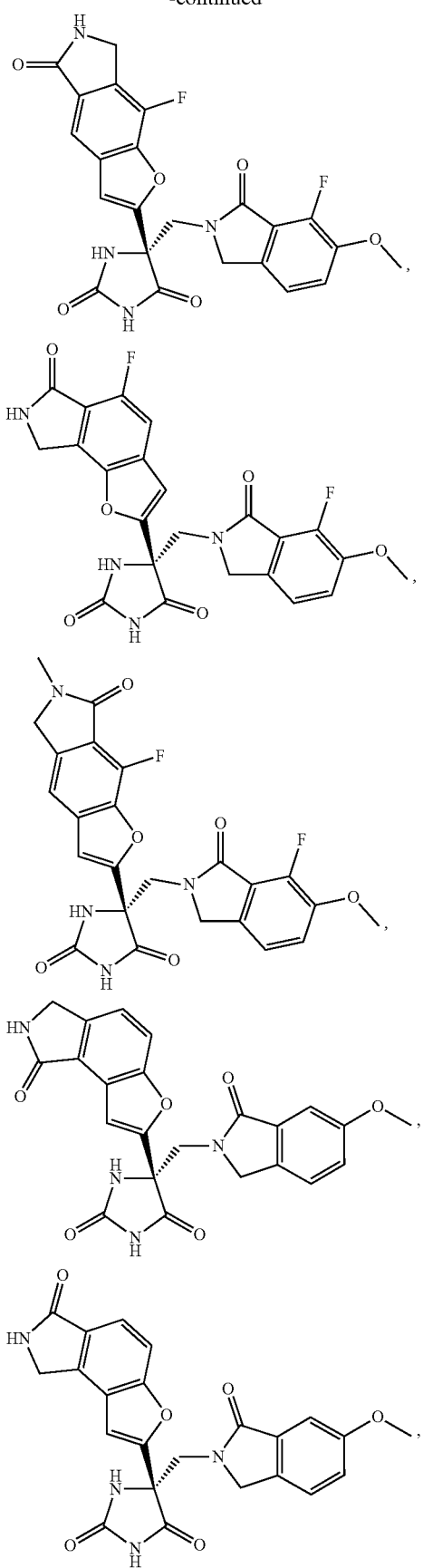
830
-continued
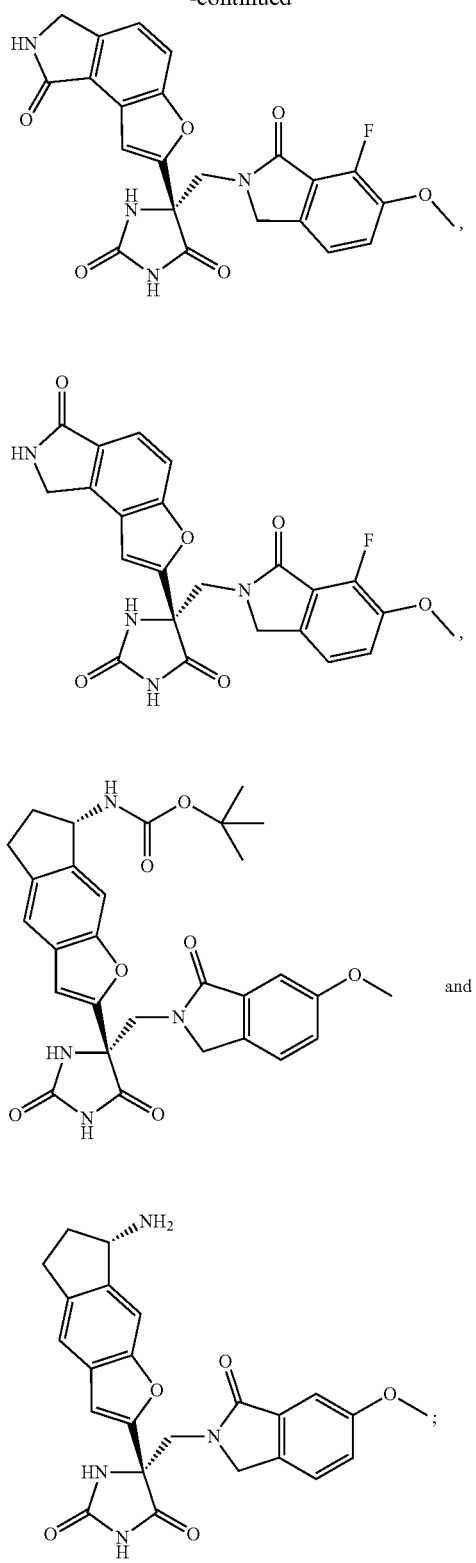
or a pharmaceutically acceptable salt thereof.
2. The compound of claim 1, selected from the group consisting of:

831
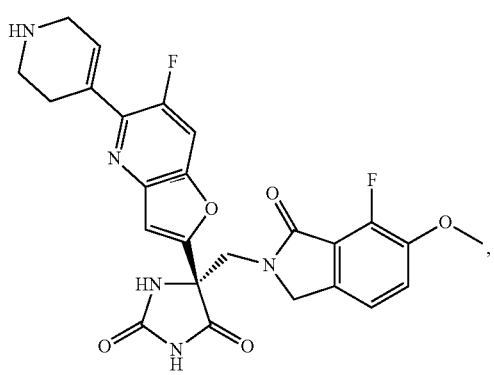
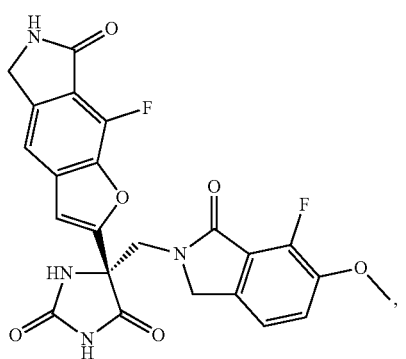
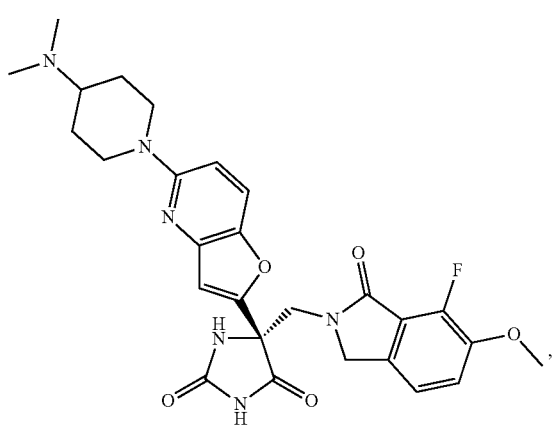
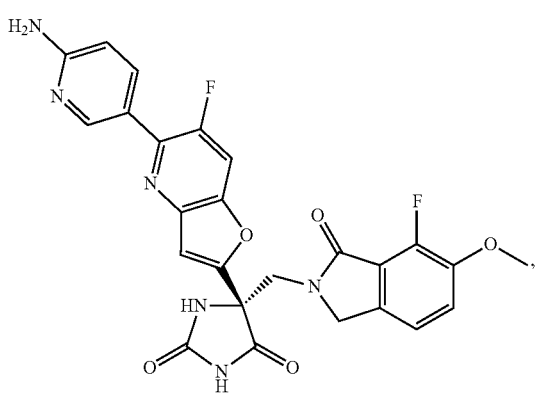
832
-continued
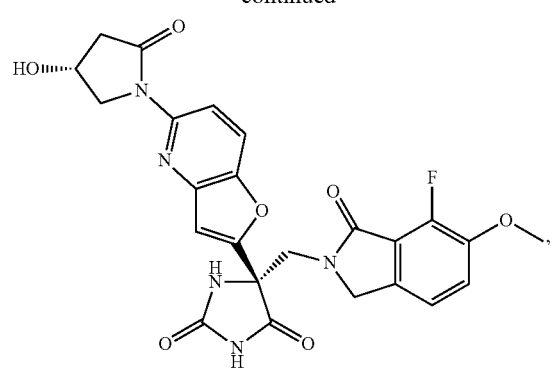
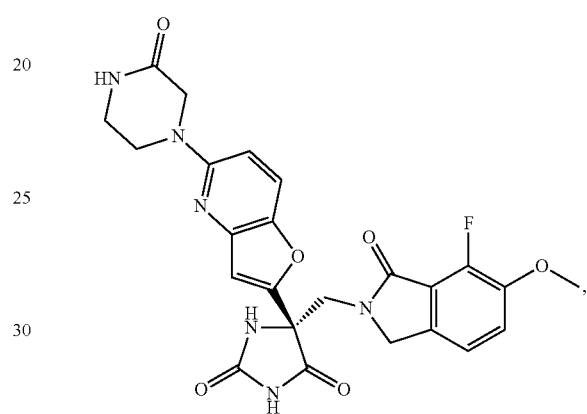
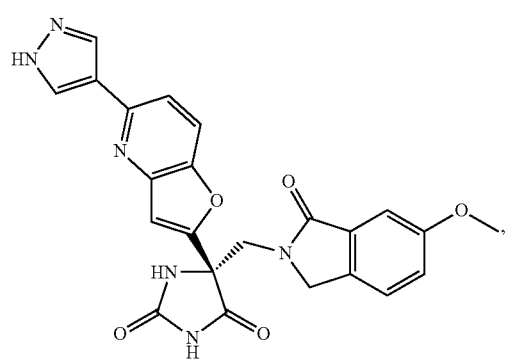

833
-continued
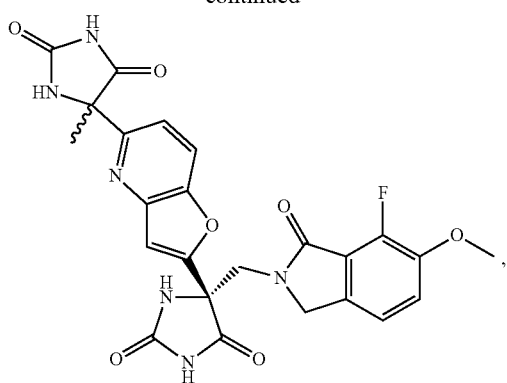
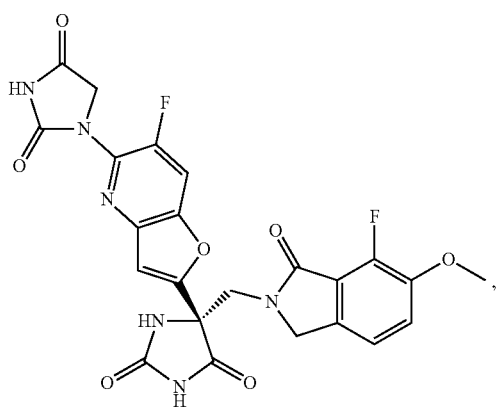
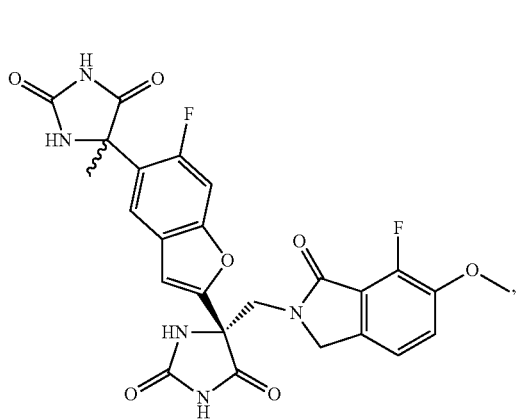
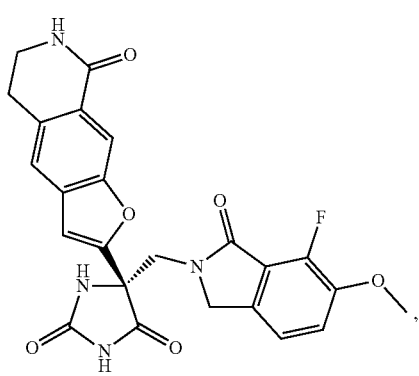
834
-continued
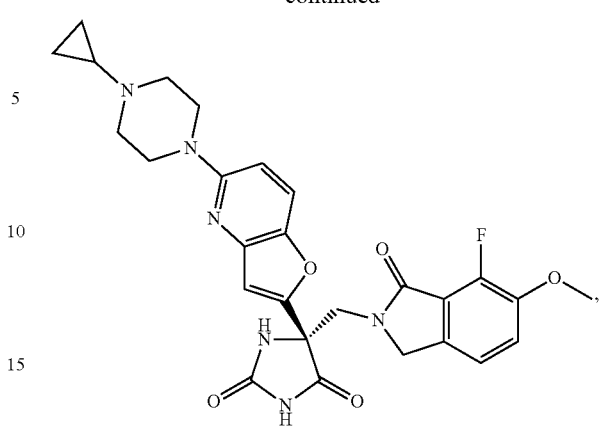
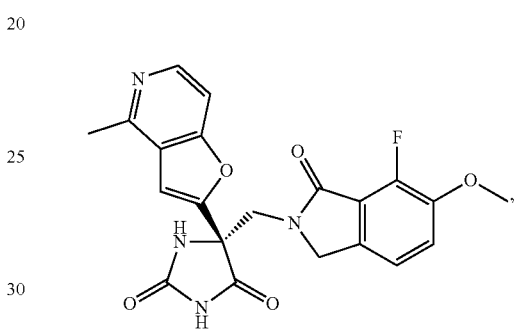
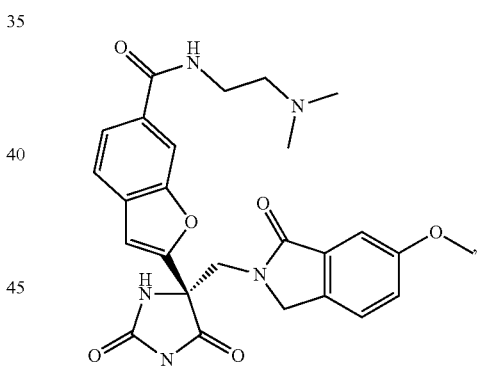
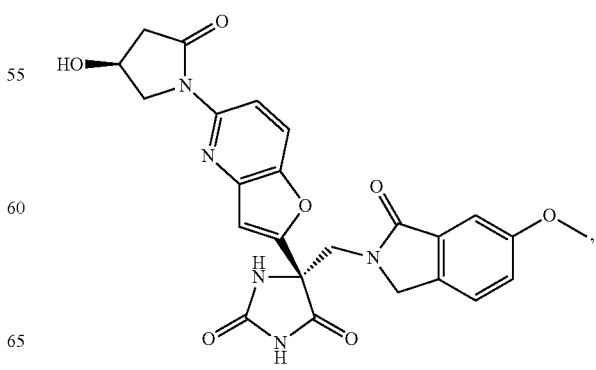

835
-continued
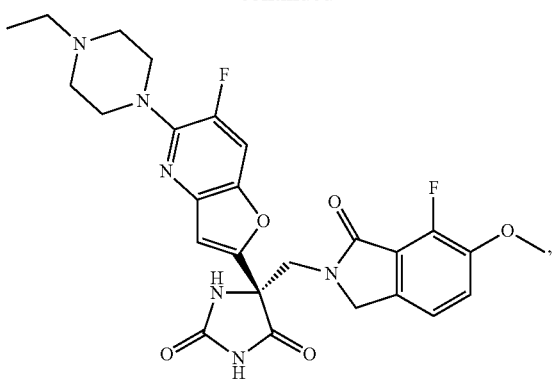
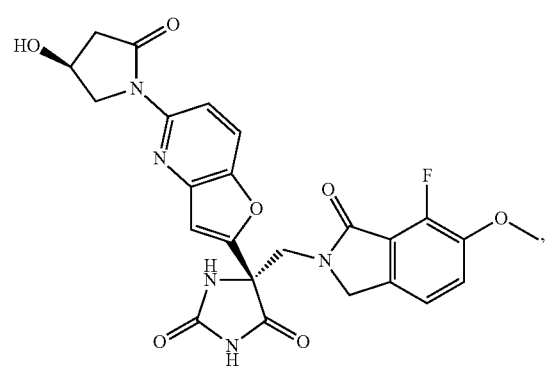
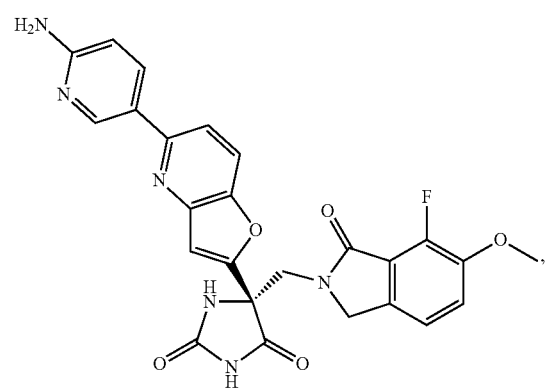
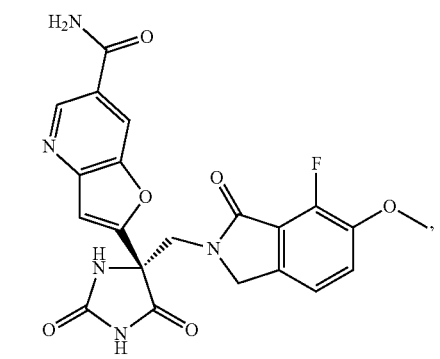
836
-continued
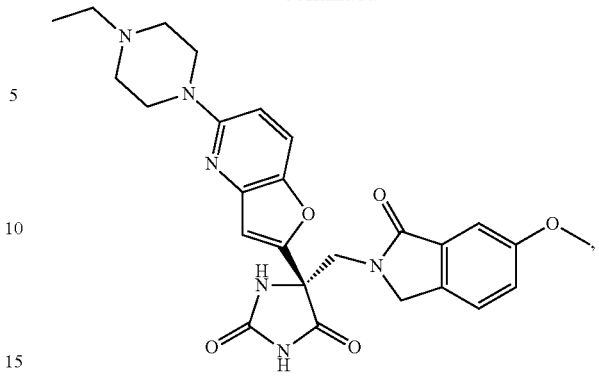
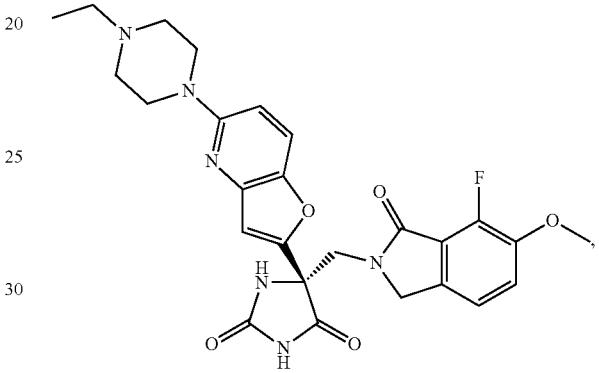
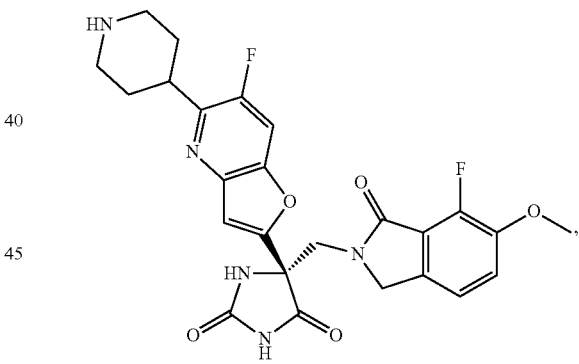
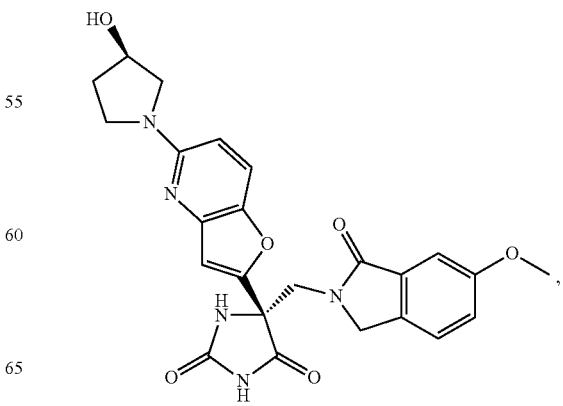

837
-continued
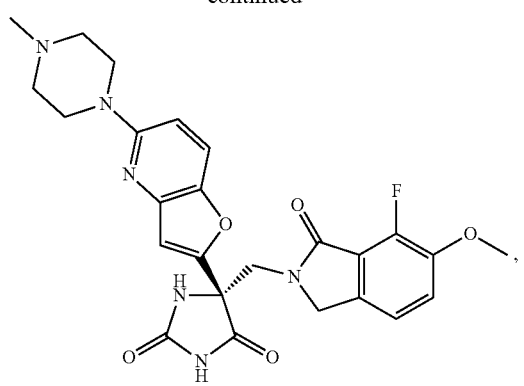
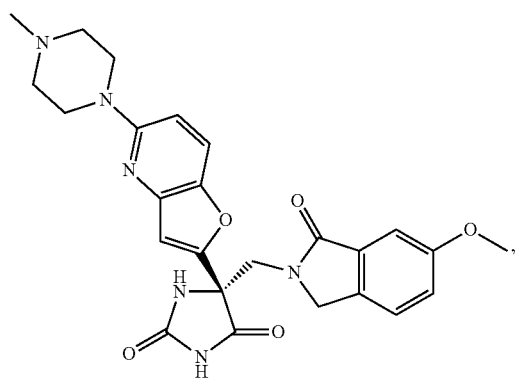
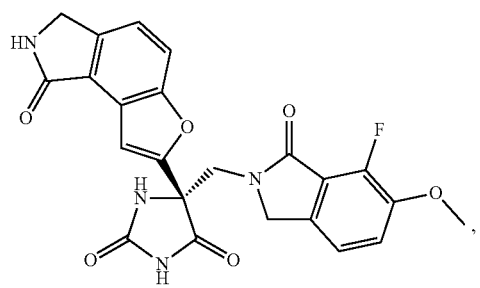
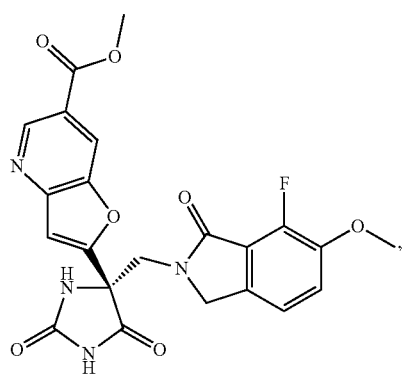
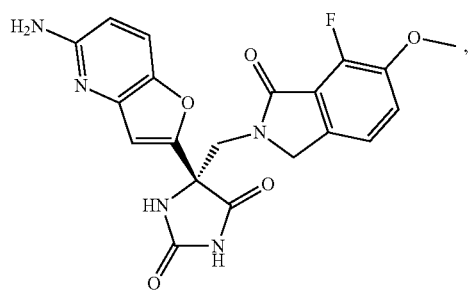
838
-continued
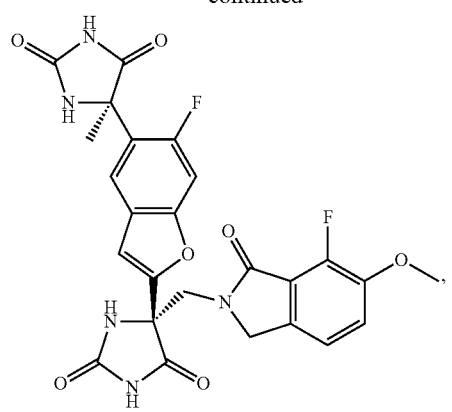
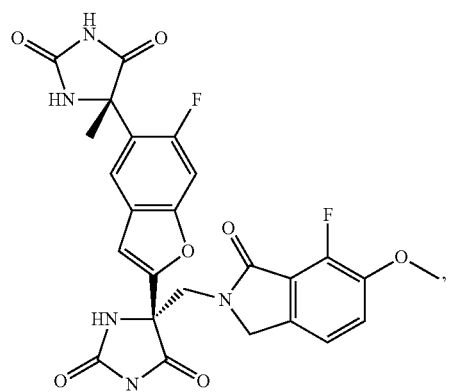
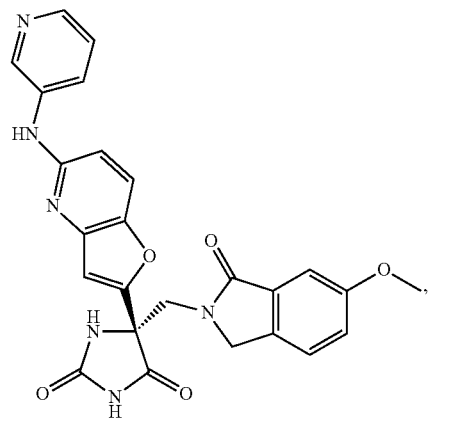
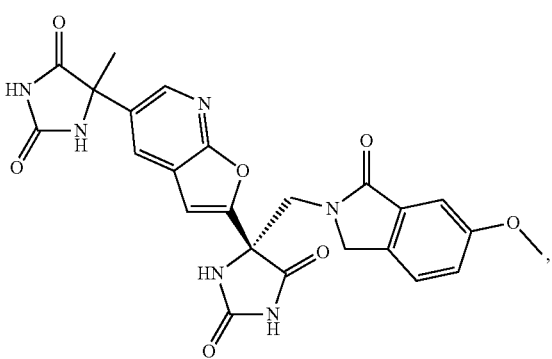

839
-continued
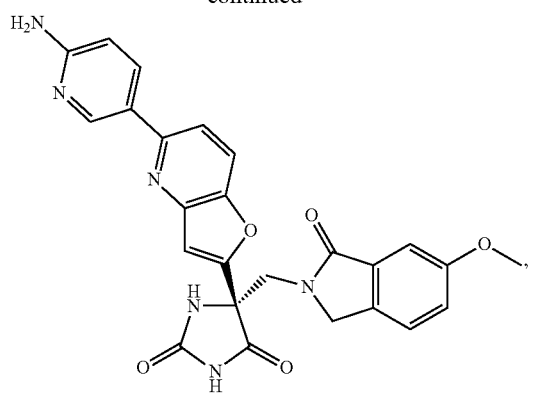
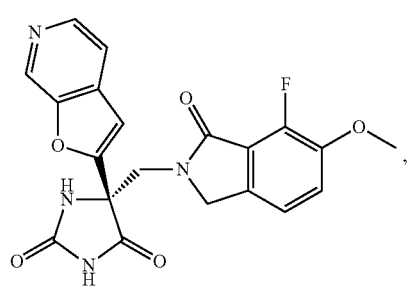
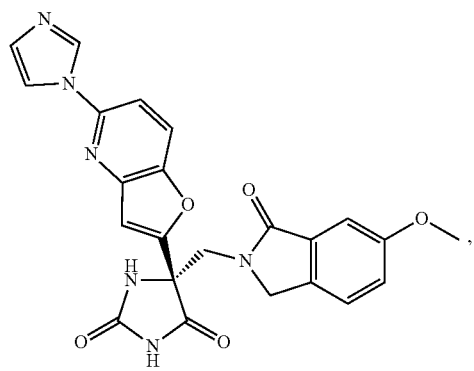
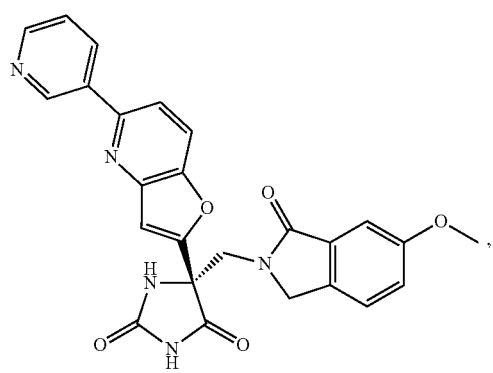
840
-continued
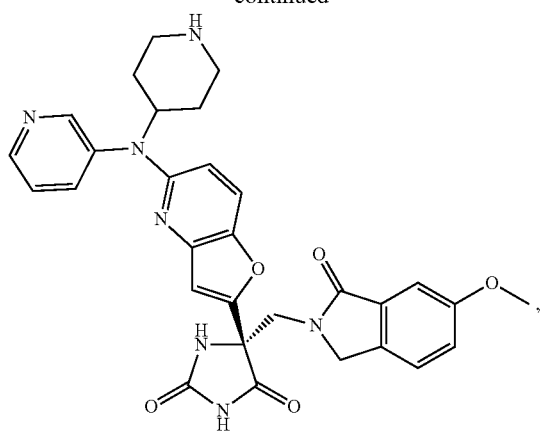
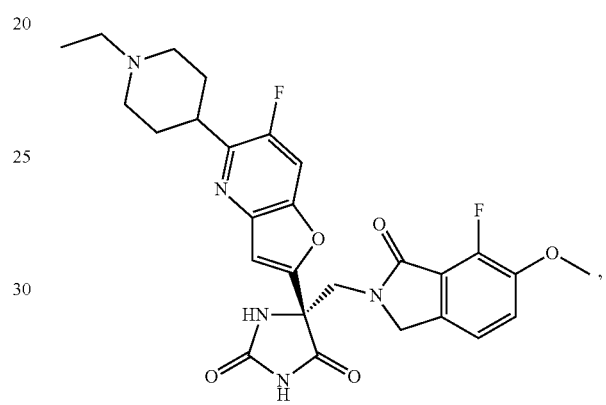
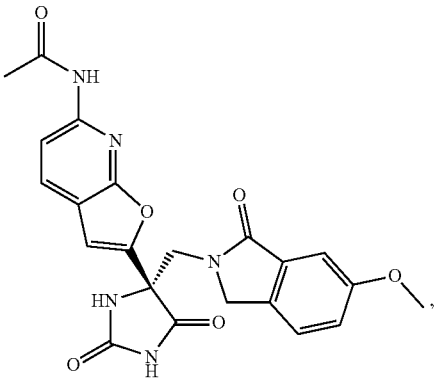

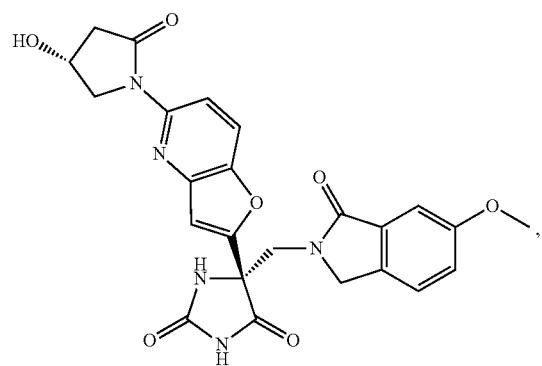
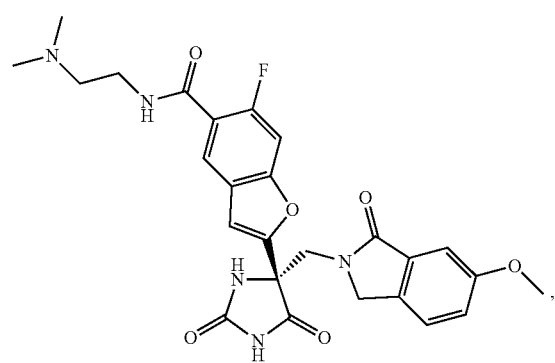
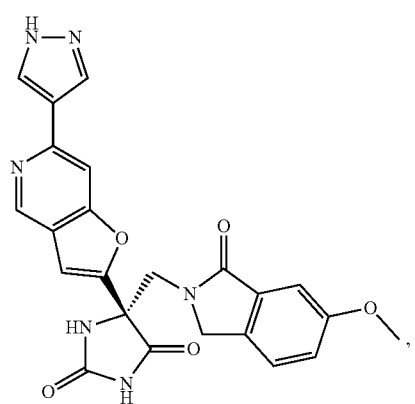
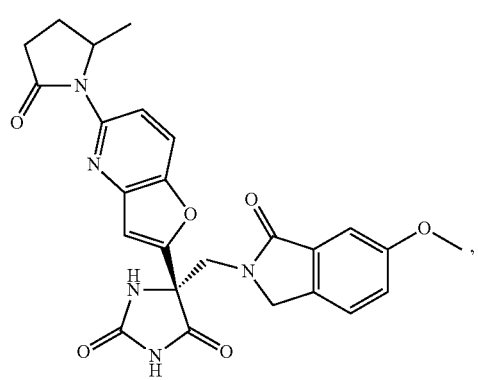
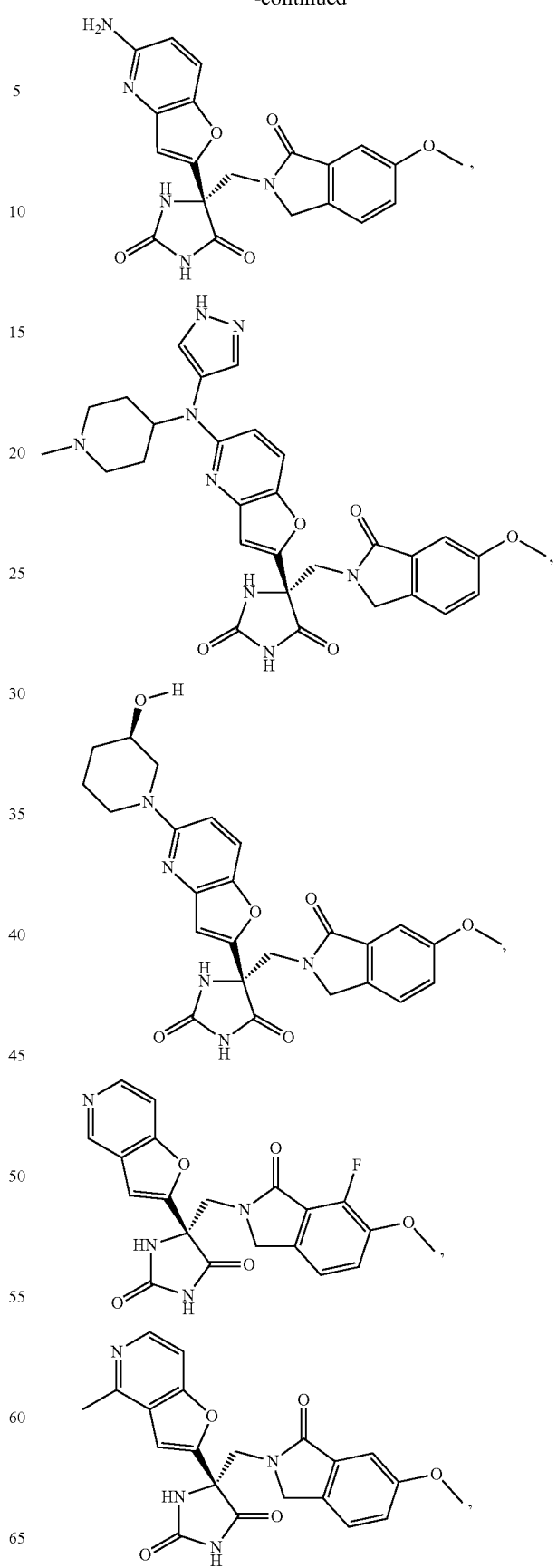

843
-continued
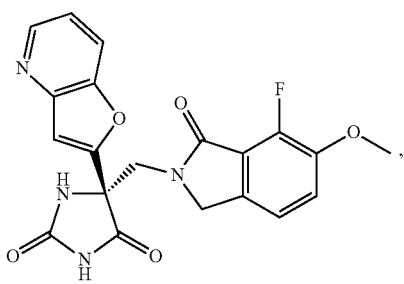
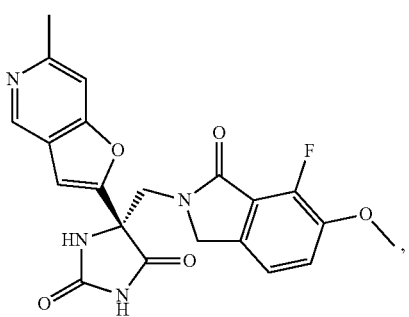
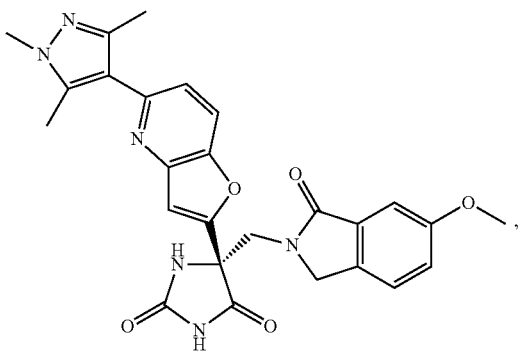
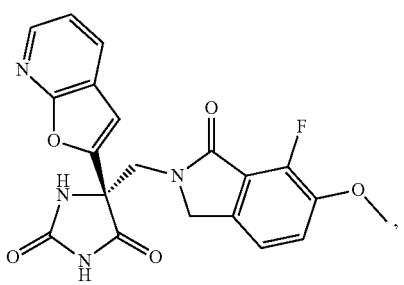
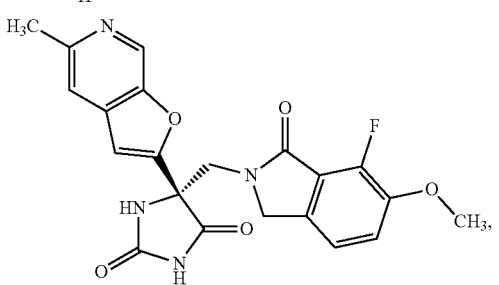
844
-continued
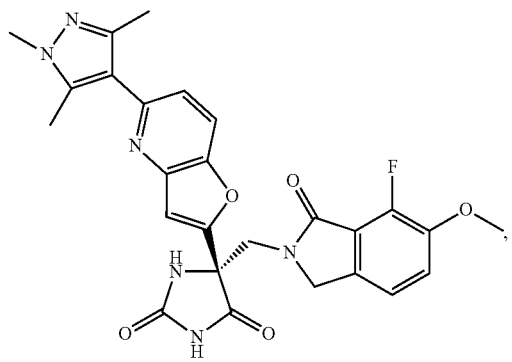
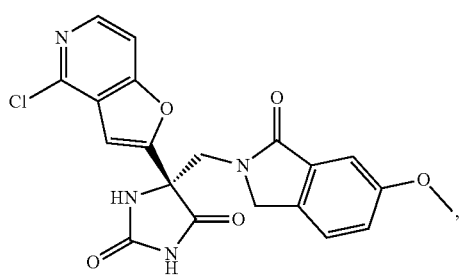
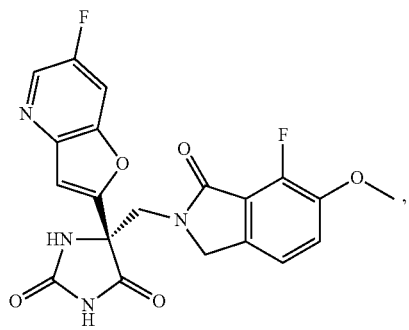
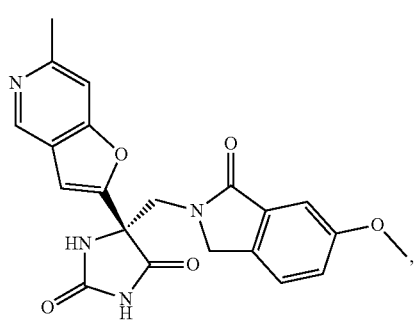
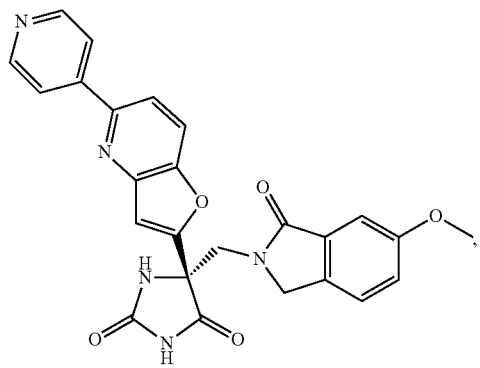

845
-continued
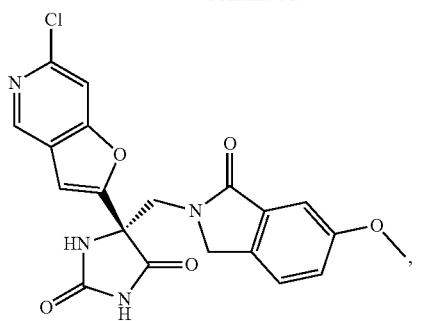
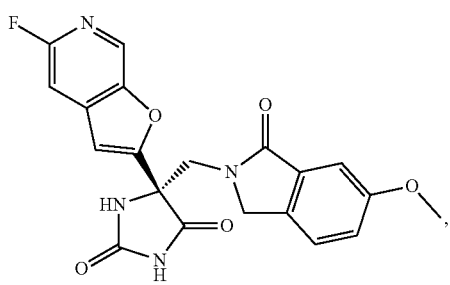
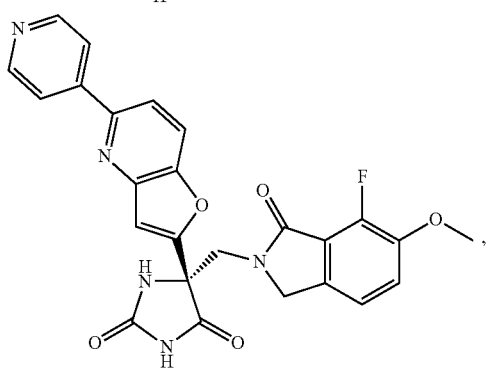
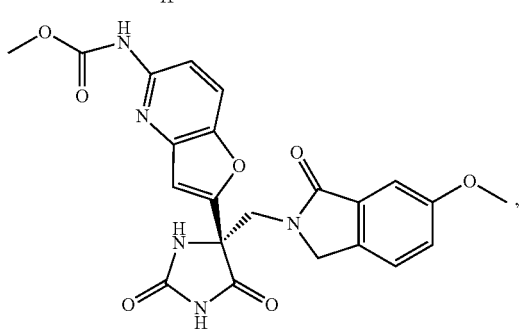
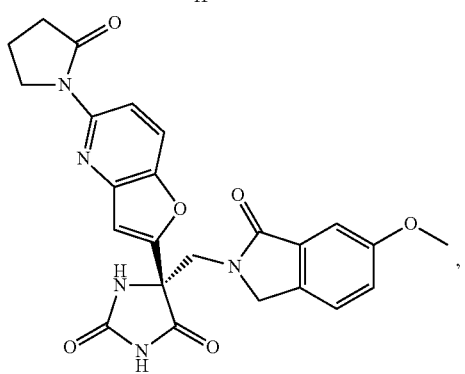
846
-continued
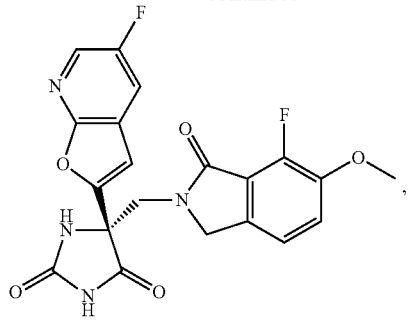
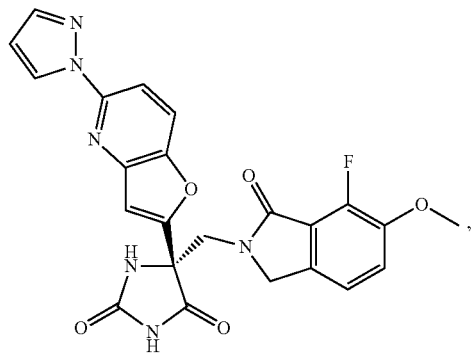
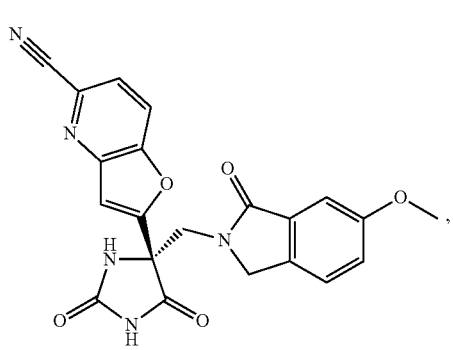
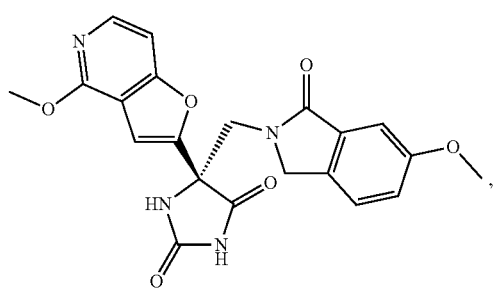
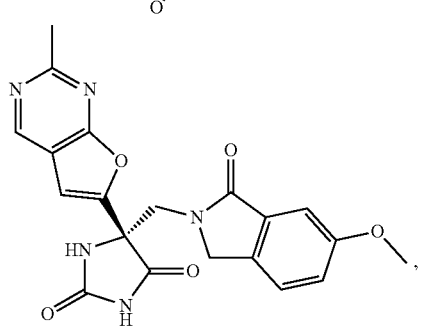

847
-continued
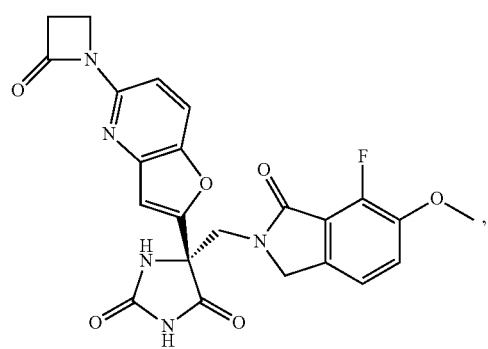
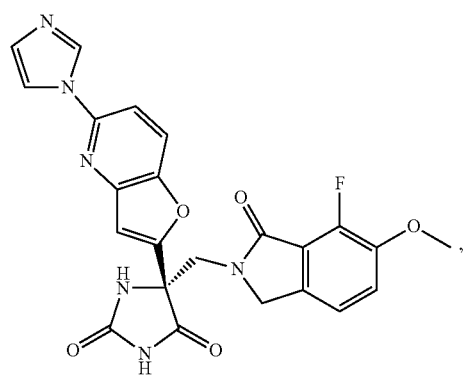
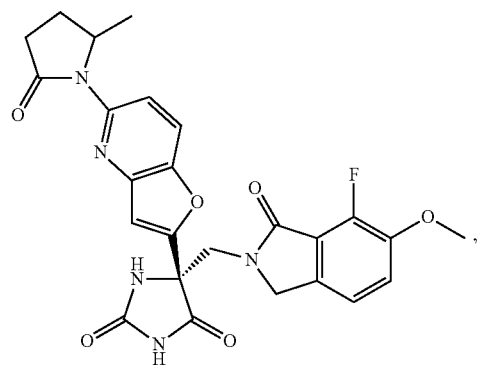
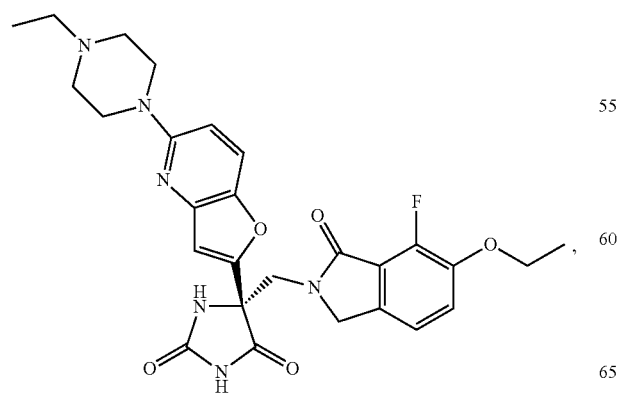
848
-continued
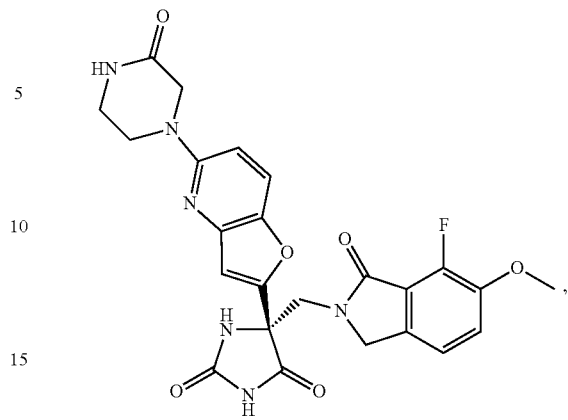
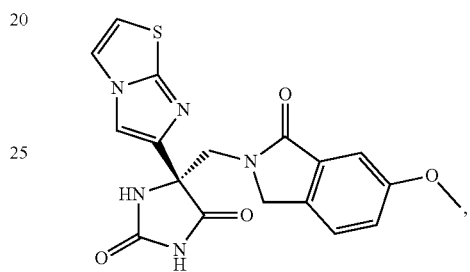
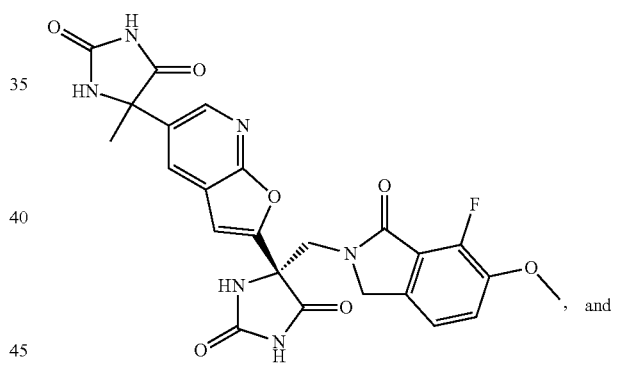
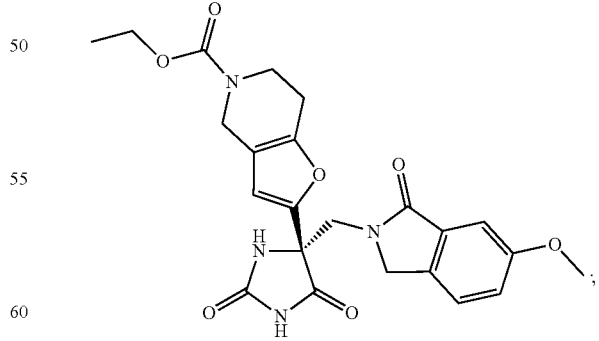
or a pharmaceutically acceptable salt thereof.
3. The compound of claim 2, selected from the group consisting of:

849
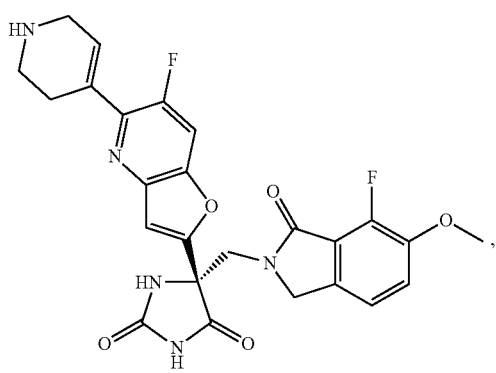
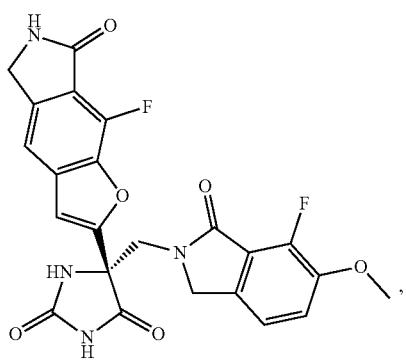
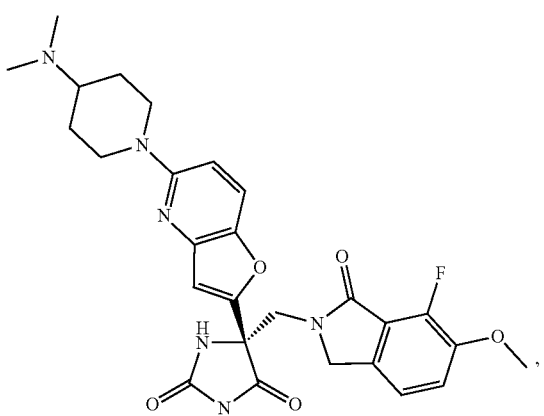
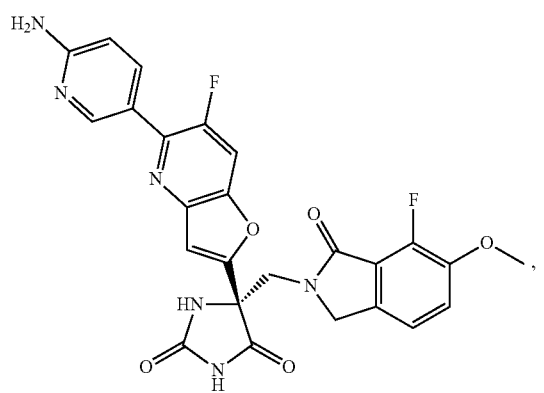
850
-continued
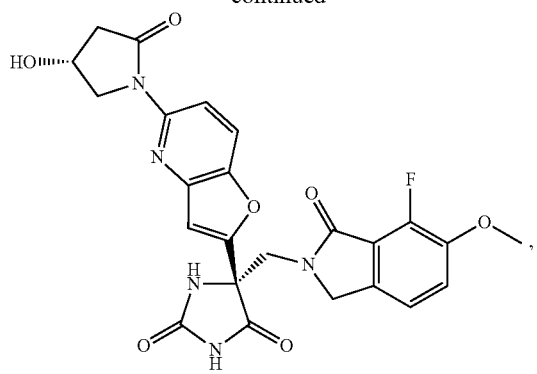
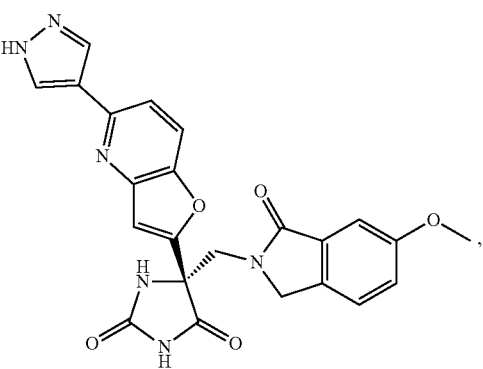

851
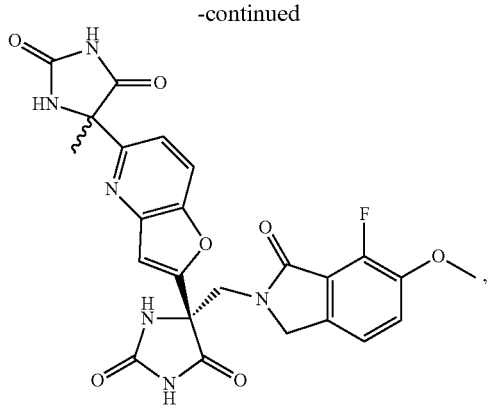
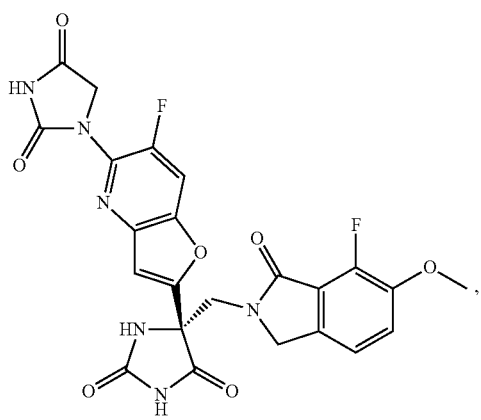
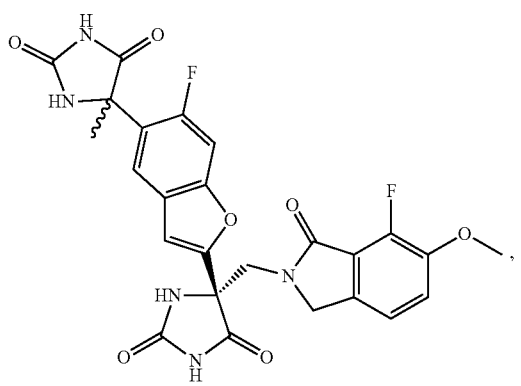
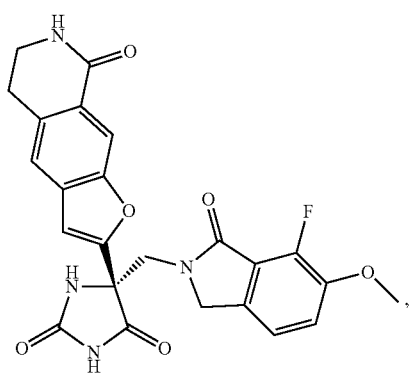
852
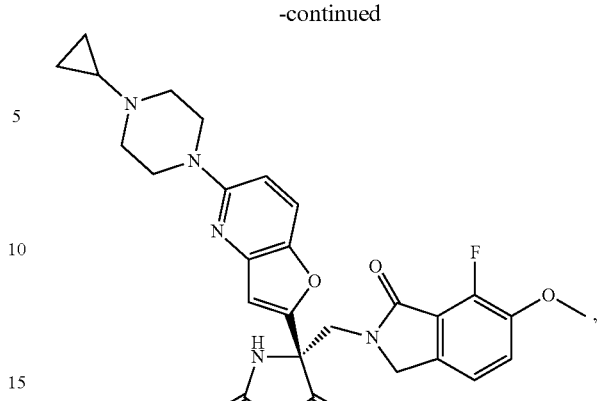
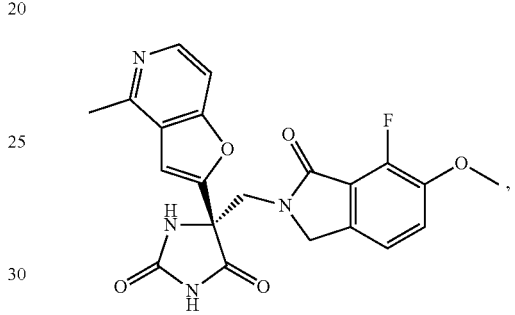
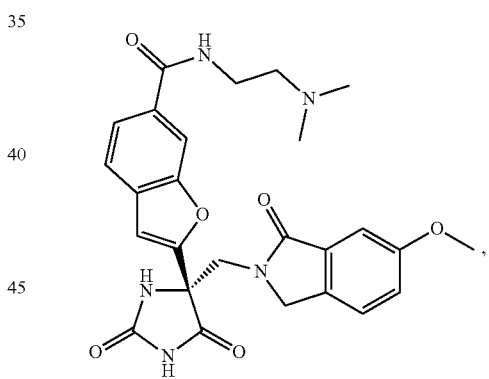
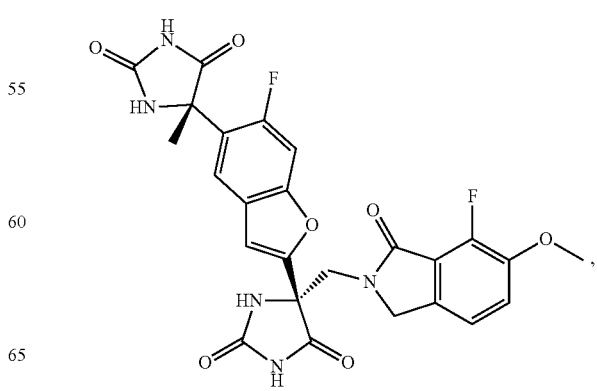

853
-continued
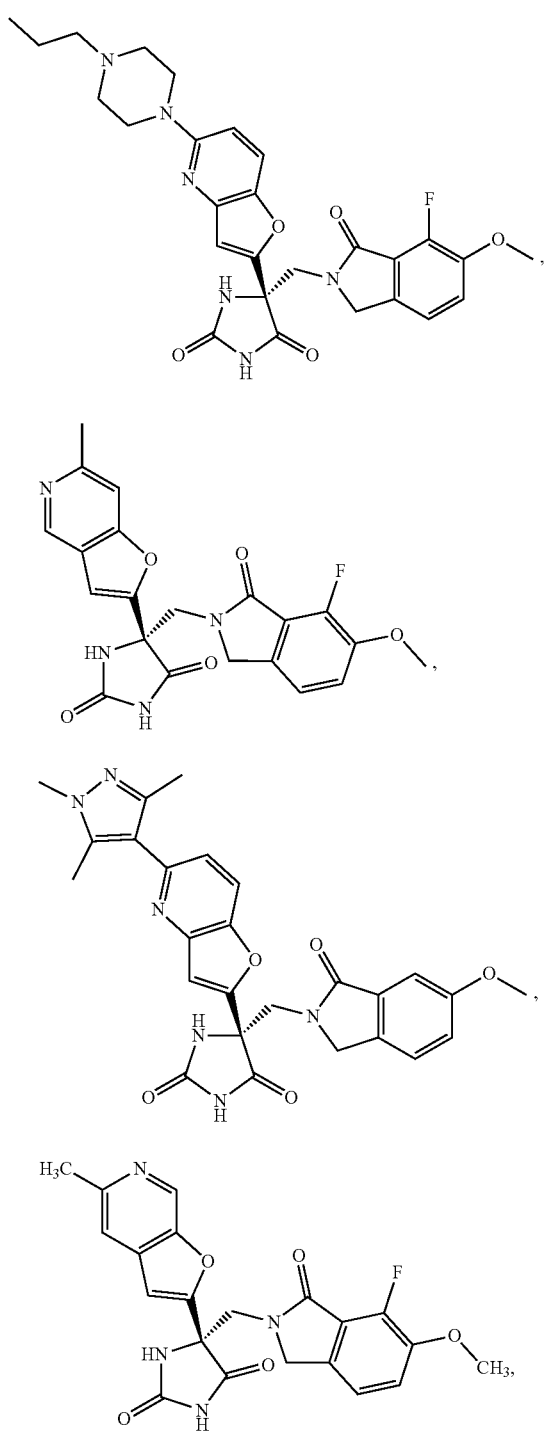
854
-continued
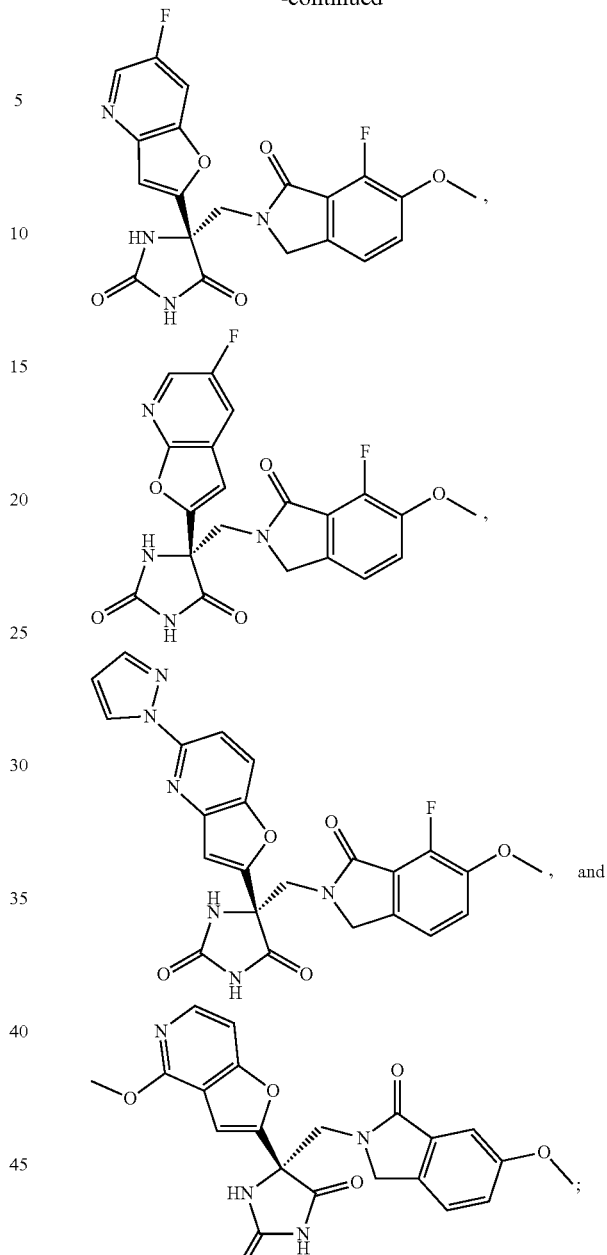
or a pharmaceutically acceptable salt thereof.
4. A pharmaceutical composition comprising at least one compound of claim 1, or a pharmaceutically acceptable salt thereof, and at least one pharmaceutically acceptable carrier.
* * * * *

UNITED STATES PATENT AND TRADEMARK OFFICE
CERTIFICATE OF CORRECTION

| | |
|---|---|
| PATENT NO. | : 8,569,336 B2 |
| APPLICATION NO. | : 13/127953 |
| DATED | : October 29, 2013 |
| INVENTOR(S) | : Tong et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 213 days.

Signed and Sealed this
Twenty-first Day of April, 2015

Michelle K. Lee
*Director of the United States Patent and Trademark Office*